US011891361B2

(12) United States Patent
La et al.

(10) Patent No.: US 11,891,361 B2
(45) Date of Patent: Feb. 6, 2024

(54) HETEROCYCLIC COMPOUND AND ORGANIC LIGHT EMITTING DEVICE COMPRISING SAME

(71) Applicant: LT MATERIALS CO., LTD., Yongin (KR)

(72) Inventors: Hyun-Ju La, Hwaseong-si (KR); Seong-Jong Park, Osan-si (KR); Won-Jang Jeong, Hwaseong-si (KR); Jin-Seok Choi, Suwon-si (KR); Dae-Hyuk Choi, Yongin-si (KR); Joo-Dong Lee, Seongnam-si (KR)

(73) Assignee: LT MATERIALS CO., LTD., Yongin-si (KR)

( * ) Notice: Subject to any disclaimer, the term of this patent is extended or adjusted under 35 U.S.C. 154(b) by 415 days.

(21) Appl. No.: 16/624,812

(22) PCT Filed: Dec. 26, 2018

(86) PCT No.: PCT/KR2018/016622
§ 371 (c)(1),
(2) Date: Dec. 19, 2019

(87) PCT Pub. No.: WO2019/132492
PCT Pub. Date: Jul. 4, 2019

(65) Prior Publication Data
US 2020/0131133 A1 Apr. 30, 2020

(30) Foreign Application Priority Data
Dec. 26, 2017 (KR) ........................ 10-2017-0179830

(51) Int. Cl.
*C07D 221/12* (2006.01)
*C07D 401/10* (2006.01)
(Continued)

(52) U.S. Cl.
CPC ......... *C07D 221/12* (2013.01); *C07D 401/10* (2013.01); *C07D 401/12* (2013.01);
(Continued)

(58) Field of Classification Search
None
See application file for complete search history.

(56) References Cited

U.S. PATENT DOCUMENTS 4,356,429 A 10/1982 Tang
2003/0168970 A1 9/2003 Tominaga et al.
(Continued)

FOREIGN PATENT DOCUMENTS

CN 105339363 A 2/2016
CN 106910833 A 6/2017
(Continued)

OTHER PUBLICATIONS

International Search Report (PCT/ISA/210) issued in PCT/KR2018/016622, dated Mar. 26, 2019.
(Continued)

*Primary Examiner* — Jay Yang
(74) *Attorney, Agent, or Firm* — Birch, Stewart, Kolasch & Birch, LLP

(57) ABSTRACT

The present specification relates to a heterocyclic compound represented by Chemical Formula 1, and an organic light emitting device comprising the same.

9 Claims, 3 Drawing Sheets

(51) Int. Cl.

| | |
|---|---|
| ***C07D 403/10*** | (2006.01) |
| ***C07D 513/02*** | (2006.01) |
| ***C07F 9/53*** | (2006.01) |
| ***C07D 401/14*** | (2006.01) |
| ***C07D 407/14*** | (2006.01) |
| ***C07D 409/14*** | (2006.01) |
| ***C07D 401/12*** | (2006.01) |
| ***C07D 413/10*** | (2006.01) |
| ***C07D 471/04*** | (2006.01) |
| ***H01L 51/00*** | (2006.01) |
| ***H10K 85/60*** | (2023.01) |
| *H10K 50/16* | (2023.01) |
| *H10K 50/17* | (2023.01) |

(52) U.S. Cl.

CPC ......... *C07D 401/14* (2013.01); *C07D 403/10* (2013.01); *C07D 407/14* (2013.01); *C07D 409/14* (2013.01); *C07D 413/10* (2013.01); *C07D 471/04* (2013.01); *C07D 513/02* (2013.01); *C07F 9/5325* (2013.01); *H10K 85/622* (2023.02); *H10K 85/626* (2023.02); *H10K 85/656* (2023.02); *H10K 85/6572* (2023.02); *H10K 85/6574* (2023.02); *H10K 85/6576* (2023.02); *H10K 50/16* (2023.02); *H10K 50/171* (2023.02)

(56) References Cited

U.S. PATENT DOCUMENTS

| | | | |
|---|---|---|---|
| 2015/0333266 | A1 | 11/2015 | Ito et al. |
| 2015/0364698 | A1 | 12/2015 | Kim et al. |
| 2016/0141514 | A1 | 5/2016 | Lee et al. |
| 2016/0172598 | A1 | 6/2016 | Lee et al. |
| 2017/0179396 | A1 | 6/2017 | Kim et al. |
| 2017/0179402 | A1 | 6/2017 | Kim et al. |
| 2017/0179407 | A1 | 6/2017 | Park et al. |
| 2018/0282295 | A1 | 10/2018 | Parham et al. |

FOREIGN PATENT DOCUMENTS

| | | | |
|---|---|---|---|
| JP | 10-251634 | A | 9/1998 |
| JP | 2002-222697 | A | 8/2002 |
| JP | 2010-270245 | A | 12/2010 |
| KR | 10-2009-0036441 | A | 4/2009 |
| KR | 10-2012-0122982 | A | 11/2012 |
| KR | 10-2013-0094628 | A | 8/2013 |
| KR | 10-2015-0143280 | A | 12/2015 |
| KR | 10-2017-0074731 | A | 6/2017 |
| KR | 10-2017-0075117 | A | 7/2017 |
| KR | 10-2017-0084190 | A | 7/2017 |
| WO | WO-2016/074755 | A1 * | 5/2016 |

OTHER PUBLICATIONS

Kuwabara et al., "Thermally Stable Multilayered Organic Electroluminescent Devices Using Novel Starburst Molecules, 4,4', 4"-Tr(N-carbazolyl)triphenylamine (TCTA) and 4,4', 4"-Tris(3-methylphenylphenyl-amino)triphenylamine (m-MTDATA), as Hole-Transport Materials," Advanced Materials, vol. 6, No. 9, 1994, pp. 677-679.

* cited by examiner

【FIG. 1】
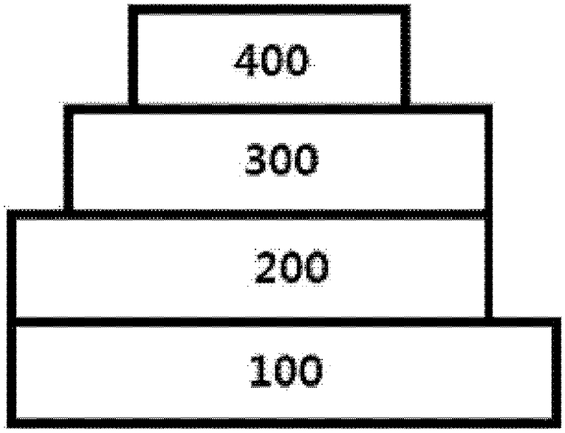
【FIG. 2】
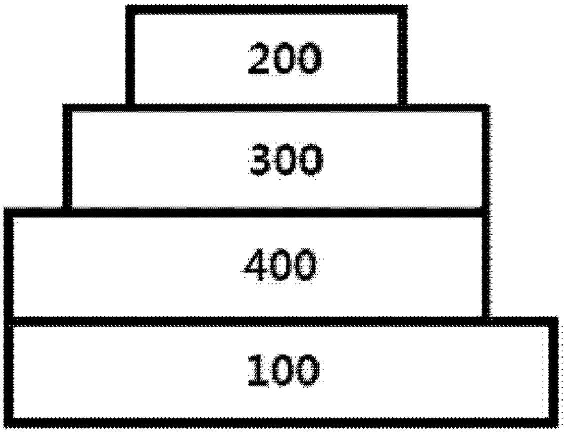

【FIG. 3】
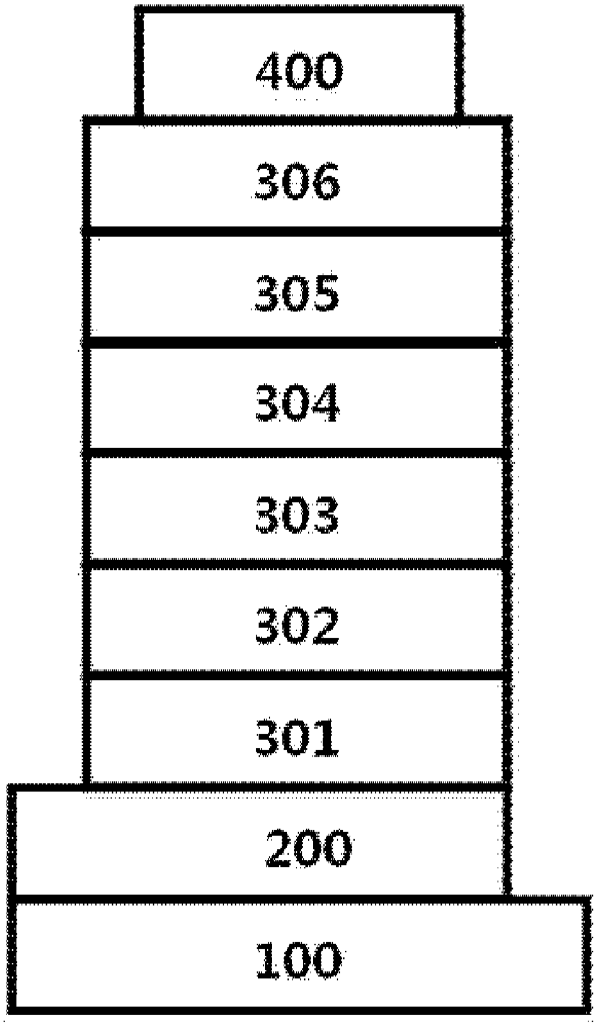

【FIG. 4】
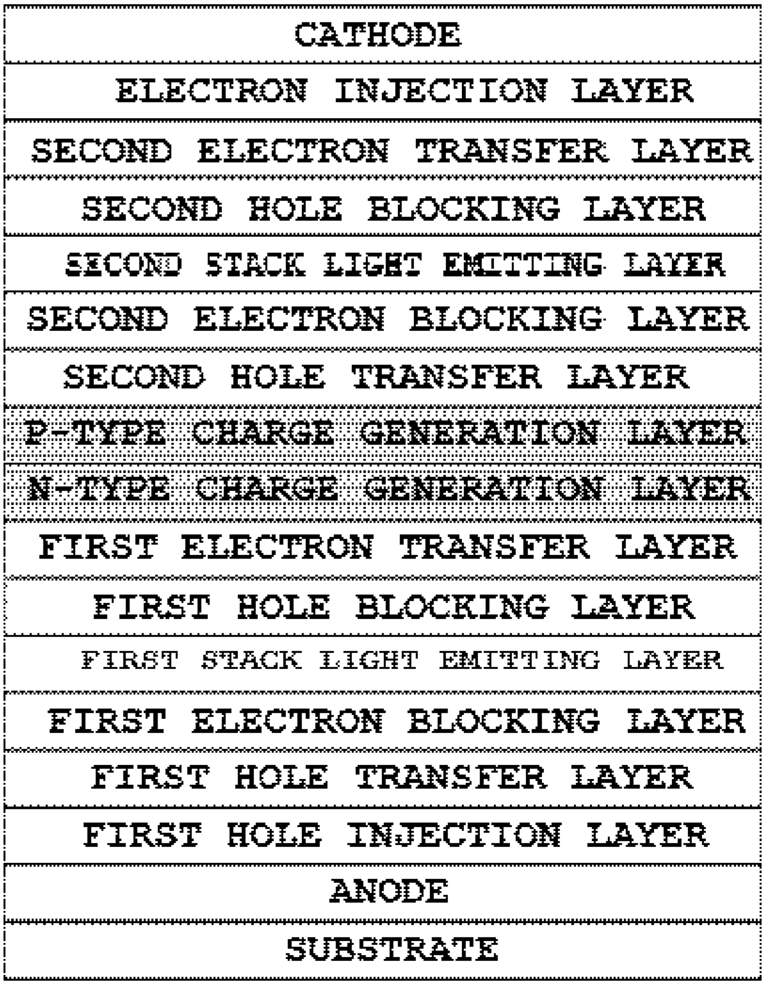

HETEROCYCLIC COMPOUND AND ORGANIC LIGHT EMITTING DEVICE COMPRISING SAME

TECHNICAL FIELD

This application claims priority to and the benefits of Korean Patent Application No. 10-2017-0179830, filed with the Korean Intellectual Property Office on Dec. 26, 2017, the entire contents of which are incorporated herein by reference.

The present specification relates to a heterocyclic compound and an organic light emitting device comprising the same.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of foaming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

DISCLOSURE

Technical Problem

The present disclosure is directed to providing a novel heterocyclic compound and an organic light emitting device comprising the same.

Technical Solution

One embodiment of the present application provides a heterocyclic compound represented by the following Chemical Formula 1.

[Chemical Formula 1]

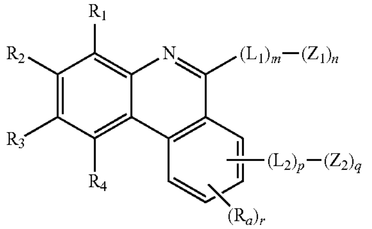

In Chemical Formula 1, $R_1$ to $R_4$ are the same as or different from each other, and each independently selected from the group consisting of hydrogen; deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; —SiRR'R"; —P(═O)RR'; and an amine group unsubstituted or substituted with a substituted or unsubstituted alkyl group, a substituted or unsubstituted aryl group, or a substituted or unsubstituted heteroaryl group, or two or more groups adjacent to each other bond to each other to form a substituted or unsubstituted aliphatic or aromatic hydrocarbon ring, $R_a$ is hydrogen; a substituted or unsubstituted alkyl group; a substituted or unsubstituted aryl group; or a substituted or unsubstituted heteroaryl group, $L_1$ and $L_2$ are the same as or different from each other, and each independently —O—; a substituted or unsubstituted arylene group; or a substituted or unsubstituted heteroarylene group, $Z_1$ and $Z_2$ are the same as or different from each other, and each independently selected from the group consisting of hydrogen; deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; —SiRR'R"; —P(═O)RR'; and an amine group unsubstituted or substituted with a substituted or unsubstituted alkyl group, a substituted or unsubstituted aryl group, or a substituted or unsubstituted heteroaryl group, R, R' and R" are the same as or different from each other, and each independently hydrogen; deuterium; —CN; a substituted or unsubstituted alkyl group; a substituted or unsubstituted cycloalkyl group; a substituted or unsubstituted aryl group; or a substituted or unsubstituted heteroaryl group, p and m are an integer of 1 to 4, q and n are an integer of 1 to 3, and r is an integer of 0 to 3.

Another embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound according to one embodiment of the present application.

Advantageous Effects

A compound described in the present specification can be used as an organic material layer material of an organic light emitting device. The compound is capable of performing a role of a hole injection material, a hole transfer material, a light emitting material, an electron transfer material, an electron injection material and the like in the organic light emitting device. Particularly, the compound can be used as an electron transfer layer material or a charge generation layer material of the organic light emitting device.

Specifically, when using the compound represented by Chemical Formula 1 in the organic material layer, a driving voltage is lowered and light efficiency is enhanced in the device, and device lifetime properties can be enhanced by thermal stability of the compound.

DESCRIPTION OF DRAWINGS

FIG. 1 to FIG. 4 are diagrams each schematically illustrating a lamination structure of an organic light emitting device according to one embodiment of the present application.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

BEST MODE

Hereinafter, the present application will be described in detail.

The term "substituted" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the halogen may be fluorine, chlorine, bromine or iodine.

In the present specification, the alkyl group comprises linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group comprises linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may comprise methoxy, ethoxy, n-propoxy, isopropoxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benxyloxy, p-methylbenzyloxy and the like, but are not limited thereto.

In the present specification, the cycloalkyl group comprises monocyclic or multicyclic having 3 to 60 carbon atoms, and may be further substituted with other substituents. Herein, the multicyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group comprises O, S, Se, N or Si as a heteroatom, comprises monocyclic or multicyclic having 2 to 60 carbon atoms, and may be further substituted with other substituents. Herein, the multicyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group comprises monocyclic or multicyclic having 6 to 60 carbon atoms, and may be further substituted with other substituents. Herein, the multicyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group comprises a spiro group. The number of carbon atoms of the aryl group may be from 6 to 60, specifically from 6 to 40 and more specifically from 6 to 25. Specific examples of the aryl group may comprise a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the silyl group is a substituent comprising Si, having the Si atom directly linked as a radical, and is represented by —$SiR_{104}R_{105}R_{106}$. $R_{104}$ to $R_{106}$ are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the silyl group may comprise a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the fluorenyl group may be substituted, and adjacent substituents may bond to each other to form a ring.

When the fluorenyl group is substituted,

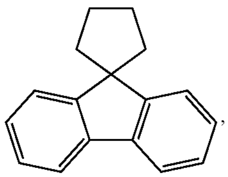
,
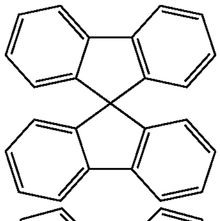
,
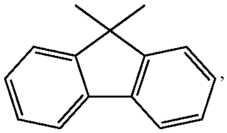
,
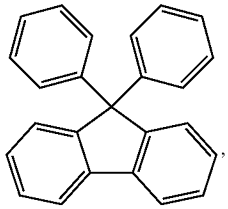
,
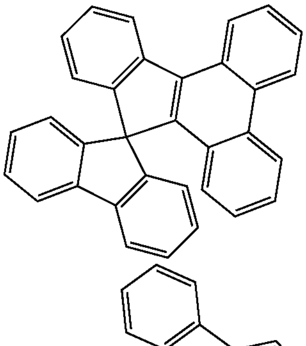
,
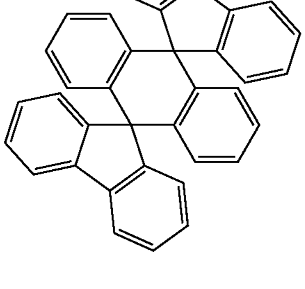

and the like may be included. However, the structure is not limited thereto.

In the present specification, the heteroaryl group comprises O, S, Se, N or Si as a heteroatom, comprises monocyclic or multicyclic having 2 to 60 carbon atoms, and may be further substituted with other substituents. Herein, the multicyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a triazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a triazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydrodibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; —$NH_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. Descriptions on the aryl group provided above may be applied thereto except for each being a divalent. In addition, the heteroarylene group means the heteroaryl group having two bonding sites, that is, a divalent group. Descriptions on the heteroaryl group provided above may be applied thereto except for each being a divalent.

In the present specification, specific examples of the phosphine oxide group may comprise a diphenylphosphine oxide group, a dinaphthylphosphine oxide group and the like, but are not limited thereto.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, the term "substituted" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; P(=O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted.

One embodiment of the present application provides a compound represented by Chemical Formula 1.

Chemical Formula 1 is a compound having specific substituents in 2 or 3 places in the phenanthridine core structure. By combining an electron-deficient substituent and an aryl or acene-based substituent, electrons are readily supplied to the electron-deficient substituent from an electron injection layer, and by the acryl or acene-based substituent stabilizing the molecule itself or transferring the supplied electrons to a light emitting layer, high molecular stability and enhanced device properties may be obtained compared to compounds in which phenanthridine is monosubstituted when used in an organic light emitting device later.

In one embodiment of the present application, $R_1$ to $R_4$ of Chemical Formula 1 are the same as or different from each other, and each independently selected from the group consisting of hydrogen; deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group, or two or more groups adjacent to each other may bond to each other to form a substituted or unsubstituted aliphatic or aromatic hydrocarbon ring.

In another embodiment, $R_1$ to $R_4$ of Chemical Formula 1 are the same as or different from each other, and each independently selected from the group consisting of hydrogen; a substituted or unsubstituted C1 to C60 aryl group; and a substituted or unsubstituted C2 to C60 heteroaryl group, or two or more groups adjacent to each other may bond to each other to form a substituted or unsubstituted aromatic hydrocarbon ring.

In another embodiment, $R_1$ to $R_4$ of Chemical Formula 1 are the same as or different from each other, and may be each independently selected from the group consisting of hydrogen; a substituted or unsubstituted C1 to C40 aryl group; and a substituted or unsubstituted C2 to C40 heteroaryl group.

In another embodiment, $R_1$ to $R_4$ of Chemical Formula 1 are the same as or different from each other, and may be each independently selected from the group consisting of hydrogen; a C1 to C40 aryl group; and a C2 to C40 heteroaryl group.

In another embodiment, $R_1$ to $R_4$ of Chemical Formula 1 are the same as or different from each other, and may be each independently hydrogen; a phenyl group; a biphenyl group; a naphthyl group; or a pyridine group.

In one embodiment of the present application, $R_1$ to $R_4$ may be hydrogen.

In one embodiment of the present application, $R_a$ of Chemical Formula 1 may be hydrogen; a substituted or unsubstituted alkyl group; a substituted or unsubstituted aryl group; or a substituted or unsubstituted heteroaryl group.

In another embodiment, $R_a$ of Chemical Formula 1 may be hydrogen; a substituted or unsubstituted C6 to C60 aryl group; or a substituted or unsubstituted C2 to C60 heteroaryl group.

In another embodiment, $R_a$ of Chemical Formula 1 may be hydrogen; a C6 to C40 aryl group; or a C2 to C40 heteroaryl group.

In another embodiment, $R_a$ of Chemical Formula 1 may be hydrogen.

In one embodiment of the present application, $L_1$ and $L_2$ of Chemical Formula 1 are the same as or different from each other, and may be each independently —O—; a substituted or unsubstituted arylene group; or a substituted or unsubstituted heteroarylene group.

In another embodiment, $L_1$ and $L_2$ of Chemical Formula 1 are the same as or different from each other, and may be each independently —O—; a substituted or unsubstituted C6 to C60 arylene group; or a substituted or unsubstituted C2 to C60 heteroarylene group.

In another embodiment, $L_1$ and $L_2$ of Chemical Formula 1 are the same as or different from each other, and may be each independently —O—; a substituted or unsubstituted C6 to C40 arylene group; or a substituted or unsubstituted C2 to C40 heteroarylene group.

In another embodiment, $L_1$ and $L_2$ of Chemical Formula 1 are the same as or different from each other, and may be each independently —O—; a C6 to C40 arylene group; or a C2 to C40 heteroarylene group unsubstituted or substituted with a C6 to C40 aryl group.

In another embodiment, $L_1$ and $L_2$ of Chemical Formula 1 are the same as or different from each other, and may be each independently —O—; a phenylene group; a biphenylene group; a naphthalene group; an anthracene group; a pyrene group; a phenanthrene group; a divalent pyridine group; a divalent pyrimidine group unsubstituted or substituted with a phenyl group; or a divalent triazine group unsubstituted or substituted with a phenyl group.

In one embodiment of the present application, $Z_1$ and $Z_2$ of Chemical Formula 1 are the same as or different from each other, and may be each independently selected from the group consisting of hydrogen; deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; —SiRR'R"; —P(═O)RR'; and an amine group unsubstituted or substituted with a substituted or unsubstituted alkyl group, a substituted or unsubstituted aryl group, or a substituted or unsubstituted heteroaryl group.

In another embodiment, $Z_1$ and $Z_2$ of Chemical Formula 1 are the same as or different from each other, and may be each independently selected from the group consisting of hydrogen; CN; a substituted or unsubstituted alkyl group; a substituted or unsubstituted aryl group; a substituted or unsubstituted heteroaryl group; —SiRR'R" and —P(═O)RR'.

In another embodiment, $Z_1$ and $Z_2$ of Chemical Formula 1 are the same as or different from each other, and may be each independently selected from the group consisting of hydrogen; —CN; a substituted or unsubstituted C1 to C60 alkyl group; a substituted or unsubstituted C6 to C60 aryl group; a substituted or unsubstituted C2 to C60 heteroaryl group; —SiRR'R" and —P(═O)RR'.

In another embodiment, $Z_1$ and $Z_2$ of Chemical Formula 1 are the same as or different from each other, and may be each independently selected from the group consisting of hydrogen; —CN; a substituted or unsubstituted C1 to C40 alkyl group; a substituted or unsubstituted C6 to C40 aryl group; a substituted or unsubstituted C2 to C40 heteroaryl group; —SiRR'R" and —P(═O)RR'.

In another embodiment, $Z_1$ and $Z_2$ of Chemical Formula 1 are the same as or different from each other, and may be each independently selected from the group consisting of hydrogen; —CN; a C1 to C40 alkyl group; a C6 to C40 aryl group unsubstituted or substituted with a C2 to C40 heteroaryl group; a C2 to C40 heteroaryl group unsubstituted or substituted with one or more substituents selected from the group consisting of a C1 to C40 alkyl group, a C6 to C40 aryl group and a C2 to C40 heteroaryl group; —SiRR'R" and —P(═O)RR'.

In another embodiment, $Z_1$ and $Z_2$ of Chemical Formula 1 are the same as or different from each other, and may be each independently selected from the group consisting of hydrogen; —CN; —SiRR'R" and —P(═O)RR'.

In another embodiment, $Z_1$ and $Z_2$ of Chemical Formula 1 are the same as or different from each other, and may be each independently a phenyl group unsubstituted or substituted with a pyridine group or a carbazole group; a biphenyl group; a naphthyl group; a phenanthrenyl group; a triphenylenyl group; or a terphenyl group.

In another embodiment, $Z_1$ and $Z_2$ of Chemical Formula 1 are the same as or different from each other, and may be each independently a pyridine group unsubstituted or substituted with a pyridine group; a triazine group unsubstituted or substituted with one or more substituents selected from the group consisting of a phenyl group, a biphenyl group, a naphthyl group and a phenanthrenyl group; a pyrimidine group unsubstituted or substituted with one or more substituents selected from the group consisting of a phenyl group, a biphenyl group, a naphthyl group and a phenanthrenyl group; a quinoline group; a quinazoline group unsubstituted or substituted with one or more substituents selected from the group consisting of a phenyl group, a naphthyl group and a biphenyl group; a phenanthridine group unsubstituted or substituted with one or more substituents selected from the group consisting of a phenyl group and a naphthyl group; a phenanthroline group unsubstituted or substituted with a phenyl group; a benzothiazole group unsubstituted or substituted with a phenyl group; a benzoxazole group; a benzimidazole group unsubstituted or substituted with one or more substituents selected from the group consisting of an ethyl group and a phenyl group; an imidazo[1,2-a]pyridine group unsubstituted or substituted with a phenyl group; a carbazole group; a dibenzofuran group; a dibenzothiophene group; a furazine group unsubstituted or substituted with a phenyl group; or a benzo[4,5]thieno[2,3-d]pyrimidine group unsubstituted or substituted with a phenyl group.

In one embodiment of the present application, $Z_1$ and $Z_2$ may be unsubstituted or substituted again with one or more substituents selected from the group consisting of a methyl group; a carbazole group; a phenyl group; a dibenzofuran group; a dibenzothiophene group; —P(═O)RR'; and a dimethylfluorenyl group.

In one embodiment of the present application, R, R' and R" are the same as or different from each other, and may be each independently hydrogen; deuterium; —CN; a substituted or unsubstituted alkyl group; a substituted or unsubstituted cycloalkyl group; a substituted or unsubstituted aryl group; or a substituted or unsubstituted heteroaryl group.

In another embodiment, R, R' and R" are the same as or different from each other, and may be each independently a substituted or unsubstituted alkyl group; or a substituted or unsubstituted aryl group.

In another embodiment, R, R' and R" are the same as or different from each other, and may be each independently a substituted or unsubstituted C1 to C60 alkyl group; or a substituted or unsubstituted C6 to C60 aryl group.

In another embodiment, R, R' and R" are the same as or different from each other, and may be each independently a substituted or unsubstituted C1 to C40 alkyl group; or a substituted or unsubstituted C6 to C40 aryl group.

In another embodiment, R, R' and R" are the same as or different from each other, and may be each independently a C1 to C40 alkyl group; or a C6 to C40 aryl group.

In another embodiment, R, R' and R" are the same as or different from each other, and may be each independently a phenyl group; or a methyl group.

In the heterocyclic compound provided in one embodiment of the present application, Chemical Formula 1 is represented by any one of the following Chemical Formulae 2 to 5.

[Chemical Formula 2]

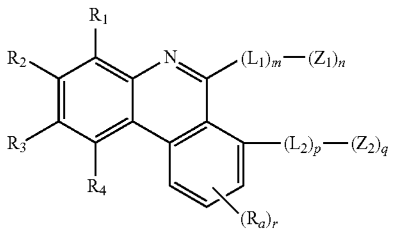

-continued

[Chemical Formula 3]

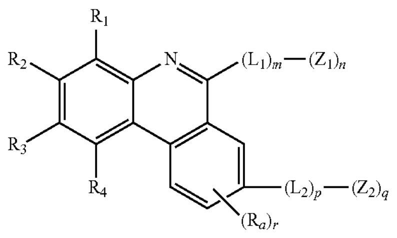

[Chemical Formula 4]

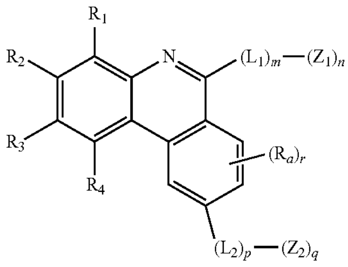

[Chemical Formula 5]

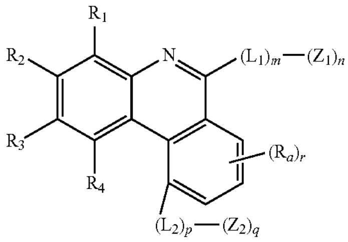

In Chemical Formulae 2 to 5, each substituent has the same definition as in Chemical Formula 1.

In the heterocyclic compound provided in one embodiment of the present application, Chemical Formula 1 is represented by any one of the following Chemical Formulae 6 to 10.

[Chemical Formula 6]

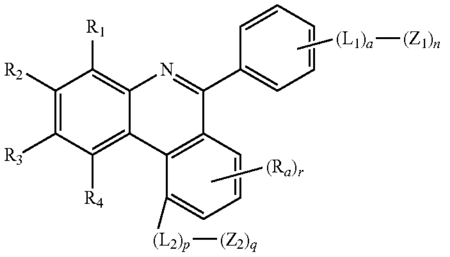

-continued

[Chemical Formula 7]

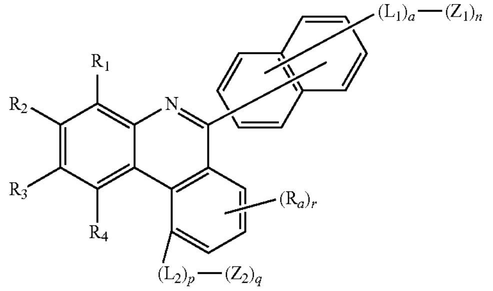

[Chemical Formula 8]

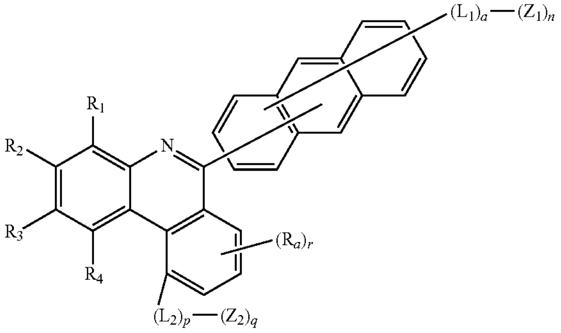

[Chemical Formula 9]

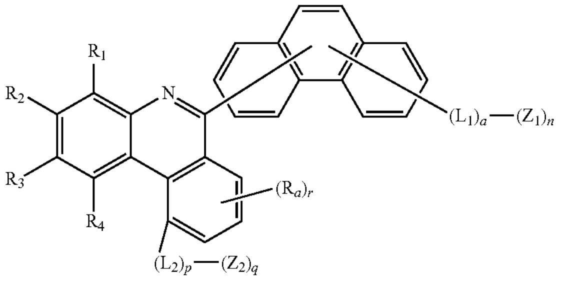

[Chemical Formula 10]

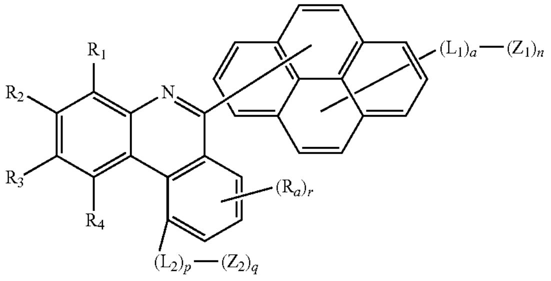

In Chemical Formulae 6 to 10, $R_1$ to $R_4$, $L_1$, $L_2$, $Z_1$, $Z_2$, Ra, p, q, r and n have the same definitions as in Chemical Formula 1, and a is an integer of 0 to 4.

In one embodiment of the present application, Chemical Formula 1 may be represented by the following Chemical Formula 11 or 12.

[Chemical Formula 11]

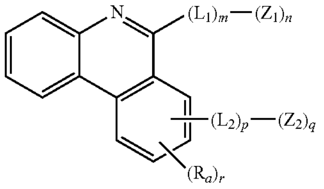

[Chemical Formula 12]

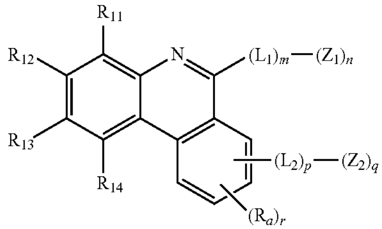

In Chemical Formulae 11 and 12, $L_1$, $L_2$, $Z_1$, $Z_2$, Ra, m, n, p, q and r have the same definitions as in Chemical Formula 1, $R_{11}$ to $R_{14}$ are hydrogen; a substituted or unsubstituted aryl group; or a substituted or unsubstituted heteroaryl group, and at least one of $R_{11}$ to $R_{14}$ is a substituted or unsubstituted aryl group; or a substituted or unsubstituted heteroaryl group.

In one embodiment of the present application, $R_{11}$ to $R_{14}$ are hydrogen; a substituted or unsubstituted aryl group; or a substituted or unsubstituted heteroaryl group, and at least one of $R_{11}$ to $R_{14}$ may be a substituted or unsubstituted aryl group; or a substituted or unsubstituted heteroaryl group.

In another embodiment, $R_{11}$ to $R_{14}$ are hydrogen; a substituted or unsubstituted C6 to C60 aryl group; or a substituted or unsubstituted C2 to C60 heteroaryl group, and at least one of $R_{11}$ to $R_{14}$ may be a substituted or unsubstituted C6 to C60 aryl group; or a substituted or unsubstituted C2 to C60 heteroaryl group.

In another embodiment, $R_{11}$ to $R_{14}$ are hydrogen; a substituted or unsubstituted C6 to C40 aryl group; or a substituted or unsubstituted C2 to C40 heteroaryl group, and at least one of $R_{11}$ to $R_{14}$ may be a substituted or unsubstituted C6 to C40 aryl group; or a substituted or unsubstituted C2 to C40 heteroaryl group.

In another embodiment, $R_{11}$ to $R_{14}$ are hydrogen; a C6 to C40 aryl group; or a C2 to C40 heteroaryl group, and at least one of $R_{11}$ to $R_{14}$ may be a C6 to C40 aryl group; or a C2 to C40 heteroaryl group.

In another embodiment, $R_{11}$ to $R_{14}$ are hydrogen; a phenyl group; a biphenyl group; a naphthyl group; or a pyridine group, and at least one of $R_{11}$ to $R_{14}$ may be a phenyl group; a biphenyl group; a naphthyl group; or a pyridine group.

In the heterocyclic compound provided in one embodiment of the present application, Chemical Formula 1 is represented by any one of the following compounds.

1

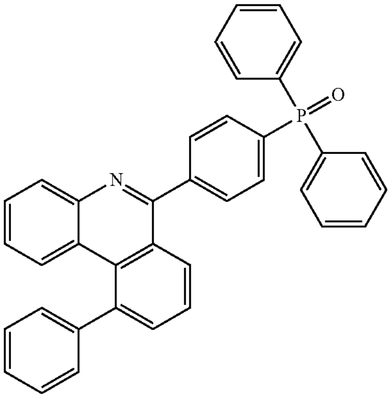

2

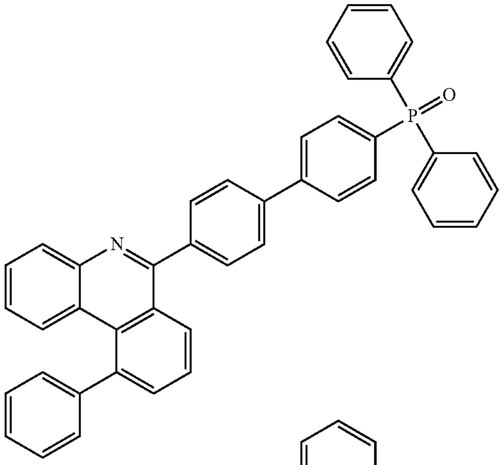

3

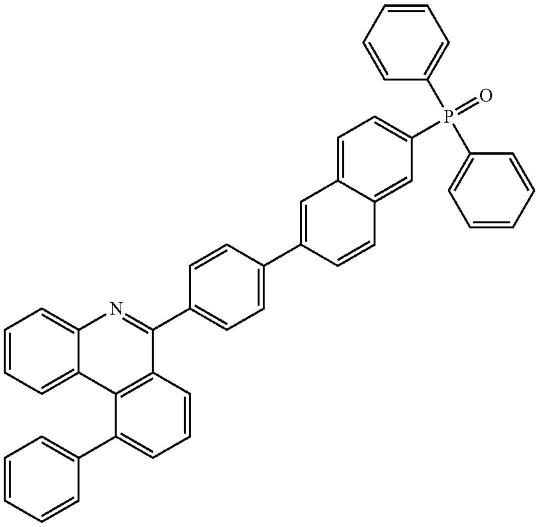

4

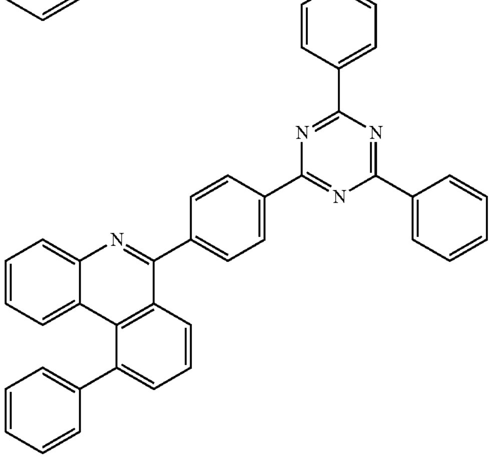

-continued
5
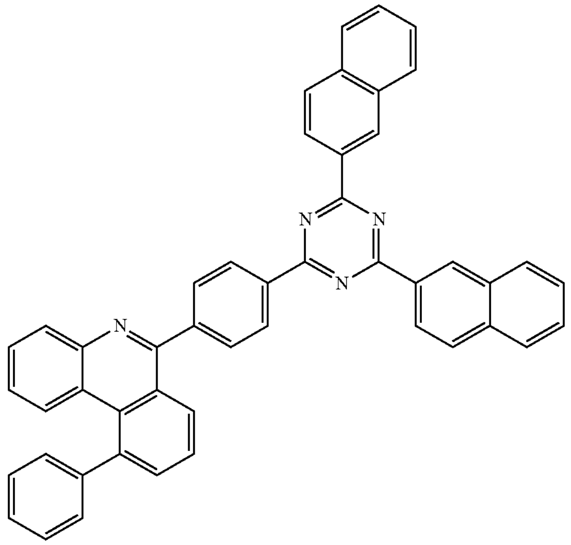
6
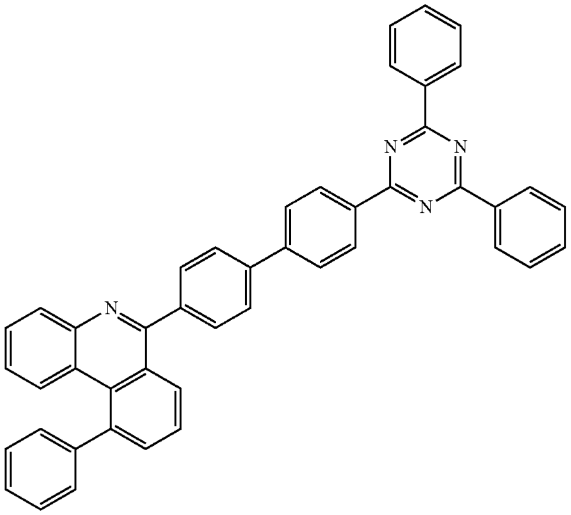
7
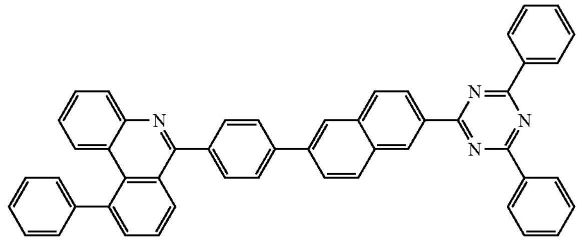
8
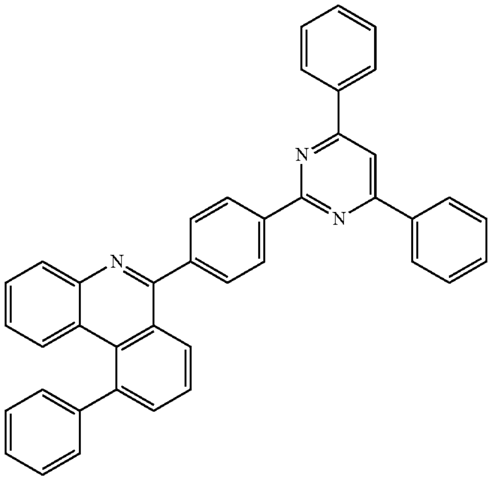
9
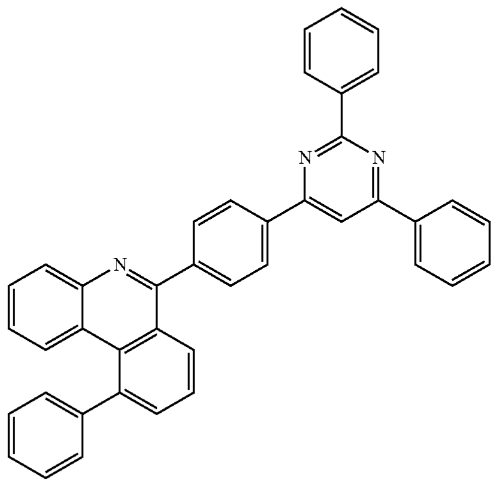
10
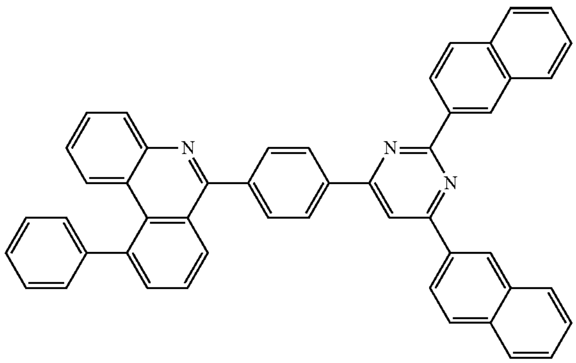

-continued
11
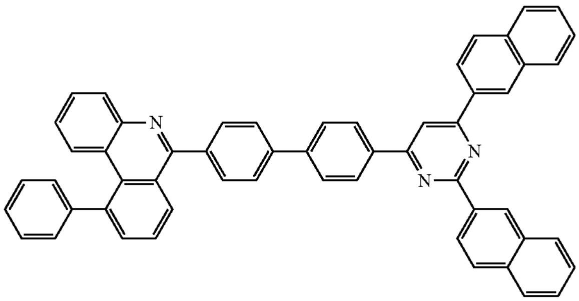
12
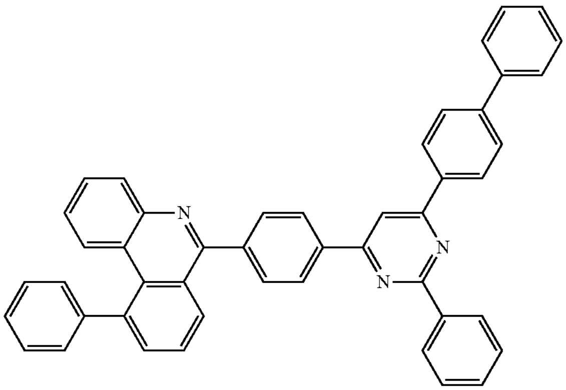
13
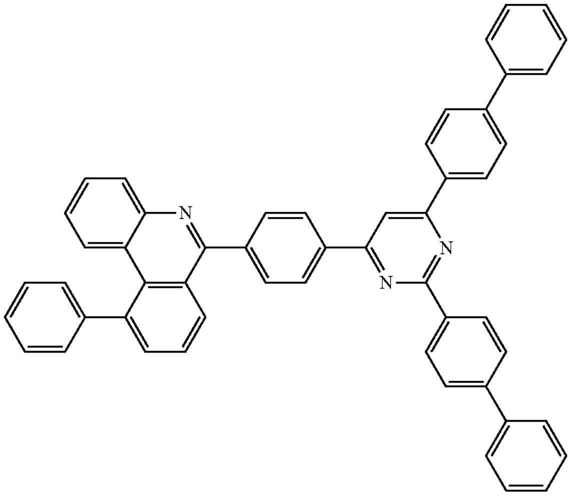
14
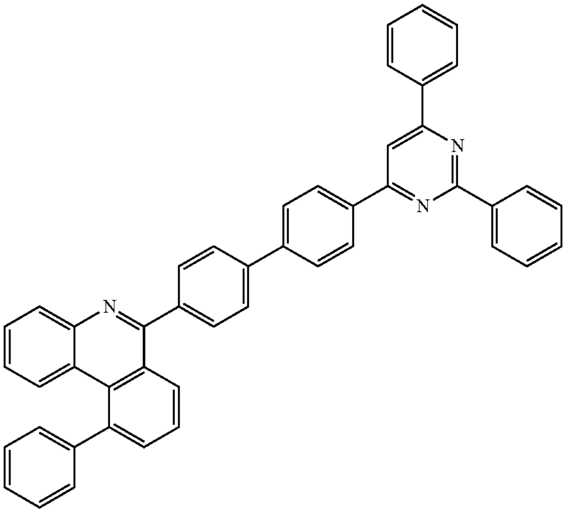
15
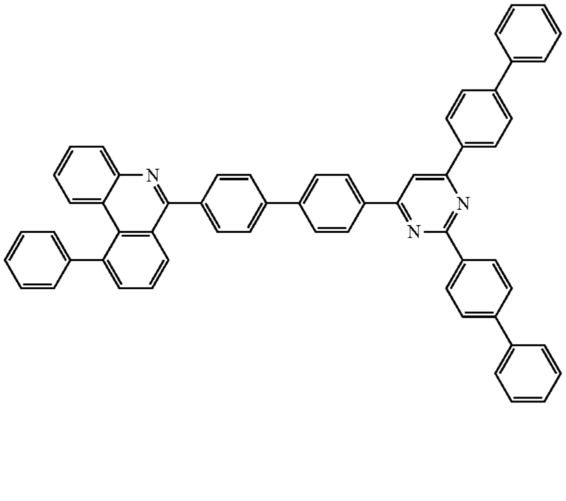
16
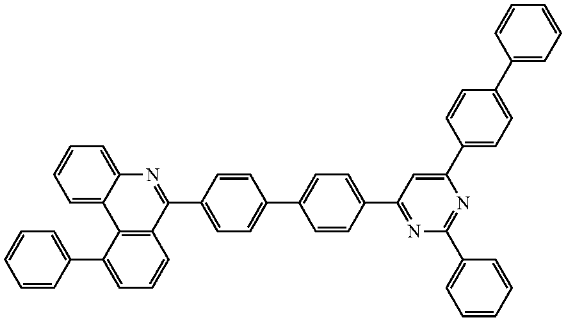

-continued
17
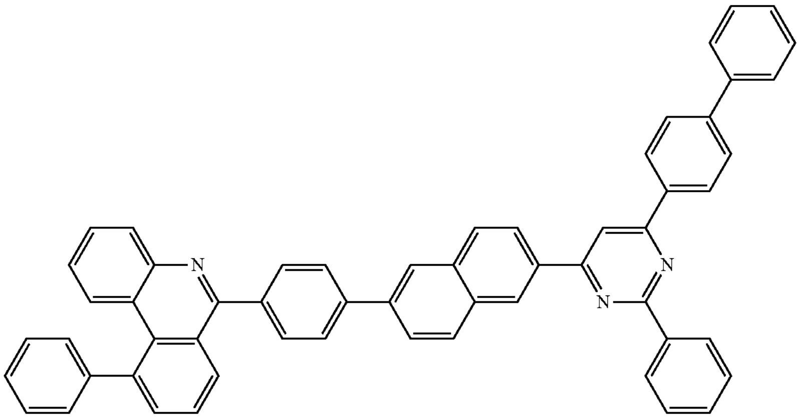
18
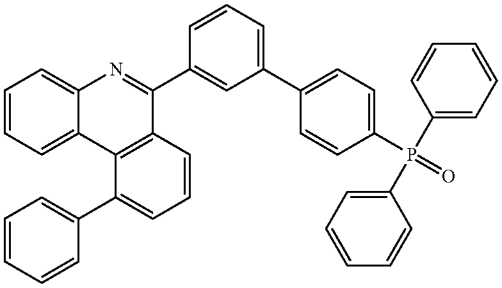
19
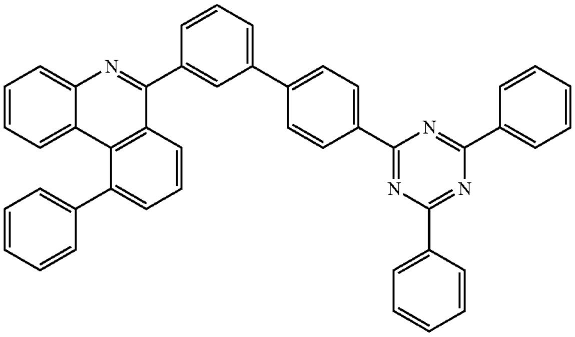
20
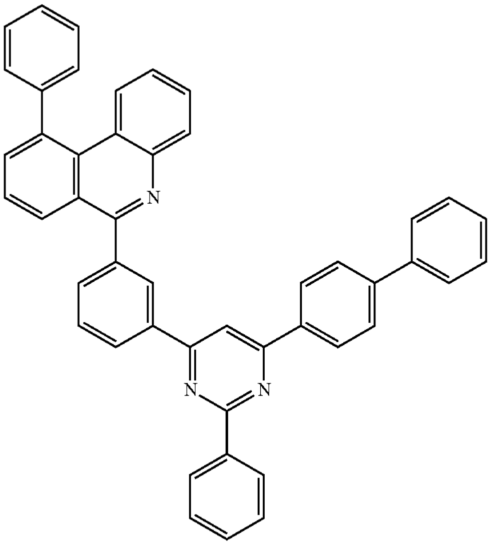
21
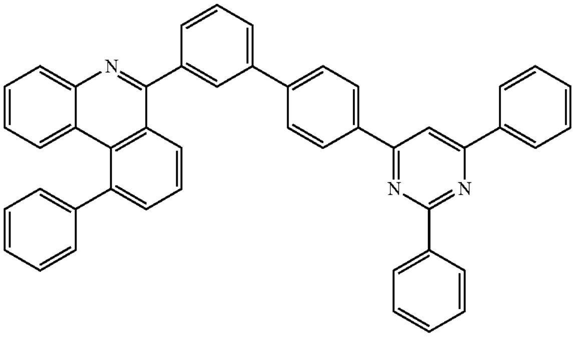

-continued
22
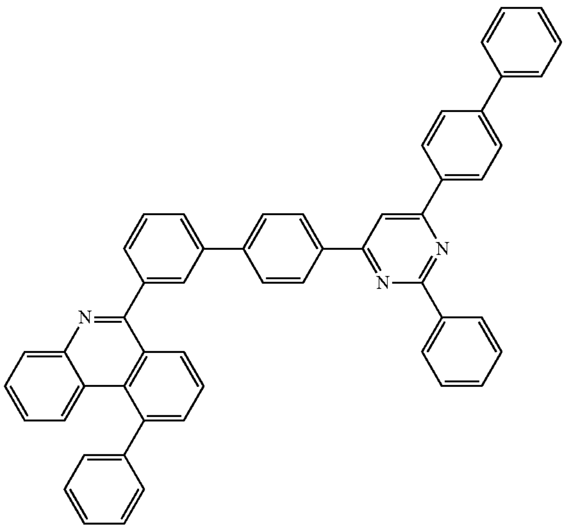
23
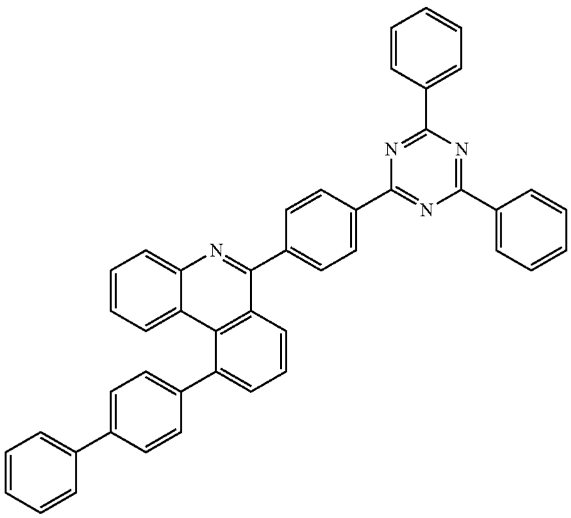
24
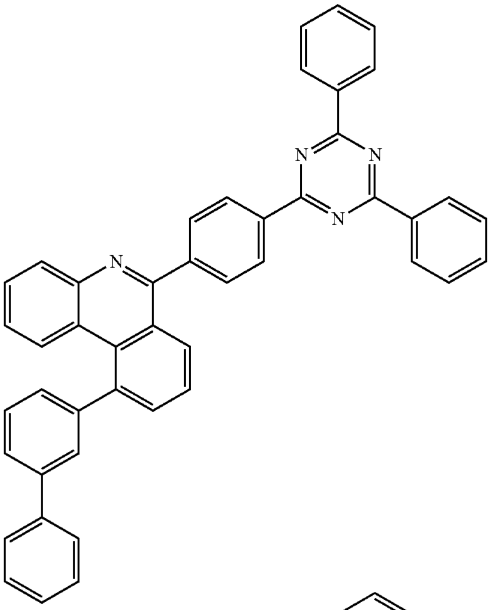
25
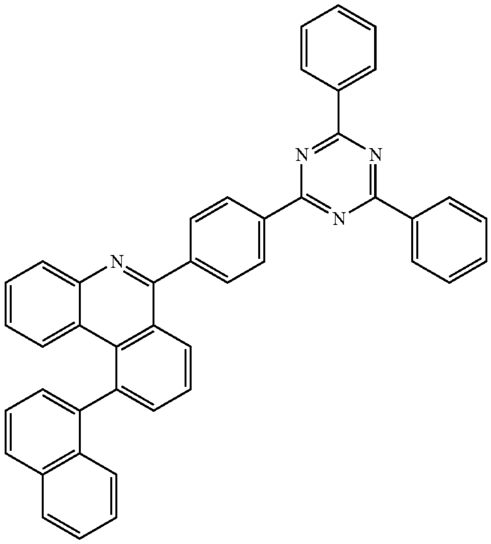
26
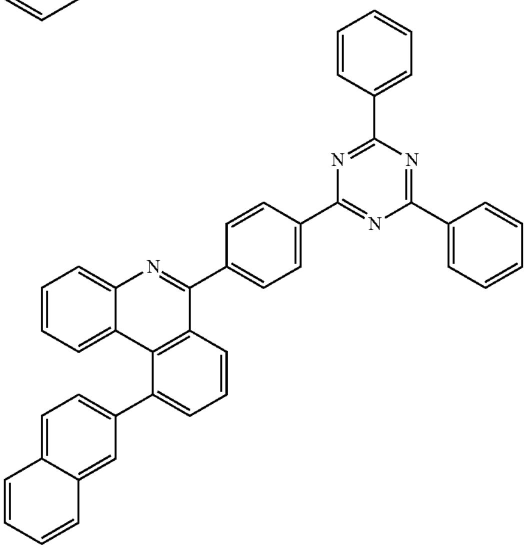
27
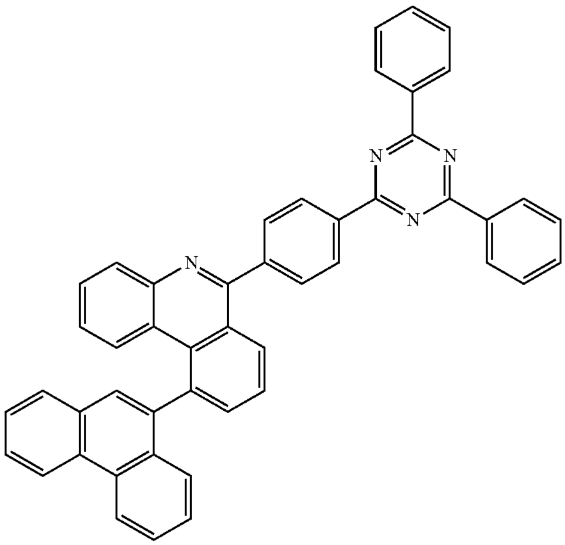

-continued
28
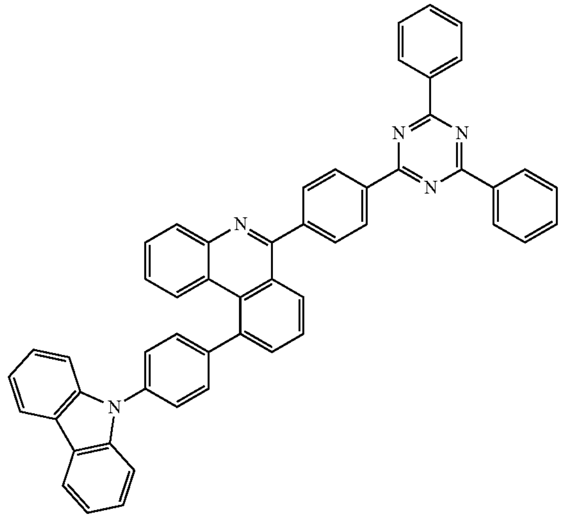
29
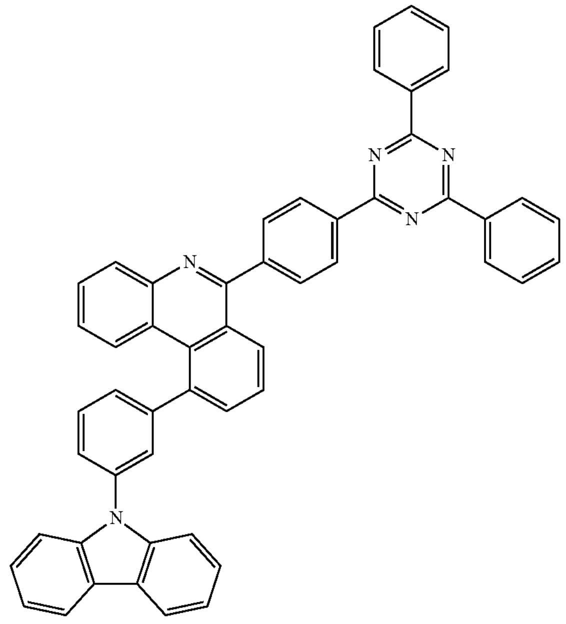
30
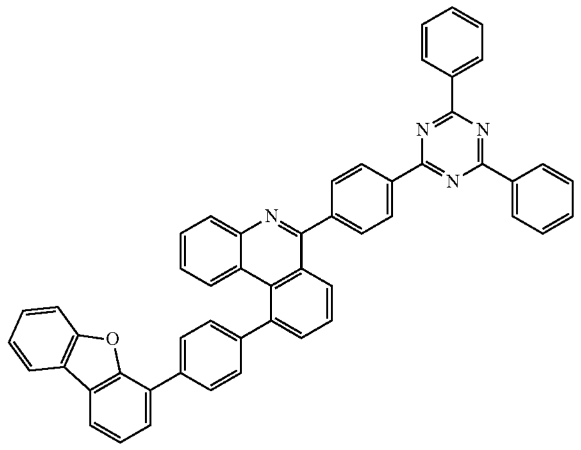
31
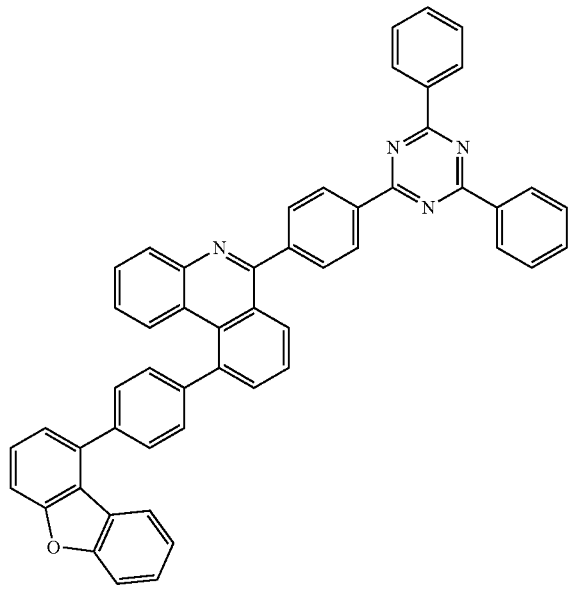

-continued
32
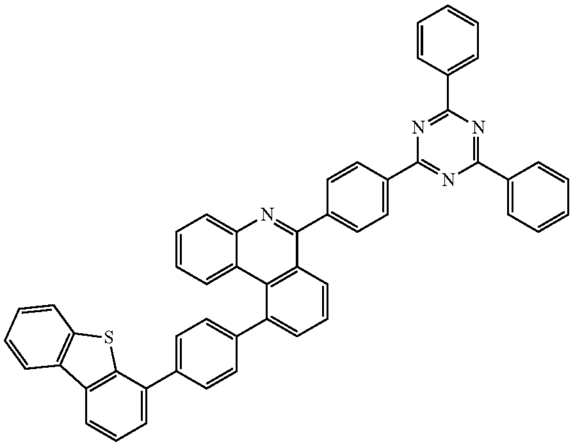
33
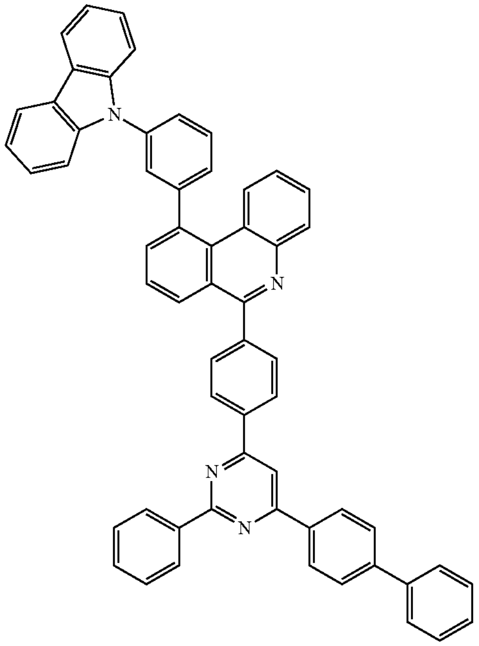
34
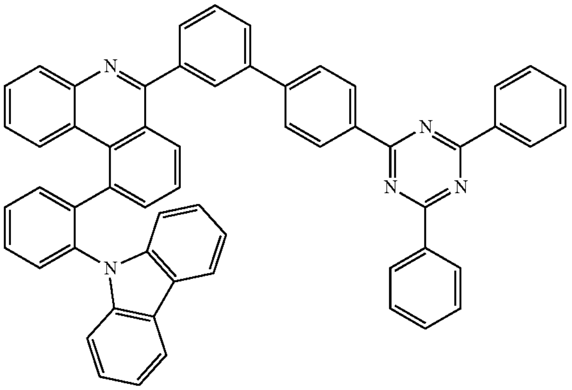
35
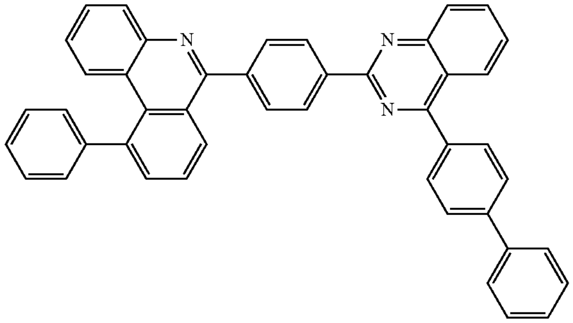
36
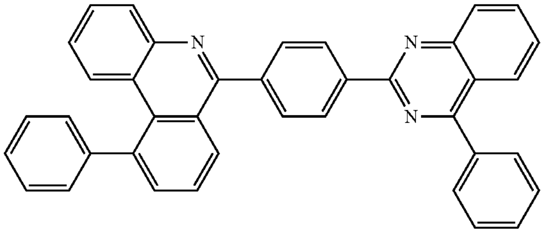
37
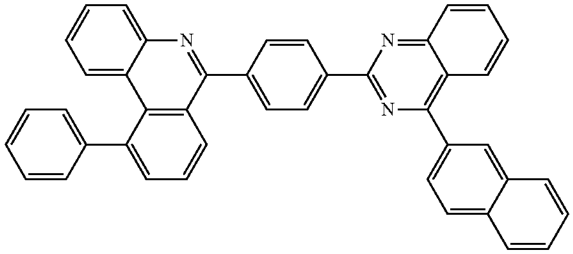
38
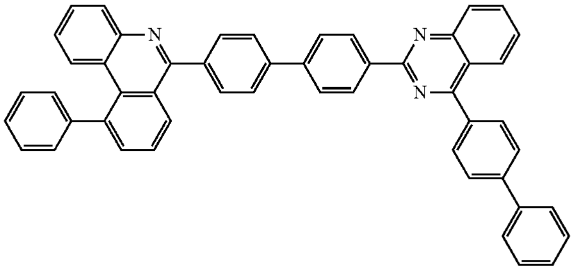
39
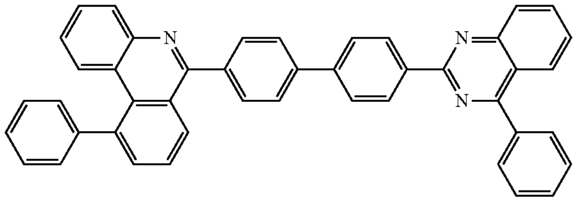

-continued
40
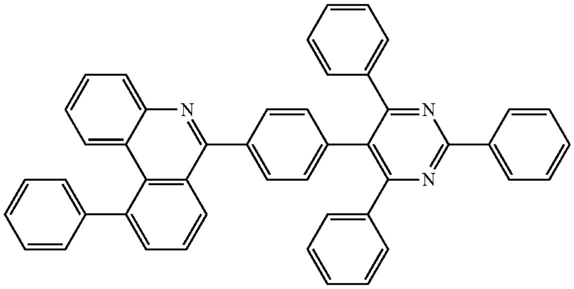
41
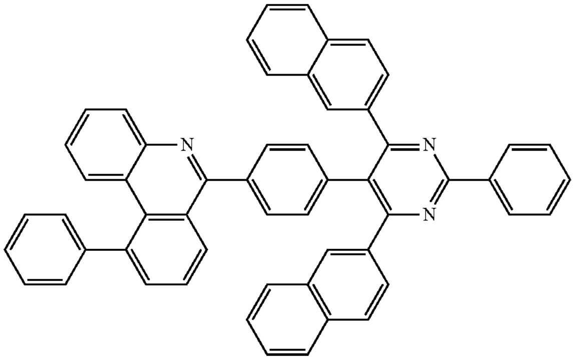
42
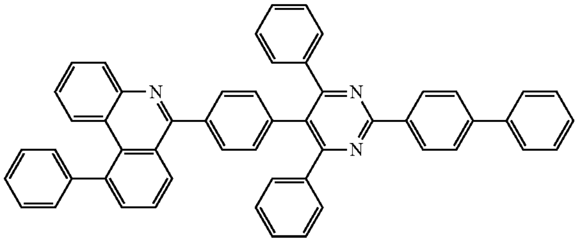
43
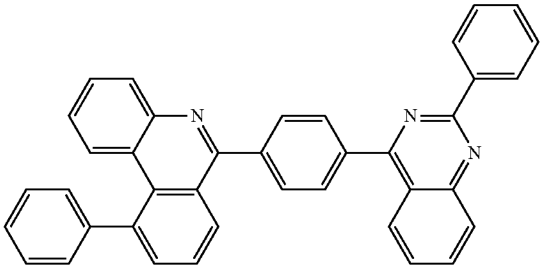
44
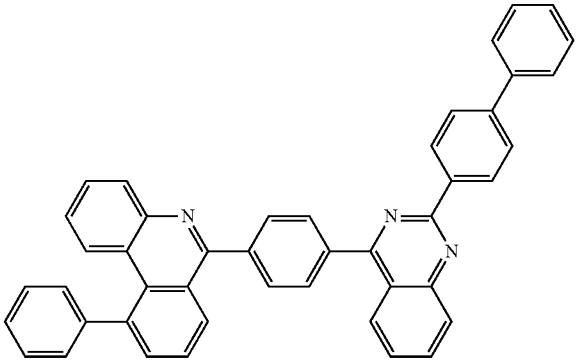
45
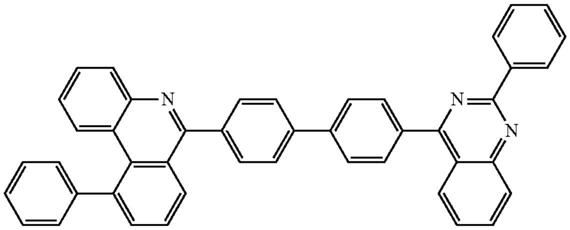
46
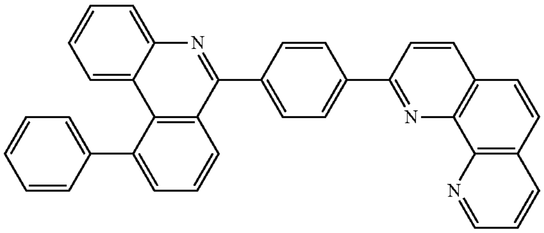
47
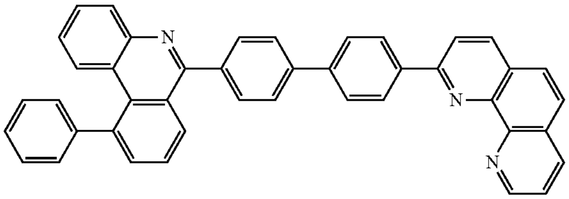

-continued
48
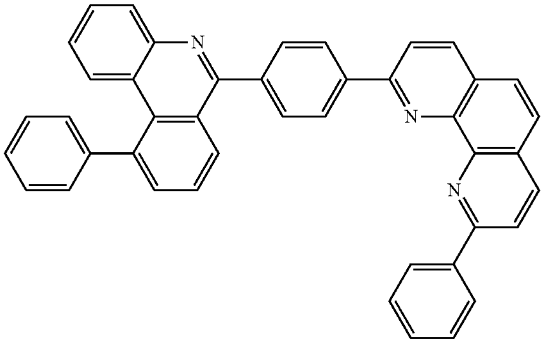
49
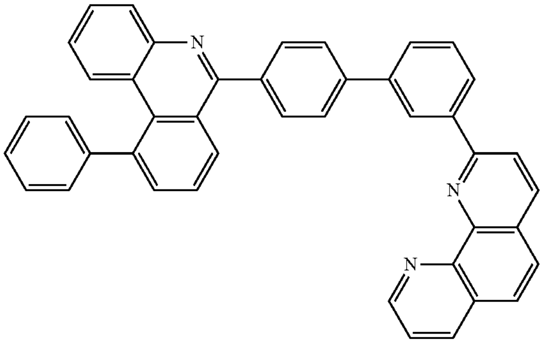
50
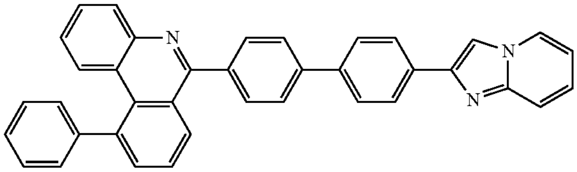
51
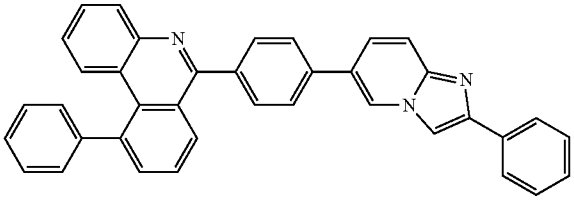
52
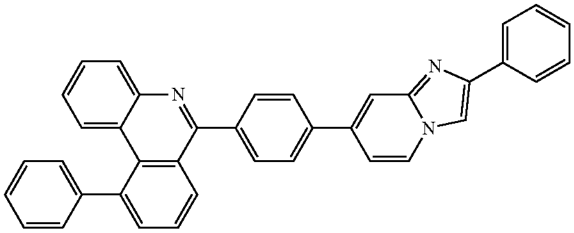
53
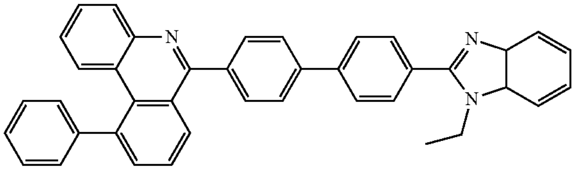
54
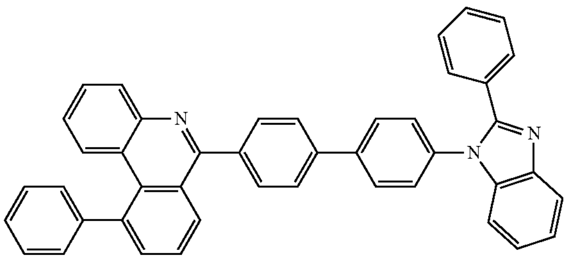
55
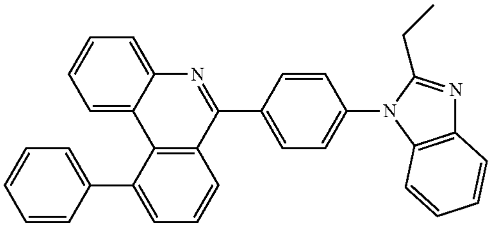
56
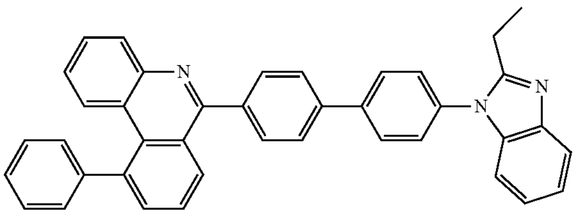
57
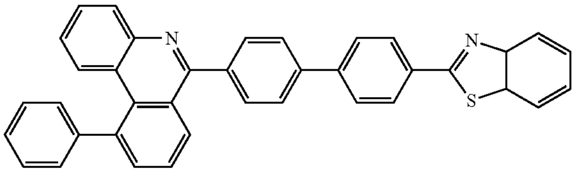

-continued
58
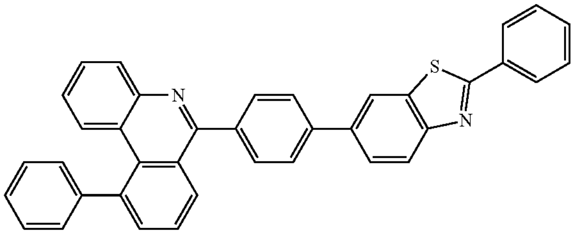
59
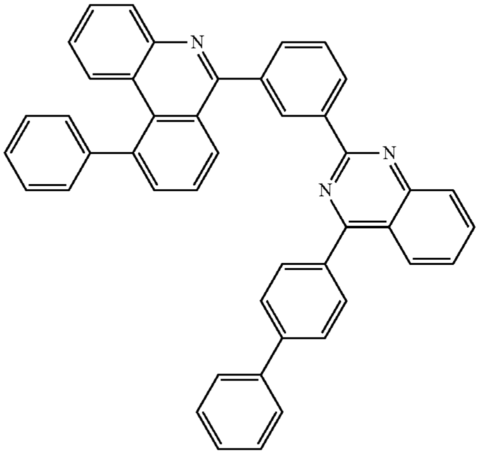
60
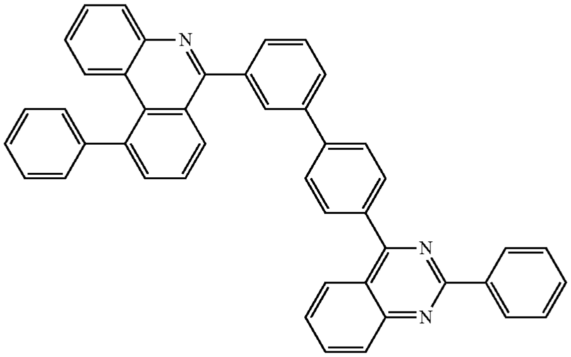
61
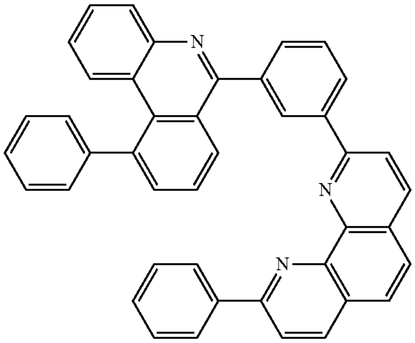
62
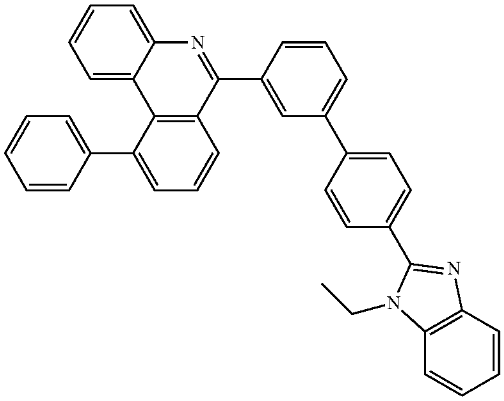
63
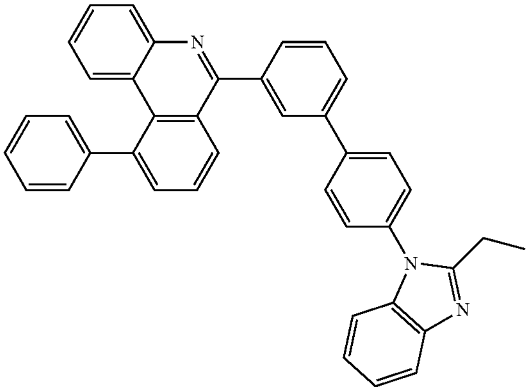

-continued
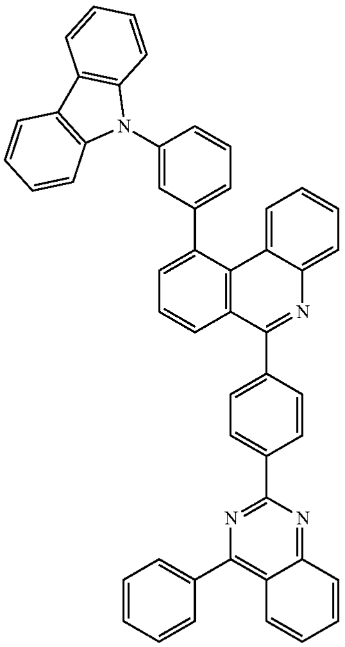
64
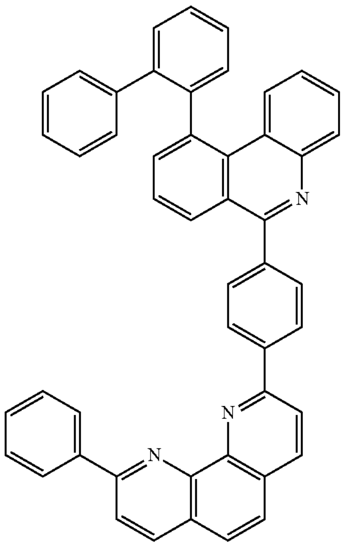
65
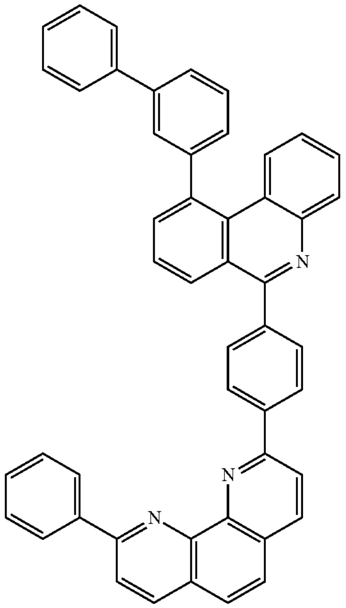
66
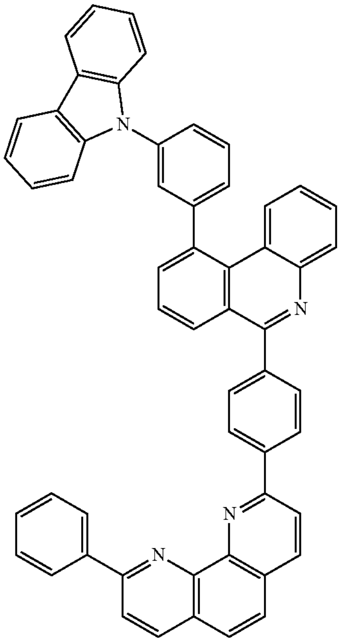
67

-continued
68
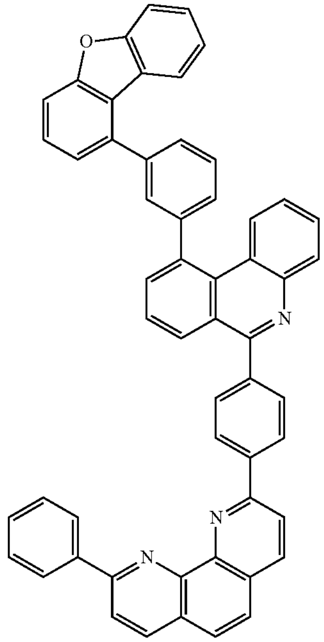
69
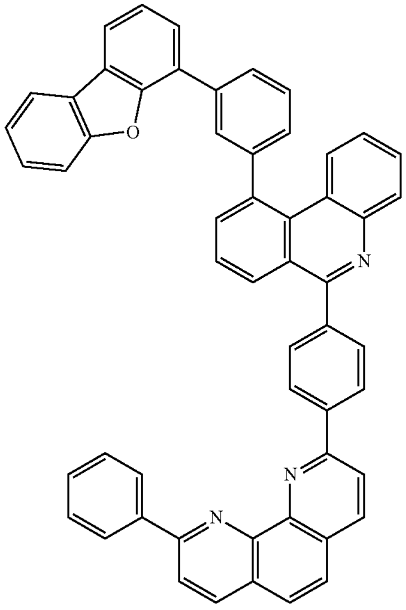
70
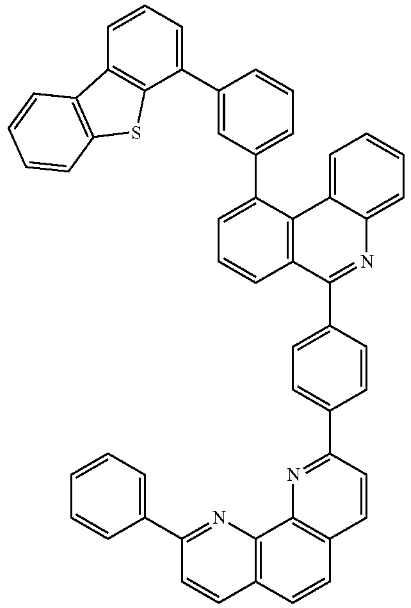
71
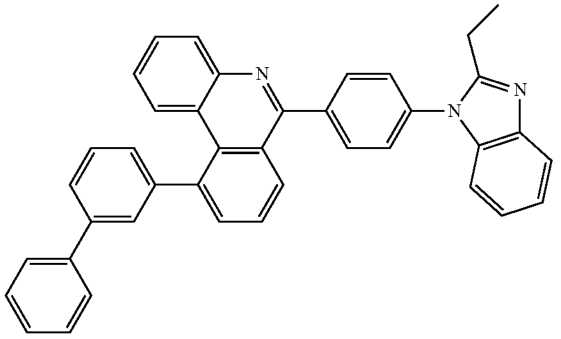
72
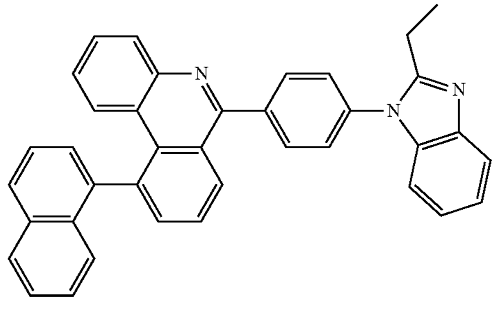
73
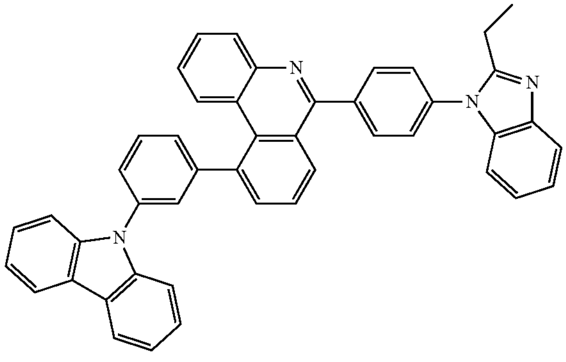

-continued
74
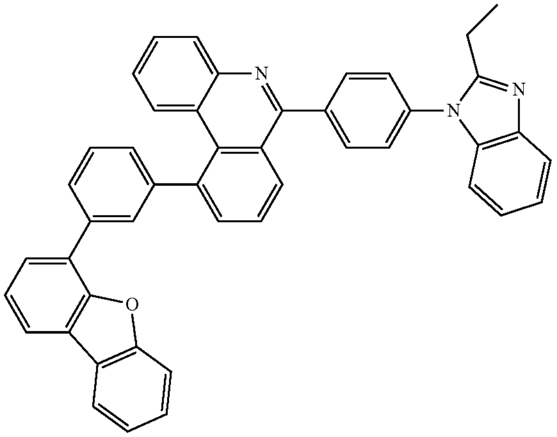
75
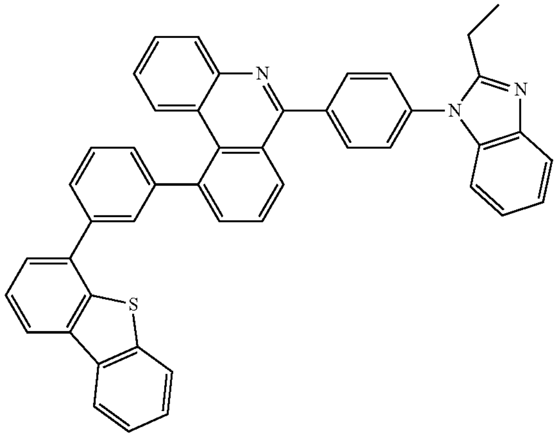
76
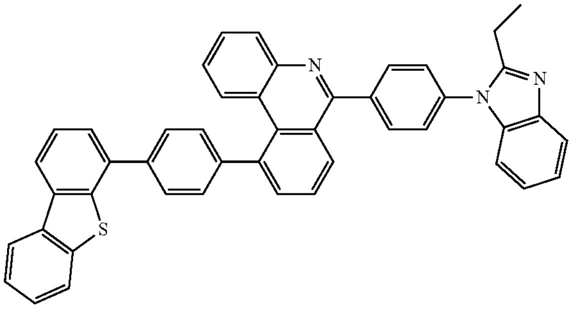
77
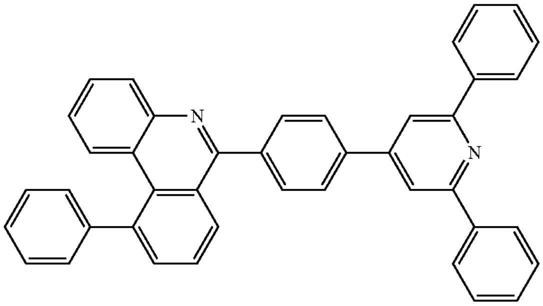
78
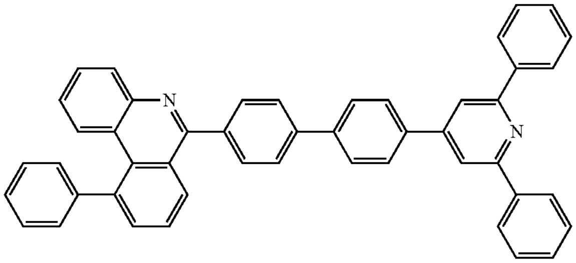
79
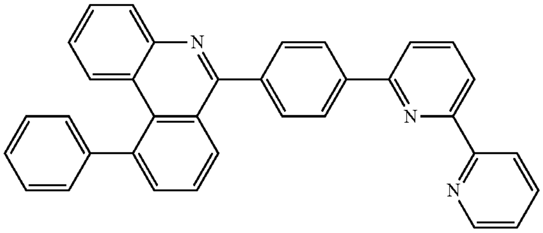
80
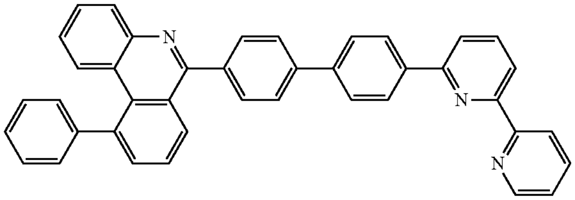
81
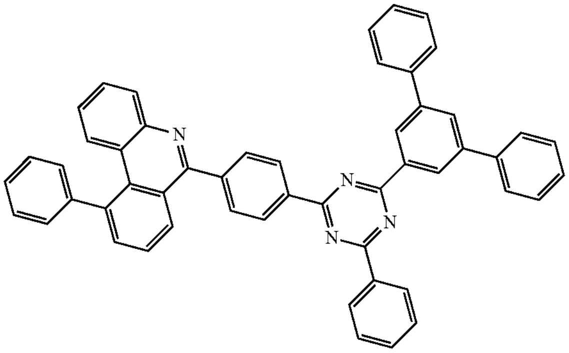

-continued
82
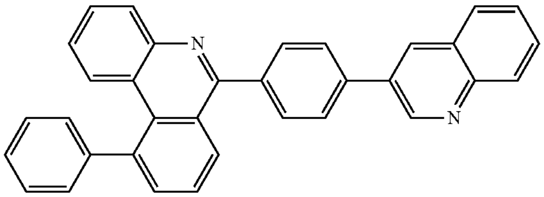
83
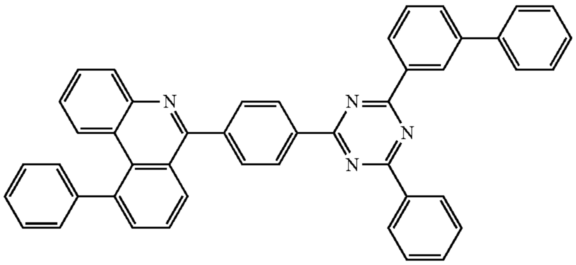
84
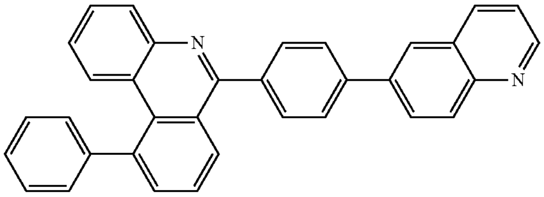
85
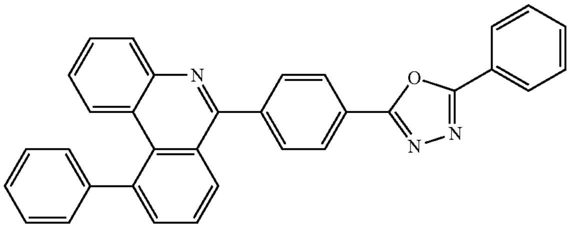
86
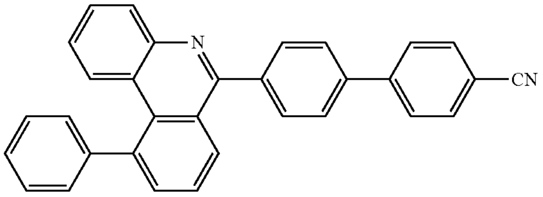
87
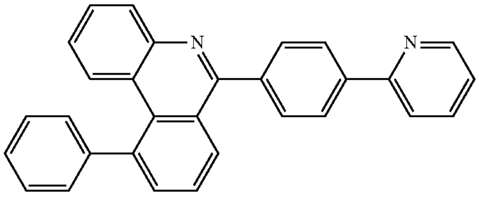
88
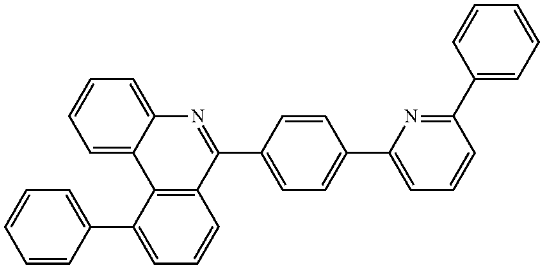
89
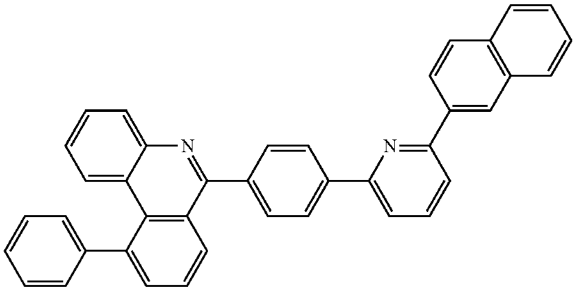
90
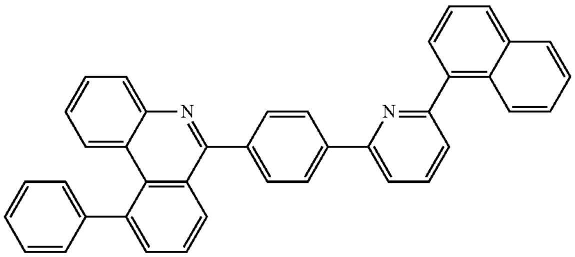
91
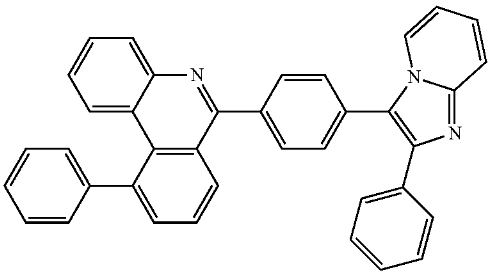

-continued
92
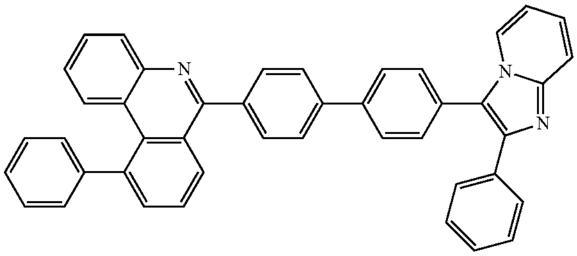
93
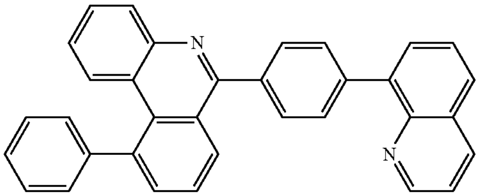
94
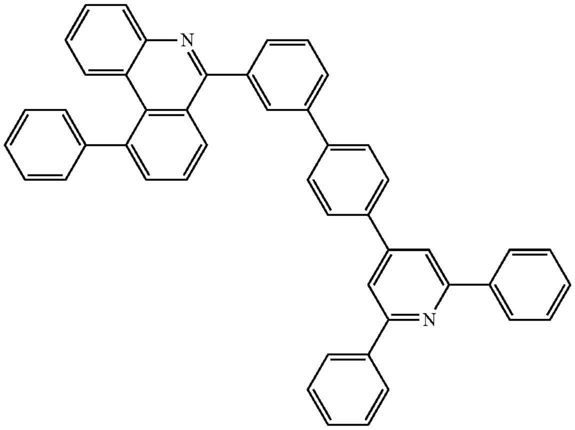
95
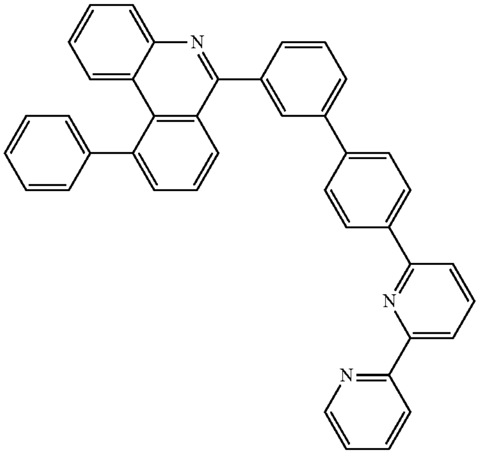
96
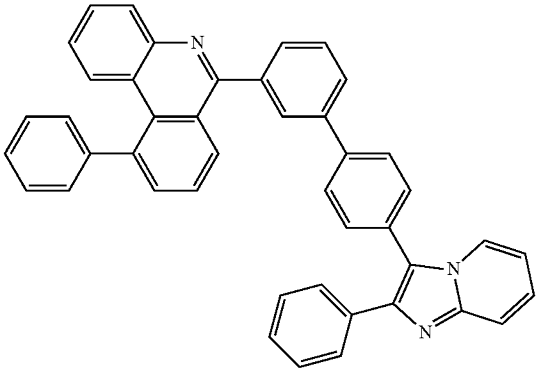
97
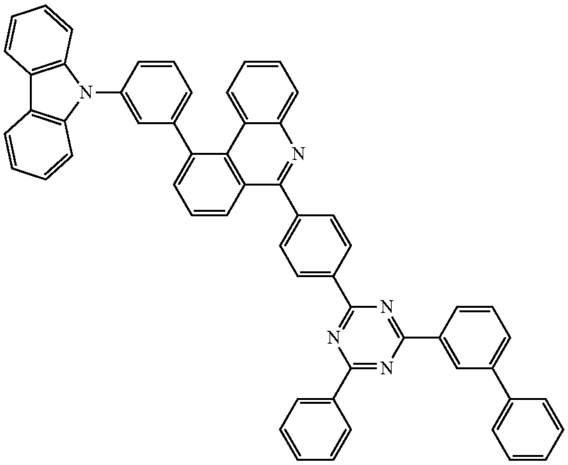

-continued
98
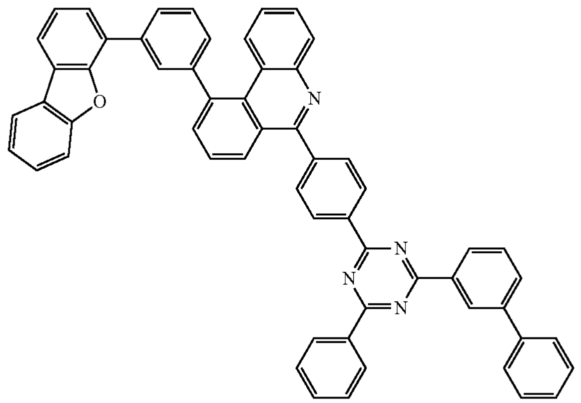
99
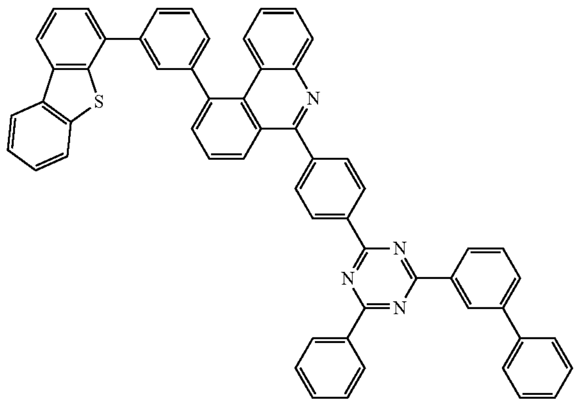
100
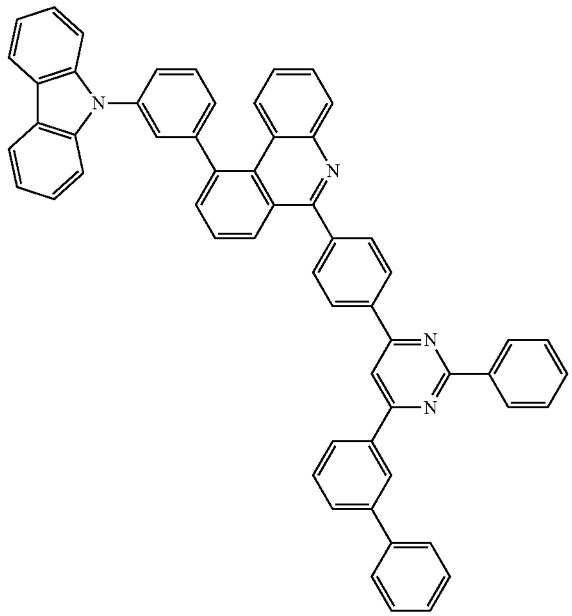
101
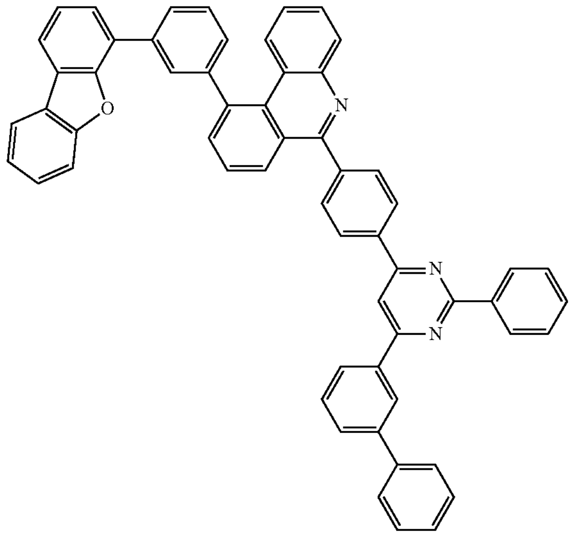
102
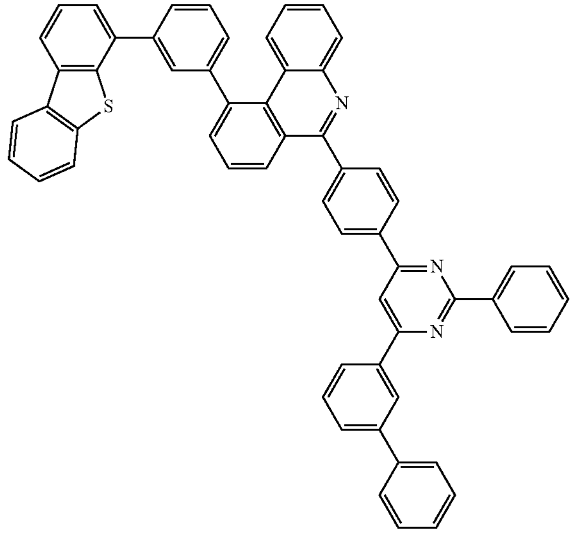
103
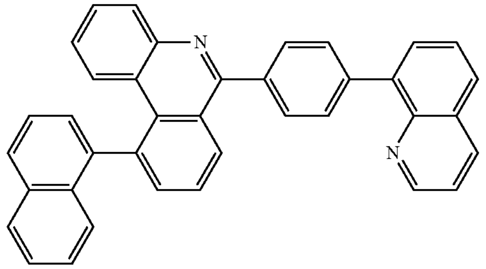

-continued
104
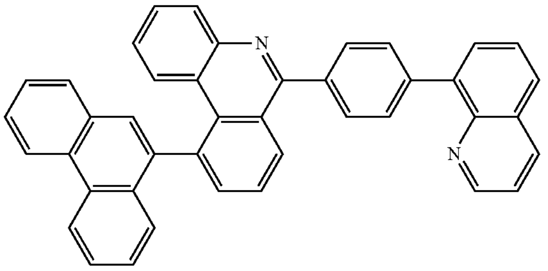
105
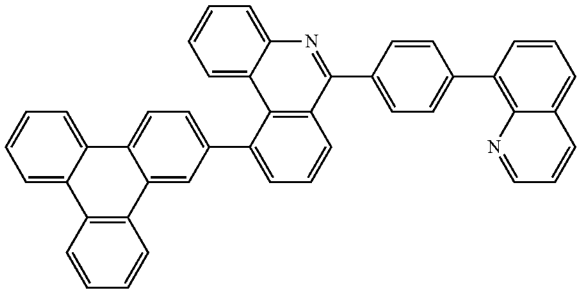
106
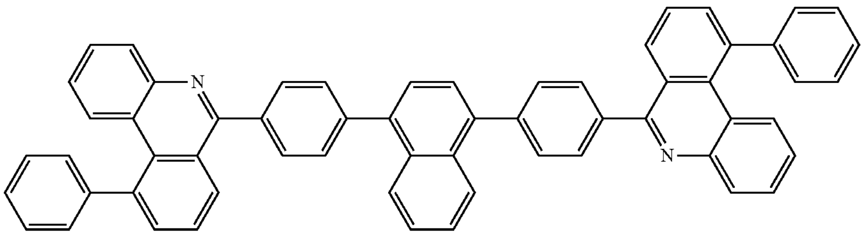
107
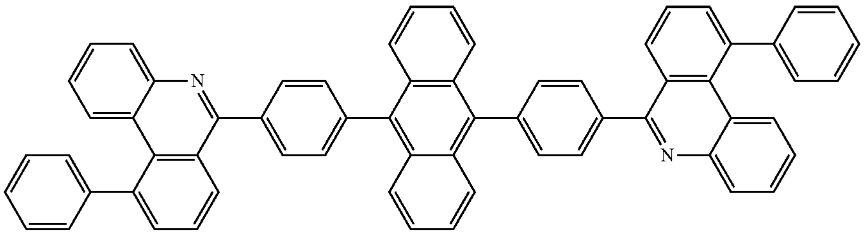
108
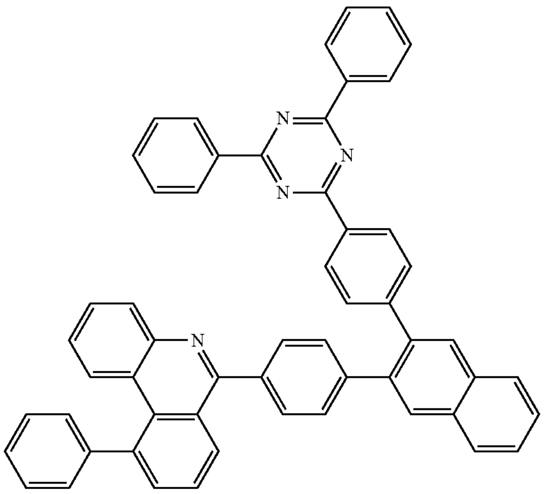
109
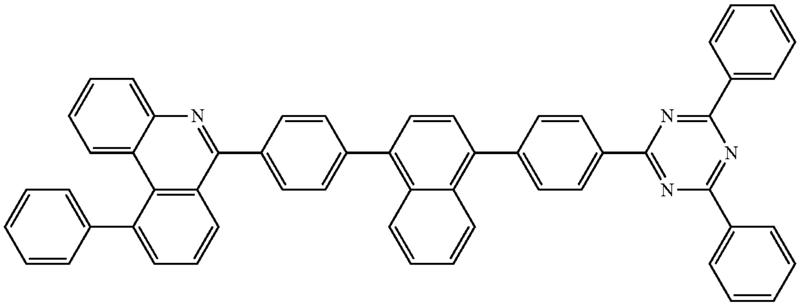

-continued
110
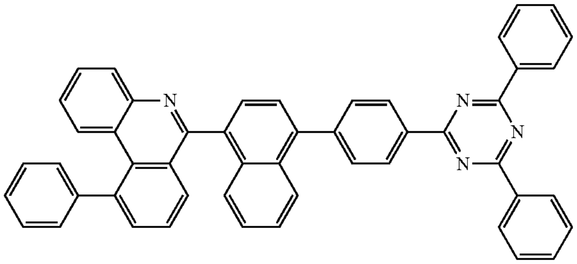
111
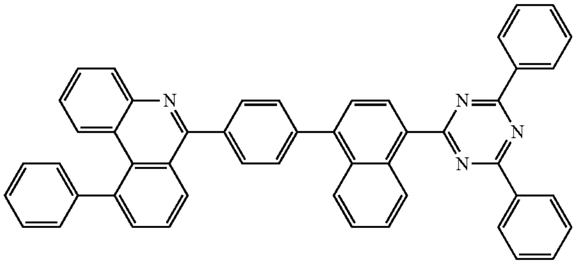
112
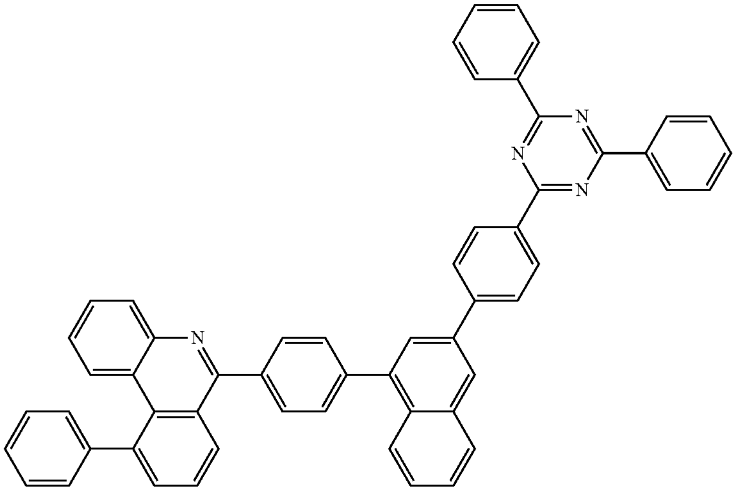
113
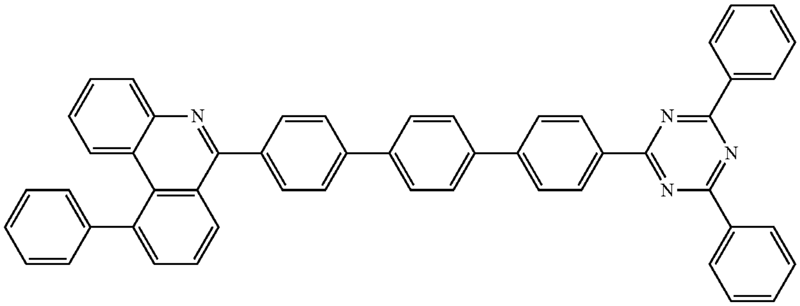
114
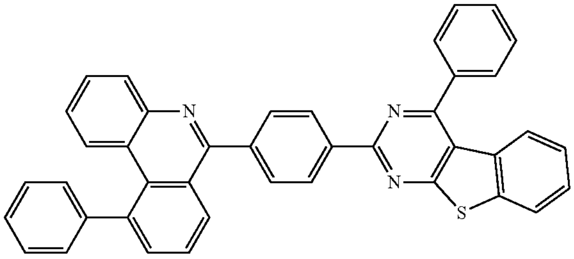
115
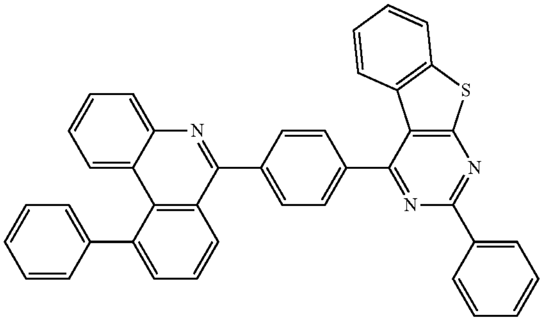

-continued
116
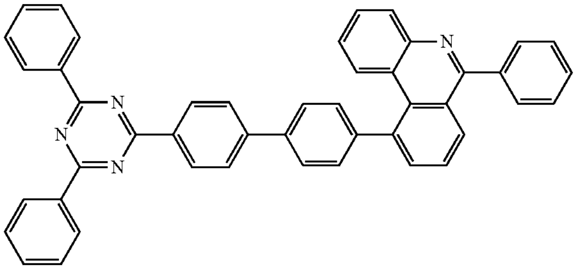
117
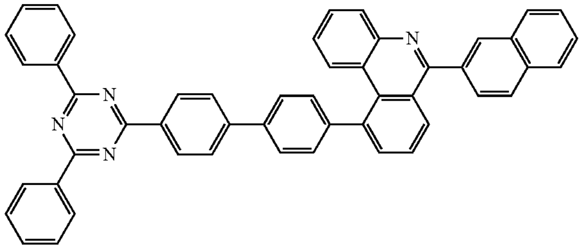
118
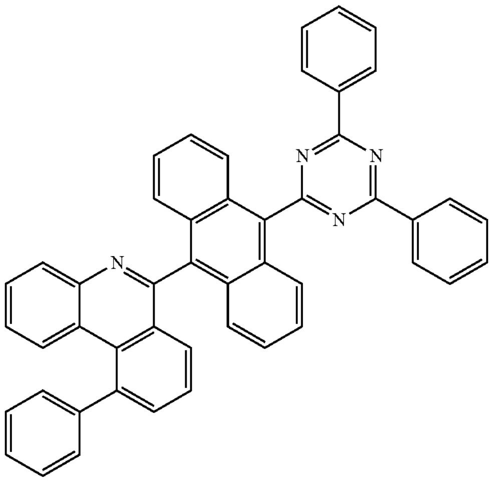
119
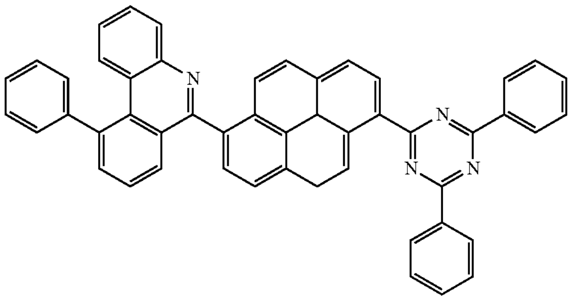
120
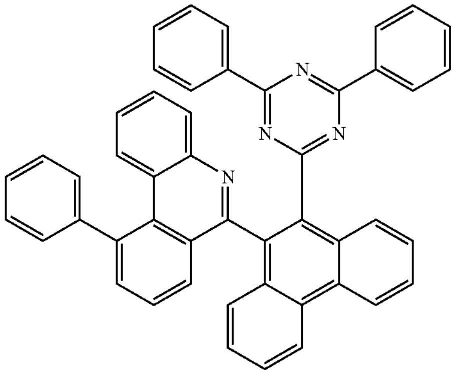
121
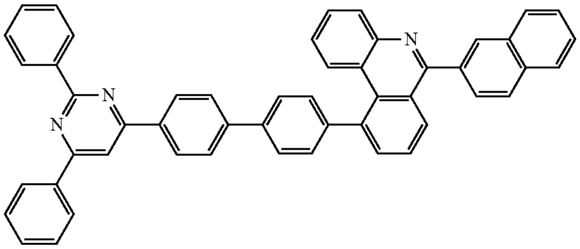
122
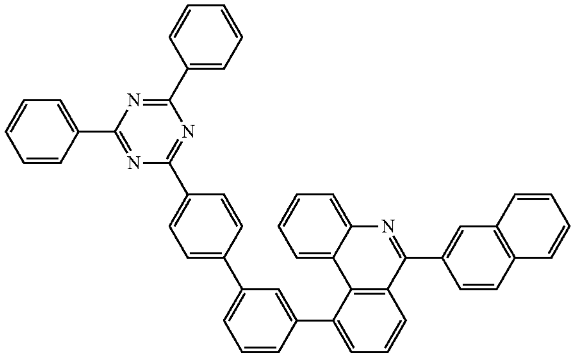

-continued
123
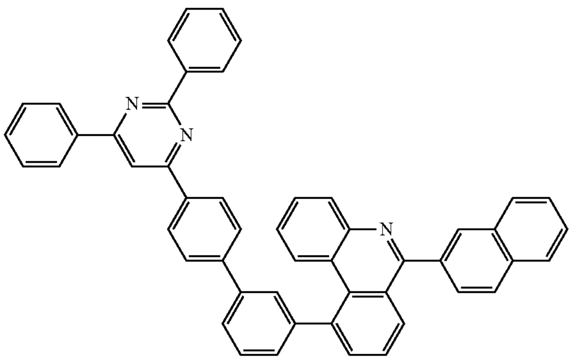
124
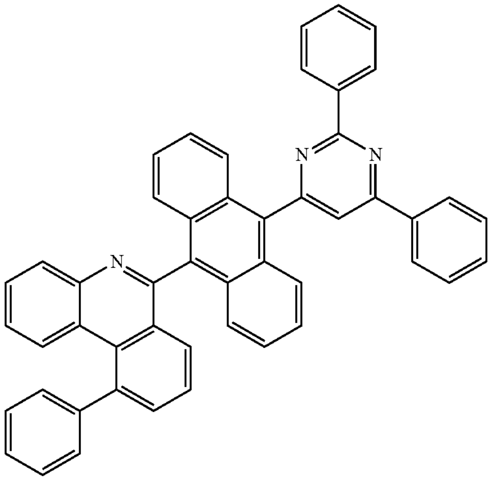
125
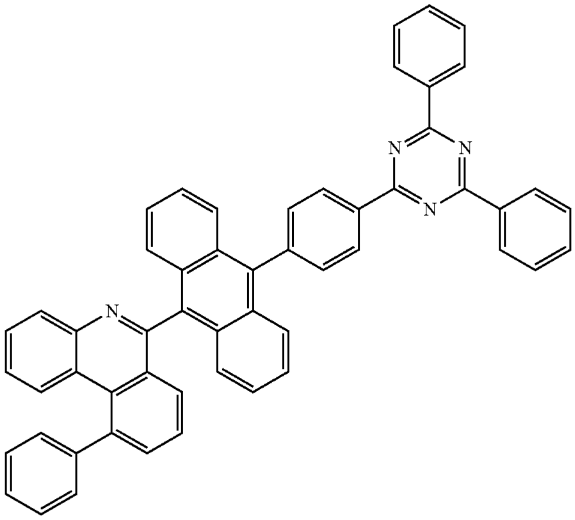
126
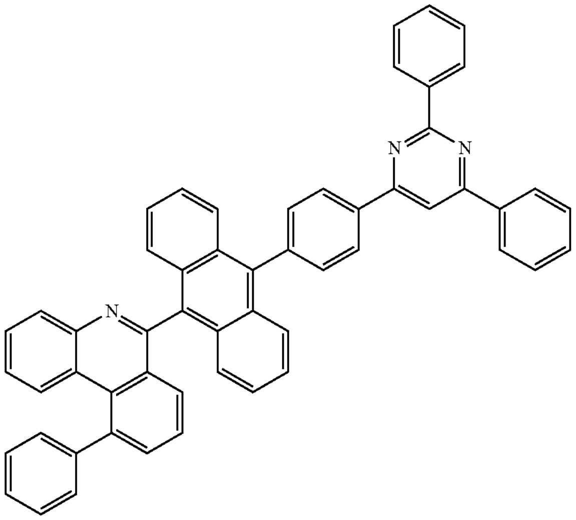
127
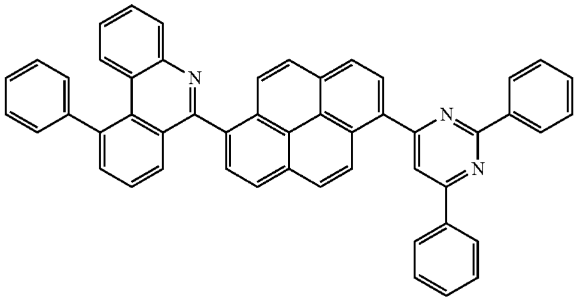

-continued
128
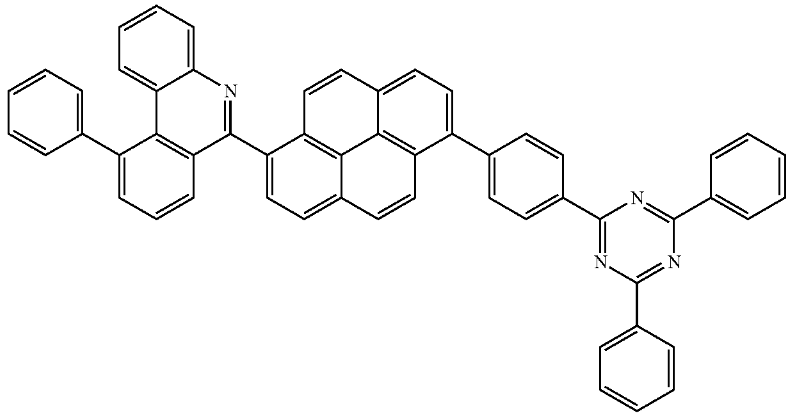
129
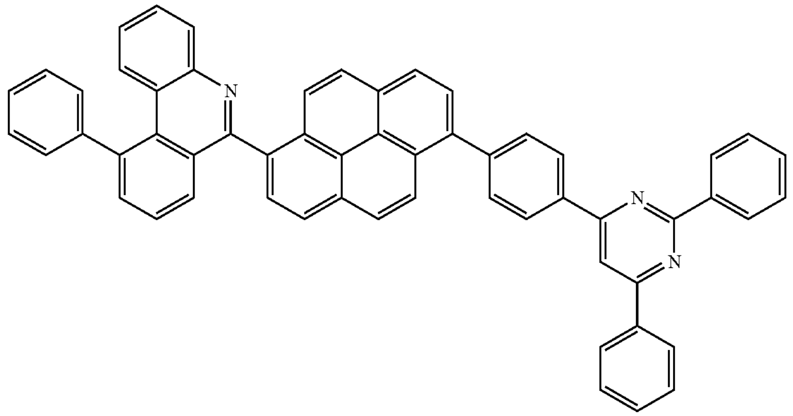
130
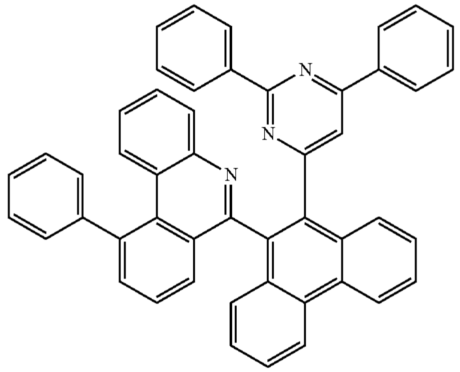
131
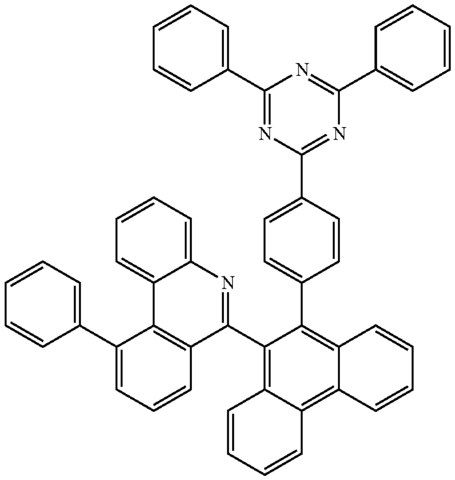

-continued
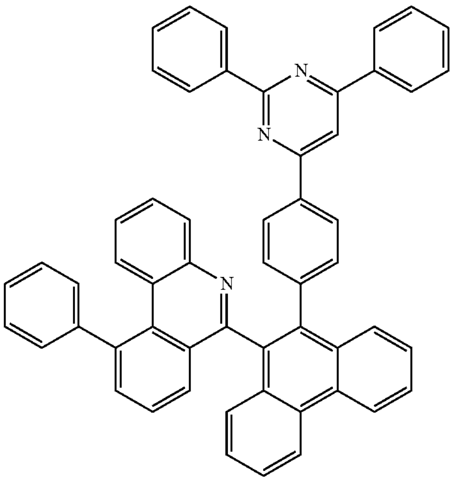
132
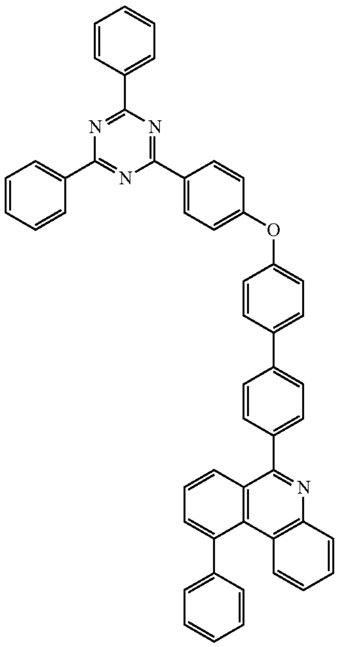
133
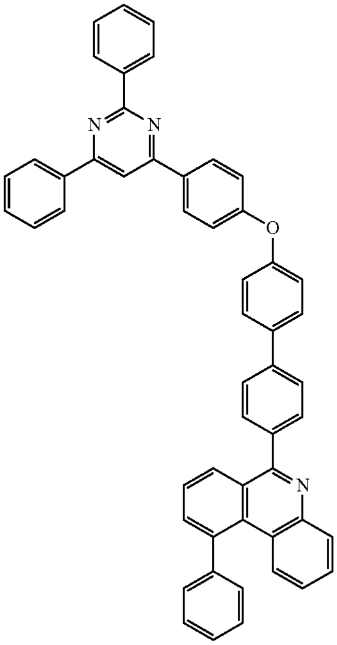
134
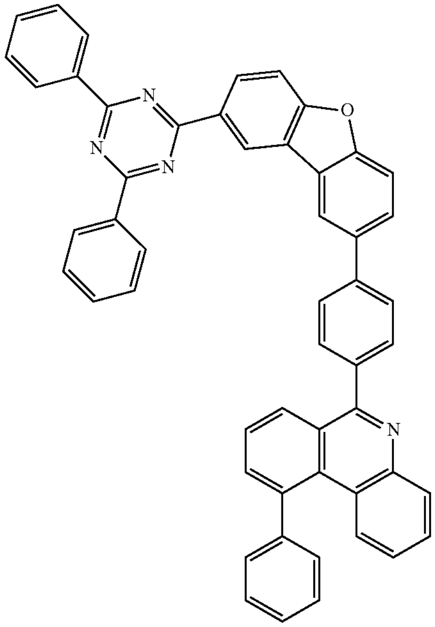
135

-continued
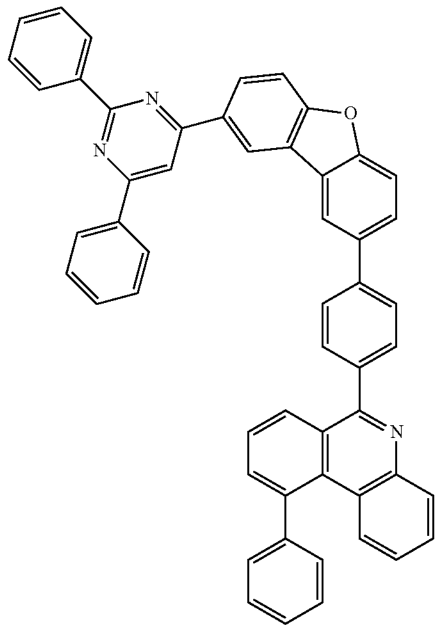
136
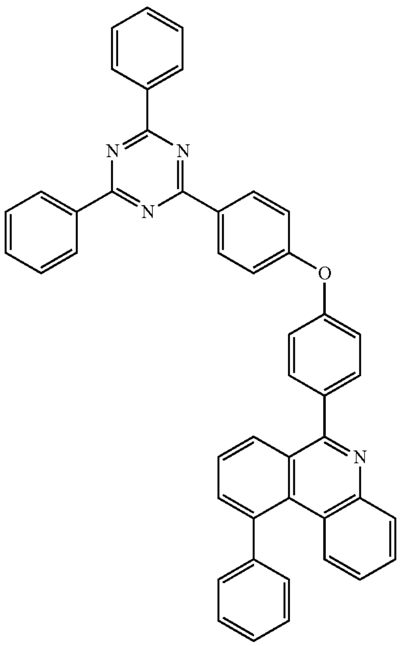
137
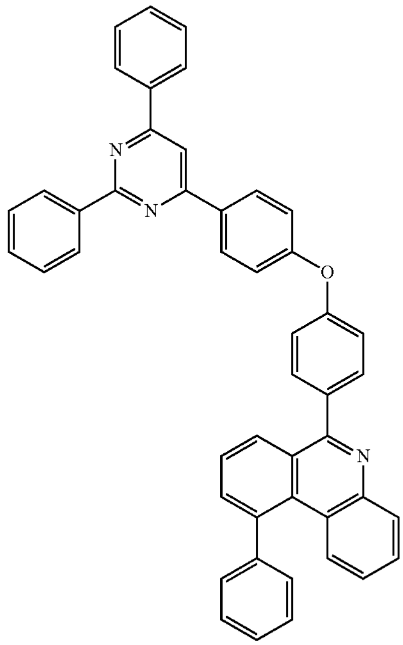
138
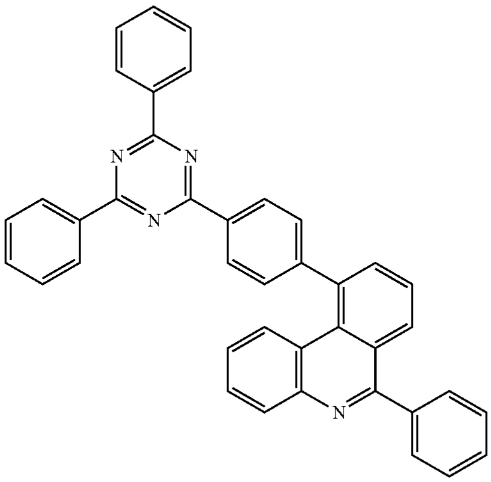
139

-continued
140
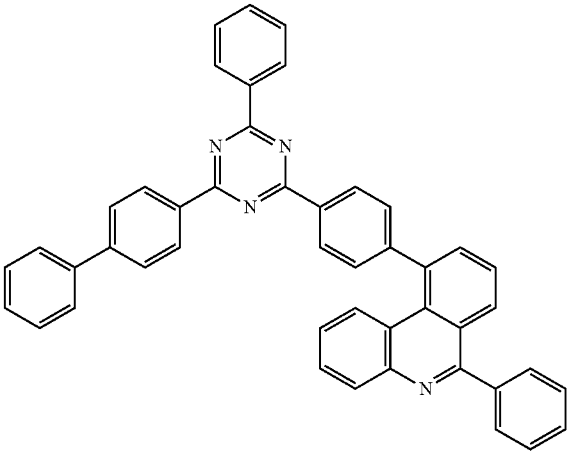
141
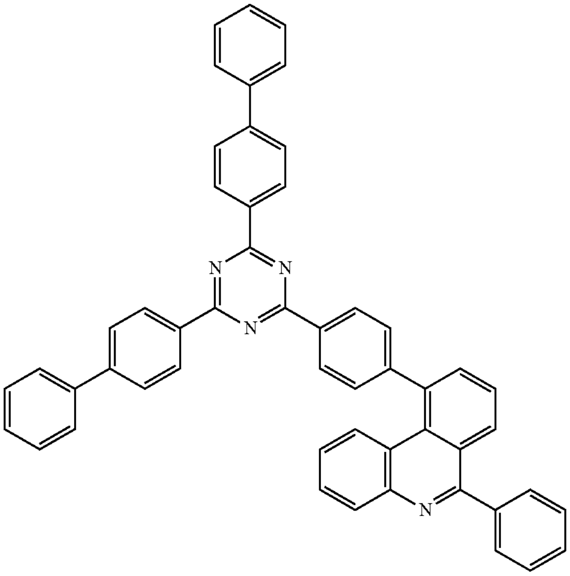
142
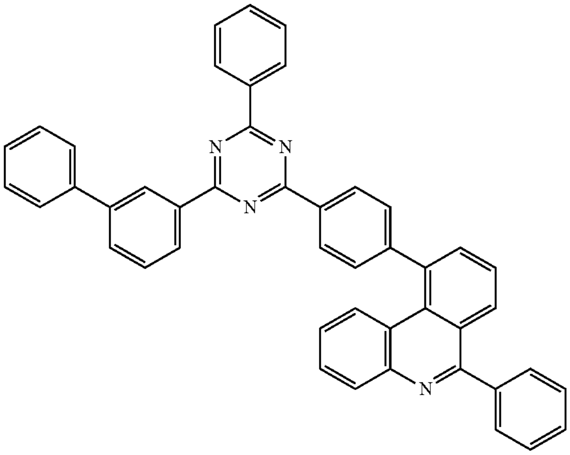
143
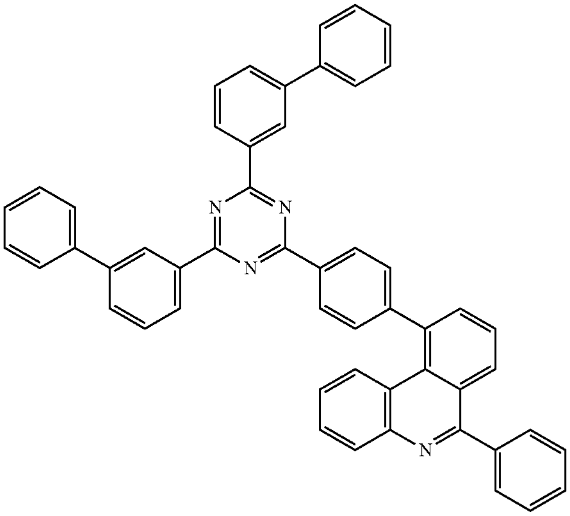

-continued
144
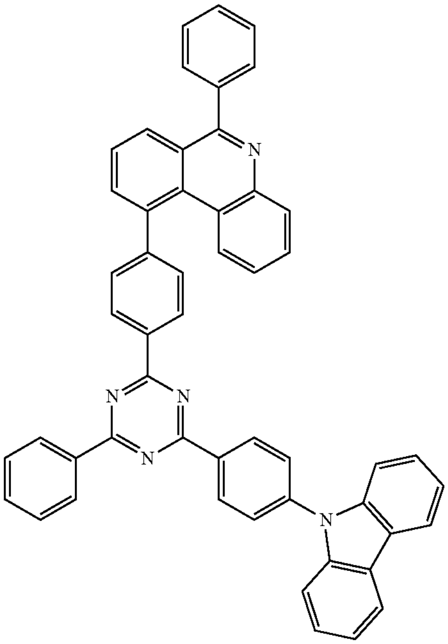
145
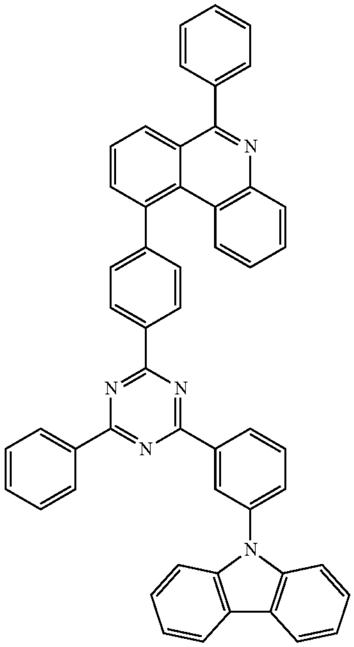
146
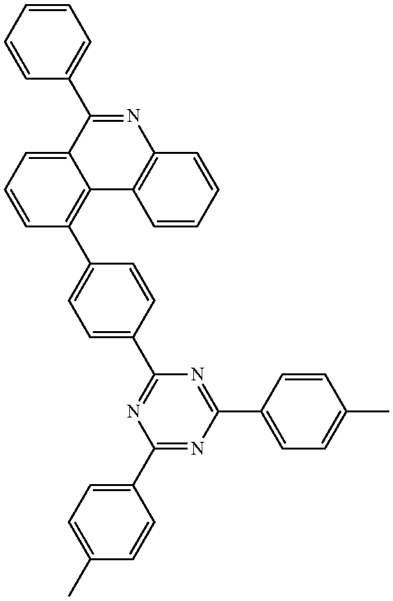
147
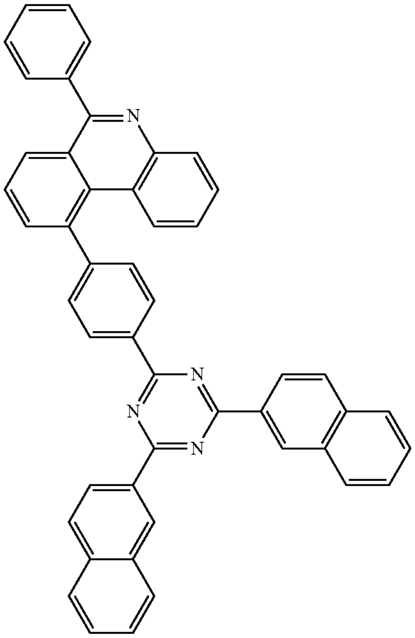

-continued
148
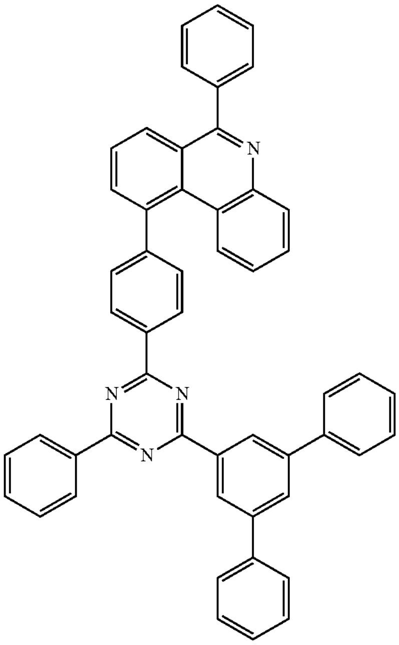
149
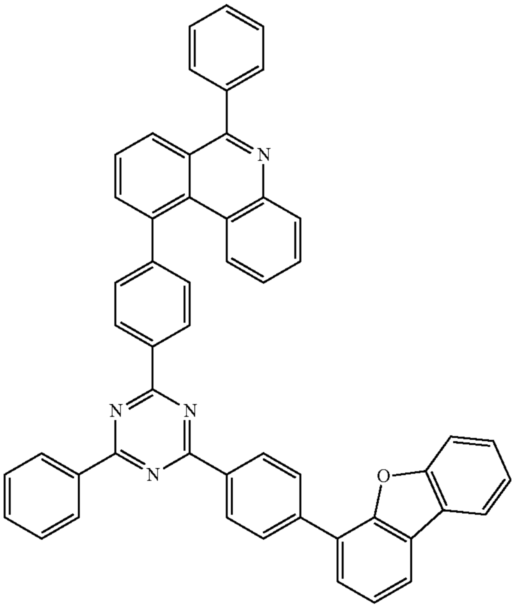
150
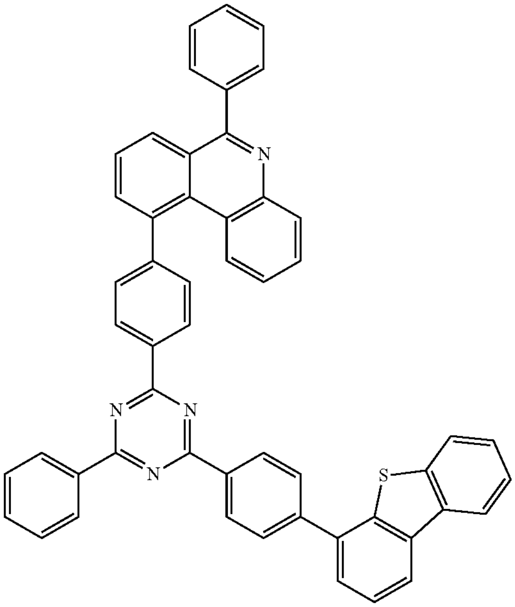
151
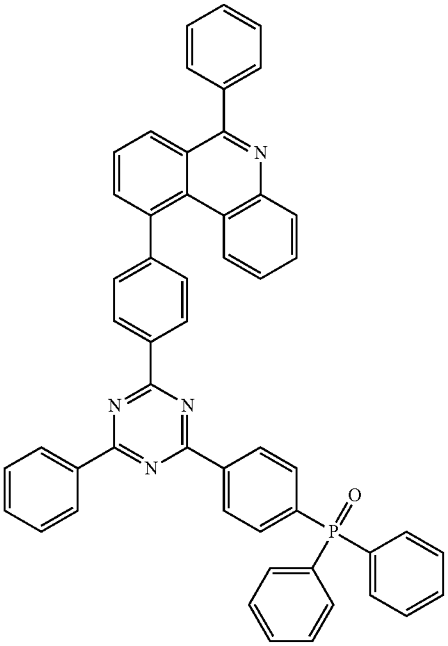

-continued
152
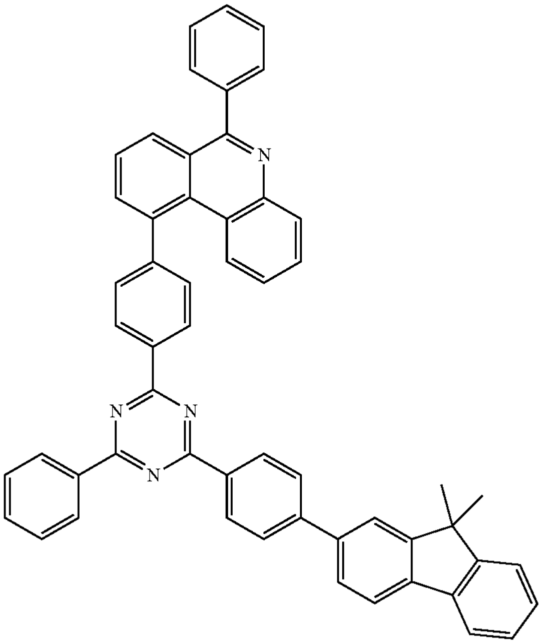
153
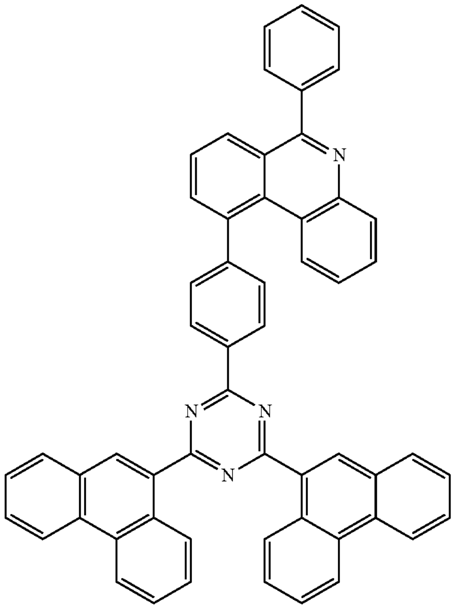
154
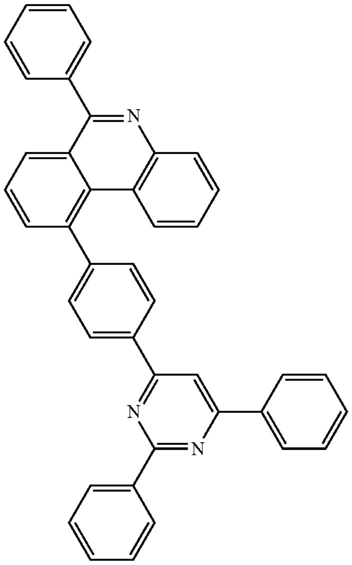
155
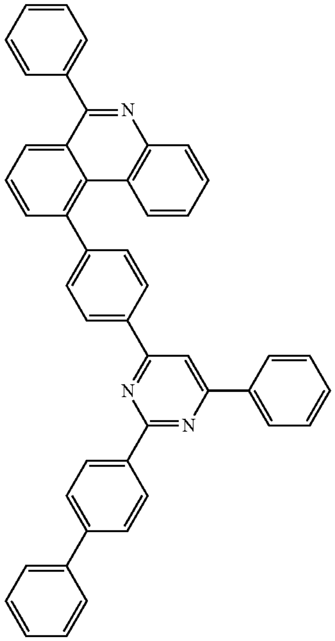

-continued
156
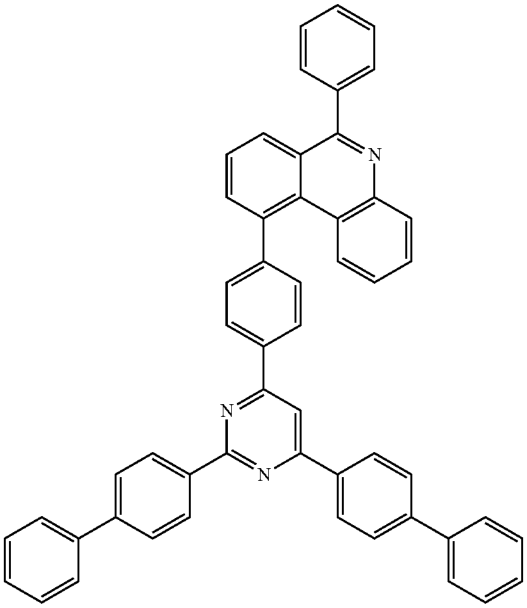
157
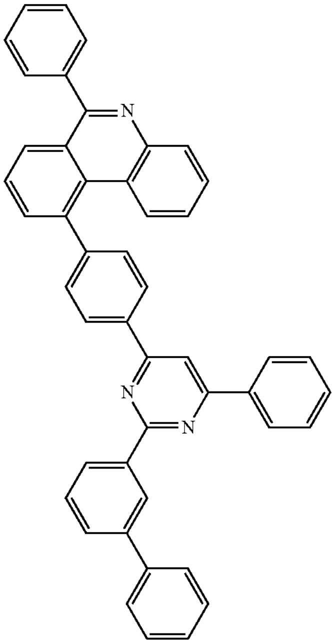
158
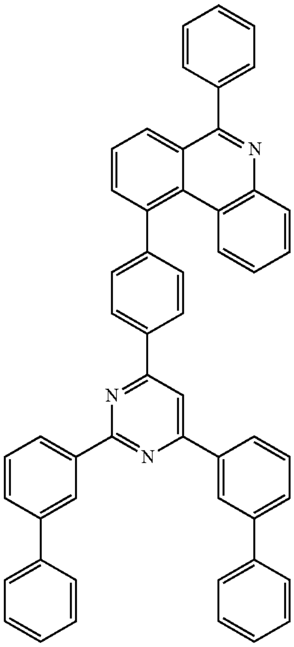
159
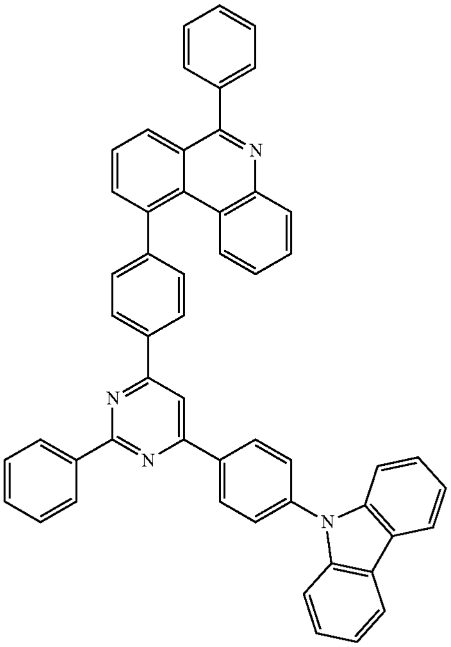

-continued
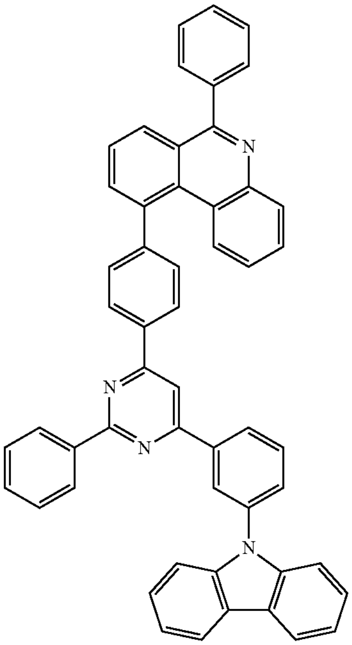
160
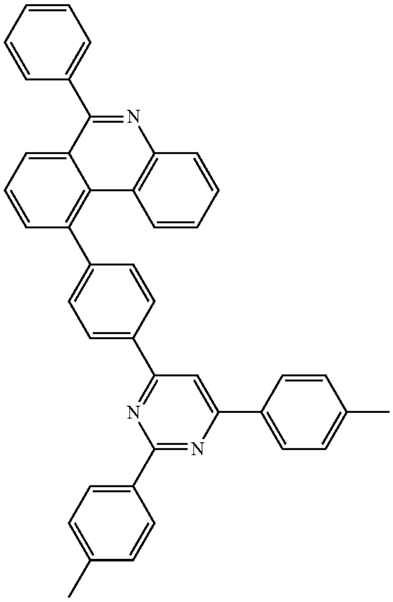
161
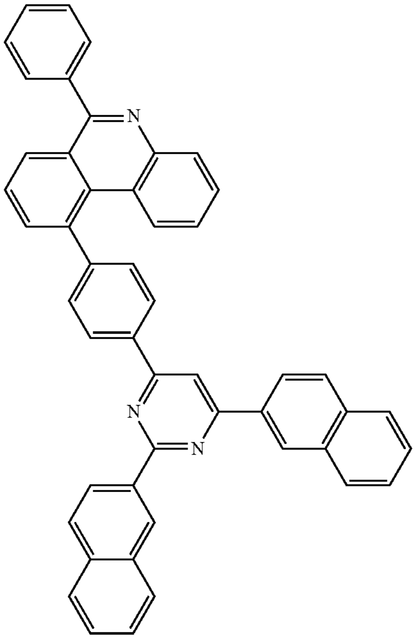
162
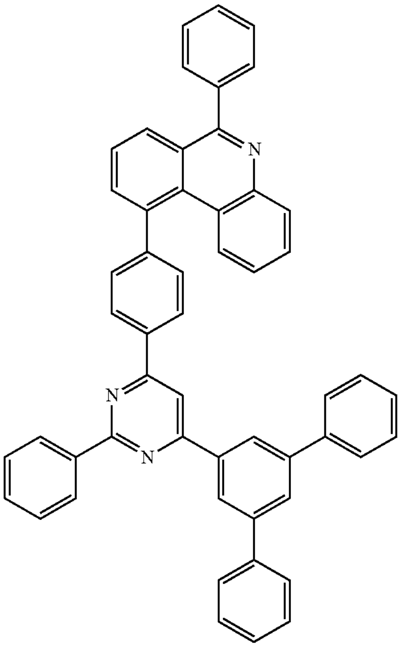
163

-continued
164
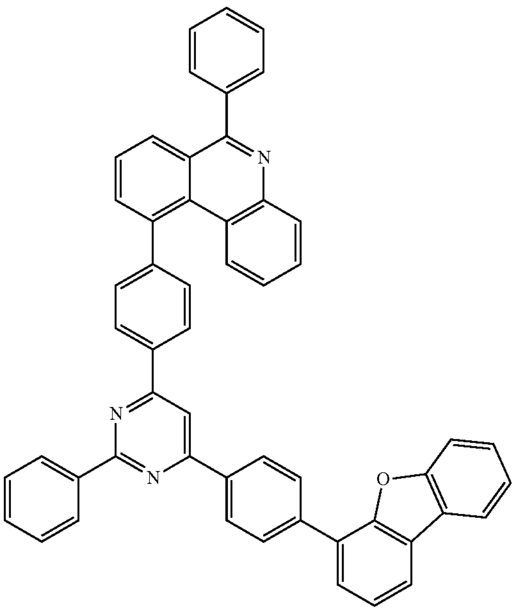
165
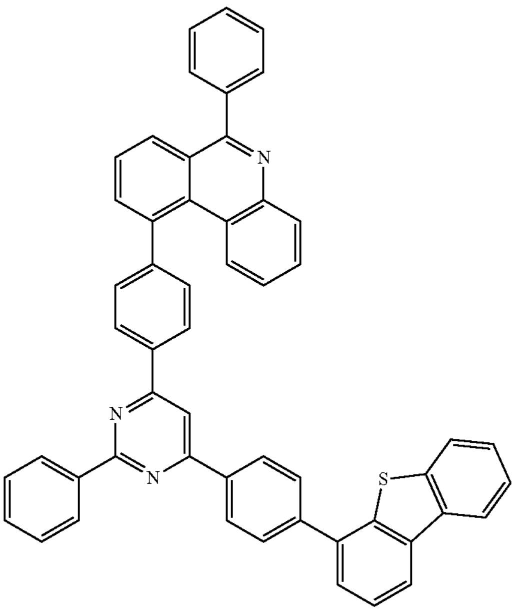
166
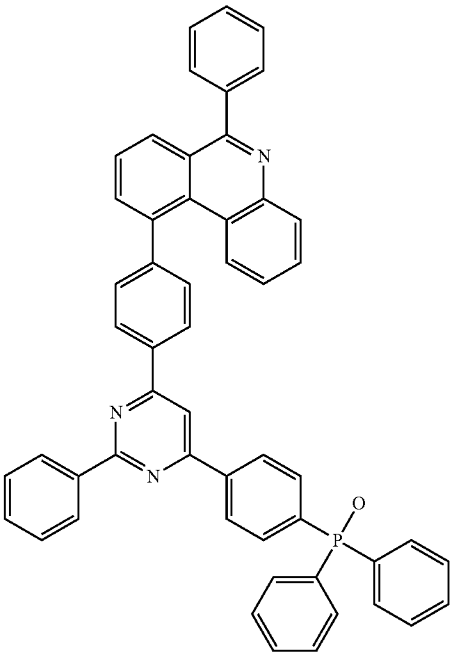
167
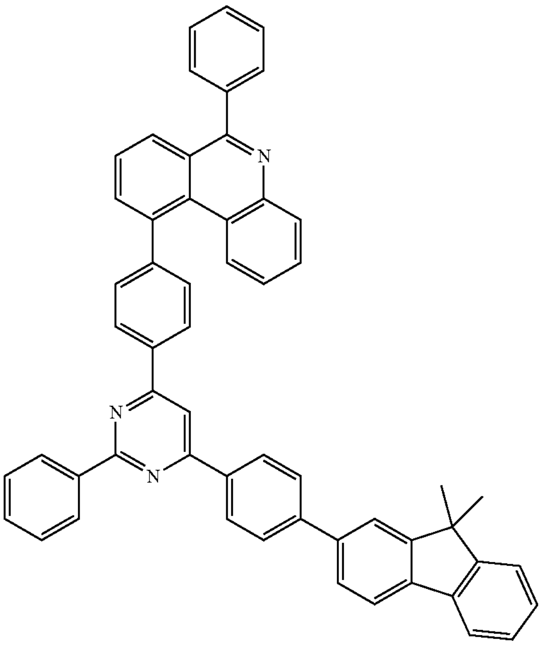

-continued
168
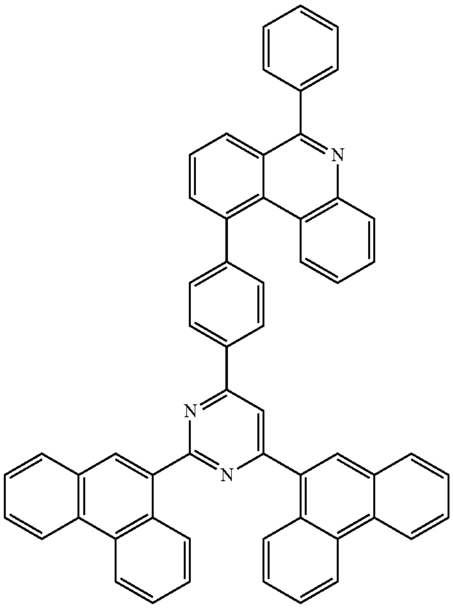
169
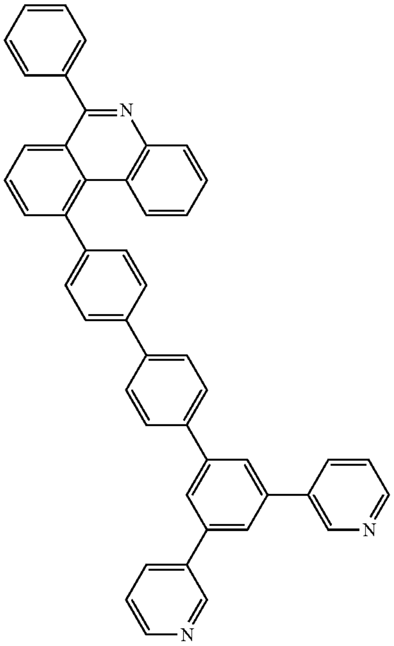
170
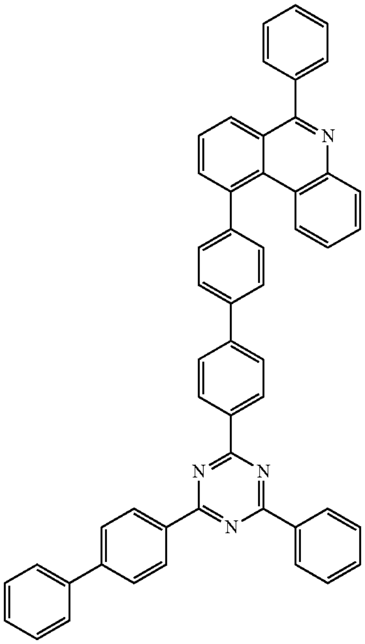
171
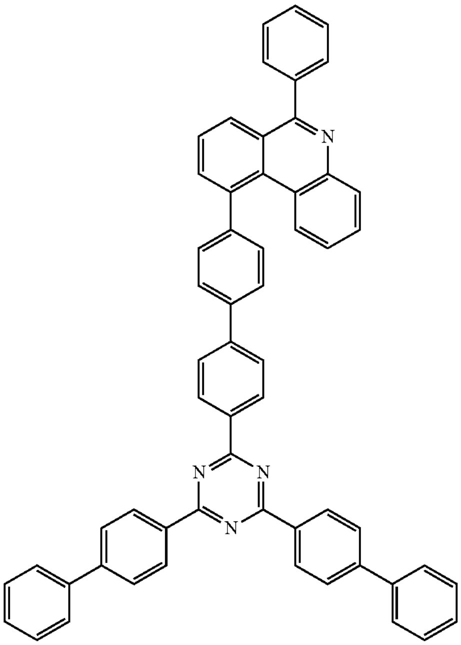

-continued
172
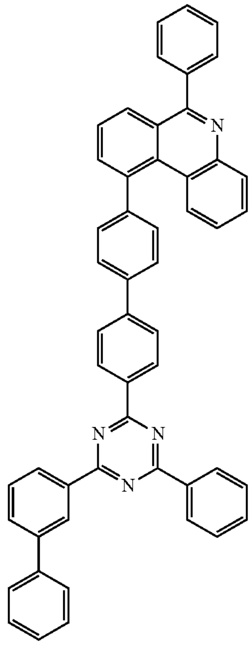
173
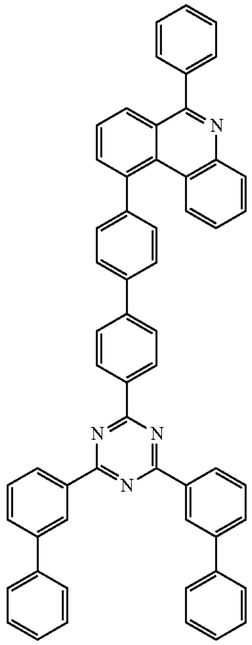
174
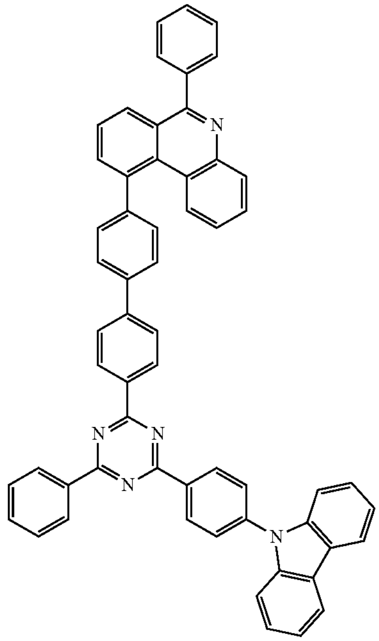
175
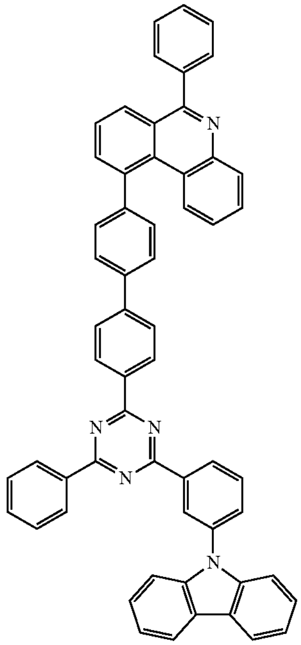

-continued
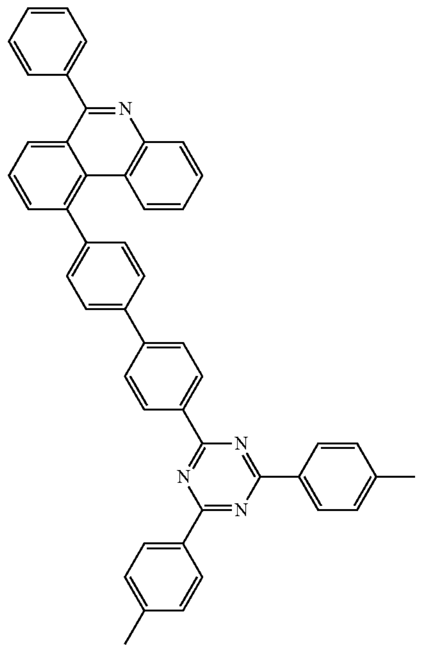
176
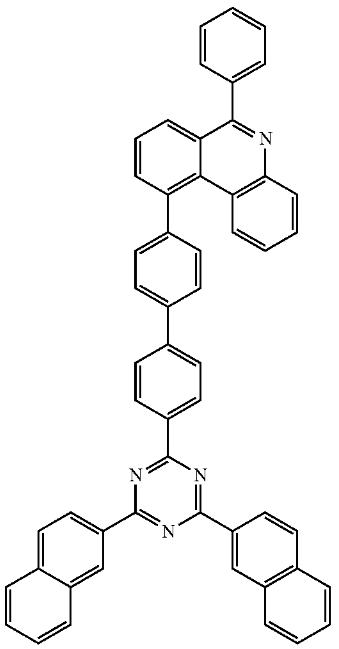
177
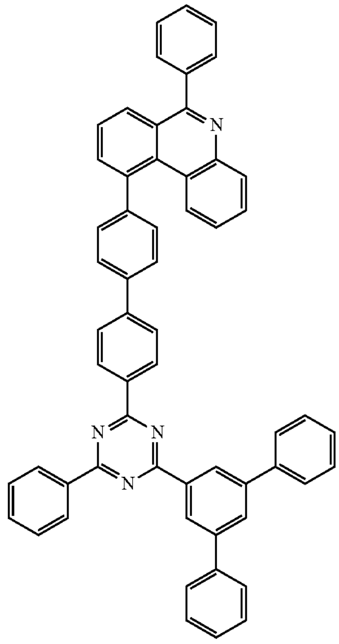
178
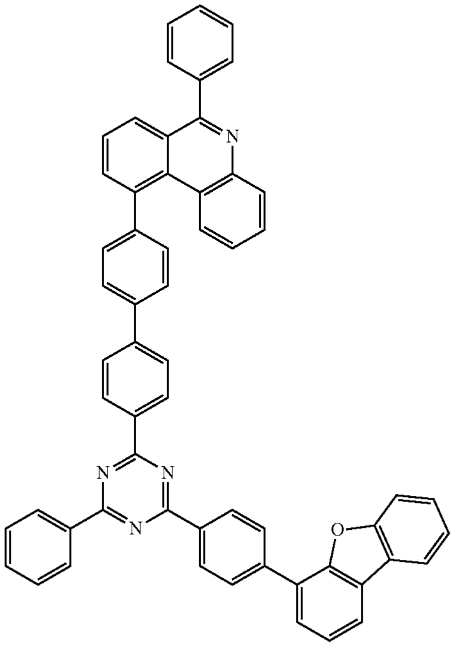
179

-continued
180
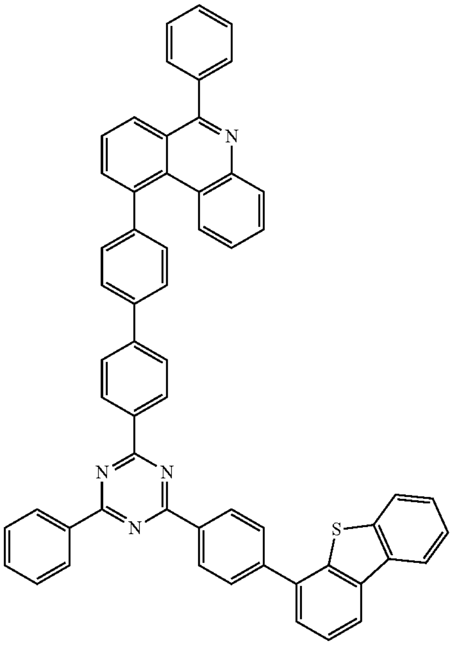
181
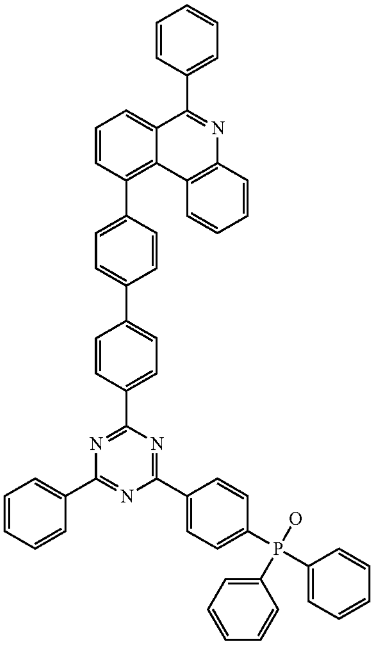
182
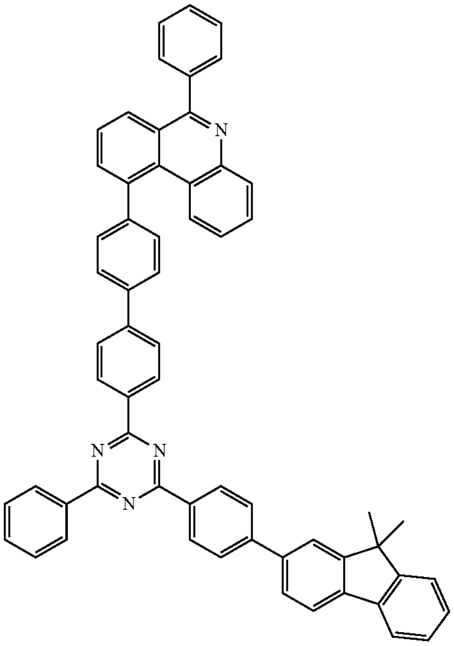
183
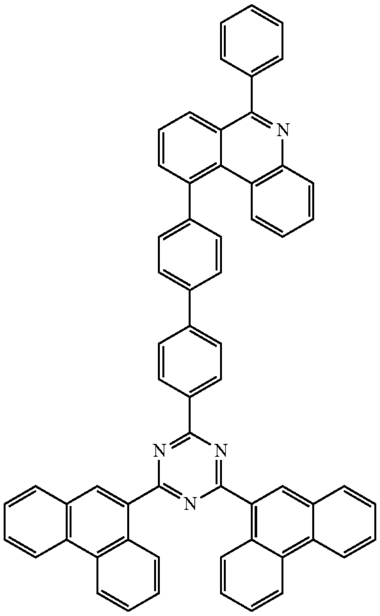

-continued
184
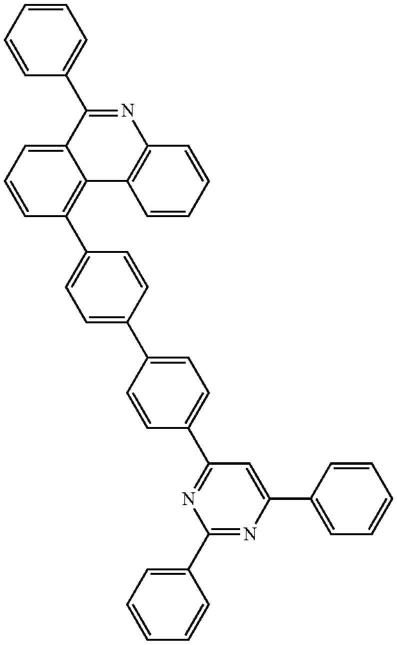
185
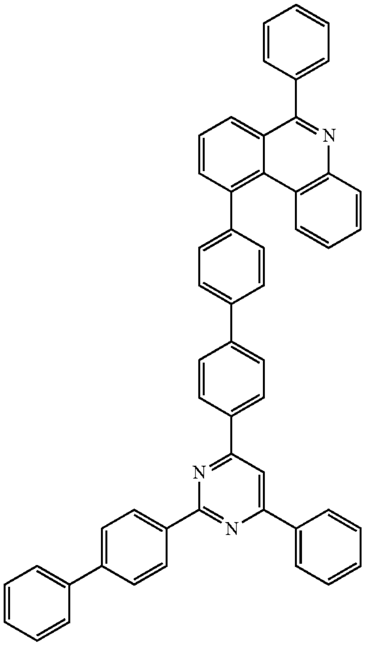
186
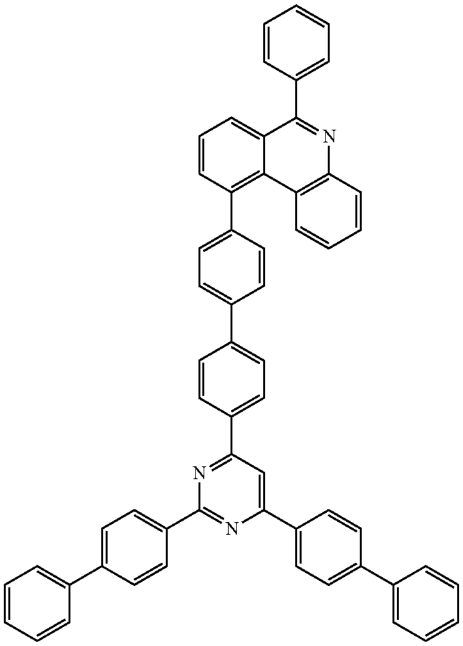
187
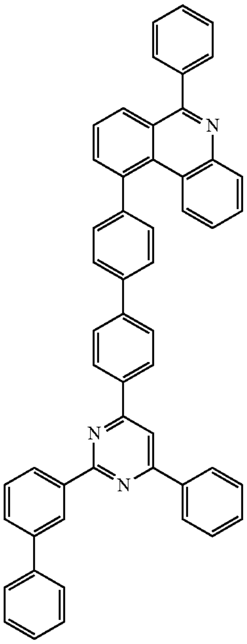

-continued
188
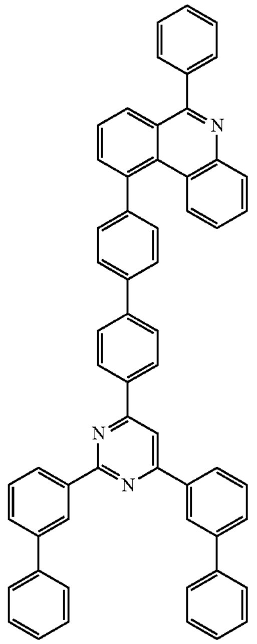
189
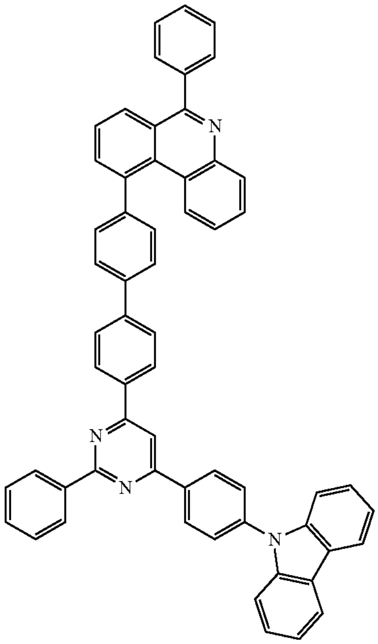
190
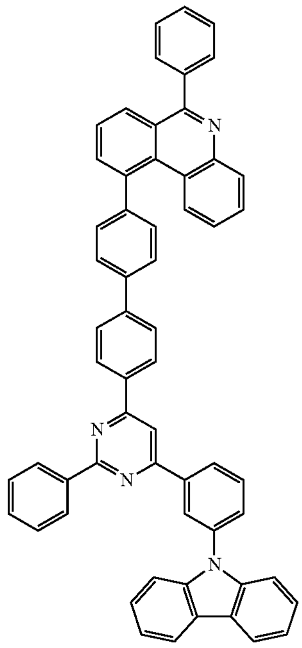
191
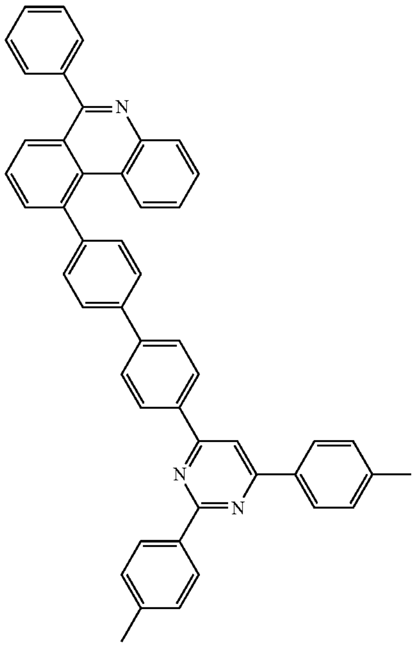

-continued
192
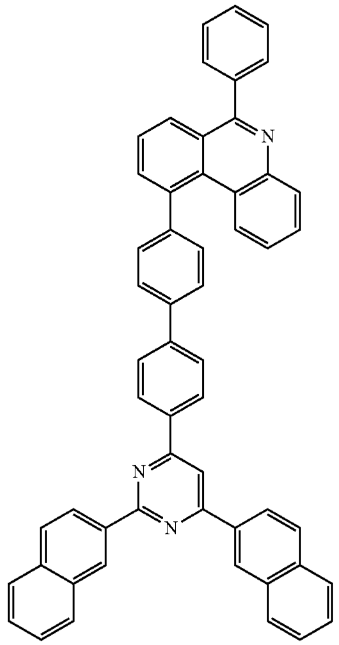
193
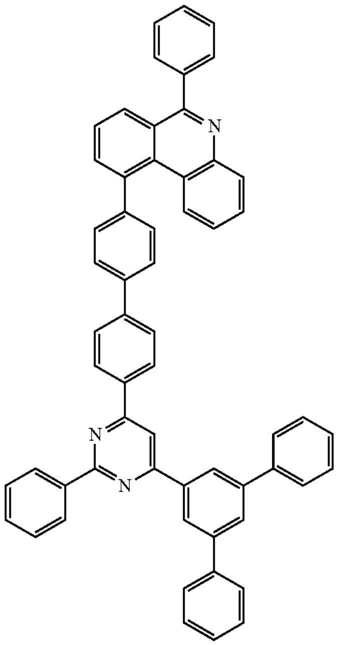
194
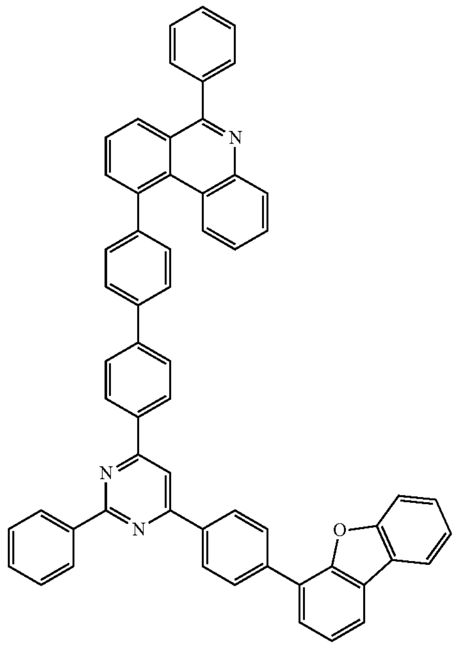
195
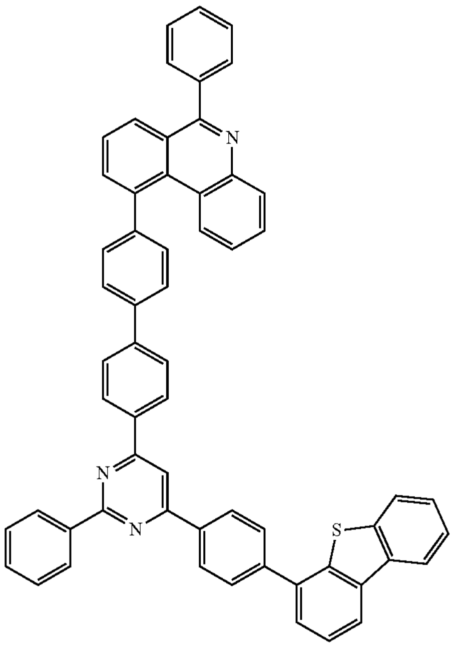

-continued
196
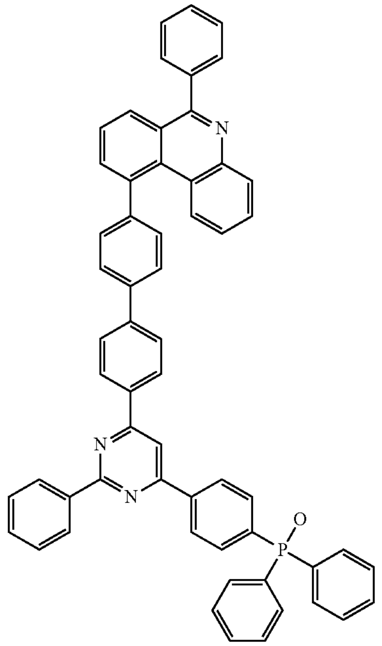
197
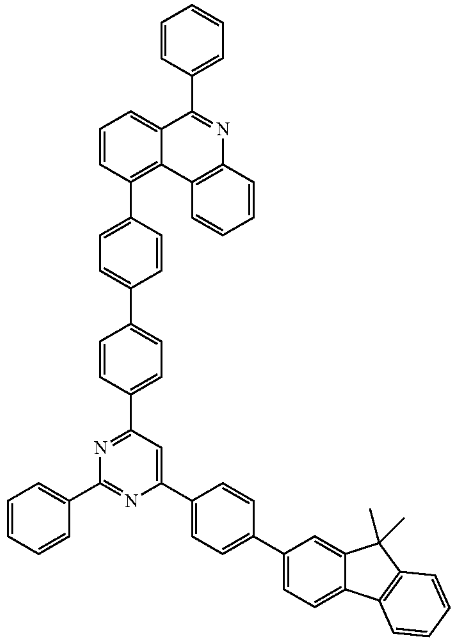
198
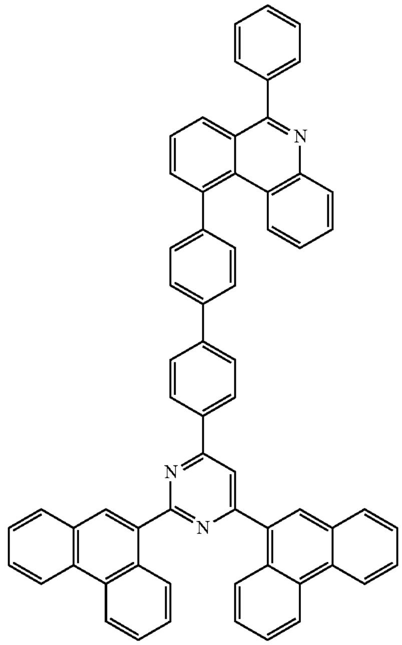
199
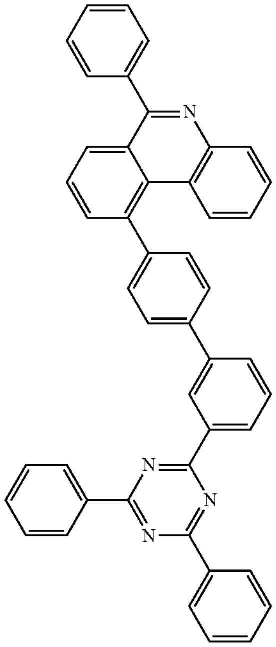

-continued
200
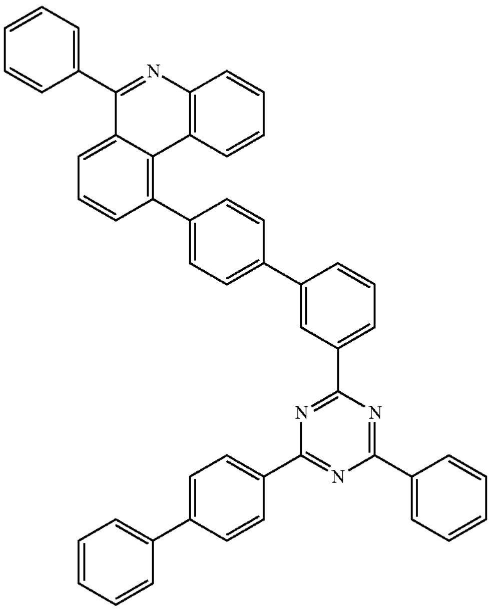
201
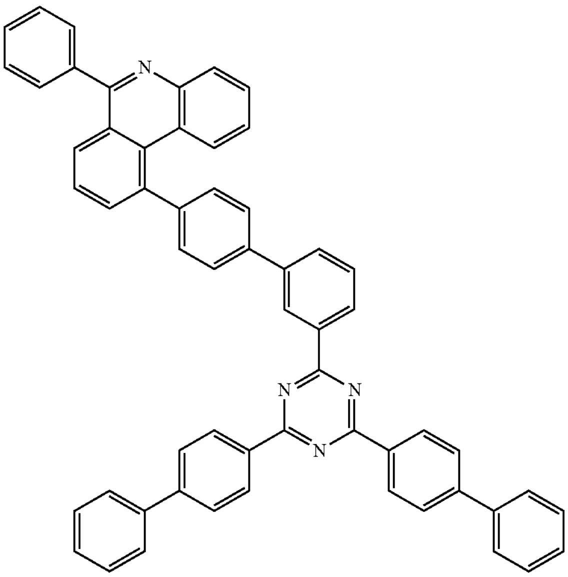
202
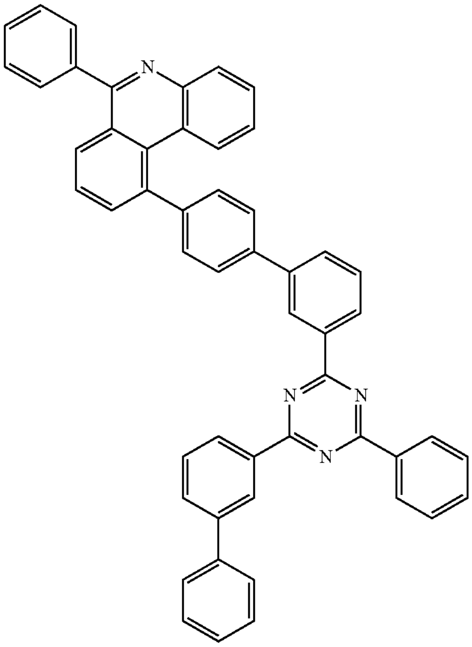
203
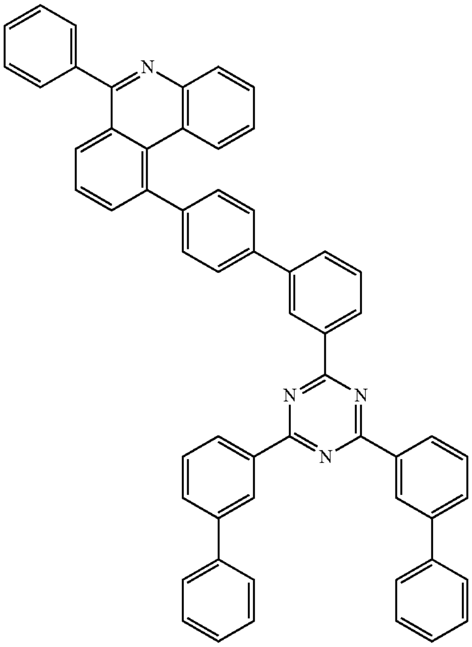

-continued
204
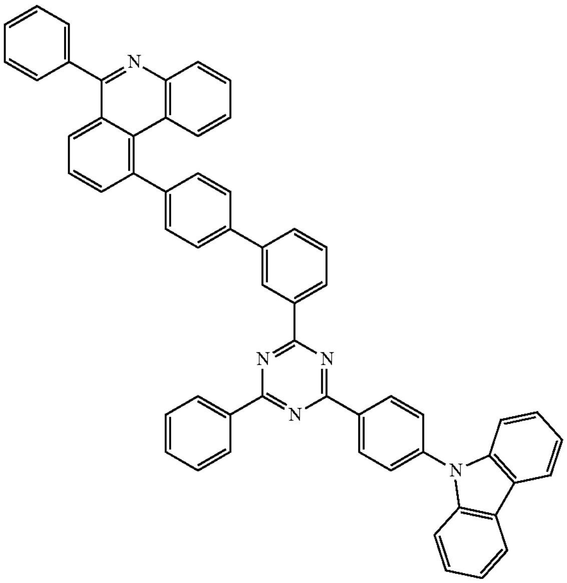
205
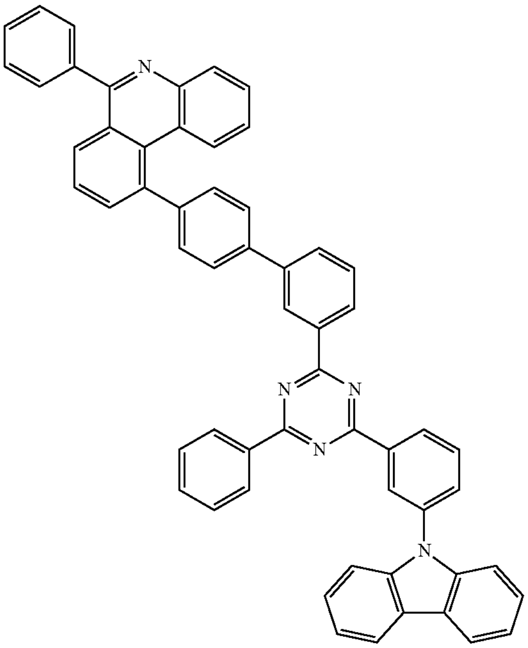
206
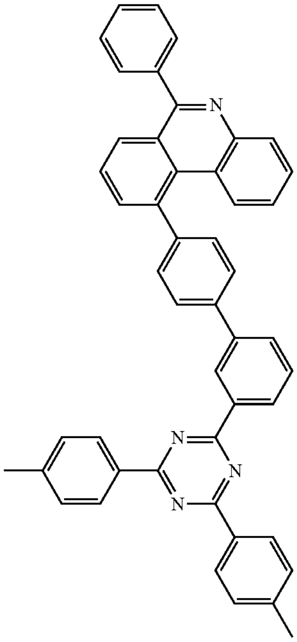
207
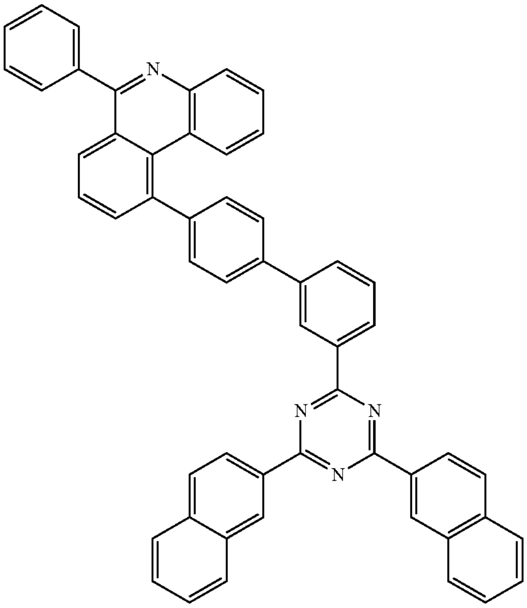

-continued
208
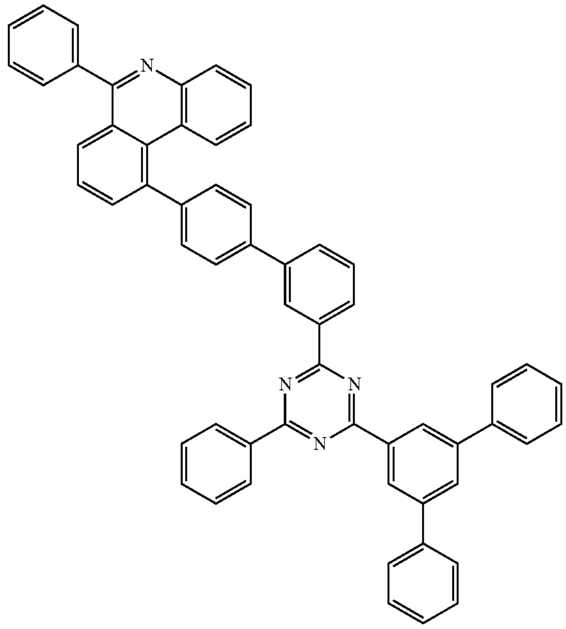
209
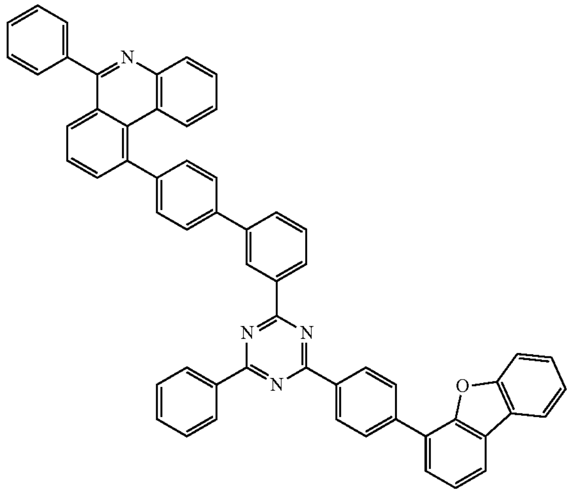
210
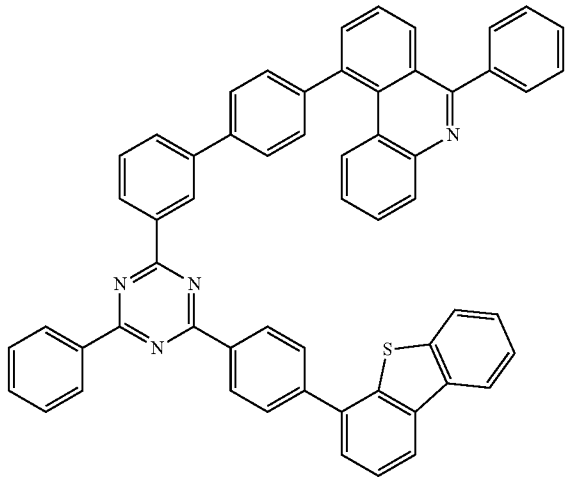
211
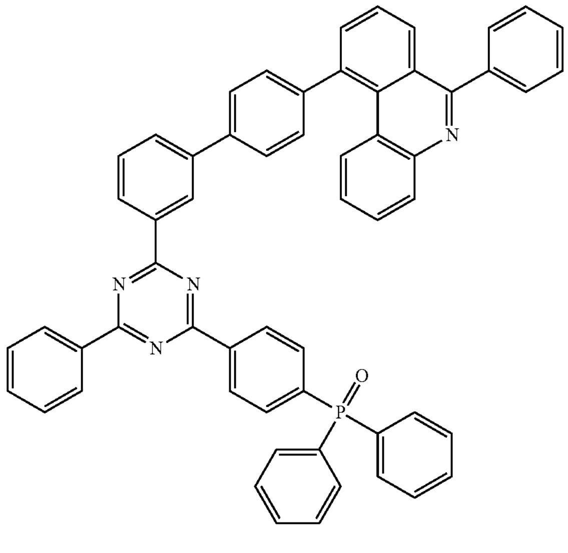

-continued
212
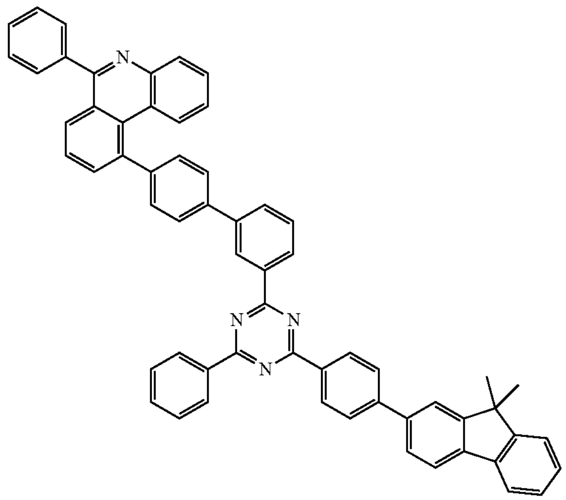
213
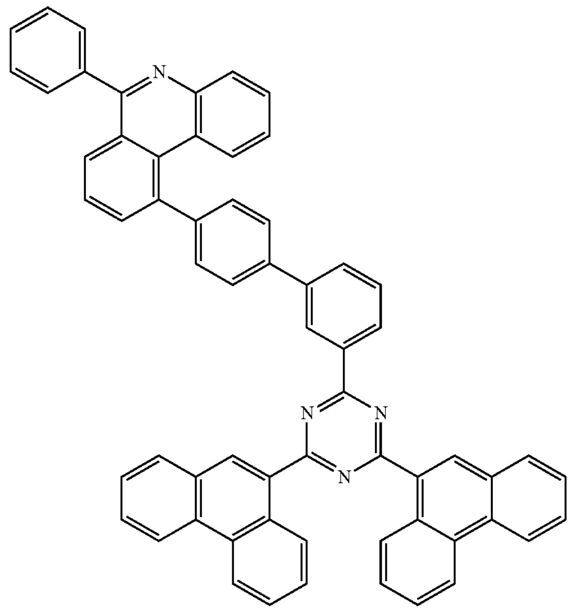
214
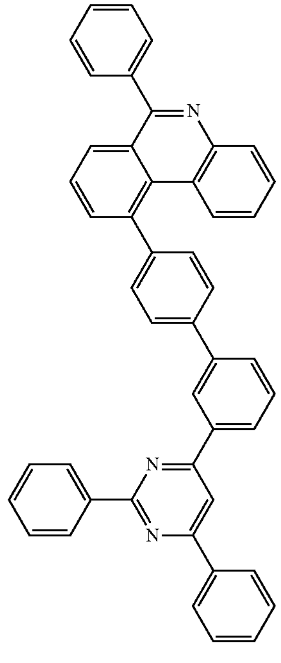
215
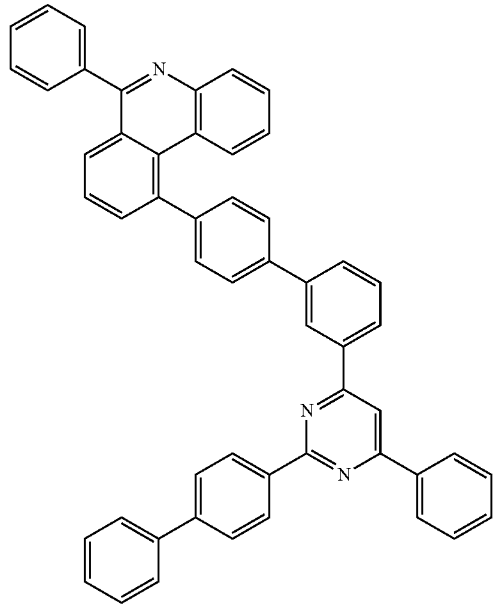

-continued
216
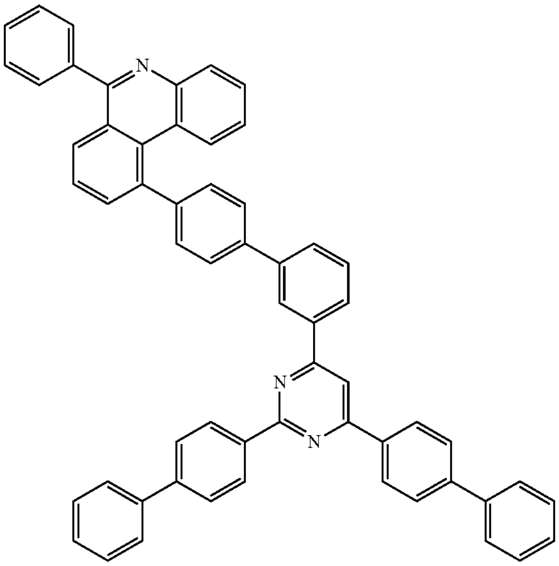
217
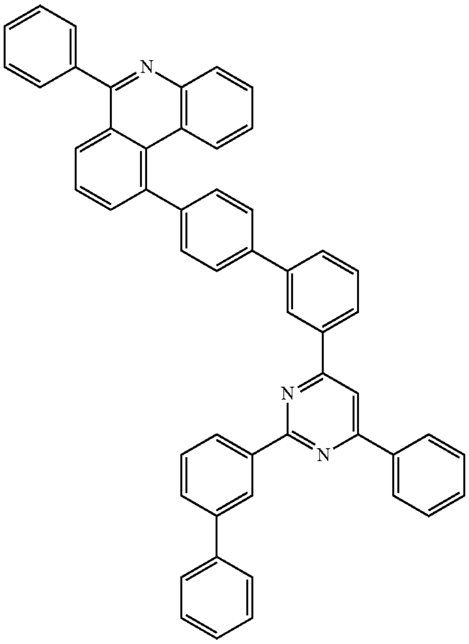
218
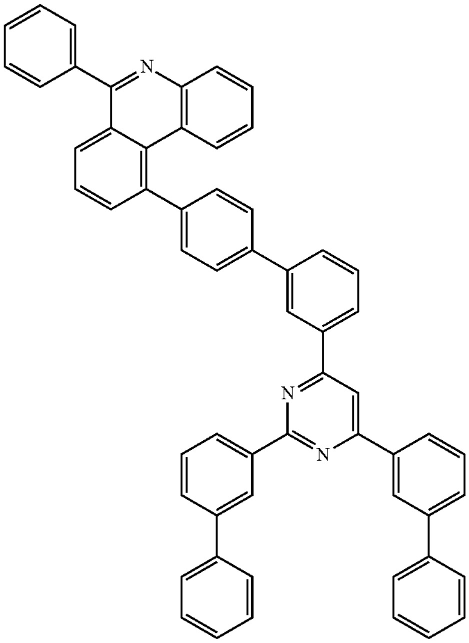
219
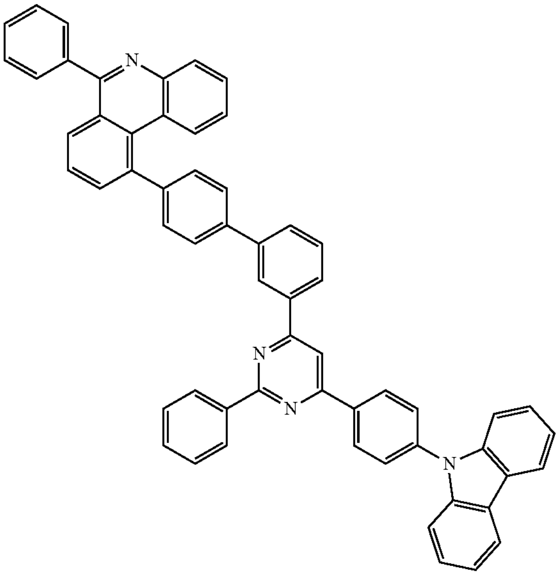

-continued
220
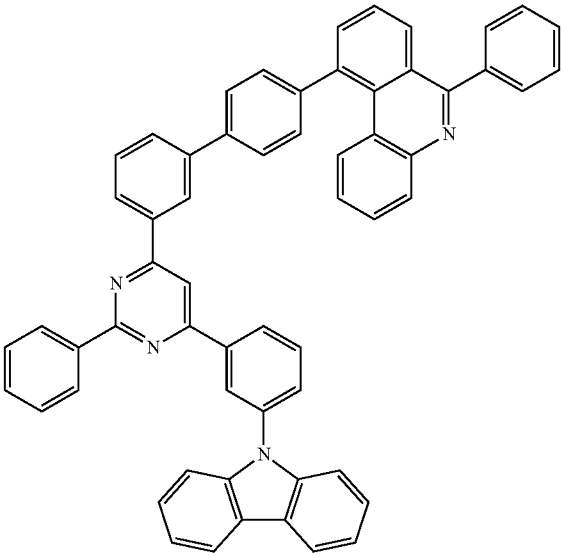
221
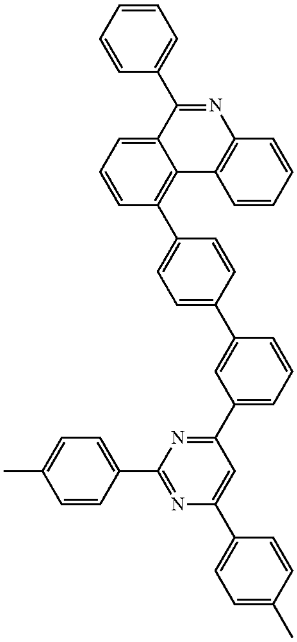
222
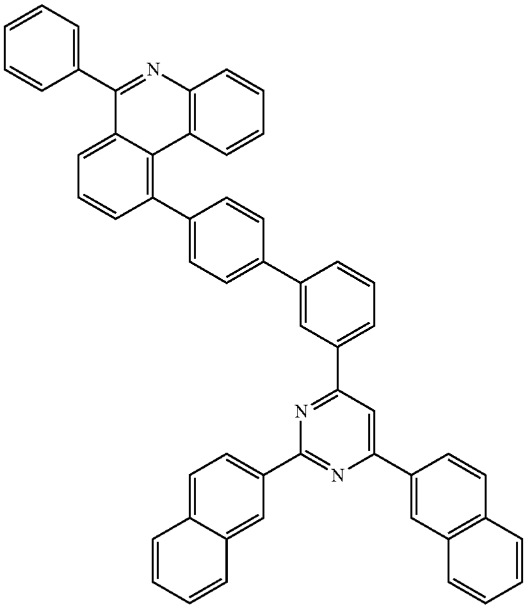
223
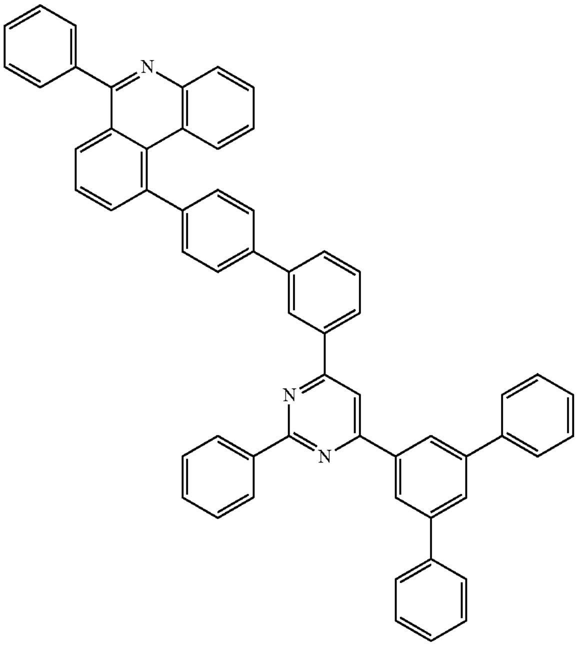

-continued
224
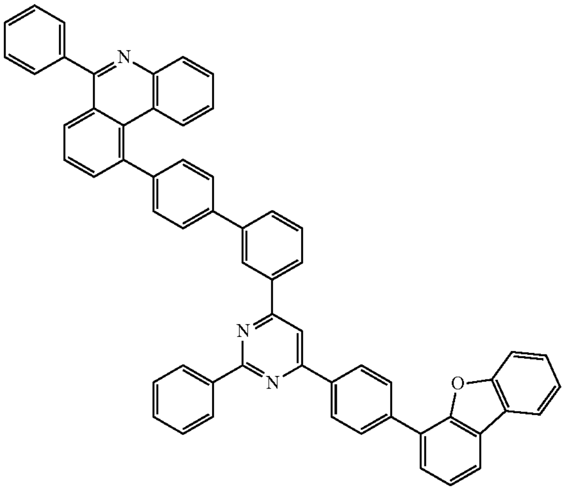
225
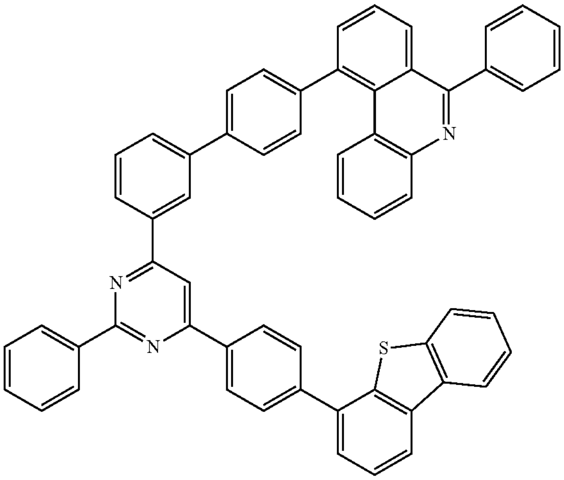
226
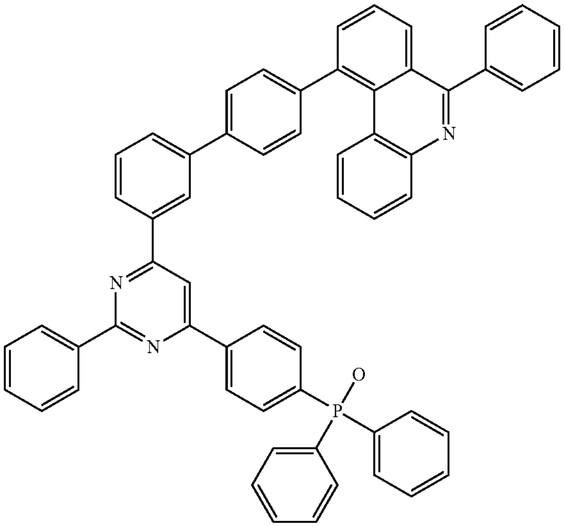
227
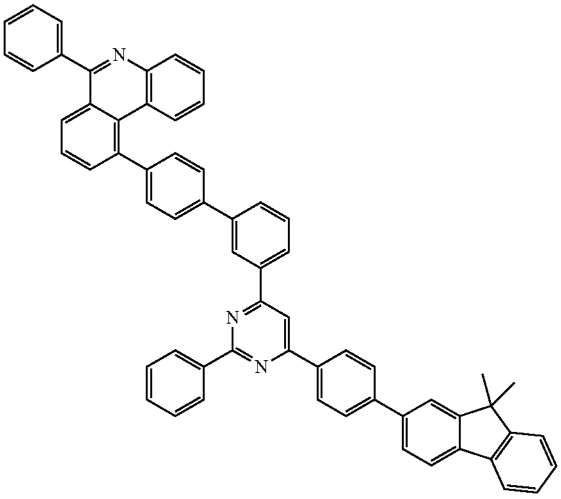

-continued
228
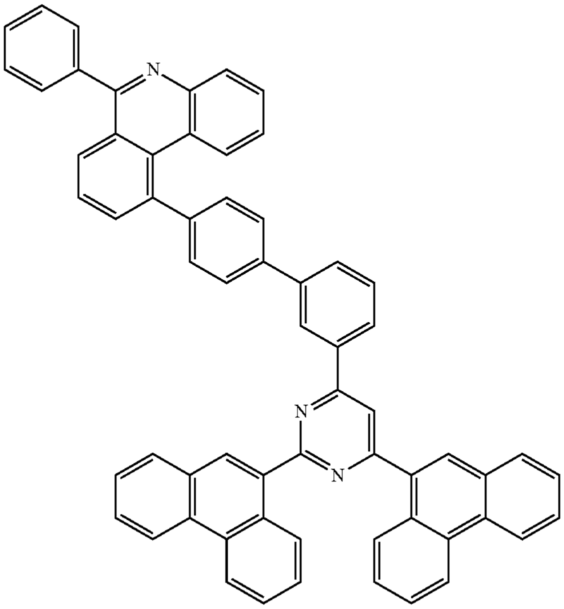
229
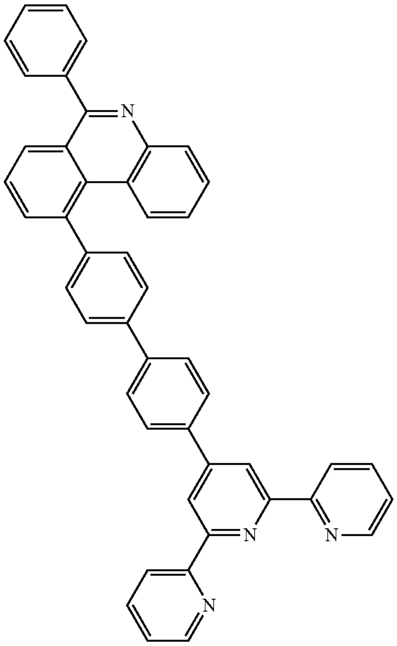
230
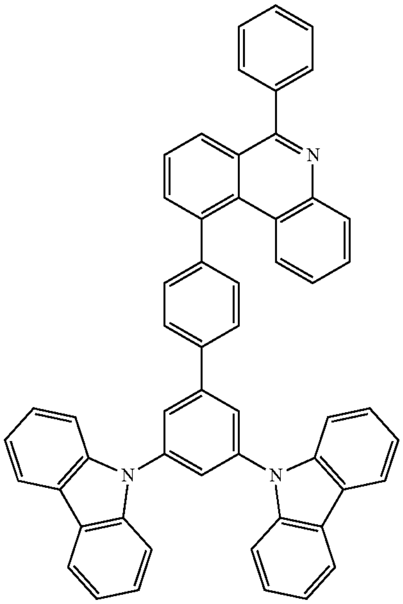
231
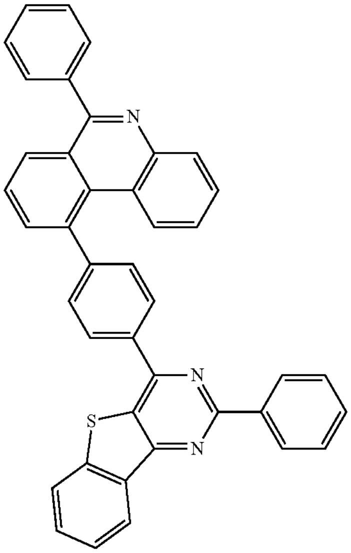

-continued
232
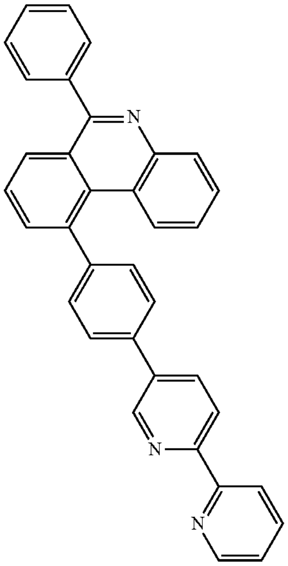
233
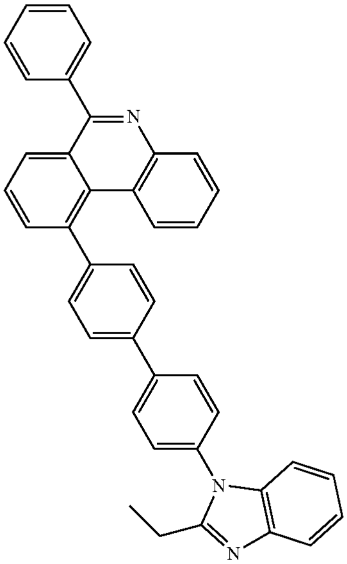
234
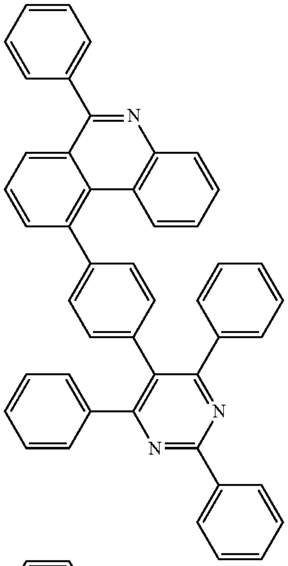
235
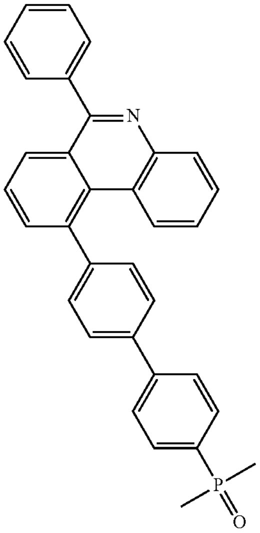
236
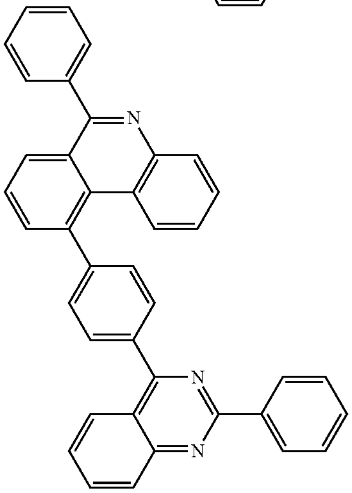
237
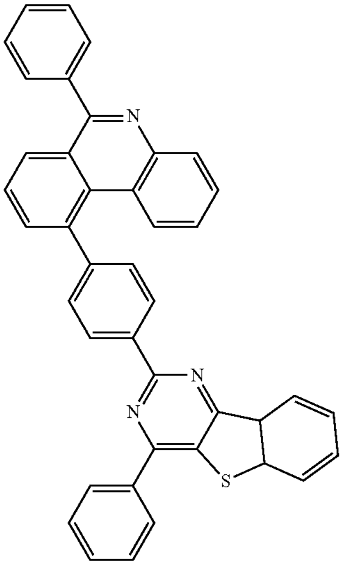

-continued
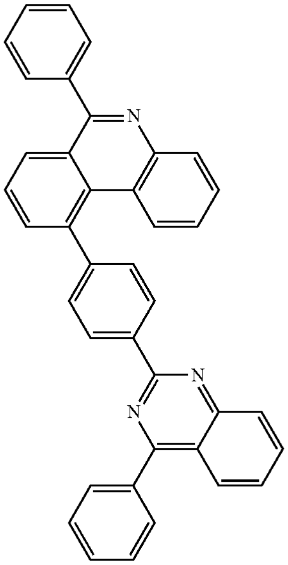
238
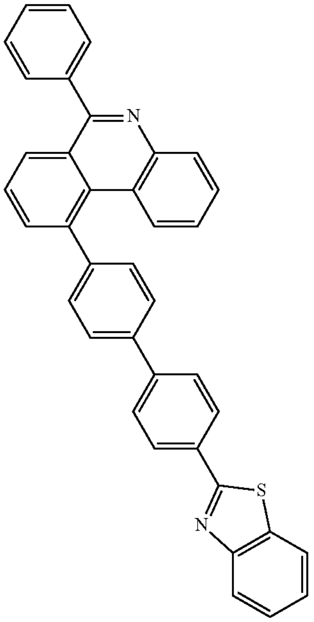
239
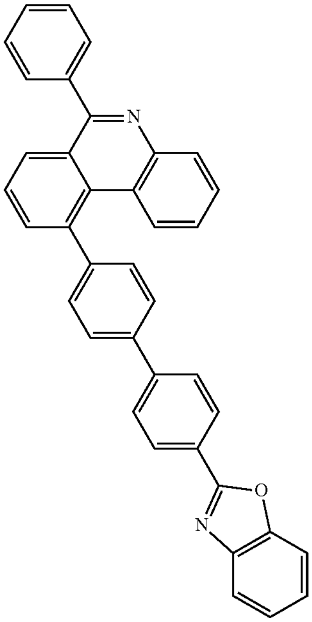
240
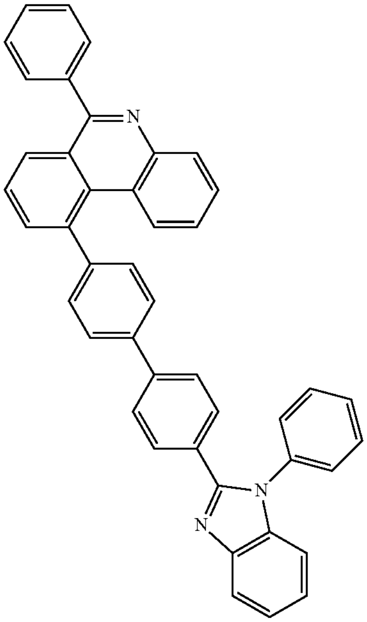
241

-continued
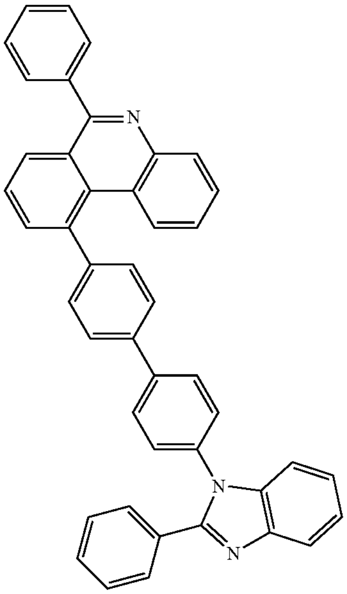
242
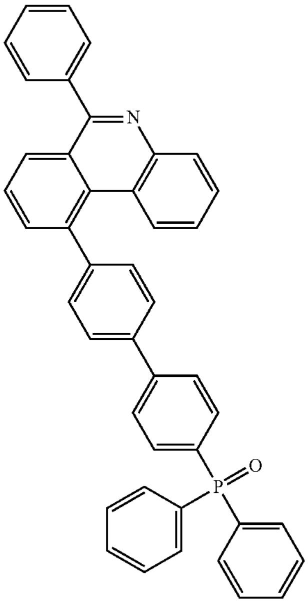
243
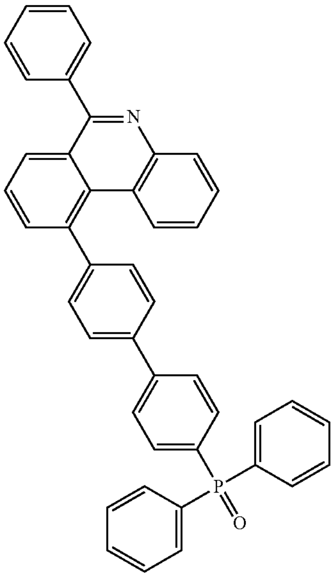
244
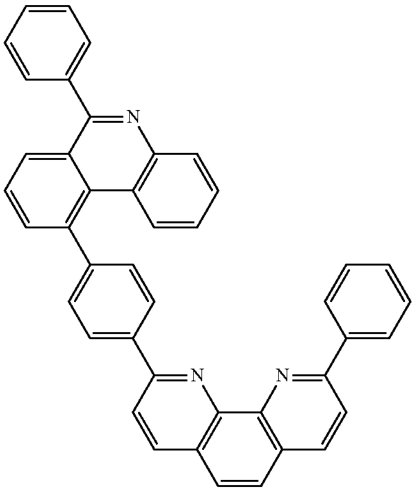
245

-continued
246
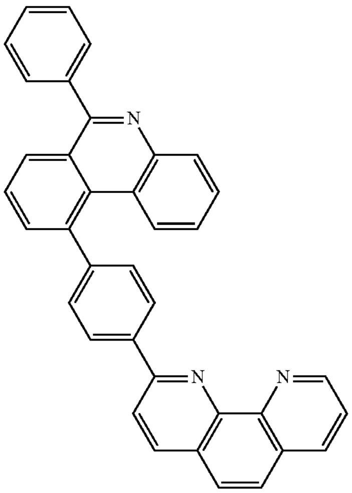
247
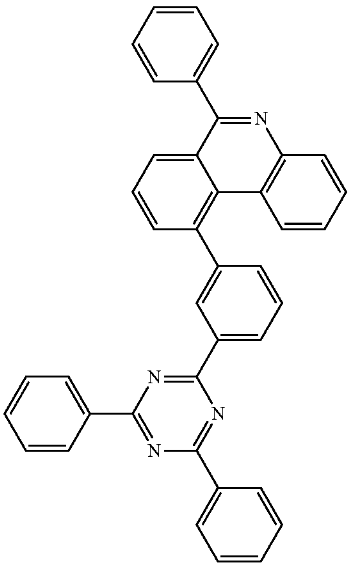
248
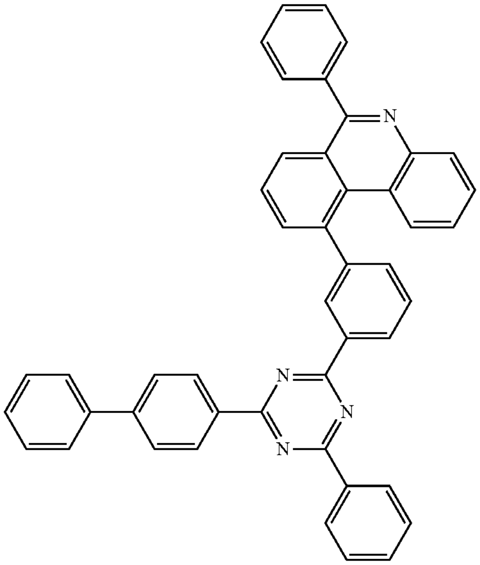
249
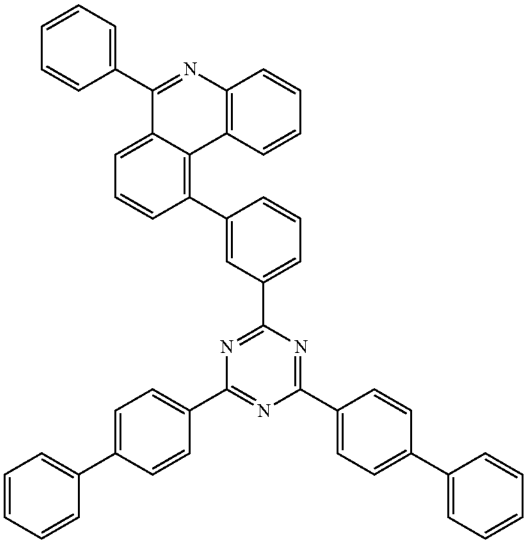

-continued
250
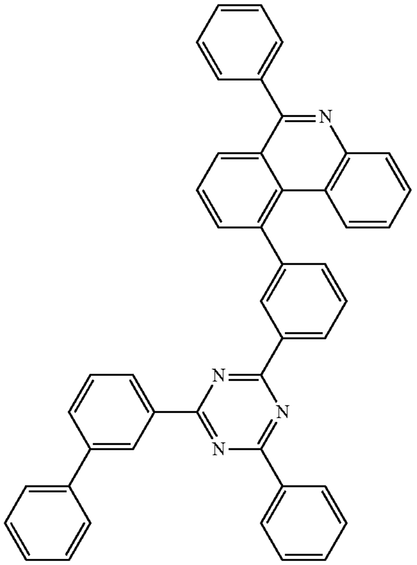
251
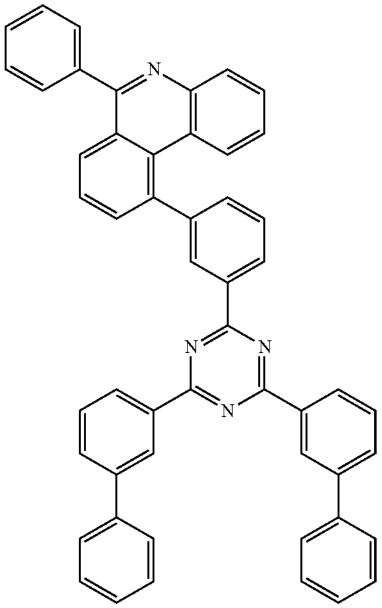
252
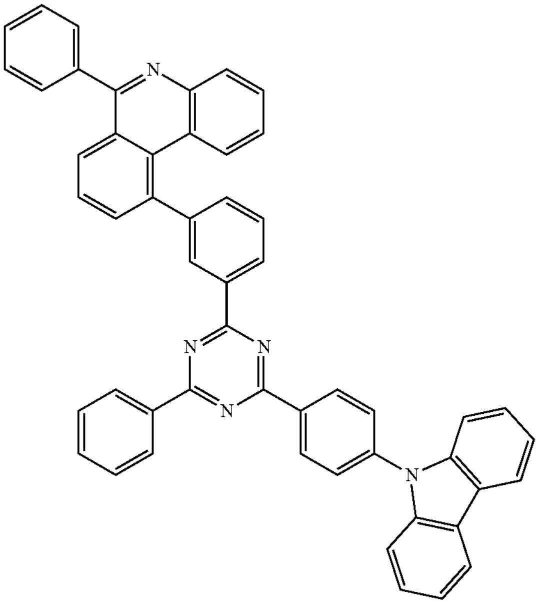
253
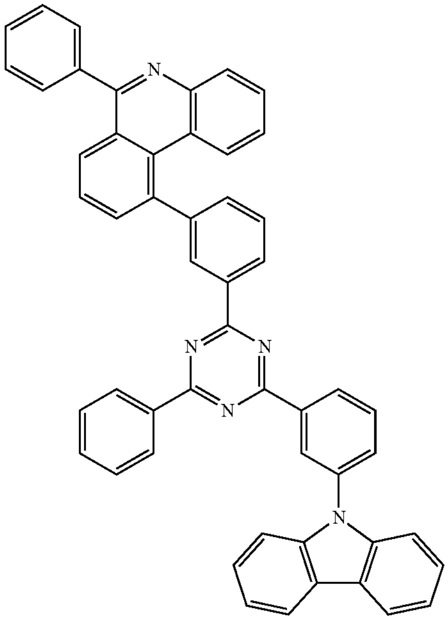

-continued
254
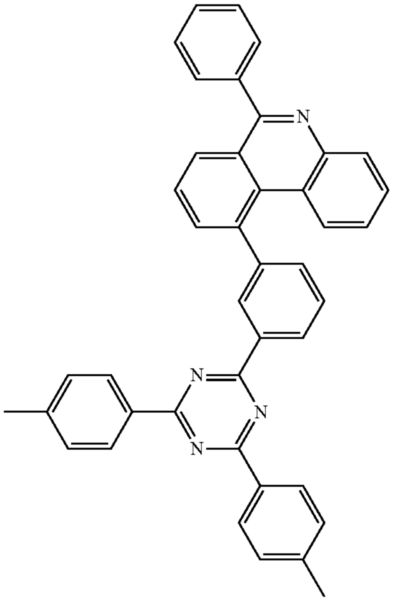
255
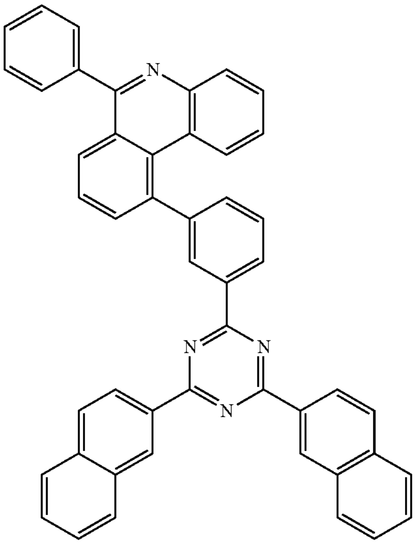
256
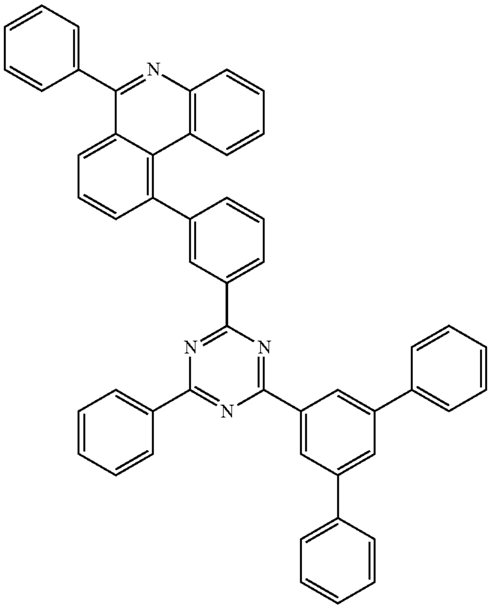
257
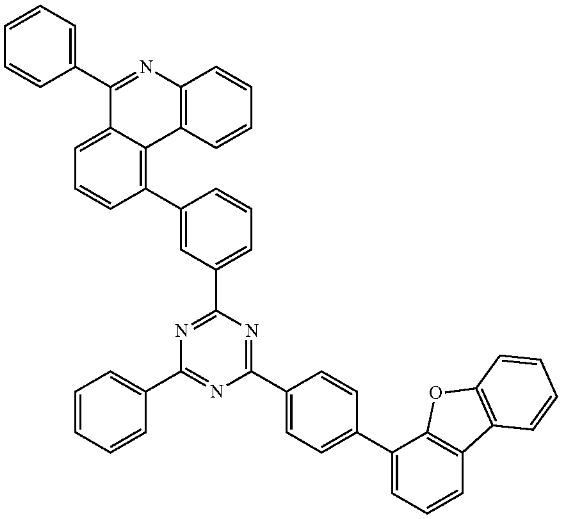

-continued
258
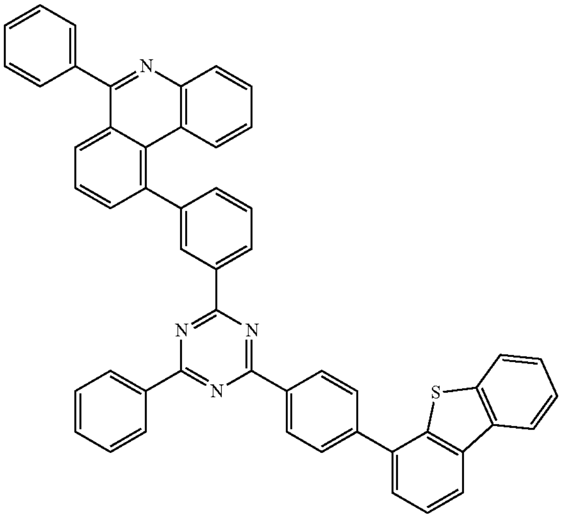
259
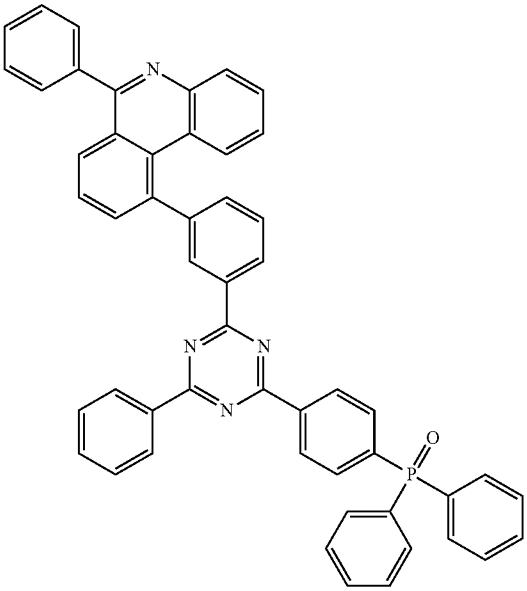
260
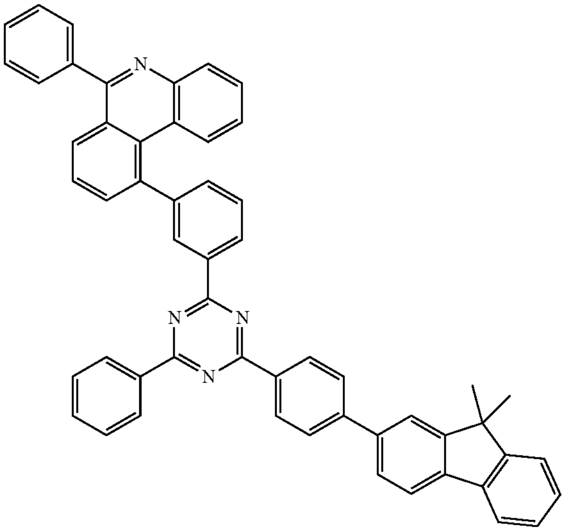
261
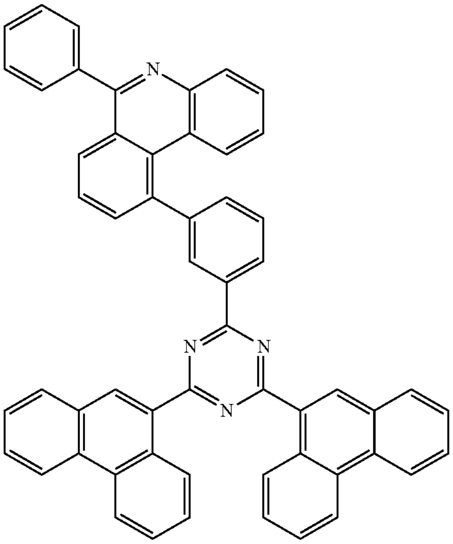

-continued
262
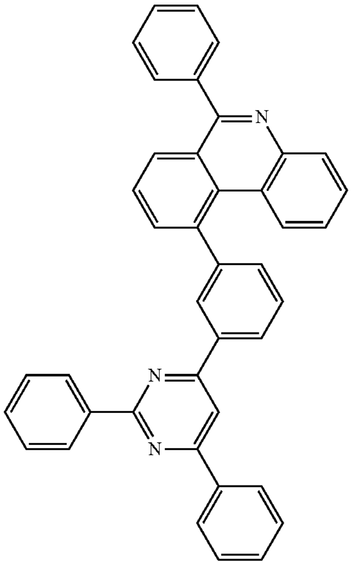
263
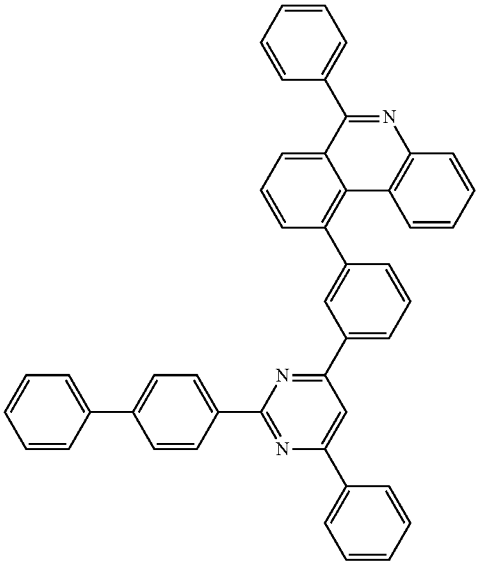
264
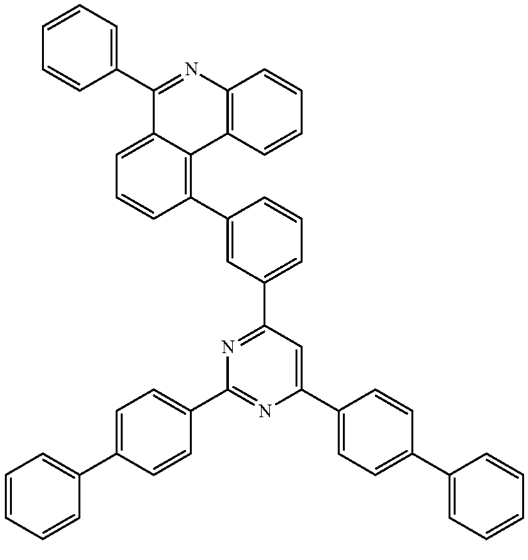
265
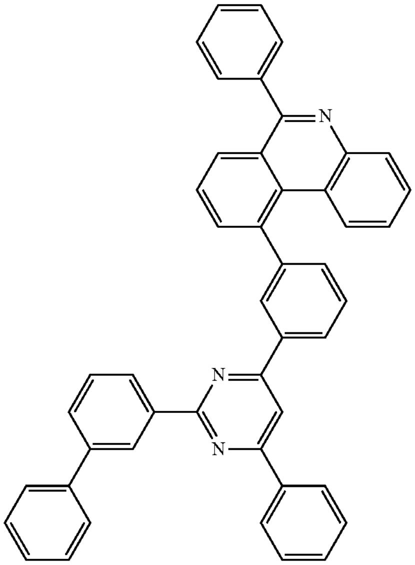

-continued
266
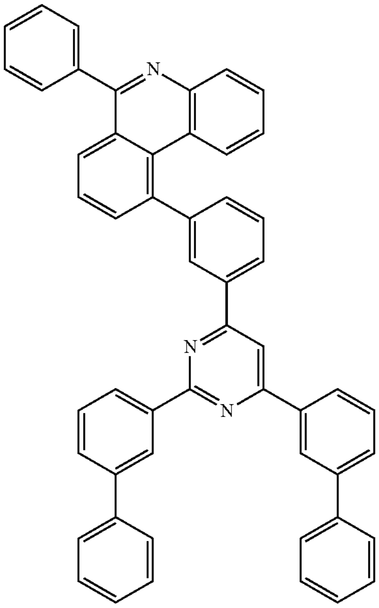
267
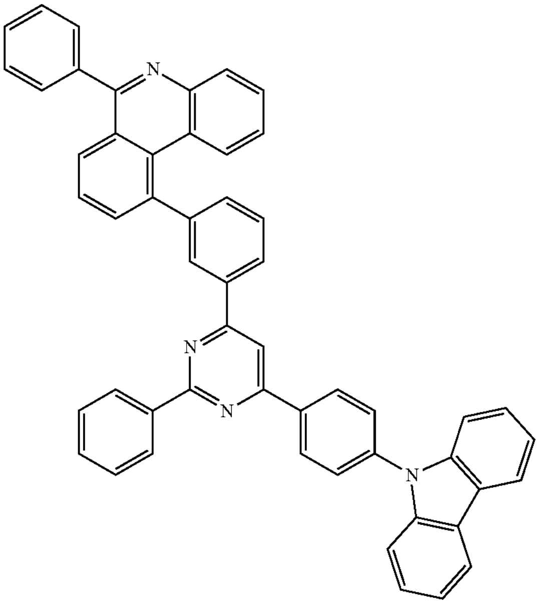
268
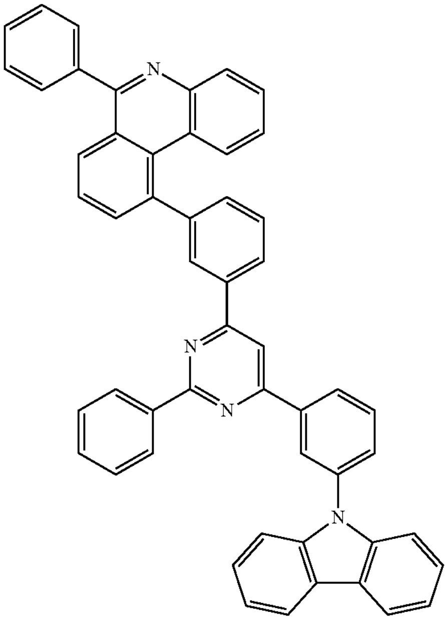
269
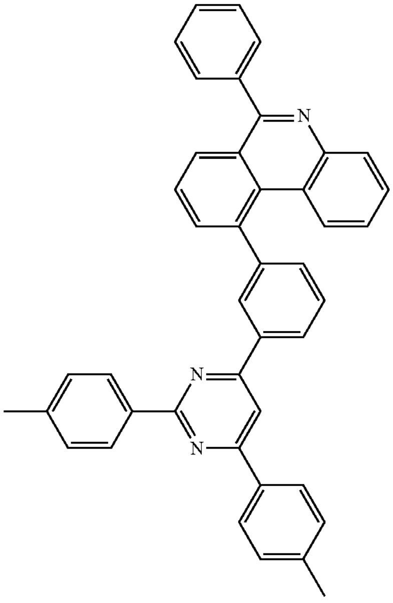

-continued
270
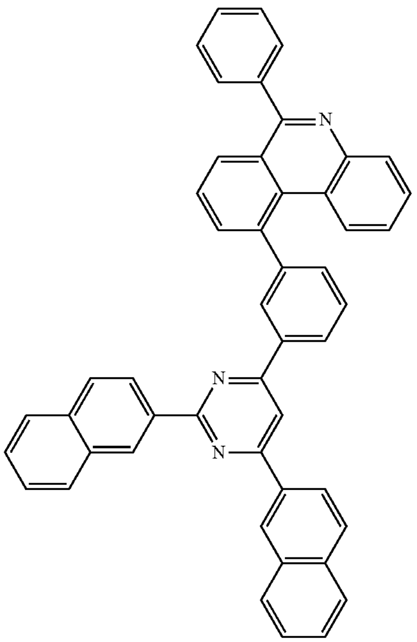
271
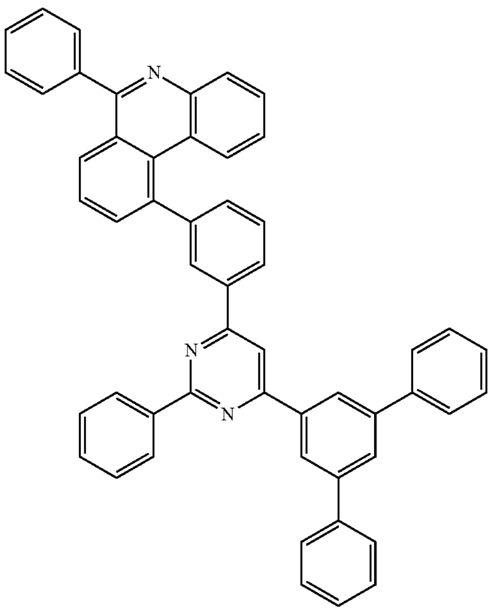
272
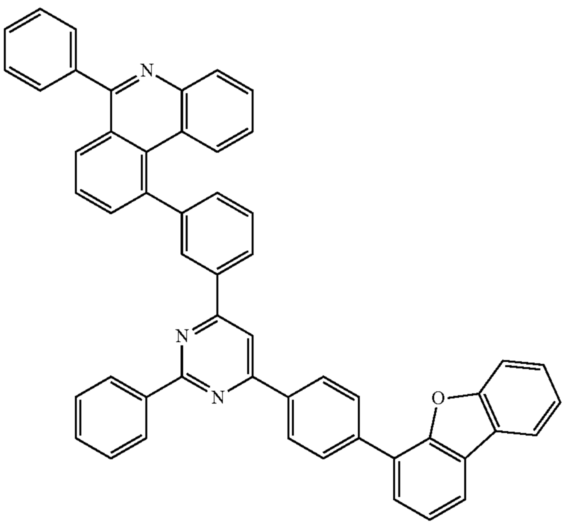
273
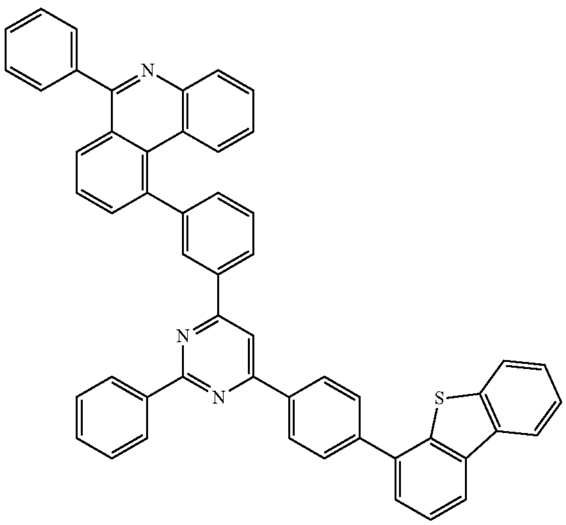

-continued
274
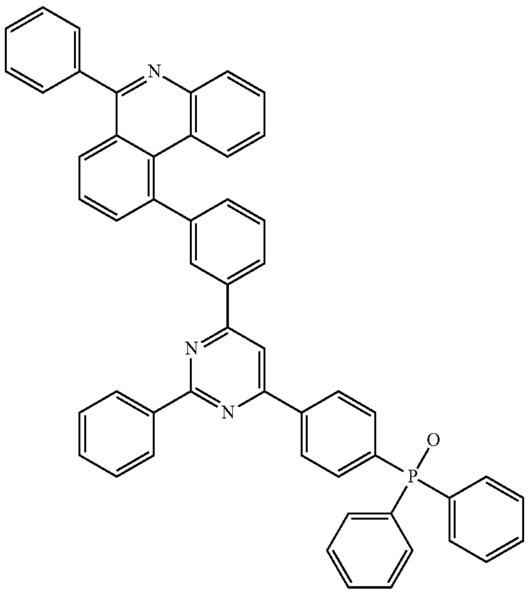
275
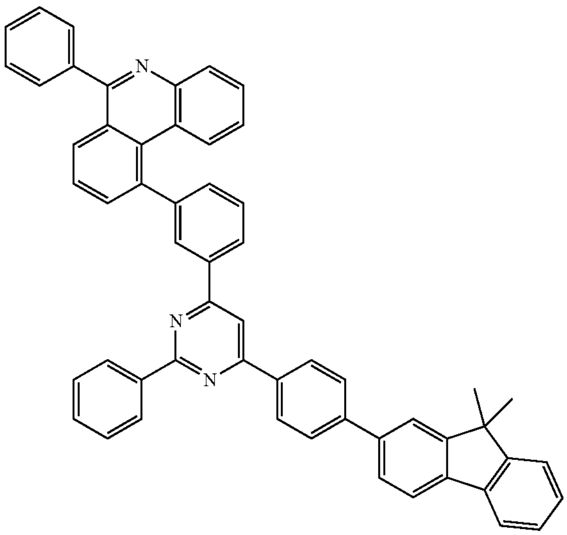
276
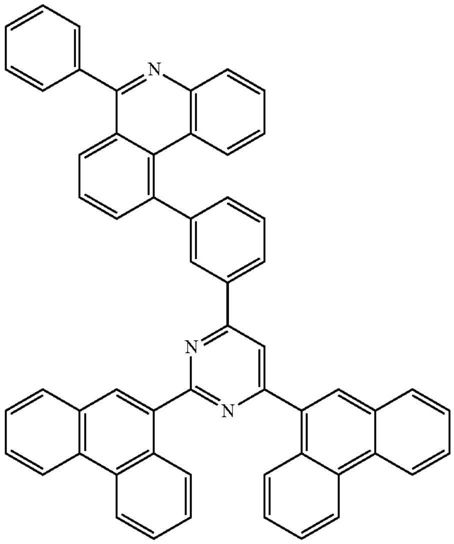
277
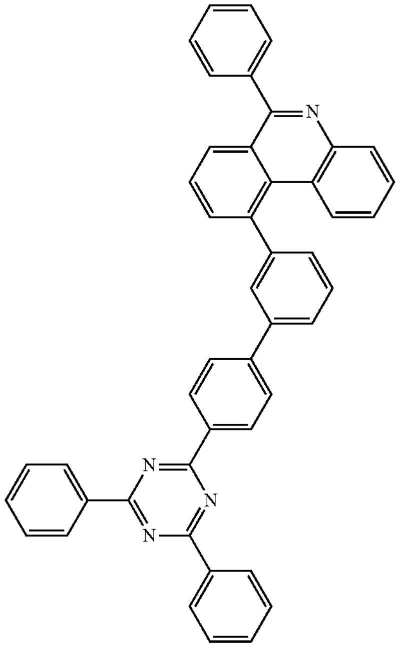

-continued
278
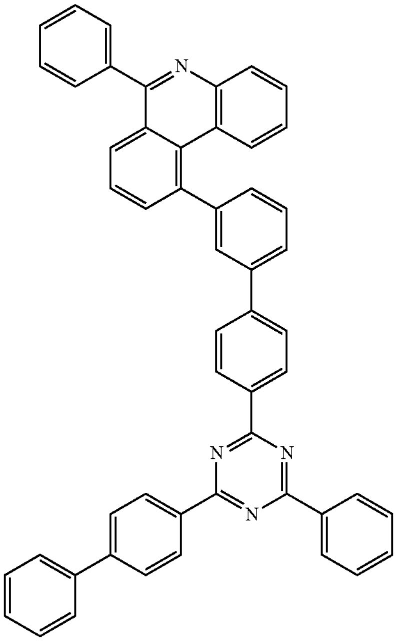
279
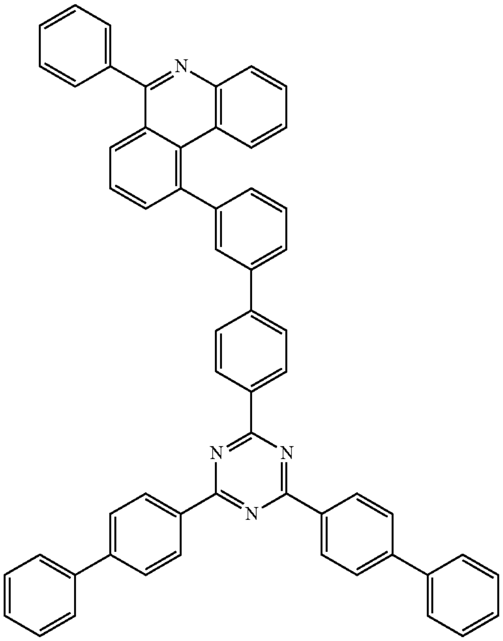
280
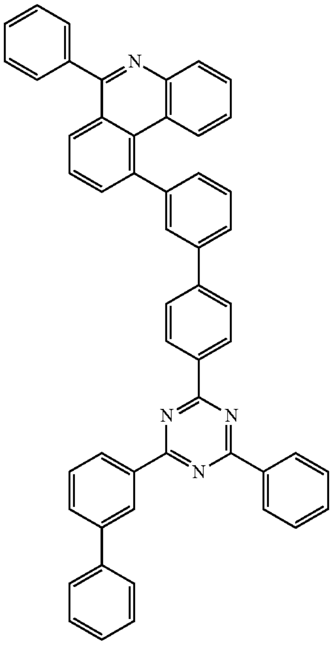
281
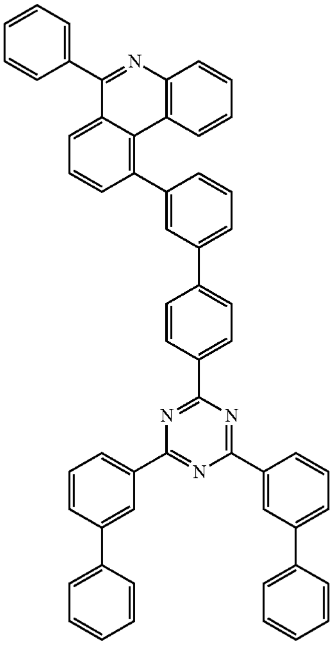

-continued
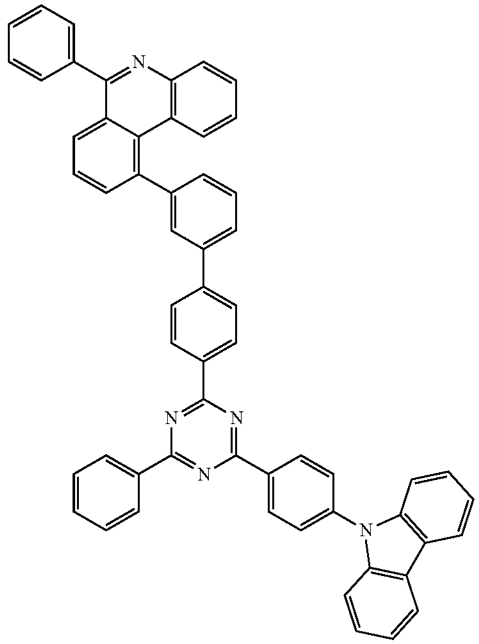
282
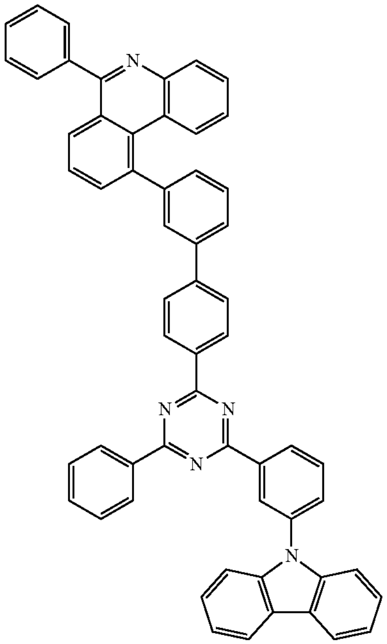
283
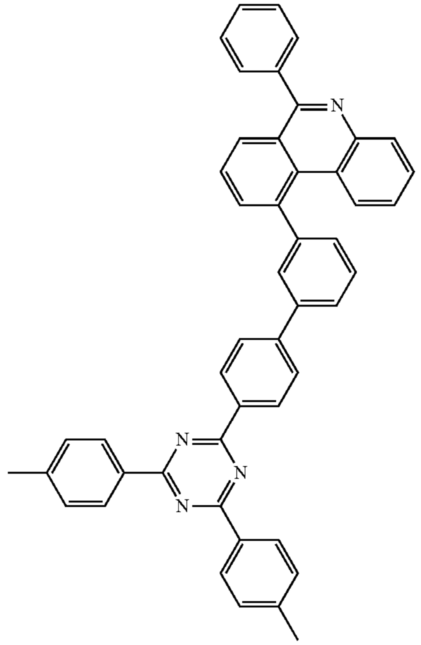
284
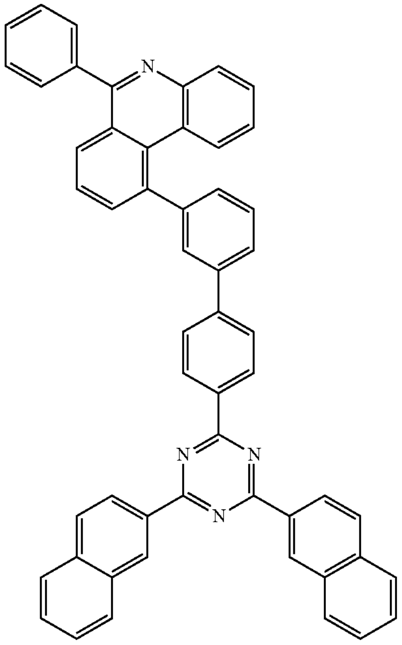
285

-continued
286
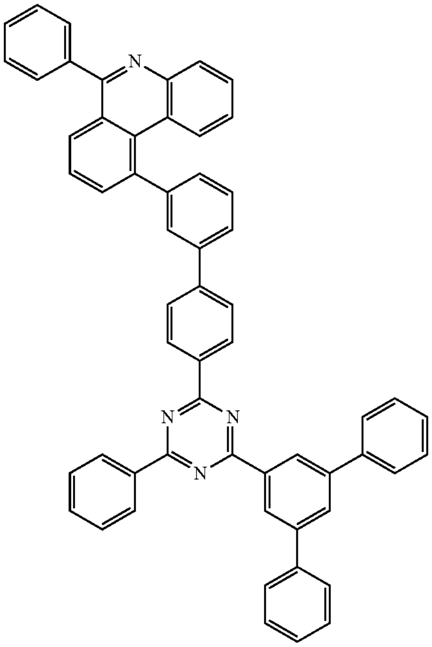
287
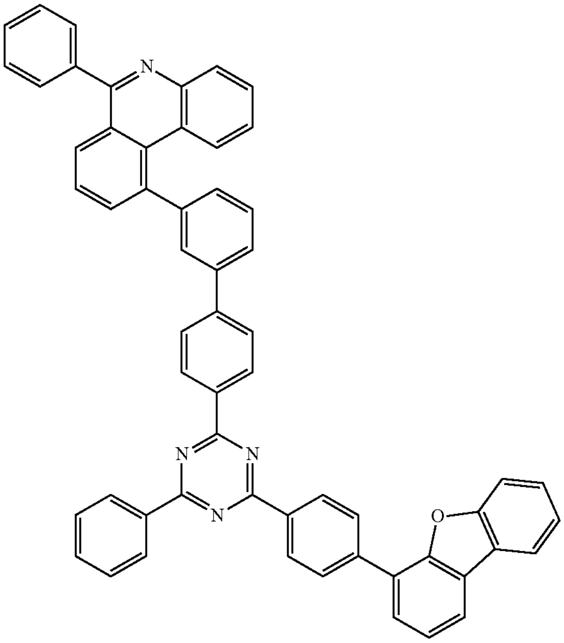
288
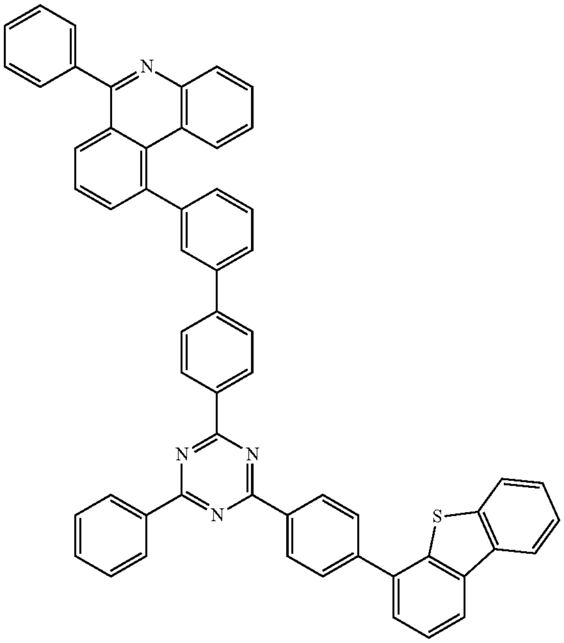
289
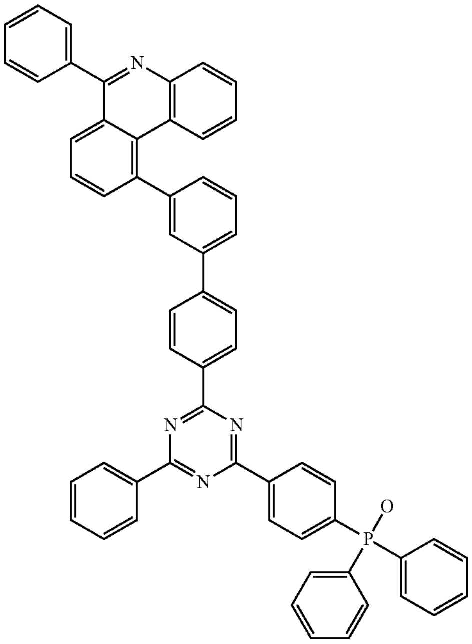

-continued
290
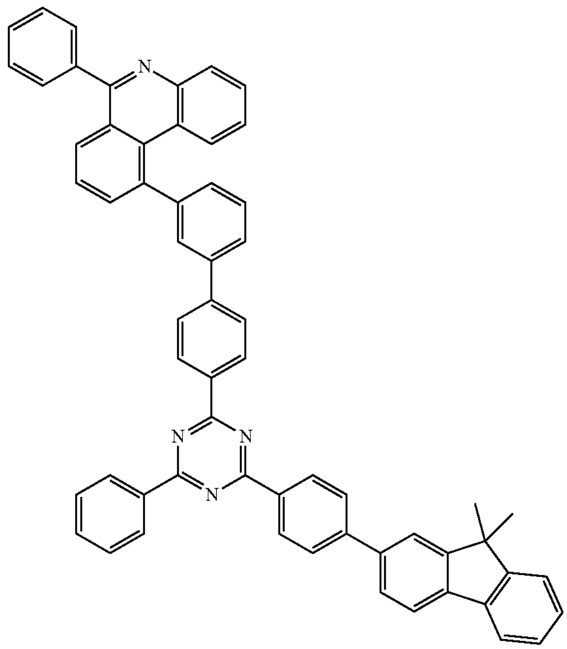
291
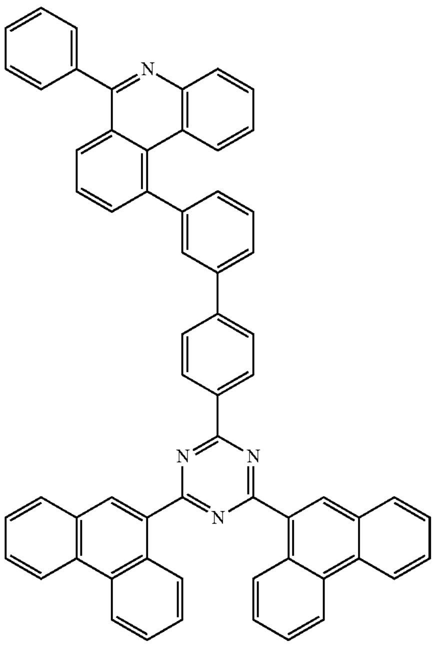
-continued
292
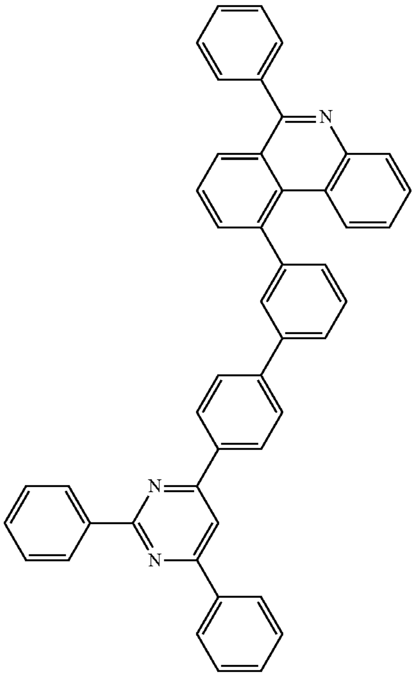
293
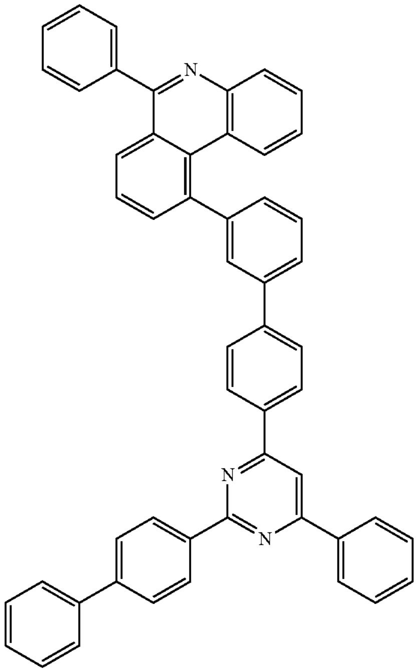

-continued
294
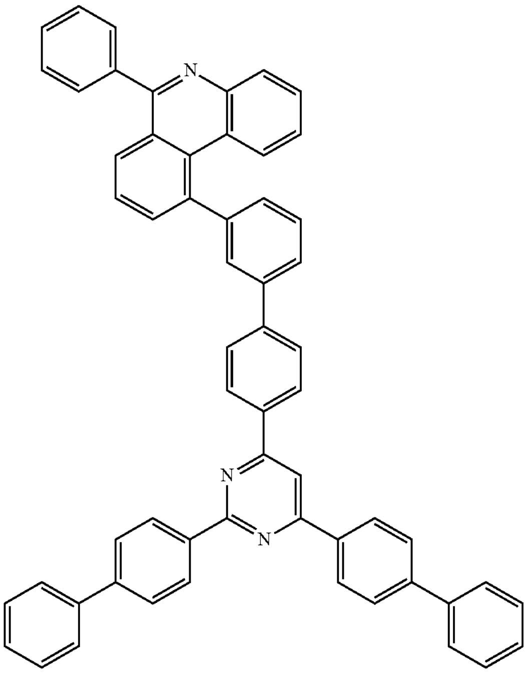
295
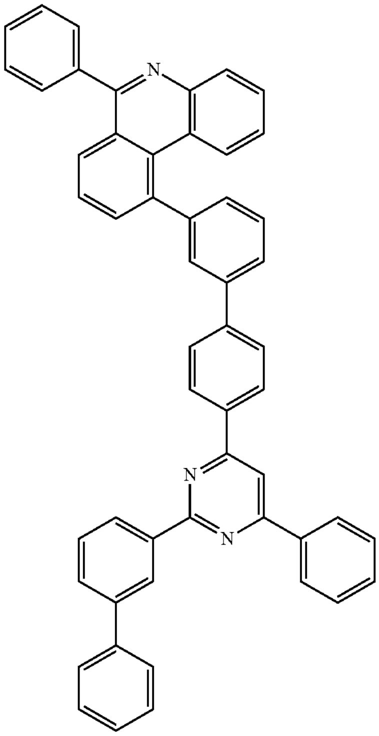
-continued
296
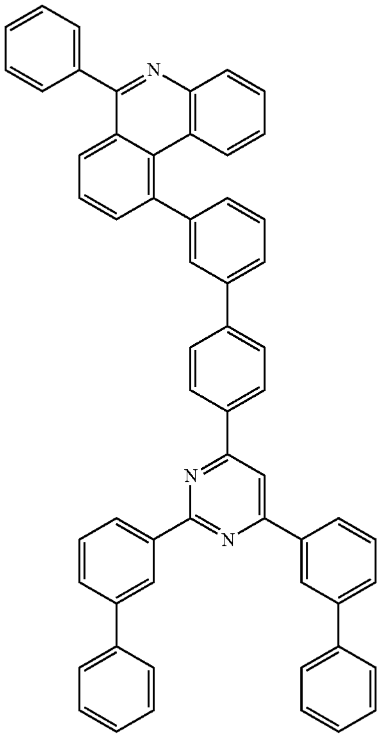
297
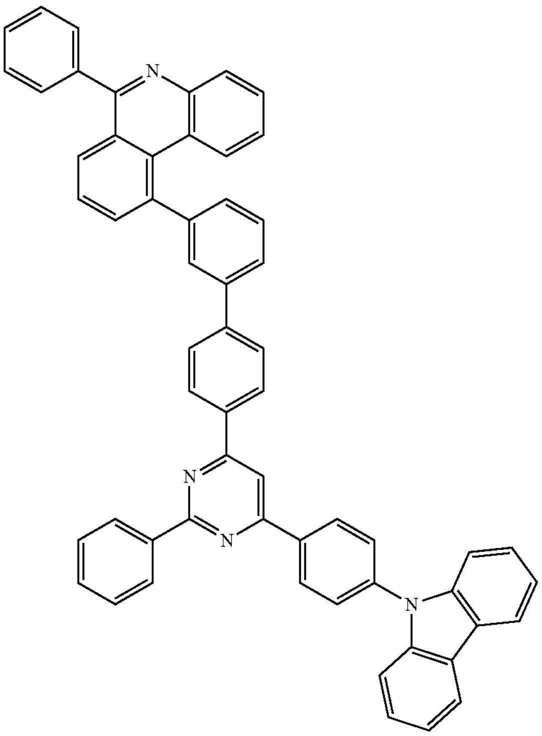

-continued
298
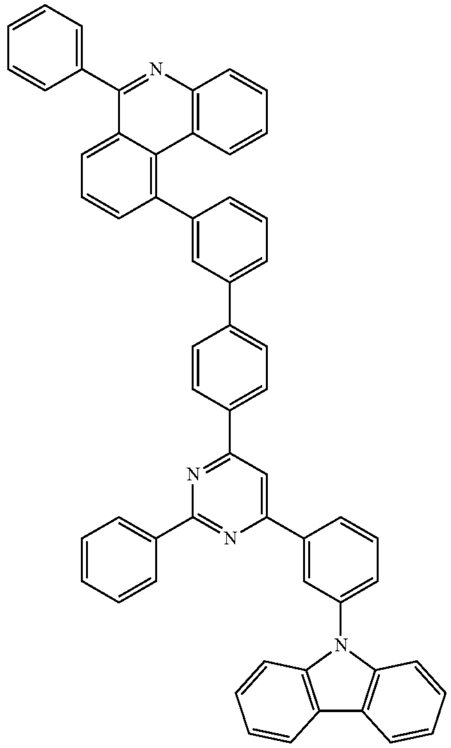
299
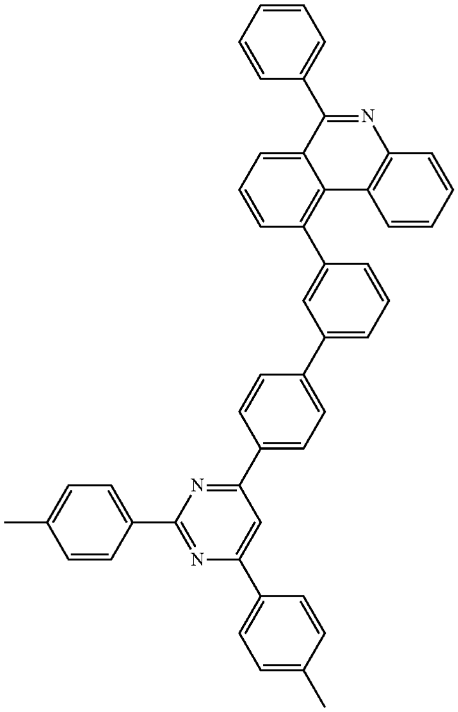
-continued
300
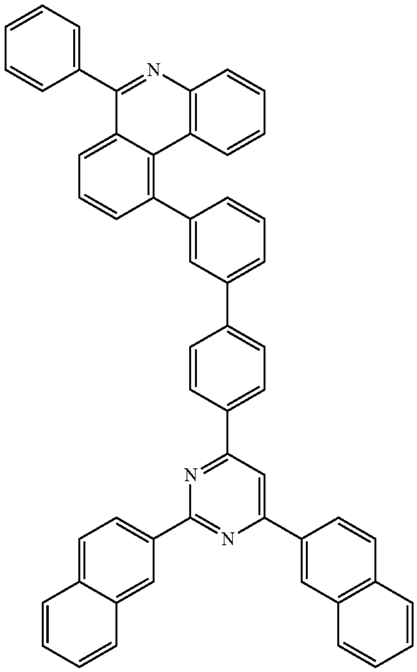
301
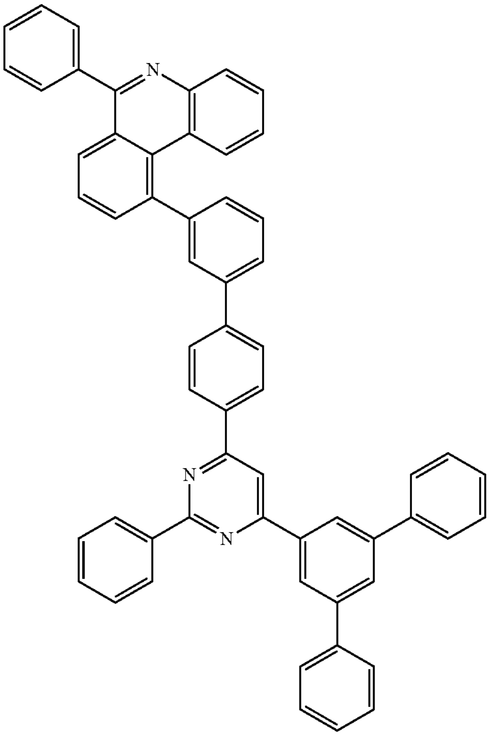

-continued
302
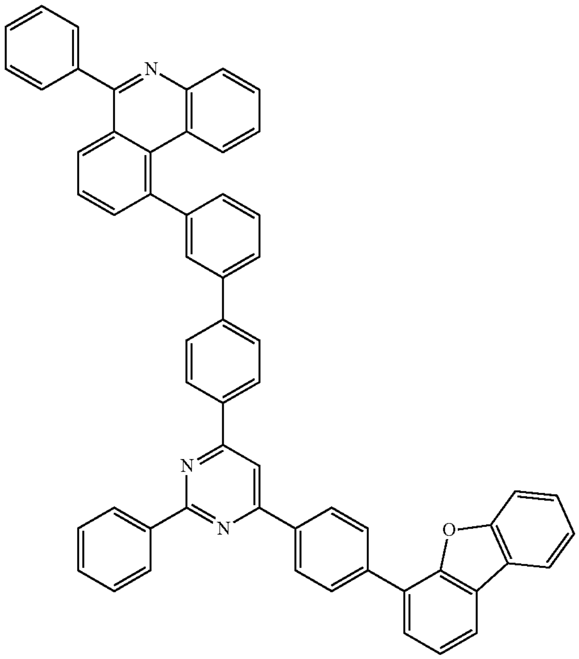
303
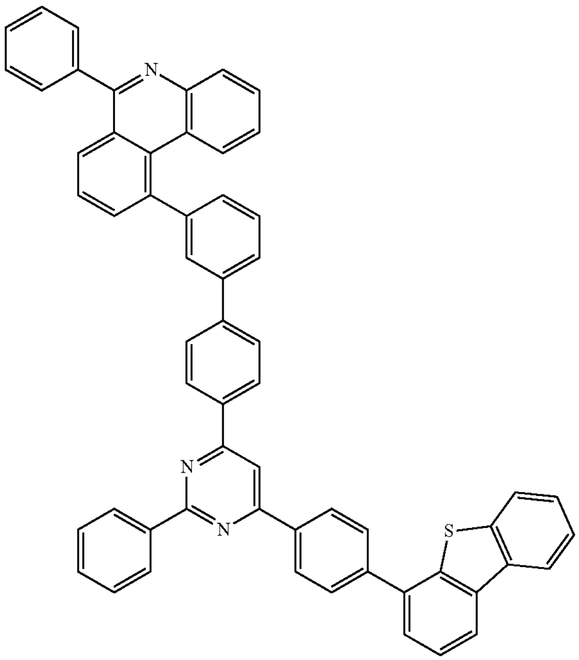
-continued
304
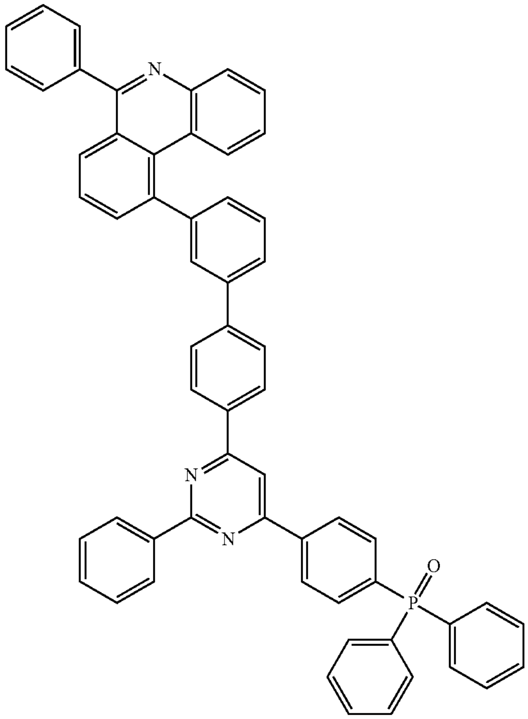
305
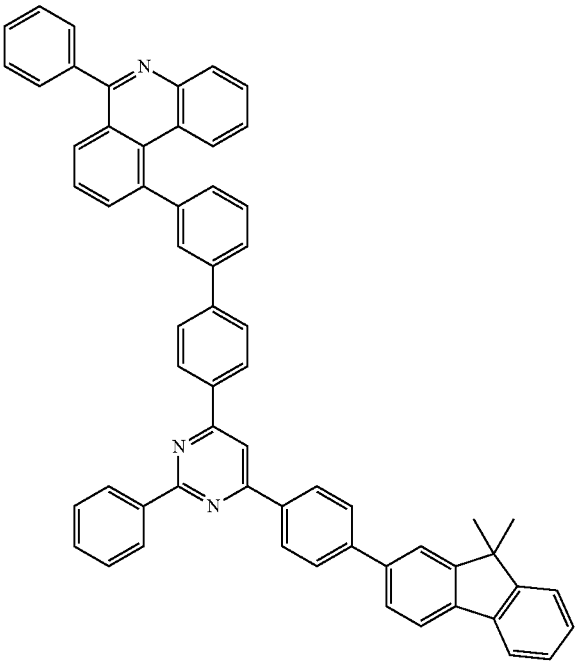

306
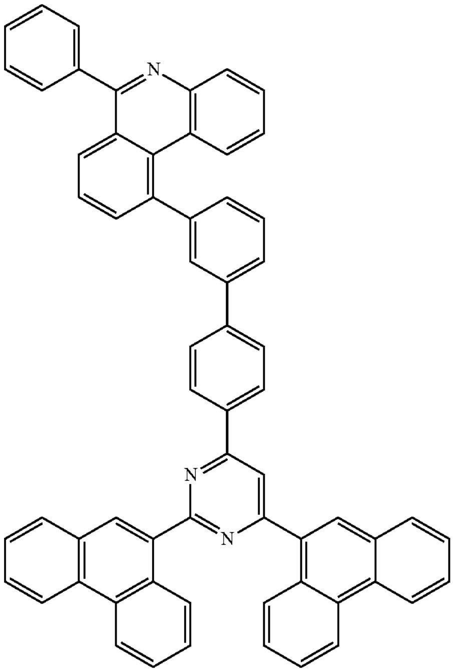
307
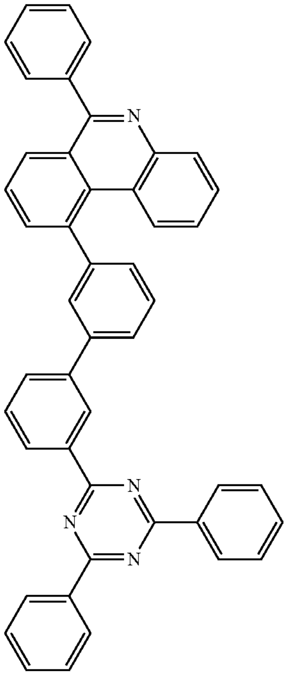
308
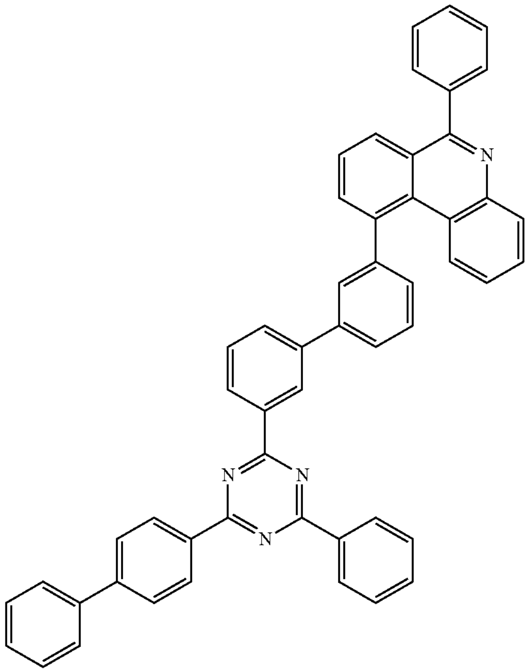
309
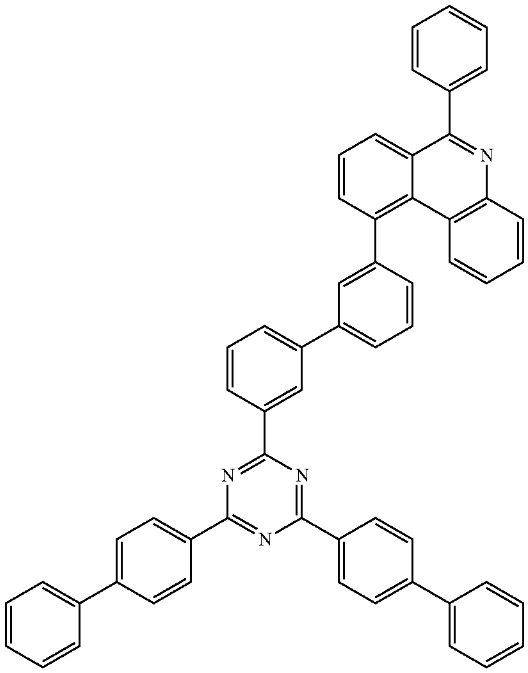

-continued
310
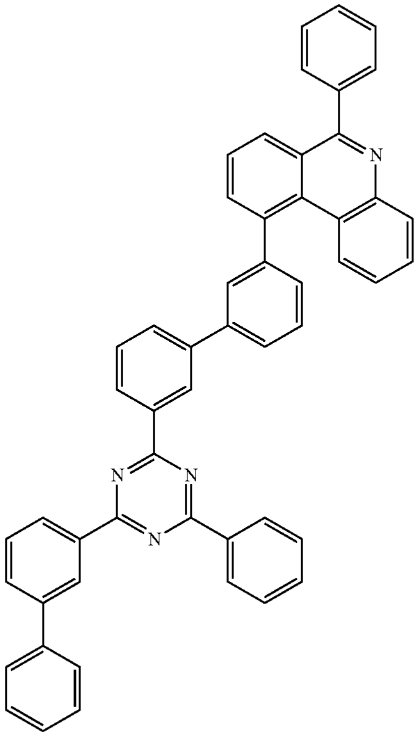
311
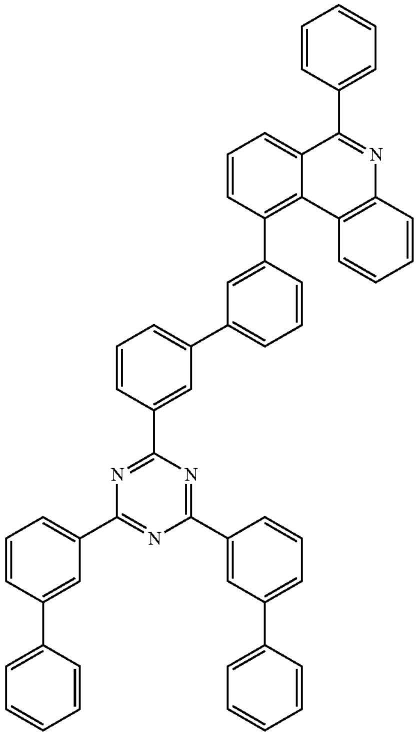
-continued
312
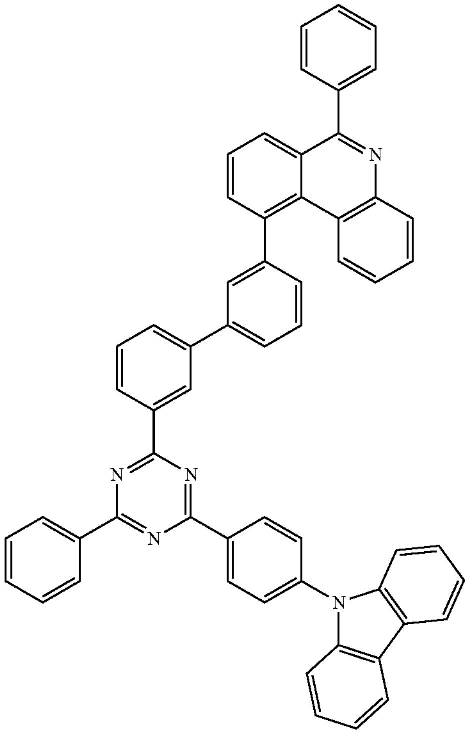
313
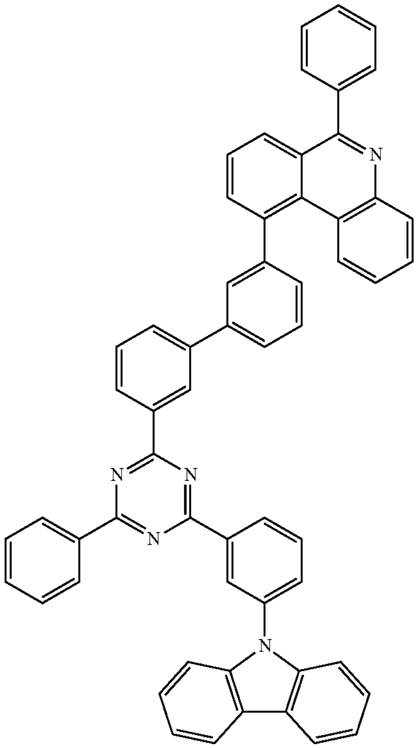

314
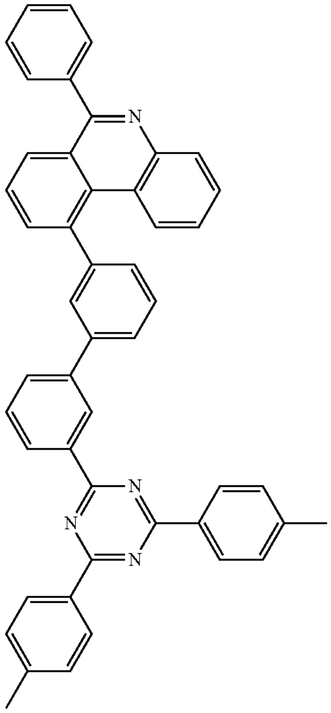
315
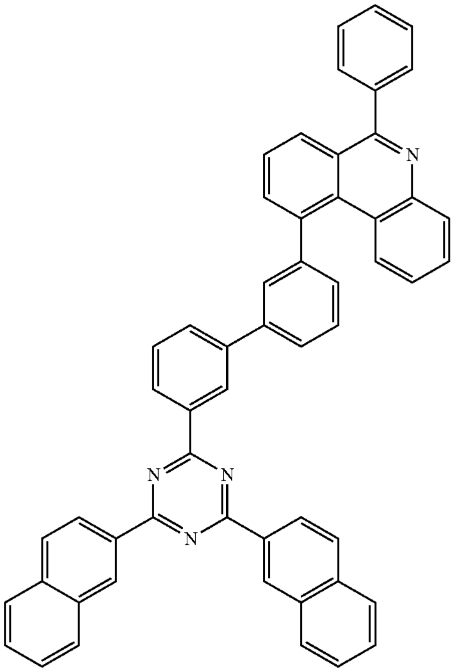
316
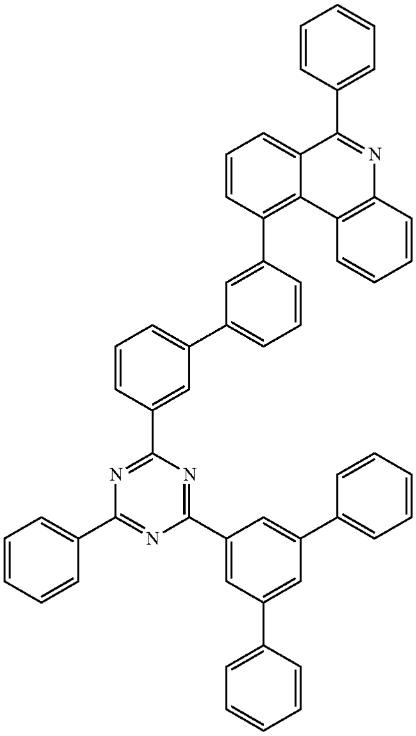
317
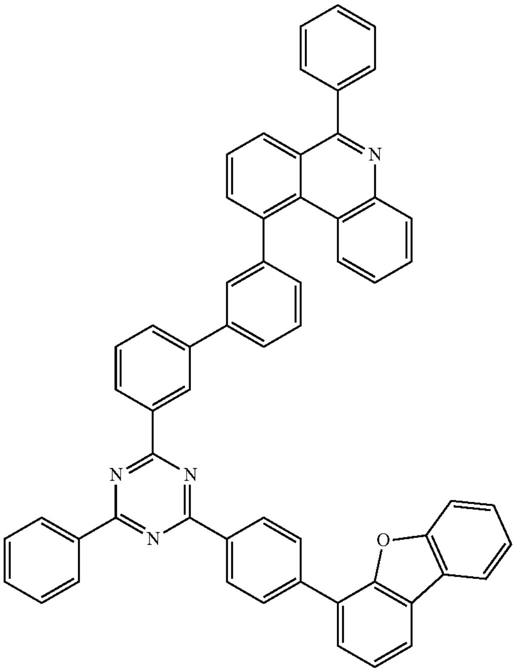

-continued
318
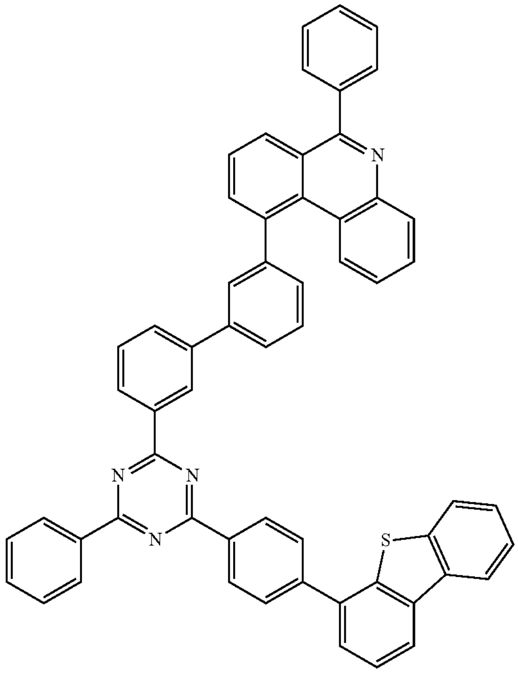
319
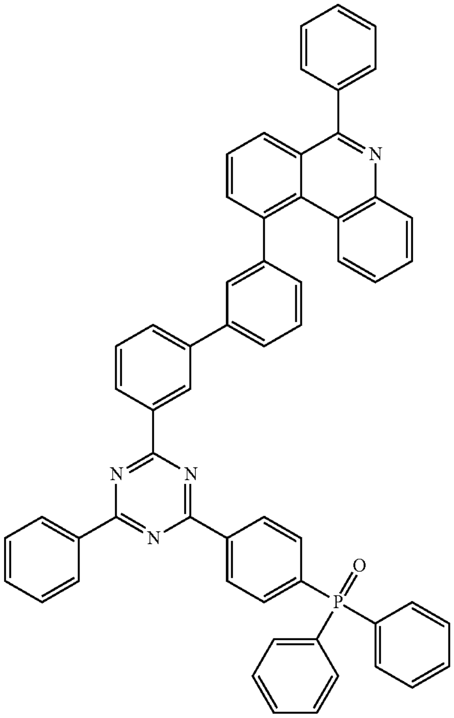
-continued
320
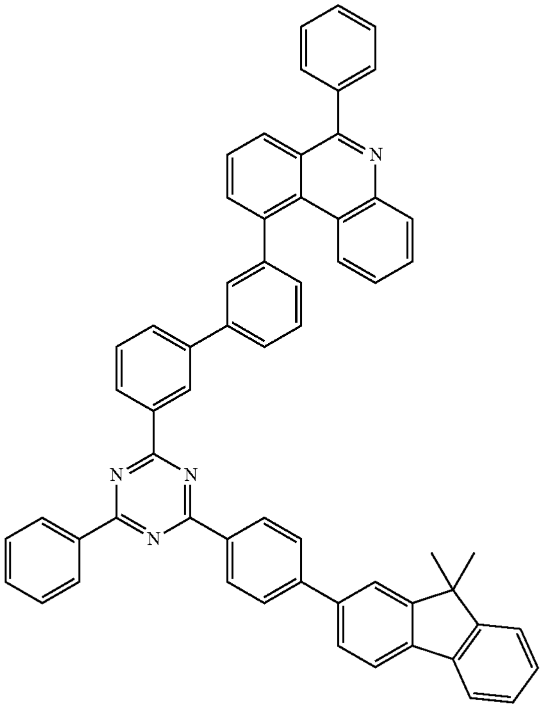
321
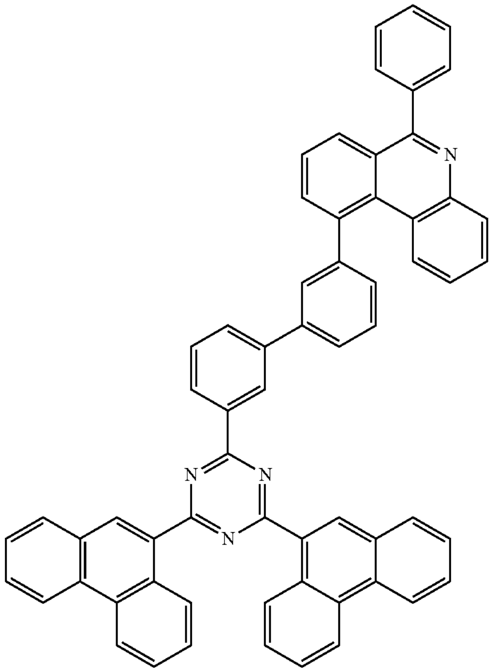

-continued
322
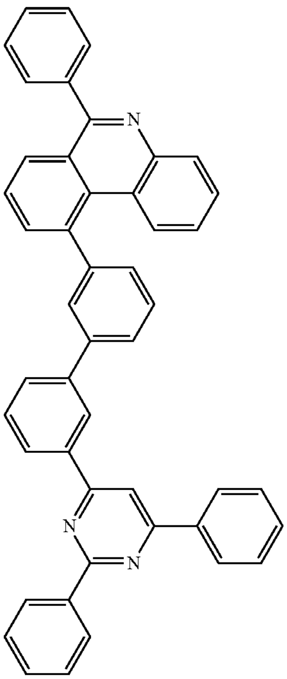
323
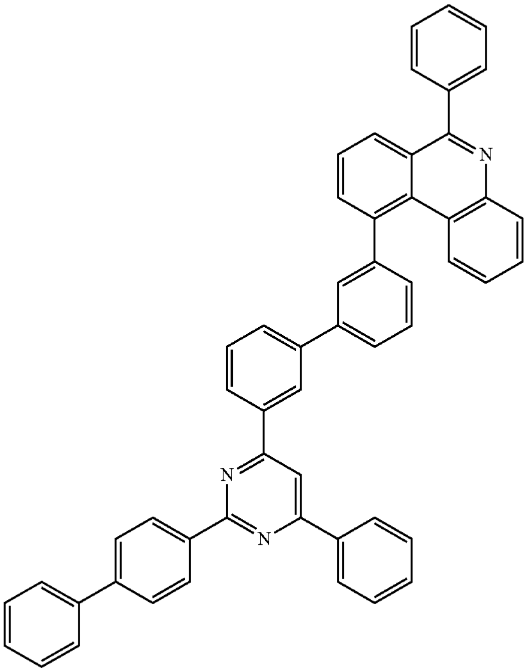
-continued
324
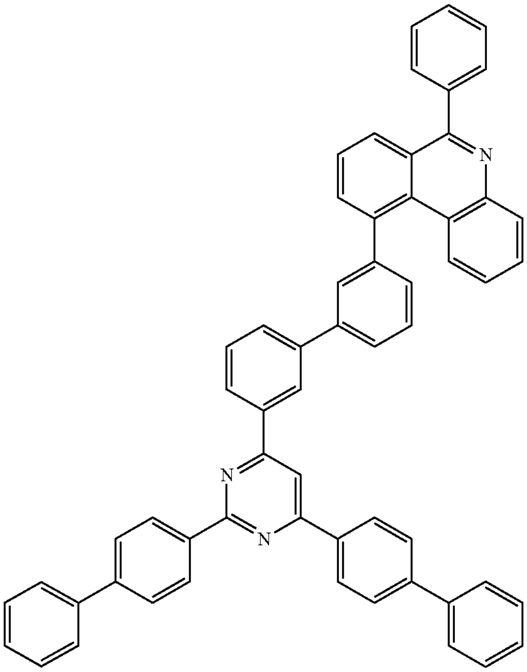
325
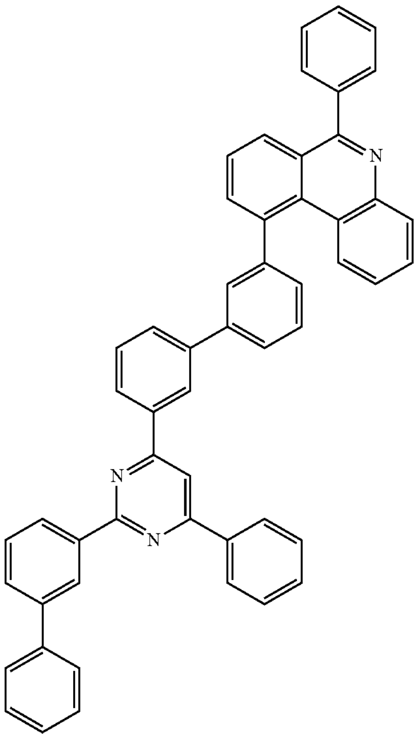

-continued
326
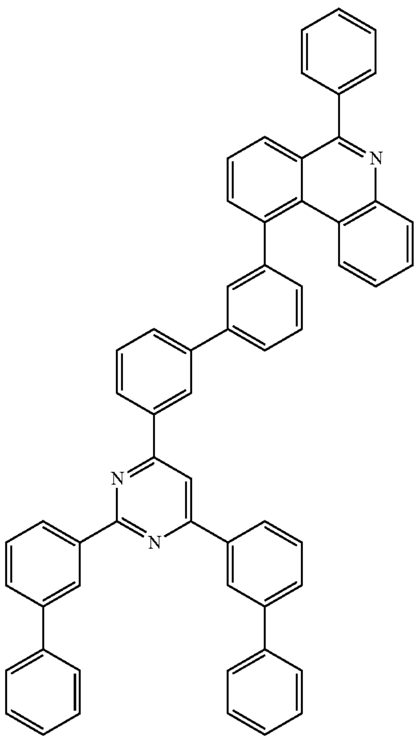
327
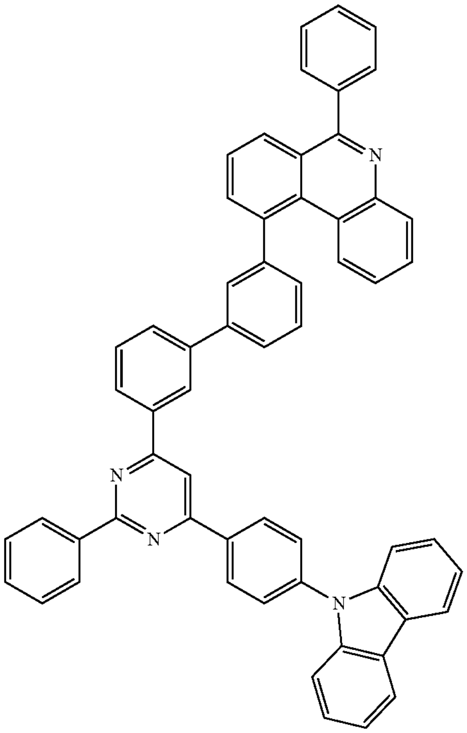
-continued
328
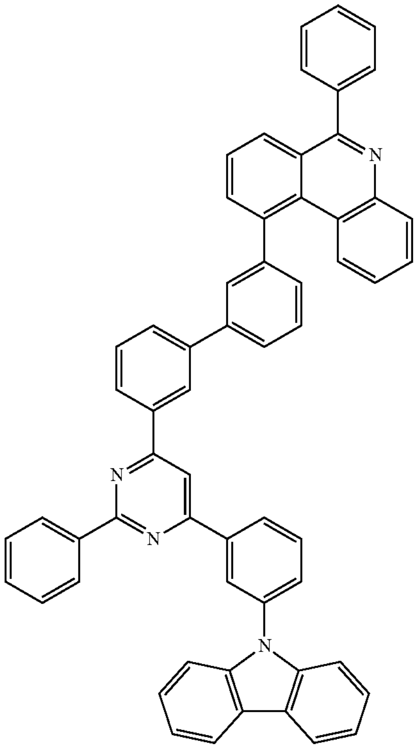
329
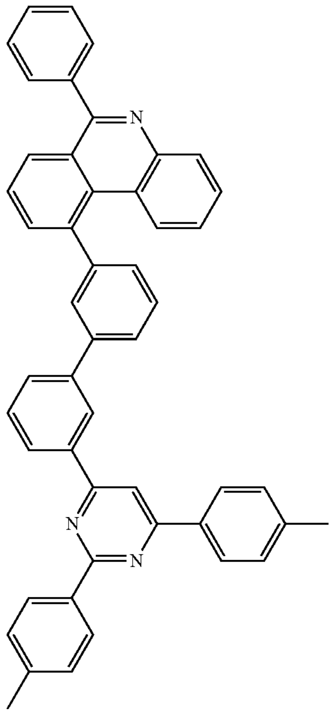

-continued
330
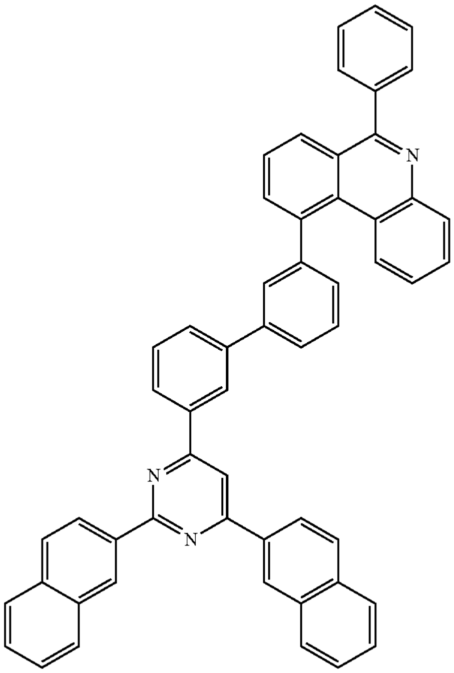
331
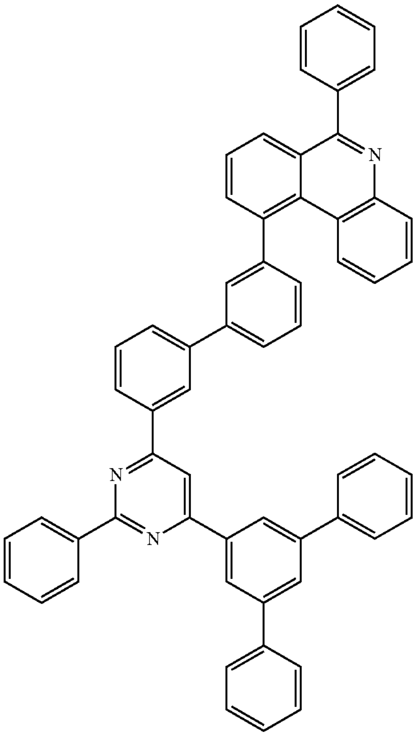
-continued
332
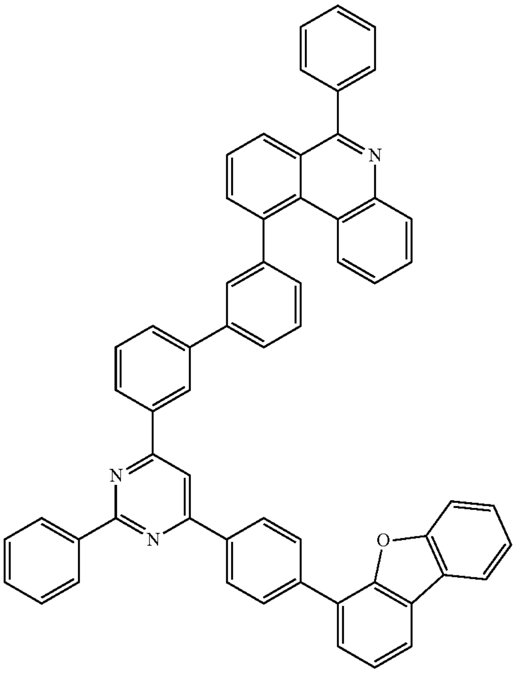
333
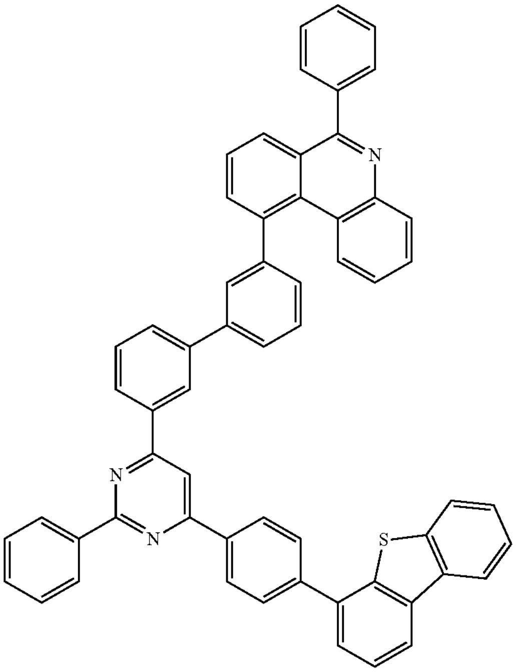

-continued
334
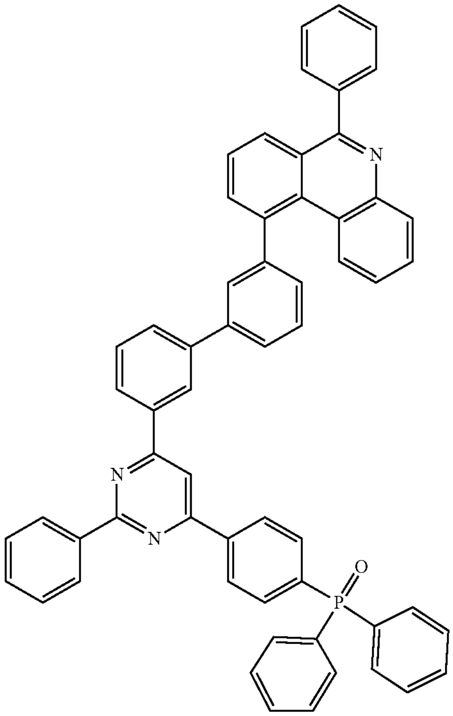
335
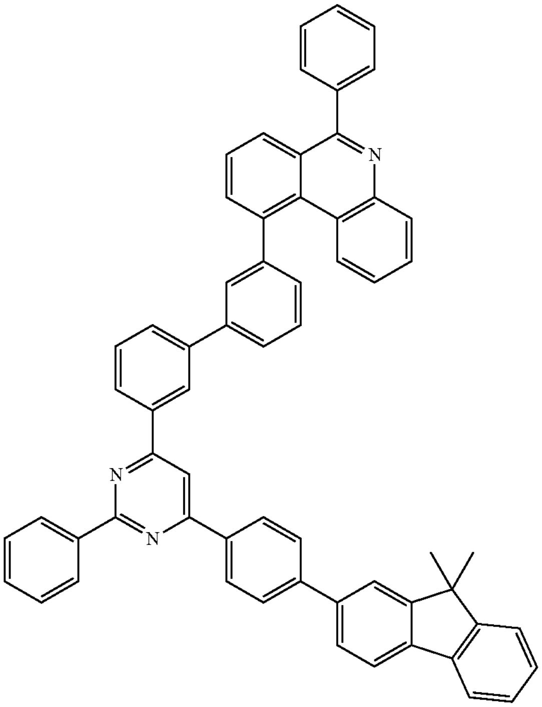
-continued
336
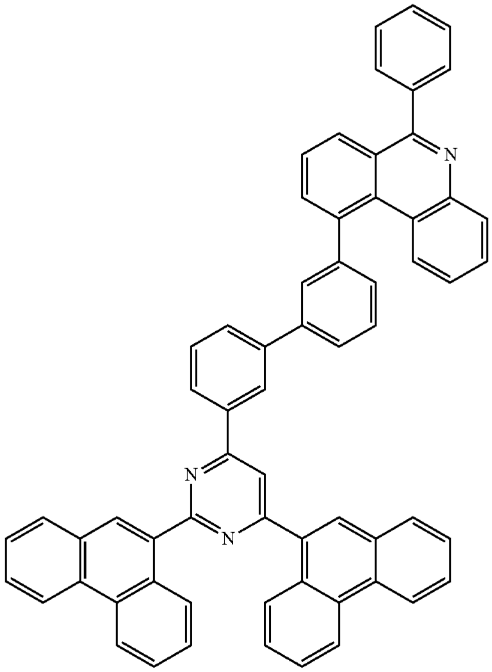
337
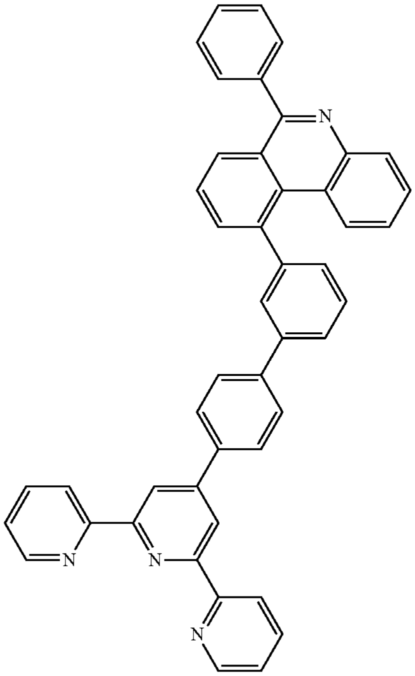

-continued
338
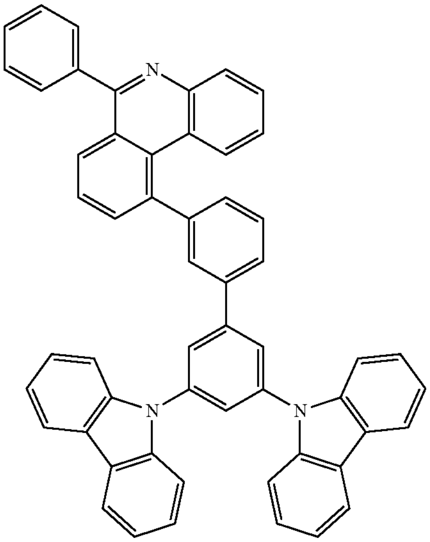
340
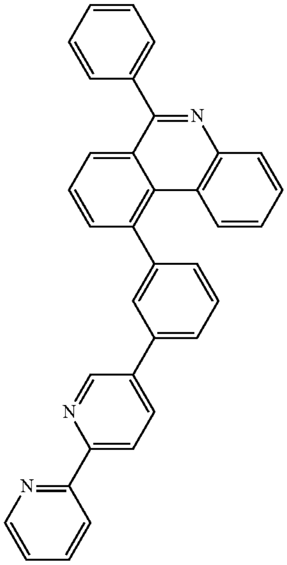
339
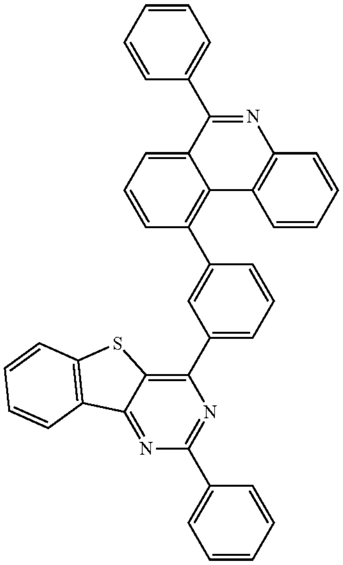
341
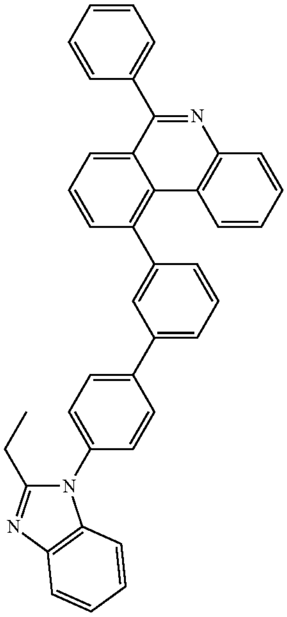

-continued
342
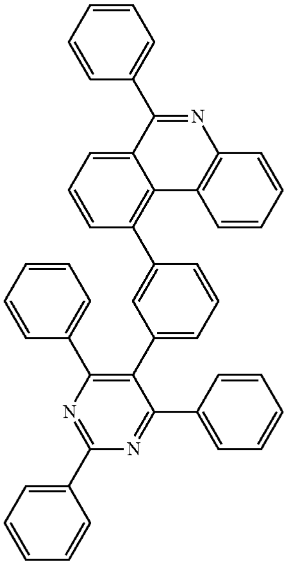
343
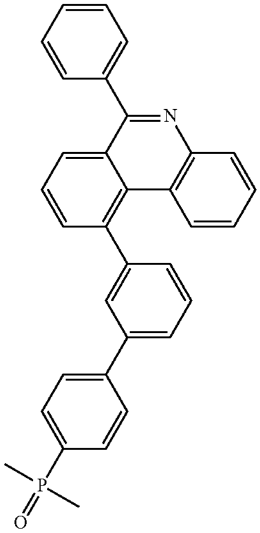
344
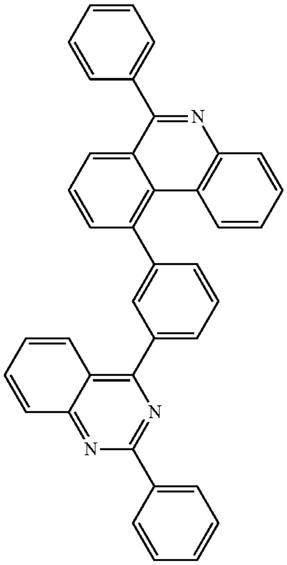
-continued
345
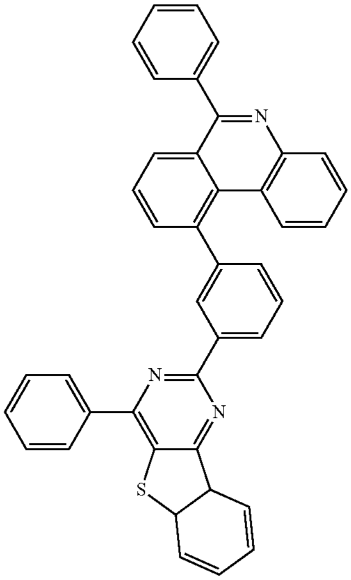
346
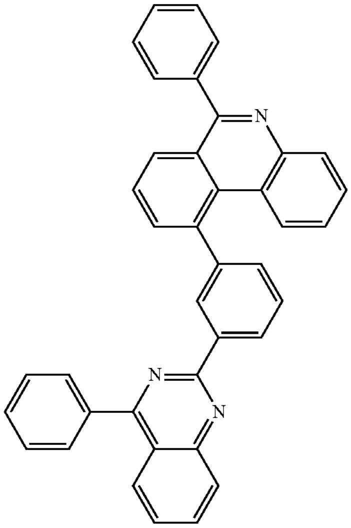

-continued
347
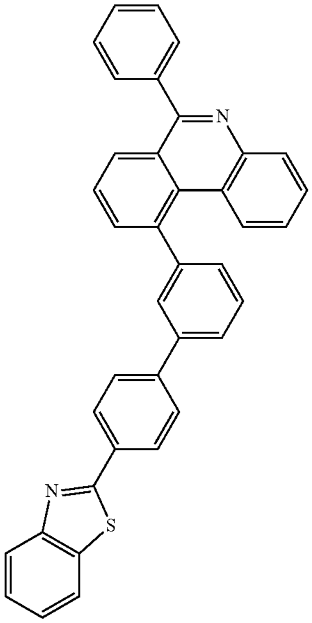
348
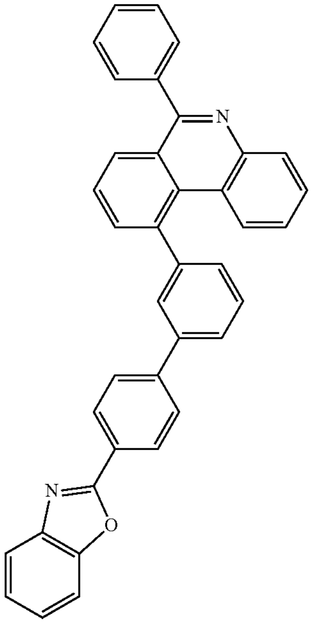
-continued
349
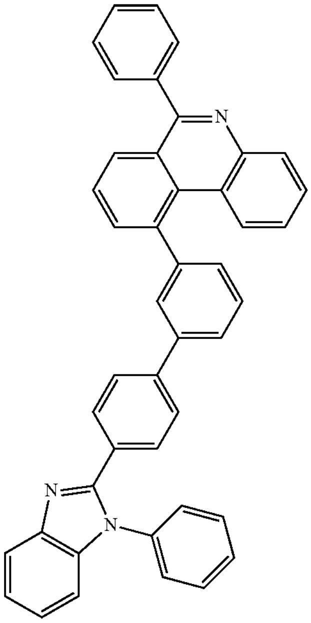
350
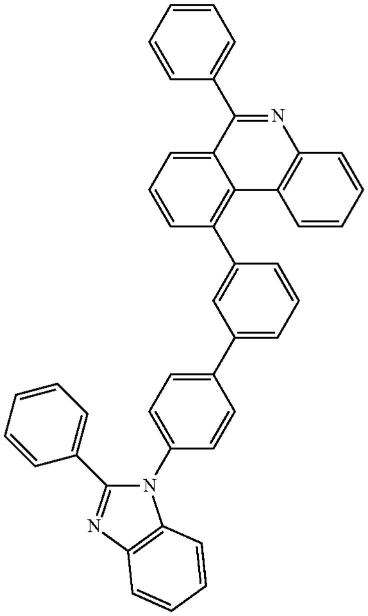

351
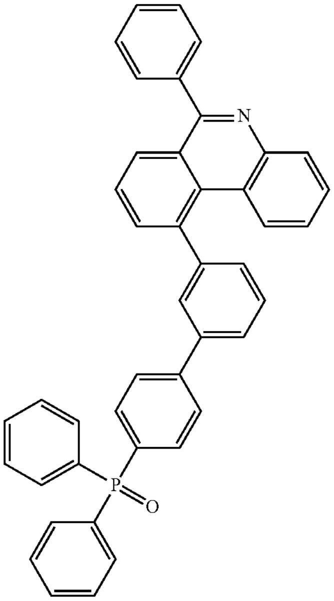
352
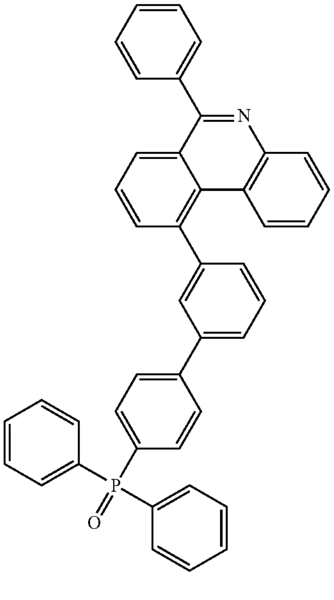
353
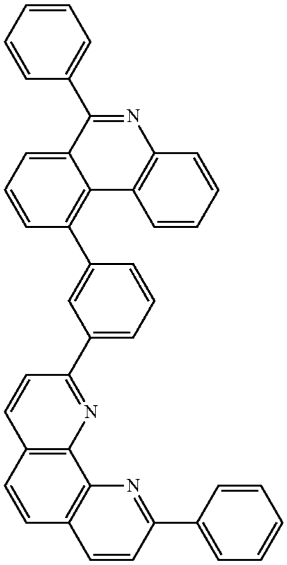
354
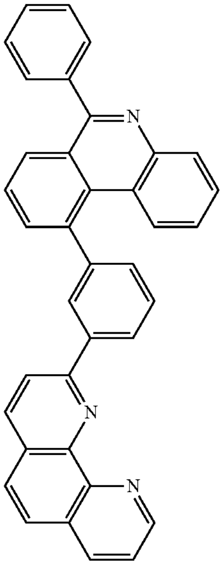
355
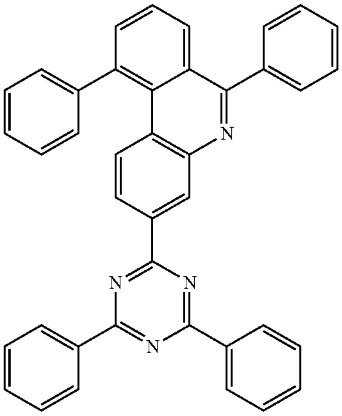

-continued
356
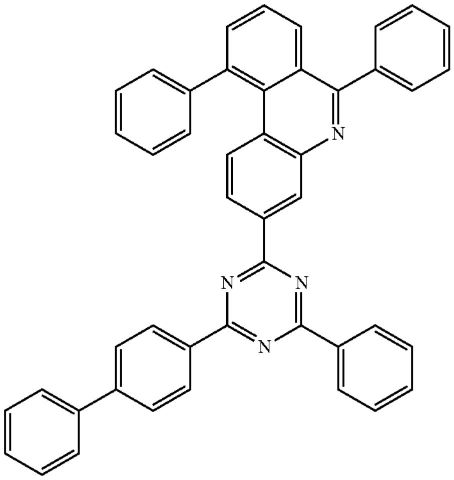
357
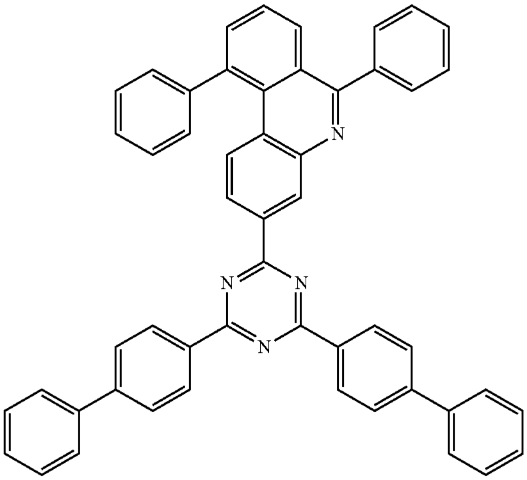
358
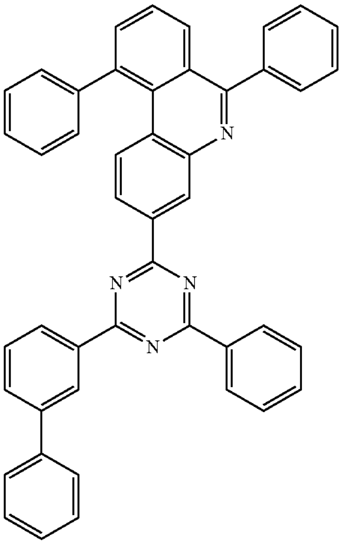
-continued
359
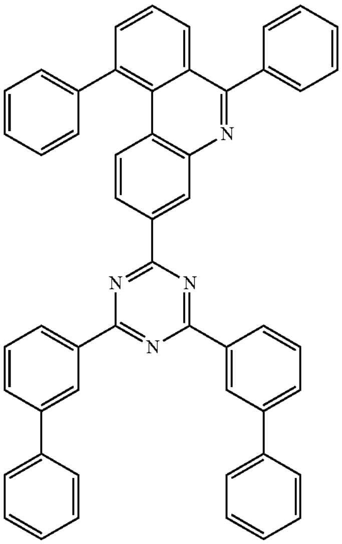
360
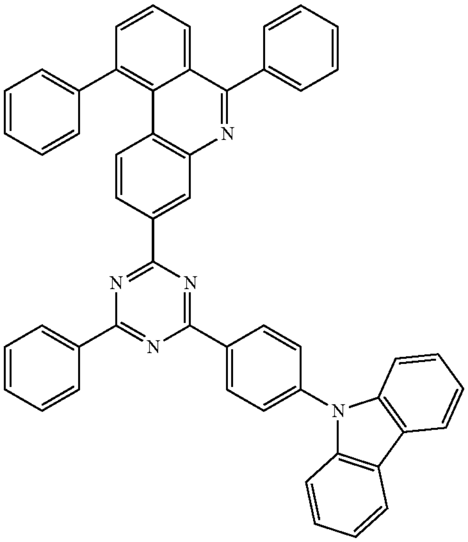
361
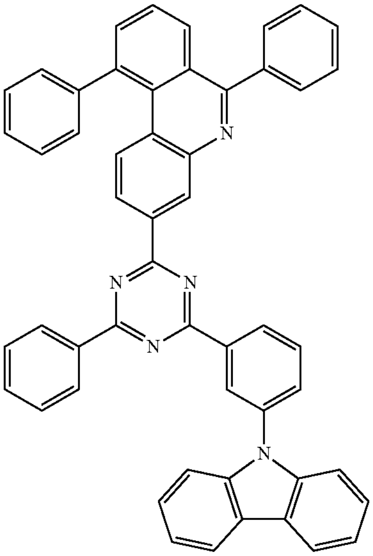

-continued
362
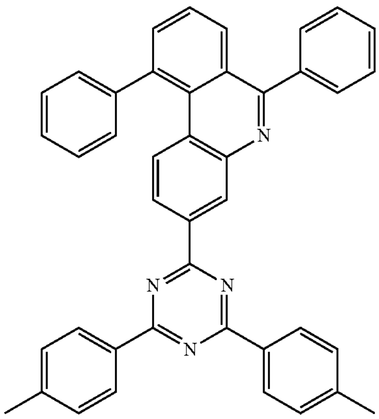
363
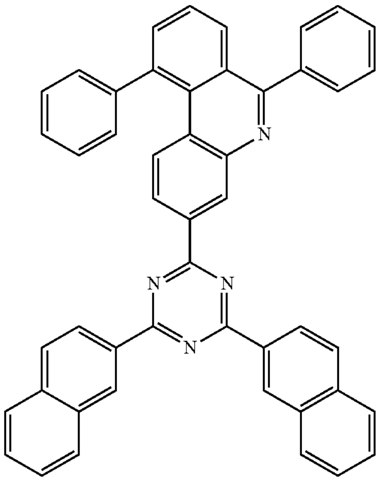
364
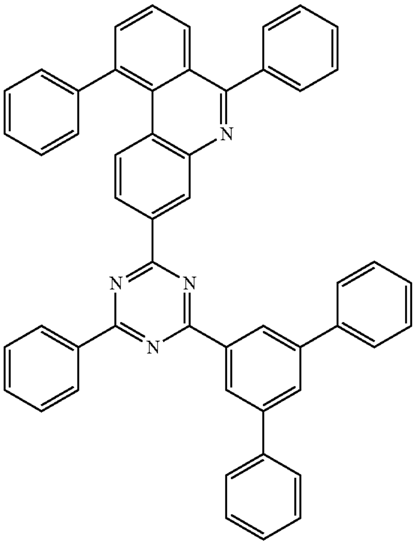
-continued
365
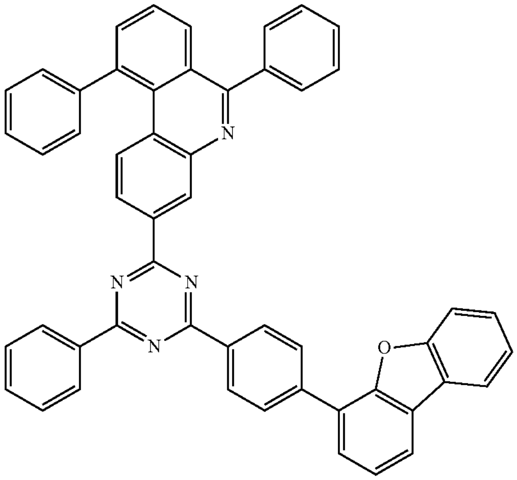
366
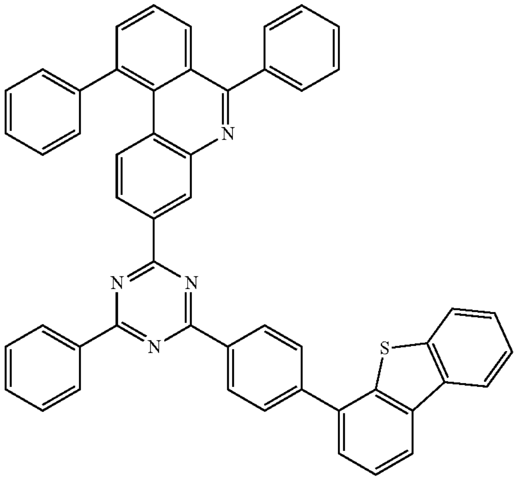
367
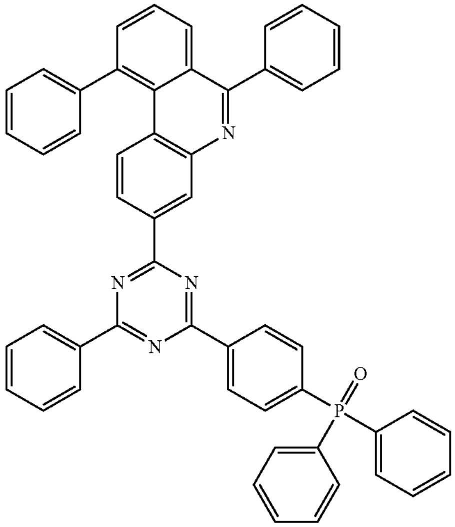

-continued
368
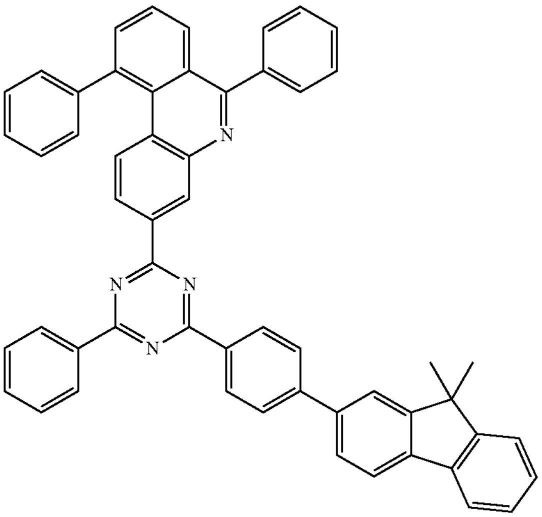
369
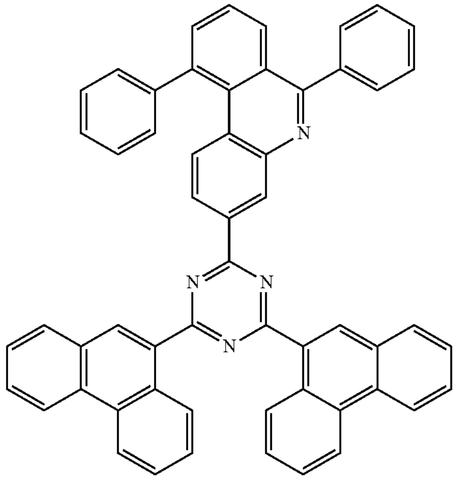
370
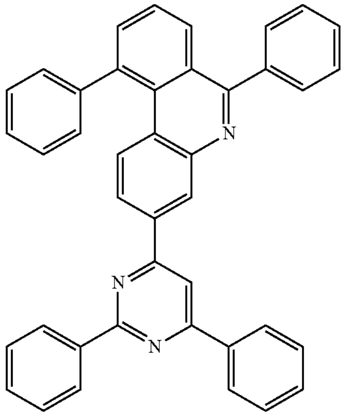
-continued
371
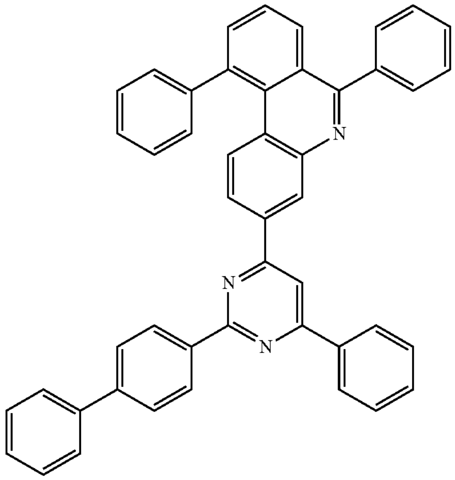
372
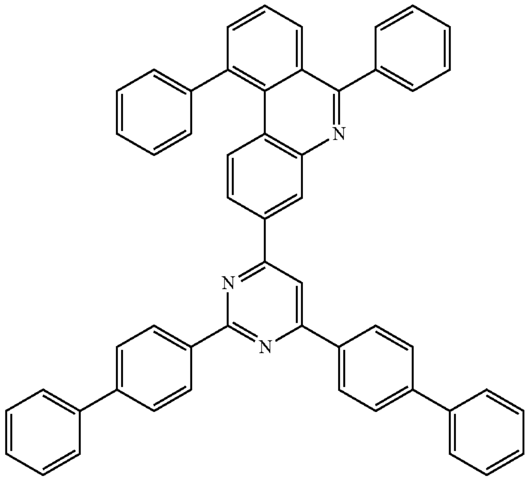
373
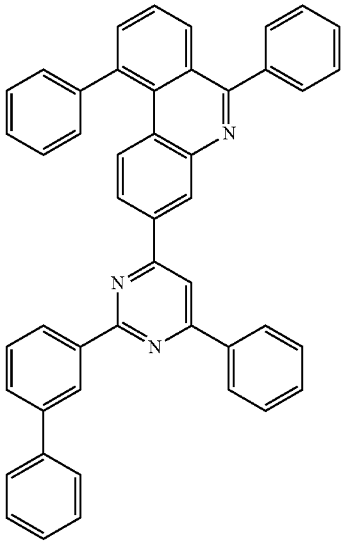

-continued
374
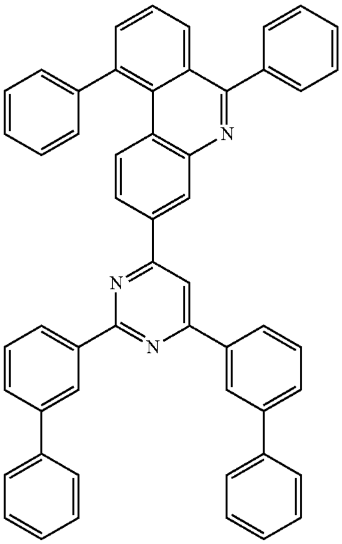
375
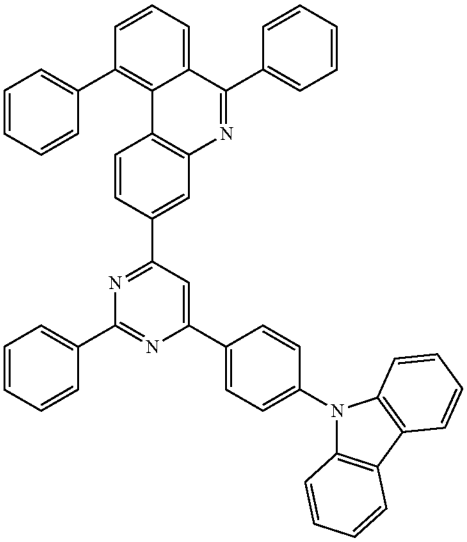
376
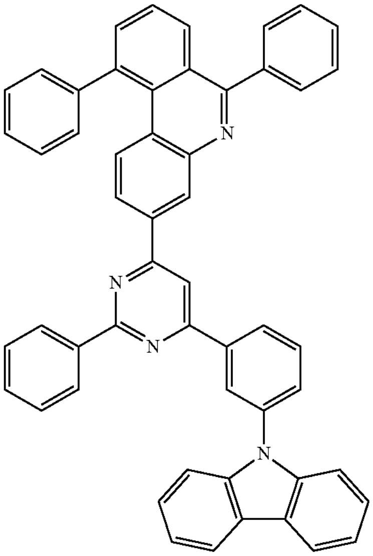
-continued
377
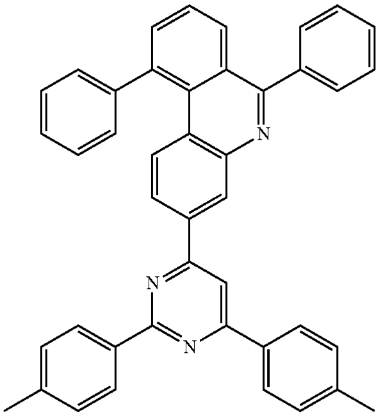
378
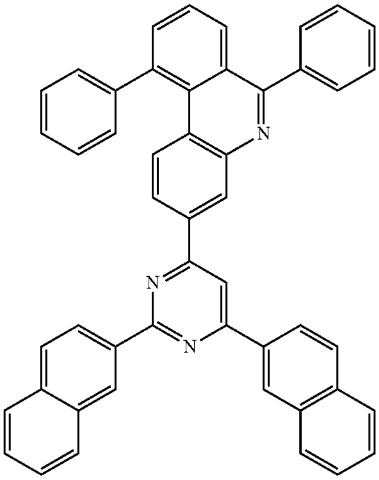
379
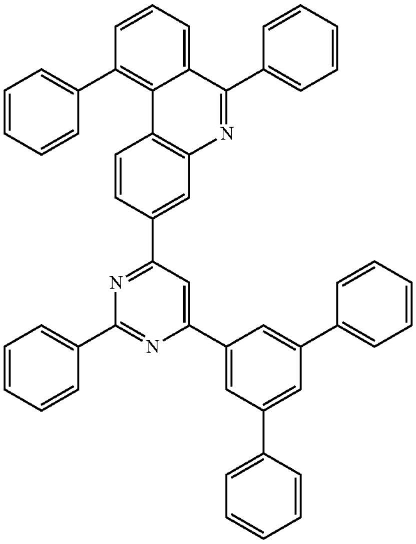

-continued
380
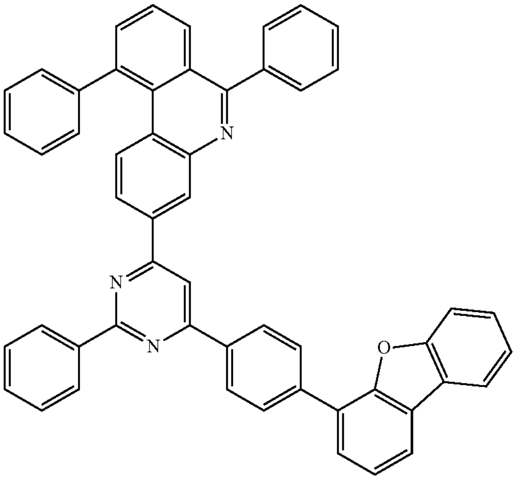
381
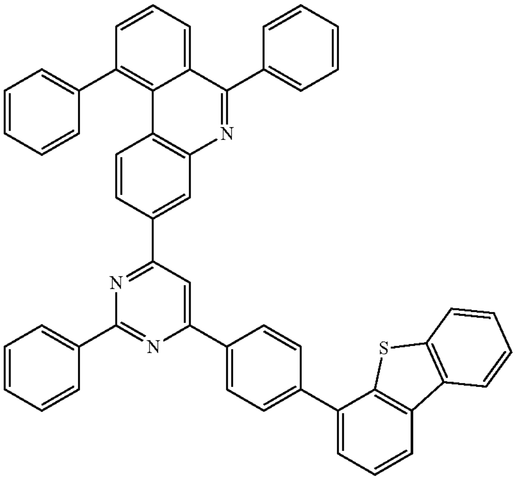
382
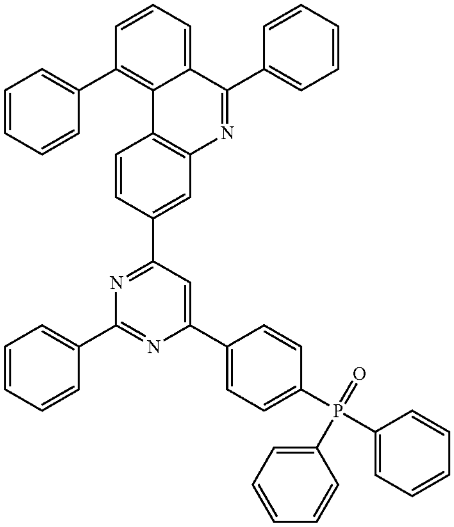
-continued
383
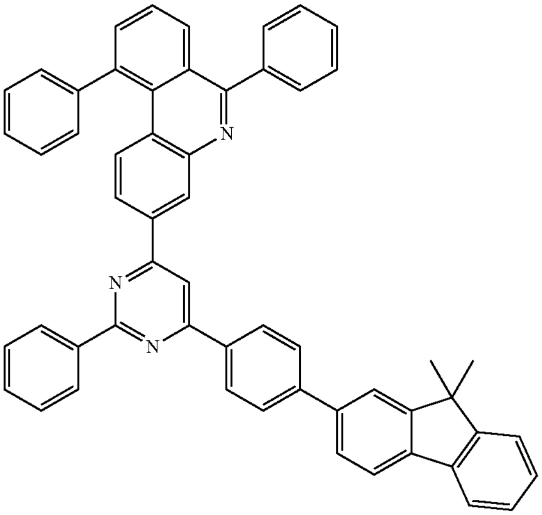
384
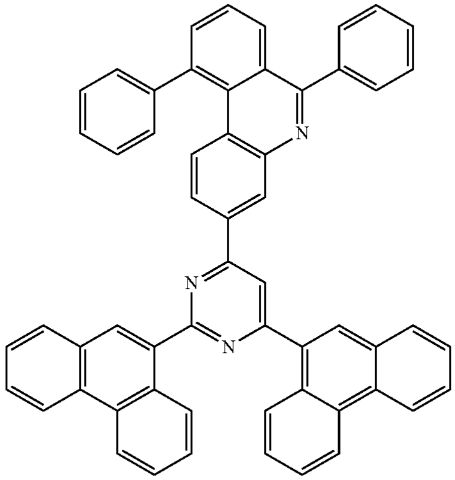
385
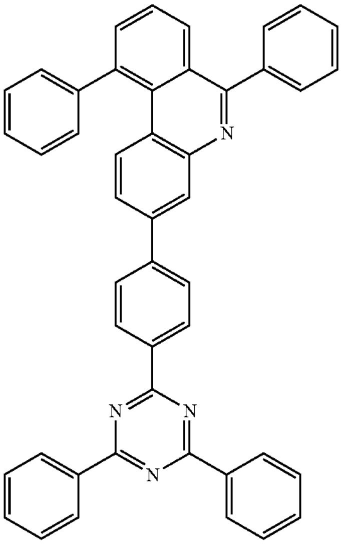

-continued
386
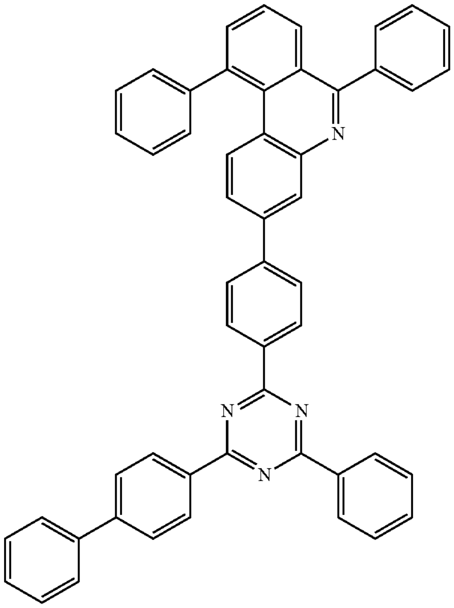
387
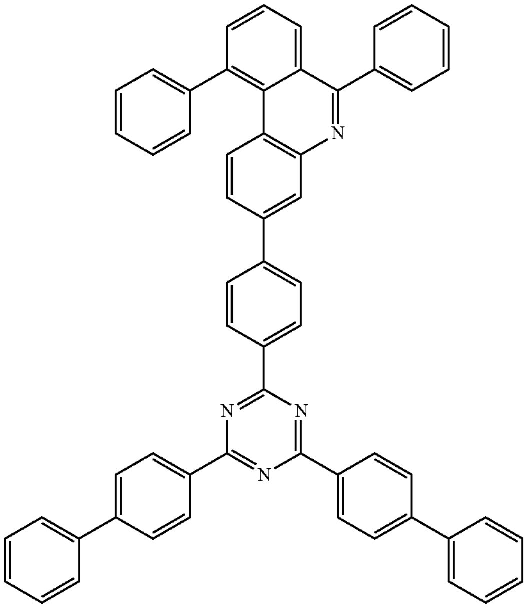
-continued
388
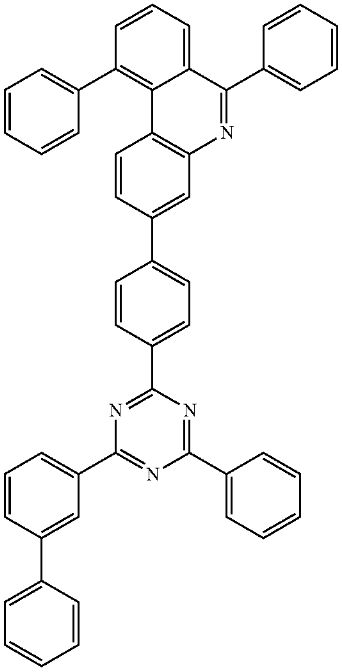
389
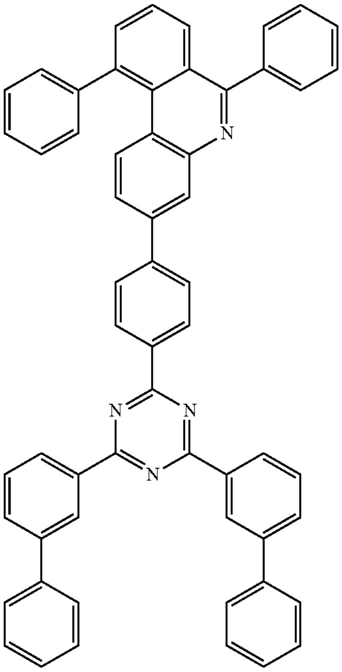

390
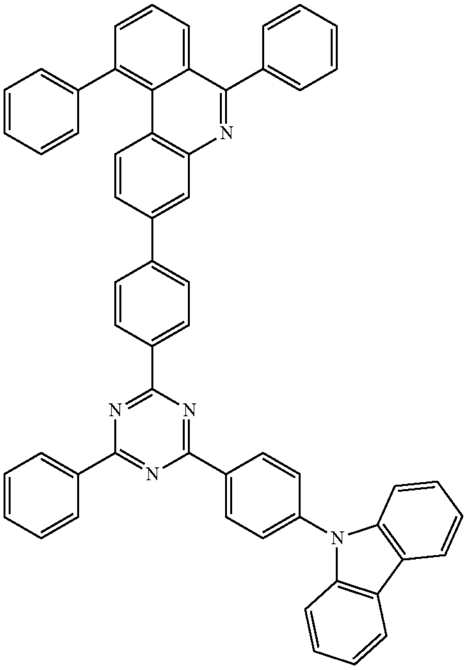
391
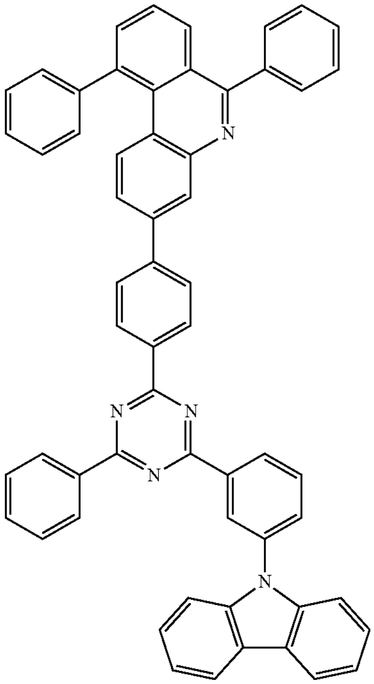
392
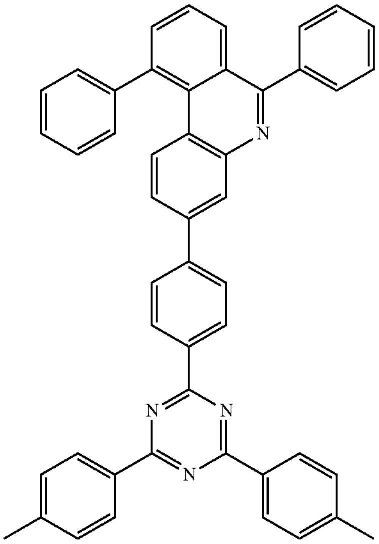
393
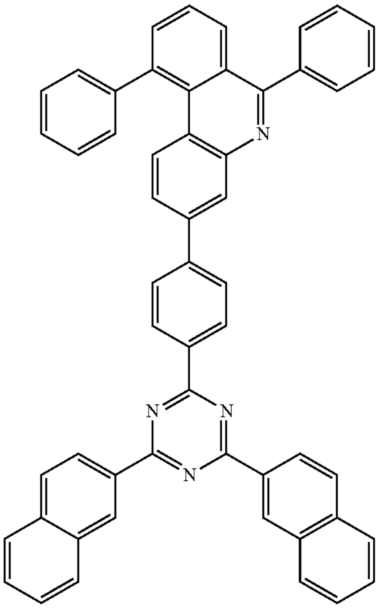

-continued
394
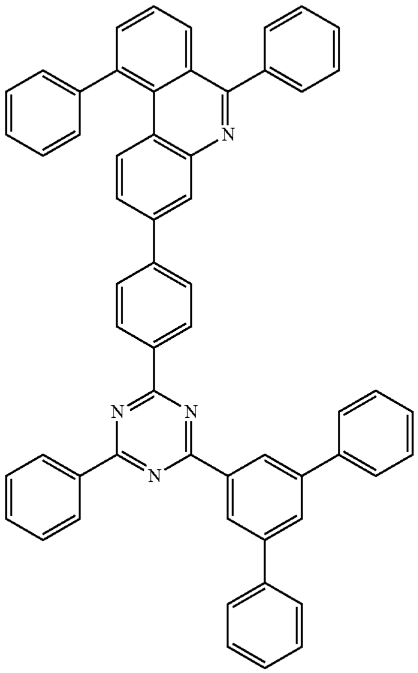
395
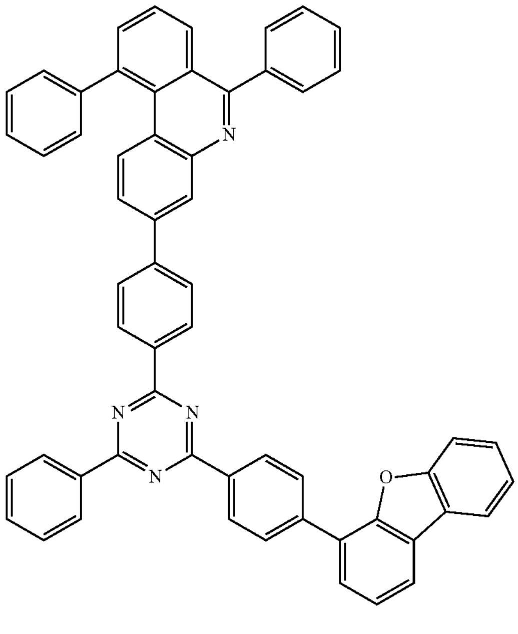
-continued
396
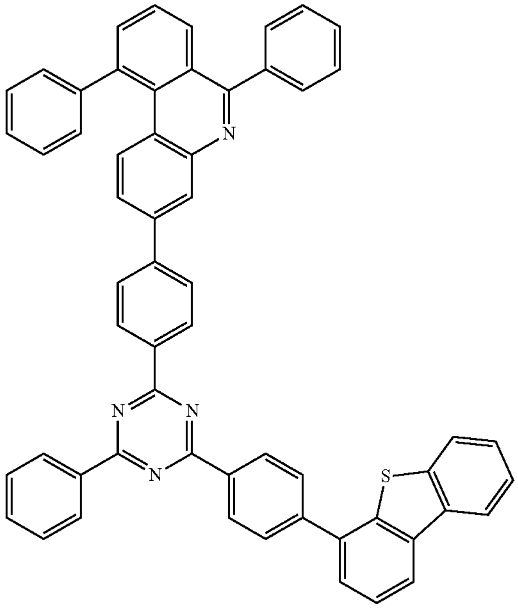
397
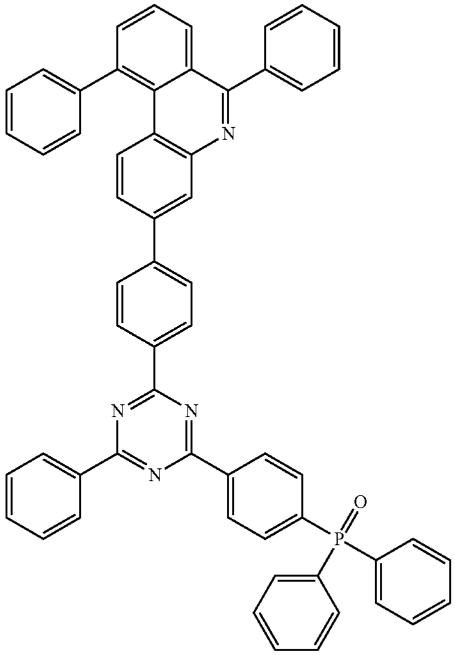

-continued
398
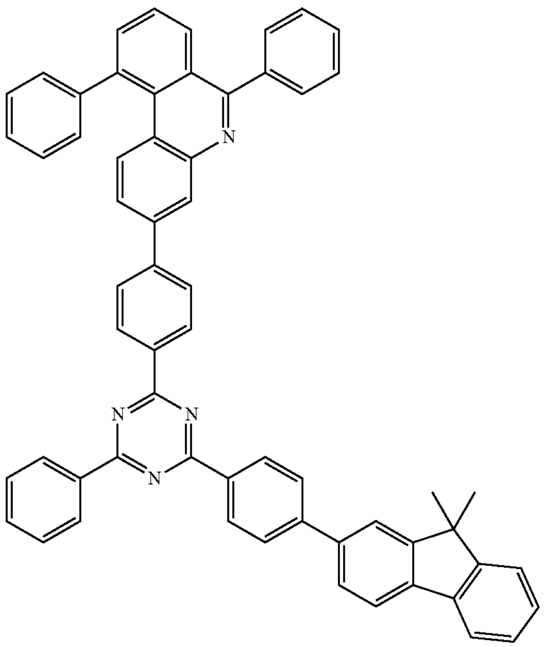
399
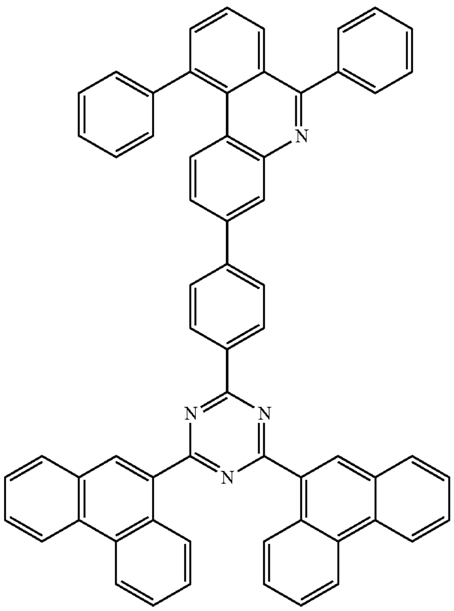
-continued
400
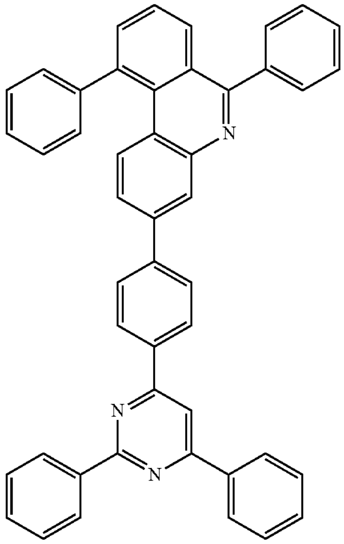
401
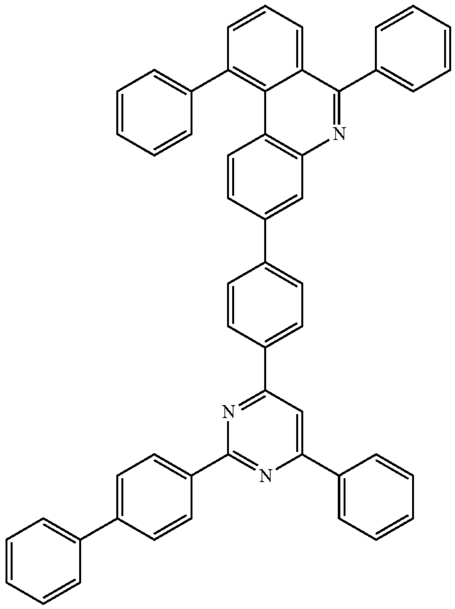

402
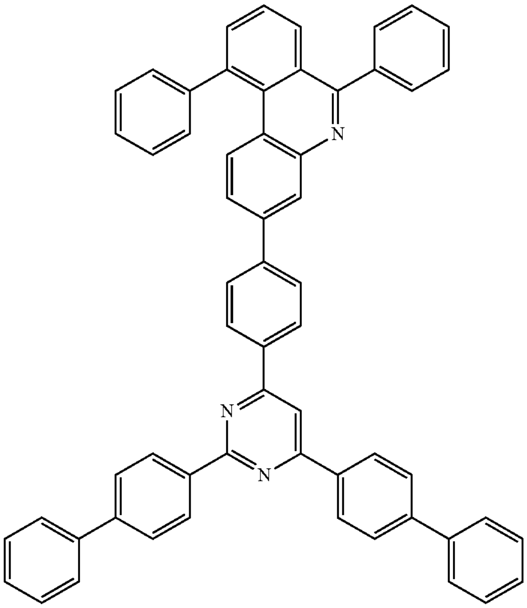
403
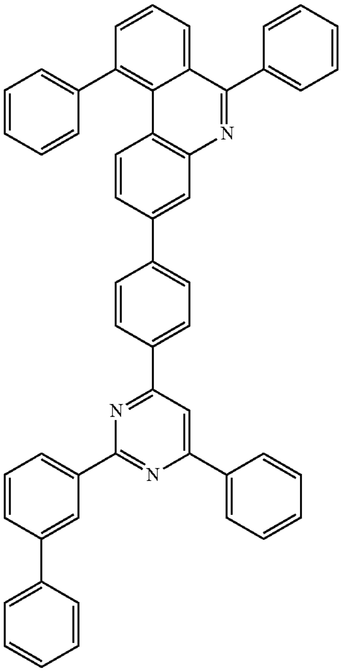
404
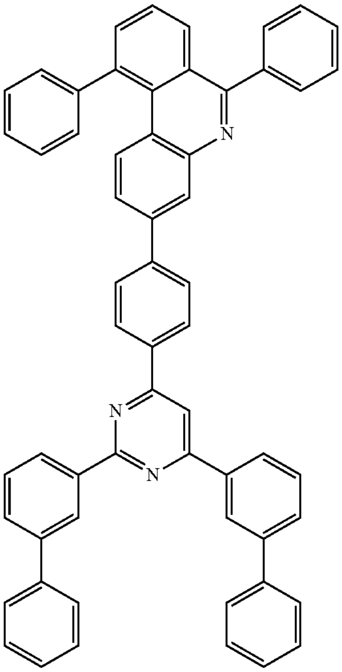
405
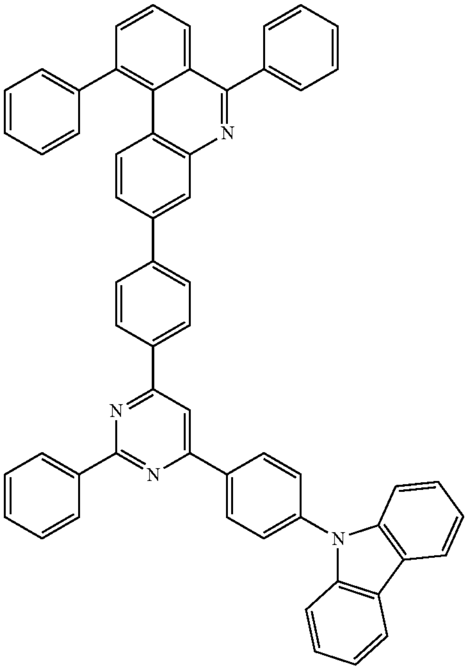

-continued
406
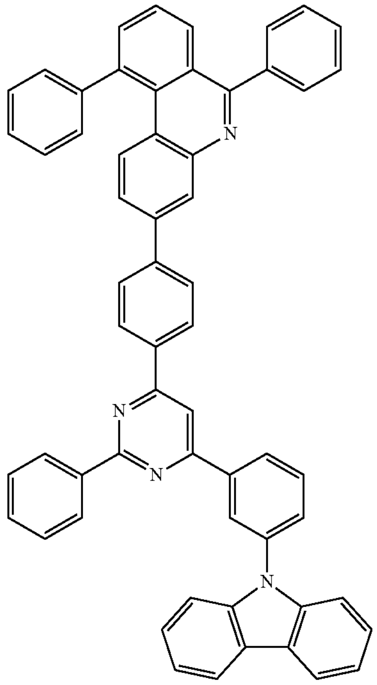
407
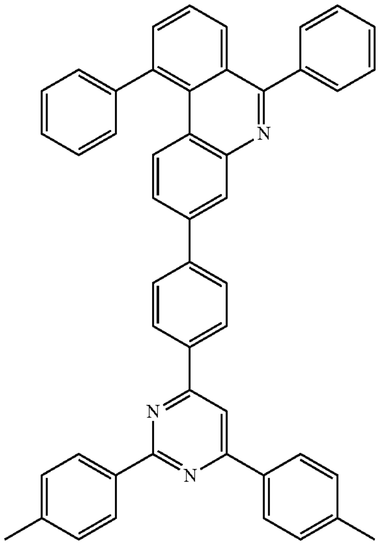
-continued
408
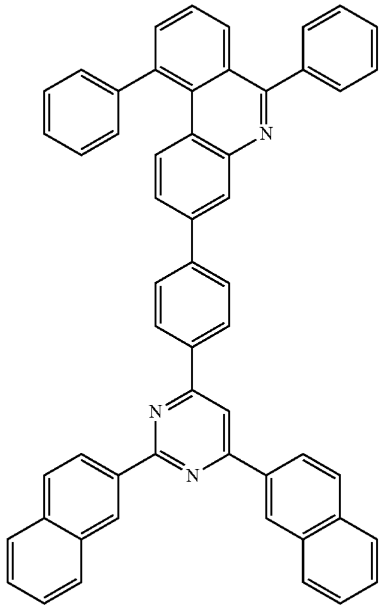
409
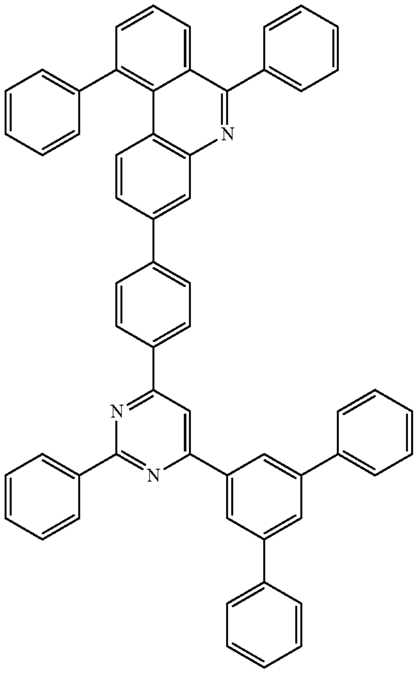

410
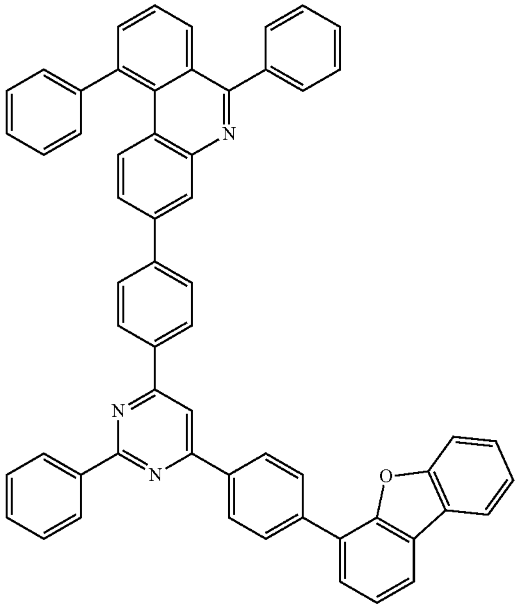
412
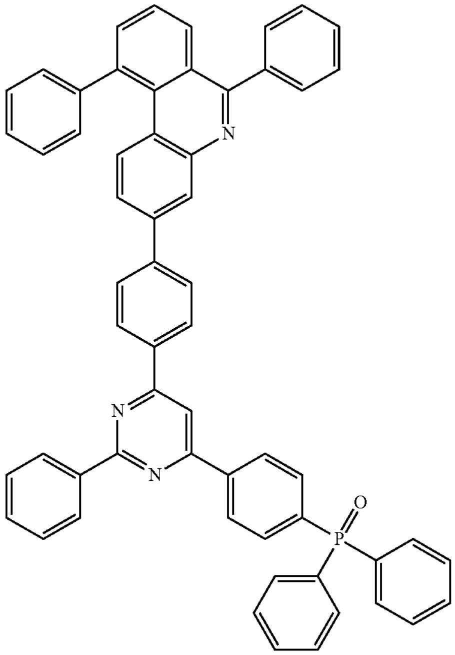
411
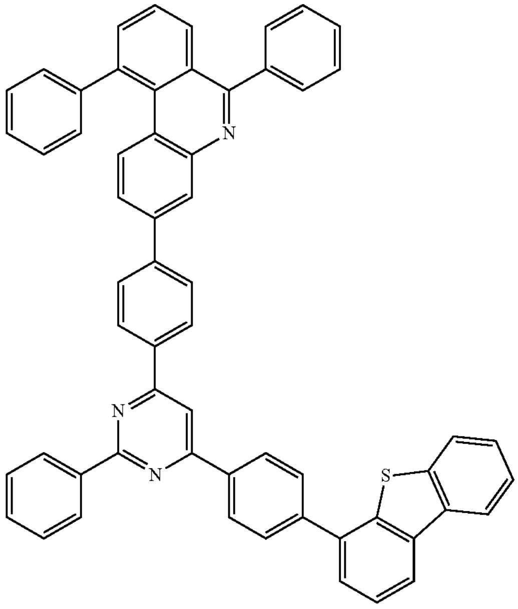
413
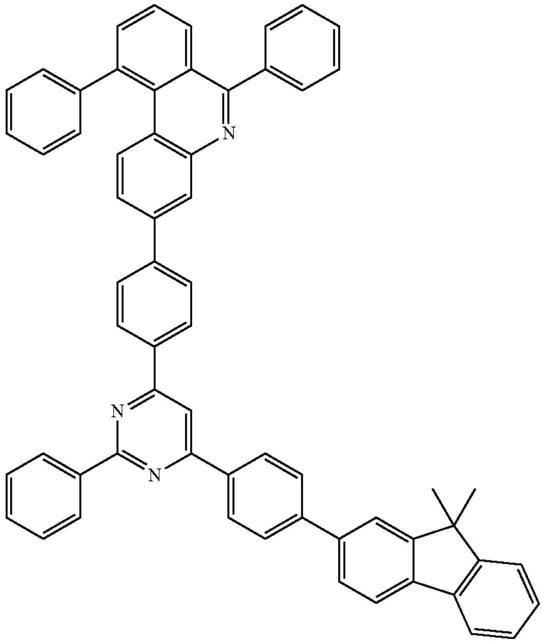

-continued
414
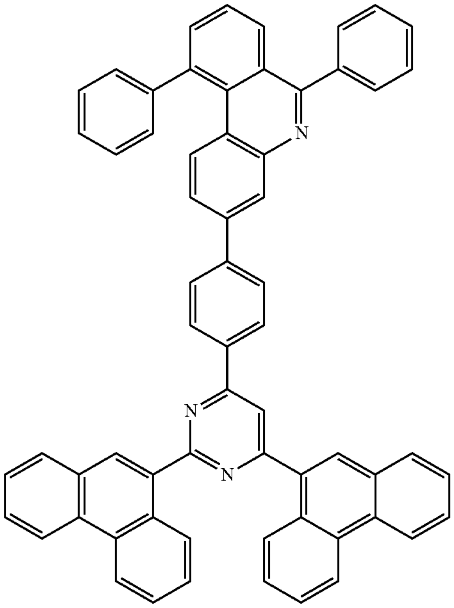
415
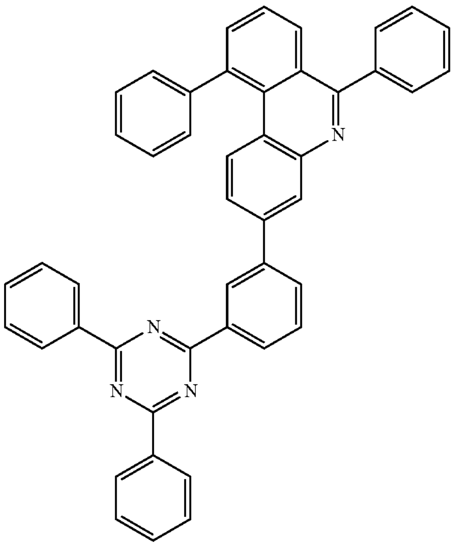
-continued
416
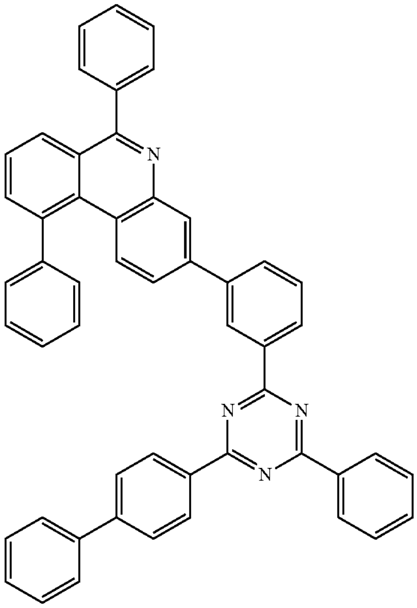
417
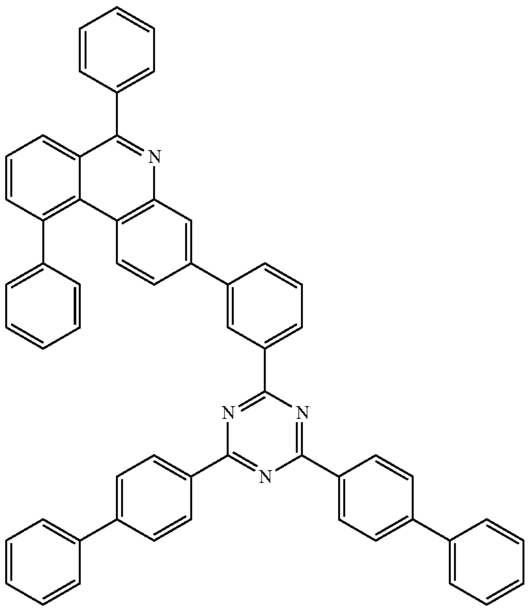

-continued
418
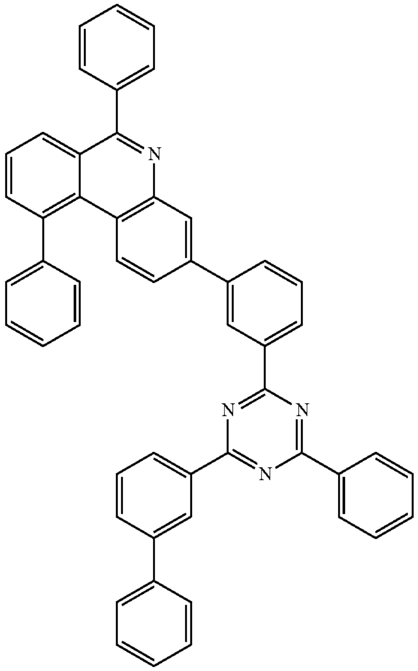
419
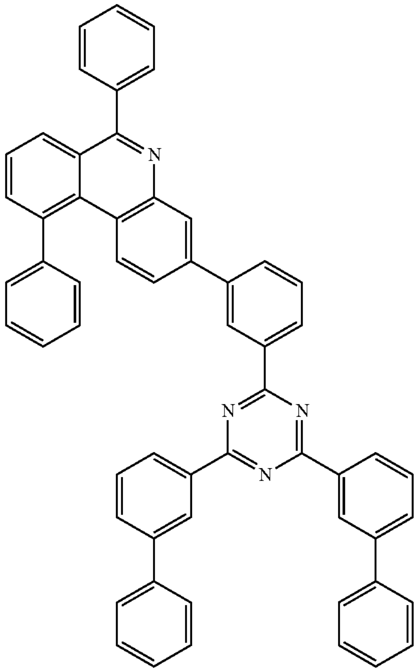
-continued
420
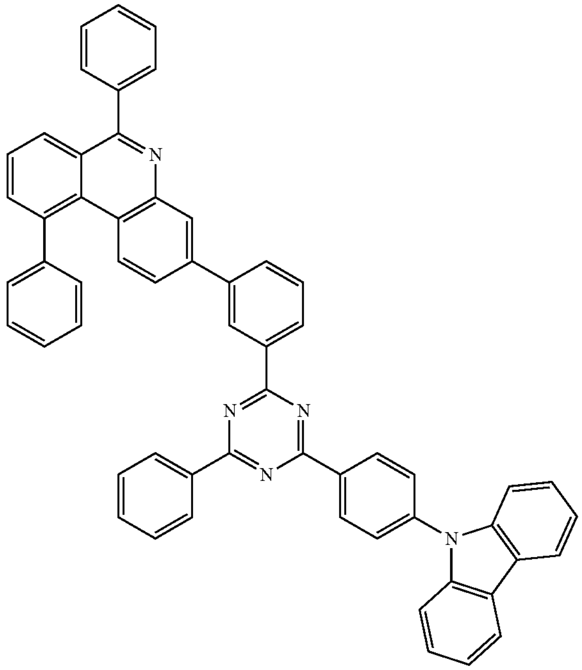
421
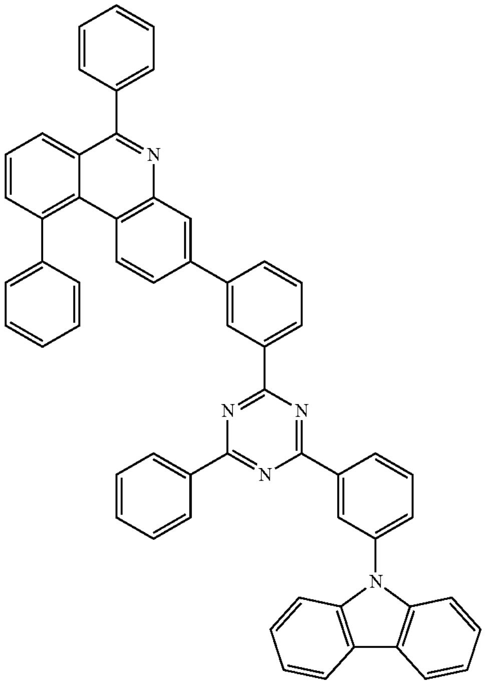

-continued
422
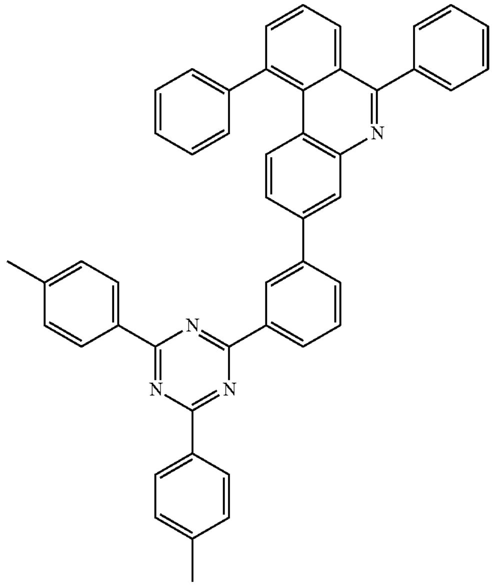
423
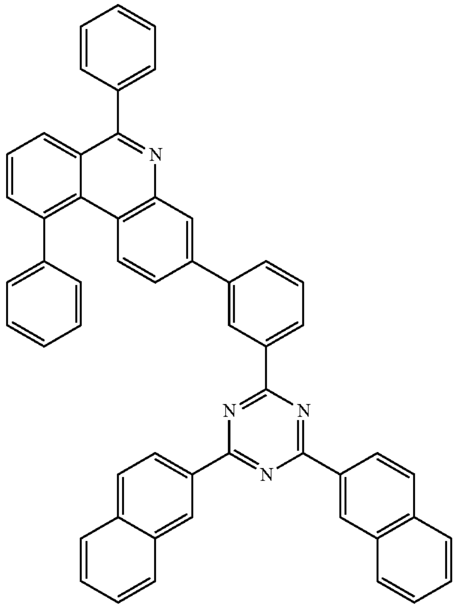
-continued
424
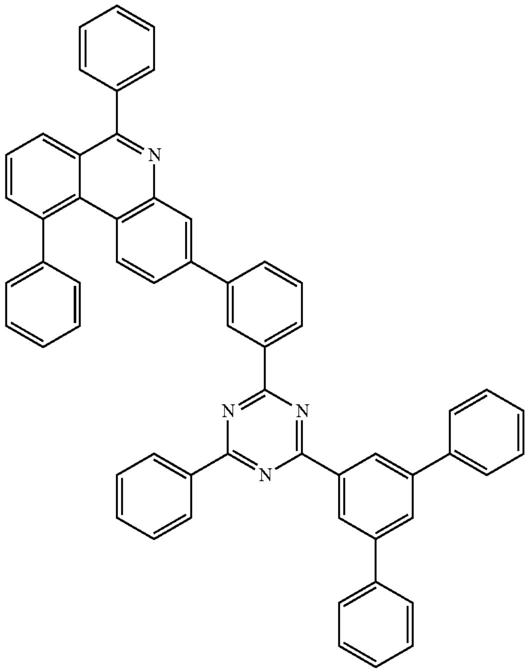
425
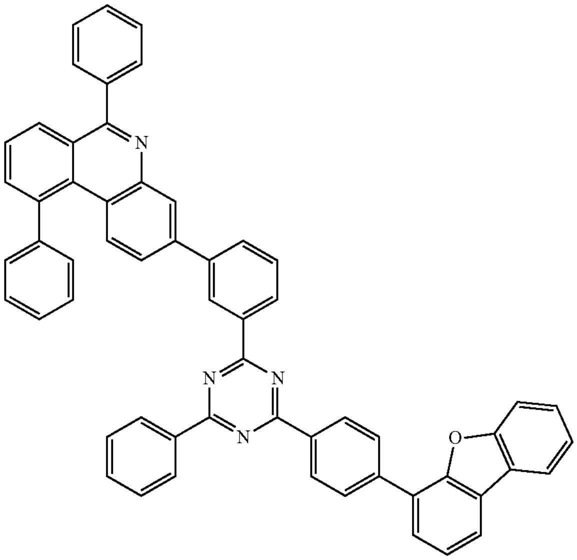

-continued
426
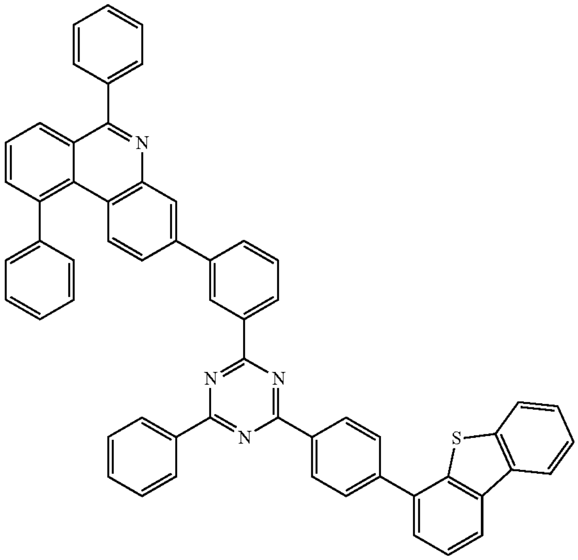
427
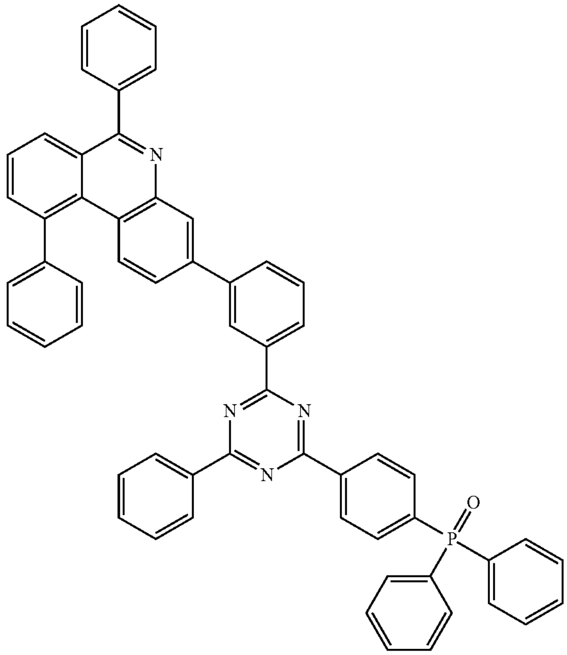
-continued
428
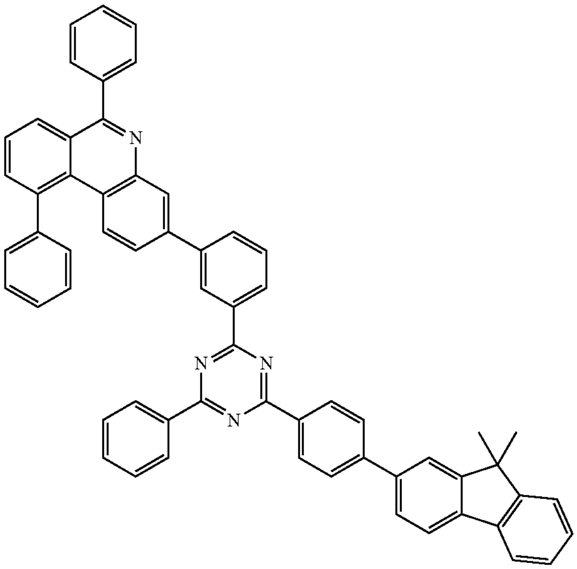
429
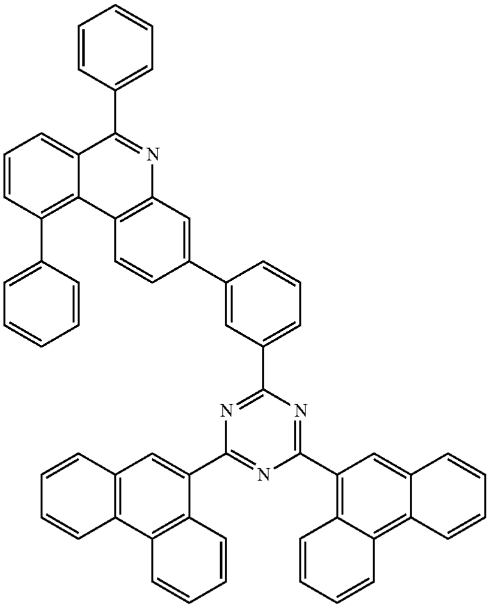

430
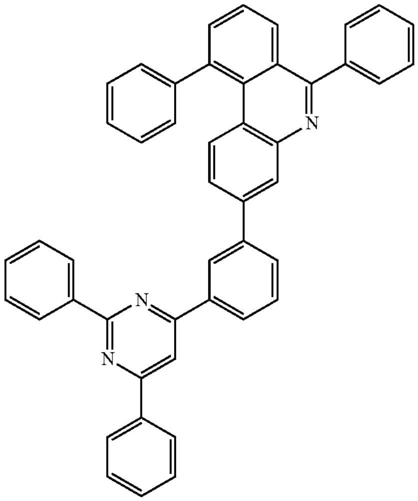
431
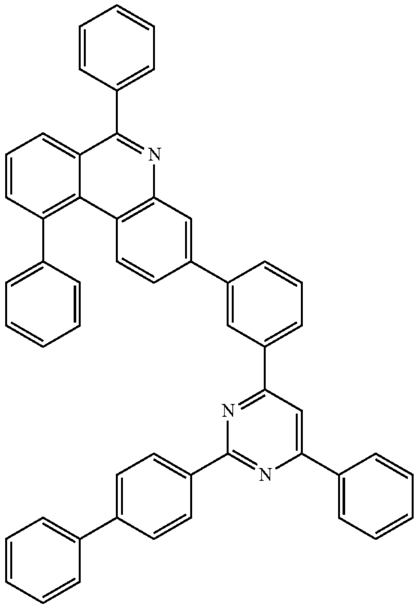
432
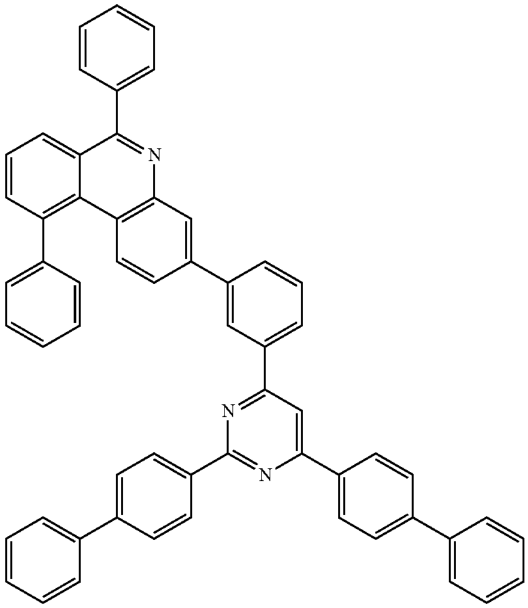
433
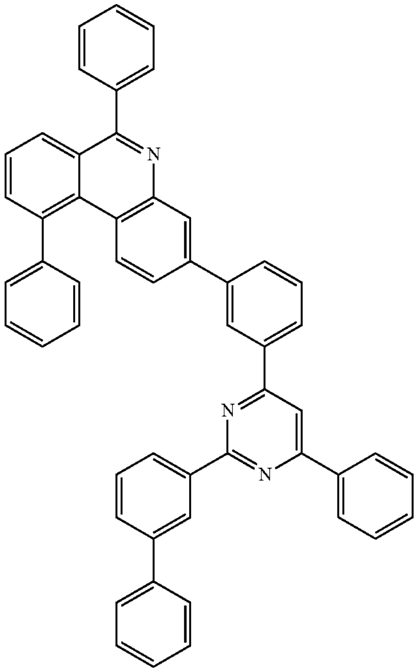

-continued
434
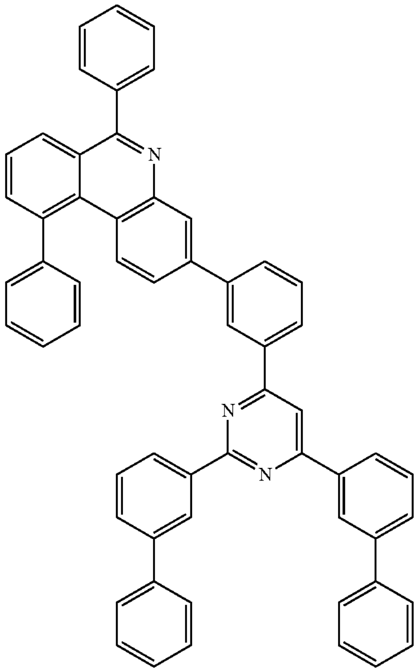
435
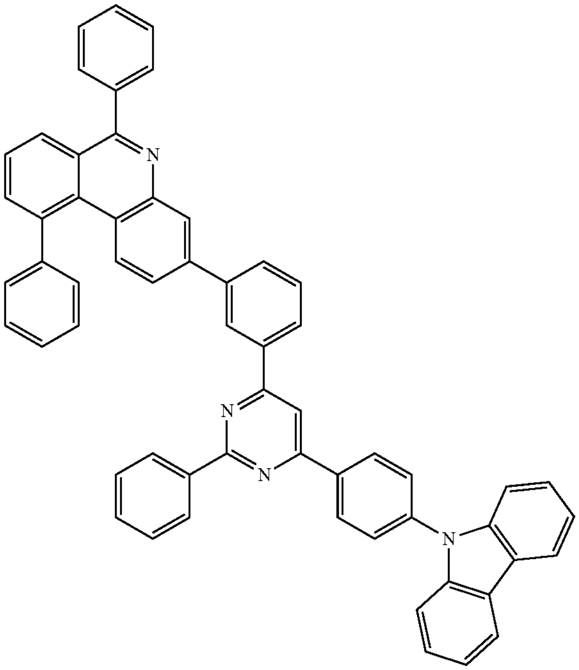
-continued
436
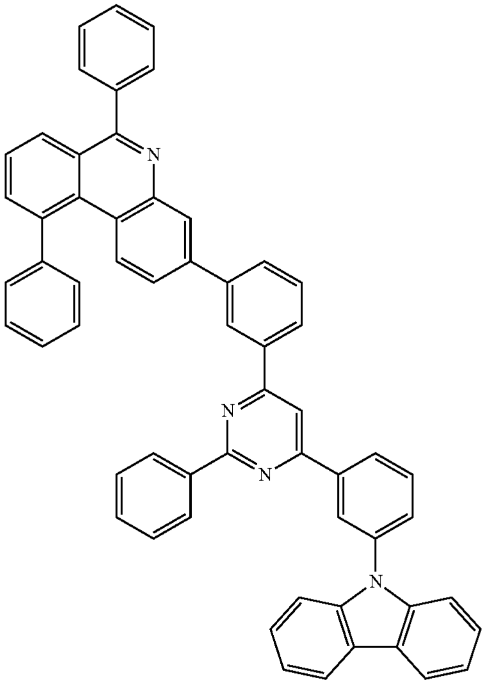
437
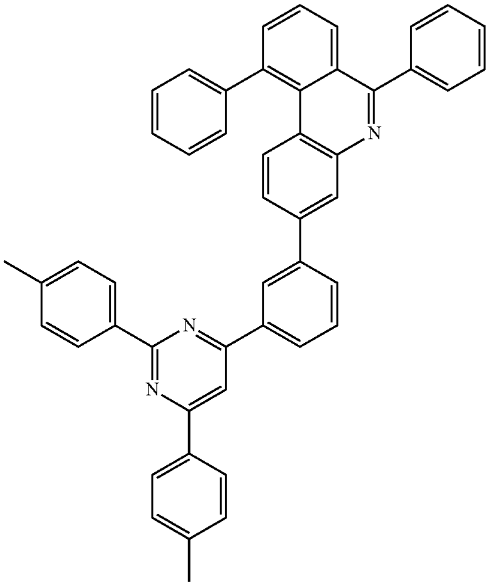

-continued
438
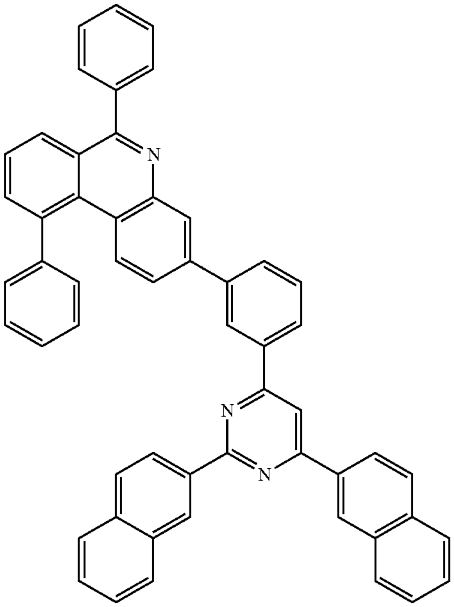
439
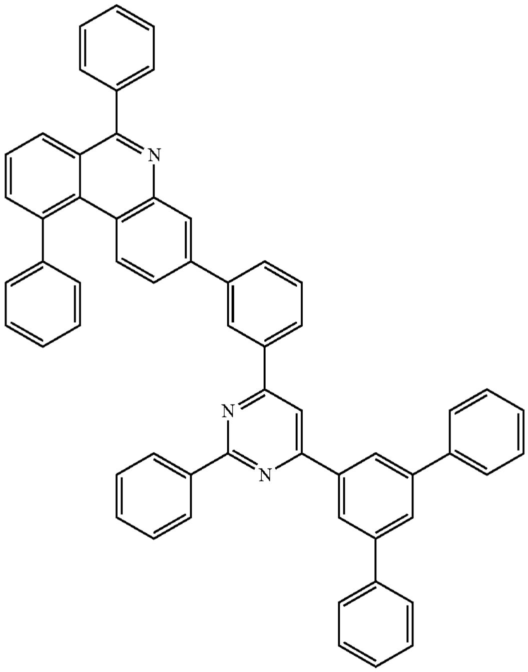
-continued
440
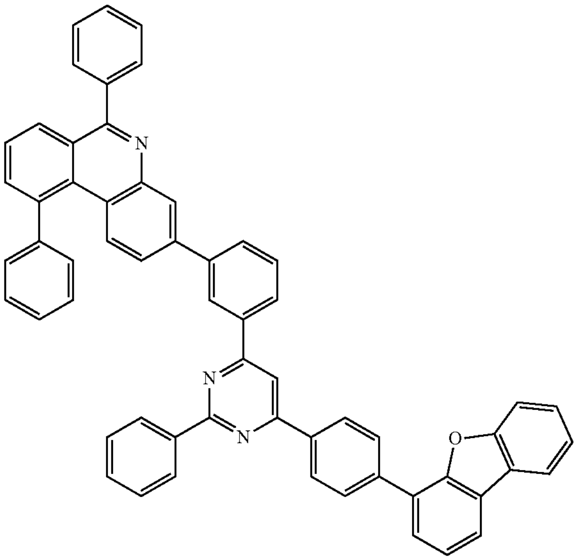
441
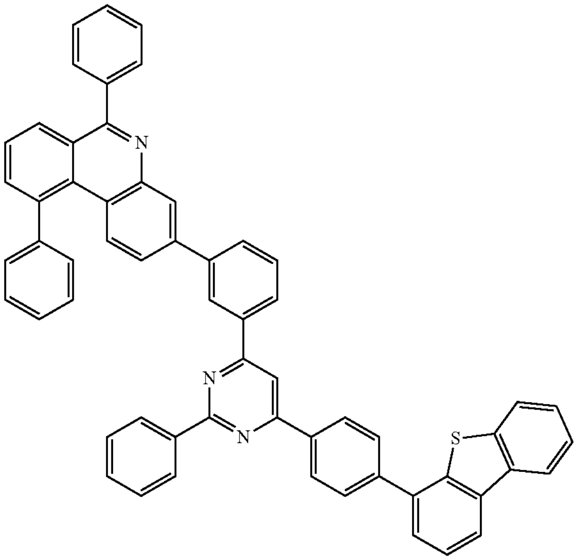

-continued
442
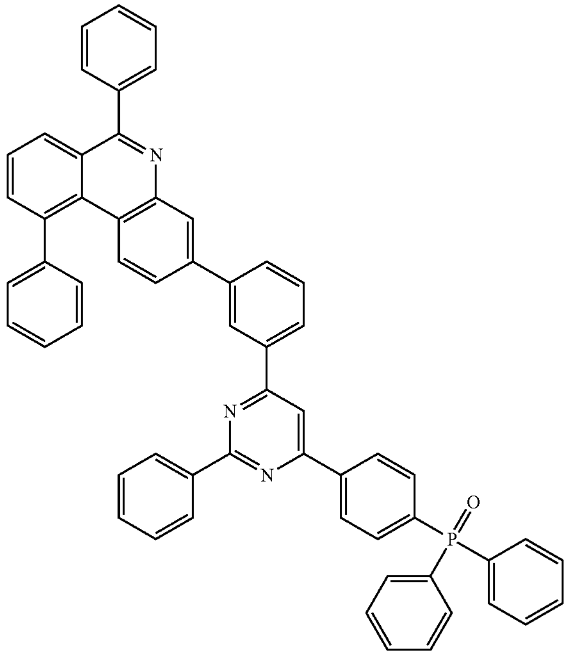
443
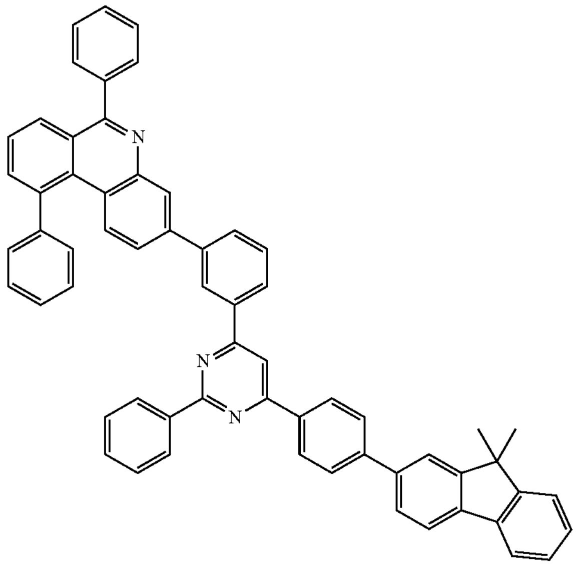
-continued
444
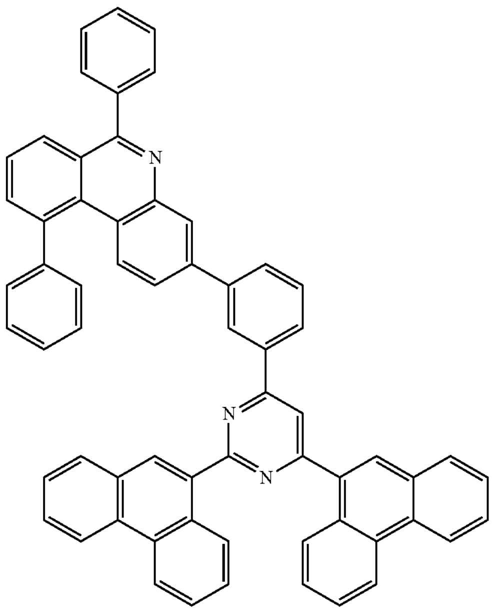
445
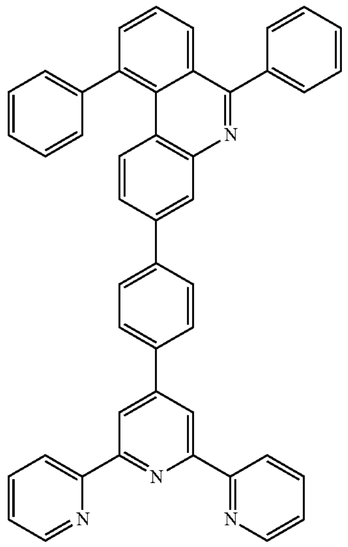
446
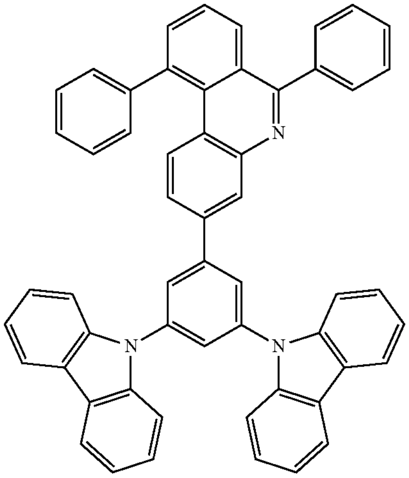

447
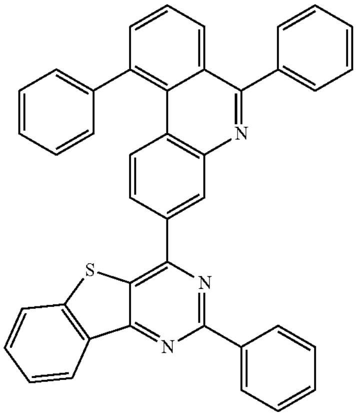
448
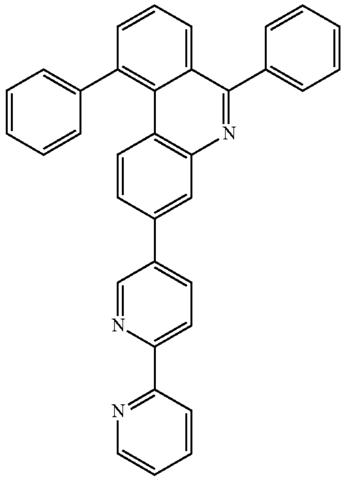
449
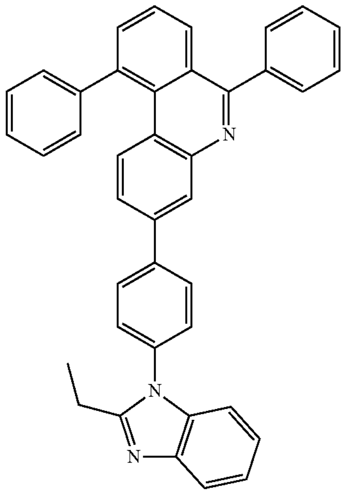
450
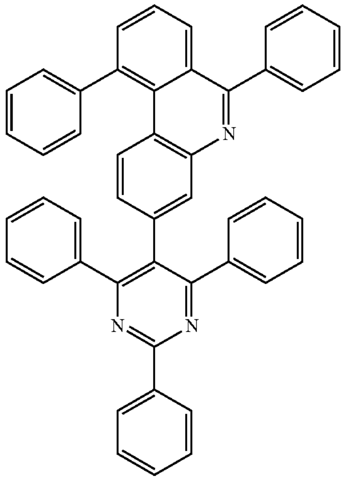
451
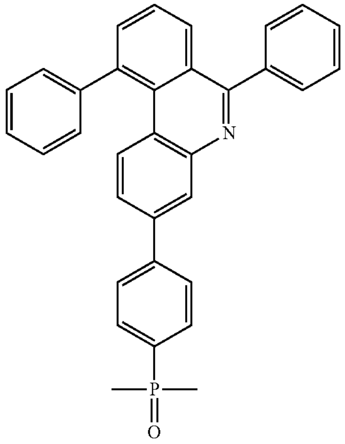
452
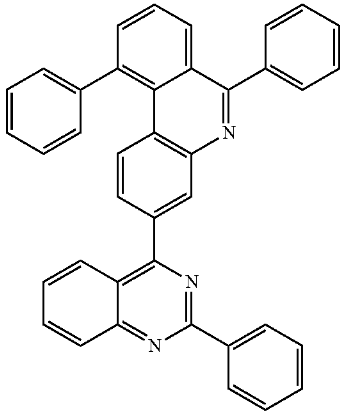

-continued
453
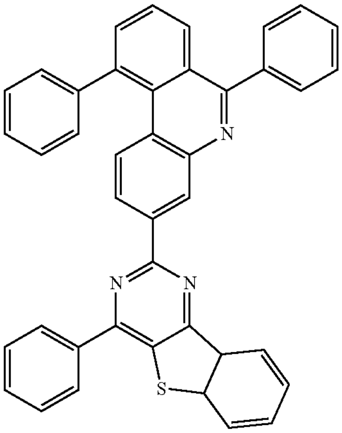
454
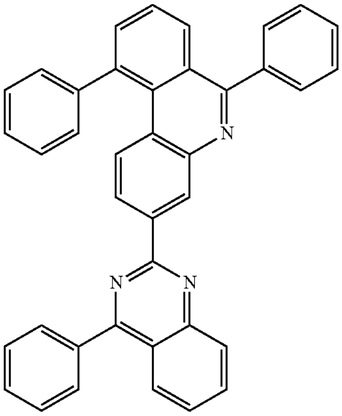
455
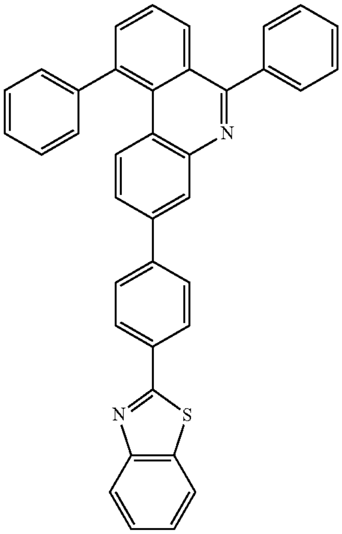
-continued
456
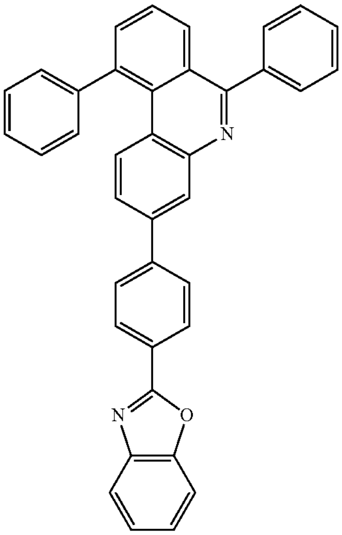
457
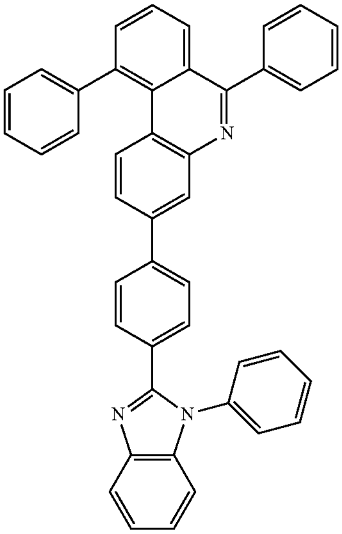
458
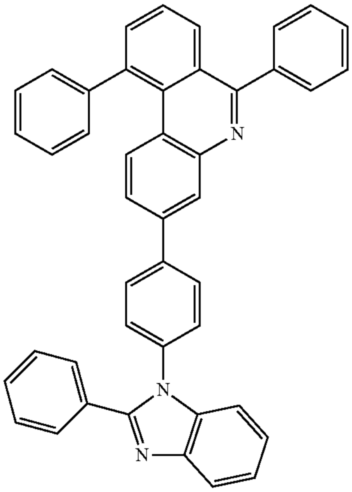

459
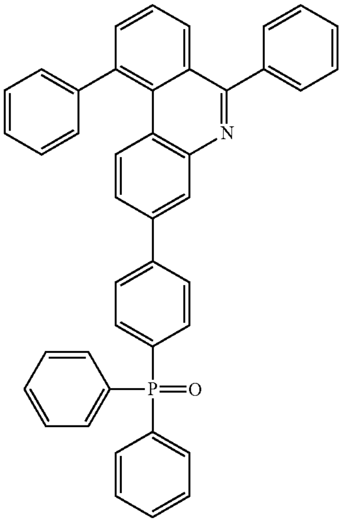
460
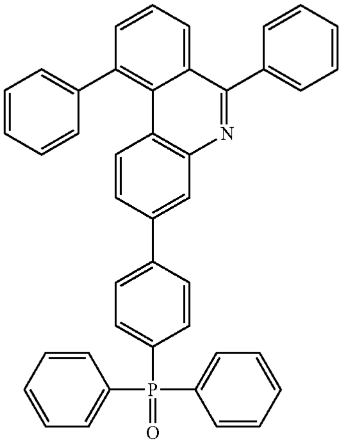
461
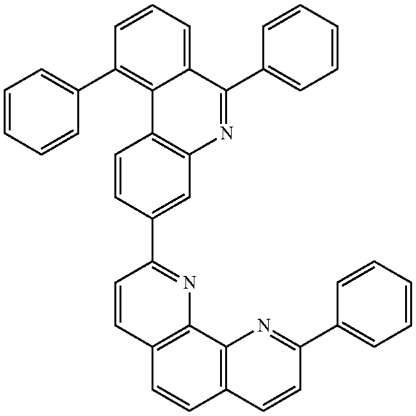
462
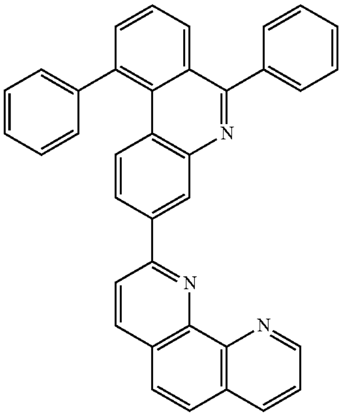
463
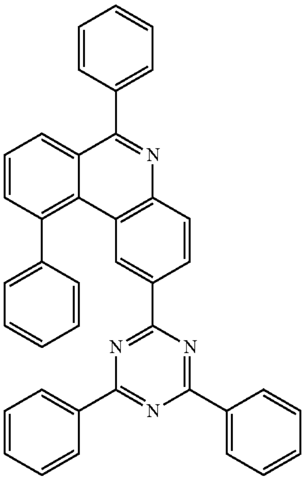
464
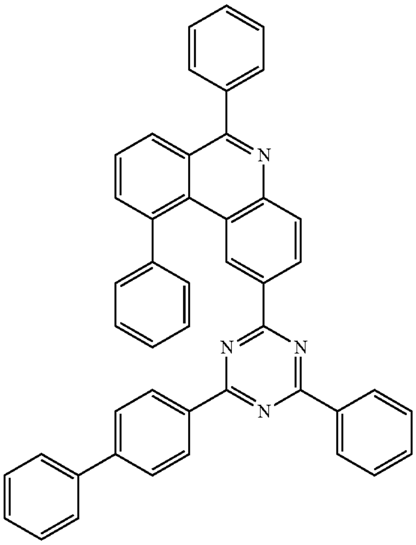

-continued
465
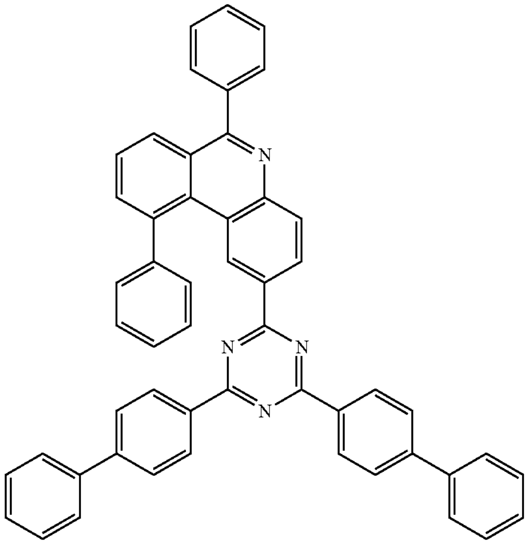
466
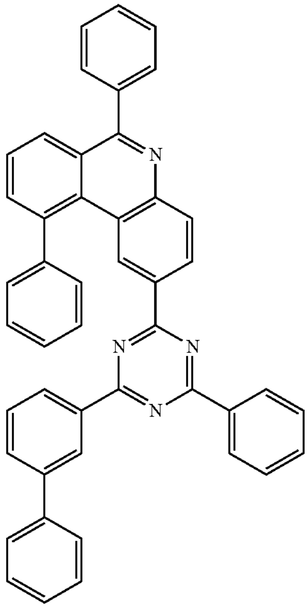
-continued
467
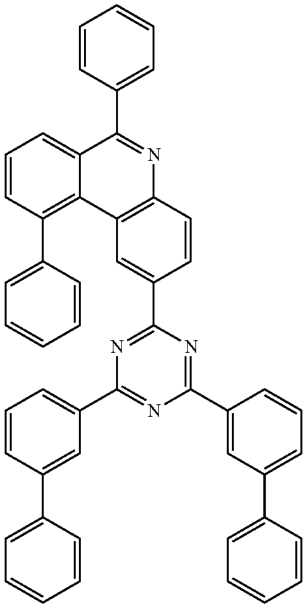
468
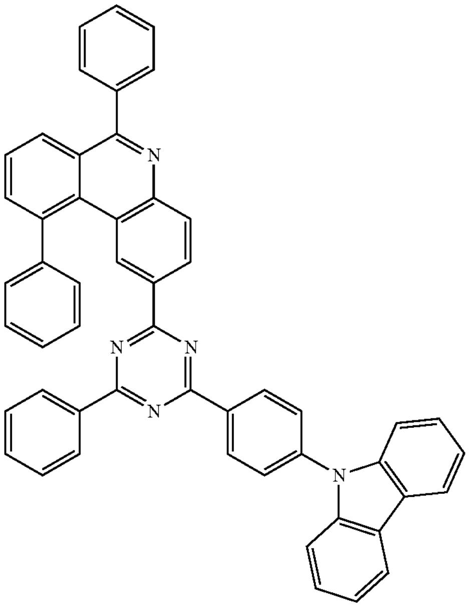

-continued
469
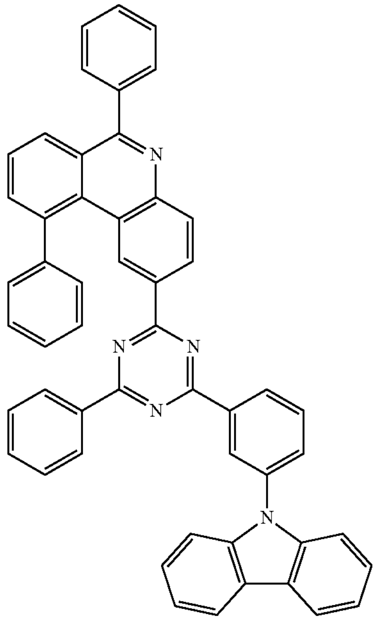
470
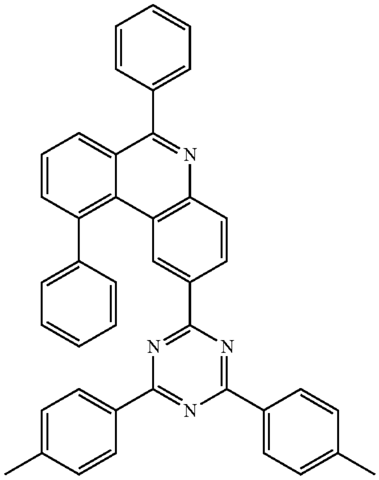
471
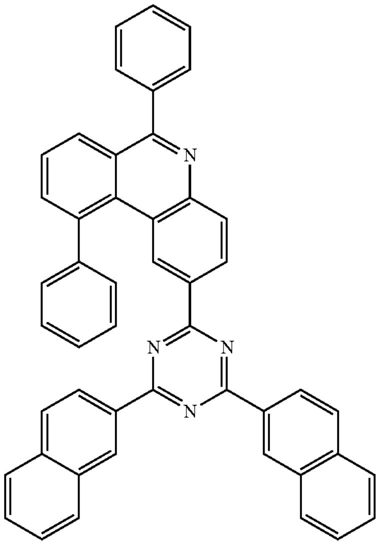
-continued
472
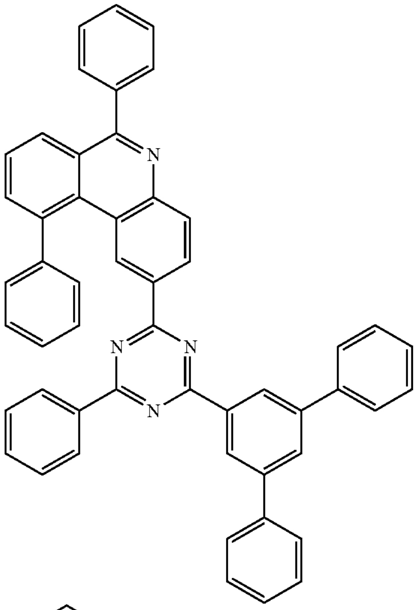
473
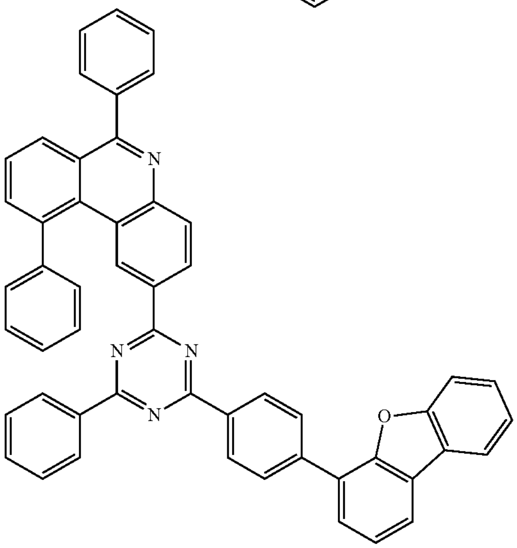
474
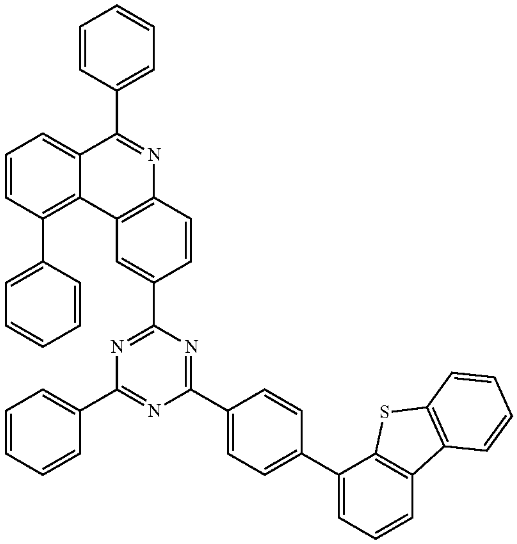

475
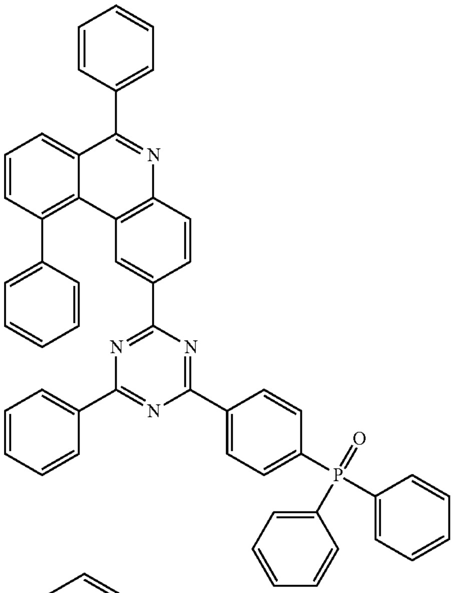
476
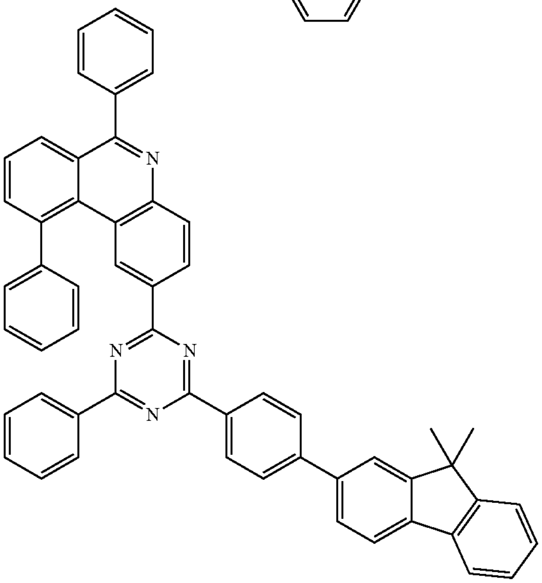
477
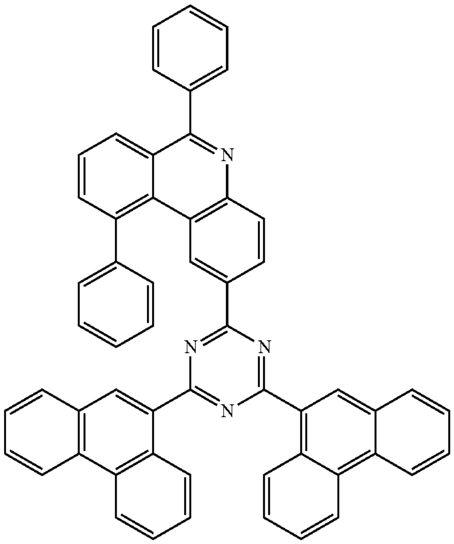
478
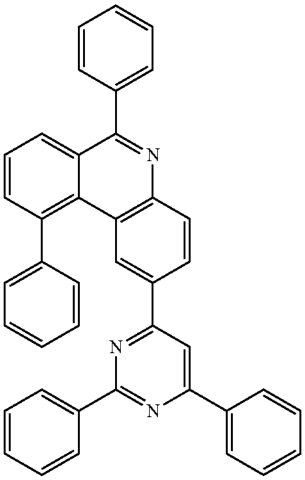
479
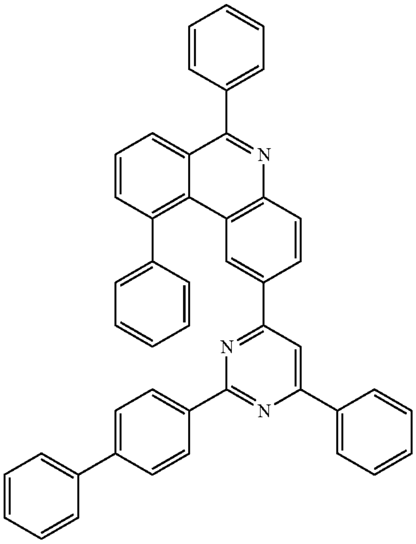
480
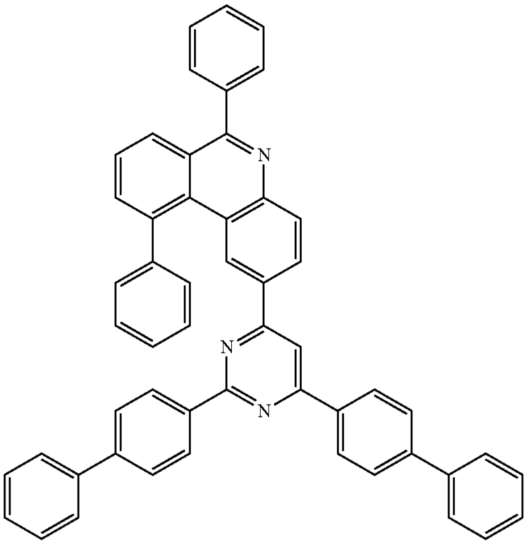

-continued
481
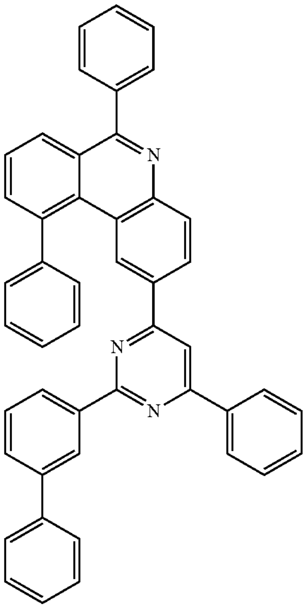
482
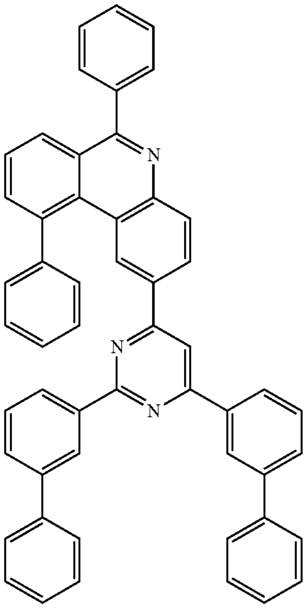
-continued
483
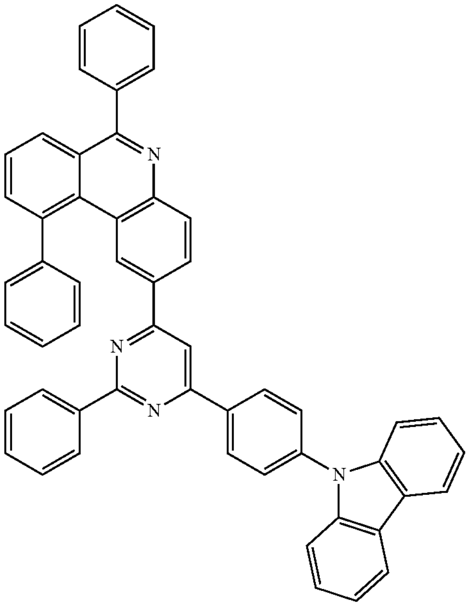
484
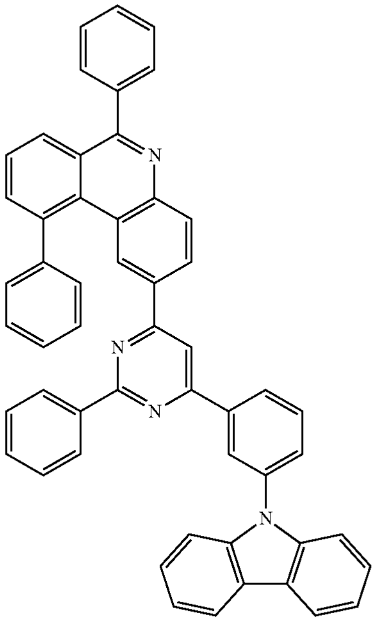

-continued
485
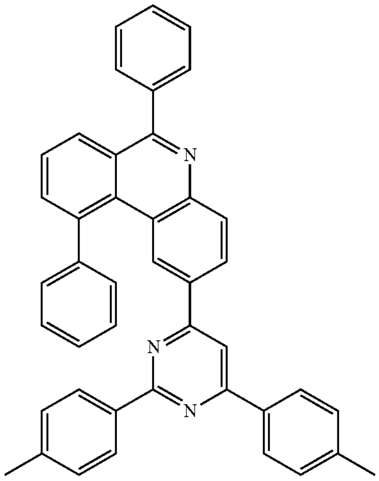
486
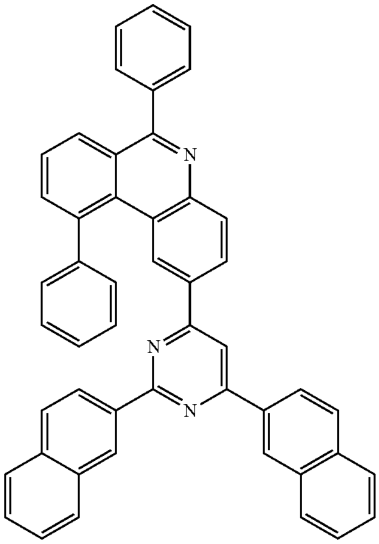
487
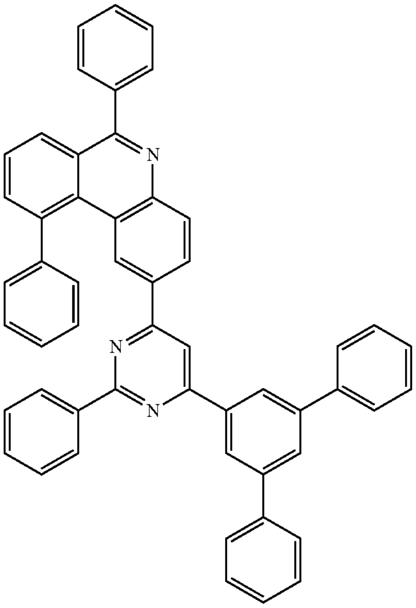
-continued
488
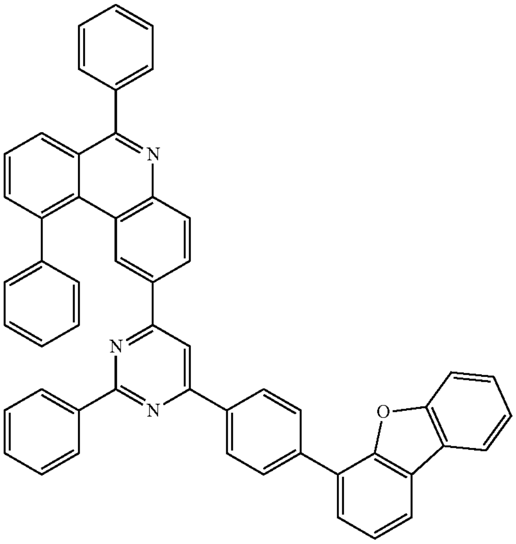
489
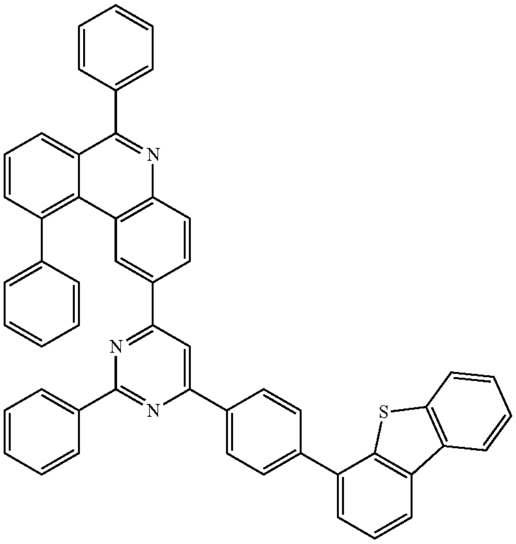
490
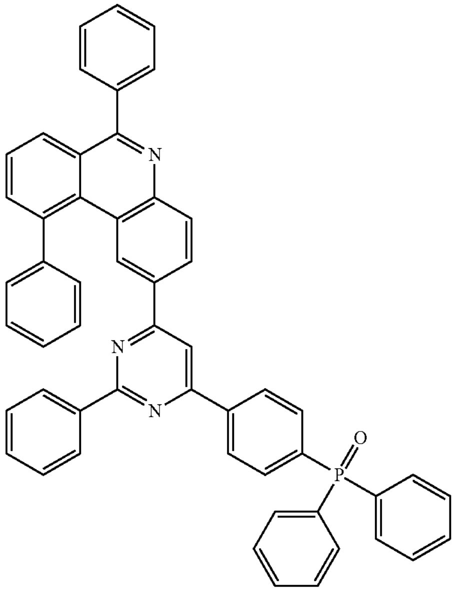

-continued
491
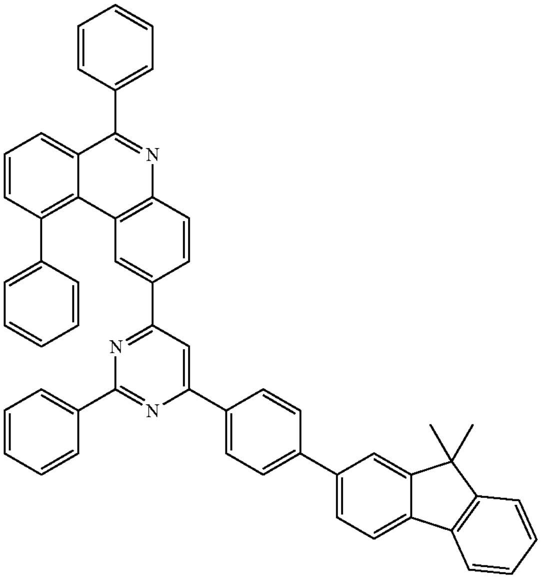
492
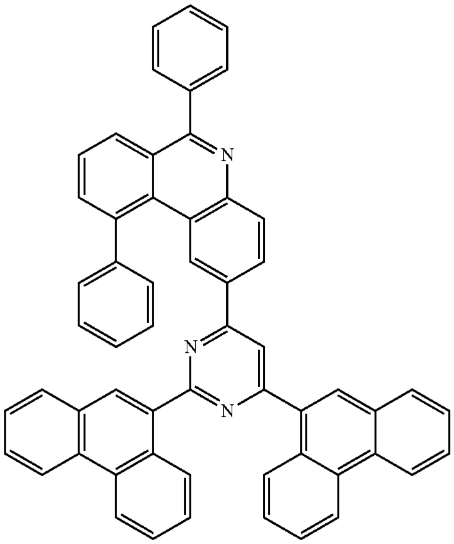
-continued
493
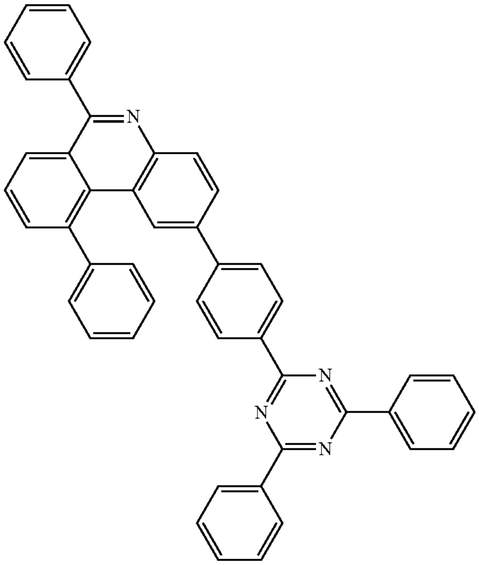
494
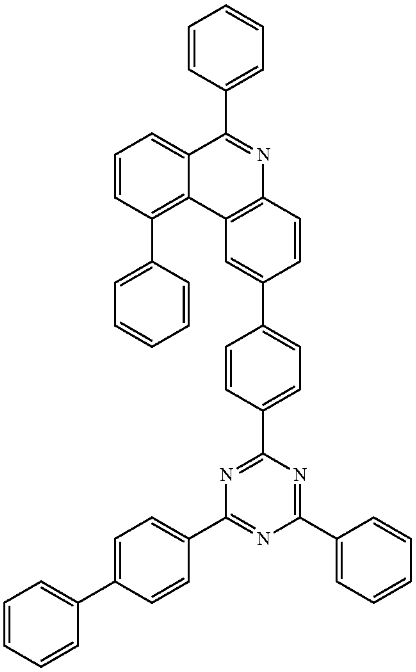

-continued
495
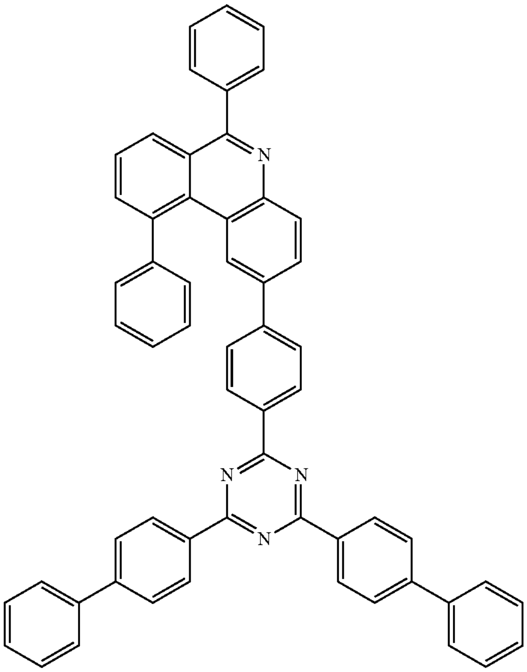
496
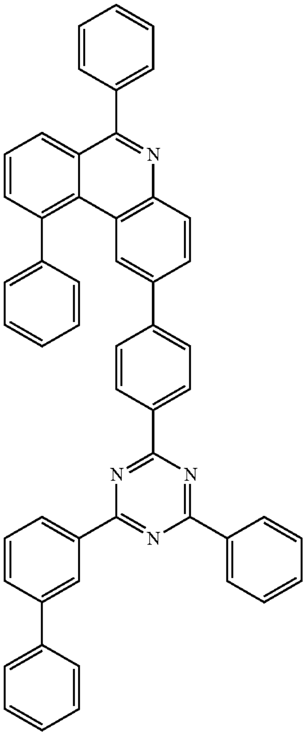
-continued
497
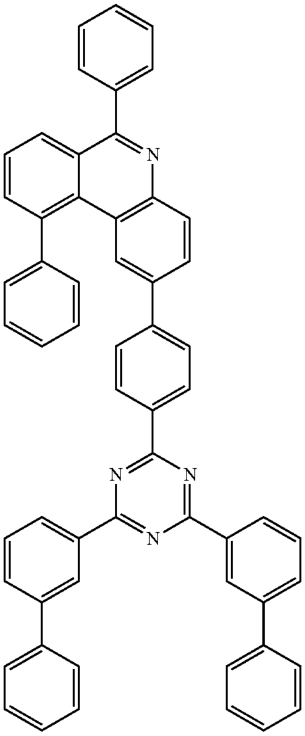
498
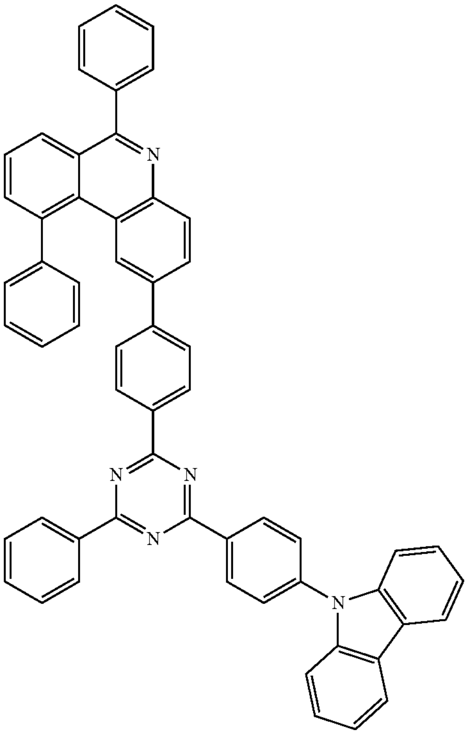

-continued
499
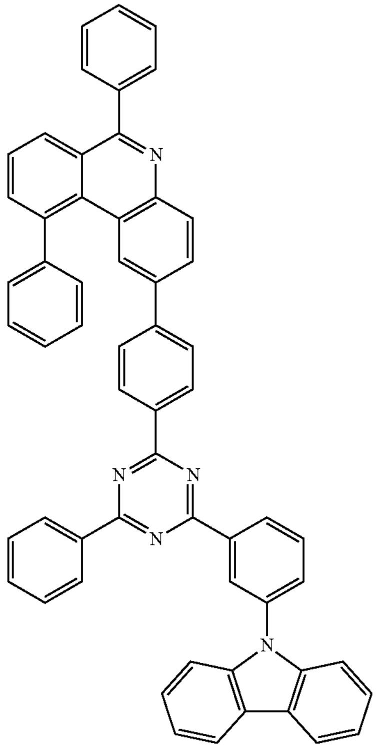
500
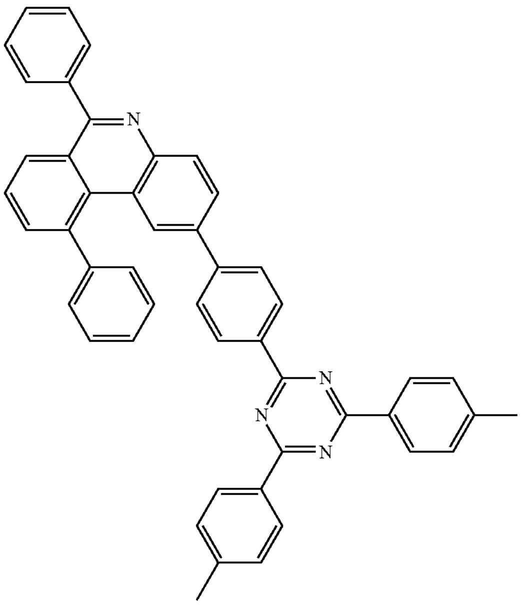
-continued
501
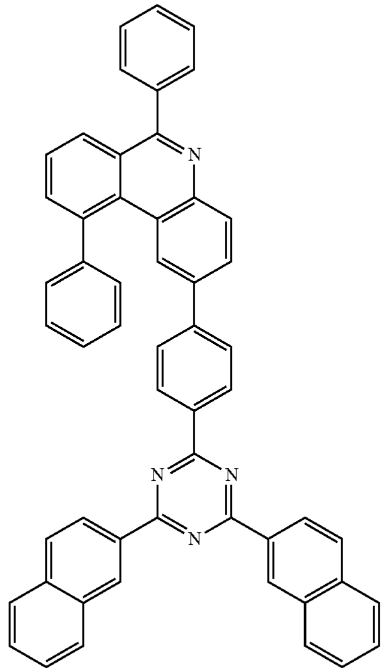
502
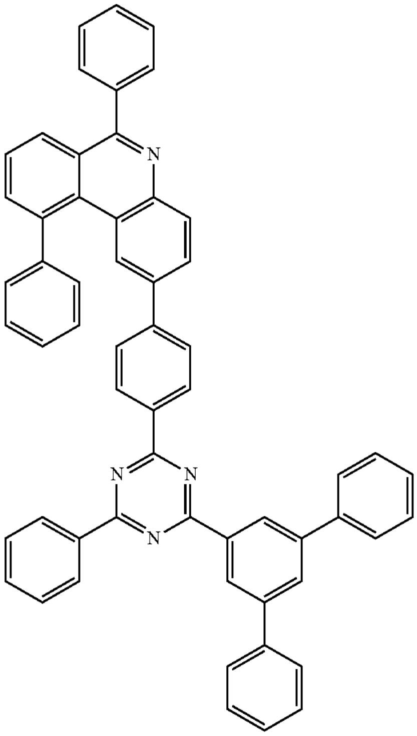

-continued
503
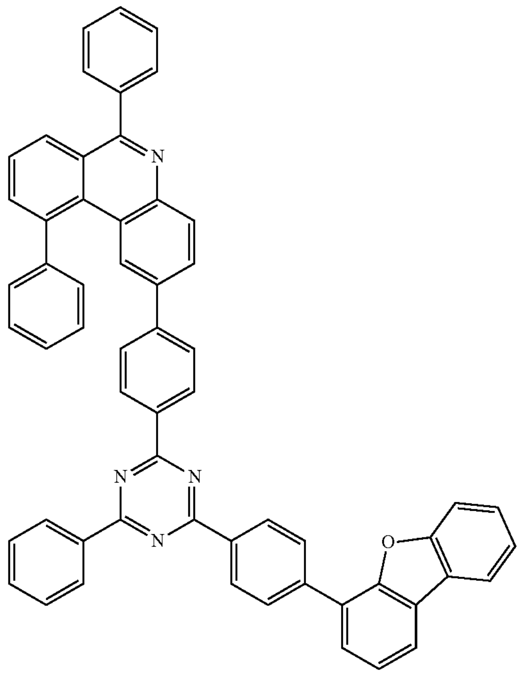
504
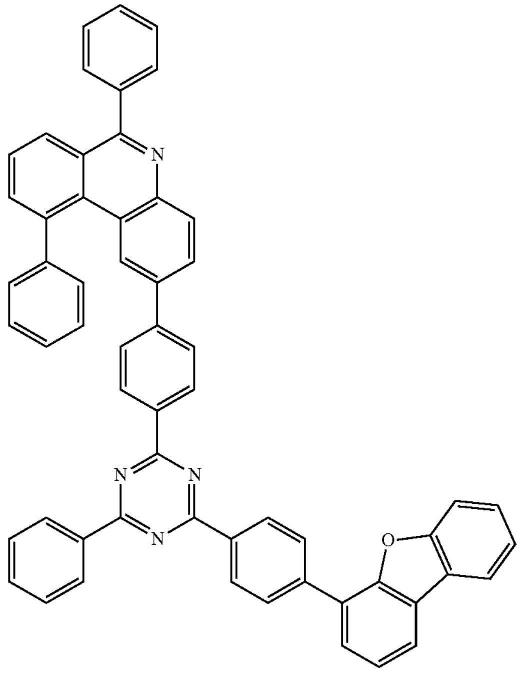
-continued
505
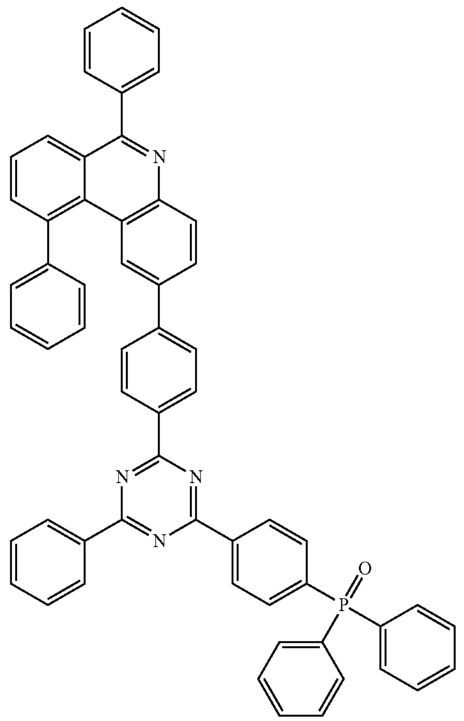
506
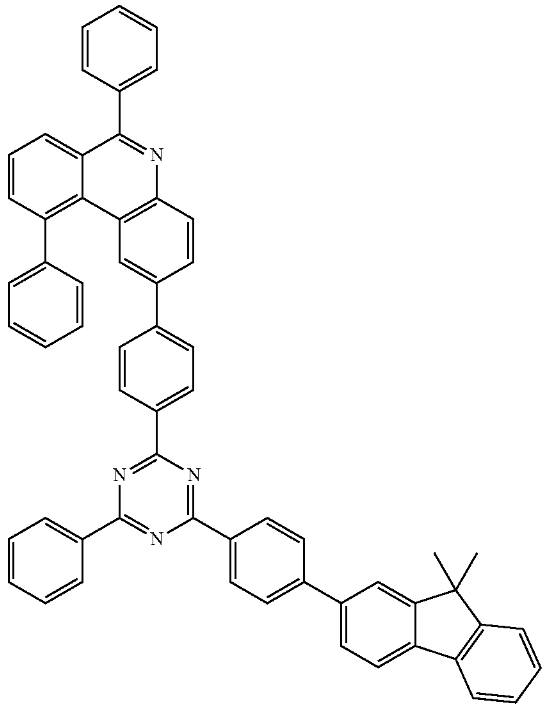

-continued
507
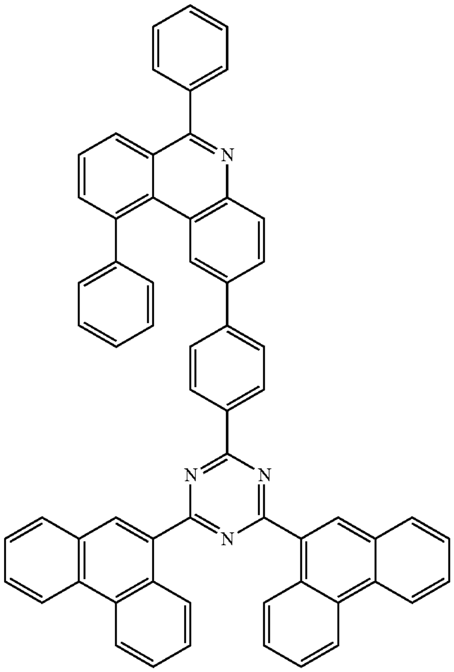
508
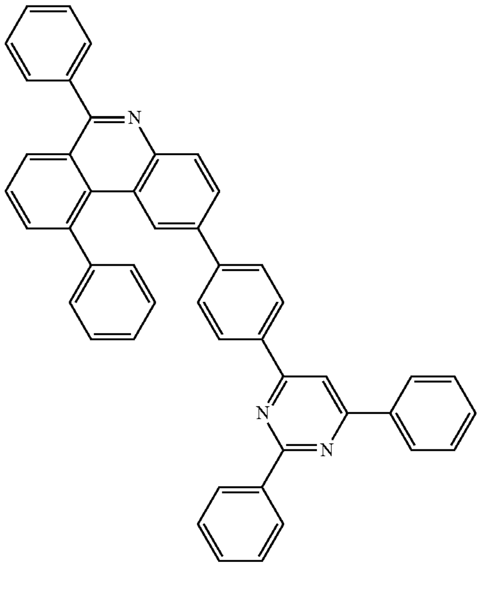
-continued
509
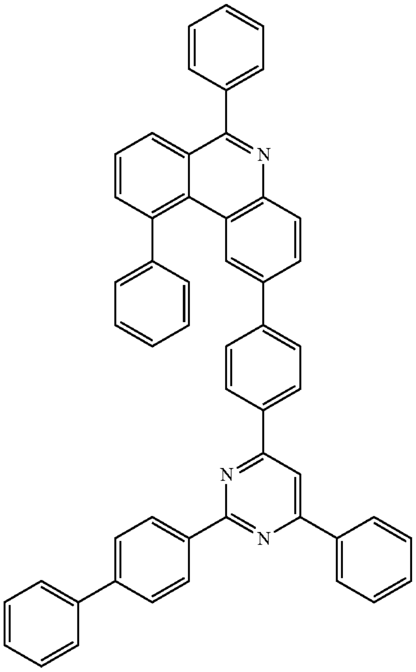
510
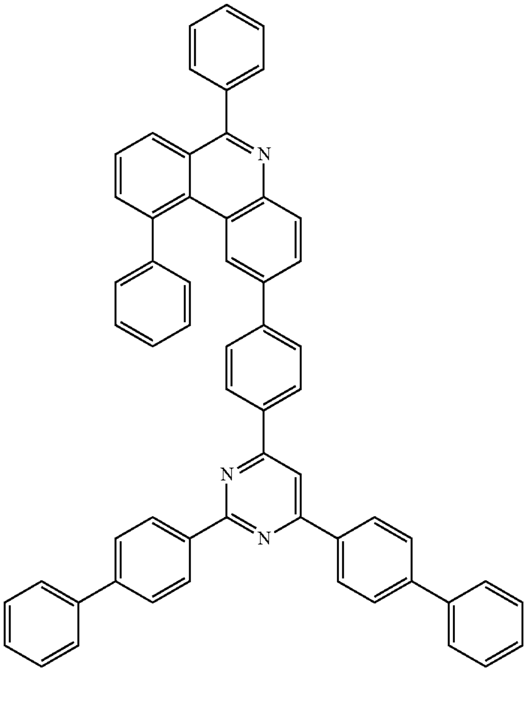

-continued
511
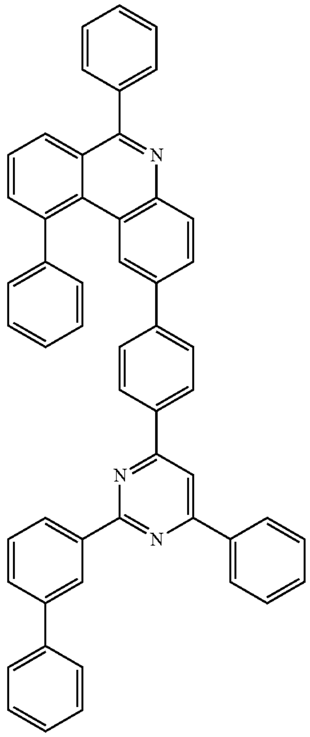
512
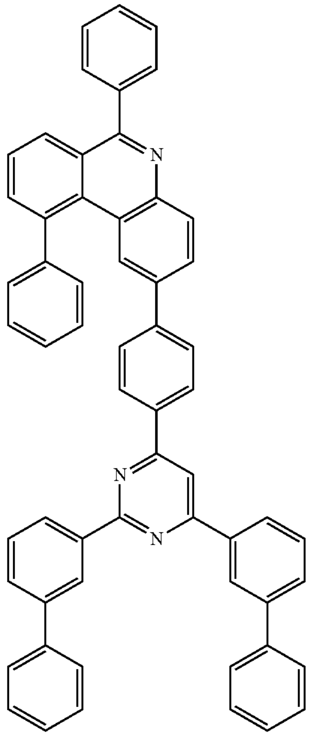
-continued
513
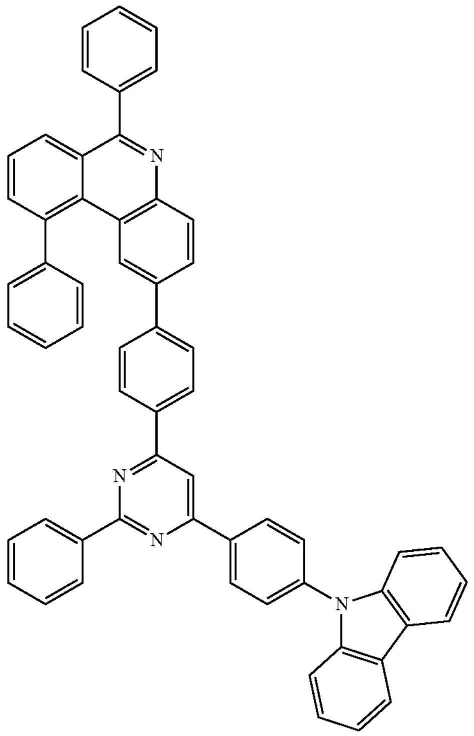
514
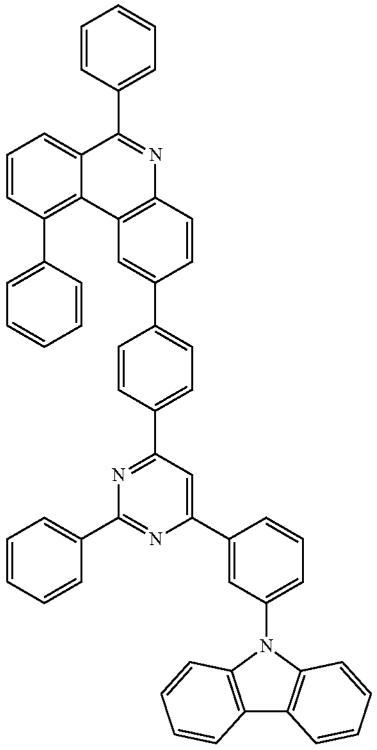

-continued
515
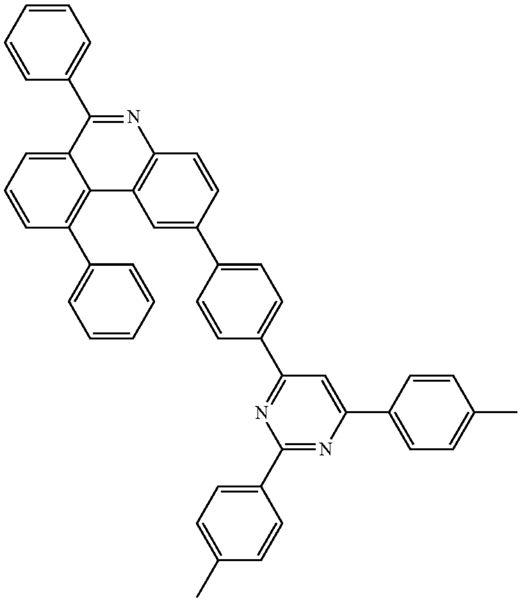
516
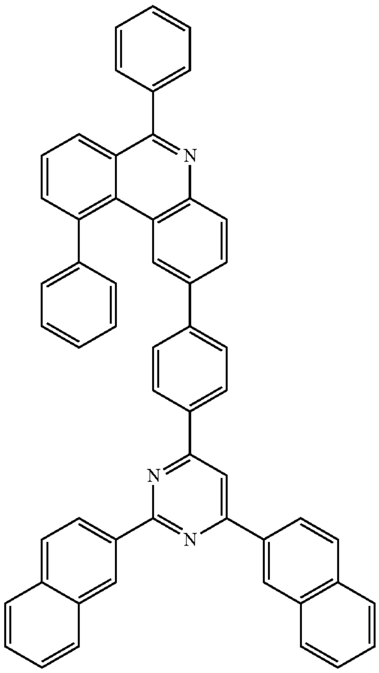
-continued
517
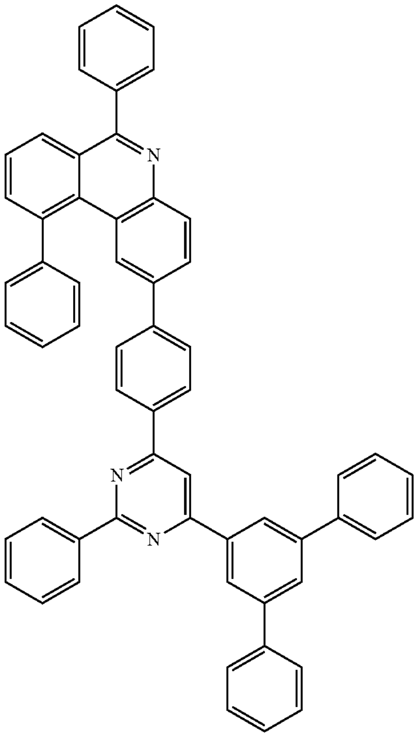
518
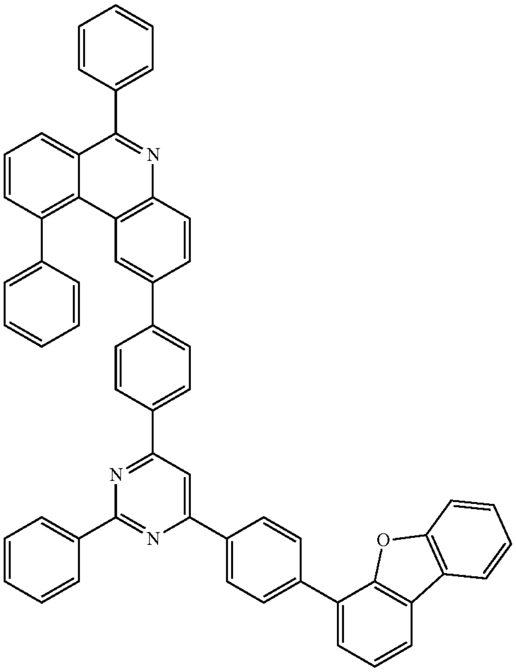

-continued
519
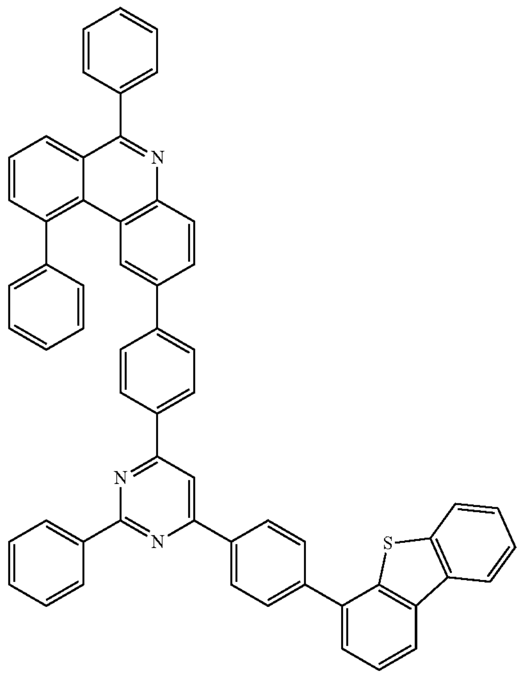
520
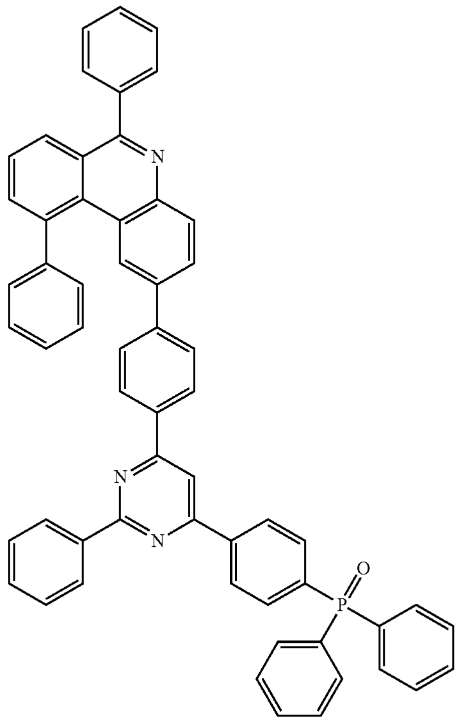
-continued
521
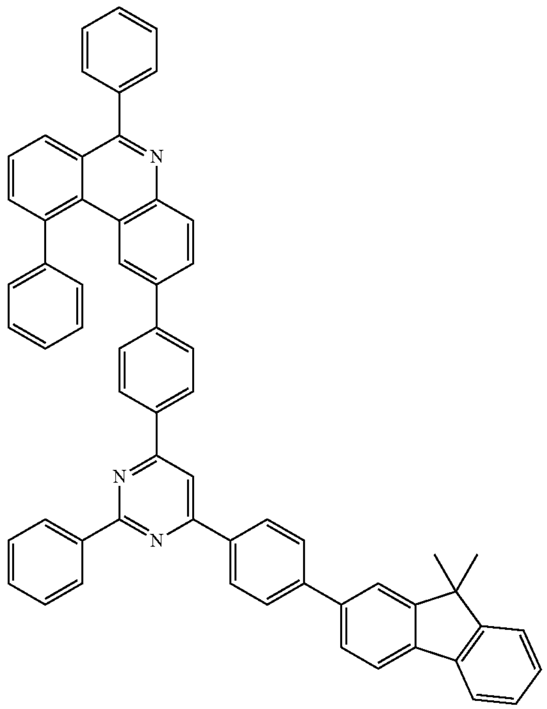
522
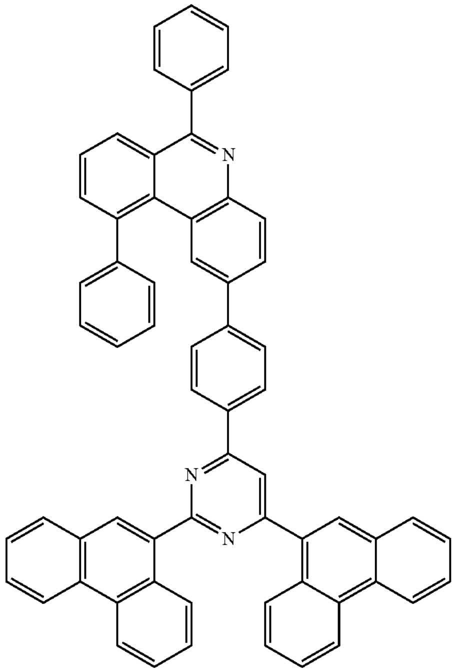

-continued
523
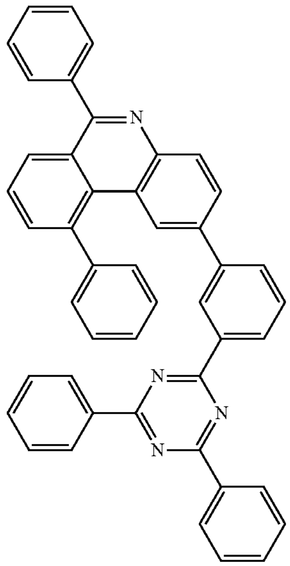
524
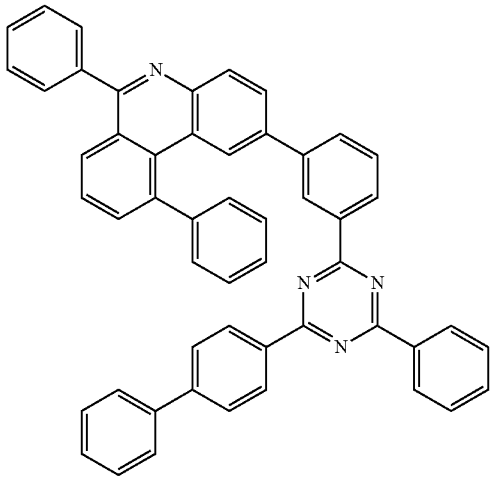
525
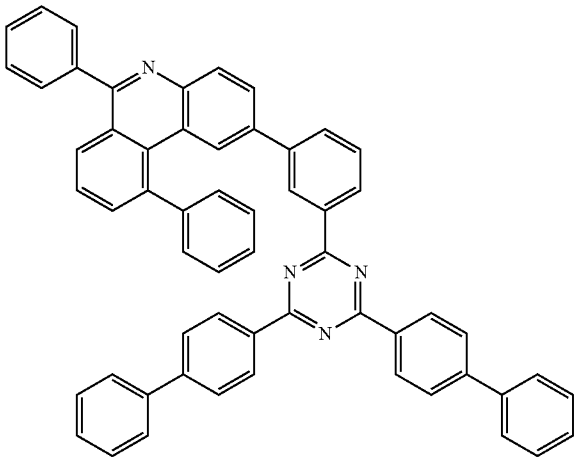
-continued
526
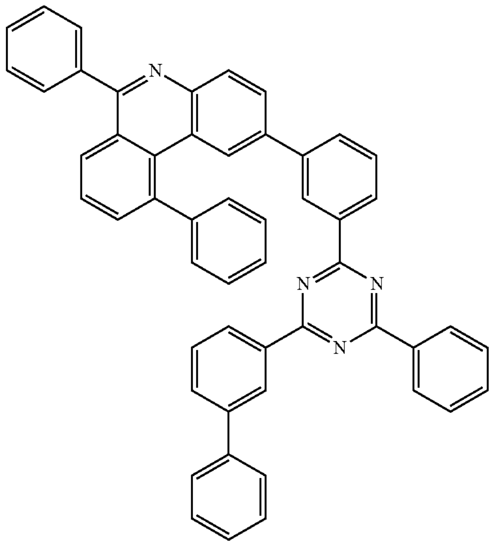
527
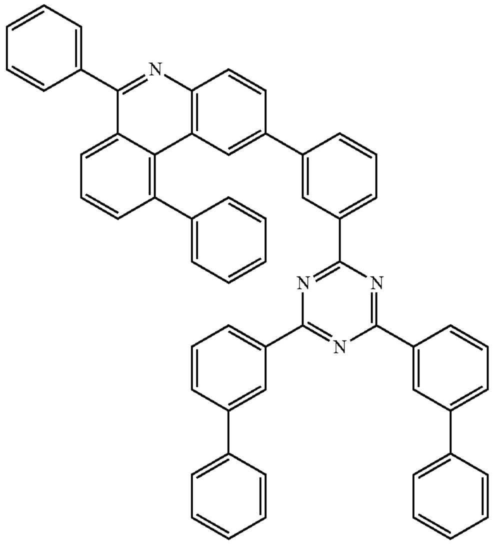
528
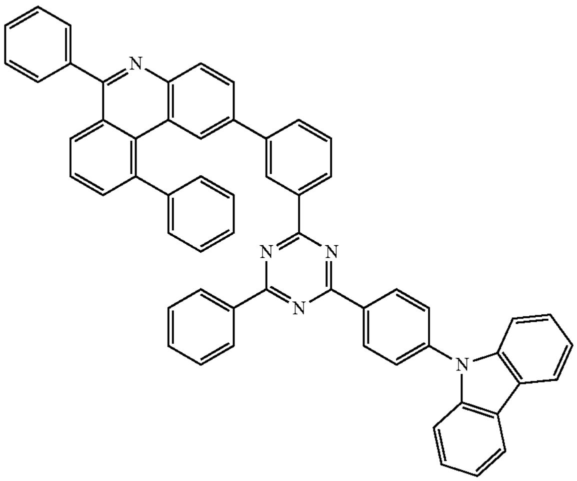

-continued
529
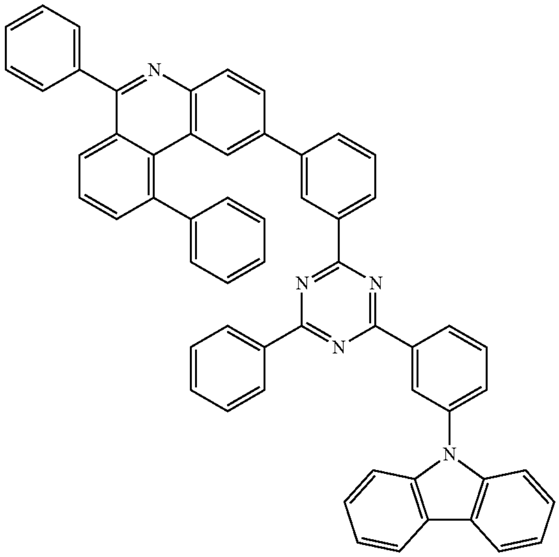
530
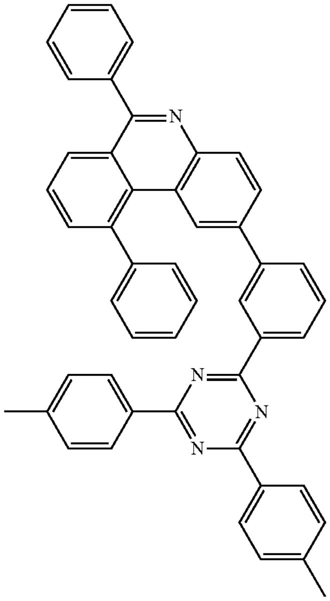
531
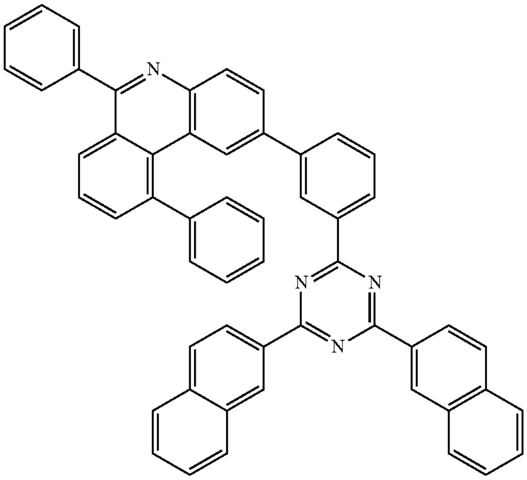
-continued
532
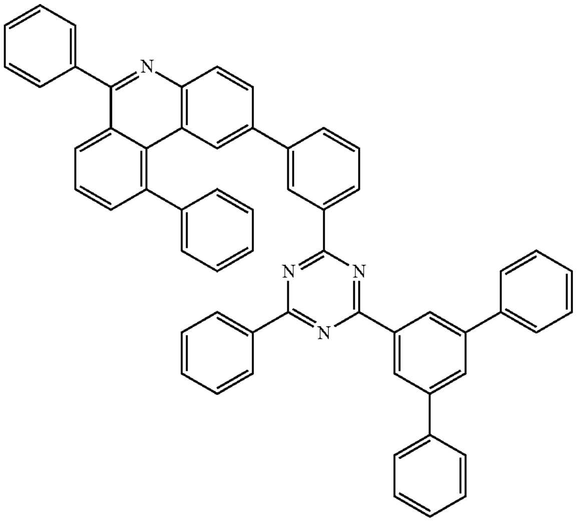
533
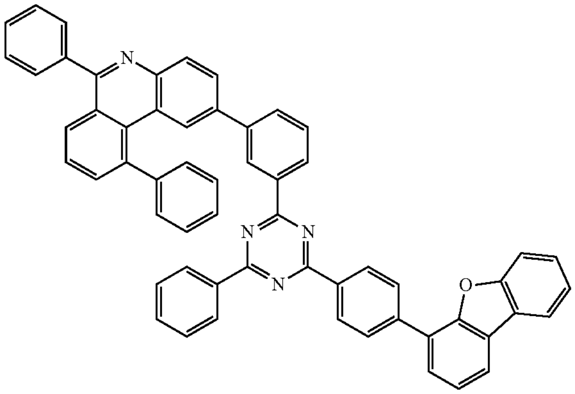
534
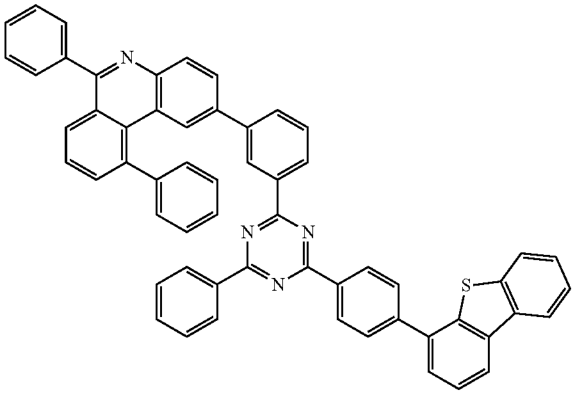

535
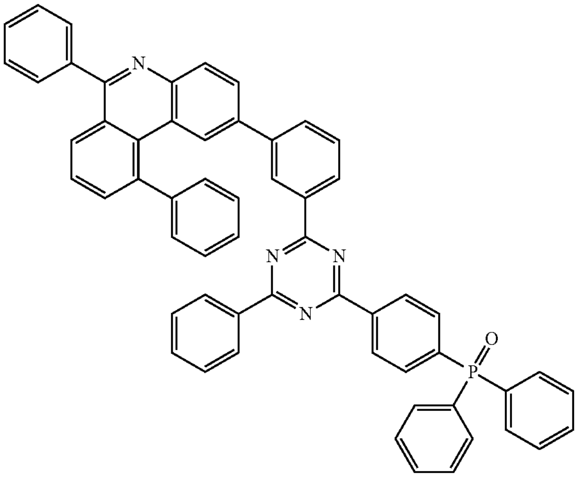
536
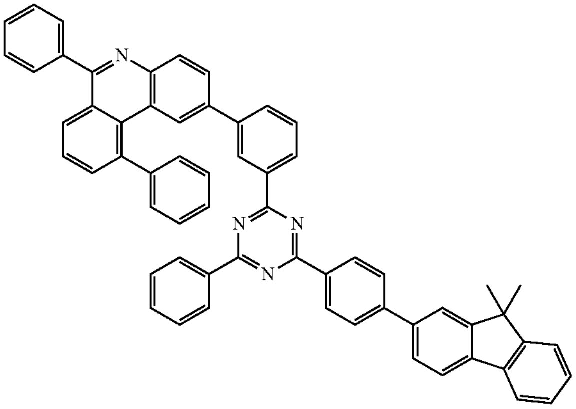
537
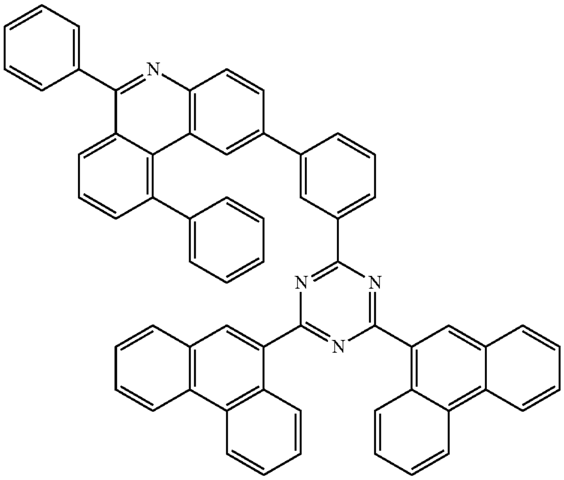
538
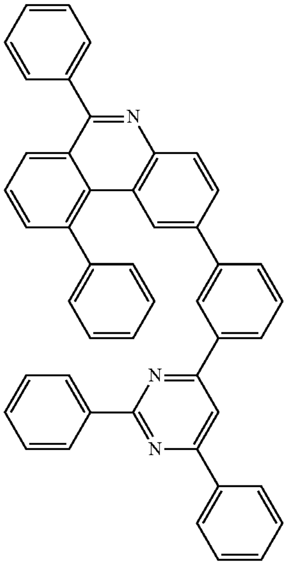
539
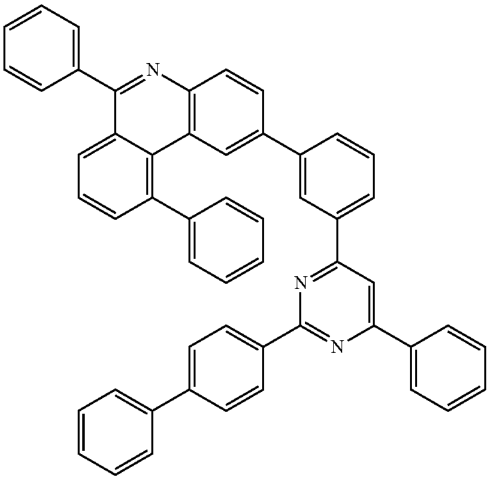
540
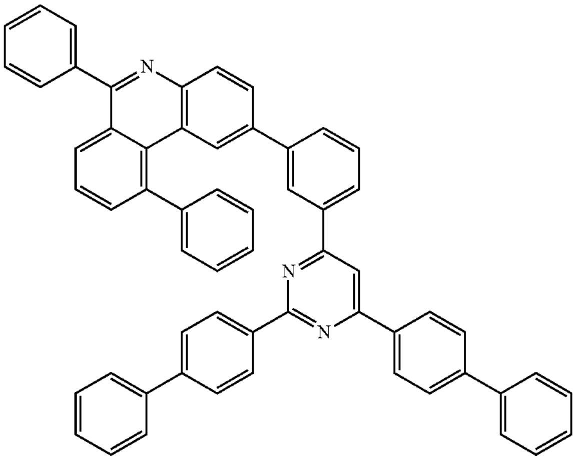

-continued
541
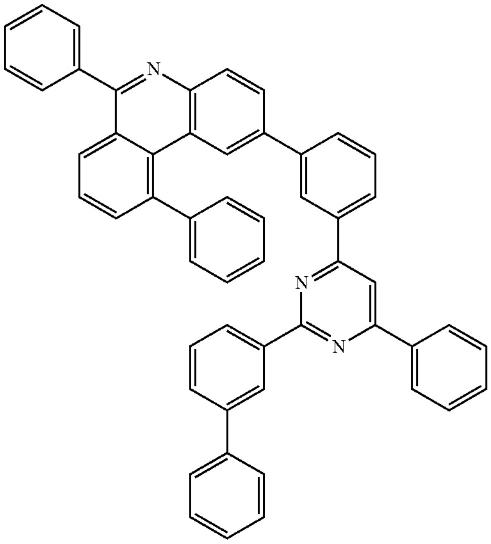
542
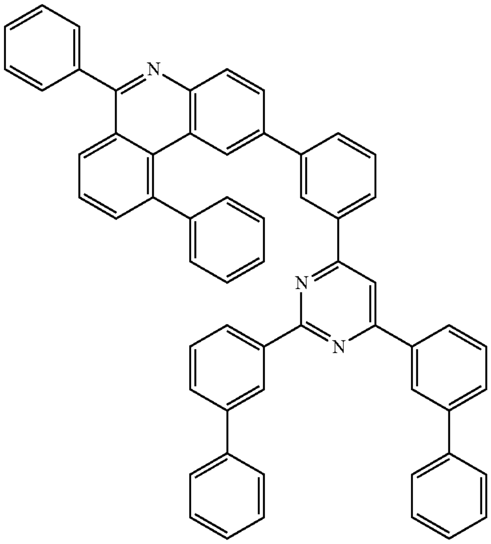
543
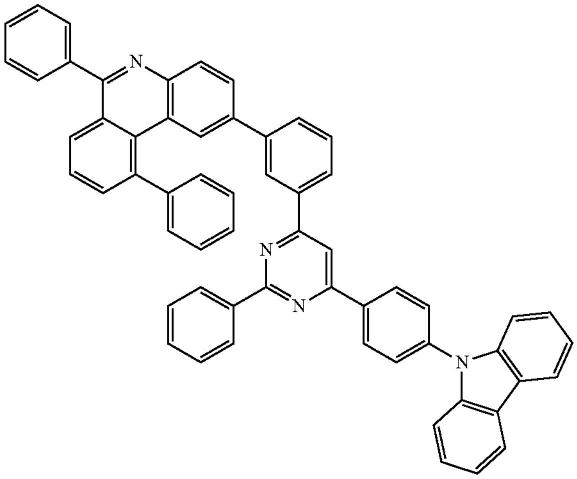
-continued
544
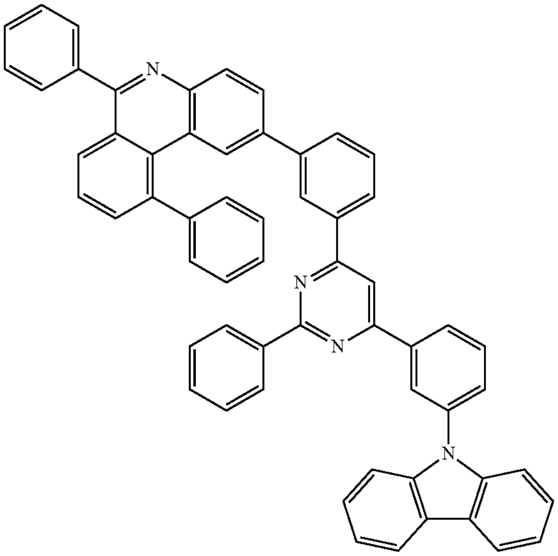
545
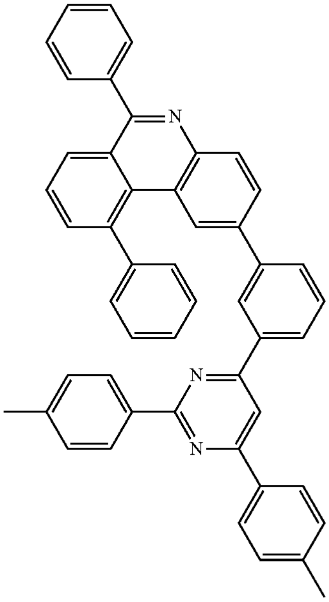
546
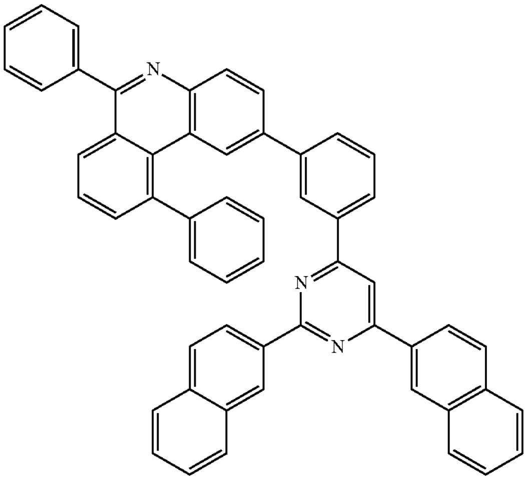

-continued
547
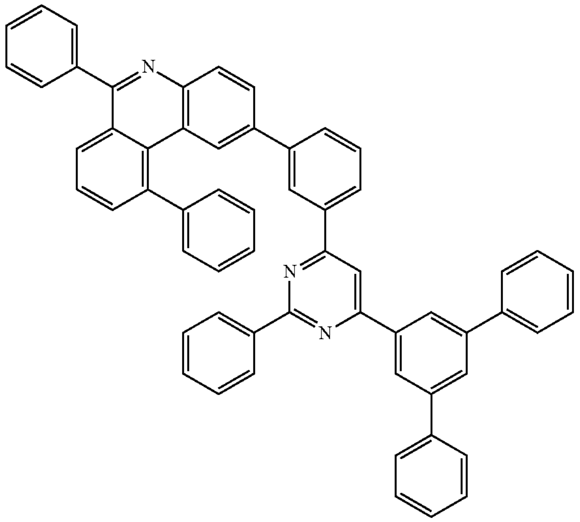
548
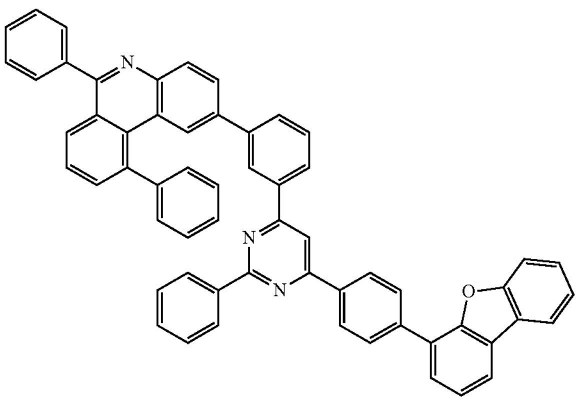
549
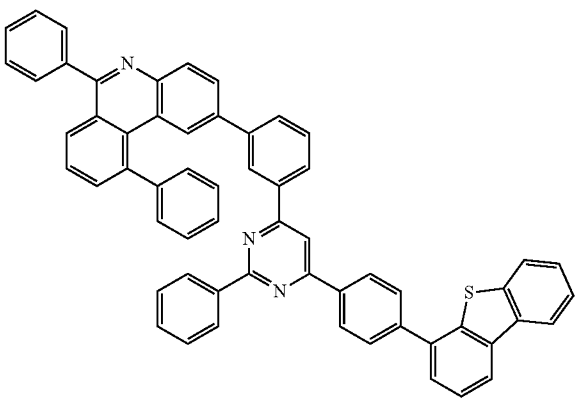
-continued
550
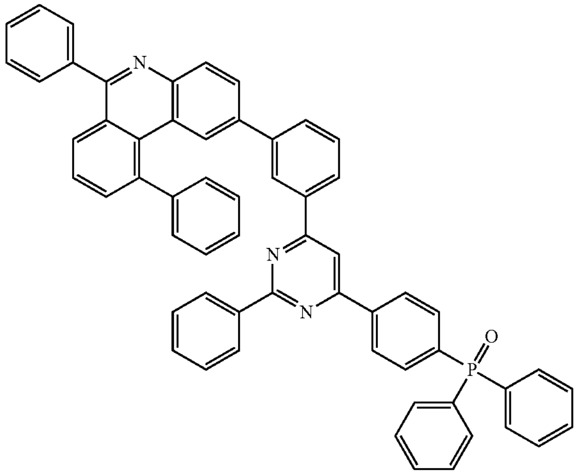
551
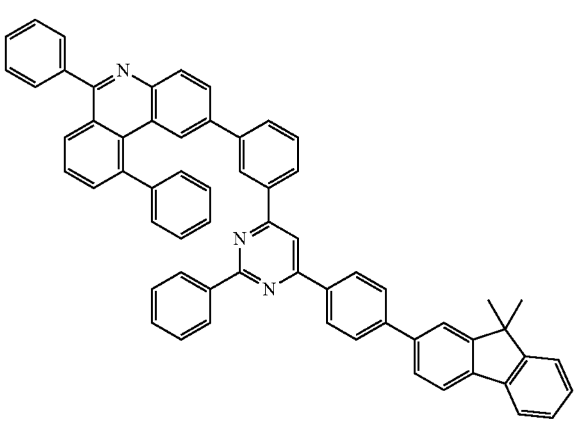
552
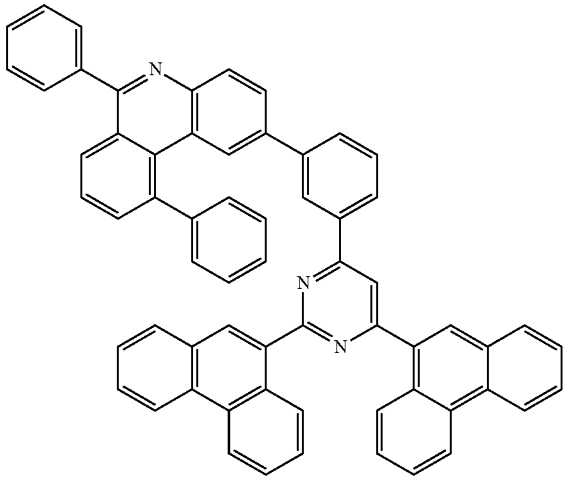

-continued
553
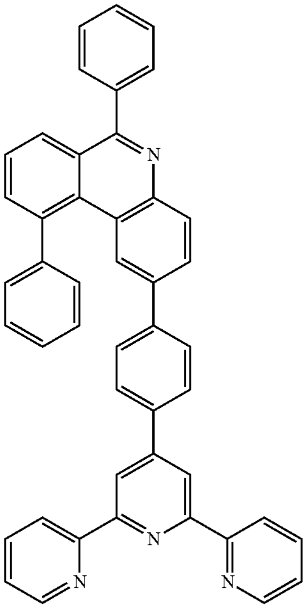
554
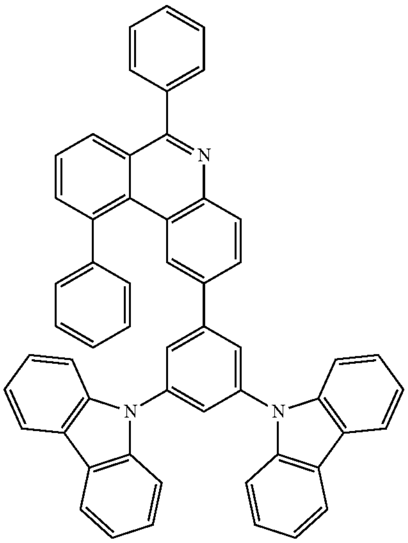
555
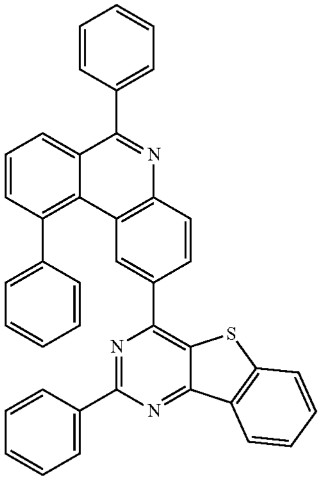
-continued
556
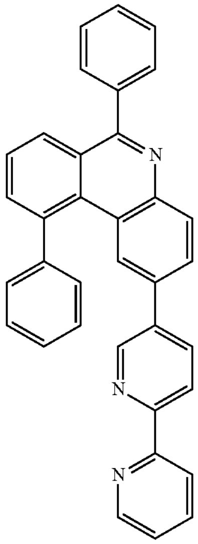
557
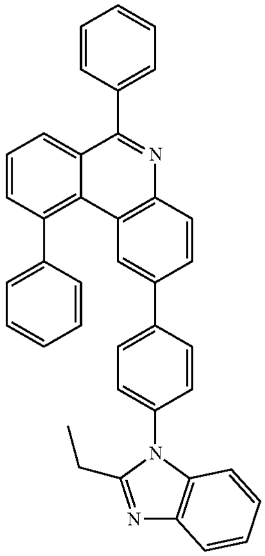

-continued
558
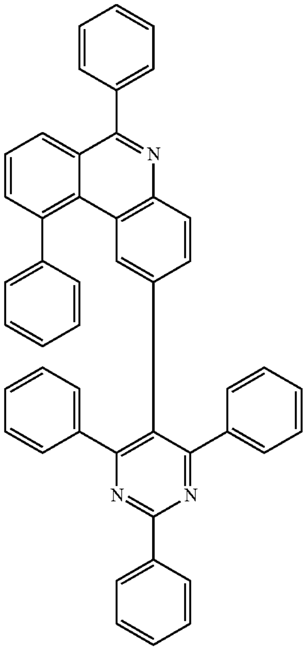
559
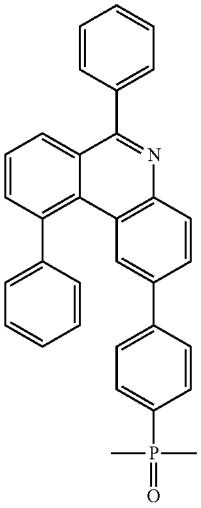
560
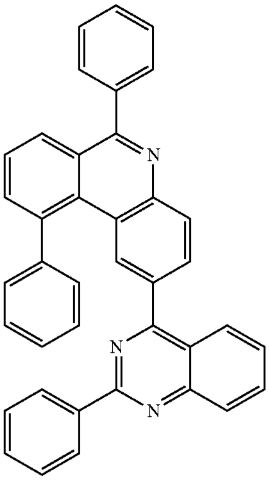
-continued
561
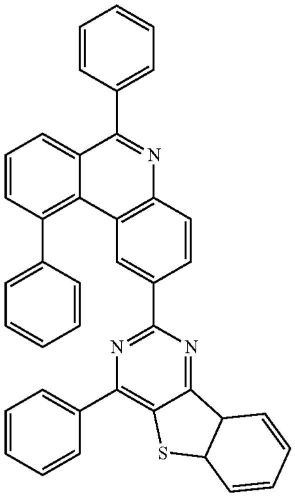
562
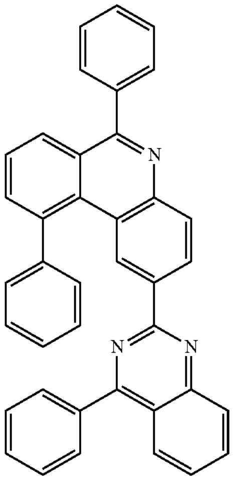
563
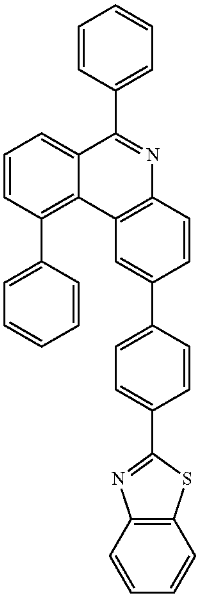

-continued
564
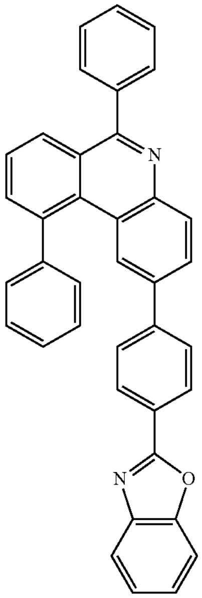
565
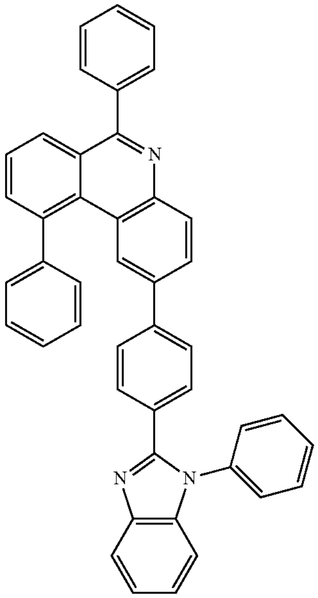
-continued
566
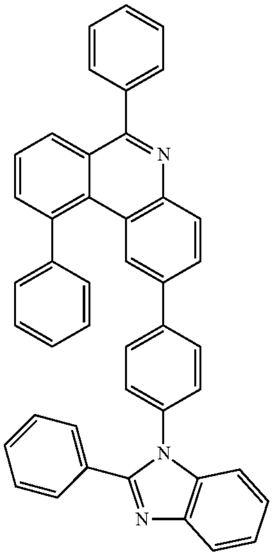
567
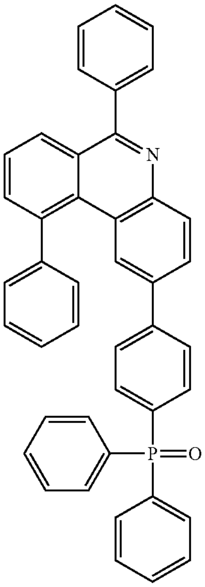
568
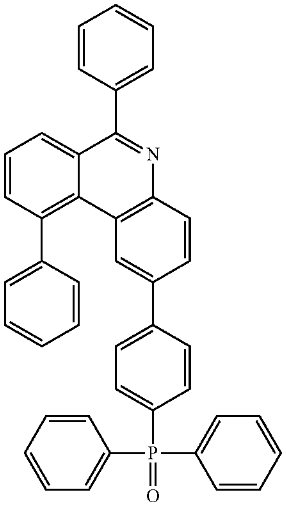

569
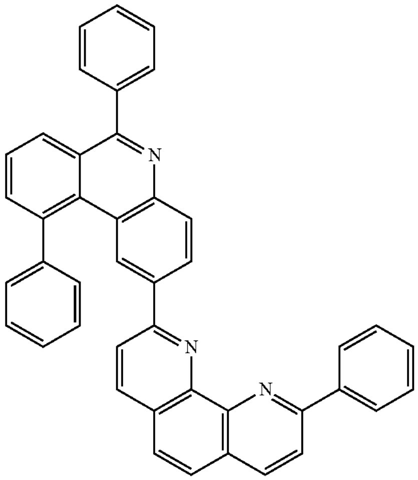
570
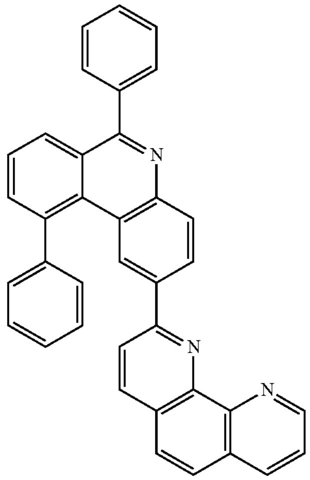
571
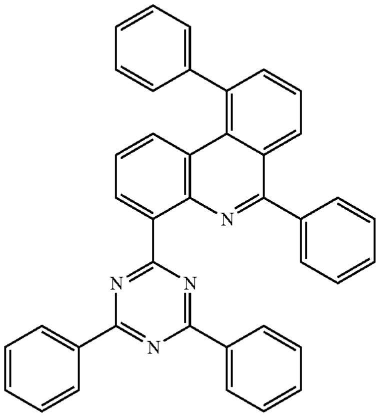
572
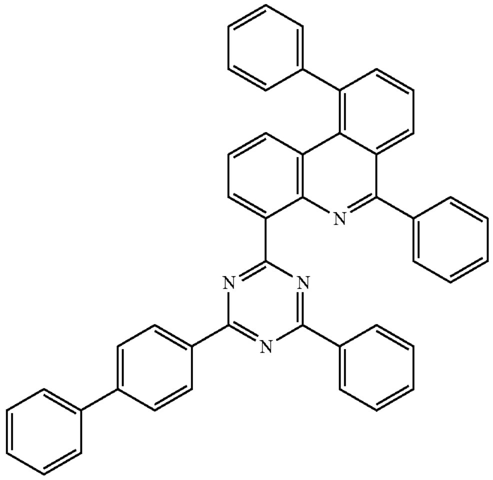
573
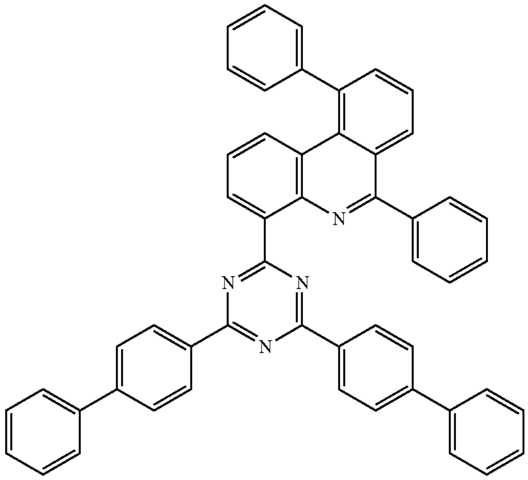
574
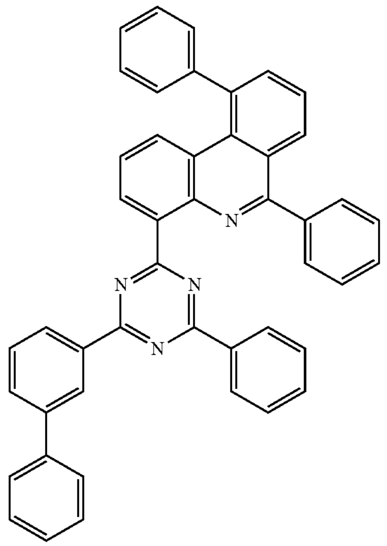

-continued
575
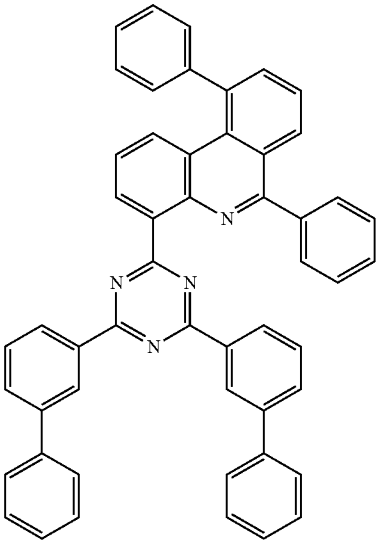
576
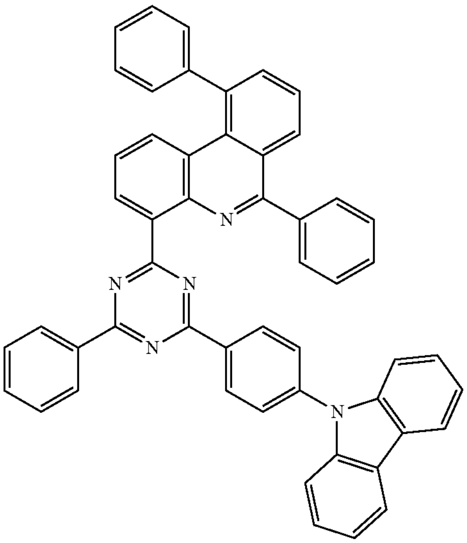
577
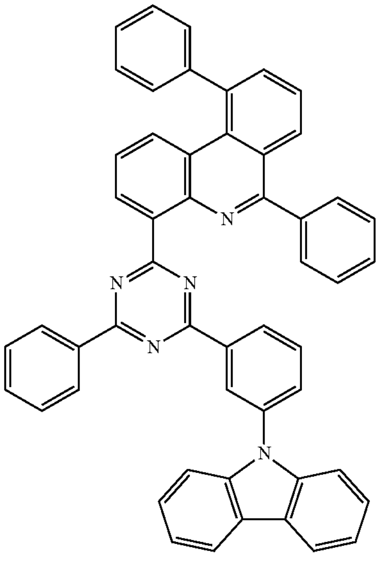
-continued
578
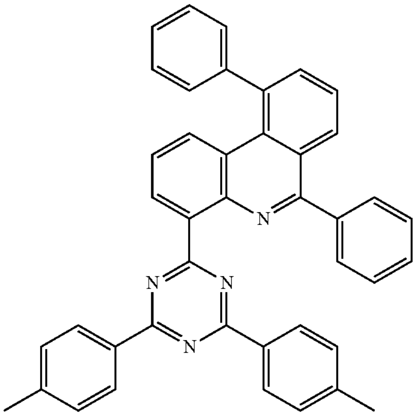
579
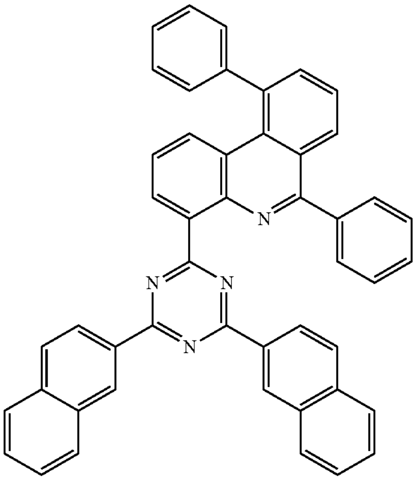
580
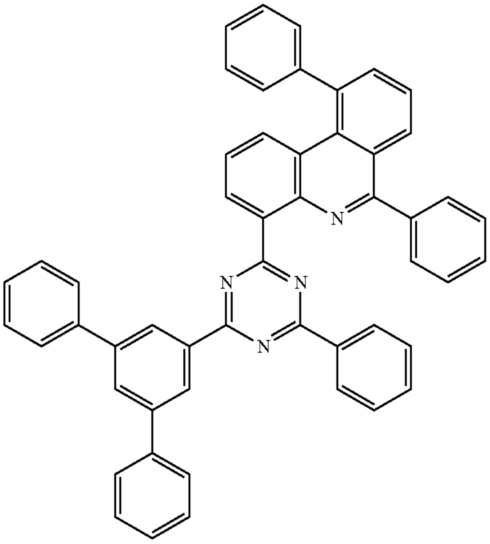

-continued
581
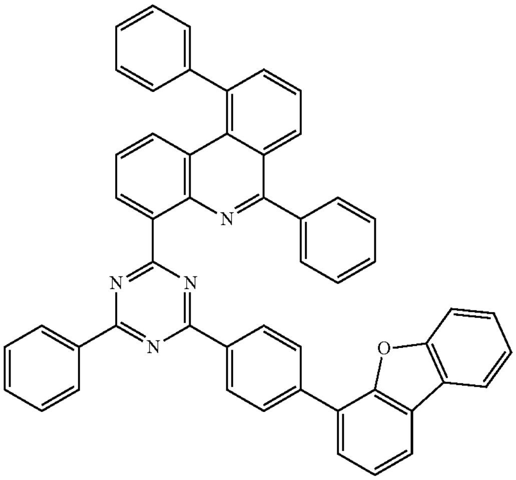
582
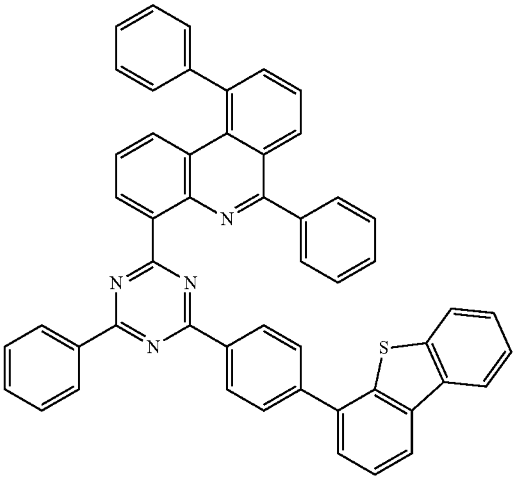
583
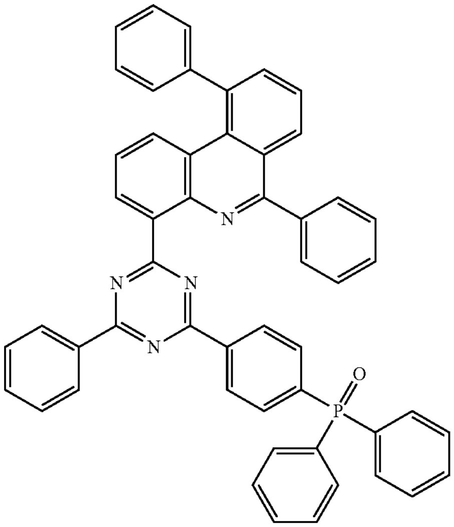
-continued
584
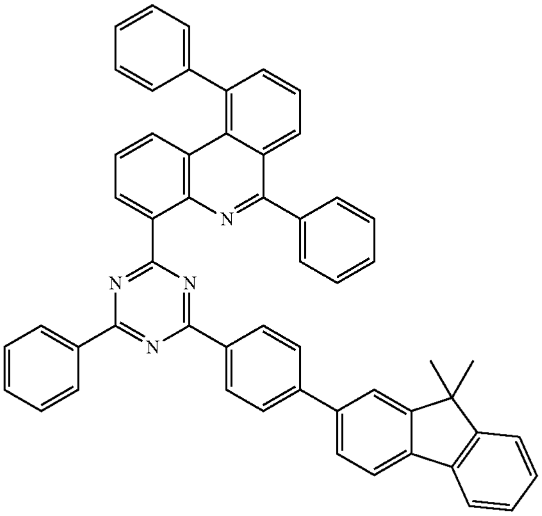
585
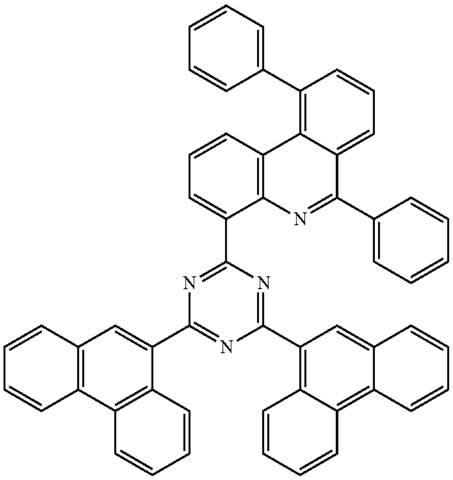
586
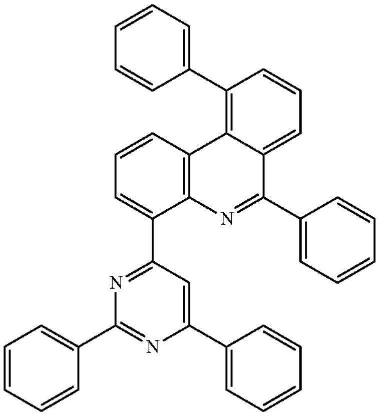

-continued
587
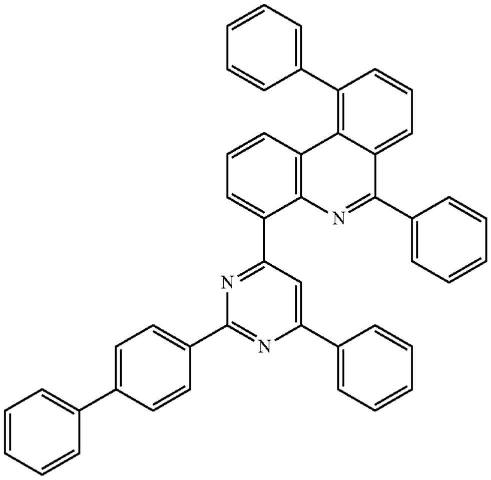
588
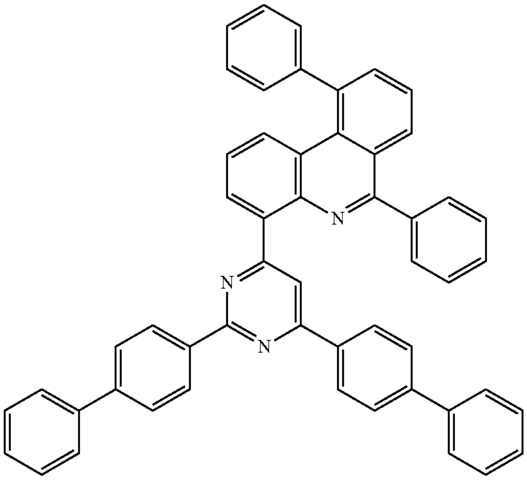
589
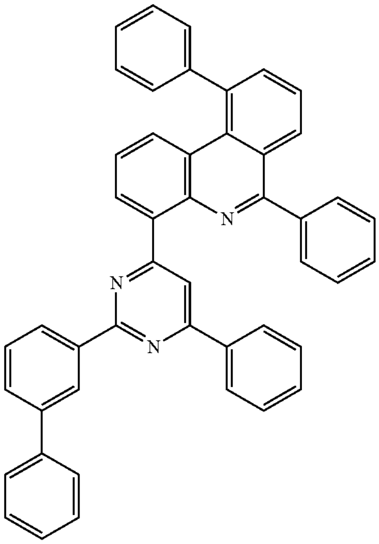
-continued
590
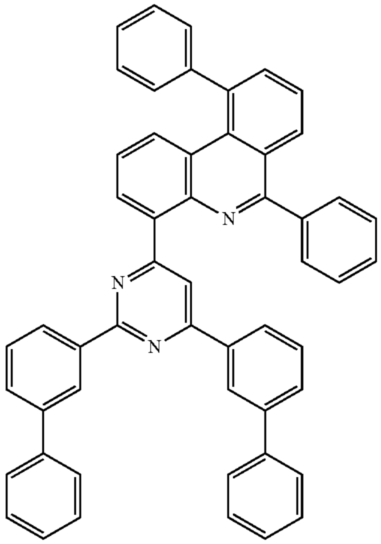
591
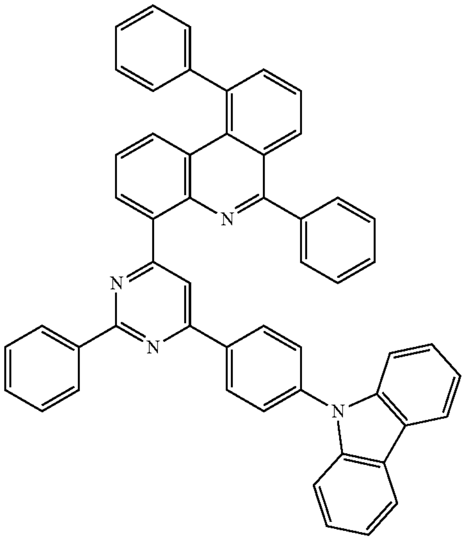
592
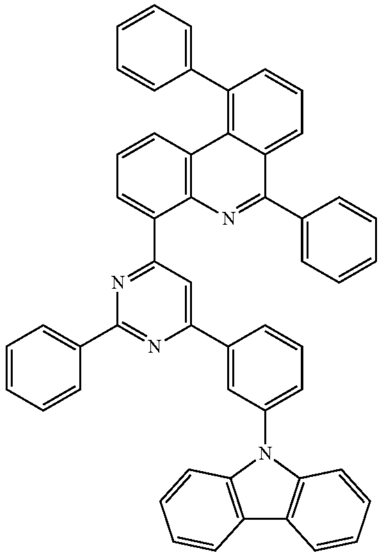

-continued
593
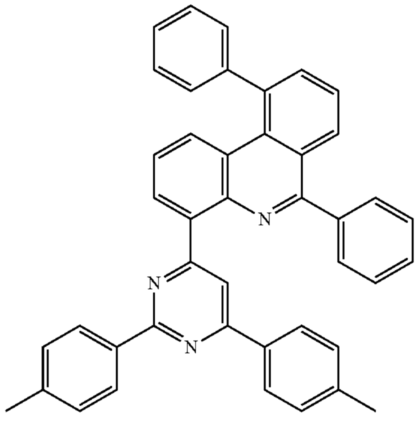
594
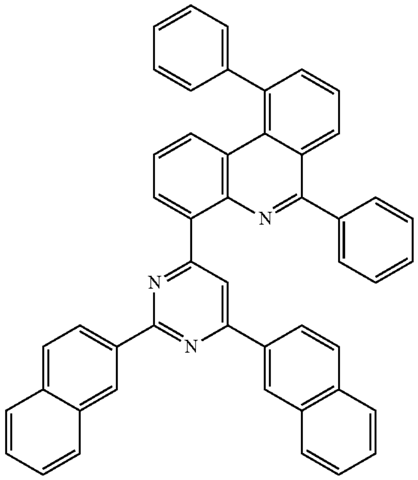
595
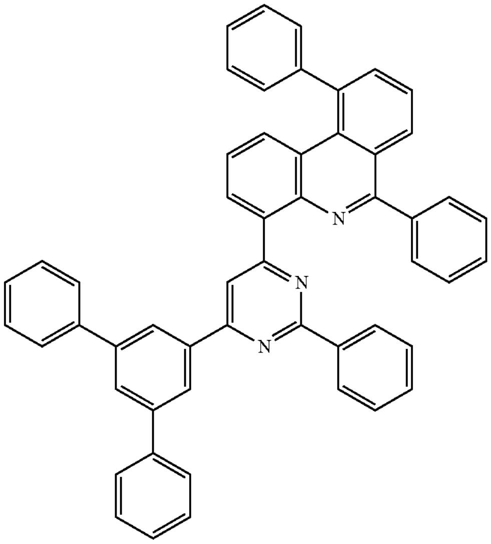
-continued
596
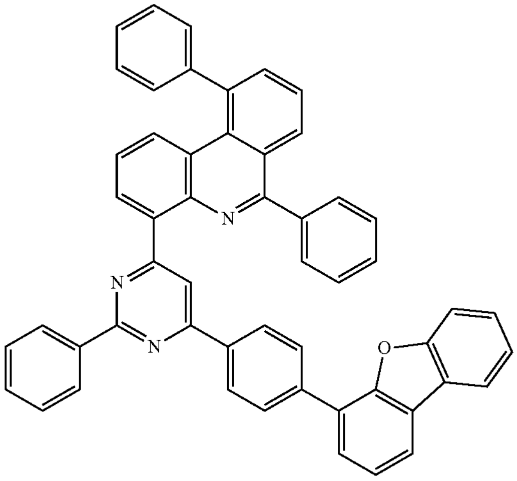
597
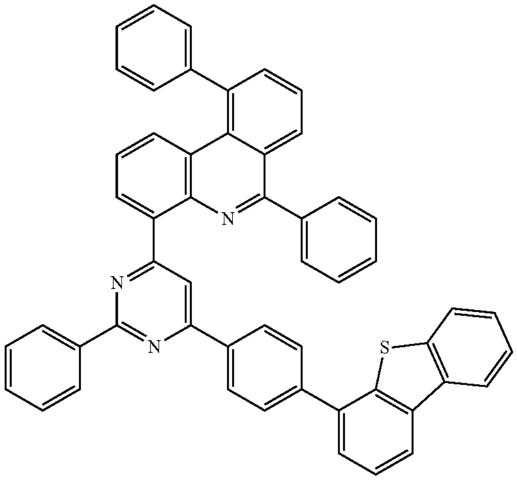
598
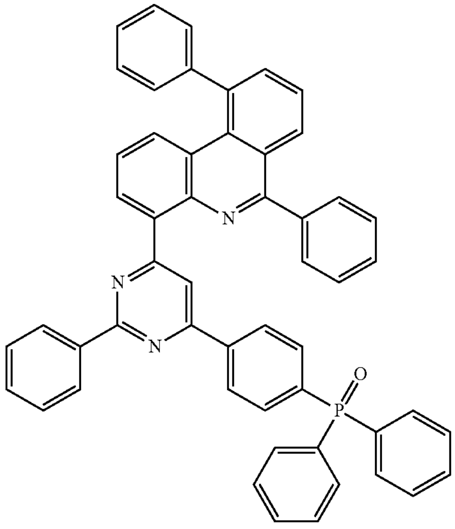

599
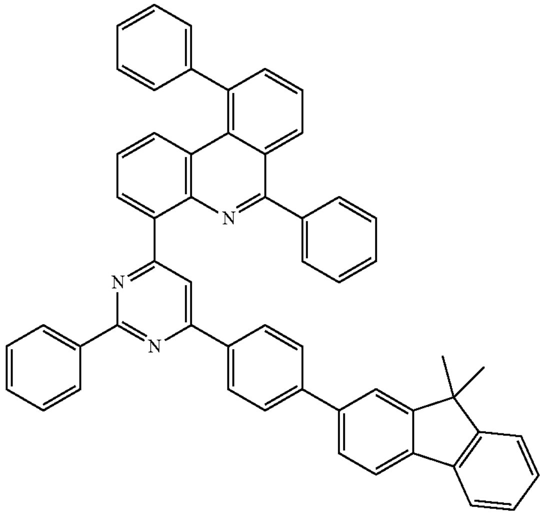
600
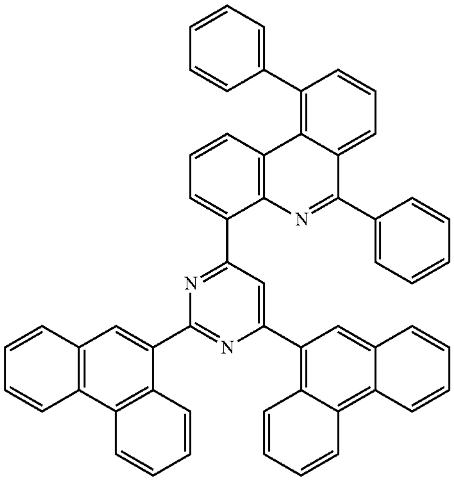
601
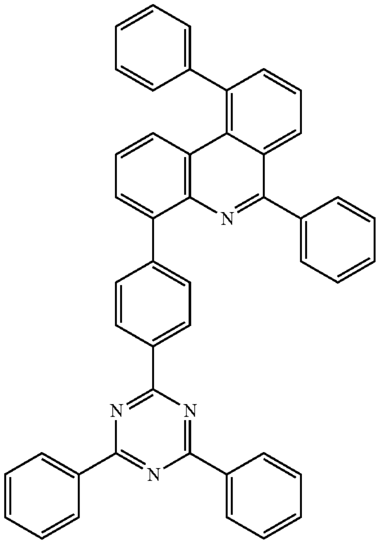
602
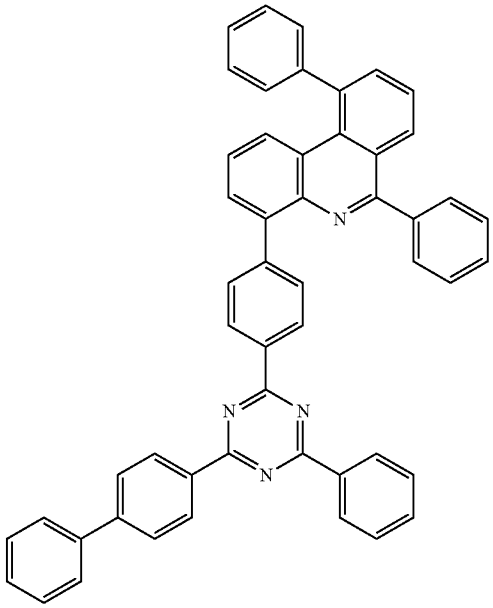
603
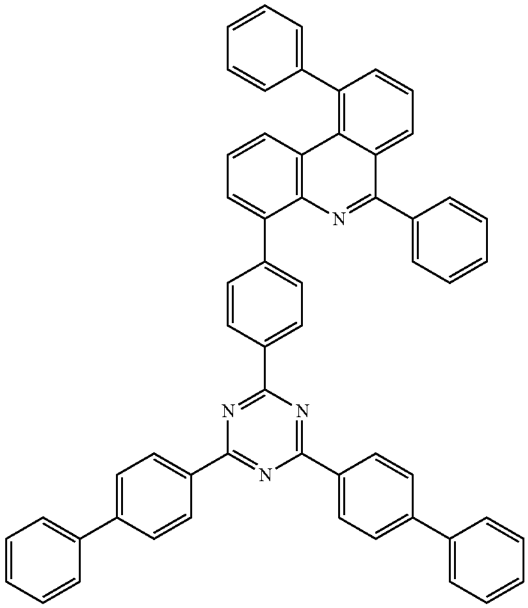

-continued
604
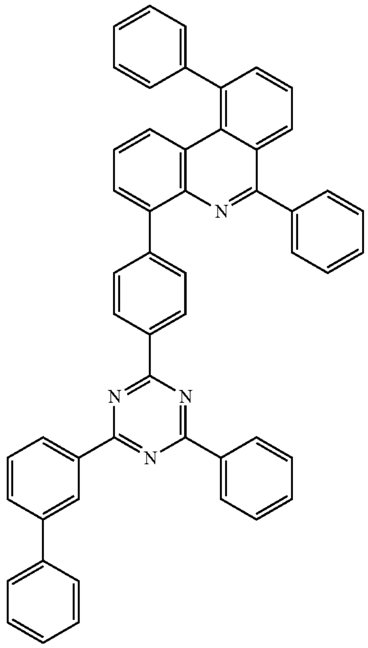
605
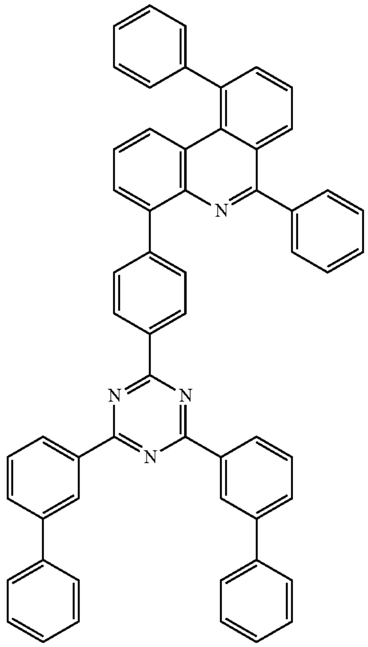
-continued
606
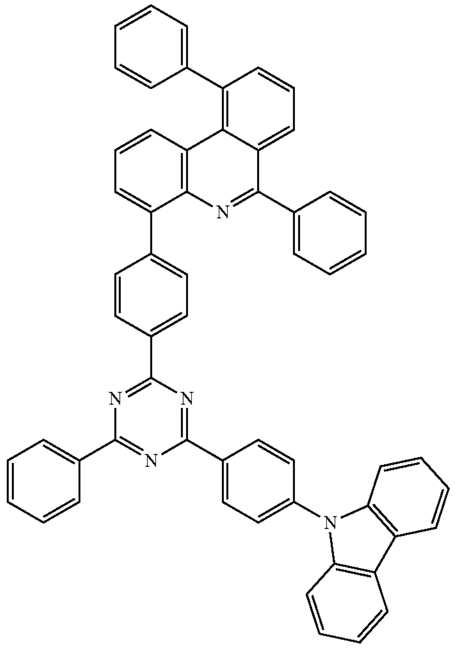
607
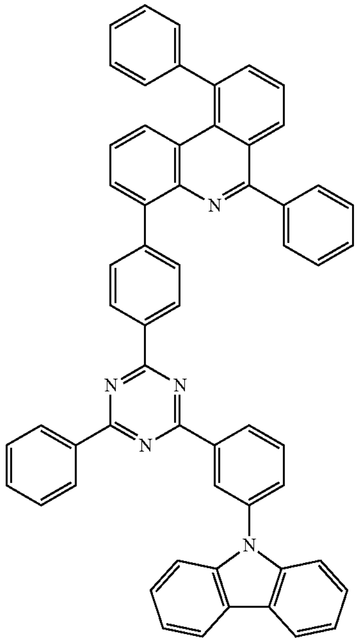

-continued
608
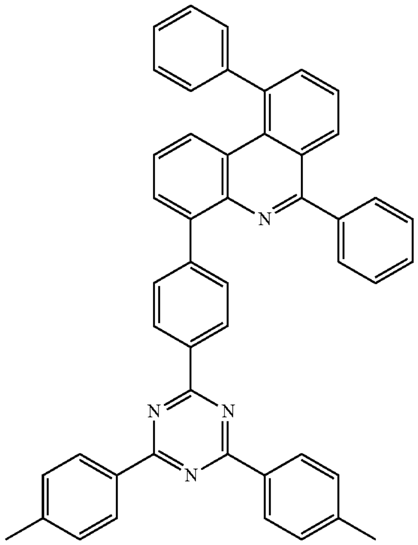
609
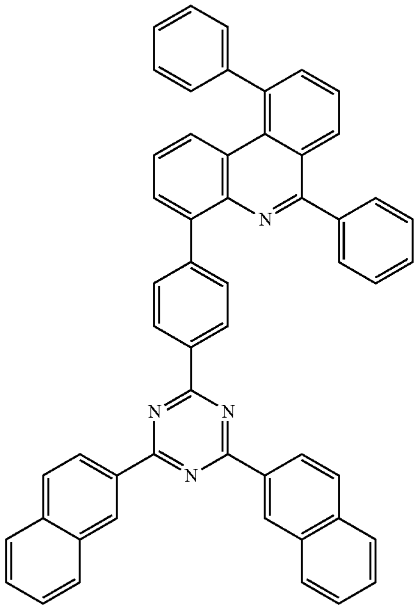
-continued
610
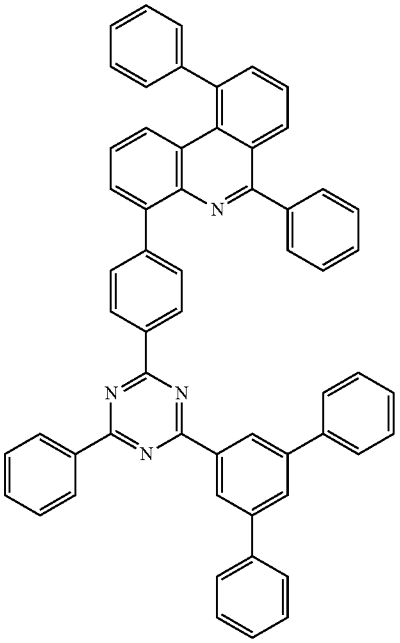
611
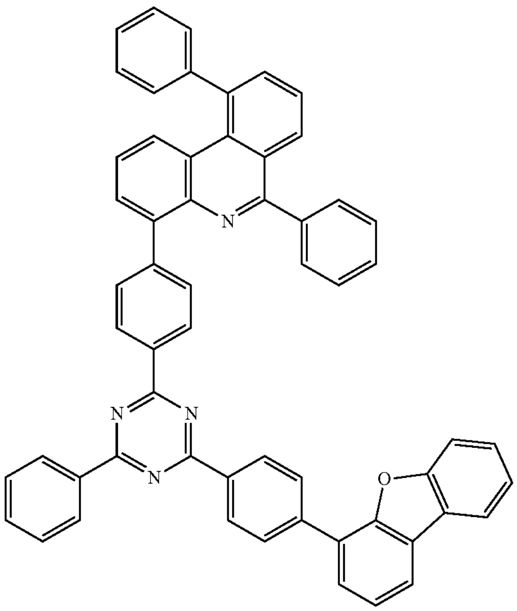

-continued
612
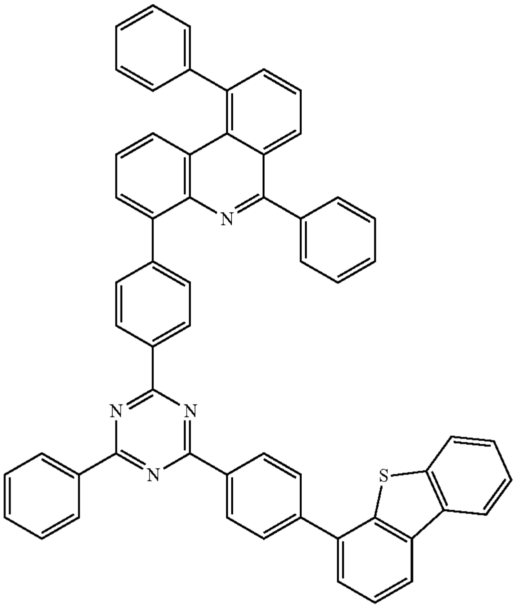
613
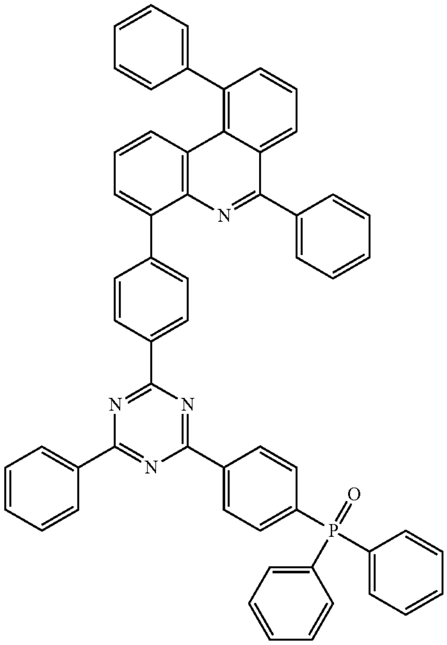
-continued
614
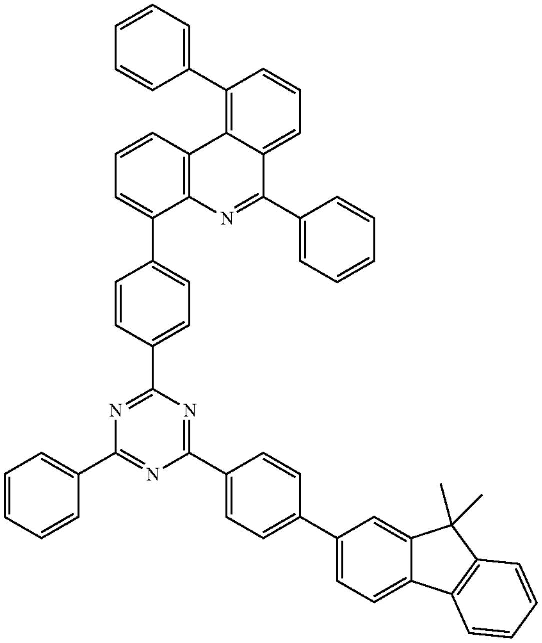
615
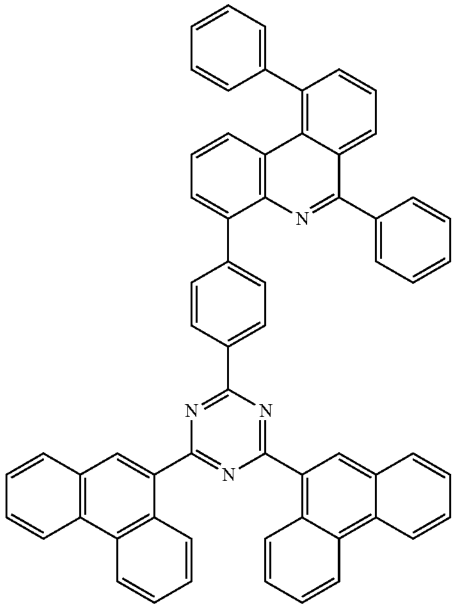

-continued
616
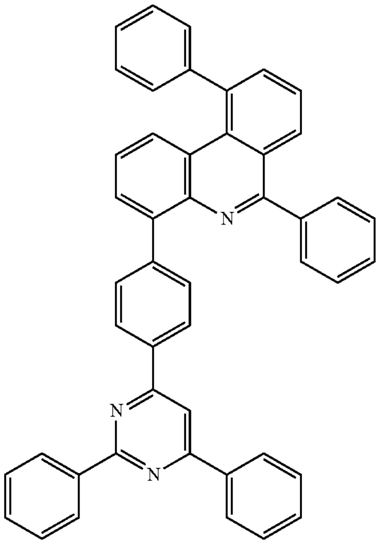
617
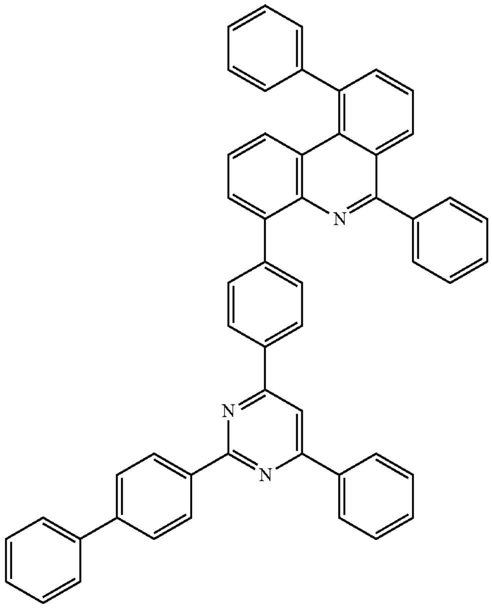
-continued
618
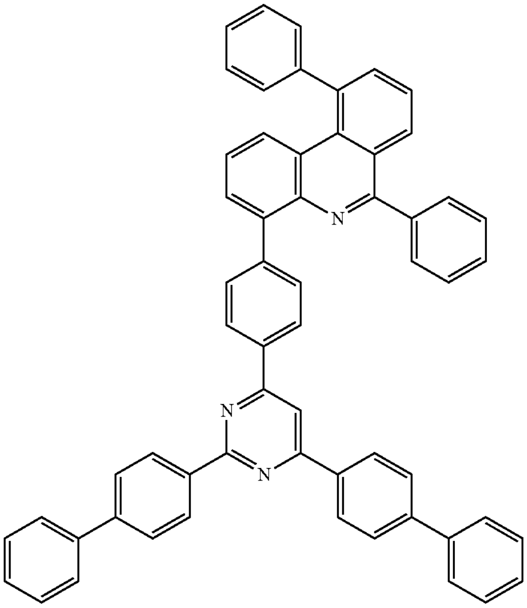
619
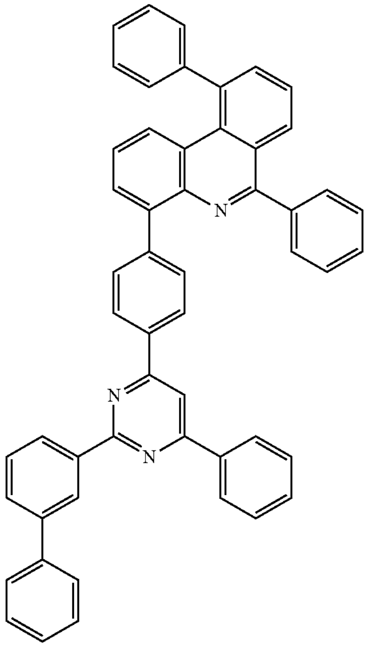

-continued
620
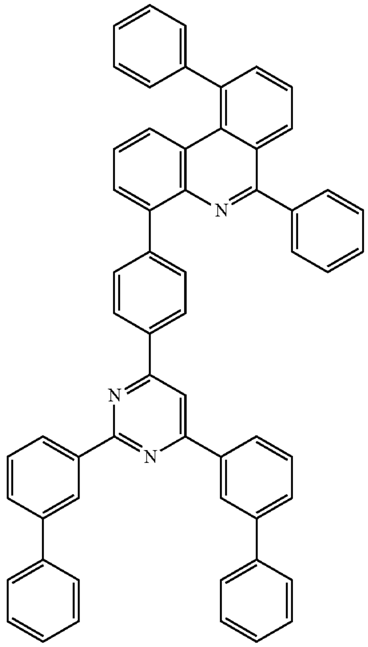
621
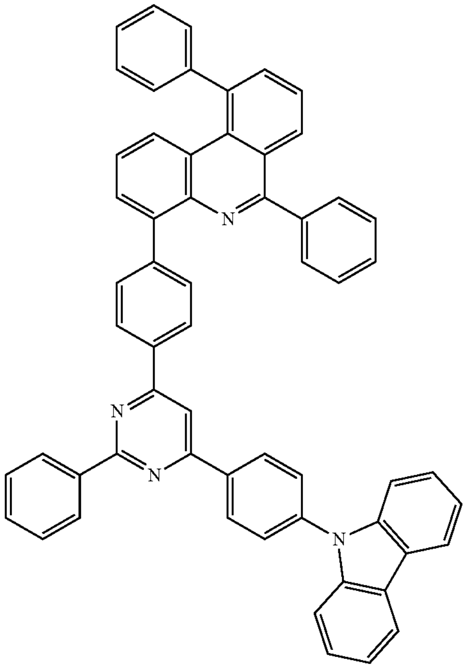
-continued
622
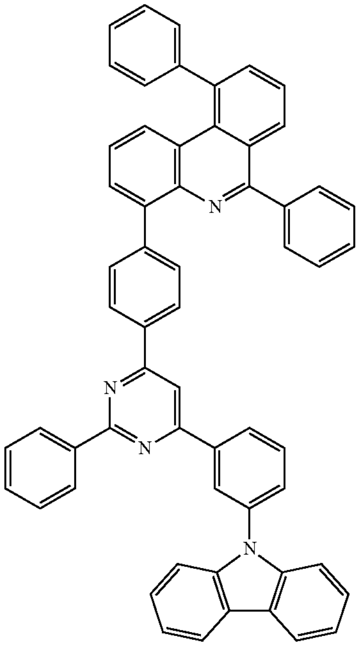
623
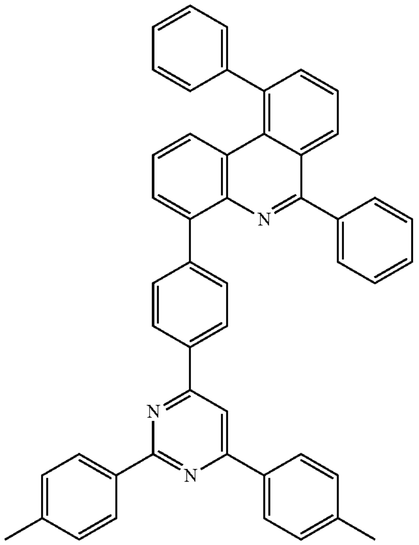

-continued
624
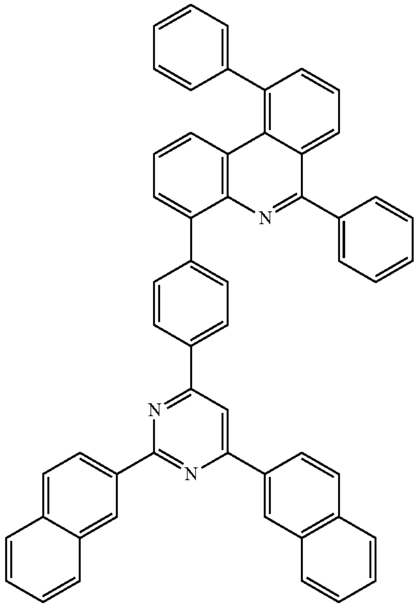
626
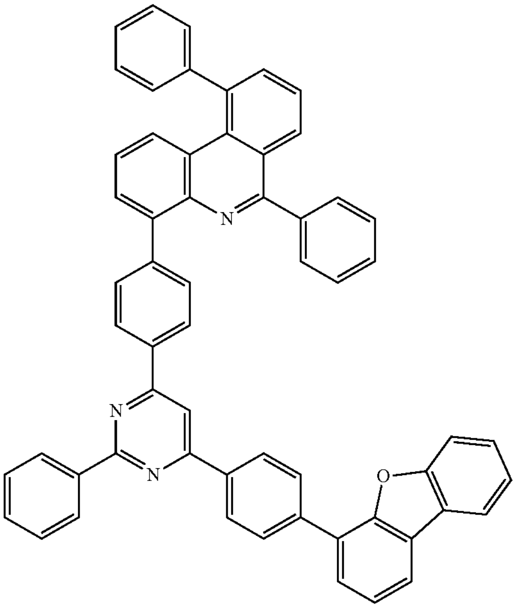
625
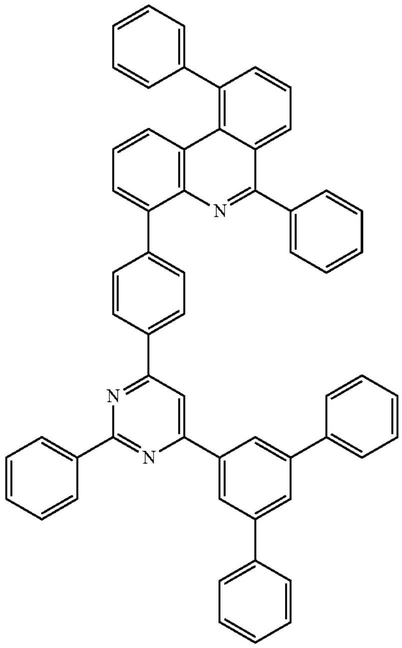
627
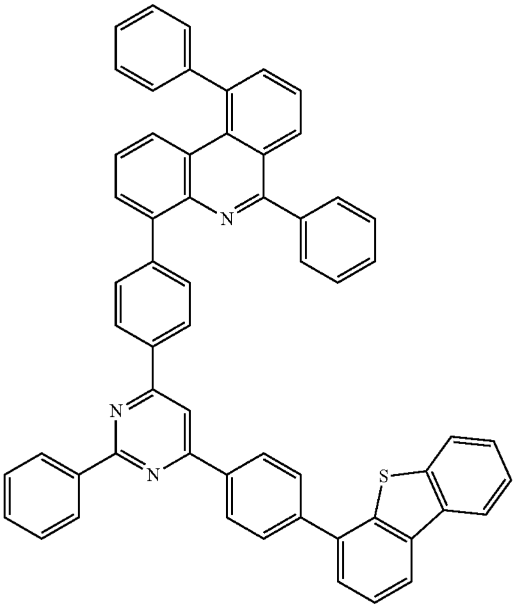

-continued
628
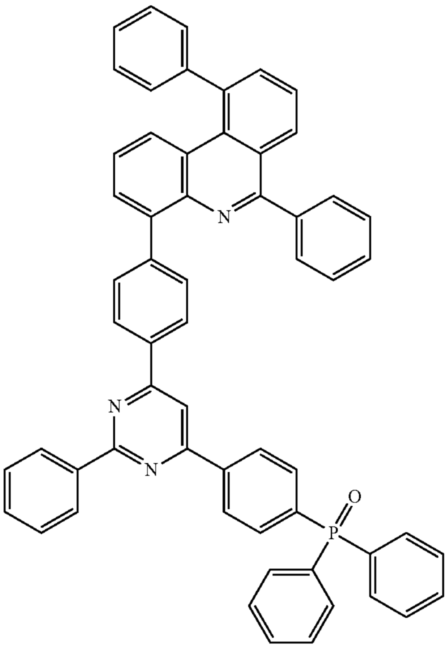
629
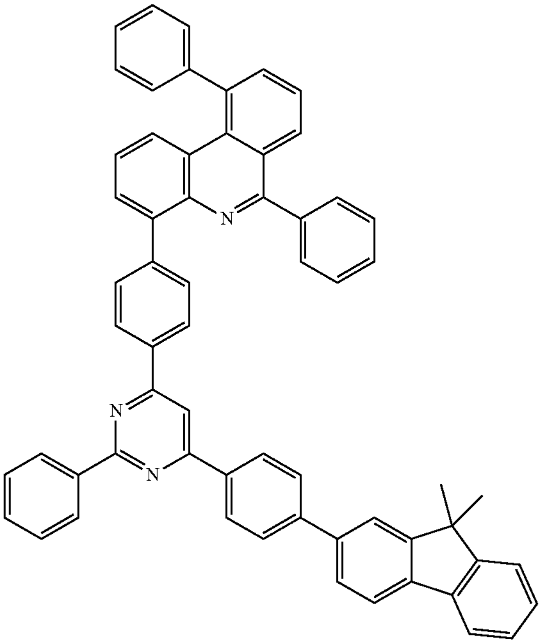
-continued
630
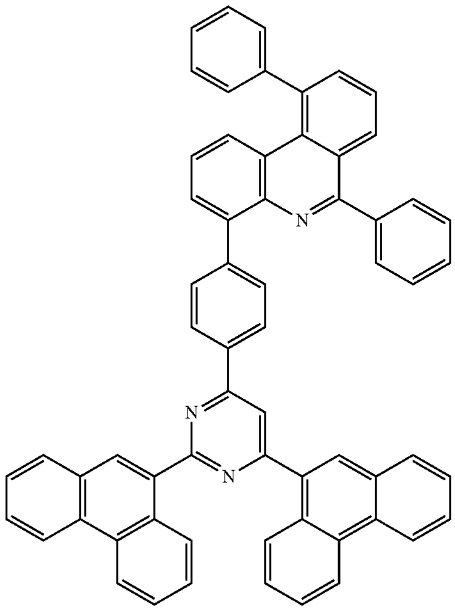
631
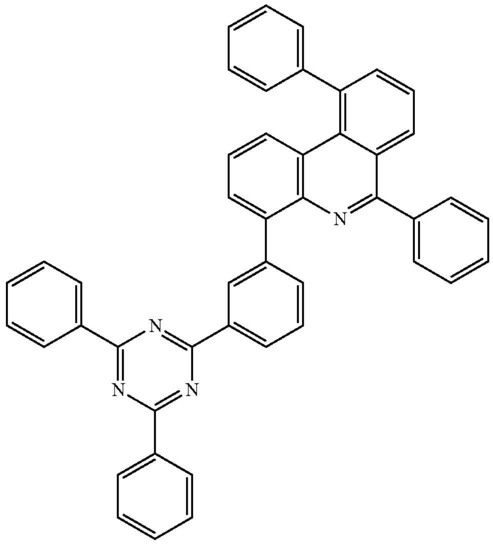

-continued
632
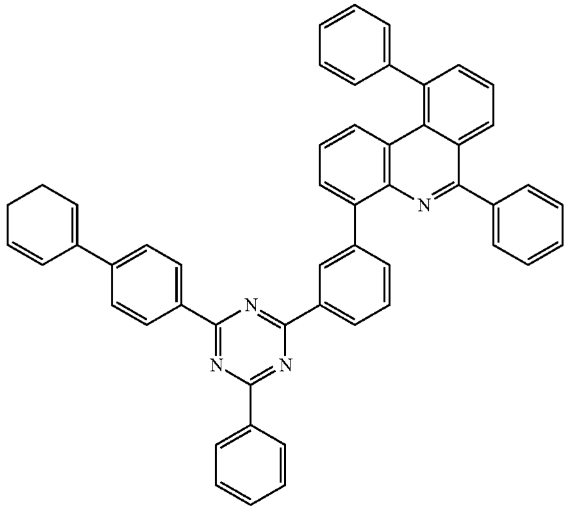
633
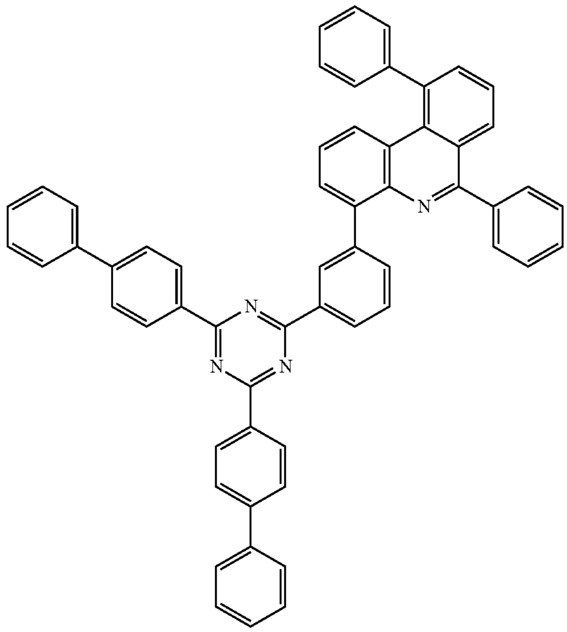
-continued
634
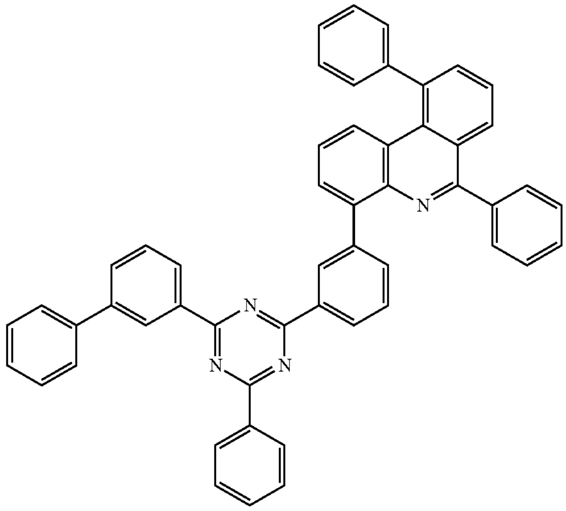
635
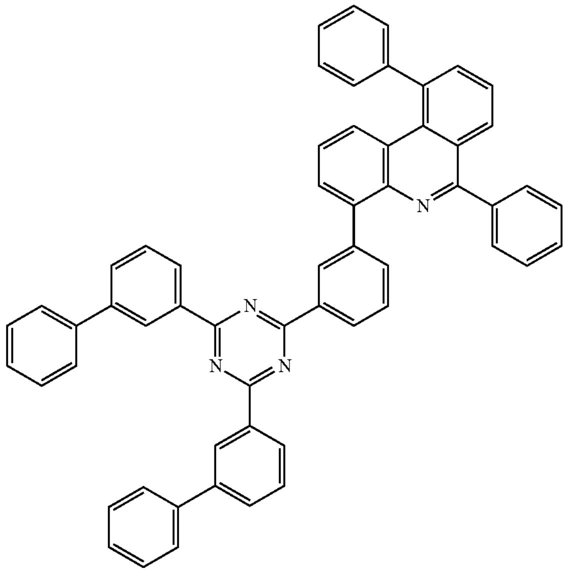

-continued
636
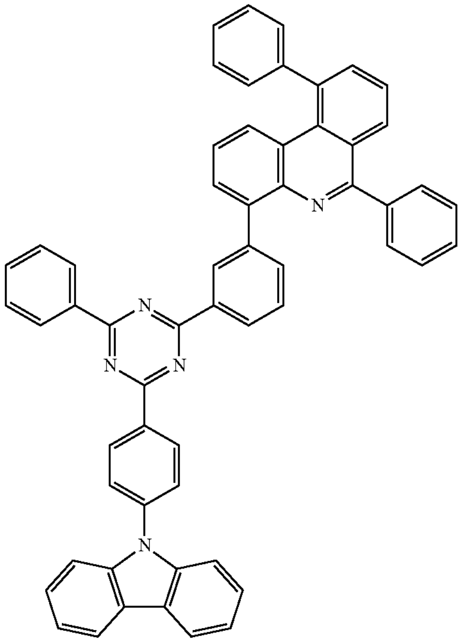
637
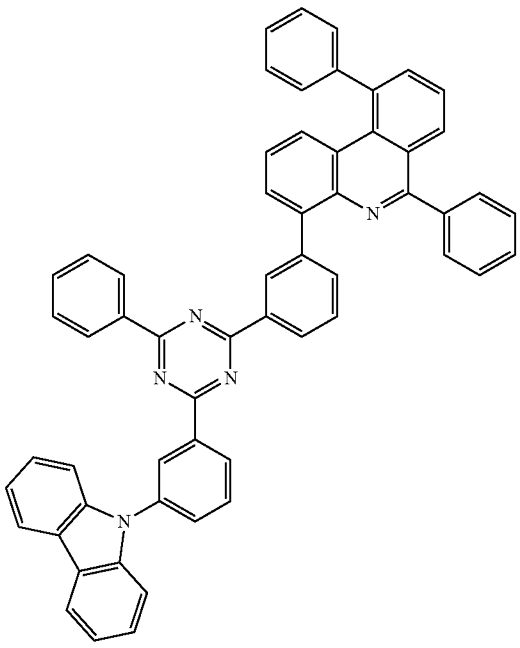
-continued
638
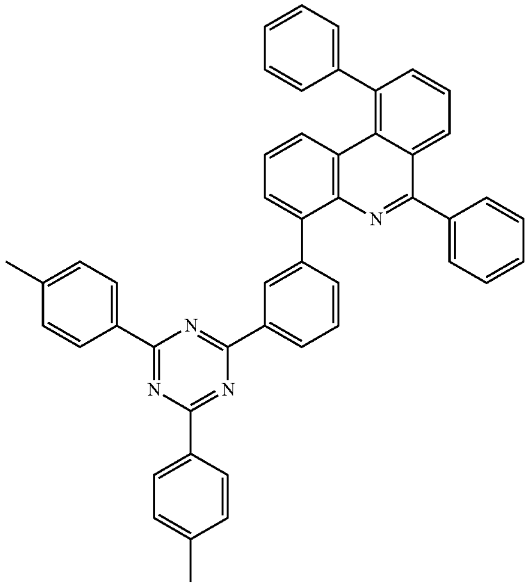
639
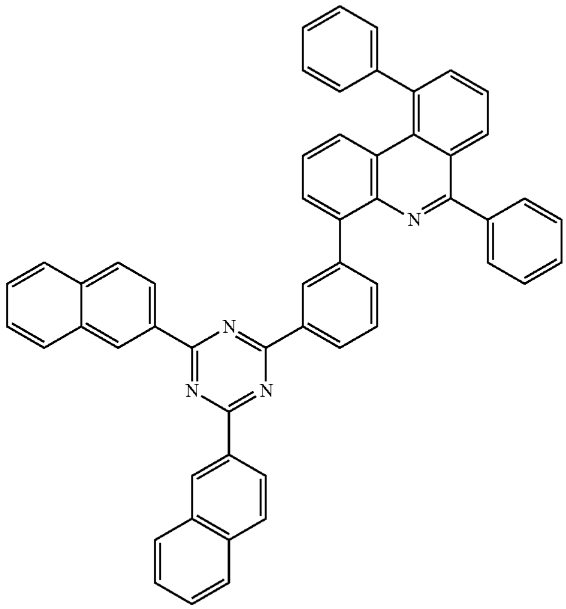

640
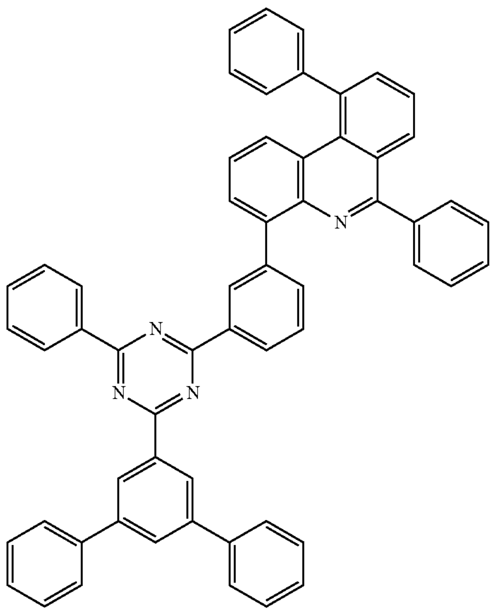
642
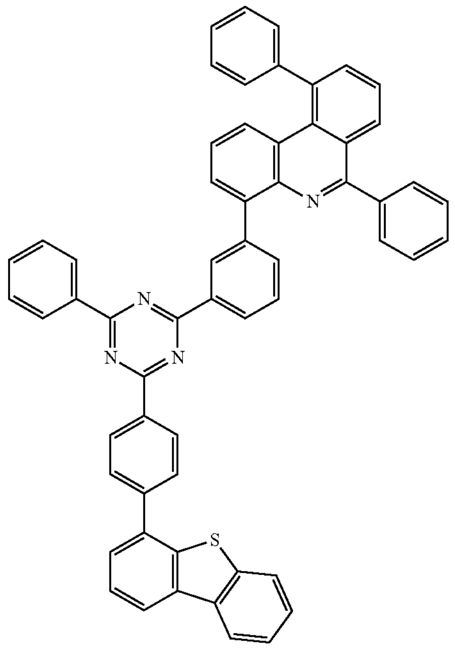
641
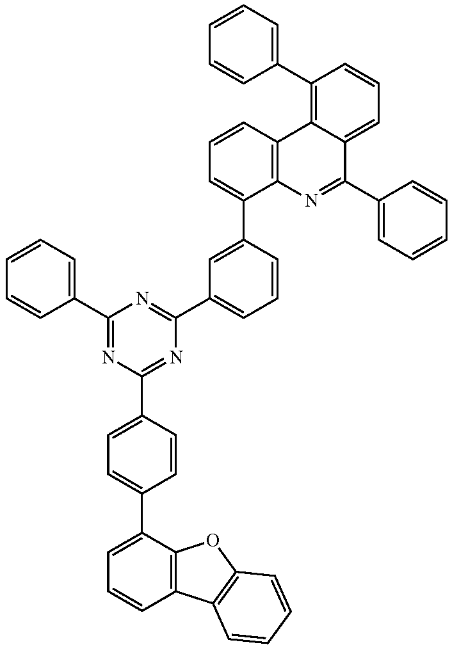
643
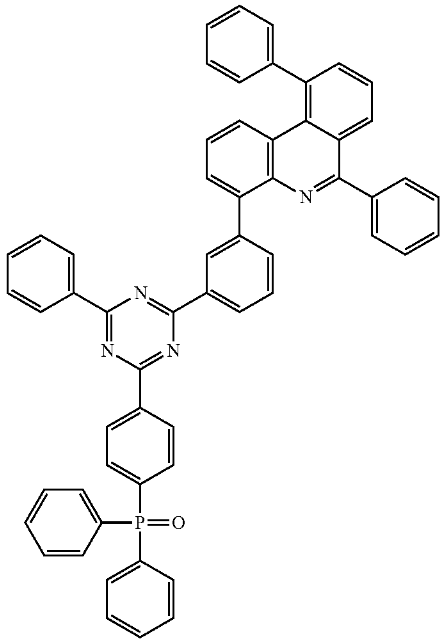

-continued
644
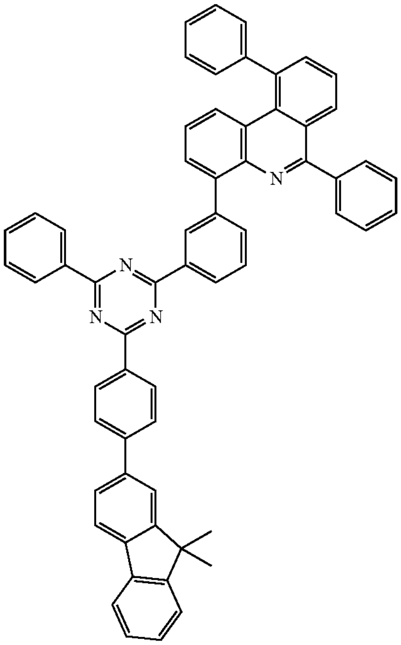
645
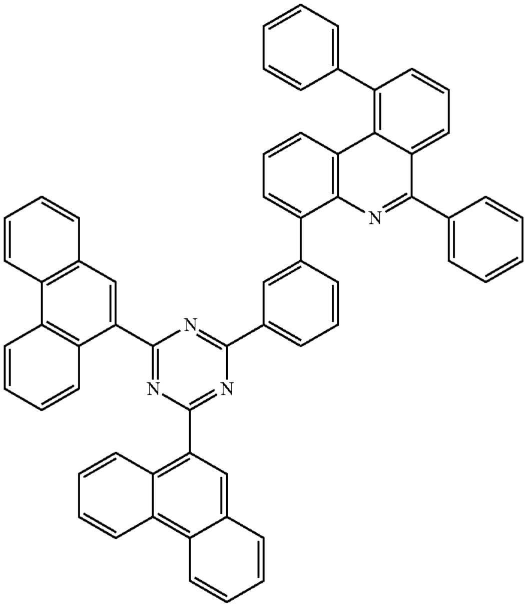
-continued
646
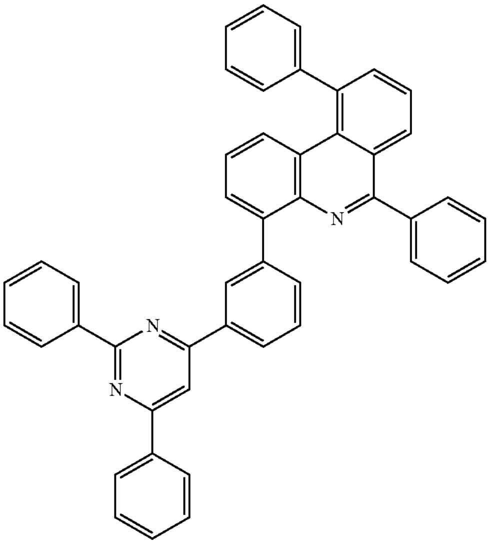
647
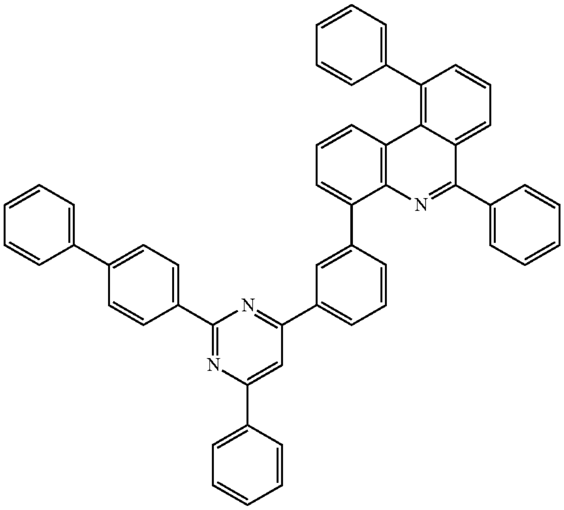

648
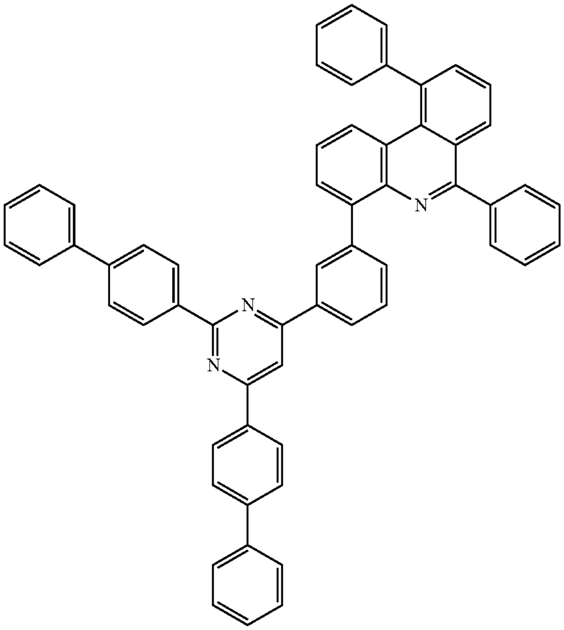
649
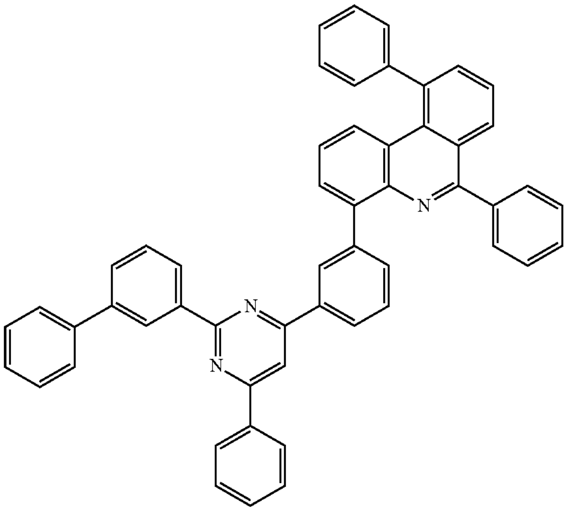
650
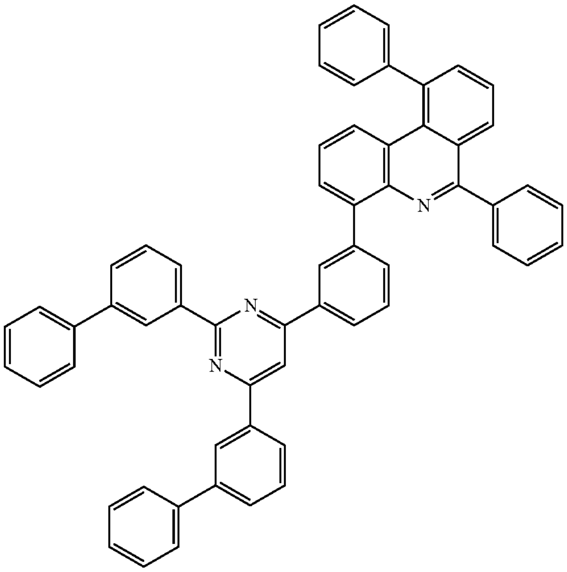
651
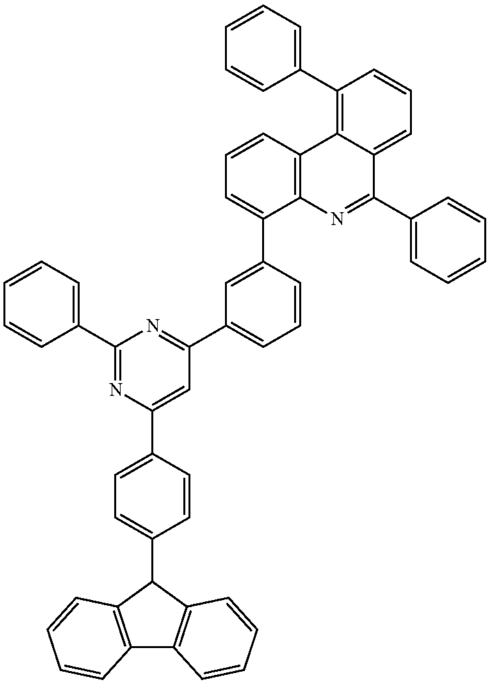

652
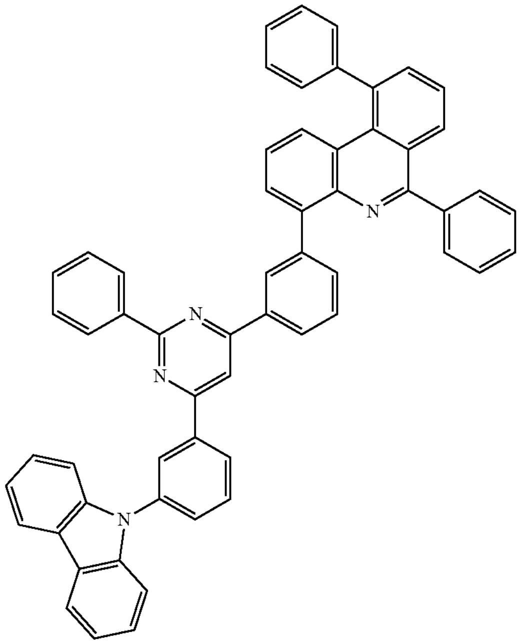
653
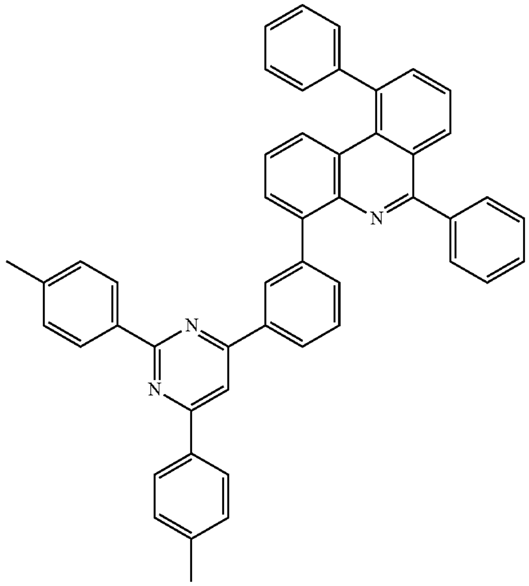
654
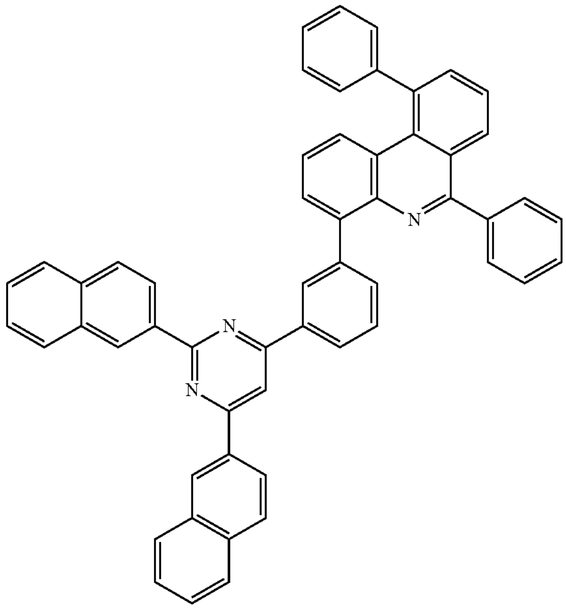
655
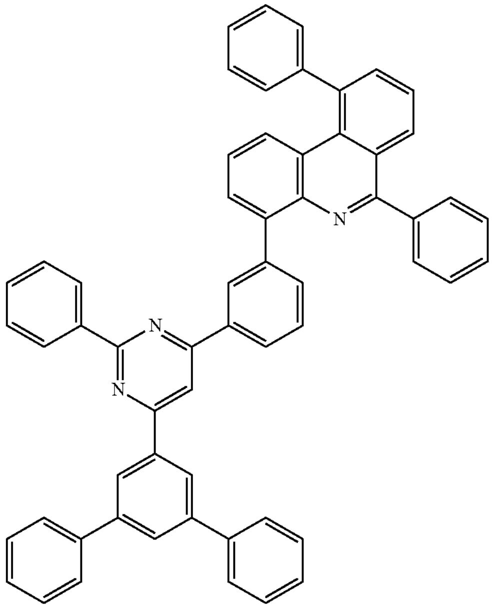

-continued
656
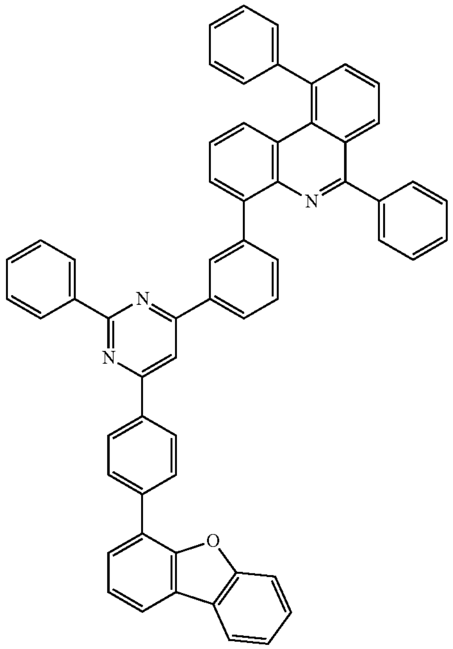
657
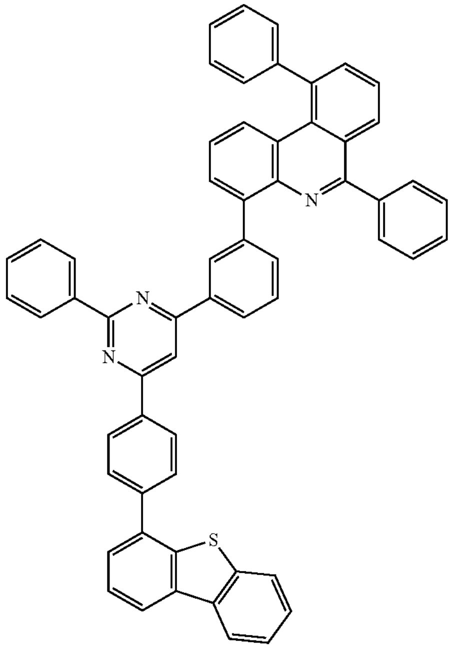
-continued
658
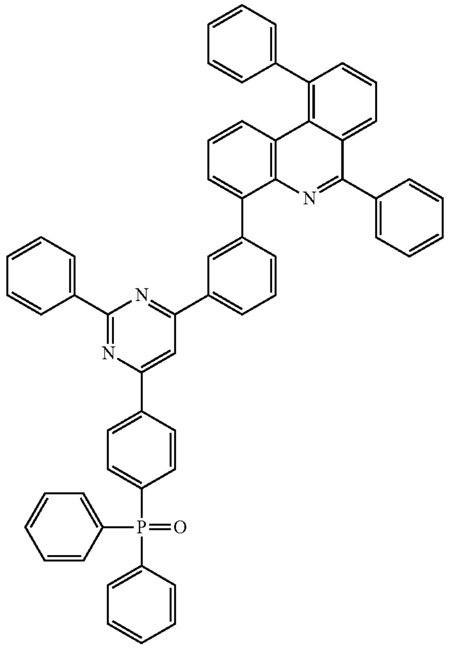
659
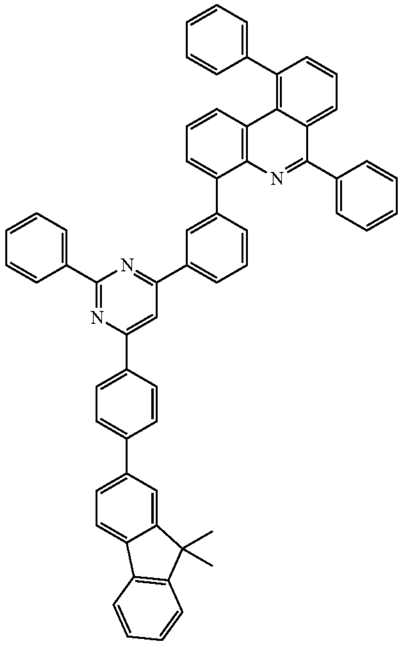

-continued
660
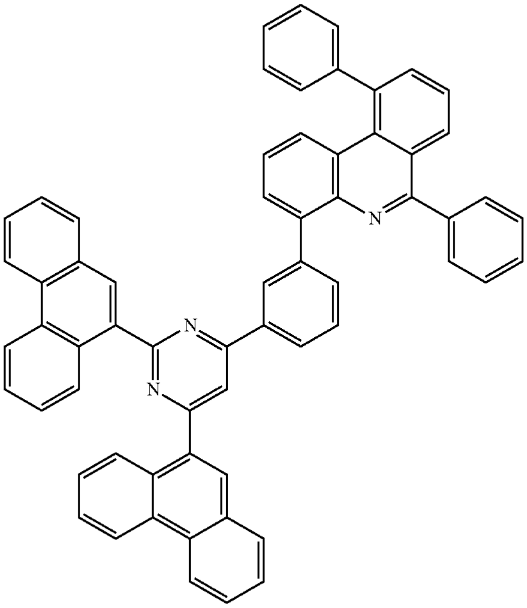
661
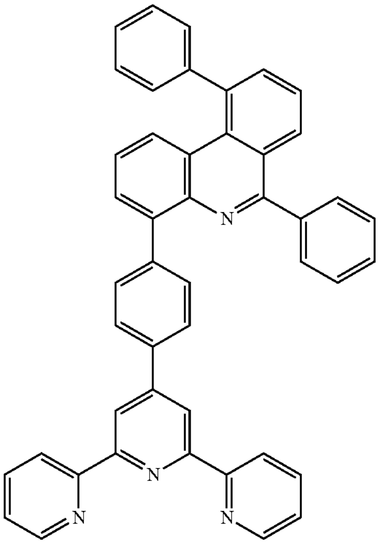
662
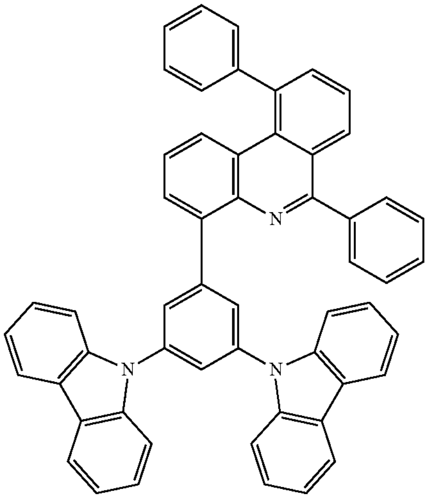
-continued
663
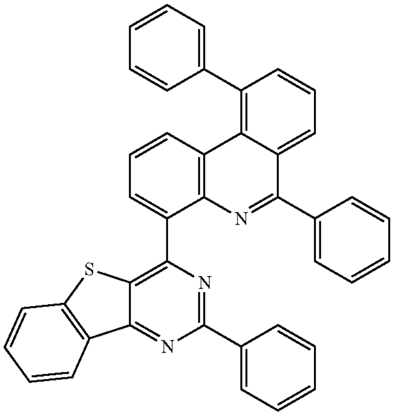
664
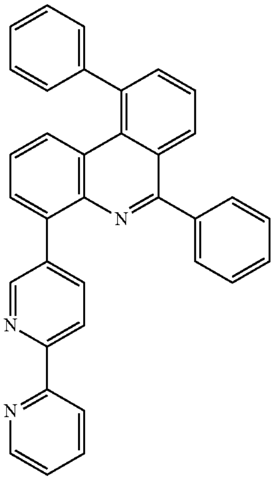
665
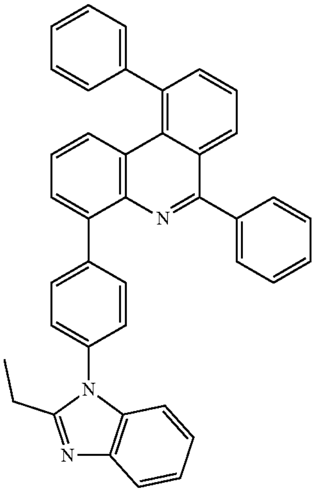

-continued
666
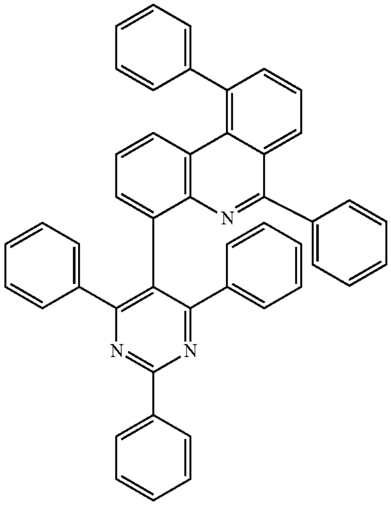
667
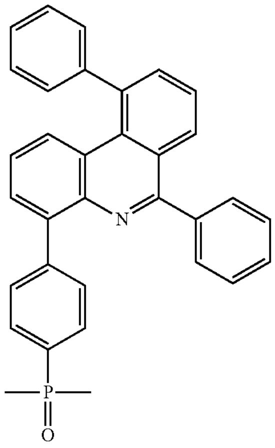
668
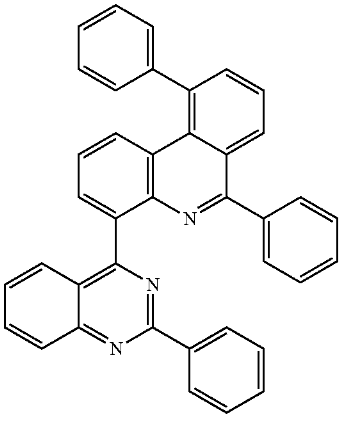
-continued
669
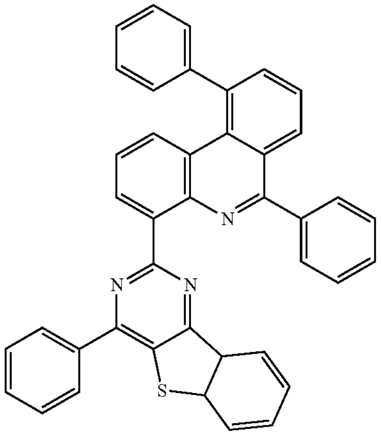
670
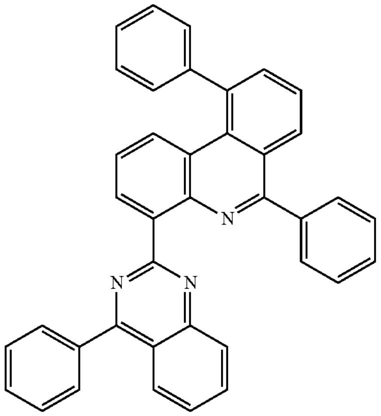
671
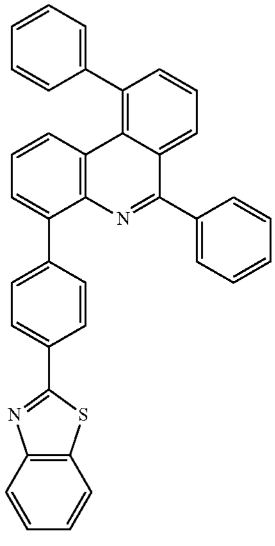

-continued
672
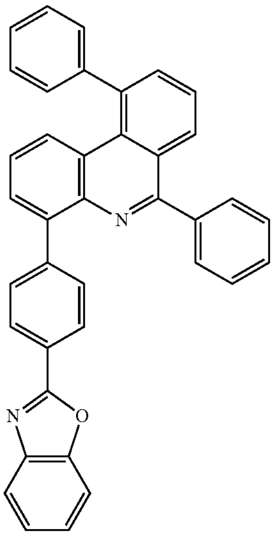
673
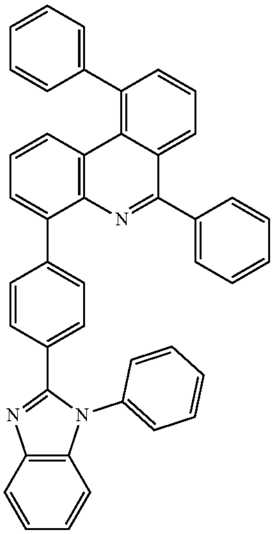
674
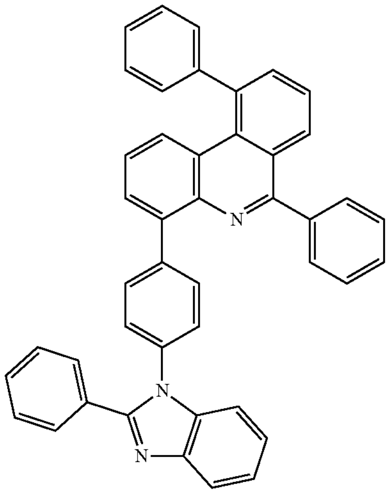
-continued
675
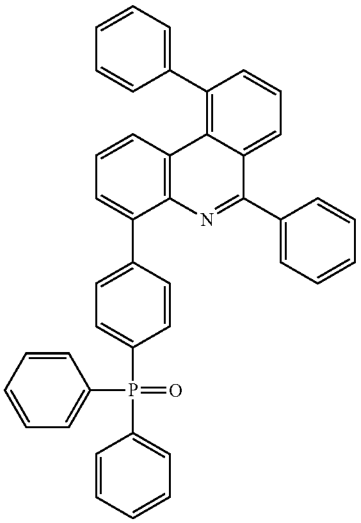
676
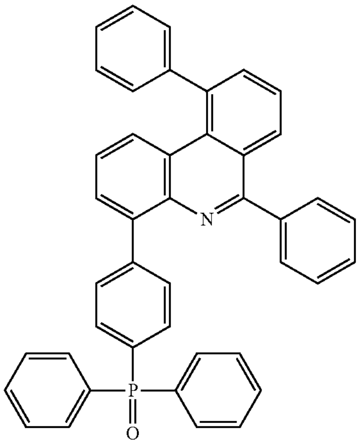
677
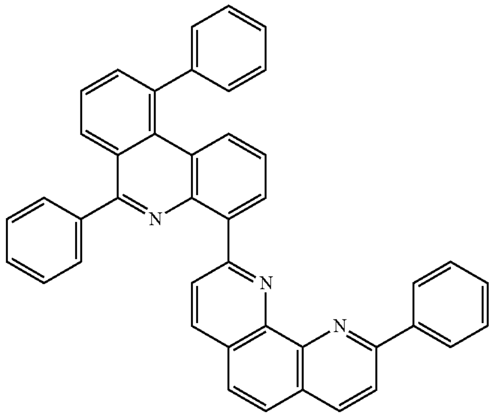

-continued
678
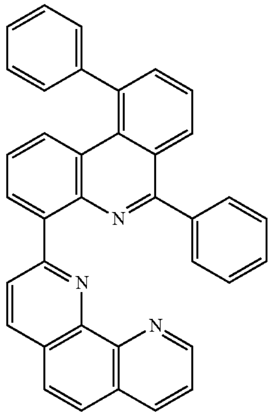
679
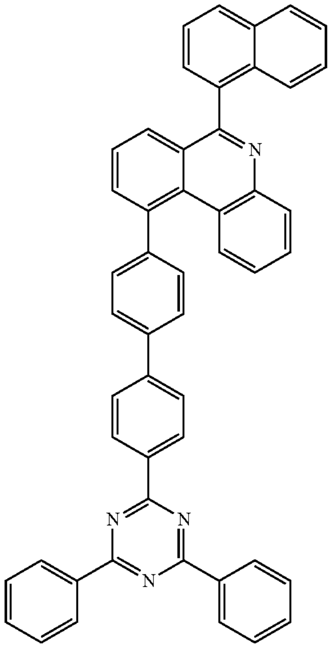
-continued
680
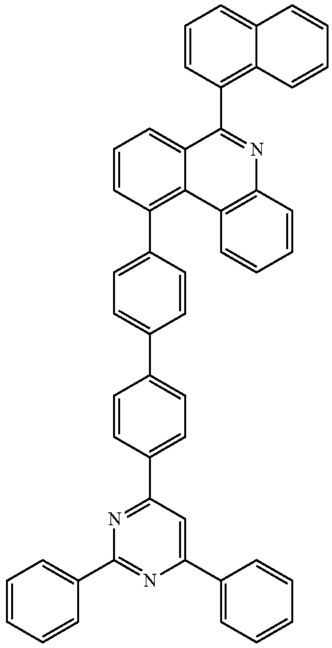
681
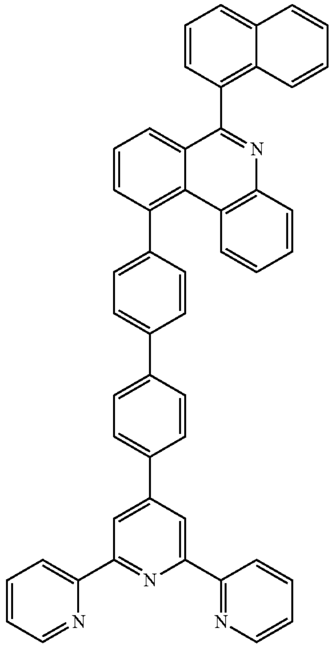

682
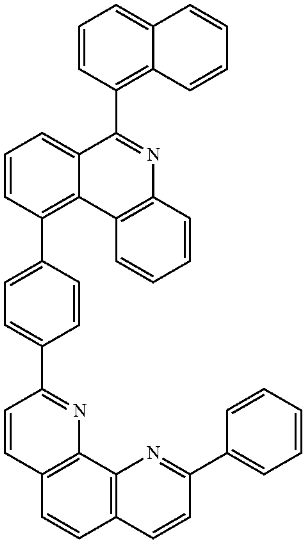
684
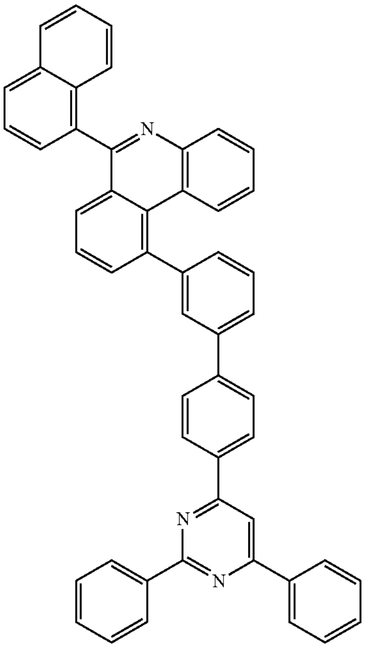
683
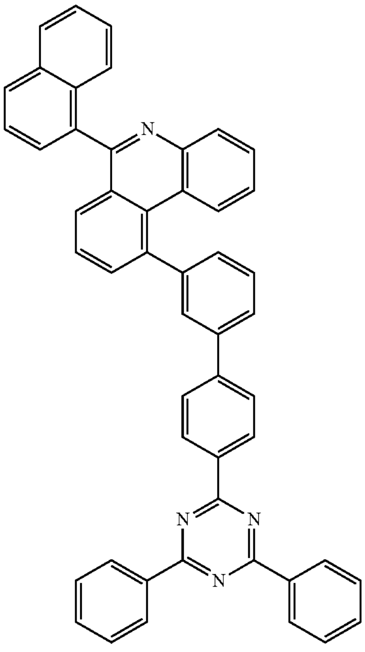
685
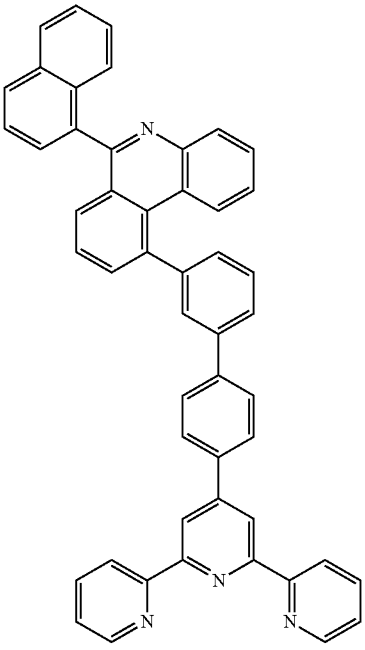

-continued
686
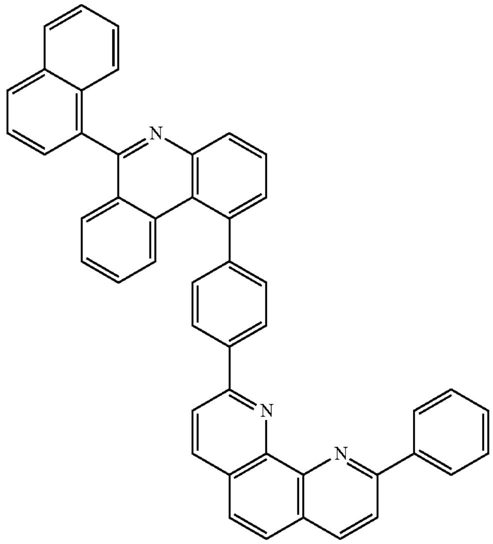
687
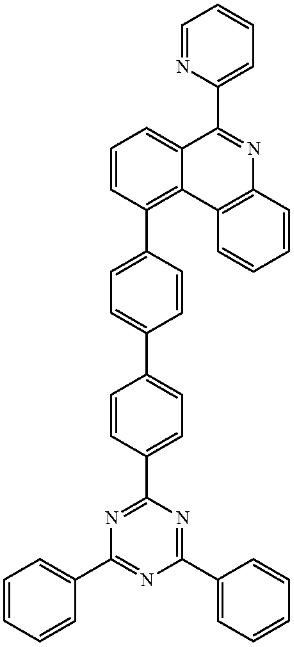
-continued
688
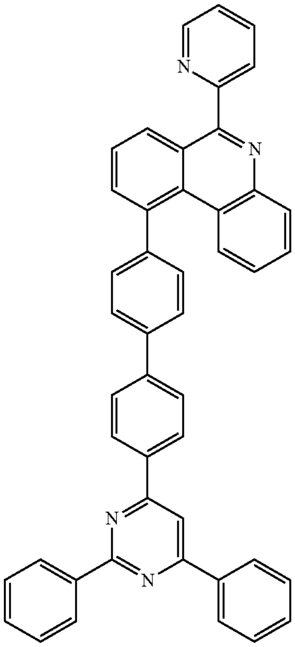
689
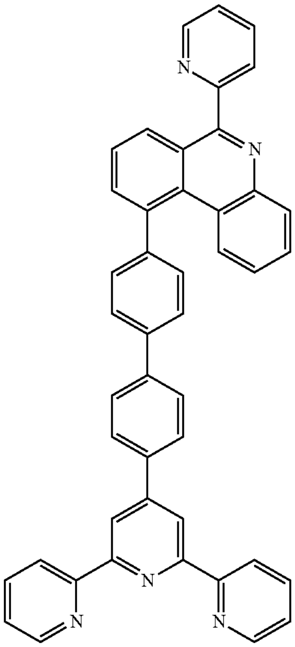

-continued
690
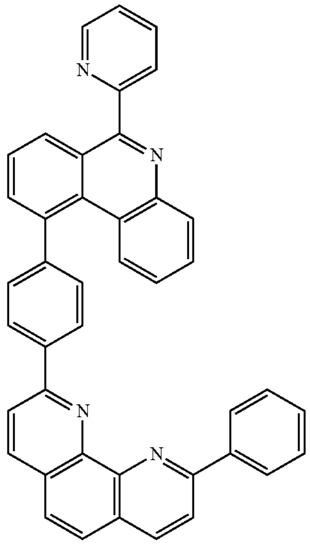
691
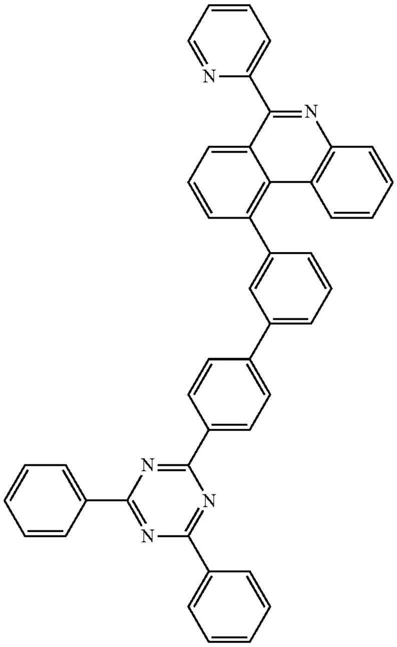
-continued
692
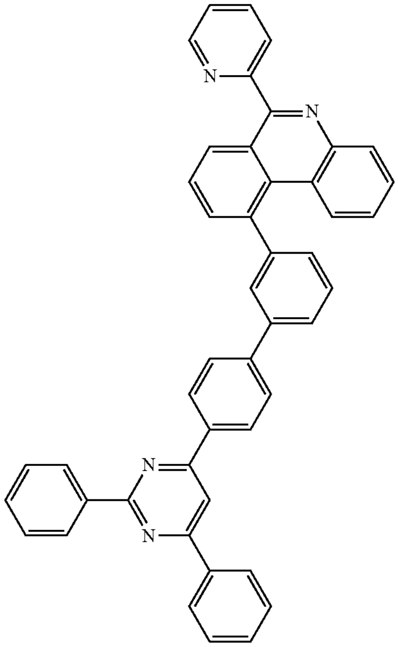
693
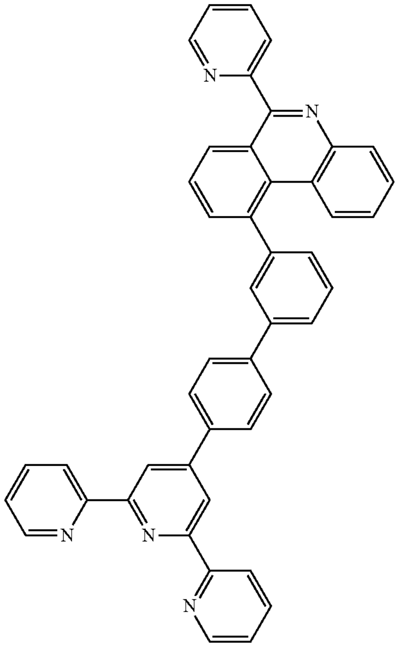

-continued
694
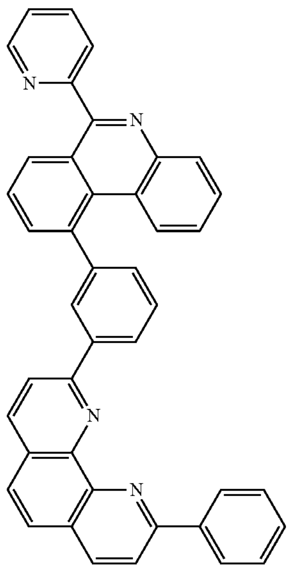
695
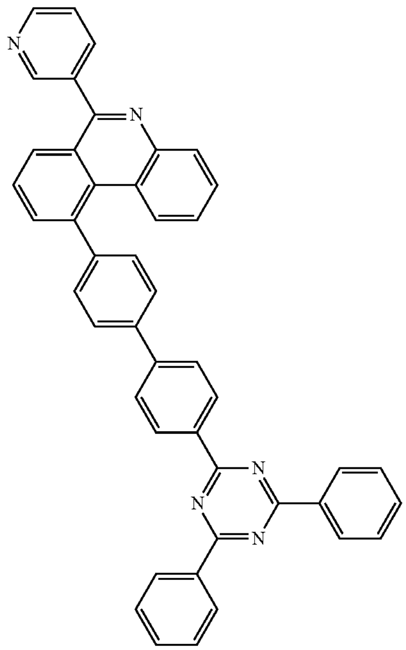
-continued
696
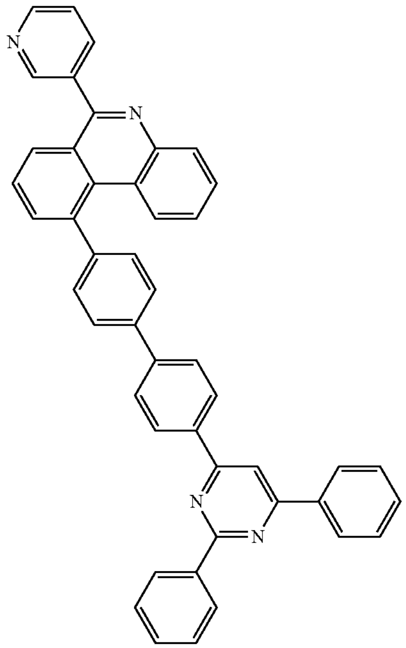
697
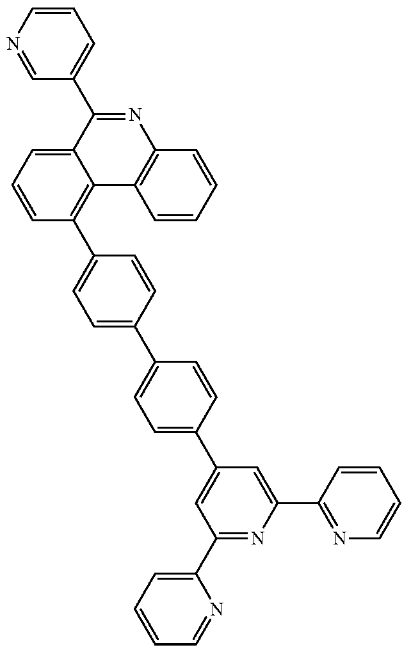

-continued
698
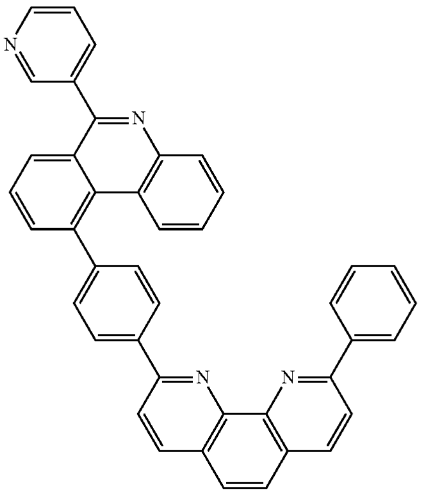
699
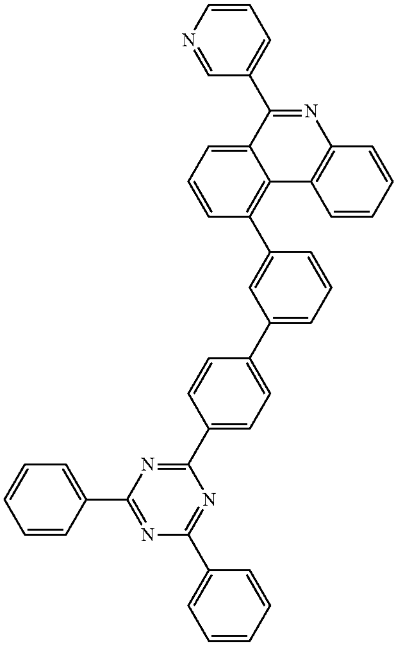
-continued
700
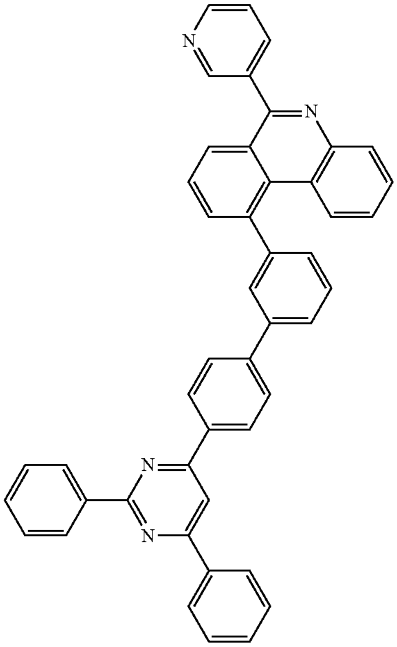
701
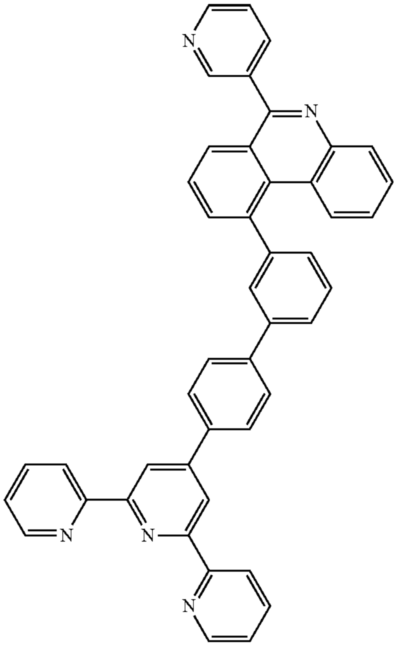

-continued
702
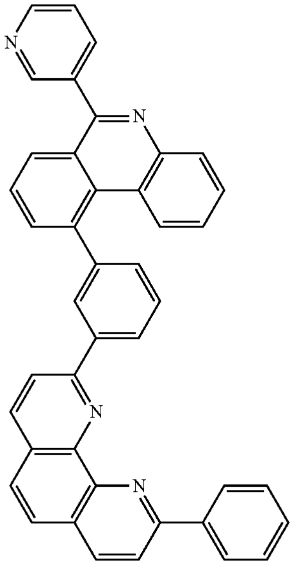
703
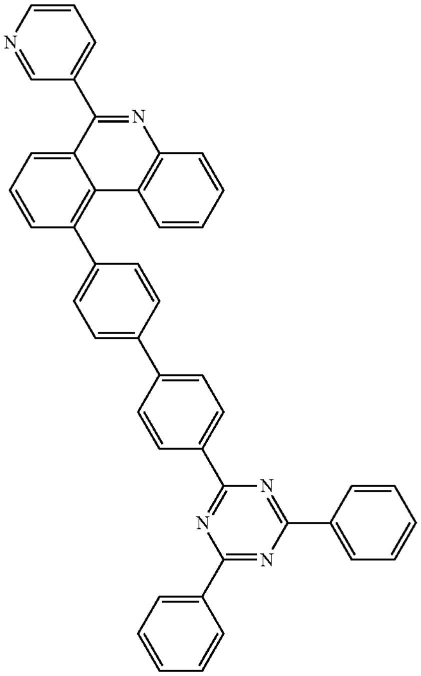
-continued
704
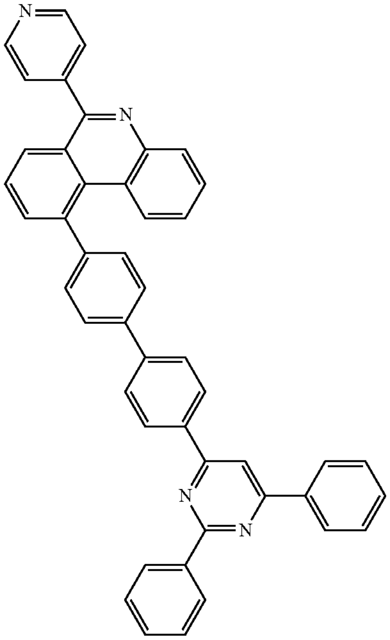
705
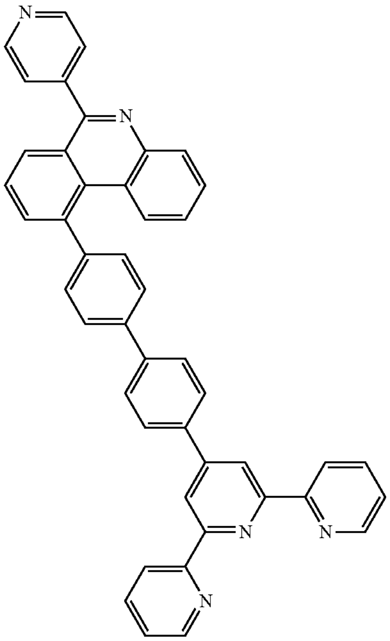

-continued
706
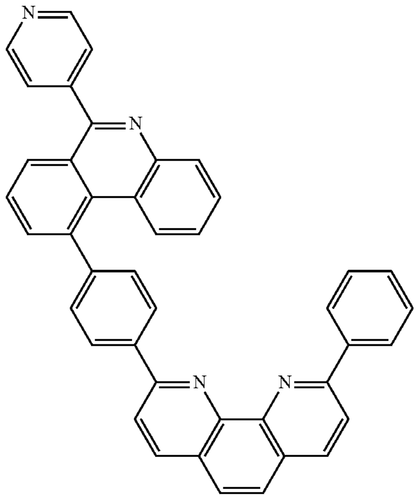
707
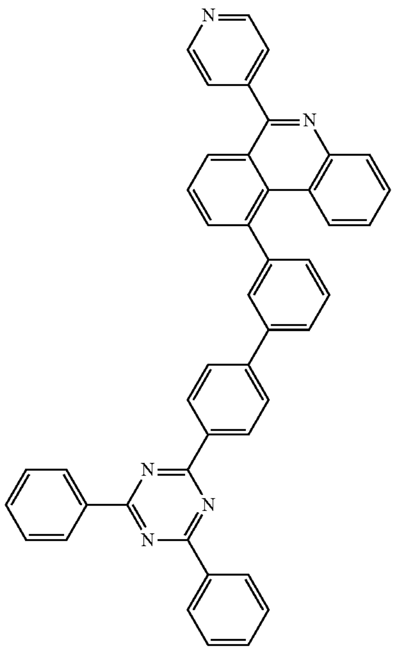
-continued
708
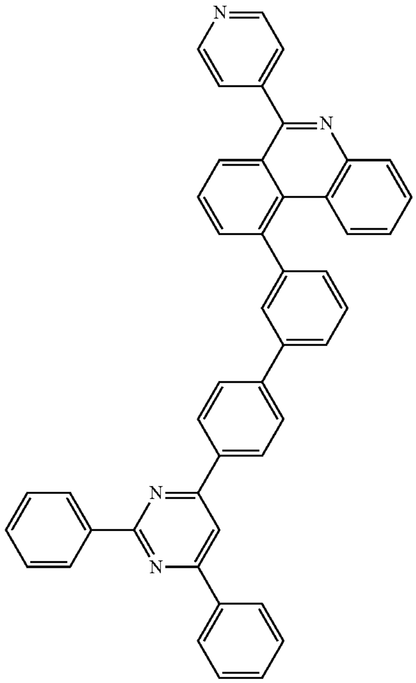
709
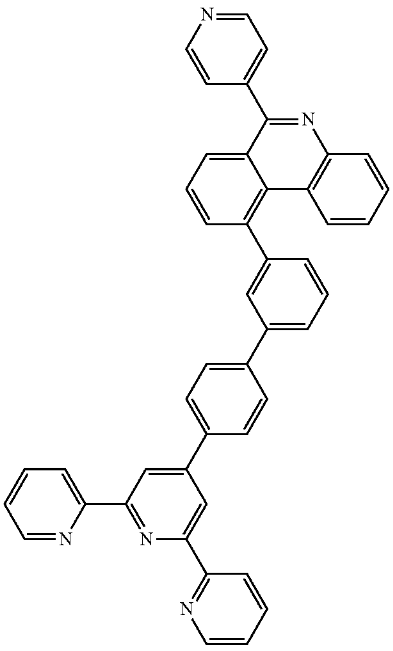

-continued
710
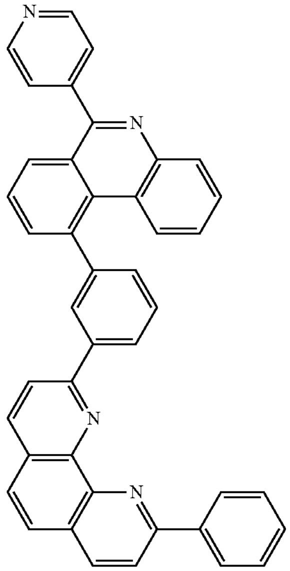
711
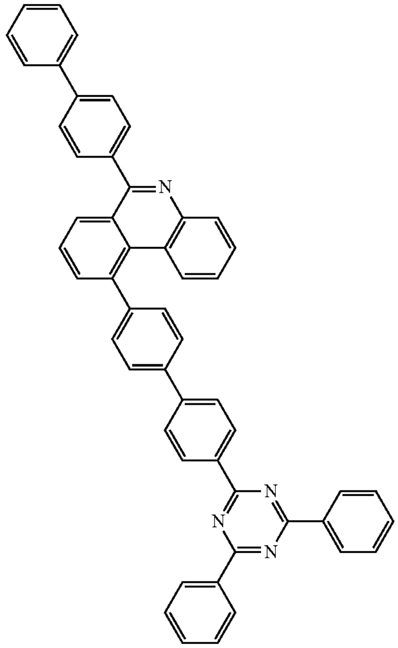
-continued
712
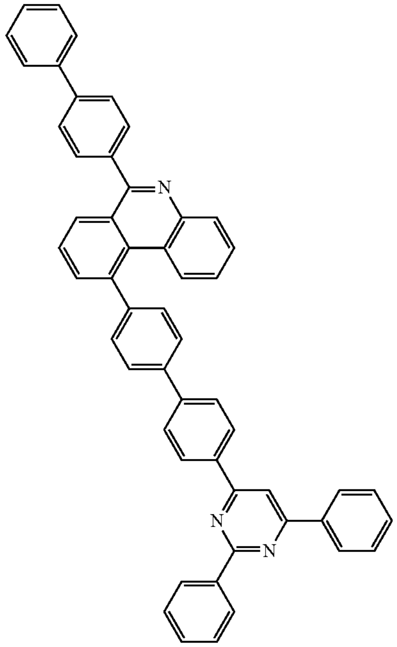
713
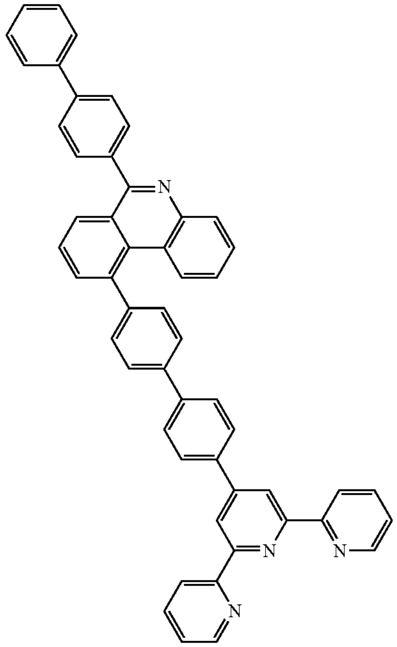

-continued
714
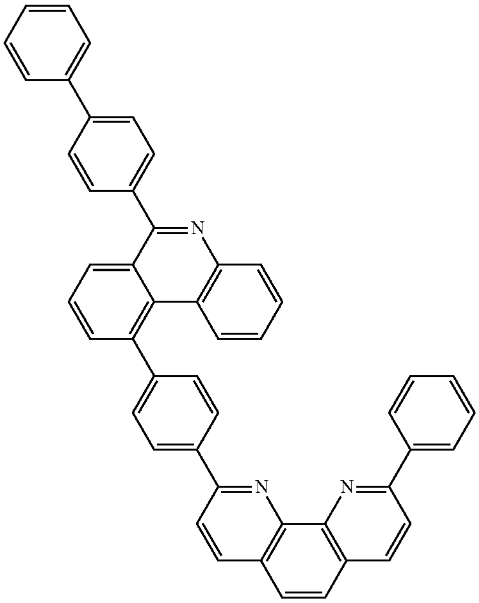
715
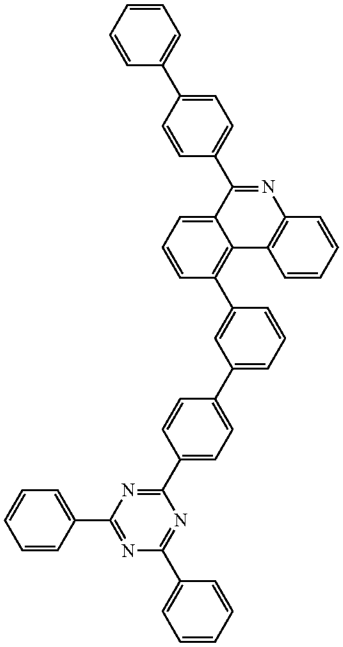
-continued
716
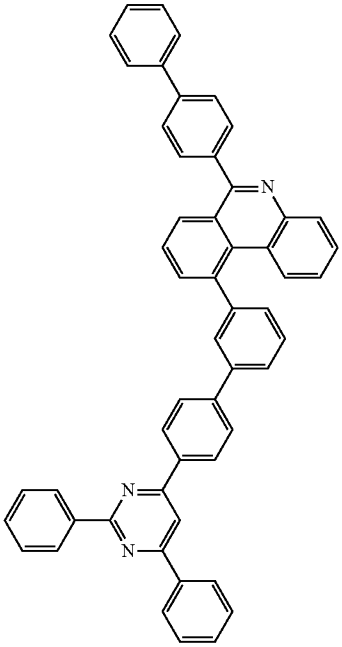
717
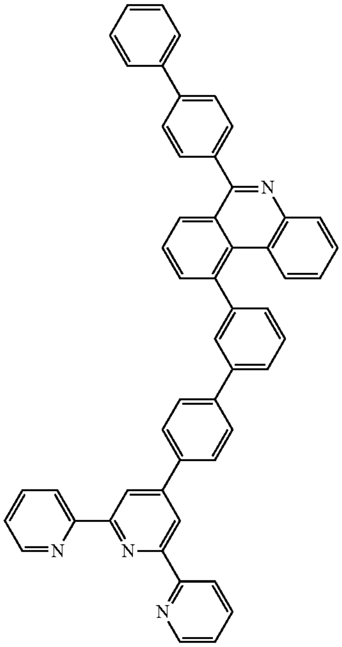

-continued
718
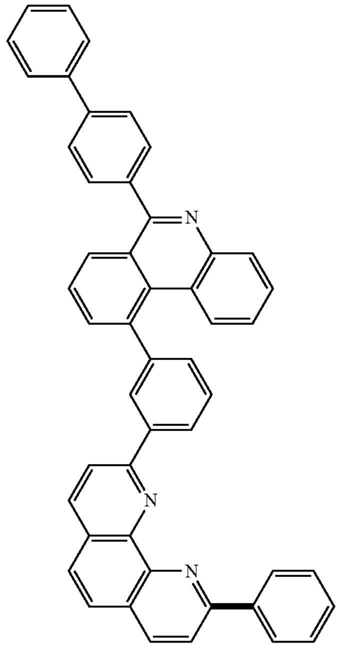
719
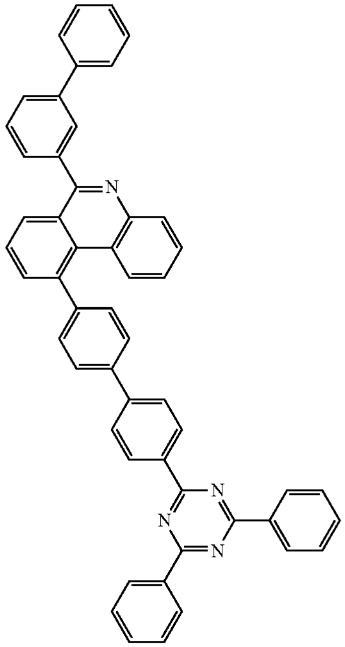
-continued
720
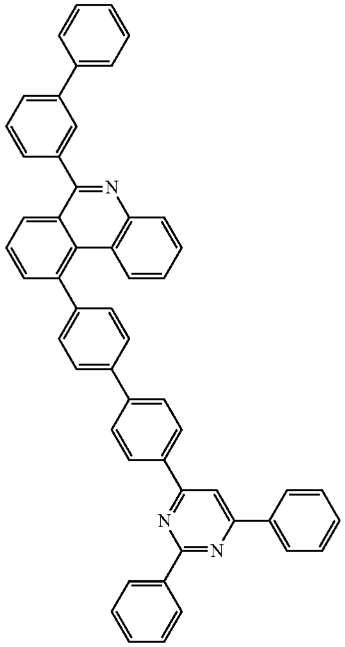
721
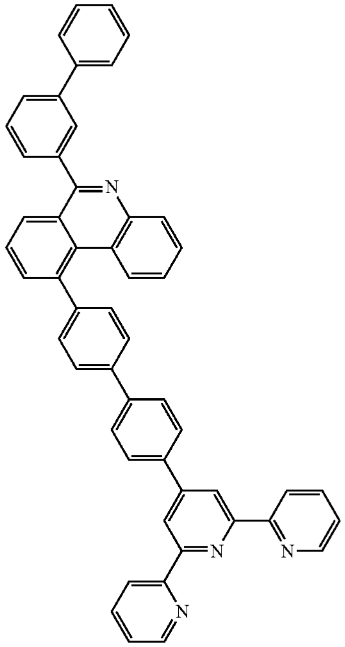

-continued
722
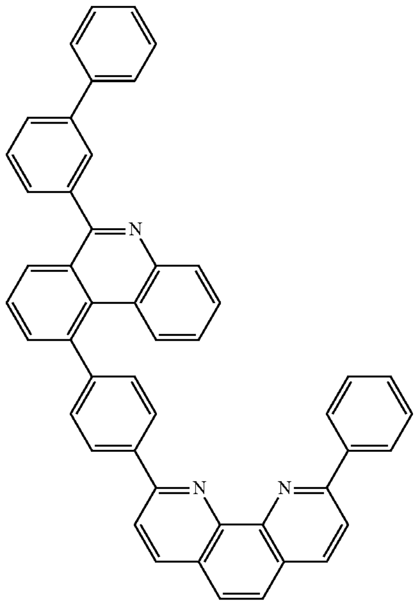
723
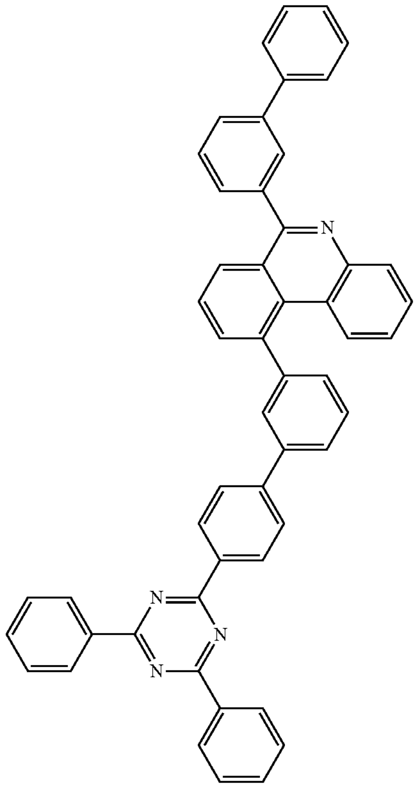
-continued
724
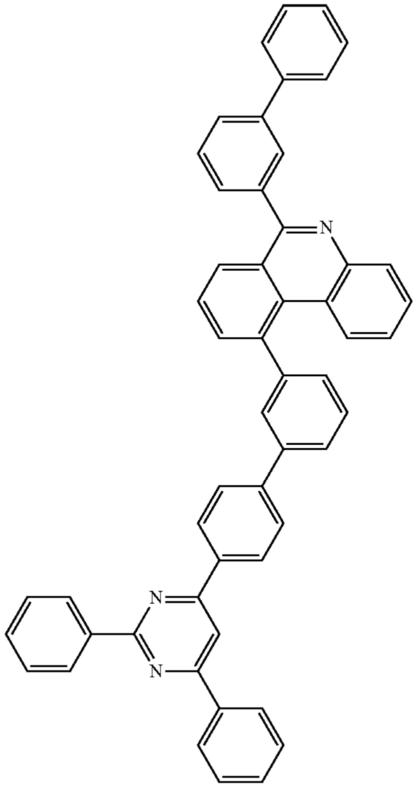
725
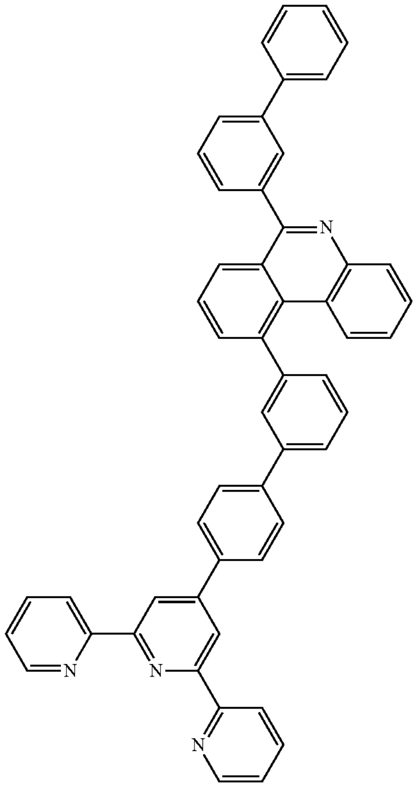

-continued
726
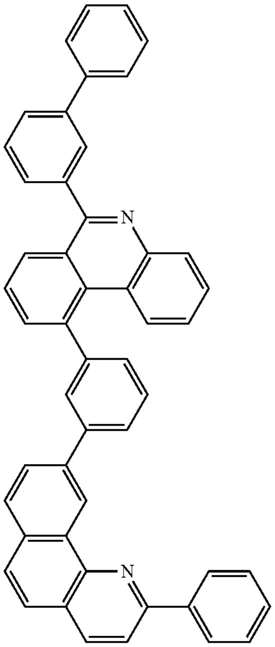
727
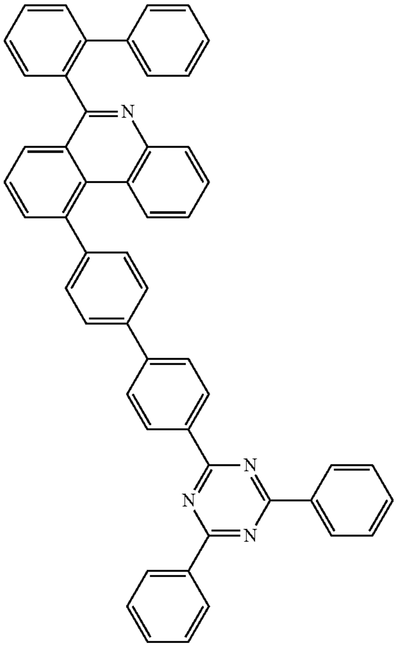
-continued
728
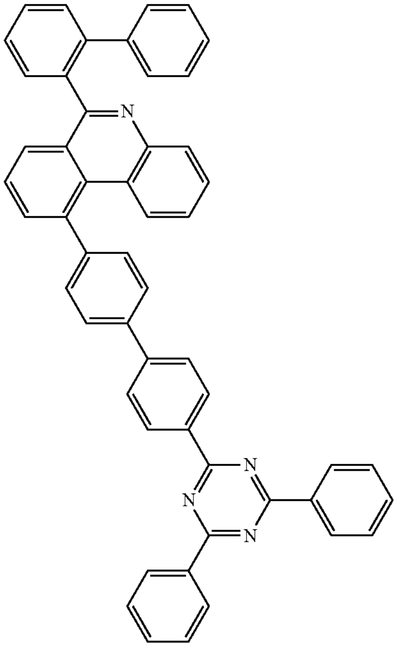
729
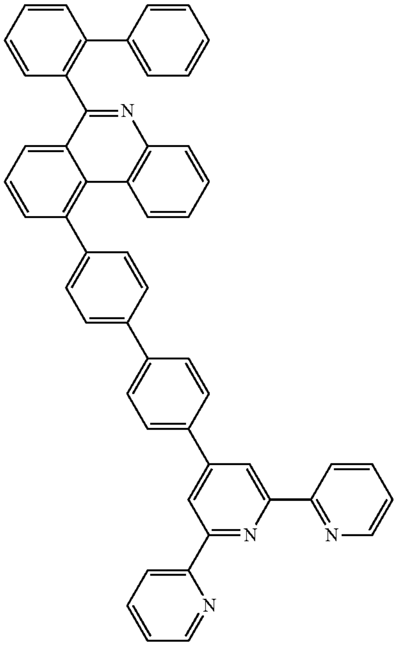

-continued
730
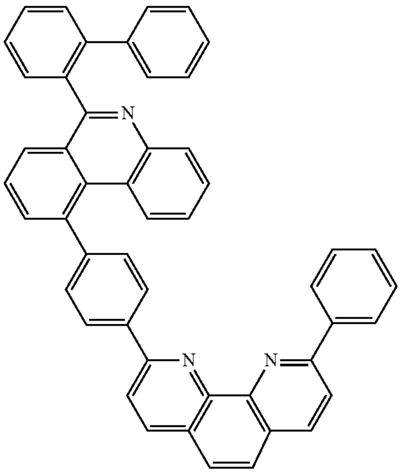
731
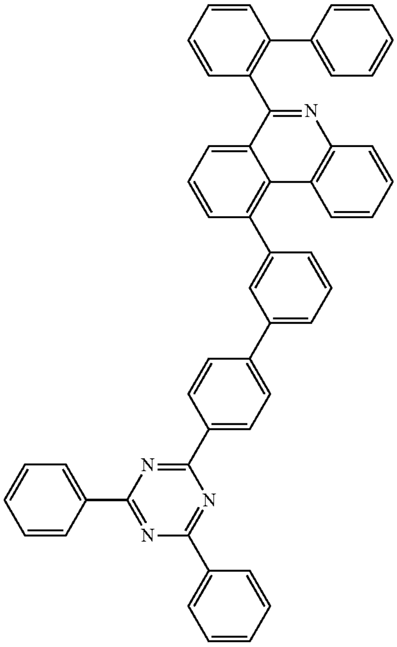
-continued
732
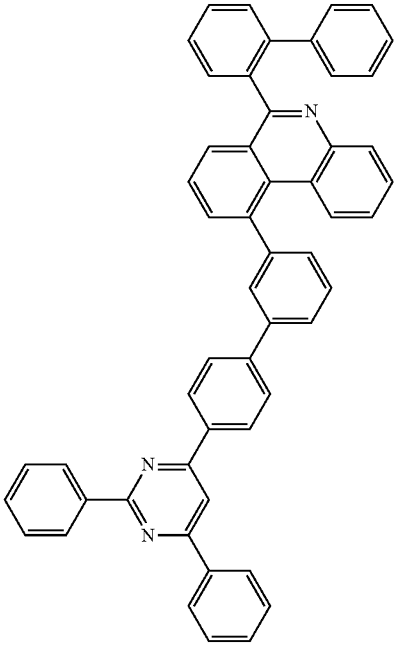
733
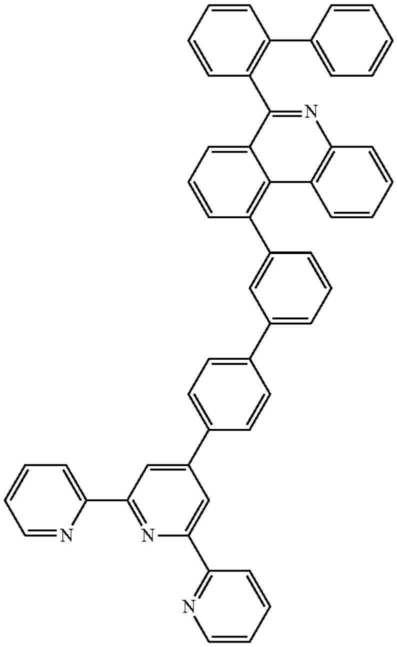

734
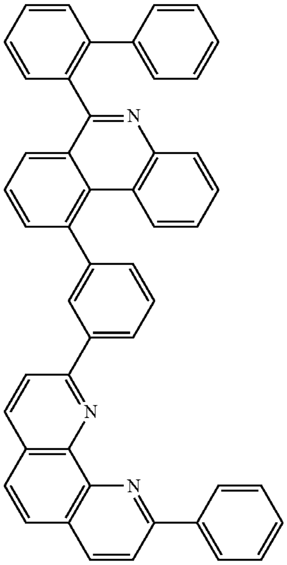
735
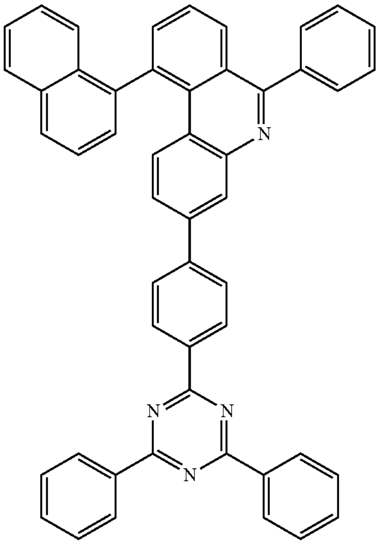
736
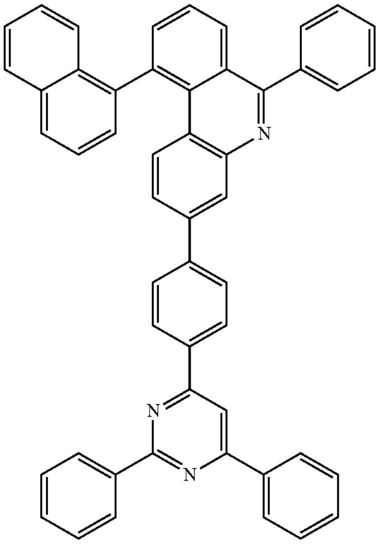
737
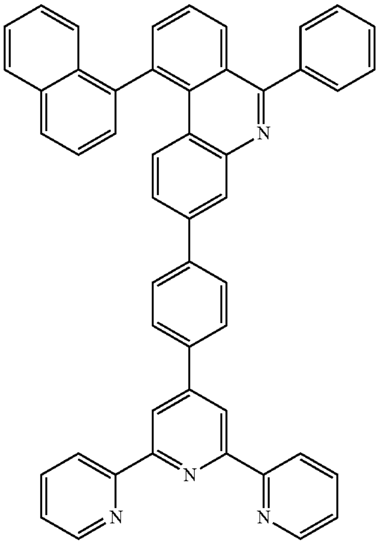
738
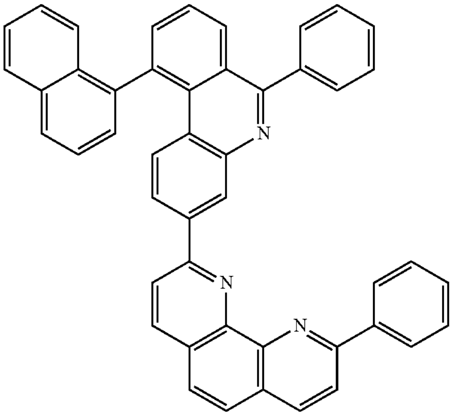
739
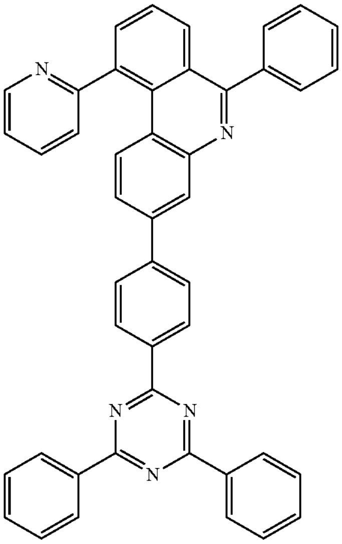

-continued
740
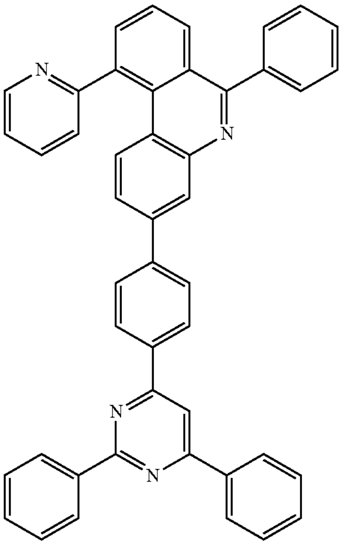
741
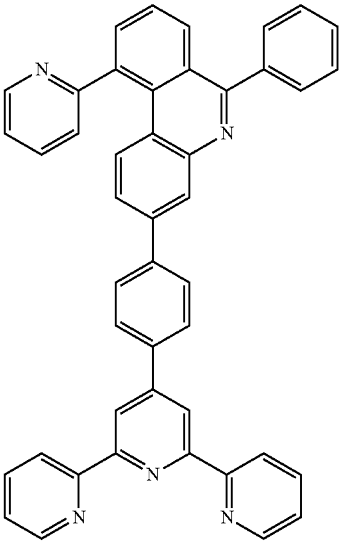
742
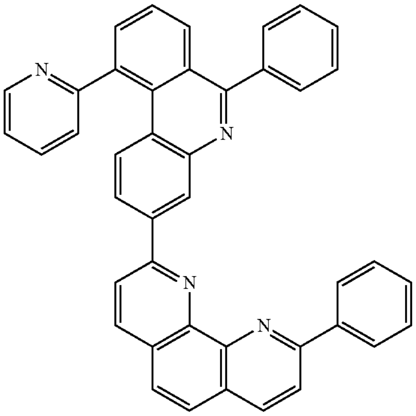
-continued
743
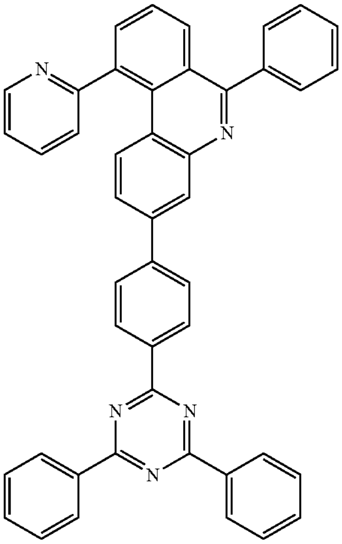
744
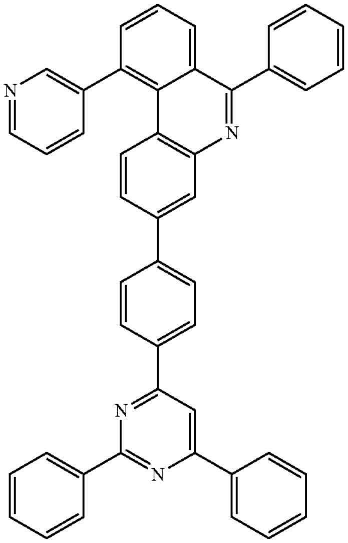
745
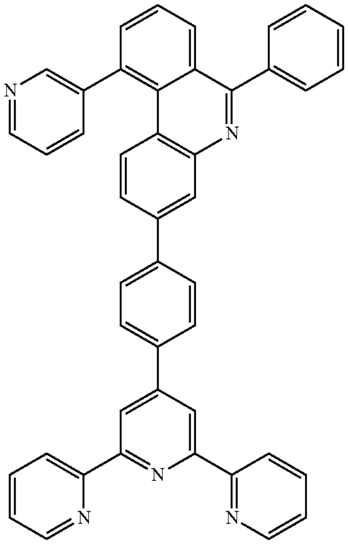

746
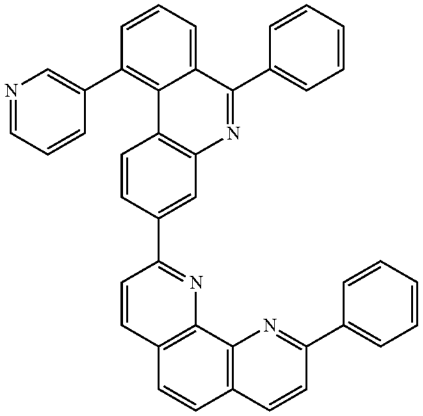
747
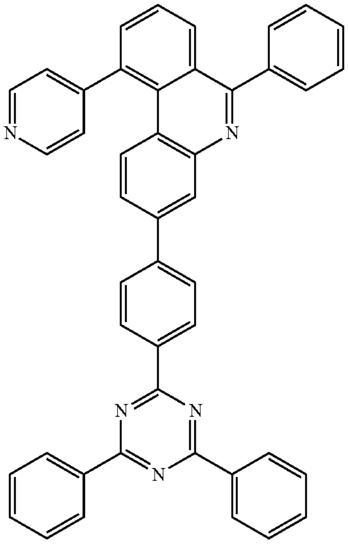
748
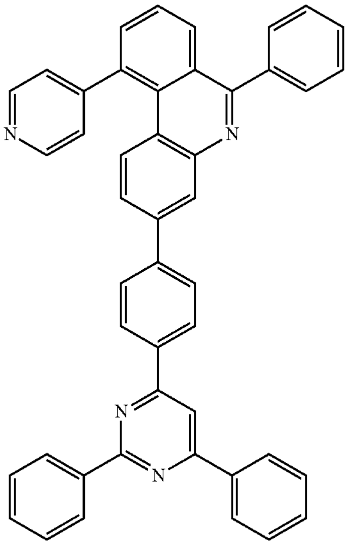
749
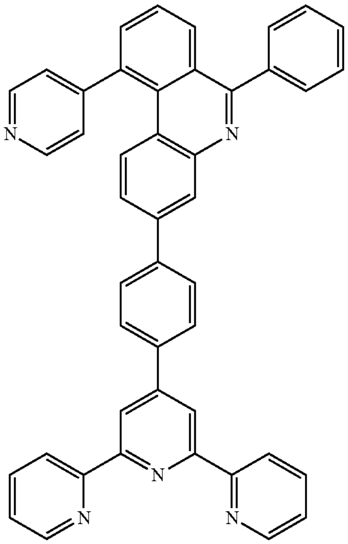
750
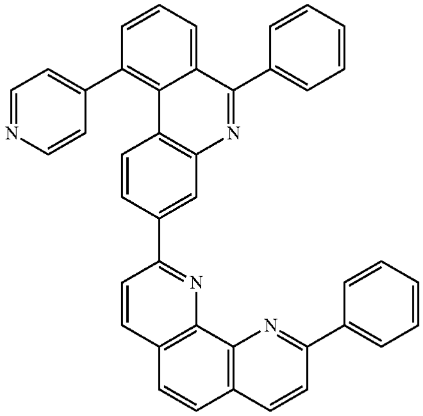
751
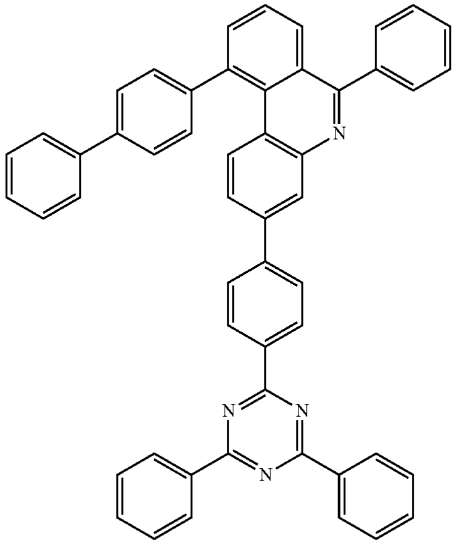

-continued
752
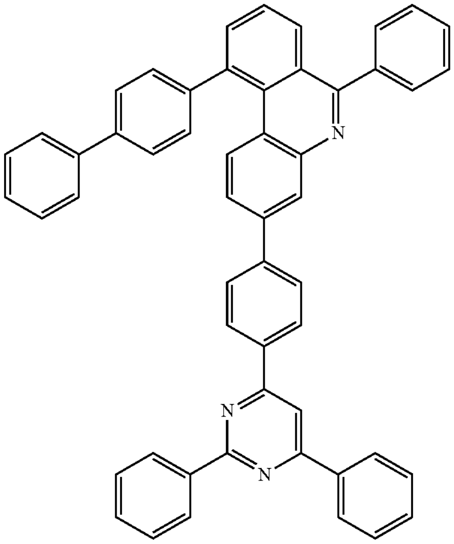
753
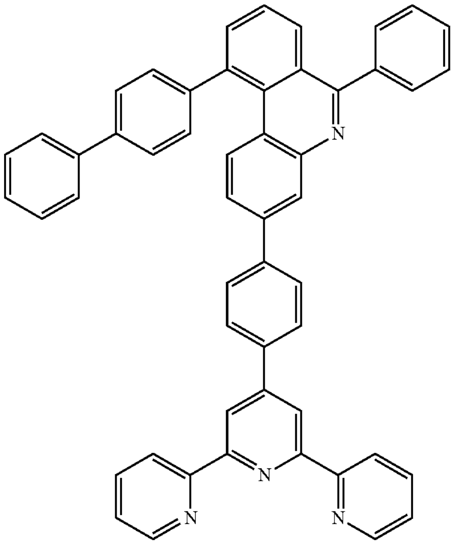
754
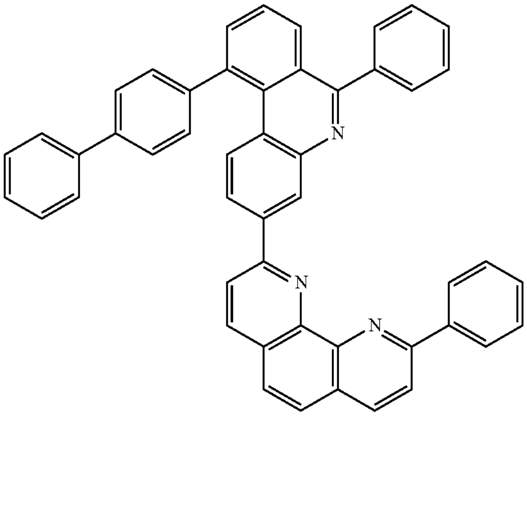
-continued
755
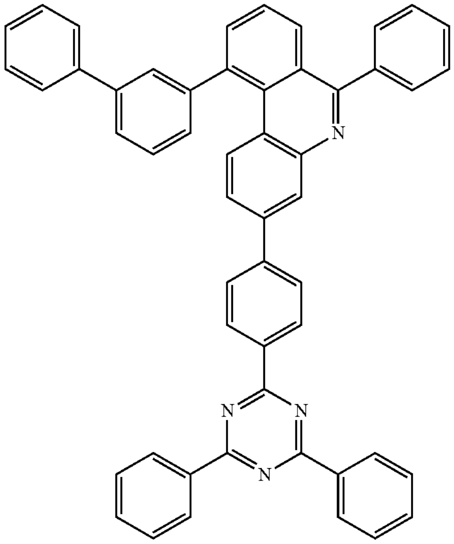
756
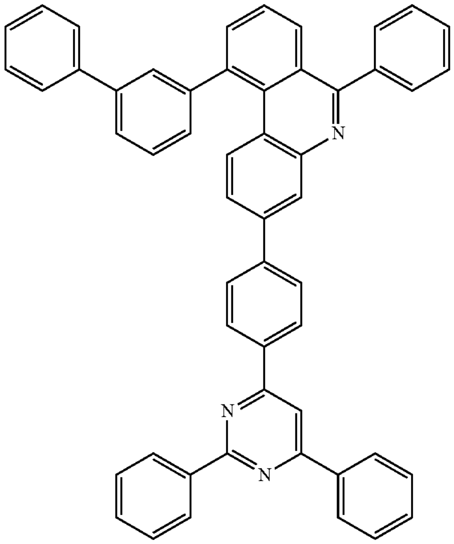
757
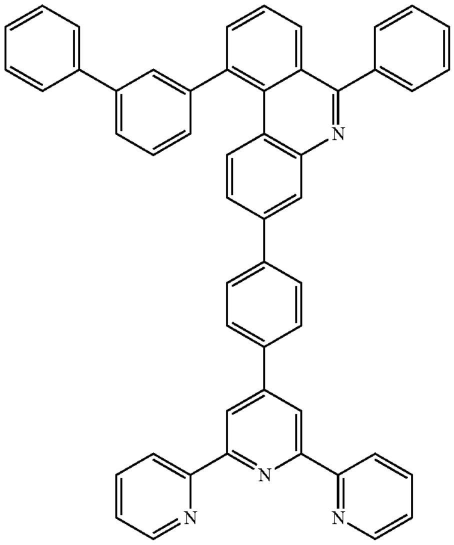

-continued
758
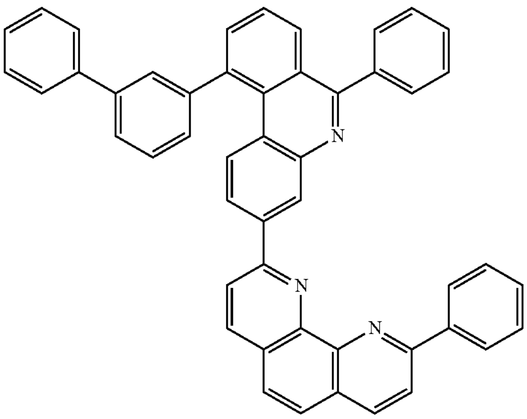
759
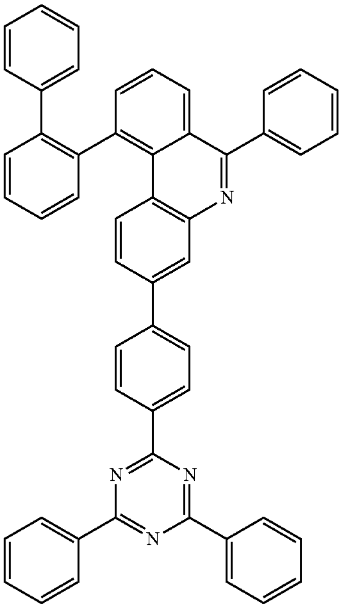
760
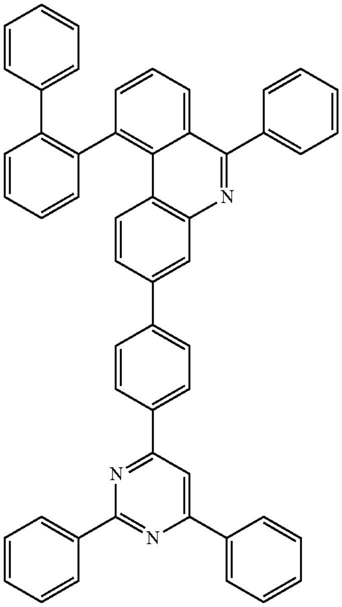
-continued
761
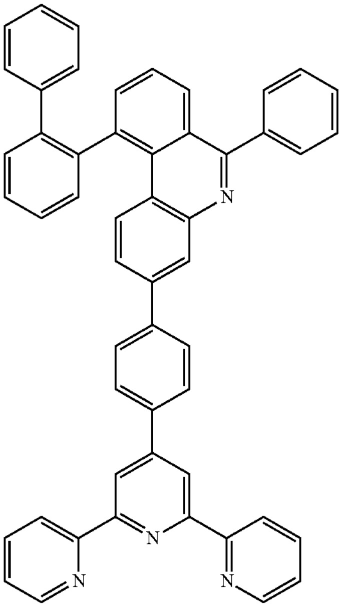
762
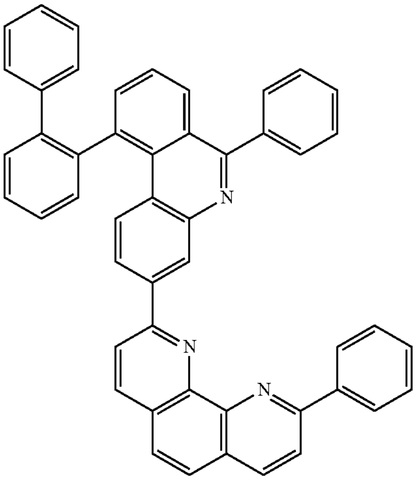
763
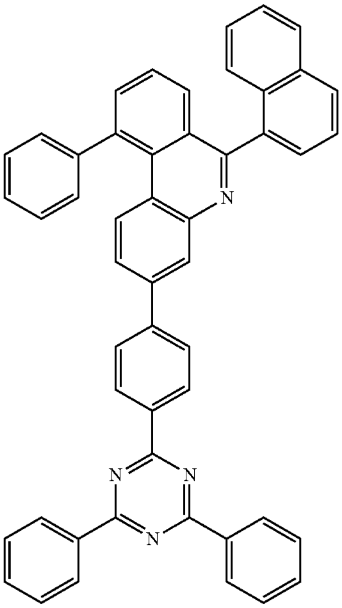

-continued
764
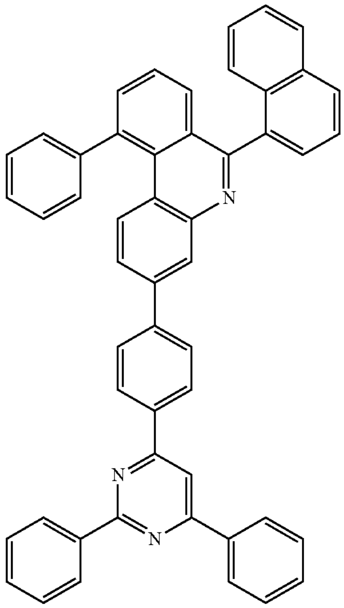
765
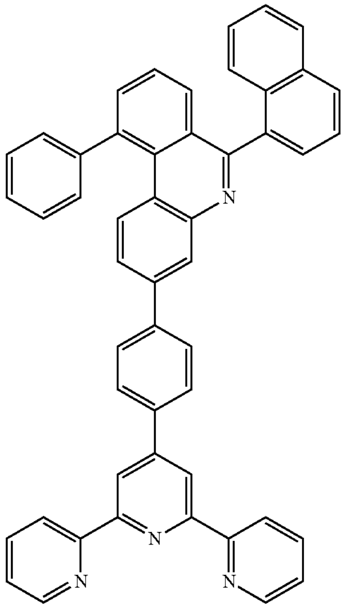
-continued
766
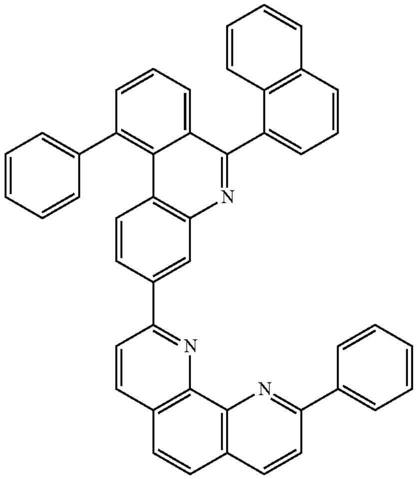
767
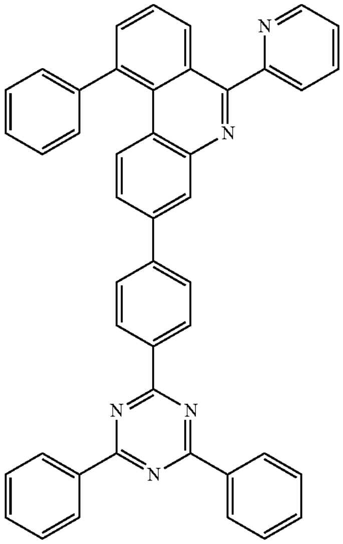
768
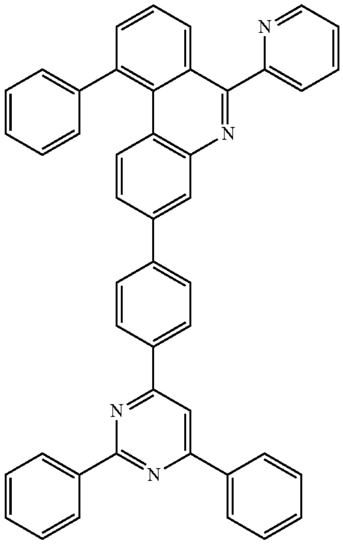

-continued
769
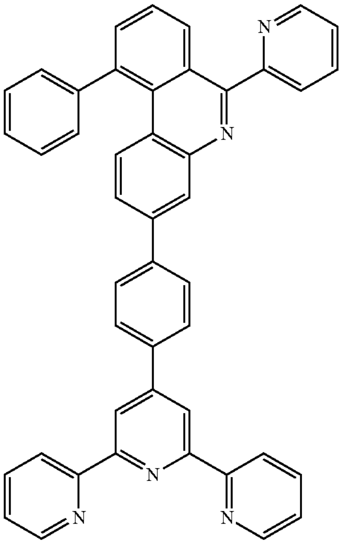
770
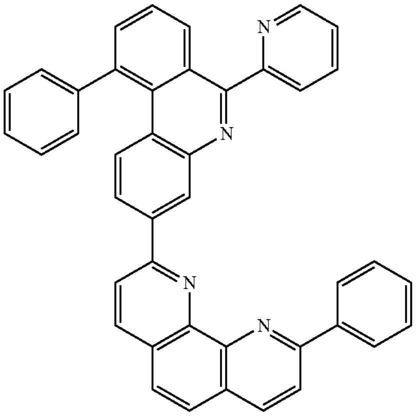
771
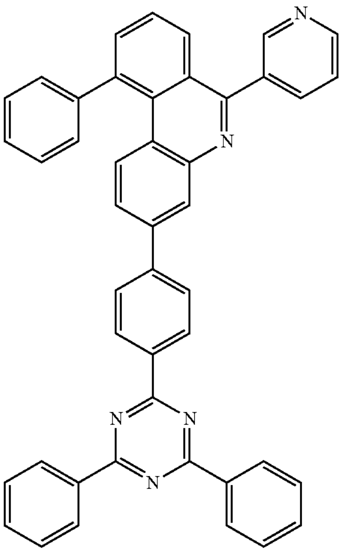
-continued
772
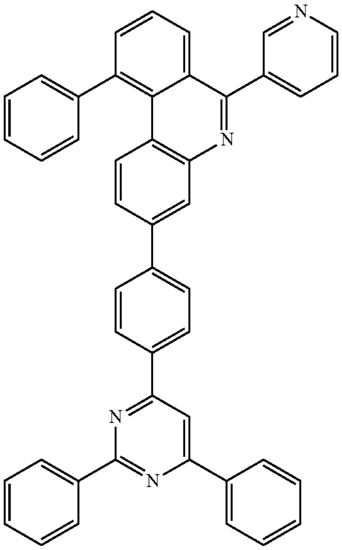
773
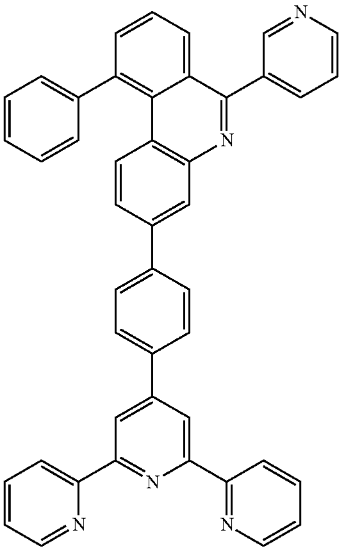
774
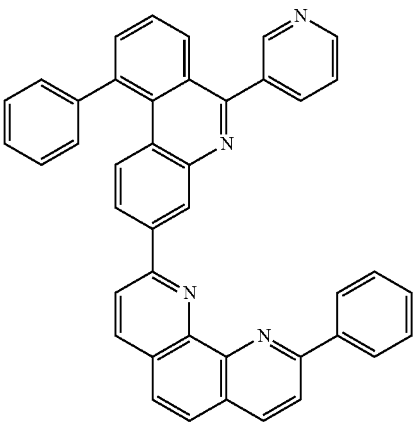

-continued
775
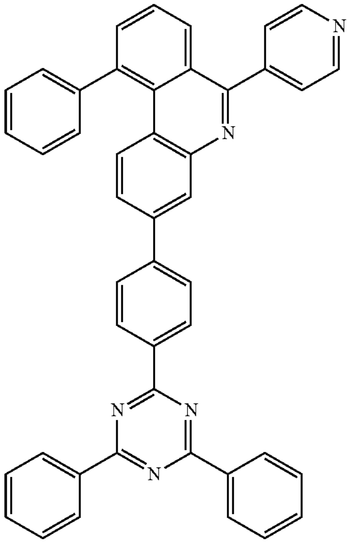
776
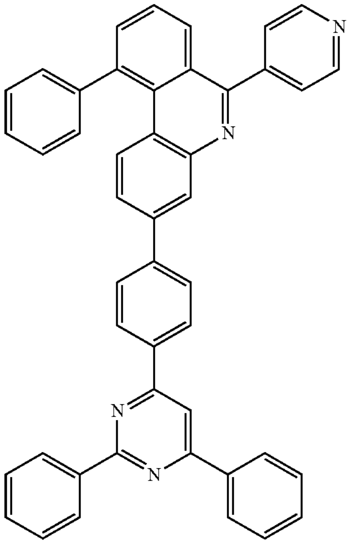
777
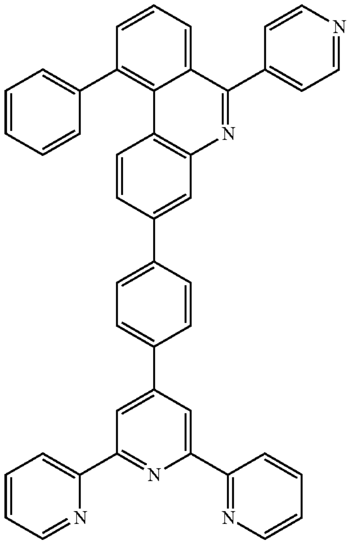
-continued
778
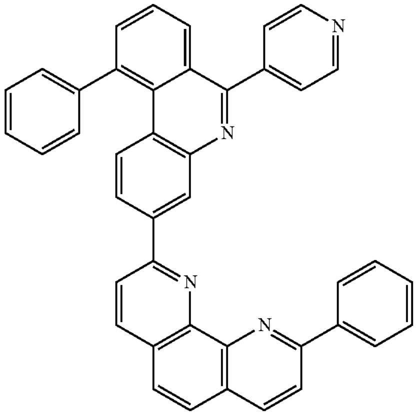
779
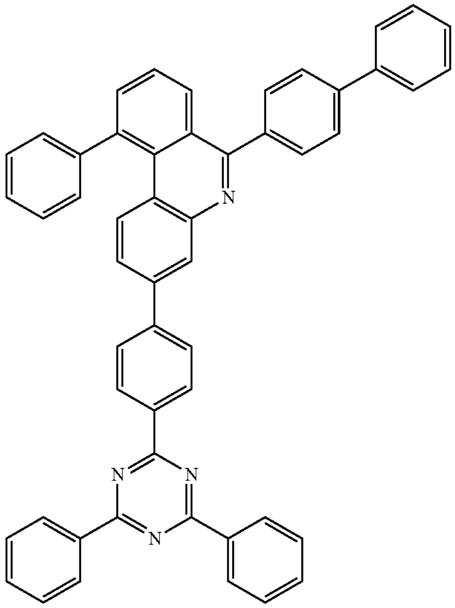
780
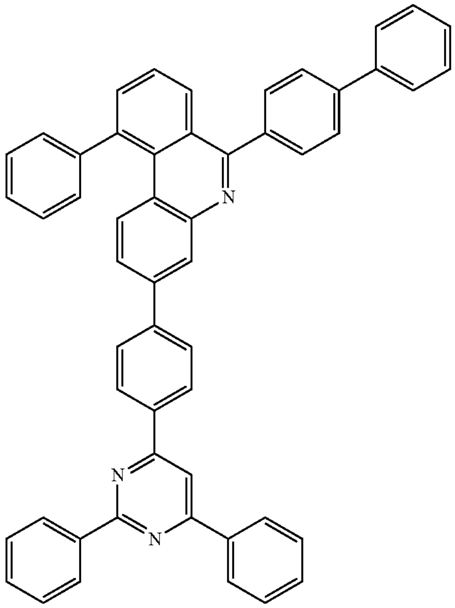

-continued
781
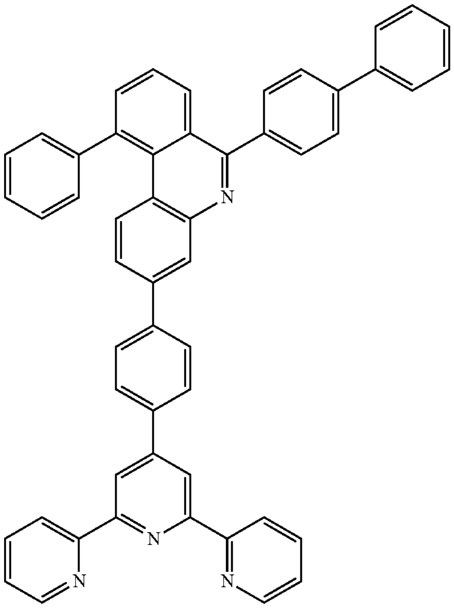
782
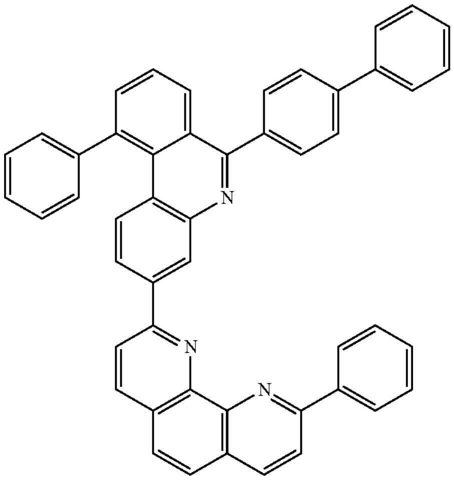
783
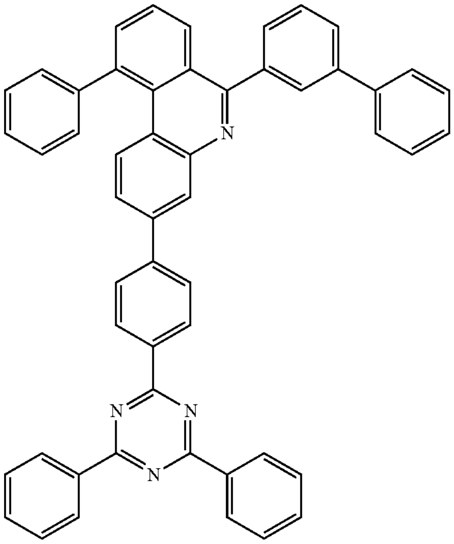
-continued
784
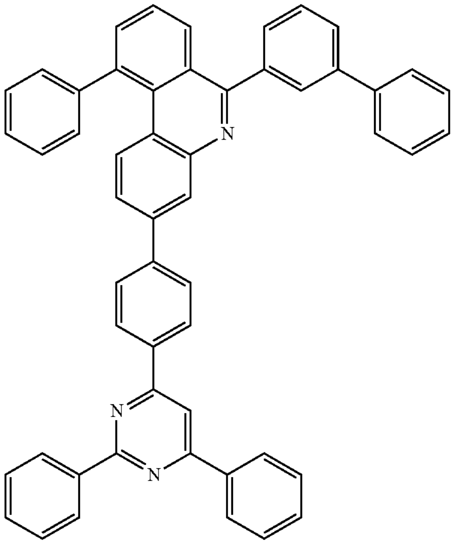
785
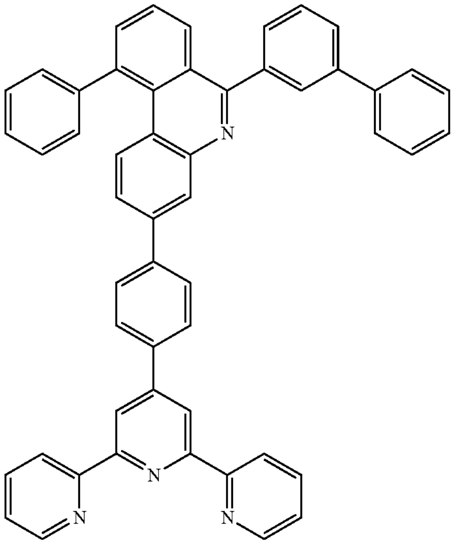
786
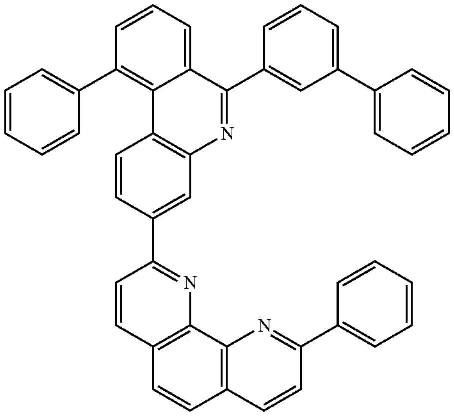

787
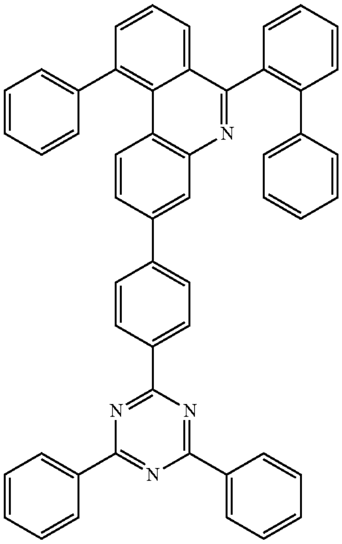
788
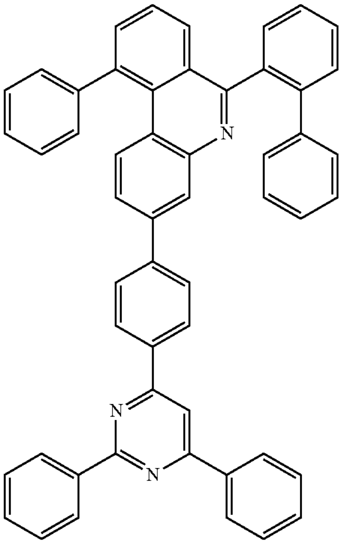
789
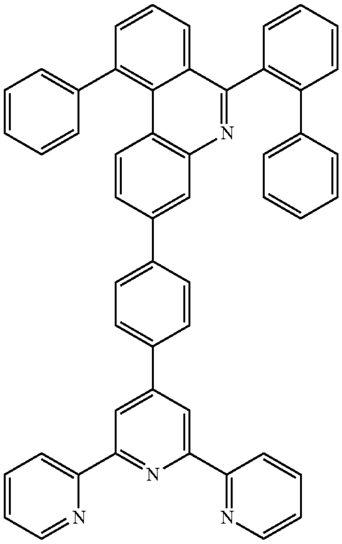
790
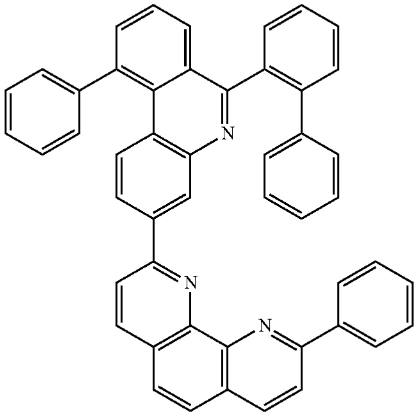
791
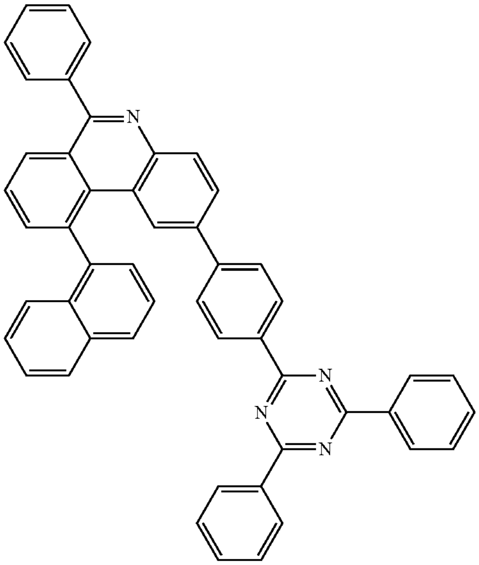
792
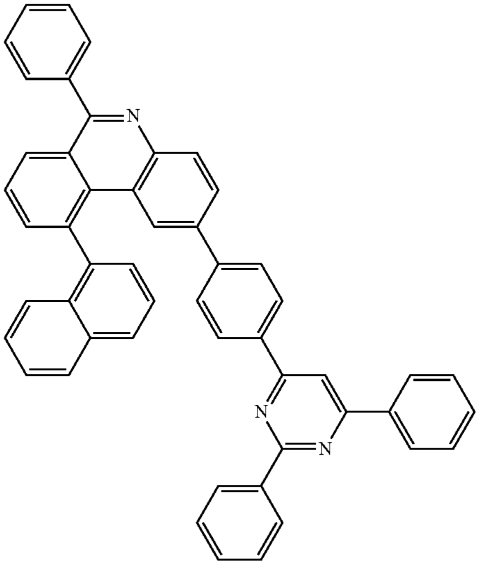

-continued
793
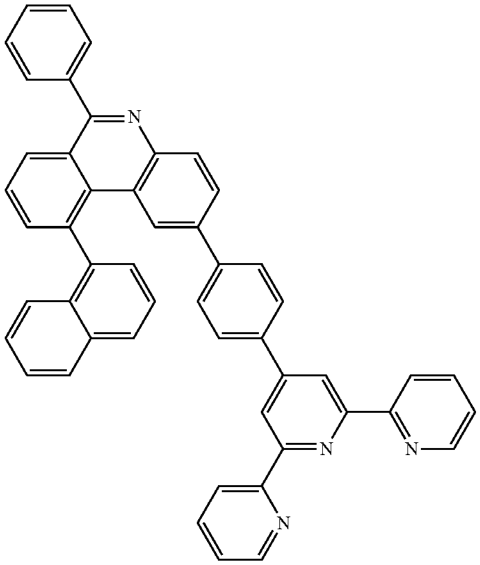
794
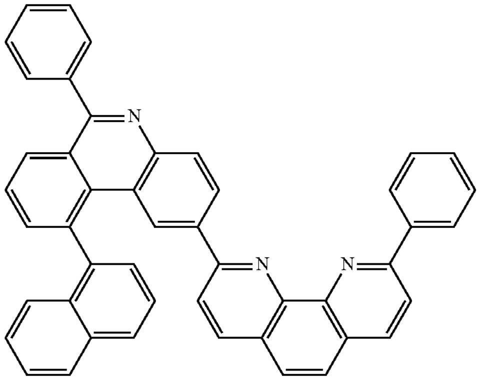
795
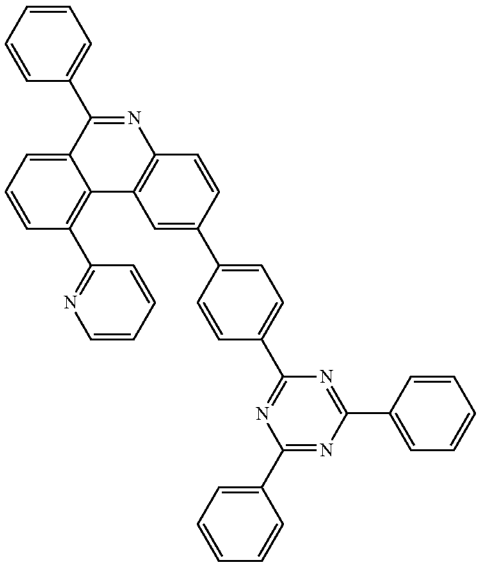
-continued
796
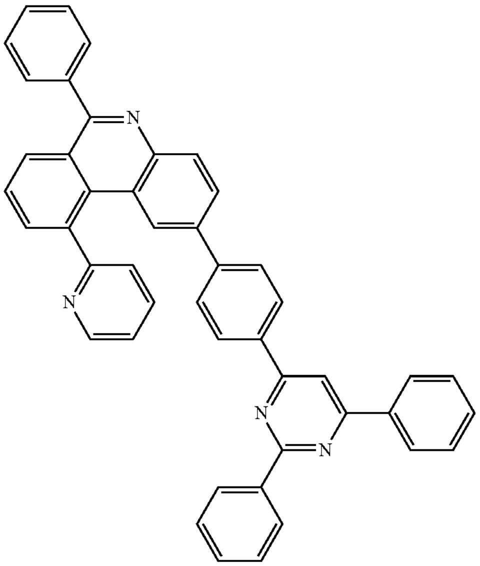
797
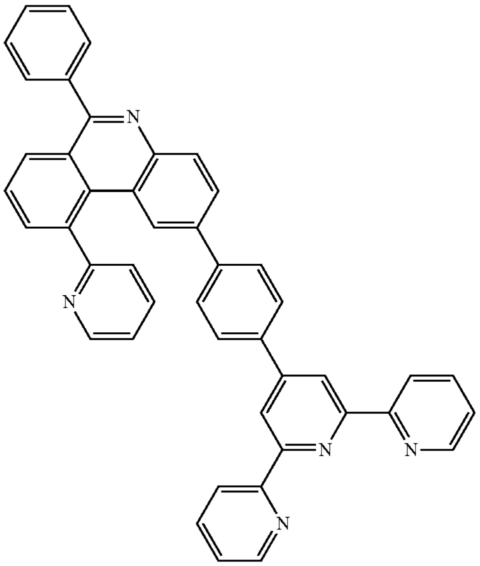
798
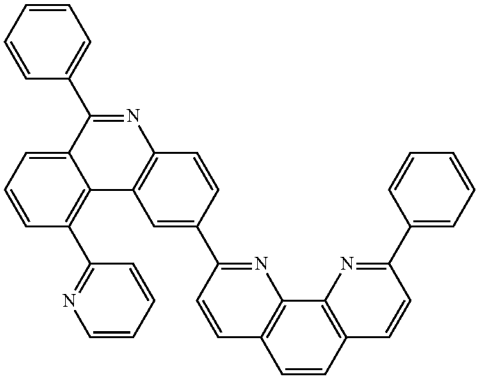

-continued
799
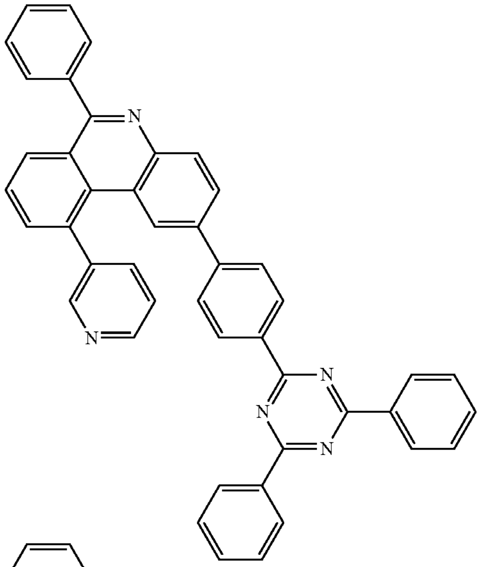
800
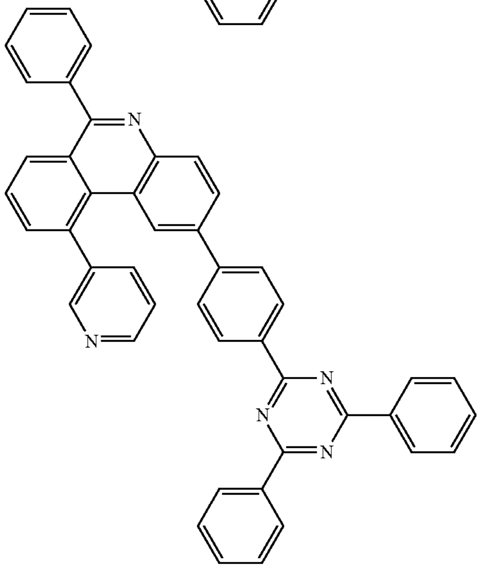
801
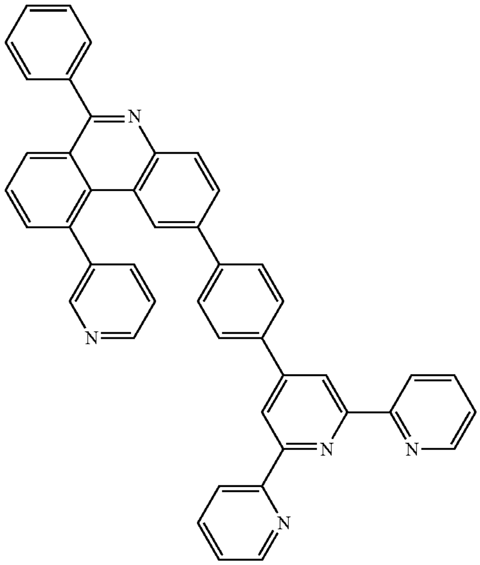
-continued
802
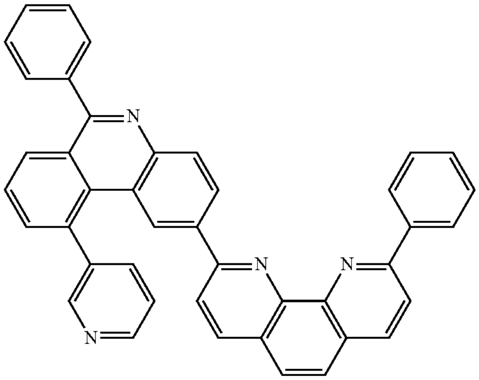
803
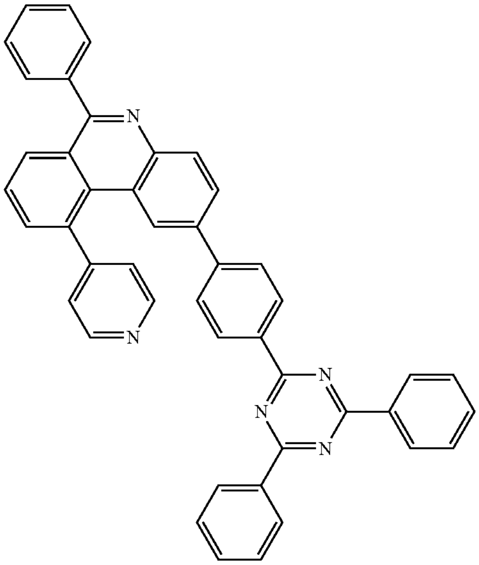
804
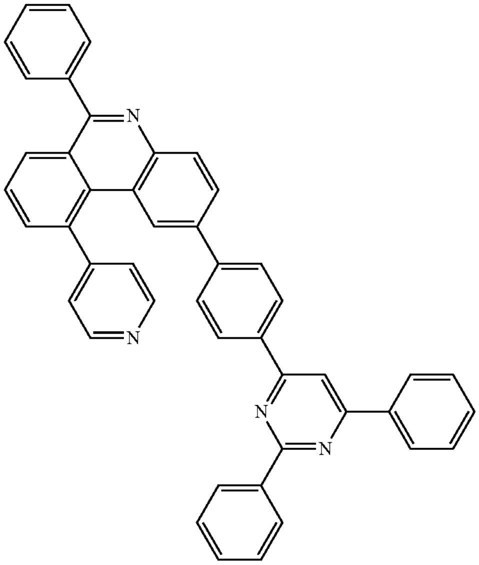

-continued
805
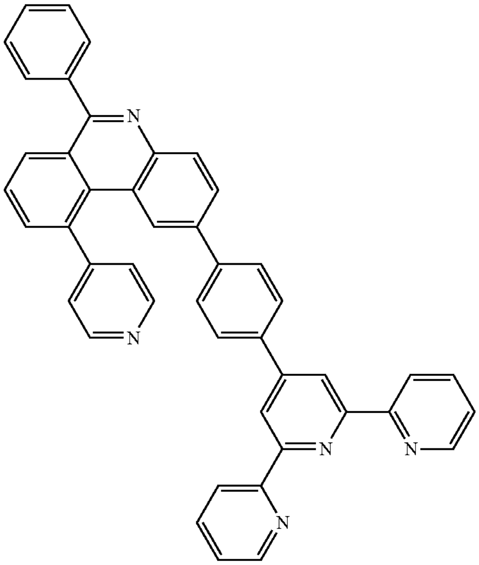
806
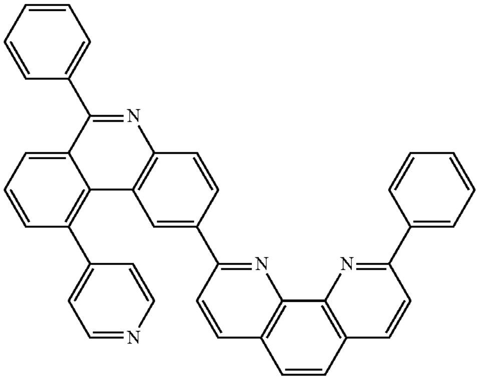
807
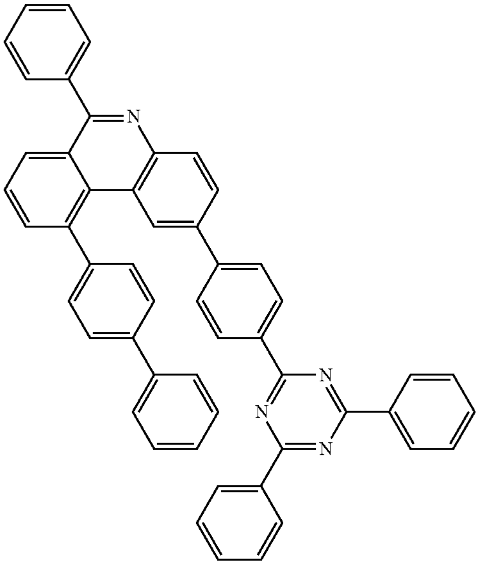
-continued
808
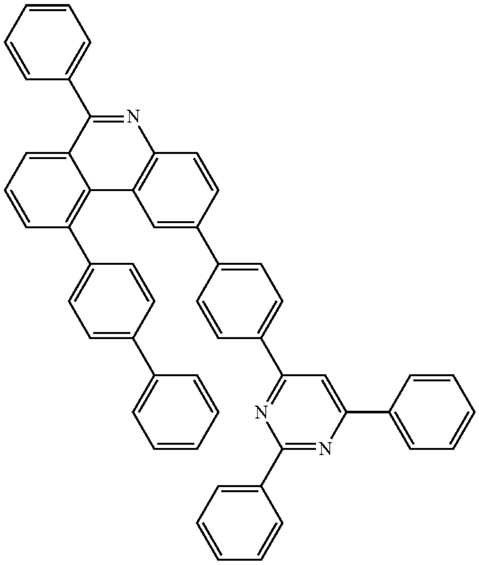
809
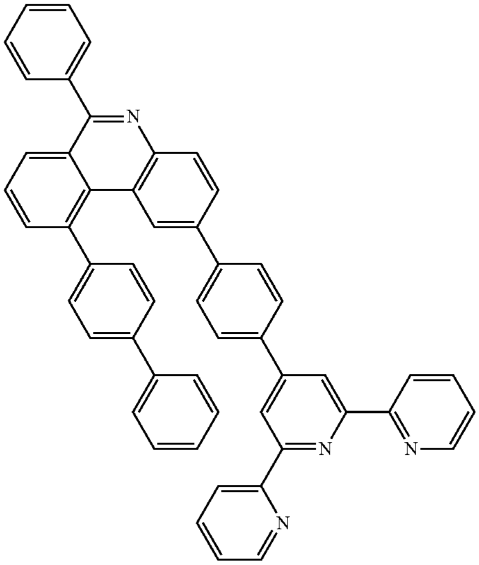
810
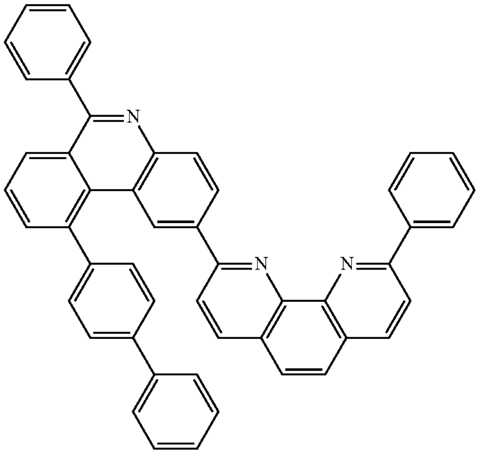

-continued
811
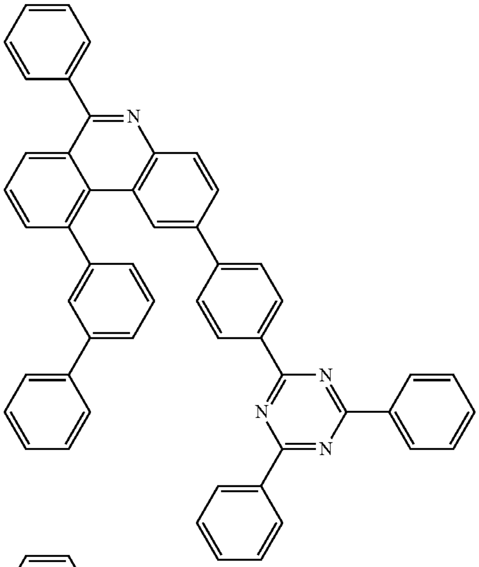
812
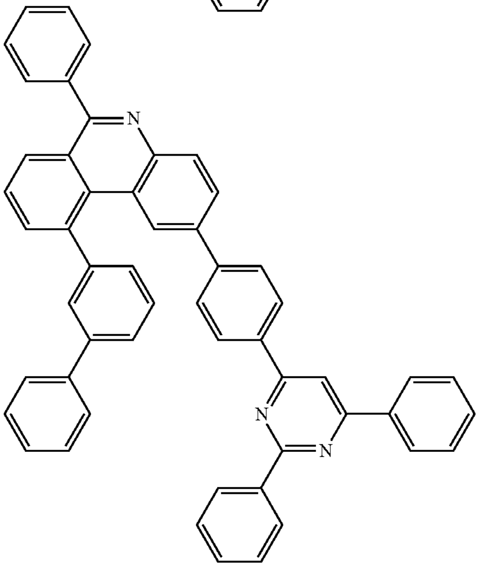
813
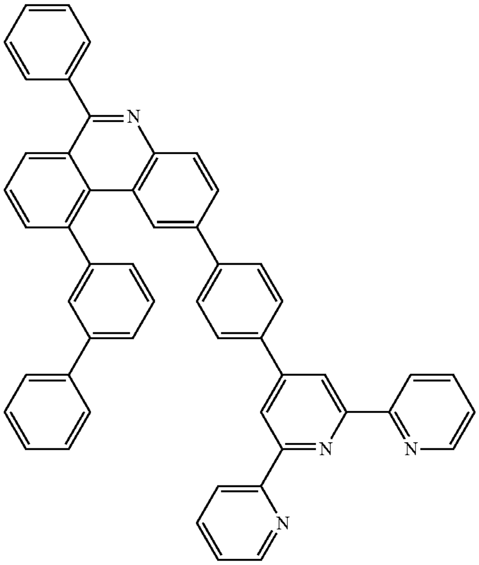
-continued
814
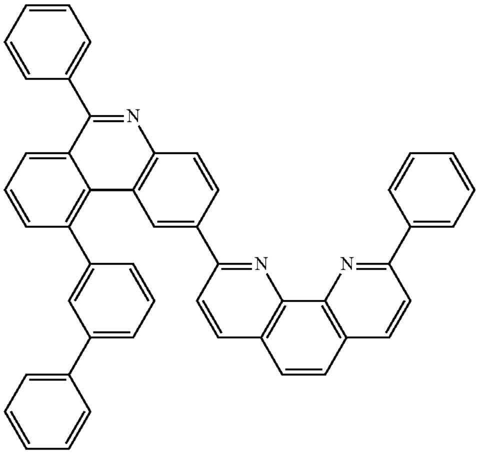
815
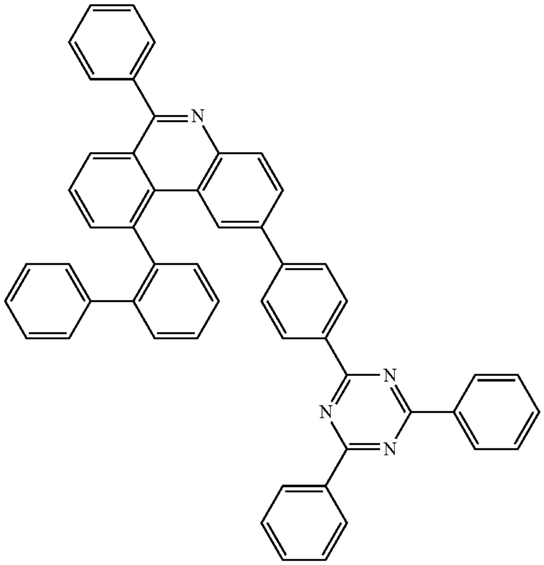
816
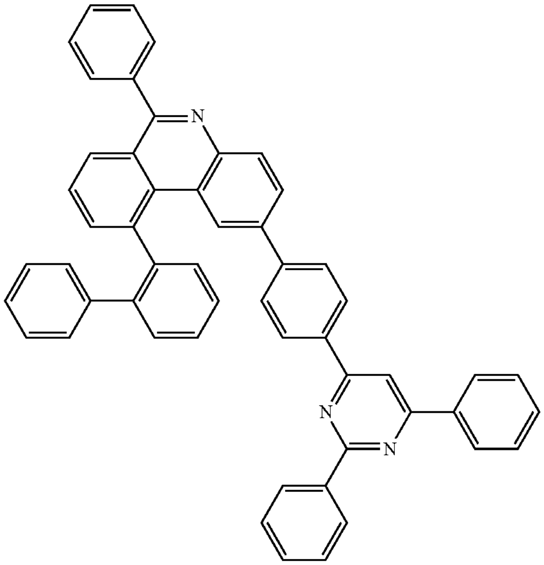

-continued
817
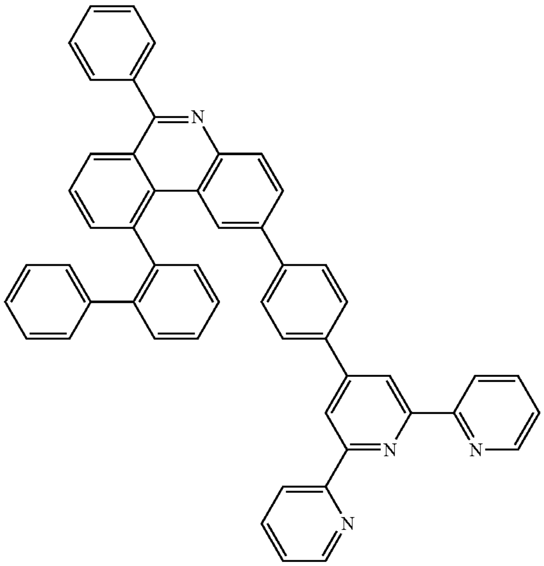
818
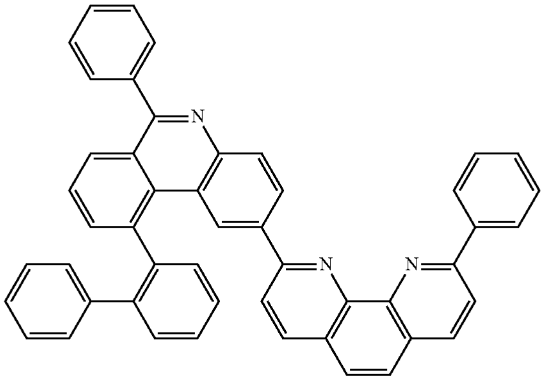
819
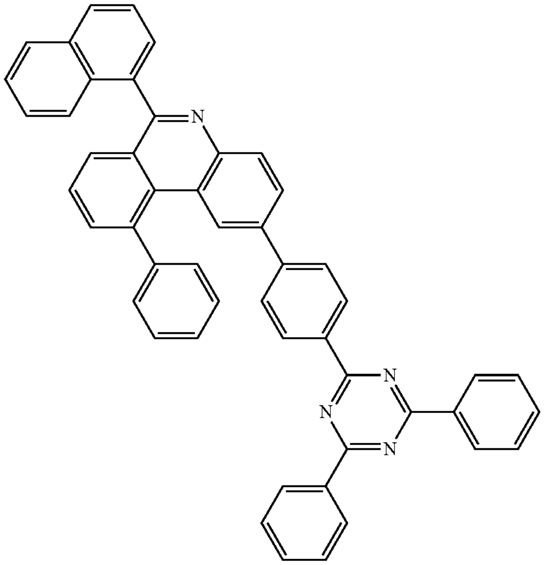
-continued
820
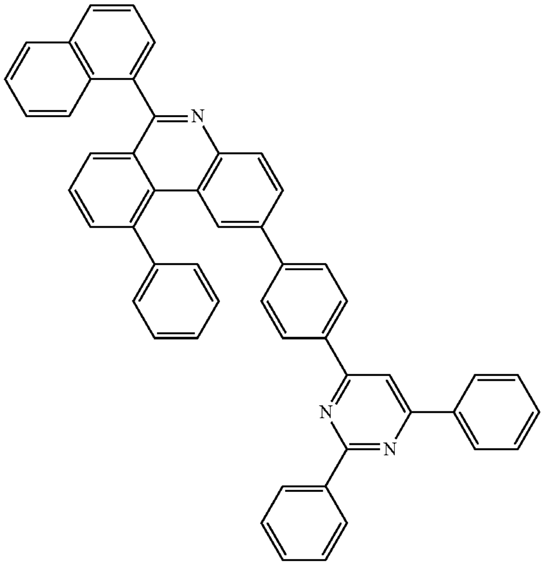
821
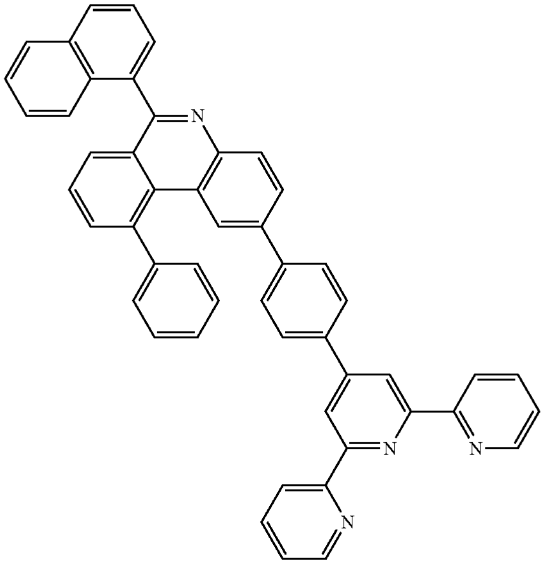
822
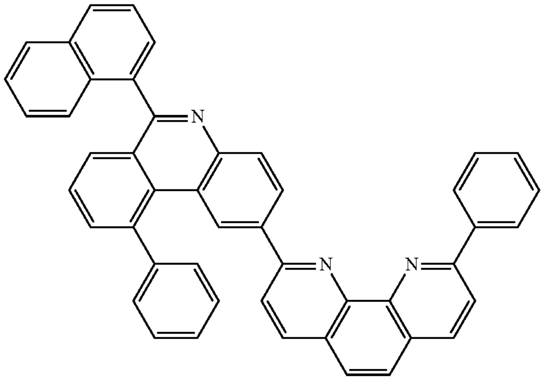

-continued
823
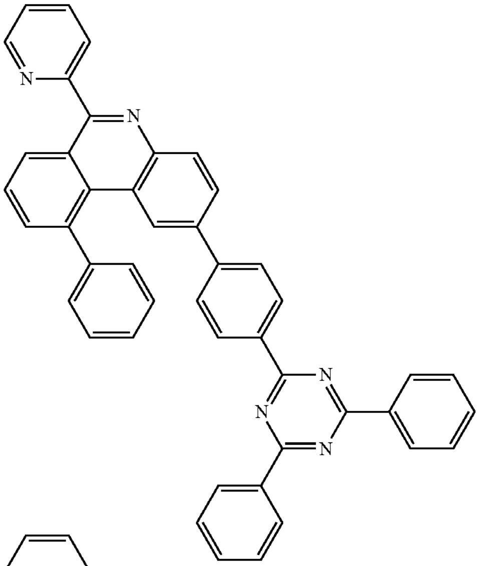
824
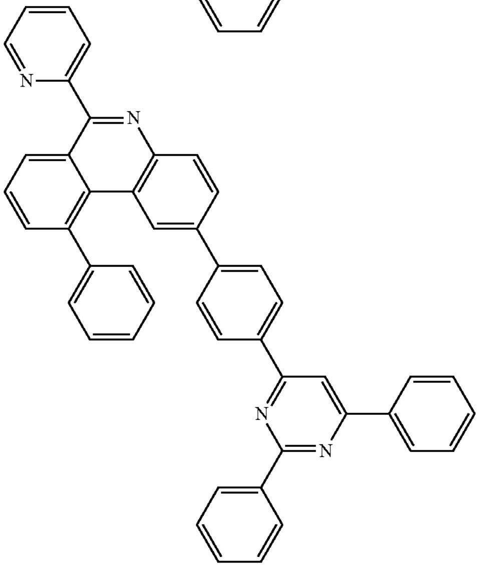
825
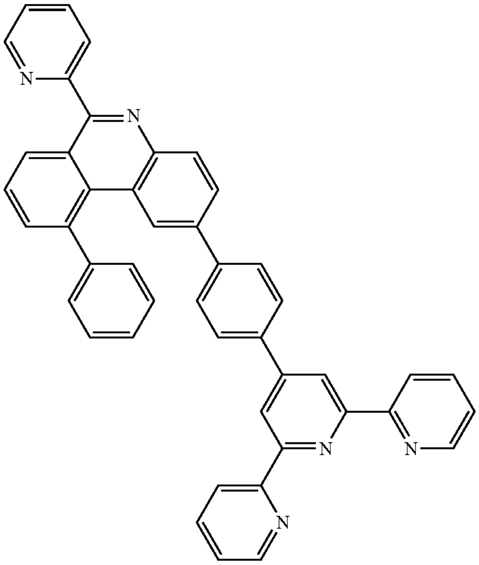
-continued
826
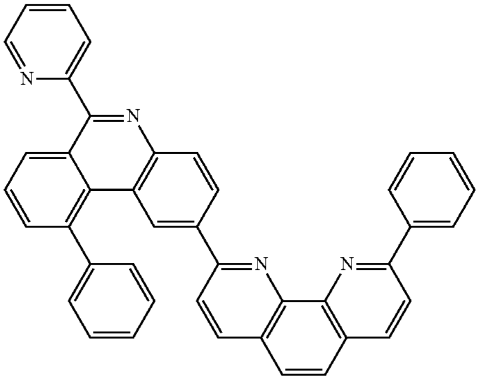
827
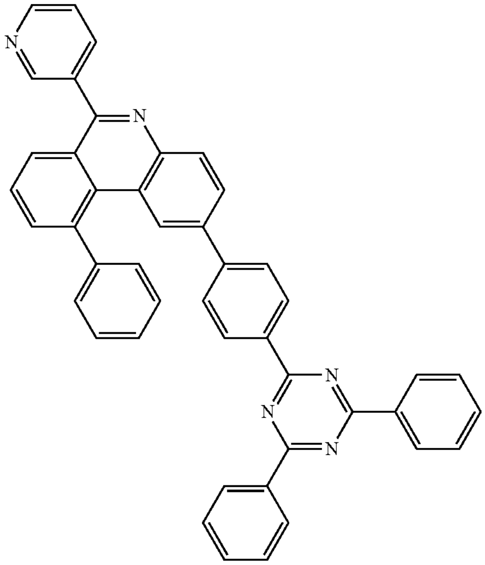
828
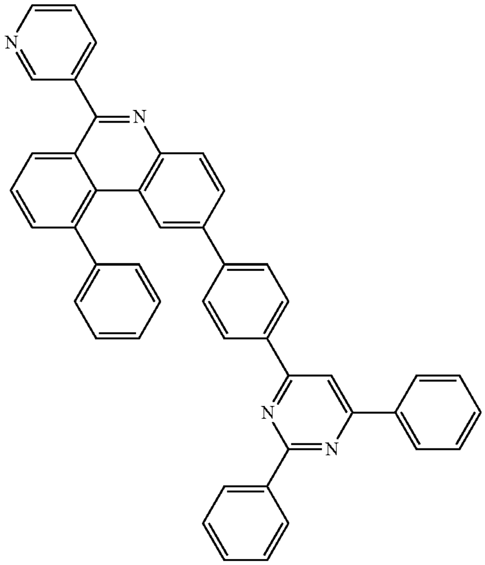

-continued
829
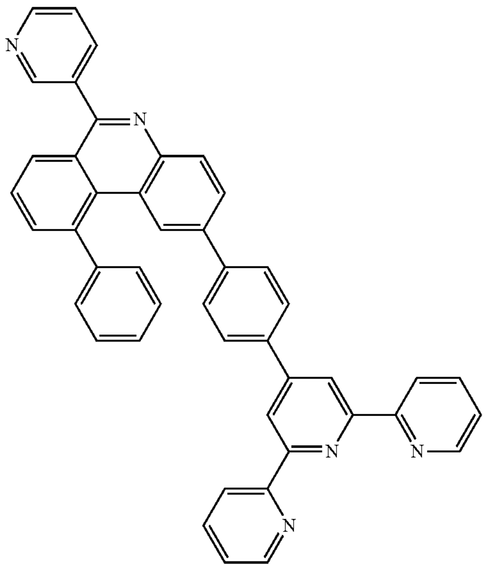
830
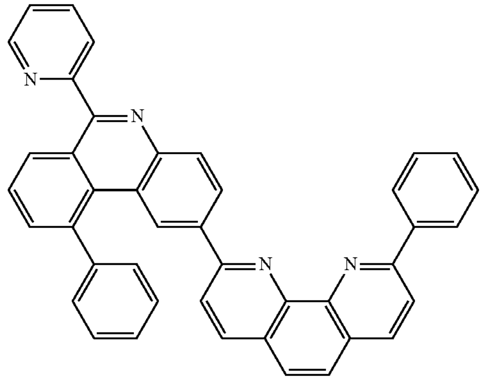
831
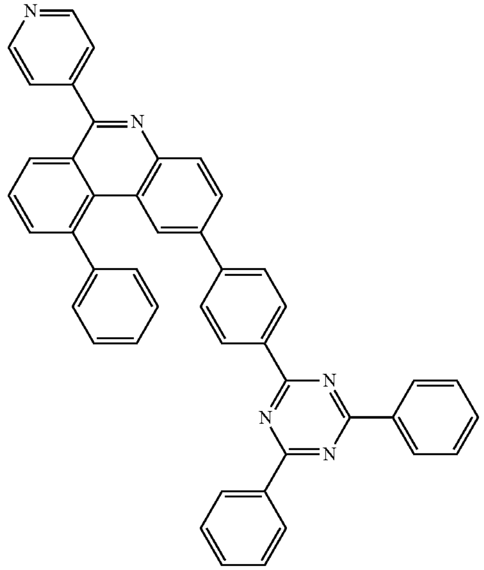
-continued
832
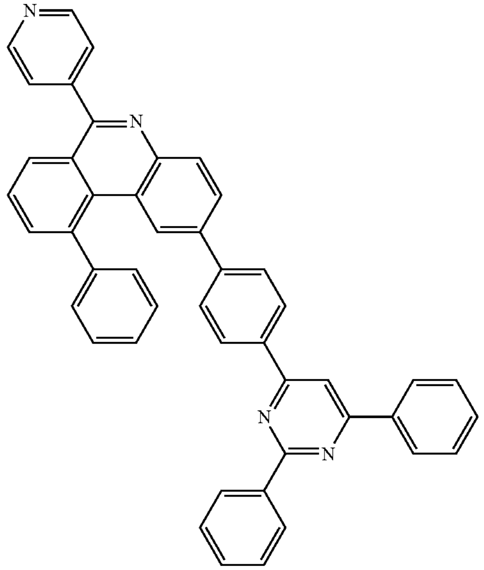
833
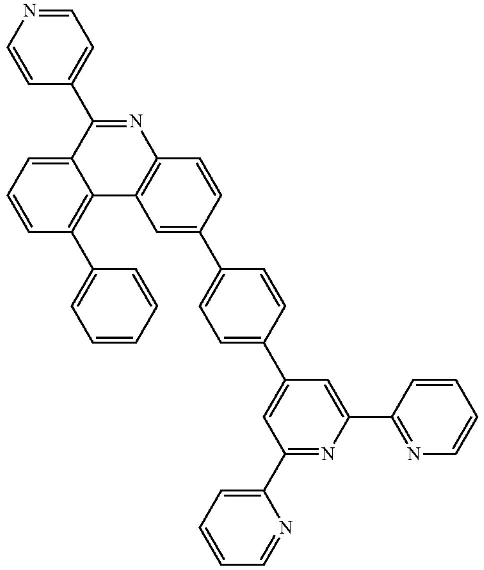
834
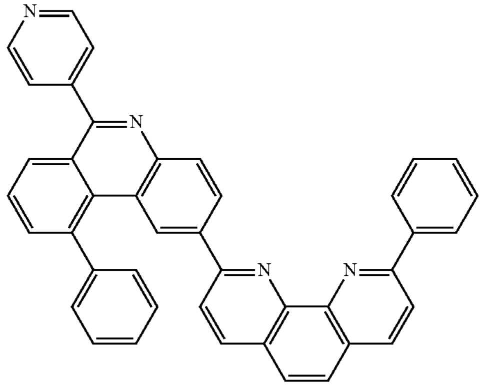

-continued
835
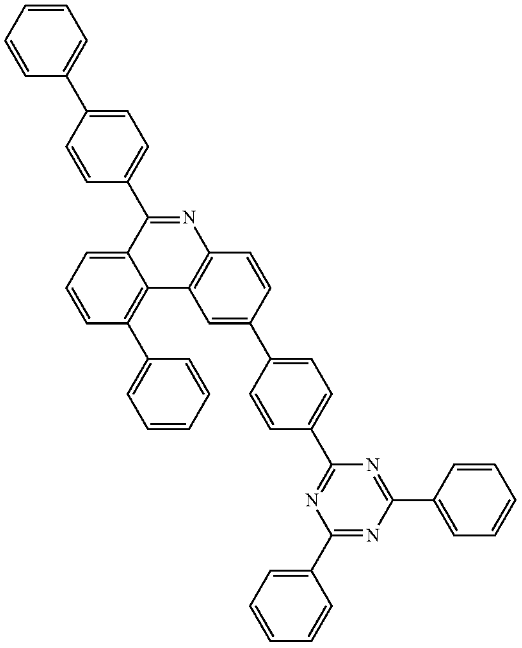
836
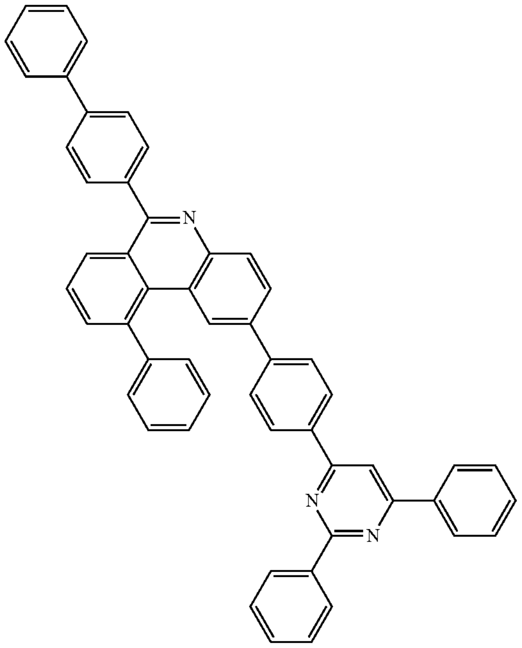
837
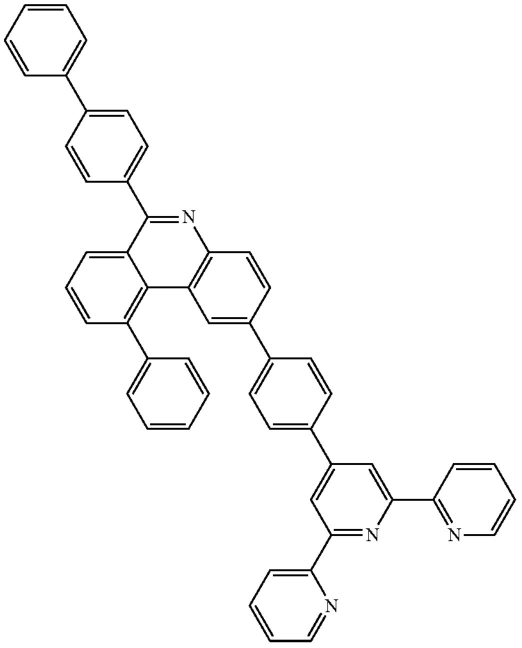
838
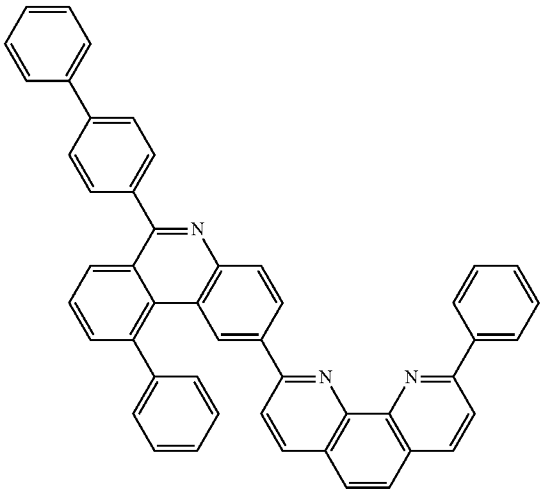

-continued
839
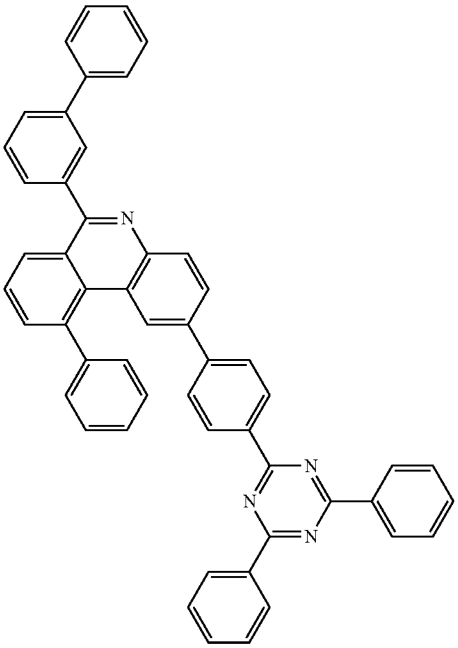
840
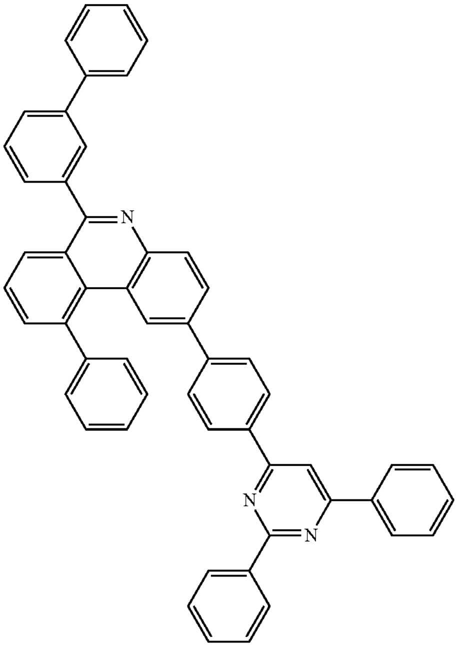
-continued
841
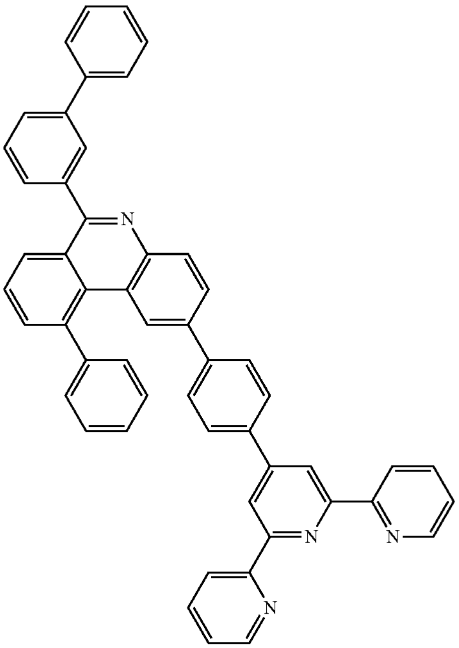
842
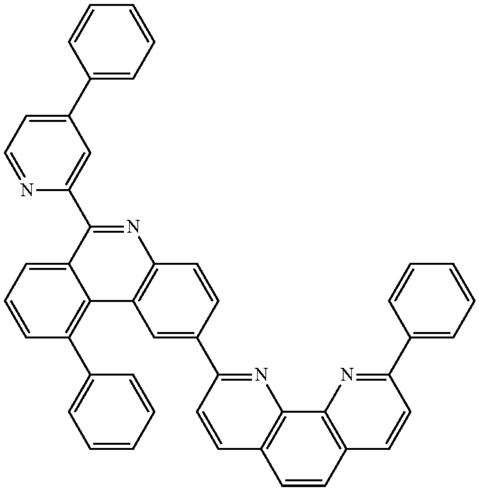

-continued
843
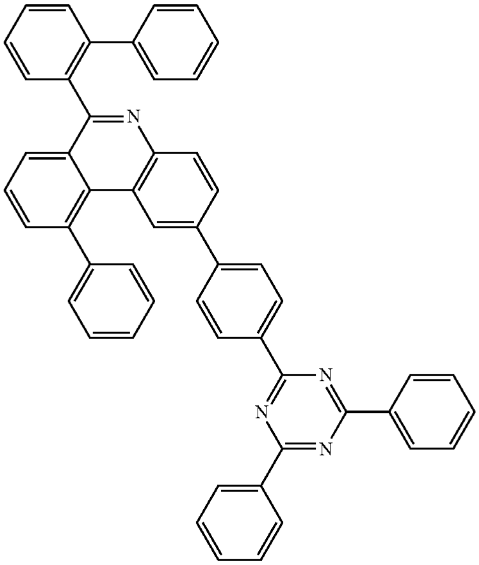
844
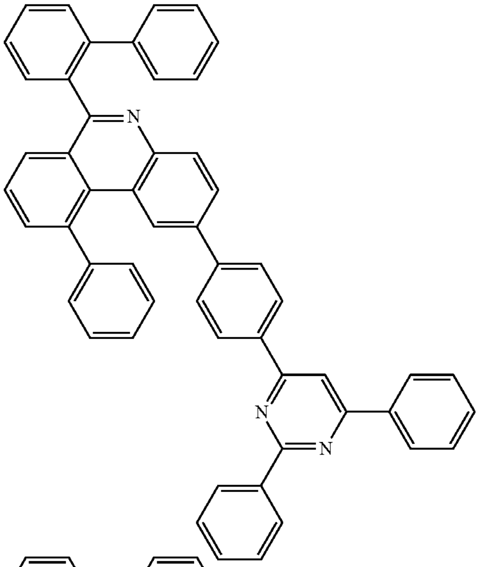
845
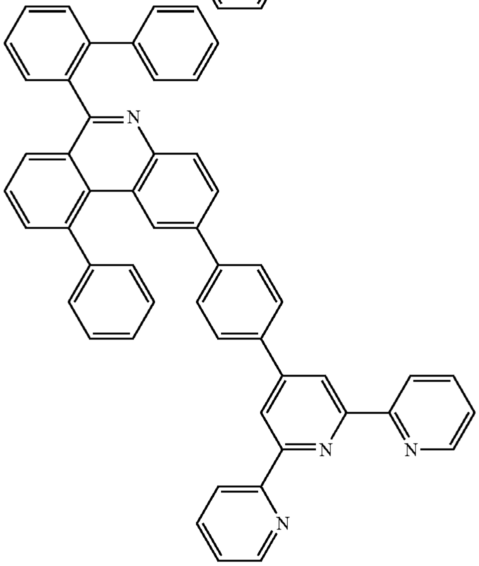
-continued
846
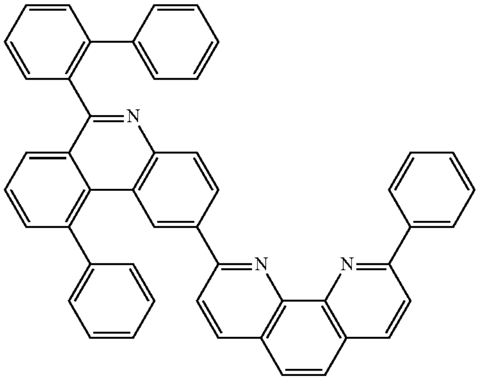
847
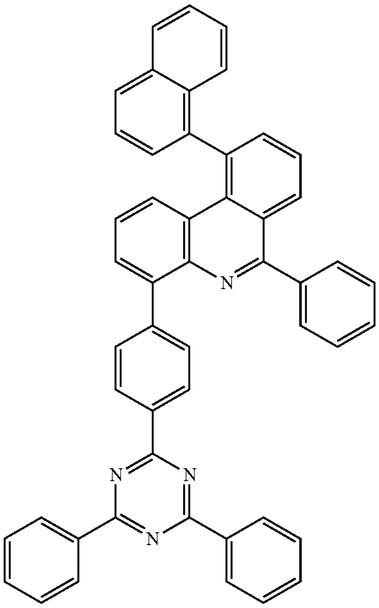
848
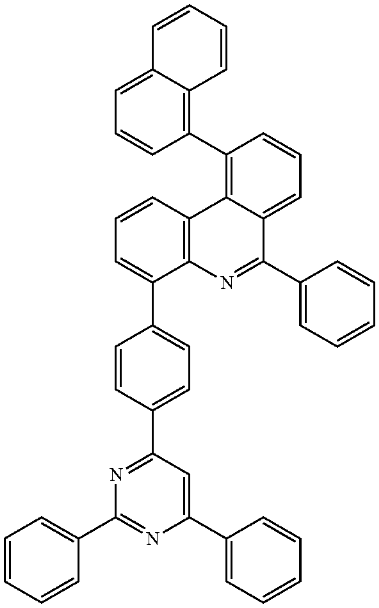

-continued
849
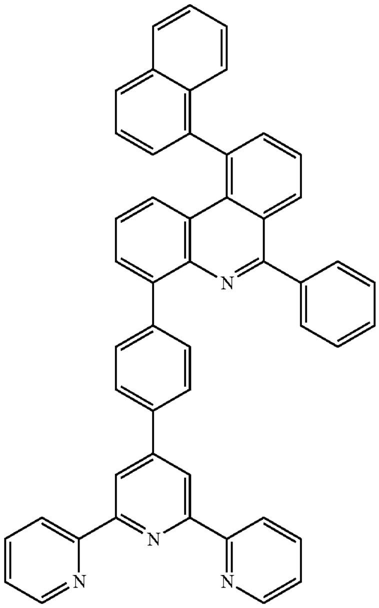
850
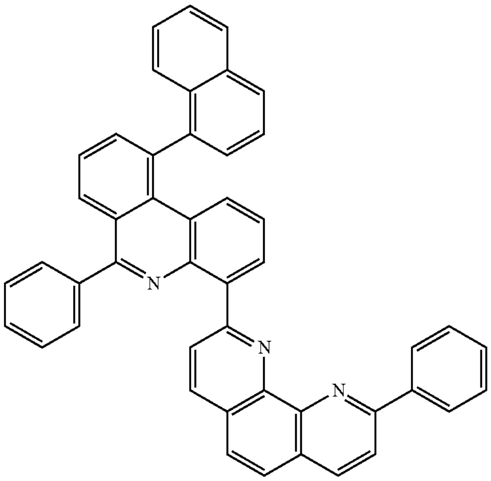
851
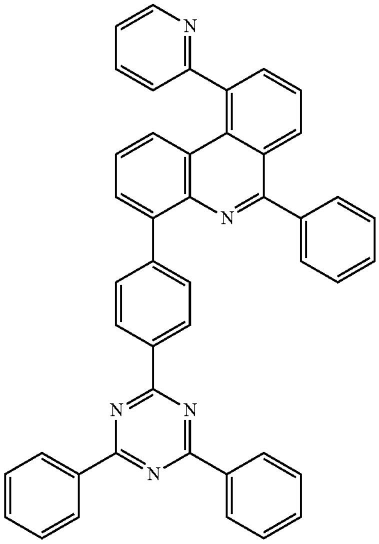
-continued
852
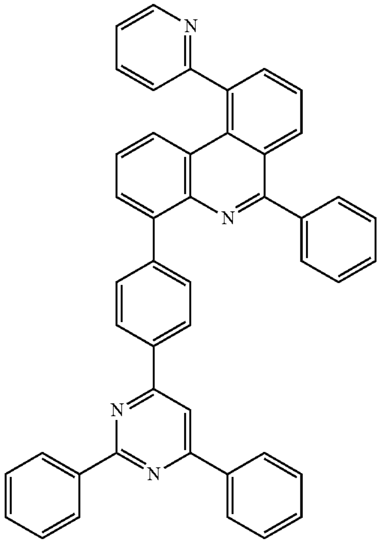
853
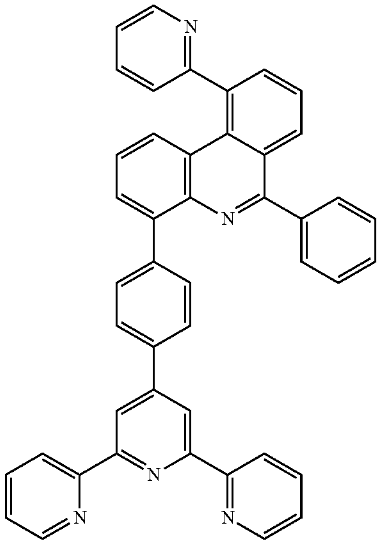
854
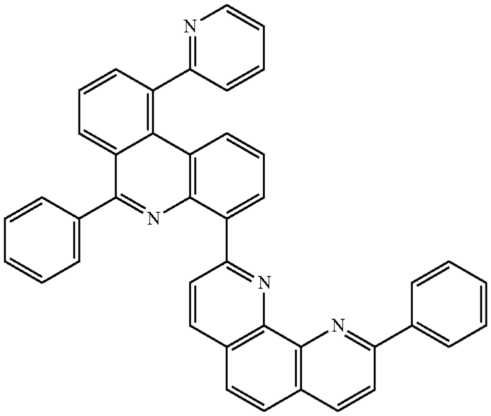

-continued
855
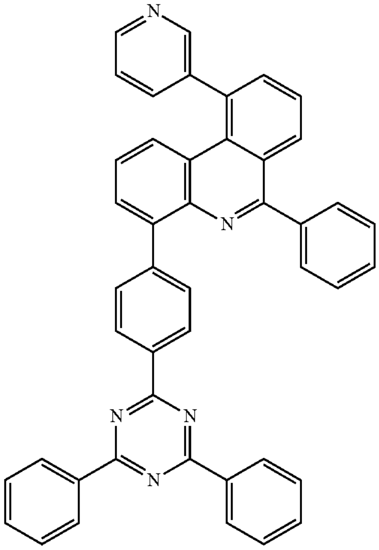
856
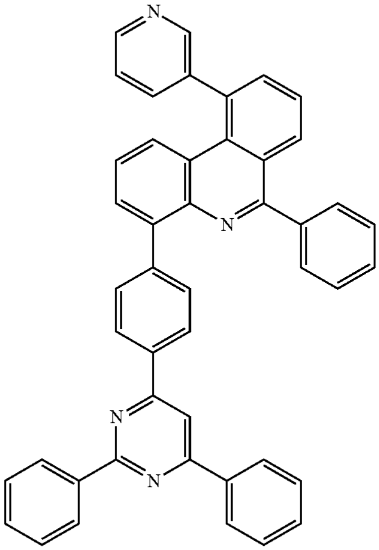
857
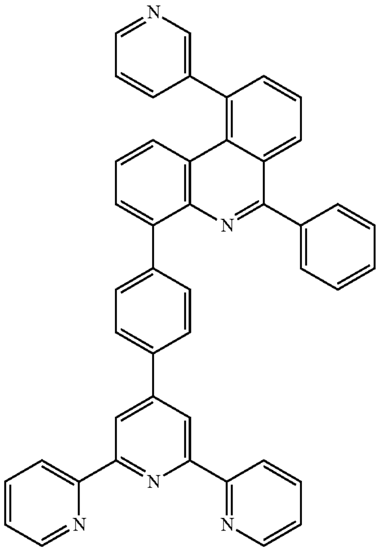
-continued
858
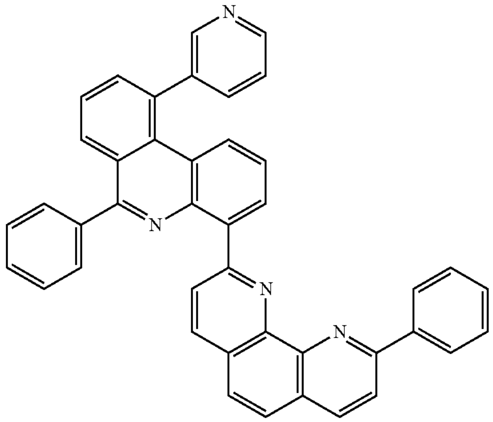
859
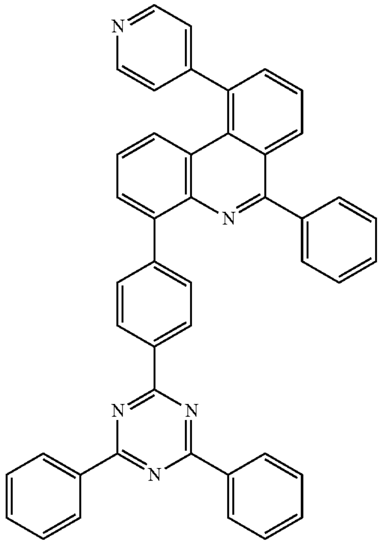
860
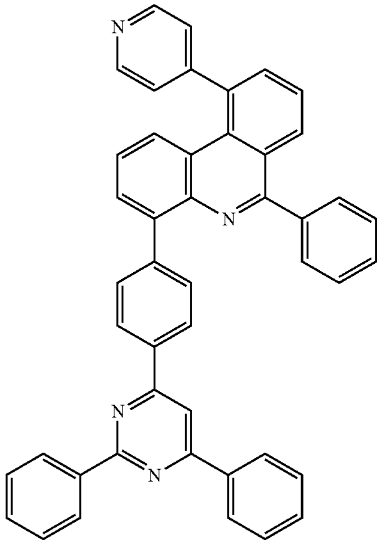

-continued
861
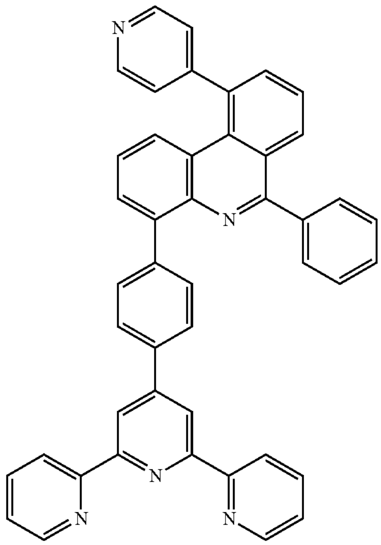
862
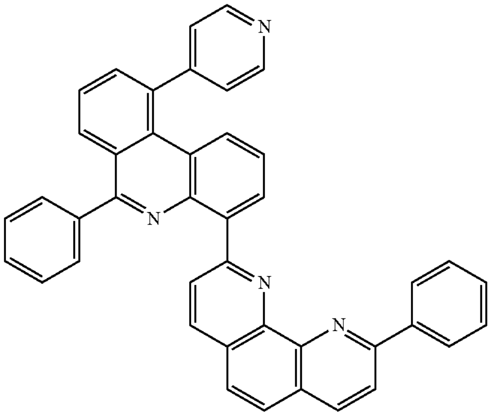
863
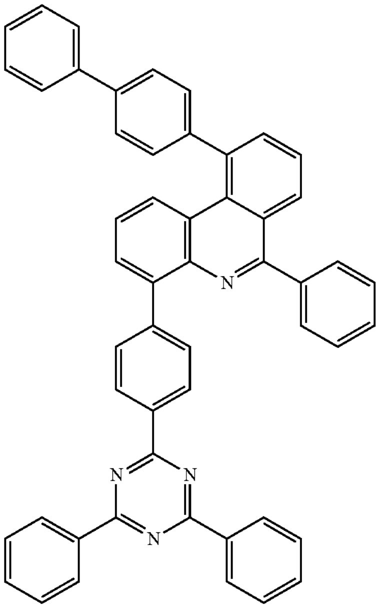
-continued
864
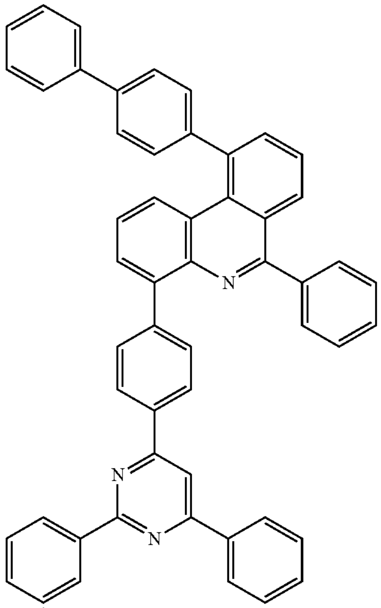
865
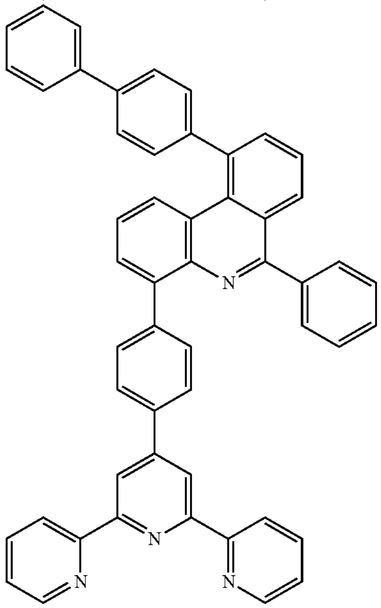
866
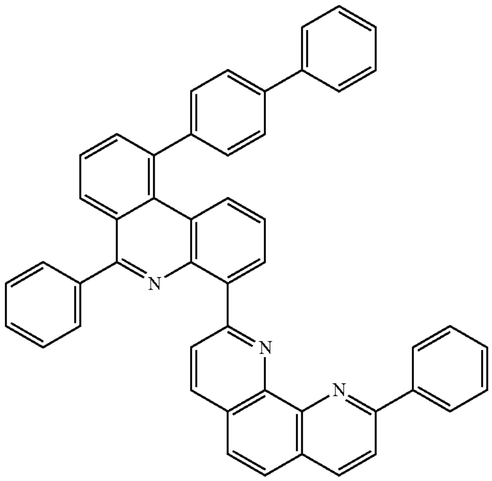

867
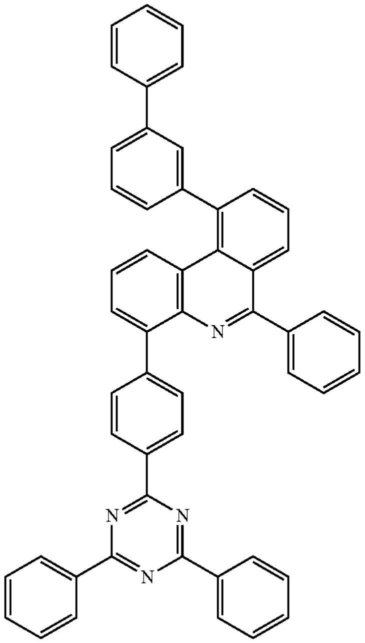
868
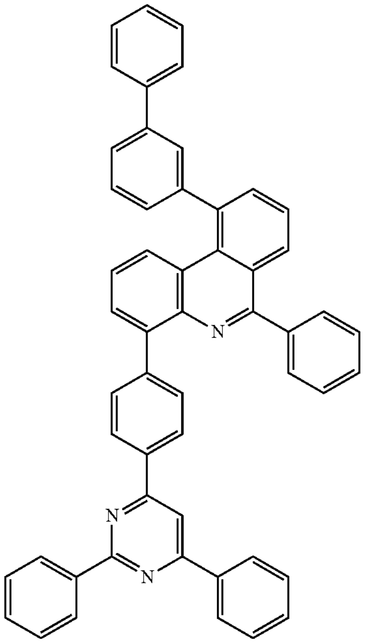
869
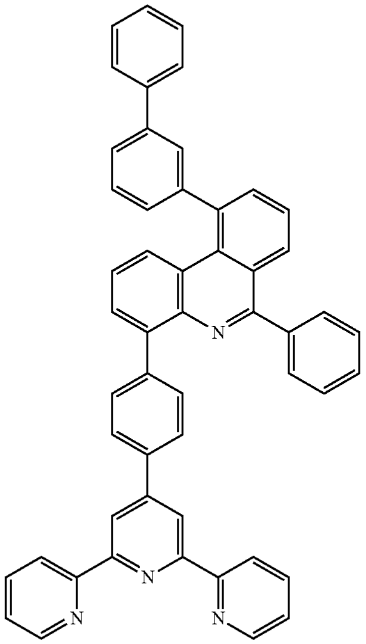
870
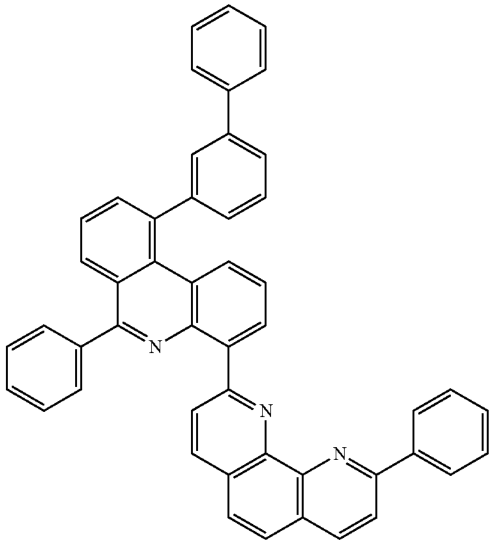

-continued
871
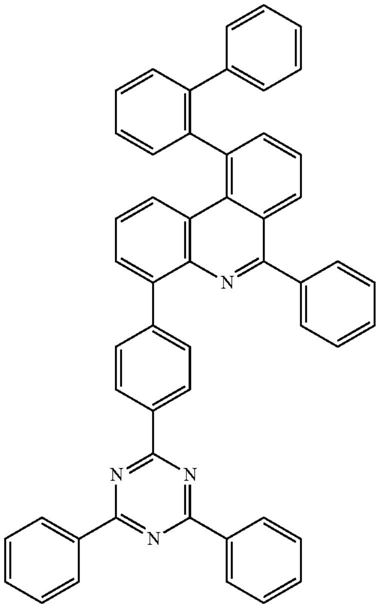
872
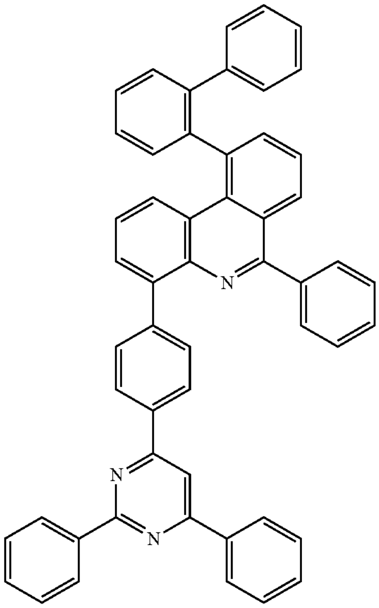
-continued
873
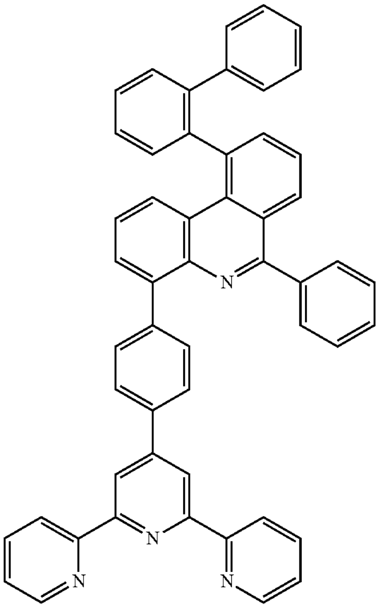
874
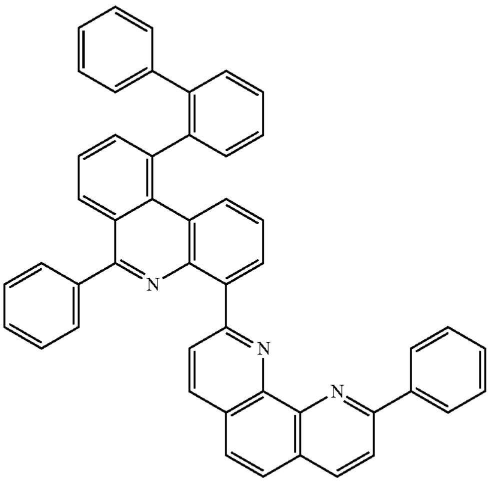
875
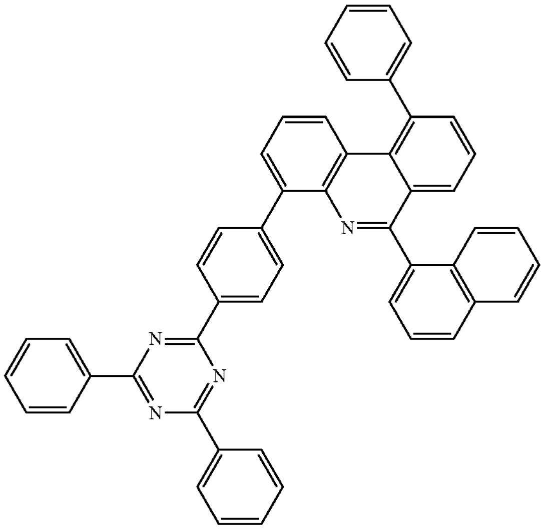

-continued
876
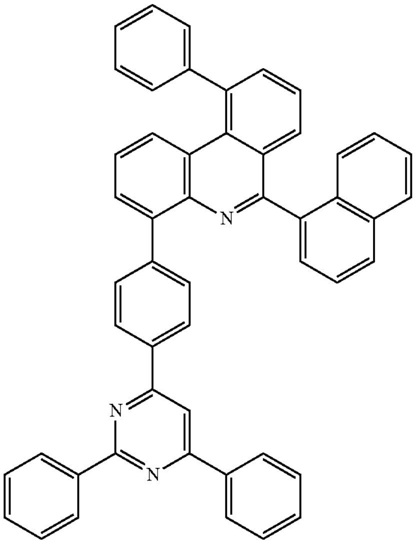
877
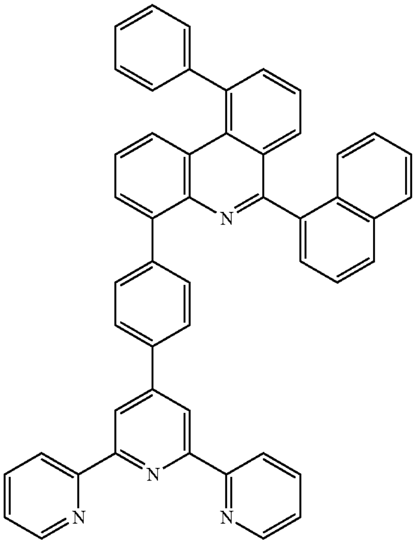
878
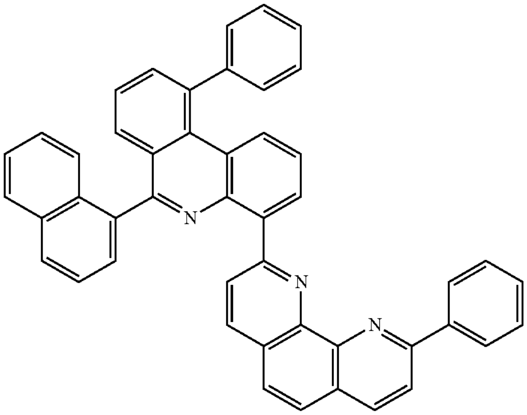
-continued
879
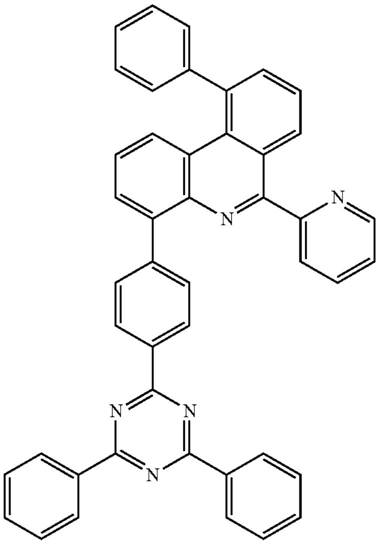
880
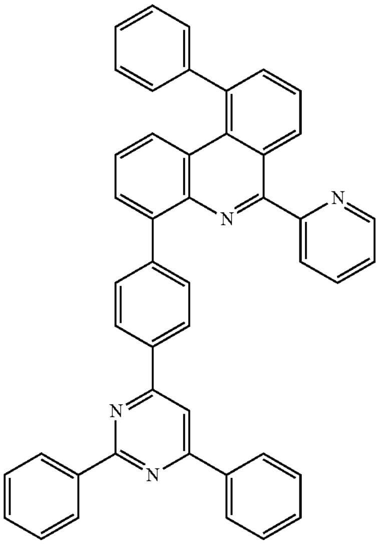
881
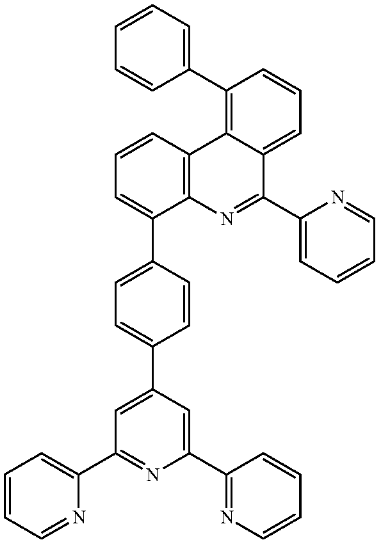

882
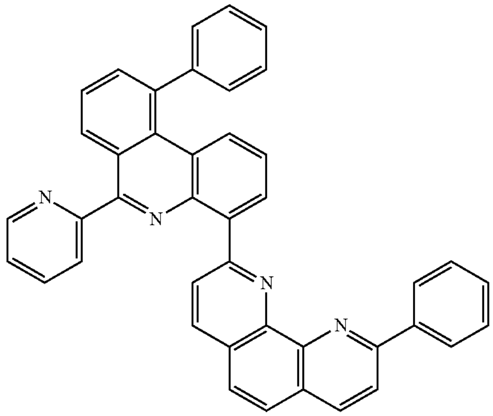
883
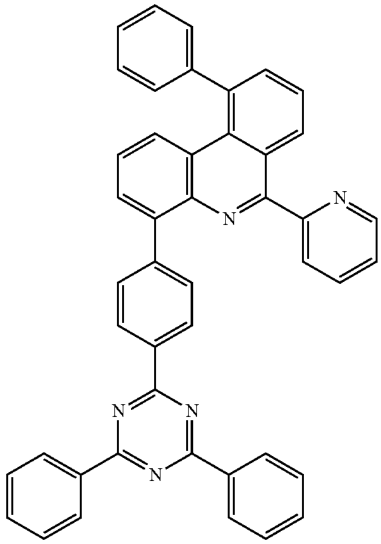
884
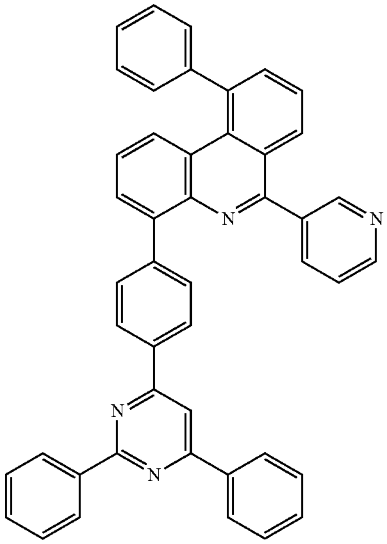
885
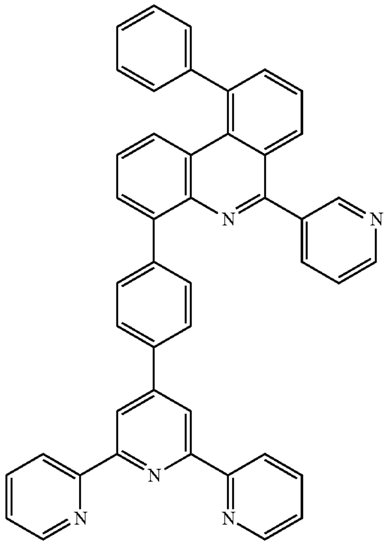
886
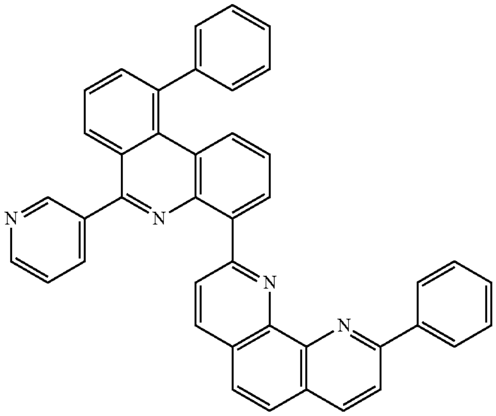
887
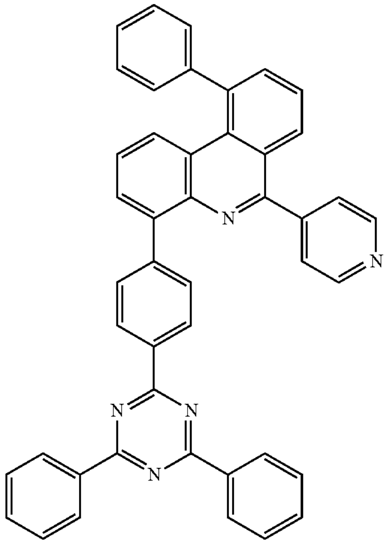

-continued
888
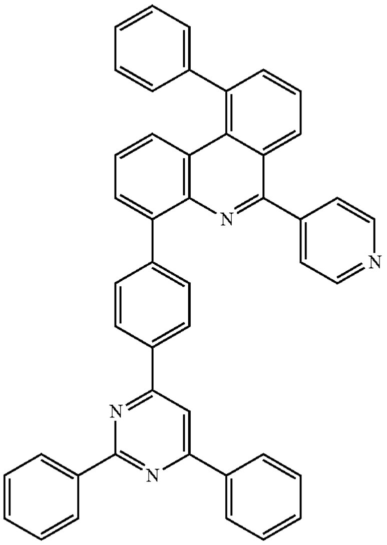
889
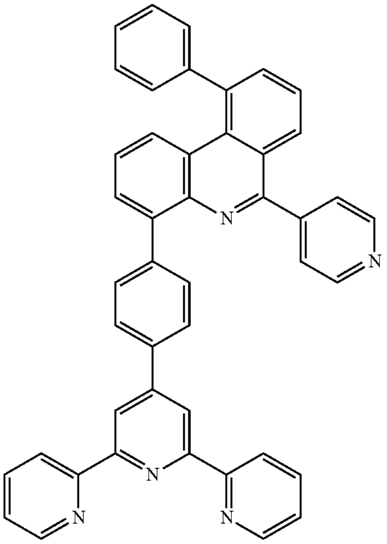
890
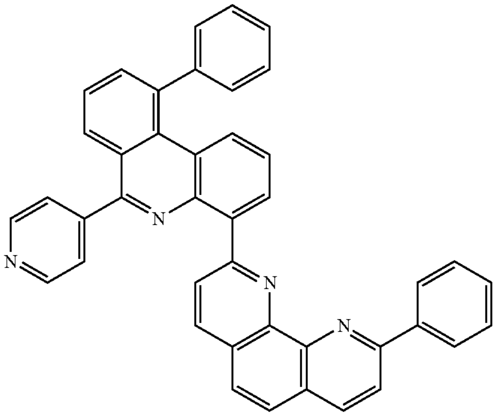
-continued
891
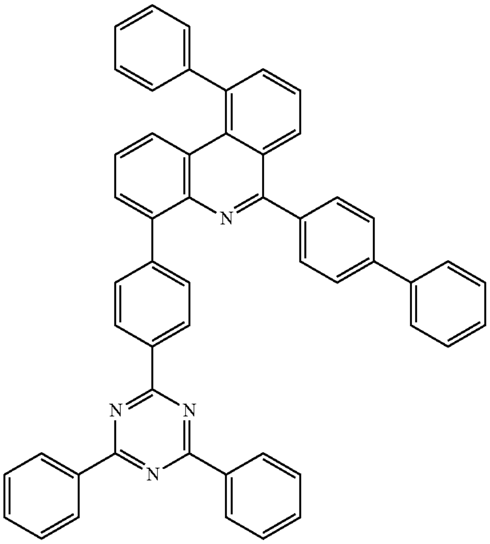
892
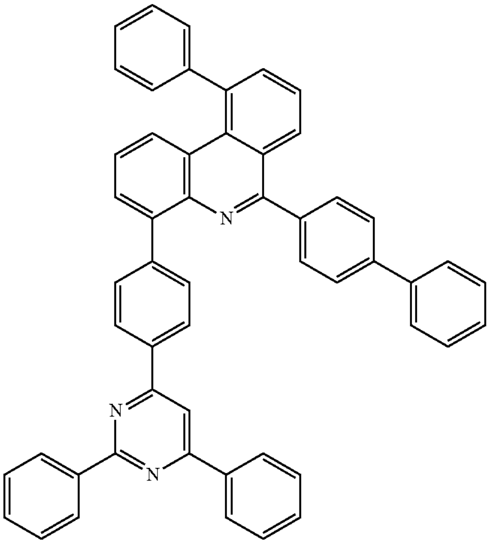
893
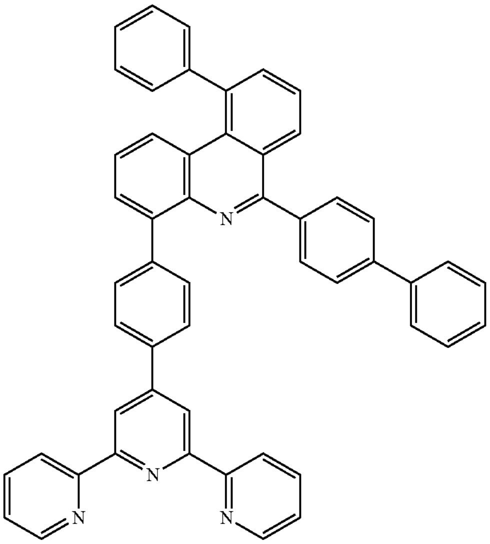

-continued
894
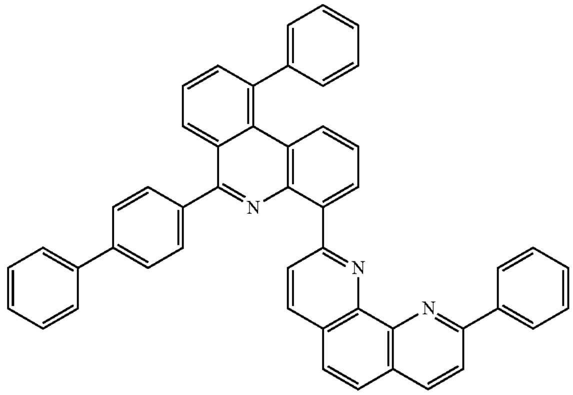
895
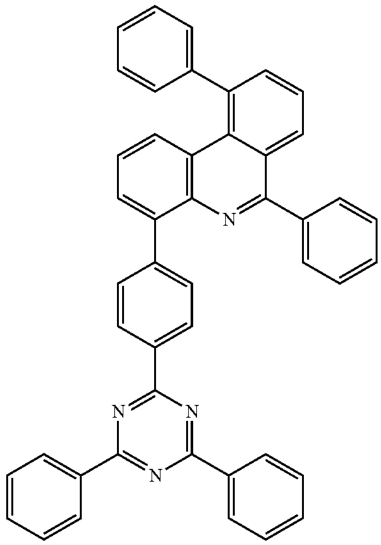
896
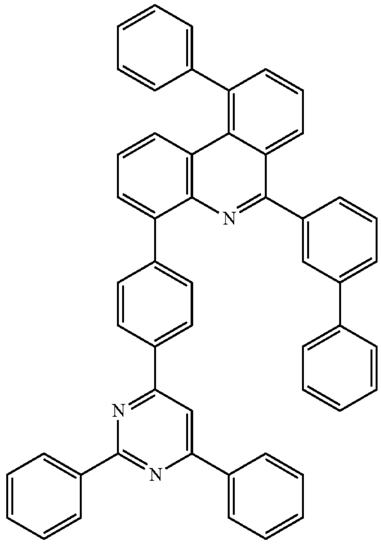
-continued
897
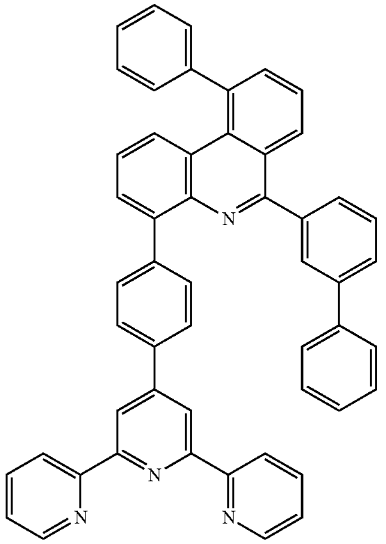
898
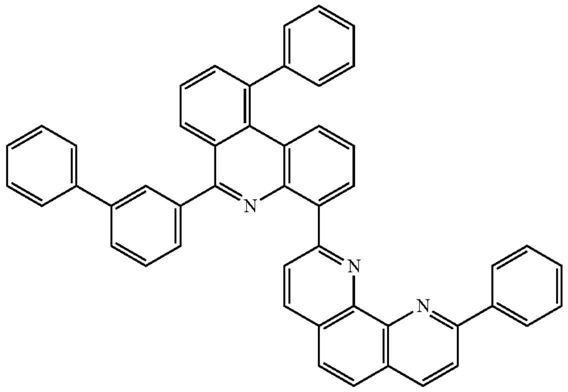
899
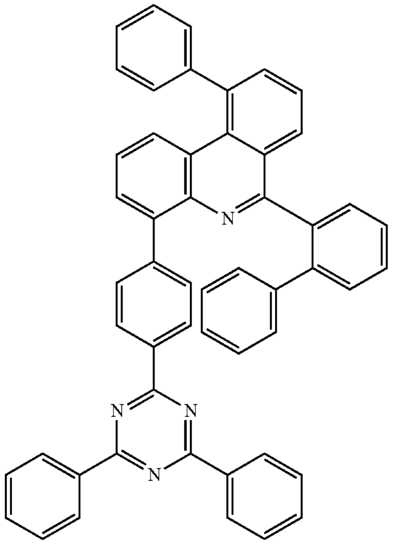

-continued
900
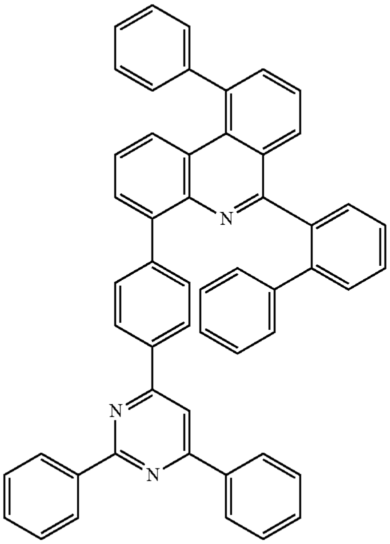
901
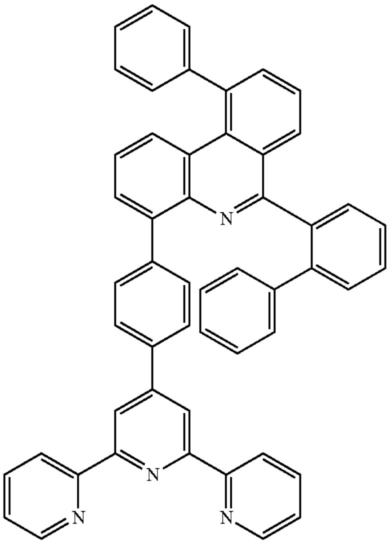
902
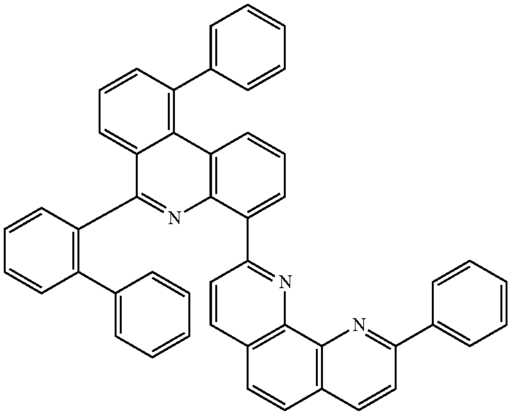
-continued
903
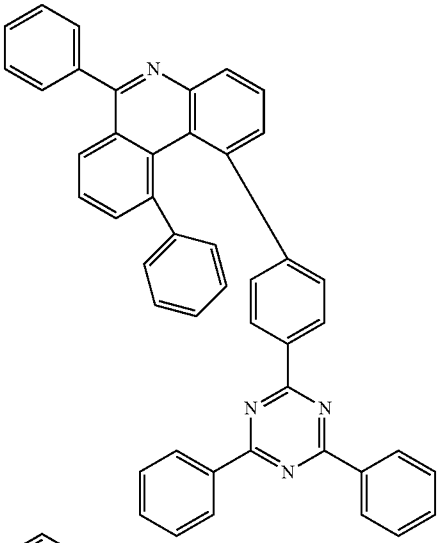
904
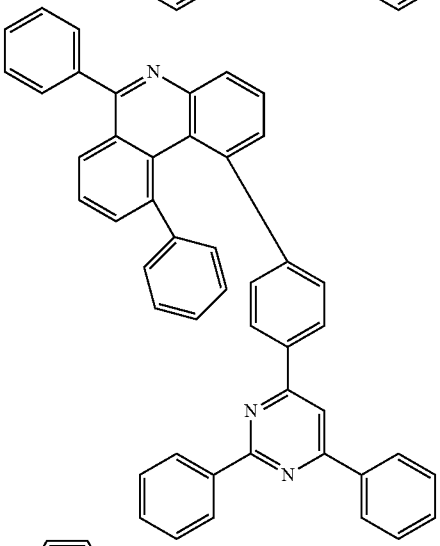
905
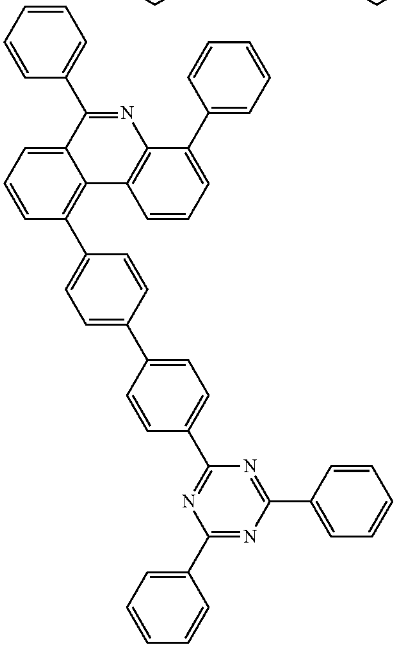

-continued
-continued
906
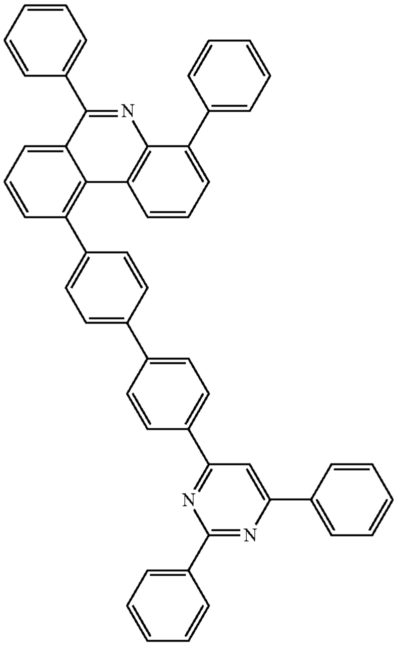
908
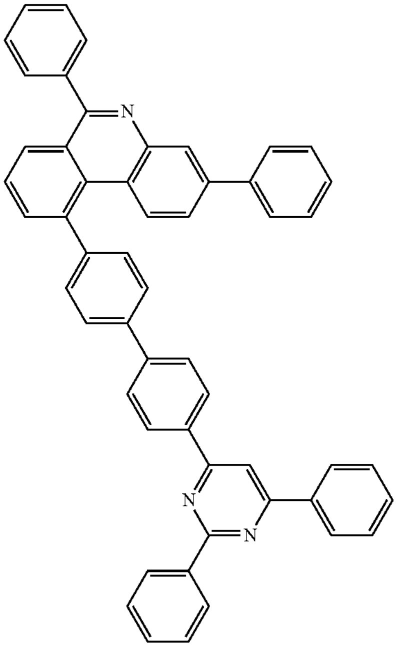
907
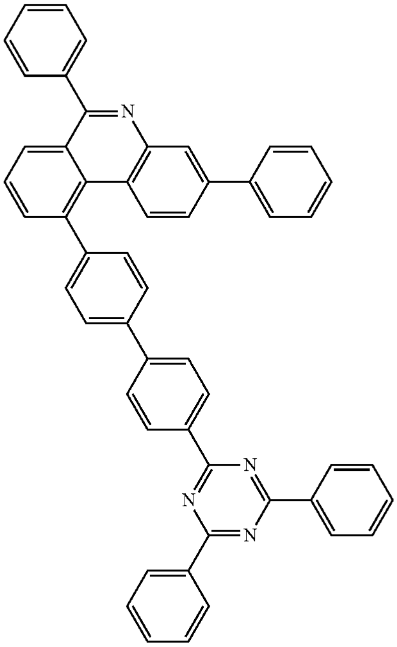
909
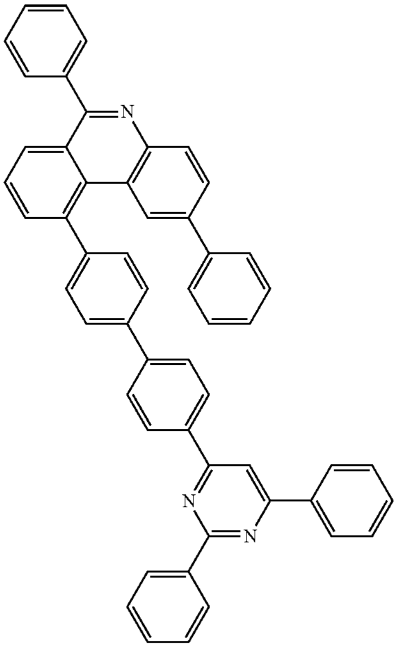

910
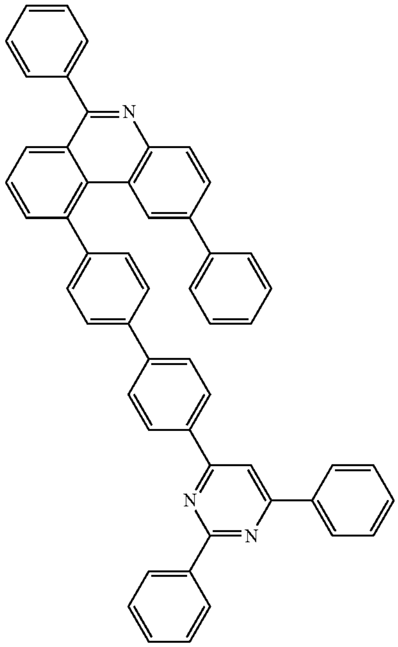
912
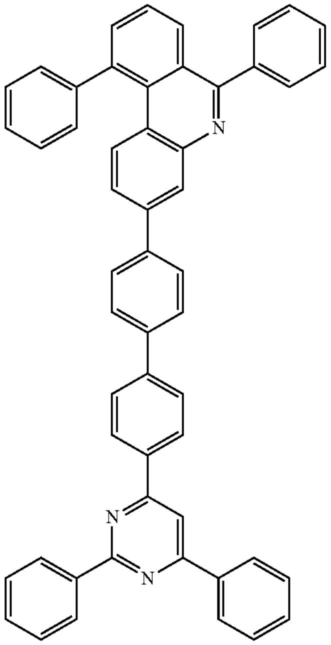
911
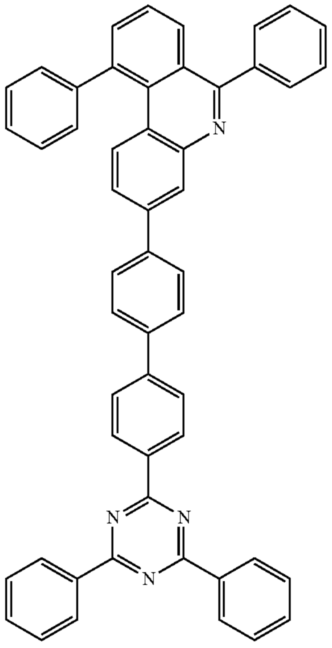
913
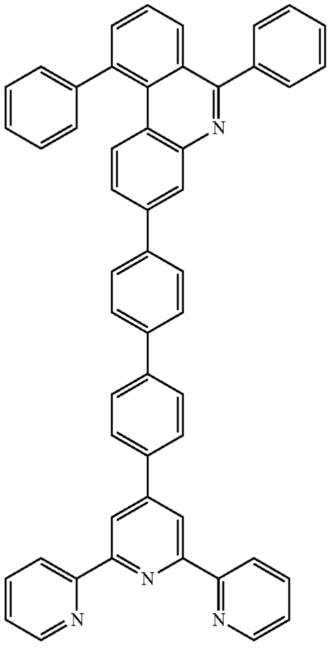

-continued
914
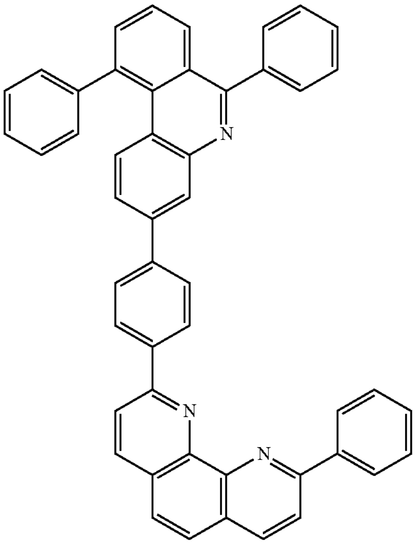
916
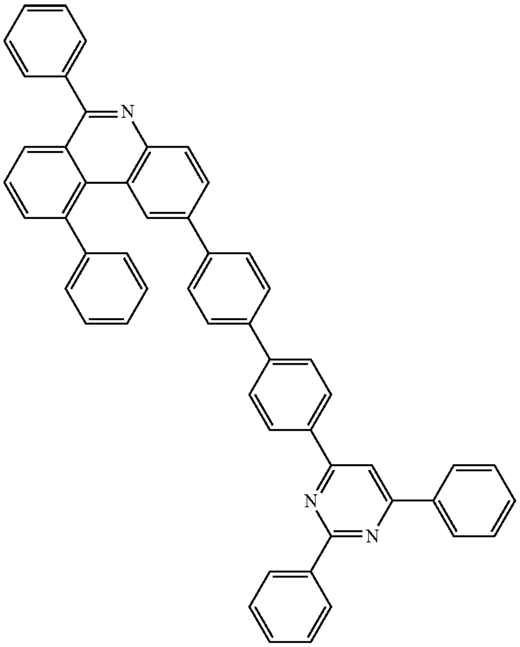
915
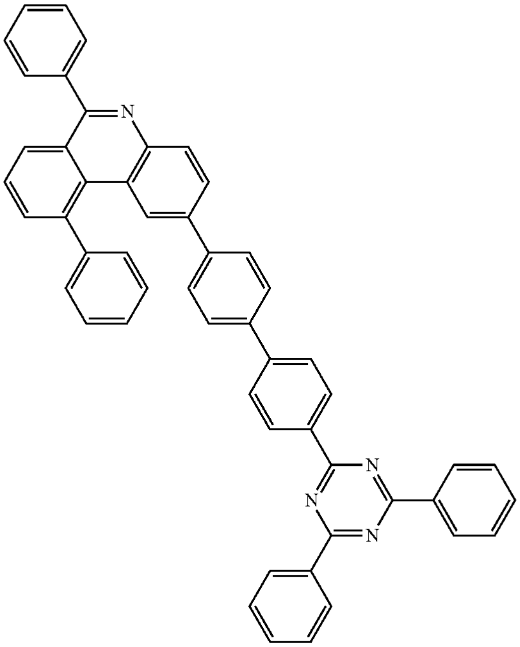
917
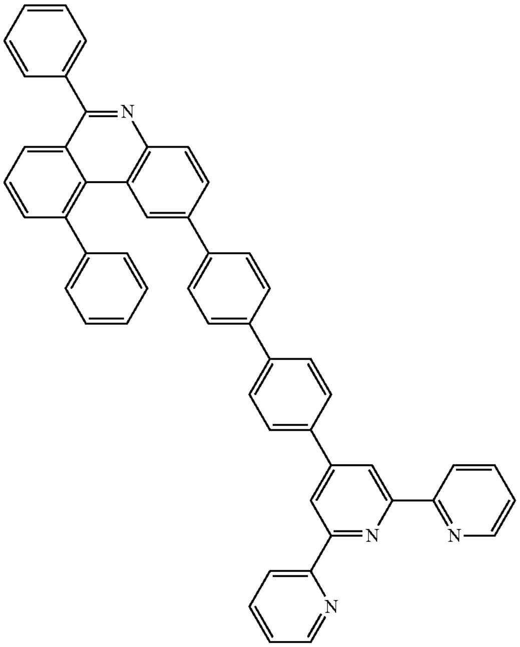

-continued
918
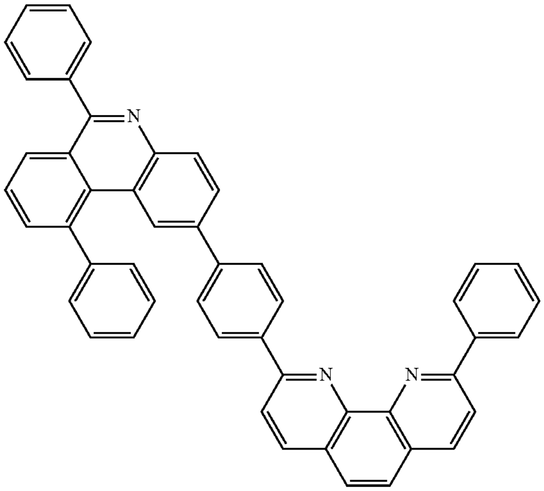
919
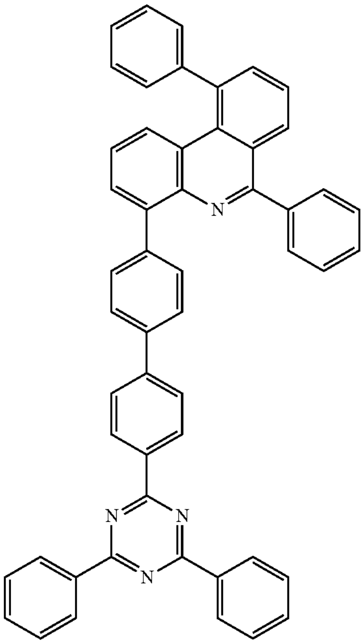
-continued
920
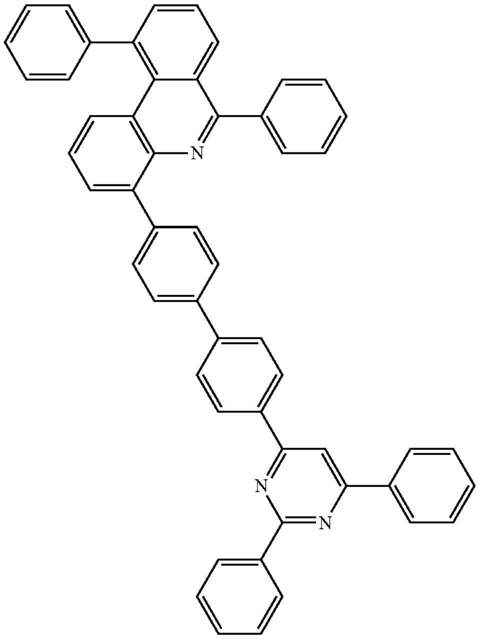
921
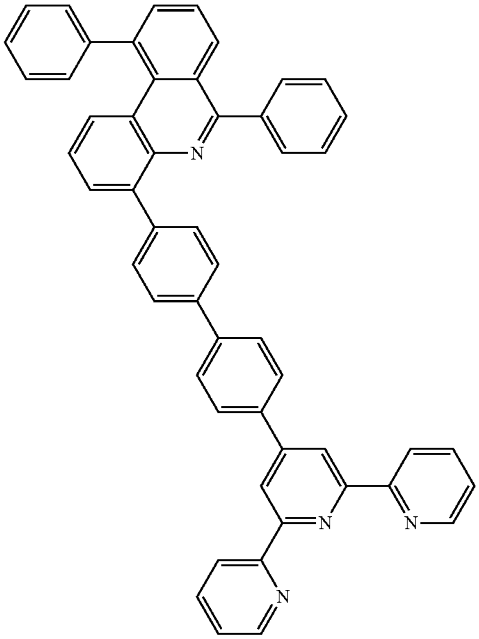

-continued
922
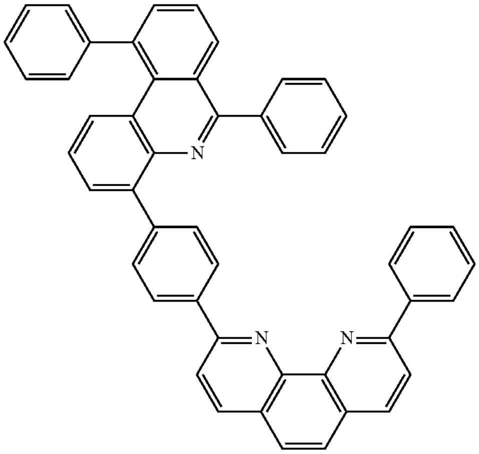
923
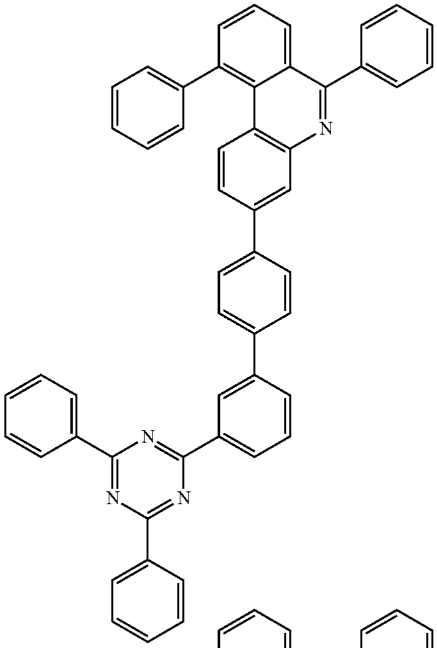
924
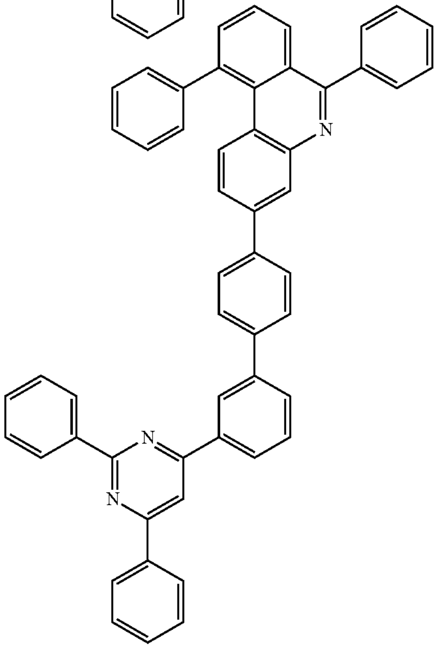
-continued
925
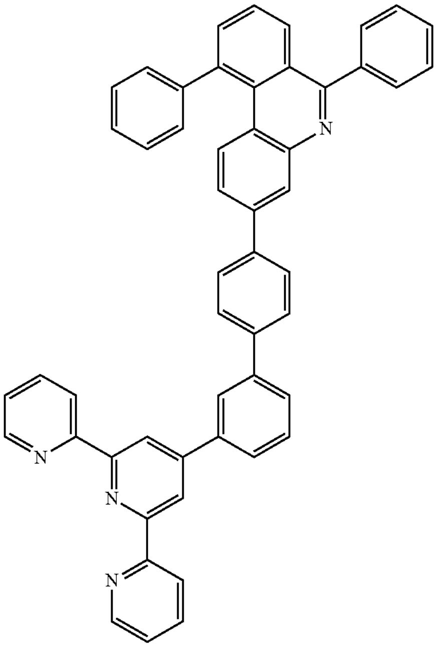
926
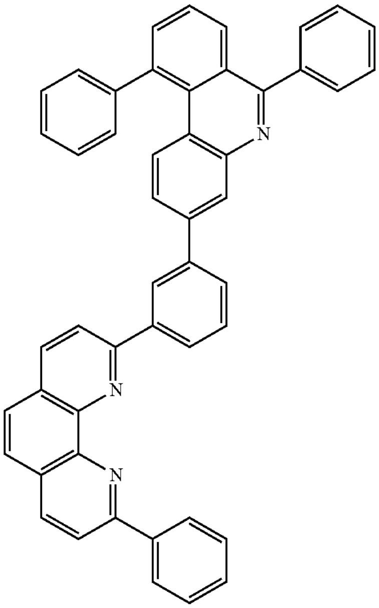

927
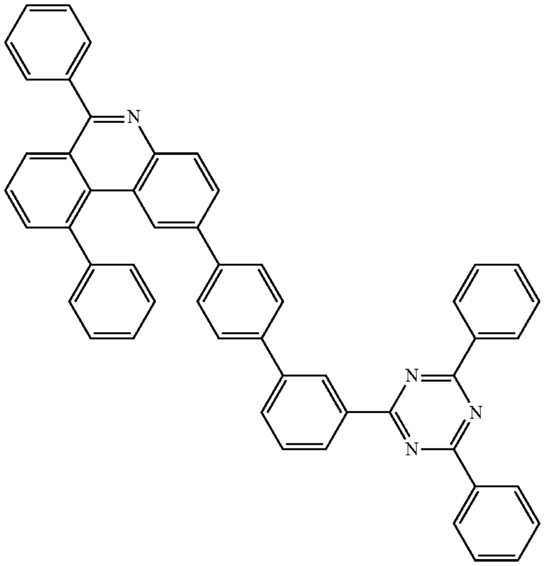
928
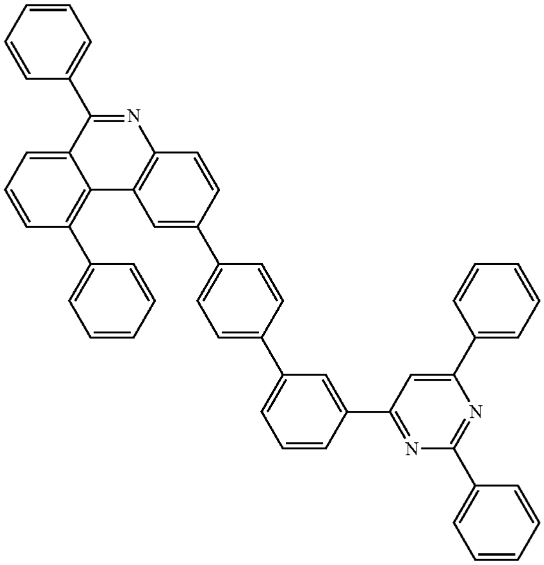
929
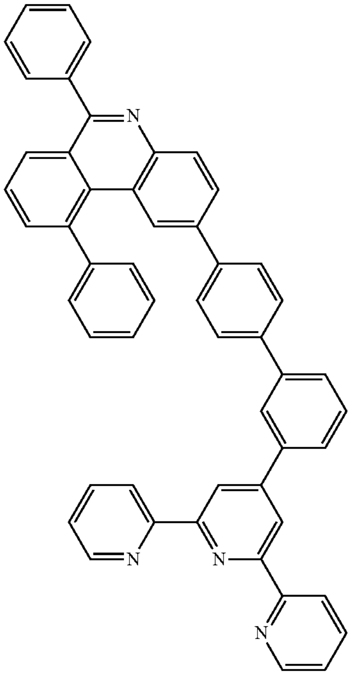
930
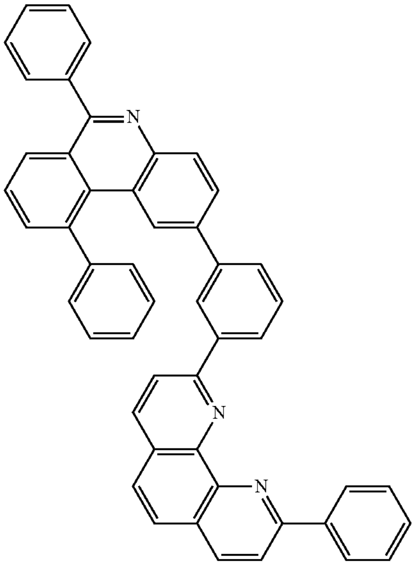

-continued
931
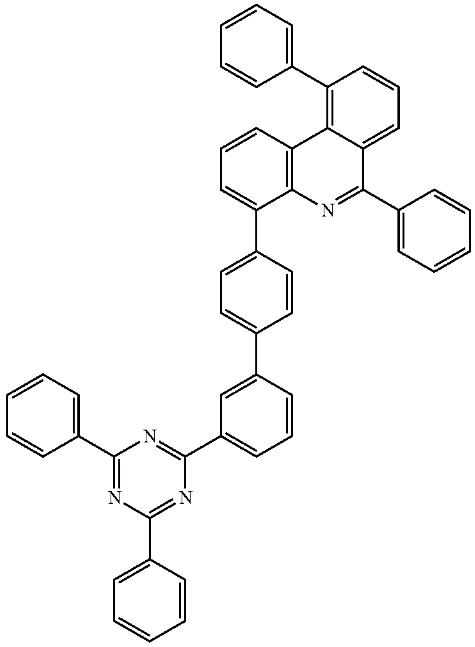
932
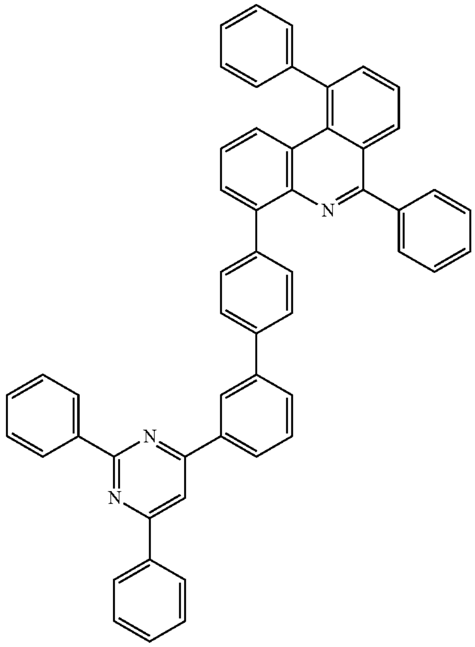
-continued
933
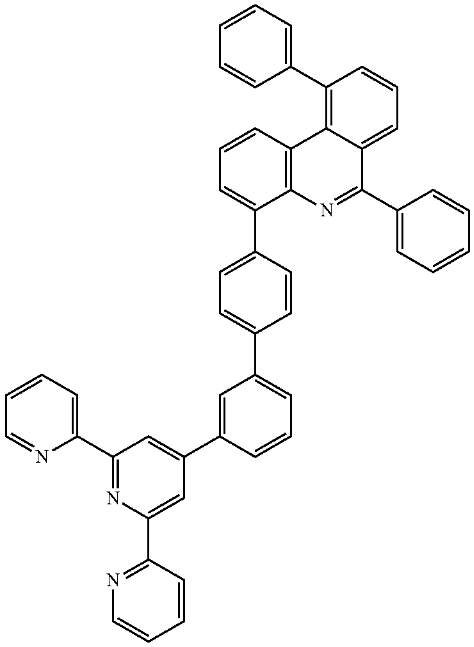
934
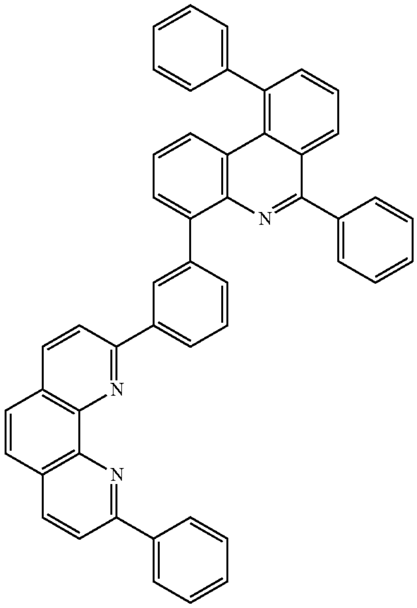

-continued
935
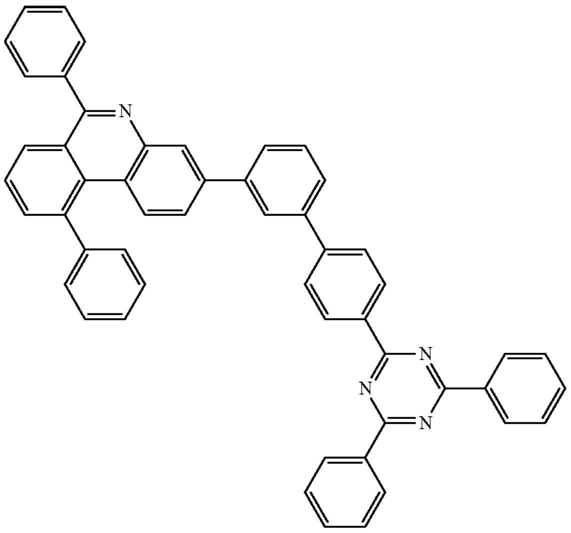
936
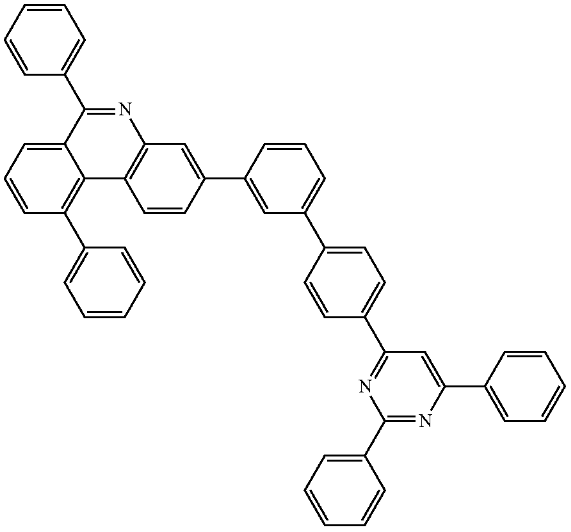
937
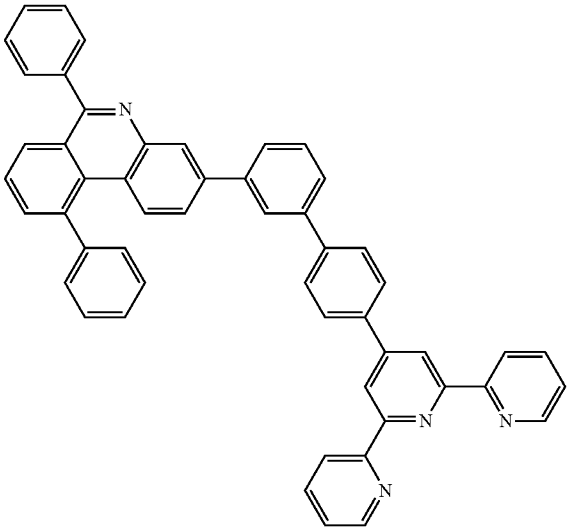
-continued
938
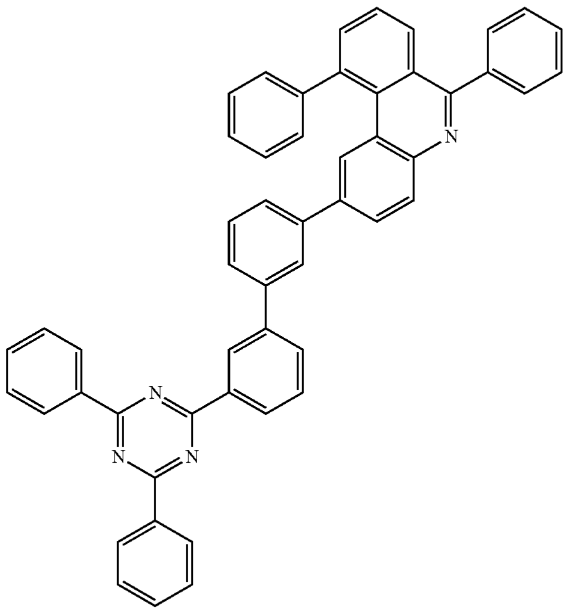
939
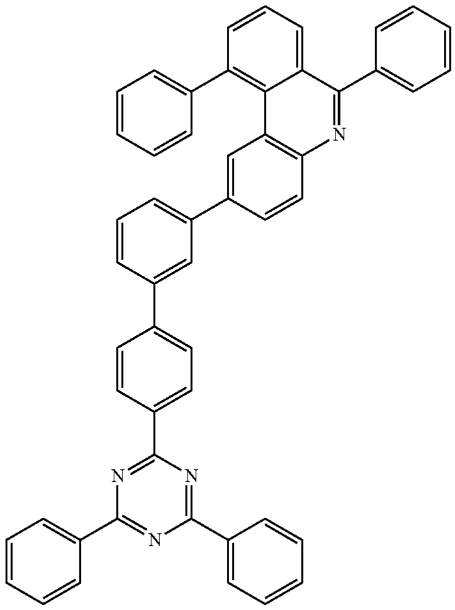

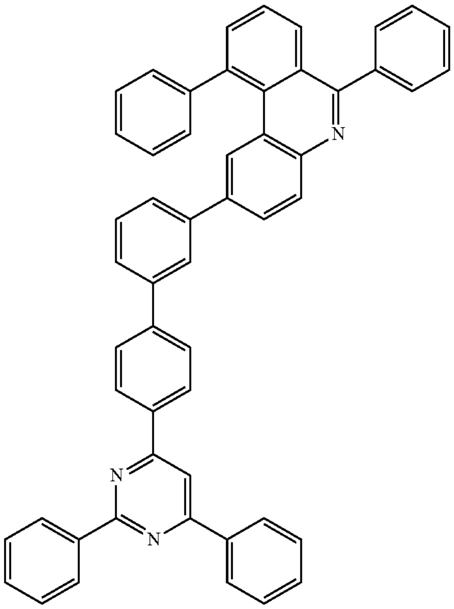
940
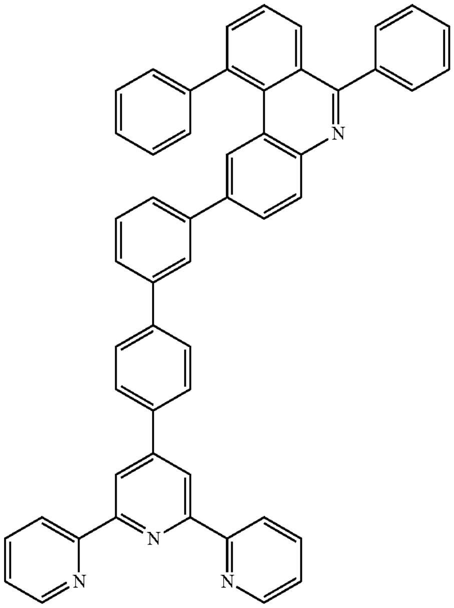
941
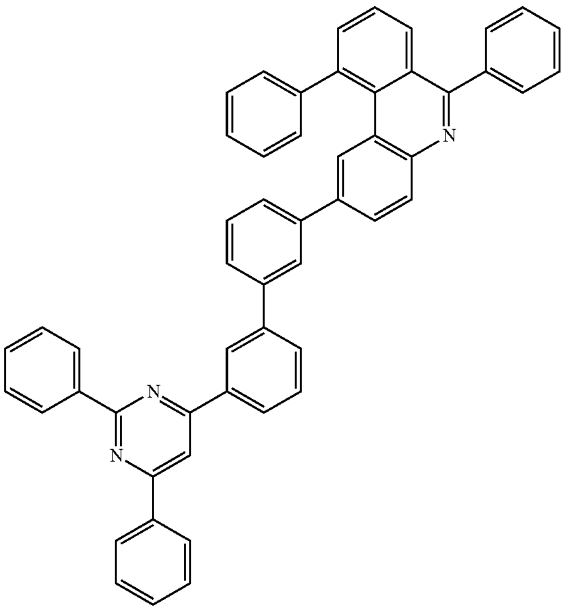
942
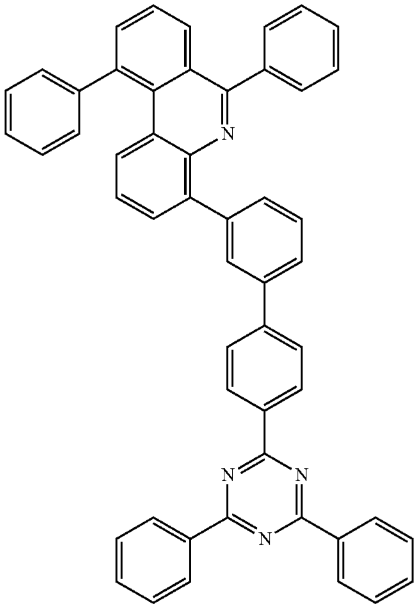
943

-continued
944
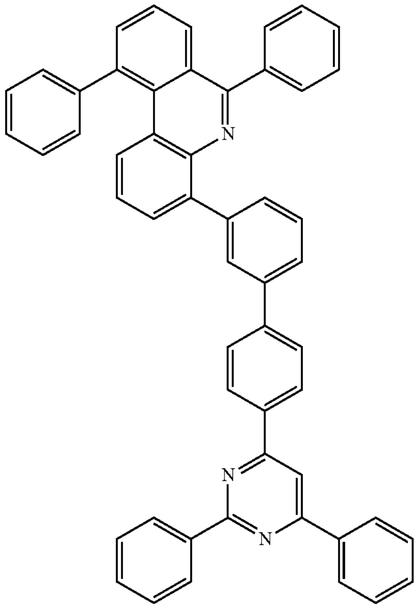
945
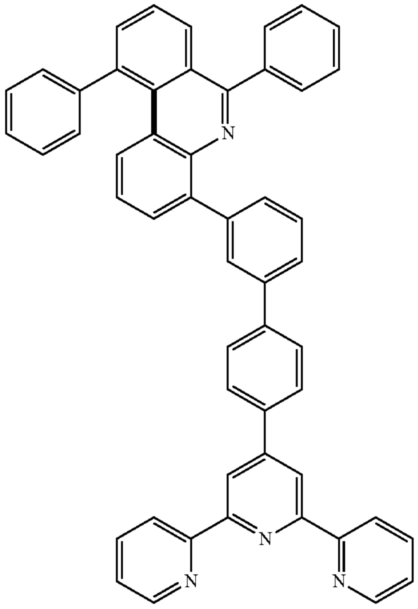
-continued
946
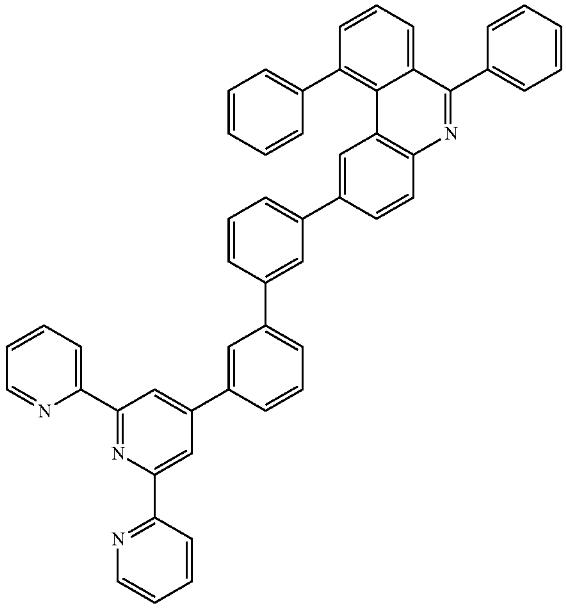
947
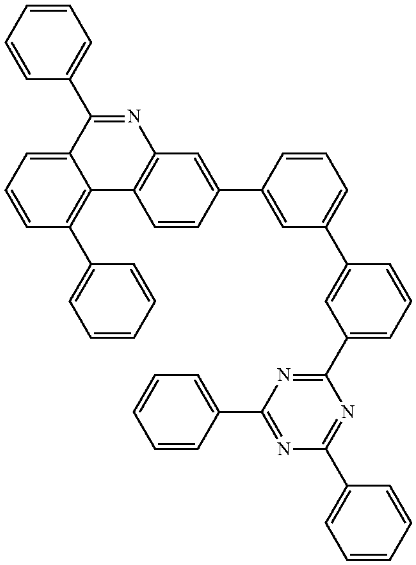

948
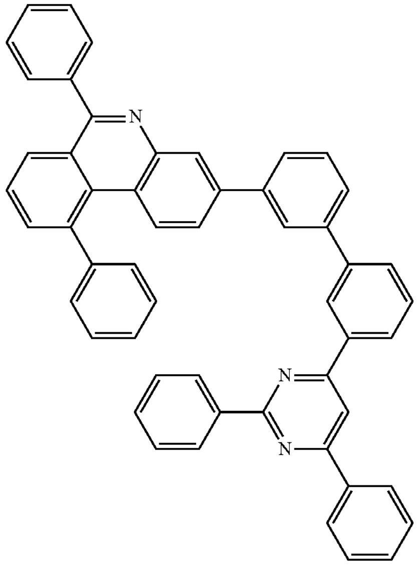
949
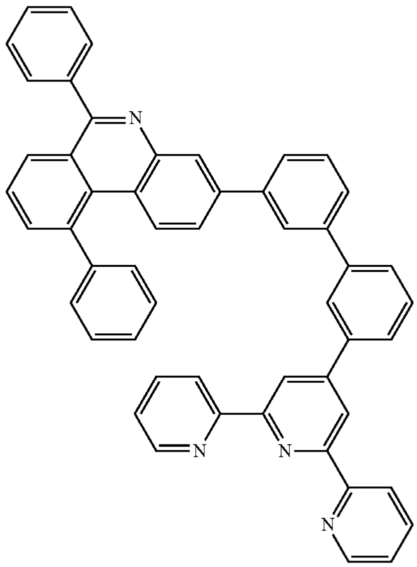
950
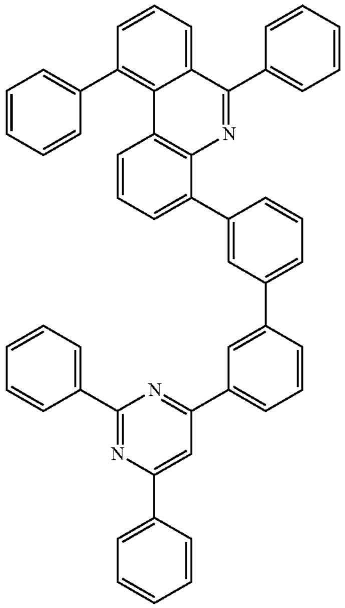
951
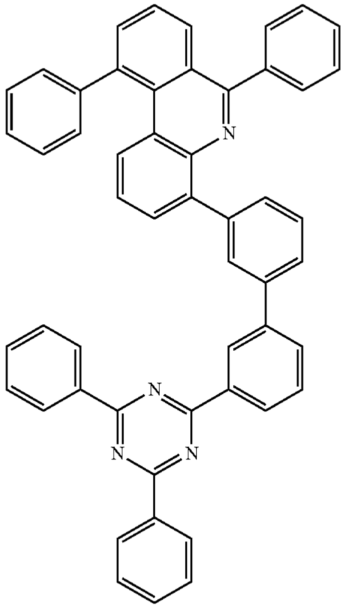

-continued

952

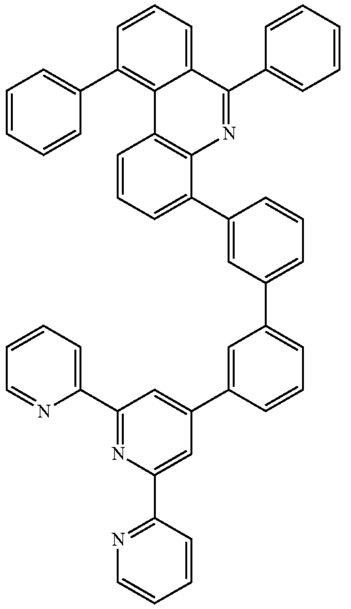

The compound according to one embodiment of the present application may be prepared according to the following General Formula 1.

(General Formula 1)

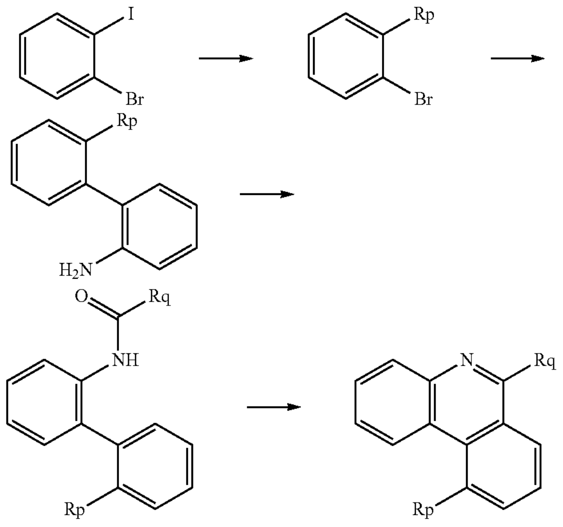

Rp in General Formula 1 has the same definition as $-(L_2)_p-(Z_2)_q$ in Chemical Formula 1, and Rq in General Formula 1 has the same definition as $-(L_1)-(Z_1)_n$ in Chemical Formula 1.

In addition, by introducing various substituents to the structure of Chemical Formulae 1 to 12, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formulae 1 to 12, the energy band gap may be finely controlled, and meanwhile, properties at interfaces between organic materials are enhanced, and material applications may become diverse.

Meanwhile, the compound has a high glass transition temperature (Tg), and has excellent thermal stability. Such an increase in the thermal stability becomes an important factor providing driving stability to a device.

The heterocyclic compound according to one embodiment of the present application may be prepared through a multistep chemical reaction. Some intermediate compounds are prepared first, and the compound of Chemical Formula 1 may be prepared from the intermediate compounds. More specifically, the heterocyclic compound according to one embodiment of the present application may be prepared based on preparation examples to describe later.

Another embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound according to Chemical Formula 1.

In one embodiment of the present application, the first electrode may be an anode, and the second electrode may be a cathode.

In another embodiment, the first electrode may be a cathode, and the second electrode may be an anode.

In one embodiment of the present application, the organic light emitting device may be a blue organic light emitting device, and the heterocyclic compound according to Chemical Formula 1 may be used as a material of the blue organic light emitting device.

In one embodiment of the present application, the organic light emitting device may be a green organic light emitting device, and the heterocyclic compound according to Chemical Formula 1 may be used as a material of the green organic light emitting device.

In one embodiment of the present application, the organic light emitting device may be a red organic light emitting device, and the heterocyclic compound according to Chemical Formula 1 may be used as a material of the red organic light emitting device.

Specific descriptions on the heterocyclic compound represented by Chemical Formula 1 are the same as the descriptions provided above.

The organic light emitting device of the present disclosure may be manufactured using common organic light emitting device manufacturing methods and materials except that one or more organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure may be formed in a single layer structure, or may also be foiled in a multilayer structure in which two or more organic material layers are laminated. For example, the organic light emitting device according to one embodiment of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may comprise less numbers of organic material layers.

In the organic light emitting device of the present disclosure, the organic material layer comprises an electron injection layer or an electron transfer layer, and the electron injection layer or the electron transfer layer may comprise the heterocyclic compound.

In the organic light emitting device of the present disclosure, the organic material layer comprises an electron transfer layer, and the electron transfer layer may comprise the heterocyclic compound.

In another organic light emitting device, the organic material layer comprises an electron blocking layer or a hole blocking layer, and the electron blocking layer or the hole blocking layer may comprise the heterocyclic compound.

In another organic light emitting device, the organic material layer comprises a hole blocking layer, and the hole blocking layer may comprise the heterocyclic compound.

In another organic light emitting device, the organic material layer comprises an electron transfer layer, a light emitting layer or a hole blocking layer, and the electron transfer layer, the light emitting layer or the hole blocking layer may comprise the heterocyclic compound.

The organic light emitting device of the present disclosure may further comprise one, two or more layers selected from the group consisting of a light emitting layer, a hole injection layer, a hole transfer layer, an electron injection layer, an electron transfer layer, an electron blocking layer and a hole blocking layer.

FIGS. 1 to 3 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, other layers except the light emitting layer may not be included, and other necessary functional layers may be further included.

The organic material layer comprising Chemical Formulae 1 to 12 may further comprise other materials as necessary.

In addition, the organic light emitting device according to one embodiment of the present application comprises an anode, a cathode, and two or more stacks provided between the anode and the cathode, wherein the two or more stacks each independently comprise a light emitting layer, a charge generation layer is included between the two or more stacks, and the charge generation layer comprises the heterocyclic compound represented by Chemical Formula 1.

In addition, the organic light emitting device according to one embodiment of the present application may comprise an anode, a first stack provided on the anode and comprising a first light emitting layer, a charge generation layer provided on the first stack, a second stack provided on the charge generation layer and comprising a second light emitting layer, and a cathode provided on the second stack. Herein, the charge generation layer may comprise the heterocyclic compound represented by Chemical Formula 1. In addition, the first stack and the second stack may each independently further comprise one or more types of the hole injection layer, the hole transfer layer, the hole blocking layer, the electron transfer layer, the electron injection layer described above and the like.

The charge generation layer may be an N-type charge generation layer, and the charge generation layer may further comprise a dopant known in the art in addition to the heterocyclic compound represented by Chemical Formula 1.

As the organic light emitting device according to one embodiment of the present application, an organic light emitting device having a 2-stack tandem structure is schematically illustrated in FIG. 4.

Herein, the first electron blocking layer, the first hole blocking layer and the second hole blocking layer and the like described in FIG. 4 may not be included in some cases.

In the organic light emitting device according to one embodiment of the present application, materials other than the compounds of Chemical Formulae 1 to 12 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrene-sulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involved in light emission together may also be used.

When mixing light emitting material hosts, same series hosts may be mixed, or different series hosts may be mixed. For example, any two or more types of materials among n-type host materials or p-type host materials may be selected, and used as a host material of a light emitting layer.

The organic light emitting device according to one embodiment of the present application may be a top-emission type, a bottom-emission type or a dual-emission type depending on the materials used.

The heterocyclic compound according to one embodiment of the present application may also be used in an organic electronic device comprising an organic solar cell, an organic photo conductor, an organic transistor and the like under a similar principle used in the organic light emitting device.

MODE FOR INVENTION

Hereinafter, the present specification will be described in more detail with reference to examples, however, these are for illustrative purposes only, and the scope of the present application is not limited thereto.

PREPARATION EXAMPLE

<Preparation Example 1> Preparation of Compound 1

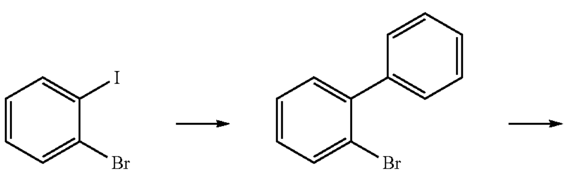

1-1

-continued

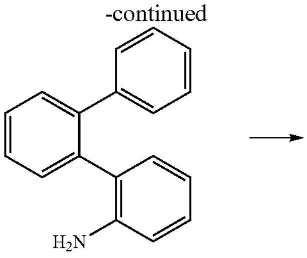

1-2

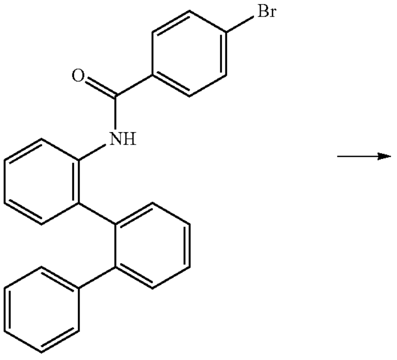

1-3

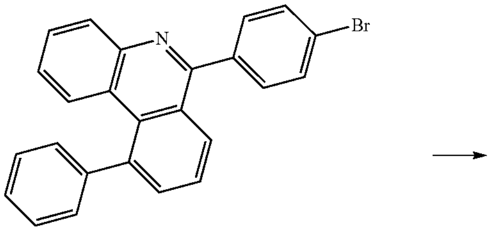

1-4

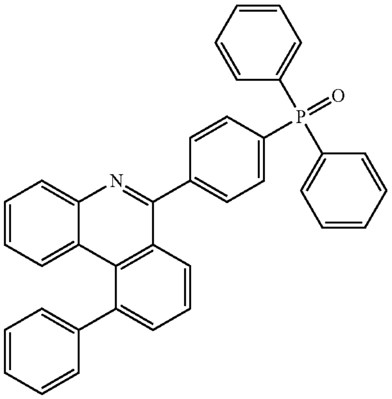

1

1) Preparation of Compound 1-1

After dissolving 1-bromo-2-iodobenzene (100 g, 353 mmol, 1 eq.) in 1,4-dioxane/$H_2O$, phenylboronic acid (42 g, 353 mmol, 1 eq.), $Pd(PPh_3)_4$ (20 g, 0.05 eq.) and $K_2CO_3$ (146 g, 3 eq.) were added thereto, and the result was stirred for 6 hours at 100° C. After the reaction was terminated, the result was cooled to room temperature, and extracted with distilled water and EA. The organic layer was dried with $MgSO_4$, and then filtered and concentrated. With ethyl acetate and hexane as a developing solvent, the concentrated residue was purified using column chromatography to obtain target Compound 1-1 (72 g, 88%).

2) Preparation of Compound 1-2

After dissolving Compound 1-1 (72 g, 310 mmol, 1 eq.) in 1,4-dioxane/$H_2O$, 2-(4,4,5,5-tetramethyl-1,3,2-dioxaborolan-2-yl)aniline (81 g, 1.2 eq.), $Pd(PPh_3)_4$ (18 g, 0.05 eq.) and $K_2CO_3$ (128 g, 3 eq.) were added thereto, and the result was stirred for 6 hours at 100° C. After the reaction was terminated, the result was cooled to room temperature, and extracted with distilled water and EA. The organic layer was dried with $MgSO_4$, and then filtered and concentrated. With ethyl acetate and hexane as a developing solvent, the concentrated residue was purified using column chromatography to obtain target Compound 1-2 (69 g, 91%).

3) Preparation of Compound 1-3

After dissolving Compound 1-2 (69 g, 282 mmol, 1 eq.) by adding THF, TEA (118 ml, 3 eq.) and 4-bromobenzoyl chloride (92 g, 1.5 eq.) were added thereto at 0° C., and the result was stirred for 1 hour at room temperature. After the reaction was terminated, the result was extracted with distilled water and EA. The organic layer was dried with $MgSO_4$, and then filtered and concentrated. With ethyl acetate and hexane as a developing solvent, the concentrated residue was purified using column chromatography to obtain target Compound 1-3 (114 g, 95%).

4) Preparation of Compound 1-4

After dissolving Compound 1-3 (114 g, 267 mmol, 1 eq.) in nitrobenzene, $POCl_3$ (37.4 mL, 1.5 eq.) was added thereto, and the result was stirred for 6 hours at 150° C. After the reaction was terminated, the result was neutralized at room temperature, and then extracted with distilled water and dichloromethane. The organic layer was dried with $MgSO_4$, and then filtered and concentrated. The concentrated residue was stirred with ethyl acetate and then filtered to obtain target Compound 1-4 (78.8 g, 72%).

5) Preparation of Compound 1

After dissolving Compound 1-4 (10 g, 24.4 mmol) in THF, 2.5 M n-butyl lithium (n-BuLi) (1.3 eq.) was slowly added dropwise thereto at −78° C., and the result was stirred for 30 minutes. After adding chlorodiphenyl phosphine (1.3 eq.) thereto, the result was stirred for 1 hour. After the reaction was completed, methanol was added thereto, and the result was stirred for 1 hour, and then extracted with distilled water and EA. After drying the organic layer with anhydrous $MgSO_4$, the solvent was removed using a rotary evaporator. After dissolving the concentrated solution by adding dichloromethane, $H_2O_2$ was added thereto, and the result was stirred for 3 hours at room temperature. After the reaction was terminated, the result was extracted with distilled water and EA. After drying the organic layer with anhydrous $MgSO_4$, the solvent was removed using a rotary evaporator, and after dissolving the result by adding toluene and heating, the result was recrystallized to obtain target Compound 1 (10.5 g, 81%).

<Preparation Example 2> Preparation of Compound 4

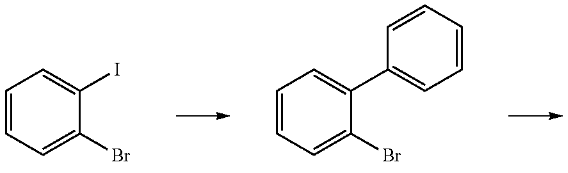

1-1

-continued

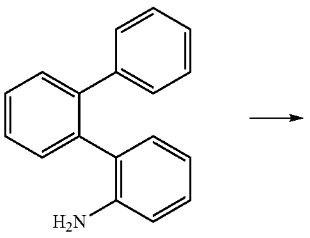

1-2

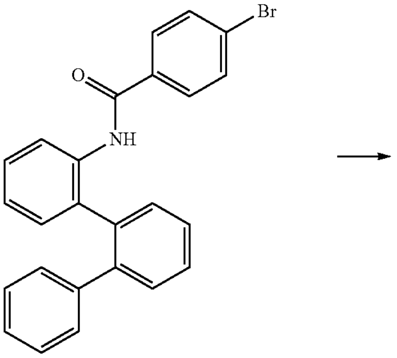

1-3

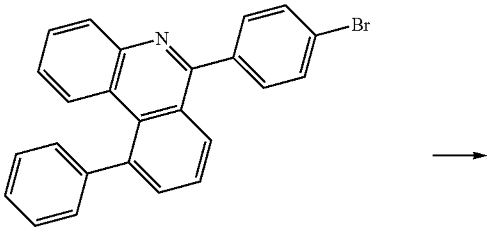

1-4

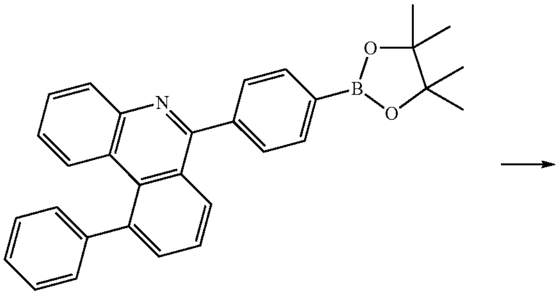

1-5

-continued

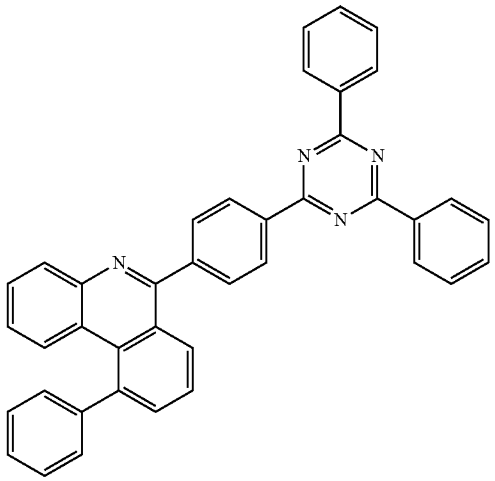

4

Preparation of Compound 1-5 After dissolving Compound 1-4 (78.8 g, 192 mmol) in 1,4-dioxane, bis(pinacolato)diboron (40 g, 2 eq.), Pd(dppf)$Cl_2$ (7.0 g, 0.05 eq.) and potassium acetate (56 g, 3.0 eq.) were added thereto, and the result was stirred for 2 hours at 110° C. After the reaction was completed, the result was extracted with distilled water and EA. After drying the organic layer with anhydrous $MgSO_4$, the solvent was removed using a rotary evaporator, and the result was passed through silica gel to obtain target Compound 1-5 (81 g, 93%).

Preparation of Compound 4

After adding 2-bromo-4,6-diphenyl-1,3,5-triazine (8.2 g, 26.2 mmol), $Pd(PPh_3)_4$ (1.25 g, 1.09 mmol), $K_2CO_3$ (25.0 g, 65.4 mmol) and toluene/EtOH/$H_2O$ to Compound 1-5 (10.0 g, 21.8 mmol), the result was stirred for 6 hours at 110° C. After the reaction was completed, the result was cooled to room temperature, and extracted with distilled water and dichloromethane. After drying the organic layer with anhydrous $MgSO_4$, the solvent was removed using a rotary evaporator, and with dichloromethane and hexane as a developing solvent, the result was purified using column chromatography to obtain target Compound 4 (10.4 g, 85%).

<Preparation Example 3> Preparation of Compound 5

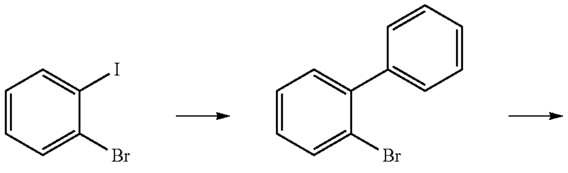

1-1

-continued

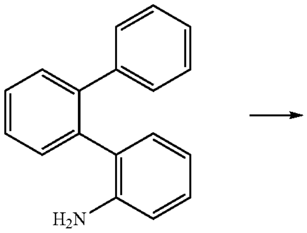

1-2

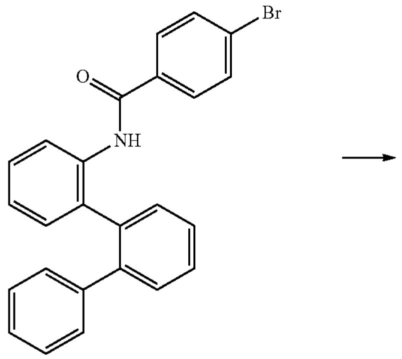

1-3

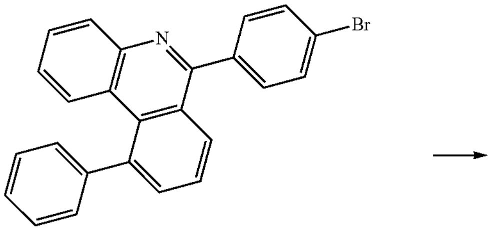

1-4

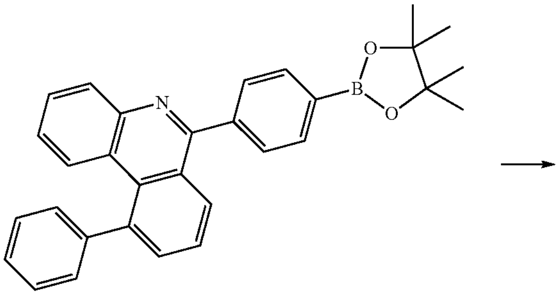

1-5

-continued

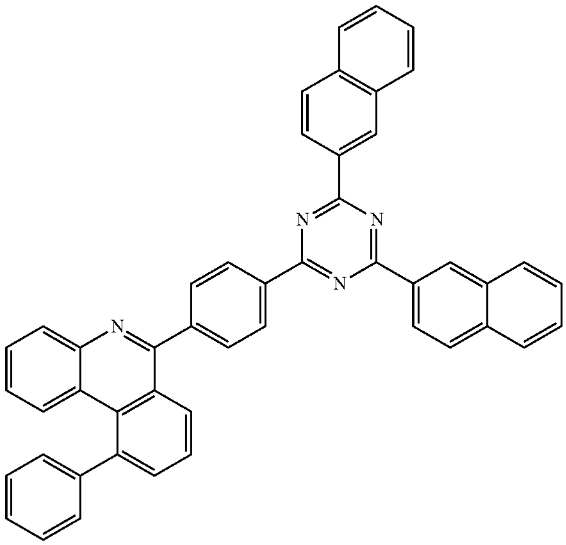

5

Preparation of Compound 5

Target Compound 5 was obtained in the same manner as in the preparation of Compound 4 of Preparation Example 2 except that 2-bromo-4,6-di(naphthalen-2-yl)-1,3,5-triazine was used instead of 2-bromo-4,6-diphenyl-1,3,5-triazine.

<Preparation Example 4> Preparation of Compound 6

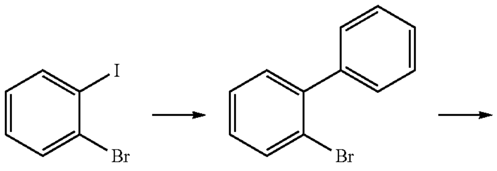

1-1

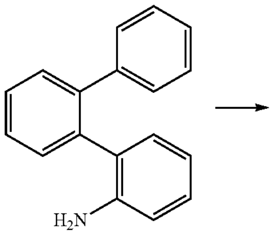

1-2

-continued

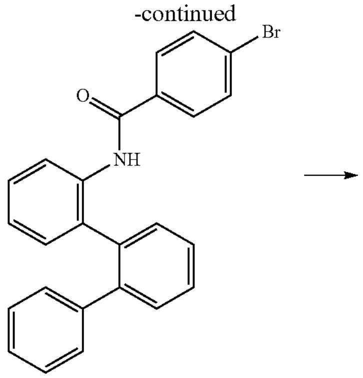

1-3

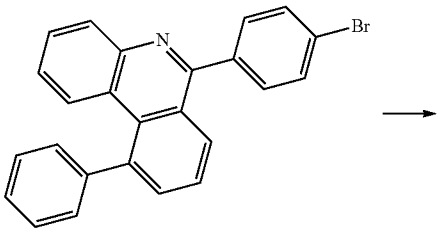

1-4

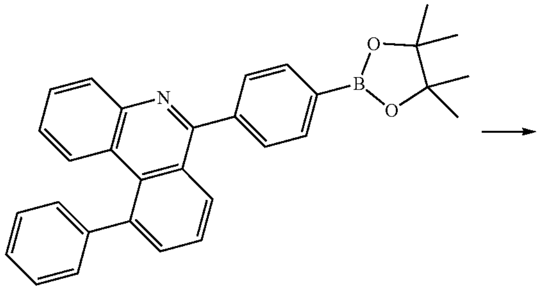

1-5

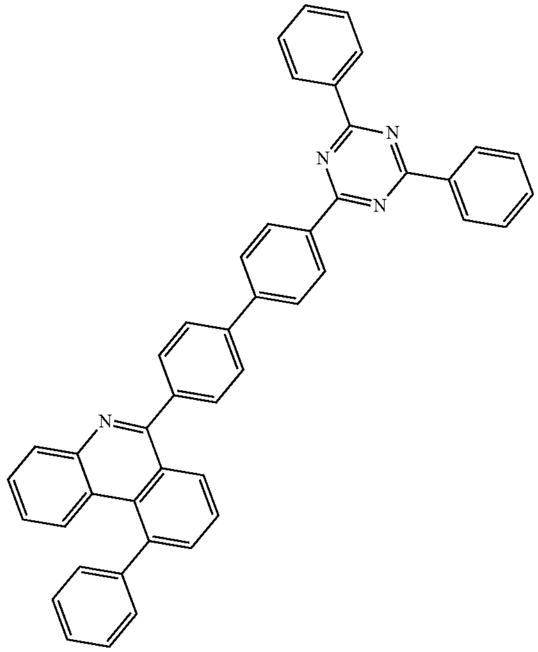

6

Target Compound 6 was obtained in the same manner as in the preparation of Compound 4 of Preparation Example 2 except that 2-(4-bromophenyl)-4,6-diphenyl-1,3,5-triazine was used instead of 2-bromo-4,6-diphenyl-1,3,5-triazine.

<Preparation Example 5> Preparation of Compound 8

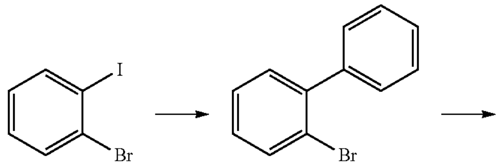

1-1

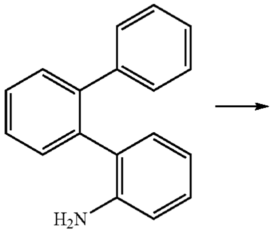

1-2

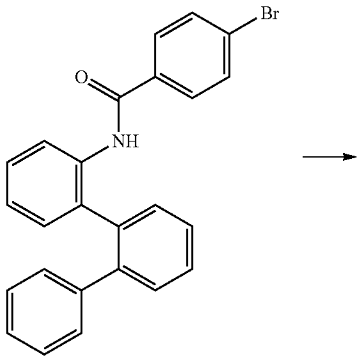

1-3

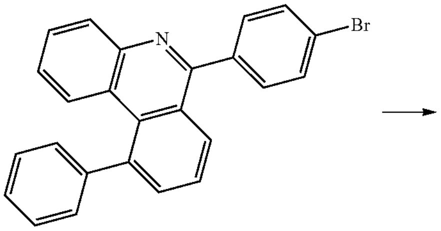

1-4

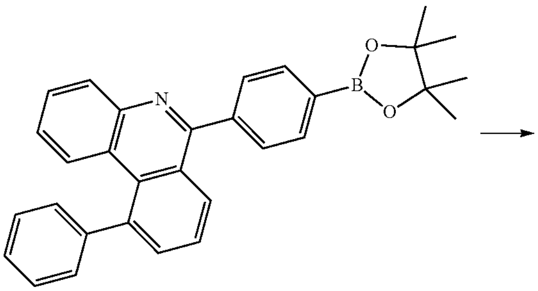

1-5

-continued

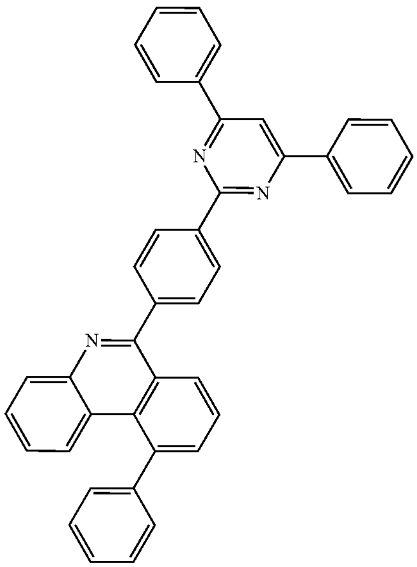

8

Target Compound 8 was obtained in the same manner as in the preparation of Compound 4 of Preparation Example 2 except that 2-chloro-4,6-diphenylpyrimidine was used instead of 2-bromo-4,6-diphenyl-1,3,5-triazine.

<Preparation Example 6> Preparation of Compound 9

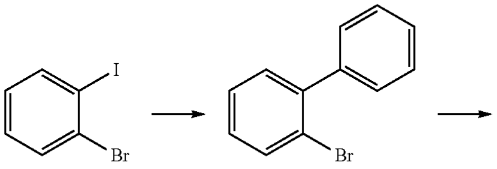

1-1

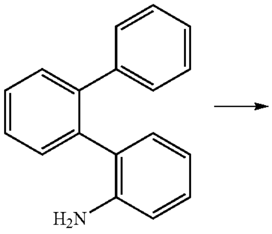

1-2

-continued
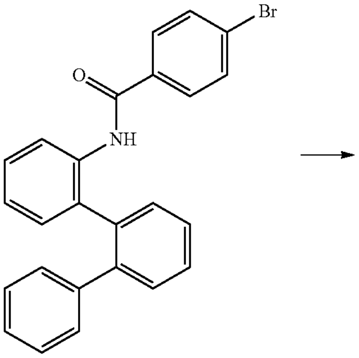
1-3
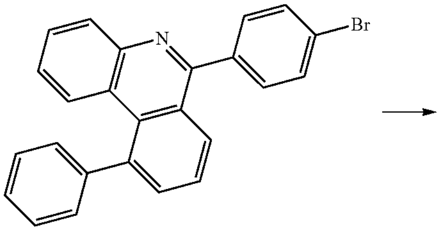
1-4
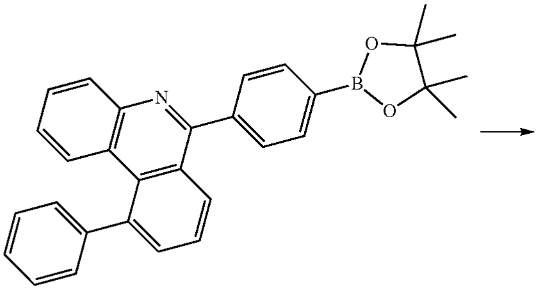
1-5
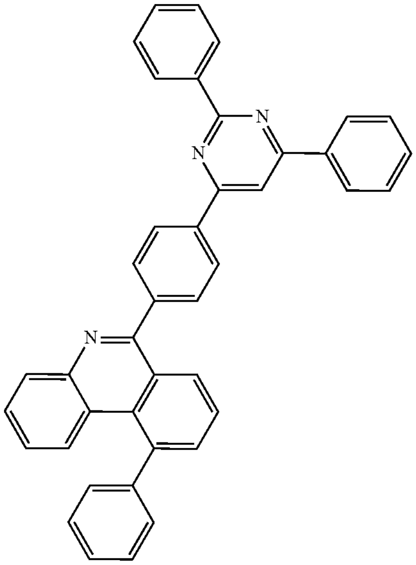
9
Target Compound 9 was obtained in the same manner as in the preparation of Compound 4 of Preparation Example 2 except that 4-chloro-2,6-diphenylpyrimidine was used instead of 2-bromo-4,6-diphenyl-1,3,5-triazine.
<Preparation Example 7> Preparation of Compound 12
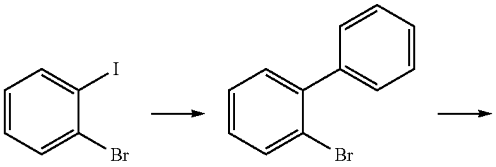
1-1
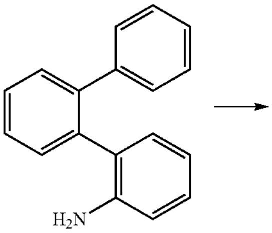
1-2
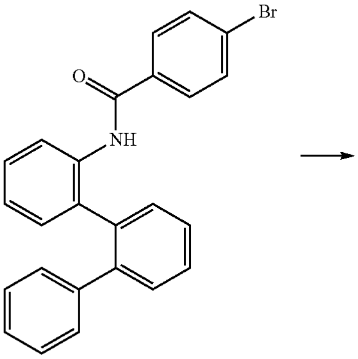
1-3
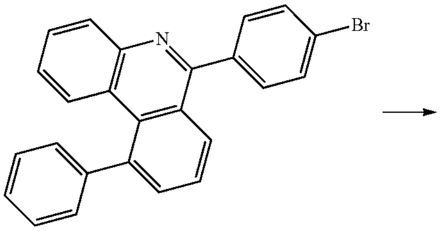
1-4
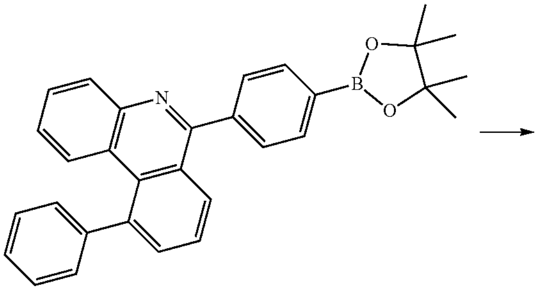
1-5

-continued

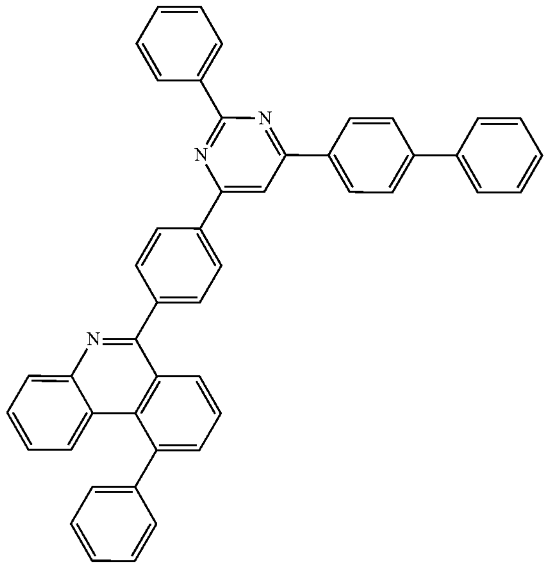

12

Target Compound 12 was obtained in the same manner as in the preparation of Compound 4 of Preparation Example 2 except that 4-([1,1'-biphenyl]-4-yl)-6-chloro-2-phenylpyrimidine was used instead of 2-bromo-4,6-diphenyl-1,3,5-triazine.

<Preparation Example 8> Preparation of Compound 16

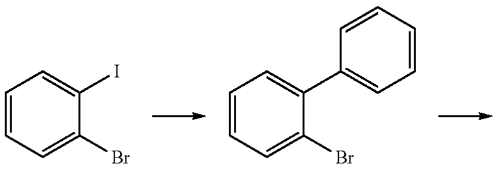

1-1

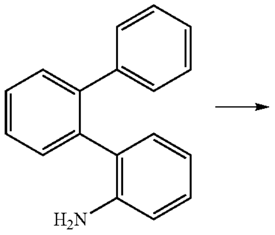

1-2

-continued

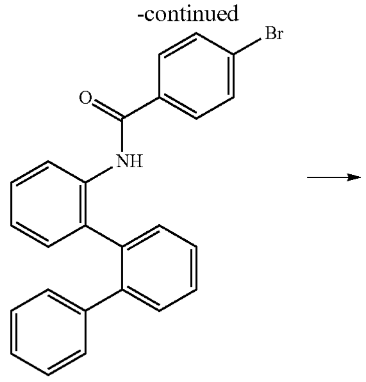

1-3

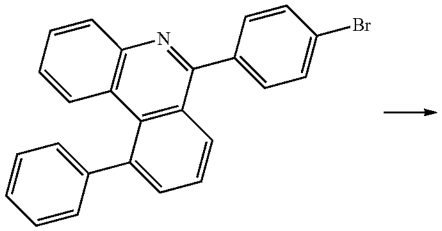

1-4

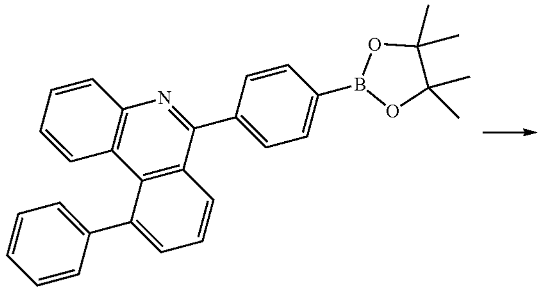

1-5

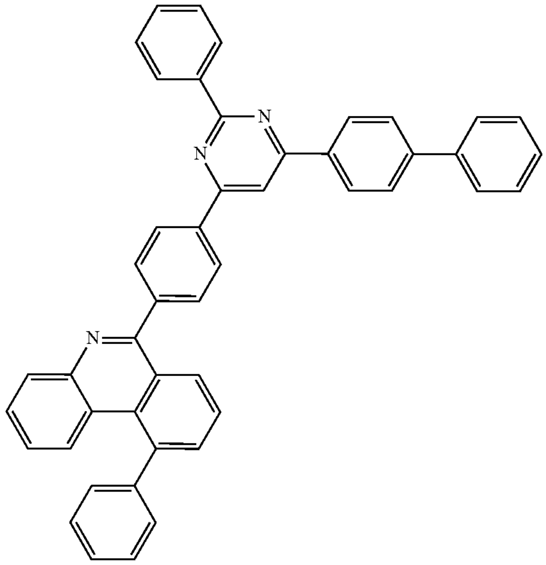

16

Target Compound 16 was obtained in the same manner as in the preparation of Compound 4 of Preparation Example 2 except that 4-([1,1'-biphenyl]-4-yl)-6-(4-bromophenyl)-2-phenylpyrimidine was used instead of 2-bromo-4,6-diphenyl-1,3,5-triazine.

<Preparation Example 9> Preparation of Compound 22

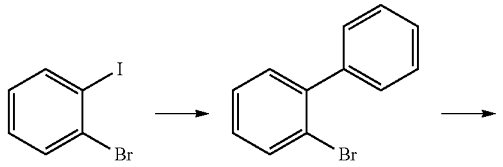

1-1

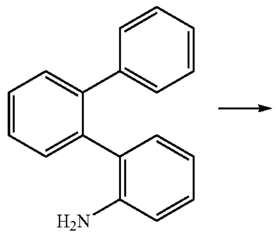

1-2

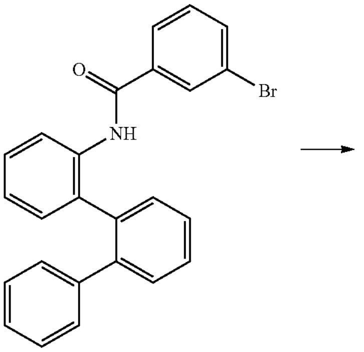

22-1

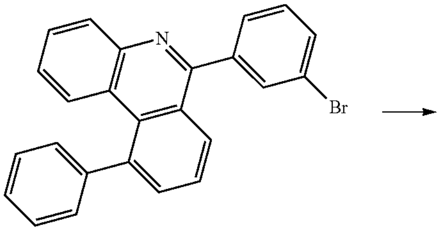

22-2

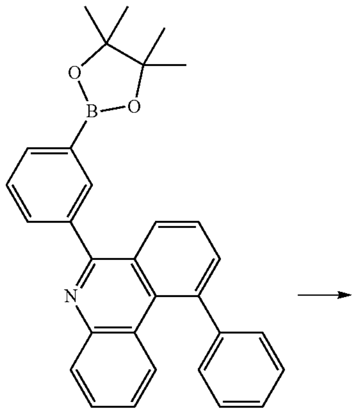

22-3

-continued

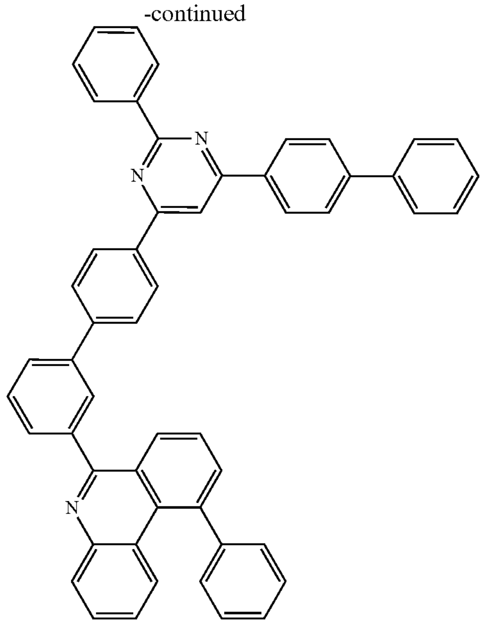

22

Preparation of Compound 22-1

After dissolving Compound 1-2 (50 g, 203 mmol, 1 eq.) by adding THF, TEA (85 ml, 3 eq.) and 3-bromobenzoyl chloride (67 g, 1.5 eq.) were added thereto at 0° C., and the result was stirred for 1 hour at room temperature. After the reaction was terminated, the result was extracted with distilled water and EA. The organic layer was dried with $MgSO_4$, and then filtered and concentrated. With ethyl acetate and hexane as a developing solvent, the concentrated residue was purified using column chromatography to obtain target Compound 22-1 (80 g, 93%).

Preparation of Compound 22-2

After dissolving Compound 22-1 (80 g, 188 mmol, 1 eq.) in nitrobenzene, $POCl_3$ (26.4 mL, 1.5 eq.) was added thereto, and the result was stirred for 6 hours at 150° C. After the reaction was terminated, the result was neutralized at room temperature, and then extracted with distilled water and dichloromethane. The organic layer was dried with $MgSO_4$, and then filtered and concentrated. The concentrated residue was stirred with ethyl acetate and then filtered to obtain target Compound 22-2 (52.4 g, 68%).

Preparation of Compound 22-3

After dissolving Compound 22-2 (52.4 g, 127 mmol) in 1,4-dioxane, bis(pinacolato)diboron (64 g, 2 eq.), Pd(dppf)$Cl_2$ (4.6 g, 0.05 eq.) and potassium acetate (37 g, 3.0 eq.) were added thereto, and the result was stirred for 2 hours at 110° C. After the reaction was completed, the result was extracted with distilled water and EA. After drying the organic layer with anhydrous $MgSO_4$, the solvent was removed using a rotary evaporator, and the result was passed through silica gel to obtain target Compound 22-3 (57 g, 98%).

Preparation of Compound 22

After adding 2-bromo-4,6-diphenyl-1,3,5-triazine (8.2 g, 26.2 mmol), $Pd(PPh_3)_4$ (1.25 g, 1.09 mmol), $K_2CO_3$ (25.0 g, 65.4 mmol) and toluene/EtOH/$H_2O$ to Compound 22-3 (10.0 g, 21.8 mmol), the result was stirred for 6 hours at 110° C. After the reaction was completed, the result was cooled to room temperature, and extracted with distilled water and dichloromethane. After drying the organic layer with anhydrous $MgSO_4$, the solvent was removed using a rotary evaporator, and with dichloromethane and hexane as a developing solvent, the result was purified using column chromatography to obtain target Compound 22 (12.7 g, 82%).

<Preparation Example 10> Preparation of Compound 25

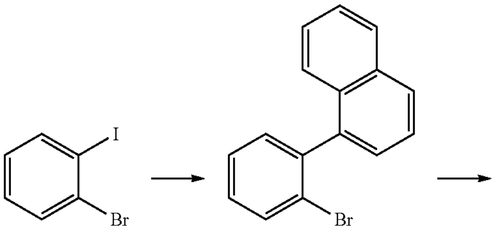

25-1

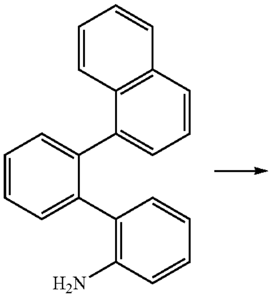

25-2

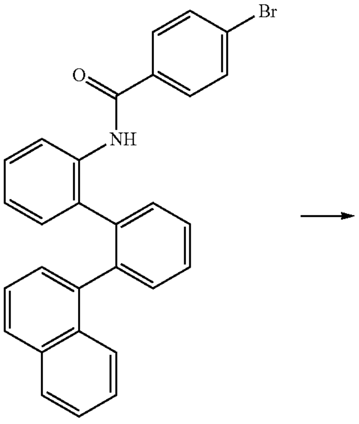

25-3

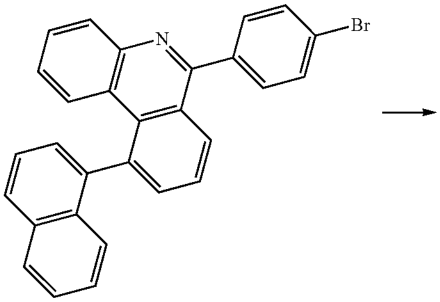

25-4

-continued

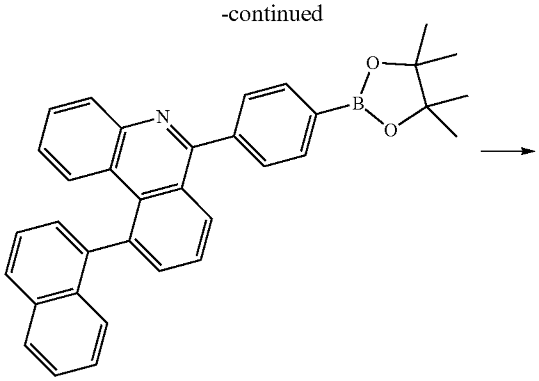

25-5

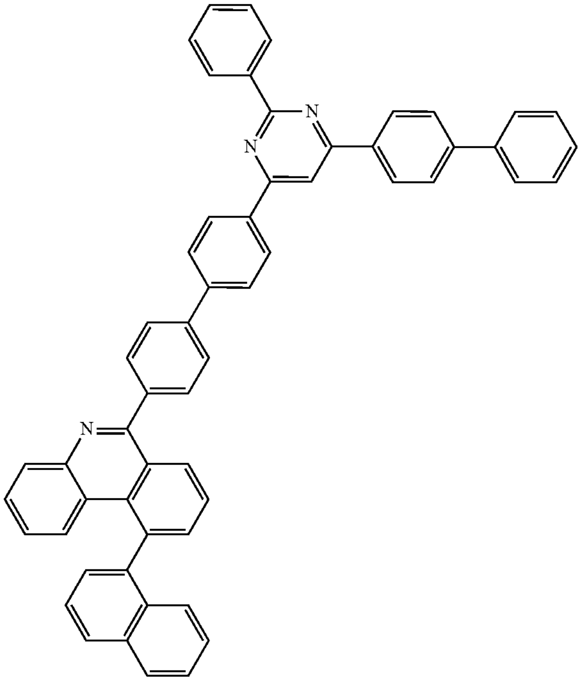

25

Preparation of Compound 25-1

After dissolving 1-bromo-2-iodobenzene (100 g, 353 mmol, 1 eq.) in 1,4-dioxane/$H_2O$, 1-naphthylboronic acid (60 g, 353 mmol, 1 eq.), $Pd(PPh_3)_4$ (20 g, 0.05 eq.) and $K_2CO_3$ (146 g, 3 eq.) were added thereto, and the result was stirred for 6 hours at 100° C. After the reaction was terminated, the result was cooled to room temperature, and extracted with distilled water and EA. The organic layer was dried with $MgSO_4$, and then filtered and concentrated. With ethyl acetate and hexane as a developing solvent, the concentrated residue was purified using column chromatography to obtain target Compound 25-1 (84 g, 84%).

Preparation of Compound 25-2

After dissolving Compound 25-1 (84 g, 296 mmol, 1 eq.) in 1,4-dioxane/$H_2O$, 2-(4,4,5,5-tetramethyl-1,3,2-dioxaborolan-2-yl)aniline (77 g, 1.2 eq.), $Pd(PPh_3)_4$ (17 g, 0.05 eq.) and $K_2CO_3$ (122 g, 3 eq.) were added thereto, and the result was stirred for 6 hours at 100° C. After the reaction was terminated, the result was cooled to room temperature, and extracted with distilled water and EA. The organic layer was dried with $MgSO_4$, and then filtered and concentrated. With ethyl acetate and hexane as a developing solvent, the concentrated residue was purified using column chromatography to obtain target Compound 25-2 (77 g, 89%).

Preparation of Compound 25-3

After dissolving Compound 25-2 (77 g, 263 mmol, 1 eq.) by adding THF, TEA (110 ml, 3 eq.) and 4-bromobenzoyl chloride (86 g, 1.5 eq.) were added thereto at 0° C., and the result was stirred for 1 hour at room temperature. After the reaction was terminated, the result was extracted with distilled water and EA. The organic layer was dried with $MgSO_4$, and then filtered and concentrated. With ethyl acetate and hexane as a developing solvent, the concentrated residue was purified using column chromatography to obtain target Compound 25-3 (123 g, 98%).

Preparation of Compound 25-4

After dissolving Compound 25-3 (123 g, 257 mmol, 1 eq.) in nitrobenzene, $POCl_3$ (36 mL, 1.5 eq.) was added thereto, and the result was stirred for 6 hours at 150° C. After the reaction was terminated, the result was neutralized at room temperature, and then extracted with distilled water and dichloromethane. The organic layer was dried with $MgSO_4$, and then filtered and concentrated. The concentrated residue was stirred with ethyl acetate and then filtered to obtain target Compound 25-4 (84 g, 71%).

Preparation of Compound 25-5

After dissolving Compound 25-4 (84 g, 182.47 mmol) in 1,4-dioxane, bis(pinacolato)diboron (92 g, 2 eq.), Pd(dppf)$Cl_2$ (6.6 g, 0.05 eq.) and potassium acetate (54 g, 3.0 eq.) were added thereto, and the result was stirred for 2 hours at 110° C. After the reaction was completed, the result was extracted with distilled water and EA. After drying the organic layer with anhydrous $MgSO_4$, the solvent was removed using a rotary evaporator, and the result was passed through silica gel to obtain target Compound 25-5 (90 g, 98%).

Preparation of Compound 25

After adding 2-chloro-4,6-diphenyl-1,3,5-triazine (6.4 g, 23.7 mmol), $Pd(PPh_3)_4$ (1.14 g, 1.00 mmol), $K_2CO_3$ (8.2 g, 59.4 mmol) and toluene/EtOH/$H_2O$ to Compound 25-5 (10.0 g, 19.8 mmol), the result was stirred for 6 hours at 110° C. After the reaction was completed, the result was cooled to room temperature, and extracted with distilled water and dichloromethane. After drying the organic layer with anhydrous $MgSO_4$, the solvent was removed using a rotary evaporator, and with dichloromethane and hexane as a developing solvent, the result was purified using column chromatography to obtain target Compound 25 (10.1 g, 84%).

<Preparation Example 11> Preparation of Compound 29

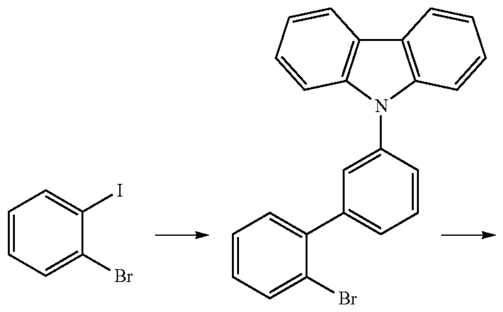

29-1

-continued

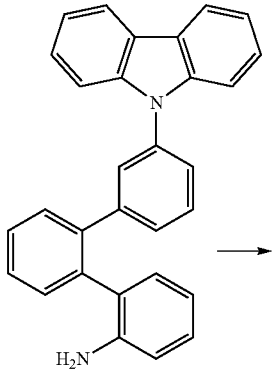

29-2

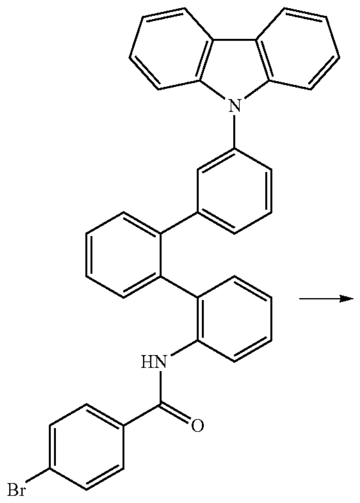

29-3

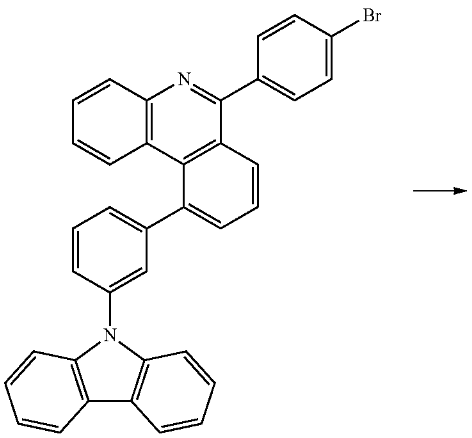

29-4

-continued

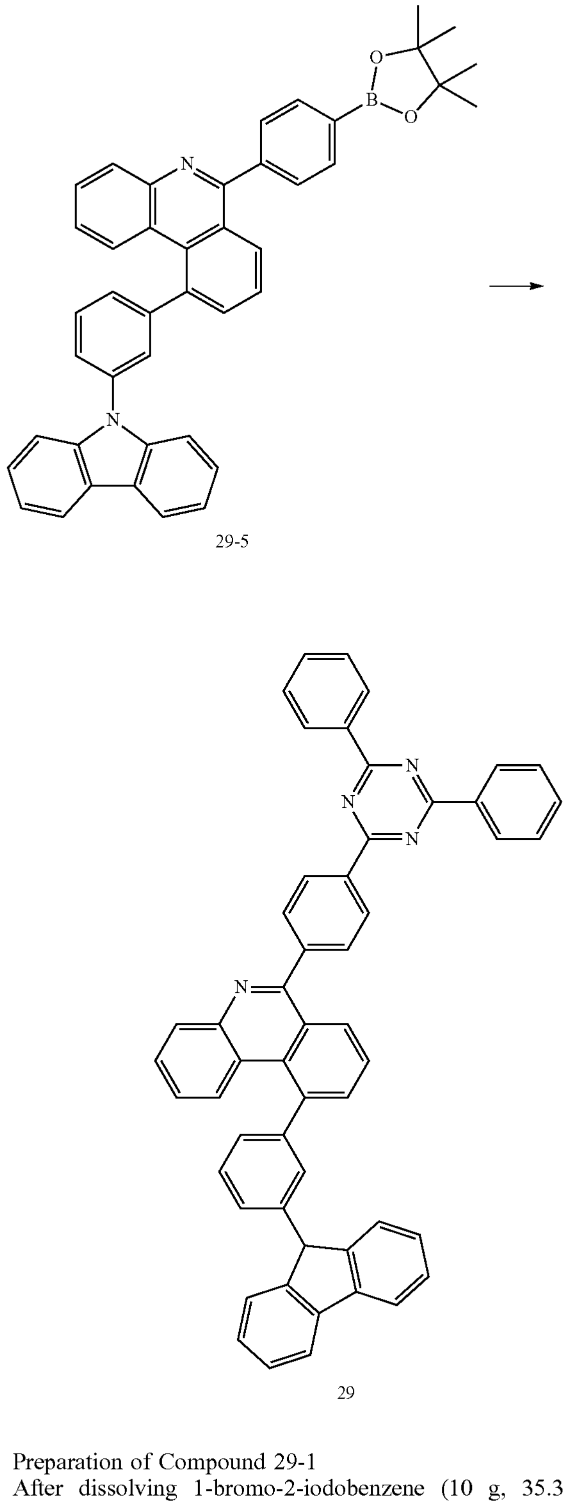

29-5

29

Preparation of Compound 29-1

After dissolving 1-bromo-2-iodobenzene (10 g, 35.3 mmol, eq.) in 1,4-dioxane/$H_2O$, 9-(3-(4,4,5,5-tetramethyl-1,3,2-dioxaborolan-2-yl)phenyl)-9H-carbazole (13 g, 35.3 mmol, 1 eq.), $Pd(PPh_3)_4$ (2.0 g, 0.05 eq.) and $K_2CO_3$ (14.6 g, 3 eq.) were added thereto, and the result was stirred for 6 hours at 100° C. After the reaction was terminated, the result was cooled to room temperature, and extracted with distilled water and EA. The organic layer was dried with $MgSO_4$, and then filtered and concentrated. With ethyl acetate and hexane as a developing solvent, the concentrated residue was purified using column chromatography to obtain target Compound 29-1 (11.5 g, 82%).

Preparation of Compound 29-2

After dissolving Compound 29-1 (11.5 g, 28.9 mmol, 1 eq.) in 1,4-dioxane/$H_2O$, 2-(4,4,5,5-tetramethyl-1,3,2-dioxaborolan-2-yl)aniline (7.7 g, 1.2 eq.), $Pd(PPh_3)_4$ (1.7 g, 0.05 eq.) and $K_2CO_3$ (12 g, 3 eq.) were added thereto, and the result was stirred for 6 hours at 100° C. After the reaction was terminated, the result was cooled to room temperature, and extracted with distilled water and EA. The organic layer was dried with $MgSO_4$, and then filtered and concentrated. With ethyl acetate and hexane as a developing solvent, the concentrated residue was purified using column chromatography to obtain target Compound 29-2 (10.8 g, 91%).

Preparation of Compound 29-3

After dissolving Compound 29-2 (10.8 g, 26.3 mmol, 1 eq.) by adding THF, TEA (11 ml, 3 eq.) and 4-bromobenzoyl chloride (8.6 g, 1.5 eq.) were added thereto at 0° C., and the result was stirred for 1 hour at room temperature. After the reaction was terminated, the result was extracted with distilled water and EA. The organic layer was dried with $MgSO_4$, and then filtered and concentrated. With ethyl acetate and hexane as a developing solvent, the concentrated residue was purified using column chromatography to obtain target Compound 29-3 (15.0 g, 96%).

Preparation of Compound 29-4

After dissolving Compound 29-3 (15.0 g, 25.2 mmol, 1 eq.) in nitrobenzene, $POCl_3$ (3.5 mL, 1.5 eq.) was added thereto, and the result was stirred for 6 hours at 150° C. After the reaction was terminated, the result was neutralized at room temperature, and then extracted with distilled water and dichloromethane. The organic layer was dried with $MgSO_4$, and then filtered and concentrated. The concentrated residue was stirred with ethyl acetate and then filtered to obtain target Compound 29-4 (10.6 g, 73%).

Preparation of Compound 29-5

After dissolving Compound 29-4 (10.6 g, 18.3 mmol) in 1,4-dioxane, bis(pinacolato)diboron (9.2 g, 2 eq.), Pd(dppf)$Cl_2$ (0.6 g, 0.05 eq.) and potassium acetate (5.4 g, 3.0 eq.) were added thereto, and the result was stirred for 2 hours at 110° C. After the reaction was completed, the result was extracted with distilled water and EA. After drying the organic layer with anhydrous $MgSO_4$, the solvent was removed using a rotary evaporator, and the result was passed through silica gel to obtain target Compound 29-5 (11 g, 97%).

Preparation of Compound 29

After adding 2-chloro-4,6-diphenyl-1,3,5-triazine (5.7 g, 23.7 mmol), $Pd(PPh_3)_4$ (1.02 g, 0.88 mmol), $K_2CO_3$ (7.3 g, 53.1 mmol) and toluene/EtOH/$H_2O$ to Compound 29-5 (11 g, 17.7 mmol), the result was stirred for 6 hours at 110° C. After the reaction was completed, the result was cooled to room temperature, and extracted with distilled water and dichloromethane. After drying the organic layer with anhydrous $MgSO_4$, the solvent was removed using a rotary evaporator, and with dichloromethane and hexane as a developing solvent, the result was purified using column chromatography to obtain target Compound 29 (10.3 g, 80%).

<Preparation Example 12> Preparation of Compound 33
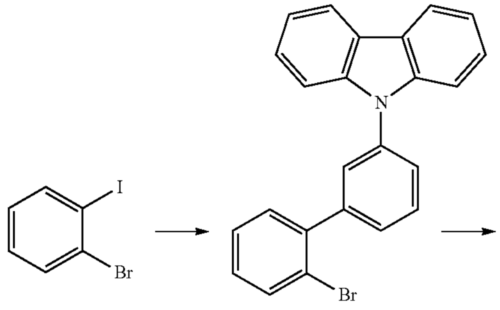
29-1
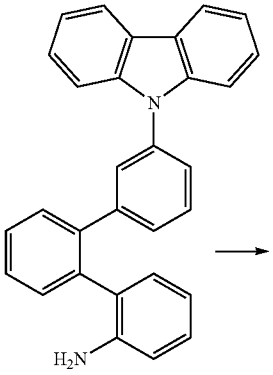
29-2
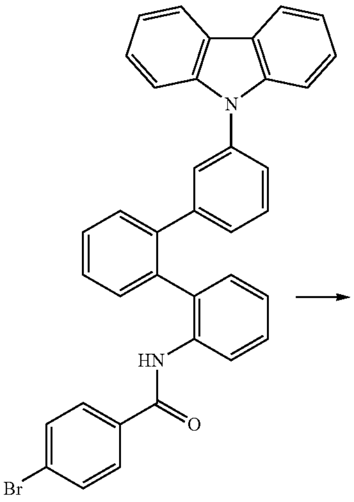
29-3
-continued
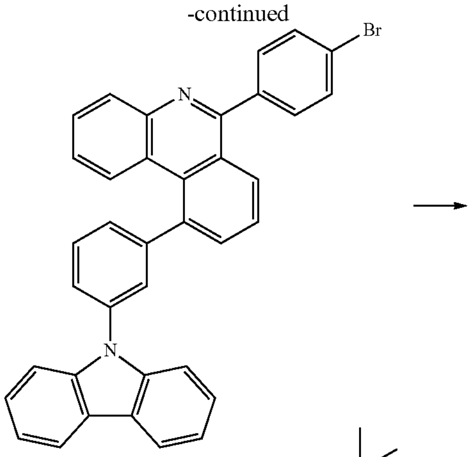
29-4
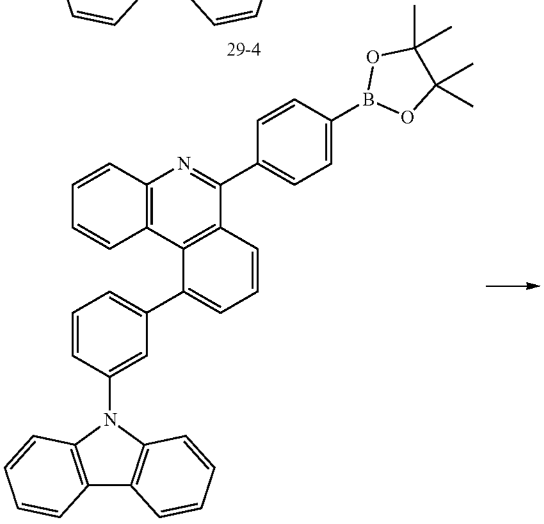
29-5
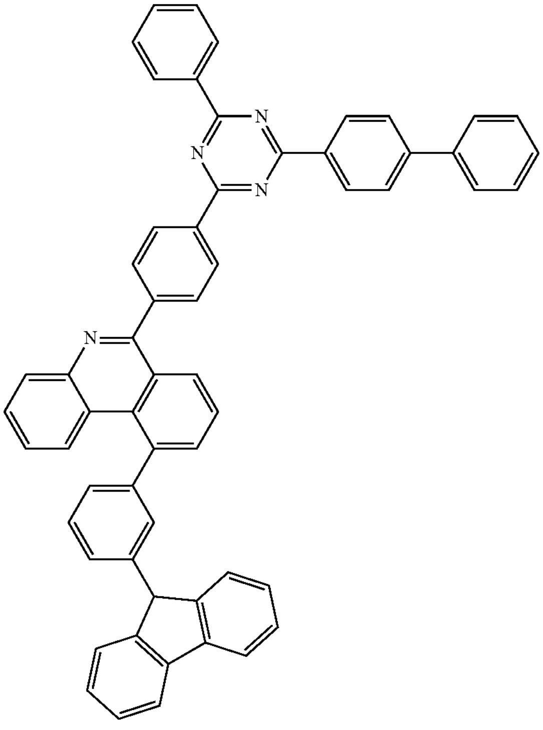
33

Target Compound 33 was obtained in the same manner as in the preparation of Compound 29 of Preparation Example 11 except that 4-([1,1'-biphenyl]-4-yl)-6-chloro-2-phenylpyrimidine was used instead of 2-chloro-4,6-diphenyl-1,3,5-triazine.

<Preparation Example 13> Preparation of Compound 35

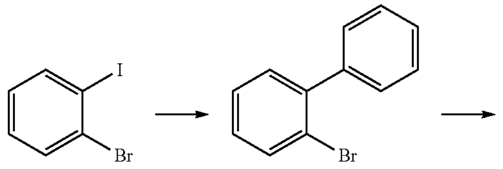

1-1

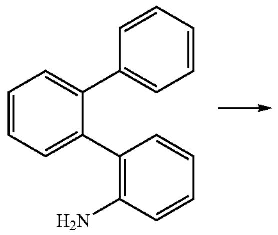

1-2

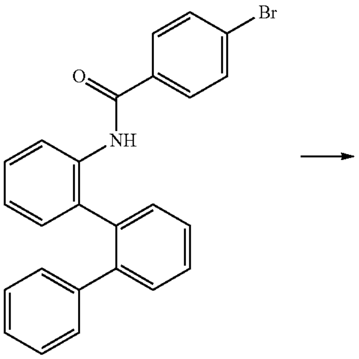

1-3

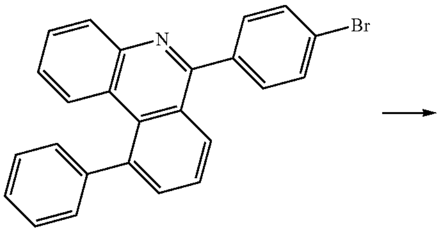

1-4

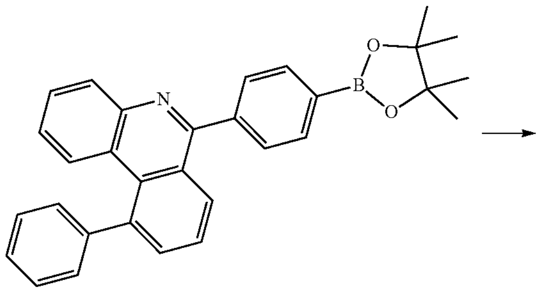

1-5

-continued

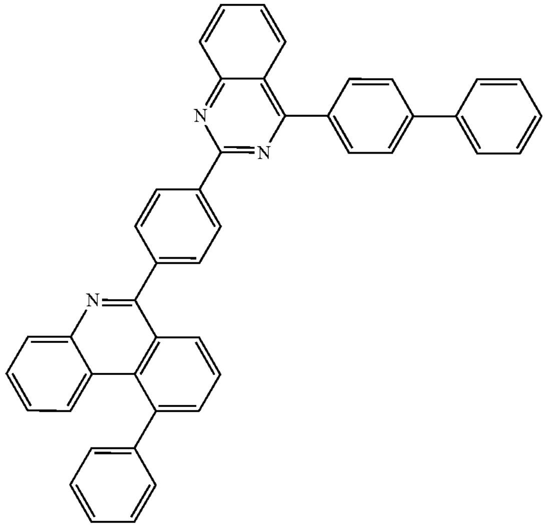

35

Target Compound 35 was obtained in the same manner as in the preparation of Compound 4 of Preparation Example 2 except that 4-([1,1'-biphenyl]-4-yl)-2-chloroquinazoline was used instead of 2-chloro-4,6-diphenyl-1,3,5-triazine.

<Preparation Example 14> Preparation of Compound 43

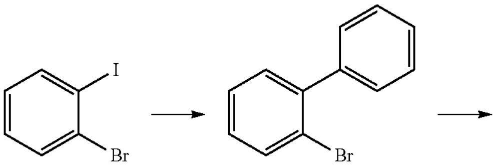

1-1

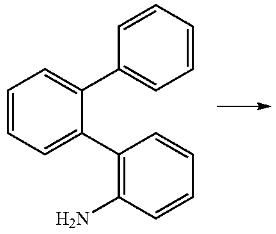

1-2

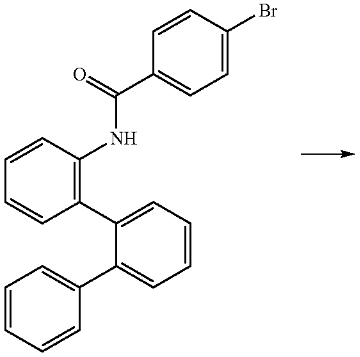

1-3

-continued

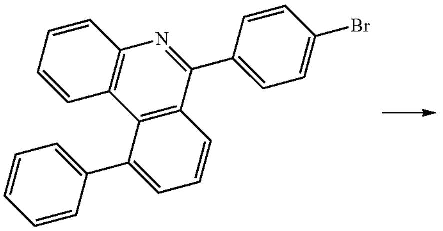

1-4

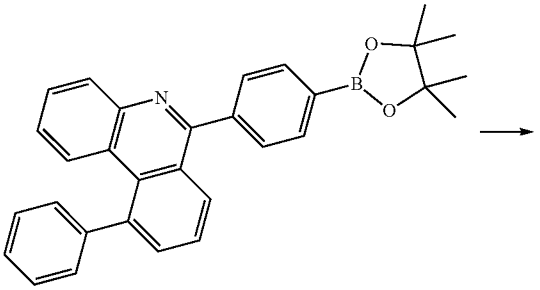

1-5

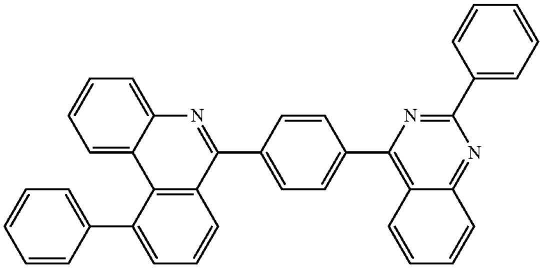

43

Target Compound 43 was obtained in the same manner as in the preparation of Compound 4 of Preparation Example 2 except that 4-chloro-2-phenylquinazoline was used instead of 2-chloro-4,6-diphenyl-1,3,5-triazine.

<Preparation Example 15> Preparation of Compound 46

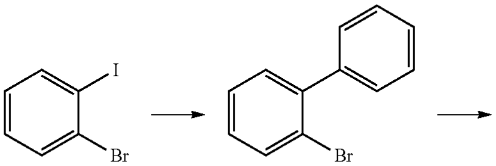

1-1

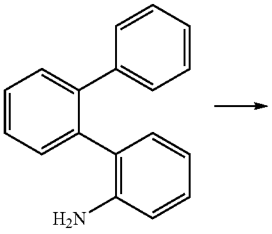

1-2

-continued

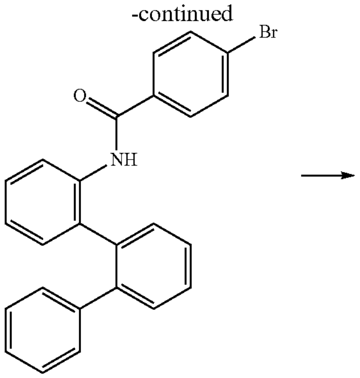

1-3

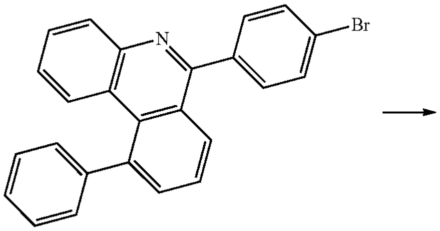

1-4

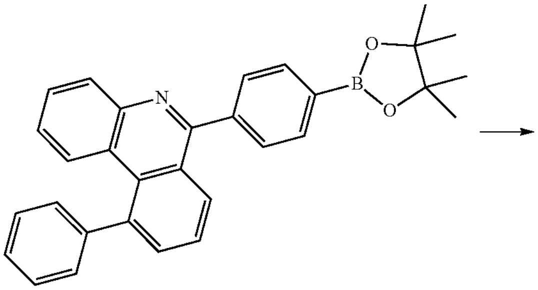

1-5

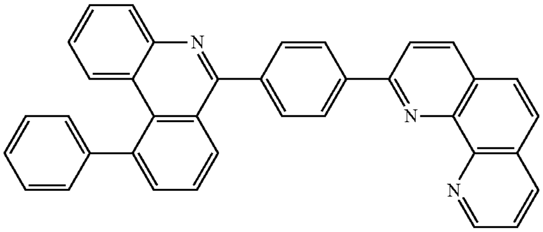

46

Target Compound 46 was obtained in the same manner as in the preparation of Compound 4 of Preparation Example 2 except that 2-chloro-1,10-phenanthroline was used instead of 2-chloro-4,6-diphenyl-1,3,5-triazine.

<Preparation Example 16> Preparation of Compound 48

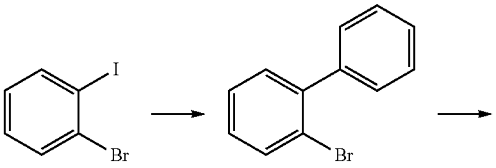

1-1

-continued
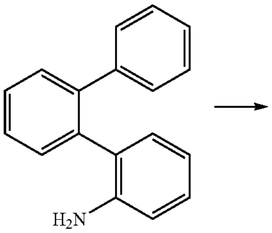
1-2
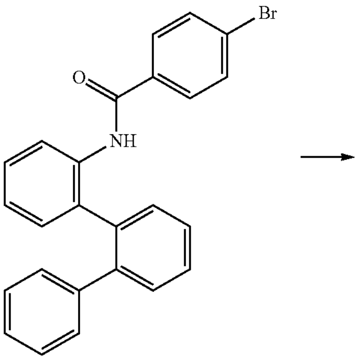
1-3
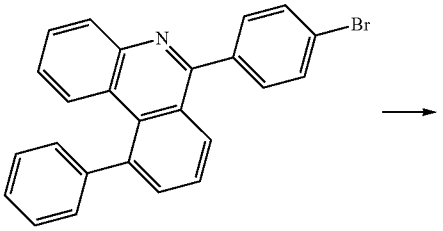
1-4
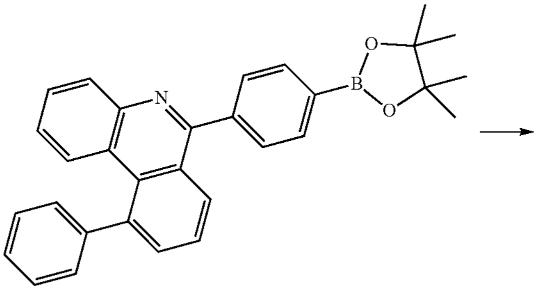
1-5
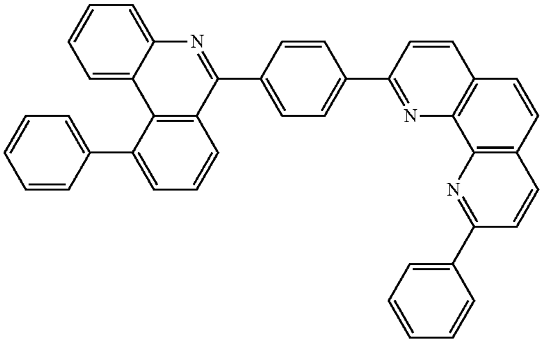
48
Target Compound 48 was obtained in the same manner as in the preparation of Compound 4 of Preparation Example 2 except that 2-chloro-9-phenyl-1,10-phenanthroline was used instead of 2-chloro-4,6-diphenyl-1,3,5-triazine.
<Preparation Example 17> Preparation of Compound 49
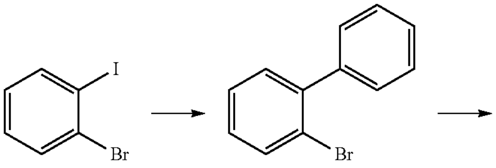
1-1
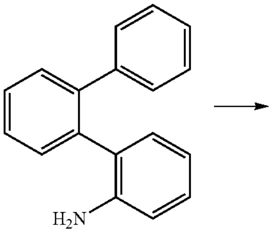
1-2
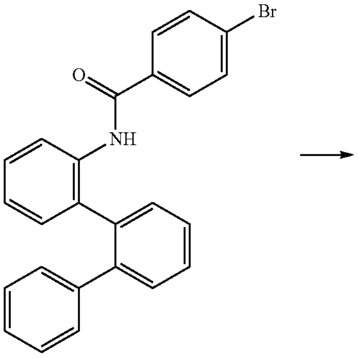
1-3
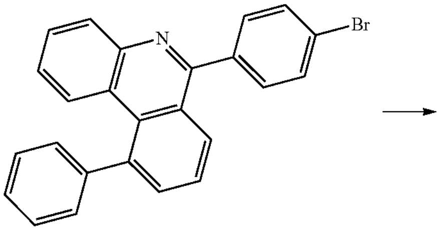
1-4
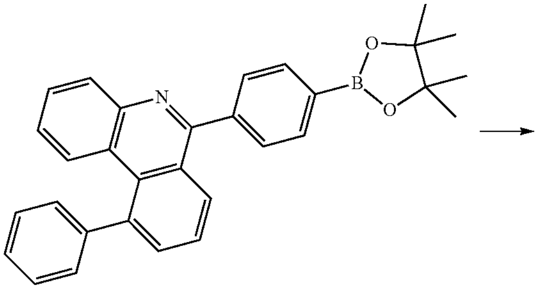
1-5

-continued

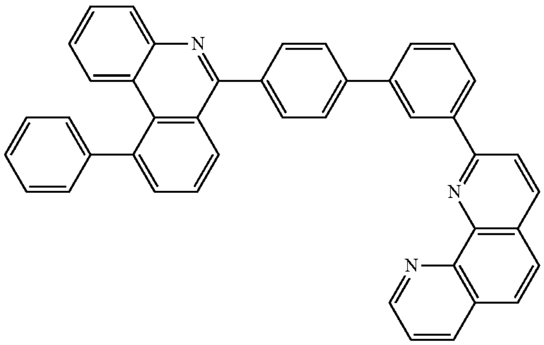

49

Target Compound 49 was obtained in the same manner as in the preparation of Compound 4 of Preparation Example 2 except that 2-(3-bromophenyl)-1,10-phenanthroline was used instead of 2-chloro-4,6-diphenyl-1,3,5-triazine.

<Preparation Example 18> Preparation of Compound 56

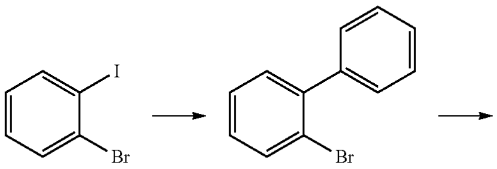

1-1

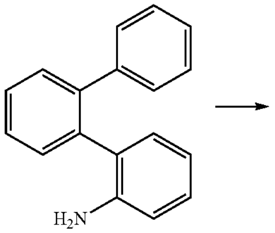

1-2

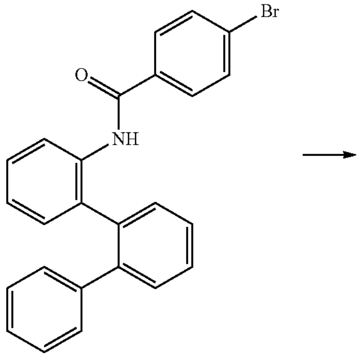

1-3

-continued

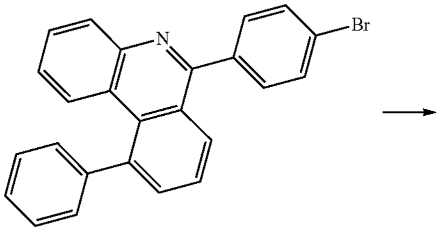

1-4

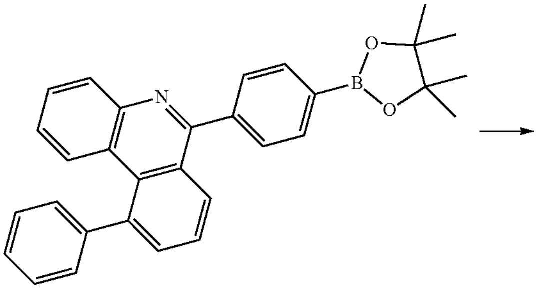

1-5

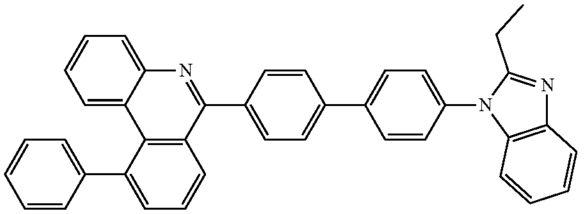

56

Target Compound 56 was obtained in the same manner as in the preparation of Compound 4 of Preparation Example 2 except that 1-(4-bromophenyl)-2-ethyl-1H-benzo[d]imidazole was used instead of 2-chloro-4,6-diphenyl-1,3,5-triazine.

<Preparation Example 19> Preparation of Compound 63

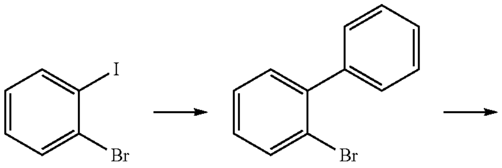

1-1

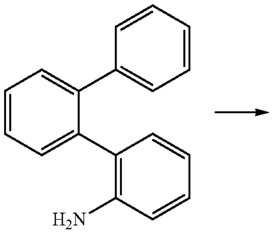

1-2

-continued
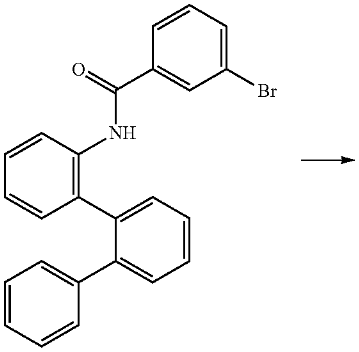
22-1
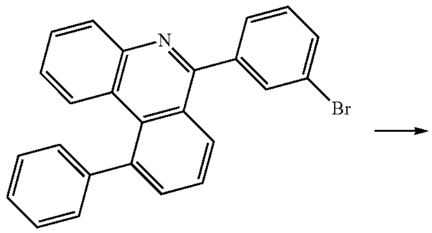
22-2
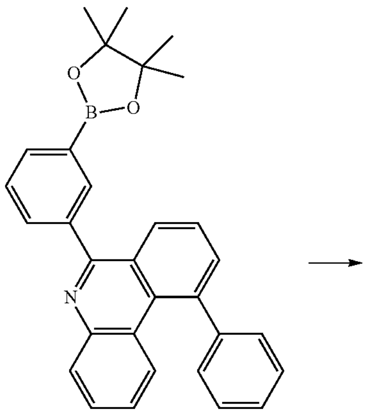
22-3
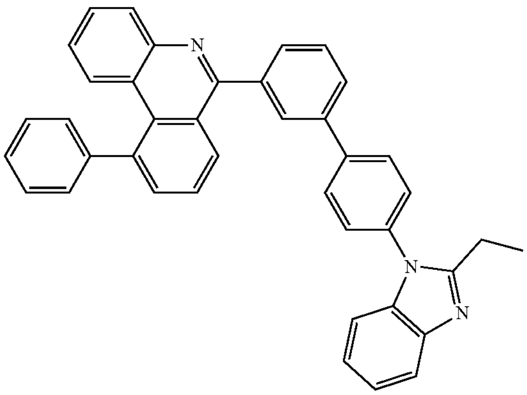
63
Target Compound 63 was obtained in the same manner as in the preparation of Compound 22 of Preparation Example 9 except that 1-(4-bromophenyl)-2-ethyl-1H-benzo[d]imidazole was used instead of 2-chloro-4,6-diphenyl-1,3,5-triazine.
<Preparation Example 20> Preparation of Compound 65
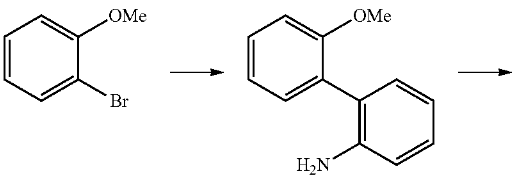
65-1
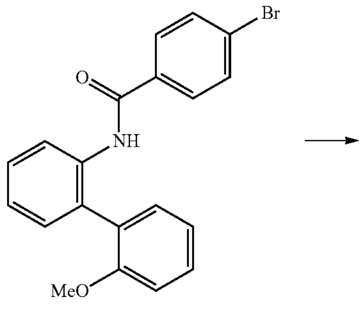
65-2
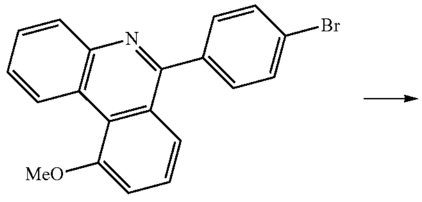
65-3
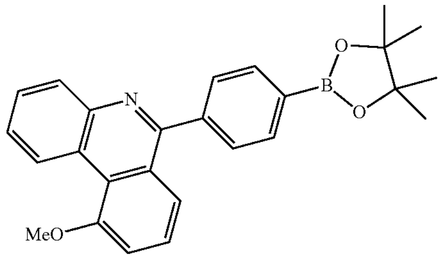
65-4
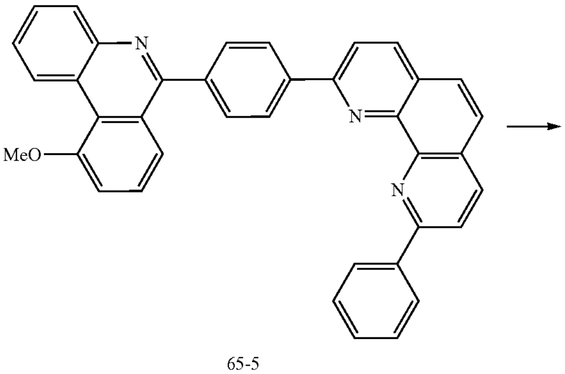
65-5

-continued

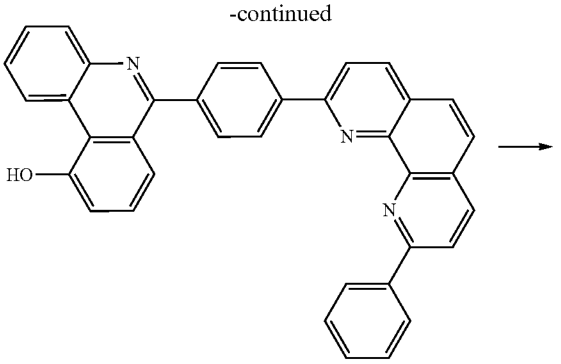

65-6

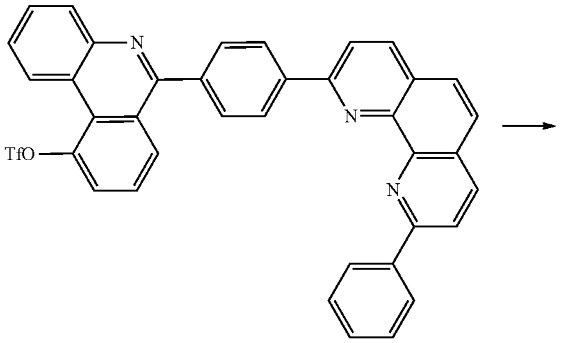

65-7

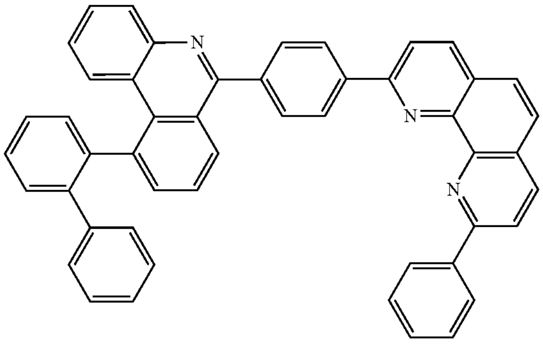

65

Preparation of Compound 65-1

After dissolving 1-bromo-2-methoxybenzene (20 g, 107 mmol, 1 eq.) in 1,4-dioxane/$H_2O$, 2-(4,4,5,5-tetramethyl-1,3,2-dioxaborolan-2-yl)aniline (28 g, 1.2 eq.), $Pd(PPh_3)_4$ (6.1 g, 0.05 eq.) and $K_2CO_3$ (44 g, 3 eq.) were added thereto, and the result was stirred for 6 hours at 100° C. After the reaction was terminated, the result was cooled to room temperature, and extracted with distilled water and EA. The organic layer was dried with $MgSO_4$, and then filtered and concentrated. With ethyl acetate and hexane as a developing solvent, the concentrated residue was purified using column chromatography to obtain target Compound 65-1 (20 g, 93%).

Preparation of Compound 65-2

After dissolving Compound 65-1 (20 g, 99 mmol, 1 eq.) by adding THF, TEA (41 ml, 3 eq.) and 4-bromobenzoyl chloride (32 g, 1.5 eq.) were added thereto at 0° C., and the result was stirred for 1 hour at room temperature. After the reaction was terminated, the result was extracted with distilled water and EA. The organic layer was dried with $MgSO_4$, and then filtered and concentrated. With ethyl acetate and hexane as a developing solvent, the concentrated residue was purified using column chromatography to obtain target Compound 65-2 (35 g, 94%).

Preparation of Compound 65-3

After dissolving Compound 65-2 (35 g, 93 mmol, 1 eq.) in nitrobenzene, $POCl_3$ (13 mL, 1.5 eq.) was added thereto, and the result was stirred for 6 hours at 150° C. After the reaction was terminated, the result was neutralized at room temperature, and then extracted with distilled water and dichloromethane. The organic layer was dried with $MgSO_4$, and then filtered and concentrated. The concentrated residue was stirred with ethyl acetate and then filtered to obtain target Compound 65-3 (23 g, 68%).

Preparation of Compound 65-4

After dissolving Compound 65-3 (23 g, 63 mmol) in 1,4-dioxane, bis(pinacolato)diboron (32 g, 2 eq.), Pd(dppf)$Cl_2$ (2.3 g, 0.05 eq.) and potassium acetate (18 g, 3.0 eq.) were added thereto, and the result was stirred for 2 hours at 110° C. After the reaction was completed, the result was extracted with distilled water and EA. After drying the organic layer with anhydrous $MgSO_4$, the solvent was removed using a rotary evaporator, and the result was passed through silica gel to obtain target Compound 65-4 (24 g, 95%).

Preparation of Compound 65-5

After adding 2-bromo-9-phenyl-1,10-phenanthroline (9.8 g, 1.2 eq.), $Pd(PPh_3)_4$ (1.4 g, 0.05 eq.), $K_2CO_3$ (10.0 g, 3.0 eq.) and toluene/EtOH/$H_2O$ to Compound 65-4 (10.0 g, 24.3 mmol), the result was stirred for 6 hours at 110° C. After the reaction was completed, the result was cooled to room temperature, and extracted with distilled water and dichloromethane. After drying the organic layer with anhydrous $MgSO_4$, the solvent was removed using a rotary evaporator, and with dichloromethane and hexane as a developing solvent, the result was purified using column chromatography to obtain target Compound 65-5 (11.1 g, 85%).

Preparation of Compound 65-6

After dissolving Compound 65-5 (11.1 g, 20.6 mmol) in dichloromethane, boron tribromide (1 M in dichloromethane) (1.5 eq.) was added thereto at once at 0° C., and the result was stirred for 18 hours at room temperature. After the reaction was completed, the result was neutralized by adding an aqueous $Na_2CO_3$ solution thereto at 0° C., and then extracted with distilled water and EA. After drying the organic layer with anhydrous $MgSO_4$, the solvent was removed using a rotary evaporator, and with dichloromethane and methanol as a developing solvent, the result was purified using column chromatography to obtain target Compound 65-6 (10.1 g, 94%).

Preparation of Compound 65-7

After dissolving Compound 65-6 (10.1 g, 19.3 mmol) in dichloromethane, pyridine (1.5 eq.) was added thereto, and triflic anhydride was added dropwise thereto at 0° C. After that, the result was stirred for 5 hours at room temperature. After the reaction was completed, the reaction solution was passed through silica, and the solvent of the filtrate was removed using a rotary evaporator. With dichloromethane and methanol as a developing solvent, the result was purified using column chromatography to obtain target Compound 65-7 (11.9 g, 94%).

Preparation of Compound 65

After adding 2-([1,1'-biphenyl]-2-yl)-4,4,5,5-tetramethyl-1,3,2-dioxaborolane (6.0 g, 1.2 eq.), $Pd(PPh_3)_4$ (1.0 g, 0.05 eq.), $K_2CO_3$ (7.5 g, 3.0 eq.) and toluene/EtOH/$H_2O$ to Compound 65-7 (11.9 g, 18.1 mmol), the result was stirred for 6 hours at 110° C. After the reaction was completed, the result was cooled to room temperature, and extracted with distilled water and dichloromethane. After drying the organic layer with anhydrous $MgSO_4$, the solvent was removed using a rotary evaporator, and with dichloromethane and hexane as a developing solvent, the result was purified using column chromatography to obtain target Compound 65 (9.3 g, 78%).
<Preparation Example 21> Preparation of Compound 67
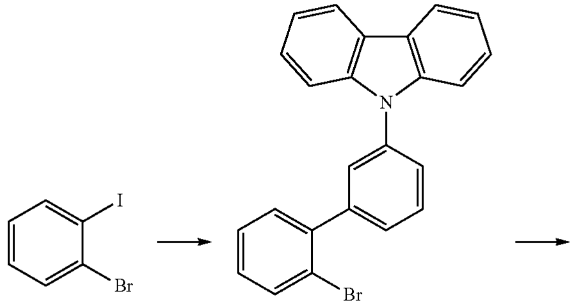
29-1
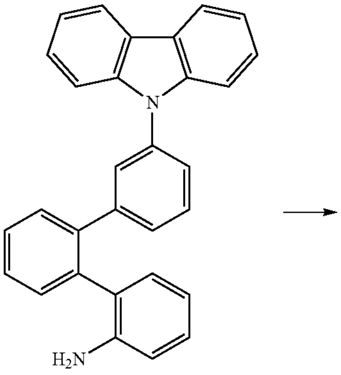
29-2
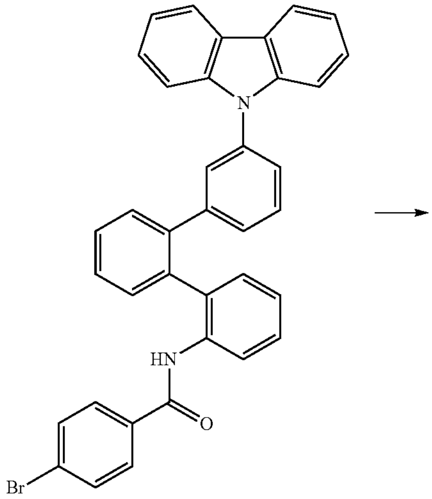
29-3
-continued
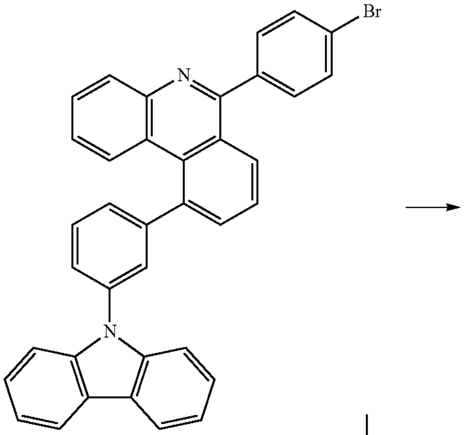
29-4
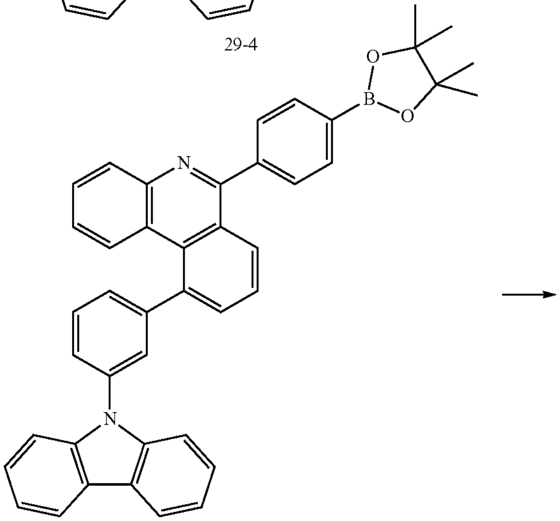
29-5
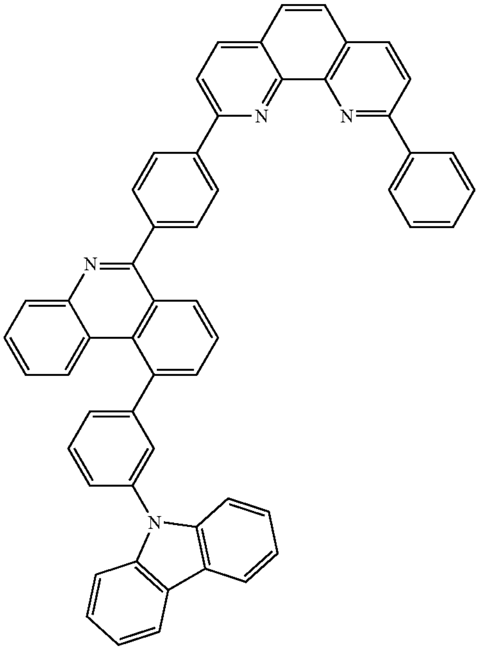
67
Target Compound 67 was obtained in the same manner as in the preparation of Compound 33 of Preparation Example 12 except that 2-bromo-9-phenyl-1,10-phenanthroline was used instead of 4-([1,1'-biphenyl]-4-yl)-6-chloro-2-phenylpyrimidine.
<Preparation Example 22> Preparation of Compound 73
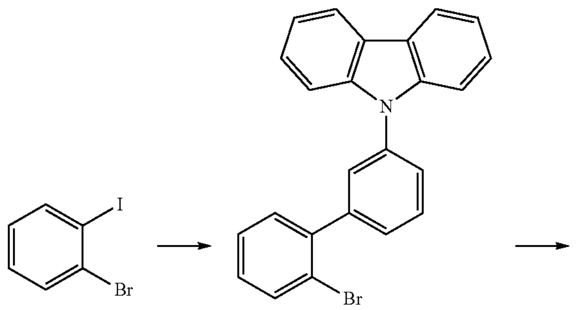
29-1
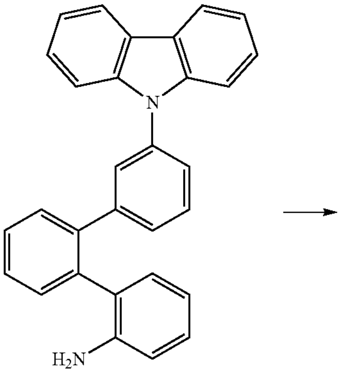
29-2
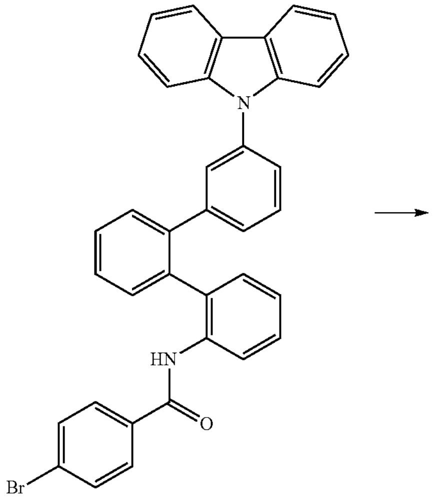
29-3
-continued
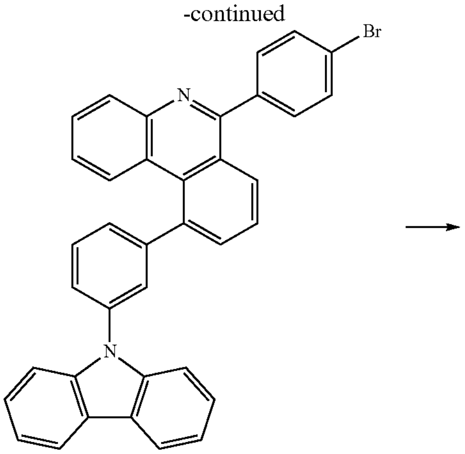
29-4
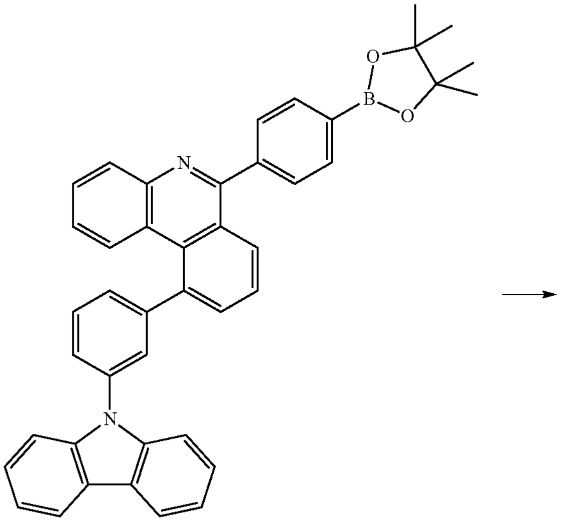
29-5
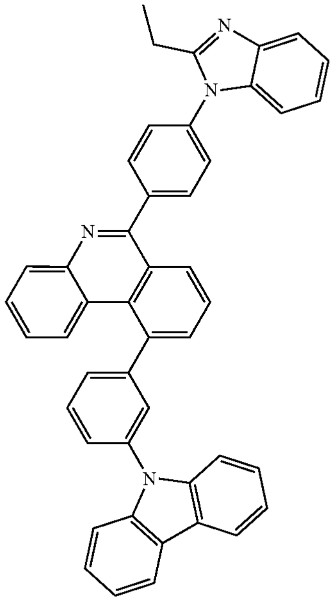
73
Target Compound 73 was obtained in the same manner as in the preparation of Compound 33 of Preparation Example 12 except that 2-ethyl-1H-benzo[d]imidazole was used instead of 4-([1,1'-biphenyl]-4-yl)-6-chloro-2-phenylpyrimidine.

<Preparation Example 23> Preparation of Compound 79

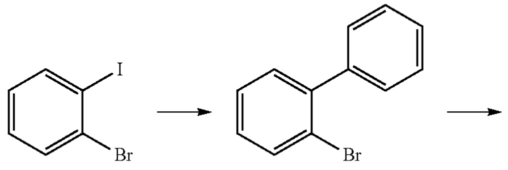

1-1

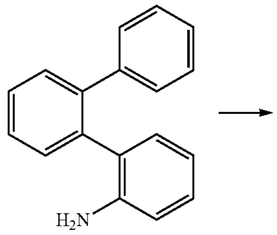

1-2

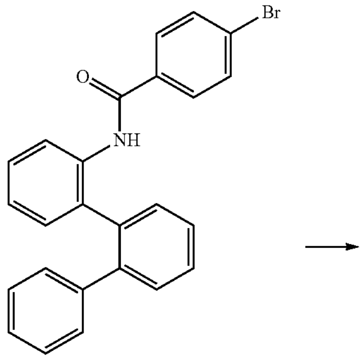

1-3

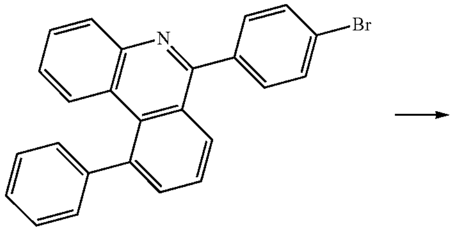

1-4

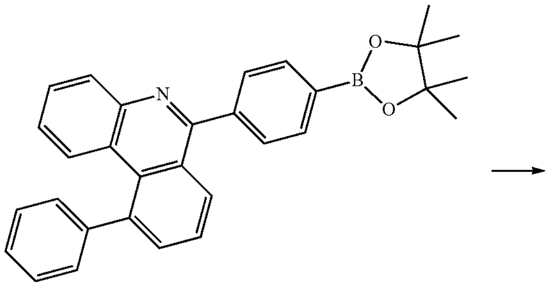

1-5

-continued

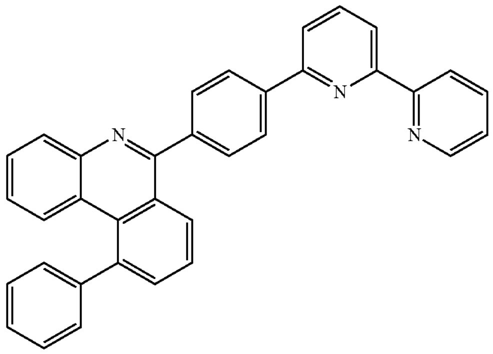

79

Target Compound 79 was obtained in the same manner as in the preparation of Compound 4 of Preparation Example 2 except that 6-bromo-2,2'-bipyridine was used instead of 2-bromo-4,6-diphenyl-1,3,5-triazine.

<Preparation Example 24> Preparation of Compound 81

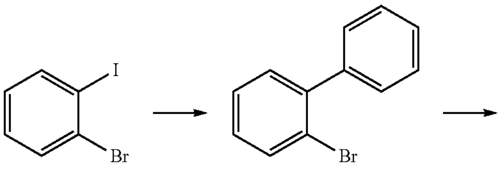

1-1

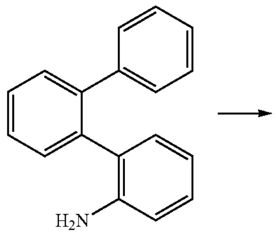

1-2

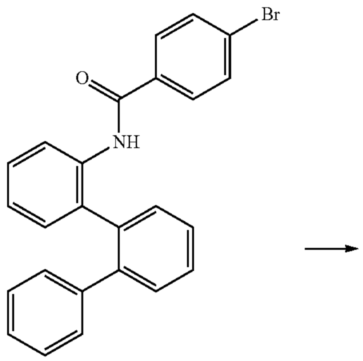

1-3

-continued
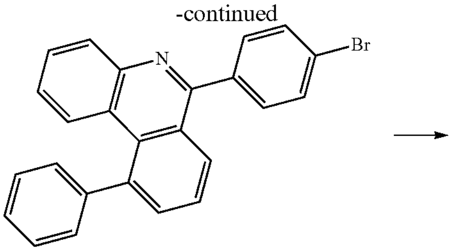
1-4
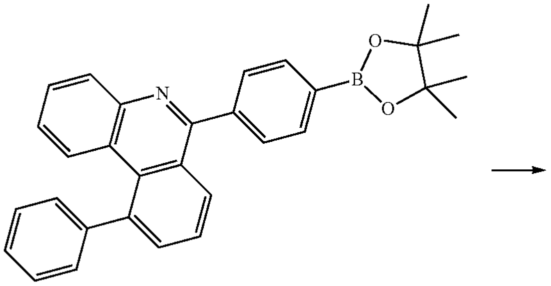
1-5
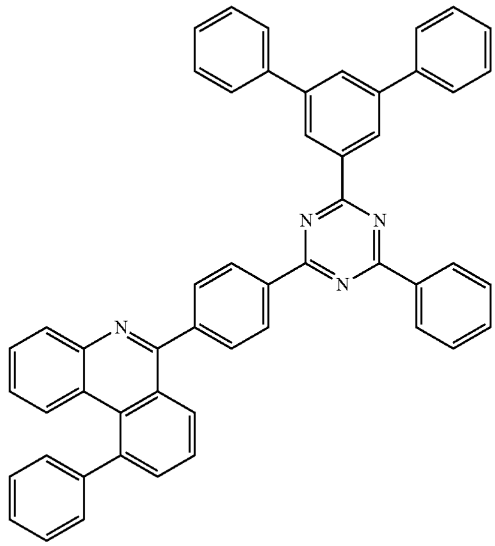
81
Target Compound 81 was obtained in the same manner as in the preparation of Compound 4 of Preparation Example 2 except that 2-([1,1':3',1"-terphenyl]-5'-yl)-4-chloro-6-phenyl-1,3,5-triazine was used instead of 2-bromo-4,6-diphenyl-1,3,5-triazine.
<Preparation Example 25> Preparation of Compound 83
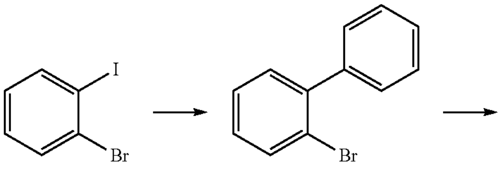
1-1
-continued
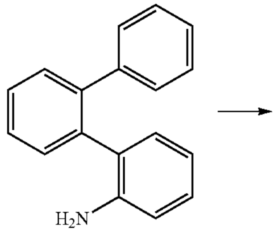
1-2
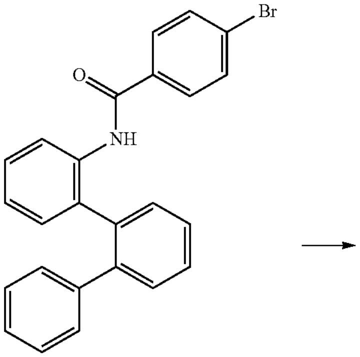
1-3
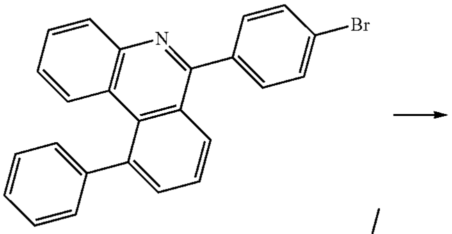
1-4
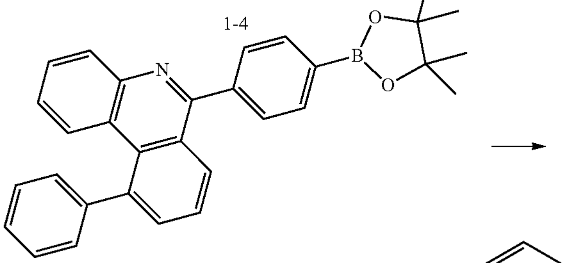
1-5
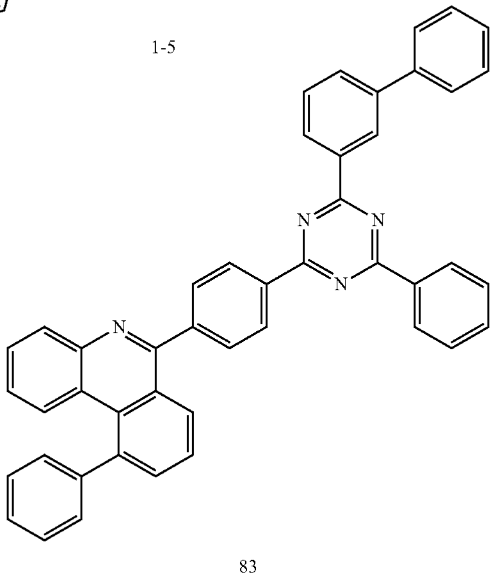
83

Preparation of Compound 83

Target Compound 83 was obtained in the same manner as in the preparation of Compound 4 of Preparation Example 2 except that 2-([1,1'-biphenyl]-3-yl)-4-chloro-6-phenyl-1,3,5-triazine was used instead of 2-bromo-4,6-diphenyl-1,3,5-triazine.

<Preparation Example 26> Preparation of Compound 100

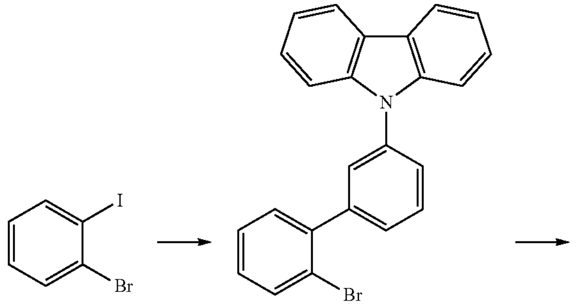

29-1

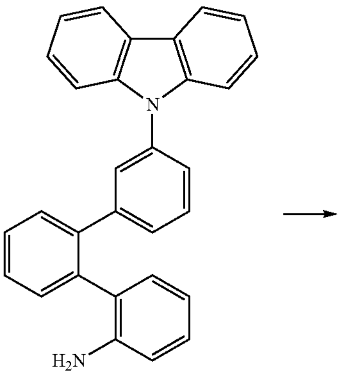

29-2

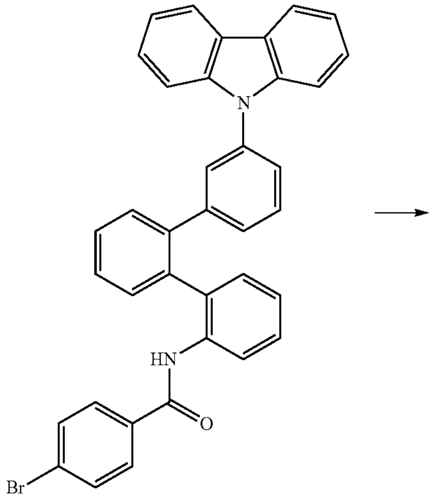

29-3

-continued

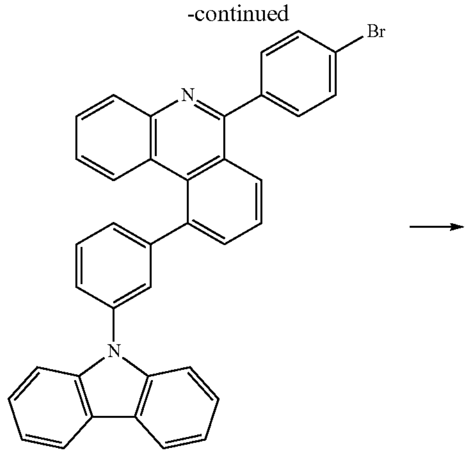

29-4

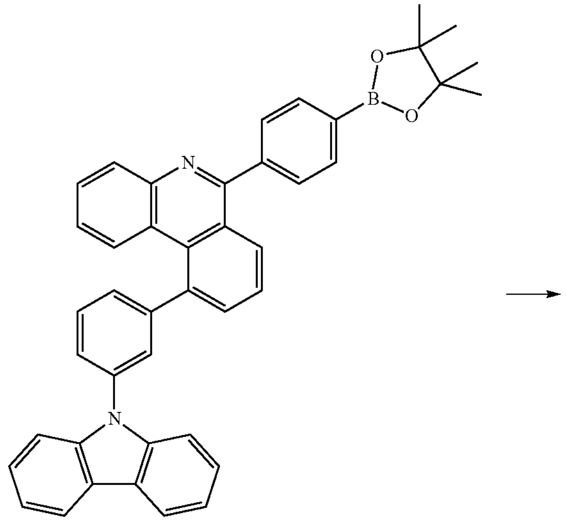

29-5

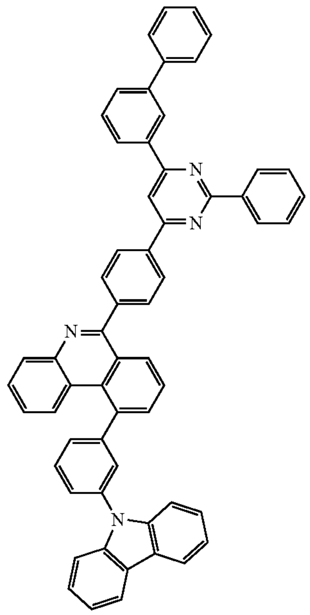

100

Target Compound 100 was obtained in the same manner as in the preparation of Compound 33 of Preparation Example 12 except that 4-([1,1'-biphenyl]-3-yl)-6-chloro-2-phenylpyrimidine was used instead of 4-([1,1'-biphenyl]-4-yl)-6-chloro-2-phenylpyrimidine.

<Preparation Example 27> Preparation of Compound 103

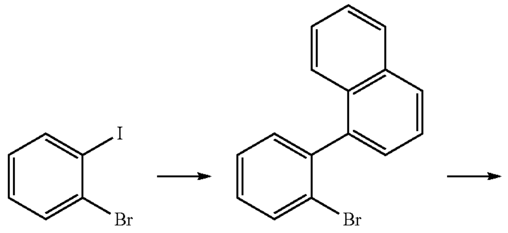

25-1

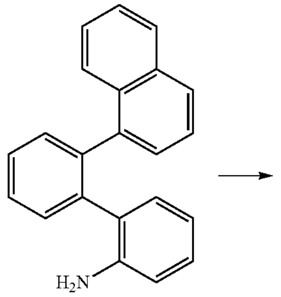

25-2

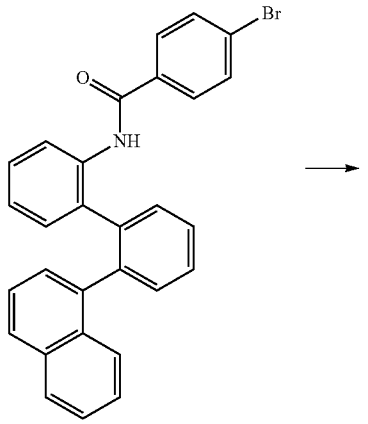

25-3

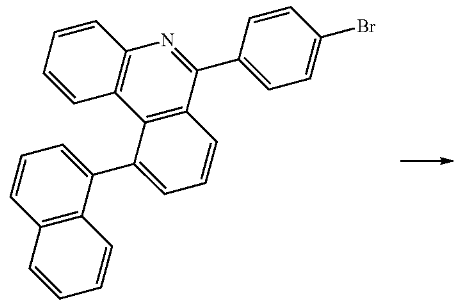

25-4

-continued

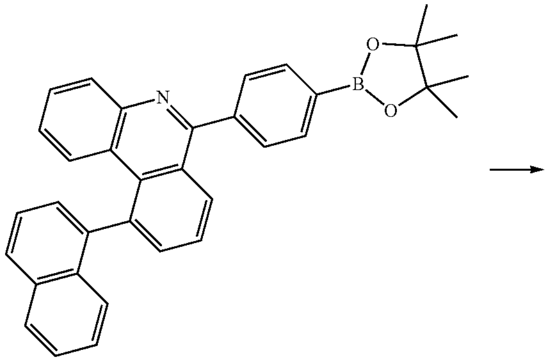

25-5

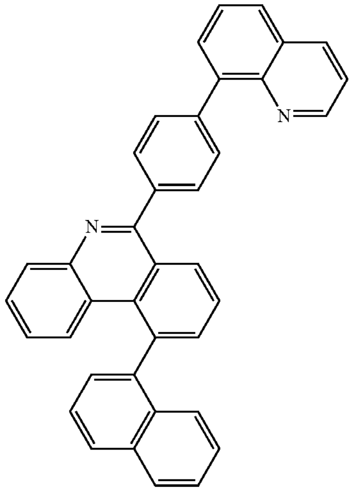

103

Target Compound 103 was obtained in the same manner as in the preparation of Compound 25 of Preparation Example 10 except that 8-bromoquinoline was used instead of 4-([1,1'-biphenyl]-4-yl)-6-(4-bromophenyl)-2-phenylpyrimidine.

<Preparation Example 28> Preparation of Compound 105

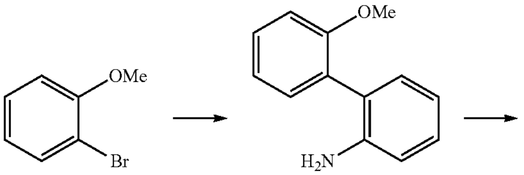

65-1

-continued

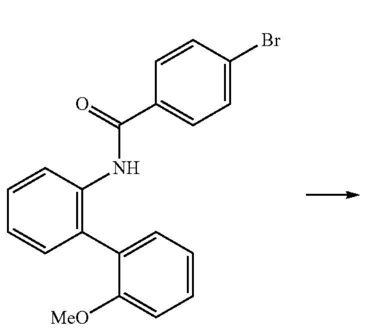

65-2

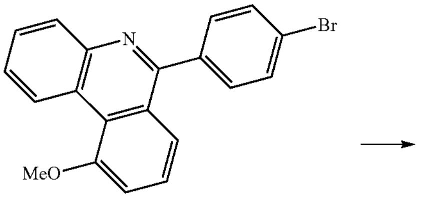

65-3

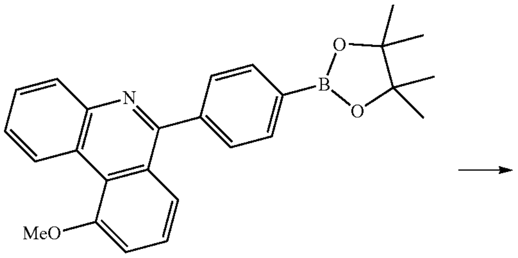

65-4

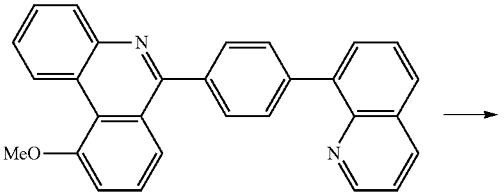

105-1

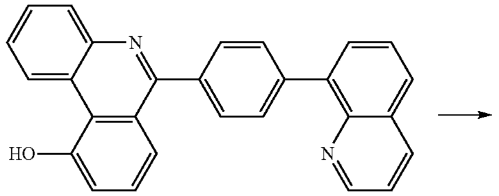

105-2

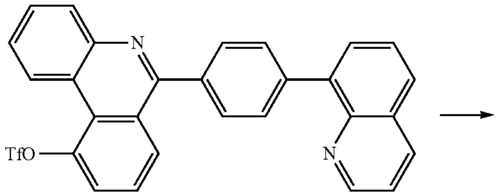

105-3

-continued

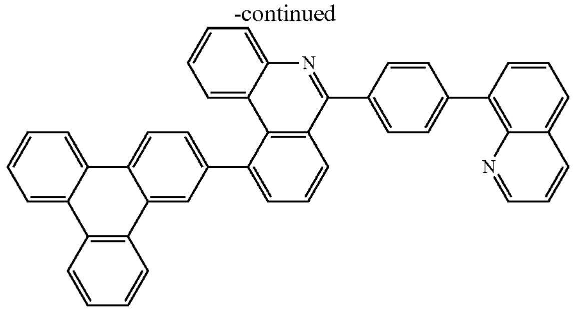

105

Preparation of Compound 105-1 After adding 8-bromoquinoline (6.0 g, 1.2 eq.), $Pd(PPh_3)_4$ (1.4 g, 0.05 eq.), $K_2CO_3$ (10.0 g, 3.0 eq.) and toluene/EtOH/$H_2O$ to Compound 65-4 (10.0 g, 24.3 mmol), the result was stirred for 6 hours at 110° C. After the reaction was completed, the result was cooled to room temperature, and extracted with distilled water and dichloromethane. After drying the organic layer with anhydrous $MgSO_4$, the solvent was removed using a rotary evaporator, and with dichloromethane and hexane as a developing solvent, the result was purified using column chromatography to obtain target Compound 105-1 (8.8 g, 88%).

Preparation of Compound 105-2

After dissolving Compound 105-1 (8.8 g, 21.3 mmol) in dichloromethane, boron tribromide (1 M in dichloromethane) (1.5 eq.) was added thereto at once at 0° C., and the result was stirred for 18 hours at room temperature. After the reaction was completed, the result was neutralized by adding an aqueous $Na_2CO_3$ solution thereto at 0° C., and then extracted with distilled water and EA. After drying the organic layer with anhydrous $MgSO_4$, the solvent was removed using a rotary evaporator, and with dichloromethane and methanol as a developing solvent, the result was purified using column chromatography to obtain target Compound 105-2 (7.8 g, 92%).

Preparation of Compound 105-3

After dissolving Compound 105-2 (7.8 g, 19.6 mmol) in dichloromethane, pyridine (1.5 eq.) was added thereto, and triflic anhydride was added dropwise thereto at 0° C. After that, the result was stirred for 5 hours at room temperature. After the reaction was completed, the reaction solution was passed through silica, and the solvent of the filtrate was removed using a rotary evaporator. With dichloromethane and methanol as a developing solvent, the result was purified using column chromatography to obtain target Compound 105-3 (9.6 g, 92%).

Preparation of Compound 105

After adding 4,4,5,5-tetramethyl-2-(triphenylen-2-yl)-1,3,2-dioxaborolane (7.6 g, 1.2 eq.), $Pd(PPh_3)_4$ (1.0 g, 0.05 eq.), $K_2CO_3$ (7.5 g, 3.0 eq.) and toluene/EtOH/$H_2O$ to Compound 105-3 (9.6 g, 18.0 mmol), the result was stirred for 6 hours at 110° C. After the reaction was completed, the result was cooled to room temperature, and extracted with distilled water and dichloromethane. After drying the organic layer with anhydrous $MgSO_4$, the solvent was removed using a rotary evaporator, and with dichloromethane and hexane as a developing solvent, the result was purified using column chromatography to obtain target Compound 105 (8.8 g, 81%).

<Preparation Example 29> Preparation of Compound 106

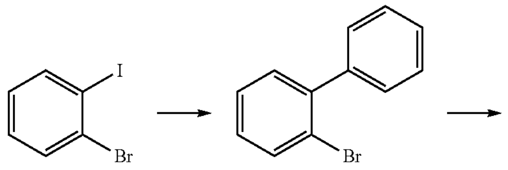

1-1

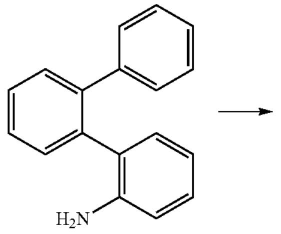

1-2

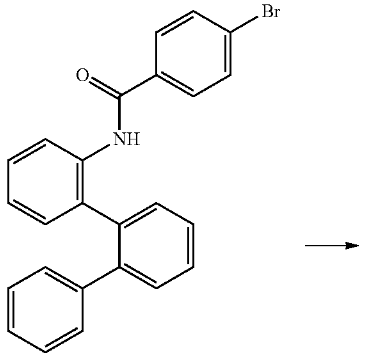

1-3

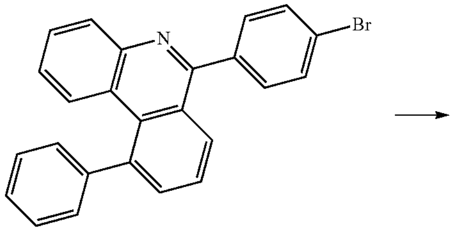

1-4

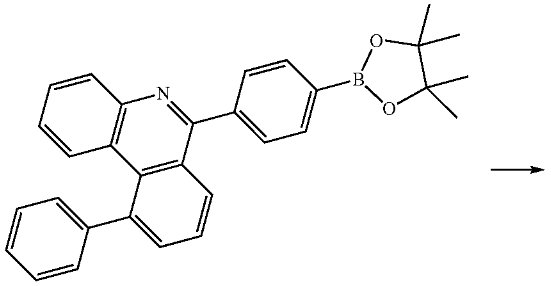

1-5

-continued

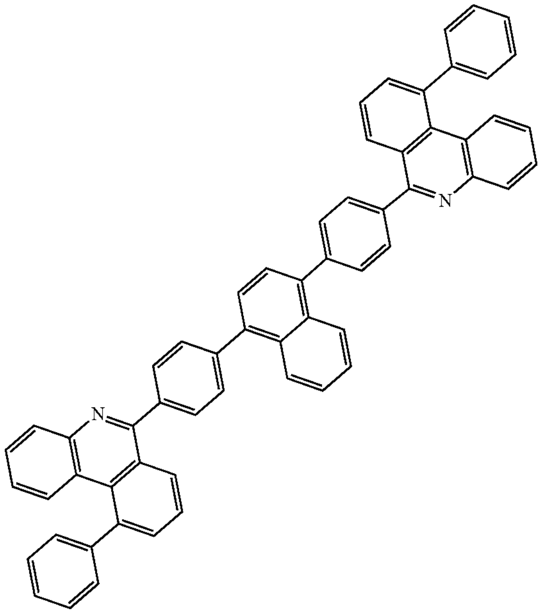

106

After adding 1,4-dibromonaphthalene (2.8 g, 0.45 eq.), $Pd(PPh_3)_4$ (1.2 g, 0.05 eq.), $K_2CO_3$ (9.0 g, 3.0 eq.) and toluene/EtOH/$H_2O$ to Compound 1-5 (10 g, 21.8 mmol), the result was stirred for 6 hours at 110° C. After the reaction was completed, the result was cooled to room temperature, and extracted with distilled water and dichloromethane. After drying the organic layer with anhydrous $MgSO_4$, the solvent was removed using a rotary evaporator, and with dichloromethane and hexane as a developing solvent, the result was purified using column chromatography to obtain target Compound 106 (6.5 g, 85%).

<Preparation Example 30> Preparation of Compound 109

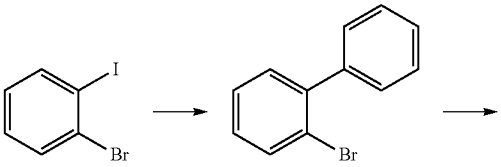

1-1

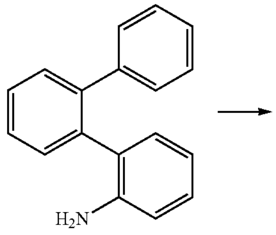

1-2

-continued
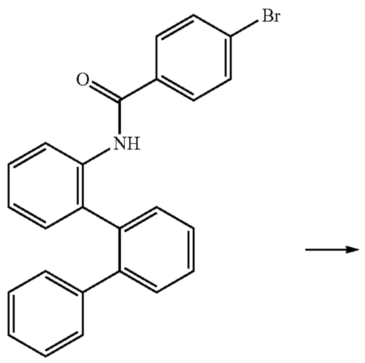
1-3
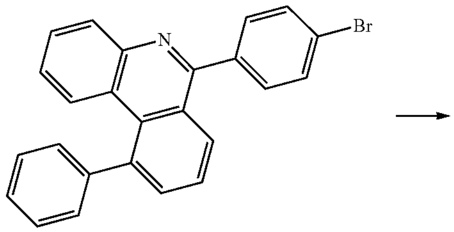
1-4
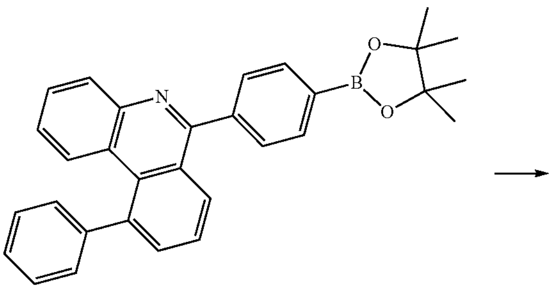
1-5
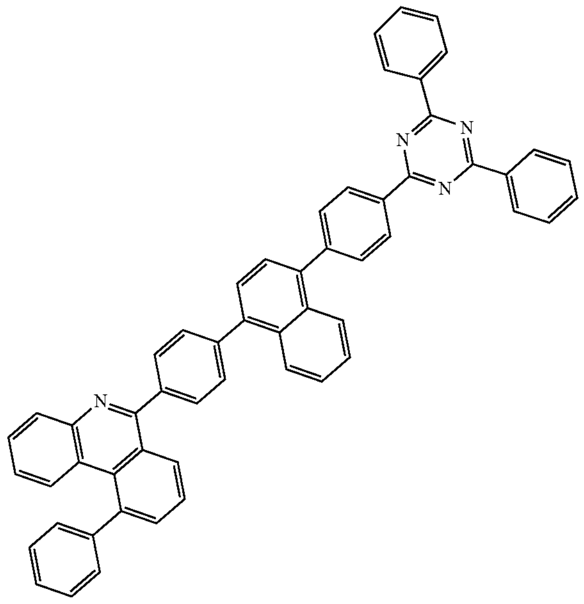
109
Target Compound 109 was obtained in the same manner as in the preparation of Compound 4 of Preparation Example
2 except that 2-(4-(4-bromonaphthalen-1-yl)phenyl)-4,6-diphenyl-1,3,5-triazine was used instead of 2-bromo-4,6-diphenyl-1,3,5-triazine.
<Preparation Example 31> Preparation of Compound 113
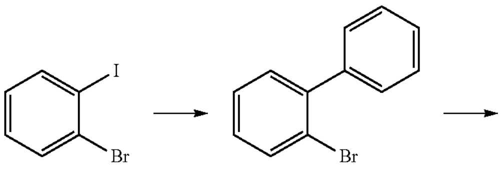
1-1
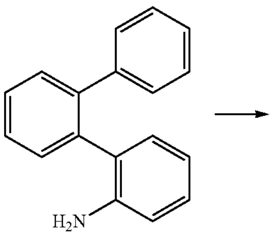
1-2
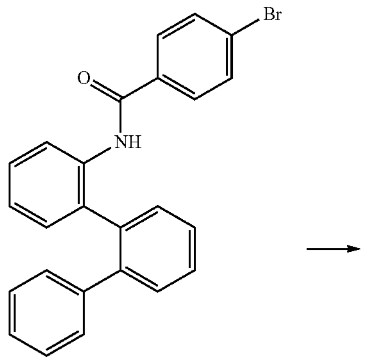
1-3
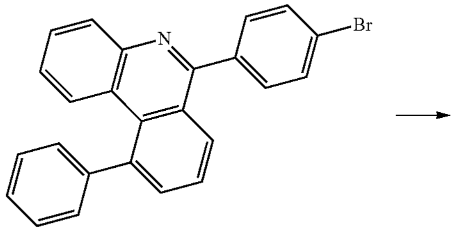
1-4
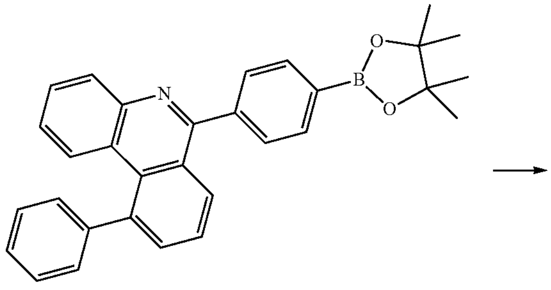
1-5

-continued
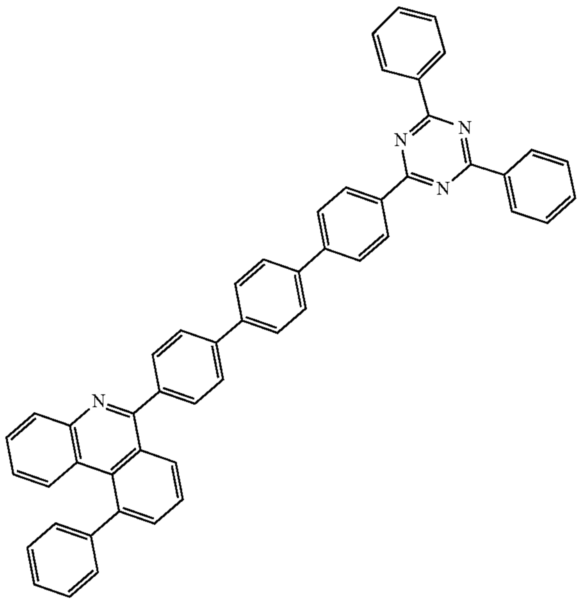
113
Target Compound 113 was obtained in the same manner as in the preparation of Compound 4 of Preparation Example 2 except that 2-(4'-bromo-[1,1'-biphenyl]-4-yl)-4,6-diphenyl-1,3,5-triazine was used instead of 2-bromo-4,6-diphenyl-1,3,5-triazine.
<Preparation Example 32> Preparation of Compound 116
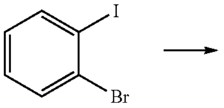
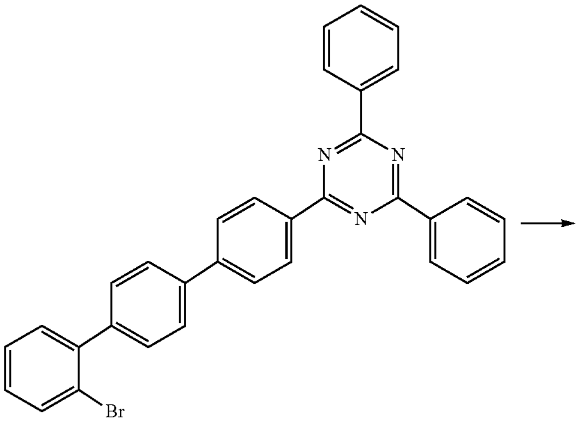
116-1
-continued
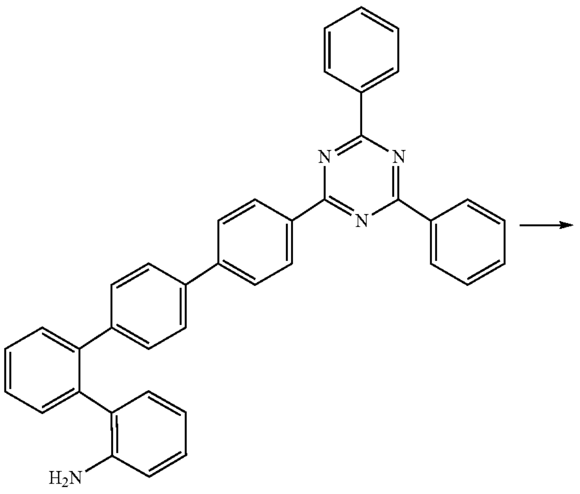
116-2
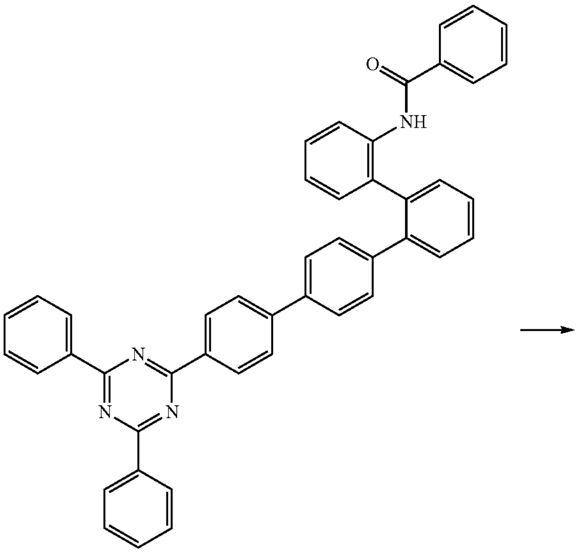
116-3
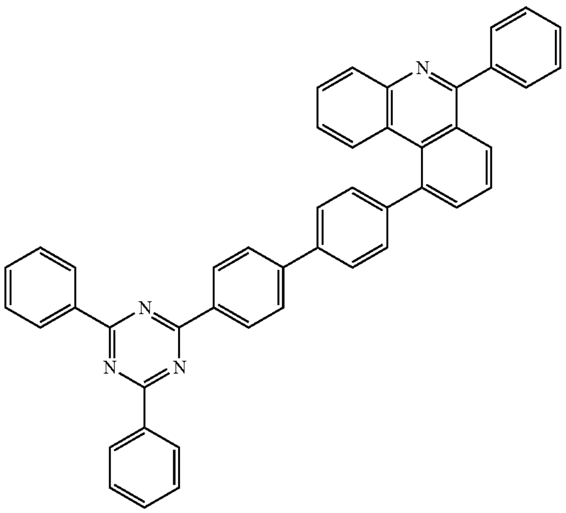
116

Preparation of Compound 116-1

After dissolving 1-bromo-2-iodobenzene (10 g, 35.3 mmol, eq.) in 1,4-dioxane/$H_2O$, 2,4-diphenyl-6-(4'-(4,4,5,5-tetramethyl-1,3,2-dioxaborolan-2-yl)-[1,1'-biphenyl]-4-yl)-1,3,5-triazine (18 g, 35.3 mmol, 1 eq.), $Pd(PPh_3)_4$ (2.0 g, 0.05 eq.) and $K_2CO_3$ (14.6 g, 3 eq.) were added thereto, and the result was stirred for 6 hours at 100° C. After the reaction was terminated, the result was cooled to room temperature, and extracted with distilled water and EA. The organic layer was dried with $MgSO_4$, and then filtered and concentrated. With ethyl acetate and hexane as a developing solvent, the concentrated residue was purified using column chromatography to obtain target Compound 116-1 (15.3 g, 80%).

Preparation of Compound 116-2

After dissolving Compound 116-1 (15.3 g, 28.2 mmol, 1 eq.) in 1,4-dioxane/$H_2O$, 2-(4,4,5,5-tetramethyl-1,3,2-dioxaborolan-2-yl)aniline (7.4 g, 1.2 eq.), $Pd(PPh_3)_4$ (1.6 g, 0.05 eq.) and $K_2CO_3$ (11 g, 3 eq.) were added thereto, and the result was stirred for 6 hours at 100° C. After the reaction was terminated, the result was cooled to room temperature, and extracted with distilled water and EA. The organic layer was dried with $MgSO_4$, and then filtered and concentrated. With ethyl acetate and hexane as a developing solvent, the concentrated residue was purified using column chromatography to obtain target Compound 116-2 (13.7 g, 88%).

Preparation of Compound 116-3

After dissolving Compound 116-2 (13.7 g, 24.8 mmol, 1 eq.) by adding THF, TEA (10 ml, 3 eq.) and bromobenzoyl chloride (5.2 g, 1.5 eq.) were added thereto at 0° C., and the result was stirred for 1 hour at room temperature. After the reaction was terminated, the result was extracted with distilled water and EA. The organic layer was dried with $MgSO_4$, and then filtered and concentrated. With ethyl acetate and hexane as a developing solvent, the concentrated residue was purified using column chromatography to obtain target Compound 116-3 (15.5 g, 95%).

Preparation of Compound 116

After dissolving Compound 116-3 (15.5 g, 23.5 mmol, 1 eq.) in nitrobenzene, $POCl_3$ (3.3 mL, 1.5 eq.) was added thereto, and the result was stirred for 6 hours at 150° C. After the reaction was terminated, the result was neutralized at room temperature, and then extracted with distilled water and dichloromethane. The organic layer was dried with $MgSO_4$, and then filtered and concentrated. The concentrated residue was stirred with ethyl acetate and then filtered to obtain target Compound 116 (7.2 g, 48%).

<Preparation Example 33> Preparation of Compound 139

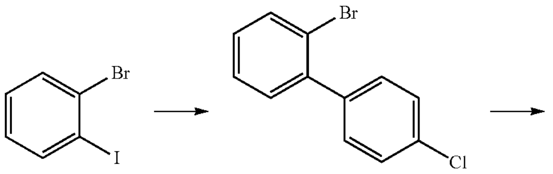

139-1

-continued

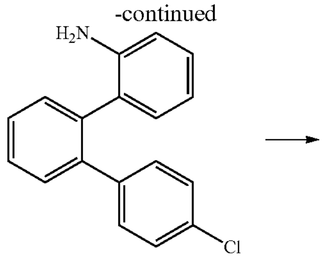

139-2

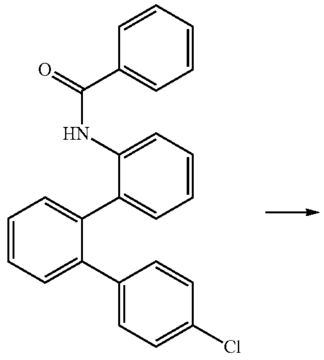

139-3

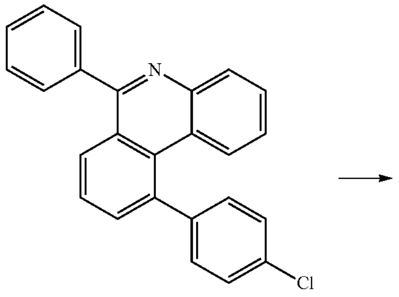

139-4

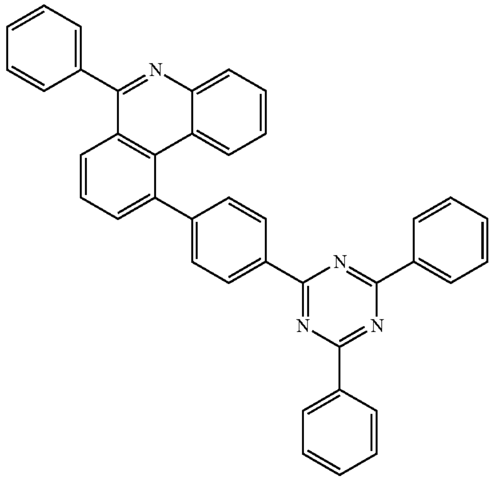

139

Preparation of Compound 139-1

After dissolving 1-bromo-2-iodobenzene (50 g, 0.176 mol, 1 eq.) in toluene/ethanol/$H_2O$, 4-chlorophenylboronic acid (25 g, 0.160 mol, 1 eq.), sodium bicarbonate (40 g, 0.481 mol, 3 eq.) and $Pd(PPh_3)_4$ (9.0 g, 0.008 eq.) were added thereto, and the result was stirred for 16 hours at 100° C. After the reaction was terminated, the result was cooled to room temperature, and extracted with distilled water and EA. The organic layer was dried with $MgSO_4$, and then filtered and concentrated. With ethyl acetate and hexane as a developing solvent, the concentrated residue was purified using column chromatography to obtain target Compound 139-1 (27 g, 57%).

Preparation of Compound 139-2

After dissolving Compound 139-1 (25 g, 0.093 mol, 1 eq.) in toluene/ethanol/$H_2O$, (2-aminophenyl)boronic acid (20 g, 0.093 mol, 1 eq.), potassium phosphate (59 g, 0.280 mol, 3 eq.) and $Pd(PPh_3)_4$ (5.3 g, 0.005 eq.) were added thereto, and the result was stirred for 14 hours at 100° C. After the reaction was terminated, the result was cooled to room temperature, and extracted with distilled water and EA. The organic layer was dried with $MgSO_4$, and then filtered and concentrated. With dichloromethane and hexane as a developing solvent, the concentrated residue was purified using column chromatography to obtain target Compound 139-2 (22 g, 84%).

Preparation of Compound 139-3

After dissolving Compound 139-2 (22 g, 0.078 mol, 1 eq.) by adding THF, triethanolamine (TEA) (27 ml, 1 eq.) and benzoyl chloride (12 ml, 1.1 eq.) were added thereto at 0° C., and the result was stirred for 1 hour at room temperature. After the reaction was terminated, the result was extracted with distilled water and EA. The organic layer was dried with $MgSO_4$, and then filtered and concentrated. With dichloromethane and hexane as a developing solvent, the concentrated residue was purified using column chromatography to obtain target Compound 139-3 (22 g, 74%).

Preparation of Compound 139-4

After dissolving Compound 139-3 (22 g, 0.059 mol, 1 eq.) in nitrobenzene, $POCl_3$ (13 mL, 1.5 eq.) was added thereto, and the result was stirred for 5 hours at 150° C. After the reaction was terminated, the result was neutralized at room temperature, and then extracted with distilled water and dichloromethane. The organic layer was dried with $MgSO_4$, and then filtered and concentrated. The concentrated residue was stirred with ethyl acetate and then filtered to obtain target Compound 139-4 (15 g, 69%).

Preparation of Compound 139-5

After dissolving Compound 139-4 (15 g, 0.041 mol, 1 eq.) in 1,4-dioxane, bis(pinacolato)diboron (11 g, 0.045 mol, 1.1 eq.), $Pd(dppf)Cl_2$ (1.6 g, 0.002 mol, 0.05 eq.) and potassium acetate (12 g, 0.123 mol, 3 eq.) were added thereto, and the result was stirred for 4 hours at 100° C. After the reaction was terminated, the result was neutralized at room temperature, and then extracted with distilled water and dichloromethane. The organic layer was dried with $MgSO_4$, and then filtered and concentrated. The concentrated residue was stirred with ethyl acetate and then filtered to obtain target Compound 139-5 (17 g, 94%).

Preparation of Compound 139

After dissolving 139-5 (8.0 g, 17.5 mmol, 1 eq.) in 1,4-dioxane/$H_2O$, 2-chloro-4,6-diphenyl-1,3,5-triazine (4.9 g, 18.3 mmol, 1.05 eq.), $Pd(PPh_3)_4$ (1.0 g, 0.87 mmol, 0.05 eq.) and $K_2CO_3$ (7.2 g, 52.5 mmol, 3 eq.) were added thereto, and the result was stirred for 15 hours at 100° C. After the reaction was terminated, the result was cooled to room temperature, and produced solids were recrystallized to obtain target Compound 139 (8.3 g, 84%).

<Preparation Example 34> Preparation of Compound 142

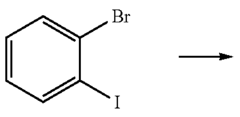

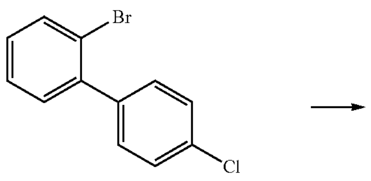

139-1

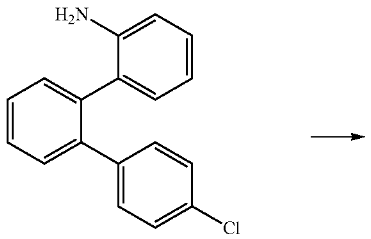

139-2

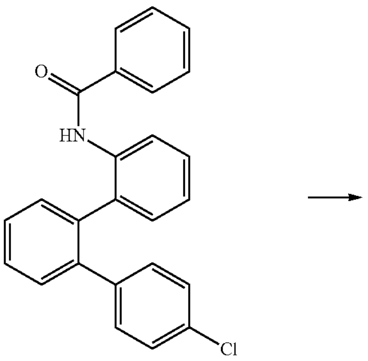

139-3

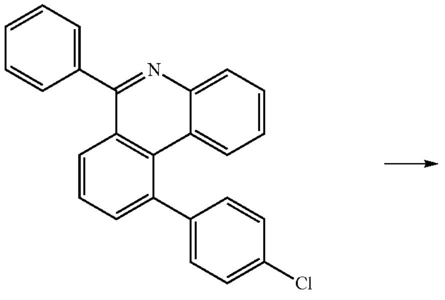

139-4

-continued
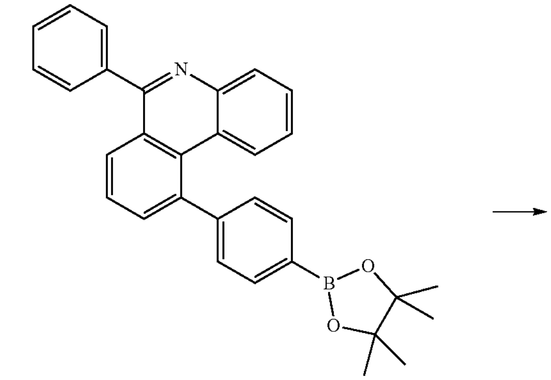
139-5
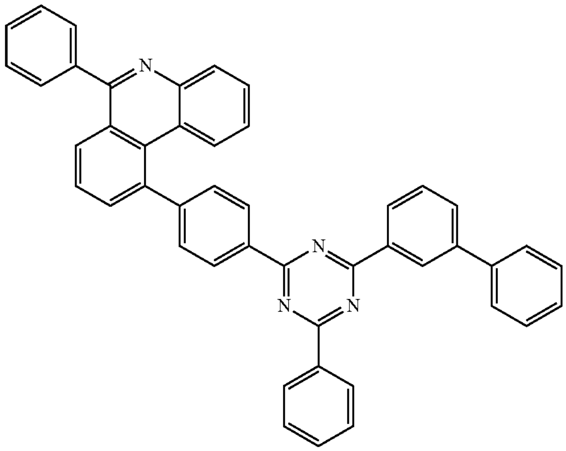
142
Preparation of Compound 142
Target Compound 142 was obtained in the same manner as in the preparation of Compound 139 of Preparation Example 33 except that 2-([1,1'-biphenyl]-3-yl)-4-chloro-6-phenyl-1,3,5-triazine was used instead of 2-chloro-4,6-diphenyl-1,3,5-triazine.
<Preparation Example 35> Preparation of Compound 145
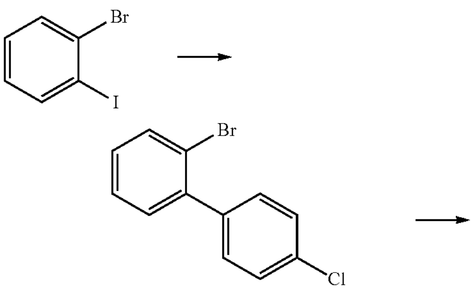
139-1
-continued
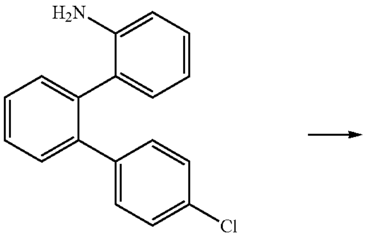
139-2
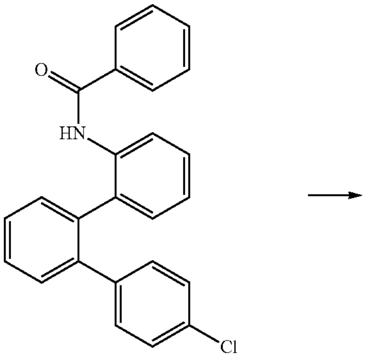
139-3
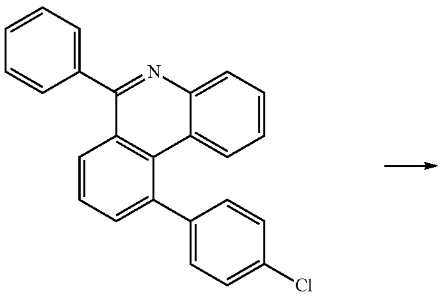
139-4
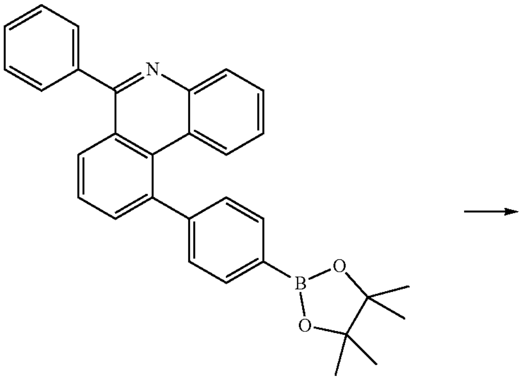
139-5

-continued

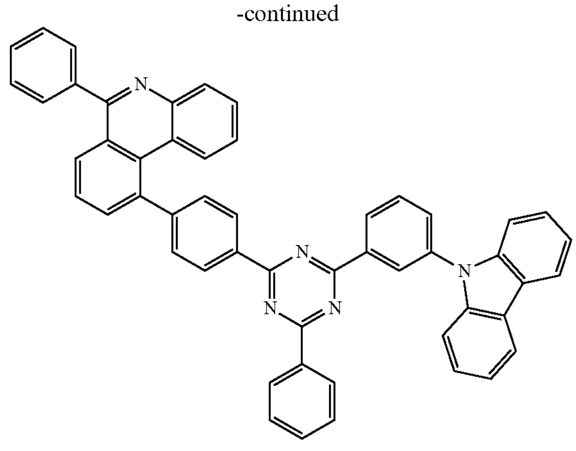

145

Target Compound 145 was obtained in the same manner as in the preparation of Compound 139 of Preparation Example 33 except that 9-(3-(4-chloro-6-phenyl-1,3,5-triazine-2-yl)phenyl)-9H-carbazole was used instead of 2-chloro-4,6-diphenyl-1,3,5-triazine.

<Preparation Example 36> Preparation of Compound 147

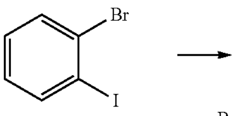

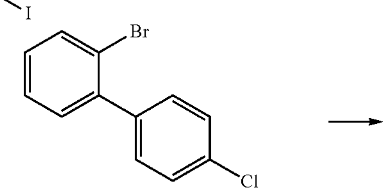

139-1

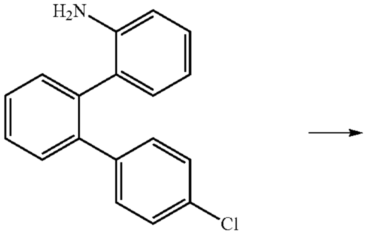

139-2

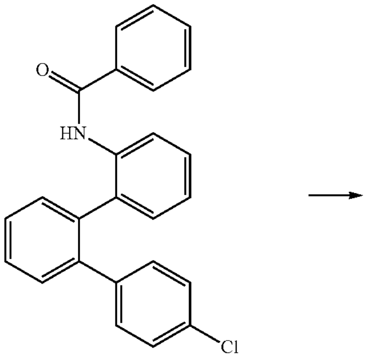

139-3

-continued

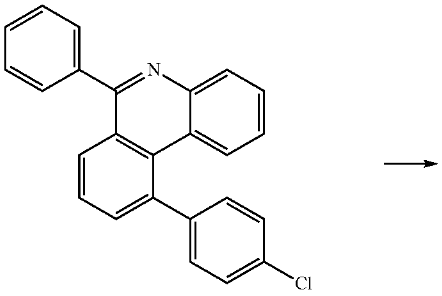

139-4

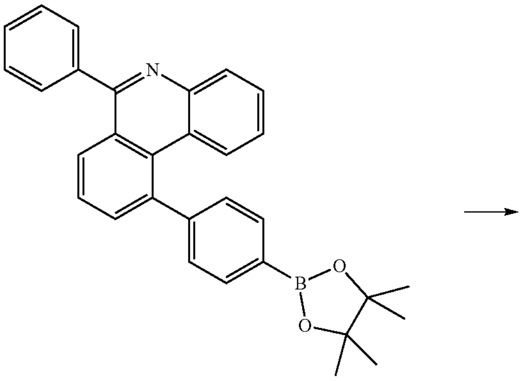

139-5

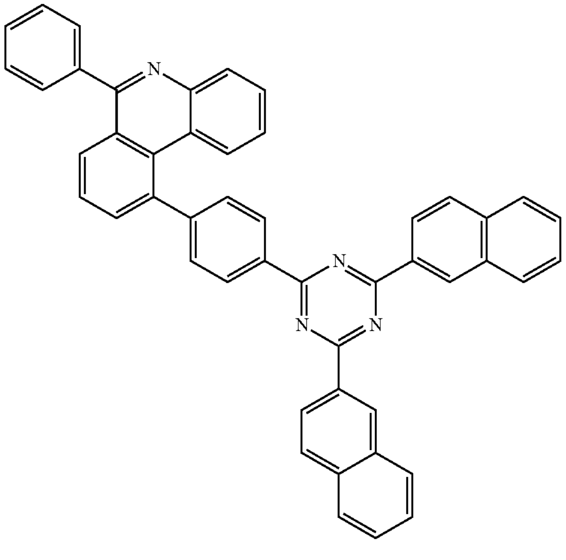

147

Target Compound 147 was obtained in the same manner as in the preparation of Compound 139 of Preparation Example 33 except that 2-chloro-4,6-di(naphthalen-2-yl)-1,3,5-triazine was used instead of 2-chloro-4,6-diphenyl-1,3,5-triazine.

<Preparation Example 37> Preparation of Compound 154
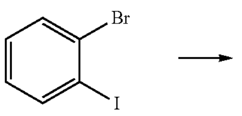
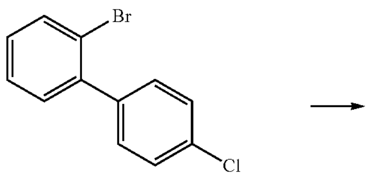
139-1
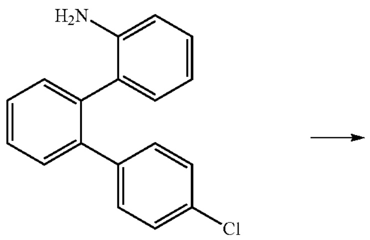
139-2
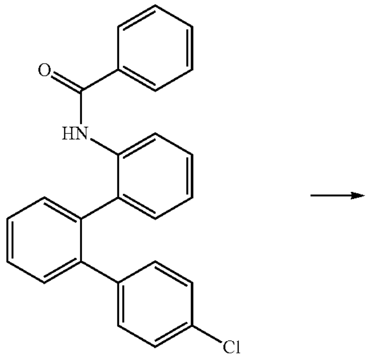
139-3
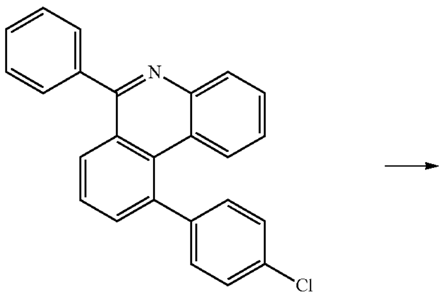
139-4
-continued
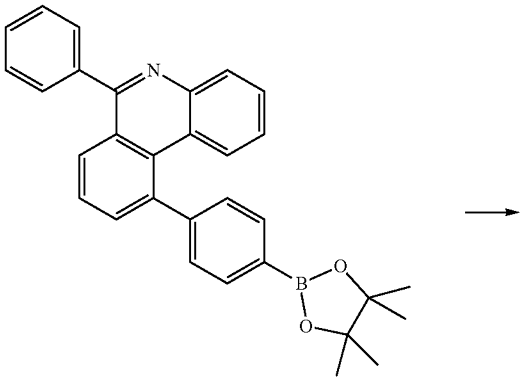
139-5
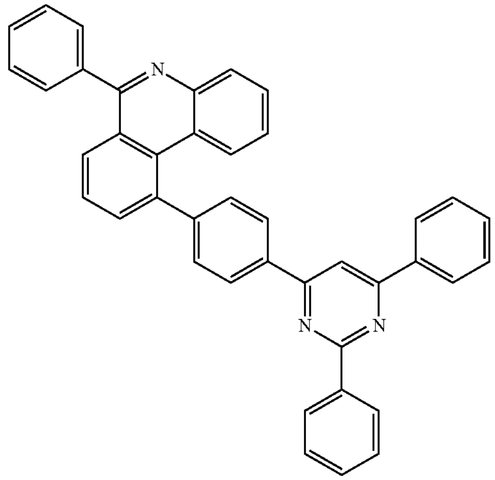
154
Target Compound 154 was obtained in the same manner as in the preparation of Compound 139 of Preparation Example 33 except that 4-chloro-2,6-diphenylpyrimidine was used instead of 2-chloro-4,6-diphenyl-1,3,5-triazine.
<Preparation Example 38> Preparation of Compound 155
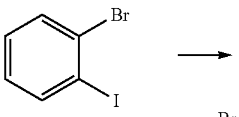
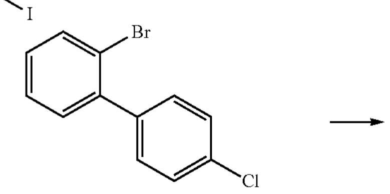
139-1

-continued
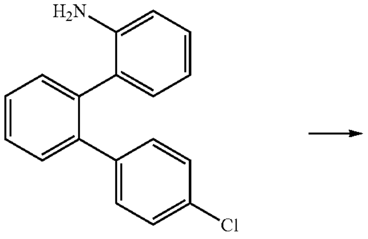
139-2
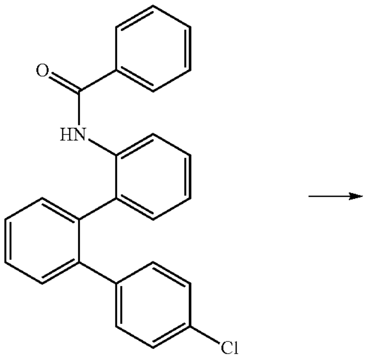
139-3
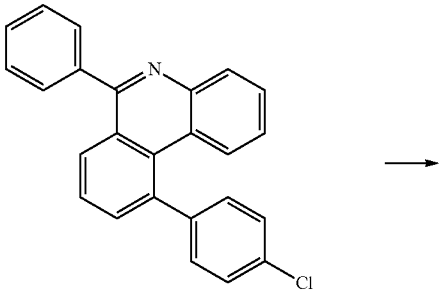
139-4
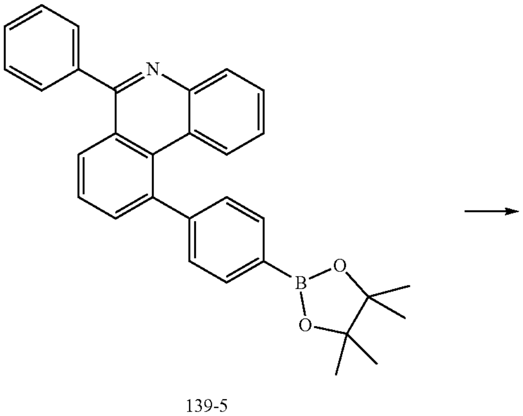
139-5
-continued
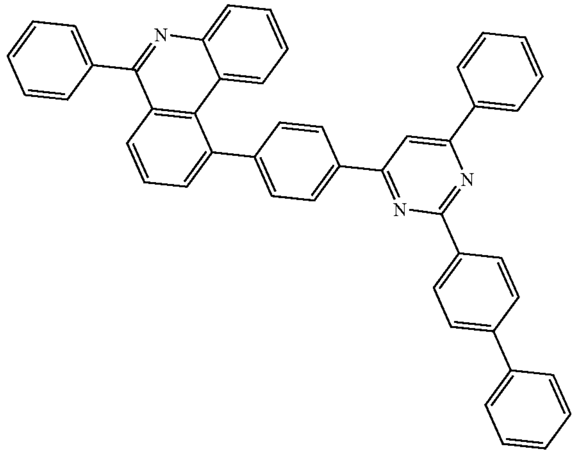
155
Target Compound 155 was obtained in the same manner as in the preparation of Compound 139 of Preparation Example 33 except that 2-([1,1'-biphenyl]-4-yl)-4-chloro-6-phenylpyrimidine was used instead of 2-chloro-4,6-diphenyl-1,3,5-triazine.
<Preparation Example 39> Preparation of Compound 160
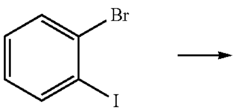
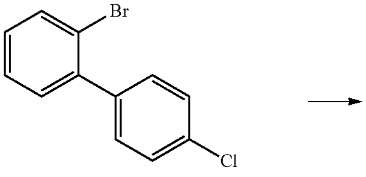
139-1
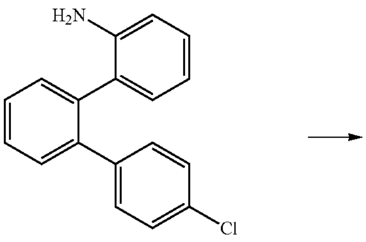
139-2

-continued
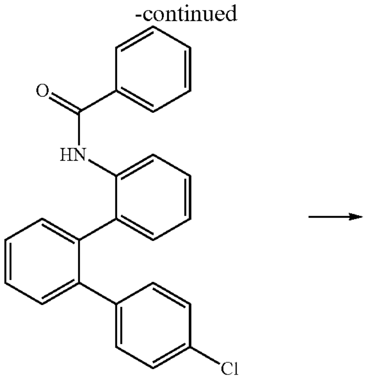
139-3
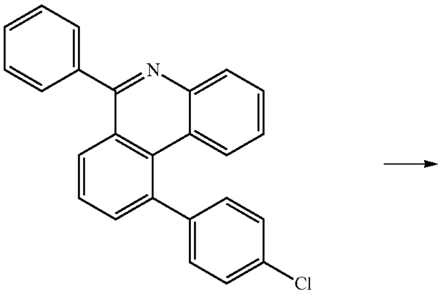
139-4
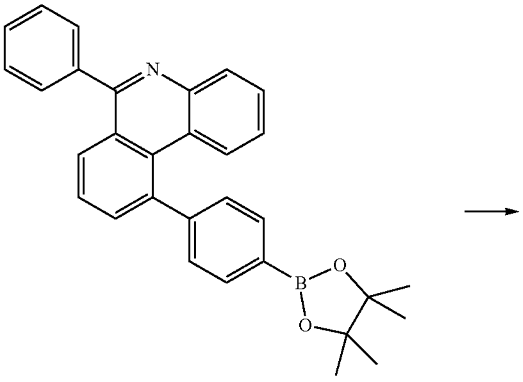
139-5
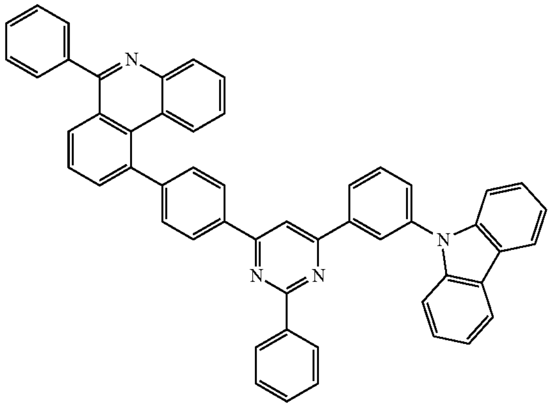
160
Target Compound 160 was obtained in the same manner as in the preparation of Compound 139 of Preparation Example 33 except that 9-(3-(6-chloro-2-phenylpyrimidin-4-yl)phenyl)-9H-carbazole was used instead of 2-chloro-4,6-diphenyl-1,3,5-triazine.
<Preparation Example 40> Preparation of Compound 164
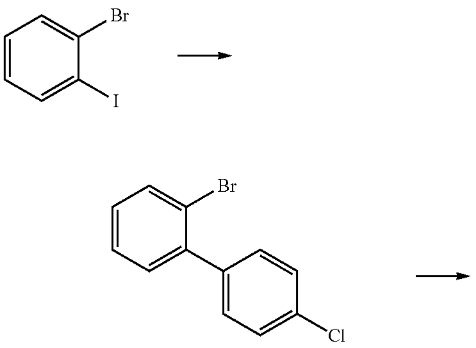
139-1
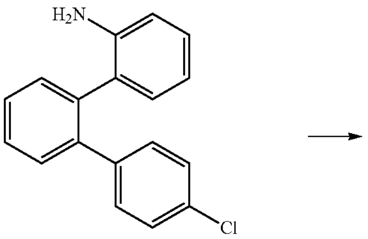
139-2
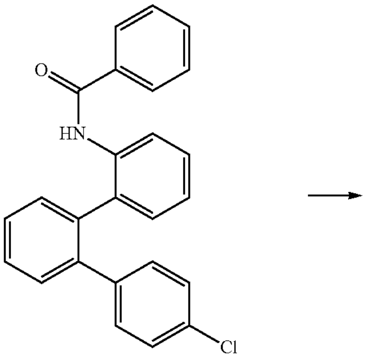
139-3
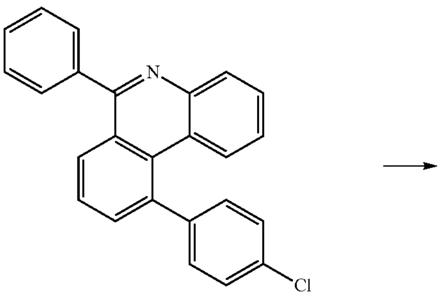
139-4

-continued

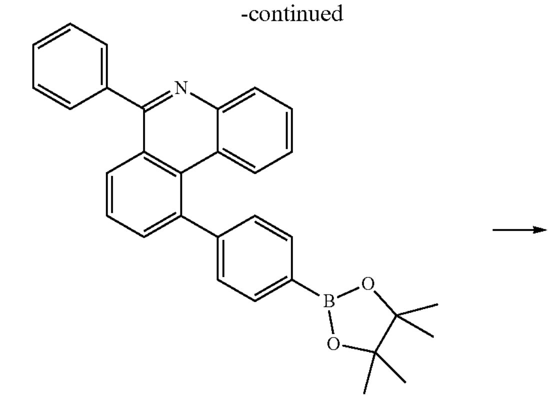

139-5

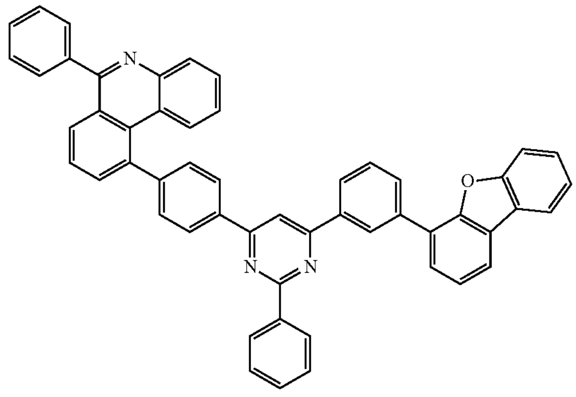

164

Target Compound 164 was obtained in the same manner as in the preparation of Compound 139 of Preparation Example 33 except that 4-chloro-6-(3-(dibenzo[b,d]furan-4-yl)phenyl)-2-phenylpyrimidine was used instead of 2-chloro-4,6-diphenyl-1,3,5-triazine.

<Preparation Example 41> Preparation of Compound 165

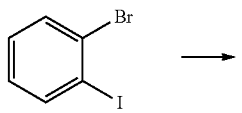

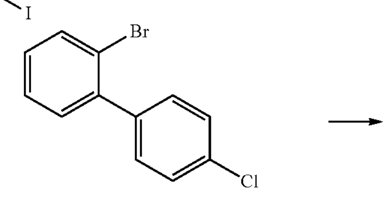

139-1

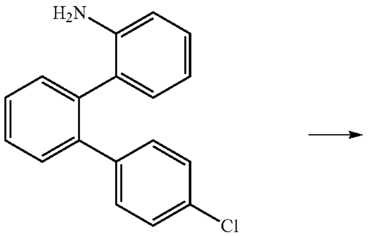

139-2

-continued

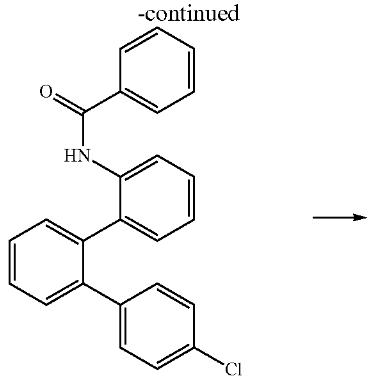

139-3

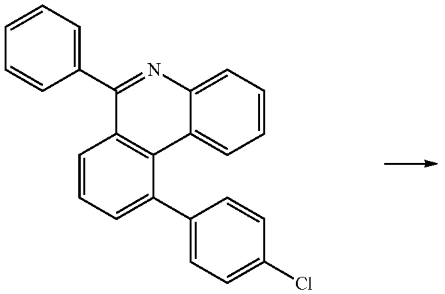

139-4

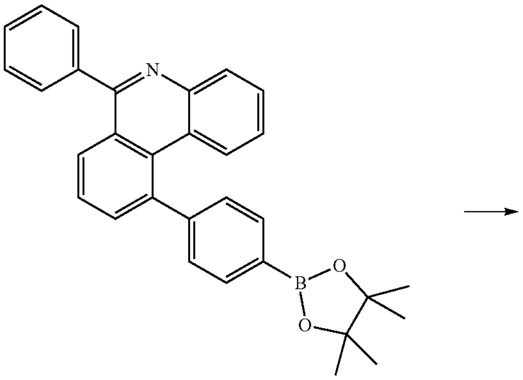

139-5

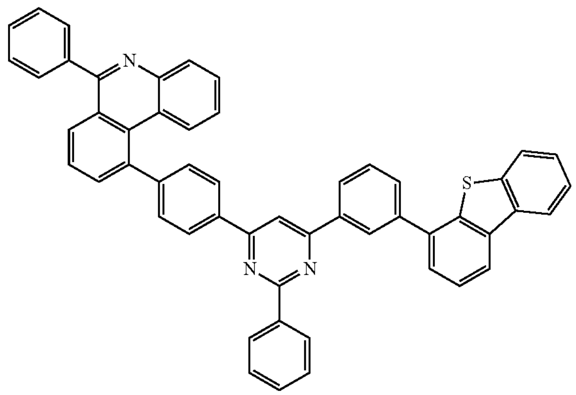

165

Target Compound 165 was obtained in the same manner as in the preparation of Compound 139 of Preparation Example 33 except that 4-chloro-6-(3-(dibenzo[b,d]thiophen-4-yl)phenyl)-2-phenylpyrimidine was used instead of 2-chloro-4,6-diphenyl-1,3,5-triazine.

<Preparation Example 42> Preparation of Compound 166
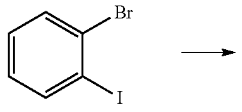
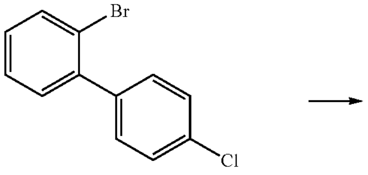
139-1
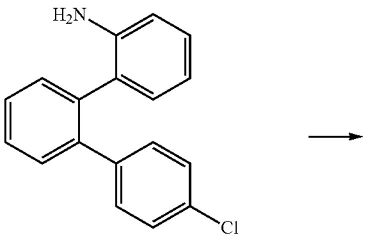
139-2
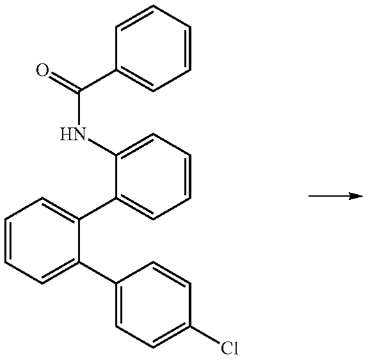
139-3
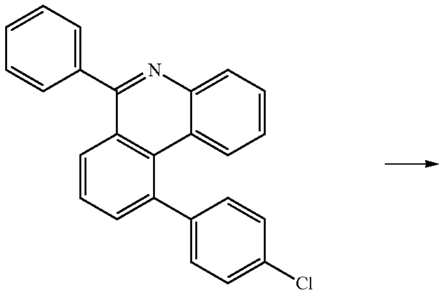
139-4
-continued
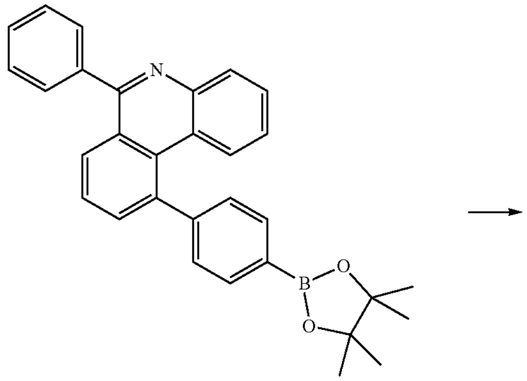
139-5
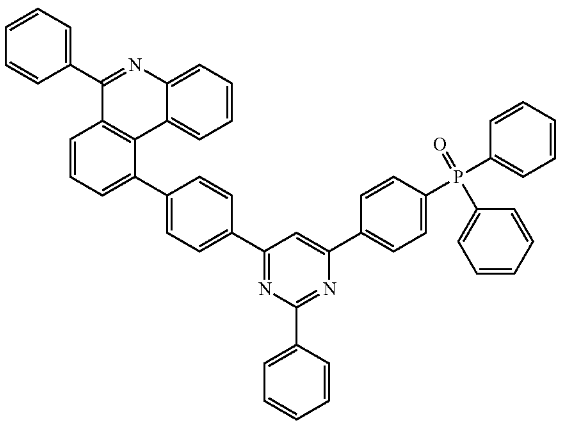
166
Target Compound 166 was obtained in the same manner as in the preparation of Compound 139 of Preparation Example 33 except that (4-(6-chloro-2-phenylpyrimidin-4-yl)phenyl)diphenylphosphine oxide was used instead of 2-chloro-4,6-diphenyl-1,3,5-triazine.
<Preparation Example 43> Preparation of Compound 184
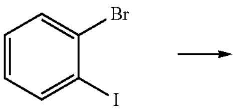
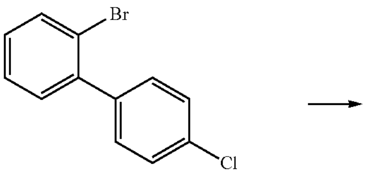
139-1

-continued
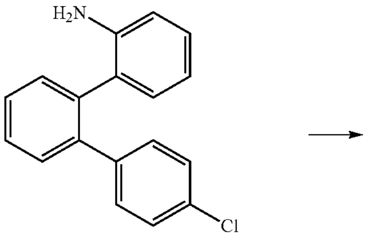
139-2
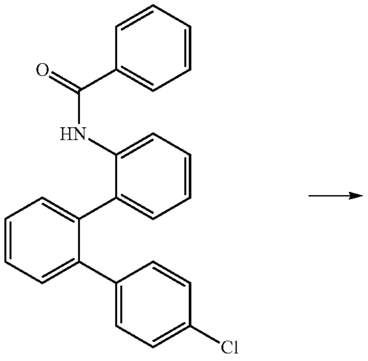
139-3
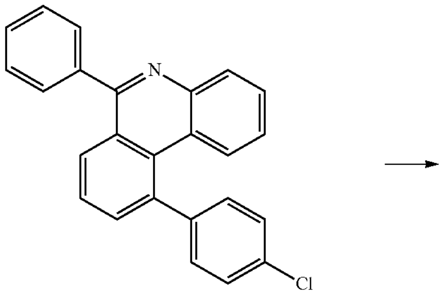
139-4
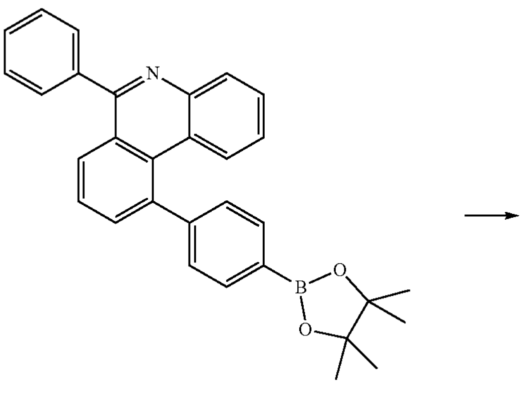
139-5
-continued
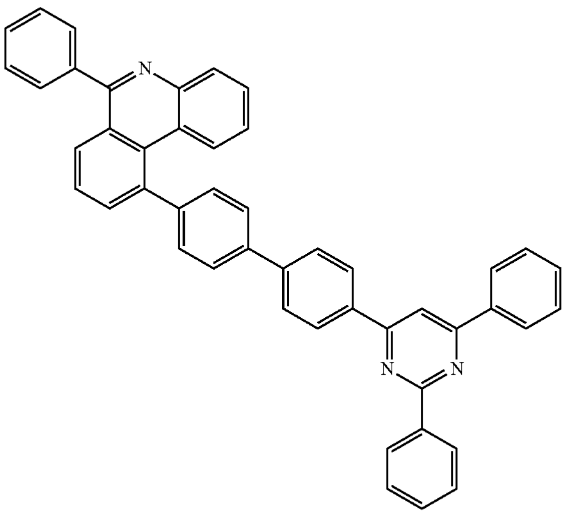
184
Target Compound 184 was obtained in the same manner as in the preparation of Compound 139 of Preparation Example 33 except that 4-(4-chlorophenyl)-2,6-diphenylpyrimidine was used instead of 2-chloro-4,6-diphenyl-1,3,5-triazine.
<Preparation Example 44> Preparation of Compound 199
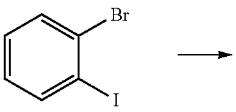
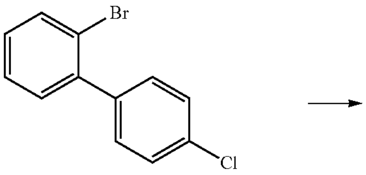
139-1
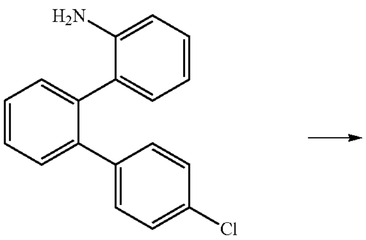
139-2

-continued
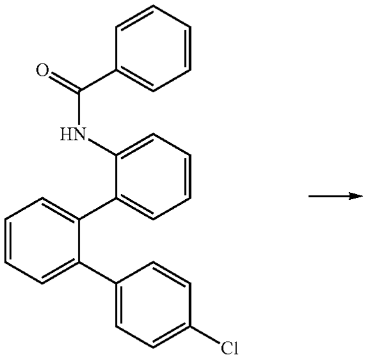
139-3
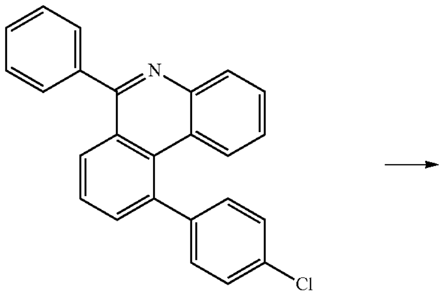
139-4
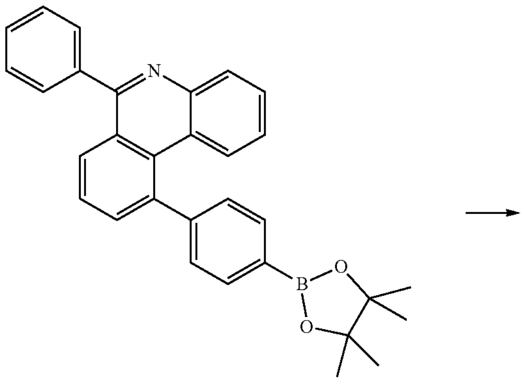
139-5
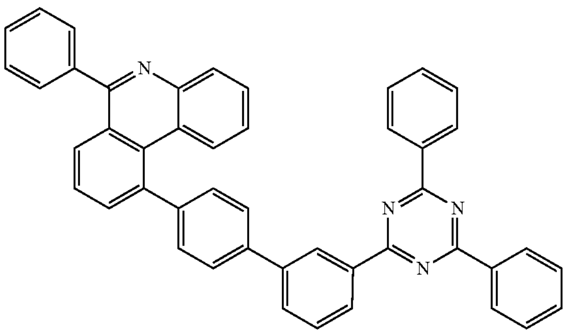
199
Target Compound 199 was obtained in the same manner as in the preparation of Compound 139 of Preparation Example 33 except that 2-(3-bromophenyl)-4,6-diphenyl-1,3,5-triazine was used instead of 2-chloro-4,6-diphenyl-1,3,5-triazine.
<Preparation Example 45> Preparation of Compound 229
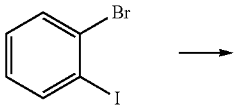
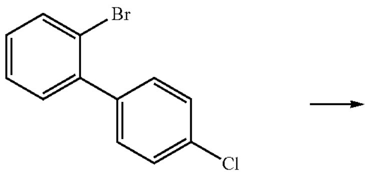
139-1
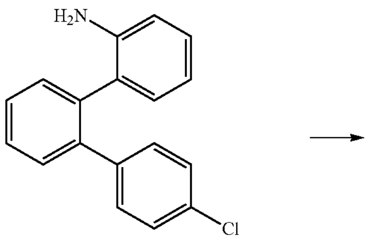
139-2
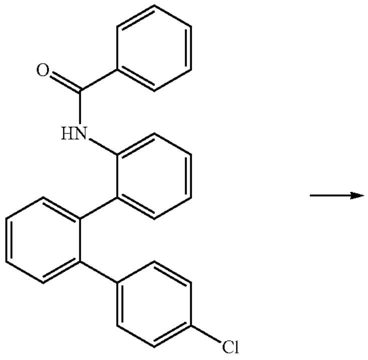
139-3
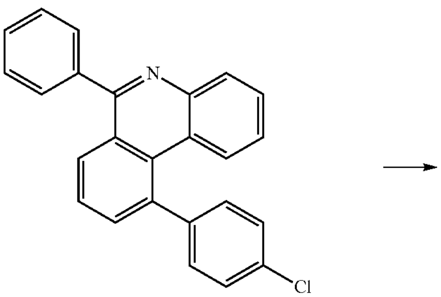
139-4

-continued
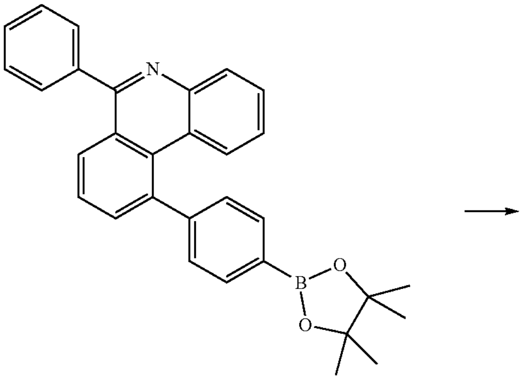
139-5
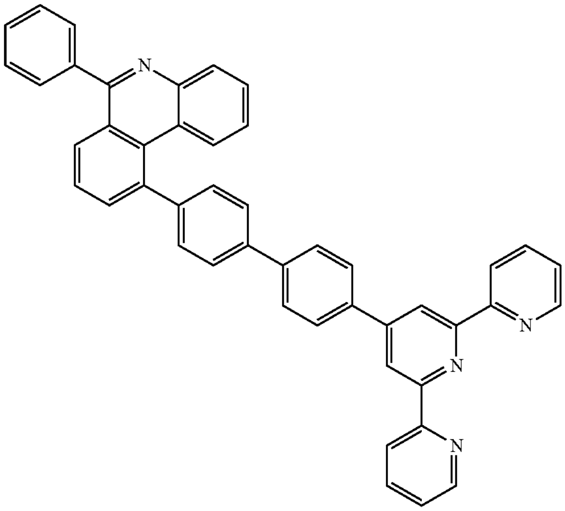
229
Target Compound 229 was obtained in the same manner as in the preparation of Compound 139 of Preparation Example 33 except that 4'-(4-bromophenyl)-2,2':6',2"-terpyridine was used instead of 2-chloro-4,6-diphenyl-1,3,5-triazine.
<Preparation Example 46> Preparation of Compound 232
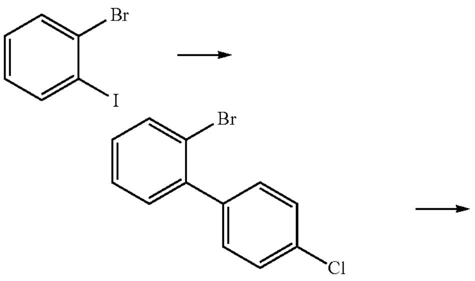
139-1
-continued
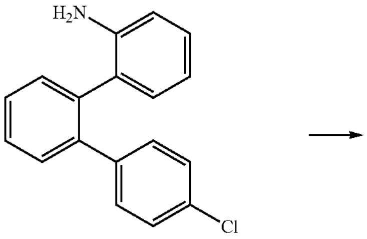
139-2
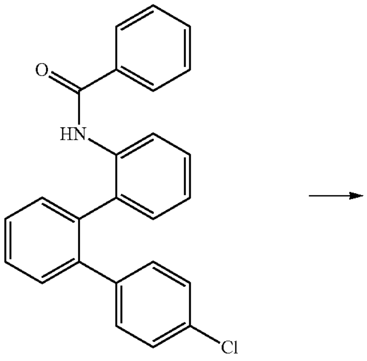
139-3
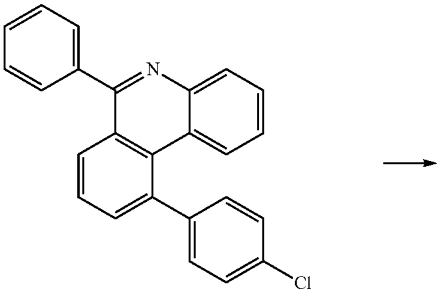
139-4
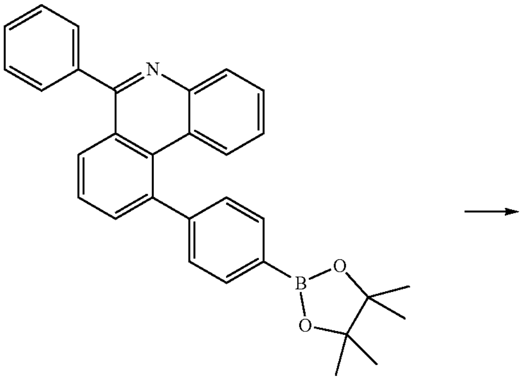
139-5

-continued

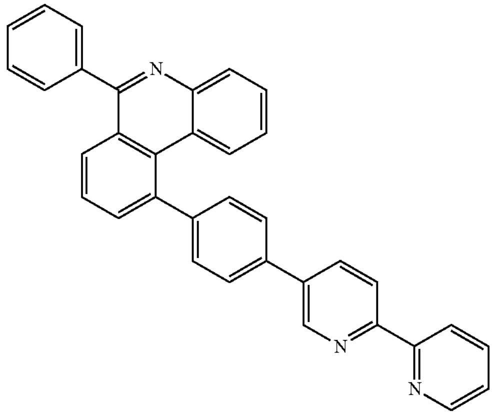

232

Target Compound 232 was obtained in the same manner as in the preparation of Compound 139 of Preparation Example 33 except that 5-bromo-2,2'-bipyridine was used instead of 2-chloro-4,6-diphenyl-1,3,5-triazine.

<Preparation Example 47> Preparation of Compound 241

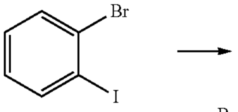

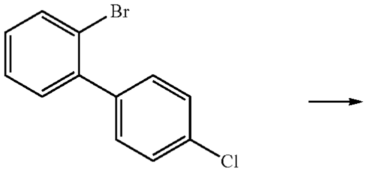

139-1

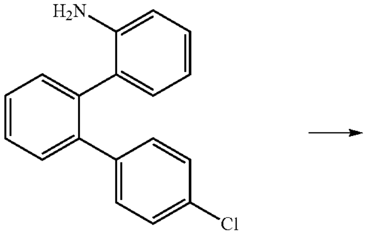

139-2

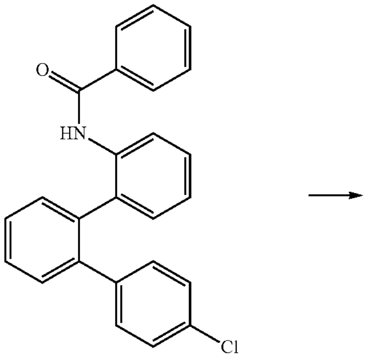

139-3

-continued

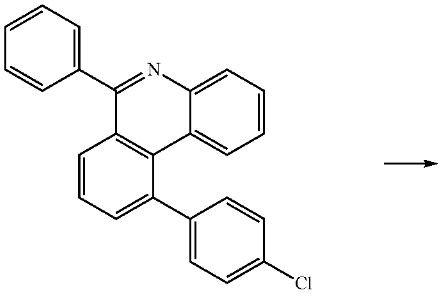

139-4

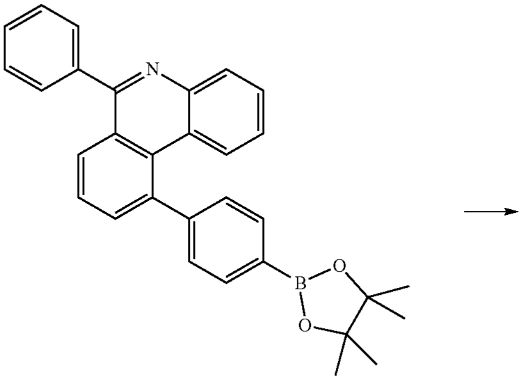

139-5

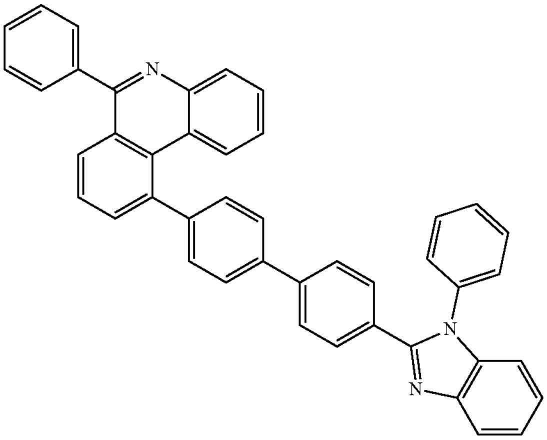

241

Target Compound 241 was obtained in the same manner as in the preparation of Compound 139 of Preparation Example 33 except that 2-(4-bromophenyl)-1-phenyl-1H-benzo[d]imidazole was used instead of 2-chloro-4,6-diphenyl-1,3,5-triazine.

<Preparation Example 48> Preparation of Compound 245

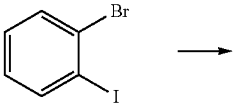

-continued
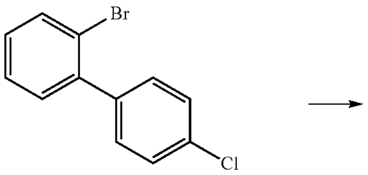
139-1
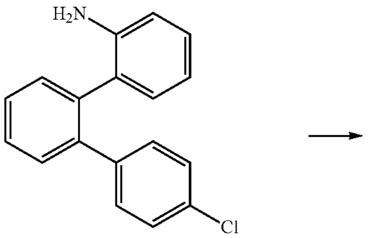
139-2
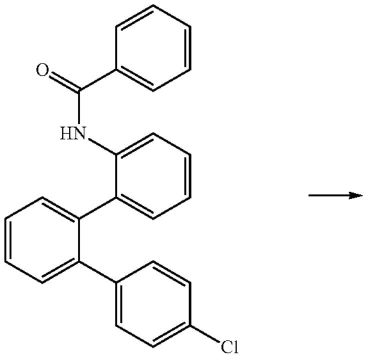
139-3
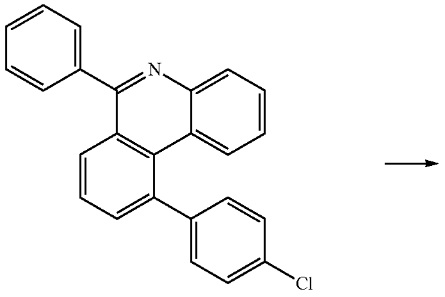
139-4
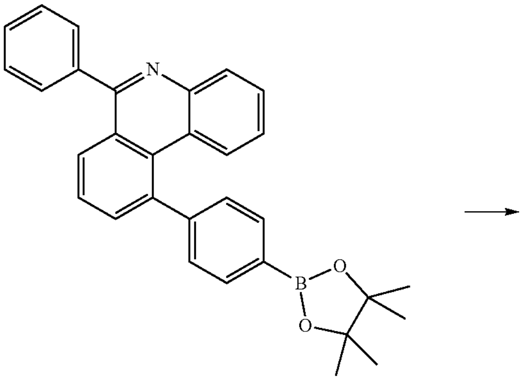
139-5
-continued
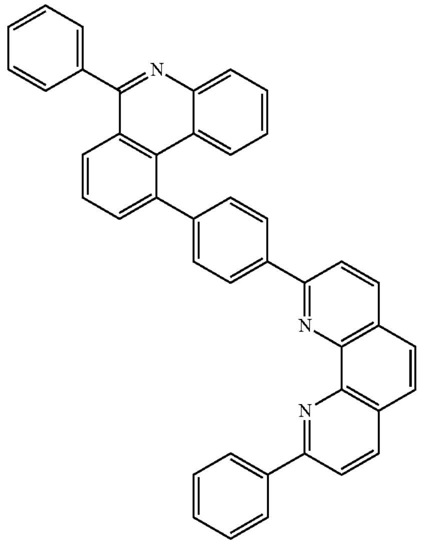
245
Target Compound 245 was obtained in the same manner as in the preparation of Compound 139 of Preparation Example 33 except that 2-bromo-9-phenyl-1,10-phenanthroline was used instead of 2-chloro-4,6-diphenyl-1,3,5-triazine.
<Preparation Example 49> Preparation of Compound 246
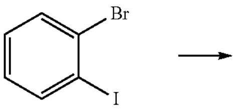
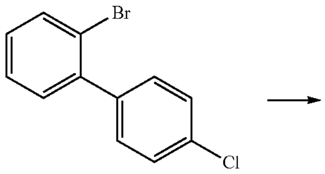
139-1
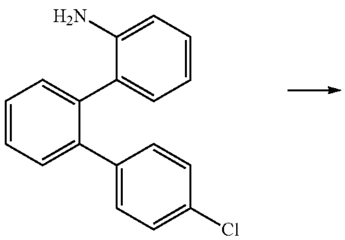
139-2

-continued
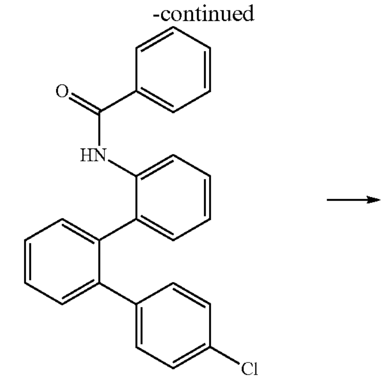
139-3
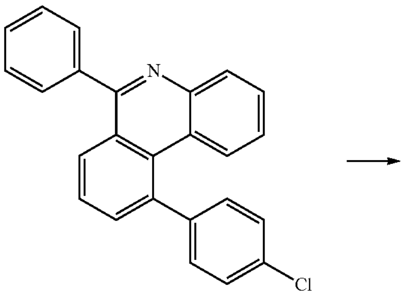
139-4
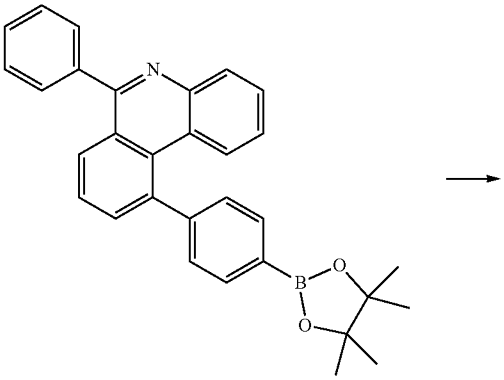
139-5
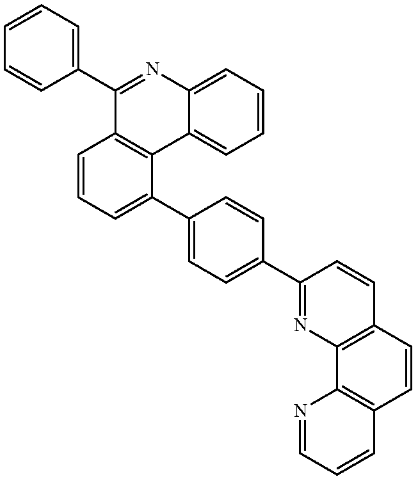
246
Target Compound 246 was obtained in the same manner as in the preparation of Compound 139 of Preparation Example 33 except that 2-bromo-1,10-phenanthroline was used instead of 2-chloro-4,6-diphenyl-1,3,5-triazine.
<Preparation Example 50> Preparation of Compound 247
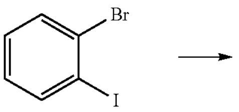
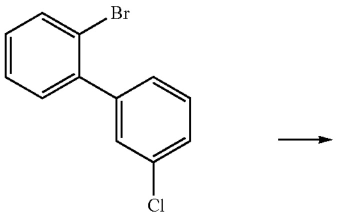
247-1
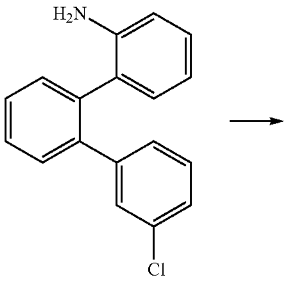
247-2
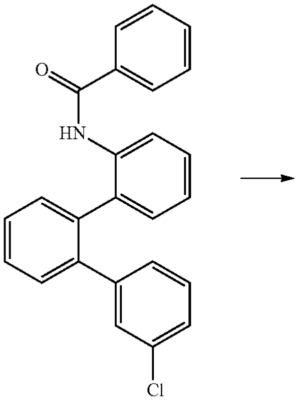
247-3
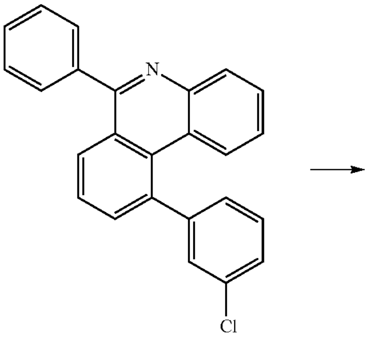
247-4

-continued

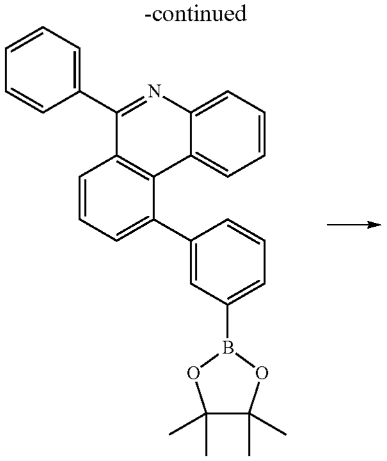

247-5

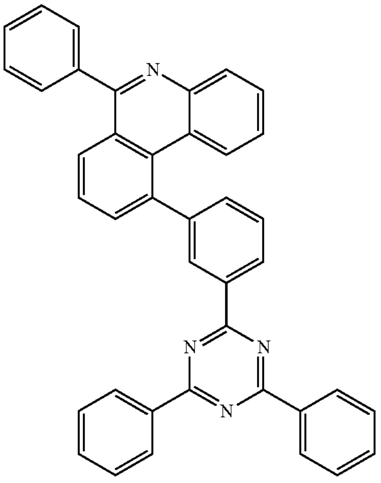

247

Preparation of Compound 247-1

After dissolving 1-bromo-2-iodobenzene (50 g, 0.176 mol, 1 eq.) in toluene/ethanol/$H_2O$, 3-chlorophenylboronic acid (25 g, 0.160 mol, 1 eq.), sodium bicarbonate (40 g, 0.481 mol, 3 eq.) and $Pd(PPh_3)_4$ (9.0 g, 0.008 eq.) were added thereto, and the result was stirred for 16 hours at 100° C. After the reaction was terminated, the result was cooled to room temperature, and extracted with distilled water and EA. The organic layer was dried with $MgSO_4$, and then filtered and concentrated. With ethyl acetate and hexane as a developing solvent, the concentrated residue was purified using column chromatography to obtain target Compound 247-1 (24 g, 52%).

Preparation of Compound 247-2

After dissolving Compound 247-1 (24 g, 0.091 mol, 1 eq.) in toluene/ethanol/$H_2O$, (2-aminophenyl)boronic acid (12 g, 0.091 mol, 1 eq.), potassium phosphate (58 g, 0.273 mol, 3 eq.) and $Pd(PPh_3)_4$ (5.2 g, 0.05 eq.) were added thereto, and the result was stirred for 14 hours at 100° C. After the reaction was terminated, the result was cooled to room temperature, and extracted with distilled water and EA. The organic layer was dried with $MgSO_4$, and then filtered and concentrated. With dichloromethane and hexane as a developing solvent, the concentrated residue was purified using column chromatography to obtain target Compound 247-2 (22 g, 86%).

Preparation of Compound 247-3

After dissolving Compound 247-2 (22 g, 0.078 mol, 1 eq.) by adding THF, TEA (27 ml, 1 eq.) and benzoyl chloride (12 ml, 1.1 eq.) were added thereto at 0° C., and the result was stirred for 1 hour at room temperature. After the reaction was terminated, the result was extracted with distilled water and EA. The organic layer was dried with $MgSO_4$, and then filtered and concentrated. With dichloromethane and hexane as a developing solvent, the concentrated residue was purified using column chromatography to obtain target Compound 247-3 (22 g, 78%).

Preparation of Compound 247-4

After dissolving Compound 247-3 (22 g, 0.060 mol, 1 eq.) in nitrobenzene, $POCl_3$ (13 mL, 1.5 eq.) was added thereto, and the result was stirred for 5 hours at 150° C. After the reaction was terminated, the result was neutralized at room temperature, and then extracted with distilled water and dichloromethane. The organic layer was dried with $MgSO_4$, and then filtered and concentrated. The concentrated residue was stirred with ethyl acetate and then filtered to obtain target Compound 247-4 (14 g, 64%).

Preparation of Compound 247-5

After dissolving Compound 247-4 (14 g, 0.038 mol, 1 eq.) in 1,4-dioxane, bis(pinacolato)diboron (10 g, 0.041 mol, 1.1 eq.), $Pd(dppf)Cl_2$ (1.6 g, 0.002 mol, 0.05 eq.) and potassium acetate (12 g, 0.122 mol, 3 eq.) were added thereto, and the result was stirred for 4 hours at 100° C. After the reaction was terminated, the result was neutralized at room temperature, and then extracted with distilled water and dichloromethane. The organic layer was dried with $MgSO_4$, and then filtered and concentrated. The concentrated residue was stirred with ethyl acetate and then filtered to obtain target Compound 247-5 (15 g, 90%).

Preparation of Compound 247

After dissolving 247-5 (8.0 g, 17.5 mmol, 1 eq.) in 1,4-dioxane/1-120, 2-chloro-4,6-diphenyl-1,3,5-triazine (4.9 g, 18.3 mmol, 1.05 eq.), $Pd(PPh_3)_4$ (1.0 g, 0.87 mmol, 0.05 eq.) and $K_2CO_3$ (7.2 g, 52.5 mmol, 3 eq.) were added thereto, and the result was stirred for 15 hours at 100° C. After the reaction was terminated, the result was cooled to room temperature, and produced solids were recrystallized to obtain target Compound 247 (8.0 g, 82%).

<Preparation Example 51> Preparation of Compound 277

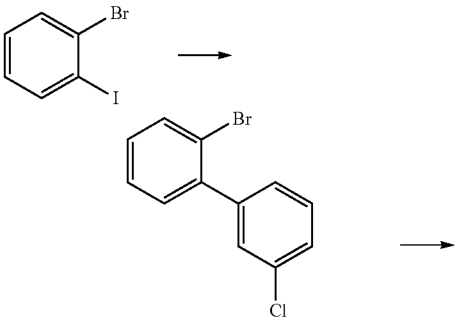

247-1

-continued
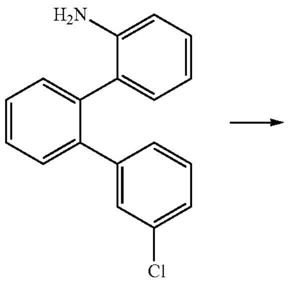
247-2
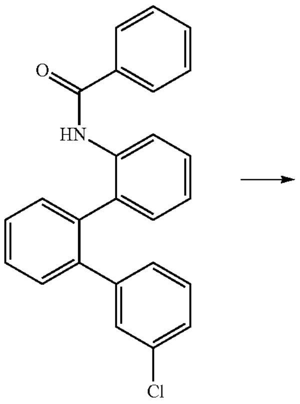
247-3
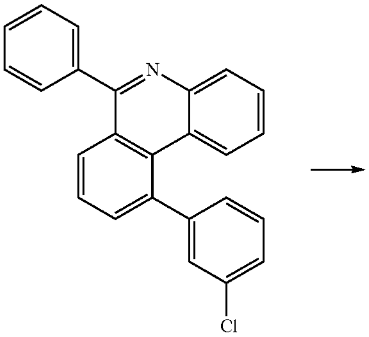
247-4
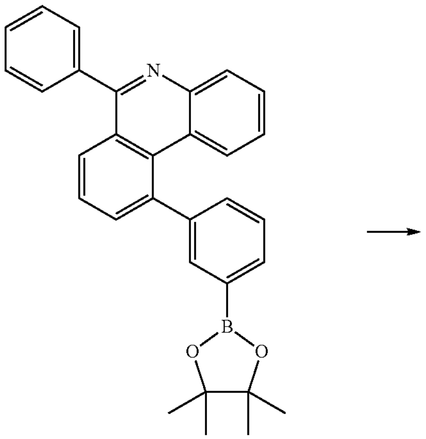
247-5
-continued
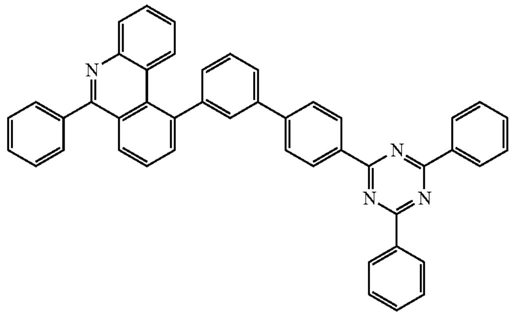
277
Target Compound 277 was obtained in the same manner as in the preparation of Compound 247 of Preparation Example 50 except that 2-(4-bromophenyl)-4,6-diphenyl-1,3,5-triazine was used instead of 2-chloro-4,6-diphenyl-1,3,5-triazine.
<Preparation Example 52> Preparation of Compound 299
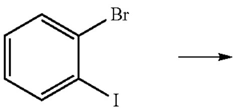
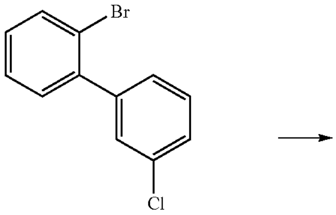
247-1
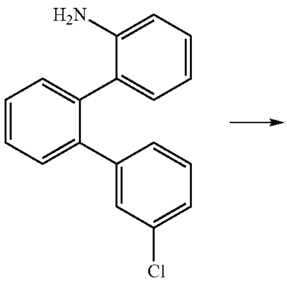
247-2

-continued
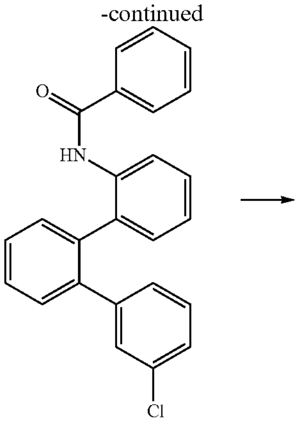
247-3
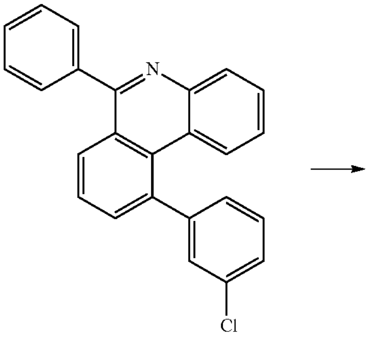
247-4
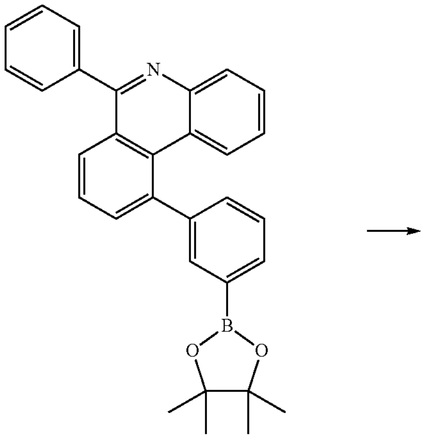
247-5
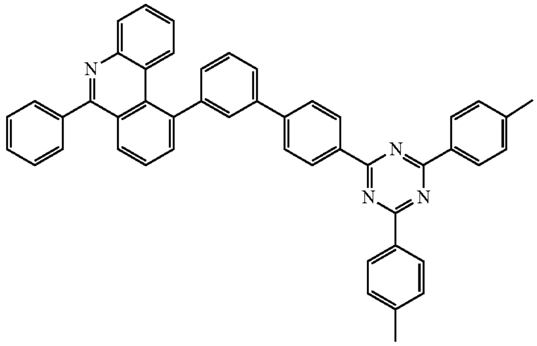
299
Target Compound 299 was obtained in the same manner as in the preparation of Compound 247 of Preparation
Example 50 except that 2-(4-bromophenyl)-4,6-di-p-tolyl-1,3,5-triazine was used instead of 2-chloro-4,6-diphenyl-1,3,5-triazine.
<Preparation Example 53> Preparation of Compound 307
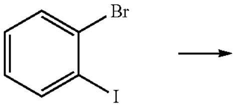
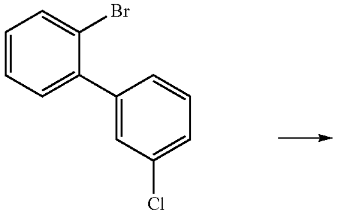
247-1
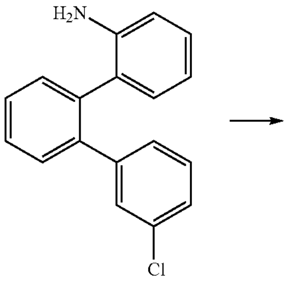
247-2
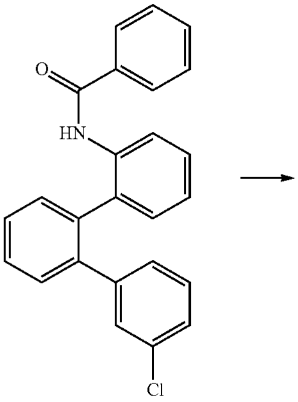
247-3
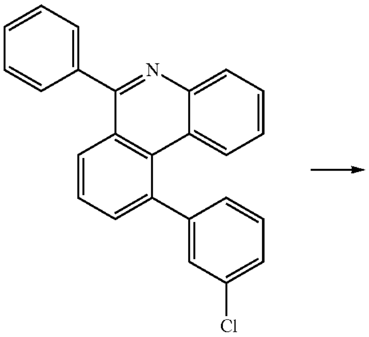
247-4

-continued

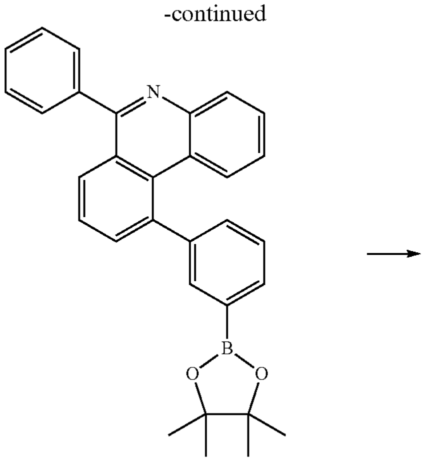

247-5

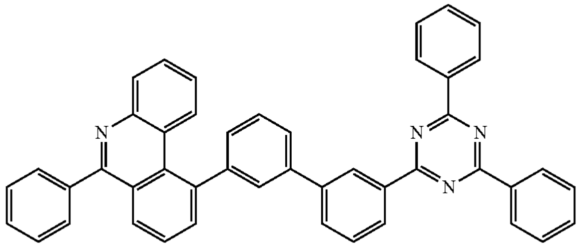

307

Target Compound 307 was obtained in the same manner as in the preparation of Compound 247 of Preparation Example 50 except that 2-(3-bromophenyl)-4,6-diphenyl-1,3,5-triazine was used instead of 2-chloro-4,6-diphenyl-1,3,5-triazine.

<Preparation Example 54> Preparation of Compound 353

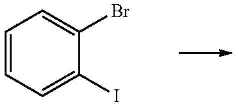

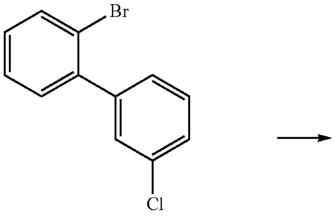

247-1

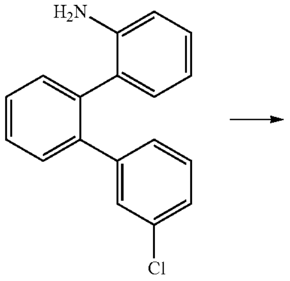

247-2

-continued

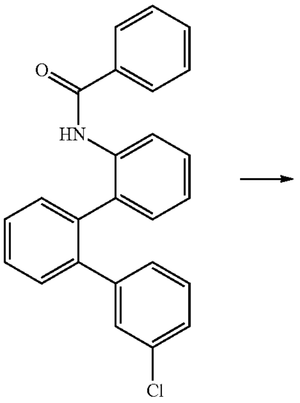

247-3

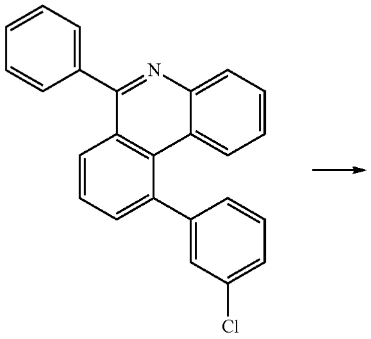

247-4

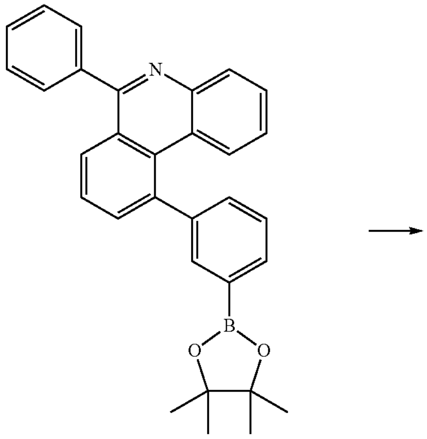

247-5

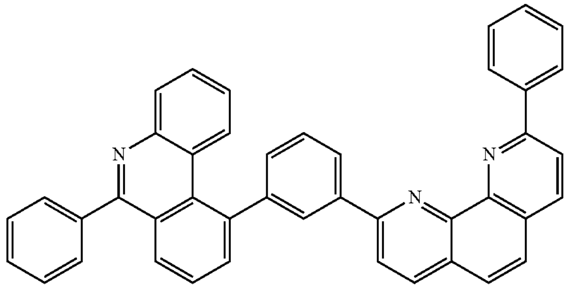

353

Target Compound 353 was obtained in the same manner as in the preparation of Compound 247 of Preparation Example 50 except that 2-bromo-9-phenyl-1,10-phenanthroline was used instead of 2-chloro-4,6-diphenyl-1,3,5-triazine.

<Preparation Example 55> Preparation of Compound 354

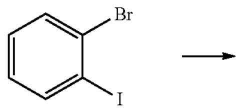

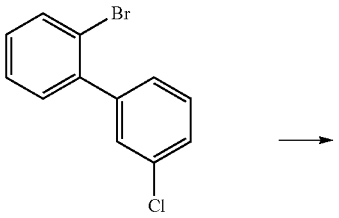

247-1

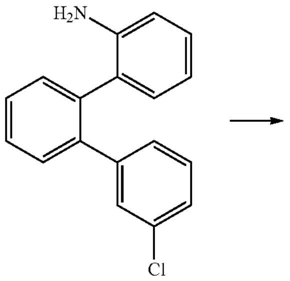

247-2

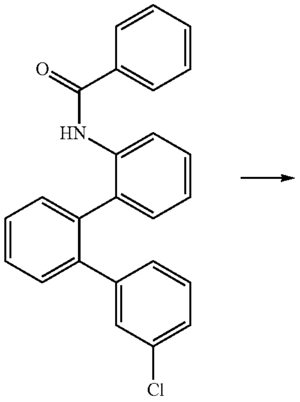

247-3

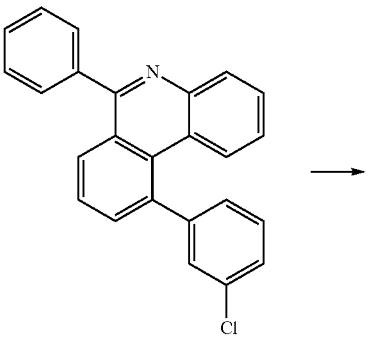

247-4

-continued

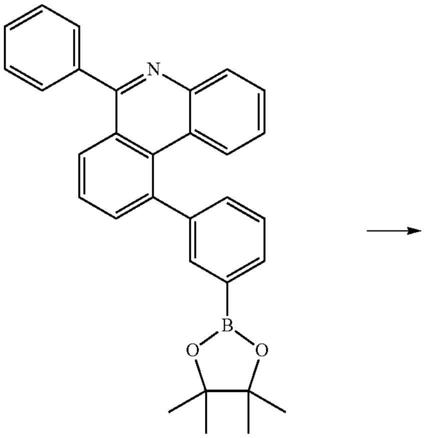

247-5

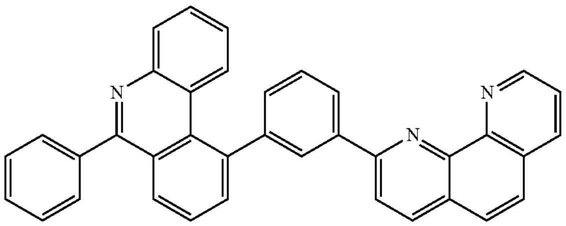

354

Target Compound 354 was obtained in the same manner as in the preparation of Compound 247 of Preparation Example 50 except that 2-bromo-1,10-phenanthroline was used instead of 2-chloro-4,6-diphenyl-1,3,5-triazine.

<Preparation Example 56> Preparation of Compound 355

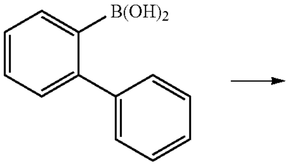

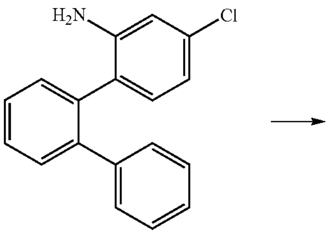

355-1

-continued

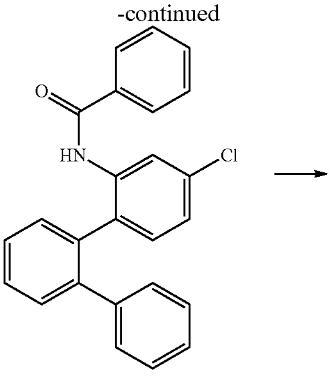

355-2

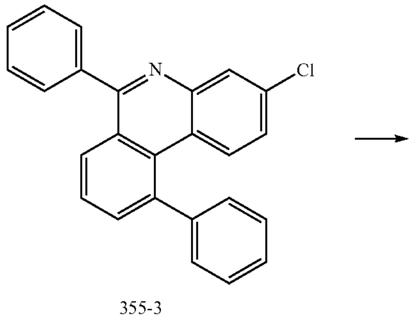

355-3

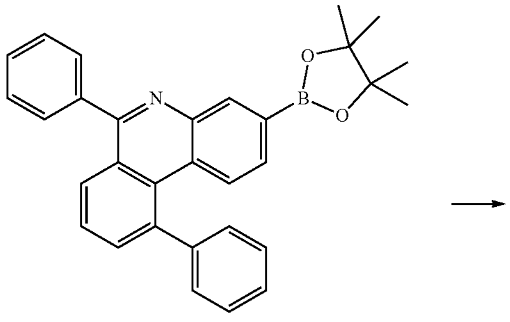

355-4

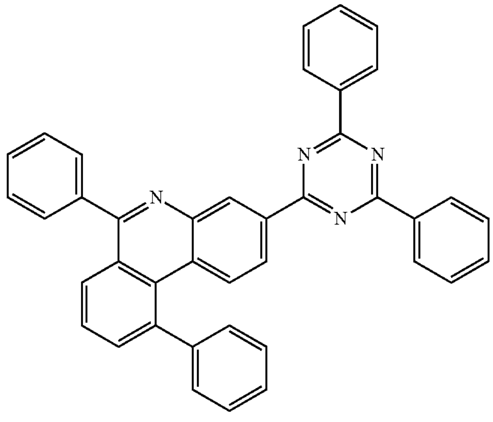

355

Preparation of Compound 355-1

After dissolving [1,1'-biphenyl]-2-ylboronic acid (50 g, 0.252 mol, 1 eq.) in toluene/ethanol/$H_2O$, 2-bromo-5-(54 g, 0.265 mol, 1.05 eq.), sodium bicarbonate (63 g, 0.757 mol, 3 eq.) and $Pd(PPh_3)_4$ (14 g, 0.05 eq.) were added thereto, and the result was stirred for 15 hours at 100° C. After the reaction was terminated, the result was cooled to room temperature, and extracted with distilled water and EA. The organic layer was dried with $MgSO_4$, and then filtered and concentrated. With ethyl acetate and hexane as a developing solvent, the concentrated residue was purified using column chromatography to obtain target Compound 355-1 (55 g, 77%).

Preparation of Compound 355-2

After dissolving Compound 355-1 (55 g, 0.196 mol, 1 eq.) by adding THF, TEA (27 ml, 1 eq.) and benzoyl chloride (25 ml, 1.1 eq.) were added thereto at 0° C., and the result was stirred for 1 hour at room temperature. After the reaction was terminated, the result was extracted with distilled water and EA. The organic layer was dried with $MgSO_4$, and then filtered and concentrated. With ethyl acetate and hexane as a developing solvent, the concentrated residue was purified using column chromatography to obtain target Compound 355-2 (43 g, 66%).

Preparation of Compound 355-3

After dissolving Compound 355-2 (43 g, 0.112 mol, 1 eq.) in nitrobenzene, $POCl_3$ (125 mL, 1.5 eq.) was added thereto, and the result was stirred for 5 hours at 150° C. After the reaction was terminated, the result was neutralized at room temperature, and then extracted with distilled water and dichloromethane. The organic layer was dried with $MgSO_4$, and then filtered and concentrated. The concentrated residue was stirred with ethyl acetate and then filtered to obtain target Compound 355-3 (33 g, 82%).

Preparation of Compound 355-4

After dissolving Compound 355-3 (33 g, 0.091 mol, 1 eq.) in 1,4-dioxane, bis(pinacolato)diboron (25 g, 0.101 mol, 1.1 eq.), $Pd(dppf)Cl_2$ (3.3 g, 4.55 mmol, 0.05 eq.) and potassium acetate (26 g, 0.273 mol, 3 eq.) were added thereto, and the result was stirred for 4 hours at 100° C. After the reaction was terminated, the result was neutralized at room temperature, and then extracted with distilled water and dichloromethane. The organic layer was dried with $MgSO_4$, and then filtered and concentrated. The concentrated residue was stirred with ethyl acetate and then filtered to obtain target Compound 355-4 (37 g, 90%).

Preparation of Compound 355

After adding Compound 355-4 (8.0 g, 21.8 mmol, 1 eq.) in 1,4-dioxane/$H_2O$, 2-chloro-4,6-diphenyl-1,3,5-triazine (6.1 g, 22.9 mmol, 1.05 eq.), $Pd(PPh_3)_4$ (1.2 g, 1.09 mmol, 0.05 eq.) and $K_2CO_3$ (9.0 g, 65.4 mmol, 3 eq.) were added thereto, and the result was stirred for 15 hours at 100° C. After the reaction was terminated, the result was cooled to room temperature, and produced solids were recrystallized to obtain target Compound 355 (9.8 g, 80%).

<Preparation Example 57> Preparation of Compound 385

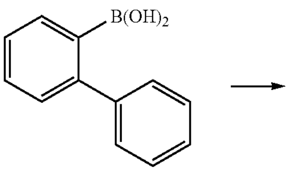

-continued
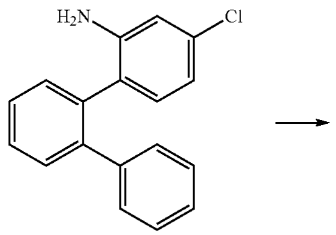
355-1
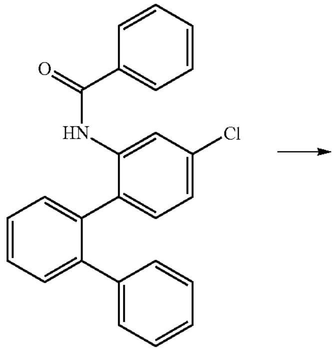
355-2
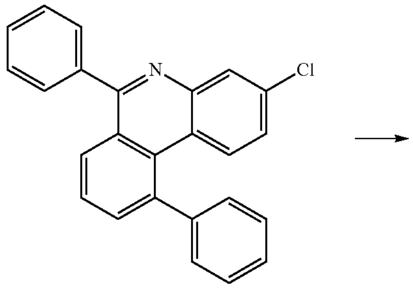
355-3
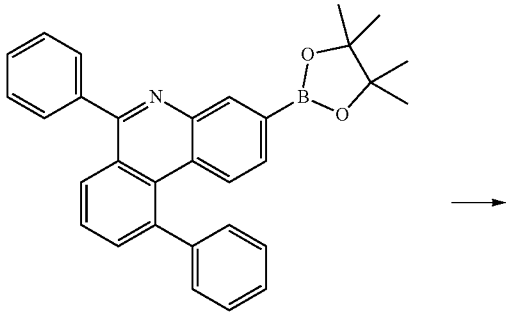
355-4
-continued
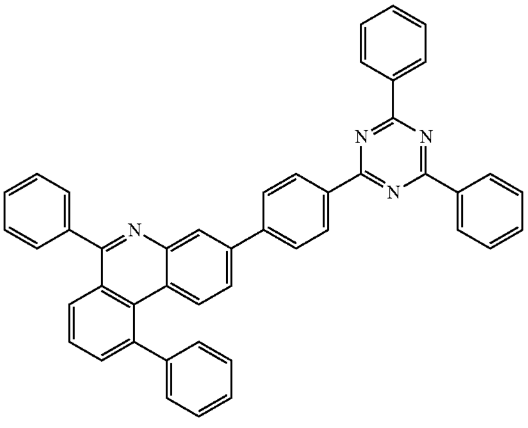
385
Preparation of Compound 385
Target Compound 385 was obtained in the same manner as in the preparation of Compound 355 of Preparation Example 56 except that 2-(4-bromophenyl)-4,6-diphenyl-1,3,5-triazine was used instead of 2-chloro-4,6-diphenyl-1,3,5-triazine.
<Preparation Example 58> Preparation of Compound 397
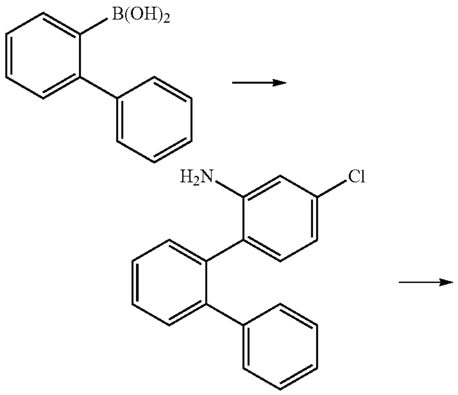
355-1
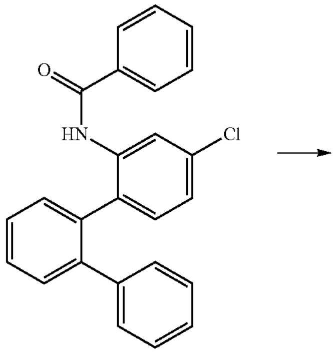
355-2

-continued
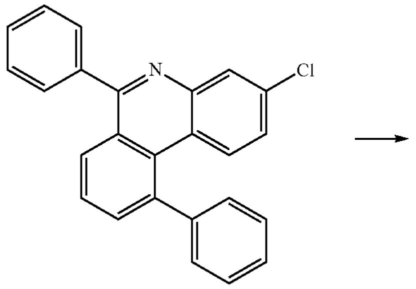
355-3
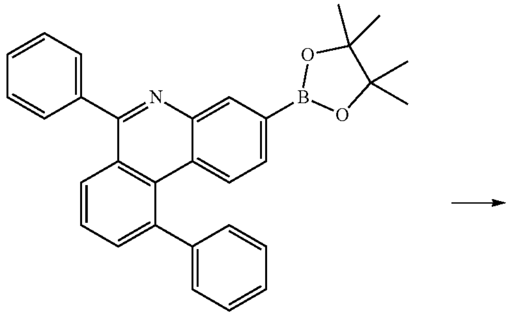
355-4
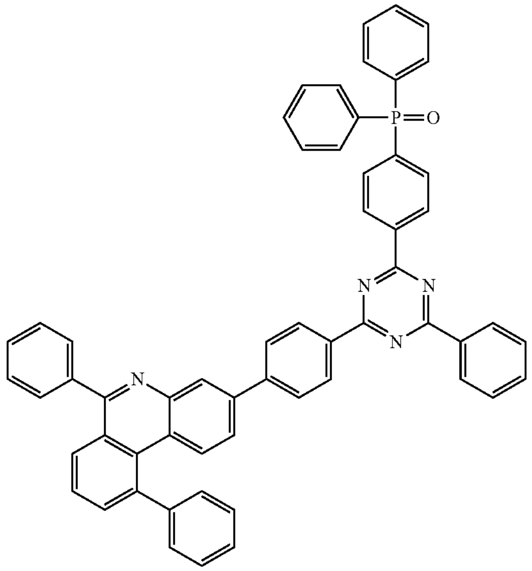
397
Preparation of Compound 397
Target Compound 397 was obtained in the same manner as in the preparation of Compound 355 of Preparation Example 56 except that (4-(4-(4-bromophenyl)-6-phenyl-1,3,5-triazin-2-yl)phenyl)diphenylphosphine oxide was used instead of 2-chloro-4,6-diphenyl-1,3,5-triazine.
<Preparation Example 59> Preparation of Compound 400
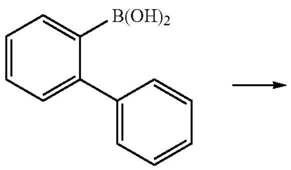
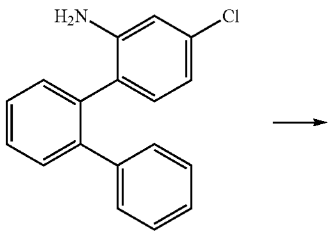
355-1
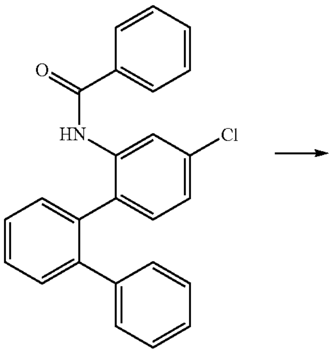
355-2
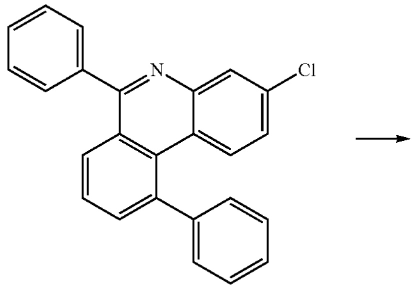
355-3
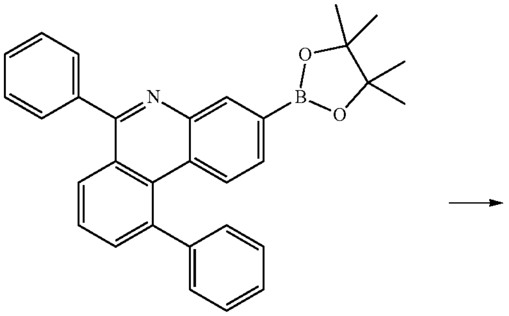
355-4

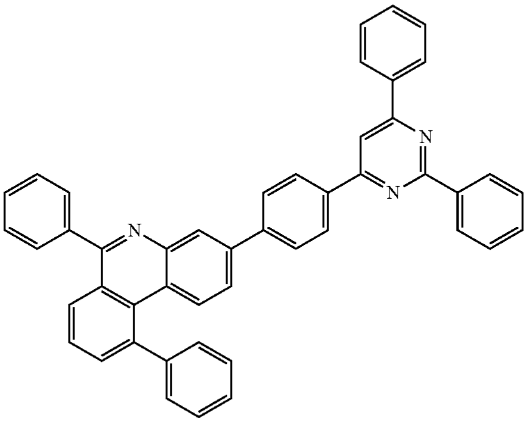

400

Preparation of Compound 400

Target Compound 400 was obtained in the same manner as in the preparation of Compound 355 of Preparation Example 56 except that 4-(4-bromophenyl)-2,6-diphenylpyrimidine was used instead of 2-chloro-4,6-diphenyl-1,3,5-triazine.

<Preparation Example 60> Preparation of Compound 412

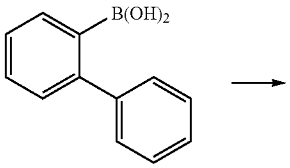

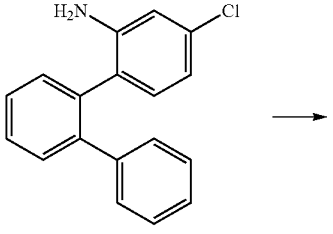

355-1

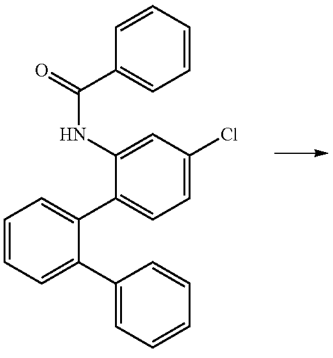

355-2

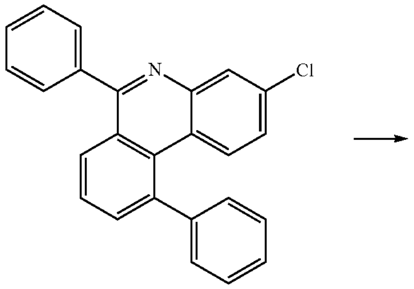

355-3

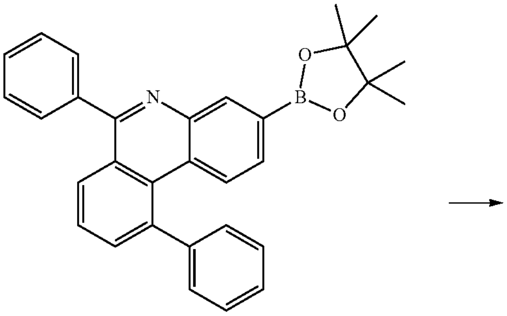

355-4

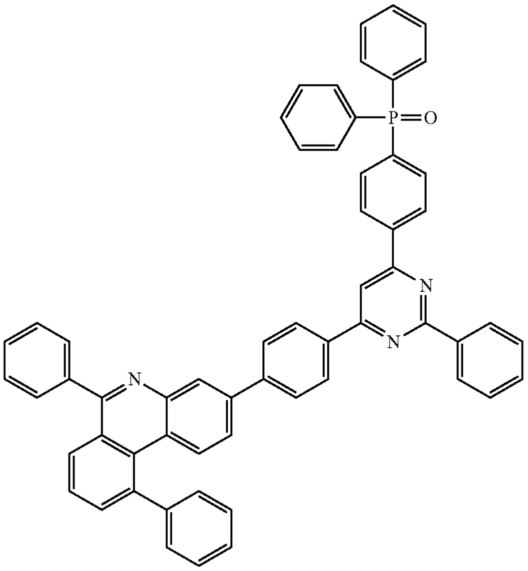

412

Preparation of Compound 412

Target Compound 412 was obtained in the same manner as in the preparation of Compound 355 of Preparation Example 56 except that (4-(6-(4-bromophenyl)-2-phenylpyrimidin-4-yl)phenyl)diphenylphosphine oxide was used instead of 2-chloro-4,6-diphenyl-1,3,5-triazine.

<Preparation Example 61> Preparation of Compound 415
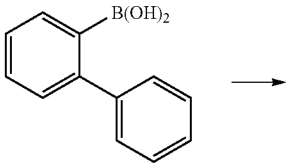
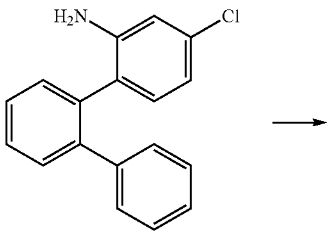
355-1
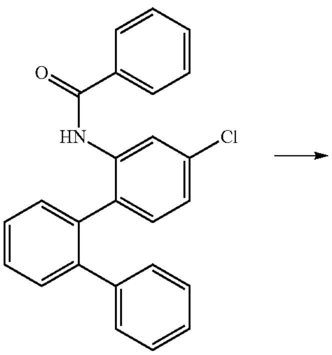
355-2
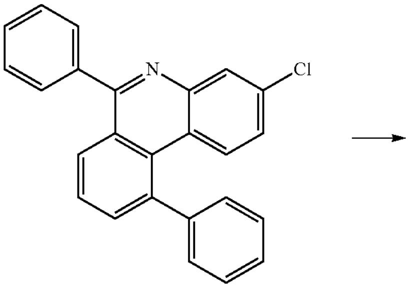
355-3
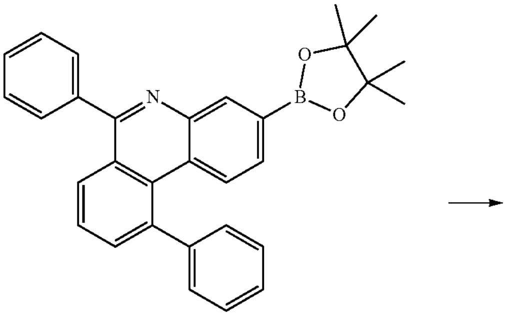
355-4
-continued
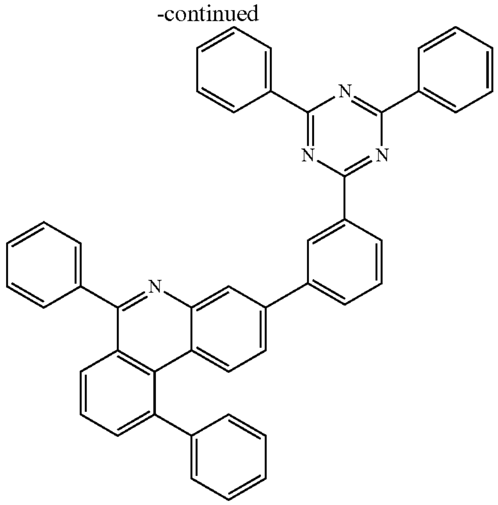
415
Preparation of Compound 415
Target Compound 415 was obtained in the same manner as in the preparation of Compound 355 of Preparation Example 56 except that 2-(3-bromophenyl)-4,6-diphenyl-1,3,5-triazine was used instead of 2-chloro-4,6-diphenyl-1,3,5-triazine.
<Preparation Example 62> Preparation of Compound 455
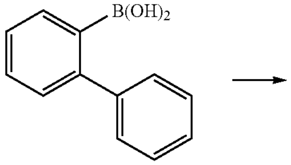
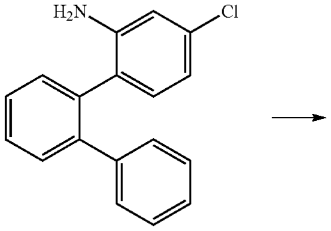
355-1
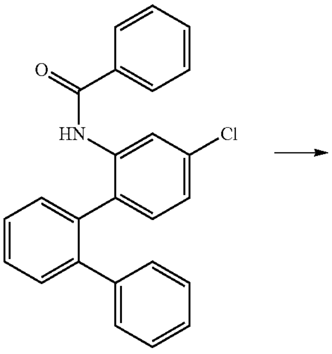
355-2

-continued
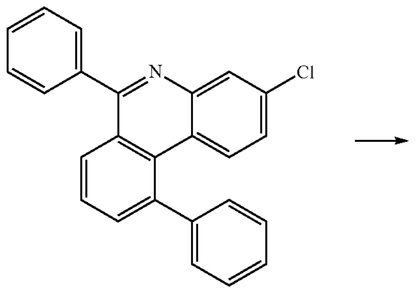
355-3
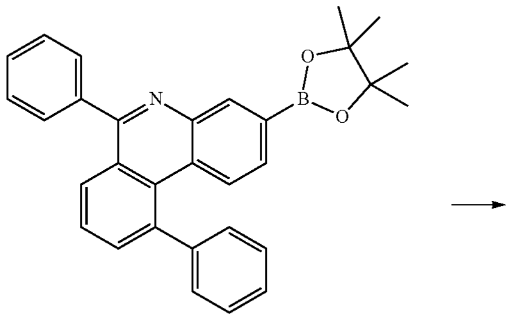
355-4
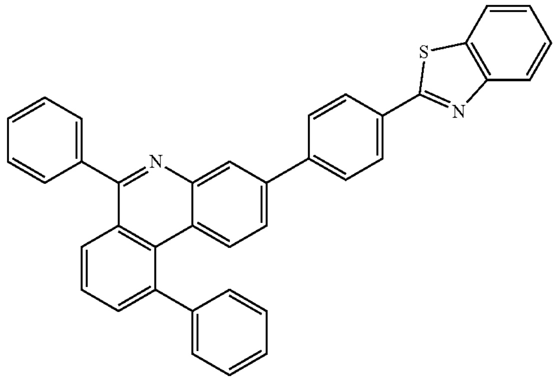
455
Preparation of Compound 455
Target Compound 455 was obtained in the same manner as in the preparation of Compound 355 of Preparation Example 56 except that 2-(4-bromophenyl)benzo[d]thiazole was used instead of 2-chloro-4,6-diphenyl-1,3,5-triazine.
<Preparation Example 63> Preparation of Compound 463
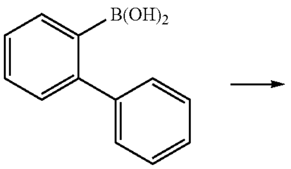
-continued
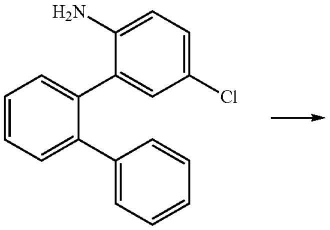
463-1
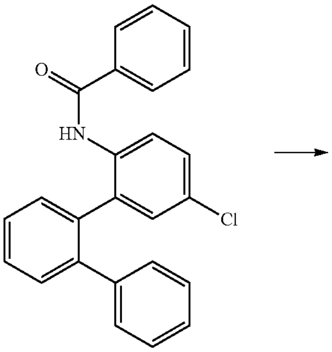
463-2
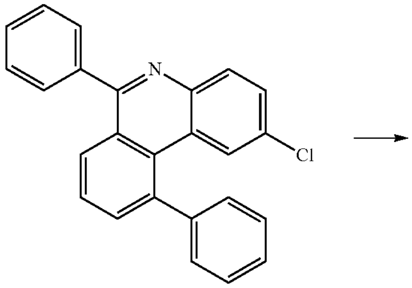
463-3
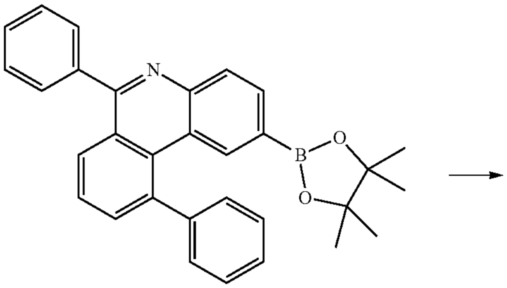
463-4
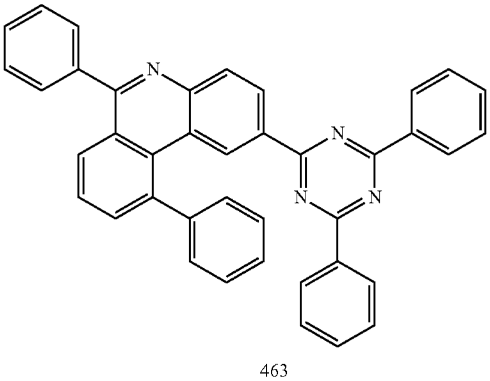
463

Preparation of Compound 463-1

After dissolving [1,1'-biphenyl]-2-ylboronic acid (50 g, 0.252 mol, 1 eq.) in toluene/ethanol/$H_2O$, 2-bromo-4-chloroaniline (54 g, 0.265 mol, 1.05 eq.), sodium bicarbonate (63 g, 0.757 mol, 3 eq.) and $Pd(PPh_3)_4$ (14 g, 0.05 eq.) were added thereto, and the result was stirred for 15 hours at 100° C. After the reaction was terminated, the result was cooled to room temperature, and extracted with distilled water and EA. The organic layer was dried with $MgSO_4$, and then filtered and concentrated. With ethyl acetate and hexane as a developing solvent, the concentrated residue was purified using column chromatography to obtain target Compound 463-1, 57 g, 82%).

Preparation of Compound 463-2

After dissolving Compound 463-1 (57 g, 0.206 mol, 1 eq.) by adding THF, TEA (62 g, 3 eq.) and benzoyl chloride (29 g, 1.1 eq.) were added thereto at 0° C., and the result was stirred for 1 hour at room temperature. After the reaction was terminated, the result was extracted with distilled water and EA. The organic layer was dried with $MgSO_4$, and then filtered and concentrated. With ethyl acetate and hexane as a developing solvent, the concentrated residue was purified using column chromatography to obtain target Compound 463-2 (57 g, 72%).

Preparation of Compound 463-3

After dissolving Compound 463-2 (57 g, 0.148 mol, 1 eq.) in nitrobenzene, $POCl_3$ (34 g, 1.5 eq.) was added thereto, and the result was stirred for 5 hours at 150° C. After the reaction was terminated, the result was neutralized at room temperature, and then extracted with distilled water and dichloromethane. The organic layer was dried with $MgSO_4$, and then filtered and concentrated. The concentrated residue was stirred with ethyl acetate and then filtered to obtain target Compound 463-3 (43 g, 80%).

Preparation of Compound 463-4

After dissolving Compound 463-3 (43 g, 0.117 mol, 1 eq.) in 1,4-dioxane, bis(pinacolato)diboron (32 g, 0.129 mol, 1.1 eq.), $Pd(dppf)Cl_2$ (4.2 g, 5.85 mmol, 0.05 eq.) and potassium acetate (34 g, 0.351 mol, 3 eq.) were added thereto, and the result was stirred for 4 hours at 100° C. After the reaction was terminated, the result was neutralized at room temperature, and then extracted with distilled water and dichloromethane. The organic layer was dried with $MgSO_4$, and then filtered and concentrated. The concentrated residue was stirred with ethyl acetate and then filtered to obtain target Compound 463-4 (49 g, 92%).

Preparation of Compound 463

After dissolving Compound 463-4 (8.0 g, 17.5 mmol, 1 eq.) in 1,4-dioxane/$H_2O$, 2-chloro-4,6-diphenyl-1,3,5-triazine (4.9 g, 18.3 mmol, 1.05 eq.), $Pd(PPh_3)_4$ (1.0 g, 0.87 mmol, 0.05 eq.) and $K_2CO_3$ (7.2 g, 52.5 mmol, 3 eq.) were added thereto, and the result was stirred for 15 hours at 100° C. After the reaction was terminated, the result was cooled to room temperature, and produced solids were recrystallized to obtain target Compound 463 (8.8 g, 79%).

<Preparation Example 64> Preparation of Compound 493

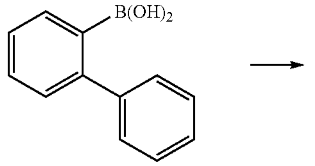

-continued

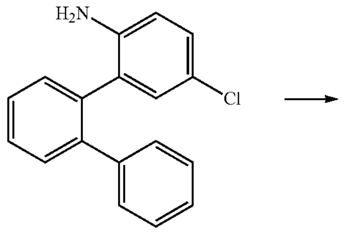

463-1

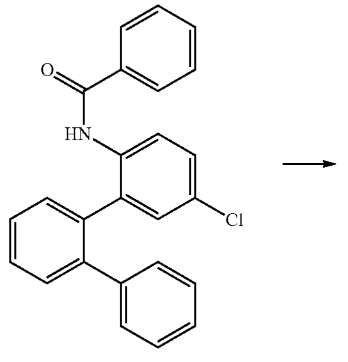

463-2

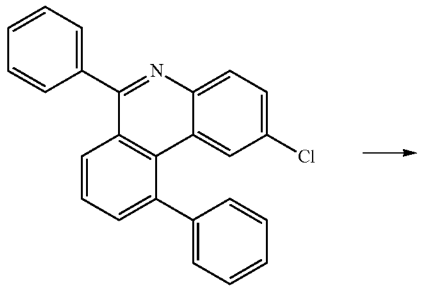

463-3

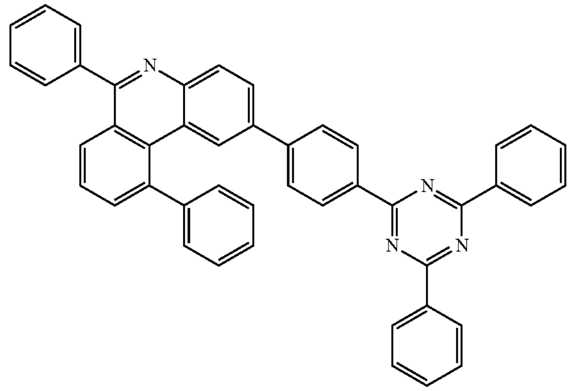

493

Preparation of Compound 493

Target Compound 493 was obtained in the same manner as in the preparation of Compound 463 of Preparation Example 63 except that 2-(4-bromophenyl)-4,6-diphenyl-1,3,5-triazine was used instead of 2-chloro-4,6-diphenyl-1,3,5-triazine.

<Preparation Example 65> Preparation of Compound 508
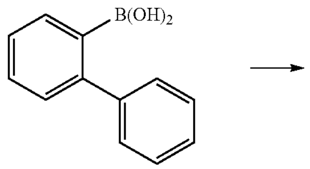
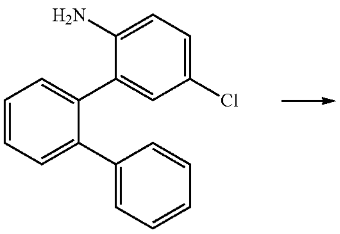
463-1
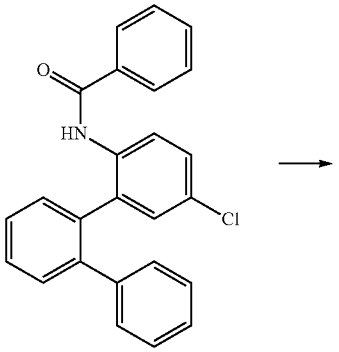
463-2
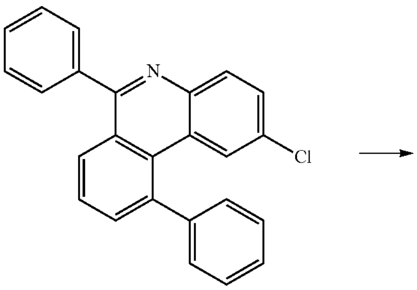
463-3
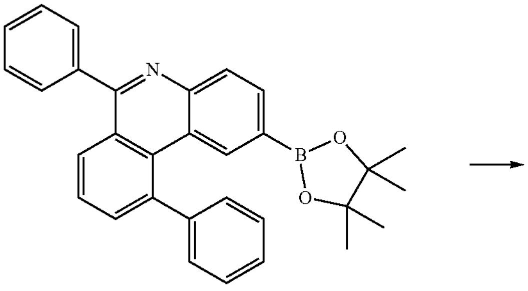
463-4
-continued
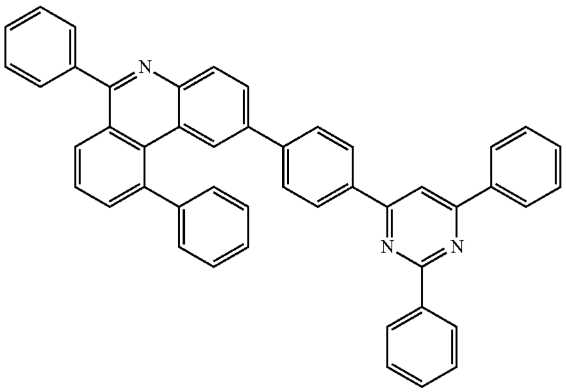
508
Preparation of Compound 508
Target Compound 508 was obtained in the same manner as in the preparation of Compound 463 of Preparation Example 63 except that 4-(4-bromophenyl)-2,6-diphenylpyrimidine was used instead of 2-chloro-4,6-diphenyl-1,3,5-triazine.
<Preparation Example 66> Preparation of Compound 523
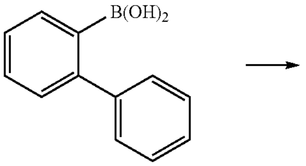
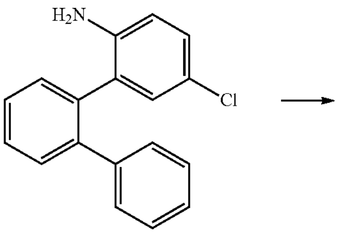
463-1
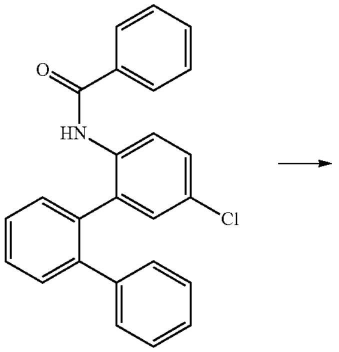
463-2

-continued
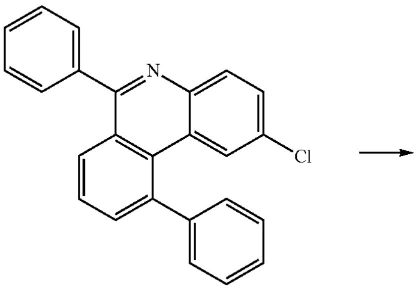
463-3
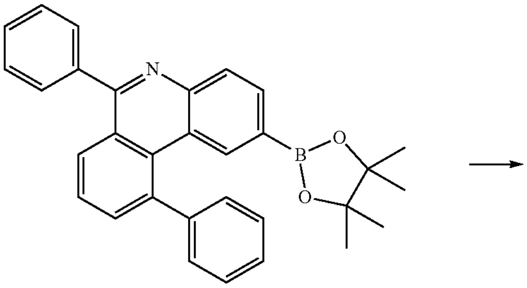
463-4
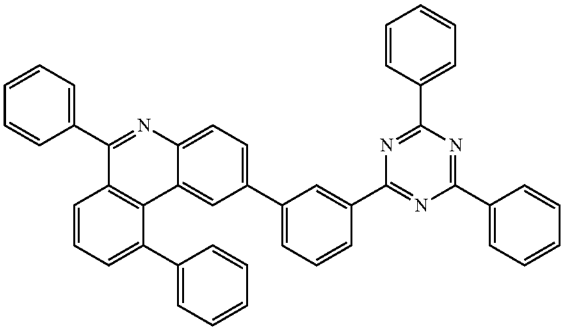
523
Preparation of Compound 523
Target Compound 523 was obtained in the same manner as in the preparation of Compound 463 of Preparation Example 63 except that 2-(3-bromophenyl)-4,6-diphenyl-1,3,5-triazine was used instead of 2-chloro-4,6-diphenyl-1,3,5-triazine.
<Preparation Example 67> Preparation of Compound 538
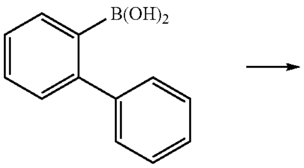
-continued
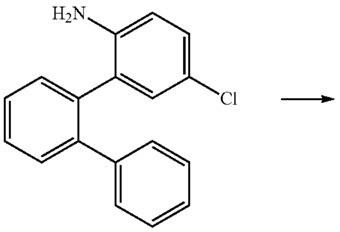
463-1
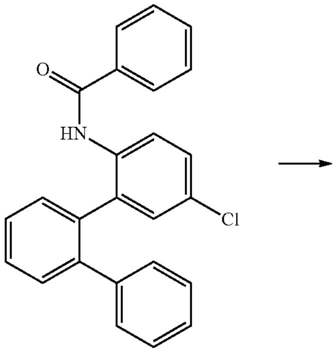
463-2
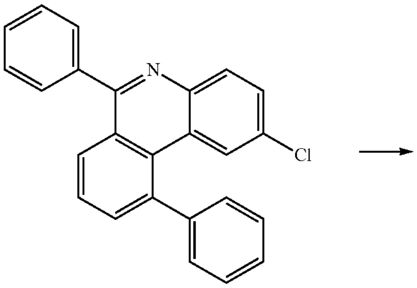
463-3
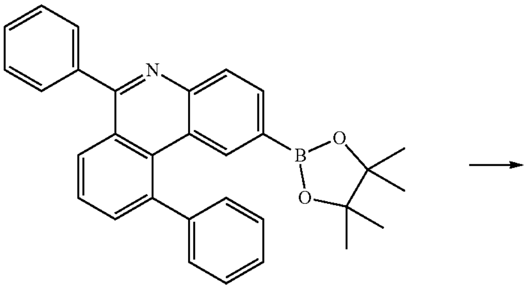
463-4
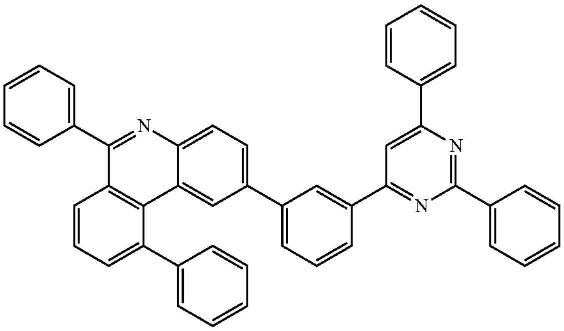
538

Preparation of Compound 538

Target Compound 538 was obtained in the same manner as in the preparation of Compound 463 of Preparation Example 63 M except that 4-(3-bromophenyl)-2,6-diphenylpyrimidine was used instead of 2-chloro-4,6-diphenyl-1,3,5-triazine.

<Preparation Example 68> Preparation of Compound 569

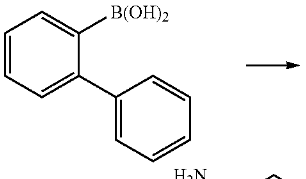

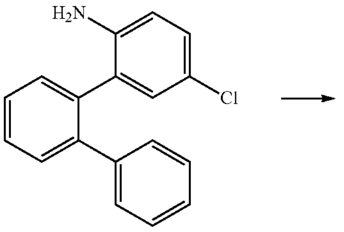

463-1

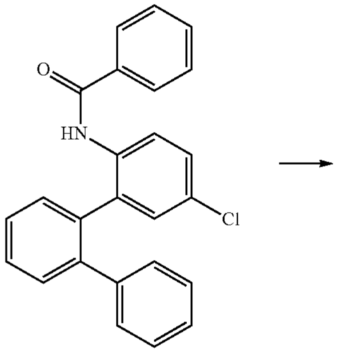

463-2

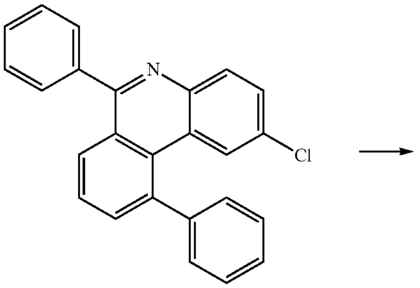

463-3

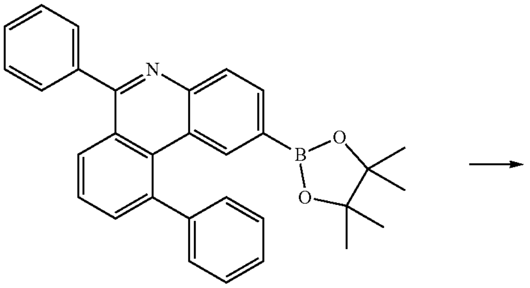

463-4

-continued

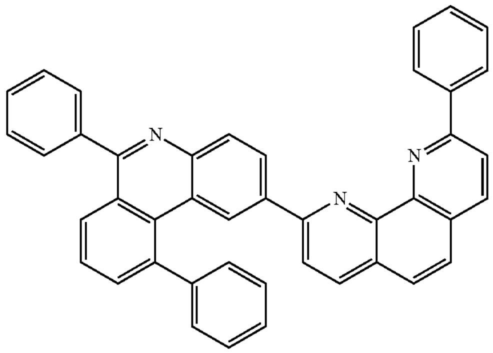

569

Preparation of Compound 569

Target Compound 569 was obtained in the same manner as in the preparation of Compound 463 of Preparation Example 63 except that 2-bromo-9-phenyl-1,10-phenanthroline was used instead of 2-chloro-4,6-diphenyl-1,3,5-triazine.

<Preparation Example 69> Preparation of Compound 601

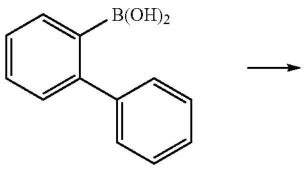

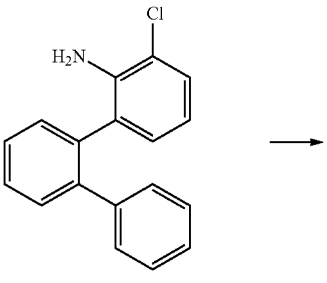

601-1

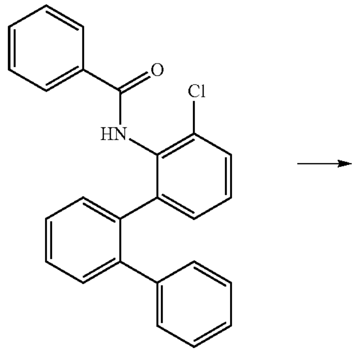

601-2

-continued

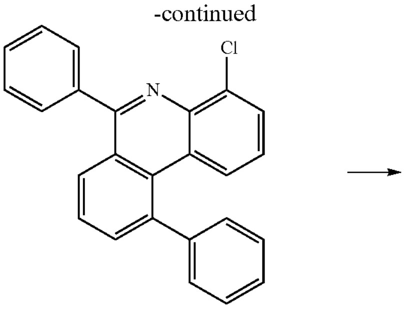

601-3

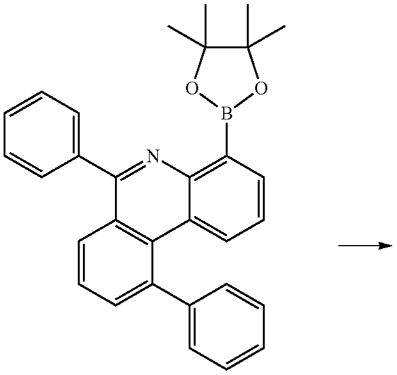

601-4

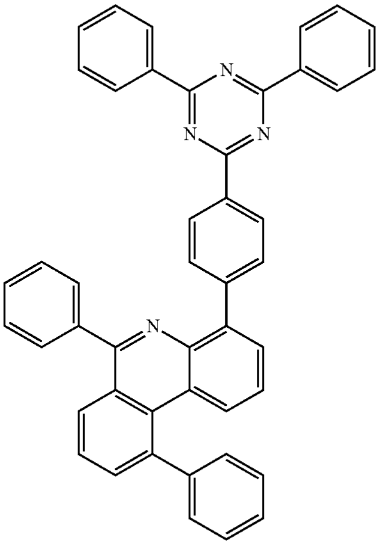

601

Preparation of Compound 601-1

After dissolving [1,1'-biphenyl]-2-ylboronic acid (50 g, 0.252 mol, 1 eq.) in toluene/ethanol/$H_2O$, 2-bromo-6-chloroaniline (54 g, 0.265 mol, 1.05 eq.), sodium bicarbonate (63 g, 0.757 mol, 3 eq.) and $Pd(PPh_3)_4$ (14 g, 0.05 eq.) were added thereto, and the result was stirred for 15 hours at 100° C.

After the reaction was terminated, the result was cooled to room temperature, and extracted with distilled water and EA. The organic layer was dried with $MgSO_4$, and then filtered and concentrated. With ethyl acetate and hexane as a developing solvent, the concentrated residue was purified using column chromatography to obtain target Compound 601-1 (56 g, 80%).

Preparation of Compound 601-2

After dissolving Compound 601-1 (56 g, 0.201 mol, 1 eq.) by adding THF, TEA (61 g, 3 eq.) and benzoyl chloride (28 g, 1.1 eq.) were added thereto at 0° C., and the result was stirred for 1 hour at room temperature. After the reaction was terminated, the result was extracted with distilled water and EA. The organic layer was dried with $MgSO_4$, and then filtered and concentrated. With ethyl acetate and hexane as a developing solvent, the concentrated residue was purified using column chromatography to obtain target Compound 601-2 (50 g, 65%).

Preparation of Compound 601-3

After dissolving Compound 601-2 (50 g, 0.130 mol, 1 eq.) in nitrobenzene, $POCl_3$ (30 g, 1.5 eq.) was added thereto, and the result was stirred for 5 hours at 150° C. After the reaction was terminated, the result was neutralized at room temperature, and then extracted with distilled water and dichloromethane.

The organic layer was dried with $MgSO_4$, and then filtered and concentrated. The concentrated residue was stirred with ethyl acetate and then filtered to obtain target Compound 601-3 (23 g, 48%).

Preparation of Compound 601-4

After dissolving Compound 601-3 (23 g, 0.062 mol, 1 eq.) in 1,4-dioxane, bis(pinacolato)diboron (17 g, 0.068 mol, 1.1 eq.), $Pd(dppf)Cl_2$ (2.3 g, 3.1 mmol, 0.05 eq.) and potassium acetate (19 g, 0.186 mol, 3 eq.) were added thereto, and the result was stirred for 4 hours at 100° C. After the reaction was terminated, the result was neutralized at room temperature, and then extracted with distilled water and dichloromethane. The organic layer was dried with $MgSO_4$, and then filtered and concentrated. The concentrated residue was stirred with ethyl acetate and then filtered to obtain target Compound 601-4 (25 g, 89%).

Preparation of Compound 601

After dissolving Compound 601-4 (8.0 g, 17.5 mmol, 1 eq.) in 1,4-dioxane/$H_2O$, 2-(4-bromophenyl)-4,6-diphenyl-1,3,5-triazine (7.1 g, 18.3 mmol, 1.05 eq.), $Pd(PPh_3)_4$ (1.0 g, 0.87 mmol, 0.05 eq.) and $K_2CO_3$ (7.2 g, 52.5 mmol, 3 eq.) were added thereto, and the result was stirred for 15 hours at 100° C. After the reaction was terminated, the result was cooled to room temperature, and produced solids were recrystallized to obtain target Compound 601 (8.4 g, 75%).

<Preparation Example 70> Preparation of Compound 616

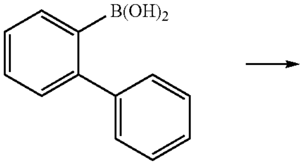

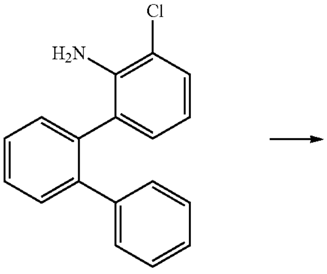

601-1

-continued
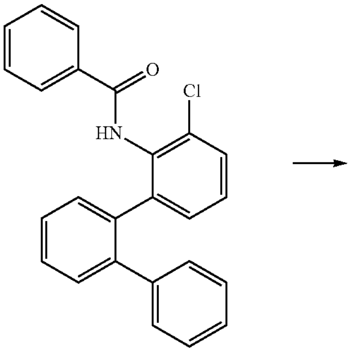
601-2
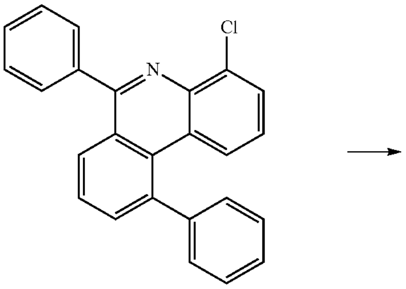
601-3
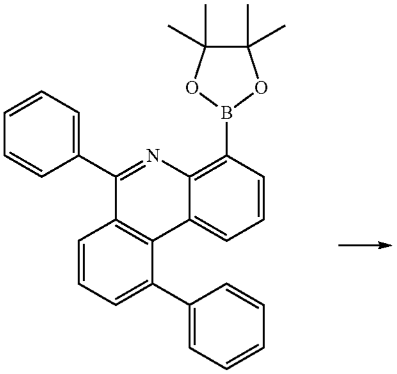
601-4
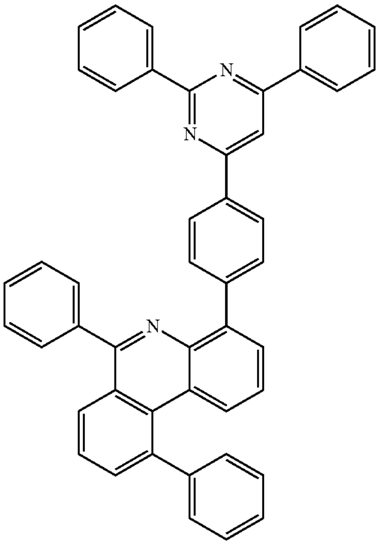
616
Preparation of Compound 616
Target Compound 616 was obtained in the same manner as in the preparation of Compound 601 of Preparation Example 69 except that 4-(4-bromophenyl)-2,6-diphenylpyrimidine was used instead of 2-chloro-4,6-diphenyl-1,3,5-triazine.
<Preparation Example 71> Preparation of Compound 631
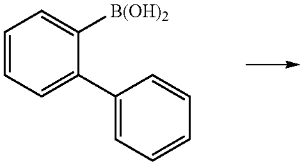
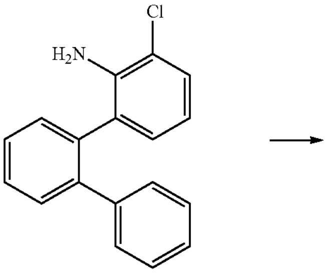
601-1
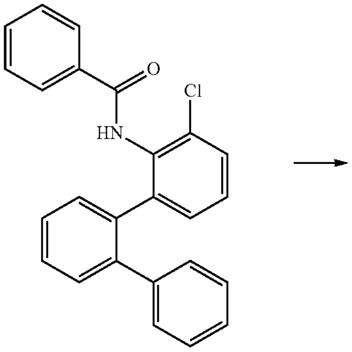
601-2
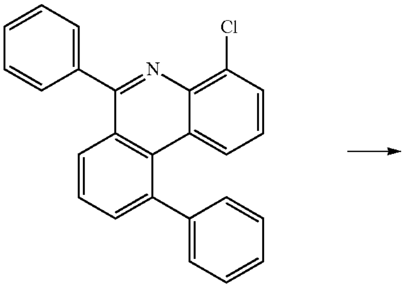
601-3

-continued
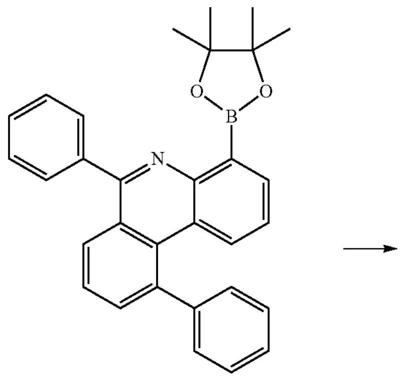
601-4
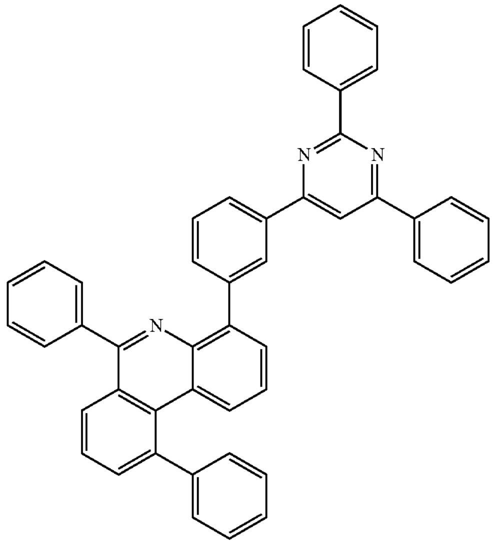
631
Preparation of Compound 631
Target Compound 631 was obtained in the same manner as in the preparation of Compound 463 of Preparation Example 63 except that 2-(3-bromophenyl)-4,6-diphenyl-1,3,5-triazine was used instead of 2-chloro-4,6-diphenyl-1,3,5-triazine.
<Preparation Example 72> Preparation of Compound 646
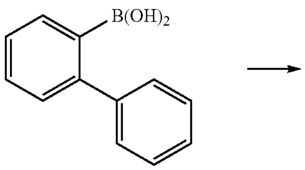
-continued
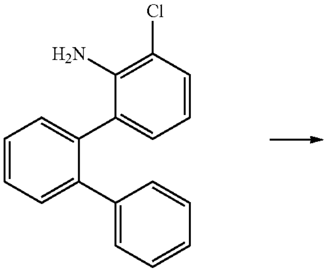
601-1
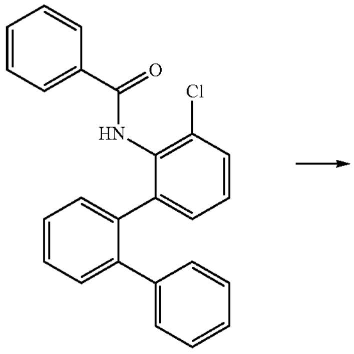
601-2
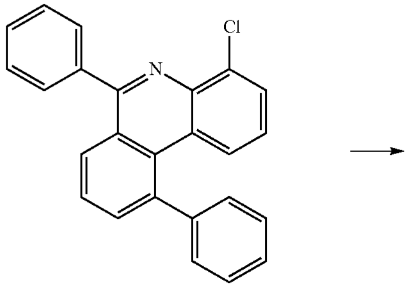
601-3
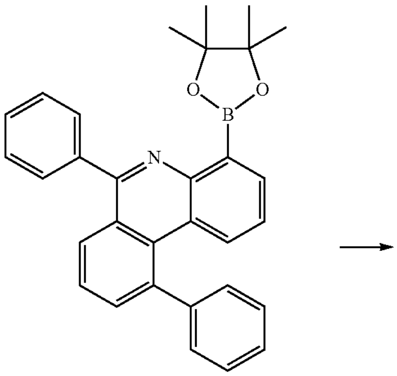
601-4

-continued
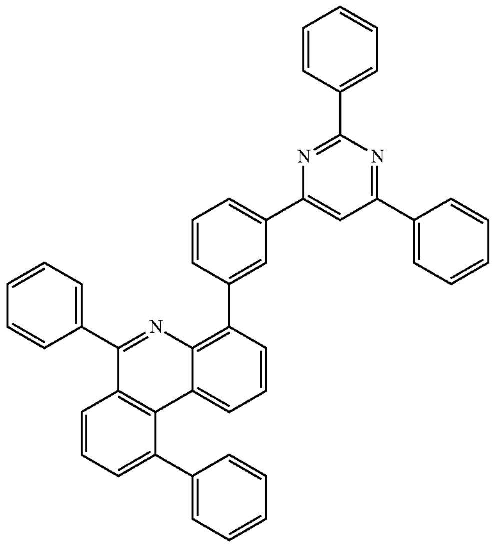
646
Preparation of Compound 646
Target Compound 646 was obtained in the same manner as in the preparation of Compound 463 of Preparation Example 63 except that 4-(3-bromophenyl)-2,6-diphenylpyrimidine was used instead of 2-chloro-4,6-diphenyl-1,3,5-triazine.
<Preparation Example 73> Preparation of Compound 661
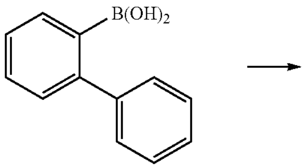
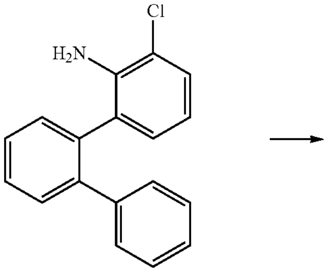
601-1
-continued
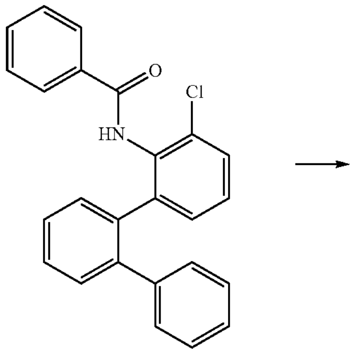
601-2
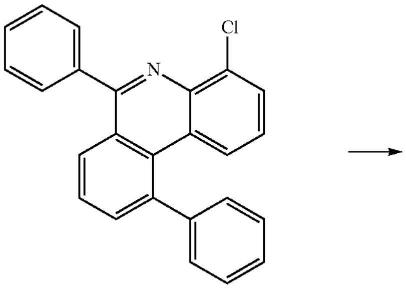
601-3
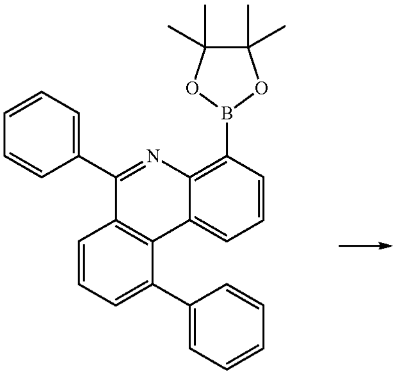
601-4
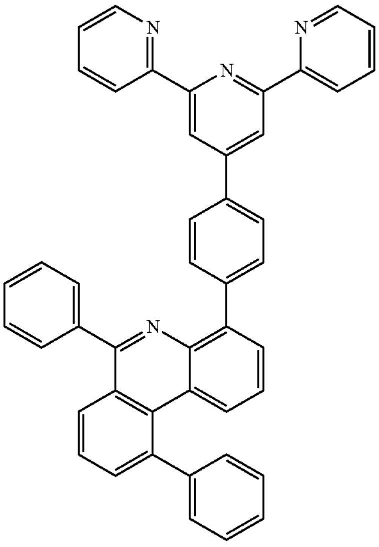
661

Preparation of Compound 661

Target Compound 661 was obtained in the same manner as in the preparation of Compound 463 of Preparation Example 63 except that 4'-(4-bromophenyl)-2,2':6',2"-terpyridine was used instead of 2-chloro-4,6-diphenyl-1,3,5-triazine.

<Preparation Example 74> Preparation of Compound 677

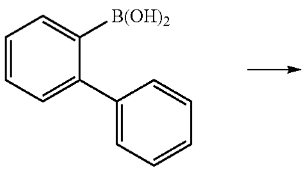

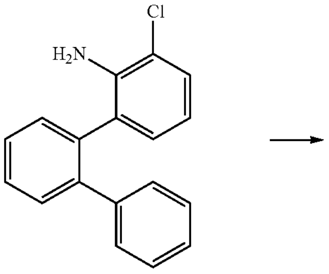

601-1

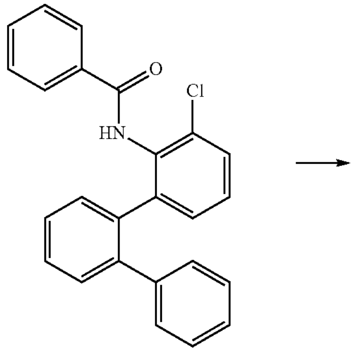

601-2

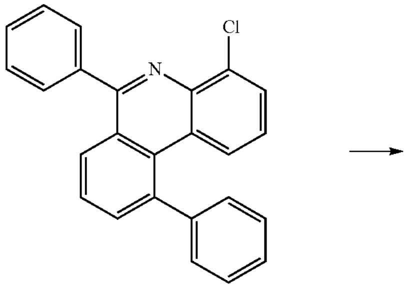

601-3

-continued

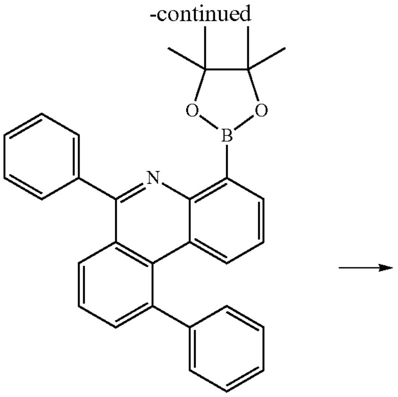

601-4

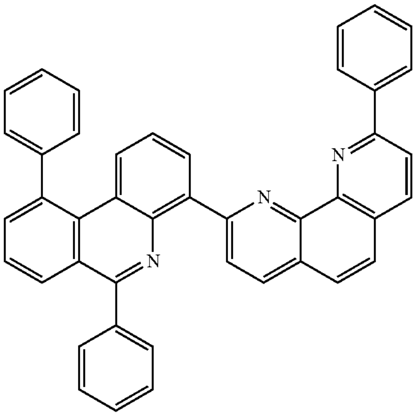

677

Preparation of Compound 677

Target Compound 677 was obtained in the same manner as in the preparation of Compound 463 of Preparation Example 63 except that 2-bromo-9-phenyl-1,10-phenanthroline was used instead of 2-chloro-4,6-diphenyl-1,3,5-triazine.

<Preparation Example 75> Preparation of Compound 679

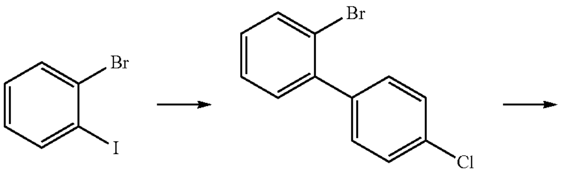

139-1

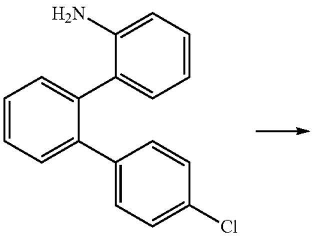

139-2

-continued

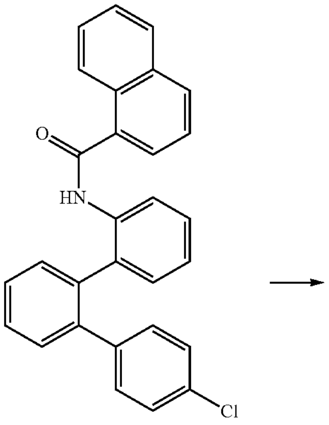

679-1

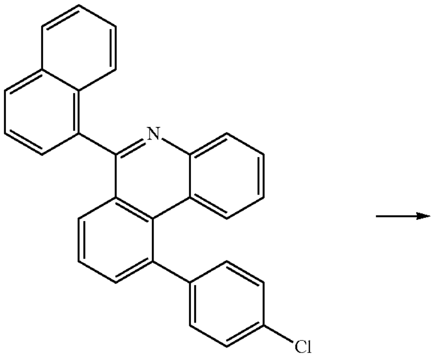

679-2

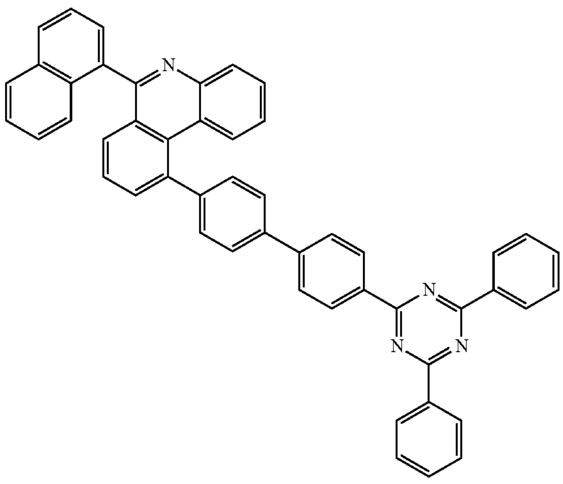

679

Preparation of Compound 679-1

After dissolving Compound 139-2 (10 g, 0.0357 mol, 1 eq.) by adding THF, TEA (15 ml, 3 eq.) and 1-naphtholyl chloride (7.5 g, 1.1 eq.) were added thereto at 0° C., and the result was stirred for 1 hour at room temperature. After the reaction was terminated, the result was extracted with distilled water and EA. The organic layer was dried with $MgSO_4$, and then filtered and concentrated. With dichloromethane and hexane as a developing solvent, the concentrated residue was purified using column chromatography to obtain target Compound 679-1 (13 g, 84%).

Preparation of Compound 679-2

After dissolving Compound 679-1 (13 g, 29.9 mmol, 1 eq.) in nitrobenzene, $POCl_3$ (4.2 mL, 1.5 eq.) was added thereto, and the result was stirred for 5 hours at 150° C. After the reaction was terminated, the result was neutralized at room temperature, and then extracted with distilled water and dichloromethane. The organic layer was dried with $MgSO_4$, and then filtered and concentrated. The concentrated residue was stirred with ethyl acetate and then filtered to obtain target Compound 679-2 (7.5 g, 61%).

Preparation of Compound 679-3

After dissolving Compound 679-2 (7.5 g, 18.2 mmol, 1 eq.) in 1,4-dioxane, bis(pinacolato)diboron (5.0 g, 20.2 mmol, 1.1 eq.), $Pd(dppf)Cl_2$ (0.6 g, 0.91 mmol, 0.05 eq.) and potassium acetate (5.3 g, 54.6 mmol, 3 eq.) were added thereto, and the result was stirred for 4 hours at 100° C. After the reaction was terminated, the result was neutralized at room temperature, and then extracted with distilled water and dichloromethane. The organic layer was dried with $MgSO_4$, and then filtered and concentrated. The concentrated residue was stirred with ethyl acetate and then filtered to obtain target Compound 679-3 (8.5 g, 92%).

Preparation of Compound 679

After dissolving Compound 679-3 (8.5 g, 16.7 mmol, 1 eq.) in 1,4-dioxane/$H_2O$, 2-(4-bromophenyl)-4,6-diphenyl-1,3,5-triazine (6.8 g, 17.5 mmol, 1.05 eq.), $Pd(PPh_3)_4$ (1.0 g, 0.84 mmol, 0.05 eq.) and $K_{2003}$ (6.9 g, 50.1 mmol, 3 eq.) were added thereto, and the result was stirred for 15 hours at 100° C. After the reaction was terminated, the result was cooled to room temperature, and produced solids were recrystallized to obtain target Compound 679 (9.6 g, 84%).

<Preparation Example 76> Preparation of Compound 699

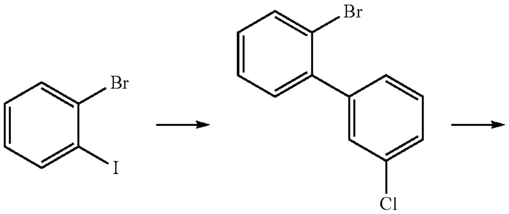

247-1

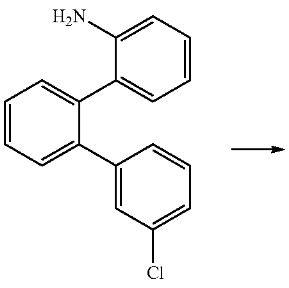

247-2

-continued

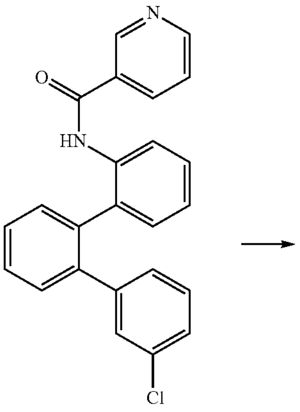

699-1

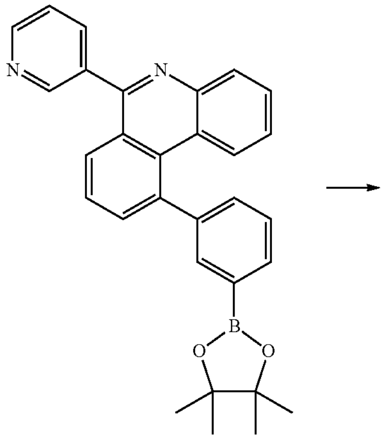

699-3

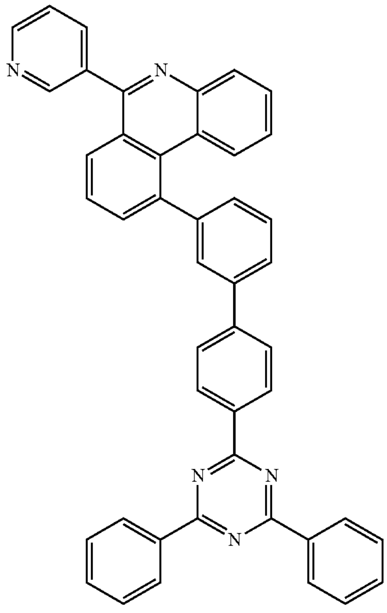

699

Preparation of Compound 699-1

After dissolving Compound 247-2 (10 g, 35.7 mmol, 1 eq.) by adding THF, TEA (15 ml, 3 eq.) and nicotinoyl chloride (5.5 g, 1.1 eq.) were added thereto at 0° C., and the result was stirred for 1 hour at room temperature. After the reaction was terminated, the result was extracted with distilled water and EA. The organic layer was dried with $MgSO_4$, and then filtered and concentrated. With dichloromethane and hexane as a developing solvent, the concentrated residue was purified using column chromatography to obtain target Compound 699-1 (8.8 g, 64%).

Preparation of Compound 699-2

After dissolving Compound 699-1 (8.8 g, 22.8 mmol, 1 eq.) in nitrobenzene, $POCl_3$ (3.2 mL, 1.5 eq.) was added thereto, and the result was stirred for 5 hours at 150° C. After the reaction was terminated, the result was neutralized at room temperature, and then extracted with distilled water and dichloromethane. The organic layer was dried with $MgSO_4$, and then filtered and concentrated. The concentrated residue was stirred with ethyl acetate and then filtered to obtain target Compound 699-2 (4.1 g, 50%).

Preparation of Compound 699-3

After dissolving Compound 699-2 (4.1 g, 11.4 mmol, 1 eq.) in 1,4-dioxane, bis(pinacolato)diboron (3.1 g, 1.1 eq.), $Pd(dppf)Cl_2$ (0.4 g, 0.05 eq.) and potassium acetate (3.3 g, 3 eq.) were added thereto, and the result was stirred for 4 hours at 100° C. After the reaction was terminated, the result was neutralized at room temperature, and then extracted with distilled water and dichloromethane. The organic layer was dried with $MgSO_4$, and then filtered and concentrated. The concentrated residue was stirred with ethyl acetate and then filtered to obtain target Compound 699-3 (4.8 g, 93%).

Preparation of Compound 699

After dissolving Compound 699-3 (4.8 g, 10.6 mmol, 1 eq.) in 1,4-dioxane/$H_2O$, 2-(4-bromophenyl)-4,6-diphenyl-1,3,5-triazine (4.3 g, 1.05 eq.), $Pd(PPh_3)_4$ (0.6 g, 0.05 eq.) and $K_2CO_3$ (4.4 g, 3 eq.) were added thereto, and the result was stirred for 15 hours at 100° C. After the reaction was terminated, the result was cooled to room temperature, and produced solids were recrystallized to obtain target Compound 699 (5.4 g, 80%).

<Preparation Example 77> Preparation of Compound 706

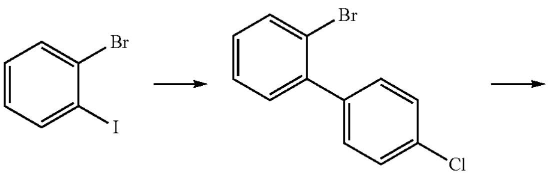

139-1

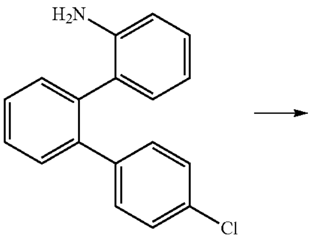

139-2

-continued

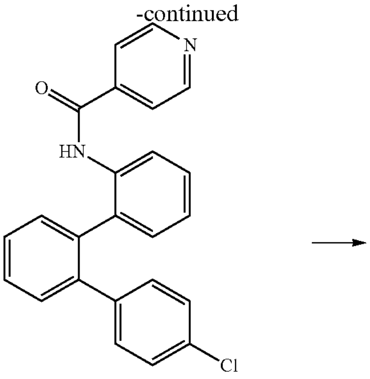

706-1

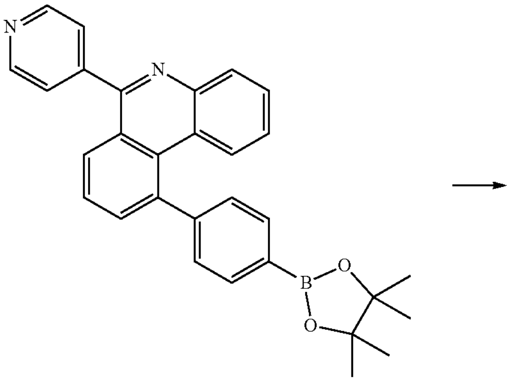

706-3

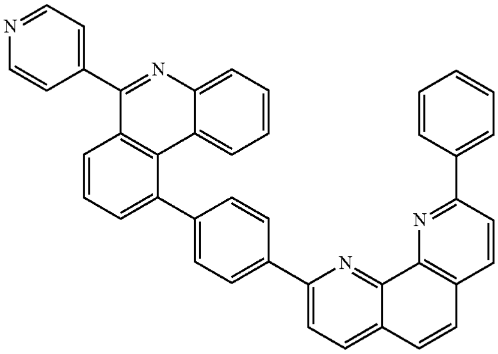

706

Preparation of Compound 706-1

After dissolving Compound 139-2 (10 g, 35.7 mmol, 1 eq.) by adding THF, TEA (15 ml, 3 eq.) and isonicotinoyl chloride (5.5 g, 1.1 eq.) were added thereto at 0° C., and the result was stirred for 1 hour at room temperature. After the reaction was terminated, the result was extracted with distilled water and EA. The organic layer was dried with $MgSO_4$, and then filtered and concentrated. With dichloromethane and hexane as a developing solvent, the concentrated residue was purified using column chromatography to obtain target Compound 706-1 (9.3 g, 68%).

Preparation of Compound 706-2

After dissolving Compound 706-1 (9.3 g, 24.2 mmol, 1 eq.) in nitrobenzene, $POCl_3$ (3.3 mL, 1.5 eq.) was added thereto, and the result was stirred for 5 hours at 150° C. After the reaction was terminated, the result was neutralized at room temperature, and then extracted with distilled water and dichloromethane. The organic layer was dried with $MgSO_4$, and then filtered and concentrated. The concentrated residue was stirred with ethyl acetate and then filtered to obtain target Compound 706-2 (4.1 g, 54%).

Preparation of Compound 706-3

After dissolving Compound 706-2 (4.1 g, 13.0 mmol, 1 eq.) in 1,4-dioxane, bis(pinacolato)diboron (3.6 g, 1.1 eq.), $Pd(dppf)Cl_2$ (0.47 g, 0.05 eq.) and potassium acetate (3.8 g, 3 eq.) were added thereto, and the result was stirred for 4 hours at 100° C. After the reaction was terminated, the result was neutralized at room temperature, and then extracted with distilled water and dichloromethane. The organic layer was dried with $MgSO_4$, and then filtered and concentrated. The concentrated residue was stirred with ethyl acetate and then filtered to obtain target Compound 706-3 (5.4 g, 91%).

Preparation of Compound 706

After dissolving Compound 706-3 (5.4 g, 11.8 mmol, 1 eq.) in 1,4-dioxane/$H_2O$, 2-bromo-9-phenyl-1,10-phenanthroline (4.1 g, 1.05 eq.), $Pd(PPh_3)_4$ (0.6 g, 0.05 eq.) and $K_2CO_3$ (4.8 g, 3 eq.) were added thereto, and the result was stirred for 15 hours at 100° C. After the reaction was terminated, the result was cooled to room temperature, and produced solids were recrystallized to obtain target Compound 706 (5.6 g, 82%).

<Preparation Example 78> Preparation of Compound 711

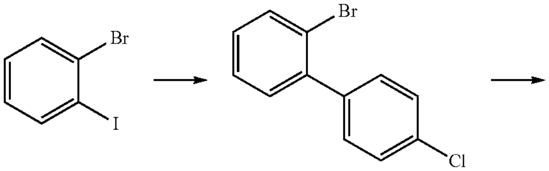

139-1

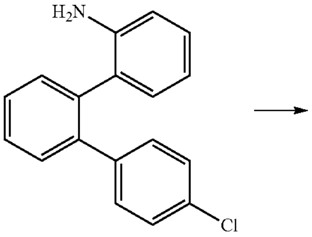

139-2

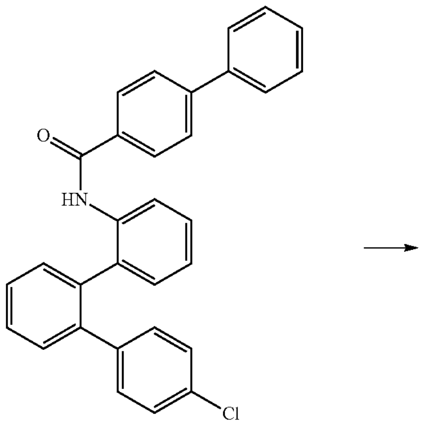

711-1

-continued

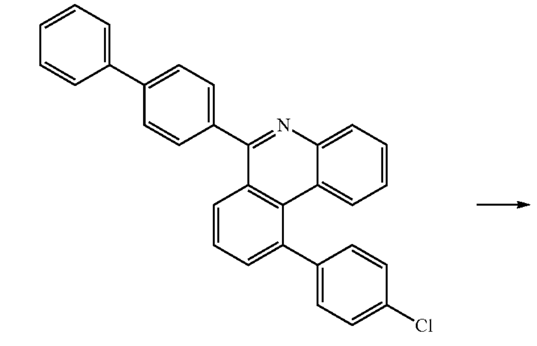

711-2

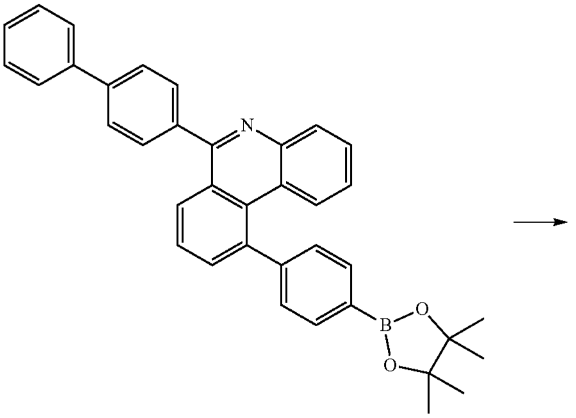

711-3

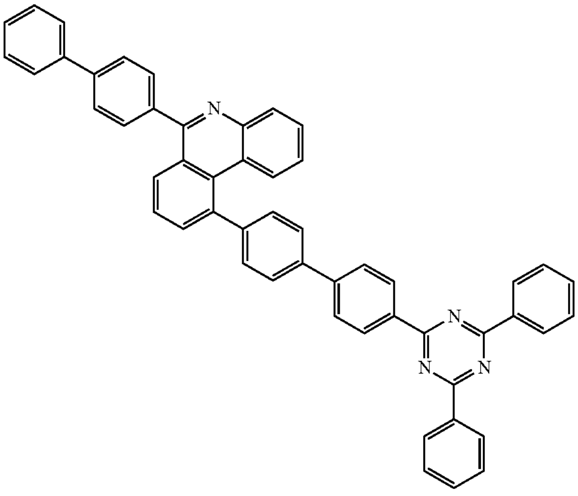

711

Preparation of Compound 711-1

After dissolving Compound 139-2 (10 g, 35.7 mmol, 1 eq.) by adding THF, TEA (15 ml, 3 eq.) and [1,1'-biphenyl]-4-carbonyl chloride (8.5 g, 1.1 eq.) were added thereto at 0° C., and the result was stirred for 1 hour at room temperature. After the reaction was terminated, the result was extracted with distilled water and EA. The organic layer was dried with $MgSO_4$, and then filtered and concentrated. With dichloromethane and hexane as a developing solvent, the concentrated residue was purified using column chromatography to obtain target Compound 711-1 (13.8 g, 84%).

Preparation of Compound 711-2

After dissolving Compound 711-1 (13.8 g, 29.9 mmol, 1 eq.) in nitrobenzene, $POCl_3$ (4.1 mL, 1.5 eq.) was added thereto, and the result was stirred for 5 hours at 150° C. After the reaction was terminated, the result was neutralized at room temperature, and then extracted with distilled water and dichloromethane. The organic layer was dried with $MgSO_4$, and then filtered and concentrated. The concentrated residue was stirred with ethyl acetate and then filtered to obtain target Compound 711-2 (7.8 g, 59%).

Preparation of Compound 711-3

After dissolving Compound 711-2 (7.8 g, 17.6 mmol, 1 eq.) in 1,4-dioxane, bis(pinacolato)diboron (5.2 g, 1.1 eq.), $Pd(dppf)Cl_2$ (0.62 g, 0.05 eq.) and potassium acetate (5.5 g, 3 eq.) were added thereto, and the result was stirred for 4 hours at 100° C. After the reaction was terminated, the result was neutralized at room temperature, and then extracted with distilled water and dichloromethane. The organic layer was dried with $MgSO_4$, and then filtered and concentrated. The concentrated residue was stirred with ethyl acetate and then filtered to obtain target Compound 711-3 (8.5 g, 91%).

Preparation of Compound 711

After dissolving Compound 711-3 (8.5 g, 16.0 mmol, 1 eq.) in 1,4-dioxane/$H_2O$, 2-(4-bromophenyl)-4,6-diphenyl-1,3,5-triazine (6.8 g, 17.5 mmol, 1.05 eq.), $Pd(PPh_3)_4$ (1.0 g, 0.84 mmol, 0.05 eq.) and $K_2CO_3$ (6.9 g, 50.1 mmol, 3 eq.) were added thereto, and the result was stirred for 15 hours at 100° C. After the reaction was terminated, the result was cooled to room temperature, and produced solids were recrystallized to obtain target Compound 711 (9.3 g, 82%).

<Preparation Example 79> Preparation of Compound 720

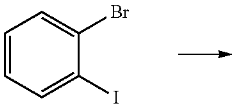

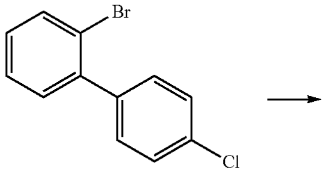

139-1

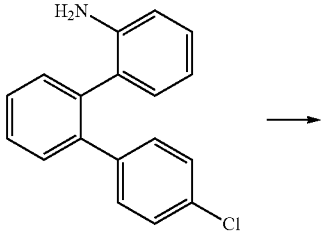

139-2

-continued

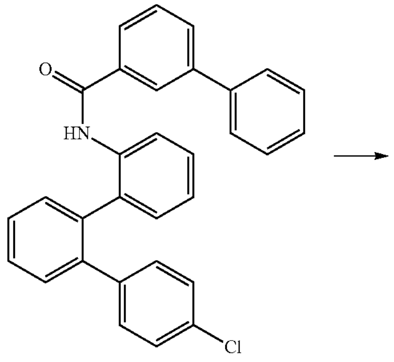

720-1

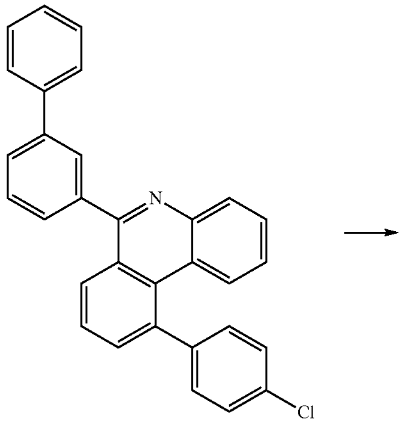

720-2

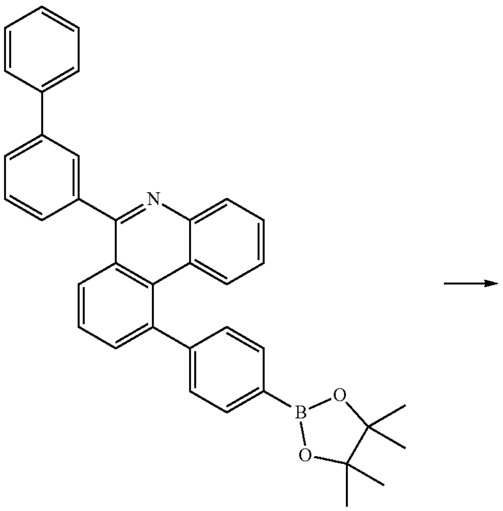

720-3

-continued

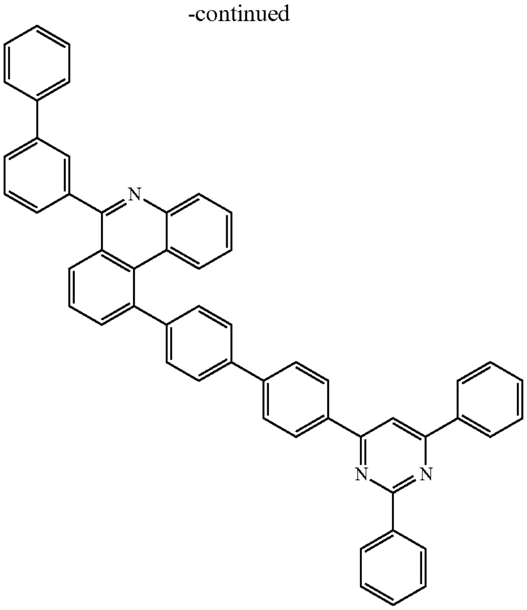

720

Preparation of Compound 720-1

After dissolving Compound 139-2 (10 g, 35.7 mmol, 1 eq.) by adding THF, TEA (15 ml, 3 eq.) and [1,1'-biphenyl]-3-carbonyl chloride (8.5 g, 1.1 eq.) were added thereto at 0° C., and the result was stirred for 1 hour at room temperature. After the reaction was terminated, the result was extracted with distilled water and EA. The organic layer was dried with $MgSO_4$, and then filtered and concentrated. With dichloromethane and hexane as a developing solvent, the concentrated residue was purified using column chromatography to obtain target Compound 720-1 (13.3 g, 81%).

Preparation of Compound 720-2

After dissolving Compound 720-1 (13.3 g, 28.9 mmol, 1 eq.) in nitrobenzene, $POCl_3$ (3.9 mL, 1.5 eq.) was added thereto, and the result was stirred for 5 hours at 150° C. After the reaction was terminated, the result was neutralized at room M temperature, and then extracted with distilled water and dichloromethane. The organic layer was dried with $MgSO_4$, and then filtered and concentrated. The concentrated residue was stirred with ethyl acetate and then filtered to obtain target Compound 720-2 (8.0 g, 63%).

Preparation of Compound 720-3

After dissolving Compound 720-2 (8.0 g, 18.2 mmol, 1 eq.) in 1,4-dioxane, bis(pinacolato)diboron (5.0 g, 1.1 eq.), $Pd(dppf)Cl_2$ (0.60 g, 0.05 eq.) and potassium acetate (5.3 g, 3 eq.) were added thereto, and the result was stirred for 4 hours at 100° C. After the reaction was terminated, the result was neutralized at room temperature, and then extracted with distilled water and dichloromethane. The organic layer was dried with $MgSO_4$, and then filtered and concentrated. The concentrated residue was stirred with ethyl acetate and then filtered to obtain target Compound 720-3 (9.7 g, 93%).

Preparation of Compound 720

After dissolving 720-3 (9.7 g, 16.0 mmol, 1 eq.) in 1,4-dioxane/$H_2O$, 4-(4-bromophenyl)-2,6-diphenylpyrimidine (7.7 g, 17.5 mmol, 1.05 eq.), $Pd(PPh_3)_4$ (1.1 g, 0.84 mmol, 0.05 eq.) and $K_2CO_3$ (7.8 g, 50.1 mmol, 3 eq.) were added thereto, and the result was stirred for 15 hours at 100° C. After the reaction was terminated, the result was cooled to room temperature, and produced solids were recrystallized to obtain target Compound 720 (9.4 g, 83%).

<Preparation Example 80> Preparation of Compound 727

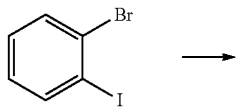

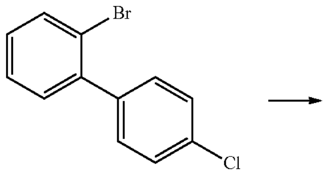

139-1

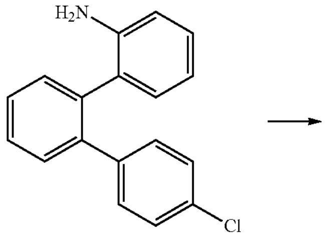

139-2

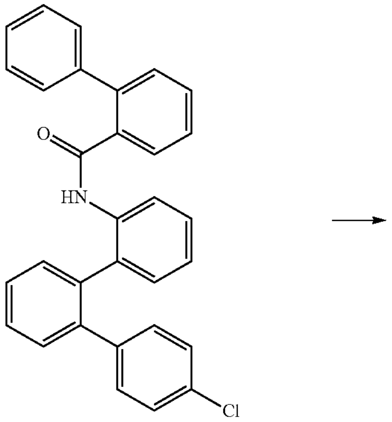

727-1

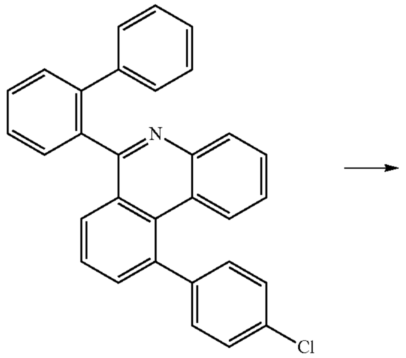

727-2

-continued

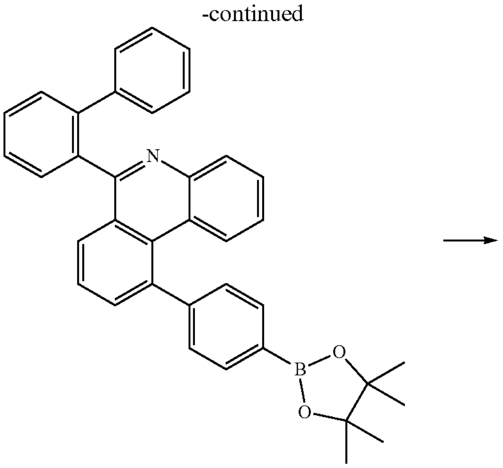

727-3

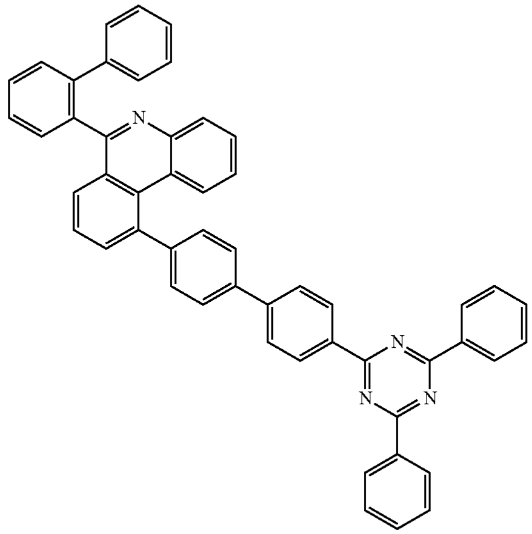

727

Preparation of Compound 727-1

After dissolving Compound 139-2 (10 g, 35.7 mmol, 1 eq.) by adding THF, TEA (15 ml, 3 eq.) and [1,1'-biphenyl]-2-carbonyl chloride (8.5 g, 1.1 eq.) were added thereto at 0° C., and the result was stirred for 1 hour at room temperature. After the reaction was terminated, the result was extracted with distilled water and EA. The organic layer was dried with $MgSO_4$, and then filtered and concentrated. With dichloromethane and hexane as a developing solvent, the concentrated residue was purified using column chromatography to obtain target Compound 727-1 (13.1 g, 80%).

Preparation of Compound 727-2

After dissolving Compound 727-1 (13.1 g, 28.5 mmol, 1 eq.) in nitrobenzene, $POCl_3$ (3.9 mL, 1.5 eq.) was added thereto, and the result was stirred for 5 hours at 150° C. After the reaction was terminated, the result was neutralized at room temperature, and then extracted with distilled water and dichloromethane. The organic layer was dried with $MgSO_4$, and then filtered and concentrated. The concentrated residue was stirred with ethyl acetate and then filtered to obtain target Compound 727-2 (6.5 g, 52%).

Preparation of Compound 727-3

After dissolving Compound 727-2 (6.5 g, 14.8 mmol, 1 eq.) in 1,4-dioxane, bis(pinacolato)diboron (4.3 g, 1.1 eq.), $Pd(dppf)Cl_2$ (0.52 g, 0.05 eq.) and potassium acetate (4.5 g, 3 eq.) were added thereto, and the result was stirred for 4 hours at 100° C. After the reaction was terminated, the result was neutralized at room temperature, and then extracted with distilled water and dichloromethane. The organic layer was dried with $MgSO_4$, and then filtered and concentrated. The concentrated residue was stirred with ethyl acetate and then filtered to obtain target Compound 727-3 (7.3 g, 93%).

Preparation of Compound 727

After dissolving Compound 727-3 (7.3 g, 13.7 mmol, 1 eq.) in 1,4-dioxane/$H_2O$, 2-(4-bromophenyl)-4,6-diphenyl-1,3,5-triazine (5.8 g, 17.5 mmol, 1.05 eq.), $Pd(PPh_3)_4$ (0.86 g, 0.84 mmol, 0.05 eq.) and $K_2CO_3$ (5.9 g, 50.1 mmol, 3 eq.) were added thereto, and the result was stirred for 15 hours at 100° C. After the reaction was terminated, the result was cooled to room temperature, and produced solids were recrystallized to obtain target Compound 727 (7.6 g, 82%).

<Preparation Example 81> Preparation of Compound 735

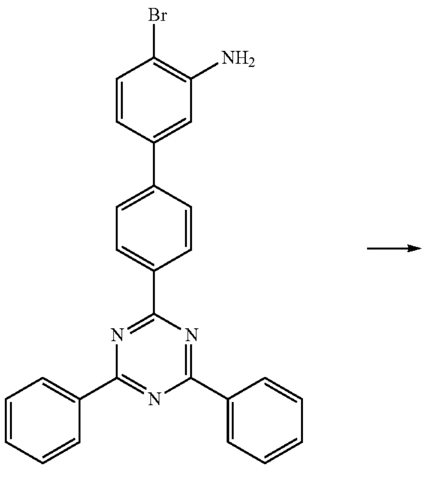

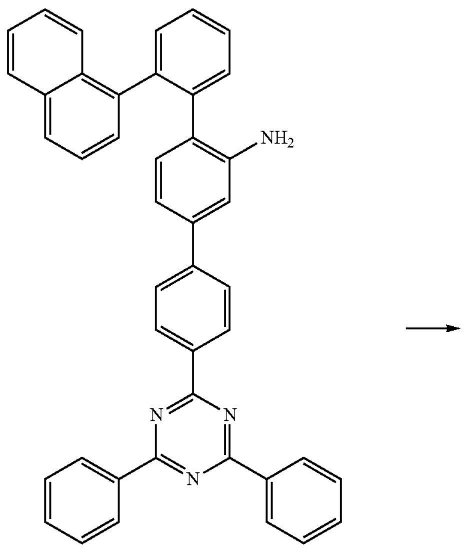

735-1

-continued

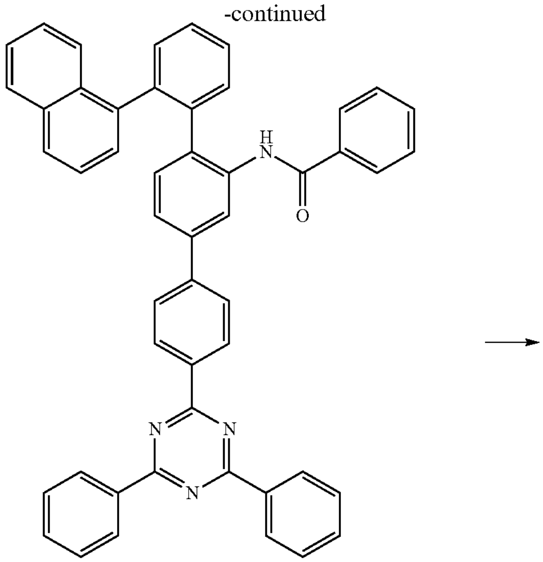

735-2

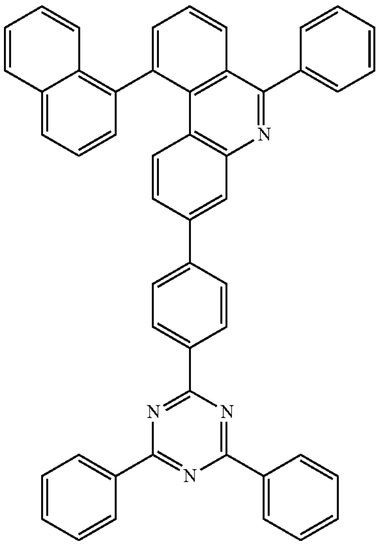

735

Preparation of Compound 735-1

After dissolving 4-bromo-4'-(4,6-diphenyl-1,3,5-triazin-2-yl)-[1,1'-biphenyl]-3-amine (10 g, 20.8 mmol, 1 eq.) in 1,4-dioxane/$H_2O$, (2-(naphthalen-1-yl)phenyl)boronic acid (5.4 g, 1.05 eq.), $Pd(PPh_3)_4$ (1.2 g, 0.05 eq.) and $K_2CO_3$ (8.6 g, 3 eq.) were added thereto, and the result was stirred for 15 hours at 100° C. After the reaction was terminated, the result was cooled to room temperature, and produced solids were recrystallized to obtain target Compound 735-1 (7.6 g, 81%).

Preparation of Compound 735-2

After dissolving Compound 735-1 (7.6 g, 16.8 mmol, 1 eq.) by adding THF, TEA (15 ml, 3 eq.) and benzoyl chloride (2.6 g, 1.1 eq.) were added thereto at 0° C., and the result was stirred for 1 hour at room temperature. After the reaction was terminated, the result was extracted with distilled water and EA. The organic layer was dried with $MgSO_4$, and then filtered and concentrated. With dichloromethane and hexane as a developing solvent, the concentrated residue was purified using column chromatography to obtain target Compound 735-2 (10 g, 86%).

Preparation of Compound 735

After dissolving Compound 735-2 (10.2 g, 14.4 mmol, 1 eq.) in nitrobenzene, $POCl_3$ (1.4 mL, 1.5 eq.) was added thereto, and the result was stirred for 5 hours at 150° C. After the reaction was terminated, the result was neutralized at room temperature, and then extracted with distilled water and dichloromethane. The organic layer was dried with $MgSO_4$, and then filtered and concentrated. The result was concentrated and recrystallized to obtain target Compound 735 (6.7 g, 68%).

<Preparation Example 82> Preparation of Compound 740

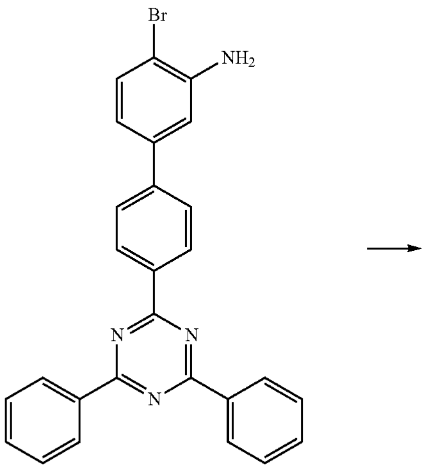

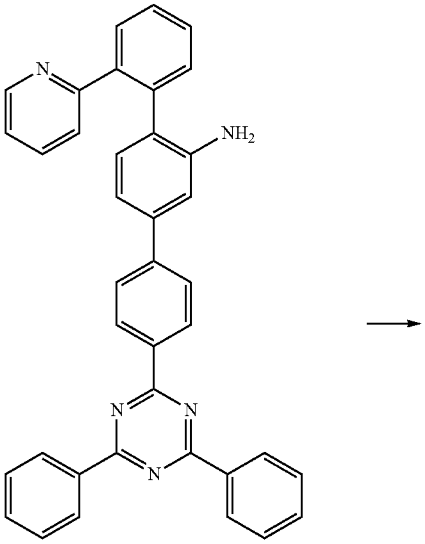

740-1

-continued

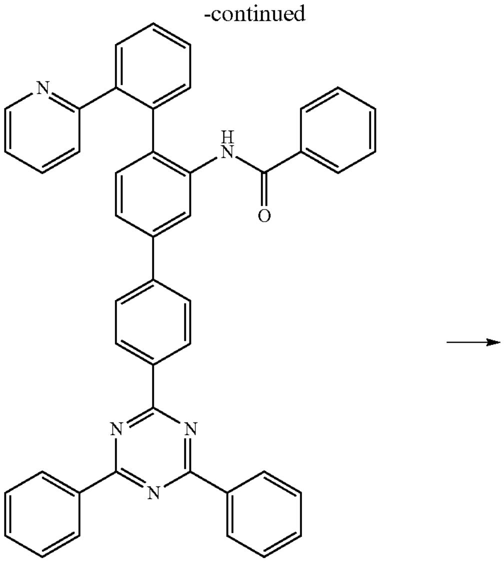

740-2

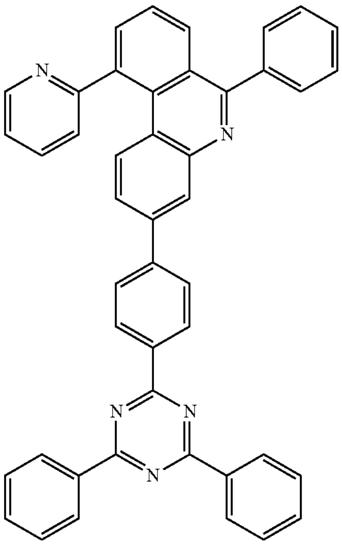

740

Preparation of Compound 740-1

After dissolving 4-bromo-4'-(4,6-diphenyl-1,3,5-triazin-2-yl)-[1,1'-biphenyl]-3-amine (10 g, 20.8 mmol, 1 eq.) in 1,4-dioxane/$H_2O$, (2-(pyridin-2-yl)phenyl)boronic acid (4.3 g, 1.05 eq.), $Pd(PPh_3)_4$ (0.96 g, 0.05 eq.) and $K_2CO_3$ (6.9 g, 3 eq.) were added thereto, and the result was stirred for 15 hours at 100° C. After the reaction was terminated, the result was cooled to room temperature, and produced solids were recrystallized to obtain target Compound 740-1 (8.8 g, 77%).

Preparation of Compound 740-2

After dissolving Compound 740-1 (8.8 g, 16.0 mmol, 1 eq.) by adding THF, TEA (13 ml, 3 eq.) and benzoyl chloride (2.3 g, 1.1 eq.) were added thereto at 0° C., and the result was stirred for 1 hour at room temperature. After the reaction was terminated, the result was extracted with distilled water and EA. The organic layer was dried with $MgSO_4$, and then filtered and concentrated. With dichloromethane and hexane as a developing solvent, the concentrated residue was purified using column chromatography to obtain target Compound 740-2 (8.4 g, 80%).

Preparation of Compound 740

After dissolving Compound 740-2 (8.4 g, 12.8 mmol, 1 eq.) in nitrobenzene, $POCl_3$ (1.1 mL, 1.5 eq.) was added thereto, and the result was stirred for 5 hours at 150° C. After the reaction was terminated, the result was neutralized at room temperature, and then extracted with distilled water and dichloromethane. The organic layer was dried with $MgSO_4$, and then filtered and concentrated. The result was concentrated and recrystallized to obtain target Compound 740 (4.5 g, 55%).

<Preparation Example 83> Preparation of Compound 755

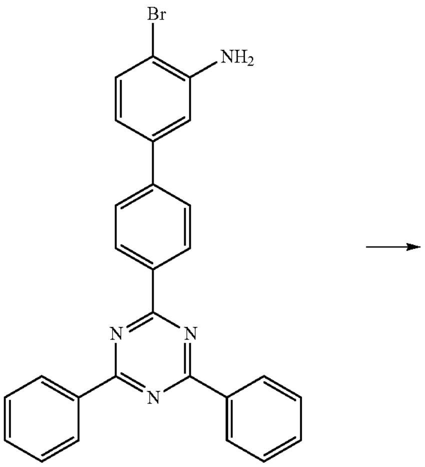

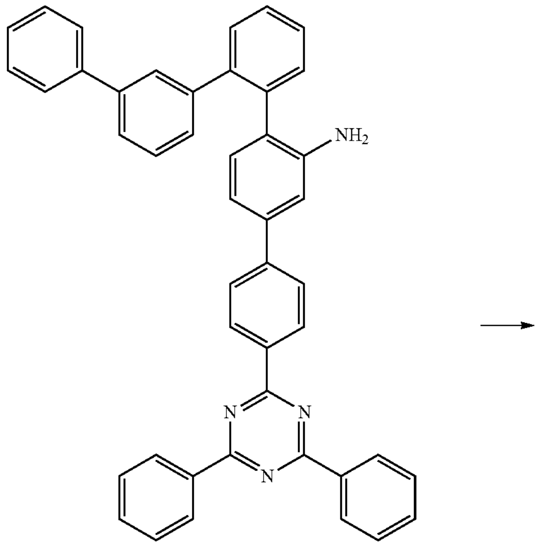

755-1

-continued

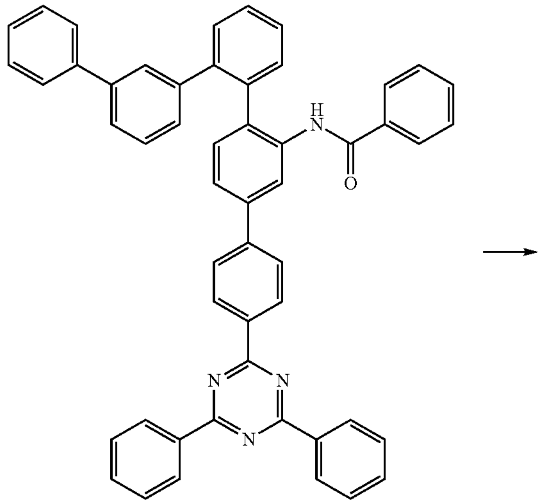

755-2

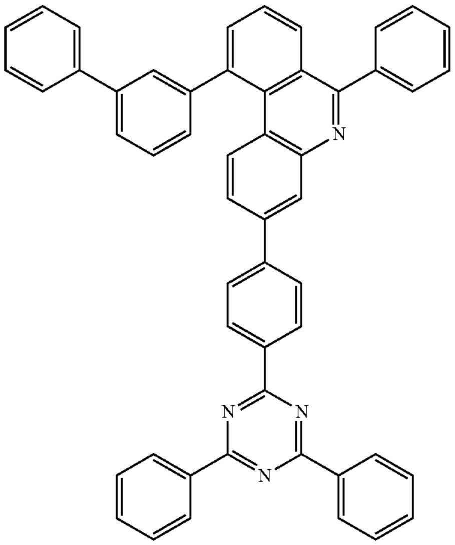

755

Preparation of Compound 755-1

After dissolving 4-bromo-4'-(4,6-diphenyl-1,3,5-triazin-2-yl)-[1,1'-biphenyl]-3-amine (10 g, 20.8 mmol, 1 eq.) in 1,4-dioxane/$H_2O$, [1,1':3',1"-terphenyl]-2-ylboronic acid (5.9 g, 1.05 eq.), $Pd(PPh_3)_4$ (1.2 g, 0.05 eq.) and $K_2CO_3$ (8.6 g, 3 eq.) were added thereto, and the result was stirred for 15 hours at 100° C. After the reaction was terminated, the result was cooled to room temperature, and produced solids were recrystallized to obtain target Compound 755-1 (11.1 g, 85%).

Preparation of Compound 755-2

After dissolving Compound 755-1 (11.1 g, 17.6 mmol, 1 eq.) by adding THF, TEA (15 ml, 3 eq.) and benzoyl chloride (3.7 g, 1.1 eq.) were added thereto at 0° C., and the result was stirred for 1 hour at room temperature. After the reaction was terminated, the result was extracted with distilled water and EA. The organic layer was dried with $MgSO_4$, and then filtered and concentrated. With dichloromethane and hexane as a developing solvent, the concentrated residue was purified using column chromatography to obtain target Compound 755-2 (10.7 g, 86%).

Preparation of Compound 755

After dissolving Compound 755-2 (10.7 g, 15.1 mmol, 1 eq.) in nitrobenzene, $POCl_3$ (1.4 mL, 1.5 eq.) was added thereto, and the result was stirred for 5 hours at 150° C. After the reaction was terminated, the result was neutralized at room temperature, and then extracted with distilled water and dichloromethane. The organic layer was dried with $MgSO_4$, and then filtered and concentrated. The result was concentrated and recrystallized to obtain target Compound 755 (6.9 g, 64%).

<Preparation Example 84> Preparation of Compound 763

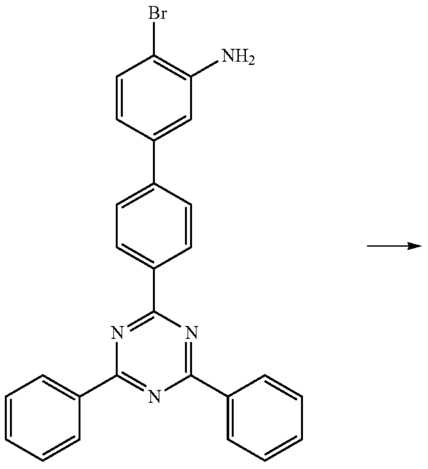

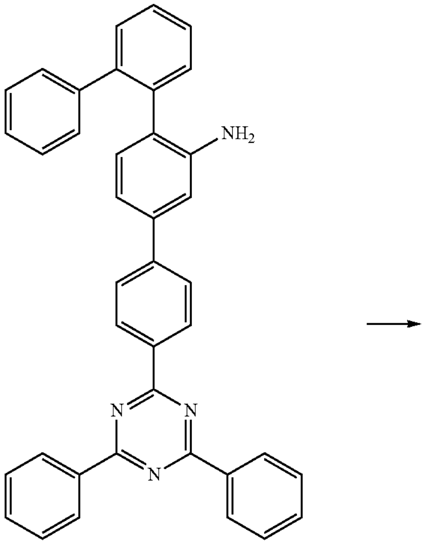

763-1

-continued

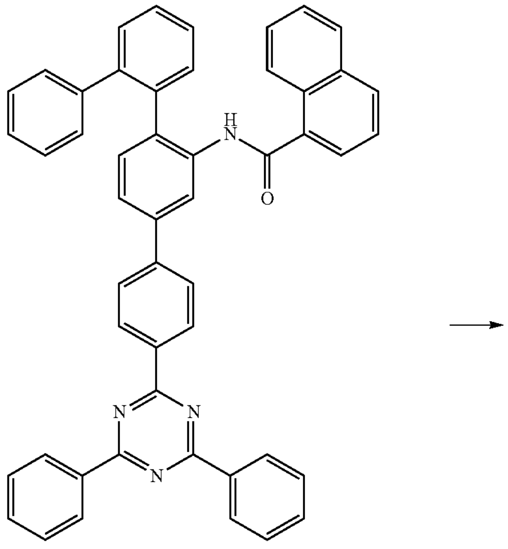

763-2

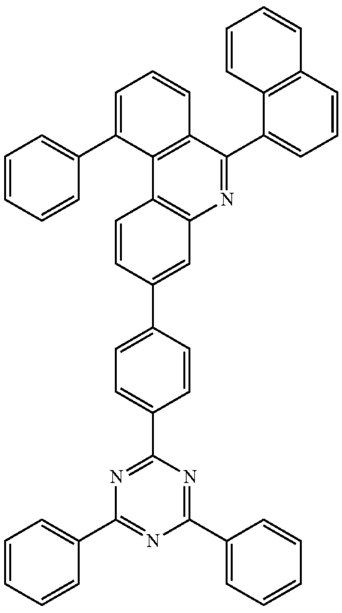

763

Preparation of Compound 763-1

After dissolving 4-bromo-4'-(4,6-diphenyl-1,3,5-triazin-2-yl)-[1,1'-biphenyl]-3-amine (10 g, 20.8 mmol, 1 eq.) in 1,4-dioxane/$H_2O$, [1,1'-biphenyl]-2-ylboronic acid (5.9 g, 1.05 eq.), $Pd(PPh_3)_4$ (1.2 g, 0.05 eq.) and $K_2CO_3$ (8.6 g, 3 eq.) were added thereto, and the result was stirred for 15 hours at 100° C. After the reaction was terminated, the result was cooled to room temperature, and produced solids were recrystallized to obtain target Compound 763-1 (9.4 g, 82%).

Preparation of Compound 763-2

After dissolving Compound 763-1 (9.4 g, 17.0 mmol, 1 eq.) by adding THE, TEA (12 ml, 3 eq.) and 1-naphtholyl chloride (3.5 g, 1.1 eq.) were added thereto at 0° C., and the result was stirred for 1 hour at room temperature. After the reaction was terminated, the result was extracted with distilled water and EA. The organic layer was dried with $MgSO_4$, and then filtered and concentrated. With dichloromethane and hexane as a developing solvent, the concentrated residue was purified using column chromatography to obtain target Compound 763-2 (9.9 g, 83%).

Preparation of Compound 763

After dissolving Compound 763-2 (9.9 g, 14.1 mmol, 1 eq.) in nitrobenzene, $POCl_3$ (1.3 mL, 1.5 eq.) was added thereto, and the result was stirred for 5 hours at 150° C. After the reaction was terminated, the result was neutralized at room temperature, and then extracted with distilled water and dichloromethane. The organic layer was dried with $MgSO_4$, and then filtered and concentrated. The result was concentrated and recrystallized to obtain target Compound 763 (6.0 g, 62%).

<Preparation Example 85> Preparation of Compound 764

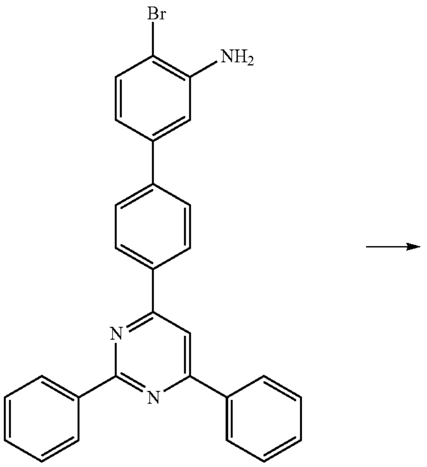

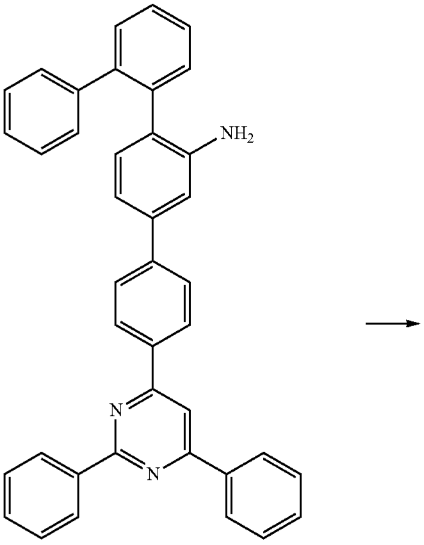

764-1

-continued

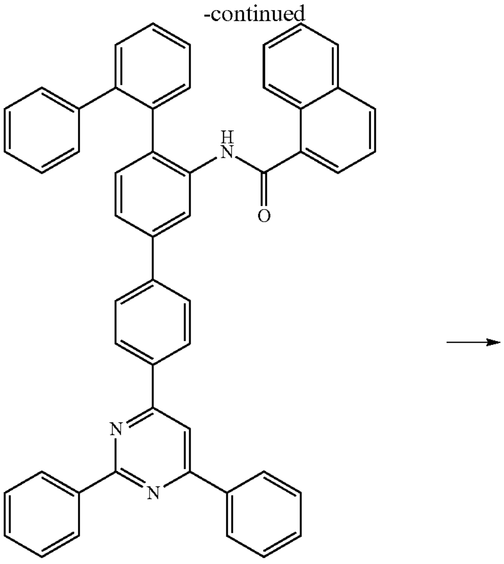

764-2

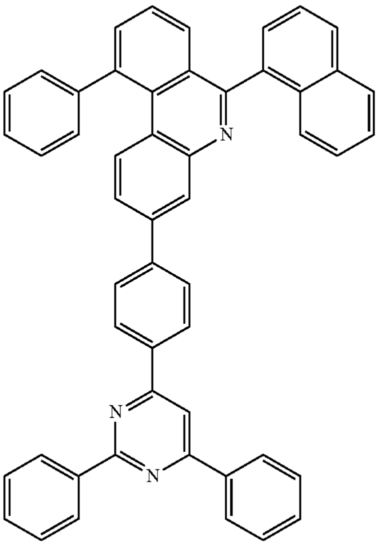

764

Preparation of Compound 764-1

After dissolving 4-bromo-4'-(2,6-diphenylpyrimidin-4-yl)-[1,1'-biphenyl]-3-amine (10 g, 20.8 mmol, 1 eq.) in 1,4-dioxane/$H_2O$, [1,1':2',1"-terphenyl]-2-ylboronic acid (5.9 g, 1.05 eq.), $Pd(PPh_3)_4$ (0.96 g, 0.05 eq.) and $K_2CO_3$ (6.9 g, 3 eq.) were added thereto, and the result was stirred for 15 hours at 100° C. After the reaction was terminated, the result was cooled to room temperature, and produced solids were recrystallized to obtain target Compound 764-1 (8.7 g, 76%).

Preparation of Compound 764-2

After dissolving Compound 764-1 (8.7 g, 15.8 mmol, 1 eq.) by adding THF, TEA (13 ml, 3 eq.) and 1-naphtholyl chloride (2.2 g, 1.1 eq.) were added thereto at 0° C., and the result was stirred for 1 hour at room temperature. After the reaction was terminated, the result was extracted with distilled water and EA. The organic layer was dried with $MgSO_4$, and then filtered and concentrated. With dichloromethane and hexane as a developing solvent, the concentrated residue was purified using column chromatography to obtain target Compound 764-2 (8.7 g, 78%).

Preparation of Compound 764

After dissolving Compound 764-2 (8.7 g, 12.3 mmol, 1 eq.) in nitrobenzene, $POCl_3$ (1.1 mL, 1.5 eq.) was added thereto, and the result was stirred for 5 hours at 150° C. After the reaction was terminated, the result was neutralized at room temperature, and then extracted with distilled water and dichloromethane. The organic layer was dried with $MgSO_4$, and then filtered and concentrated. The result was concentrated and recrystallized to obtain target Compound 764 (4.9 g, 58%).

<Preparation Example 86> Preparation of Compound 776

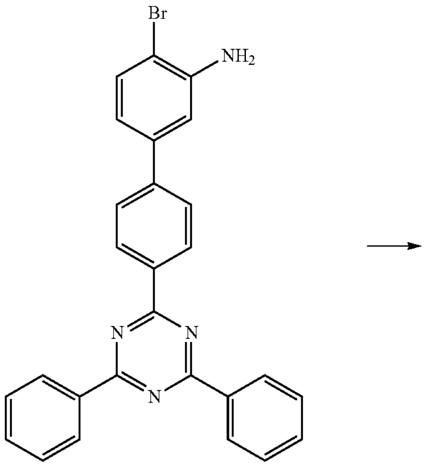

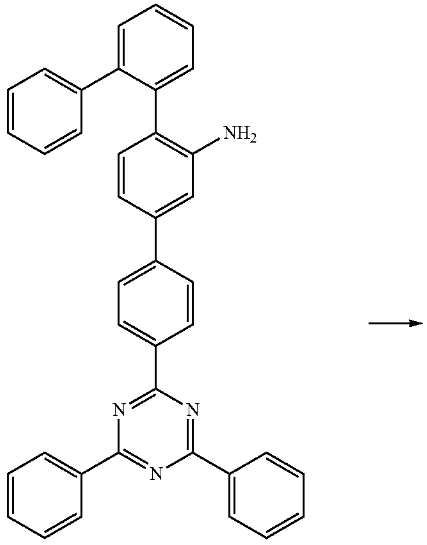

764-1

-continued

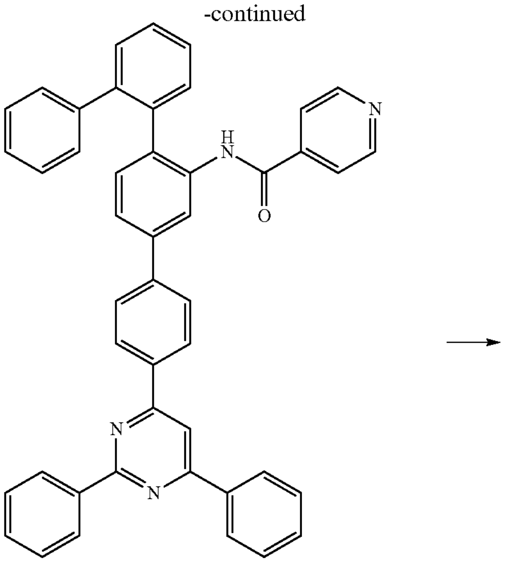

776-1

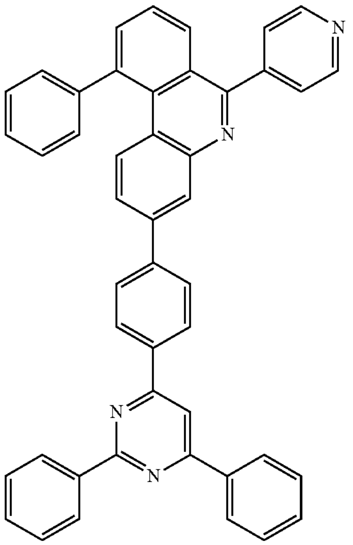

776

Preparation of Compound 764-1

After dissolving 4-bromo-4'-(2,6-diphenylpyrimidin-4-yl)-[1,1'-biphenyl]-3-amine (10 g, 20.8 mmol, 1 eq.) in 1,4-dioxane/$H_2O$, [1,1':2',1"-terphenyl]-2-ylboronic acid (5.9 g, 1.05 eq.), $Pd(PPh_3)_4$ (0.96 g, 0.05 eq.) and $K_2CO_3$ (6.9 g, 3 eq.) were added thereto, and the result was stirred for 15 hours at 100° C. After the reaction was terminated, the result was cooled to room temperature, and produced solids were recrystallized to obtain target Compound 764-1 (8.7 g, 76%).

Preparation of Compound 776-1

After dissolving Compound 764-1 (8.7 g, 15.8 mmol, 1 eq.) by adding THF, TEA (13 ml, 3 eq.) and isonicotinoyl chloride (2.4 g, 1.1 eq.) were added thereto at 0° C., and the result was stirred for 1 hour at room temperature. After the reaction was terminated, the result was extracted with distilled water and EA. The organic layer was dried with $MgSO_4$, and then filtered and concentrated. With dichloromethane and hexane as a developing solvent, the concentrated residue was purified using column chromatography to obtain target Compound 776-1 (6.0 g, 58%).

Preparation of Compound 776

After dissolving Compound 776-1 (6.0 g, 12.3 mmol, 1 eq.) in nitrobenzene, $POCl_3$ (1.7 mL, 1.5 eq.) was added thereto, and the result was stirred for 5 hours at 150° C. After the reaction was terminated, the result was neutralized at room temperature, and then extracted with distilled water and dichloromethane. The organic layer was dried with $MgSO_4$, and then filtered and concentrated. The result was concentrated and recrystallized to obtain target Compound 776 (4.0 g, 52%).

<Preparation Example 87> Preparation of Compound 779

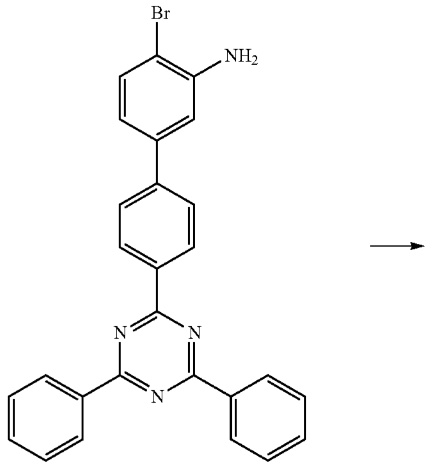

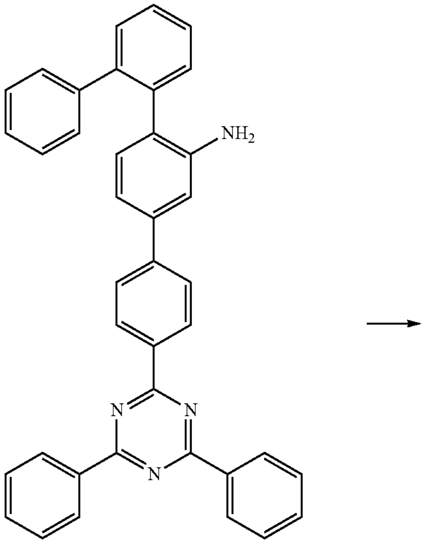

763-1

-continued

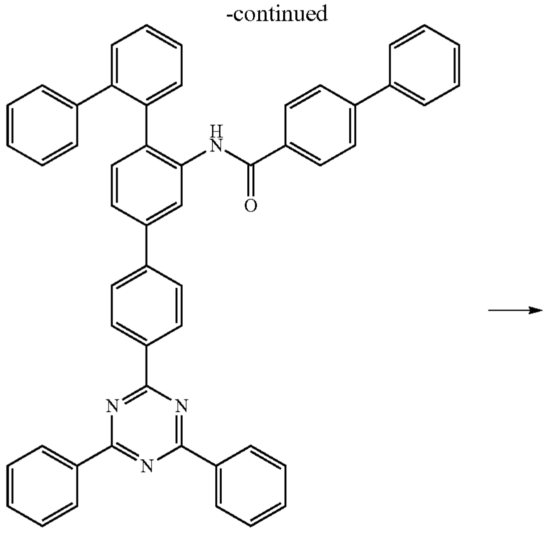

779-1

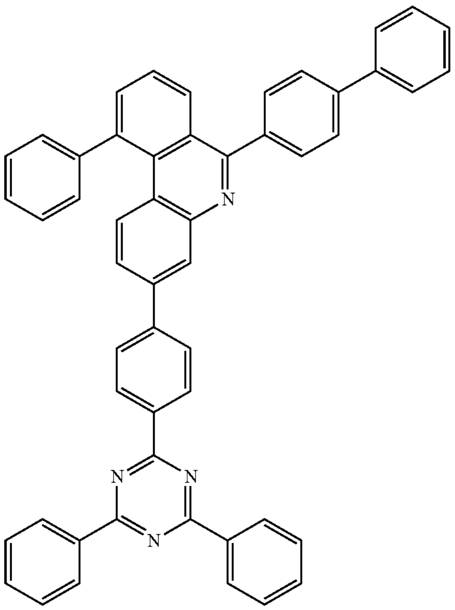

779

Preparation of Compound 763-1

After dissolving 4-bromo-4'-(4,6-diphenyl-1,3,5-triazin-2-yl)-[1,1'-biphenyl]-3-amine (10 g, 20.8 mmol, 1 eq.) in 1,4-dioxane/$H_2O$, [1,1'-biphenyl]-2-ylboronic acid (5.9 g, 1.05 eq.), $Pd(PPh_3)_4$ (1.2 g, 0.05 eq.) and $K_2CO_3$ (8.6 g, 3 eq.) were added thereto, and the result was stirred for 15 hours at 100° C. After the reaction was terminated, the result was cooled to room temperature, and produced solids were recrystallized to obtain target Compound 763-1 (9.4 g, 82%).

Preparation of Compound 779-1

After dissolving Compound 763-1 (9.4 g, 17.0 mmol, 1 eq.) by adding THF, TEA (12 ml, 3 eq.) and [1,1'-biphenyl]-4-carbonyl chloride (4.0 g, 1.1 eq.) were added thereto at 0° C., and the result was stirred for 1 hour at room temperature. After the reaction was terminated, the result was extracted with distilled water and EA. The organic layer was dried with $MgSO_4$, and then filtered and concentrated. With dichloromethane and hexane as a developing solvent, the concentrated residue was purified using column chromatography to obtain target Compound 779-1 (10 g, 81%).

Preparation of Compound 779

After dissolving Compound 779-1 (10 g, 13.7 mmol, 1 eq.) in nitrobenzene, $POCl_3$ (1.9 mL, 1.5 eq.) was added thereto, and the result was stirred for 5 hours at 150° C. After the reaction was terminated, the result was neutralized at room temperature, and then extracted with distilled water and dichloromethane. The organic layer was dried with $MgSO_4$, and then filtered and concentrated. The concentrated residue was recrystallized to obtain target Compound 779 (6.6 g, 68%).

<Preparation Example 88> Preparation of Compound 827

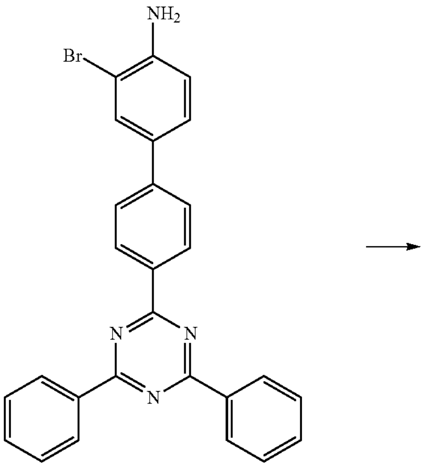

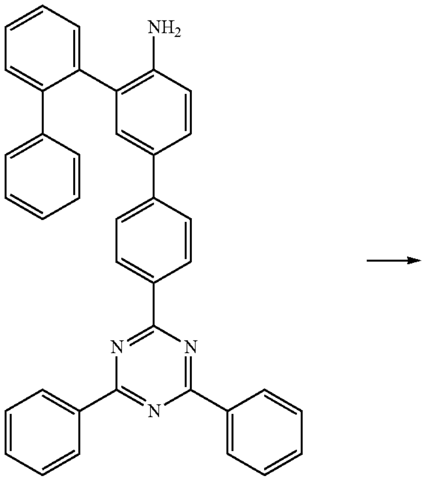

827-1

-continued

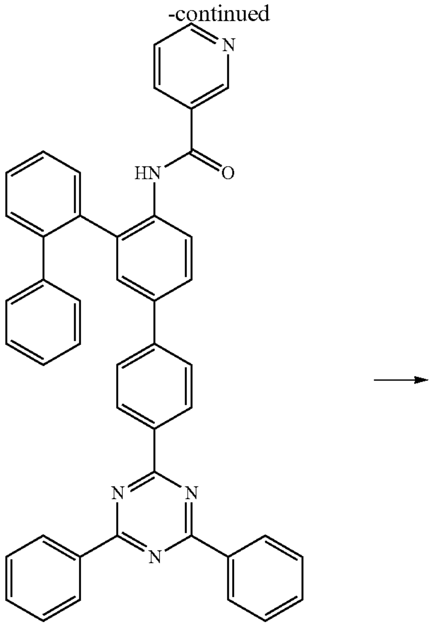

827-2

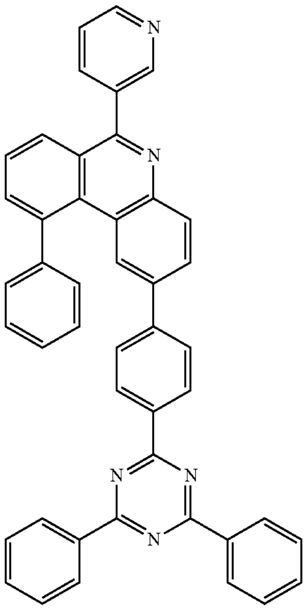

827

Preparation of Compound 827-1

After dissolving 3-bromo-4'-(4,6-diphenyl-1,3,5-triazin-2-yl)-[1,1'-biphenyl]-4-amine (10 g, 20.8 mmol, 1 eq.) in 1,4-dioxane/$H_2O$, [1,1'-biphenyl]-2-ylboronic acid (5.9 g, 1.05 eq.), $Pd(PPh_3)_4$ (1.2 g, 0.05 eq.) and $K_2CO_3$ (8.6 g, 3 eq.) were added thereto, and the result was stirred for 15 hours at 100° C. After the reaction was terminated, the result was cooled to room temperature, and produced solids were recrystallized to obtain target Compound 827-1 (9.4 g, 82%).

Preparation of Compound 827-2

After dissolving Compound 827-1 (9.4 g, 17.0 mmol, 1 eq.) by adding THF, TEA (12 ml, 3 eq.) and isonicotinoyl chloride (2.6 g, 1.1 eq.) were added thereto at 0° C., and the result was stirred for 1 hour at room temperature. After the reaction was terminated, the result was extracted with distilled water and EA. The organic layer was dried with $MgSO_4$, and then filtered and concentrated. With dichloromethane and hexane as a developing solvent, the concentrated residue was purified using column chromatography to obtain target Compound 827-2 (7.1 g, 64%).

Preparation of Compound 827

After dissolving Compound 827-2 (7.1 g, 10.8 mmol, 1 eq.) in nitrobenzene, $POCl_3$ (1.5 mL, 1.5 eq.) was added thereto, and the result was stirred for 5 hours at 150° C. After the reaction was terminated, the result was neutralized at room temperature, and then extracted with distilled water and dichloromethane. The organic layer was dried with $MgSO_4$, and then filtered and concentrated. The result was concentrated and recrystallized to obtain target Compound 827 (3.7 g, 54%).

<Preparation Example 89> Preparation of Compound 831

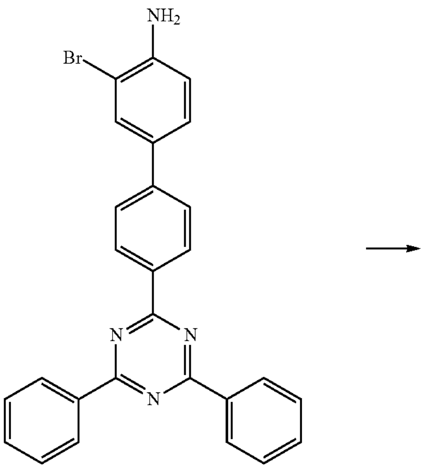

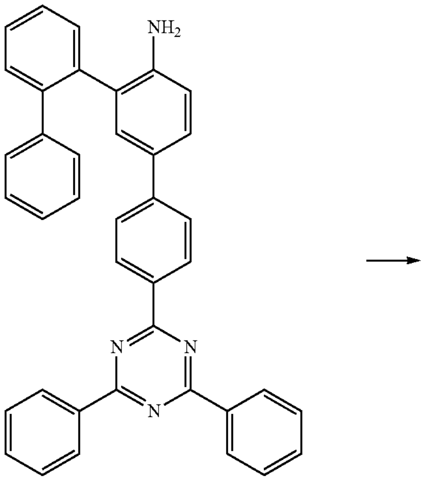

827-1

-continued

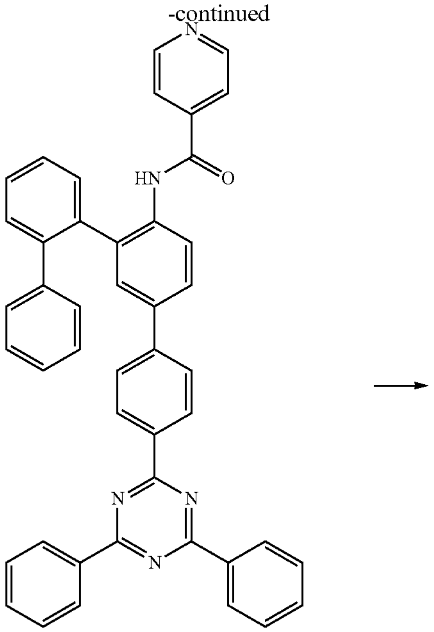

831-1

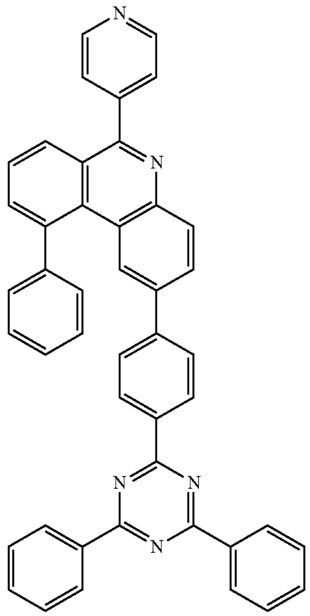

831

Preparation of Compound 827-1

After dissolving 3-bromo-4'-(4,6-diphenyl-1,3,5-triazin-2-yl)-[1,1'-biphenyl]-4-amine (10 g, 20.8 mmol, 1 eq.) in 1,4-dioxane/$H_2O$, [1,1'-biphenyl]-2-ylboronic acid (5.9 g, 1.05 eq.), $Pd(PPh_3)_4$ (1.2 g, 0.05 eq.) and $K_2CO_3$ (8.6 g, 3 eq.) were added thereto, and the result was stirred for 15 hours at 100° C. After the reaction was terminated, the result was cooled to room temperature, and produced solids were recrystallized to obtain target Compound 827-1 (9.4 g, 82%).

Preparation of Compound 831-1

After dissolving Compound 827-1 (9.4 g, 17.0 mmol, 1 eq.) by adding THF, TEA (12 ml, 3 eq.) and nicotinoyl chloride (2.6 g, 1.1 eq.) were added thereto at 0° C., and the result was stirred for 1 hour at room temperature. After the reaction was terminated, the result was extracted with distilled water and EA. The organic layer was dried with $MgSO_4$, and then filtered and concentrated. With dichloromethane and hexane as a developing solvent, the concentrated residue was purified using column chromatography to obtain target Compound 831-1 (6.9 g, 62%).

Preparation of Compound 831

After dissolving Compound 831-1 (6.9 g, 10.8 mmol, 1 eq.) in nitrobenzene, $POCl_3$ (1.5 mL, 1.5 eq.) was added thereto, and the result was stirred for 5 hours at 150° C. After the reaction was terminated, the result was neutralized at room temperature, and then extracted with distilled water and dichloromethane. The organic layer was dried with $MgSO_4$, and then filtered and concentrated. The result was concentrated and recrystallized to obtain target Compound 831 (3.6 g, 52%).

<Preparation Example 90> Preparation of Compound 848

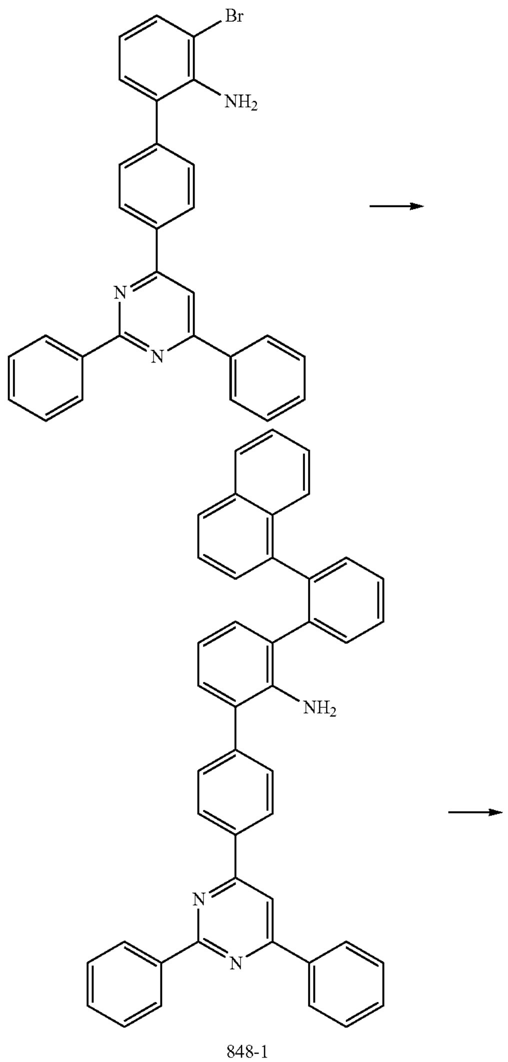

848-1

-continued

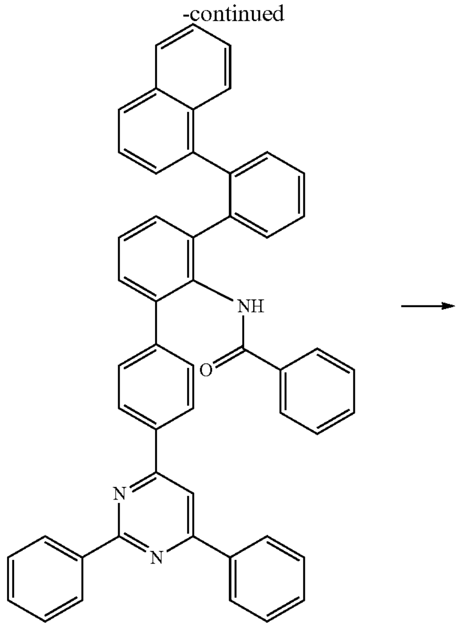

848-2

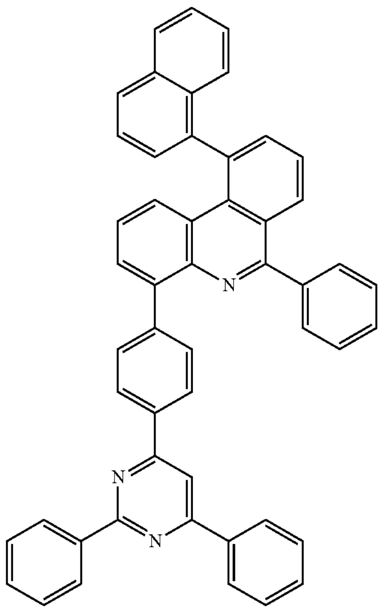

848

Preparation of Compound 848-1

After dissolving 3-bromo-4'-(2,6-diphenylpyrimidin-4-yl)-[1,1'-biphenyl]-2-amine (10 g, 20.8 mmol, 1 eq.) in 1,4-dioxane/$H_2O$, (2-(naphthalen-1-yl)phenyl)boronic acid (5.4 g, 1.05 eq.), $Pd(PPh_3)_4$ (1.2 g, 0.05 eq.) and $K_2CO_3$ (8.6 g, 3 eq.) were added thereto, and the result was stirred for 15 hours at 100° C. After the reaction was terminated, the result was cooled to room temperature, and produced solids were recrystallized to obtain target Compound 848-1 (10.1 g, 81%).

Preparation of Compound 848-2

After dissolving Compound 848-1 (10.1 g, 16.8 mmol, 1 eq.) by adding THF, TEA (7.0 ml, 3 eq.) and benzoyl chloride (10.9 g, 1.1 eq.) were added thereto at 0° C., and the result was stirred for 1 hour at room temperature. After the reaction was terminated, the result was extracted with distilled water and EA. The organic layer was dried with $MgSO_4$, and then filtered and concentrated. With dichloromethane and hexane as a developing solvent, the concentrated residue was purified using column chromatography to obtain target Compound 848-2 (7.1 g, 60%).

Preparation of Compound 848

After dissolving Compound 848-2 (7.1 g, 10.0 mmol, 1 eq.) in nitrobenzene, $POCl_3$ (1.5 mL, 1.5 eq.) was added thereto, and the result was stirred for 5 hours at 150° C. After the reaction was terminated, the result was neutralized at room temperature, and then extracted with distilled water and dichloromethane. The organic layer was dried with $MgSO_4$, and then filtered and concentrated. The result was concentrated and recrystallized to obtain target Compound 848 (3.5 g, 52%).

<Preparation Example 91> Preparation of Compound 856

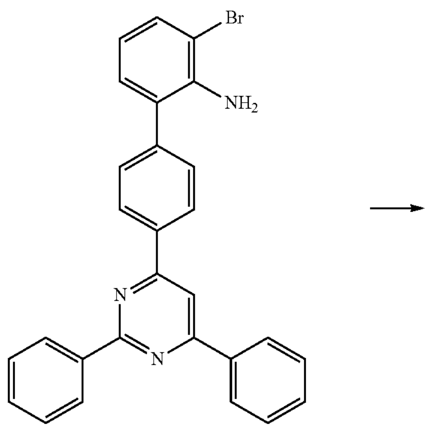

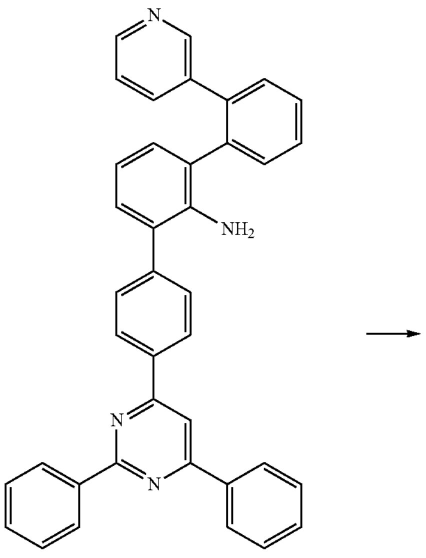

856-1

-continued

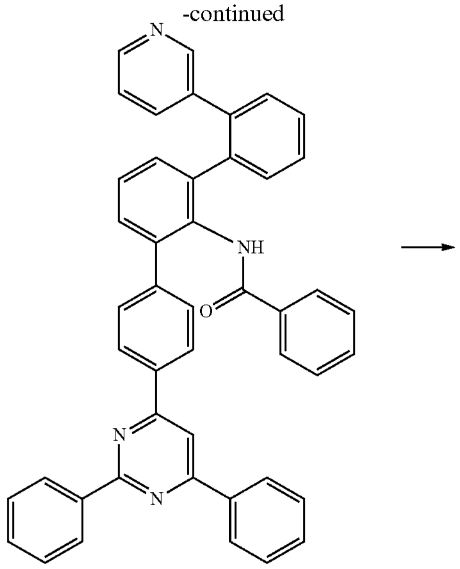

856-2

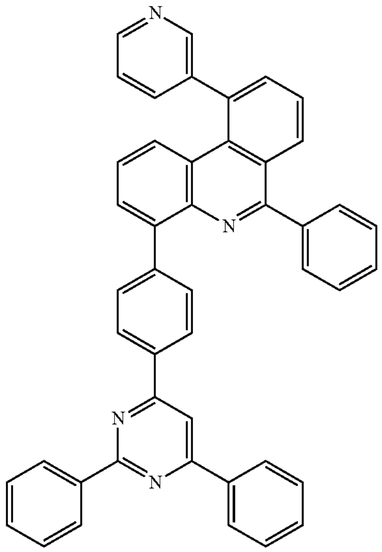

856

Preparation of Compound 856-1

After dissolving 3-bromo-4'-(2,6-diphenylpyrimidin-4-yl)-[1,1'-biphenyl]-2-amine (10 g, 20.8 mmol, 1 eq.) in 1,4-dioxane/$H_2O$, (2-(pyridin-3-yl)phenyl)boronic acid (4.3 g, 1.05 eq.), $Pd(PPh_3)_4$ (1.2 g, 0.05 eq.) and $K_2CO_3$ (8.6 g, 3 eq.) were added thereto, and the result was stirred for 15 hours at 100° C. After the reaction was terminated, the result was cooled to room temperature, and produced solids were recrystallized to obtain target Compound 856-1 (9.0 g, 79%).

Preparation of Compound 856-2

After dissolving Compound 856-1 (9.0 g, 16.8 mmol, 1 eq.) by adding THF, TEA (7.0 ml, 3 eq.) and benzoyl chloride (2.6 g, 1.1 eq.) were added thereto at 0° C., and the result was stirred for 1 hour at room temperature. After the reaction was terminated, the result was extracted with distilled water and EA. The organic layer was dried with $MgSO_4$, and then filtered and concentrated. With dichloromethane and hexane as a developing solvent, the concentrated residue was purified using column chromatography to obtain target Compound 856-2 (7.5 g, 68%).

Preparation of Compound 856

After dissolving Compound 856-2 (7.5 g, 11.4 mmol, 1 eq.) in nitrobenzene, $POCl_3$ (1.0 mL, 1.5 eq.) was added thereto, and the result was stirred for 5 hours at 150° C. After the reaction was terminated, the result was neutralized at room temperature, and then extracted with distilled water and dichloromethane. The organic layer was dried with $MgSO_4$, and then filtered and concentrated. The concentrated residue was recrystallized to obtain target Compound 856 (4.2 g, 58%).

<Preparation Example 92> Preparation of Compound 875

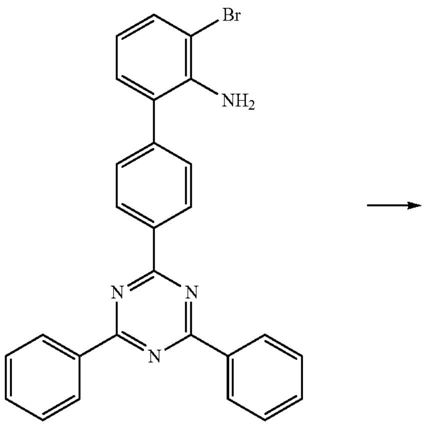

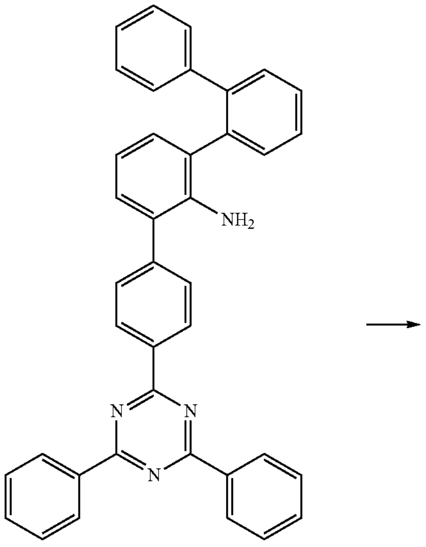

875-1

-continued

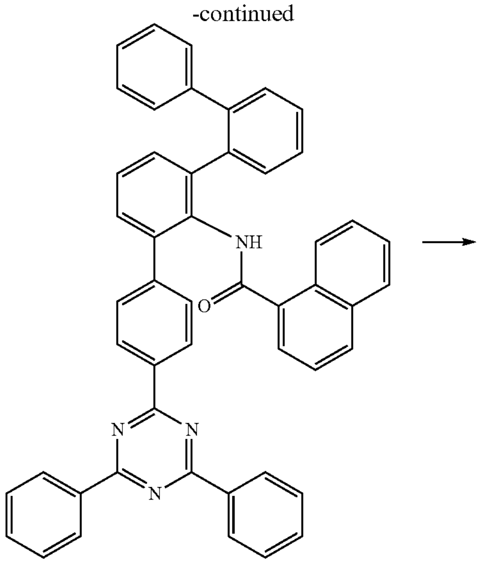

875-2

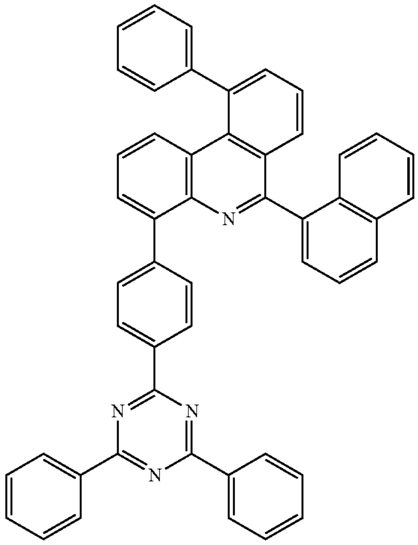

875

Preparation of Compound 875-1

After dissolving 3-bromo-4'-(4,6-diphenyl-1,3,5-triazin-2-yl)-[1,1'-biphenyl]-2-amine (10 g, 20.8 mmol, 1 eq.) in 1,4-dioxane/$H_2O$, [1,1'-biphenyl]-2-ylboronic acid (4.3 g, 1.05 eq.), $Pd(PPh_3)_4$ (1.2 g, 0.05 eq.) and $K_2CO_3$ (8.6 g, 3 eq.) were added thereto, and the result was stirred for 15 hours at 100° C. After the reaction was terminated, the result was cooled to room temperature, and produced solids were recrystallized to obtain target Compound 875-1 (9.6 g, 84%).

Preparation of Compound 875-2

After dissolving Compound 875-1 (9.6 g, 17.4 mmol, 1 eq.) by adding THF, TEA (7.2 ml, 3 eq.) and 1-naphtholyl chloride (3.6 g, 1.1 eq.) were added thereto at 0° C., and the result was stirred for 1 hour at room temperature. After the reaction was terminated, the result was extracted with distilled water and EA. The organic layer was dried with $MgSO_4$, and then filtered and concentrated. With dichloromethane and hexane as a developing solvent, the concentrated residue was purified using column chromatography to obtain target Compound 875-2 (10.3 g, 84%).

Preparation of Compound 875

After dissolving Compound 875-2 (10.3 g, 14.6 mmol, 1 eq.) in nitrobenzene, $POCl_3$ (2.0 mL, 1.5 eq.) was added thereto, and the result was stirred for 5 hours at 150° C. After the reaction was terminated, the result was neutralized at room temperature, and then extracted with distilled water and dichloromethane. The organic layer was dried with $MgSO_4$, and then filtered and concentrated. The concentrated residue was recrystallized to obtain target Compound 875 (6.9 g, 69%).

<Preparation Example 93> Preparation of Compound 908

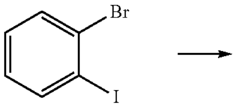

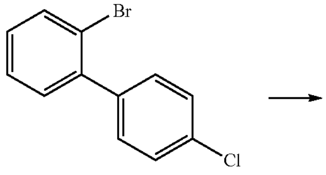

139-1

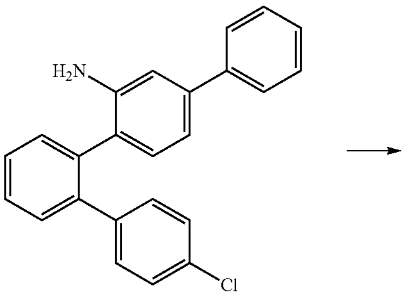

908-1

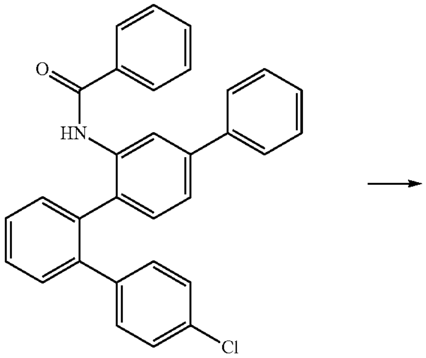

908-2

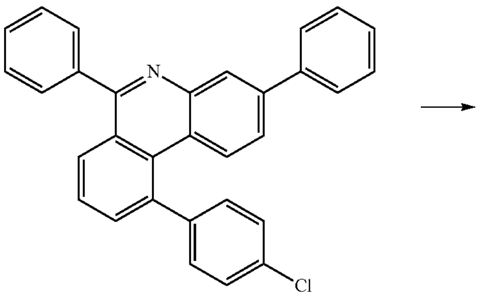

908-3

-continued

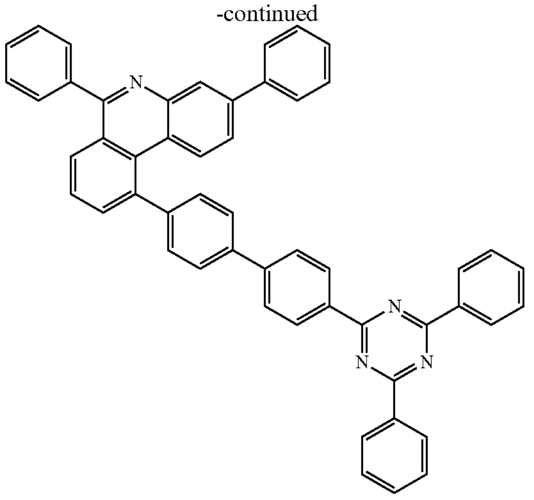

908

Preparation of Compound 139-1

After dissolving 1-bromo-2-iodobenzene (50 g, 0.176 mol, 1 eq.) in toluene/ethanol/$H_2O$, 4-chlorophenylboronic acid (25 g, 0.160 mol, 1 eq.), sodium bicarbonate (40 g, 0.481 mol, 3 eq.) and $Pd(PPh_3)_4$ (9.0 g, 0.008 eq.) were added thereto, and the result was stirred for 16 hours at 100° C. After the reaction was terminated, the result was cooled to room temperature, and extracted with distilled water and EA. The organic layer was dried with $MgSO_4$, and then filtered and concentrated. With ethyl acetate and hexane as a developing solvent, the concentrated residue was purified using column chromatography to obtain target Compound 139-1 (27 g, 57%).

Preparation of Compound 908-1

After dissolving Compound 139-1 (25 g, 0.093 mol, 1 eq.) in Toluene/ethanol/$H_2O$, 4-(4,4,5,5-tetramethyl-1,3,2-dioxaborolan-2-yl)-[1,1'-biphenyl]-3-amine (27 g, 1 eq.), potassium phosphate (59 g, 3 eq.) and $Pd(PPh_3)_4$ (5.3 g, 0.005 eq.) were added thereto, and the result was stirred for 14 hours at 100° C. After the reaction was terminated, the result was cooled to room temperature, and extracted with distilled water and EA. The organic layer was dried with $MgSO_4$, and then filtered and concentrated. With dichloromethane and hexane as a developing solvent, the concentrated residue was purified using column chromatography to obtain target Compound 908-1 (27 g, 84%).

Preparation of Compound 908-2

After dissolving Compound 908-1 (27 g, 0.078 mol, 1 eq.) by adding THF, TEA (27 ml, 1 eq.) and benzoyl chloride (12 ml, 1.1 eq.) were added thereto at 0° C., and the result was stirred for 1 hour at room temperature. After the reaction was terminated, the result was extracted with distilled water and EA. The organic layer was dried with $MgSO_4$, and then filtered and concentrated. With dichloromethane and hexane as a developing solvent, the concentrated residue was purified using column chromatography to obtain target Compound 908-2 (28 g, 78%).

Preparation of Compound 908-3

After dissolving Compound 908-2 (28 g, 0.060 mol, 1 eq.) in nitrobenzene, $POCl_3$ (13 mL, 1.5 eq.) was added thereto, and the result was stirred for 5 hours at 150° C. After the reaction was terminated, the result was neutralized at room temperature, and then extracted with distilled water and dichloromethane. The organic layer was dried with $MgSO_4$, and then filtered and concentrated. The concentrated residue was stirred with ethyl acetate and then filtered to obtain target Compound 908-3 (15 g, 64%).

Preparation of Compound 908

After dissolving Compound 908-3 (8.0 g, 18.1 mmol, 1 eq.) in 1,4-dioxane/$H_2O$, 2,4-diphenyl-6-(4-(4,4,5,5-tetramethyl-1,3,2-dioxaborolan-2-yl)phenyl)-1,3,5-triazine (8.3 g, 18.3 mmol, 1.05 eq.), $Pd(PPh_3)_4$ (1.0 g, 0.87 mmol, 0.05 eq.) and $K_2CO_3$ (7.2 g, 52.5 mmol, 3 eq.) were added thereto, and the result was stirred for 15 hours at 100° C. After the reaction was terminated, the result was cooled to room temperature, and produced solids were recrystallized to obtain target Compound 908 (10.3 g, 80%).

<Preparation Example 94> Preparation of Compound 911

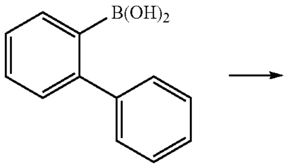

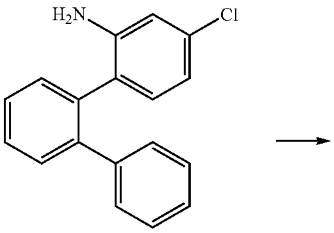

355-1

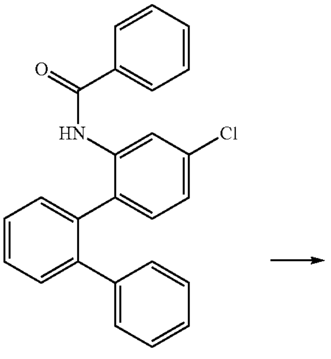

355-2

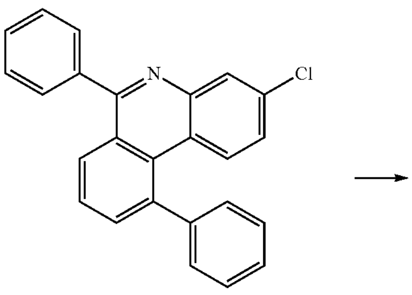

355-3

-continued

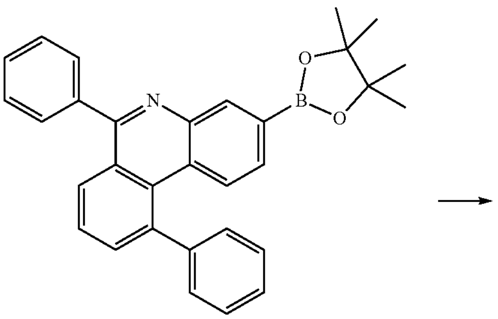

355-4

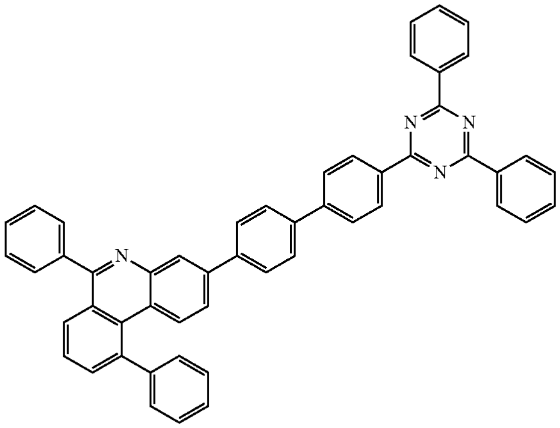

911

Preparation of Compound 911

Target Compound 911 was obtained in the same manner as in the preparation of Compound 355 of Preparation Example 56 except that 2-(4'-bromo-[1,1'-biphenyl]-4-yl)-4,6-diphenyl-1,3,5-triazine was used instead of 2-chloro-4,6-diphenyl-1,3,5-triazine.

<Preparation Example 95> Preparation of Compound 912

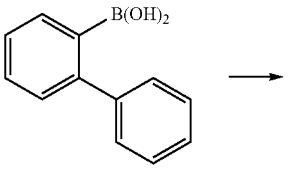

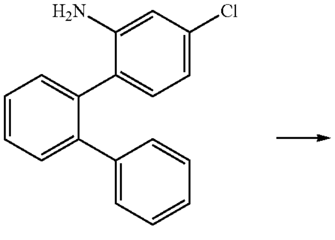

355-1

-continued
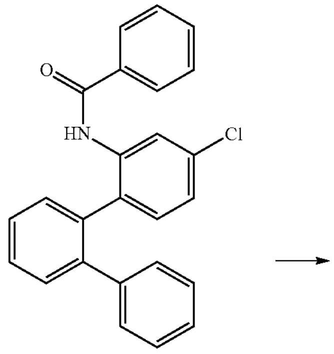
355-2
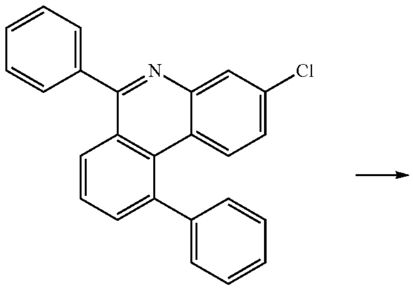
355-3
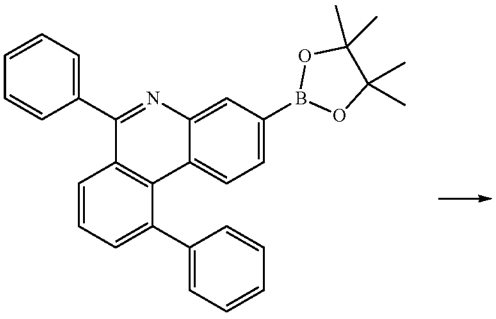
355-4
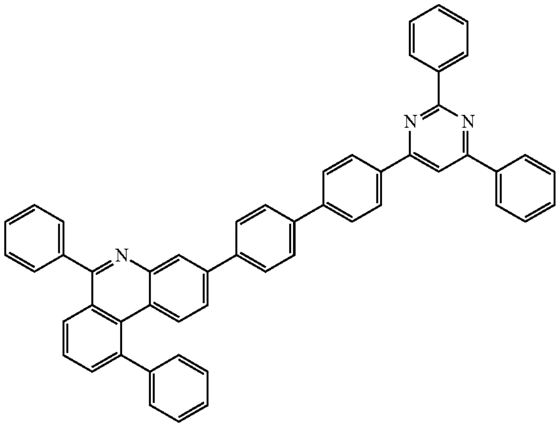
912
Preparation of Compound 912
Target Compound 912 was obtained in the same manner as in the preparation of Compound 355 of Preparation Example 56 except that 4-(4'-bromo-[1,1'-biphenyl]-4-yl)-2,6-diphenylpyrimidine was used instead of 2-chloro-4,6-diphenyl-1,3,5-triazine.
<Preparation Example 96> Preparation of Compound 914
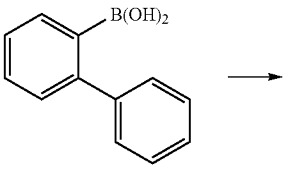
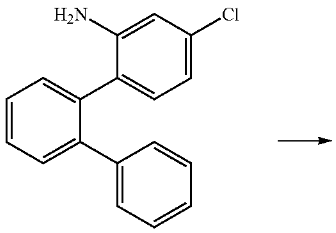
355-1
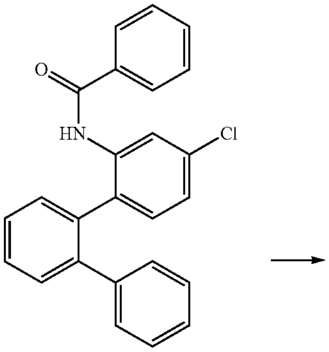
355-2
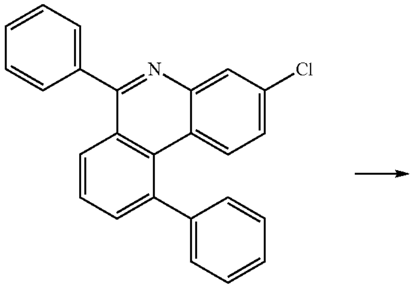
355-3
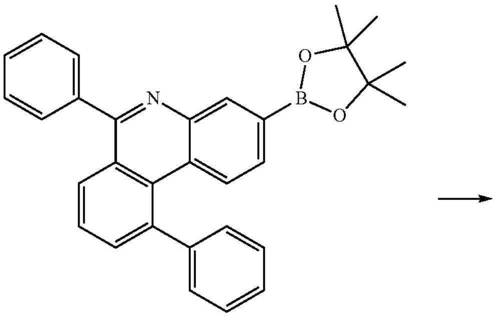
355-4

-continued

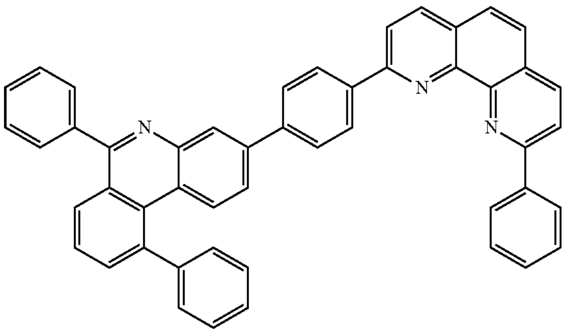

914

Preparation of Compound 914

Target Compound 914 was obtained in the same manner as in the preparation of Compound 355 of Preparation Example 56 except that 2-(4-bromophenyl)-9-phenyl-1,10-phenanthroline was used instead of 2-chloro-4,6-diphenyl-1,3,5-triazine.

<Preparation Example 97> Preparation of Compound 935

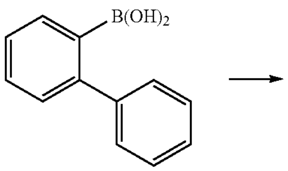

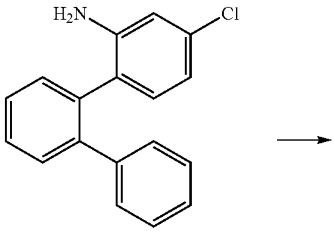

355-1

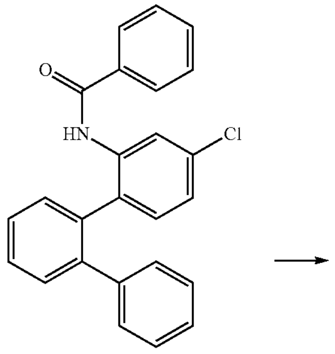

355-2

-continued

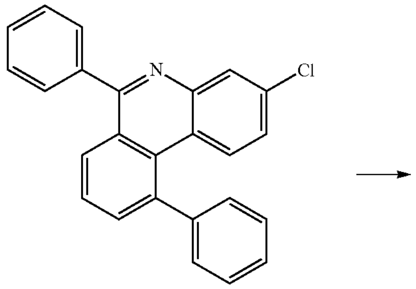

355-3

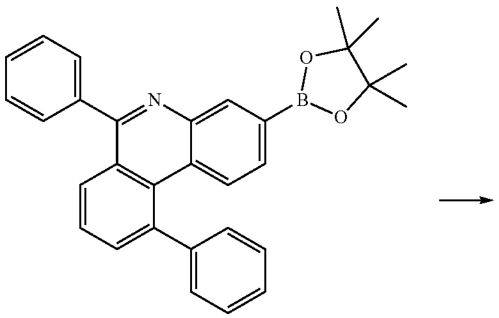

355-4

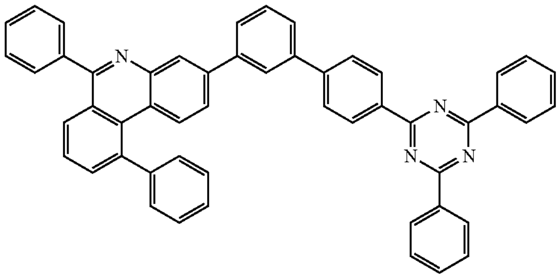

935

Preparation of Compound 935

Target Compound 935 was obtained in the same manner as in the preparation of Compound 355 of Preparation Example 56 except that 2-(3'-bromo-[1,1'-biphenyl]-4-yl)-4,6-diphenyl-1,3,5-triazine was used instead of 2-chloro-4,6-diphenyl-1,3,5-triazine.

<Preparation Example 98> Preparation of Compound 936

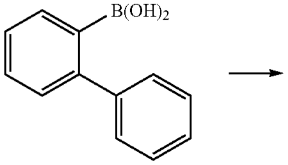

-continued

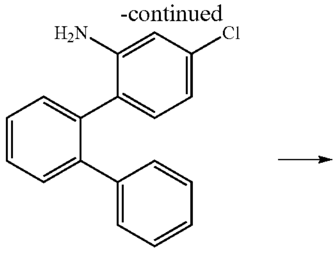

355-1

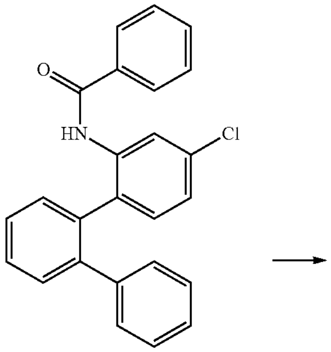

355-2

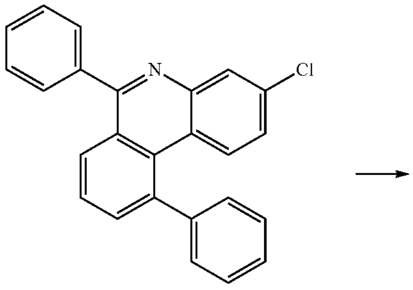

355-3

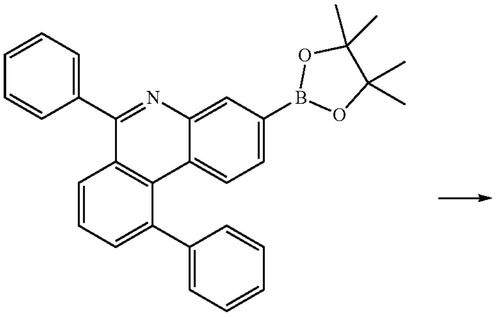

355-4

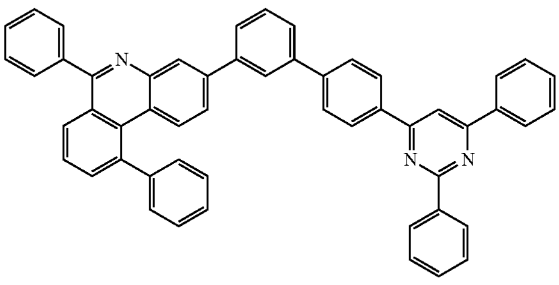

936

Preparation of Compound 936

Target Compound 936 was obtained in the same manner as in the preparation of Compound 355 of Preparation Example 56 except that 4-(3'-bromo-[1,1'-biphenyl]-4-yl)-2,6-diphenylpyrimidine was used instead of 2-chloro-4,6-diphenyl-1,3,5-triazine.

Compounds other than the compounds described in Preparation Example 1 to Preparation Example 98 were also prepared in the same manner as in the preparation examples described above.

The following Table 1 and Table 2 present 1H NMR data and FD-MS data of the synthesized compounds, and through the following data, syntheses of target compounds may be identified.

TABLE 1

| NO | $^1$H NMR ($CDCl_3$, 300 Mz) |
|---|---|
| 1 | 7.41-7.58 (m, 11H), 7.70-7.96 (m, 12H), 8.20 (d, 1H), 8.36 (d, 2H) |
| 4 | 7.41-7.58 (m, 11H), 7.70 (t, 1H), 7.79-7.96 (m, 7H), 7.79 (d, 1H), 8.36-8.38 (m, 4H), 8.69 (d, 2H) |
| 5 | 7.41-7.46 (m, 3H), 7.57-8.20 (m, 21H), 8.49 (d, 2H), 8.69 (d, 2H), 9.09 (s, 2H) |
| 6 | 7.25 (d, 2H), 7.41-7.58 (m, 11H), 7.70 (m, 1H), 7.79-7.96 (m, 9H), 8.20 (d, 1H), 8.36-8.38 (m, 4H), 8.69 (d, 2H) |
| 8 | 7.41-7.58 (m, 11H), 7.70 (m, 1H), 7.79-7.96 (m, 11H), 8.20-8.23 (m, 2H), 8.69 (d, 2H) |
| 9 | 7.41-7.58 (m, 11H), 7.70-7.79 (m, 8H), 8.20-8.23 (m, 2H), 8.30-8.35 (m, 4H), 8.69 (d, 2H) |
| 12 | 7.41-7.58 (m, 11H), 7.75-7.93 (m, 10H), 8.20-8.35 (m, 8H), 8.69 (d, 2H) |
| 16 | 7.41-7.58 (m, 11H), 7.70-7.85 (m, 14H), 8.20-8.23 (m, 2H), 8.30-8.35 (m, 6H), 8.69 (d, 2H) |
| 22 | 7.41-7.61 (m, 12H), 7.75-7.94 (m, 15H), 8.20-8.35 (m, 10H), |
| 25 | 7.39 (m, 1H), 7.50-7.58 (m, 9H), 7.70-7.96 (m, 7H), 8.09 (d, 1H), 8.20 (d, 2H), 8.36-8.38 (m, 4H), 8.50 (d, 1H), 8.69 (d, 2H), 8.95 (d, 1H) |
| 29 | 7.16-7.20 (m, 2H), 7.35 (m, 1H), 7.47-7.70 (m, 14H), 7.85-7.96 (m, 6H), 8.20-8.21 (m, 2H), 8.36-8.38 (m, 4H), 8.55 (d, 1H), 8.69 (d, 2H) |
| 33 | 7.16-7.20 (m, 2H), 7.35-7.75 (m, 17H), 7.84-7.94 (m, 6H), 8.20-8.35 (m, 10H), 8.55 (d, 1H), 8.69 (d, 2H) |
| 35 | 7.41-7.58 (m, 9H), 7.70-7.96 (m, 14H), 8.13-8.20 (m, 2H), 8.30 (d, 2H), 8.69 (d, 2H) |
| 43 | 7.41-7.58 (m, 9H), 7.70-7.94 (m, 8H), 8.13-8.20 (m, 2H), 8.30-8.35 (m, 4H), 8.69 d, 2H) |
| 46 | 7.29 (d, 1H), 7.41-7.58 (m, 6H), 7.70-7.94 (m, 7H), 8.20 (d, 2H), 8.45 (d, 1H), 8.69-8.71 (m, 5H), 8.80 (d, 1H) |
| 48 | 7.29 (d, 2H), 7.41-7.58 (m, 8H), 7.70 (m, 1H), 7.79-7.94 (m, 6H), 8.20 (d, 2H), 8.33 (d, 2H), 8.69-8.71 (m, 6H) |
| 49 | 7.29 (d, 1H), 7.41-7.94 (m, 17H), 8.20 (d, 2H), 8.33 (d, 2H), 8.45 (d, 1H), 8.69-8.71 (m, 3H), 8.80 (d, 1H) |
| 55 | 1.30 (t, 3H), 2.85 (m, 2H), 7.21-7.28 (m, 2H), 7.41-7.58 (m, 6H), 7.70-7.94 (m, 8H), 8.16-8.20 (m, 3H), 8.56 (d, 1H) |
| 56 | 1.30 (t, 3H), 2.85 (m, 2H), 7.21-7.28 (m, 2H), 7.41-7.58 (m, 6H), 7.70-7.94 (m, 12H), 8.20 (d, 1H), 8.56 (d, 1H), 8.69 (d, 2H) |
| 63 | 1.30 (t, 3H), 2.85 (m, 2H), 7.21-7.28 (m, 2H), 7.41-7.61 (m, 7H), 7.70-7.94 (m, 11H), 8.20 (d, 1H), 8.33 (m, 2H), 8.56 (d, 1H) |
| 65 | 7.29 (d, 2H), 7.41-7.60 (m, 10H), 7.70-7.96 (m, 9H), 8.20 (d, 2H), 8.33 (d, 2H), 8.69-8.71 (m, 6H) |
| 67 | 7.16-7.20 (m, 2H), 7.29-7.35 (m, 3H), 7.49-7.70 (m, 11H), 7.85-7.94 (m, 5H), 8.19-8.21 (m, 4H), 8.33 (d, 2H), 8.55 (d, 1H), 8.69-8.71 (m, 6H) |
| 71 | 1.30 (t, 3H), 2.85 (m, 2H), 7.21-7.28 (m, 2H), 7.41-7.94 (m, 18H), 8.16-8.20 (m, 3H), 8.56 (d, 1H) |
| 73 | 1.30 (t, 3H), 2.85 (m, 2H), 7.16-7.35 (m, 5H), 7.50-7.70 (m, 9H), 7.80-7.94 (m, 6H), 8.16-8.21 (m, 5H), 8.55-8.56 (m, 2H), |
| 77 | 7.41-7.58 (m, 11H), 7.70-7.94 (m, 8H), 8.20-8.29 (m, 7H), 8.69 (d, 2H) |
| 79 | 6.88 (d, 1H), 7.23 (t, 1H), 7.37-7.46 (m, 4H), 7.57-7.58 (m, 2H), 7.70-7.94 (m, 7H), 8.20 (d, 1H), 8.55 (d, 1H), 8.69 (s, 4H), 8.78 (d, 1H), 9.18 (d, 1H) |
| 81 | 7.41-7.58 (m, 14H), 7.70-7.94 (m, 12H), 8.04 (s, 3H), 8.20 (d, 1H), 8.36 (d, 2H), 8.69 (d,2H) |
| 83 | 7.41-7.61 (m, 12H), 7.70-7.94 (m, 12H), 8.20 (d, 1H), 8.36-8.38 (m, 3H), 8.69 (d, 2H) |

TABLE 1-continued

| NO | $^1$H NMR ($CDCl_3$, 300 Mz) |
|---|---|
| 100 | 7.16-7.20 (m, 2H), 7.35-7.75 (m, 19H), 7.85-7.94 (m, 6H), 8.19-8.23 (m, 4H), 8.30-8.35 (m, 4H), 8.55 (d, 1H), 8.69 (d, 2H) |
| 103 | 7.25 (d, 2H), 7.39-8.09 (m, 14H), 8.20 (d, 2H), 8.50-8.55 (m, 2H), 8.69 (d, 2H), 8.87-8.95 (m, 2H) |
| 105 | 7.25 (d, 2H), 7.49-7.70 (m, 11H), 7.85-7.96 (m, 4H), 8.05 (d, 1H), 8.20 (d, 1H), 8.23-8.33 (m, 3H), 8.55 (d, 1H), 8.69 (d, 2H), 8.87 (d, 1H), 9.27 (s, 1H), 9.60 (d, 1H) |
| 106 | 7.25 (d, 4H), 7.39-7.61 (m, 14H), 7.70-7.94 (m, 12H), 8.20 (d, 2H), 8.69 (d, 4H), 9.00 (d, 2H) |
| 109 | 7.25 (d, 4H), 7.39-7.61 (m, 15H), 7.70-7.96 (m, 8H), 8.20 (d, 1H), 8.36 (d, 4H), 8.69 (d, 2H), 9.00 (d, 2H) |
| 113 | 7.25 (m, 6H), 7.41-7.58 (m, 11H), 7.70 (t, 1H), 7.79-7.96 (m, 9H), 8.20 (d, 1H), 8.36 (d, 4H), 8.69 (d, 2H) |
| 116 | 7.25 (m, 6H), 7.49-7.70 (m, 12H), 7.85-7.96 (m, 5H), 8.19-8.20 (m, 3H), 8.36 (m, 4H) |
| 117 | 7.25 (m, 6H), 7.50-7.70 (m, 11H), 7.85-8.06 (m, 8H), 8.20 (d, 1H), 8.36-8.38 (m, 5H), 8.85 (s, 1H) |
| 121 | 7.25 (s, 4H), 7.49-7.70 (m, 11H), 7.85-8.06 (m, 10H), 8.20-8.37 (m, 7H), 8.85 (s, 1H) |
| 122 | 7.25 (d, 2H), 7.50-7.73 (m, 14H), 7.85-8.06 (m, 9H), 8.20 (d, 1H), 8.36-8.38 (m, 4H), 8.85 (s, 1H) |
| 124 | 7.41-7.58 (m, 15H), 7.70 (m, 1H), 7.79-7.94 (m, 7H), 8.20-8.23 (m, 6H), 8.35 (d, 2H) |
| 135 | 7.41-7.58 (m, 11H), 7.70-7.93 (m, 14H), 8.20 (d, 1H), 8.36 (d, 4H), 8.69 (d, 2H) |
| 136 | 7.41-7.58 (m, 11H), 7.70-7.94 (m, 16H), 8.20-8.23 (m, 2H), 8.35 (d, 2H), 8.69 (d, 2H) |
| 137 | 6.93 (d, 2H), 7.25 (d, 2H), 7.41-7.58 (m, 11H), 7.70 (m, 1H), 7.79-7.94 (m, 7H), 8.20-8.22 (m, 3H), 8.36 (d, 4H) |
| 139 | 7.25 (d, 2H), 7.49-7.70 (m, 12H), 7.85-7.96 (m, 5H), 8.19-8.26 (m, 3H), 8.36 (m, 4H) |
| 142 | 7.25 (d, 2H), 7.41-7.75 (m, 16H), 7.85-7.96 (m, 6H), 8.19-8.26 (m, 3H), 8.36-8.38 (m, 3H) |
| 145 | 7.16-7.25 (m, 4H), 7.35 (m, 1H), 7.49-7.70 (m, 13H), 7.85-7.96 (m, 6H), 8.19-8.24 (m, 6H), 8.36 (d, 2H), 8.55 (d, 1H) |
| 147 | 7.25 (d, 2H), 7.49-7.70 (m, 10H), 7.93-8.19 (m, 14H), 8.49 (d, 2H), 9.09 (s, 2H) |
| 154 | 7.25 (d, 2H), 7.49-7.70 (m, 12H), 7.85-7.94 (m, 5H), 8.30-8.35 (m, 4H) |
| 155 | 7.25 (d, 4H), 7.41-7.70 (m, 14H), 7.85-7.96 (m, 7H), 8.19-8.23 (m, 4H), 8.30 (d, 2H) |
| 160 | 7.16-7.25 (m, 4H), 7.35 (m, 1H), 7.49-7.70 (m, 13H), 7.80-7.94 (m, 5H), 8.19-8.35 (m, 10H), 8.55 (d, 1H) |
| 164 | 7.25-7.70 (m, 17H), 7.85-8.08 (m, 6H), 8.19-8.35 (m, 10H) |
| 165 | 7.25 (d, 4H), 7.49-7.70 (m, 12H), 7.85-7.94 (m, 4H), 8.19-8.35 (m, 11H), 8.45 (d, 1H), 8.55 (d, 1H) |
| 166 | 7.25 (d, 2H), 7.50-7.97 (m, 26H), 8.19-8.23 (m, 4H), 8.30-8.35 (m, 4H) |
| 184 | 7.25 (d, 4H), 7.49-7.70 (m, 12H), 7.85-7.94 (m, 7H), 8.19-8.23 (m, 4H), 8.30-8.35 (m, 4H) |
| 199 | 7.25 (d, 4H), 7.49-7.73 (m, 14H), 7.85-7.94 (m, 4H), 8.19-8.20 (m, 3H), 8.36-8.38 (m, 5H) |
| 229 | 7.23-7.25 (m, 10H), 7.49-7.57 (m, 2H), 7.58-7.74 (m, 6H), 7.85-7.94 (m, 3H), 8.19-8.20 (m, 3H), 8.55 (d, 2H), 9.14-9.18 (m, 4H) |
| 232 | 7.23-7.25 (m, 5H), 7.49-7.74 (m, 7H), 7.85-8.00 (m, 4H), 8.19-8.20 (m, 3H), 8.55 (d, 1H), 8.93-8.97 (m, 2H), 9.18 (d, 1H) |
| 241 | 7.25-7.28 (m, 7H), 7.38 (d, 2H), 7.48-7.70 (m, 10H), 7.81-7.96 (m, 6H), 8.19-8.20 (m, 3H), 8.56 (d, 1H) |
| 245 | 7.25-7.29 (m, 4H), 7.49-7.70 (m, 9H), 7.85-7.94 (m, 4H), 8.19-8.20 (m, 4H), 8.33 (d, 2H), 8.69-8.71 (m, 4H) |
| 246 | 7.25-7.29 (m, 3H), 7.49-7.70 (m, 7H), 7.85-7.94 (m, 4H), 8.19-8.20 (m, 4H), 8.45 (d, 1H), 8.69-8.71 (m, 3H), 8.80 (d, 1H) |
| 247 | 7.49-7.73 (m, 14H), 7.85-7.94 (m, 4H), 8.19-8.20 (m, 3H), 8.36-8.38 (m, 5H) |
| 277 | 7.25 (d, 2H), 7.49-7.73 (m, 15H), 7.85-7.96 (m, 6H), 8.19-8.20 (m, 3H), 8.36 (d, 4H) |
| 299 | 2.34 (s, 6H), 7.15 (m, 2H), 7.45-7.73 (m, 13H), 7.85-7.94 (m, 6H), 8.19-8.23 (m, 4H), 8.30 (d, 2H), 8.60 (d, 2H) |
| 307 | 7.49-7.73 (m, 17H), 7.85-7.94 (m, 5H), 8.19-8.20 (m, 3H), 8.36-8.38 (m, 5H) |
| 353 | 7.29 (d, 2H), 7.49-7.73 (m, 11H), 7.85-7.94 (m, 4H), 8.19-8.20 (m, 4H), 8.33 (m, 4H), 8.71 (d, 2H) |
| 354 | 7.29 (d, 1H), 7.49-7.73 (m, 9H), 7.85-7.94 (m, 4H), 8.19-8.20 (m, 4H), 8.33 (m, 2H), 8.45 (d, 1H), 8.71 (d, 1H), 8.80 (d, 1H) |

TABLE 1-continued

| NO | $^1$H NMR ($CDCl_3$, 300 Mz) |
|---|---|
| 355 | 7.41-7.65 (m, 14H), 7.79 (d, 2H), 7.93 (d, 1H), 8.19-8.24 (m, 3H), 8.36-8.37 (m, 6H) |
| 385 | 7.25 (d, 2H), 7.41-7.65 (m, 14H), 7.79 (d, 2H), 7.90-7.96 (m, 4H), 8.19-8.23 (m, 3H), 8.36 (d, 4H), 8.45 (d, 1H) |
| 397 | 7.25 (d, 2H), 7.41-7.65 (m, 17H), 7.77-7.79 (m, 6H), 7.90-7.97 (m, 8H), 8.19-8.23 (m, 3H), 8.36 (d, 2H), 8.45 (d, 1H) |
| 400 | 7.41-7.65 (m, 14H), 7.79-7.94 (m, 8H), 8.19-8.35 (m, 8H), 8.45 (d, 1H) |
| 412 | 7.41-7.65 (m, 17H), 7.77-7.97 (m, 14H), 8.19-8.23 (m, 4H), 8.30-8.35 (m, 4H), 8.45 (d, 1H) |
| 415 | 7.41-7.79 (m, 18H), 7.90-7.94 (m, 3H), 8.19-8.23 (m, 3H), 8.36-8.45 (m, 6H) |
| 455 | 7.25 (d, 2H), 7.41-7.65 (m, 10H), 7.79 (d, 2H), 7.90-8.02 (m, 5H), 8.18-8.23 (m, 4H), |
| 463 | 7.46-7.65 (m, 14H), 7.79 (d, 2H), 7.93 (d, 1H), 8.08 (s, 1H), 8.19-8.25 (m, 3H), 8.36 (d, 4H) |
| 493 | 7.25 (d, 2H), 7.41-7.65 (m, 14H), 7.79 (d, 2H), 7.93-7.96 (m, 4H), 8.09 (d, 1H), 8.19 (d, 2H), 8.31-8.36 (m, 5H) |
| 508 | 7.41-7.65 (m, 14H), 7.79-7.94 (m, 8H), 8.09 (d, 1H), 8.19-8.23 (m, 3H), 8.30-8.35 (m, 5H) |
| 523 | 7.41-7.79 (m, 18H), 7.93-7.94 (m, 3H), 8.09 (d, 1H), 8.19 (d, 2H), 8.31-8.38 (m, 6H) |
| 538 | 7.41-7.73 (m, 18H), 7.93-7.94 (m ,6H), 8.09 (d, 1H), 8.19-8.23 (m, 3H), 8.31-8.35 (m, 3H) |
| 569 | 7.29 (d, 2H), 7.41-7.65 (m, 11H), 7.79 (d, 1H), 7.90-7.93 (m, 2H), 8.19-8.33 (m, 6H), 8.47 (s, 1H), 8.71 (d, 2H), 8.82 (d, 1H) |
| 601 | 7.25 (d, 2H), 7.41-7.65 (m, 15H), 7.79 (d, 2H), 7.93-7.98 (m, 4H), 8.14-8.19 (m, 3H), 8.36 (d, 4H) |
| 616 | 7.25 (d, 2H), 7.41-7.65 (m, 15H), 7.79 (d, 2H), 7.93-7.98 (m, 4H), 8.14-8.23 (m, 4H), 8.30-8.35 (m, 4H) |
| 631 | 7.41-7.79 (m, 19H), 7.93-7.98 (m, 3H), 8.14-8.19 (m, 3H), 8.36-8.38 (m, 5H) |
| 646 | 7.41-7.79 (m, 19H), 7.93-7.98 (m, 6H), 8.14-8.23 (m, 4H), 8.35 (d, 2H) |
| 661 | 7.23-7.25 (m, 6H), 7.41-7.79 (m, 13H), 7.93-7.98 (m, 2H), 8.14-8.19 (m, 3H), 8.55 (d, 2H), 9.14-9.18 (m, 4H) |
| 677 | 7.29 (d, 2H), 7.41-7.65 (m, 11H), 7.79-7.93 (m, 5H), 8.19-8.20 (m, 3H), 8.30-8.33 (m, 3H), 8.71 (d, 2H), 9.04 (d, 1H) |
| 679 | 7.25 (d, 6H), 7.50-7.59 (m, 10H), 7.70 (m, 1H), 7.85-8.00 (m, 6H), 8.15-8.25 (m, 3H), 8.36 (d, 4H), 8.49 (d, 1H), 8.97 (d, 1H) |
| 699 | 7.25 (d, 2H), 7.50-7.73 (m, 13H), 7.83 (m, 1H), 7.93-7.96 (m, 5H), 8.14 (d, 1H), 8.36 (d, 4H), 8.70 (d, 1H), 8.81 (d, 1H), 9.63 (s, 1H) |
| 706 | 7.25-7.29 (m, 4H), 7.49-7.58 (m, 5H), 7.69 (m, 1H), 7.83-7.96 (m, 4H), 8.14-8.20 (m, 2H), 8.33 (d, 2H), 8.69-8.75 (m, 6H) |
| 711 | 7.25 (d, 6H), 7.41-7.58 (m, 11H), 7.70-7.75 (m, 3H), 7.85-7.96 (m, 7H), 8.20 (d, 1H), 8.36 (d, 4H), 8.69 (d, 2H) |
| 720 | 7.25 (s, 4H), 7.41-7.61 (m, 12H), 7.70-7.75 (m, 4H), 7.85-7.94 (m, 7H), 8.20-8.23 (m, 2H), 8.30-8.35 (m, 6H) |
| 727 | 7.25 (d, 6H), 7.41-7.60 (m, 13H), 7.70 (m, 1H), 7.79-7.96 (m, 8H), 8.20 (d, 1H), 8.35-8.36(m, 5H) |
| 735 | 7.25 (d, 2H), 7.39 (m, 1H), 7.49-7.65 (m, 12H), 7.77 (m, 1H), 7.90-7.96 (m, 4H), 8.09 (d, 1H), 8.19-8.23 (m, 4H), 8.36 (d, 4H), 8.45-8.50 (m, 2H), 8.95 (d, 1H) |
| 740 | 6.90 (m, 1H), 7.14 (d, 1H), 7.38 (m, 1H), 7.49-7.65 (m, 9H), 7.80-7.94 (m, 6H), 8.09 (d, 1H), 8.19-8.45 (m, 11H) |
| 755 | 7.25 (d, 2H), 7.41-7.75 (m, 19H), 7.90-7.96 (m, 5H), 8.19-8.23 (m, 3H), 8.36 (d, 4H), 8.45 (d, 1H) |
| 763 | 7.25 (d, 2H), 7.41-7.59 (m, 13H), 7.79 (d, 2H), 7.90-8.00 (m, 5H), 8.15 (d, 1H), 8.23-8.25 (m, 2H), 8.36 (d, 4H), 8.45-8.49 (m, 2H), 8.97 (d, 1H) |
| 764 | 7.41-7.59 (m, 13H), 7.79-8.00 (m, 9H), 8.15 (d, 1H), 8.23-8.35 (m, 7H), 8.45-8.49 (d, 2H), 8.97 (d, 1H) |
| 776 | 7.41-7.58 (m, 11H), 7.79-7.94 (m, 8H), 8.23-8.38 (m, 9H), 8.75 (d, 2H) |
| 779 | 7.25 (d, 2H), 7.41-7.58 (m, 14H), 7.75-7.96 (m, 10H), 8.23 (s, 1H), 8.36 (d, 4H), 8.45 (d, 1H), 8.69 (d, 2H) |
| 827 | 7.25 (d, 2H), 7.41-7.58 (m, 12H), 7.79 (d, 2H), 7.88-7.96 (m, 4H), 8.07 (d, 1H), 8.33-8.36 (m, 5H), 8.70 (d, 1H), 8.81 (d, 1H), 9.63 (s, 1H) |
| 831 | 7.25 (d, 2H), 7.41-7.58 (m, 11H), 7.79 (d, 2H), 7.88-7.96 (m, 4H), 8.07 (d, 1H), 8.33-8.38 (m, 7H), 8.75 (d, 2H) |
| 848 | 7.25 (d, 2H), 7.39-7.65 (m, 14H), 7.77 (m, 1H), 7.93-7.98 (m, 4H), 8.09-8.23 (m, 6H), 8.30-8.35 (m, 4H), 8.50 (d, 1H), 8.95 (d, 1H) |

TABLE 1-continued

| NO | $^1H$ NMR ($CDCl_3$, 300 Mz) |
|---|---|
| 856 | 7.25 (d, 2H), 7.49-7.65 (m, 11H), 7.80 (m, 1H), 7.94-8.42 (m, 14H), 8.70 (d, 1H), 9.24 (s, 1H) |
| 875 | 7.25 (d, 2H), 7.41-7.65 (m, 14H), 7.79 (d, 2H), 7.93-8.00 (m, 5H), 8.14-8.15 (m, 2H), 8.25 (d, 1H), 8.36 (d, 4H), 8.49 (d, 1H), 8.97 (d, 1H) |
| 908 | 7.25 (s, 4H), 7.41-7.65 (m, 14H), 7.75 (d, 2H), 7.85-7.94 (m, 6H), 8.19-8.35 (m, 8H), 8.45 (d, 1H) |
| 911 | 7.25 (m, 6H), 7.41-7.65 (m, 14H), 7.79 (d, 2H), 7.90-7.96 (m, 4H), 8.19 (d, 2H), 8.36 (d, 4H), 8.45 (d, 1H) |
| 912 | 7.25 (s, 4H), 7.41-7.65 (m, 14H), 7.79-7.93 (m, 8H), 8.19-8.35 (m, 7H), 8.45 (d, 1H) |
| 914 | 7.29 (d, 2H), 7.41-7.65 (m, 11H), 7.79-7.93 (m, 7H), 8.19-8.23 (m, 4H), 8.33 (d, 2H), 8.45 (d, 1H), 8.69-8.71 (m, 3H) |
| 935 | 7.25 (d, 2H), 7.41-7.79 (m, 19H), 7.90-7.96 (m, 5H), 8.19-8.23 (m, 3H), 8.36 (d, 4H), 8.45 (d, 1H) |
| 936 | 7.41-7.94 (m, 26H), 8.19-8.35 (m, 8H), 8.45 (d, 1H) |

TABLE 2

| Compound | FD-MS |
|---|---|
| 1 | m/z = 531.58 (C37H26NOP = 531.18) |
| 2 | m/z = 607.68 (C43H30NOP = 607.21) |
| 3 | m/z = 657.74 (C47H32NOP = 657.22) |
| 4 | m/z = 562.66 (C40H26N4 = 562.22) |
| 5 | m/z = 662.78 (C48H30N4 = 662.25) |
| 6 | m/z = 638.76 (C46H30N4 = 638.25) |
| 7 | m/z = 688.82 (C50H32N4 = 688.26) |
| 8 | m/z = 561.67 (C41H27N3 = 561.22) |
| 9 | m/z = 561.67 (C41H27N3 = 561.22) |
| 10 | m/z = 661.79 (C49H31N3 = 661.25) |
| 11 | m/z = 737.89 (C55H35N3 = 737.28) |
| 12 | m/z = 637.77 (C47H31N3 = 637.25) |
| 13 | m/z = 713.87 (C53H35N3 = 713.28) |
| 14 | m/z = 637.77 (C47H31N3 = 637.25) |
| 15 | m/z = 789.96 (C59H39N3 = 789.31) |
| 16 | m/z = 713.87 (C53H35N3 = 713.28) |
| 17 | m/z = 763.92 (C57H37N3 = 763.30) |
| 18 | m/z = 607.68 (C43H3ONOP = 607.21) |
| 19 | m/z = 638.76 (C46H30N4 = 638.25) |
| 20 | m/z = 637.77 (C47H31N3 = 637.25) |
| 21 | m/z = 637.77 (C47H31N3 = 637.25) |
| 22 | m/z = 713.87 (C53H35N3 = 713.28) |
| 23 | m/z = 638.76 (C46H30N4 = 638.25) |
| 24 | m/z = 638.76 (C46H30N4 = 638.25) |
| 25 | m/z = 612.72 (C44H28N4 = 612.23) |
| 26 | m/z = 612.72 (C44H28N4 = 612.23) |
| 27 | m/z = 662.78 (C48H30N4 = 662.25) |
| 28 | m/z = 727.85 (C52H33N5 = 727.27) |
| 29 | m/z = 727.85 (C52H33N5 = 727.27) |
| 30 | m/z = 728.84 (C52H32N40 = 728.26) |
| 31 | m/z = 728.84 (C52H32N40 = 728.26) |
| 32 | m/z = 744.90 (C52H32N4S = 744.23) |
| 33 | m/z = 802.96 (C59H38N4 = 802.31) |
| 34 | m/z = 803.95 (C58H37N5 = 803.30) |
| 35 | m/z = 611.73 (C45H29N3 = 611.24) |
| 36 | m/z = 535.64 (C39H25N3 = 535.20) |
| 37 | m/z = 585.69 (C43H27N3 = 585.22) |
| 38 | m/z = 687.83 (C51H33N3 = 687.27) |
| 39 | m/z = 611.73 (C45H29N3 = 611.24) |
| 40 | m/z = 637.77 (C47H31N3 = 637.25) |
| 41 | m/z = 737.89 (C55H35N3 = 737.28) |
| 42 | m/z = 713.87 (C53H35N3 = 713.28) |
| 43 | m/z = 535.64 (C39H25N3 = 535.20) |
| 44 | m/z = 611.73 (C45H29N3 = 611.24) |
| 45 | m/z = 611.73 (C45H29N3 = 611.24) |
| 46 | m/z = 509.60 (C37H23N3 = 509.19) |
| 47 | m/z = 585.69 (C47H23N3 = 585.22) |
| 48 | m/z = 585.69 (C47H23N3 = 585.22) |
| 49 | m/z = 585.69 (C47H23N3 = 585.22) |
| 50 | m/z = 523.63 (C38H25N3 = 523.20) |
| 51 | m/z = 523.63 (C38H25N3 = 523.20) |
| 52 | m/z = 523.63 (C38H25N3 = 523.20) |
| 53 | m/z = 551.68 (C40H29N3 = 551.24) |
| 54 | m/z = 559.72 (C44H29N3 = 559.24) |

TABLE 2-continued

| Compound | FD-MS |
|---|---|
| 55 | m/z = 475.58 (C34H25N3 = 475.20) |
| 56 | m/z = 551.68 (C40H29N3 = 551.24) |
| 57 | m/z = 540.68 (C38H24N2S = 540.17) |
| 58 | m/z = 540.68 (C38H24N2S = 540.17) |
| 59 | m/z = 611.73 (C45H29N3 = 611.24) |
| 60 | m/z = 611.73 (C45H29N3 = 611.24) |
| 61 | m/z = 585.69 (C47H23N3 = 585.22) |
| 62 | m/z = 551.68 (C40H29N3 = 551.24) |
| 63 | m/z = 551.68 (C40H29N3 = 551.24) |
| 64 | m/z = 700.83 (C51H32N4 = 700.26) |
| 65 | m/z = 661.79 (C49H31N3 = 661.25) |
| 66 | m/z = 661.79 (C49H31N3 = 661.25) |
| 67 | m/z = 750.89 (C55H34N4 = 750.28) |
| 68 | m/z = 751.87 (C55H33N3O = 751.26) |
| 69 | m/z = 751.87 (C55H33N3O = 751.26) |
| 70 | m/z = 767.94 (C55H33N3S = 767.24) |
| 71 | m/z = 551.68 (C40H29N3 = 551.24) |
| 72 | m/z = 525.64 (C38H27N3 = 525.22) |
| 73 | m/z = 640.77 (C46H32N4 = 640.26) |
| 74 | m/z = 641.76 (C46H31N30 = 641.25) |
| 75 | m/z = 657.82 (C46H31N3S = 657.22) |
| 76 | m/z = 657.82 (C46H31N3S = 657.22) |
| 77 | m/z = 560.69 (C42H28N2 = 560.23) |
| 78 | m/z = 636.78 (C48H32N2 = 636.26) |
| 79 | m/z = 485.58 (C35H23N3 = 485.19) |
| 80 | m/z = 561.67 (C41H27N3 = 561.22) |
| 81 | m/z = 714.85 (C52H34N4 = 714.28) |
| 82 | m/z = 458.55 (C34H22N2 = 458.18) |
| 83 | m/z = 638.76 (C46H30N4 = 638.25) |
| 84 | m/z = 458.55 (C34H22N2 = 458.18) |
| 85 | m/z = 475.54 (C33H21N30 = 475.17) |
| 86 | m/z = 432.51 (C32H20N2 = 432.16) |
| 87 | m/z = 408.49 (C30H20N2 = 408.16) |
| 88 | m/z = 484.59 (C36H24N2 = 484.19) |
| 89 | m/z = 534.65 (C40H26N2 = 534.21) |
| 90 | m/z = 534.65 (C40H26N2 = 534.21) |
| 91 | m/z = 523.63 (C38H25N3 = 523.20) |
| 92 | m/z = 599.72 (C44H29N3 = 599.24) |
| 93 | m/z = 458.55 (C34H22N2 = 458.18) |
| 94 | m/z = 636.78 (C48H32N2 = 636.26) |
| 95 | m/z = 561.67 (C41H27N3 = 561.22) |
| 96 | m/z = 599.72 (C44H29N3 = 599.24) |
| 97 | m/z = 803.95 (C58H37N5 = 803.30) |
| 98 | m/z = 804.93 (C58H36N40 = 804.29) |
| 99 | m/z = 821.00 (C58H36N4S = 820.27) |
| 100 | m/z = 802.96 (C59H38N4 = 802.31) |
| 101 | m/z = 803.94 (C59H37N30 = 803.29) |
| 102 | m/z = 820.01 (C59H37N3S = 819.27) |
| 103 | m/z = 508.61 (C38H24N4 = 508.19) |
| 104 | m/z = 558.67 (C42H26N2 = 558.21) |
| 105 | m/z = 608.73 (C46H28N2 = 608.23) |
| 106 | m/z = 786.96 (C60H38N2 = 786.30) |
| 107 | m/z = 837.02 (C64H40N2 = 836.32) |
| 108 | m/z = 764.91 (C56H36N4 = 764.29) |
| 109 | m/z = 764.91 (C56H36N4 = 764.29) |
| 110 | m/z = 688.82 (C50H32N4 = 688.26) |
| 111 | m/z = 688.82 (C50H32N4 = 688.26) |
| 112 | m/z = 764.91 (C56H36N4 = 764.29) |
| 113 | m/z = 714.85 (C52H34N4 = 714.28) |
| 114 | m/z = 591.72 (C41H25N3S = 591.18) |
| 115 | m/z = 591.72 (C41H25N3S = 591.18) |
| 116 | m/z = 638.76 (C46H30N4 = 638.25) |
| 117 | m/z = 688.82 (C50H32N4 = 688.26) |
| 118 | m/z = 662.24 (C48H30N4 = 662.79) |
| 119 | m/z = 688.26 (C50H32N4 = 688.83) |
| 120 | m/z = 662.24 (C48H30N4 = 662.79) |
| 121 | m/z = 687.27 (C51H33N3 = 687.83) |
| 122 | m/z = 688.26 (C50H32N4 = 688.82) |
| 123 | m/z = 687.27 (C51H33N3 = 687.83) |
| 124 | m/z = 661.25 (C49H31N3 = 661.79) |
| 125 | m/z = 738.28 (C54H34N4 = 738.87) |
| 126 | m/z = 737.28 (C55H35N3 = 737.89) |
| 127 | m/z = 685.25 (C51H31N3 = 685.81) |
| 128 | m/z = 762.28 (C56H34N4 = 762.90) |
| 129 | m/z = 761.28 (C57H35N3 = 761.91) |
| 130 | m/z = 661.25 (C49H31N3 = 661.79) |
| 131 | m/z = 738.28 (C54H34N4 = 738.87) |
| 132 | m/z = 737.28 (C55H35N3 = 737.90) |

TABLE 2-continued

| Compound | FD-MS |
|---|---|
| 133 | m/z = 730.27 (C52H34N4O = 730.87) |
| 134 | m/z = 729.27 (C53H35N3O = 729.88) |
| 135 | m/z = 728.25 (C52H32N4O = 728.85) |
| 136 | m/z = 727.26 (C53H33N3O = 727.86) |
| 137 | m/z = 654.24 (C46H30N4O = 654.77) |
| 138 | m/z = 653.24 (C47H31N3O = 653.78) |
| 139 | m/z = 562.21 (C40H26N4 = 562.67) |
| 140 | m/z = 638.24 (C46H30N4 = 638.77) |
| 141 | m/z = 714.27 (C52H34N4 = 714.87) |
| 142 | m/z = 638.24 (C46H30N4 = 638.77) |
| 143 | m/z = 714.27 (C52H34N4 = 714.87) |
| 144 | m/z = 727.27 (C52H33N5 = 727.87) |
| 145 | m/z = 727.27 (C52H33N5 = 727.87) |
| 146 | m/z = 590.24 (C42H30N4 = 590.73) |
| 147 | m/z = 662.24 (C48H30N4 = 662.79) |
| 148 | m/z = 714.27 (C52H34N4 = 714.87) |
| 149 | m/z = 728.25 (C52H32N4O = 728.85) |
| 150 | m/z = 744.23 (C52H32N4S = 744.91) |
| 151 | m/z = 762.25(C52H35N40P = 762.85) |
| 152 | m/z = 754.30 (C55H38N4 = 754.93) |
| 153 | m/z = 762.27 (C56H34N4 = 762.91) |
| 154 | m/z = 561.22 (C41H27N3 = 561.68) |
| 155 | m/z = 637.25 (C47H31N3 = 637.78) |
| 156 | m/z = 713.28 (C55H35N3 = 713.88) |
| 157 | m/z = 637.25 (C47H31N3 = 637.78) |
| 158 | m/z = 713.28 (C55H35N3 = 713.88) |
| 159 | m/z = 726.27 (C53H34N4 = 726.88) |
| 160 | m/z = 726.27 (C53H34N4 = 726.88) |
| 161 | m/z = 589.25 (C43H31N3 = 589.74) |
| 162 | m/z = 661.25 (C49H31N3 = 661.80) |
| 163 | m/z = 713.28 (C55H35N3 = 713.88) |
| 164 | m/z = 727.26 (C53H33N30 = 727.86) |
| 165 | m/z = 743.23 (C53H33N3S = 743.92) |
| 166 | m/z = 761.25 (C53H36N3OP = 761.86) |
| 167 | m/z = 753.31 (C56H39N3 = 753.94) |
| 168 | m/z = 761.28 (C57H35N3 = 761.92) |
| 169 | m/z = 637.25 (C47H31N3 = 637.78) |
| 170 | m/z = 714.27 (C52H34N4 = 714.87) |
| 171 | m/z = 790.30 (C58H38N4 = 790.97) |
| 172 | m/z = 714.27 (C52H34N4 = 714.87) |
| 173 | m/z = 790.30 (C58H38N4 = 790.97) |
| 174 | m/z = 803.30 (C58H37N5 = 803.96) |
| 175 | m/z = 803.30 (C58H37N5 = 803.96) |
| 176 | m/z = 666.27 (C48H34N4 = 666.82) |
| 177 | m/z = 738.27 (C54H34N4 = 738.89) |
| 178 | m/z = 790.30 (C58H38N4 = 790.97) |
| 179 | m/z = 804.28 (C58H36N40 = 804.95) |
| 180 | m/z = 820.26 (C58H36N4S = 821.01) |
| 181 | m/z = 838.28 (C58H39N4OP = 838.95) |
| 182 | m/z = 830.34 (C61H42N4 = 831.03) |
| 183 | m/z = 838.30 (C62H38N4 = 839.01) |
| 184 | m/z = 637.25 (C47H31N3 = 637.78) |
| 185 | m/z = 713.28 (C55H35N3 = 713.88) |
| 186 | m/z = 789.31 (C59H39N3 = 789.98) |
| 187 | m/z = 713.28 (C55H35N3 = 713.88) |
| 188 | m/z = 789.31 (C59H39N3 = 789.98) |
| 189 | m/z = 802.30 (C59H38N4 = 802.98) |
| 190 | m/z = 802.30 (C59H38N4 = 802.98) |
| 191 | m/z = 665.28 (C49H35N3 = 665.84) |
| 192 | m/z = 737.28 (C55H35N3 = 737.90) |
| 193 | m/z = 789.31 (C59H39N3 = 789.98) |
| 194 | m/z = 803.29 (C59H37N3O = 803.96) |
| 195 | m/z = 819.27 (C59H37N3S = 820.02) |
| 196 | m/z = 837.29 (C59H40N3OP = 837.96) |
| 197 | m/z = 829.34 (C62H43N3 = 830.04) |
| 198 | m/z = 837.31 (C63H39N3 = 838.02) |
| 199 | m/z = 638.24 (C46H30N4 = 638.77) |
| 200 | m/z = 714.27 (C52H34N4 = 714.87) |
| 201 | m/z = 790.30 (C58H38N4 = 790.97) |
| 202 | m/z = 714.27 (C52H34N4 = 714.87) |
| 203 | m/z = 790.30 (C58H38N4 = 790.97) |
| 204 | m/z = 803.30 (C58H37N5 = 803.96) |
| 205 | m/z = 803.30 (C58H37N5 = 803.96) |
| 206 | m/z = 666.27 (C48H34N4 = 666.82) |
| 207 | m/z = 738.27 (C54H34N4 = 738.89) |
| 208 | m/z = 790.30 (C58H38N4 = 790.97) |
| 209 | m/z = 804.28 (C58H36N4O = 804.95) |
| 210 | m/z = 820.26 (C58H36N4S = 821.01) |

TABLE 2-continued

| Compound | FD-MS |
|---|---|
| 211 | m/z = 838.28 (C58H39N4OP = 838.95) |
| 212 | m/z = 830.34 (C61H42N4 = 831.03) |
| 213 | m/z = 838.30 (C62H38N4 = 839.01) |
| 214 | m/z = 637.25 (C47H31N3 = 637.78) |
| 215 | m/z = 713.28 (C55H35N3 = 713.88) |
| 216 | m/z = 789.31 (C59H39N3 = 789.98) |
| 217 | m/z = 713.28 (C55H35N3 = 713.88) |
| 218 | m/z = 789.31 (C59H39N3 = 789.98) |
| 219 | m/z = 802.30 (C59H38N4 = 802.98) |
| 220 | m/z = 802.30 (C59H38N4 = 802.98) |
| 221 | m/z = 665.28 (C49H35N3 = 665.84) |
| 222 | m/z = 737.28 (C55H35N3 = 737.90) |
| 223 | m/z = 789.31 (C59H39N3 = 789.98) |
| 224 | m/z = 803.29 (C59H37N3O = 803.96) |
| 225 | m/z = 819.27 (C59H37N3S = 820.02) |
| 226 | m/z = 837.29 (C59H40N3OP = 837.96) |
| 227 | m/z = 829.34 (C62H43N3 = 830.04) |
| 228 | m/z = 837.31 (C63H39N3 = 838.02) |
| 229 | m/z = 638.24 (C46H30N4 = 638.77) |
| 230 | m/z = 737.28 (C55H35N3 = 737.90) |
| 231 | m/z = 591.17 (C41H25N3S = 591.73) |
| 232 | m/z = 485.18 (C35H23N3 = 485.59) |
| 233 | m/z = 551.23 (C40H29N3 = 551.69) |
| 234 | m/z = 637.25 (C47H31N3 = 637.78) |
| 235 | m/z = 483.17 (C33H26NOP = 483.55) |
| 236 | m/z = 535.20 (C39H25N3 = 535.65) |
| 237 | m/z = 593.19 (C41H27N3S = 593.74) |
| 238 | m/z = 535.20 (C39H25N3 = 535.65) |
| 239 | m/z = 540.16 (C38H24N2S = 540.68) |
| 240 | m/z = 524.18 (C38H24N2O = 524.62) |
| 241 | m/z = 599.23 (C44H29N3 = 599.73) |
| 242 | m/z = 599.23 (C44H29N3 = 599.73) |
| 243 | m/z = 607.20 (C43H30NOP = 607.69) |
| 244 | m/z = 607.20 (C43H30NOP = 607.69) |
| 245 | m/z = 585.22 (C43H27N3 = 585.71) |
| 246 | m/z = 509.18 (C37H23N3 = 509.61) |
| 247 | m/z = 562.21 (C40H26N4 = 562.67) |
| 248 | m/z = 638.24 (C46H30N4 = 638.77) |
| 249 | m/z = 714.27 (C52H34N4 = 714.87) |
| 250 | m/z = 638.24 (C46H30N4 = 638.77) |
| 251 | m/z = 714.27 (C52H34N4 = 714.87) |
| 252 | m/z = 727.27 (C52H33N5 = 727.87) |
| 253 | m/z = 727.27 (C52H33N5 = 727.87) |
| 254 | m/z = 590.24 (C42H30N4 = 590.73) |
| 255 | m/z = 662.24 (C48H30N4 = 662.79) |
| 256 | m/z = 714.27 (C52H34N4 = 714.87) |
| 257 | m/z = 728.25 (C52H32N40 = 728.85) |
| 258 | m/z = 744.23 (C52H32N4S = 744.91) |
| 259 | m/z = 762.25 (C52H35N4OP = 762.85) |
| 260 | m/z = 754.30 (C55H38N4 = 754.93) |
| 261 | m/z = 762.27 (C56H34N4 = 762.91) |
| 262 | m/z = 561.22 (C41H27N3 = 561.68) |
| 263 | m/z = 637.25 (C47H31N3 = 637.78) |
| 264 | m/z = 713.28 (C55H35N3 = 713.88) |
| 265 | m/z = 637.25 (C47H31N3 = 637.78) |
| 266 | m/z = 713.28 (C55H35N3 = 713.88) |
| 267 | m/z = 726.27 (C53H34N4 = 726.88) |
| 268 | m/z = 726.27 (C53H34N4 = 726.88) |
| 269 | m/z = 589.25 (C43H31N3 = 589.74) |
| 270 | m/z = 661.25 (C49H31N3 = 661.80) |
| 271 | m/z = 713.28 (C55H35N3 = 713.88) |
| 272 | m/z = 727.26 (C53H33N3O = 727.86) |
| 273 | m/z = 743.23 (C53H33N3S = 743.92) |
| 274 | m/z = 761.25 (C53H36N3OP = 761.86) |
| 275 | m/z = 753.31 (C56H39N3 = 753.94) |
| 276 | m/z = 761.28 (C57H35N3 = 761.92) |
| 277 | m/z = 638.24 (C46H30N4 = 638.77) |
| 278 | m/z = 714.27 (C52H34N4 = 714.87) |
| 279 | m/z = 790.30 (C58H38N4 = 790.97) |
| 280 | m/z = 714.27 (C52H34N4 = 714.87) |
| 281 | m/z = 790.30 (C58H38N4 = 790.97) |
| 282 | m/z = 803.30 (C58H37N5 = 803.96) |
| 283 | m/z = 803.30 (C58H37N5 = 803.96) |
| 284 | m/z = 666.27 (C48H34N4 = 666.82) |
| 285 | m/z = 738.27 (C54H34N4 = 738.89) |
| 286 | m/z = 790.30 (C58H38N4 = 790.97) |
| 287 | m/z = 804.28 (C58H36N4O = 804.95) |
| 288 | m/z = 820.26 (C58H36N4S = 821.01) |

TABLE 2-continued

| Compound | FD-MS |
|---|---|
| 289 | m/z = 838.28 (C58H39N4OP = 838.95) |
| 290 | m/z = 830.34 (C61H42N4 = 831.03) |
| 291 | m/z = 838.30 (C62H38N4 = 839.01) |
| 292 | m/z = 637.25 (C47H31N3 = 637.78) |
| 293 | m/z = 713.28 (C55H35N3 = 713.88) |
| 294 | m/z = 789.31 (C59H39N3 = 789.98) |
| 295 | m/z = 713.28 (C55H35N3 = 713.88) |
| 296 | m/z = 789.31 (C59H39N3 = 789.98) |
| 297 | m/z = 802.30 (C59H38N4 = 802.98) |
| 298 | m/z = 802.30 (C59H38N4 = 802.98) |
| 299 | m/z = 665.28 (C49H35N3 = 665.84) |
| 300 | m/z = 737.28 (C55H35N3 = 737.90) |
| 301 | m/z = 789.31 (C59H39N3 = 789.98) |
| 302 | m/z = 803.29 (C59H37N3O = 803.96) |
| 303 | m/z = 819.27 (C59H37N3S = 820.02) |
| 304 | m/z = 837.29 (C59H40N3OP = 837.96) |
| 305 | m/z = 829.34 (C62H43N3 = 830.04) |
| 306 | m/z = 837.31 (C63H39N3 = 838.02) |
| 307 | m/z = 638.24 (C46H30N4 = 638.77) |
| 308 | m/z = 714.27 (C52H34N4 = 714.87) |
| 309 | m/z = 790.30 (C58H38N4 = 790.97) |
| 310 | m/z = 714.27 (C52H34N4 = 714.87) |
| 311 | m/z = 790.30 (C58H38N4 = 790.97) |
| 312 | m/z = 803.30 (C58H37N5 = 803.96) |
| 313 | m/z = 803.30 (C58H37N5 = 803.96) |
| 314 | m/z = 666.27 (C48H34N4 = 666.82) |
| 315 | m/z = 738.27 (C54H34N4 = 738.89) |
| 316 | m/z = 790.30 (C58H38N4 = 790.97) |
| 317 | m/z = 804.28 (C58H36N4O = 804.95) |
| 318 | m/z = 820.26 (C58H36N4S = 821.01) |
| 319 | m/z = 838.28 (C58H39N4OP = 838.95) |
| 320 | m/z = 830.34 (C61H42N4 = 831.03) |
| 321 | m/z = 838.30 (C62H38N4 = 839.01) |
| 322 | m/z = 637.25 (C47H31N3 = 637.78) |
| 323 | m/z = 713.28 (C55H35N3 = 713.88) |
| 324 | m/z = 789.31 (C59H39N3 = 789.98) |
| 325 | m/z = 713.28 (C55H35N3 = 713.88) |
| 326 | m/z = 789.31 (C59H39N3 = 789.98) |
| 327 | m/z = 802.30 (C59H38N4 = 802.98) |
| 328 | m/z = 802.30 (C59H38N4 = 802.98) |
| 329 | m/z = 665.28 (C49H35N3 = 665.84) |
| 330 | m/z = 737.28 (C55H35N3 = 737.90) |
| 331 | m/z = 789.31 (C59H39N3 = 789.98) |
| 332 | m/z = 803.29 (C59H37N3O = 803.96) |
| 333 | m/z = 819.27 (C59H37N3S = 820.02) |
| 334 | m/z = 837.29 (C59H40N3OP = 837.96) |
| 335 | m/z = 829.34 (C62H43N3 = 830.04) |
| 336 | m/z = 837.31 (C63H39N3 = 838.02) |
| 337 | m/z = 638.24 (C46H30N4 = 638.77) |
| 338 | m/z = 737.28 (C55H35N3 = 737.90) |
| 339 | m/z = 591.17 (C41H25N3S = 591.73) |
| 340 | m/z = 485.18 (C35H23N3 = 485.59) |
| 341 | m/z = 551.23 (C40H29N3 = 551.69) |
| 342 | m/z = 637.25 (C47H31N3 = 637.78) |
| 343 | m/z = 483.17 (C33H26NOP = 483.55) |
| 344 | m/z = 535.20 (C39H25N3 = 535.65) |
| 345 | m/z = 593.19 (C41H27N3S = 593.74) |
| 346 | m/z = 535.20 (C39H25N3 = 535.65) |
| 347 | m/z = 540.16 (C38H24N2S = 540.68) |
| 348 | m/z = 524.18 (C38H24N2O = 524.62) |
| 349 | m/z = 599.23 (C44H29N3 = 599.73) |
| 350 | m/z = 599.23 (C44H29N3 = 599.73) |
| 351 | m/z = 607.20 (C43H30NOP = 607.69) |
| 352 | m/z = 607.20 (C43H30NOP = 607.69) |
| 353 | m/z = 585.22 (C43H27N3 = 585.71) |
| 354 | m/z = 509.18 (C37H23N3 = 509.61) |
| 355 | m/z = 562.21 (C40H26N4 = 562.67) |
| 356 | m/z = 638.24 (C46H30N4 = 638.77) |
| 357 | m/z = 714.27 (C52H34N4 = 714.87) |
| 358 | m/z = 638.24 (C46H30N4 = 638.77) |
| 359 | m/z = 714.27 (C52H34N4 = 714.87) |
| 360 | m/z = 727.27 (C52H33N5 = 727.87) |
| 361 | m/z = 727.27 (C52H33N5 = 727.87) |
| 362 | m/z = 590.24 (C42H30N4 = 590.73) |
| 363 | m/z = 662.24 (C48H30N4 = 662.79) |
| 364 | m/z = 714.27 (C52H34N4 = 714.87) |
| 365 | m/z = 728.25 (C52H32N4O = 728.85) |
| 366 | m/z = 744.23 (C52H32N4S = 744.91) |

TABLE 2-continued

| Compound | FD-MS |
|---|---|
| 367 | m/z = 762.25(C52H35N4OP = 762.85) |
| 368 | m/z = 754.30 (C55H38N4 = 754.93) |
| 369 | m/z = 762.27 (C56H34N4 = 762.91) |
| 370 | m/z = 561.22 (C41H27N3 = 561.68) |
| 371 | m/z = 637.25 (C47H31N3 = 637.78) |
| 372 | m/z = 713.28 (C55H35N3 = 713.88) |
| 373 | m/z = 637.25 (C47H31N3 = 637.78) |
| 374 | m/z = 713.28 (C55H35N3 = 713.88) |
| 375 | m/z = 726.27 (C53H34N4 = 726.88) |
| 376 | m/z = 726.27 (C53H34N4 = 726.88) |
| 377 | m/z = 589.25 (C43H31N3 = 589.74) |
| 378 | m/z = 661.25 (C49H31N3 = 661.80) |
| 379 | m/z = 713.28 (C55H35N3 = 713.88) |
| 380 | m/z = 727.26 (C53H33N30 = 727.86) |
| 381 | m/z = 743.23 (C53H33N3S = 743.92) |
| 382 | m/z = 761.25 (C53H36N3OP = 761.86) |
| 383 | m/z = 753.31 (C56H39N3 = 753.94) |
| 384 | m/z = 761.28 (C57H35N3 = 761.92) |
| 385 | m/z = 638.24 (C46H30N4 = 638.77) |
| 386 | m/z = 714.27 (C52H34N4 = 714.87) |
| 387 | m/z = 790.30 (C58H38N4 = 790.97) |
| 388 | m/z = 714.27 (C52H34N4 = 714.87) |
| 389 | m/z = 790.30 (C58H38N4 = 790.97) |
| 390 | m/z = 803.30 (C58H37N5 = 803.96) |
| 391 | m/z = 803.30 (C58H37N5 = 803.96) |
| 392 | m/z = 666.27 (C48H34N4 = 666.82) |
| 393 | m/z = 738.27 (C54H34N4 = 738.89) |
| 394 | m/z = 790.30 (C58H38N4 = 790.97) |
| 395 | m/z = 804.28 (C58H36N4O = 804.95) |
| 396 | m/z = 820.26 (C58H36N4S = 821.01) |
| 397 | m/z = 838.28 (C58H39N4OP = 838.95) |
| 398 | m/z = 830.34 (C61H42N4 = 831.03) |
| 399 | m/z = 838.30 (C62H38N4 = 839.01) |
| 400 | m/z = 637.25 (C47H31N3 = 637.78) |
| 401 | m/z = 713.28 (C55H35N3 = 713.88) |
| 402 | m/z = 789.31 (C59H39N3 = 789.98) |
| 403 | m/z = 713.28 (C55H35N3 = 713.88) |
| 404 | m/z = 789.31 (C59H39N3 = 789.98) |
| 405 | m/z = 802.30 (C59H38N4 = 802.98) |
| 406 | m/z = 802.30 (C59H38N4 = 802.98) |
| 407 | m/z = 665.28 (C49H35N3 = 665.84) |
| 408 | m/z = 737.28 (C55H35N3 = 737.90) |
| 409 | m/z = 789.31 (C59H39N3 = 789.98) |
| 410 | m/z = 803.29 (C59H37N3O = 803.96) |
| 411 | m/z = 819.27 (C59H37N3S = 820.02) |
| 412 | m/z = 837.29 (C59H40N3OP = 837.96) |
| 413 | m/z = 829.34 (C62H43N3 = 830.04) |
| 414 | m/z = 837.31 (C63H39N3 = 838.02) |
| 415 | m/z = 638.24 (C46H30N4 = 638.77) |
| 416 | m/z = 714.27 (C52H34N4 = 714.87) |
| 417 | m/z = 790.30 (C58H38N4 = 790.97) |
| 418 | m/z = 714.27 (C52H34N4 = 714.87) |
| 419 | m/z = 790.30 (C58H38N4 = 790.97) |
| 420 | m/z = 803.30 (C58H37N5 = 803.96) |
| 421 | m/z = 803.30 (C58H37N5 = 803.96) |
| 422 | m/z = 666.27 (C48H34N4 = 666.82) |
| 423 | m/z = 738.27 (C54H34N4 = 738.89) |
| 424 | m/z = 790.30 (C58H38N4 = 790.97) |
| 425 | m/z = 804.28 (C58H36N4O = 804.95) |
| 426 | m/z = 820.26 (C58H36N4S = 821.01) |
| 427 | m/z = 838.28 (C58H39N4OP = 838.95) |
| 428 | m/z = 830.34 (C61H42N4 = 831.03) |
| 429 | m/z = 838.30 (C62H38N4 = 839.01) |
| 430 | m/z = 637.25 (C47H31N3 = 637.78) |
| 431 | m/z = 713.28 (C55H35N3 = 713.88) |
| 432 | m/z = 789.31 (C59H39N3 = 789.98) |
| 433 | m/z = 713.28 (C55H35N3 = 713.88) |
| 434 | m/z = 789.31 (C59H39N3 = 789.98) |
| 435 | m/z = 802.30 (C59H38N4 = 802.98) |
| 436 | m/z = 802.30 (C59H38N4 = 802.98) |
| 437 | m/z = 665.28 (C49H35N3 = 665.84) |
| 438 | m/z = 737.28 (C55H35N3 = 737.90) |
| 439 | m/z = 789.31 (C59H39N3 = 789.98) |
| 440 | m/z = 803.29 (C59H37N3O = 803.96) |
| 441 | m/z = 819.27 (C59H37N3S = 820.02) |
| 442 | m/z = 837.29 (C59H40N3OP = 837.96) |
| 443 | m/z = 829.34 (C62H43N3 = 830.04) |
| 444 | m/z = 837.31 (C63H39N3 = 838.02) |

TABLE 2-continued

| Compound | FD-MS |
|---|---|
| 445 | m/z = 638.24 (C46H30N4 = 638.77) |
| 446 | m/z = 737.28 (C55H35N3 = 737.90) |
| 447 | m/z = 591.17 (C41H25N3S = 591.73) |
| 448 | m/z = 485.18 (C35H23N3 = 485.59) |
| 449 | m/z = 551.23 (C40H29N3 = 551.69) |
| 450 | m/z = 637.25 (C47H31N3 = 637.78) |
| 451 | m/z = 483.17 (C33H26NO2 = 483.55) |
| 452 | m/z = 535.20 (C39H25N3 = 535.65) |
| 453 | m/z = 593.19 (C41H27N3S = 593.74) |
| 454 | m/z = 535.20 (C39H25N3 = 535.65) |
| 455 | m/z = 540.16 (C38H24N2S = 540.68) |
| 456 | m/z = 524.18 (C38H24N2O = 524.62) |
| 457 | m/z = 599.23 (C44H29N3 = 599.73) |
| 458 | m/z = 599.23 (C441129N3 = 599.73) |
| 459 | m/z = 607.20 (C43H30NOP = 607.69) |
| 460 | m/z = 607.20 (C43H30NOP = 607.69) |
| 461 | m/z = 585.22 (C43H27N3 = 585.71) |
| 462 | m/z = 509.18 (C37H23N3 = 509.61) |
| 463 | m/z = 562.21 (C40H26N4 = 562.67) |
| 464 | m/z = 638.24 (C46H30N4 = 638.77) |
| 465 | m/z = 714.27 (C52H34N4 = 714.87) |
| 466 | m/z = 638.24 (C46H30N4 = 638.77) |
| 467 | m/z = 714.27 (C52H34N4 = 714.87) |
| 468 | m/z = 727.27 (C52H33N5 = 727.87) |
| 469 | m/z = 727.27 (C52H33N5 = 727.87) |
| 470 | m/z = 590.24 (C42H30N4 = 590.73) |
| 471 | m/z = 662.24 (C48H30N4 = 662.79) |
| 472 | m/z = 714.27 (C52H34N4 = 714.87) |
| 473 | m/z = 728.25 (C52H32N4O = 728.85) |
| 474 | m/z = 744.23 (C52H32N4S = 744.91) |
| 475 | m/z = 762.25 (C52H35N4OP = 762.85) |
| 476 | m/z = 754.30 (C55H38N4 = 754.93) |
| 477 | m/z = 762.27 (C56H34N4 = 762.91) |
| 478 | m/z = 561.22 (C41H27N3 = 561.68) |
| 479 | m/z = 637.25 (C47H31N3 = 637.78) |
| 480 | m/z = 713.28 (C55H35N3 = 713.88) |
| 481 | m/z = 637.25 (C47H31N3 = 637.78) |
| 482 | m/z = 713.28 (C55H35N3 = 713.88) |
| 483 | m/z = 726.27 (C53H34N4 = 726.88) |
| 484 | m/z = 726.27 (C53H34N4 = 726.88) |
| 485 | m/z = 589.25 (C43H31N3 = 589.74) |
| 486 | m/z = 661.25 (C49H31N3 = 661.80) |
| 487 | m/z = 713.28 (C55H35N3 = 713.88) |
| 488 | m/z = 727.26 (C53H33N3O = 727.86) |
| 489 | m/z = 743.23 (C53H33N3S = 743.92) |
| 490 | m/z = 761.25 (C53H36N3OP = 761.86) |
| 491 | m/z = 753.31 (C56H39N3 = 753.94) |
| 492 | m/z = 761.28 (C57H35N3 = 761.92) |
| 493 | m/z = 638.24 (C46H30N4 = 638.77) |
| 494 | m/z = 714.27 (C52H34N4 = 714.87) |
| 495 | m/z = 790.30 (C58H38N4 = 790.97) |
| 496 | m/z = 714.27 (C52H34N4 = 714.87) |
| 497 | m/z = 790.30 (C58H38N4 = 790.97) |
| 498 | m/z = 803.30 (C58H37N5 = 803.96) |
| 499 | m/z = 803.30 (C58H37N5 = 803.96) |
| 500 | m/z = 666.27 (C48H34N4 = 666.82) |
| 501 | m/z = 738.27 (C54H34N4 = 738.89) |
| 502 | m/z = 790.30 (C58H38N4 = 790.97) |
| 503 | m/z = 804.28 (C58H36N4O = 804.95) |
| 504 | m/z = 820.26 (C58H36N4S = 821.01) |
| 505 | m/z = 838.28 (C58H39N4OP = 838.95) |
| 506 | m/z = 830.34 (C61H42N4 = 831.03) |
| 507 | m/z = 838.30 (C62H38N4 = 839.01) |
| 508 | m/z = 637.25 (C47H31N3 = 637.78) |
| 509 | m/z = 713.28 (C55H35N3 = 713.88) |
| 510 | m/z = 789.31 (C59H39N3 = 789.98) |
| 511 | m/z = 713.28 (C55H35N3 = 713.88) |
| 512 | m/z = 789.31 (C59H39N3 = 789.98) |
| 513 | m/z = 802.30 (C59H38N4 = 802.98) |
| 514 | m/z = 802.30 (C59H38N4 = 802.98) |
| 515 | m/z = 665.28 (C49H35N3 = 665.84) |
| 516 | m/z = 737.28 (C55H35N3 = 737.90) |
| 517 | m/z = 789.31 (C59H39N3 = 789.98) |
| 518 | m/z = 803.29 (C59H37N3O = 803.96) |
| 519 | m/z = 819.27 (C59H37N3S = 820.02) |
| 520 | m/z = 837.29 (C59H40N3OP = 837.96) |
| 521 | m/z = 829.34 (C62H43N3 = 830.04) |
| 522 | m/z = 837.31 (C63H39N3 = 838.02) |

TABLE 2-continued

| Compound | FD-MS |
|---|---|
| 523 | m/z = 638.24 (C46H30N4 = 638.77) |
| 524 | m/z = 714.27 (C52H34N4 = 714.87) |
| 525 | m/z = 790.30 (C58H38N4 = 790.97) |
| 526 | m/z = 714.27 (C52H34N4 = 714.87) |
| 527 | m/z = 790.30 (C58H38N4 = 790.97) |
| 528 | m/z = 803.30 (C58H37N5 = 803.96) |
| 529 | m/z = 803.30 (C58H37N5 = 803.96) |
| 530 | m/z = 666.27 (C48H34N4 = 666.82) |
| 531 | m/z = 738.27 (C54H34N4 = 738.89) |
| 532 | m/z = 790.30 (C58H38N4 = 790.97) |
| 533 | m/z = 804.28 (C58H36N4O = 804.95) |
| 534 | m/z = 820.26 (C58H36N4S = 821.01) |
| 535 | m/z = 838.28 (C58H39N4OP = 838.95) |
| 536 | m/z = 830.34 (C61H42N4 = 831.03) |
| 537 | m/z = 838.30 (C62H38N4 = 839.01) |
| 538 | m/z = 637.25 (C47H31N3 = 637.78) |
| 539 | m/z = 713.28 (C55H35N3 = 713.88) |
| 540 | m/z = 789.31 (C59H39N3 = 789.98) |
| 541 | m/z = 713.28 (C55H35N3 = 713.88) |
| 542 | m/z = 789.31 (C59H39N3 = 789.98) |
| 543 | m/z = 802.30 (C59H38N4 = 802.98) |
| 544 | m/z = 802.30 (C59H38N4 = 802.98) |
| 545 | m/z = 665.28 (C49H35N3 = 665.84) |
| 546 | m/z = 737.28 (C55H35N3 = 737.90) |
| 547 | m/z = 789.31 (C59H39N3 = 789.98) |
| 548 | m/z = 803.29 (C59H37N3O = 803.96) |
| 549 | m/z = 819.27 (C59H37N3S = 820.02) |
| 550 | m/z = 837.29 (C59H40N3OP = 837.96) |
| 551 | m/z = 829.34 (C62H43N3 = 830.04) |
| 552 | m/z = 837.31 (C63H39N3 = 838.02) |
| 553 | m/z = 638.24 (C46H30N4 = 638.77) |
| 554 | m/z = 737.28 (C55H35N3 = 737.90) |
| 555 | m/z = 591.17 (C41H25N3S = 591.73) |
| 556 | m/z = 485.18 (C35H23N3 = 485.59) |
| 557 | m/z = 551.23 (C40H29N3 = 551.69) |
| 558 | m/z = 637.25 (C47H31N3 = 637.78) |
| 559 | m/z = 483.17 (C33H26NOP = 483.55) |
| 560 | m/z = 535.20 (C39H25N3 = 535.65) |
| 561 | m/z = 593.19 (C41H27N3S = 593.74) |
| 562 | m/z = 535.20 (C39H25N3 = 535.65) |
| 563 | m/z = 540.16 (C38H24N2S = 540.68) |
| 564 | m/z = 524.18 (C38H24N2O = 524.62) |
| 565 | m/z = 599.23 (C44H29N3 = 599.73) |
| 566 | m/z = 599.23 (C44H29N3 = 599.73) |
| 567 | m/z = 607.20 (C43H30NOP = 607.69) |
| 568 | m/z = 607.20 (C43H30NOP = 607.69) |
| 569 | m/z = 585.22 (C43H27N3 = 585.71) |
| 570 | m/z = 509.18 (C37H23N3 = 509.61) |
| 571 | m/z = 562.21 (C40H26N4 = 562.67) |
| 572 | m/z = 638.24 (C46H30N4 = 638.77) |
| 573 | m/z = 714.27 (C52H34N4 = 714.87) |
| 574 | m/z = 638.24 (C46H30N4 = 638.77) |
| 575 | m/z = 714.27 (C52H34N4 = 714.87) |
| 576 | m/z = 727.27 (C52H33N5 = 727.87) |
| 577 | m/z = 727.27 (C52H33N5 = 727.87) |
| 578 | m/z = 590.24 (C42H30N4 = 590.73) |
| 579 | m/z = 662.24 (C48H30N4 = 662.79) |
| 580 | m/z = 714.27 (C52H34N4 = 714.87) |
| 581 | m/z = 728.25 (C52H32N4O = 728.85) |
| 582 | m/z = 744.23 (C52H32N4S = 744.91) |
| 583 | m/z = 762.25(C52H35N4OP = 762.85) |
| 584 | m/z = 754.30 (C55H38N4 = 754.93) |
| 585 | m/z = 762.27 (C56H34N4 = 762.91) |
| 586 | m/z = 561.22 (C41H27N3 = 561.68) |
| 587 | m/z = 637.25 (C47H31N3 = 637.78) |
| 588 | m/z = 713.28 (C55H35N3 = 713.88) |
| 589 | m/z = 637.25 (C47H31N3 = 637.78) |
| 590 | m/z = 713.28 (C55H35N3 = 713.88) |
| 591 | m/z = 726.27 (C53H34N4 = 726.88) |
| 592 | m/z = 726.27 (C53H34N4 = 726.88) |
| 593 | m/z = 589.25 (C43H31N3 = 589.74) |
| 594 | m/z = 661.25 (C49H31N3 = 661.80) |
| 595 | m/z = 713.28 (C55H35N3 = 713.88) |
| 596 | m/z = 727.26 (C53H33N3O = 727.86) |
| 597 | m/z = 743.23 (C53H33N3S = 743.92) |
| 598 | m/z = 761.25 (C53H36N3OP = 761.86) |
| 599 | m/z = 753.31 (C56H39N3 = 753.94) |
| 600 | m/z = 761.28 (C57H35N3 = 761.92) |

TABLE 2-continued

| Compound | FD-MS |
|---|---|
| 601 | m/z = 638.24 (C46H30N4 = 638.77) |
| 602 | m/z = 714.27 (C52H34N4 = 714.87) |
| 603 | m/z = 790.30 (C58H38N4 = 790.97) |
| 604 | m/z = 714.27 (C52H34N4 = 714.87) |
| 605 | m/z = 790.30 (C58H38N4 = 790.97) |
| 606 | m/z = 803.30 (C58H37N5 = 803.96) |
| 607 | m/z = 803.30 (C58H37N5 = 803.96) |
| 608 | m/z = 666.27 (C48H34N4 = 666.82) |
| 609 | m/z = 738.27 (C54H34N4 = 738.89) |
| 610 | m/z = 790.30 (C58H38N4 = 790.97) |
| 611 | m/z = 804.28 (C58H36N4O = 804.95) |
| 612 | m/z = 820.26 (C58H36N4S = 821.01) |
| 613 | m/z = 838.28 (C58H39N4OP = 838.95) |
| 614 | m/z = 830.34 (C61H42N4 = 831.03) |
| 615 | m/z = 838.30 (C62H38N4 = 839.01) |
| 616 | m/z = 637.25 (C47H31N3 = 637.78) |
| 617 | m/z = 713.28 (C55H35N3 = 713.88) |
| 618 | m/z = 789.31 (C59H39N3 = 789.98) |
| 619 | m/z = 713.28 (C55H35N3 = 713.88) |
| 620 | m/z = 789.31 (C59H39N3 = 789.98) |
| 621 | m/z = 802.30 (C59H38N4 = 802.98) |
| 622 | m/z = 802.30 (C59H38N4 = 802.98) |
| 623 | m/z = 665.28 (C49H35N3 = 665.84) |
| 624 | m/z = 737.28 (C55H35N3 = 737.90) |
| 625 | m/z = 789.31 (C59H39N3 = 789.98) |
| 626 | m/z = 803.29 (C59H37N3O = 803.96) |
| 627 | m/z = 819.27 (C59H37N3S = 820.02) |
| 628 | m/z = 837.29 (C59H40N3OP = 837.96) |
| 629 | m/z = 829.34 (C62H43N3 = 830.04) |
| 630 | m/z = 837.31 (C63H39N3 = 838.02) |
| 631 | m/z = 638.24 (C46H30N4 = 638.77) |
| 632 | m/z = 714.27 (C52H34N4 = 714.87) |
| 633 | m/z = 790.30 (C58H38N4 = 790.97) |
| 634 | m/z = 714.27 (C52H34N4 = 714.87) |
| 635 | m/z = 790.30 (C58H38N4 = 790.97) |
| 636 | m/z = 803.30 (C58H37N5 = 803.96) |
| 637 | m/z = 803.30 (C58H37N5 = 803.96) |
| 638 | m/z = 666.27 (C48H34N4 = 666.82) |
| 639 | m/z = 738.27 (C54H34N4 = 738.89) |
| 640 | m/z = 790.30 (C58H38N4 = 790.97) |
| 641 | m/z = 804.28 (C58H36N4O = 804.95) |
| 642 | m/z = 820.26 (C58H36N4S = 821.01) |
| 643 | m/z = 838.28 (C58H39N4OP = 838.95) |
| 644 | m/z = 830.34 (C61H42N4 = 831.03) |
| 645 | m/z = 838.30 (C62H38N4 = 839.01) |
| 646 | m/z = 637.25 (C47H31N3 = 637.78) |
| 647 | m/z = 713.28 (C55H35N3 = 713.88) |
| 648 | m/z = 789.31 (C59H39N3 = 789.98) |
| 649 | m/z = 713.28 (C55H35N3 = 713.88) |
| 650 | m/z = 789.31 (C59H39N3 = 789.98) |
| 651 | m/z = 802.30 (C59538N4 = 802.98) |
| 652 | m/z = 802.30 (C59H38N4 = 802.98) |
| 653 | m/z = 665.28 (C49H35N3 = 665.84) |
| 654 | m/z = 737.28 (C55H35N3 = 737.90) |
| 655 | m/z = 789.31 (C59H39N3 = 789.98) |
| 656 | m/z = 803.29 (C59H37N3O = 803.96) |
| 657 | m/z = 819.27 (C59H37N3S = 820.02) |
| 658 | m/z = 837.29 (C59540N3OP = 837.96) |
| 659 | m/z = 829.34 (C62H43N3 = 830.04) |
| 660 | m/z = 837.31 (C63H39N3 = 838.02) |
| 661 | m/z = 638.24 (C46H30N4 = 638.77) |
| 662 | m/z = 737.28 (C55H35N3 = 737.90) |
| 663 | m/z = 591.17 (C41H25N3S = 591.73) |
| 664 | m/z = 485.18 (C35H23N3 = 485.59) |
| 665 | m/z = 551.23 (C40H29N3 = 551.69) |
| 666 | m/z = 637.25 (C47H31N3 = 637.78) |
| 667 | m/z = 483.17 (C33H26NOP = 483.55) |
| 668 | m/z = 535.20 (C39H25N3 = 535.65) |
| 669 | m/z = 593.19 (C41H27N3S = 593.74) |
| 670 | m/z = 535.20 (C39H25N3 = 535.65) |
| 671 | m/z = 540.16 (C38H24N2S = 540.68) |
| 672 | m/z = 524.18 (C38H24N2O = 524.62) |
| 673 | m/z = 599.23 (C44H29N3 = 599.73) |
| 674 | m/z = 599.23 (C44H29N3 = 599.73) |
| 675 | m/z = 607.20 (C43H30NOP = 607.69) |
| 676 | m/z = 607.20 (C43H30NOP = 607.69) |
| 677 | m/z = 585.22 (C43H27N3 = 585.71) |
| 678 | m/z = 509.18 (C37H23N3 = 509.61) |

TABLE 2-continued

| Compound | FD-MS |
|---|---|
| 679 | m/z = 688.26 (C50H32N4 = 688.83) |
| 680 | m/z = 687.26 (C51H33N3 = 687.84) |
| 681 | m/z = 688.26 (C50H32N4 = 688.83) |
| 682 | m/z = 635.23 (C47H29N3 = 635.77) |
| 683 | m/z = 688.26 (C50H32N4 = 688.83) |
| 684 | m/z = 687.26 (C51H33N3 = 687.84) |
| 685 | m/z = 688.26 (C50H32N4 = 688.83) |
| 686 | m/z = 635.23 (C47H29N3 = 635.77) |
| 687 | m/z = 639.24 (C45529N5 = 639.76) |
| 688 | m/z = 638.24 (C46H38N4 = 638.77) |
| 689 | m/z = 639.24 (C45H29N5 = 639.76) |
| 690 | m/z = 586.21 (C42H26N4 = 586.69) |
| 691 | m/z = 639.24 (C45H29N5 = 639.76) |
| 692 | m/z = 638.24 (C46538N4 = 638.77) |
| 693 | m/z = 639.24 (C45H29N5 = 639.76) |
| 694 | m/z = 586.21 (C42H26N4 = 586.69) |
| 695 | m/z = 639.24 (C45529N5 = 639.76) |
| 696 | m/z = 638.24 (C46H38N4 = 638.77) |
| 697 | m/z = 639.24 (C45H29N5 = 639.76) |
| 698 | m/z = 586.21 (C42526N4 = 586.69) |
| 699 | m/z = 639.24 (C45H29N5 = 639.76) |
| 700 | m/z = 638.24 (C46H38N4 = 638.77) |
| 701 | m/z = 639.24 (C45529N5 = 639.76) |
| 702 | m/z = 586.21 (C42526N4 = 586.69) |
| 703 | m/z = 639.24 (C45H29N5 = 639.76) |
| 704 | m/z = 638.24 (C46H38N4 = 638.77) |
| 705 | m/z = 639.24 (C45H29N5 = 639.76) |
| 706 | m/z = 586.21 (C42526N4 = 586.69) |
| 707 | m/z = 639.24 (C45H29N5 = 639.76) |
| 708 | m/z = 638.24 (C46H38N4 = 638.77) |
| 709 | m/z = 639.24 (C45H29N5 = 639.76) |
| 710 | m/z = 586.21 (C42H26N4 = 586.69) |
| 711 | m/z = 714.27 (C52H34N4 = 714.87) |
| 712 | m/z = 713.28 (C55H35N3 = 713.88) |
| 713 | m/z = 714.27 (C52H34N4 = 714.87) |
| 714 | m/z = 661.25 (C49H31N3 = 661.80) |
| 715 | m/z = 714.27 (C52H34N4 = 714.87) |
| 716 | m/z = 713.28 (C55H35N3 = 713.88) |
| 717 | m/z = 714.27 (C52H34N4 = 714.87) |
| 718 | m/z = 661.25 (C49H31N3 = 661.80) |
| 719 | m/z = 714.27 (C52H34N4 = 714.87) |
| 720 | m/z = 713.28 (C55H35N3 = 713.88) |
| 721 | m/z = 714.27 (C52H34N4 = 714.87) |
| 722 | m/z = 661.25 (C49H31N3 = 661.80) |
| 723 | m/z = 714.27 (C52H34N4 = 714.87) |
| 724 | m/z = 713.28 (C55H35N3 = 713.88) |
| 725 | m/z = 714.27 (C52H34N4 = 714.87) |
| 726 | m/z = 661.25 (C49H31N3 = 661.80) |
| 727 | m/z = 714.27 (C52H34N4 = 714.87) |
| 728 | m/z = 713.28 (C55H35N3 = 713.88) |
| 729 | m/z = 714.27 (C52H34N4 = 714.87) |
| 730 | m/z = 661.25 (C49H31N3 = 661.80) |
| 731 | m/z = 714.27 (C52H34N4 = 714.87) |
| 732 | m/z = 713.28 (C55H35N3 = 713.88) |
| 733 | m/z = 714.27 (C52H34N4 = 714.87) |
| 734 | m/z = 661.25 (C49H31N3 = 661.80) |
| 735 | m/z = 688.26 (C50H32N4 = 688.83) |
| 736 | m/z = 687.26 (C51H33N3 = 687.84) |
| 737 | m/z = 688.26 (C50H32N4 = 688.83) |
| 738 | m/z = 635.23 (C47H29N3 = 635.77) |
| 739 | m/z = 639.24 (C45H29N5 = 639.76) |
| 740 | m/z = 638.24 (C46H38N4 = 638.77) |
| 741 | m/z = 639.24 (C45H29N5 = 639.76) |
| 742 | m/z = 586.21 (C42H26N4 = 586.69) |
| 743 | m/z = 639.24 (C45H29N5 = 639.76) |
| 744 | m/z = 638.24 (C46H38N4 = 638.77) |
| 745 | m/z = 639.24 (C45H29N5 = 639.76) |
| 746 | m/z = 586.21 (C42H26N4 = 586.69) |
| 747 | m/z = 639.24 (C45H29N5 = 639.76) |
| 748 | m/z = 638.24 (C46H38N4 = 638.77) |
| 749 | m/z = 639.24 (C45H29N5 = 639.76) |
| 750 | m/z = 586.21 (C42H26N4 = 586.69) |
| 751 | m/z = 714.27 (C52H34N4 = 714.87) |
| 720 | m/z = 713.28 (C55H35N3 = 713.88) |
| 753 | m/z = 714.27 (C52H34N4 = 714.87) |
| 722 | m/z = 661.25 (C49H31N3 = 661.80) |
| 755 | m/z = 714.27 (C52H34N4 = 714.87) |
| 720 | m/z = 713.28 (C55H35N3 = 713.88) |

TABLE 2-continued

| Compound | FD-MS |
| --- | --- |
| 757 | m/z = 714.27 (C52H34N4 = 714.87) |
| 722 | m/z = 661.25 (C49H31N3 = 661.80) |
| 759 | m/z = 714.27 (C52H34N4 = 714.87) |
| 720 | m/z = 713.28 (C55H35N3 = 713.88) |
| 761 | m/z = 714.27 (C52H34N4 = 714.87) |
| 722 | m/z = 661.25 (C49H31N3 = 661.80) |
| 763 | m/z = 688.26 (C50H32N4 = 688.83) |
| 736 | m/z = 687.26 (C51H33N3 = 687.84) |
| 765 | m/z = 688.26 (C50H32N4 = 688.83) |
| 738 | m/z = 635.23 (C47H29N3 = 635.77) |
| 767 | m/z = 639.24 (C45H29N5 = 639.76) |
| 748 | m/z = 638.24 (C46H38N4 = 638.77) |
| 769 | m/z = 639.24 (C45H29N5 = 639.76) |
| 750 | m/z = 586.21 (C42H26N4 = 586.69) |
| 771 | m/z = 639.24 (C45H29N5 = 639.76) |
| 748 | m/z = 638.24 (C46H38N4 = 638.77) |
| 773 | m/z = 639.24 (C45H29N5 = 639.76) |
| 750 | m/z = 586.21 (C42H26N4 = 586.69) |
| 775 | m/z = 639.24 (C45H29N5 = 639.76) |
| 748 | m/z = 638.24 (C46H38N4 = 638.77) |
| 777 | m/z = 639.24 (C45H29N5 = 639.76) |
| 750 | m/z = 586.21 (C42H26N4 = 586.69) |
| 779 | m/z = 714.27 (C52H34N4 = 714.87) |
| 720 | m/z = 713.28 (C55H35N3 = 713.88) |
| 781 | m/z = 714.27 (C52H34N4 = 714.87) |
| 722 | m/z = 661.25 (C49H31N3 = 661.80) |
| 783 | m/z = 714.27 (C52H34N4 = 714.87) |
| 720 | m/z = 713.28 (C55H35N3 = 713.88) |
| 785 | m/z = 714.27 (C52H34N4 = 714.87) |
| 722 | m/z = 661.25 (C49H31N3 = 661.80) |
| 787 | m/z = 714.27 (C52H34N4 = 714.87) |
| 720 | m/z = 713.28 (C55H35N3 = 713.88) |
| 789 | m/z = 714.27 (C52H34N4 = 714.87) |
| 722 | m/z = 661.25 (C49H31N3 = 661.80) |
| 791 | m/z = 688.26 (C50H32N4 = 688.83) |
| 736 | m/z = 687.26 (C51H33N3 = 687.84) |
| 793 | m/z = 688.26 (C50H32N4 = 688.83) |
| 738 | m/z = 635.23 (C47H29N3 = 635.77) |
| 795 | m/z = 639.24 (C45H29N5 = 639.76) |
| 748 | m/z = 638.24 (C46H38N4 = 638.77) |
| 797 | m/z = 639.24 (C45H29N5 = 639.76) |
| 750 | m/z = 586.21 (C42H26N4 = 586.69) |
| 799 | m/z = 639.24 (C45H29N5 = 639.76) |
| 748 | m/z = 638.24 (C46H38N4 = 638.77) |
| 801 | m/z = 639.24 (C45H29N5 = 639.76) |
| 750 | m/z = 586.21 (C42H26N4 = 586.69) |
| 803 | m/z = 639.24 (C45H29N5 = 639.76) |
| 748 | m/z = 638.24 (C46H38N4 = 638.77) |
| 805 | m/z = 639.24 (C45H29N5 = 639.76) |
| 750 | m/z = 586.21 (C42H26N4 = 586.69) |
| 807 | m/z = 714.27 (C52H34N4 = 714.87) |
| 720 | m/z = 713.28 (C55H35N3 = 713.88) |
| 809 | m/z = 714.27 (C52H34N4 = 714.87) |
| 722 | m/z = 661.25 (C49H31N3 = 661.80) |
| 811 | m/z = 714.27 (C52H34N4 = 714.87) |
| 720 | m/z = 713.28 (C55H35N3 = 713.88) |
| 813 | m/z = 714.27 (C52H34N4 = 714.87) |
| 722 | m/z = 661.25 (C49H31N3 = 661.80) |
| 815 | m/z = 714.27 (C52H34N4 = 714.87) |
| 720 | m/z = 713.28 (C55H35N3 = 713.88) |
| 817 | m/z = 714.27 (C52H34N4 = 714.87) |
| 722 | m/z = 661.25 (C49H31N3 = 661.80) |
| 819 | m/z = 688.26 (C50H32N4 = 688.83) |
| 736 | m/z = 687.26 (C51H33N3 = 687.84) |
| 821 | m/z = 688.26 (C50H32N4 = 688.83) |
| 738 | m/z = 635.23 (C47H29N3 = 635.77) |
| 823 | m/z = 639.24 (C45H29N5 = 639.76) |
| 748 | m/z = 638.24 (C46H38N4 = 638.77) |
| 825 | m/z = 639.24 (C45H29N5 = 639.76) |
| 750 | m/z = 586.21 (C42H26N4 = 586.69) |
| 827 | m/z = 639.24 (C45H29N5 = 639.76) |
| 748 | m/z = 638.24 (C46H38N4 = 638.77) |
| 829 | m/z = 639.24 (C45H29N5 = 639.76) |
| 750 | m/z = 586.21 (C42H26N4 = 586.69) |
| 831 | m/z = 639.24 (C45H29N5 = 639.76) |
| 748 | m/z = 638.24 (C46H38N4 = 638.77) |
| 833 | m/z = 639.24 (C45H29N5 = 639.76) |
| 750 | m/z = 586.21 (C42H26N4 = 586.69) |

TABLE 2-continued

| Compound | FD-MS |
| --- | --- |
| 835 | m/z = 714.27 (C52H34N4 = 714.87) |
| 720 | m/z = 713.28 (C55H35N3 = 713.88) |
| 837 | m/z = 714.27 (C52H34N4 = 714.87) |
| 722 | m/z = 661.25 (C49H31N3 = 661.80) |
| 839 | m/z = 714.27 (C52H34N4 = 714.87) |
| 720 | m/z = 713.28 (C55H35N3 = 713.88) |
| 841 | m/z = 714.27 (C52H34N4 = 714.87) |
| 722 | m/z = 661.25 (C49H31N3 = 661.80) |
| 843 | m/z = 714.27 (C52H34N4 = 714.87) |
| 720 | m/z = 713.28 (C55H35N3 = 713.88) |
| 845 | m/z = 714.27 (C52H34N4 = 714.87) |
| 722 | m/z = 661.25 (C49H31N3 = 661.80) |
| 847 | m/z = 688.26 (C50H32N4 = 688.83) |
| 736 | m/z = 687.26 (C51H33N3 = 687.84) |
| 849 | m/z = 688.26 (C50H32N4 = 688.83) |
| 738 | m/z = 635.23 (C47H29N3 = 635.77) |
| 851 | m/z = 639.24 (C45H29N5 = 639.76) |
| 748 | m/z = 638.24 (C46H38N4 = 638.77) |
| 853 | m/z = 639.24 (C45H29N5 = 639.76) |
| 750 | m/z = 586.21 (C42H26N4 = 586.69) |
| 855 | m/z = 639.24 (C45H29N5 = 639.76) |
| 748 | m/z = 638.24 (C46H38N4 = 638.77) |
| 857 | m/z = 639.24 (C45H29N5 = 639.76) |
| 750 | m/z = 586.21 (C42H26N4 = 586.69) |
| 859 | m/z = 639.24 (C45H29N5 = 639.76) |
| 748 | m/z = 638.24 (C46H38N4 = 638.77) |
| 861 | m/z = 639.24 (C45H29N5 = 639.76) |
| 750 | m/z = 586.21 (C42H26N4 = 586.69) |
| 863 | m/z = 714.27 (C52H34N4 = 714.87) |
| 720 | m/z = 713.28 (C55H35N3 = 713.88) |
| 865 | m/z = 714.27 (C52H34N4 = 714.87) |
| 722 | m/z = 661.25 (C49H31N3 = 661.80) |
| 867 | m/z = 714.27 (C52H34N4 = 714.87) |
| 720 | m/z = 713.28 (C55H35N3 = 713.88) |
| 869 | m/z = 714.27 (C52H34N4 = 714.87) |
| 722 | m/z = 661.25 (C49H31N3 = 661.80) |
| 871 | m/z = 714.27 (C52H34N4 = 714.87) |
| 720 | m/z = 713.28 (C55H35N3 = 713.88) |
| 873 | m/z = 714.27 (C52H34N4 = 714.87) |
| 722 | m/z = 661.25 (C49H31N3 = 661.80) |
| 875 | m/z = 688.26 (C50H32N4 = 688.83) |
| 736 | m/z = 687.26 (C51H33N3 = 687.84) |
| 877 | m/z = 688.26 (C50H32N4 = 688.83) |
| 738 | m/z = 635.23 (C47H29N3 = 635.77) |
| 879 | m/z = 639.24 (C45H29N5 = 639.76) |
| 748 | m/z = 638.24 (C46H38N4 = 638.77) |
| 881 | m/z = 639.24 (C45H29N5 = 639.76) |
| 750 | m/z = 586.21 (C42H26N4 = 586.69) |
| 883 | m/z = 639.24 (C45H29N5 = 639.76) |
| 748 | m/z = 638.24 (C46H38N4 = 638.77) |
| 885 | m/z = 639.24 (C45H29N5 = 639.76) |
| 750 | m/z = 586.21 (C42H26N4 = 586.69) |
| 887 | m/z = 639.24 (C45H29N5 = 639.76) |
| 748 | m/z = 638.24 (C46H38N4 = 638.77) |
| 889 | m/z = 639.24 (C45H29N5 = 639.76) |
| 750 | m/z = 586.21 (C42H26N4 = 586.69) |
| 891 | m/z = 714.27 (C52H34N4 = 714.87) |
| 720 | m/z = 713.28 (C55H35N3 = 713.88) |
| 893 | m/z = 714.27 (C52H34N4 = 714.87) |
| 722 | m/z = 661.25 (C49H31N3 = 661.80) |
| 895 | m/z = 714.27 (C52H34N4 = 714.87) |
| 720 | m/z = 713.28 (C55H35N3 = 713.88) |
| 897 | m/z = 714.27 (C52H34N4 = 714.87) |
| 722 | m/z = 661.25 (C49H31N3 = 661.80) |
| 899 | m/z = 714.27 (C52H34N4 = 714.87) |
| 720 | m/z = 713.28 (C55H35N3 = 713.88) |
| 901 | m/z = 714.27 (C52H34N4 = 714.87) |
| 722 | m/z = 661.25 (C49H31N3 = 661.80) |
| 903 | m/z = 638.24 (C46H38N4 = 638.77) |
| 904 | m/z = 637.25 (C47H31N3 = 637.78) |
| 905 | m/z = 714.27 (C52H34N4 = 714.87) |
| 906 | m/z = 713.28 (C55H35N3 = 713.88) |
| 907 | m/z = 714.27 (C52H34N4 = 714.87) |
| 908 | m/z = 713.28 (C55H35N3 = 713.88) |
| 909 | m/z = 713.28 (C55H35N3 = 713.88) |
| 910 | m/z = 713.28 (C55H35N3 = 713.88) |
| 911 | m/z = 714.27 (C52H34N4 = 714.87) |
| 908 | m/z = 713.28 (C55H35N3 = 713.88) |

TABLE 2-continued

| Compound | FD-MS |
|---|---|
| 913 | m/z = 714.27 (C52H34N4 = 714.87) |
| 722 | m/z = 661.25 (C49H31N3 = 661.80) |
| 915 | m/z = 714.27 (C52H34N4 = 714.87) |
| 908 | m/z = 713.28 (C55H35N3 = 713.88) |
| 917 | m/z = 714.27 (C52H34N4 = 714.87) |
| 722 | m/z = 661.25 (C49H31N3 = 661.80) |
| 919 | m/z = 714.27 (C52H34N4 = 714.87) |
| 908 | m/z = 713.28 (C55H35N3 = 713.88) |
| 921 | m/z = 714.27 (C52H34N4 = 714.87) |
| 722 | m/z = 661.25 (C49H31N3 = 661.80) |
| 923 | m/z = 714.27 (C52H34N4 = 714.87) |
| 908 | m/z = 713.28 (C55H35N3 = 713.88) |
| 925 | m/z = 714.27 (C52H34N4 = 714.87) |
| 722 | m/z = 661.25 (C49H31N3 = 661.80) |
| 927 | m/z = 714.27 (C52H34N4 = 714.87) |
| 908 | m/z = 713.28 (C55H35N3 = 713.88) |
| 929 | m/z = 714.27 (C52H34N4 = 714.87) |
| 722 | m/z = 661.25 (C49H31N3 = 661.80) |
| 931 | m/z = 714.27 (C52H34N4 = 714.87) |
| 908 | m/z = 713.28 (C55H35N3 = 713.88) |
| 933 | m/z = 714.27 (C52H34N4 = 714.87) |
| 722 | m/z = 661.25 (C49H31N3 = 661.80) |
| 935 | m/z = 714.27 (C52H34N4 = 714.87) |
| 908 | m/z = 713.28 (C55H35N3 = 713.88) |
| 937 | m/z = 714.27 (C52H34N4 = 714.87) |
| 938 | m/z = 714.27 (C52H34N4 = 714.87) |
| 939 | m/z = 714.27 (C52H34N4 = 714.87) |
| 908 | m/z = 713.28 (C55H35N3 = 713.88) |
| 941 | m/z = 714.27 (C52H34N4 = 714.87) |
| 908 | m/z = 713.28 (C55H35N3 = 713.88) |
| 943 | m/z = 714.27 (C52H34N4 = 714.87) |
| 908 | m/z = 713.28 (C55H35N3 = 713.88) |
| 945 | m/z = 714.27 (C52H34N4 = 714.87) |
| 946 | m/z = 714.27 (C52H34N4 = 714.87) |
| 947 | m/z = 714.27 (C52H34N4 = 714.87) |
| 908 | m/z = 713.28 (C55H35N3 = 713.88) |
| 949 | m/z = 714.27 (C52H34N4 = 714.87) |
| 908 | m/z = 713.28 (C55H35N3 = 713.88) |
| 951 | m/z = 714.27 (C52H34N4 = 714.87) |
| 952 | m/z = 714.27 (C52H34N4 = 714.87) |

<Experimental Example 1> Manufacture of Organic Light Emitting Device

1) Manufacture of Organic Light Emitting Device

A transparent indium tin oxide (ITO) electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum deposition apparatus, and the following 4,4',4''-tris(N,N-(2-naphthyl)-phenylamino)triphenylamine (2-TNATA) was introduced to a cell in the vacuum deposition apparatus.

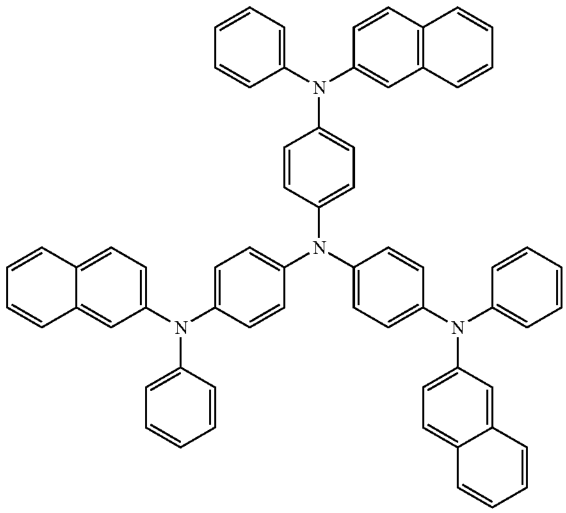

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell of the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

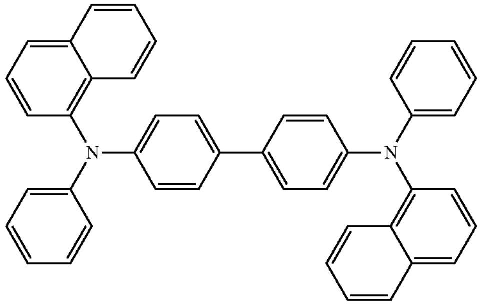

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

H1

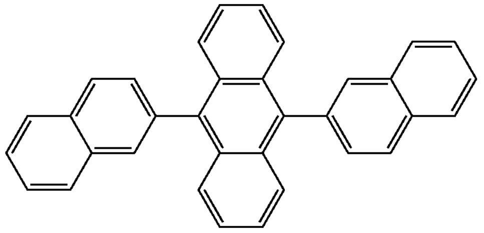

D1

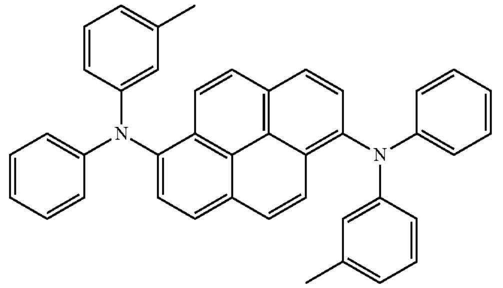

Subsequently, a compound of the following Table 3 was deposited to a thickness of 300 Å as an electron transfer layer.

As an electron injection layer, lithium fluoride (LiF) was deposited to a thickness of 10 Å, and an Al cathode was employed to a thickness of 1,000 Å to manufacture an OLED.

Meanwhile, all the organic compounds required to manufacture the OLED were vacuum sublimation purified under $10^{-6}$ torr to $10^{-8}$ torr by each material to be used in the OLED manufacture.

2) Driving Voltage and Light Emission Efficiency of Organic Light Emitting Device For the organic light emitting devices manufactured as above, electroluminescent light emission (EL) properties were measured using M7000 manufactured by McScience Inc., and with the measurement results, $T_{95}$ when standard luminance was 700 cd/m$^2$ was measured using a lifetime measurement system (M6000) manufactured by McScience Inc. Results of measuring a driving voltage, light emission efficiency, external quantum efficiency and a color coordinate (CIE) of the blue organic light emitting device manufactured according to the present disclosure are as shown in the following Table 3.

TABLE 3

| | Compound | Driving Voltage (V) | Light Emission Efficiency (cd/A) | CIE (x, y) | Life-time (T95) |
|---|---|---|---|---|---|
| Example 1 | 1 | 5.03 | 6.68 | (0.134, 0.101) | 65 |
| Example 2 | 4 | 4.92 | 6.83 | (0.134, 0.102) | 43 |
| Example 3 | 5 | 4.90 | 6.76 | (0.134, 0.101) | 42 |
| Example 4 | 6 | 4.84 | 6.98 | (0.134, 0.103) | 43 |
| Example 5 | 8 | 5.05 | 6.32 | (0.134, 0.102) | 37 |
| Example 6 | 9 | 4.81 | 6.97 | (0.134, 0.101) | 42 |
| Example 7 | 12 | 4.79 | 7.10 | (0.134, 0.102) | 42 |
| Example 8 | 16 | 4.78 | 7.11 | (0.134, 0.101) | 42 |
| Example 9 | 22 | 4.81 | 7.01 | (0.134, 0.101) | 41 |
| Example 10 | 25 | 4.90 | 6.88 | (0.134, 0.100) | 44 |
| Example 11 | 29 | 4.85 | 6.89 | (0.134, 0.101) | 54 |
| Example 12 | 33 | 4.78 | 7.05 | (0.134, 0.100) | 50 |
| Example 13 | 35 | 5.01 | 6.67 | (0.134, 0.100) | 41 |
| Example 14 | 43 | 4.78 | 7.17 | (0.134, 0.100) | 43 |

TABLE 3-continued

| | Compound | Driving Voltage (V) | Light Emission Efficiency (cd/A) | CIE (x, y) | Life-time (T95) |
|---|---|---|---|---|---|
| Example 15 | 46 | 4.85 | 6.81 | (0.134, 0.100) | 44 |
| Example 16 | 48 | 4.80 | 6.90 | (0.134, 0.100) | 44 |
| Example 17 | 49 | 4.81 | 6.96 | (0.134, 0.102) | 43 |
| Example 18 | 55 | 4.76 | 7.00 | (0.134, 0.101) | 39 |
| Example 19 | 56 | 4.74 | 7.05 | (0.134, 0.102) | 40 |
| Example 20 | 63 | 4.77 | 7.02 | (0.134, 0.100) | 39 |
| Example 21 | 65 | 4.85 | 6.83 | (0.134, 0.103) | 43 |
| Example 22 | 67 | 4.85 | 6.86 | (0.134, 0.100) | 55 |
| Example 23 | 71 | 4.79 | 6.88 | (0.134, 0.102) | 41 |
| Example 24 | 73 | 4.79 | 6.99 | (0.134, 0.101) | 56 |
| Example 25 | 77 | 4.85 | 6.89 | (0.134, 0.100) | 37 |
| Example 26 | 79 | 4.82 | 6.90 | (0.134, 0.102) | 40 |
| Example 27 | 81 | 4.83 | 6.98 | (0.134, 0.103) | 44 |
| Example 28 | 83 | 4.83 | 6.91 | (0.134, 0.100) | 39 |
| Example 29 | 100 | 4.77 | 7.00 | (0.134, 0.103) | 54 |
| Example 30 | 103 | 4.98 | 6.62 | (0.134, 0.102) | 43 |
| Example 31 | 105 | 4.92 | 6.71 | (0.134, 0.100) | 45 |
| Example 32 | 106 | 4.99 | 6.71 | (0.134, 0.099) | 44 |
| Example 33 | 109 | 4.85 | 6.88 | (0.134, 0.102) | 45 |
| Example 34 | 113 | 4.85 | 6.91 | (0.134, 0.100) | 46 |
| Example 35 | 116 | 4.85 | 6.91 | (0.134, 0.103) | 43 |
| Example 36 | 117 | 4.92 | 6.65 | (0.134, 0.102) | 45 |
| Example 37 | 121 | 4.79 | 6.72 | (0.134, 0.101) | 40 |
| Example 38 | 122 | 4.85 | 6.62 | (0.134, 0.102) | 43 |
| Example 39 | 124 | 4.70 | 6.92 | (0.134, 0.102) | 45 |
| Example 40 | 135 | 4.83 | 6.83 | (0.134, 0.101) | 43 |
| Example 41 | 136 | 4.81 | 6.88 | (0.134, 0.101) | 42 |
| Example 42 | 137 | 4.86 | 6.81 | (0.134, 0.099) | 40 |
| Example 43 | 139 | 4.95 | 6.83 | (0.134, 0.101) | 56 |
| Example 44 | 142 | 5.06 | 6.89 | (0.134, 0.102) | 56 |
| Example 45 | 145 | 5.04 | 6.86 | (0.134, 0.101) | 72 |
| Example 46 | 147 | 4.97 | 6.80 | (0.134, 0.101) | 57 |
| Example 47 | 154 | 4.94 | 7.01 | (0.134, 0.100) | 53 |
| Example 48 | 155 | 4.88 | 6.99 | (0.134, 0.101) | 53 |
| Example 49 | 160 | 4.92 | 6.94 | (0.134, 0.100) | 60 |
| Example 50 | 164 | 5.04 | 6.70 | (0.134, 0.100) | 59 |
| Example 51 | 165 | 5.03 | 6.80 | (0.134, 0.100) | 60 |
| Example 52 | 166 | 5.09 | 6.64 | (0.134, 0.100) | 75 |
| Example 53 | 184 | 4.84 | 7.19 | (0.134, 0.100) | 51 |
| Example 54 | 199 | 5.07 | 7.07 | (0.134, 0.102) | 44 |
| Example 55 | 229 | 4.90 | 6.77 | (0.134, 0.101) | 50 |
| Example 56 | 232 | 4.92 | 6.77 | (0.134, 0.102) | 47 |
| Example 57 | 241 | 5.01 | 7.01 | (0.134, 0.100) | 55 |
| Example 58 | 245 | 4.85 | 6.92 | (0.134, 0.103) | 58 |
| Example 59 | 246 | 4.84 | 6.94 | (0.134, 0.100) | 48 |
| Example 60 | 247 | 5.03 | 7.11 | (0.134, 0.102) | 52 |
| Example 61 | 277 | 5.09 | 7.03 | (0.134, 0.101) | 53 |
| Example 62 | 299 | 4.84 | 7.20 | (0.134, 0.100) | 45 |
| Example 63 | 307 | 4.87 | 7.07 | (0.134, 0.102) | 44 |
| Example 64 | 353 | 5.05 | 6.70 | (0.134, 0.103) | 53 |
| Example 65 | 354 | 5.04 | 6.83 | (0.134, 0.100) | 42 |
| Example 66 | 355 | 5.04 | 6.83 | (0.134, 0.103) | 50 |
| Example 67 | 385 | 4.90 | 7.01 | (0.134, 0.102) | 60 |
| Example 68 | 397 | 5.10 | 6.51 | (0.134, 0.100) | 75 |
| Example 69 | 400 | 4.77 | 7.26 | (0.134, 0.099) | 59 |
| Example 70 | 412 | 5.07 | 6.58 | (0.134, 0.102) | 73 |
| Example 71 | 415 | 4.84 | 7.25 | (0.134, 0.100) | 42 |
| Example 72 | 455 | 4.90 | 6.70 | (0.134, 0.101) | 49 |
| Example 73 | 463 | 5.05 | 6.76 | (0.134, 0.102) | 57 |
| Example 74 | 493 | 4.99 | 6.83 | (0.134, 0.101) | 60 |
| Example 75 | 508 | 4.95 | 6.92 | (0.134, 0.101) | 55 |
| Example 76 | 523 | 4.98 | 6.80 | (0.134, 0.100) | 48 |
| Example 77 | 538 | 4.95 | 6.86 | (0.134, 0.101) | 45 |
| Example 78 | 569 | 5.02 | 6.75 | (0.134, 0.100) | 52 |
| Example 79 | 601 | 4.83 | 7.19 | (0.134, 0.100) | 57 |
| Example 80 | 616 | 4.79 | 7.20 | (0.134, 0.100) | 54 |
| Example 81 | 631 | 4.81 | 7.20 | (0.134, 0.100) | 52 |
| Example 82 | 646 | 4.78 | 7.20 | (0.134, 0.100) | 50 |
| Example 83 | 661 | 5.03 | 6.91 | (0.134, 0.102) | 51 |
| Example 84 | 677 | 5.05 | 6.83 | (0.134, 0.101) | 52 |
| Example 85 | 679 | 4.84 | 7.25 | (0.134, 0.102) | 57 |
| Example 86 | 699 | 4.83 | 7.25 | (0.134, 0.100) | 52 |
| Example 87 | 706 | 5.03 | 6.86 | (0.134, 0.103) | 48 |
| Example 88 | 711 | 4.85 | 7.06 | (0.134, 0.100) | 53 |
| Example 89 | 720 | 4.79 | 7.12 | (0.134, 0.102) | 50 |

TABLE 3-continued

| | Compound | Driving Voltage (V) | Light Emission Efficiency (cd/A) | CIE (x, y) | Life-time (T95) |
|---|---|---|---|---|---|
| Example 90 | 727 | 4.89 | 7.02 | (0.134, 0.101) | 53 |
| Example 91 | 735 | 4.90 | 6.90 | (0.134, 0.100) | 52 |
| Example 92 | 740 | 4.98 | 6.80 | (0.134, 0.102) | 54 |
| Example 93 | 755 | 4.96 | 6.82 | (0.134, 0.103) | 55 |
| Example 94 | 763 | 5.01 | 6.78 | (0.134, 0.100) | 57 |
| Example 95 | 764 | 5.06 | 6.85 | (0.134, 0.103) | 54 |
| Example 96 | 776 | 5.03 | 6.92 | (0.134, 0.102) | 51 |
| Example 97 | 779 | 4.97 | 6.93 | (0.134, 0.100) | 50 |
| Example 98 | 827 | 5.02 | 6.80 | (0.134, 0.099) | 52 |
| Example 99 | 831 | 5.01 | 6.79 | (0.134, 0.102) | 51 |
| Example 100 | 848 | 5.01 | 6.92 | (0.134, 0.100) | 52 |
| Example 101 | 856 | 4.96 | 6.82 | (0.134, 0.100) | 51 |
| Example 102 | 875 | 4.90 | 6.99 | (0.134, 0.100) | 53 |
| Example 103 | 908 | 4.78 | 7.29 | (0.134, 0.100) | 48 |
| Example 104 | 911 | 4.76 | 7.32 | (0.134, 0.100) | 52 |
| Example 105 | 912 | 4.76 | 7.32 | (0.134, 0.102) | 49 |
| Example 106 | 914 | 5.04 | 6.67 | (0.134, 0.101) | 53 |
| Example 107 | 935 | 4.98 | 6.80 | (0.134, 0.102) | 54 |
| Example 108 | 936 | 4.92 | 7.41 | (0.134, 0.100) | 50 |
| Comparative Example 2-1 | E1 | 5.56 | 5.91 | (0.134, 0.100) | 28 |
| Comparative Example 2-2 | E2 | 5.52 | 6.09 | (0.134, 0.101) | 28 |
| Comparative Example 2-3 | BBQB | 5.50 | 6.10 | (0.134, 0.101) | 30 |
| Comparative Example 2-4 | TBQB | 5.51 | 6.15 | (0.134, 0.102) | 29 |

E1

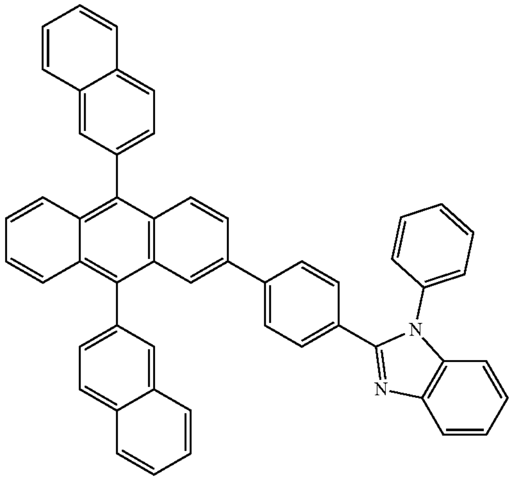

E2

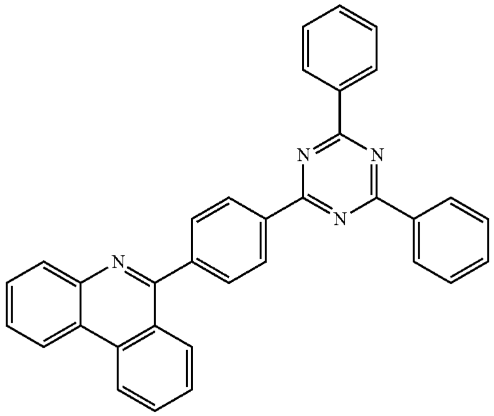

-continued

BBQB

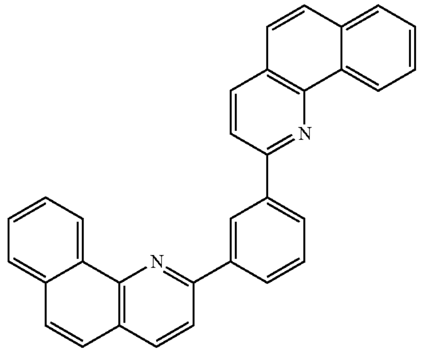

TBQB

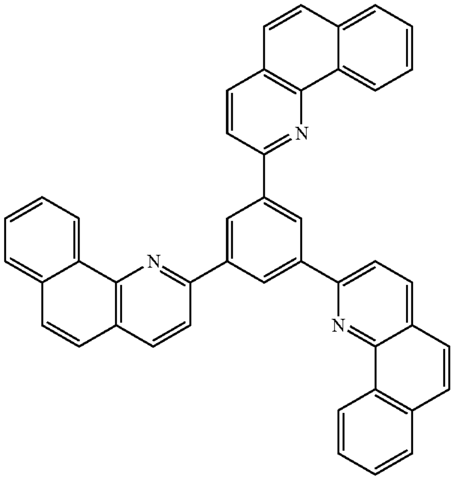

As seen from the results of Table 3, the organic light emitting device using the electron transfer layer material of the blue organic light emitting device of the present disclosure had a lower driving voltage and significantly improved light emission efficiency and lifetime compared to Comparative Examples 2-1 to 2-4. Particularly, it was identified that Compounds 43, 56, 184, 299, 400, 415, 601, 616, 679, 699, 908, 911, 912 and 936 were superior in all aspects of driving, efficiency and lifetime.

Such a result is considered to be due to the fact that, when using the disclosed compound having proper length, strength and flat properties as an electron transfer layer, a compound in an excited state is made by receiving electrons under a specific condition, and particularly when a hetero-skeleton site of the compound is formed in an excited state, excited energy moves to a stable state before the excited hetero-skeleton site goes through other reactions, and a relatively stabilized compound is capable of efficiently transferring electrons without the compound being decomposed or destroyed. For reference, those that are stable when excited are considered to be aryl or acene-based compounds or polycyclic hetero-compounds. Accordingly, it is considered that excellent results in all aspects of driving, efficiency and lifetime were obtained by the compound of the present disclosure enhancing enhanced electron-transfer properties or improved stability.

<Experimental Example 2> Manufacture of Organic Light Emitting Device

1) Manufacture of Organic Light Emitting Device

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used. Next, an ITO substrate was installed in a substrate folder of a vacuum deposition apparatus, and the following 4,4',4"-tris(N,N-(2-naphthyl)-phenylamino)triphenylamine (2-TNATA) was introduced to a cell in the vacuum deposition apparatus.

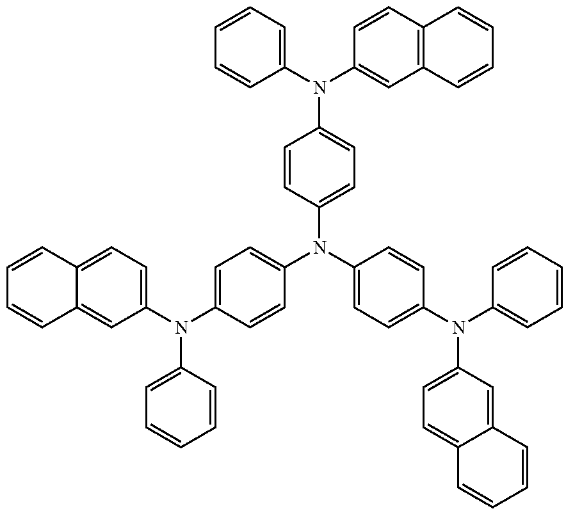

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate. To another cell of the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

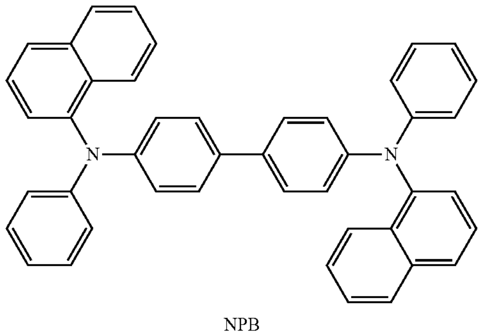 [SMILES: c1ccc(N(c2ccc(-c3ccc(N(c4ccccc4)c4cccc5ccccc45)cc3)cc2)c2cccc3ccccc23)cc1 ; "NPB"]

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

H1

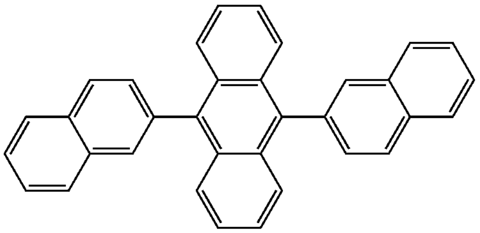

D1

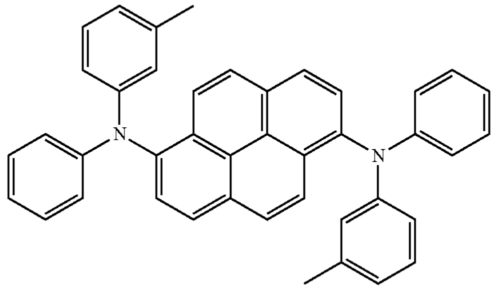

Subsequently, a compound of the following structural formula E1 was deposited to a thickness of 300 Å as an electron transfer layer.

E1

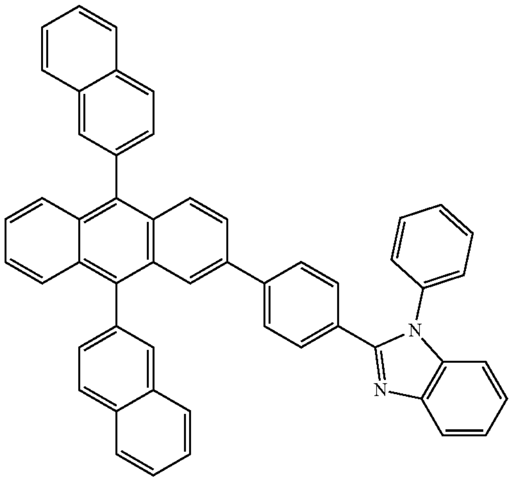

E2

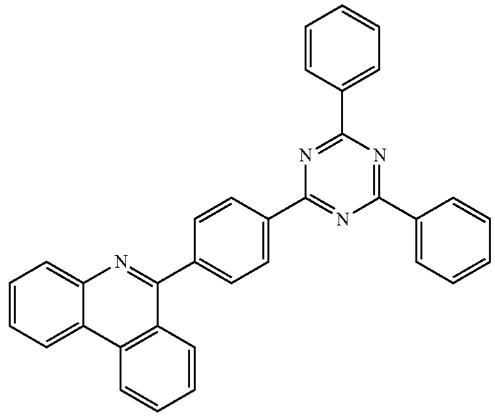

-continued

BBQB

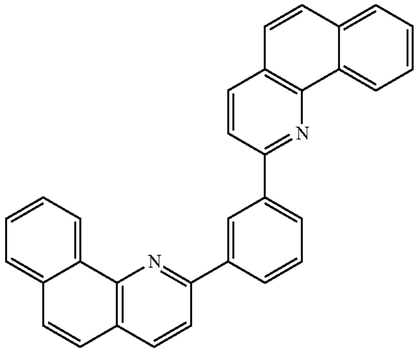

TBQB

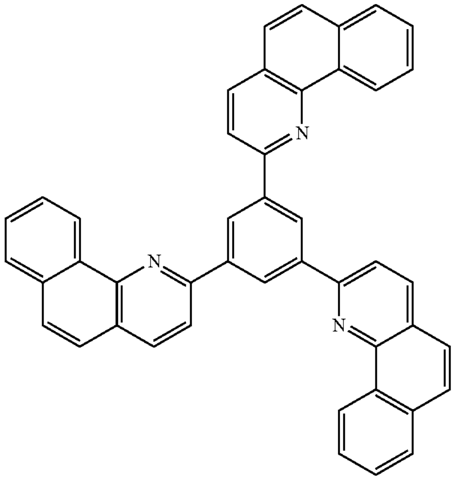

As an electron injection layer, lithium fluoride (LiF) was deposited to a thickness of 10 Å, and an Al cathode was employed to a thickness of 1,000 Å to manufacture an OLED. Meanwhile, all the organic compounds required to manufacture the OLED were vacuum sublimation purified under $10^{-6}$ torr to $10^{-8}$ torr by each material to be used in the OLED manufacture.

An electroluminescent device was manufactured in the same manner as in Experimental Example 2 except that, after forming the electron transfer layer E1 to a thickness of 250 Å, a hole blocking layer was formed on the electron transfer layer using a compound presented in Table 4 to a thickness of 50 Å. Results of measuring a driving voltage, light emission efficiency, a color coordinate (CIE) and a lifetime of the blue organic light emitting device manufactured according to the present disclosure are as shown in Table 4.

TABLE 4

| | Compound | Driving voltage (V) | Light Emission Efficiency (cd/A) | CIE (x, y) | Life-time (T95) |
|---|---|---|---|---|---|
| Example 1 | 1 | 5.03 | 6.68 | (0.134, 0.101) | 55 |
| Example 2 | 4 | 4.92 | 6.83 | (0.134, 0.102) | 43 |
| Example 3 | 5 | 4.90 | 6.76 | (0.134, 0.101) | 42 |
| Example 4 | 6 | 4.84 | 6.98 | (0.134, 0.103) | 43 |
| Example 5 | 8 | 5.05 | 6.32 | (0.134, 0.102) | 37 |
| Example 6 | 9 | 4.81 | 6.97 | (0.134, 0.101) | 42 |
| Example 7 | 12 | 4.79 | 7.10 | (0.134, 0.102) | 42 |
| Example 8 | 16 | 4.78 | 7.11 | (0.134, 0.101) | 42 |

TABLE 4-continued

| | Compound | Driving voltage (V) | Light Emission Efficiency (cd/A) | CIE (x, y) | Life-time (T95) |
|---|---|---|---|---|---|
| Example 9 | 22 | 4.81 | 7.01 | (0.134, 0.101) | 41 |
| Example 10 | 25 | 4.90 | 6.88 | (0.134, 0.100) | 44 |
| Example 11 | 29 | 4.69 | 7.50 | (0.134, 0.101) | 60 |
| Example 12 | 33 | 4.69 | 7.49 | (0.134, 0.100) | 60 |
| Example 13 | 35 | 5.01 | 6.67 | (0.134, 0.100) | 41 |
| Example 14 | 43 | 4.78 | 7.17 | (0.134, 0.100) | 43 |
| Example 15 | 46 | 4.85 | 6.81 | (0.134, 0.100) | 44 |
| Example 16 | 48 | 4.80 | 6.90 | (0.134, 0.100) | 44 |
| Example 17 | 49 | 4.81 | 6.96 | (0.134, 0.102) | 43 |
| Example 18 | 55 | 4.76 | 7.00 | (0.134, 0.101) | 39 |
| Example 19 | 56 | 4.74 | 7.05 | (0.134, 0.102) | 40 |
| Example 20 | 63 | 4.77 | 7.02 | (0.134, 0.100) | 39 |
| Example 21 | 65 | 4.85 | 6.83 | (0.134, 0.103) | 43 |
| Example 22 | 67 | 4.85 | 6.86 | (0.134, 0.100) | 55 |
| Example 23 | 71 | 4.79 | 6.88 | (0.134, 0.102) | 41 |
| Example 24 | 73 | 4.79 | 6.99 | (0.134, 0.101) | 56 |
| Example 25 | 77 | 4.85 | 6.89 | (0.134, 0.100) | 37 |
| Example 26 | 79 | 4.82 | 6.90 | (0.134, 0.102) | 40 |
| Example 27 | 81 | 4.83 | 6.98 | (0.134, 0.103) | 44 |
| Example 28 | 83 | 4.83 | 6.91 | (0.134, 0.100) | 39 |
| Example 29 | 100 | 4.69 | 7.49 | (0.134, 0.100) | 60 |
| Example 30 | 103 | 4.98 | 6.62 | (0.134, 0.102) | 43 |
| Example 31 | 105 | 4.92 | 6.71 | (0.134, 0.100) | 45 |
| Example 32 | 106 | 4.99 | 6.71 | (0.134, 0.099) | 44 |
| Example 33 | 109 | 4.85 | 6.88 | (0.134, 0.102) | 45 |
| Example 34 | 113 | 4.85 | 6.91 | (0.134, 0.100) | 46 |
| Example 35 | 116 | 4.85 | 6.91 | (0.134, 0.103) | 43 |
| Example 36 | 117 | 4.92 | 6.65 | (0.134, 0.102) | 45 |
| Example 37 | 121 | 4.79 | 6.72 | (0.134, 0.101) | 40 |
| Example 38 | 122 | 4.85 | 6.62 | (0.134, 0.102) | 43 |
| Example 39 | 124 | 4.70 | 6.92 | (0.134, 0.102) | 45 |
| Example 40 | 135 | 4.83 | 6.83 | (0.134, 0.101) | 43 |
| Example 41 | 136 | 4.81 | 6.88 | (0.134, 0.101) | 42 |
| Example 42 | 137 | 4.86 | 6.81 | (0.134, 0.099) | 40 |
| Example 43 | 139 | 4.95 | 6.83 | (0.134, 0.101) | 56 |
| Example 44 | 142 | 5.06 | 6.89 | (0.134, 0.102) | 56 |
| Example 45 | 145 | 5.04 | 6.86 | (0.134, 0.101) | 72 |
| Example 46 | 147 | 4.97 | 6.80 | (0.134, 0.101) | 57 |
| Example 47 | 154 | 4.94 | 7.01 | (0.134, 0.100) | 53 |
| Example 48 | 155 | 4.88 | 6.99 | (0.134, 0.101) | 53 |
| Example 49 | 160 | 4.69 | 7.49 | (0.134, 0.100) | 60 |
| Example 50 | 164 | 5.04 | 6.70 | (0.134, 0.100) | 59 |
| Example 51 | 165 | 5.03 | 6.80 | (0.134, 0.100) | 60 |
| Example 52 | 166 | 5.09 | 6.64 | (0.134, 0.100) | 75 |
| Example 53 | 184 | 4.84 | 7.19 | (0.134, 0.100) | 51 |
| Example 54 | 199 | 5.07 | 7.07 | (0.134, 0.102) | 44 |
| Example 55 | 229 | 4.90 | 6.77 | (0.134, 0.101) | 50 |
| Example 56 | 232 | 4.92 | 6.77 | (0.134, 0.102) | 47 |
| Example 57 | 241 | 5.01 | 7.01 | (0.134, 0.100) | 55 |
| Example 58 | 245 | 4.85 | 6.92 | (0.134, 0.103) | 58 |
| Example 59 | 246 | 4.84 | 6.94 | (0.134, 0.100) | 48 |
| Example 60 | 247 | 5.03 | 7.11 | (0.134, 0.102) | 52 |
| Example 61 | 277 | 5.09 | 7.03 | (0.134, 0.101) | 53 |
| Example 62 | 299 | 4.84 | 7.20 | (0.134, 0.100) | 45 |
| Example 63 | 307 | 4.87 | 7.07 | (0.134, 0.102) | 44 |
| Example 64 | 353 | 5.05 | 6.70 | (0.134, 0.103) | 53 |
| Example 65 | 354 | 5.04 | 6.83 | (0.134, 0.100) | 42 |
| Example 66 | 355 | 5.04 | 6.83 | (0.134, 0.103) | 50 |
| Example 67 | 385 | 4.90 | 7.01 | (0.134, 0.102) | 60 |
| Example 68 | 397 | 5.10 | 6.51 | (0.134, 0.100) | 75 |
| Example 69 | 400 | 4.77 | 7.26 | (0.134, 0.099) | 59 |
| Example 70 | 412 | 5.07 | 6.58 | (0.134, 0.102) | 73 |
| Example 71 | 415 | 4.84 | 7.25 | (0.134, 0.100) | 42 |
| Example 72 | 455 | 4.90 | 6.70 | (0.134, 0.101) | 49 |
| Example 73 | 463 | 5.05 | 6.76 | (0.134, 0.102) | 57 |
| Example 74 | 493 | 4.99 | 6.83 | (0.134, 0.101) | 60 |
| Example 75 | 508 | 4.95 | 6.92 | (0.134, 0.101) | 55 |
| Example 76 | 523 | 4.98 | 6.80 | (0.134, 0.100) | 48 |
| Example 77 | 538 | 4.95 | 6.86 | (0.134, 0.101) | 45 |
| Example 78 | 569 | 5.02 | 6.75 | (0.134, 0.100) | 52 |
| Example 79 | 601 | 4.83 | 7.19 | (0.134, 0.100) | 57 |
| Example 80 | 616 | 4.79 | 7.20 | (0.134, 0.100) | 54 |
| Example 81 | 631 | 4.81 | 7.20 | (0.134, 0.100) | 52 |
| Example 82 | 646 | 4.78 | 7.20 | (0.134, 0.100) | 50 |
| Example 83 | 661 | 5.03 | 6.91 | (0.134, 0.102) | 51 |

TABLE 4-continued

| | Compound | Driving voltage (V) | Light Emission Efficiency (cd/A) | CIE (x, y) | Life-time (T95) |
|---|---|---|---|---|---|
| Example 84 | 677 | 5.05 | 6.83 | (0.134, 0.101) | 52 |
| Example 85 | 679 | 4.84 | 7.25 | (0.134, 0.102) | 57 |
| Example 86 | 699 | 4.83 | 7.25 | (0.134, 0.100) | 52 |
| Example 87 | 706 | 5.03 | 6.86 | (0.134, 0.103) | 48 |
| Example 88 | 711 | 4.85 | 7.06 | (0.134, 0.100) | 53 |
| Example 89 | 720 | 4.79 | 7.12 | (0.134, 0.102) | 50 |
| Example 90 | 727 | 4.89 | 7.02 | (0.134, 0.101) | 53 |
| Example 91 | 735 | 4.90 | 6.90 | (0.134, 0.100) | 52 |
| Example 92 | 740 | 4.98 | 6.80 | (0.134, 0.102) | 54 |
| Example 93 | 755 | 4.96 | 6.82 | (0.134, 0.103) | 55 |
| Example 94 | 763 | 5.01 | 6.78 | (0.134, 0.100) | 57 |
| Example 95 | 764 | 5.06 | 6.85 | (0.134, 0.103) | 54 |
| Example 96 | 776 | 5.03 | 6.92 | (0.134, 0.102) | 51 |
| Example 97 | 779 | 4.97 | 6.93 | (0.134, 0.100) | 50 |
| Example 98 | 827 | 5.02 | 6.80 | (0.134, 0.099) | 52 |
| Example 99 | 831 | 5.01 | 6.79 | (0.134, 0.102) | 51 |
| Example 100 | 848 | 5.01 | 6.92 | (0.134, 0.100) | 52 |
| Example 101 | 856 | 4.96 | 6.82 | (0.134, 0.100) | 51 |
| Example 102 | 875 | 4.90 | 6.99 | (0.134, 0.100) | 53 |
| Example 103 | 908 | 4.78 | 7.29 | (0.134, 0.100) | 48 |
| Example 104 | 911 | 4.76 | 7.32 | (0.134, 0.100) | 52 |
| Example 105 | 912 | 4.76 | 7.32 | (0.134, 0.102) | 49 |
| Example 106 | 914 | 5.04 | 6.67 | (0.134, 0.101) | 53 |
| Example 107 | 935 | 4.98 | 6.80 | (0.134, 0.102) | 54 |
| Example 108 | 936 | 4.92 | 7.41 | (0.134, 0.100) | 50 |
| Comparative Example 2-1 | E2 | 5.42 | 6.11 | (0.134, 0.101) | 28 |
| Comparative Example 2-2 | BBQB | 5.45 | 6.12 | (0.134, 0.101) | 29 |
| Comparative Example 2-3 | TBQB | 5.46 | 6.15 | (0.134, 0.102) | 28 |

As seen from the results of Table 4, the organic light emitting device using the hole blocking layer material of the blue organic light emitting device of the present disclosure had a lower driving voltage and significantly improved light emission efficiency and lifetime compared to Comparative Examples 2-1 to 2-3. Particularly, it was identified that Compounds 29, 33, 100 and 160 were significantly superior in all aspects of driving, efficiency and lifetime. Such a reason is due to the fact that the compounds are a bipolar type having both a p-type and an n-type, and capable of preventing hole leakage and effectively trapping excitons in the light emitting layer.

<Experimental Example 3> Manufacture of Organic Light Emitting Device

1) Manufacture of Organic Light Emitting Device

A glass substrate on which ITO was coated as a thin film to a thickness of 1500 Å was cleaned with distilled water ultrasonic waves. After the cleaning with distilled water was finished, the substrate was ultrasonic cleaned with solvents such as acetone, methanol and isopropyl alcohol, then dried, and UVO treatment was performed for 5 minutes using UV in a UV cleaner. After that, the substrate was transferred to a plasma cleaner (PT), and plasma treatment was performed under vacuum for ITO work function and residual film removal, and the substrate was transferred to a thermal deposition apparatus for organic deposition.

On the transparent ITO electrode (anode), an organic material was formed in a 2 stack white organic light emitting device (WOLED) structure. As for the first stack, TAPC was the/mal vacuum deposited to a thickness of 300 Å first to foam a hole transfer layer. After foaming the hole transfer layer, a light emitting layer was the/mal vacuum deposited thereon as follows. The light emitting layer was deposited to 300 Å by doping FIrpic to TCz1, a host, by 8% as a blue phosphorescent dopant. After firming an electron transfer layer to 400 Å using TmPyPB, a charge generation layer was formed to 100 Å by doping $Cs_2CO_3$ to the compound listed in the following Table 5 by 20%.

As for the second stack, $MoO_3$ was thermal vacuum deposited to a thickness of 50 Å first to form a hole injection layer. A hole transfer layer, a common layer, was formed by doping $MoO_3$ to TAPC by 20% to 100 Å and then depositing TAPC to 300 Å. A light emitting layer was deposited thereon to 300 Å by doping $Ir(ppy)_3$, a green phosphorescent dopant, to TCz1, a host, by 8%, and an electron transfer layer was formed to 600 Å using TmPyPB. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å to manufacture an organic light emitting device.

Meanwhile, all the organic compounds required to manufacture the OLED were vacuum sublimation purified under $10^{-6}$ torr to $10^{-8}$ torr by each material to be used in the OLED manufacture.

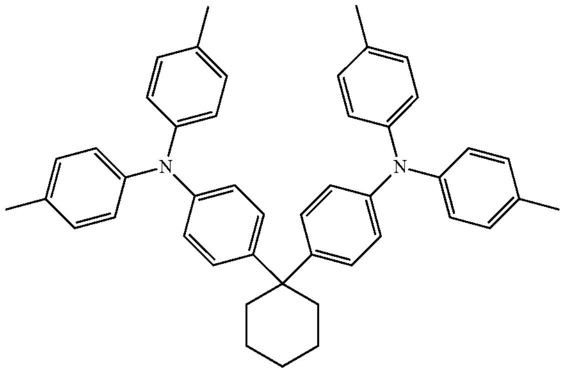

TAPC

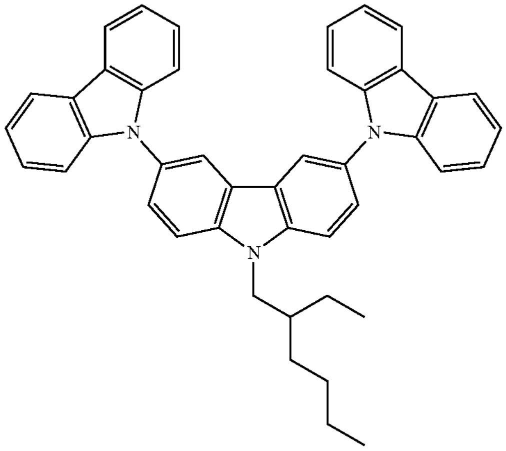

TCz1

-continued

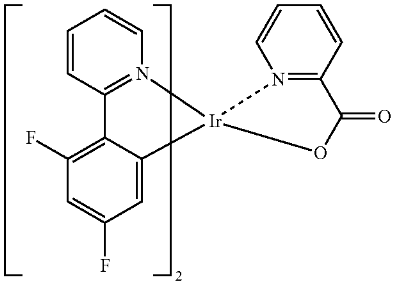

FIrpic

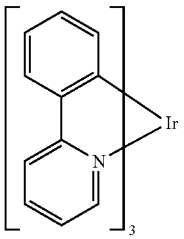

Ir(ppy)3

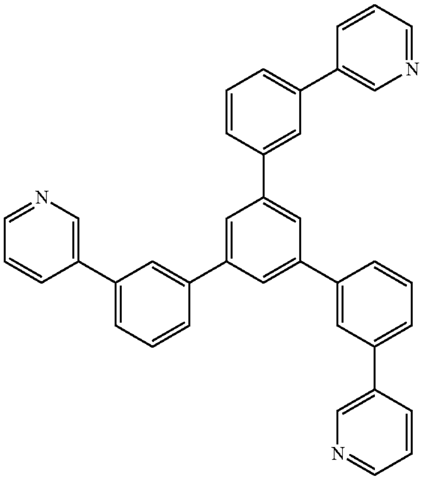

TmPyPB

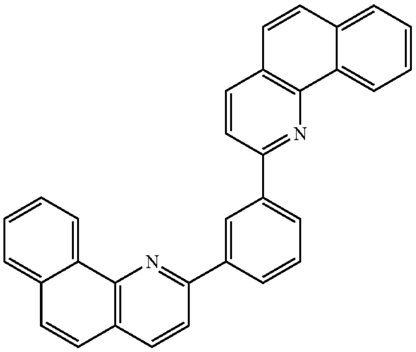

BBQB

-continued

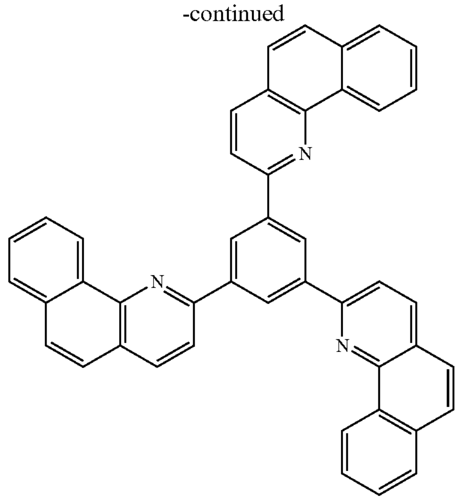

TBQB

E2

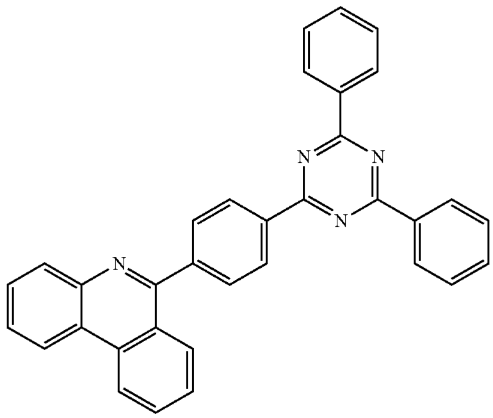

2) Driving Voltage and Light Emission Efficiency of Organic Light Emitting Device For the organic light emitting devices manufactured as above, electroluminescent light emission (EL) properties were measured using M7000 manufactured by McScience Inc., and with the measurement results, $T_{95}$ when standard luminance was 3,500 cd/m$^2$ was measured using a lifetime measurement system (M6000) manufactured by McScience Inc. Results of measuring a driving voltage, light emission efficiency, external quantum efficiency and a color coordinate (CIE) of the white organic light emitting device manufactured according to the present disclosure are as shown in Table 5.

TABLE 5

| | Compound | Driving voltage (V) | Light Emission Efficiency (cd/A) | CIE (x, y) | Life-time (T95) |
|---|---|---|---|---|---|
| Example 1 | 1 | 7.78 | 63.95 | (0.218, 0.427) | 61 |
| Example 2 | 4 | 7.60 | 65.45 | (0.220, 0.431) | 40 |
| Example 3 | 5 | 7.57 | 64.75 | (0.220, 0.431) | 39 |
| Example 4 | 6 | 7.48 | 66.88 | (0.200, 0.421) | 40 |
| Example 5 | 8 | 7.81 | 60.55 | (0.228, 0.436) | 35 |
| Example 6 | 9 | 7.44 | 66.74 | (0.243, 0.442) | 39 |
| Example 7 | 12 | 7.41 | 67.99 | (0.221, 0.433) | 39 |
| Example 8 | 16 | 7.39 | 68.12 | (0.208, 0.415) | 39 |
| Example 9 | 22 | 7.44 | 67.13 | (0.233, 0.433) | 38 |
| Example 10 | 25 | 7.57 | 65.89 | (0.238, 0.438) | 41 |

TABLE 5-continued

| | Compound | Driving voltage (V) | Light Emission Efficiency (cd/A) | CIE (x, y) | Life-time (T95) |
|---|---|---|---|---|---|
| Example 11 | 29 | 7.50 | 66.01 | (0.225, 0.429) | 50 |
| Example 12 | 33 | 7.39 | 67.56 | (0.209, 0.415) | 47 |
| Example 13 | 35 | 7.74 | 63.89 | (0.231, 0.440) | 38 |
| Example 14 | 43 | 7.39 | 68.71 | (0.211, 0.419) | 40 |
| Example 15 | 46 | 7.49 | 65.26 | (0.209, 0.419) | 41 |
| Example 16 | 48 | 7.27 | 69.54 | (0.207, 0.409) | 54 |
| Example 17 | 49 | 7.53 | 64.66 | (0.208, 0.415) | 32 |
| Example 18 | 55 | 7.35 | 67.06 | (0.214, 0.420) | 36 |
| Example 19 | 56 | 7.33 | 67.56 | (0.224, 0.429) | 37 |
| Example 20 | 63 | 7.37 | 67.21 | (0.221, 0.434) | 36 |
| Example 21 | 65 | 7.28 | 69.61 | (0.212, 0.422) | 53 |
| Example 22 | 67 | 7.49 | 65.70 | (0.228, 0.418) | 51 |
| Example 23 | 71 | 7.40 | 65.89 | (0.231, 0.420) | 38 |
| Example 24 | 73 | 7.41 | 66.98 | (0.219, 0.411) | 52 |
| Example 25 | 77 | 7.50 | 65.98 | (0.219, 0.411) | 35 |
| Example 26 | 79 | 7.45 | 66.11 | (0.210, 0.412) | 37 |
| Example 27 | 81 | 7.47 | 66.84 | (0.218, 0.421) | 41 |
| Example 28 | 83 | 7.46 | 66.21 | (0.209, 0.432) | 36 |
| Example 29 | 100 | 7.38 | 67.04 | (0.231, 0.418) | 50 |
| Example 30 | 103 | 7.69 | 63.38 | (0.243, 0.442) | 40 |
| Example 31 | 105 | 7.61 | 64.23 | (0.205, 0.411) | 42 |
| Example 32 | 106 | 7.72 | 64.22 | (0.243, 0.442) | 41 |
| Example 33 | 109 | 7.50 | 65.88 | (0.209, 0.419) | 42 |
| Example 34 | 113 | 7.49 | 66.18 | (0.210, 0.420) | 43 |
| Example 35 | 116 | 7.50 | 66.20 | (0.231, 0.419) | 40 |
| Example 36 | 117 | 7.49 | 66.24 | (0.229, 0.420) | 40 |
| Example 37 | 121 | 7.31 | 66.80 | (0.224, 0.423) | 35 |
| Example 38 | 122 | 7.45 | 66.27 | (0.220, 0.424) | 37 |
| Example 39 | 124 | 7.29 | 67.57 | (0.221, 0.430) | 40 |
| Example 40 | 135 | 7.48 | 65.82 | (0.220, 0.429) | 41 |
| Example 41 | 136 | 7.45 | 66.00 | (0.221, 0.430) | 40 |
| Example 42 | 137 | 7.50 | 65.87 | (0.222, 0.410) | 39 |
| Example 43 | 139 | 7.61 | 64.44 | (0.218, 0.427) | 47 |
| Example 44 | 142 | 7.77 | 65.02 | (0.220, 0.431) | 47 |
| Example 45 | 145 | 7.74 | 64.77 | (0.220, 0.431) | 60 |
| Example 46 | 147 | 7.63 | 64.19 | (0.200, 0.421) | 48 |
| Example 47 | 154 | 7.60 | 66.18 | (0.228, 0.436) | 44 |
| Example 48 | 155 | 7.50 | 66.00 | (0.243, 0.442) | 45 |
| Example 49 | 160 | 7.56 | 65.47 | (0.221, 0.433) | 50 |
| Example 50 | 164 | 7.75 | 63.27 | (0.208, 0.415) | 49 |
| Example 51 | 165 | 7.73 | 64.20 | (0.233, 0.433) | 50 |
| Example 52 | 166 | 7.82 | 62.64 | (0.238, 0.438) | 63 |
| Example 53 | 184 | 7.44 | 67.91 | (0.225, 0.429) | 43 |
| Example 54 | 199 | 7.79 | 66.76 | (0.209, 0.415) | 37 |
| Example 55 | 229 | 7.52 | 63.86 | (0.231, 0.440) | 41 |
| Example 56 | 232 | 7.56 | 63.86 | (0.211, 0.419) | 39 |
| Example 57 | 241 | 7.69 | 66.18 | (0.209, 0.419) | 46 |
| Example 58 | 245 | 7.27 | 69.48 | (0.207, 0.409) | 55 |
| Example 59 | 246 | 7.64 | 65.52 | (0.208, 0.415) | 27 |
| Example 60 | 247 | 7.73 | 67.16 | (0.214, 0.420) | 43 |
| Example 61 | 277 | 7.82 | 66.33 | (0.224, 0.429) | 44 |
| Example 62 | 299 | 7.43 | 67.93 | (0.221, 0.434) | 38 |
| Example 63 | 307 | 7.48 | 66.76 | (0.212, 0.422) | 36 |
| Example 64 | 353 | 7.28 | 69.70 | (0.228, 0.418) | 53 |
| Example 65 | 354 | 7.75 | 64.50 | (0.231, 0.420) | 35 |
| Example 66 | 355 | 7.74 | 64.44 | (0.219, 0.411) | 42 |
| Example 67 | 385 | 7.52 | 66.18 | (0.219, 0.411) | 50 |
| Example 68 | 397 | 7.83 | 61.47 | (0.210, 0.412) | 63 |
| Example 69 | 400 | 7.32 | 68.52 | (0.218, 0.421) | 49 |
| Example 70 | 412 | 7.78 | 62.11 | (0.209, 0.432) | 61 |
| Example 71 | 415 | 7.43 | 68.44 | (0.231, 0.418) | 35 |
| Example 72 | 455 | 7.53 | 63.26 | (0.243, 0.442) | 41 |
| Example 73 | 463 | 7.75 | 63.85 | (0.205, 0.411) | 47 |
| Example 74 | 493 | 7.67 | 64.44 | (0.243, 0.442) | 50 |
| Example 75 | 508 | 7.61 | 65.35 | (0.209, 0.419) | 46 |
| Example 76 | 523 | 7.65 | 64.16 | (0.210, 0.420) | 40 |
| Example 77 | 538 | 7.61 | 64.74 | (0.231, 0.419) | 37 |
| Example 78 | 569 | 7.28 | 69.51 | (0.229, 0.420) | 54 |
| Example 79 | 601 | 7.43 | 67.88 | (0.224, 0.423) | 48 |
| Example 80 | 616 | 7.36 | 67.94 | (0.220, 0.424) | 45 |
| Example 81 | 631 | 7.39 | 67.92 | (0.221, 0.430) | 44 |
| Example 82 | 646 | 7.34 | 68.00 | (0.220, 0.429) | 41 |
| Example 83 | 661 | 7.73 | 65.21 | (0.221, 0.430) | 43 |
| Example 84 | 677 | 7.24 | 69.51 | (0.222, 0.410) | 52 |
| Example 85 | 679 | 7.44 | 68.44 | (0.219, 0.411) | 48 |
| Example 86 | 699 | 7.42 | 68.45 | (0.210, 0.412) | 43 |
| Example 87 | 706 | 7.26 | 69.50 | (0.218, 0.421) | 53 |
| Example 88 | 711 | 7.45 | 66.60 | (0.209, 0.432) | 44 |
| Example 89 | 720 | 7.36 | 67.18 | (0.231, 0.418) | 41 |
| Example 90 | 727 | 7.52 | 66.30 | (0.243, 0.442) | 44 |
| Example 91 | 735 | 7.53 | 65.13 | (0.205, 0.411) | 44 |
| Example 92 | 740 | 7.65 | 64.20 | (0.243, 0.442) | 45 |
| Example 93 | 755 | 7.61 | 64.41 | (0.209, 0.419) | 46 |
| Example 94 | 763 | 7.69 | 64.04 | (0.210, 0.420) | 48 |
| Example 95 | 764 | 7.77 | 64.62 | (0.231, 0.419) | 45 |
| Example 96 | 776 | 7.72 | 65.28 | (0.219, 0.411) | 43 |
| Example 97 | 779 | 7.63 | 65.45 | (0.210, 0.412) | 41 |
| Example 98 | 827 | 7.72 | 64.20 | (0.218, 0.421) | 43 |
| Example 99 | 831 | 7.69 | 64.13 | (0.209, 0.432) | 43 |
| Example 100 | 848 | 7.70 | 65.28 | (0.231, 0.418) | 44 |
| Example 101 | 856 | 7.62 | 64.35 | (0.243, 0.442) | 42 |
| Example 102 | 875 | 7.52 | 65.93 | (0.205, 0.411) | 44 |
| Example 103 | 908 | 7.34 | 68.84 | (0.243, 0.442) | 40 |
| Example 104 | 911 | 7.31 | 69.06 | (0.209, 0.419) | 43 |
| Example 105 | 912 | 7.31 | 69.08 | (0.210, 0.420) | 41 |
| Example 106 | 914 | 7.24 | 62.93 | (0.231, 0.419) | 54 |
| Example 107 | 935 | 7.65 | 64.15 | (0.220, 0.431) | 45 |
| Example 108 | 936 | 7.56 | 69.95 | (0.220, 0.431) | 42 |
| Comparative Example 1-1 | TmPyPB | 8.57 | 57.61 | (0.212, 0.433) | 24 |
| Comparative Example 1-2 | BBQB | 8.43 | 58.11 | (0.220, 0,429) | 27 |
| Comparative Example 1-3 | TBQB | 8.47 | 58.90 | (0.222, 0,430) | 28 |
| Comparative Example 1-4 | E2 | 8.45 | 58.05 | (0.221, 0,431) | 25 |

As seen from the results of Table 5, the organic light emitting device using the charge generation layer material of the 2-stack white organic light emitting device of the present disclosure had a lower driving voltage and improved light emission efficiency compared to the comparative examples. Particularly, it was identified that Compounds 48, 65, 245, 353, 569, 677, 706 and 914 were significantly superior in all aspects of driving, efficiency and lifetime.

Such a result is considered to be due to the fact that the compound of the present disclosure used as the N-type charge generation layer foamed with the disclosed skeleton having proper length, strength and flat properties and a proper hetero-compound capable of binding with a metal forms a gap state in the N-type charge generation layer by doping an alkali metal or an alkaline earth metal, and electrons produced from the P-type charge generation layer are readily injected to the electron transfer layer through the gap state produced in the N-type charge generation layer. Accordingly, it is considered that the P-type charge generation layer favorably injects and transfers electrons to the N-type charge generation layer, and as a result, a driving voltage was lowered, and efficiency and lifetime were improved in the organic light emitting device.

In addition, by the core structure of the present application having substituents at two places, an electron-deficient substituent and an aryl or acene-based substituent are combined so that the electron-deficient substituent readily receives electrons from the electron injection layer, and device properties may be enhanced by the aryl or acene-based substituent stabilizing the molecule itself or transferring the supplied electrons to a light emitting layer. Therefore, enhanced molecular stability and device properties may be exhibited compared to materials in which phenanthridine is mono-substituted like E2 in Comparative Example 1-4.

The invention claimed is:
1. A heterocyclic compound represented by any one of the following compounds:
1
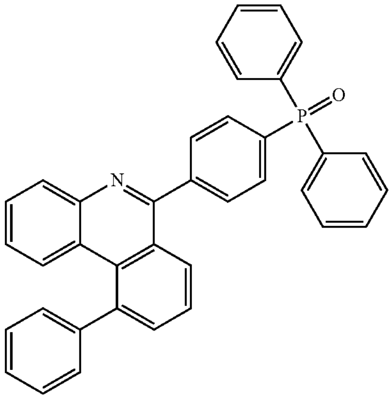
2
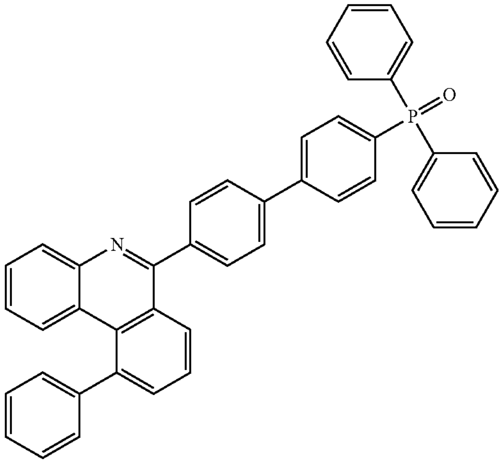
3
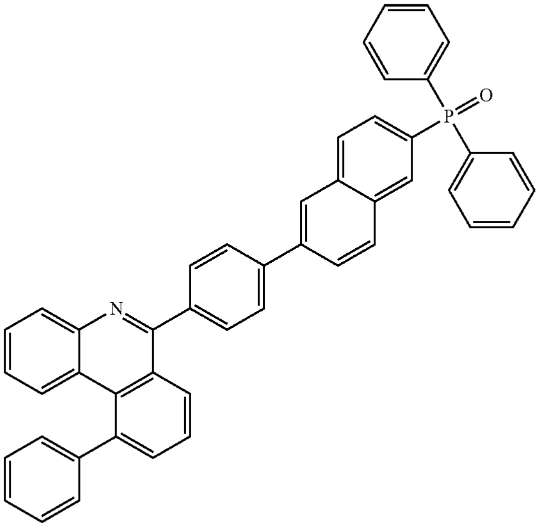
-continued
4
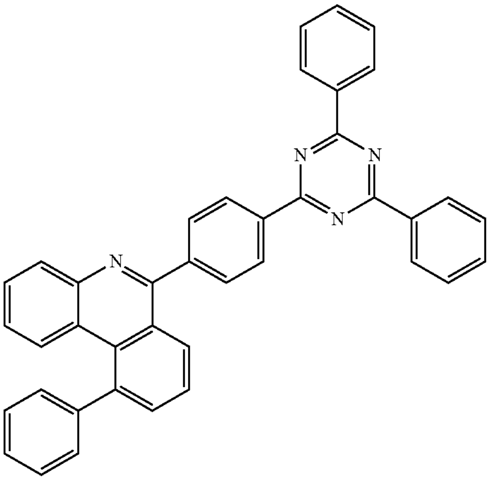
5
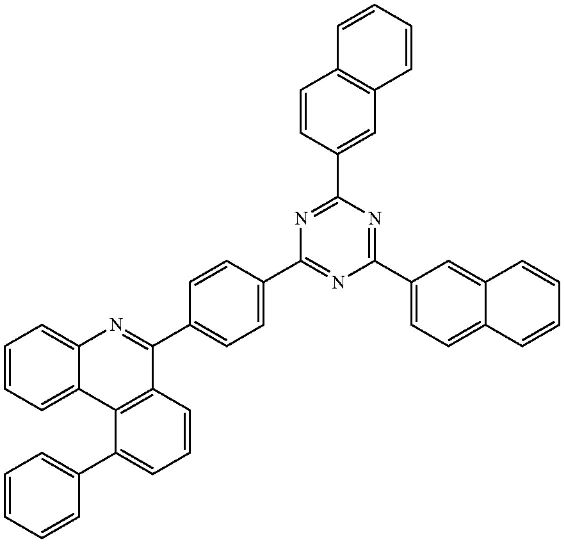
6
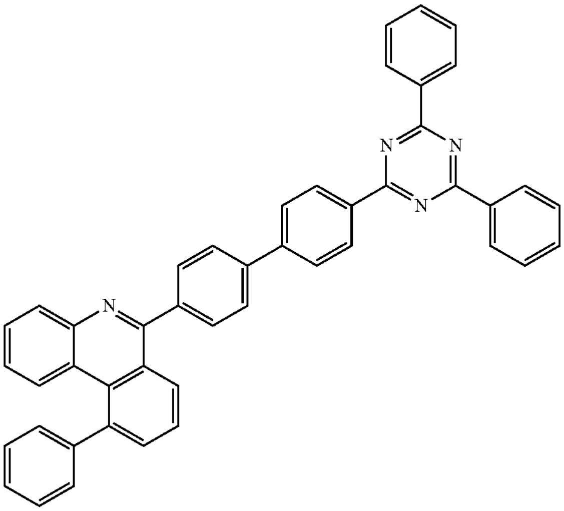

-continued
7
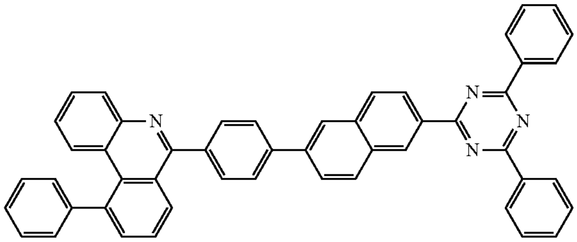
8
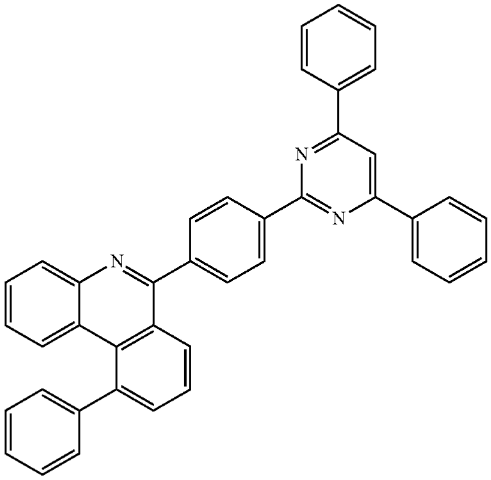
9
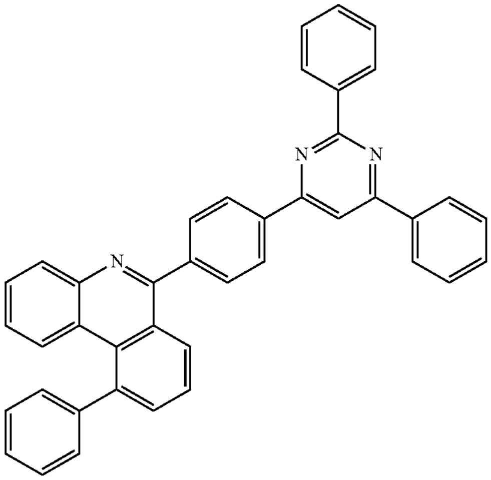
10
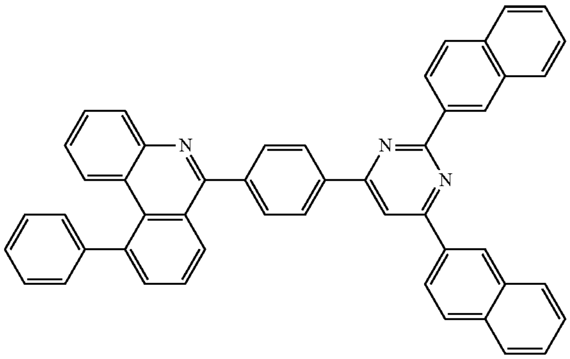
-continued
11
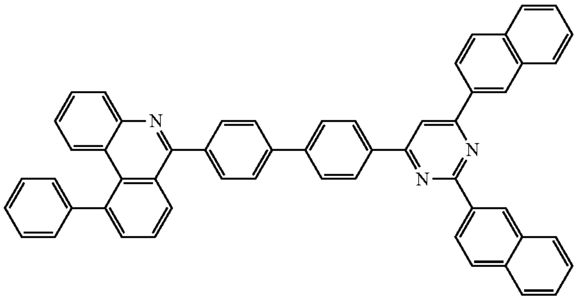
12
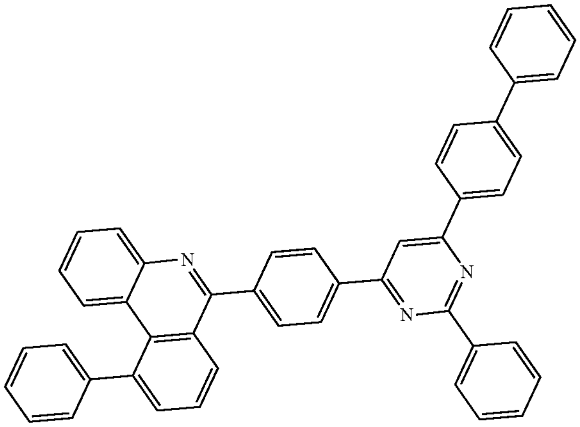
13
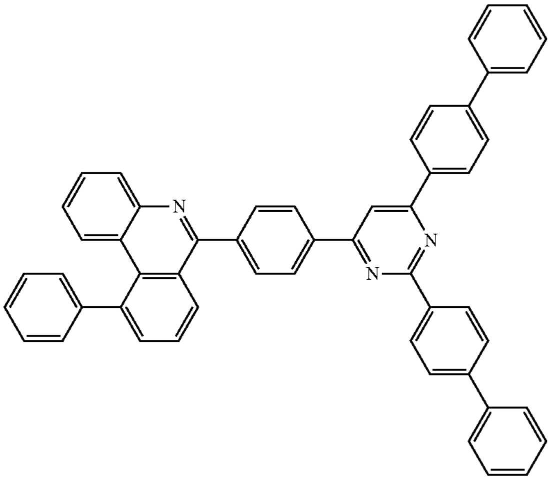

-continued
14
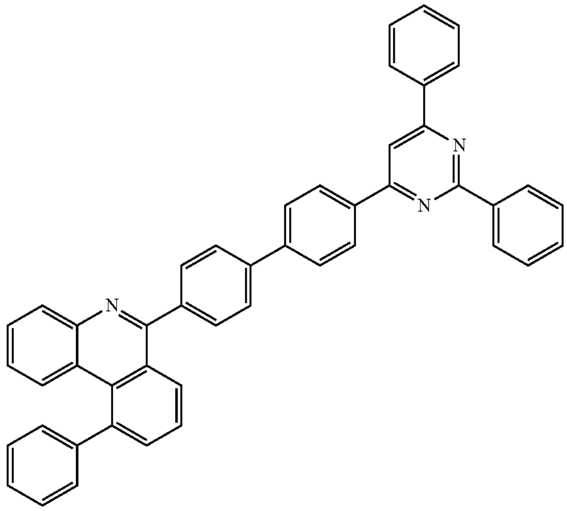
15
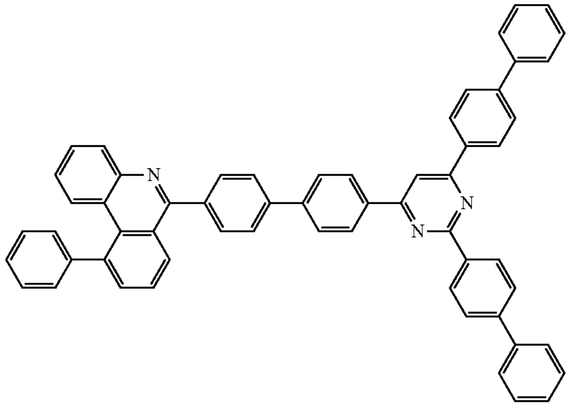
16
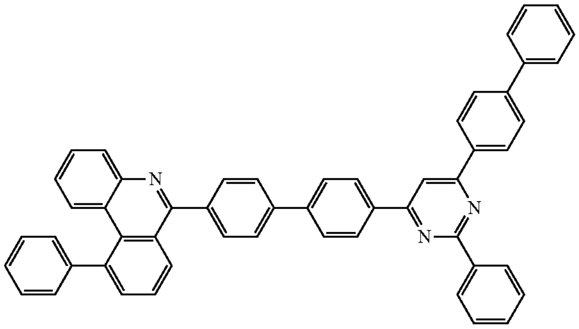
17
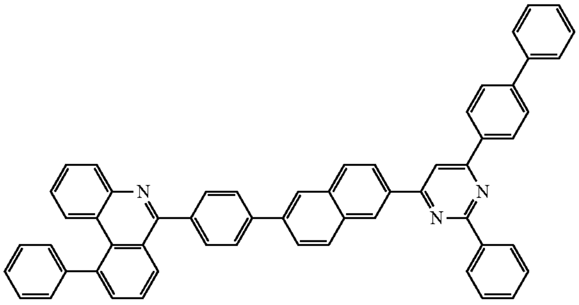
-continued
18
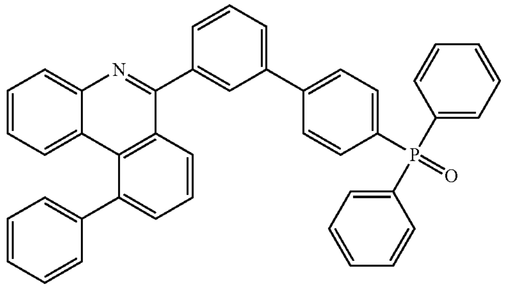
19
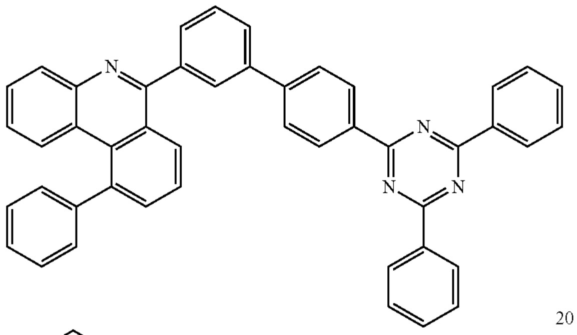
20
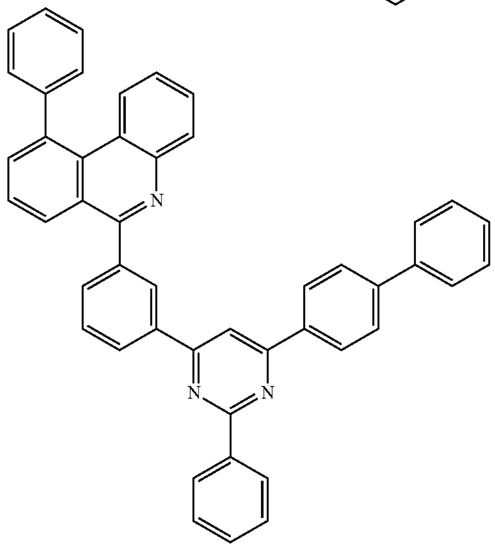
21
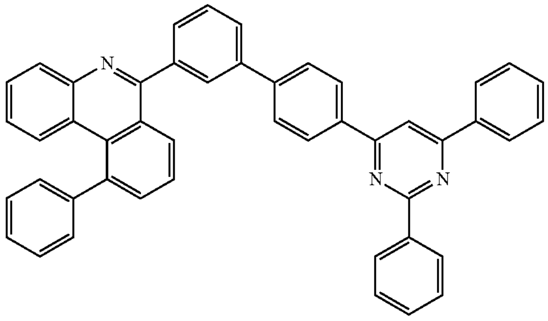

-continued
22
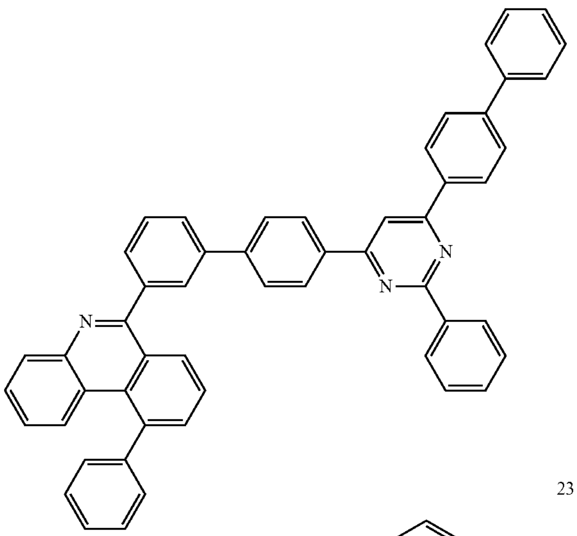
23
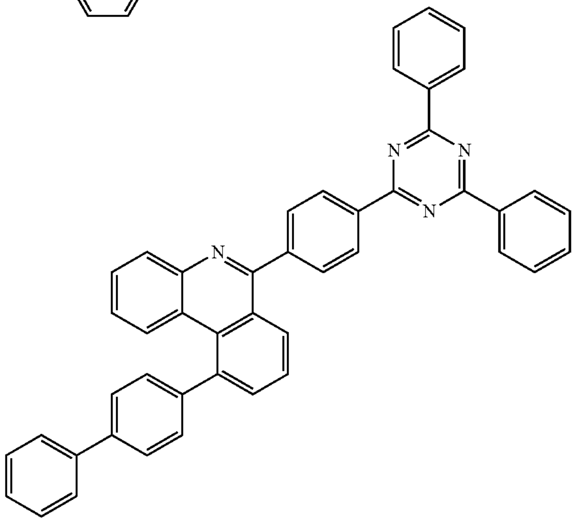
24
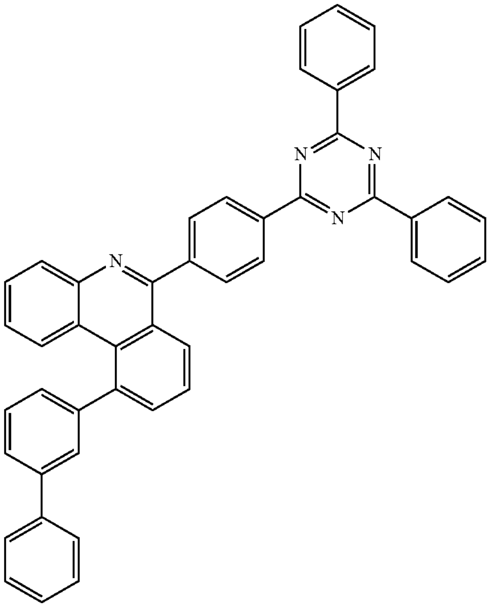
-continued
25
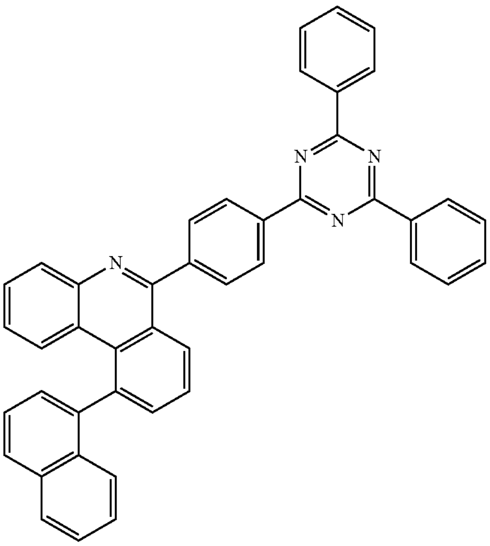
26
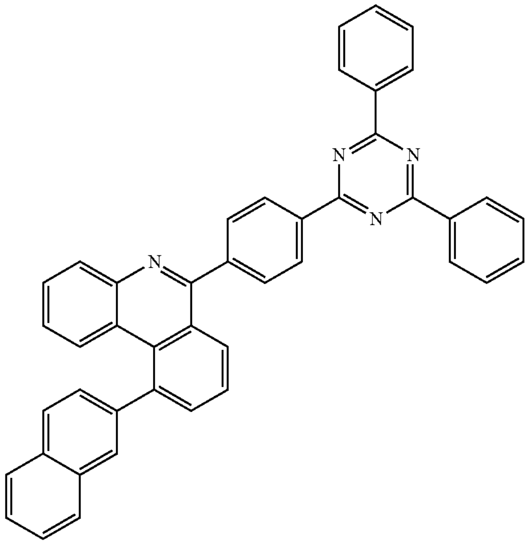
27
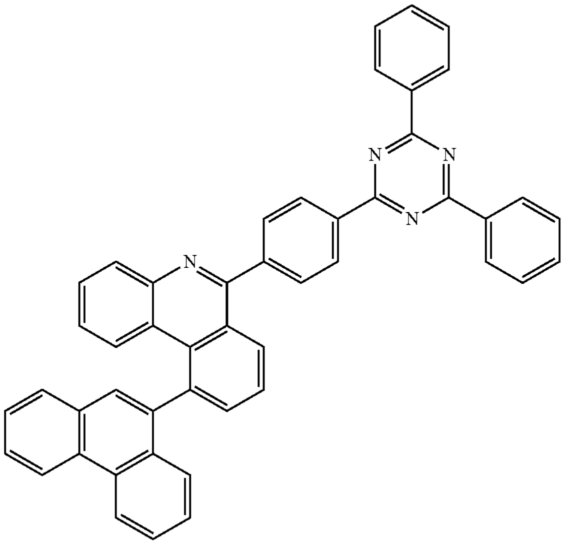

-continued
28
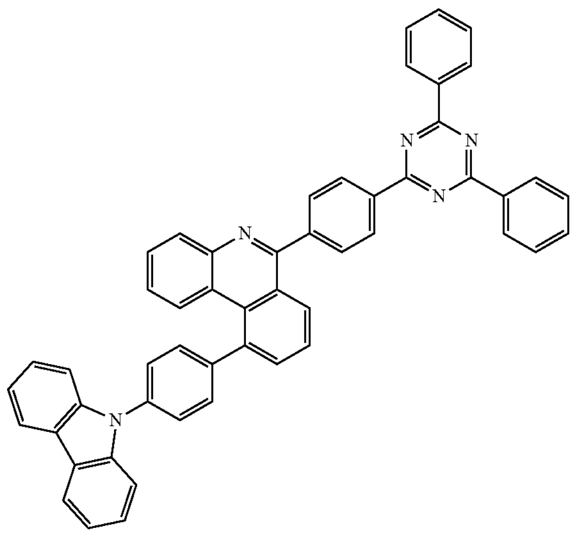
29
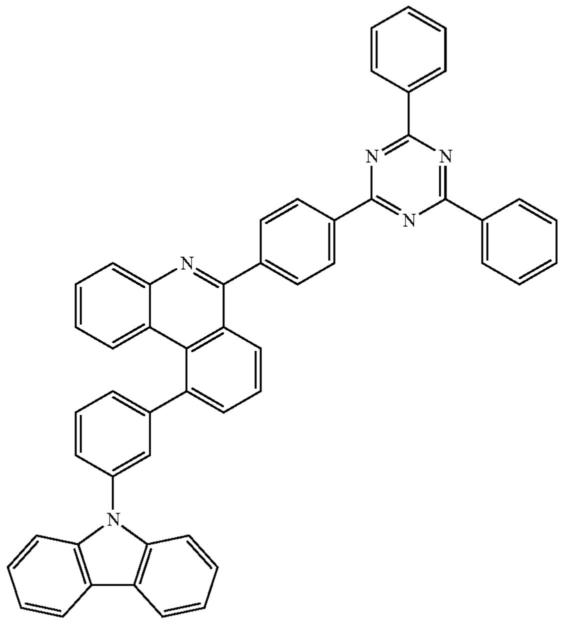
30
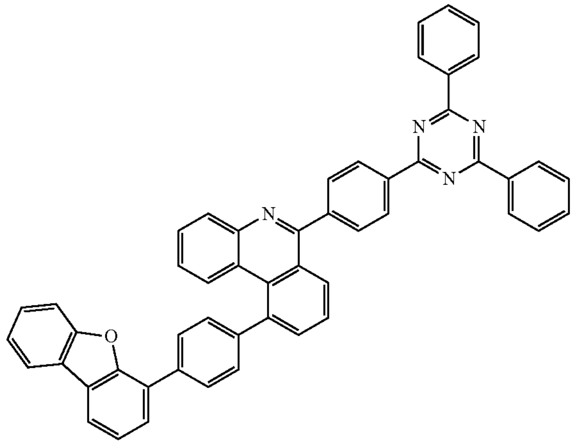
-continued
31
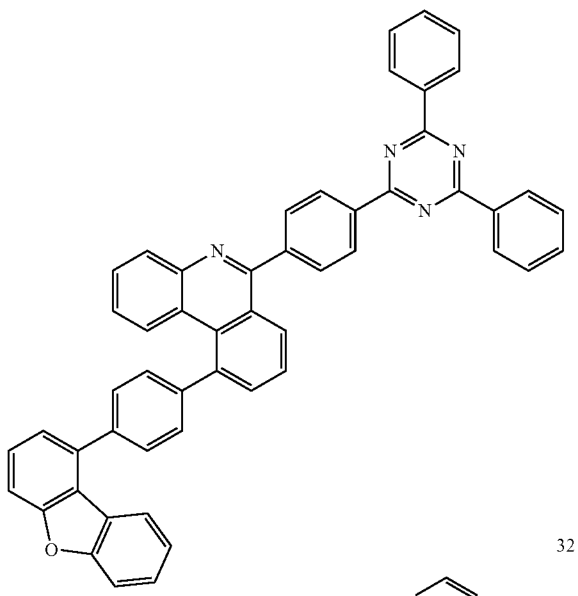
32
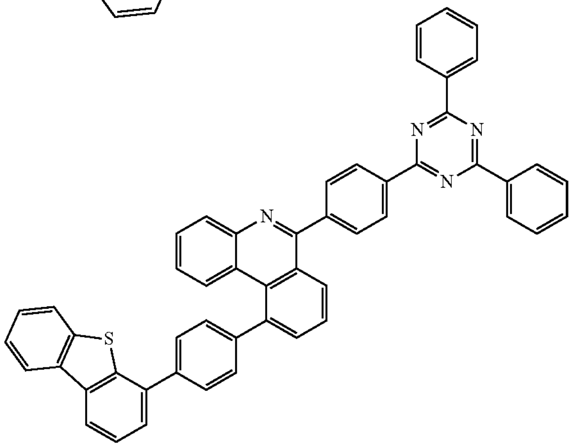
33
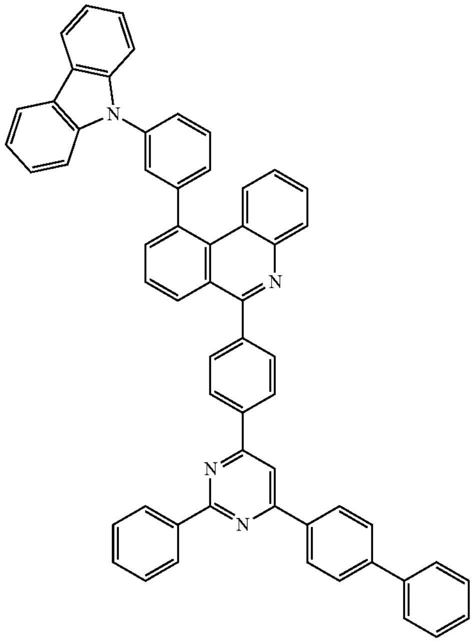

-continued
34
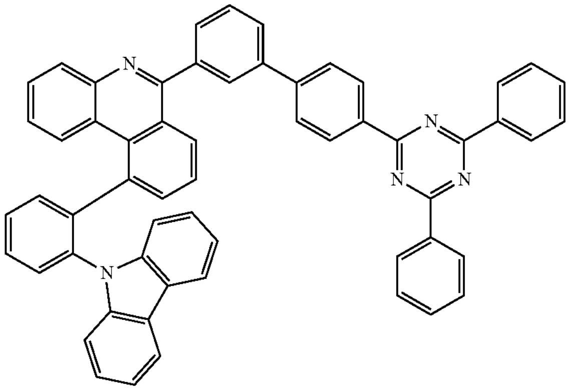
35
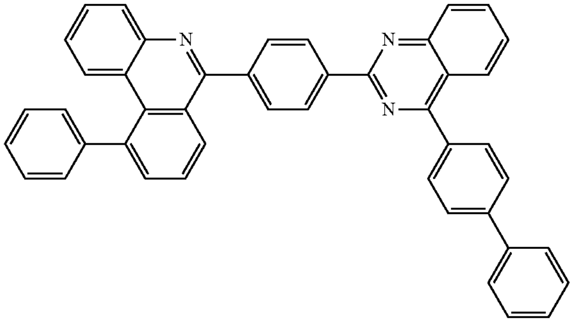
36
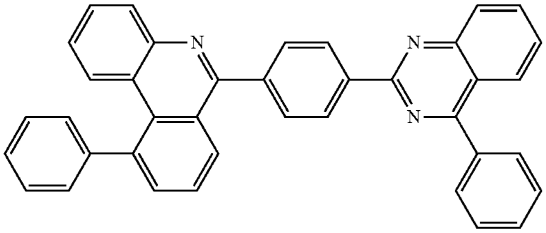
37
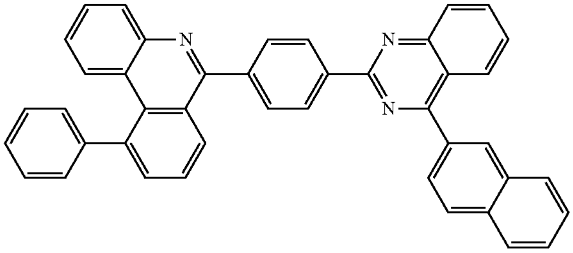
38
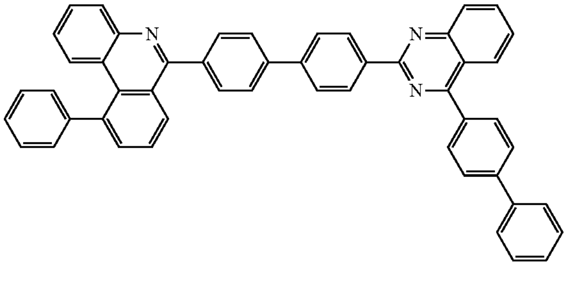
-continued
39
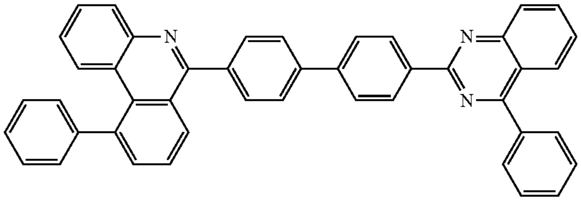
40
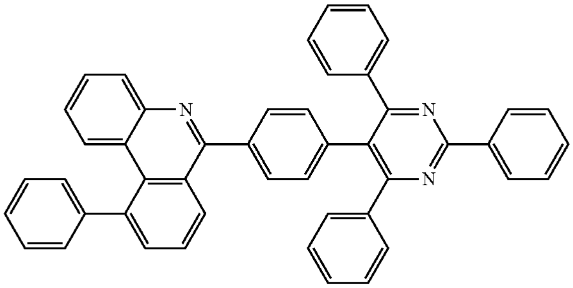
41
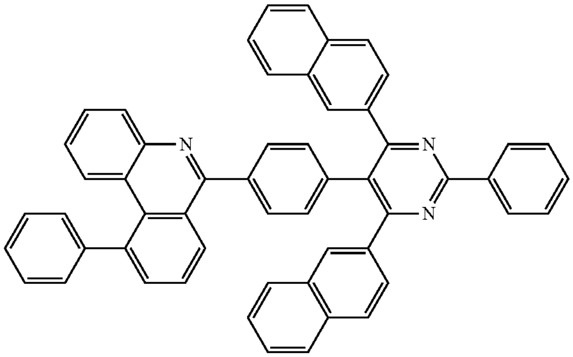
42
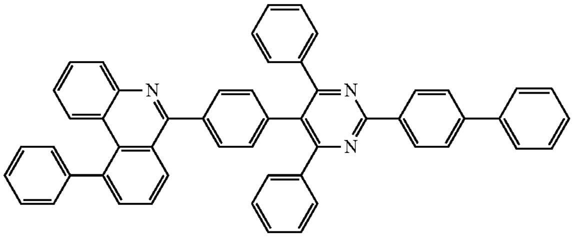
43
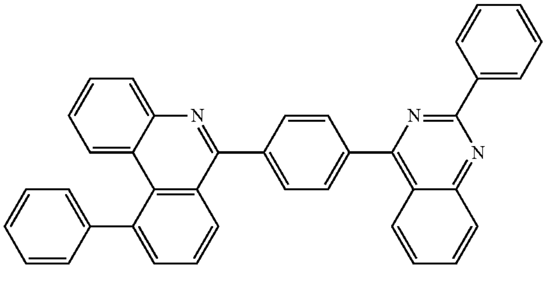

-continued
44
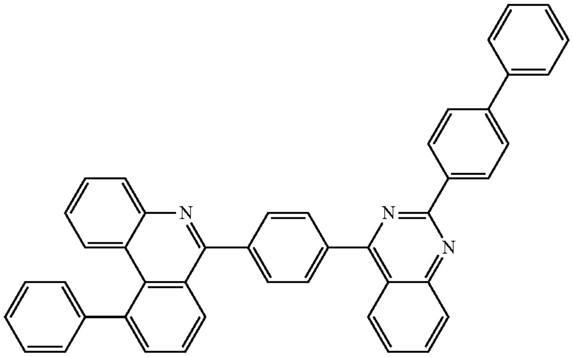
45
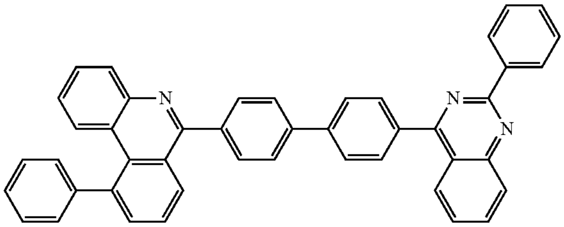
46
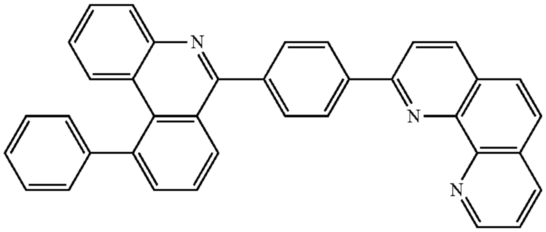
47
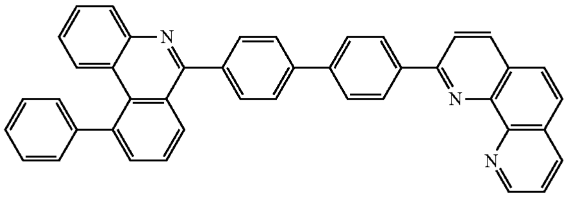
48
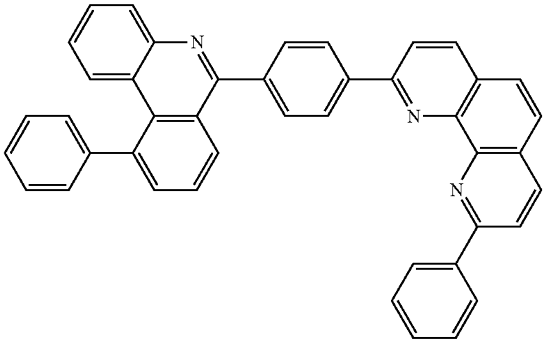
-continued
49
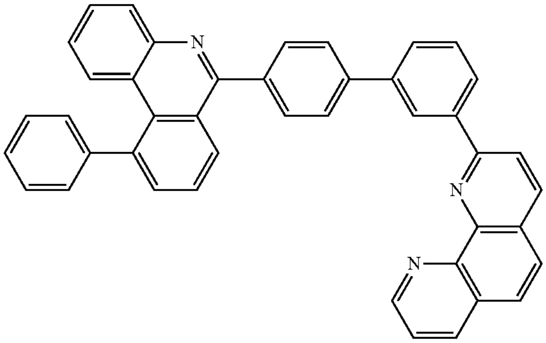
50
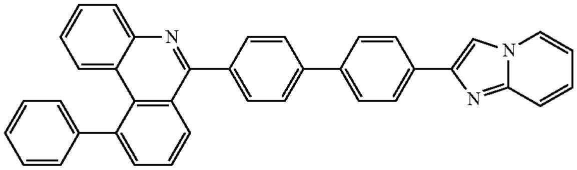
51
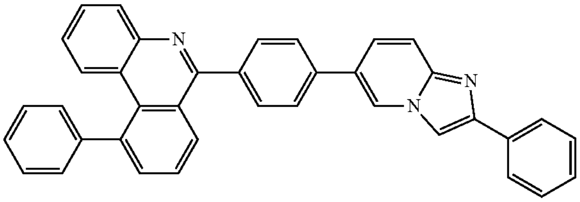
52
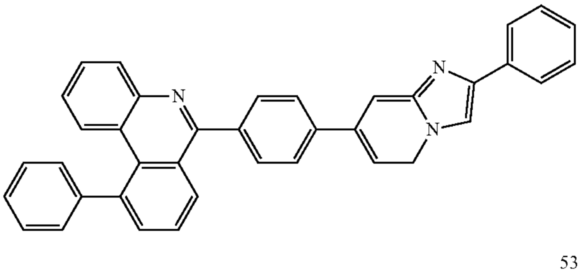
53
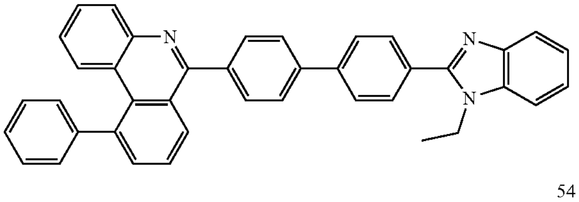
54
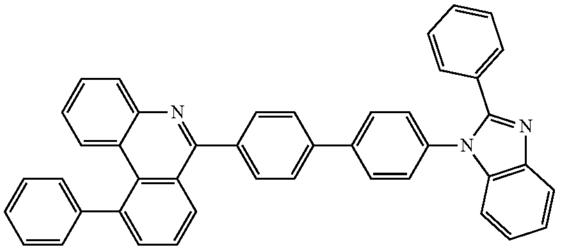

-continued
55
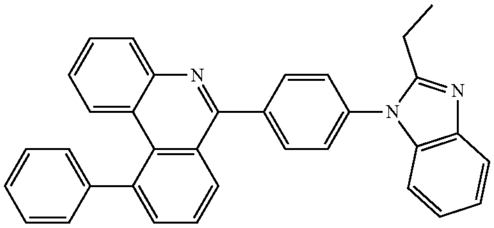
56
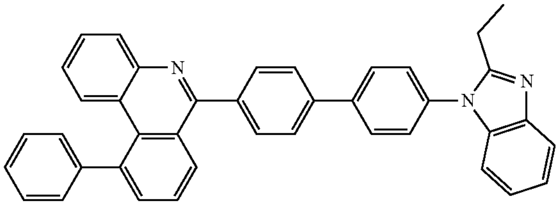
57
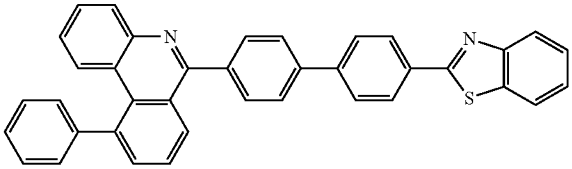
58
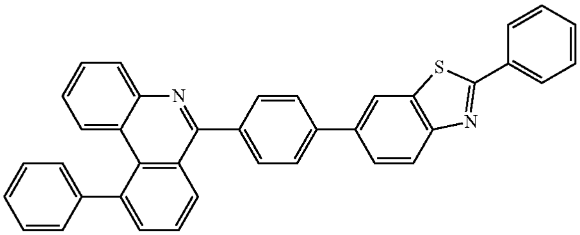
59
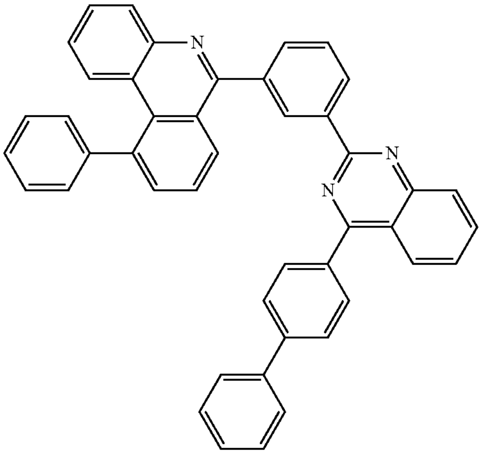
-continued
60
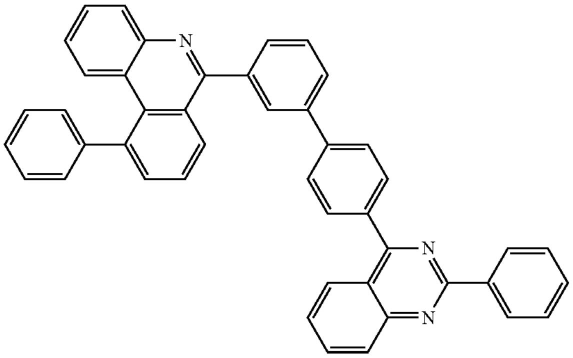
61
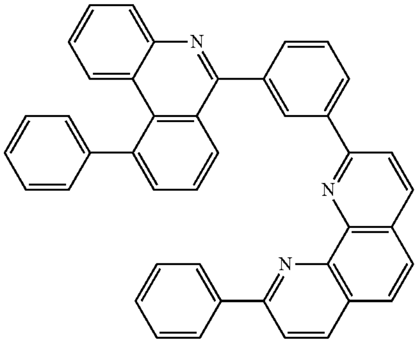
62
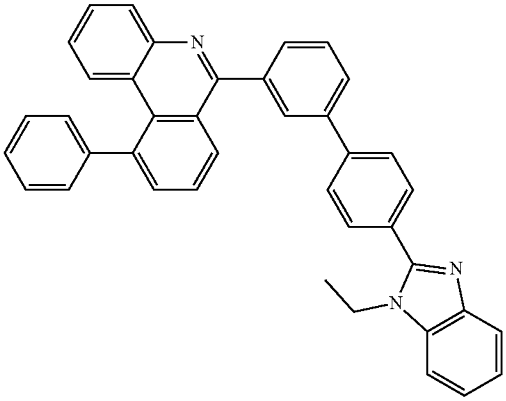
63
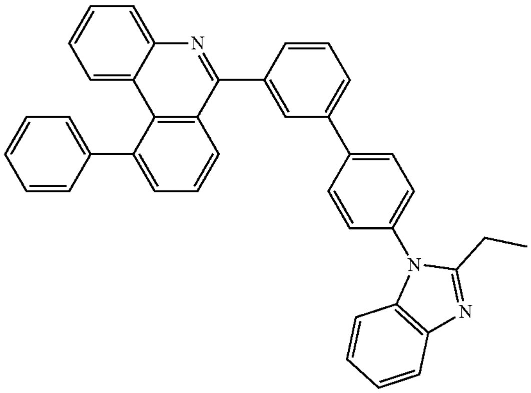

64
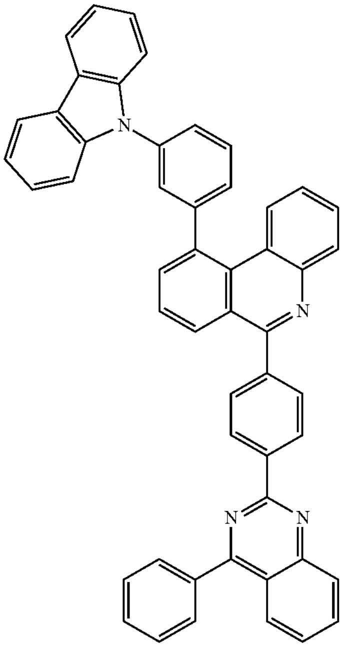
65
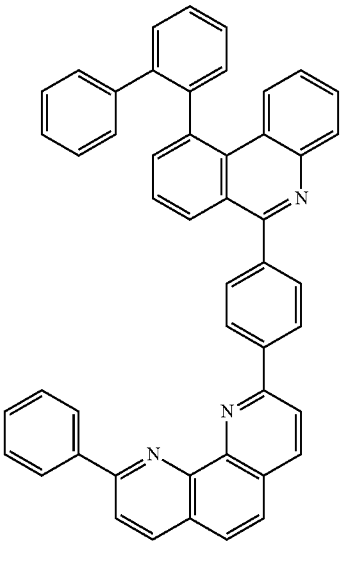
66
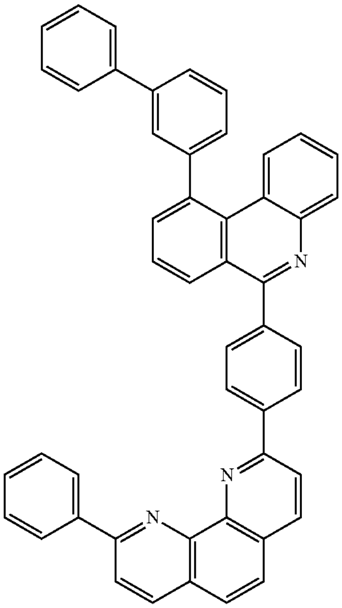
67
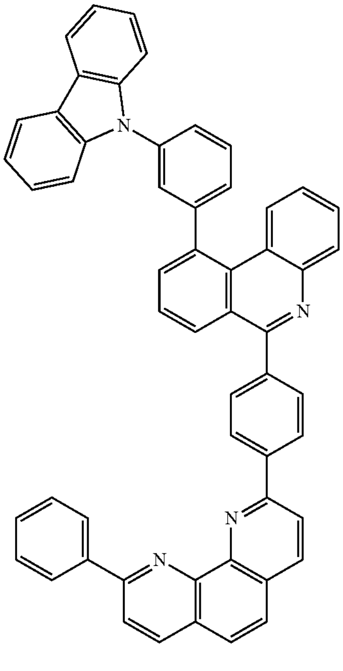

-continued
68
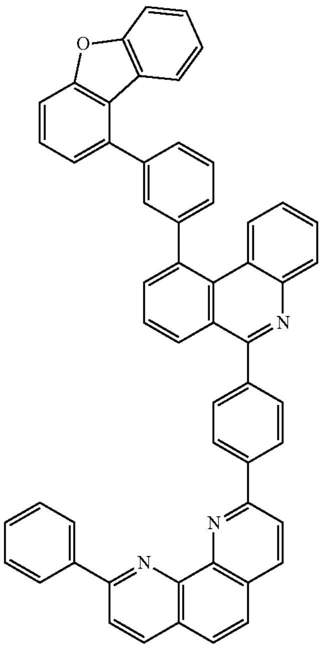
69
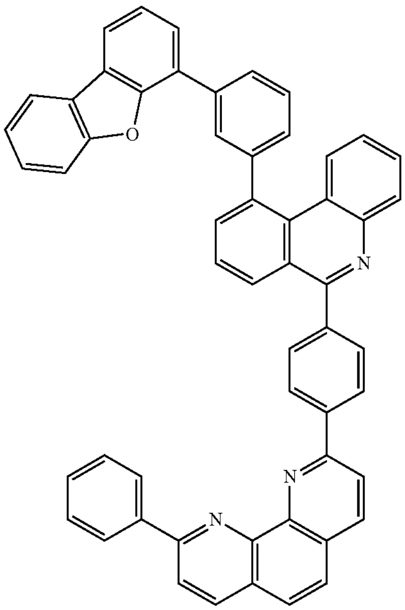
-continued
70
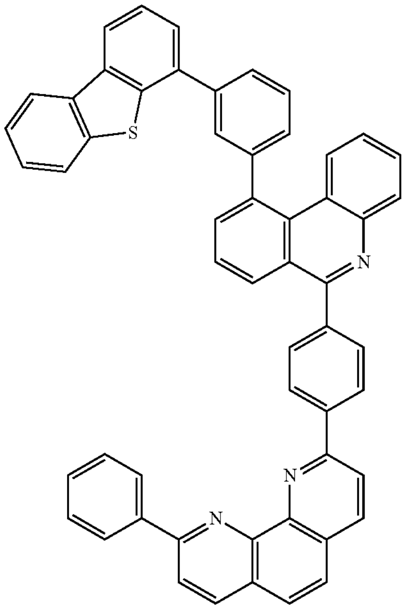
71
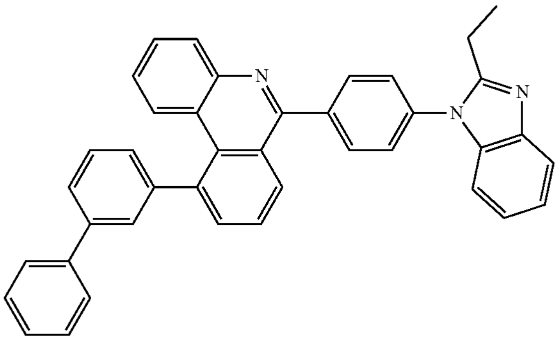
72
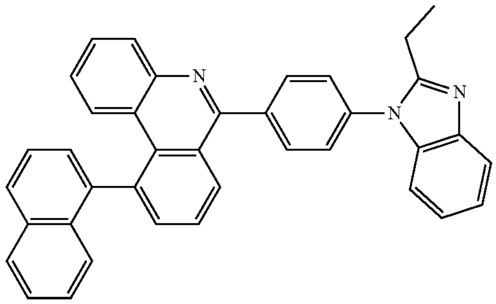

-continued
73
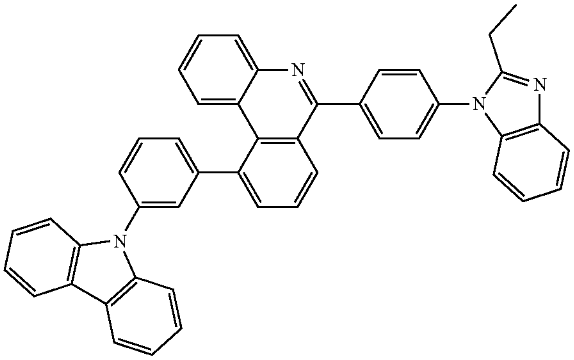
74
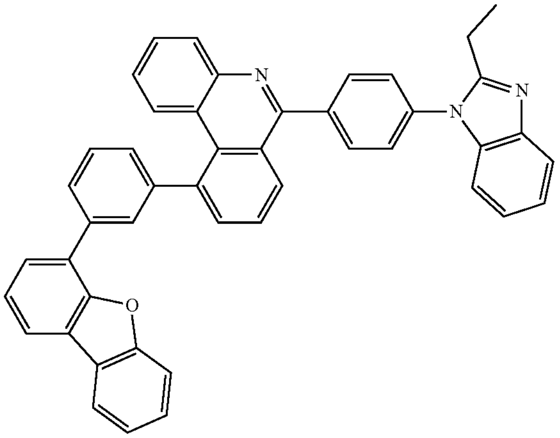
75
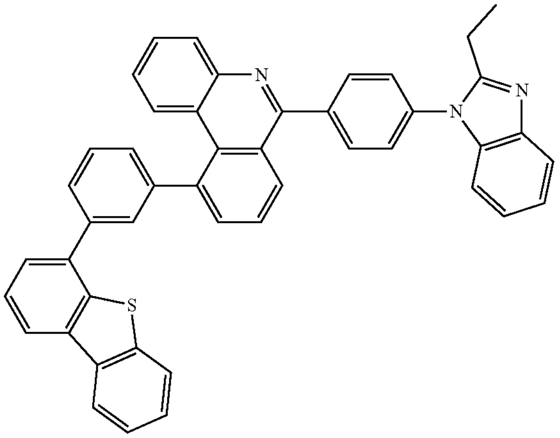
76
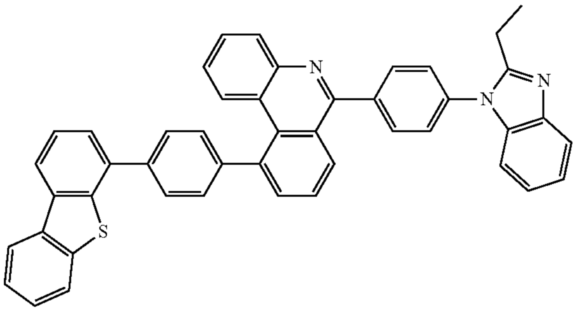
-continued
77
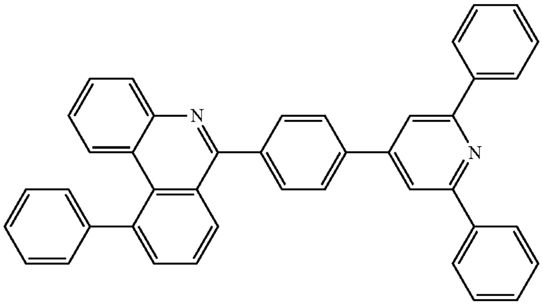
78
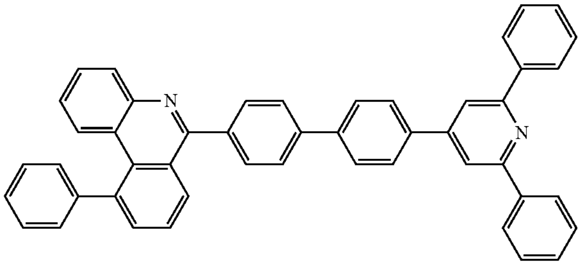
79
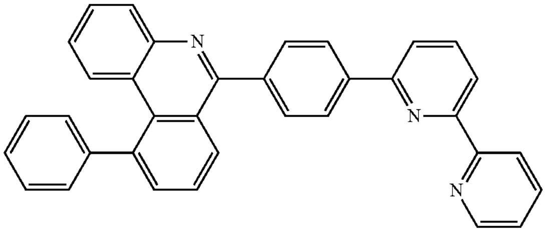
80
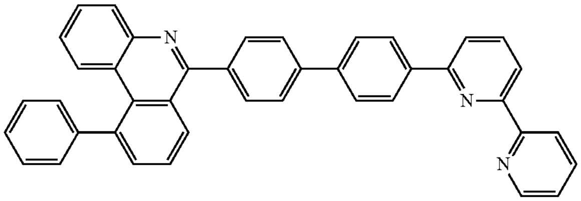
81
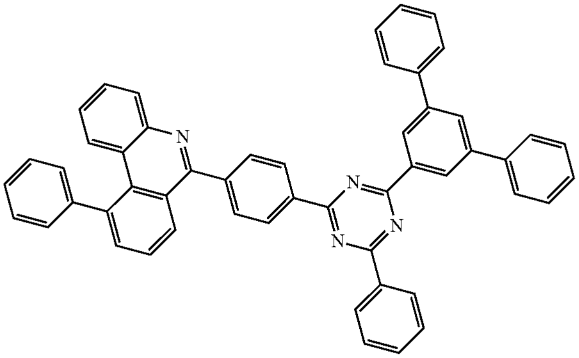

-continued
82
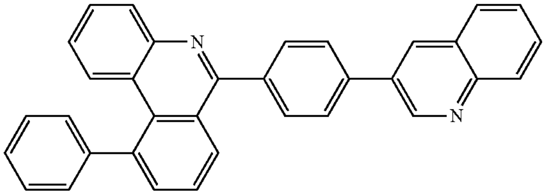
83
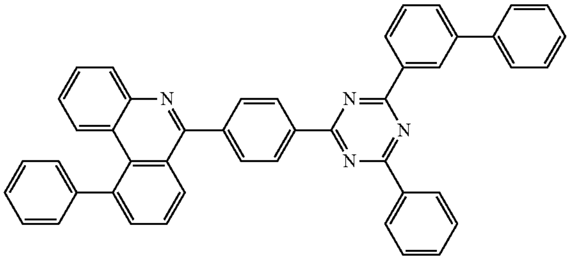
84
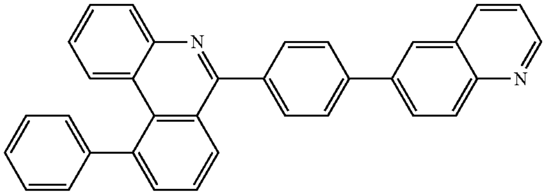
85
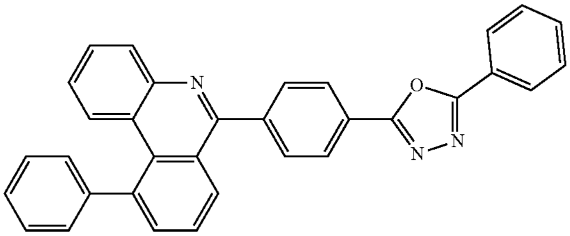
86
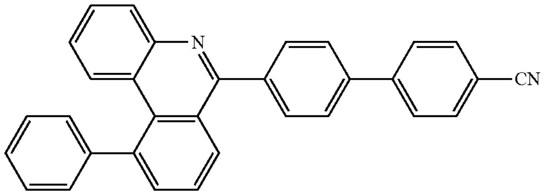
87
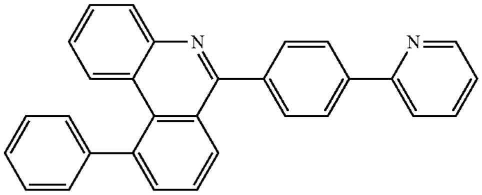
-continued
88
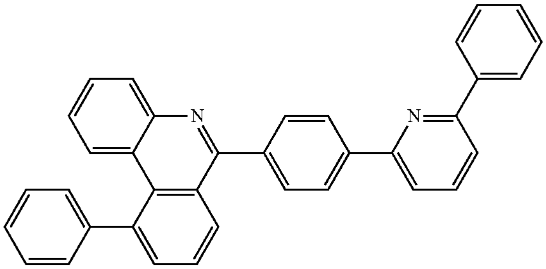
89
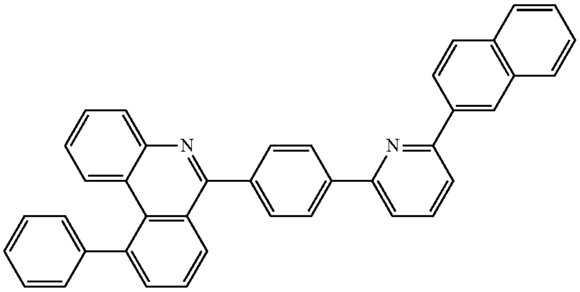
90
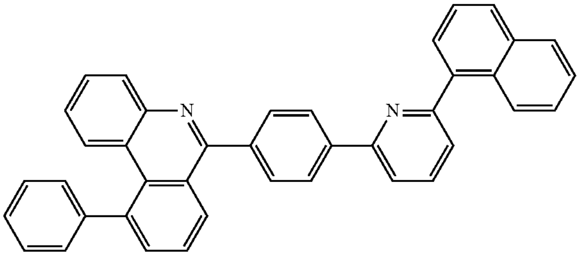
91
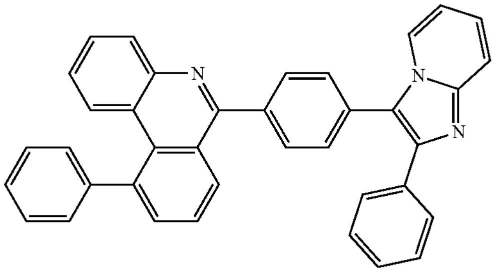
92
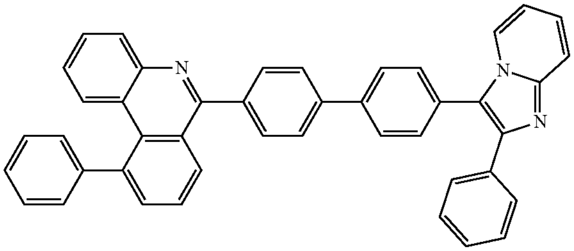

93
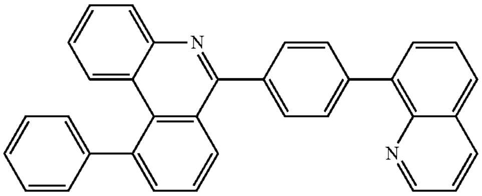
94
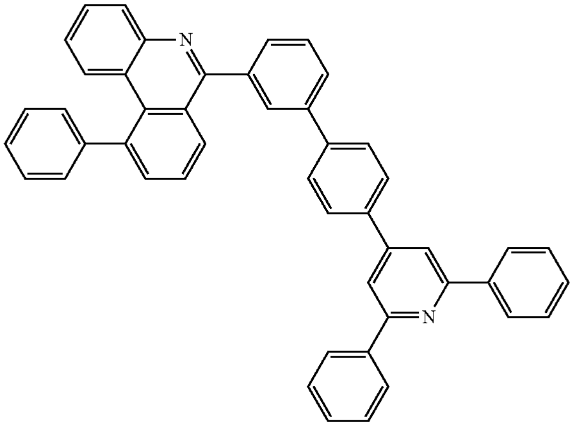
95
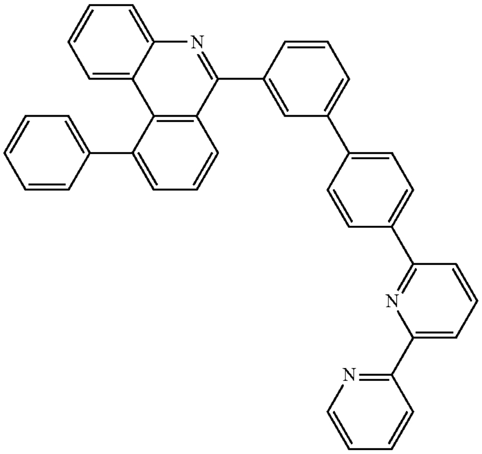
96
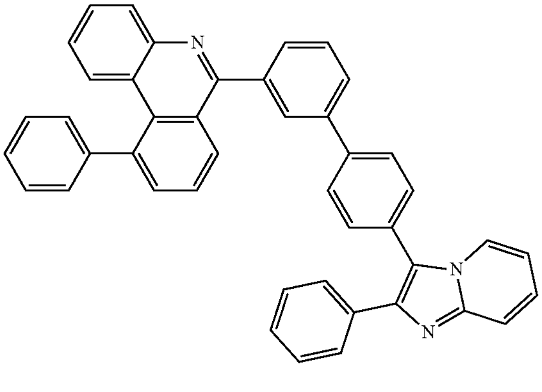
97
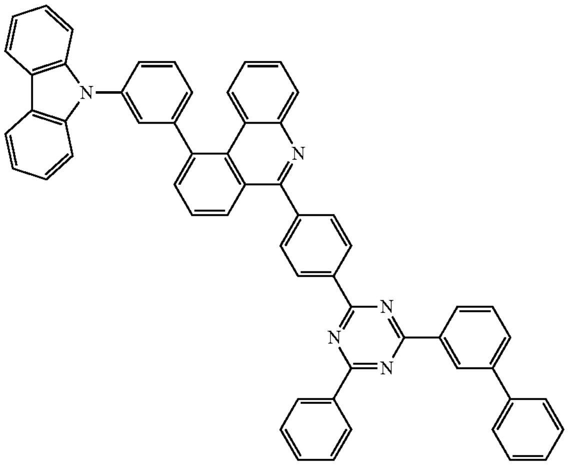
98
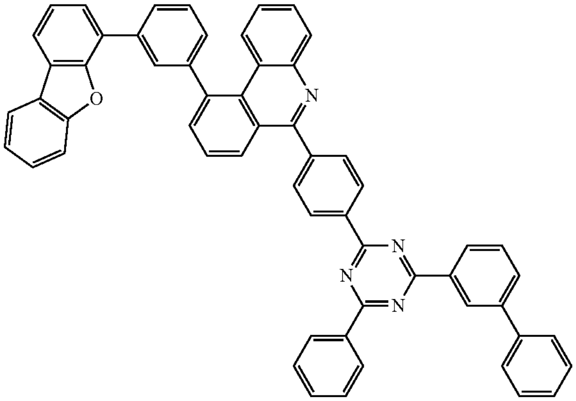
99
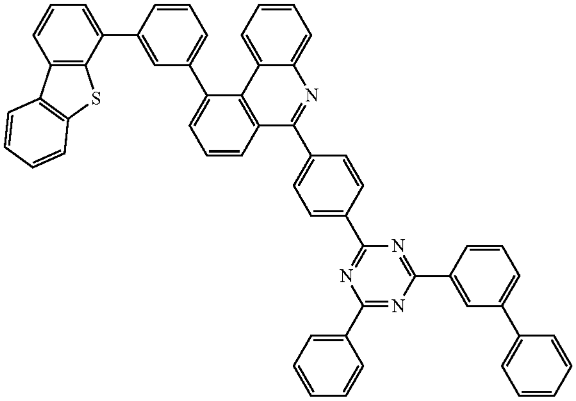

100
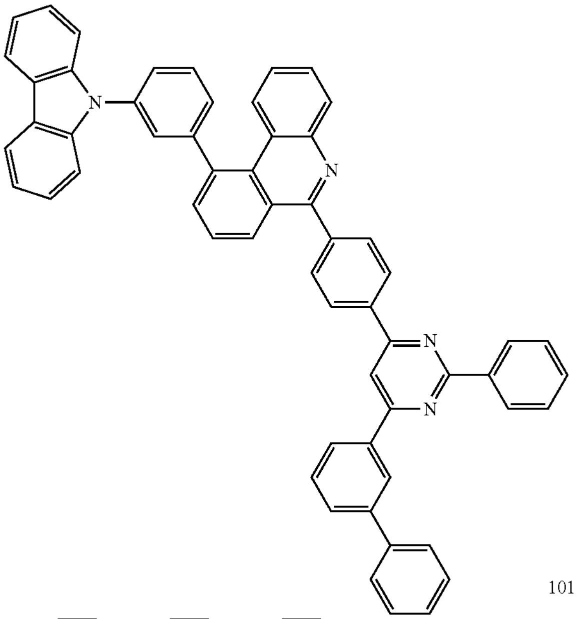
101
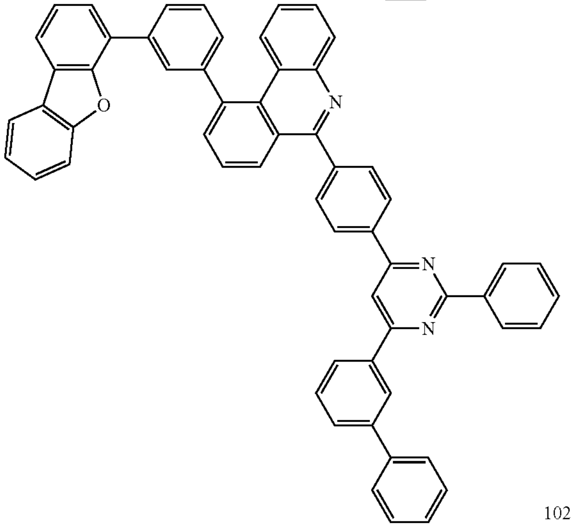
102
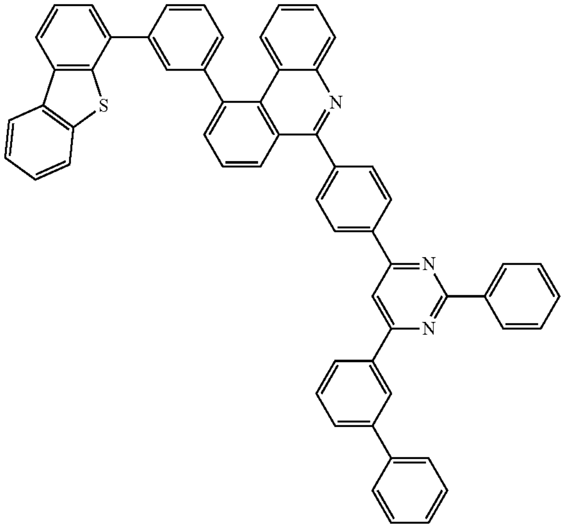
103
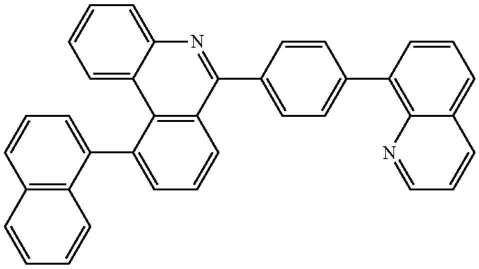
104
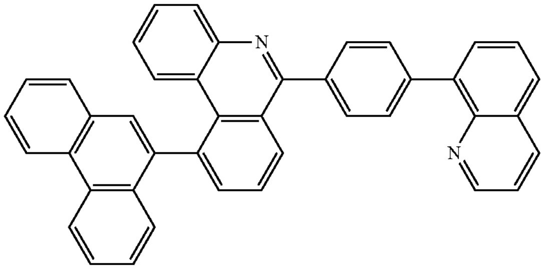
105
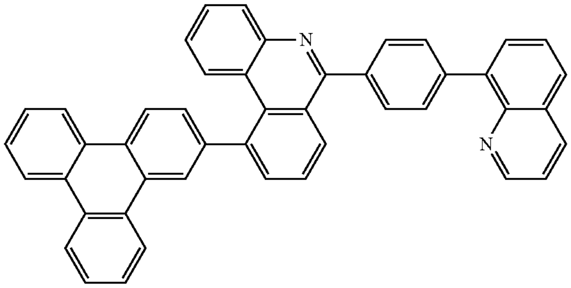
106
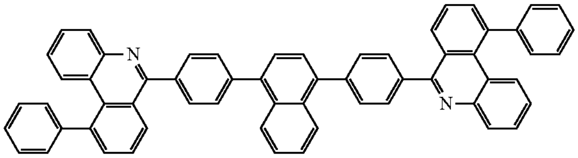
107
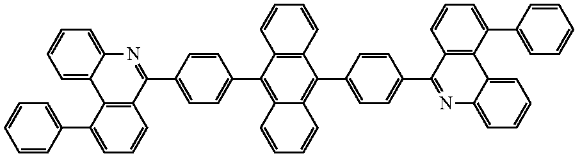

-continued
108
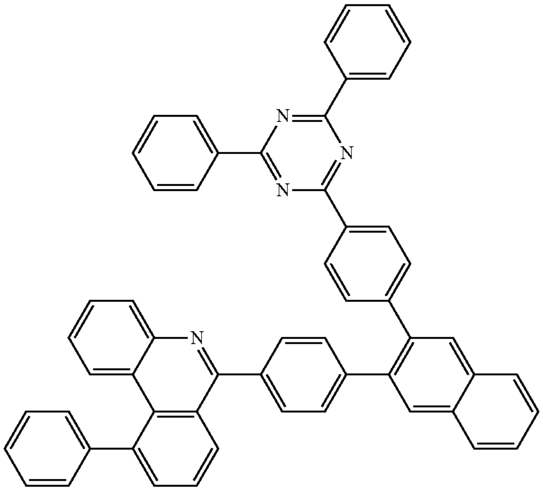
109
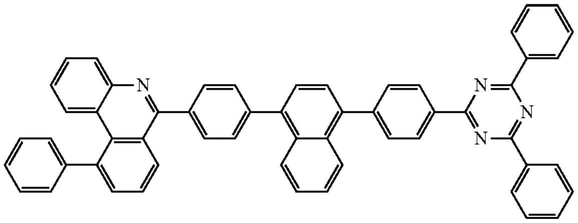
110
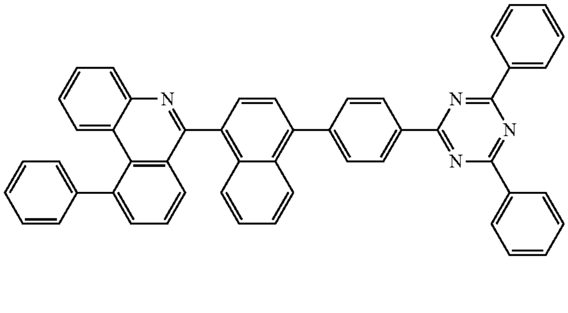
111
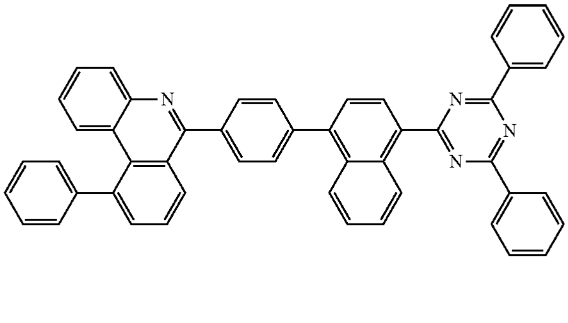
-continued
112
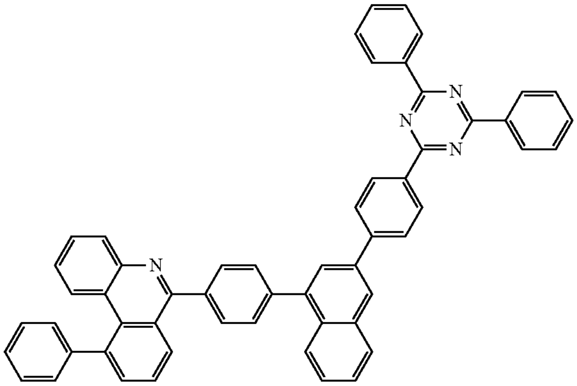
113
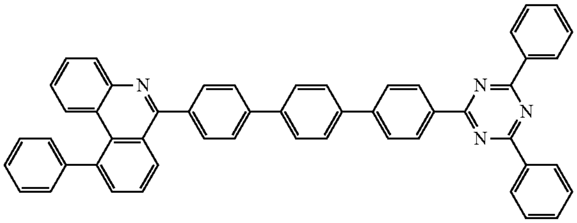
114
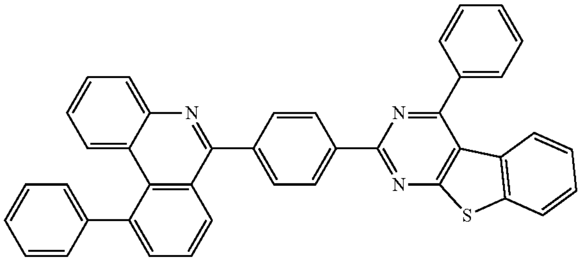
115
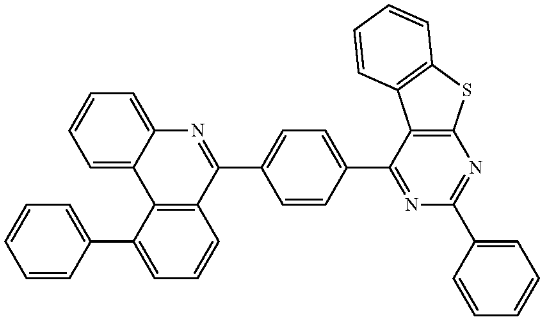
116
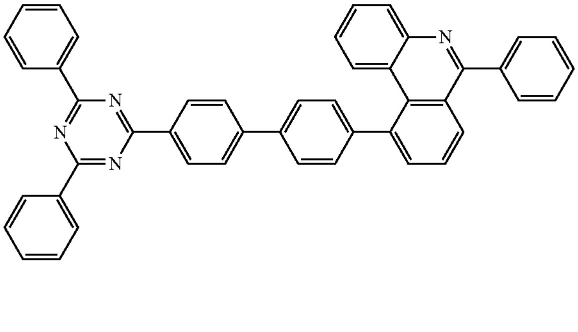

117
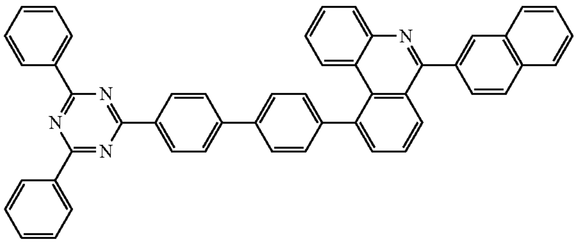
118
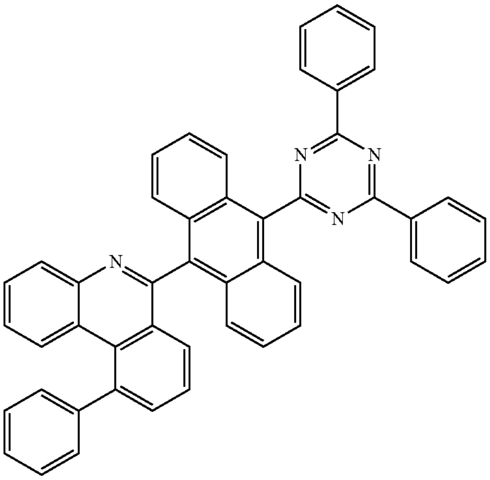
119
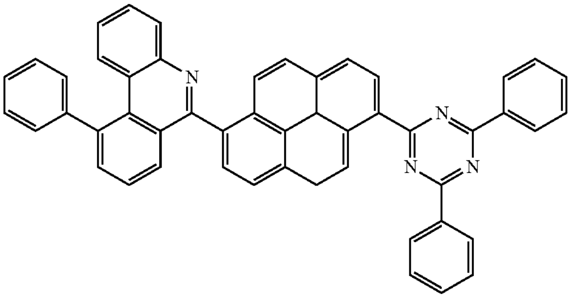
120
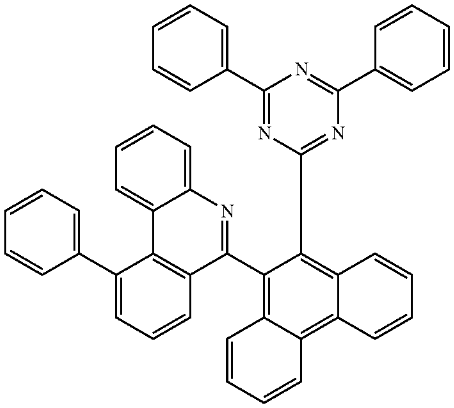
121
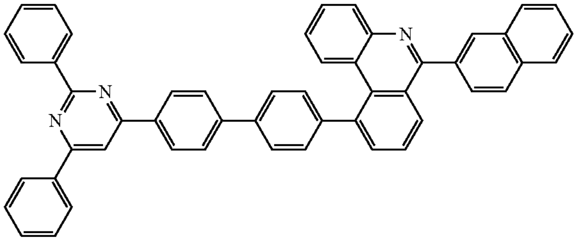
122
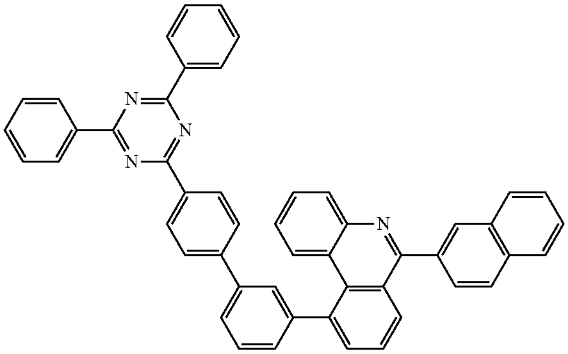
123
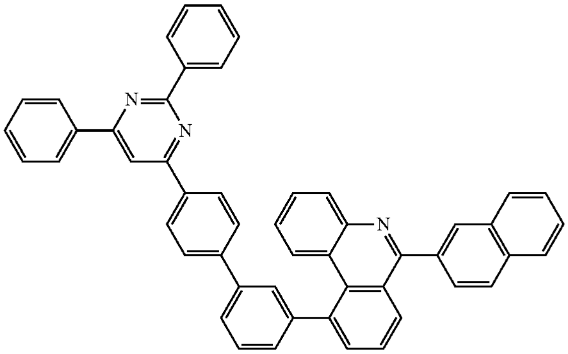
124
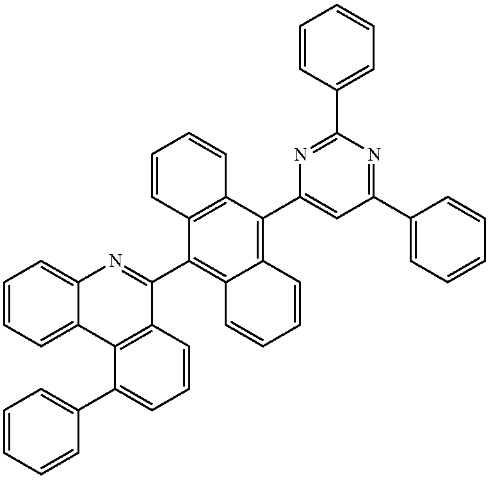

-continued
125
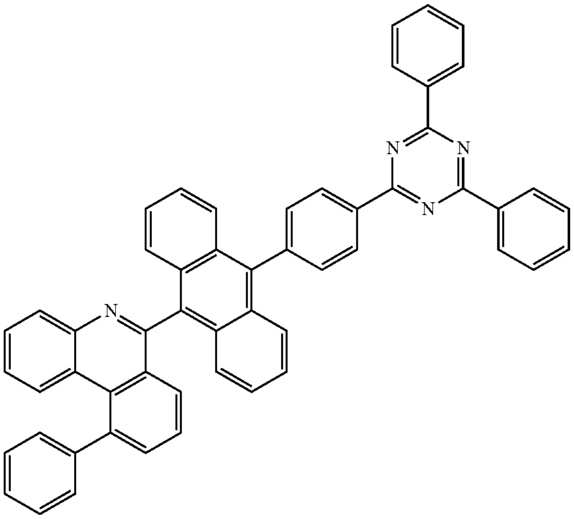
126
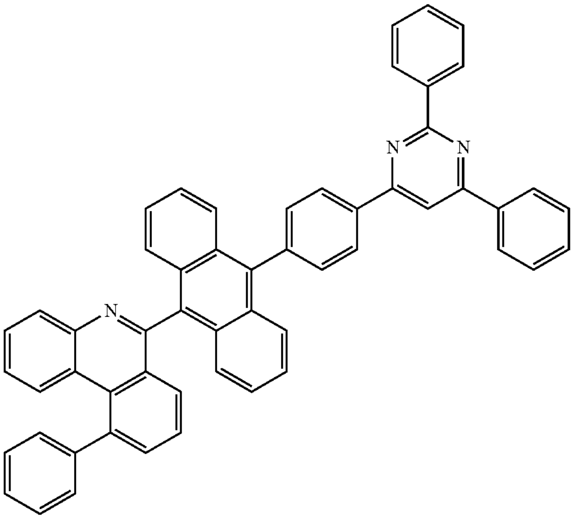
127
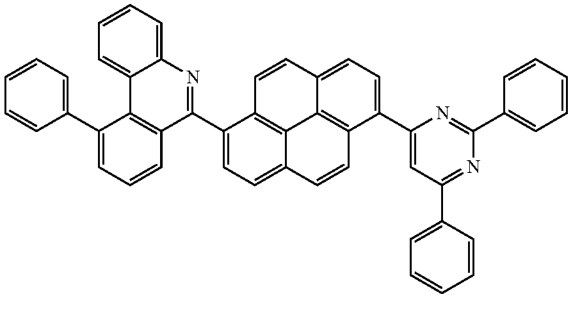
-continued
128
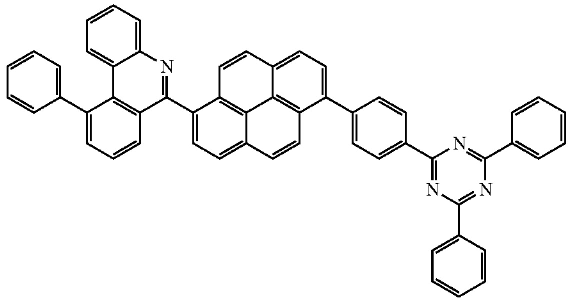
129
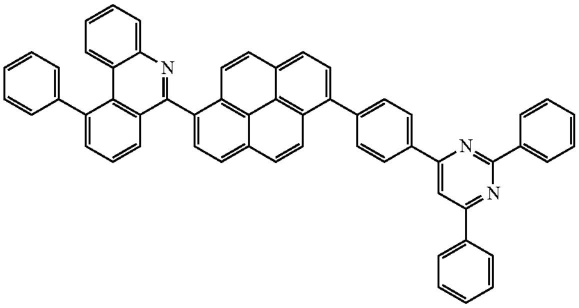
130
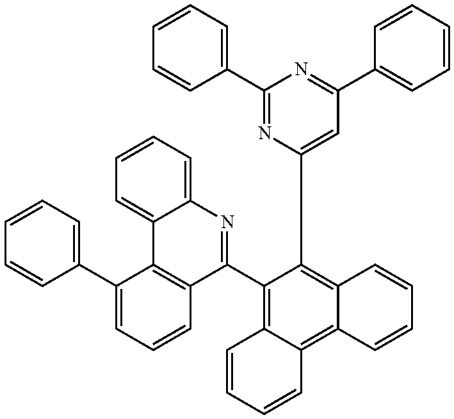
131
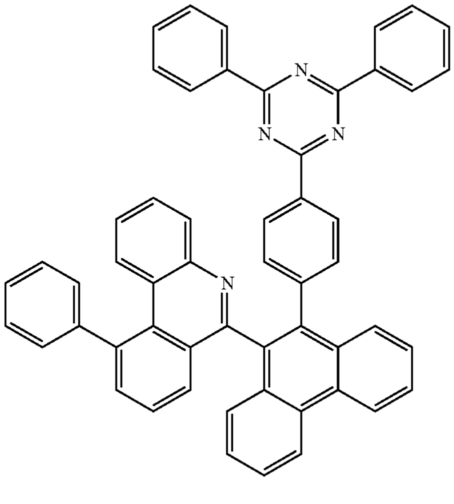

132
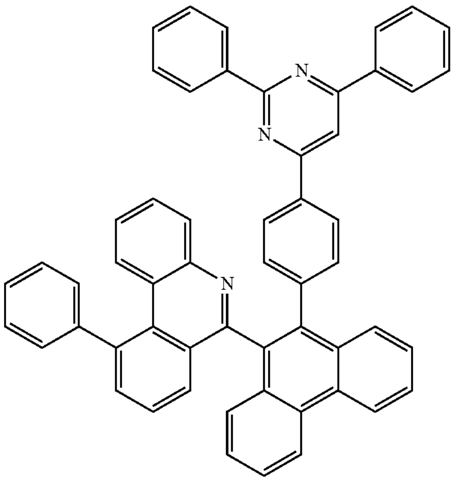
133
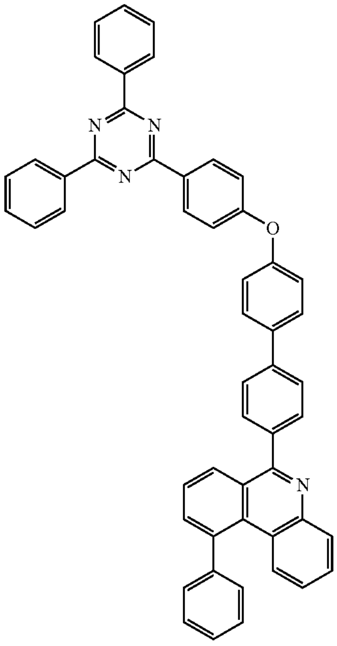
134
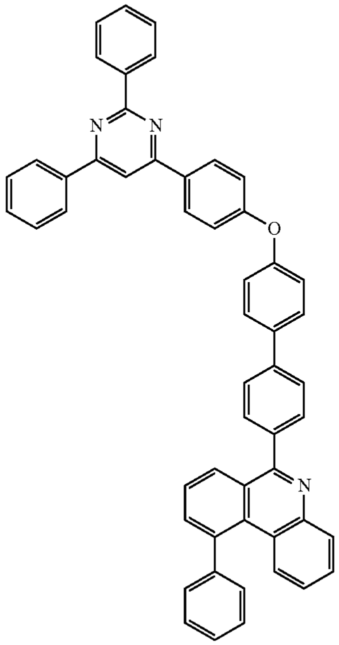
135
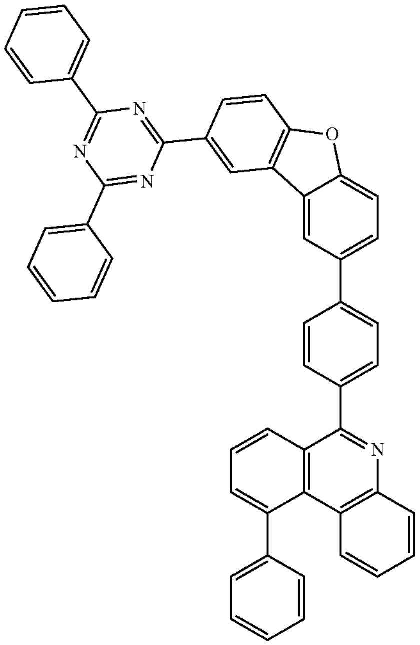

136
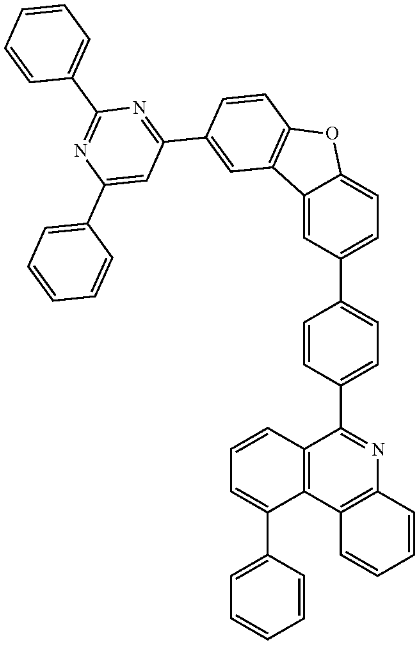
137
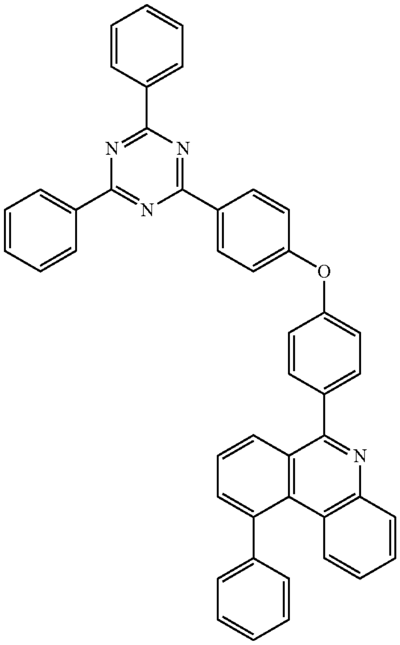
138
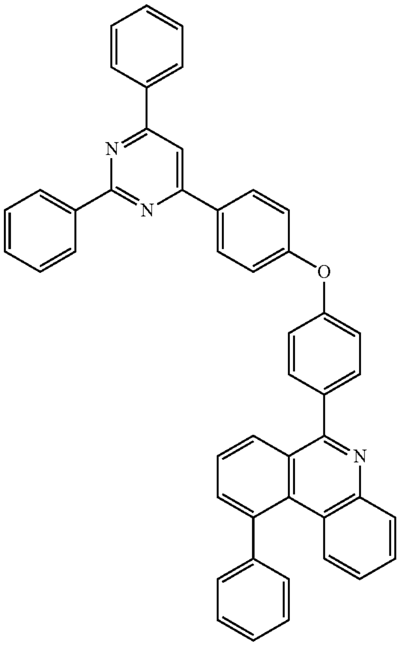
139
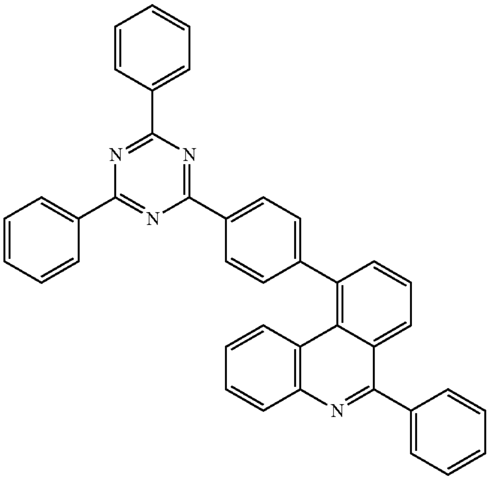
140
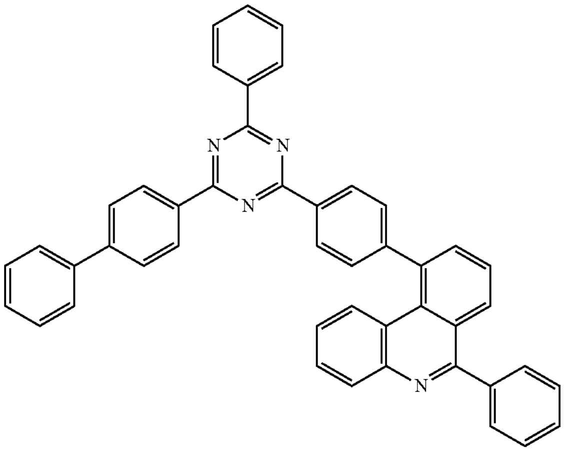

-continued
141
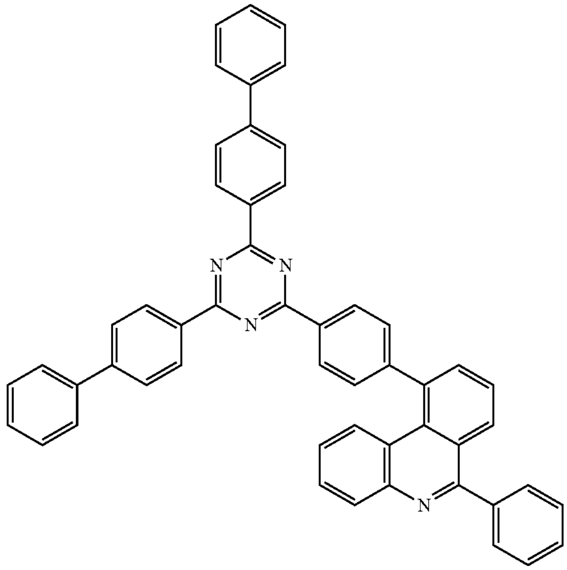
142
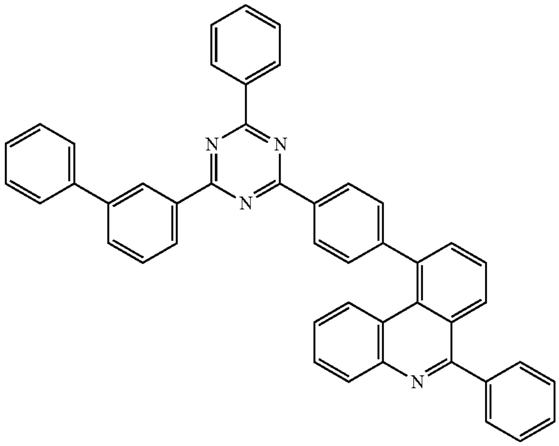
143
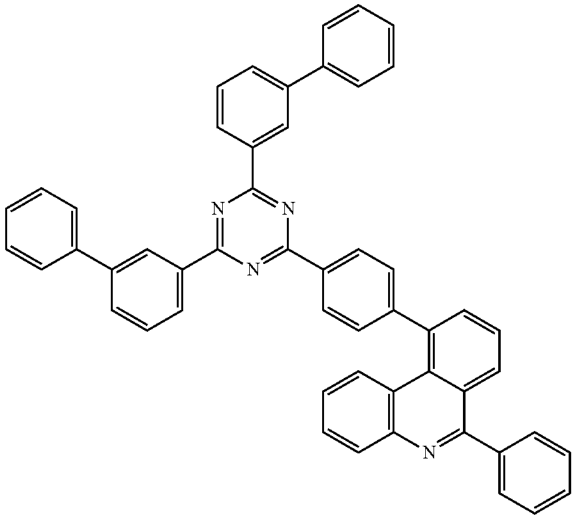
-continued
144
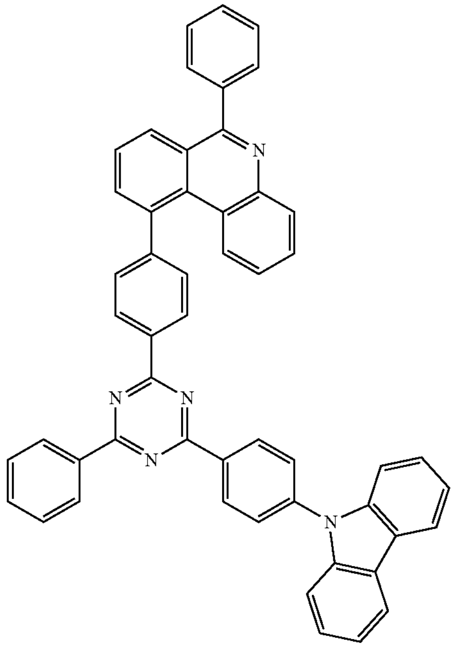
145
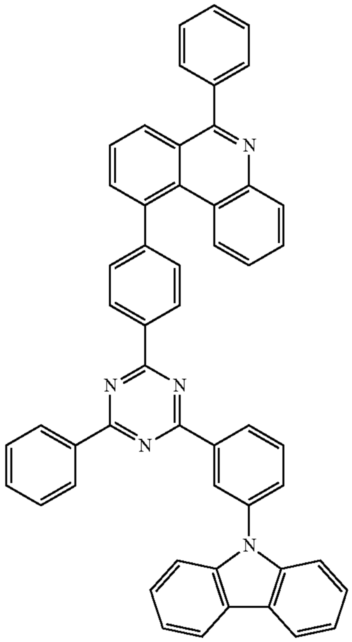

-continued
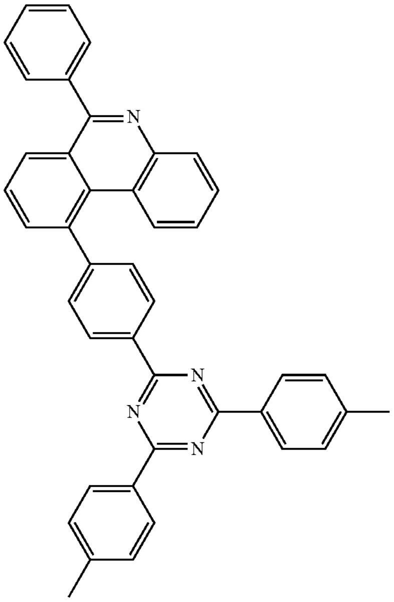
146
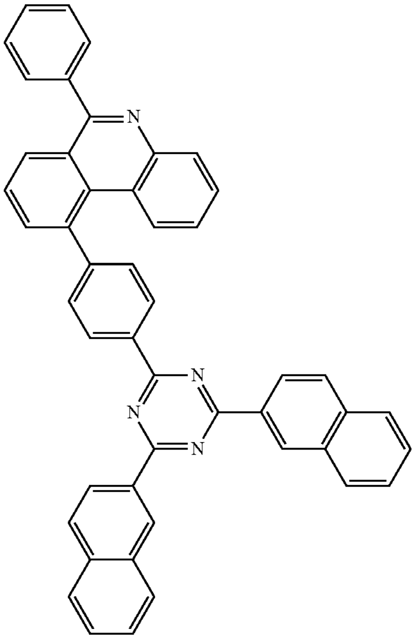
147
-continued
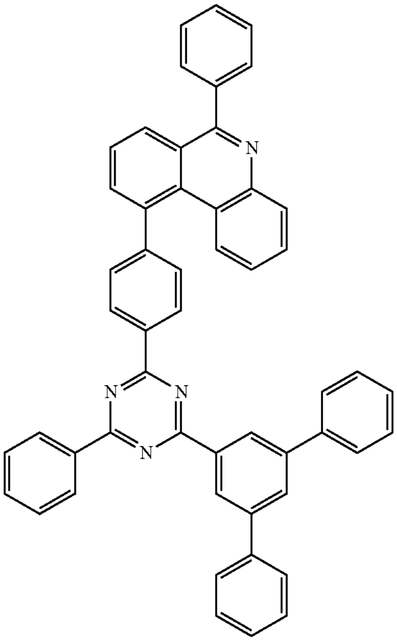
148
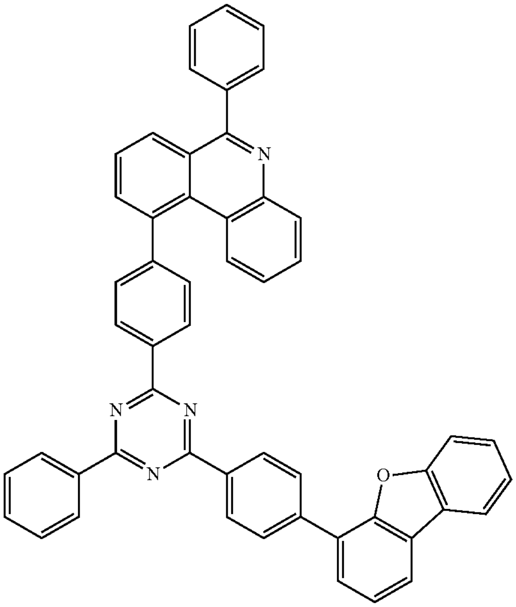
149

-continued
150
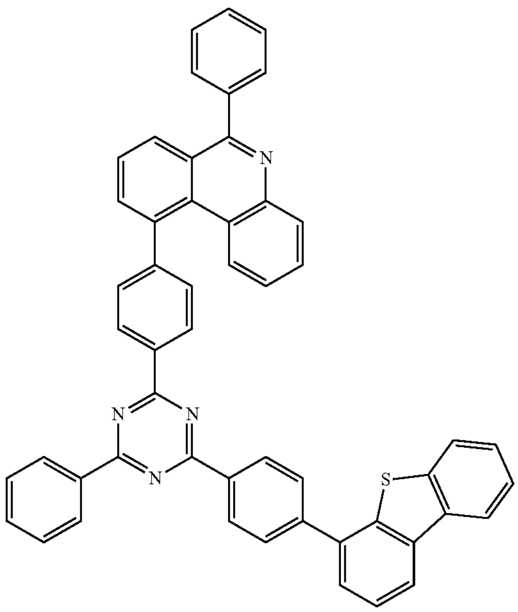
151
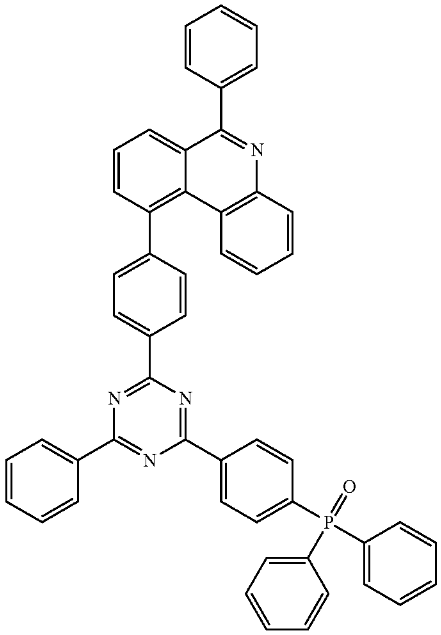
-continued
152
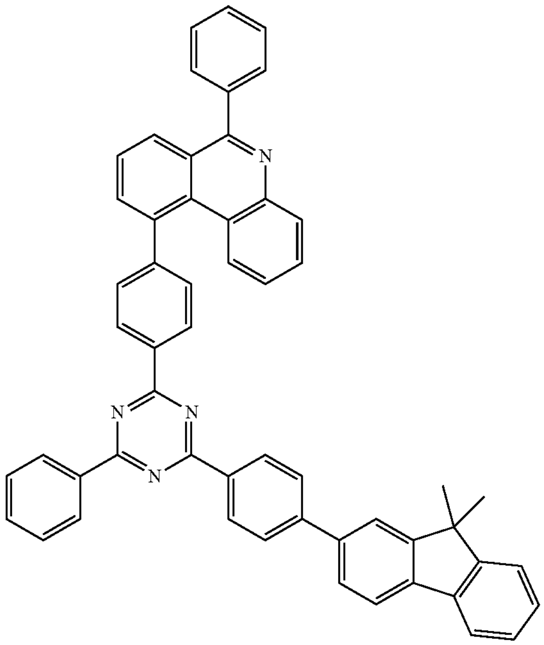
153
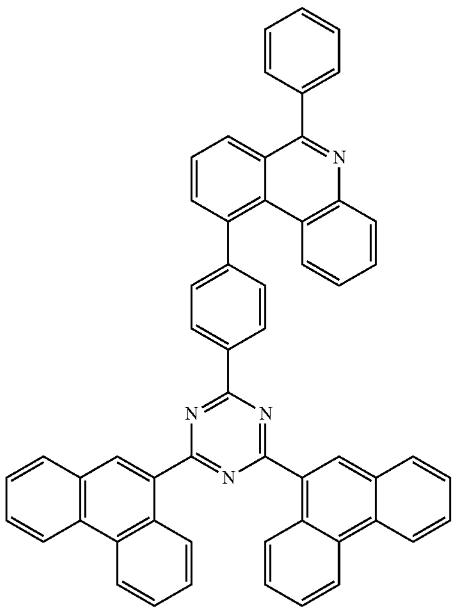

-continued
154
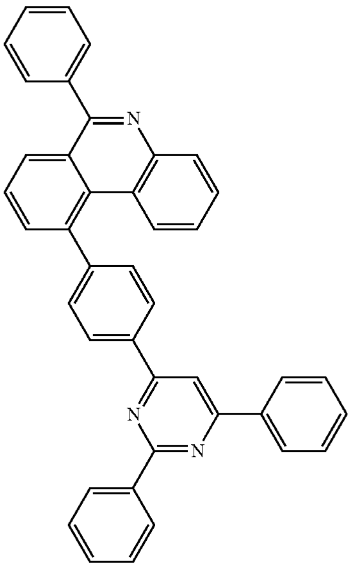
155
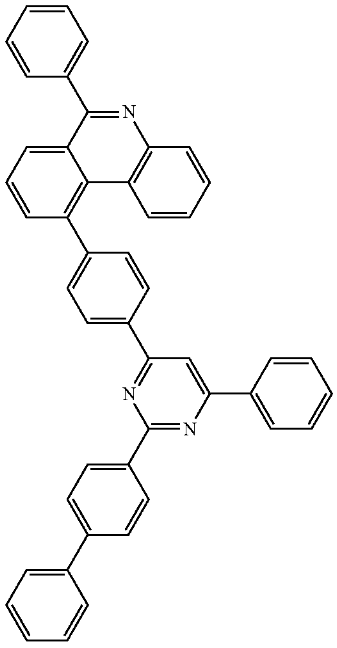
-continued
156
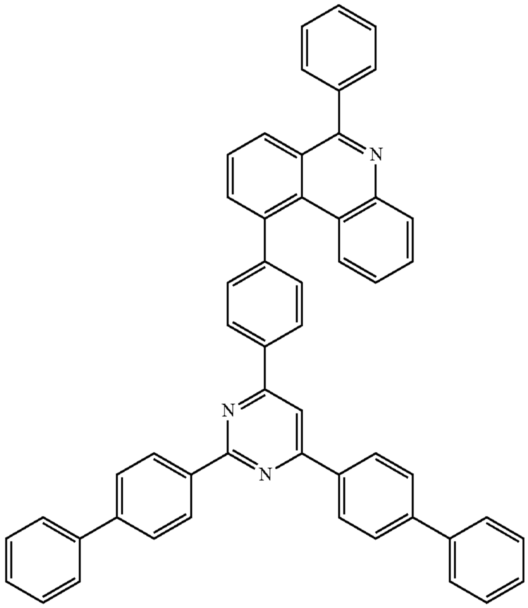
157
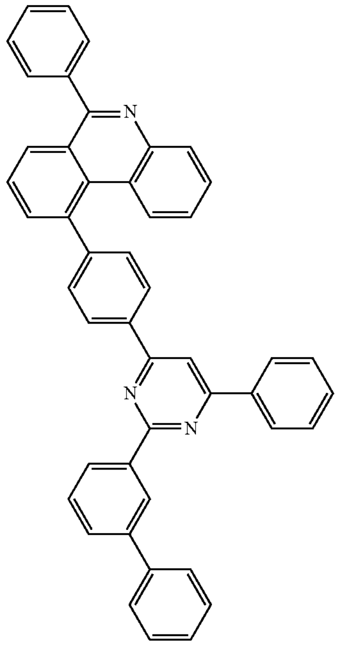

-continued
158
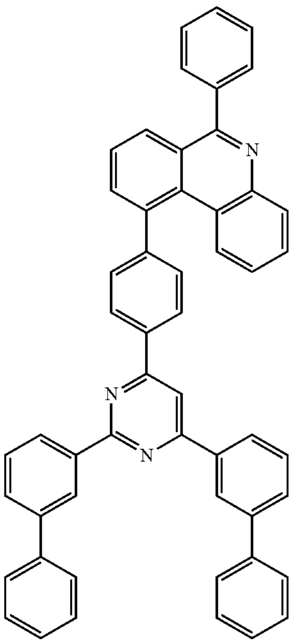
159
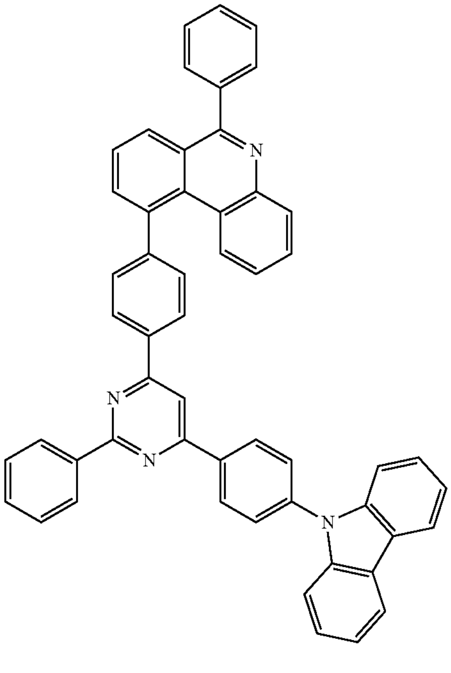
-continued
160
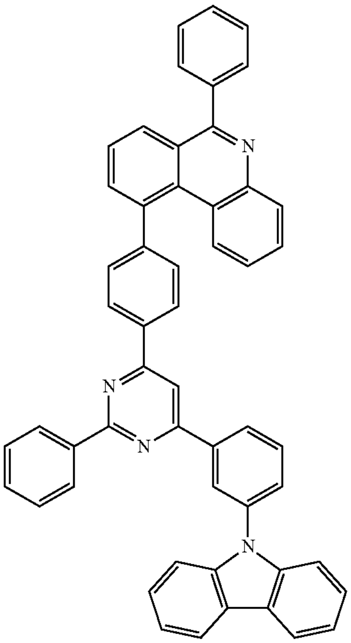
161
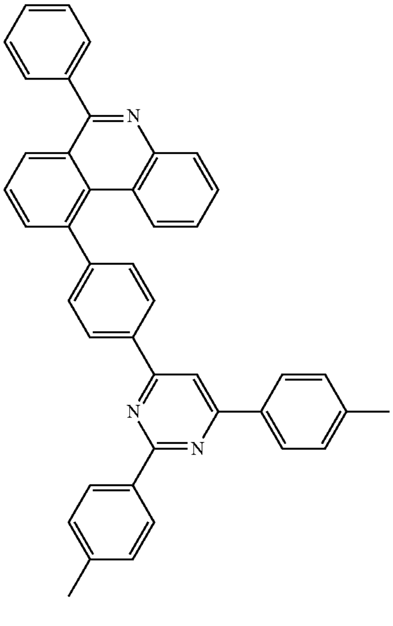

-continued
162
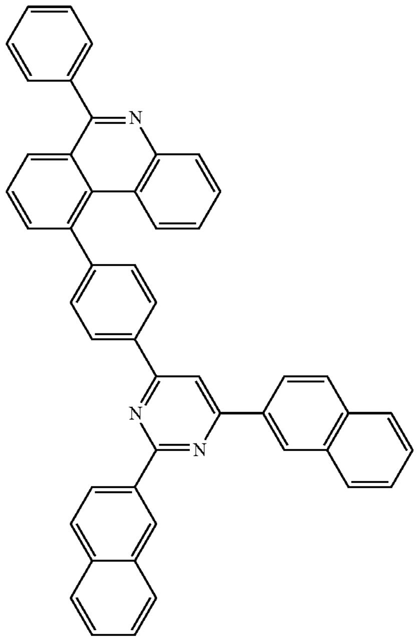
163
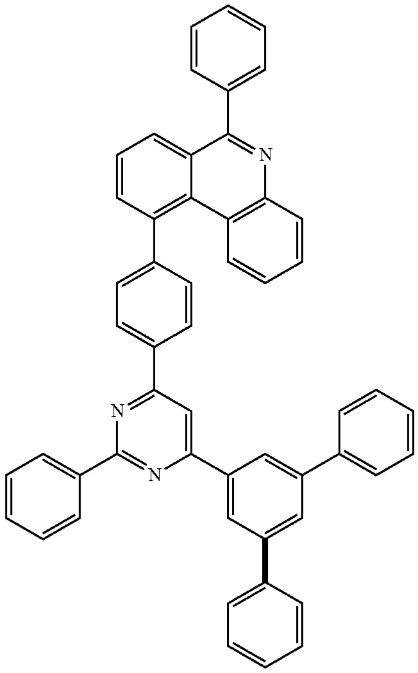
-continued
164
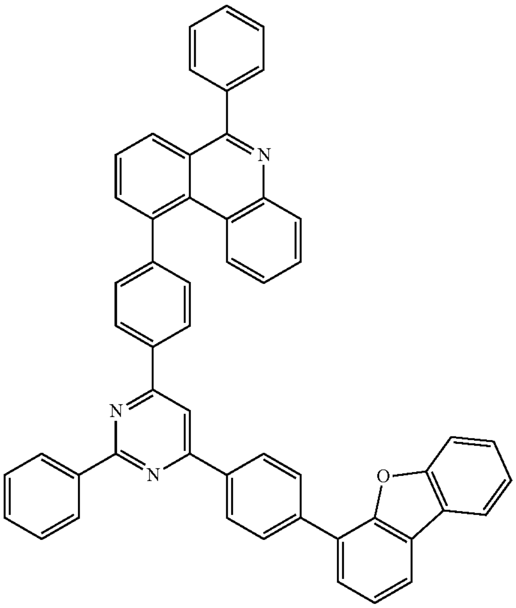
165
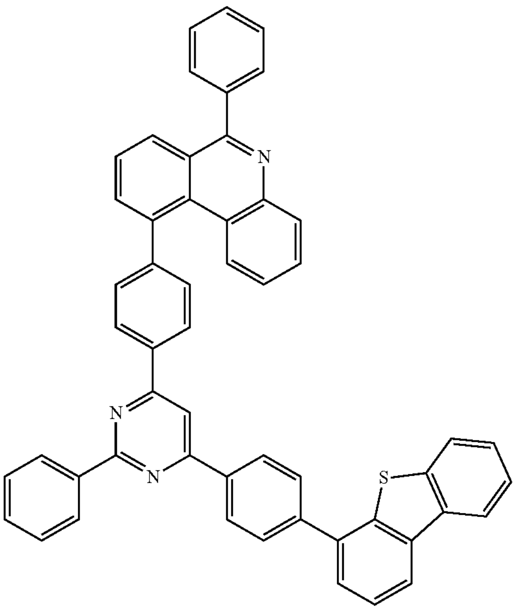

166
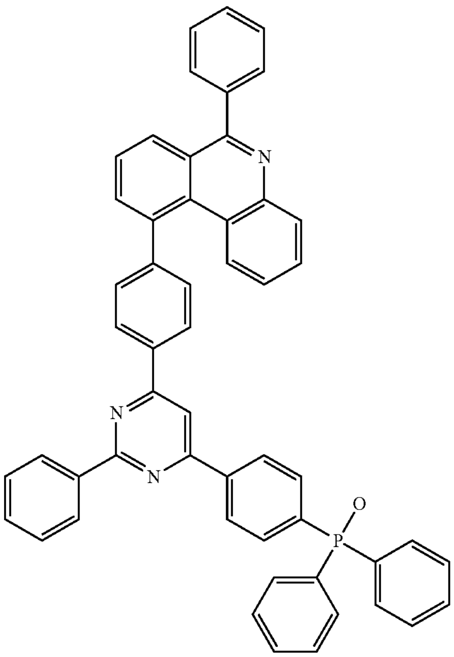
168
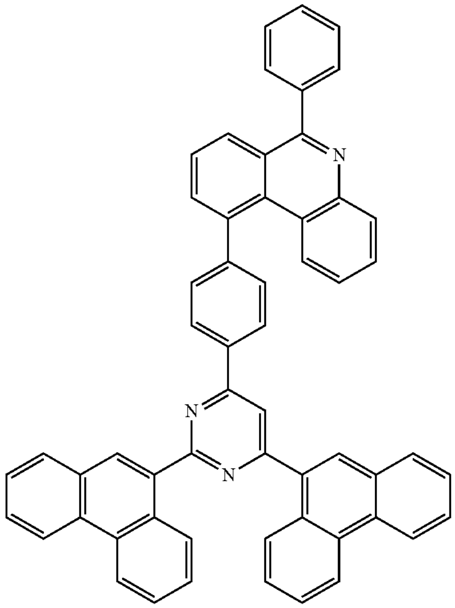
167
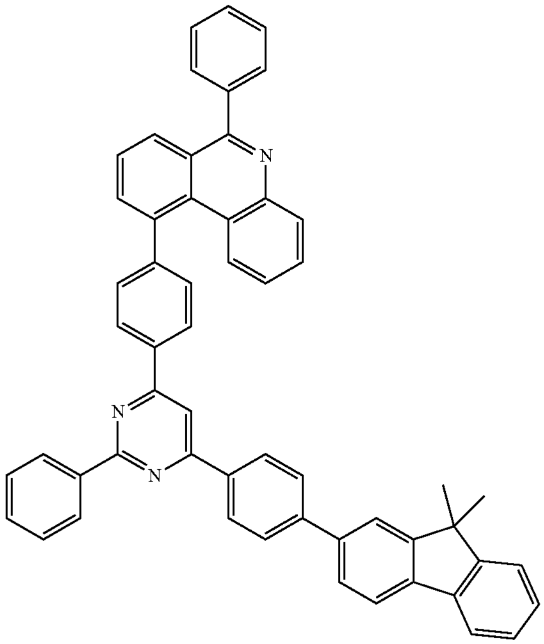
169
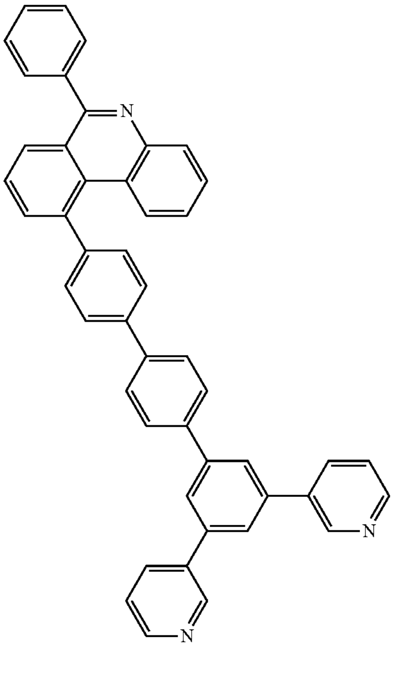

-continued
170
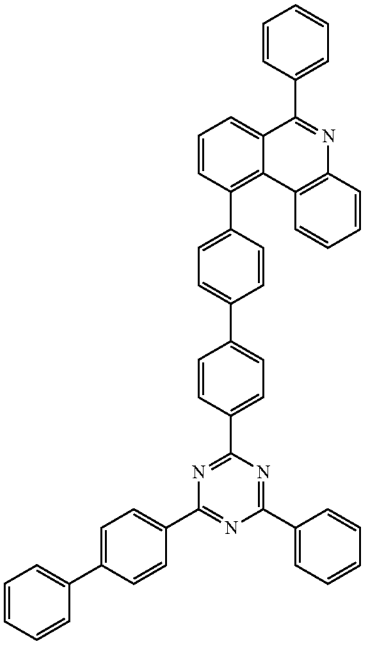
171
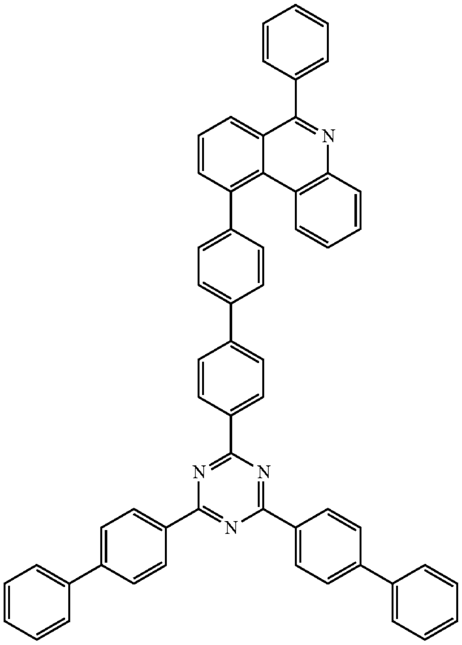
-continued
172
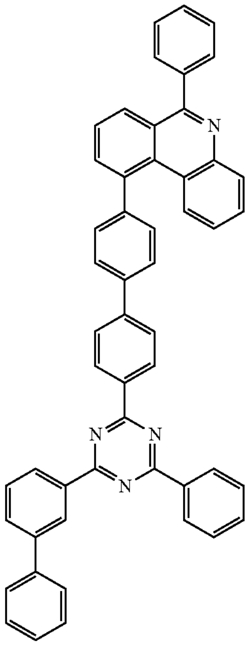
173
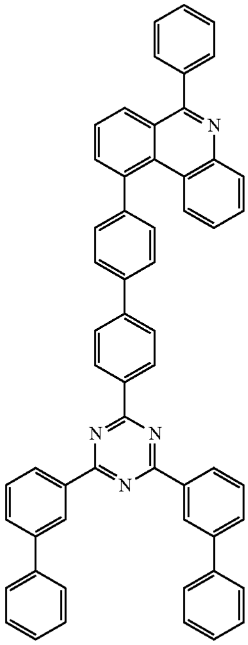

-continued
174
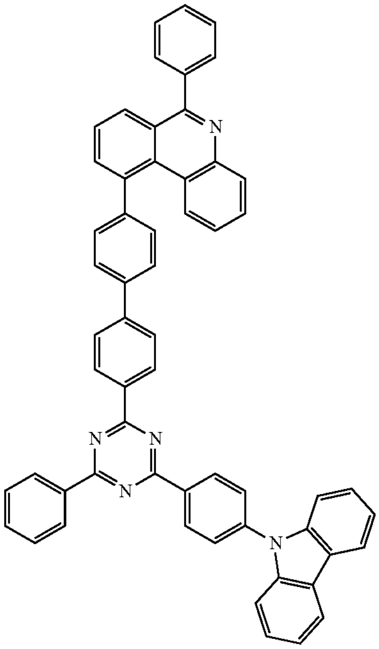
175
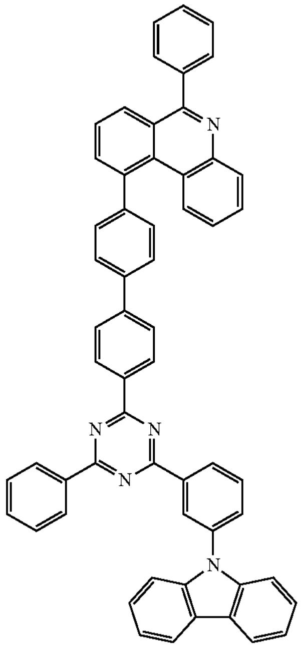
-continued
176
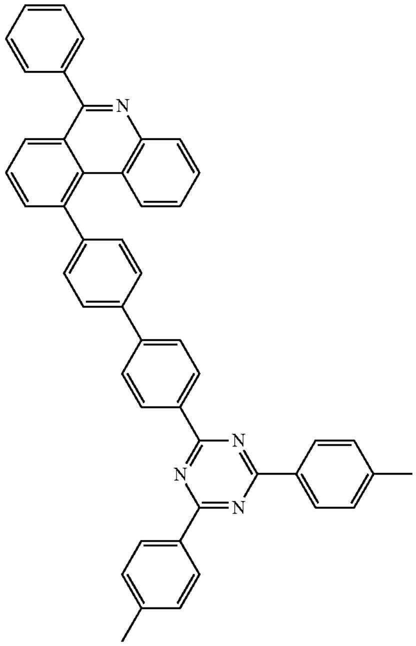
177
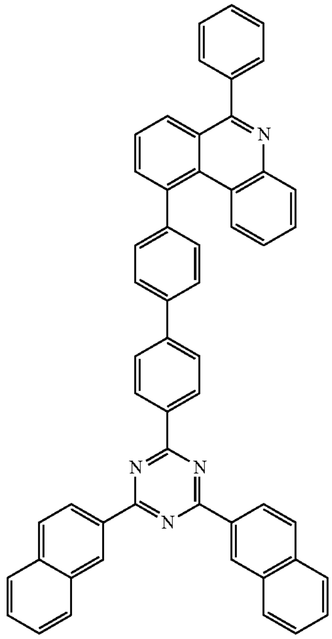

-continued
178
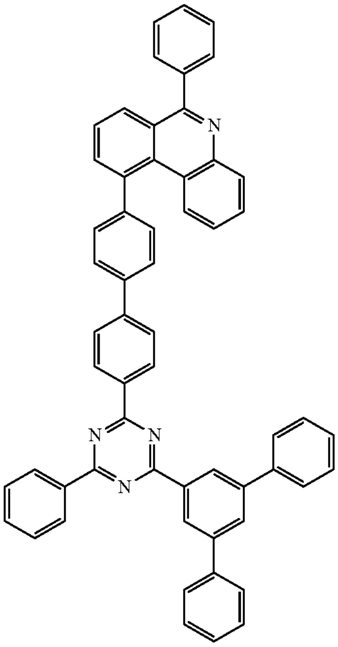
179
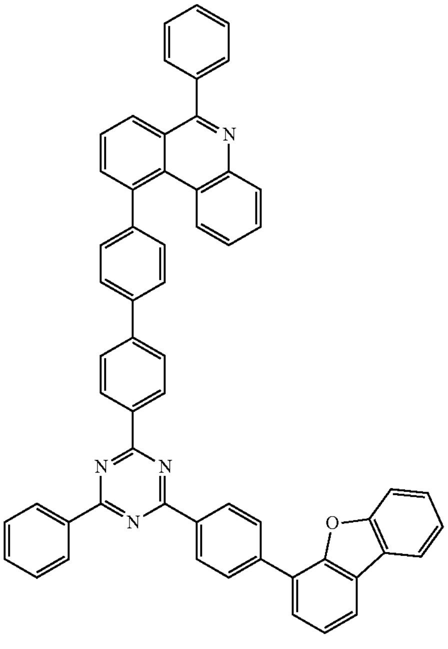
-continued
180
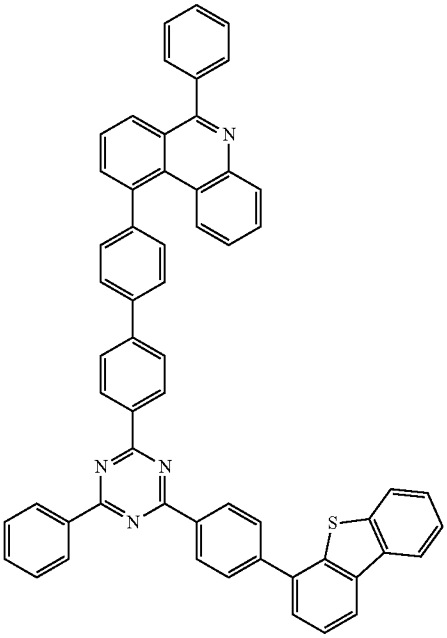
181
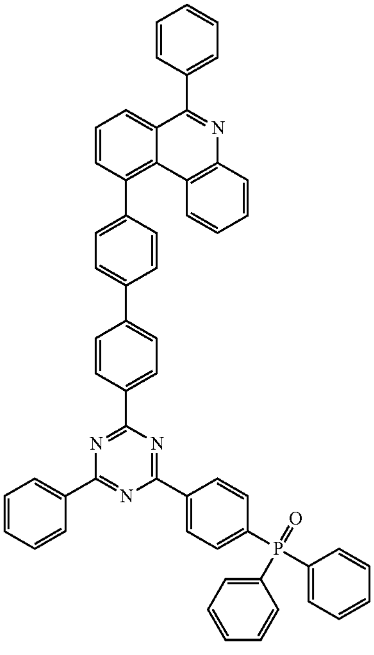

182
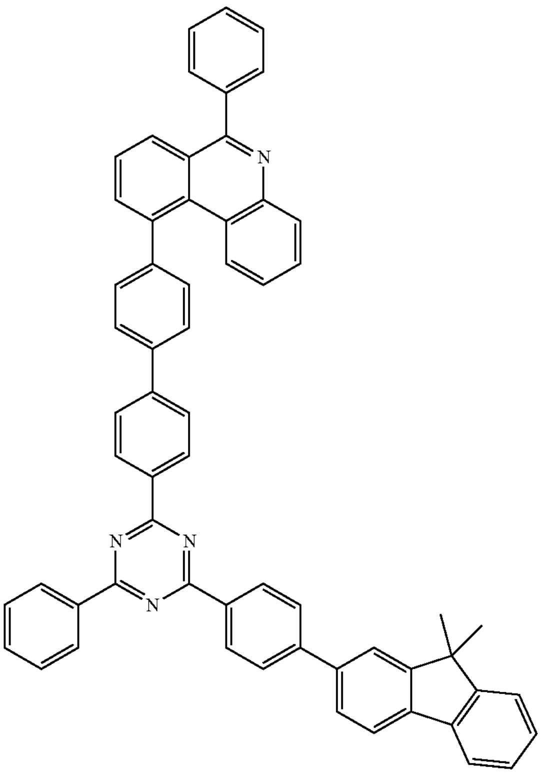
184
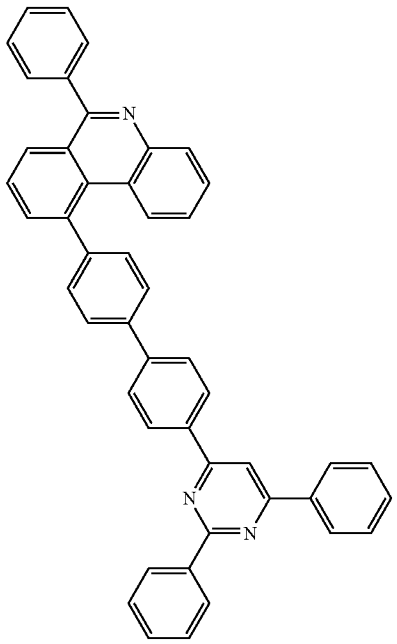
183
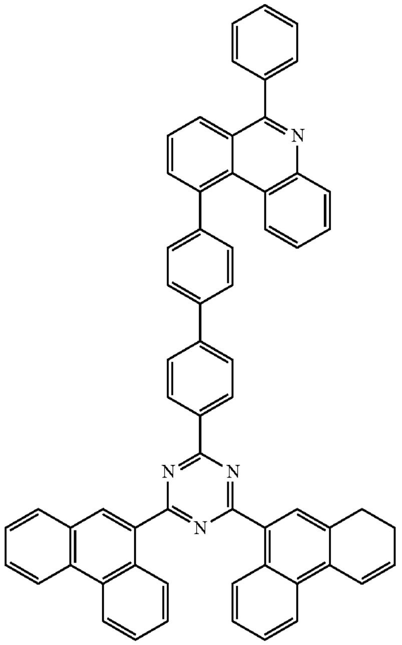
185
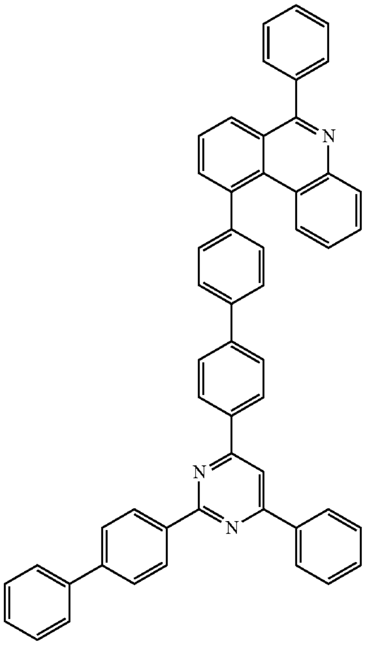

-continued
186
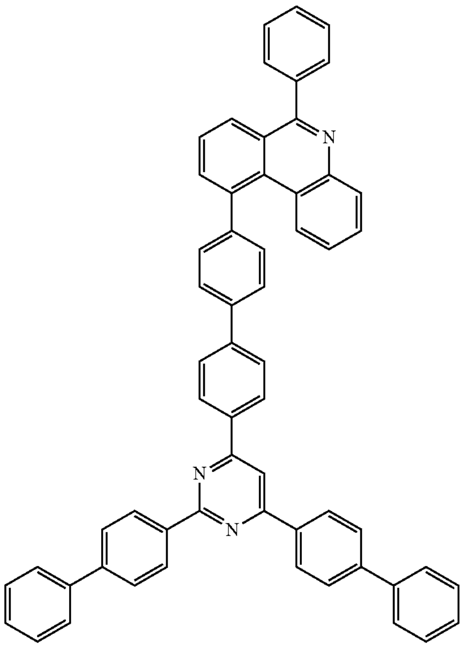
187
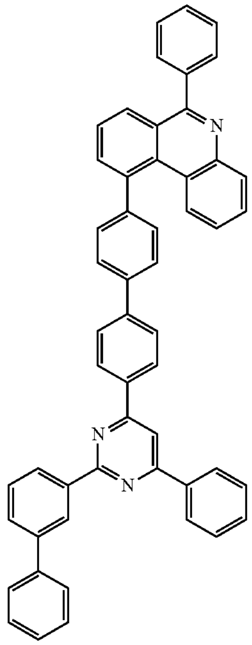
-continued
188
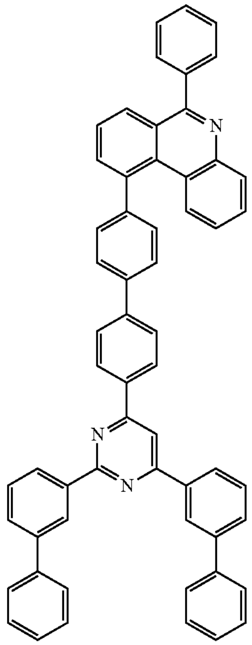
189
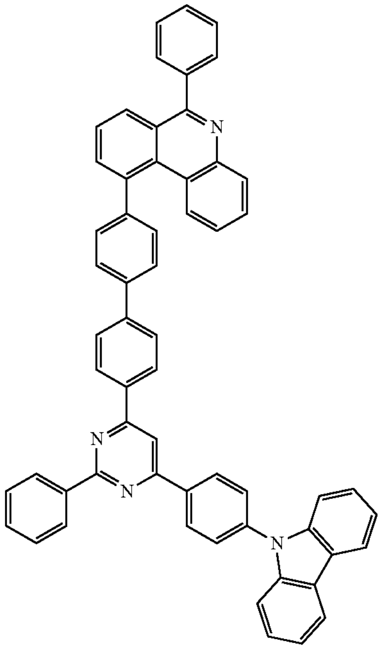

-continued
190
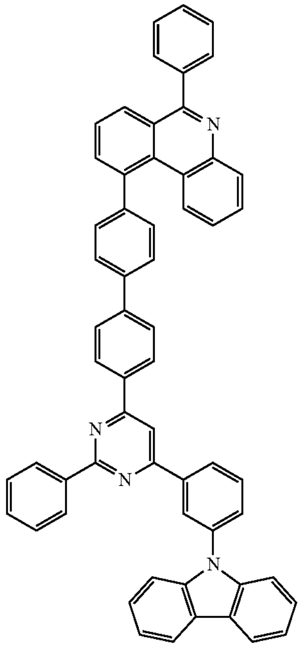
191
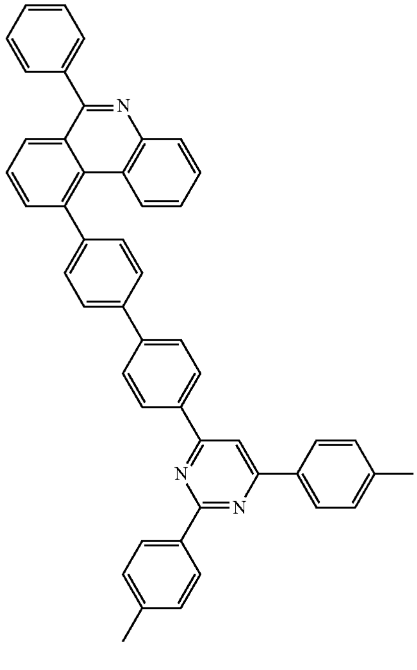
-continued
192
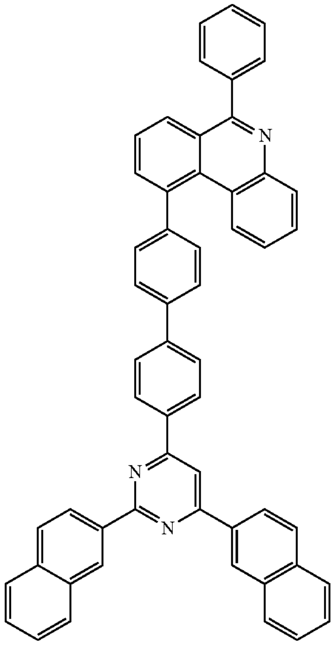
193
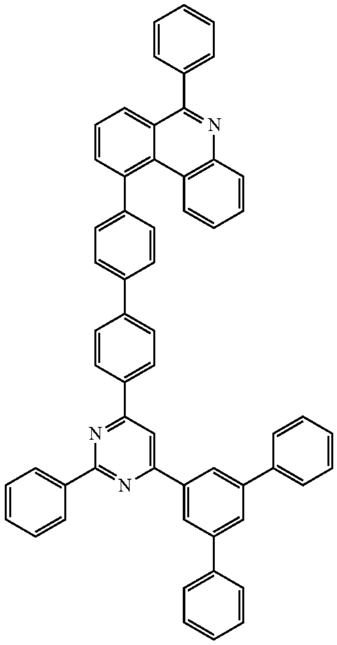

-continued
194
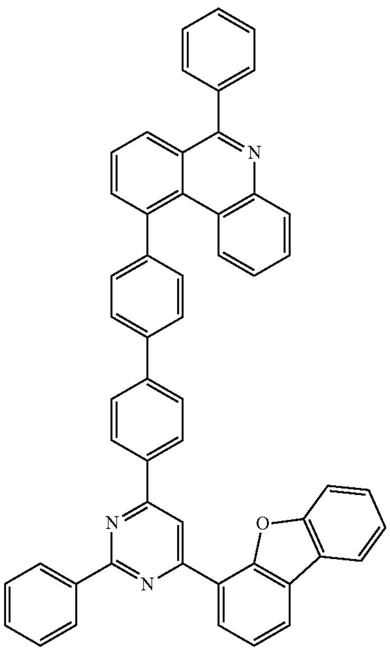
195
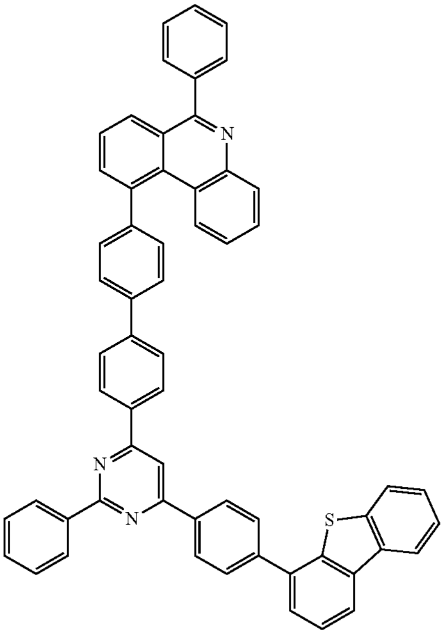
-continued
196
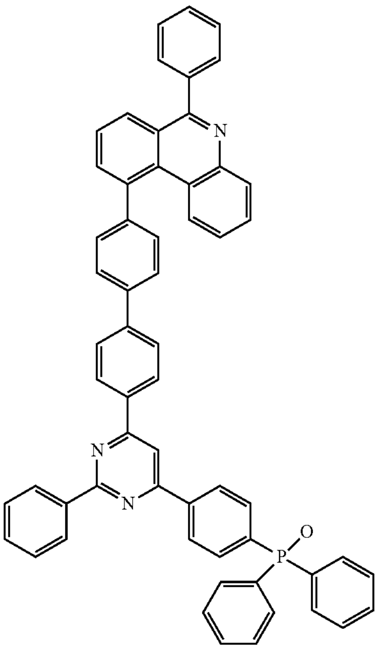
197
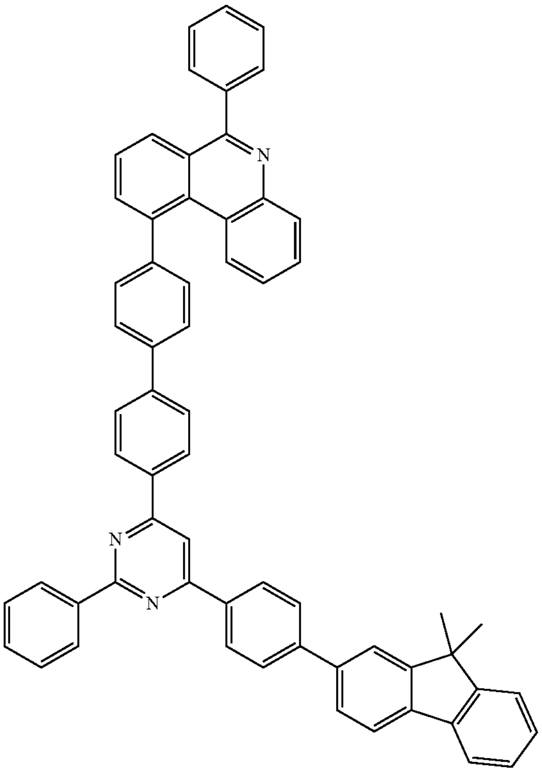

-continued
198
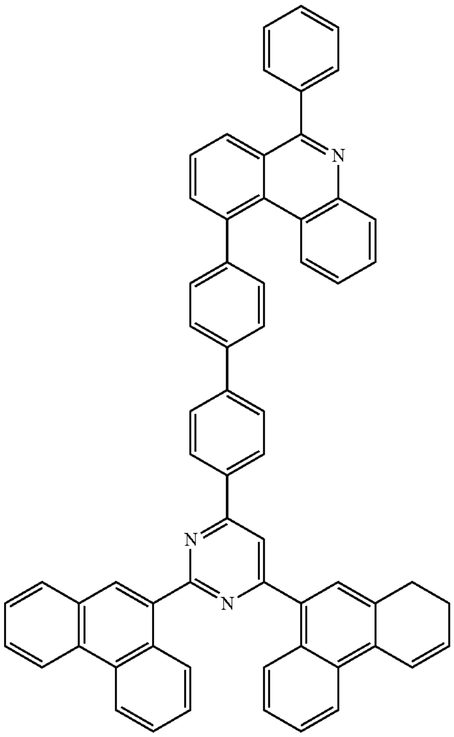
199
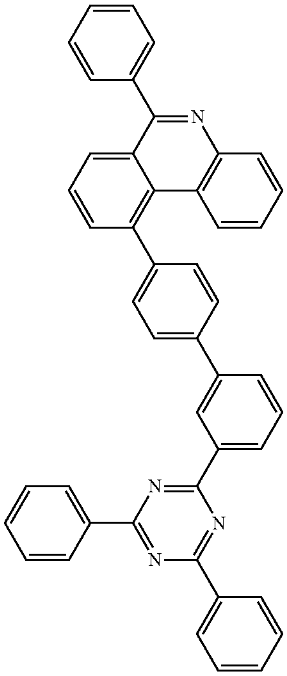
-continued
200
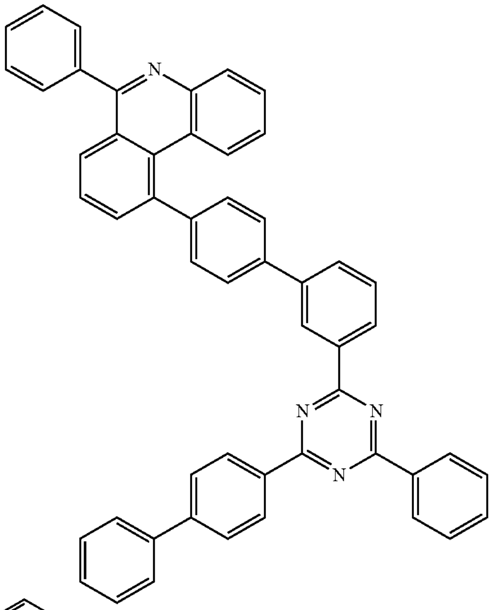
201
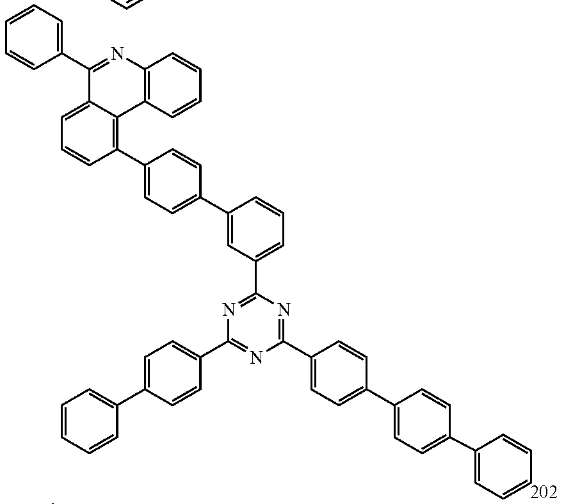
202
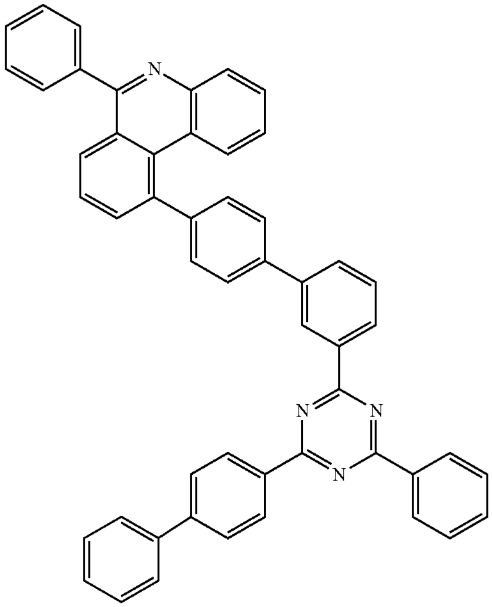

-continued
203
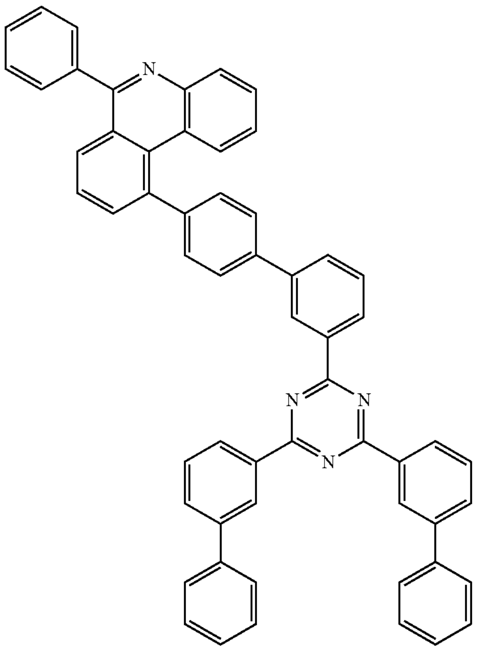
204
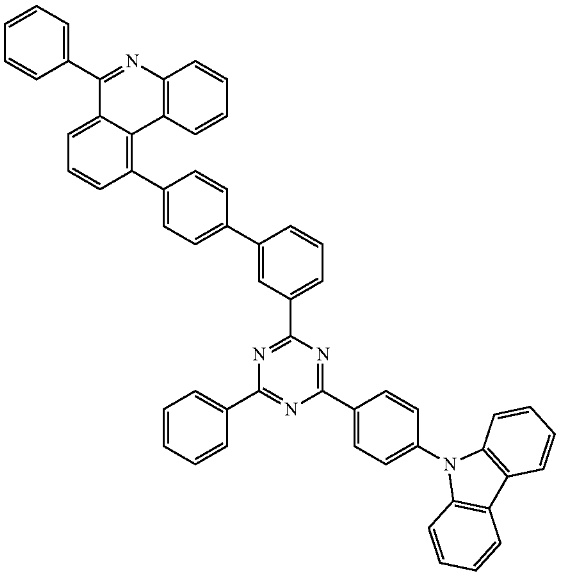
-continued
205
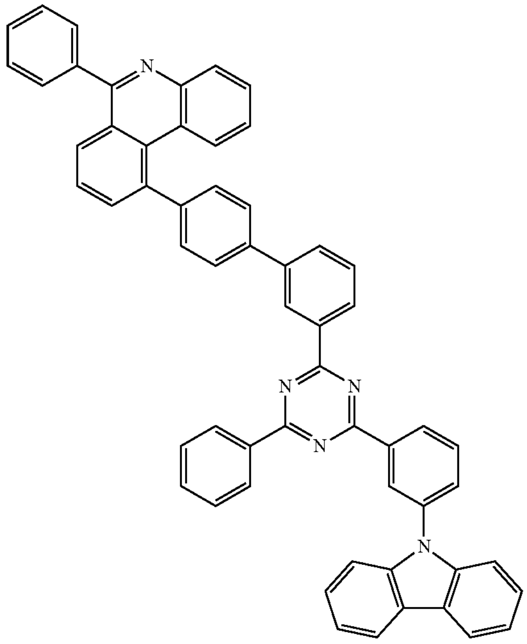
206
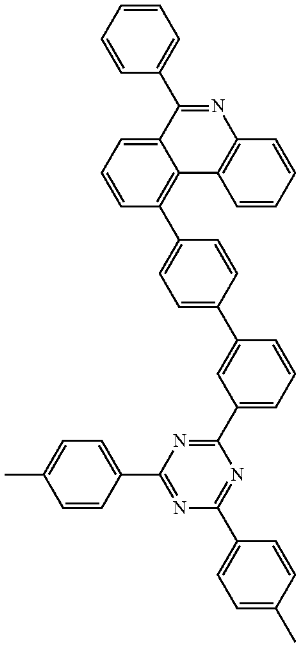

207
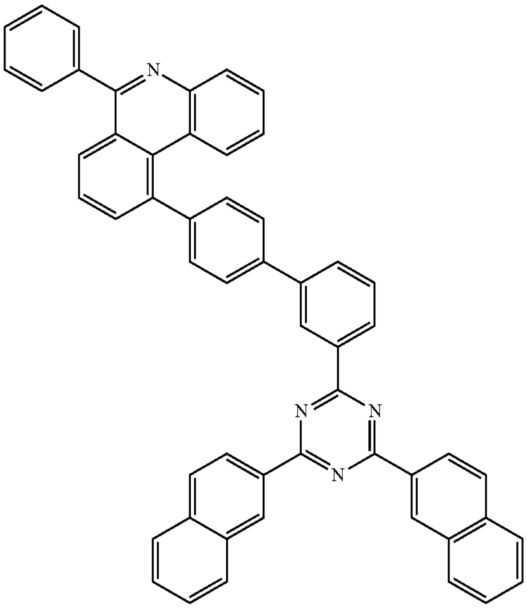
208
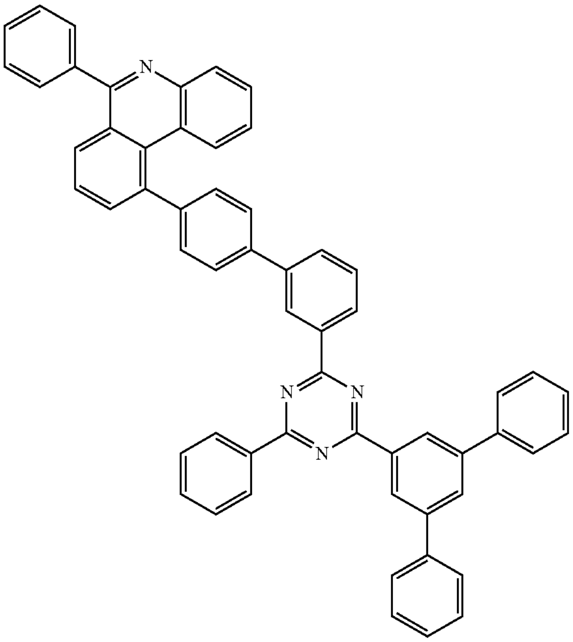
207
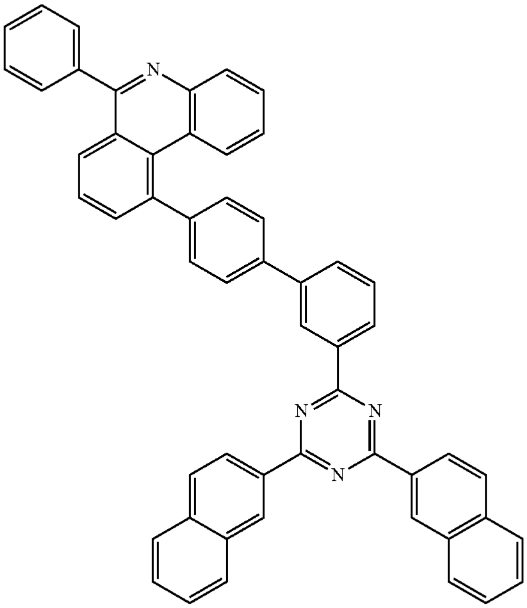
209
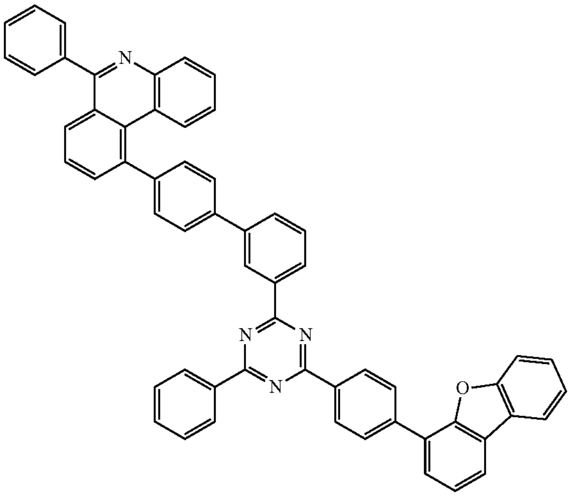

-continued
210
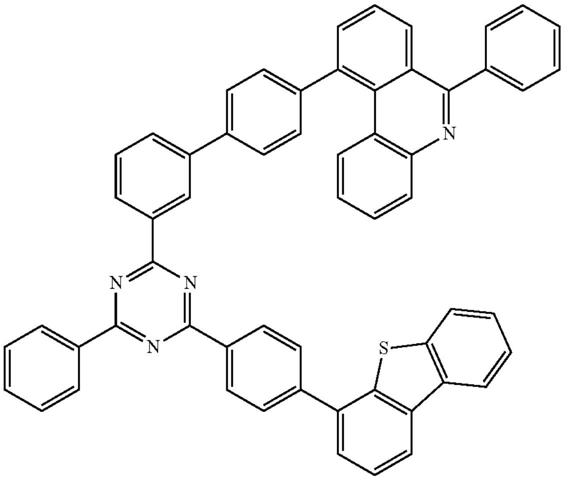
211
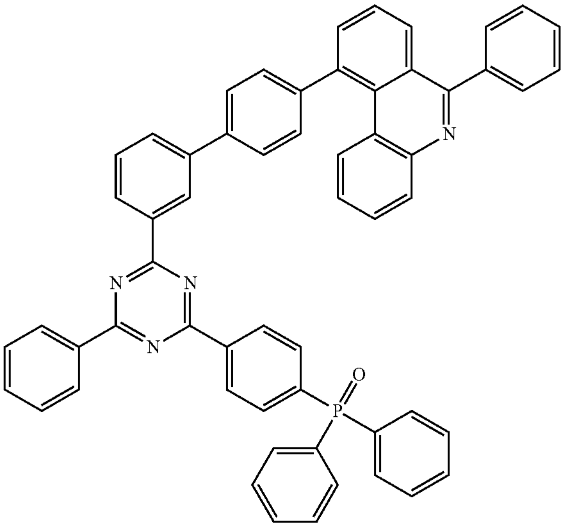
212
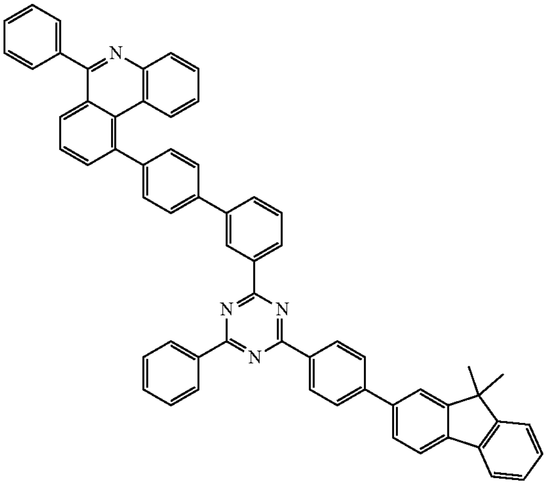
-continued
213
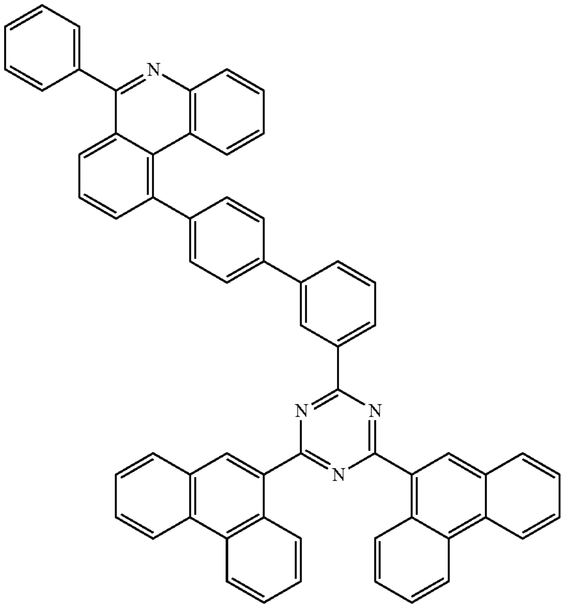
214
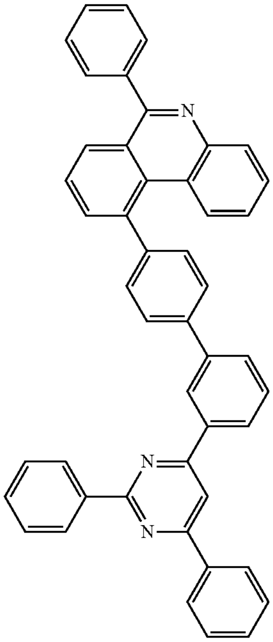

-continued
215
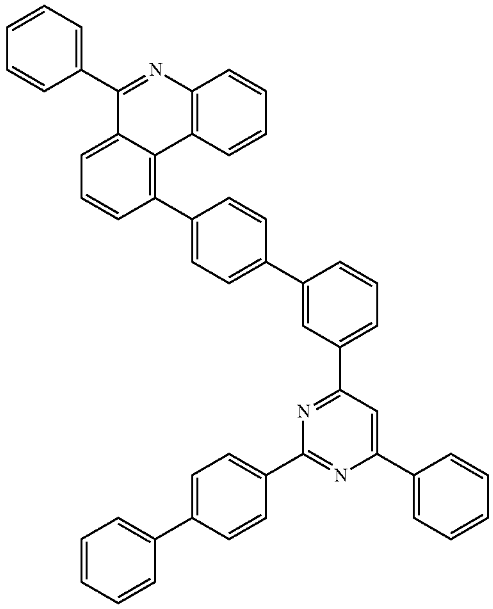
216
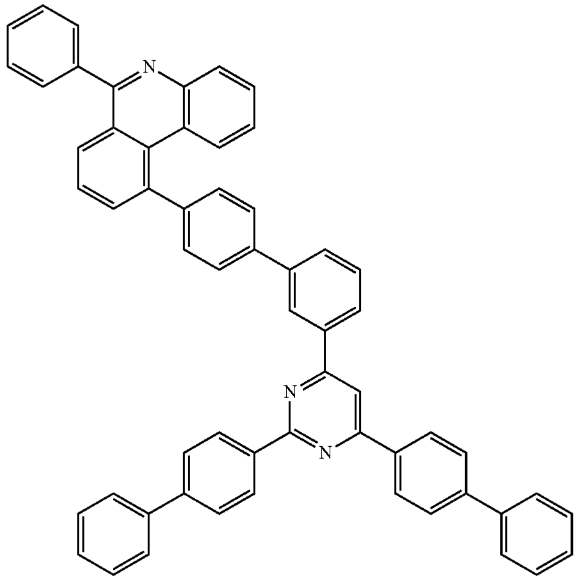
-continued
217
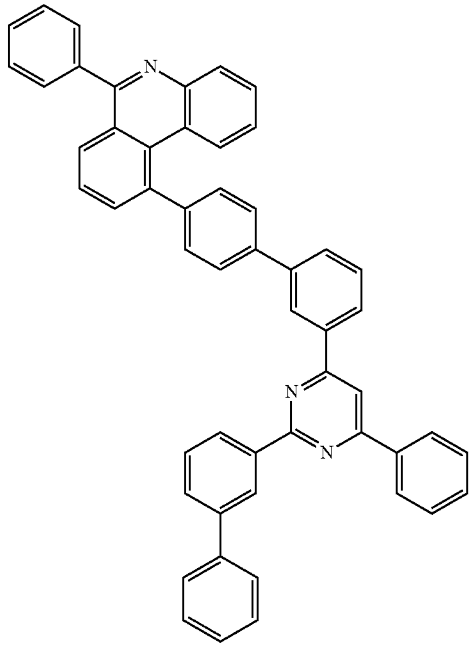
218
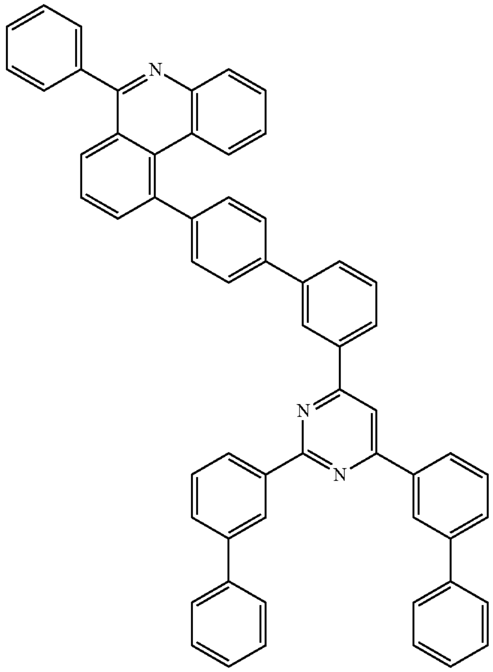

-continued
219
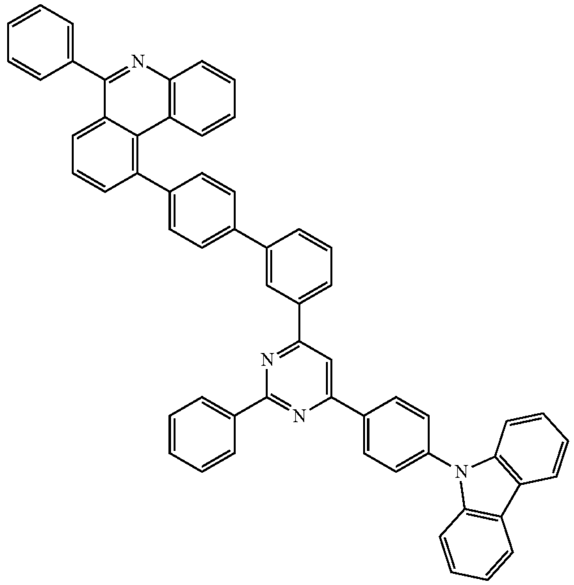
221
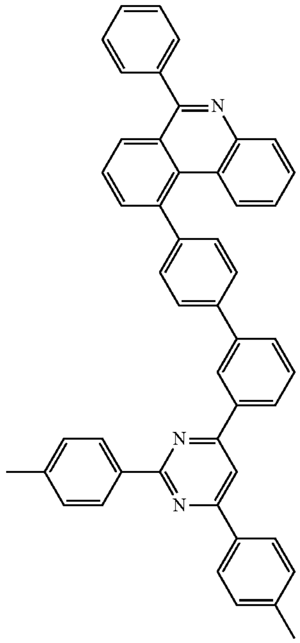
220
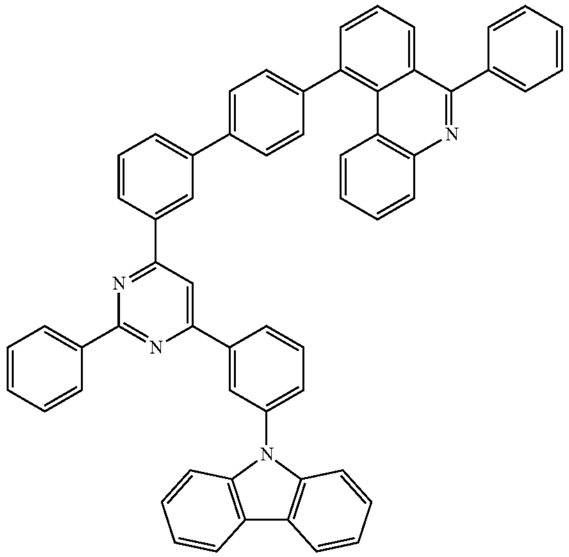
222
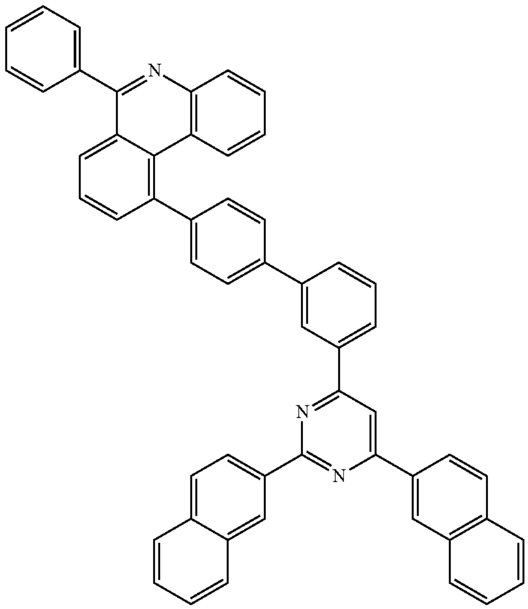

-continued
223
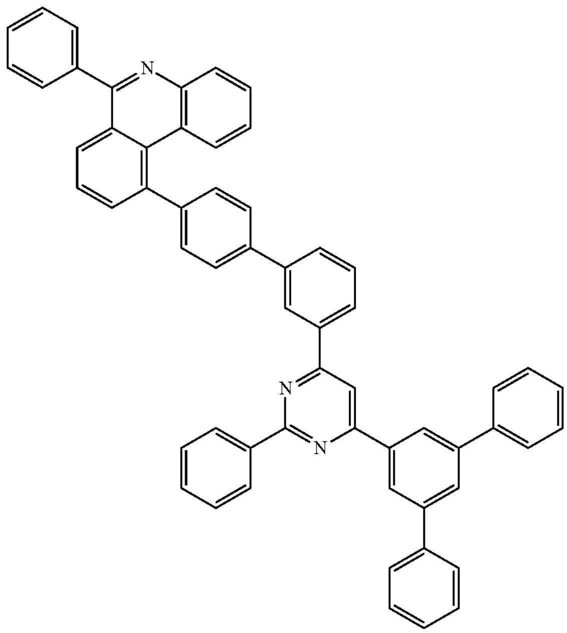
224
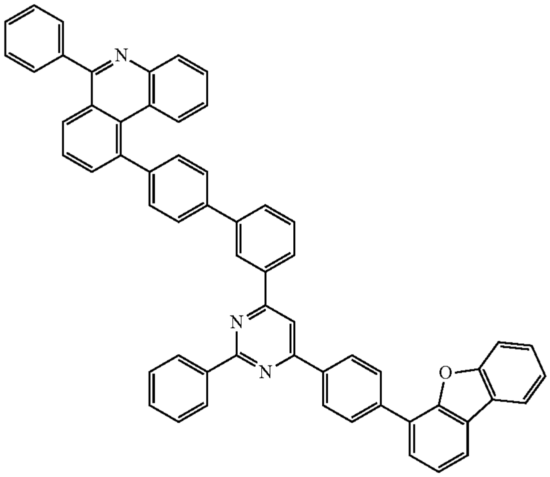
225
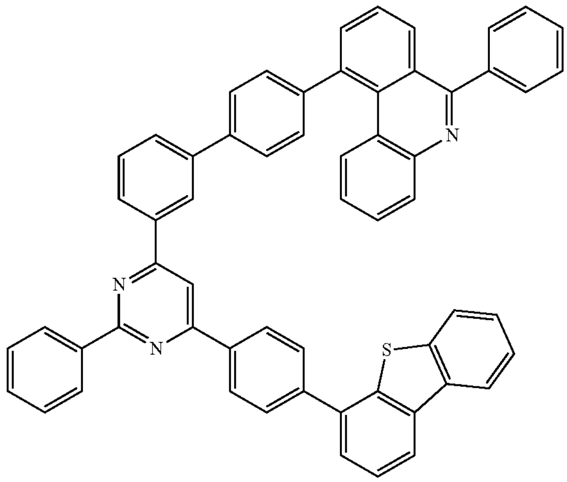
-continued
226
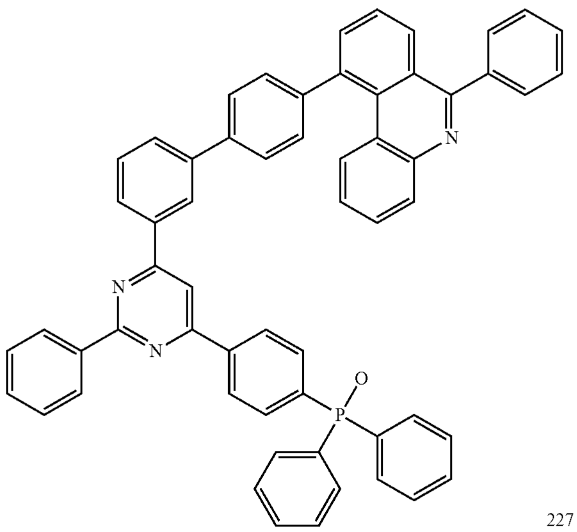
227
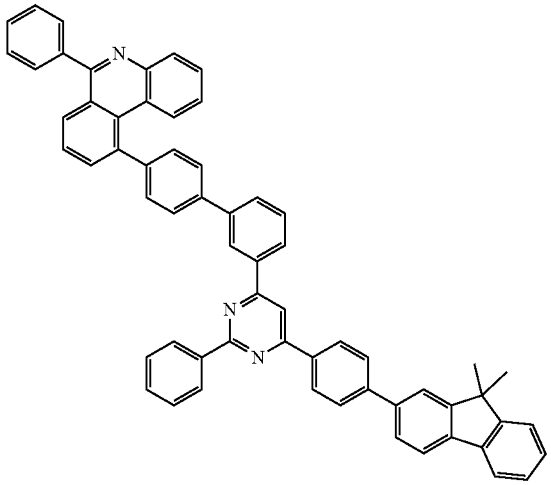
228
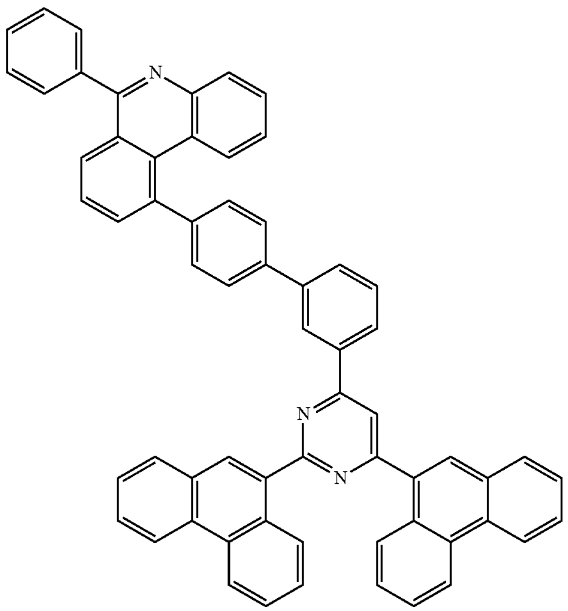

-continued
229
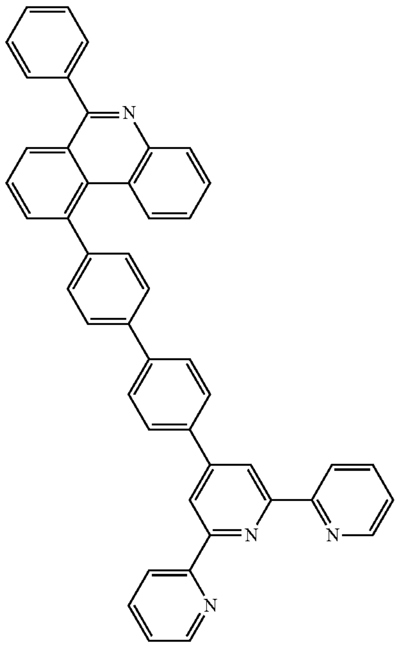
230
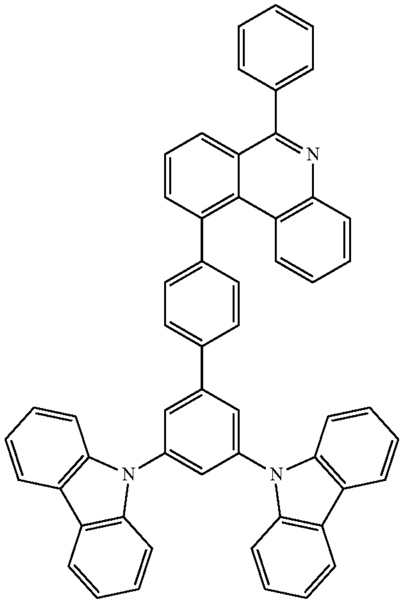
-continued
231
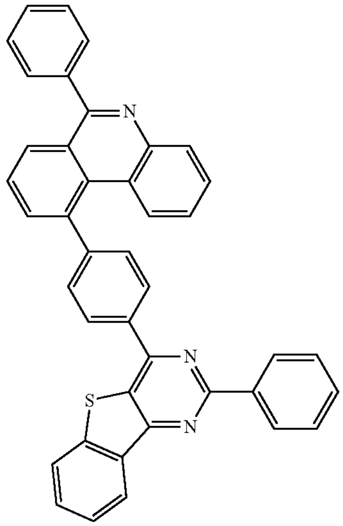
232
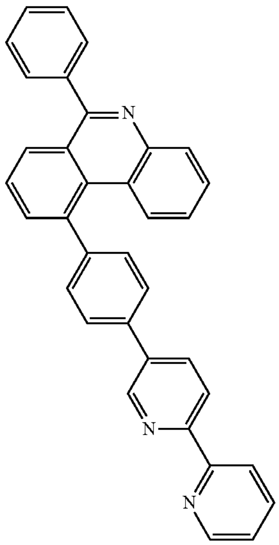
233
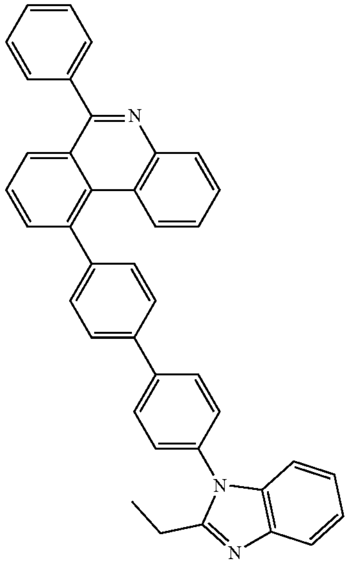

-continued
234
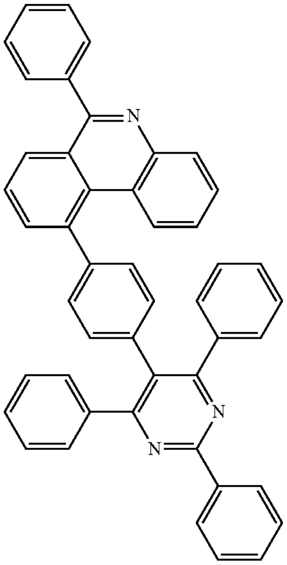
235
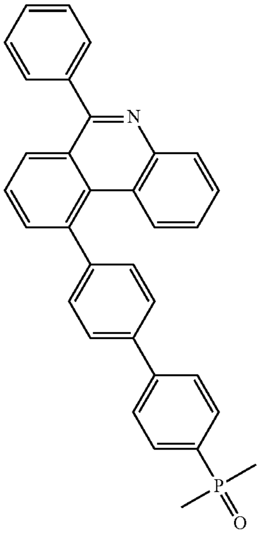
236
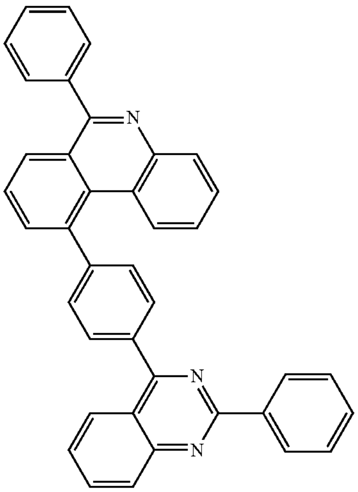
-continued
237
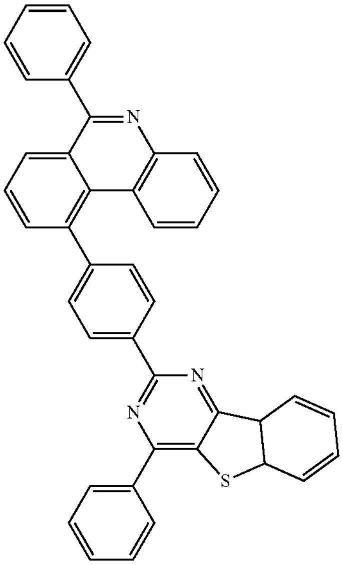
238
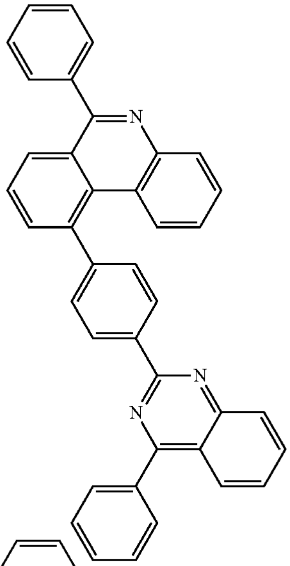
239
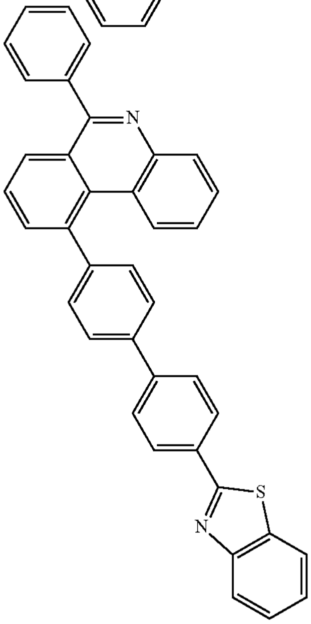

240
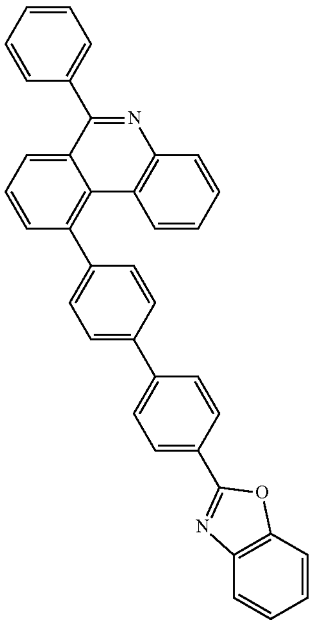
241
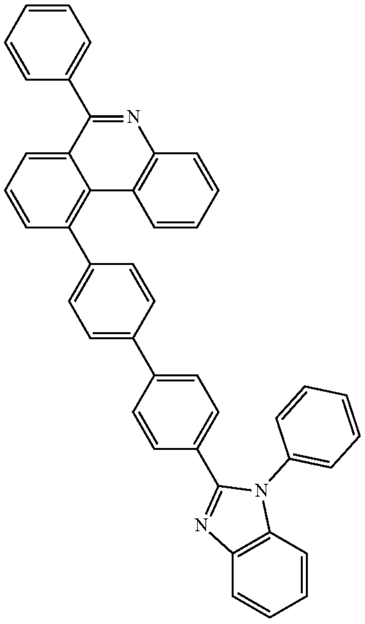
242
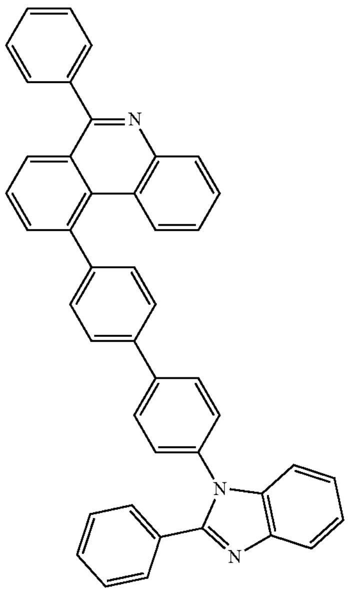
243
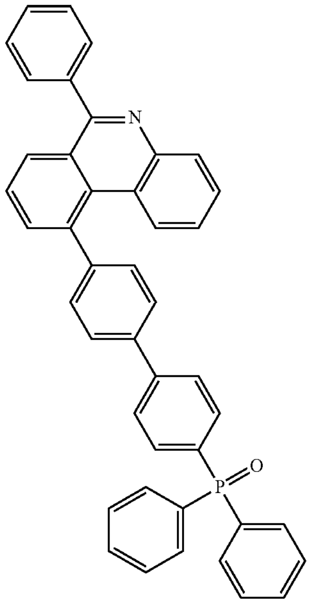

244
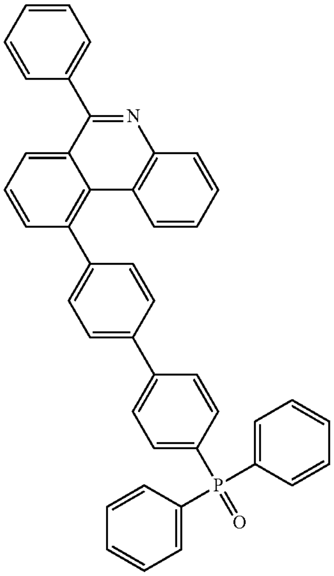
245
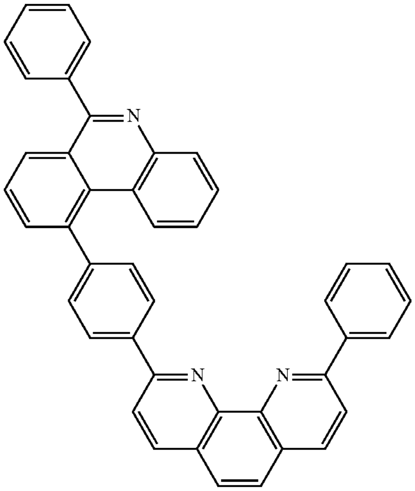
246
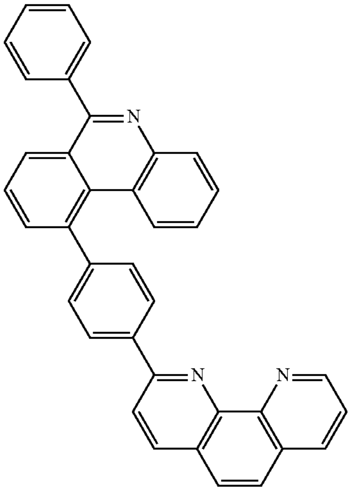
247
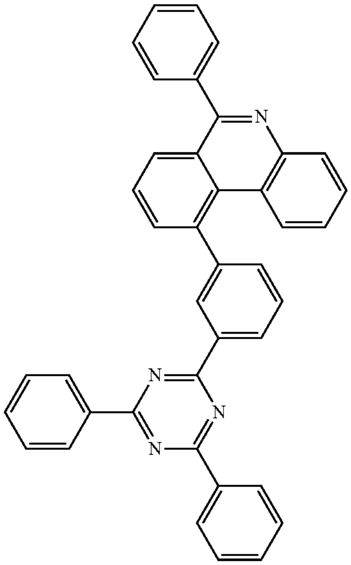
248
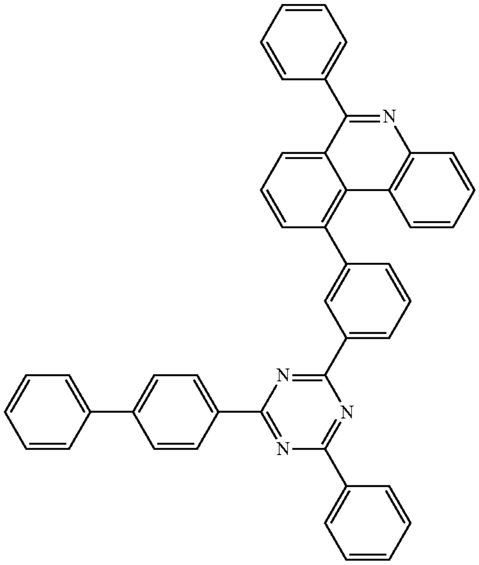
249
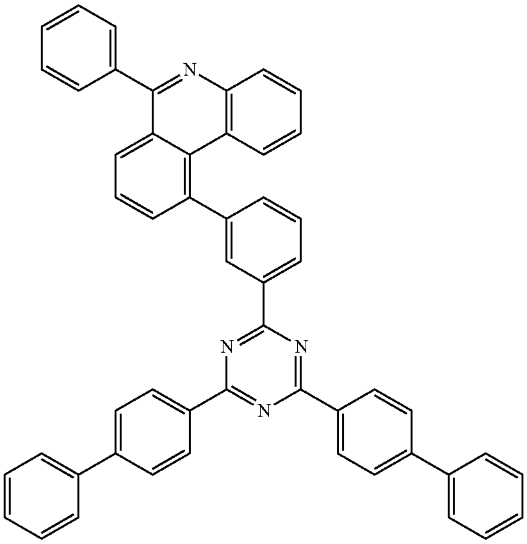

-continued
250
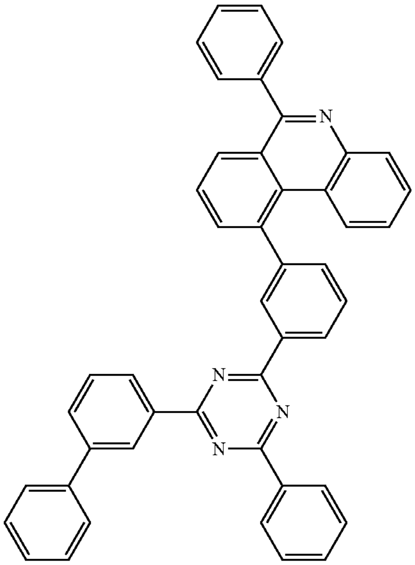
251
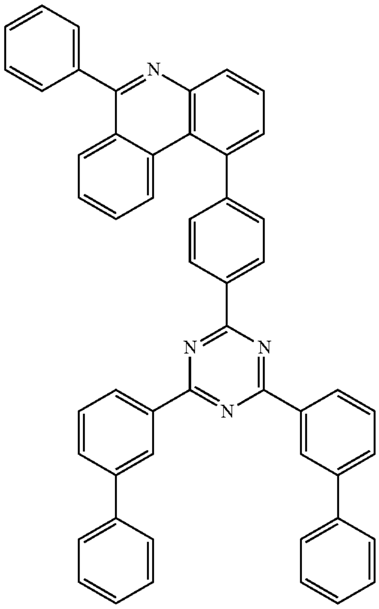
-continued
252
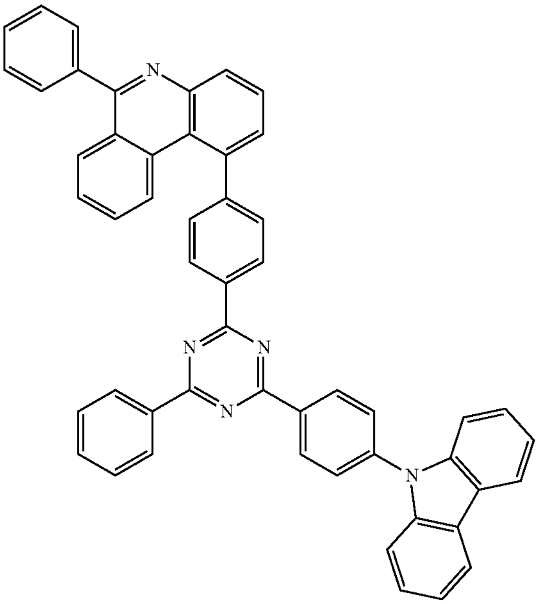
253
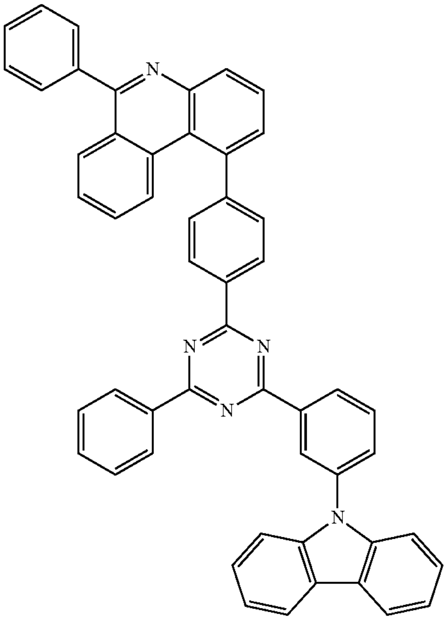

-continued
254
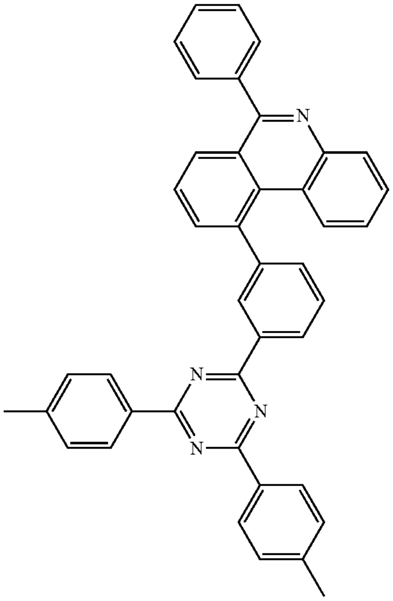
255
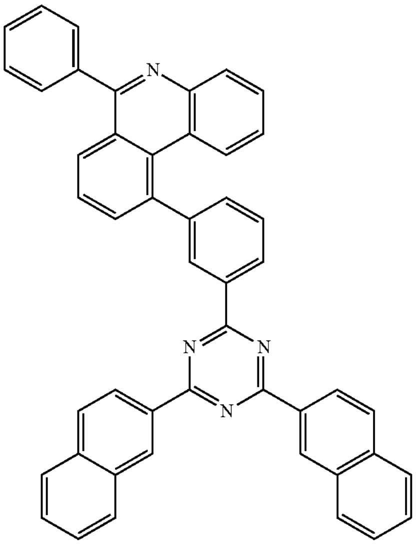
-continued
256
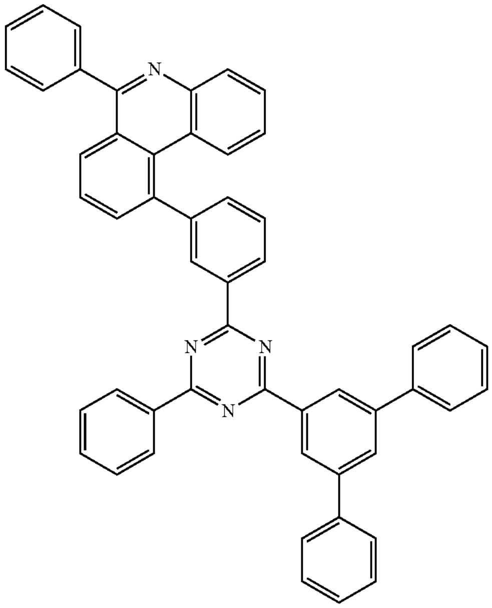
257
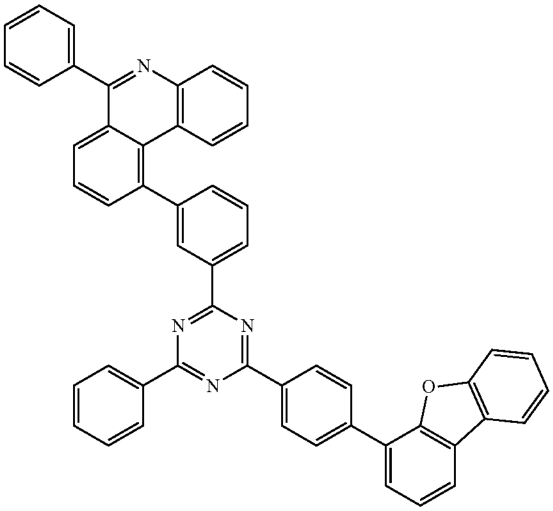

-continued
258
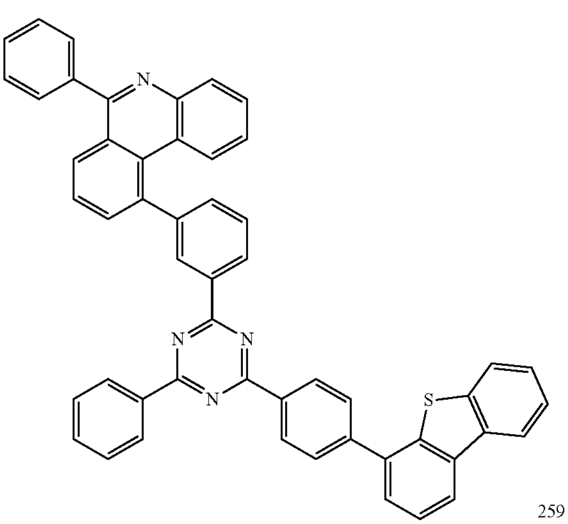
259
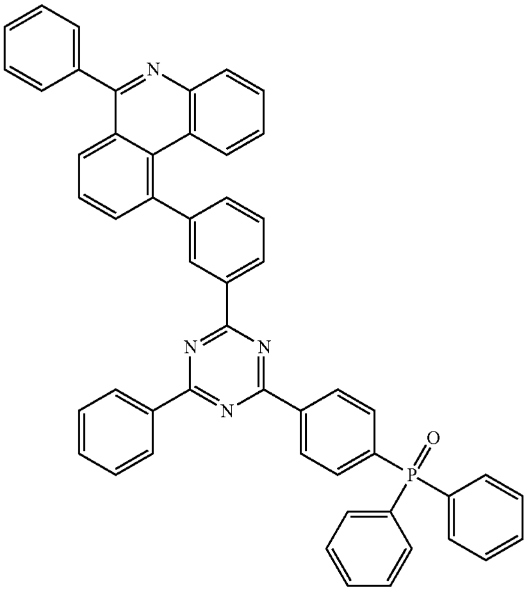
260
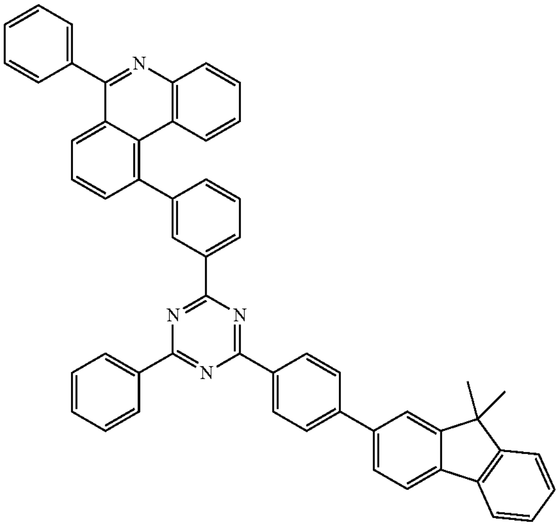
-continued
261
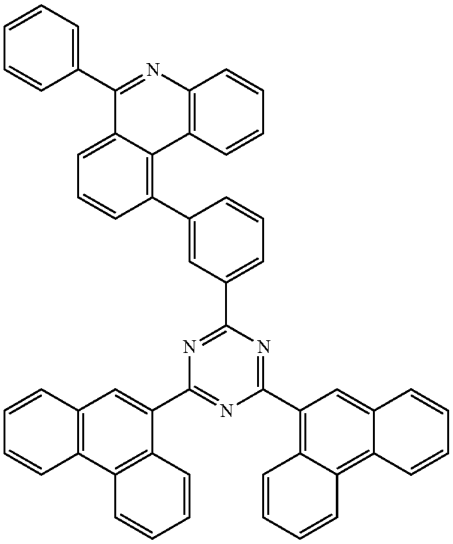
262
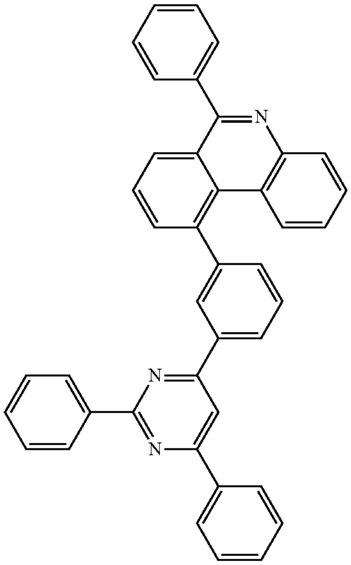
263
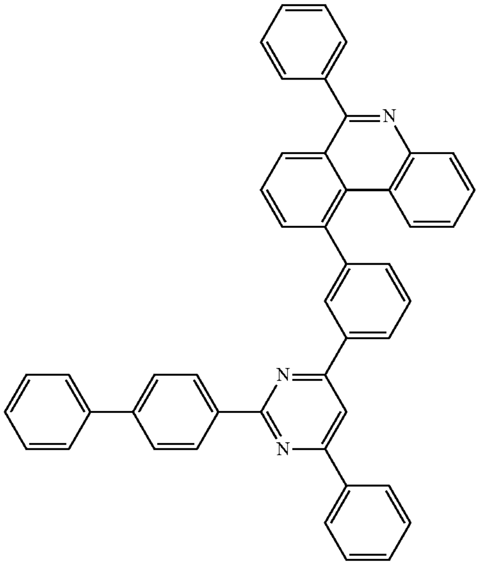

-continued
264
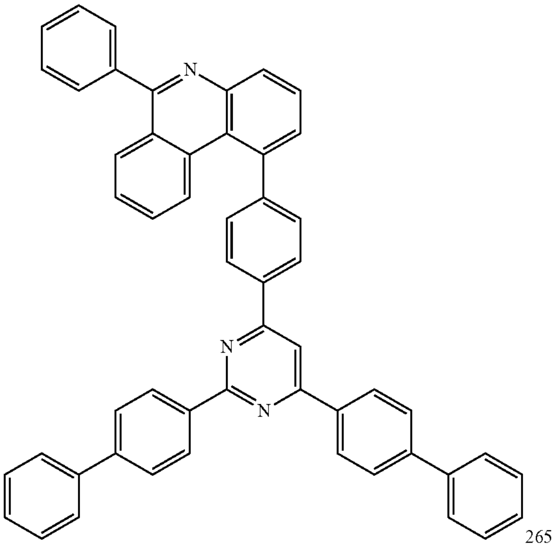
265
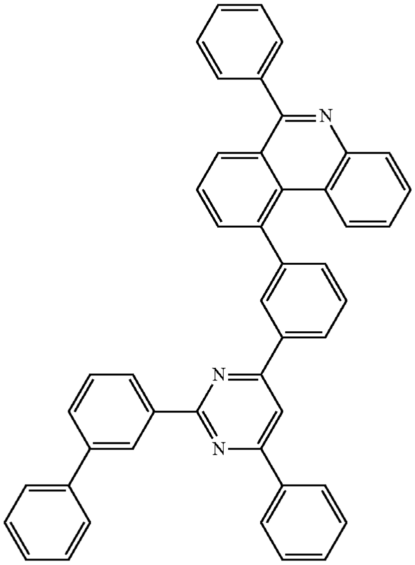
266
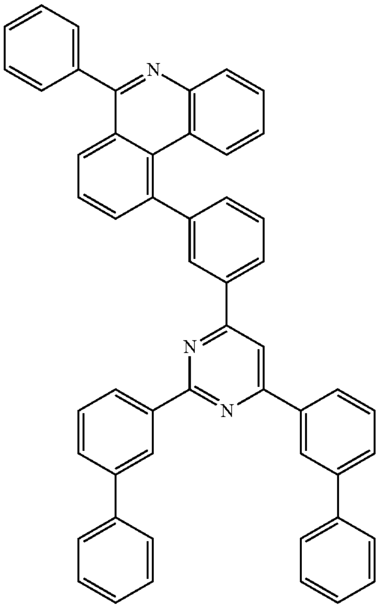
-continued
267
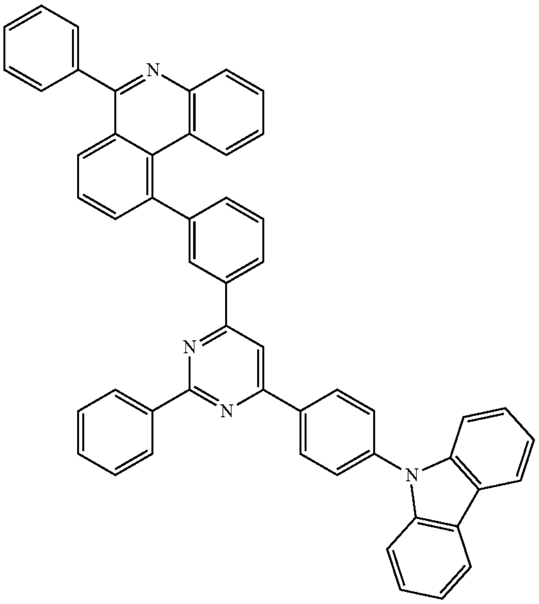
268
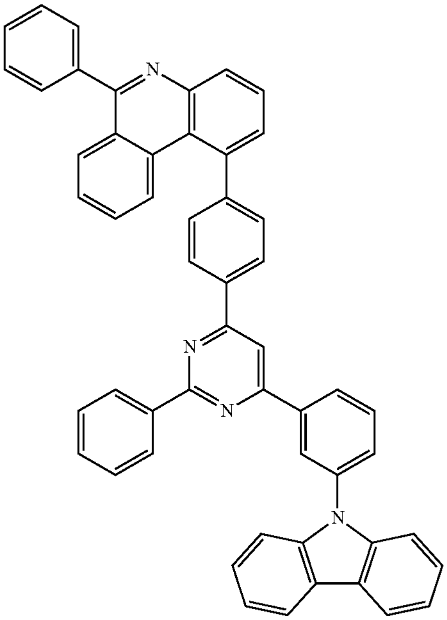

-continued
269
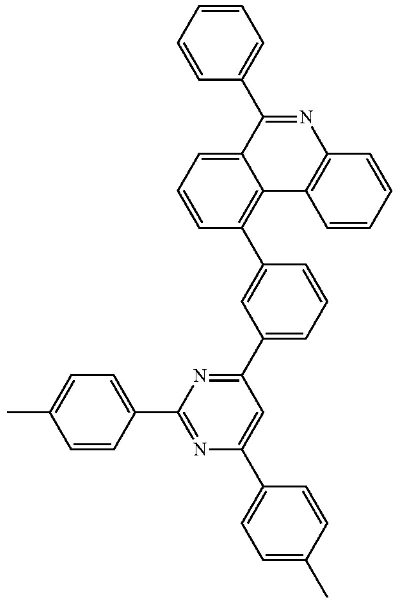
270
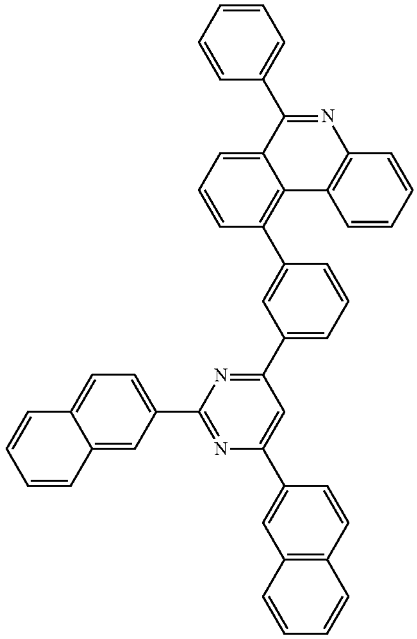
-continued
271
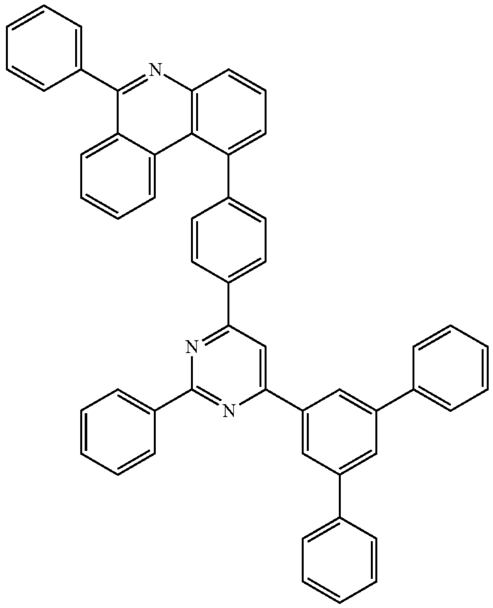
272
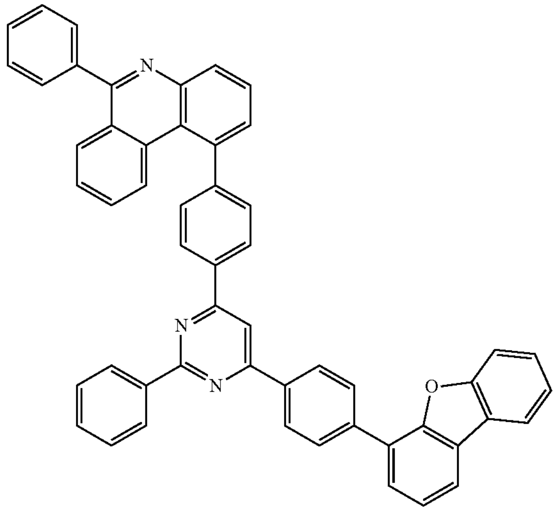
273
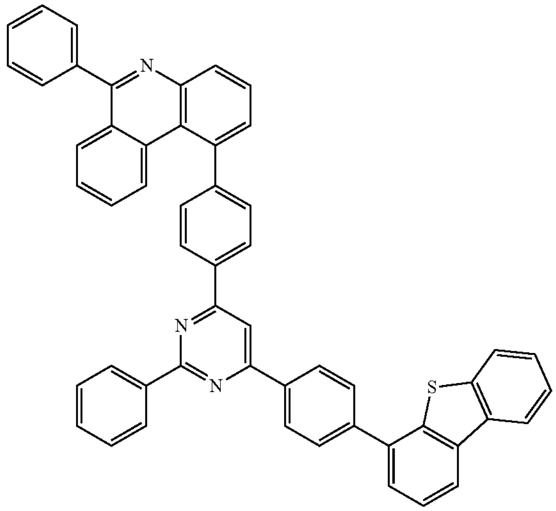

-continued
274
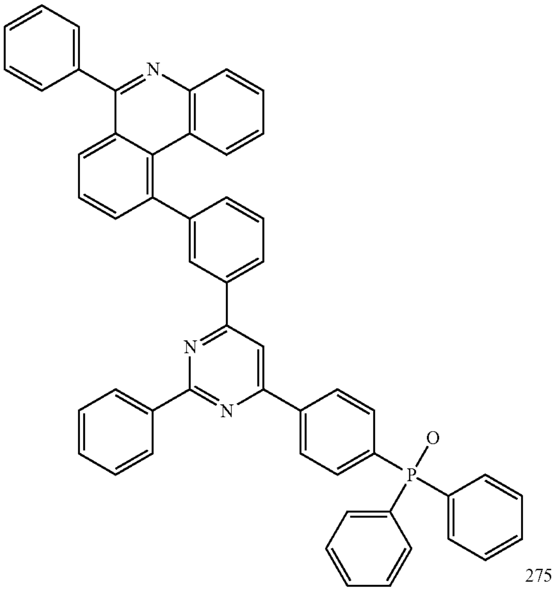
275
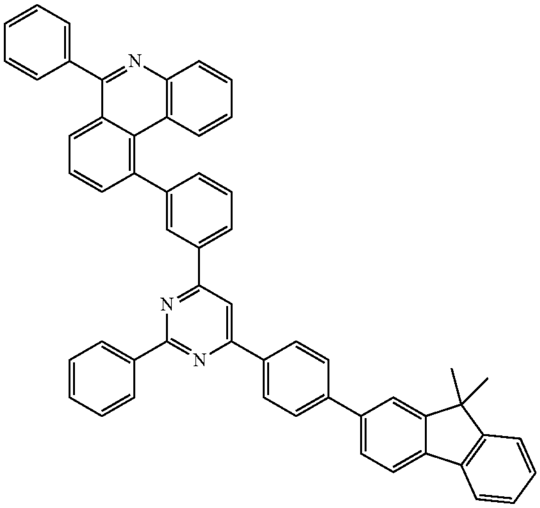
276
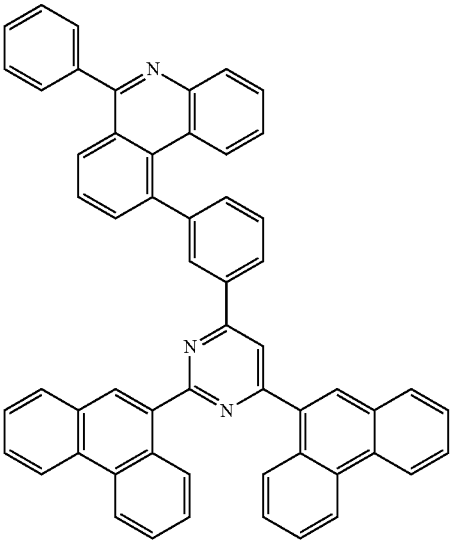
-continued
277
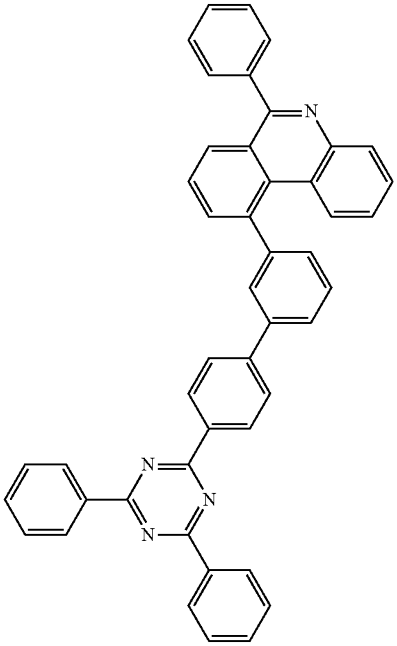
278
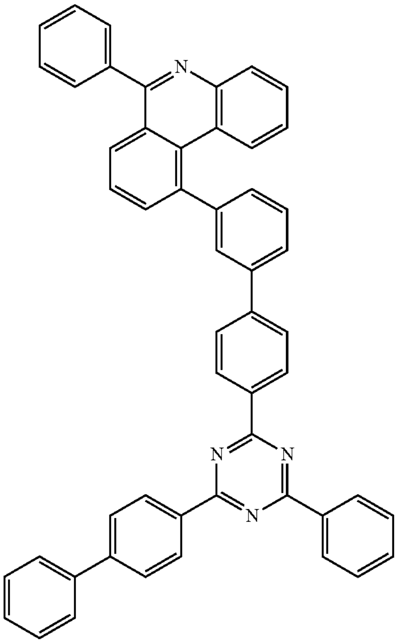

279
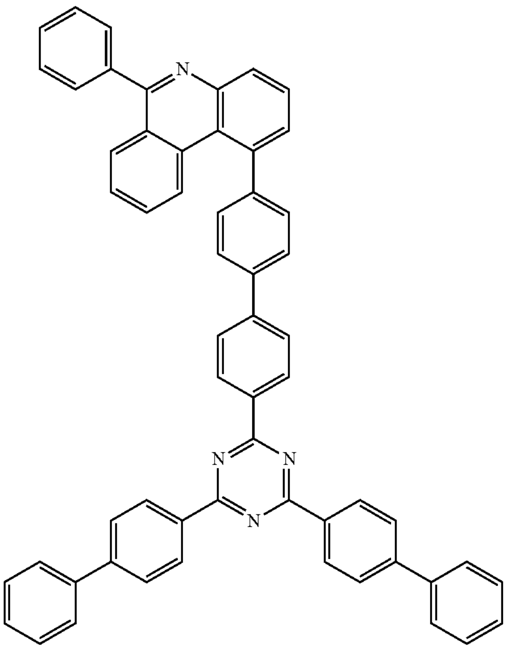
280
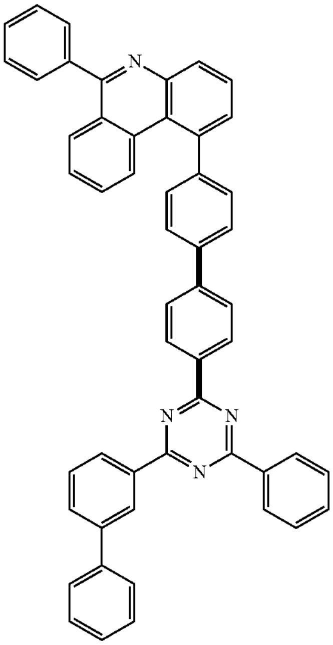
281
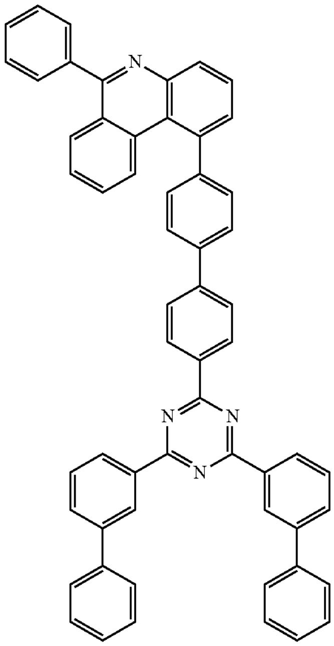
282
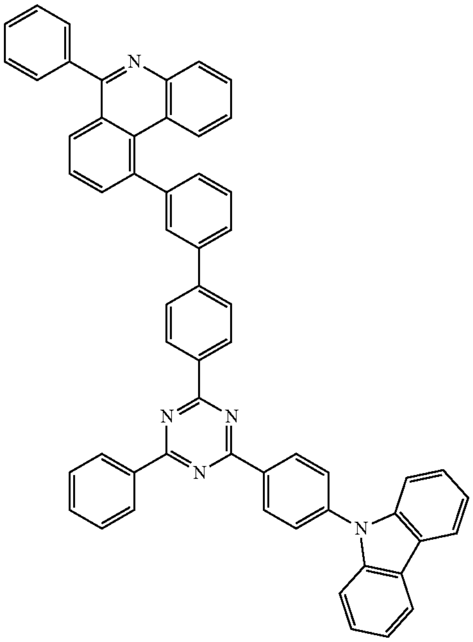

-continued
283
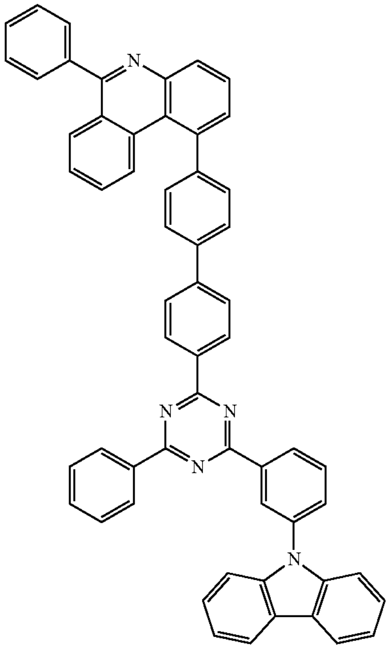
284
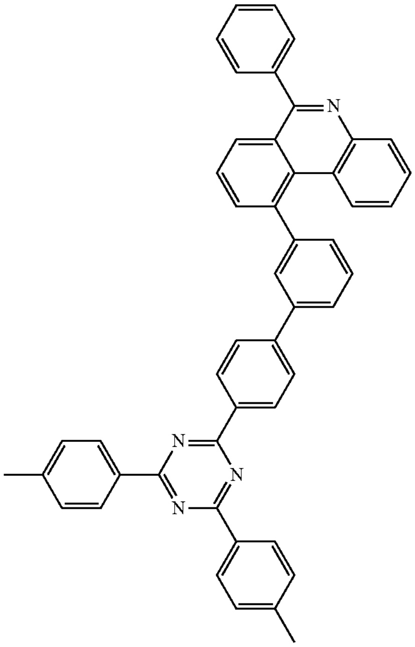
-continued
285
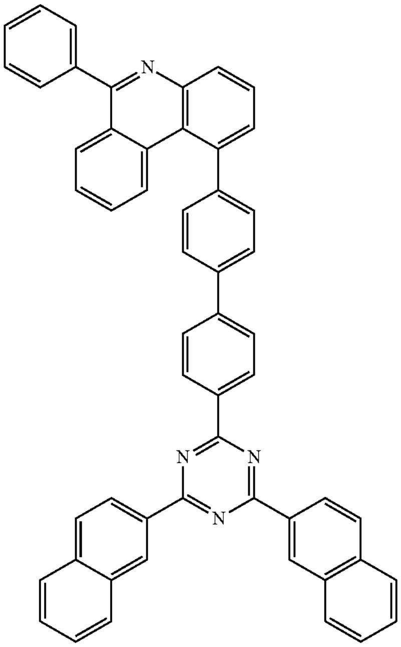
286
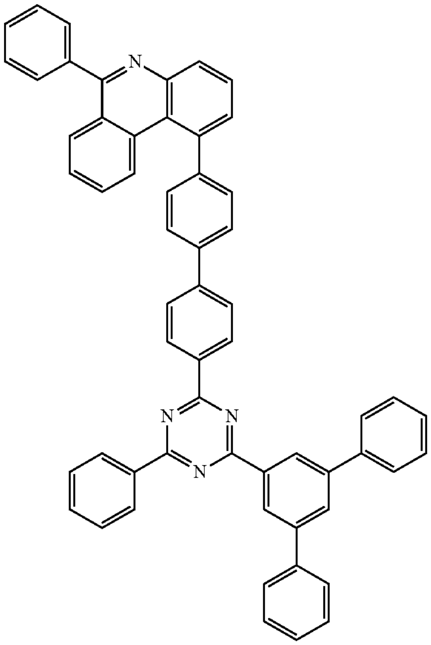

-continued
287
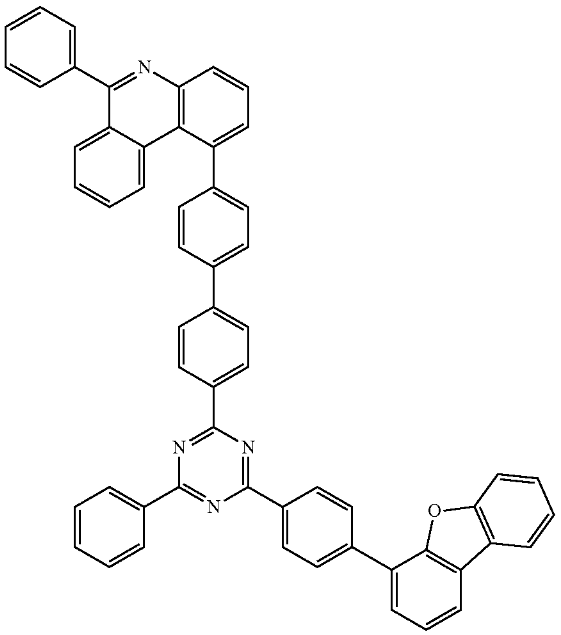
288
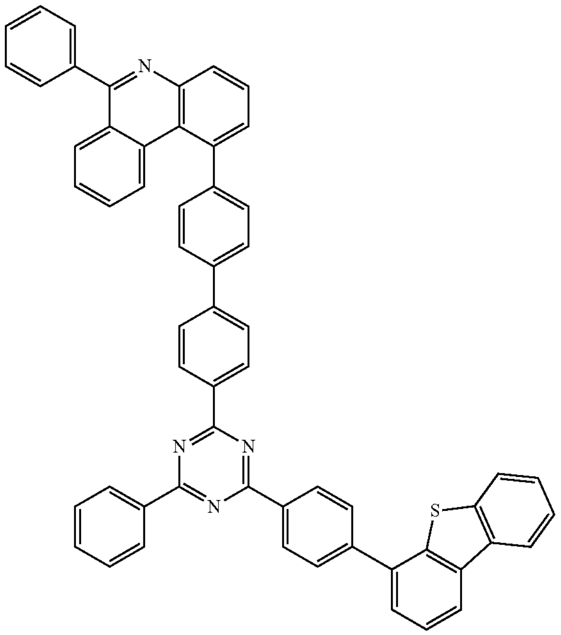
-continued
289
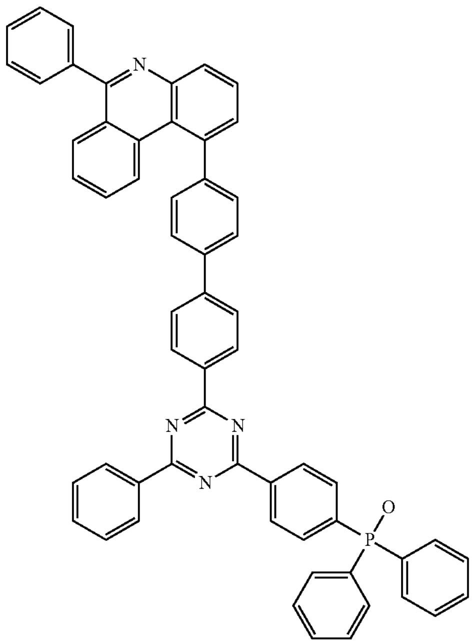
290
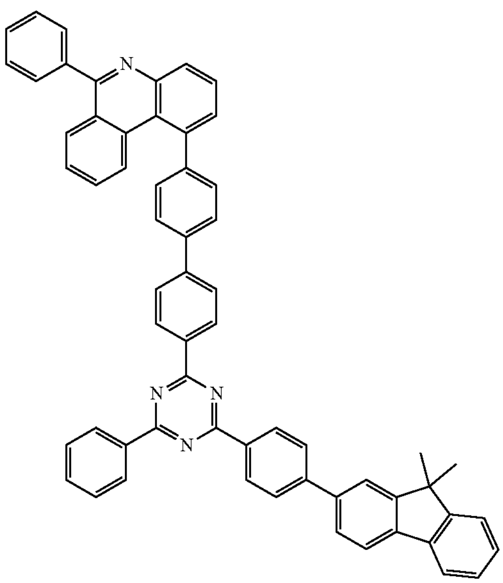

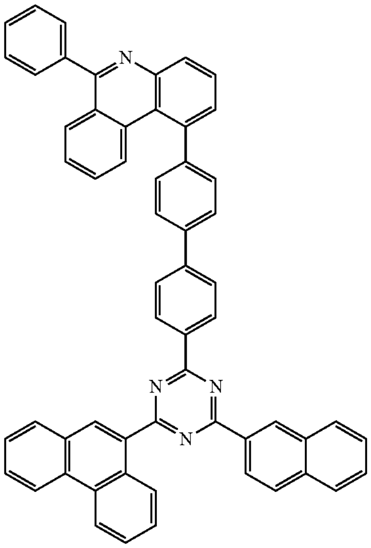
291
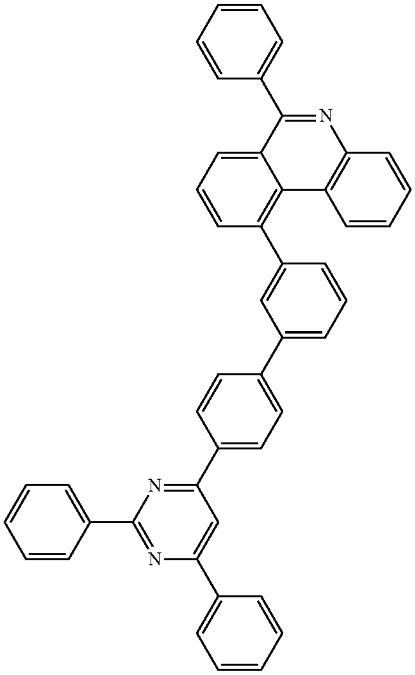
292
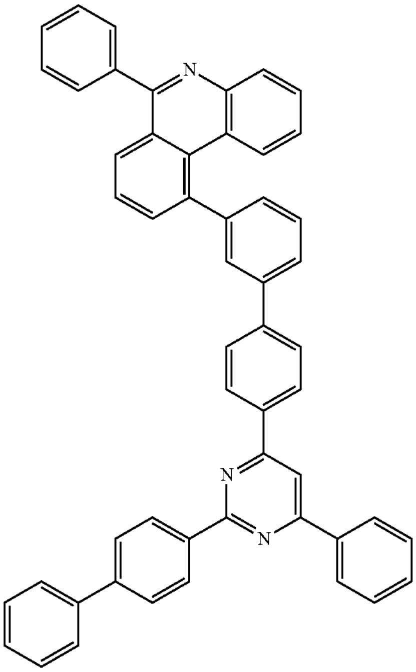
293
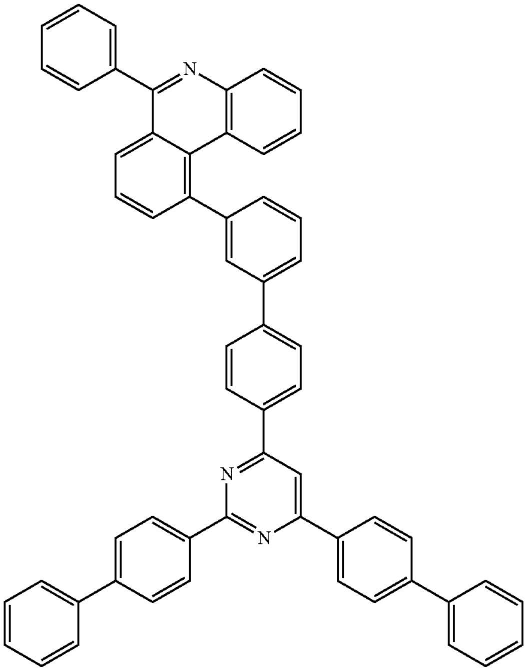
294

-continued
295
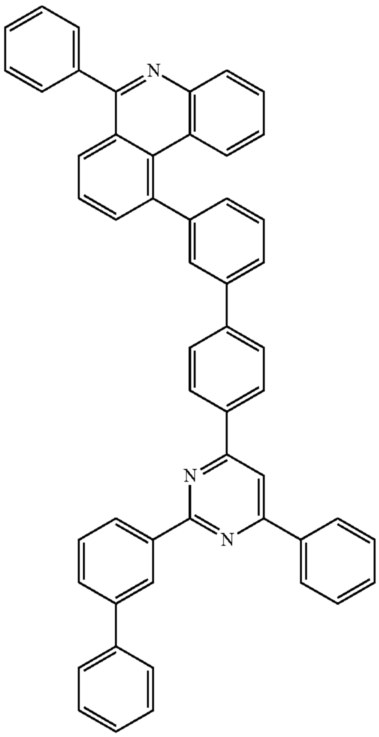
296
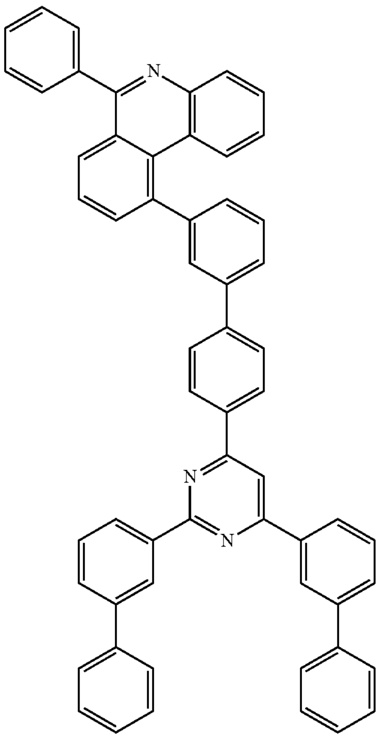
-continued
297
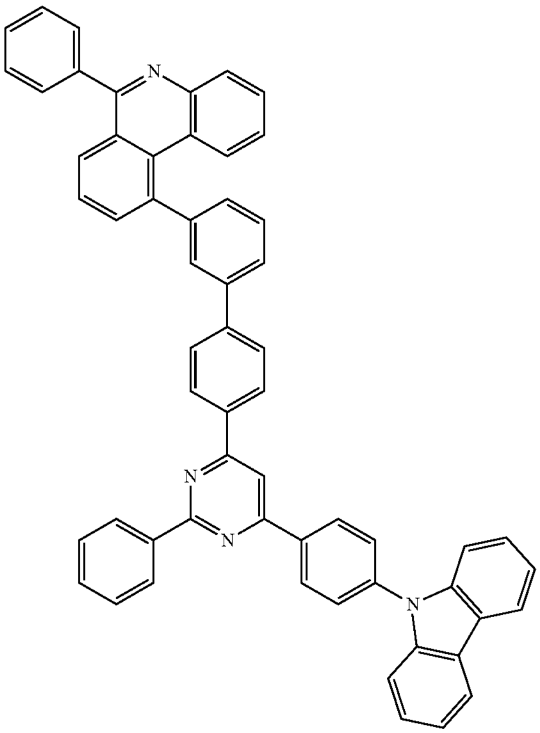
298
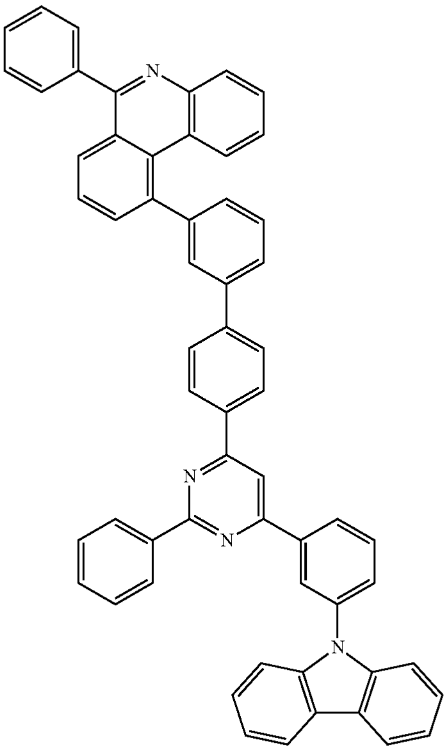

299
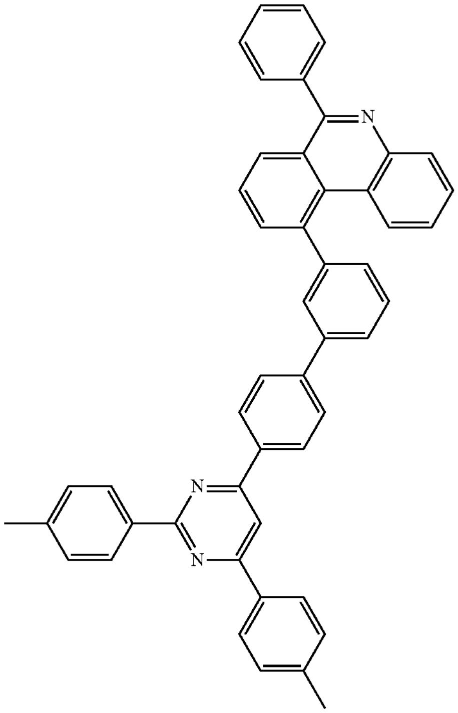
300
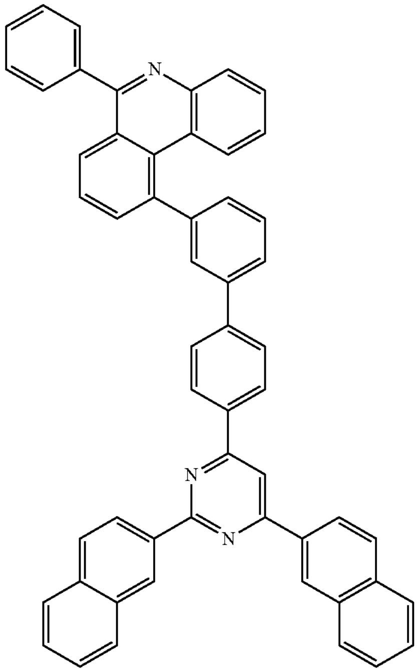
301
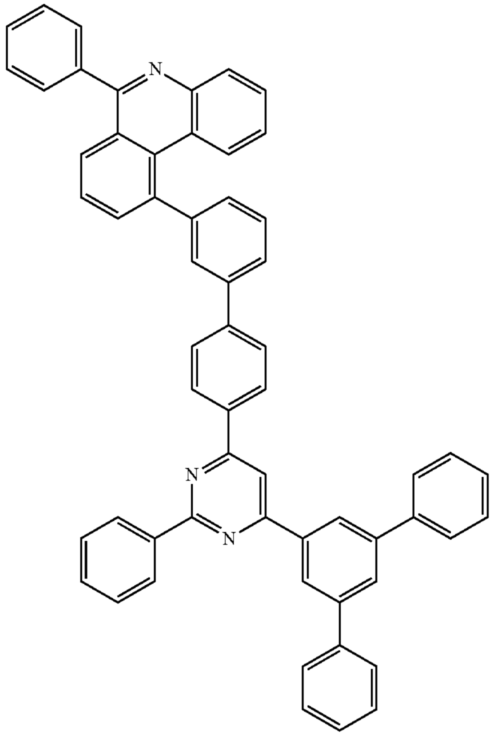
302
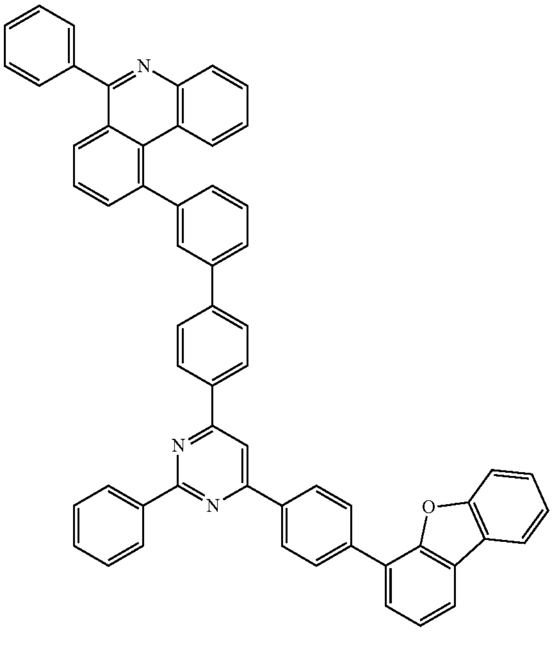

-continued
303
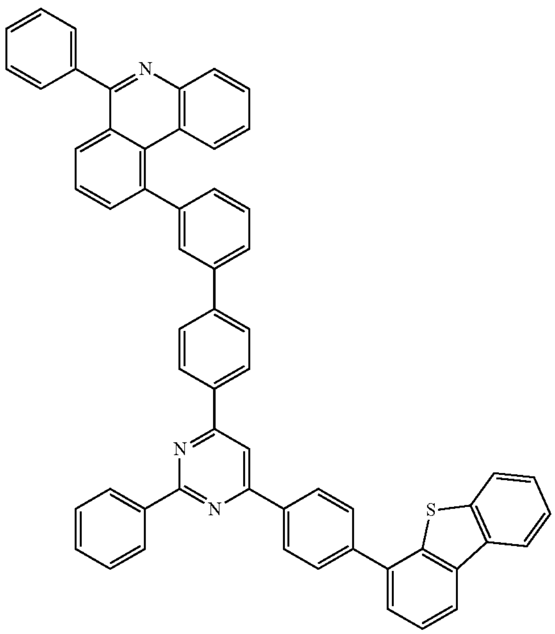
304
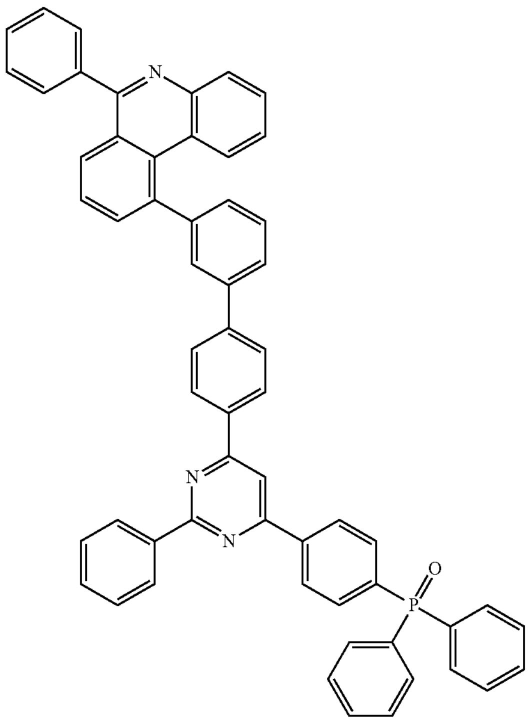
-continued
305
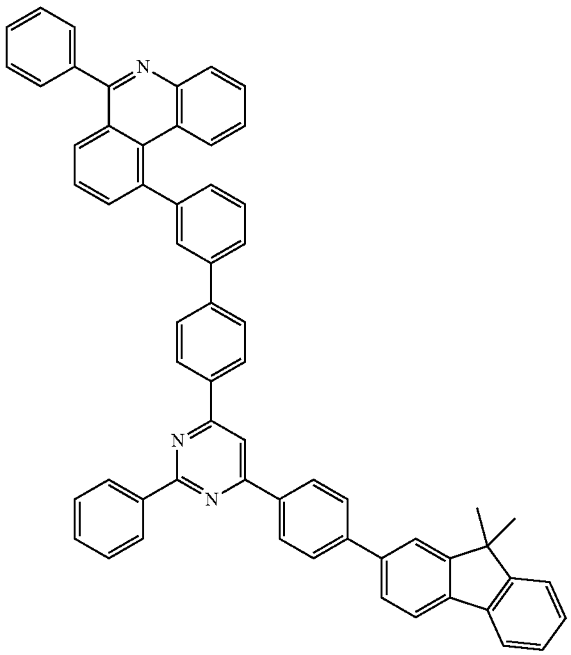
306
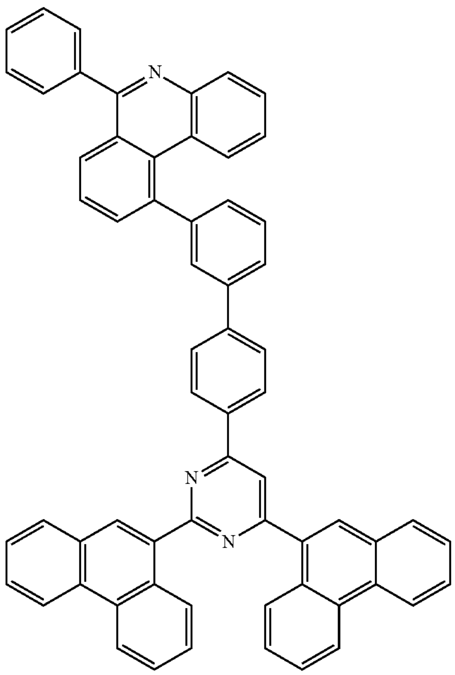

-continued
307
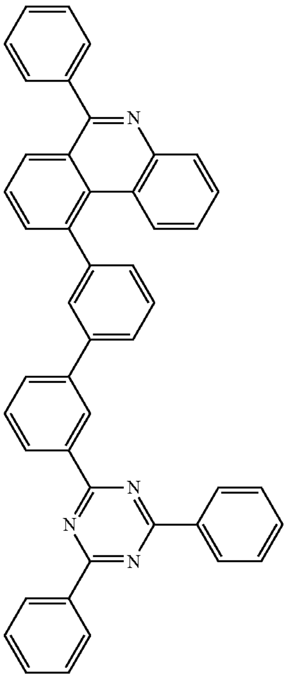
308
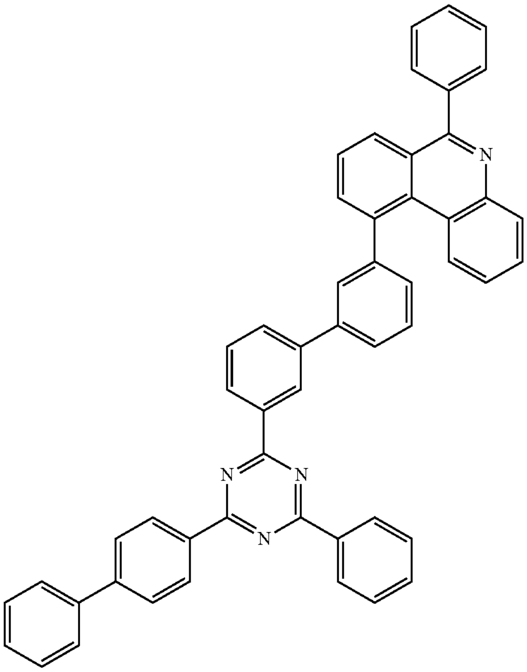
-continued
309
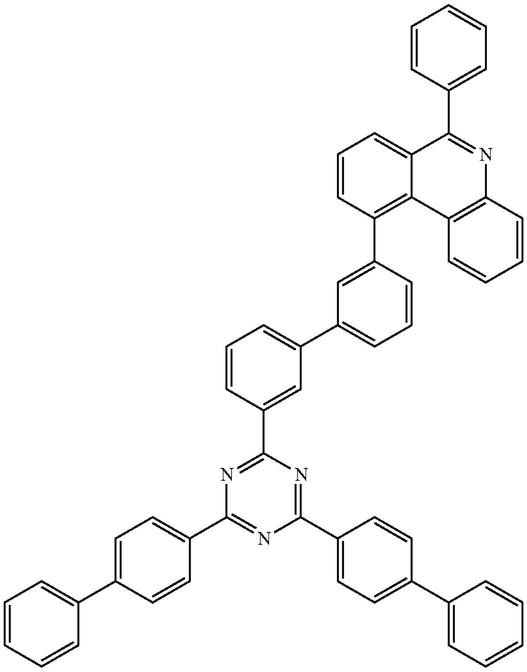
310
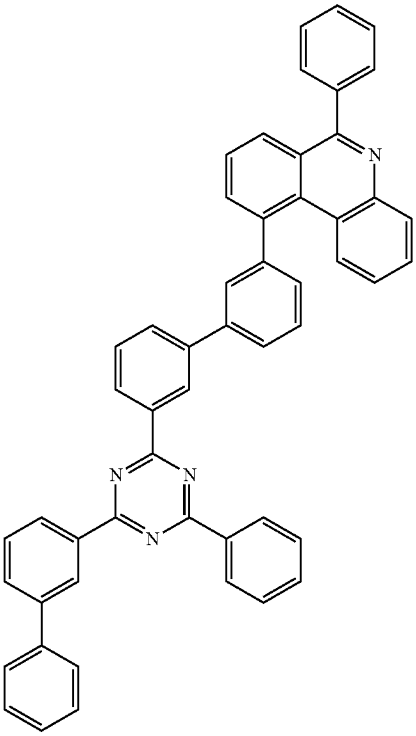

-continued
311
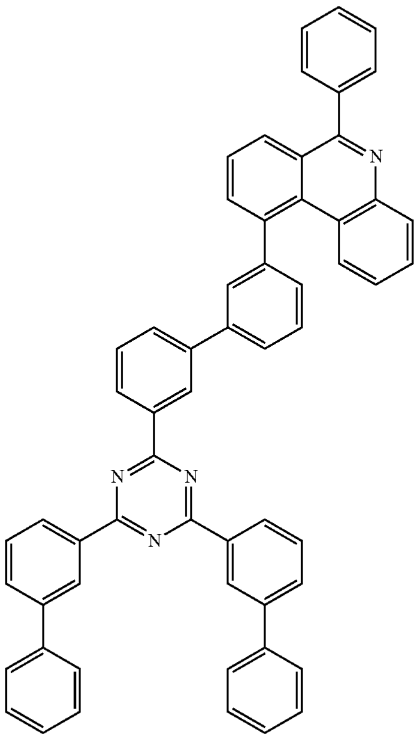
312
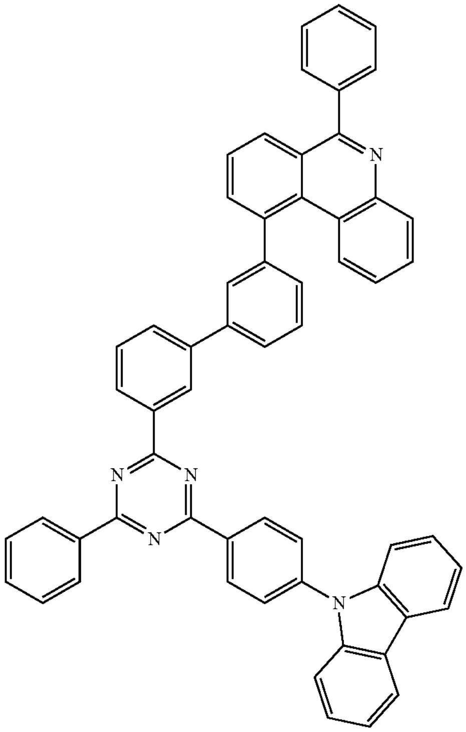
-continued
313
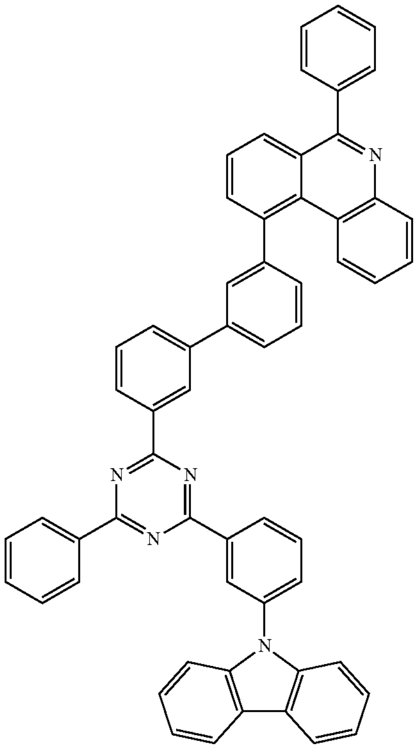
314
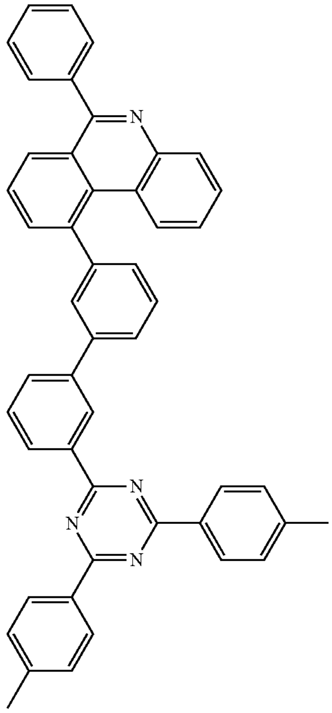

-continued
315
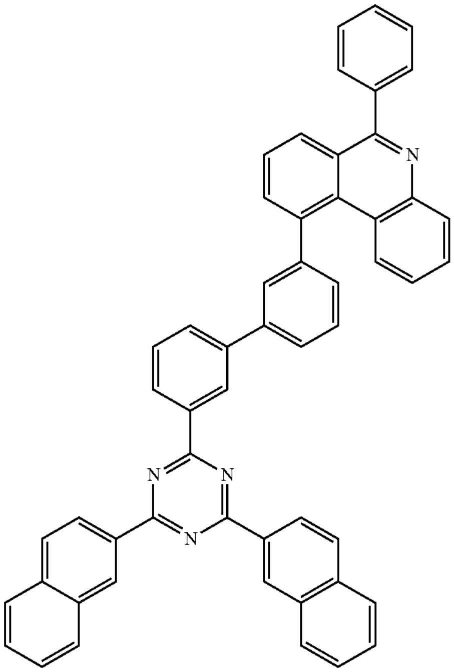
316
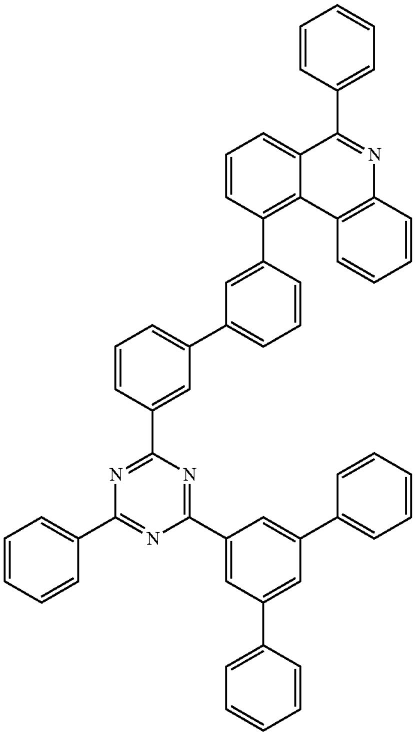
-continued
317
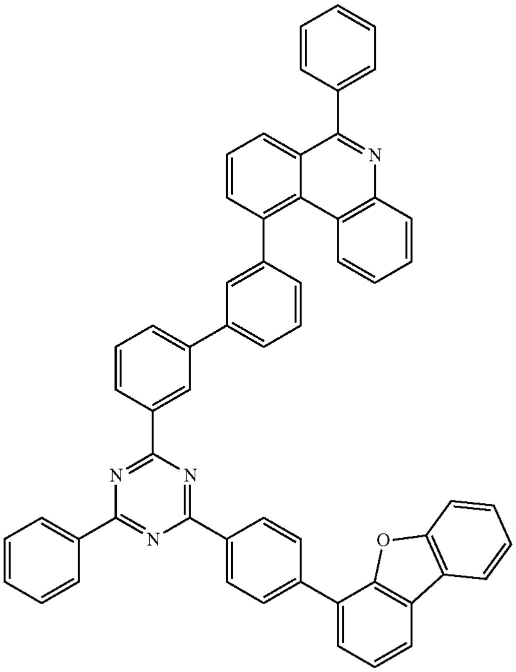
318
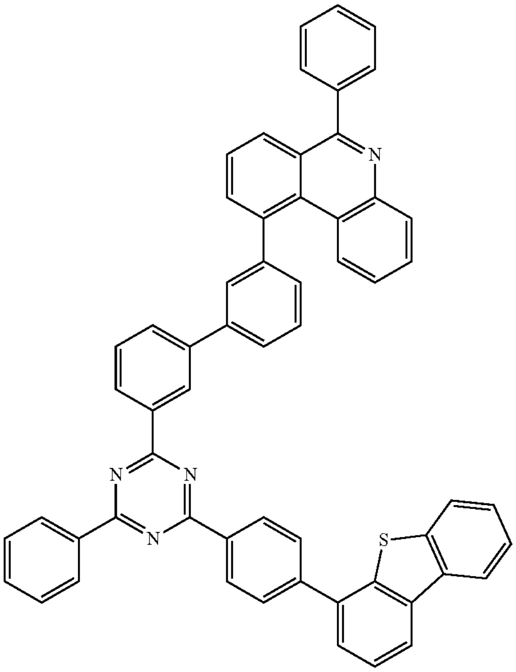

319
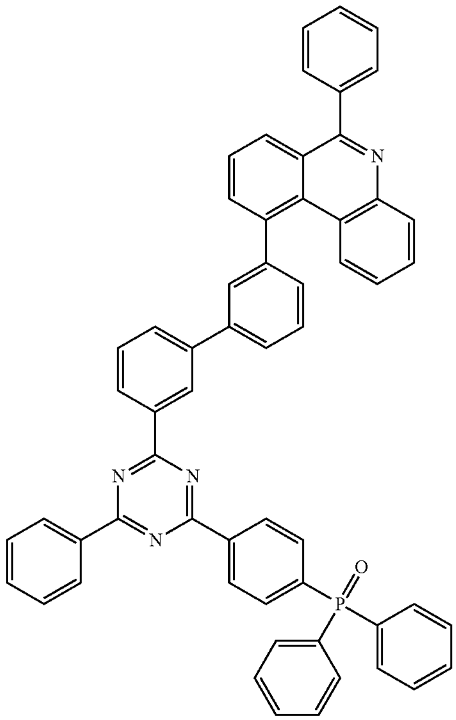
320
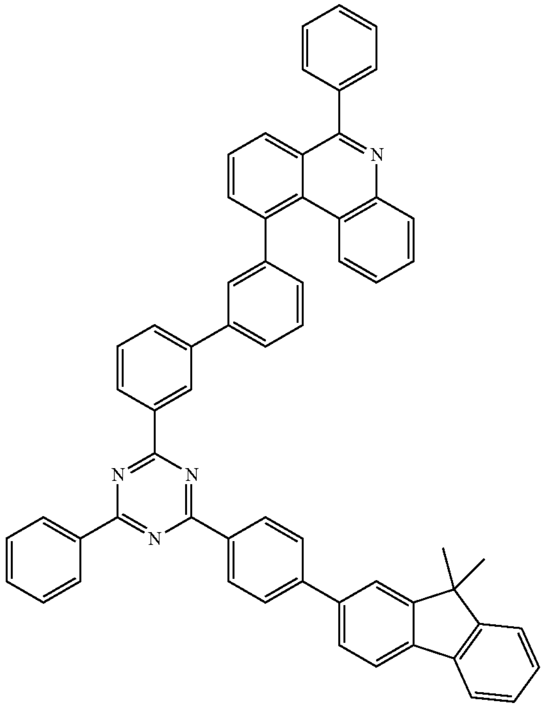
321
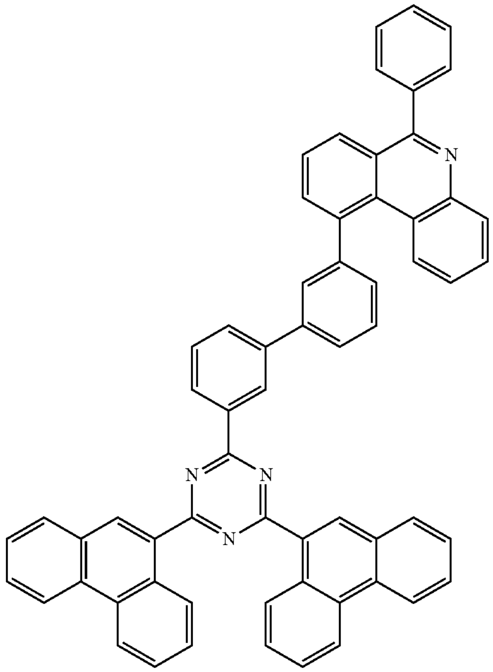
322
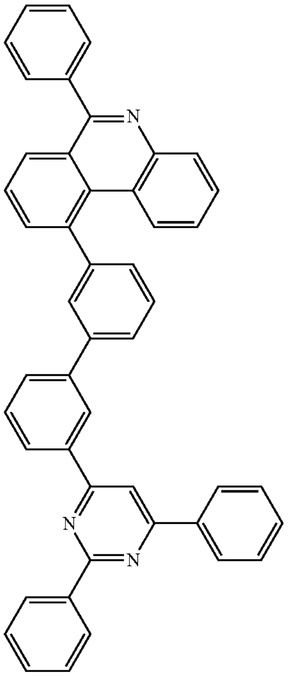

-continued
323
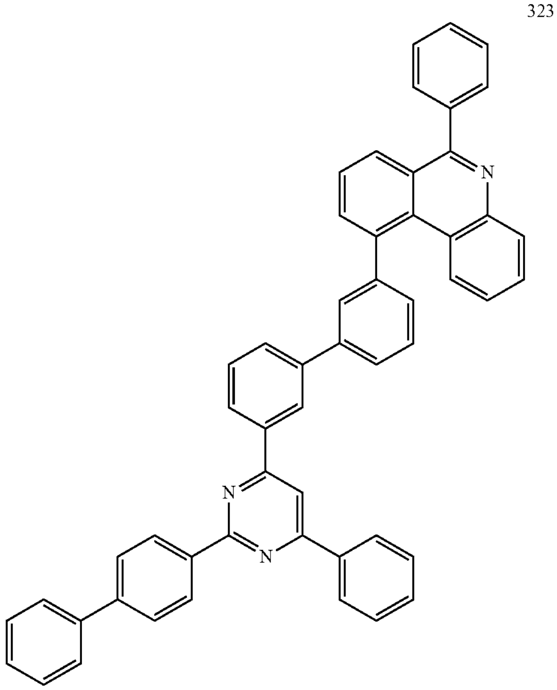
324
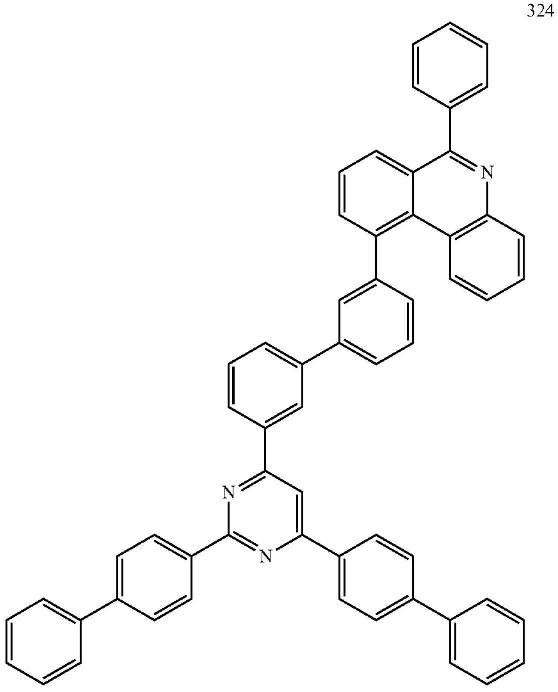
-continued
325
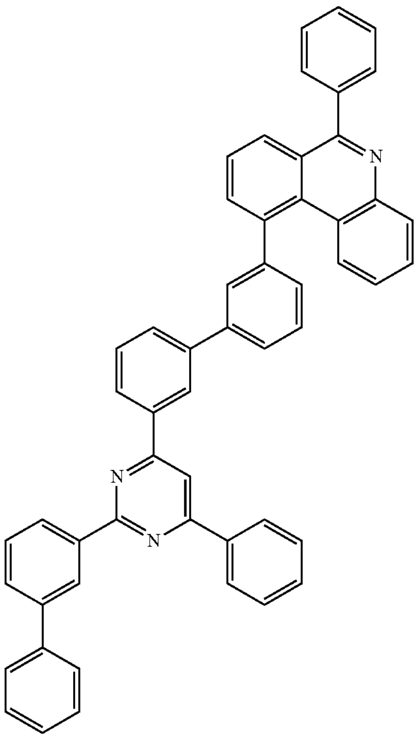
326
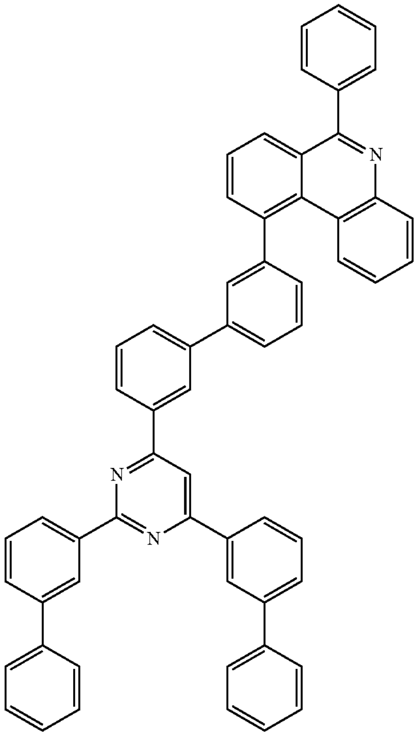

-continued
327
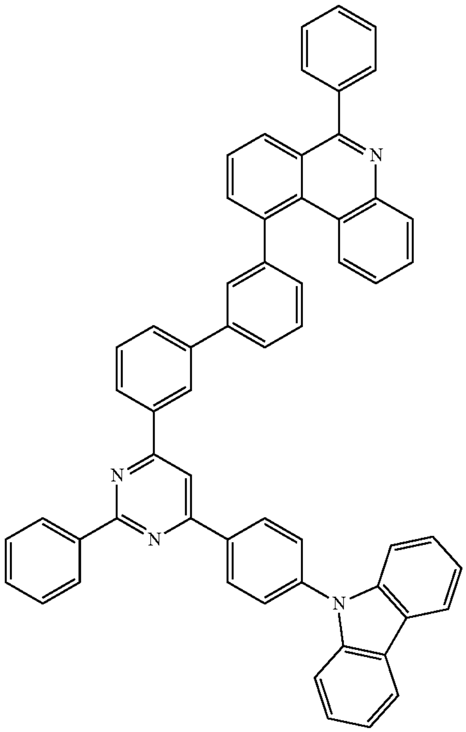
328
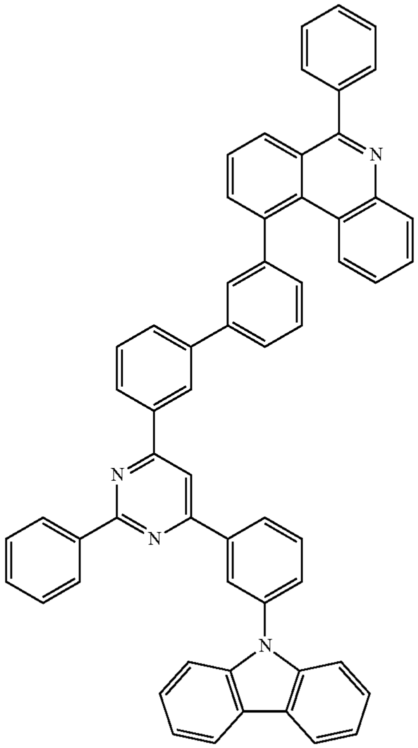
-continued
329
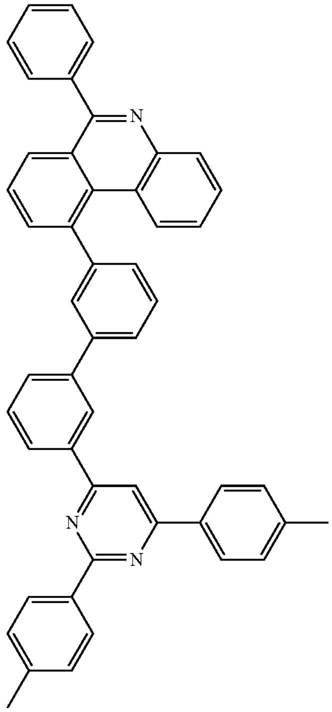
330
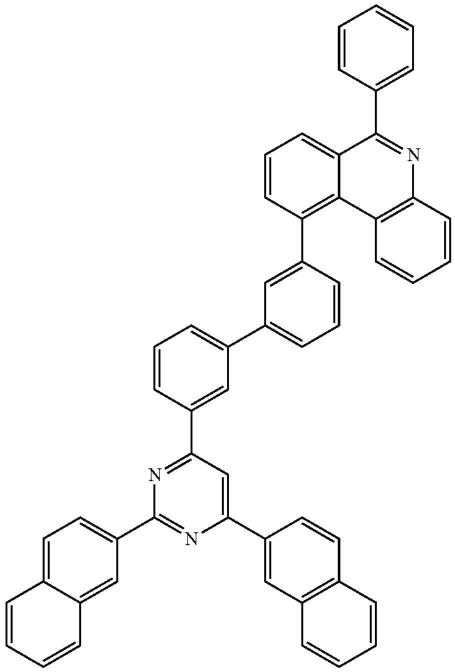

-continued
331
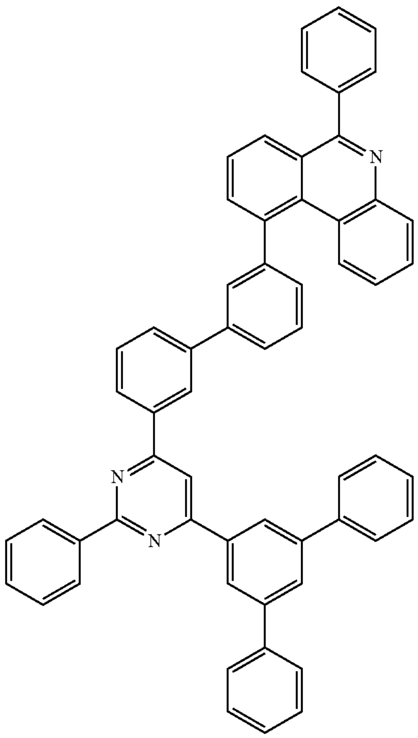
332
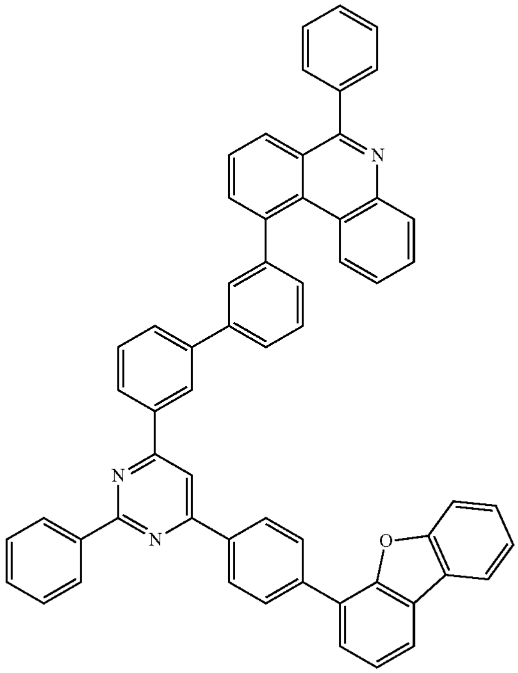
-continued
333
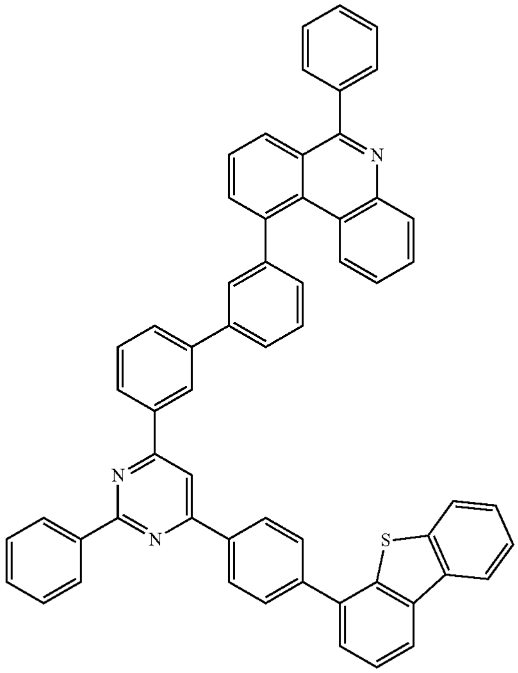
334
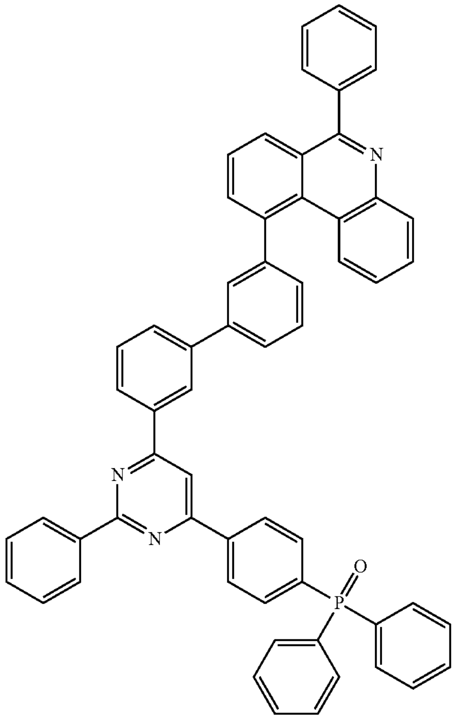

-continued
335
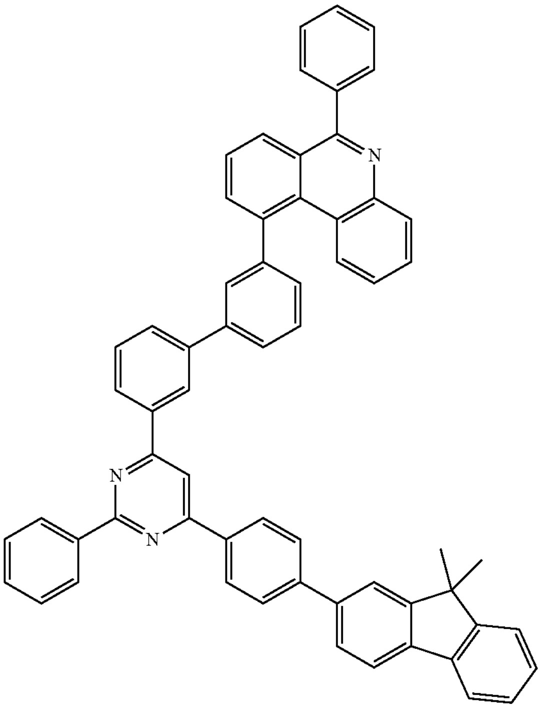
336
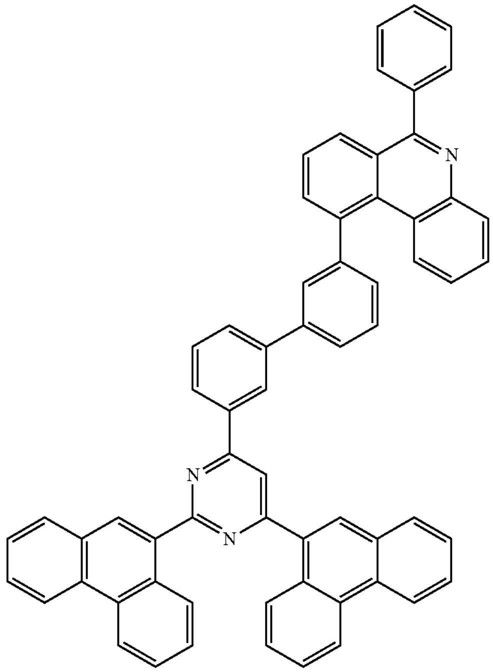
-continued
337
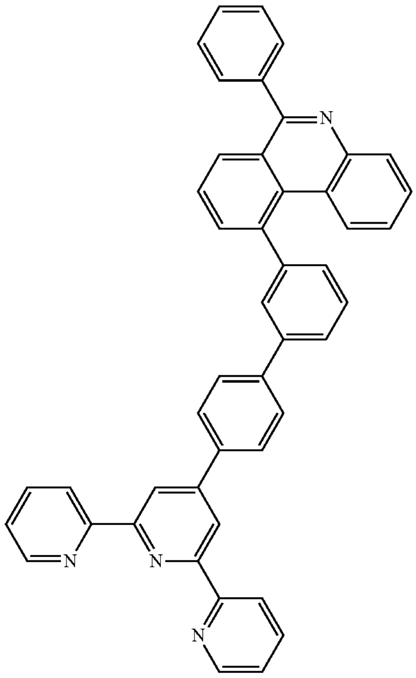
338
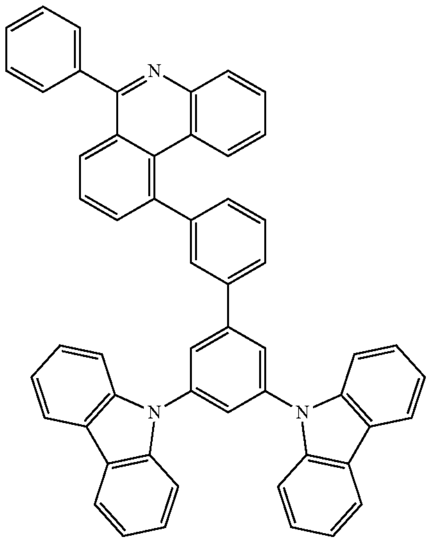

-continued
339
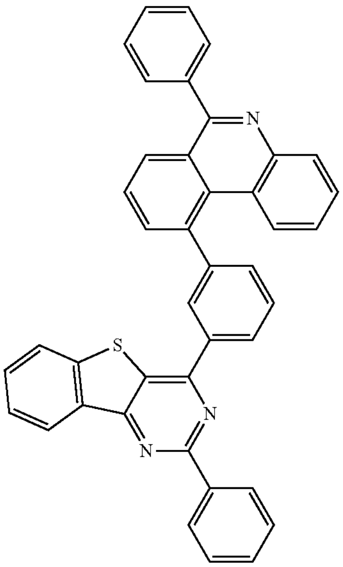
340
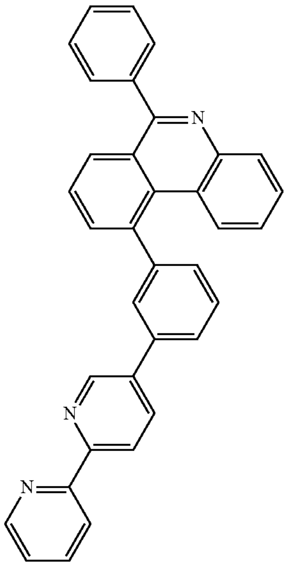
-continued
341
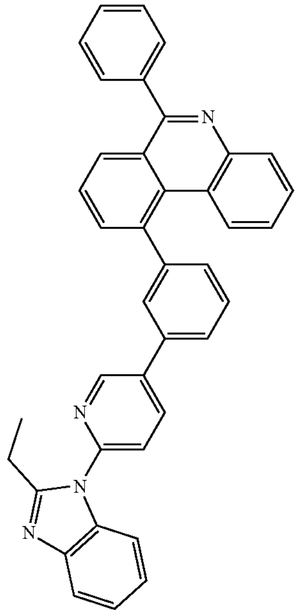
342
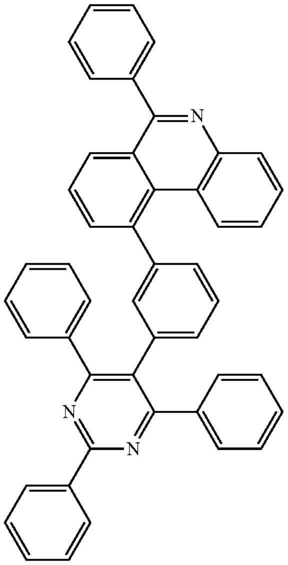

-continued
3434
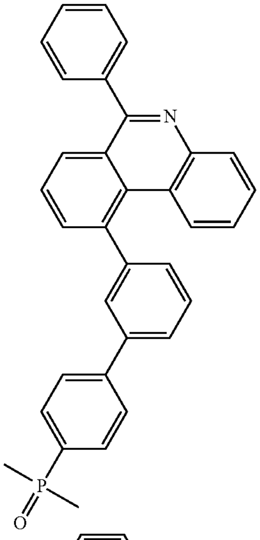
344
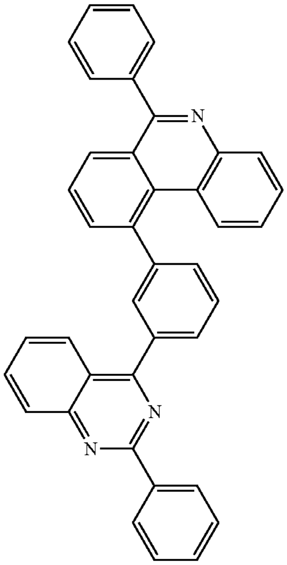
345
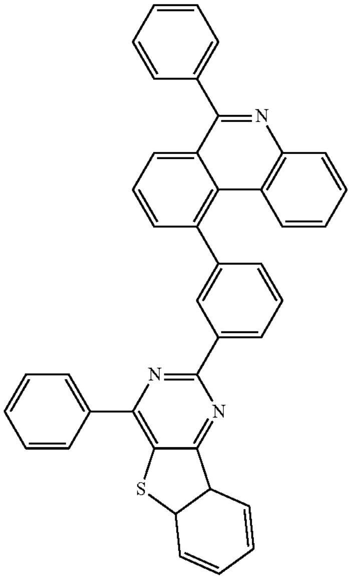
-continued
346
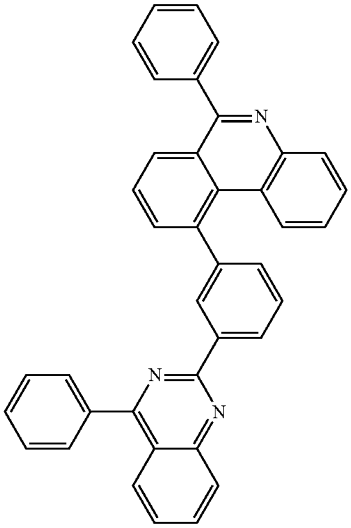
347
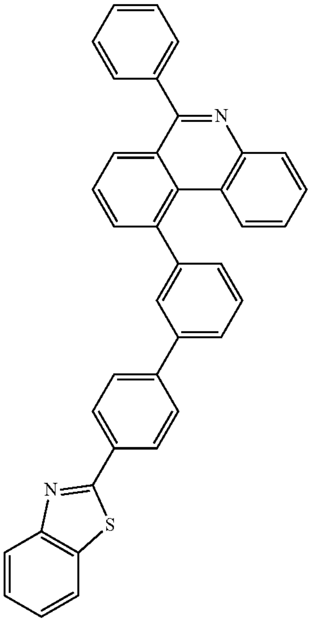

-continued
348
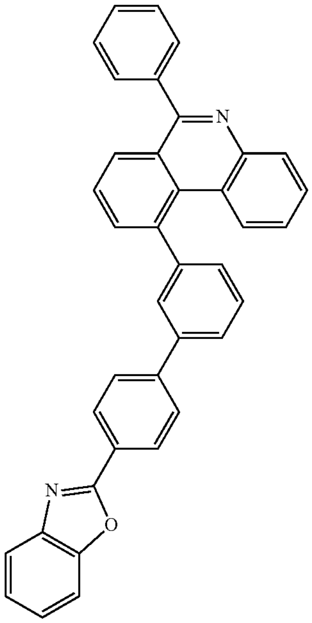
349
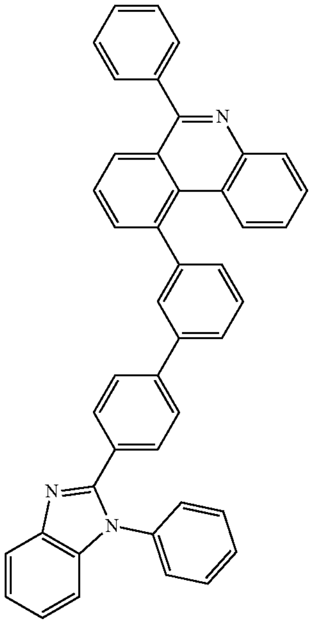
-continued
350
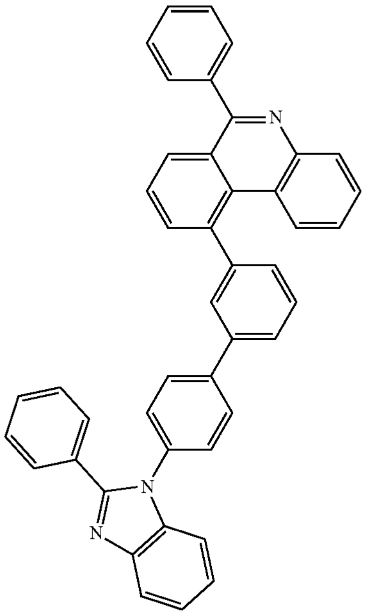
351
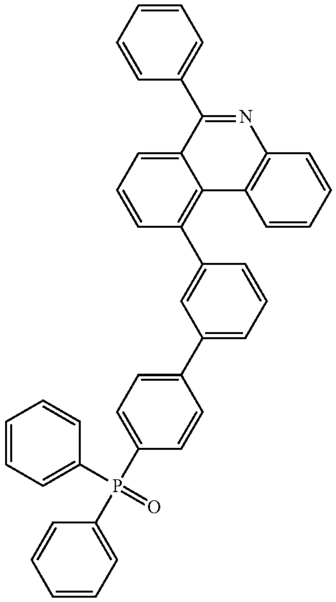

352
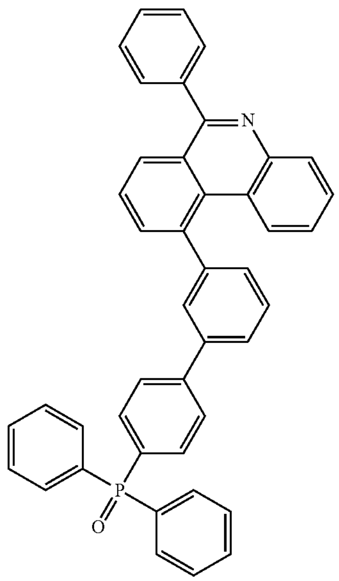
353
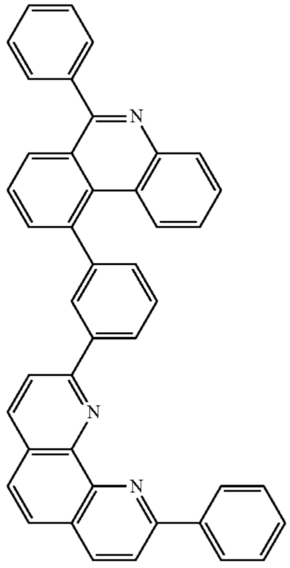
354
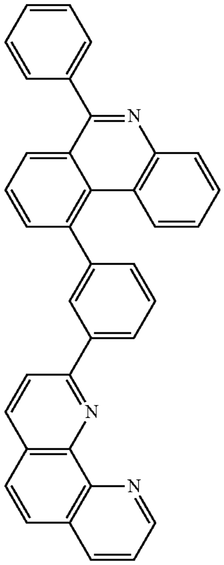
355
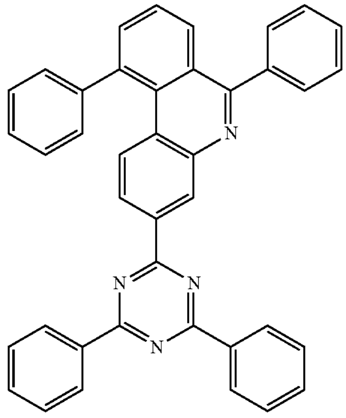
356
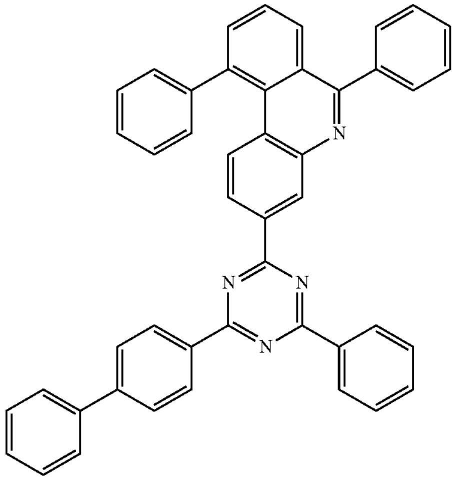

357
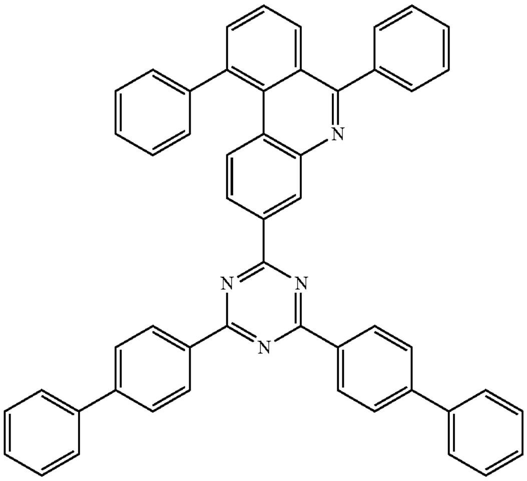
358
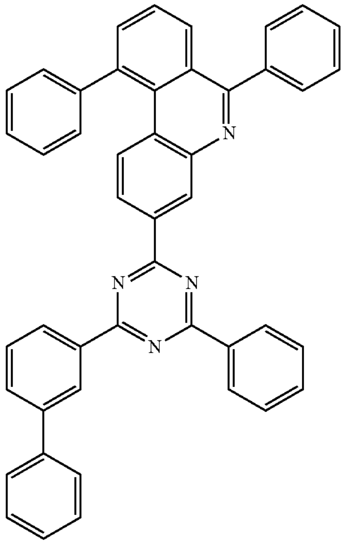
359
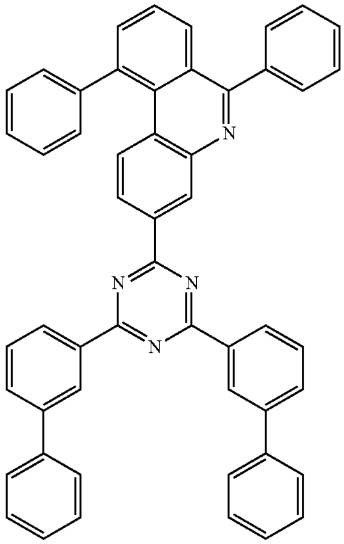
360
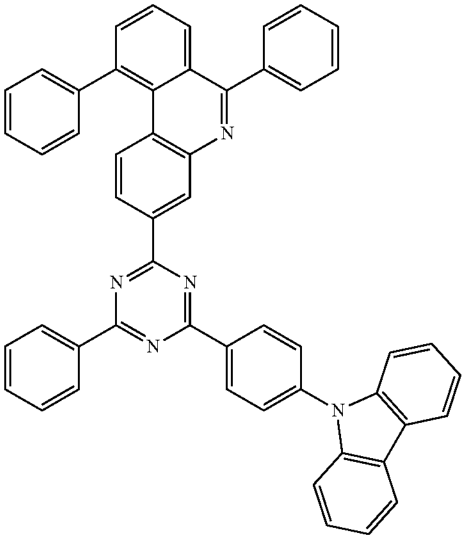
361
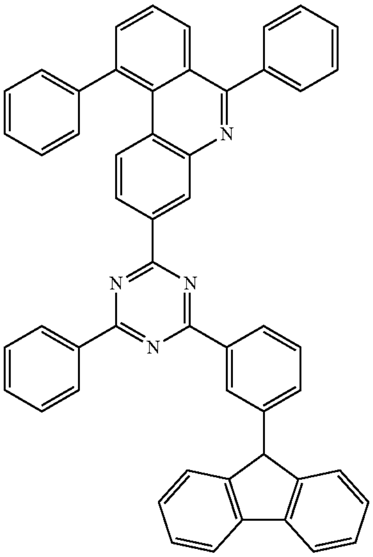
362
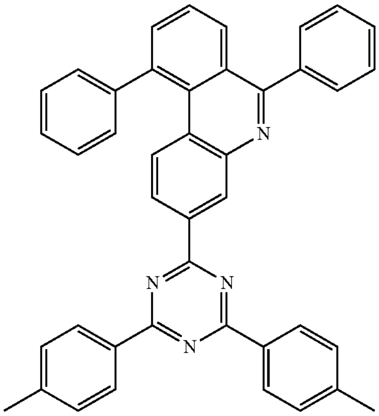

-continued
363
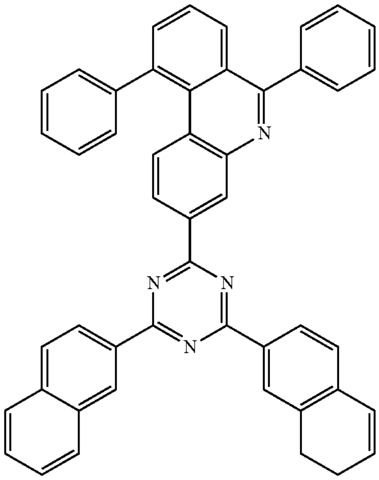
364
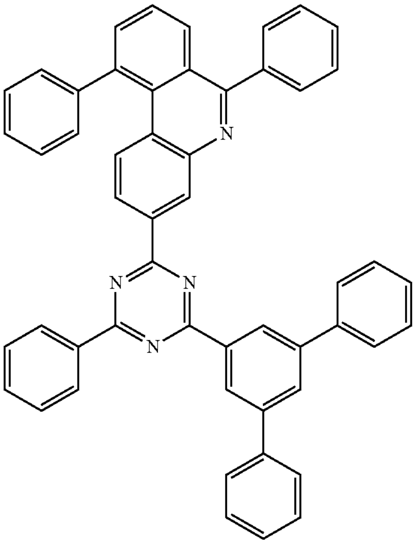
365
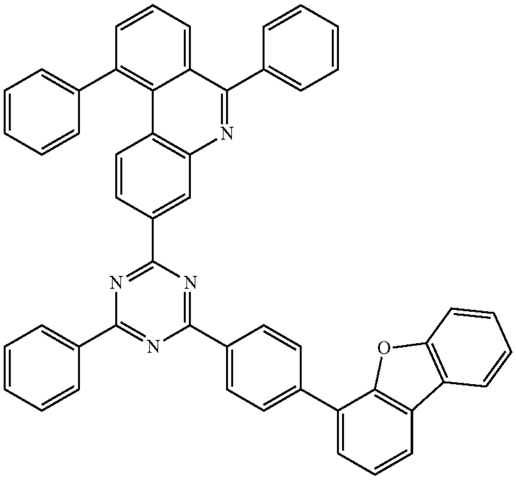
-continued
366
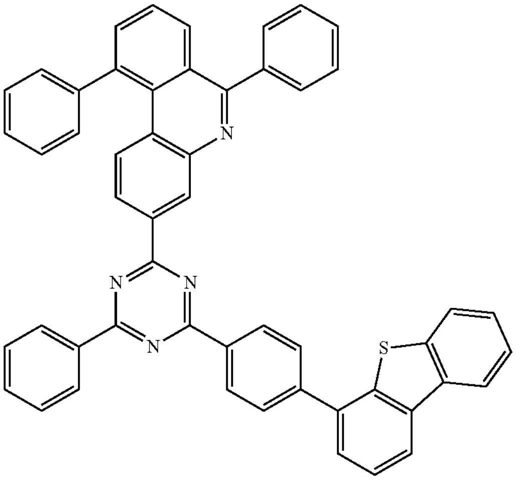
367
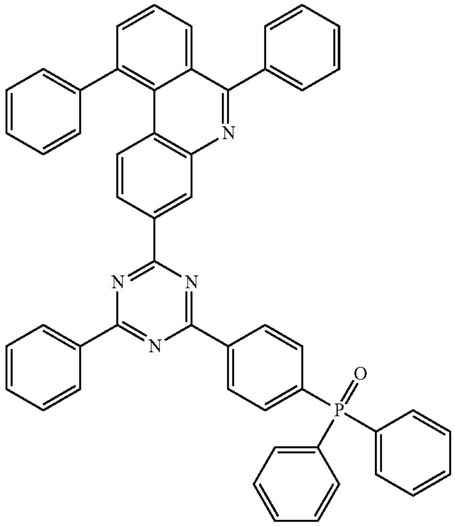
368
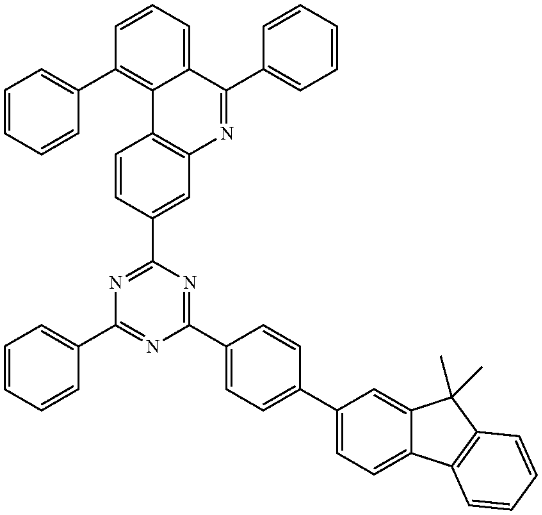

-continued
369
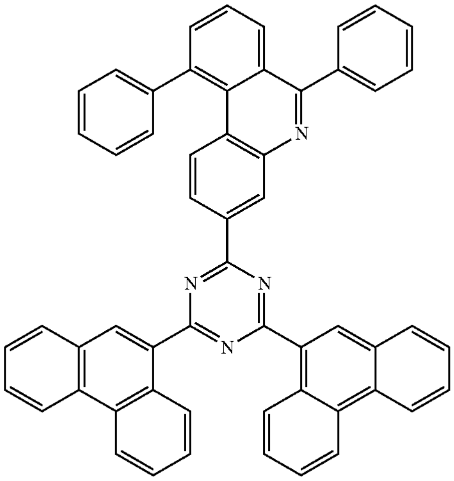
370
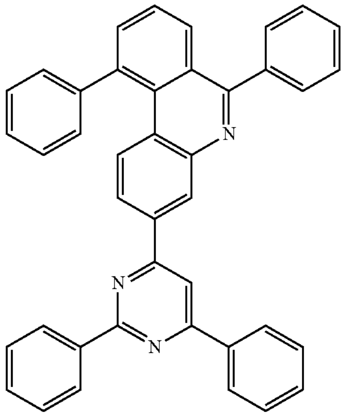
371
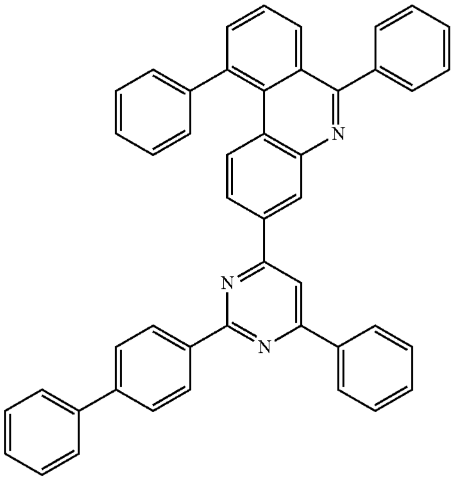
-continued
372
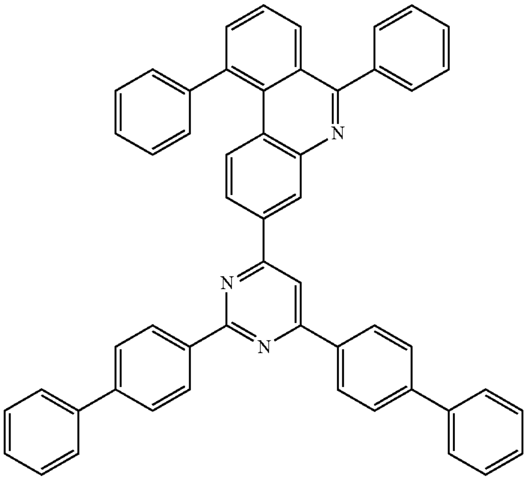
373
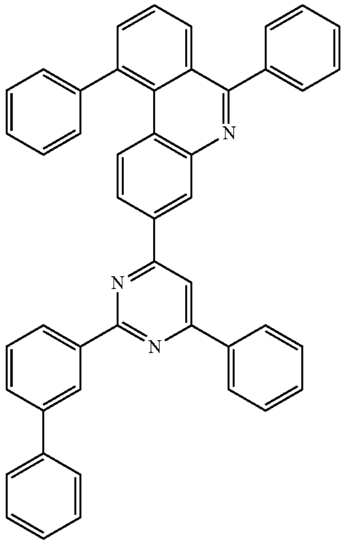
374
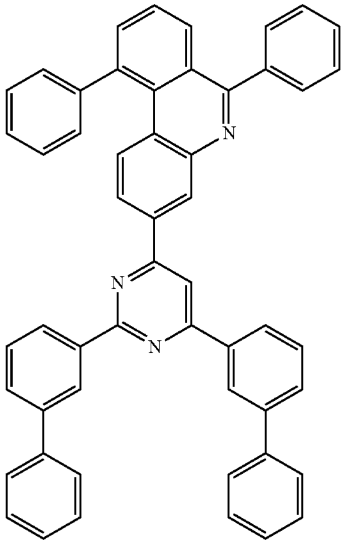

-continued
375
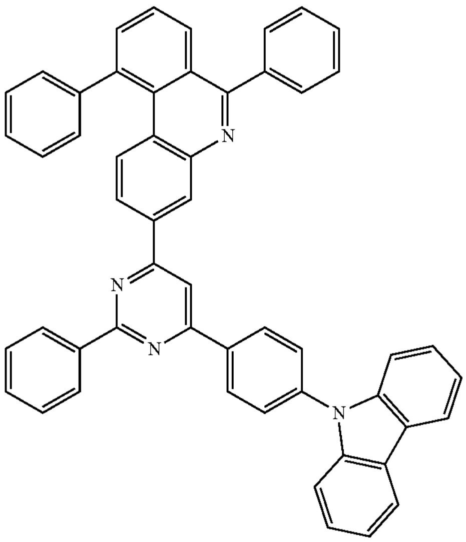
376
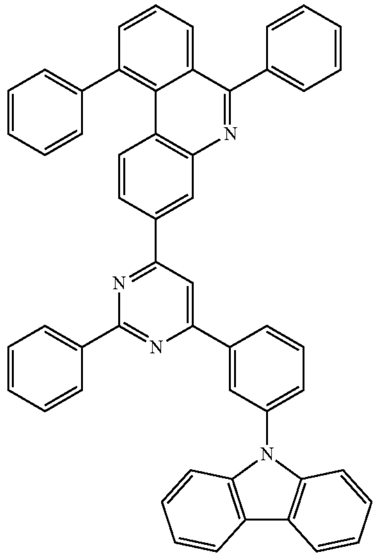
377
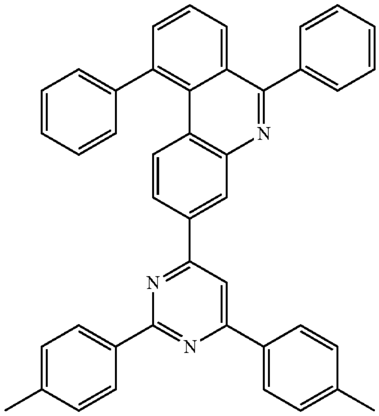
-continued
378
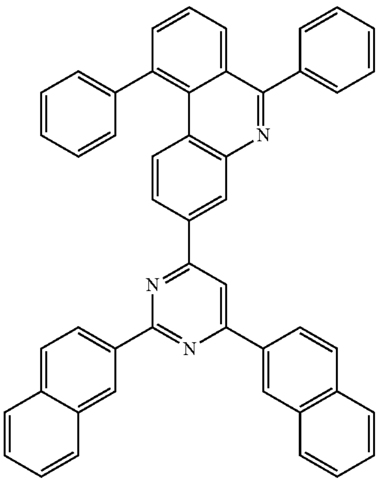
379
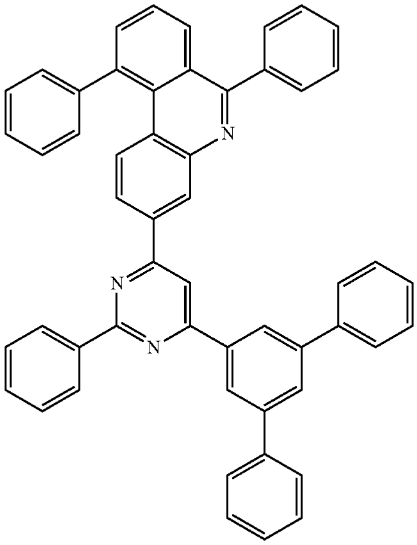
380
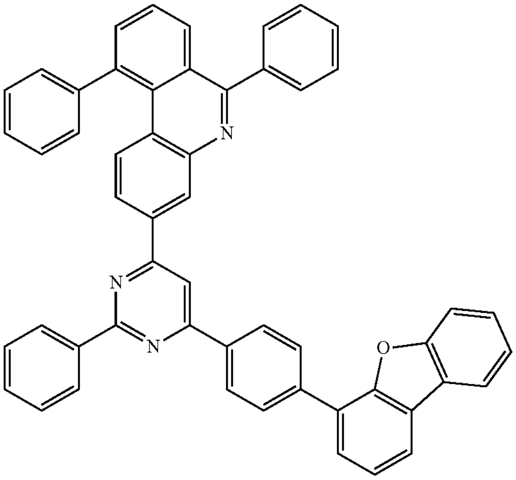

-continued
381
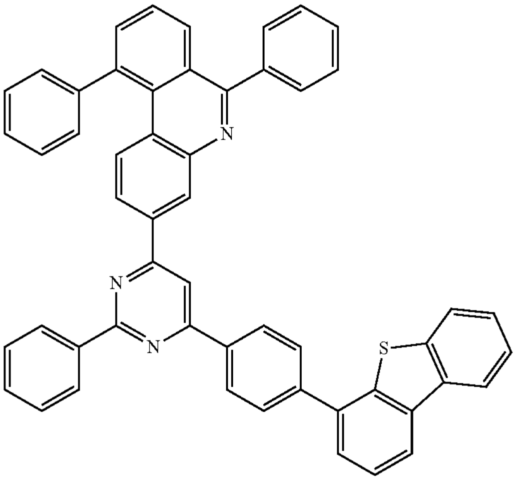
382
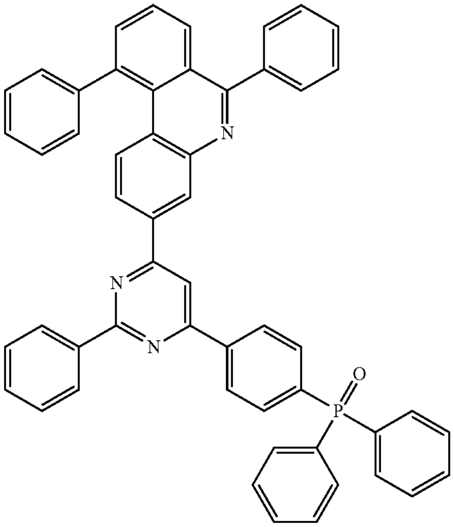
383
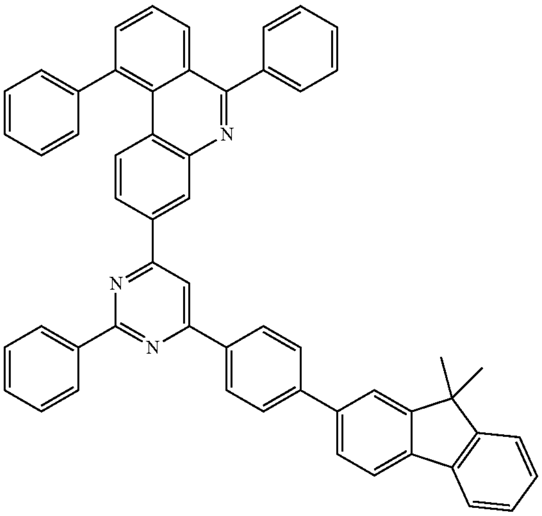
-continued
384
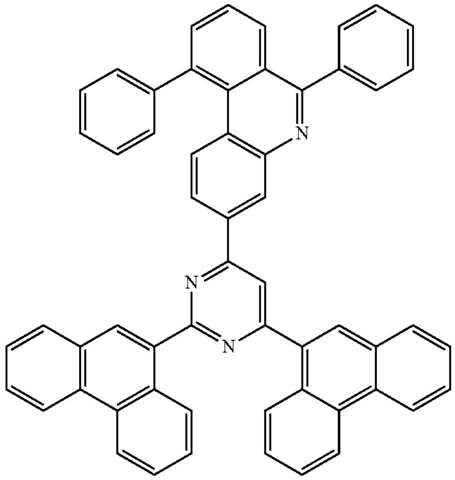
385
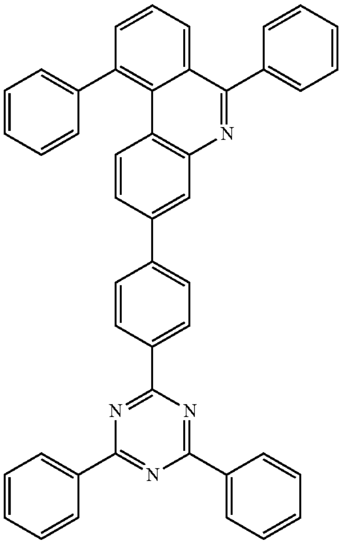
386
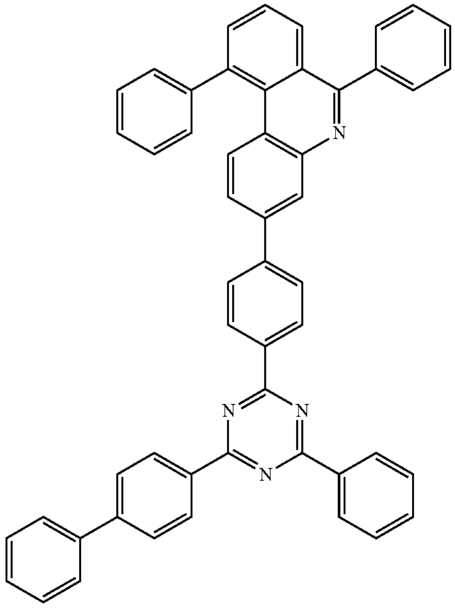

-continued
387
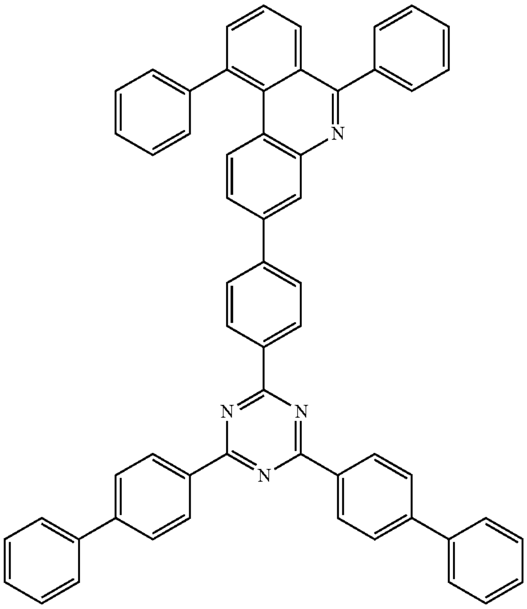
388
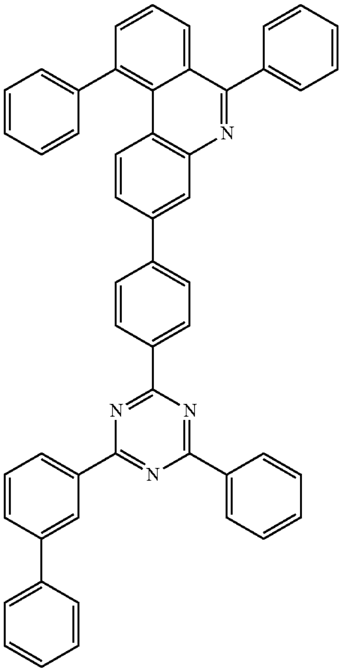
-continued
389
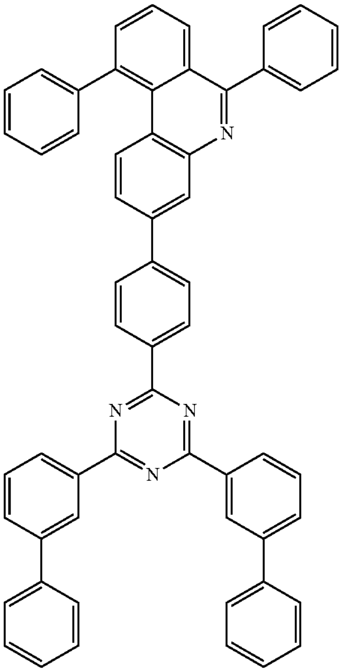
390
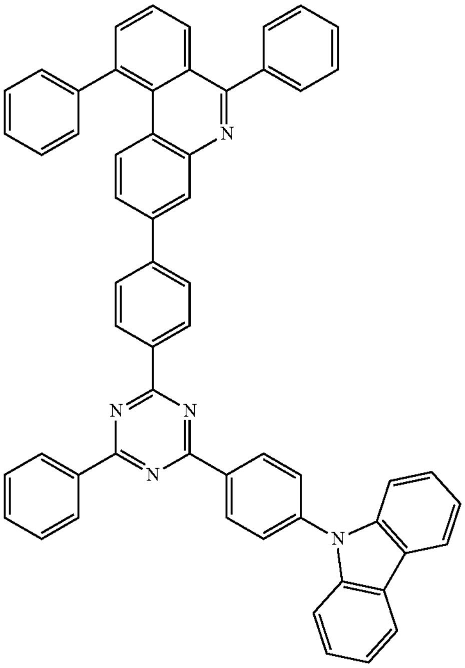

-continued
391
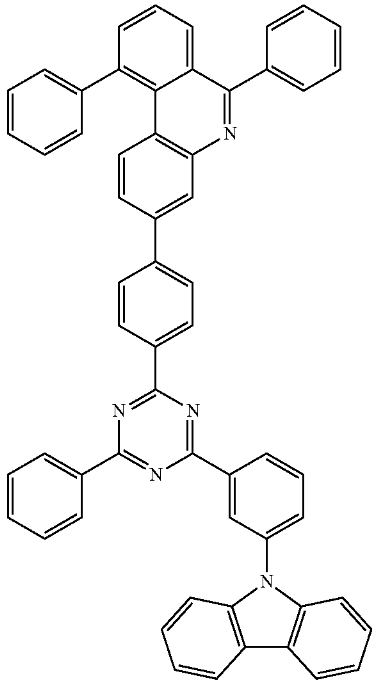
392
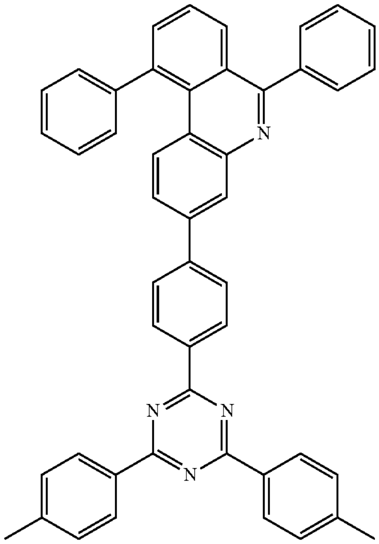
-continued
393
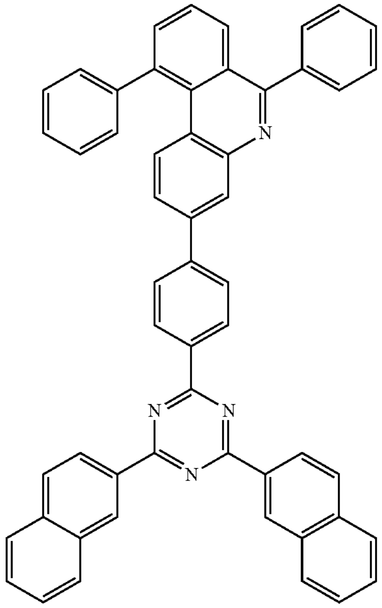
394
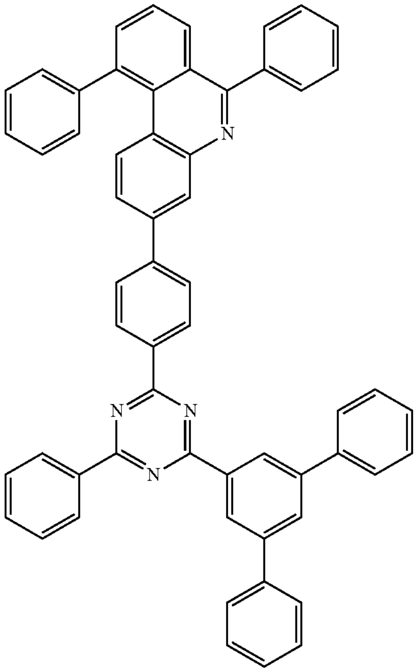

-continued
395
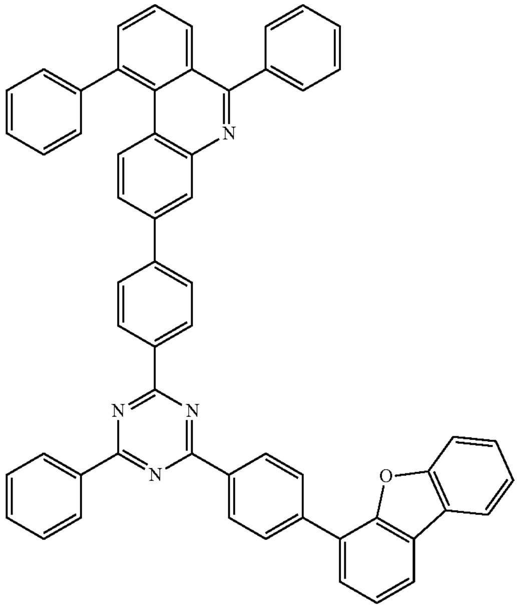
396
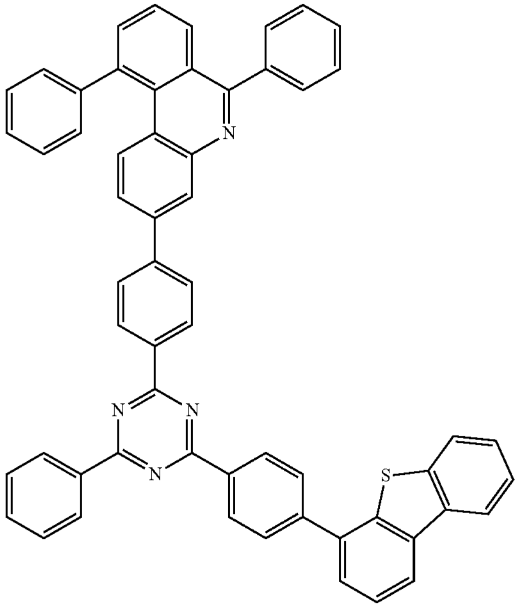
-continued
397
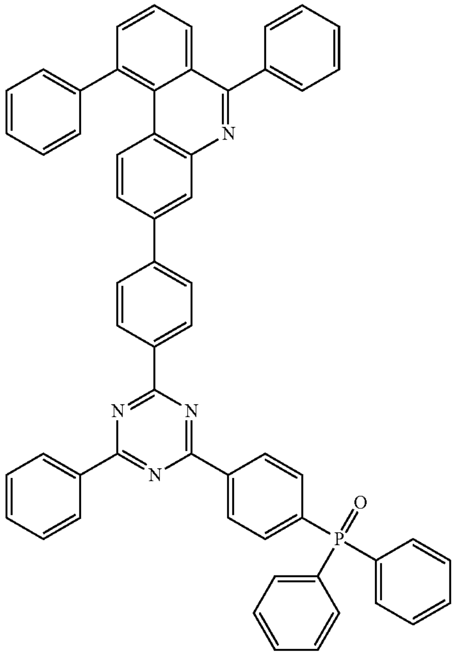
398
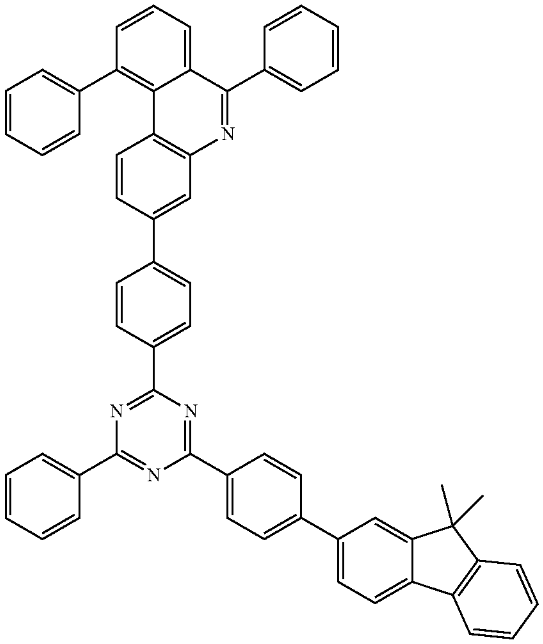

-continued
399
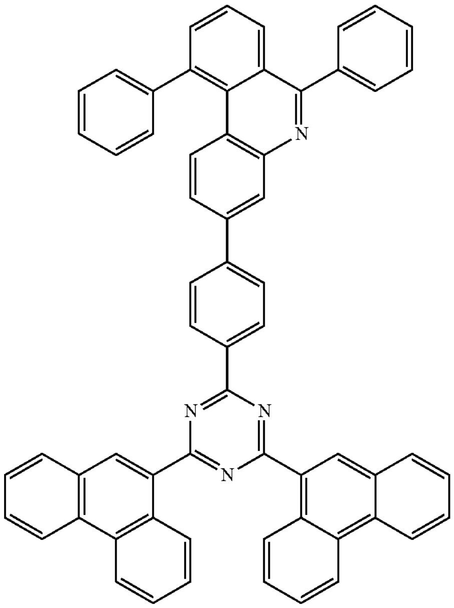
400
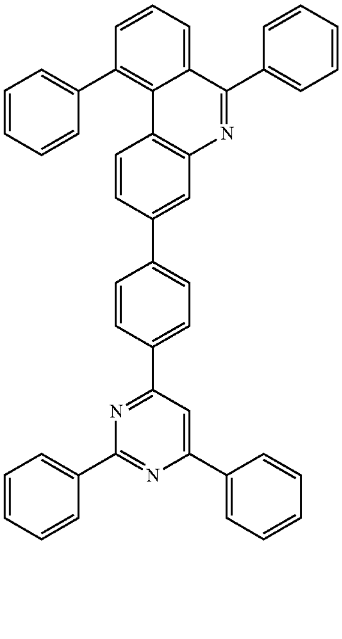
-continued
401
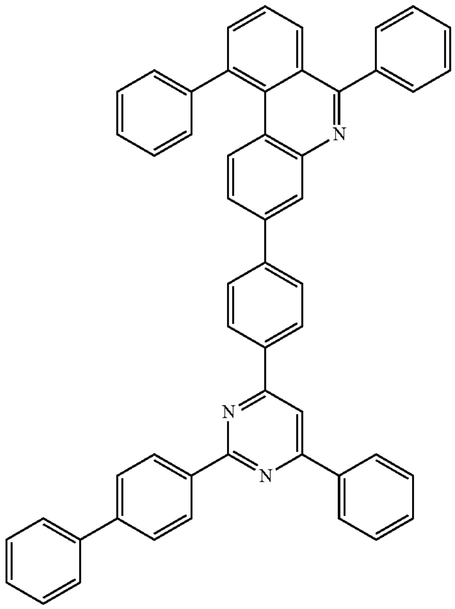
402
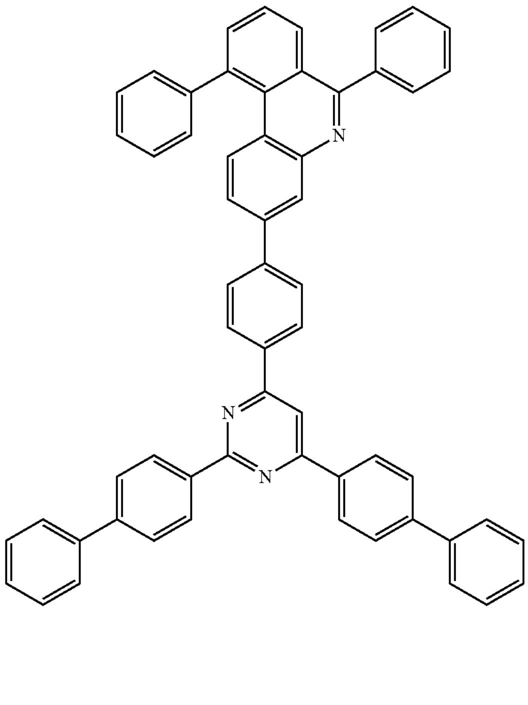

-continued
403
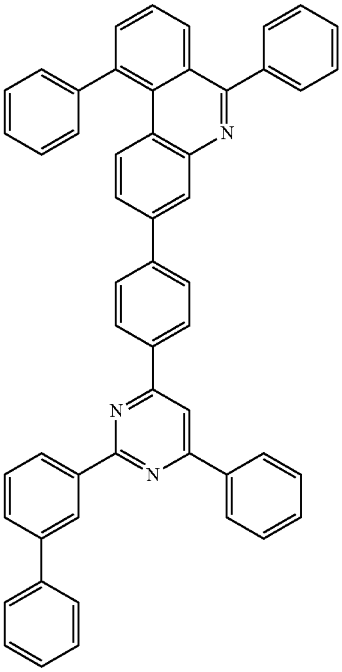
404
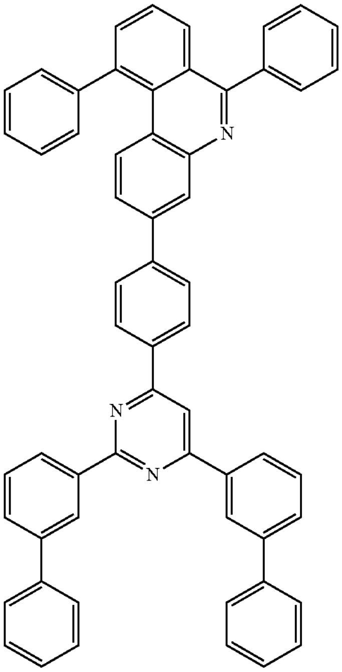
-continued
405
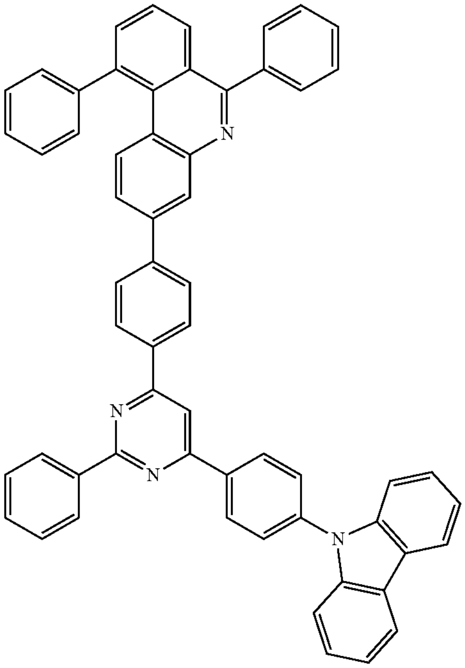
406
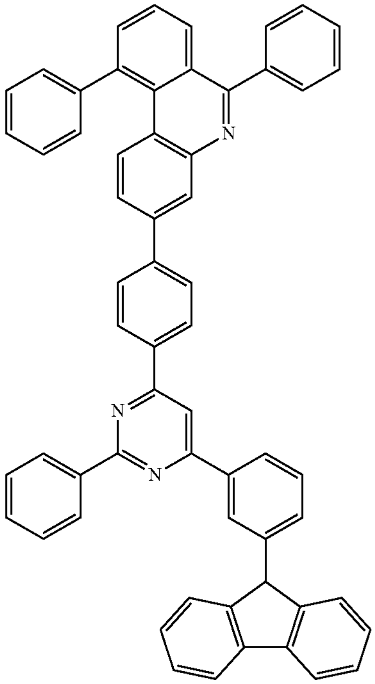

-continued
407
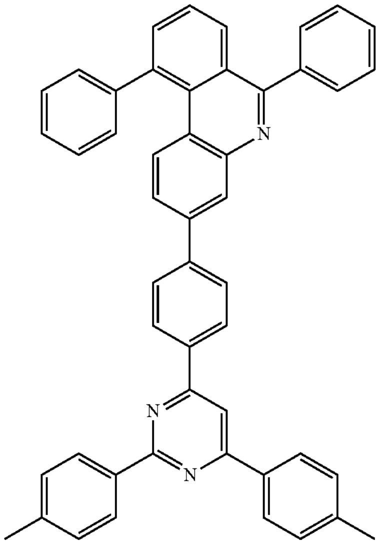
409
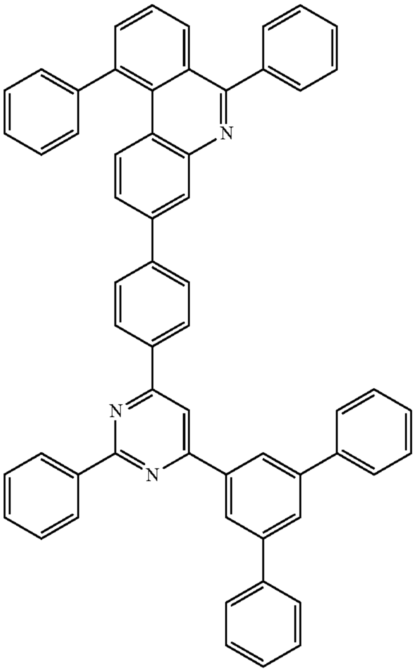
408
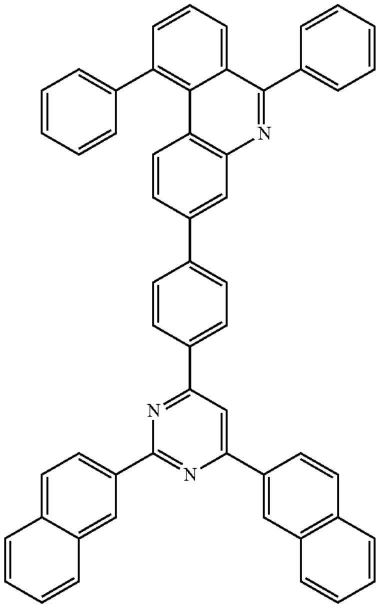
410
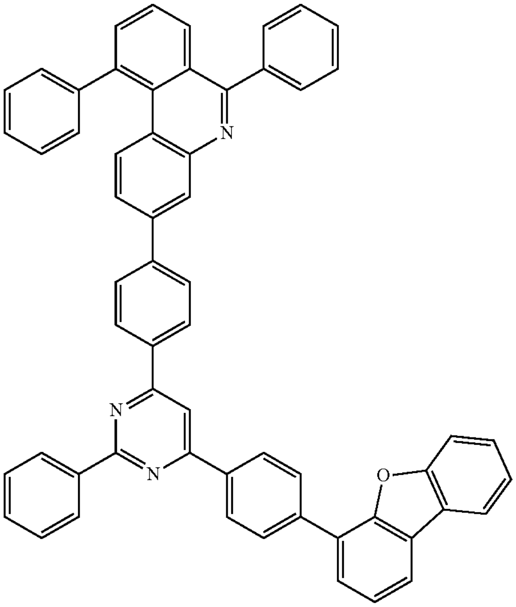

-continued
-continued
411
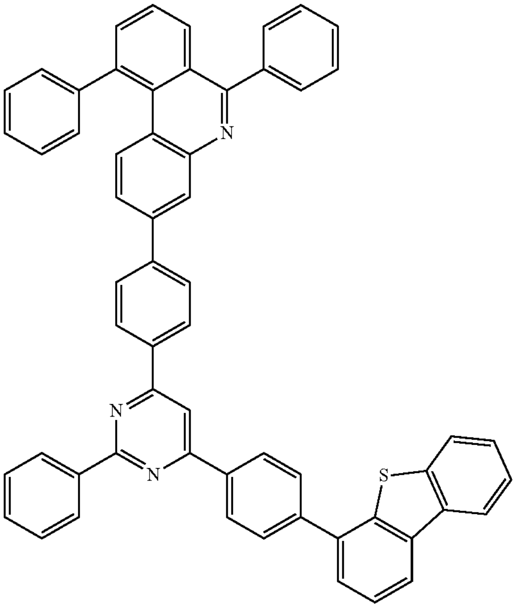
413
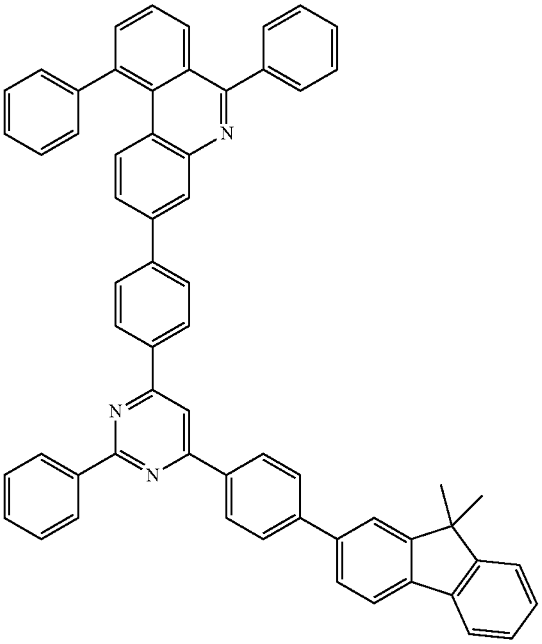
412
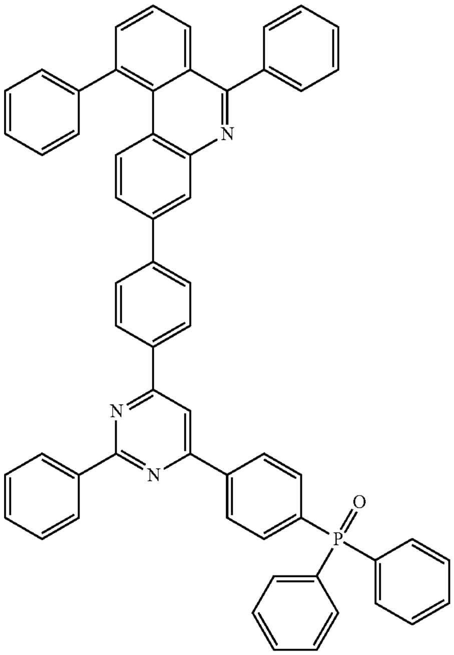
414
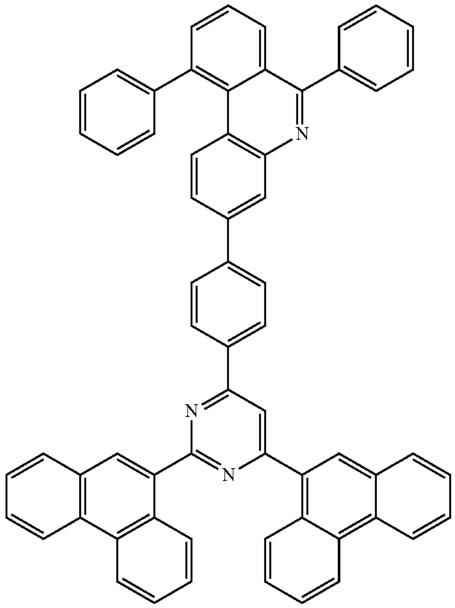

-continued
415
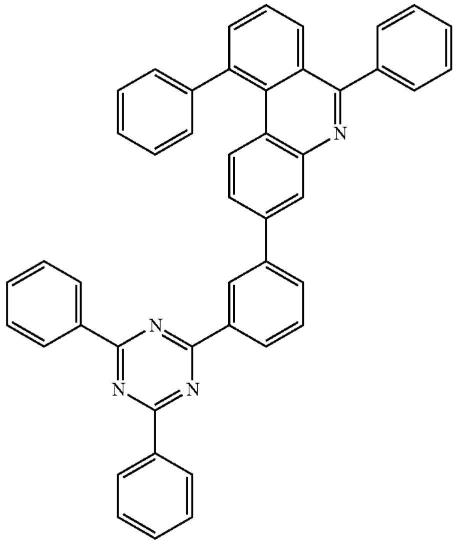
416
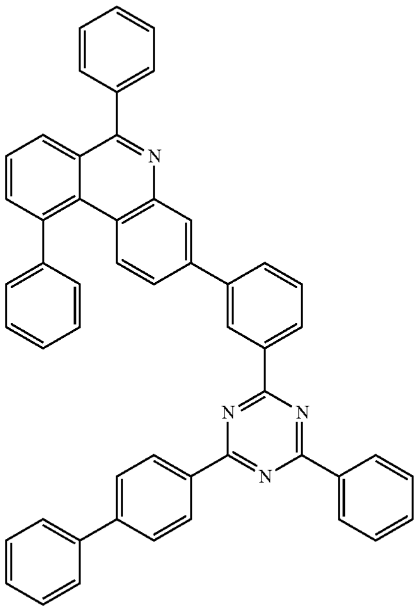
-continued
417
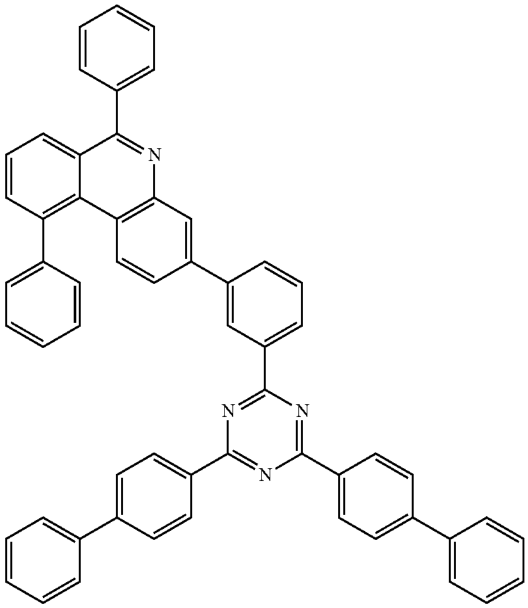
418
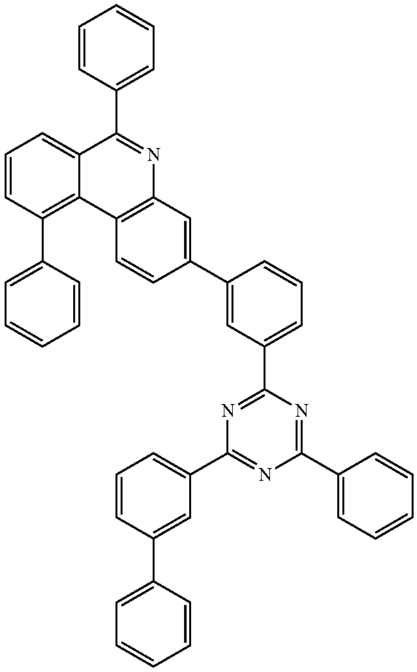

-continued
419
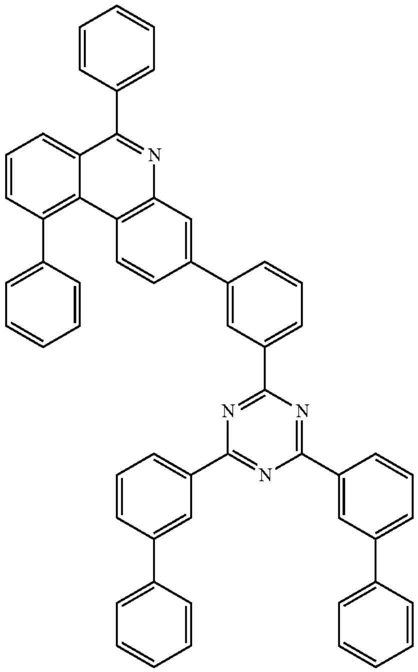
420
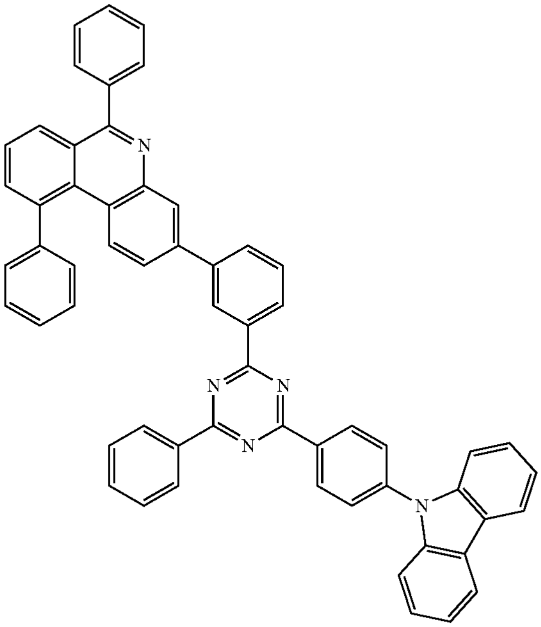
-continued
421
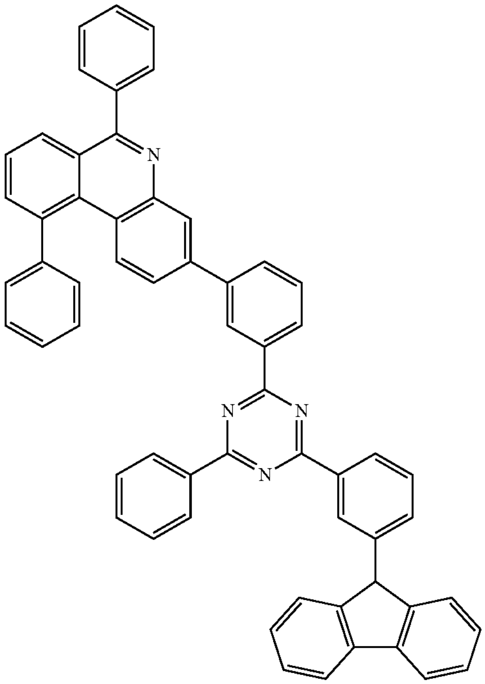
422
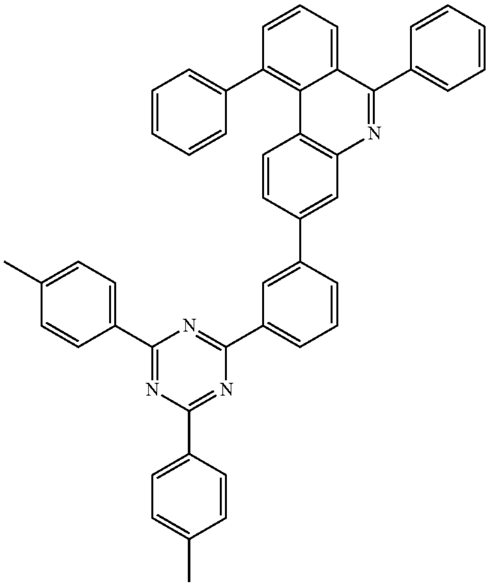

-continued
423
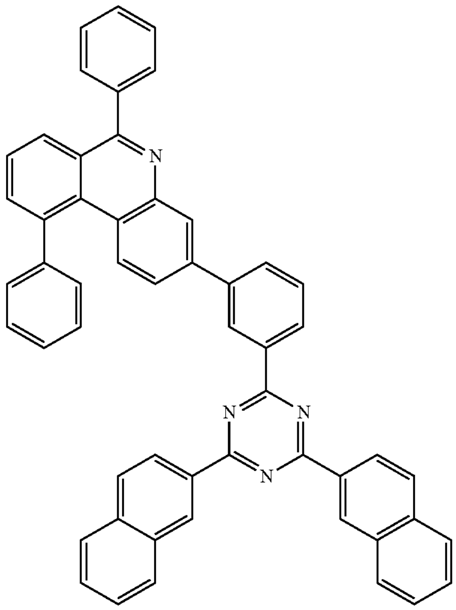
424
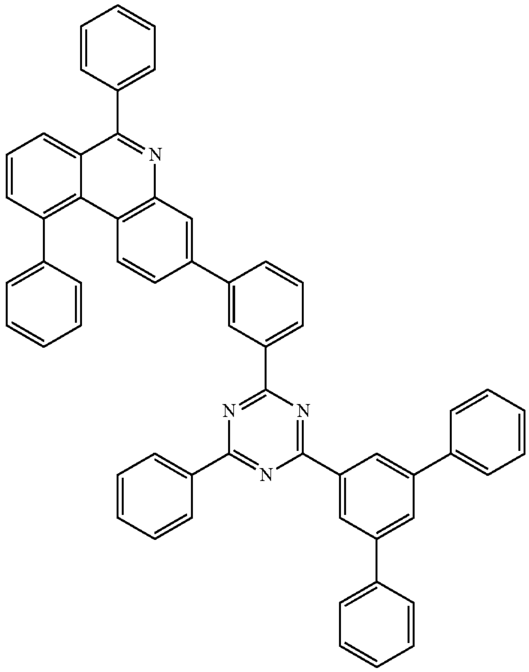
-continued
425
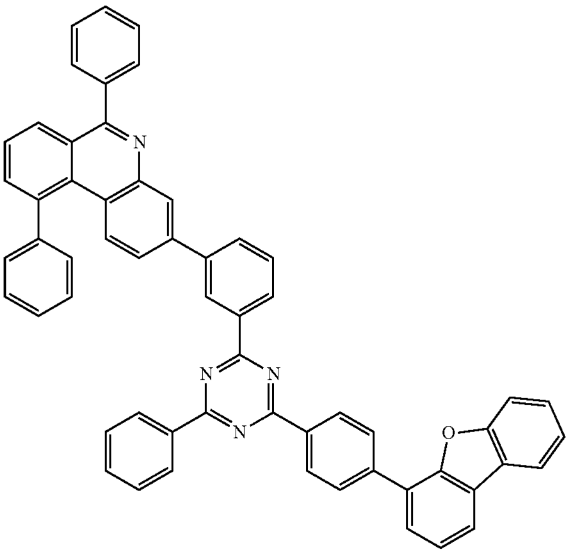
426
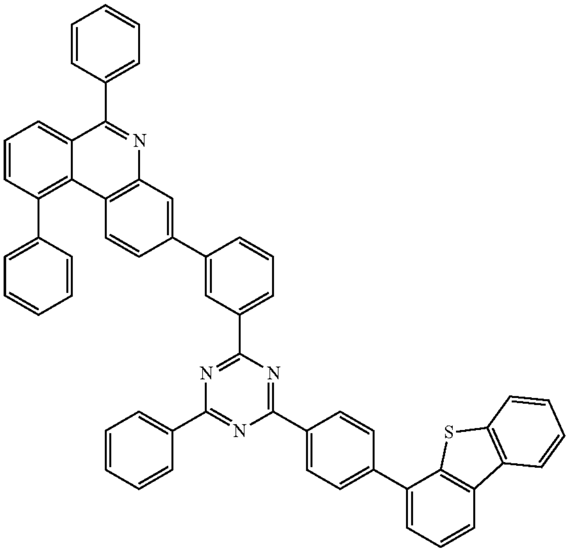

427
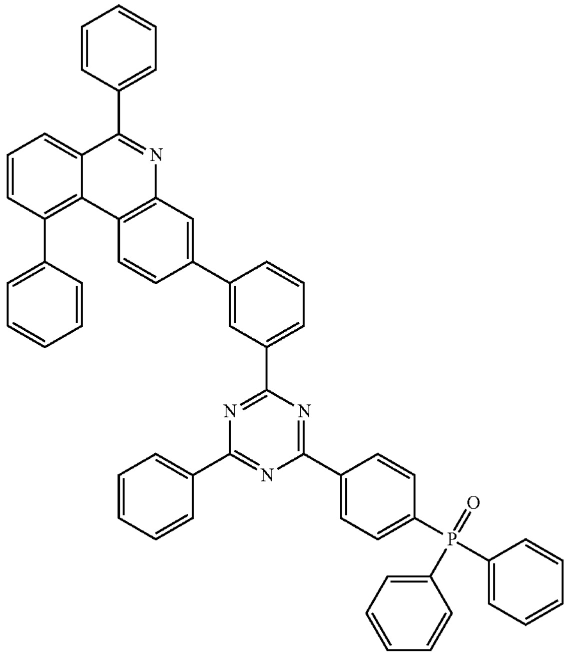
428
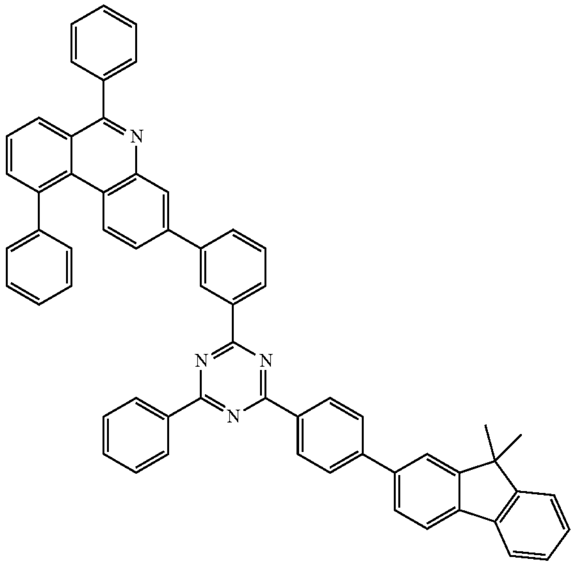
429
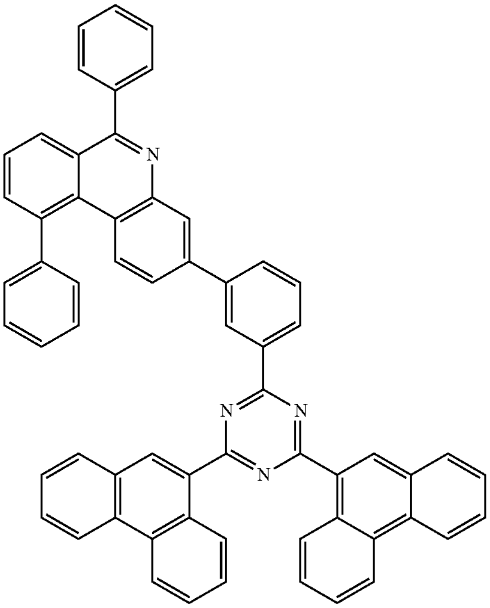
430
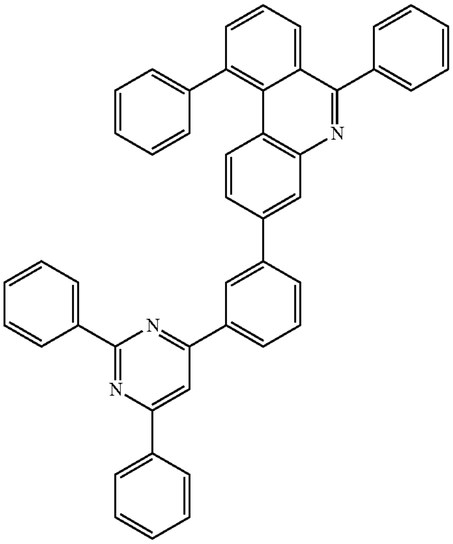

431
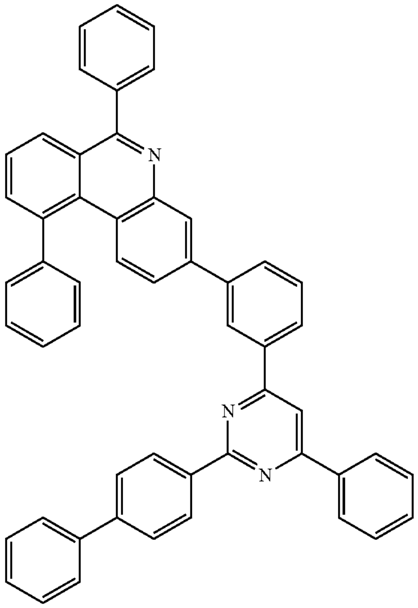
432
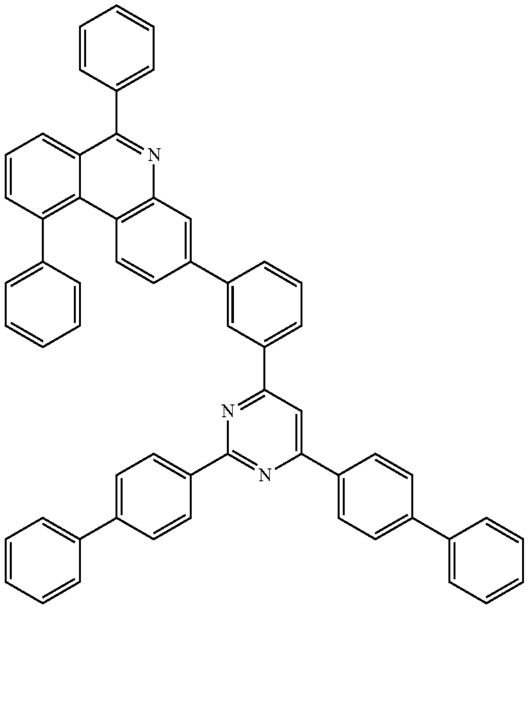
433
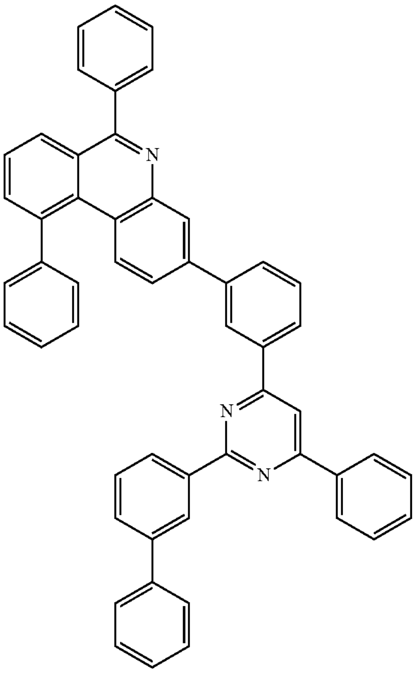
434
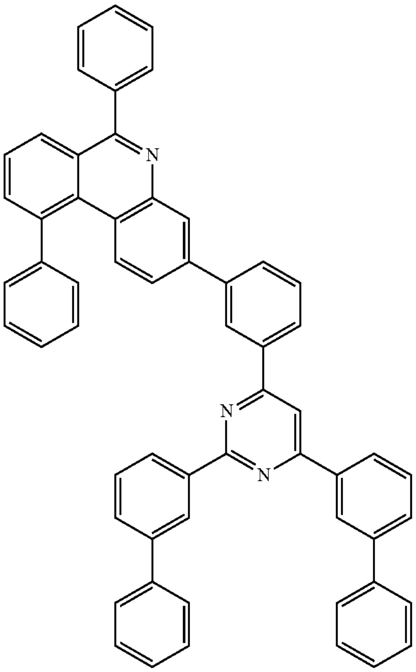

-continued
435
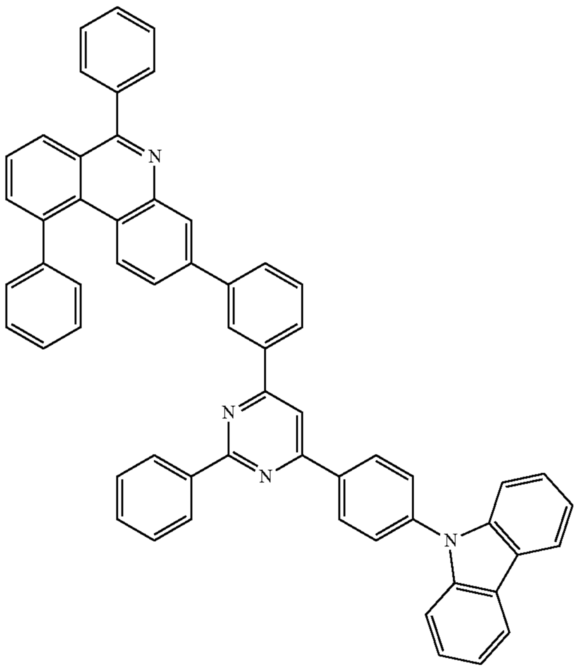
436
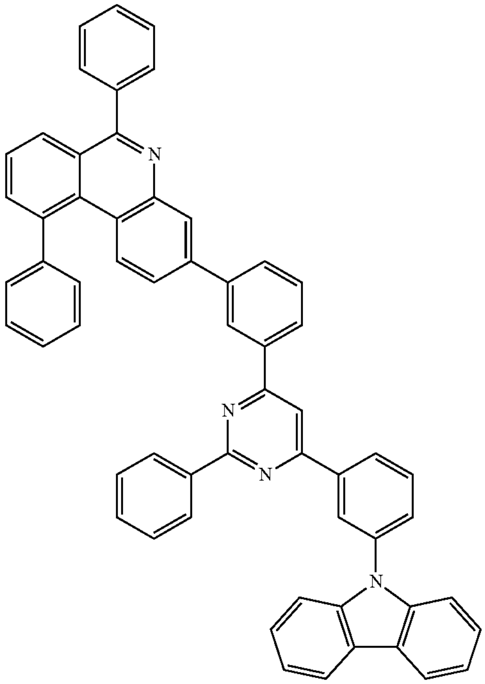
-continued
437
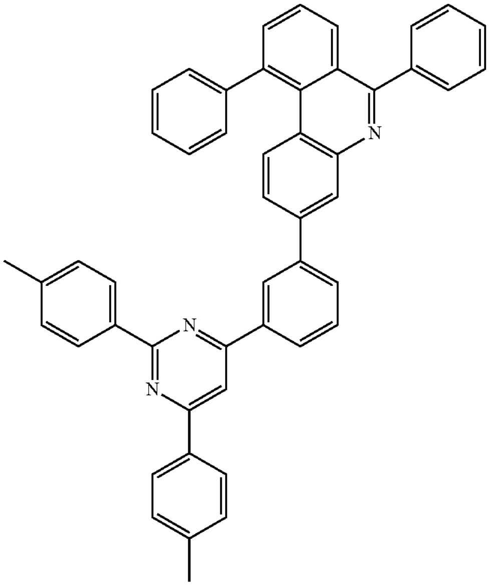
438
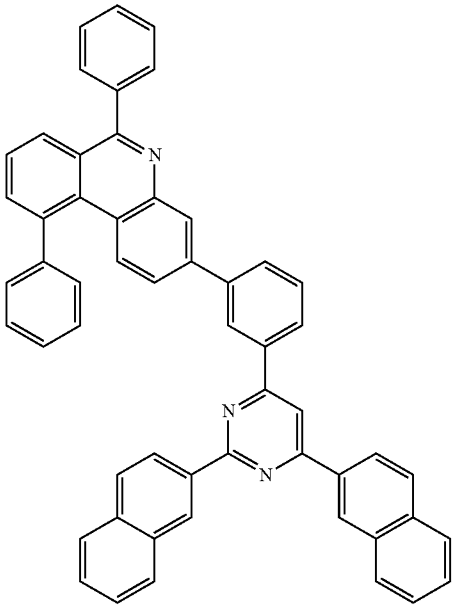

-continued
439
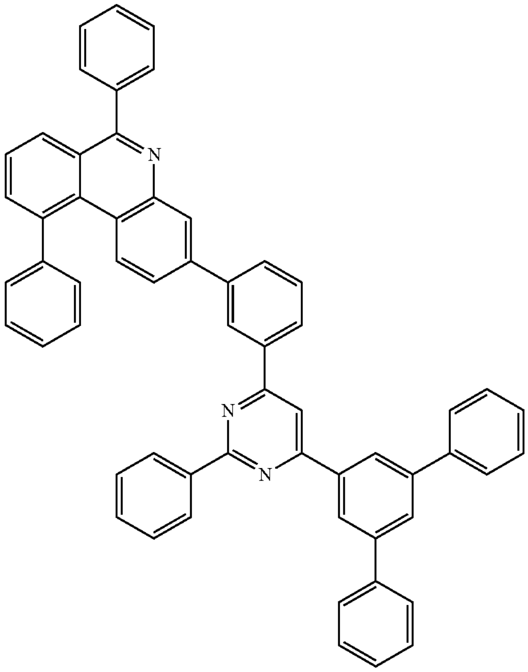
440
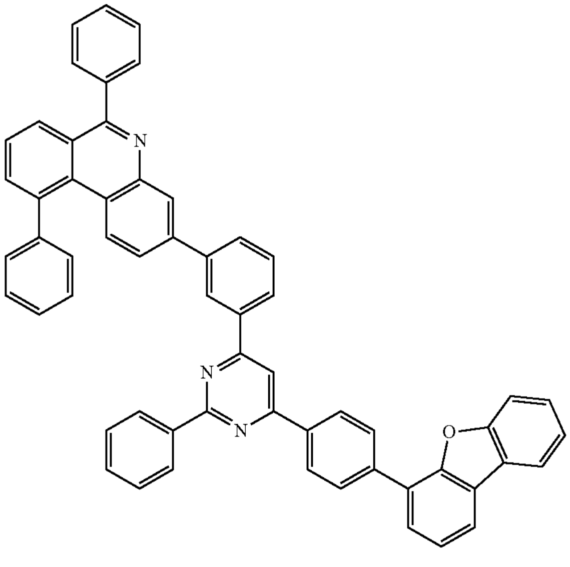
-continued
441
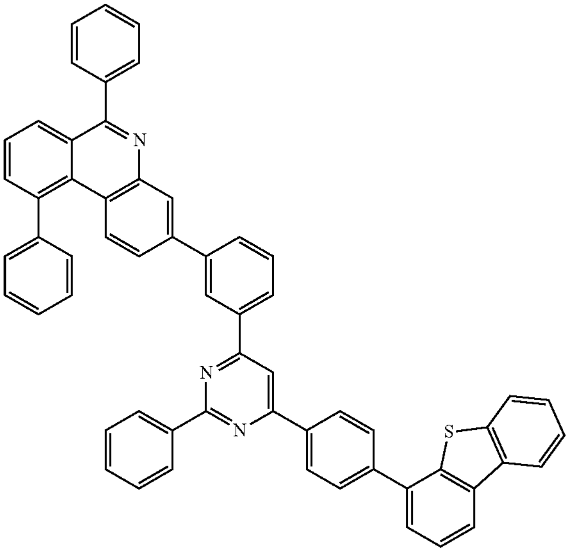
442
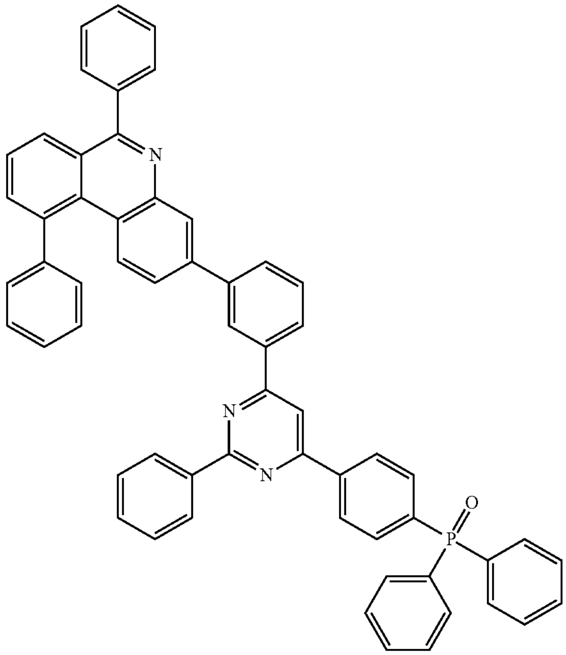

-continued
443
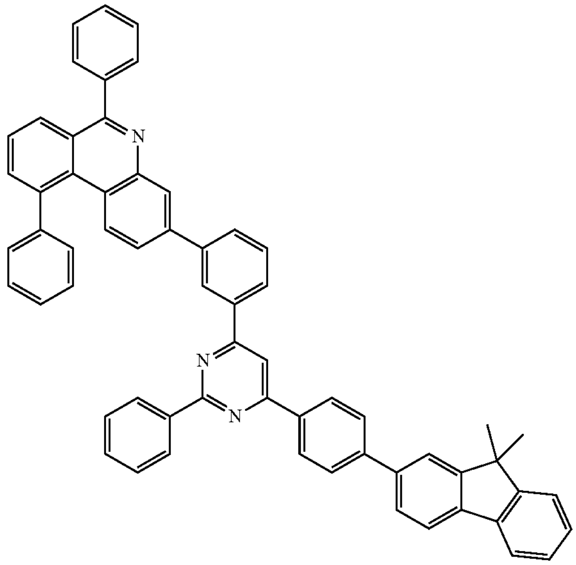
444
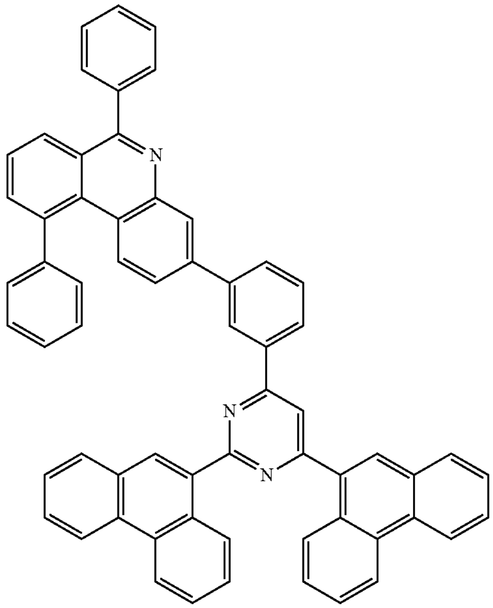
-continued
445
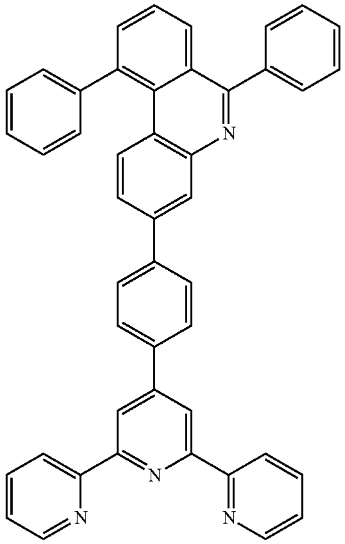
446
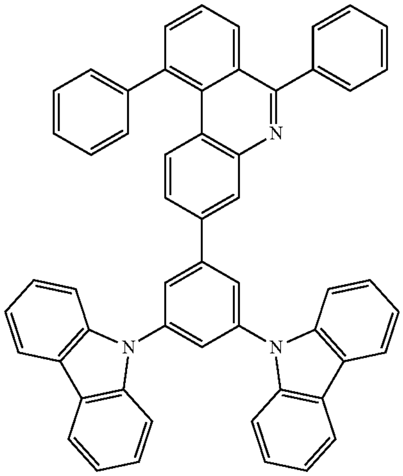
447
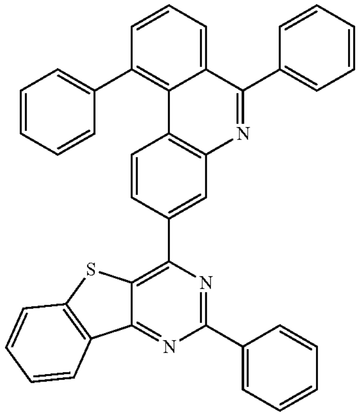

448
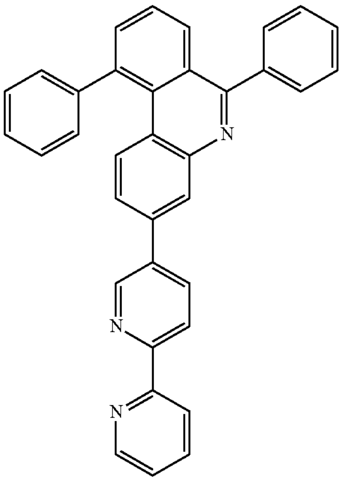
449
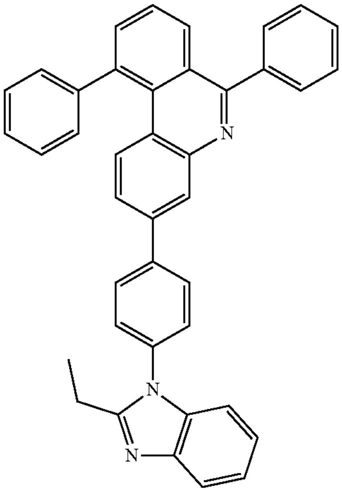
450
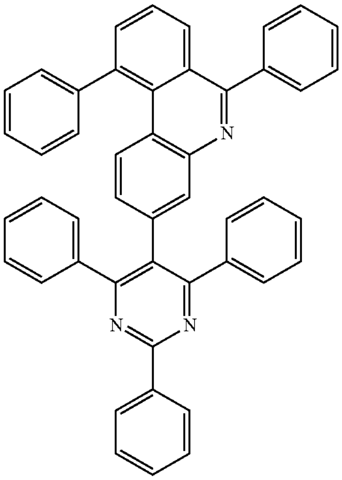
451
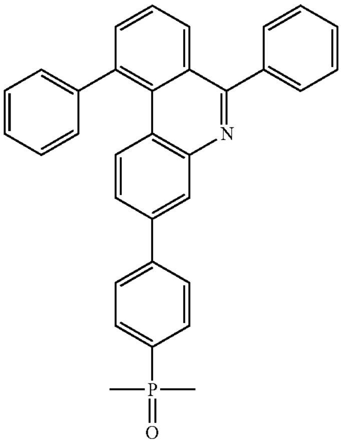
452
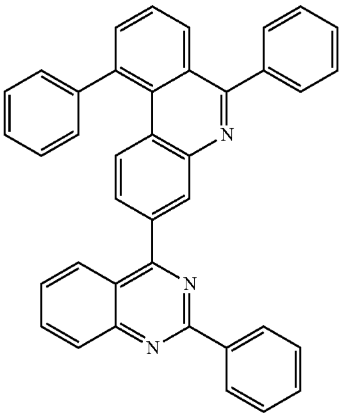
453
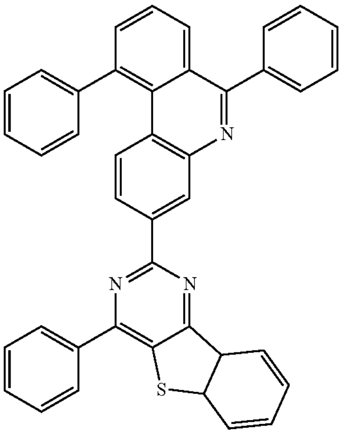

-continued
454
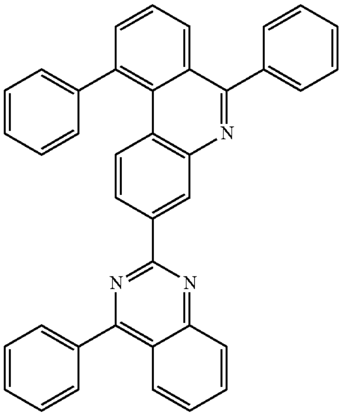
455
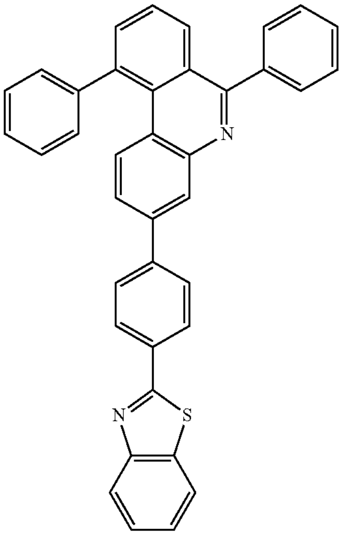
456
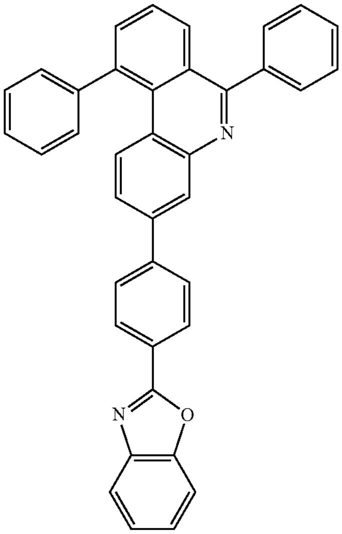
-continued
457
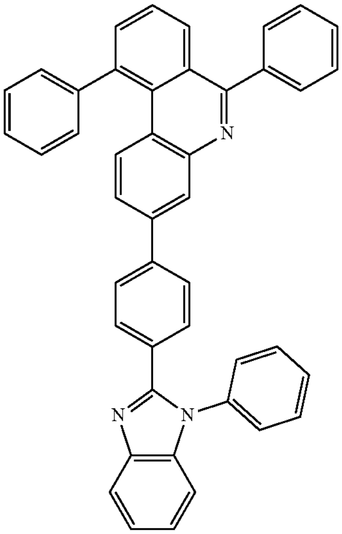
458
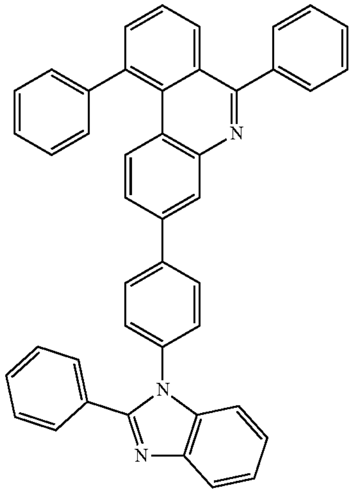
459
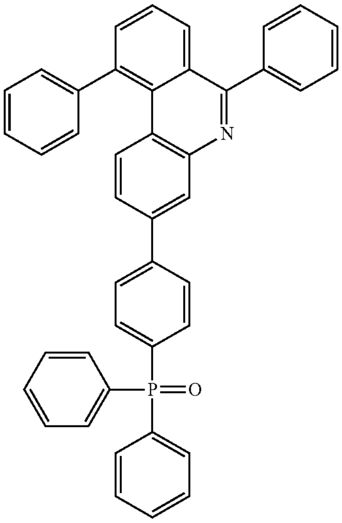

-continued
460
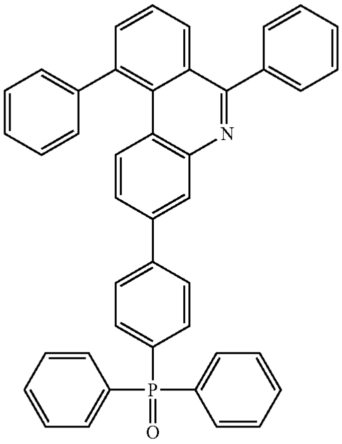
461
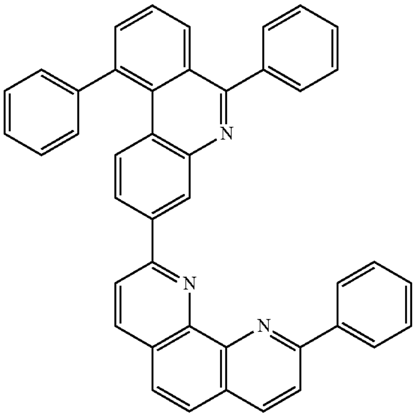
462
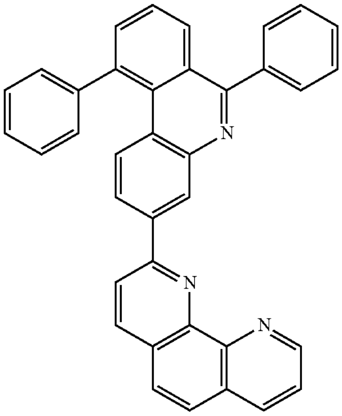
-continued
463
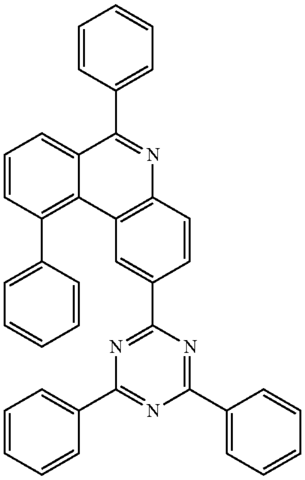
464
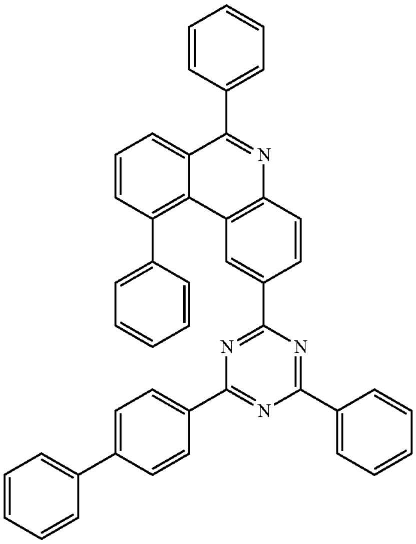
465
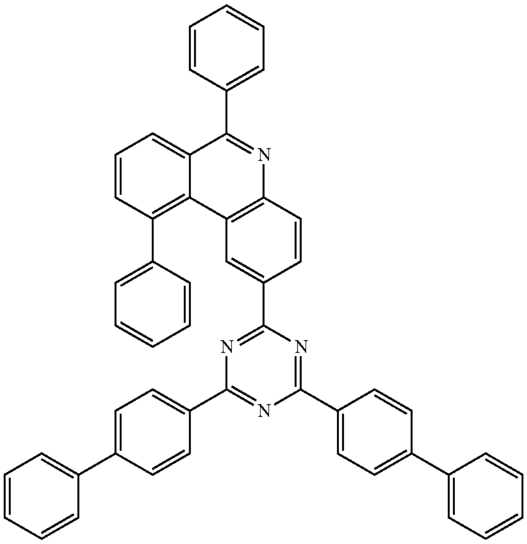

-continued
466
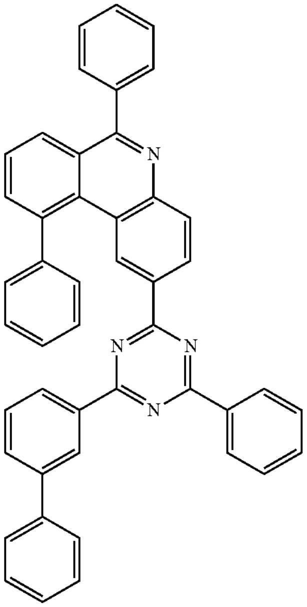
467
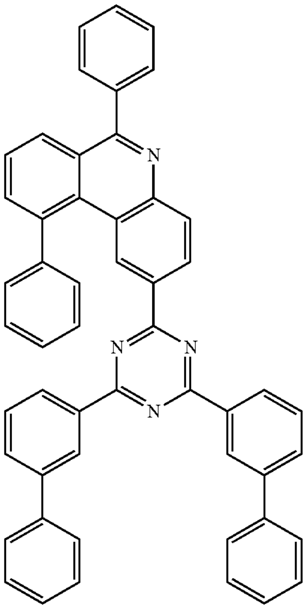
-continued
468
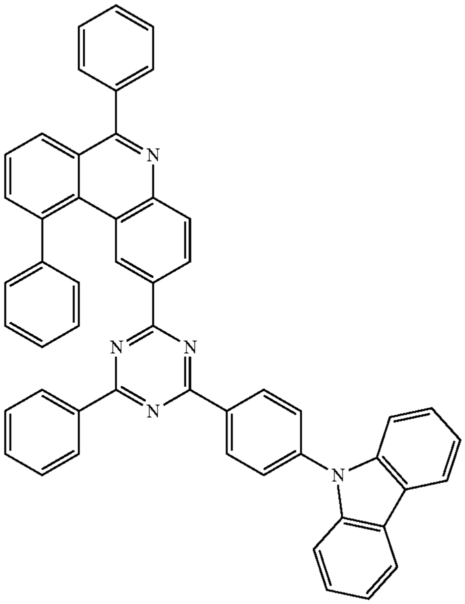
469
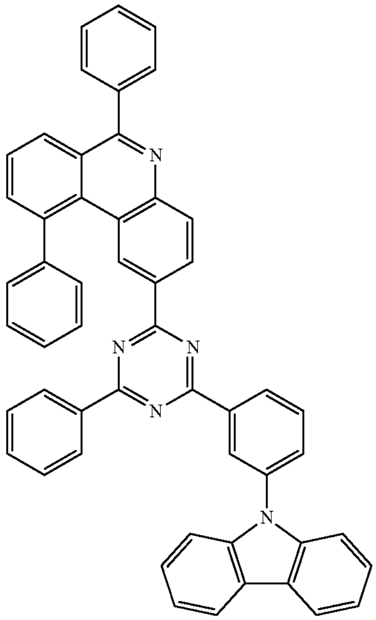

-continued
470
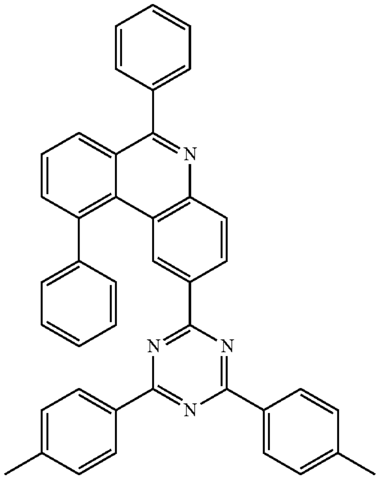
471
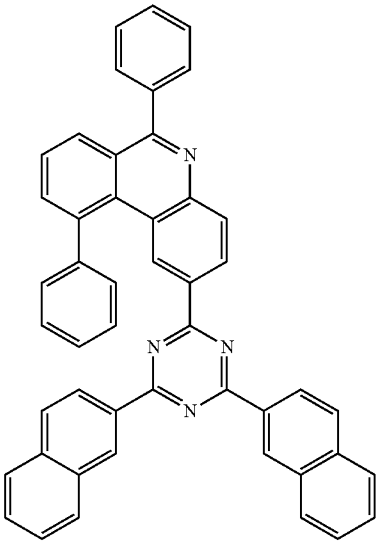
472
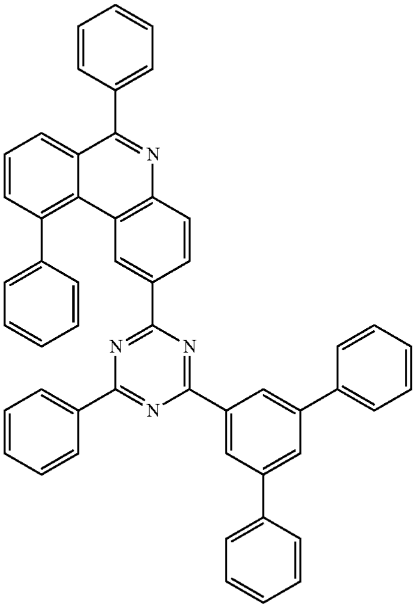
-continued
473
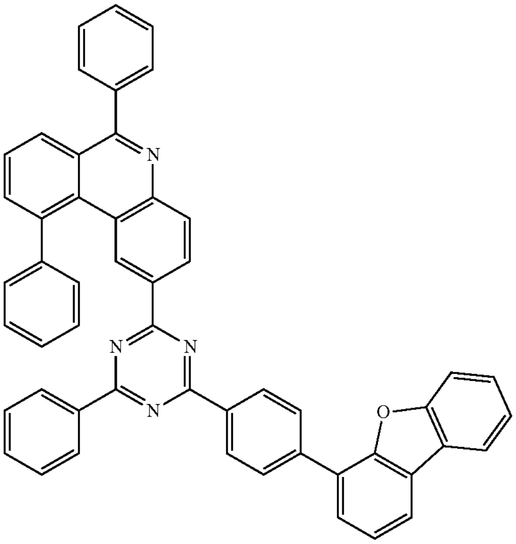
474
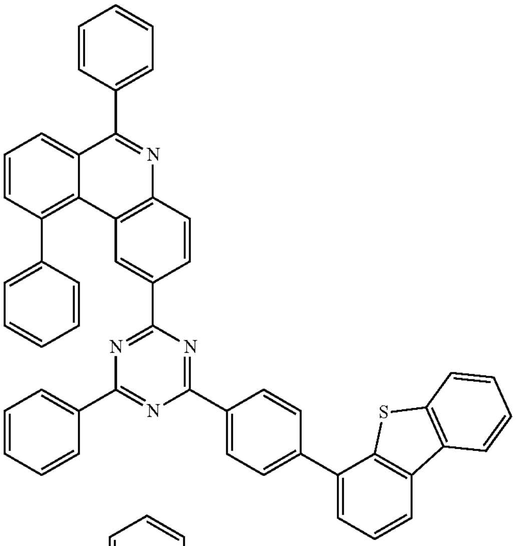
475
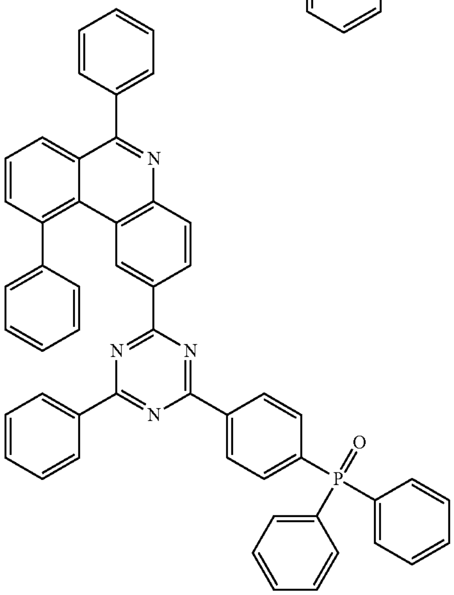

-continued
476
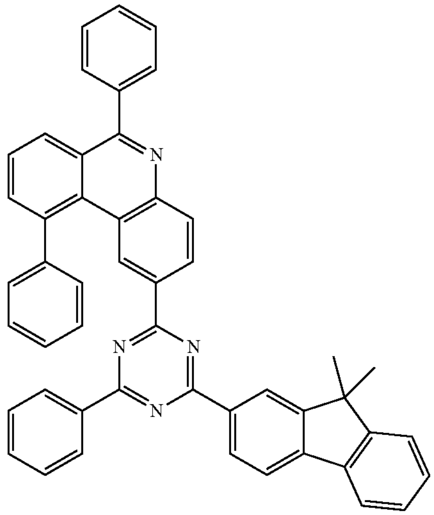
477
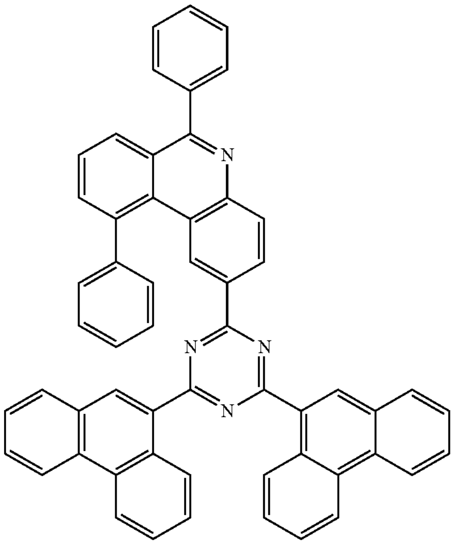
478
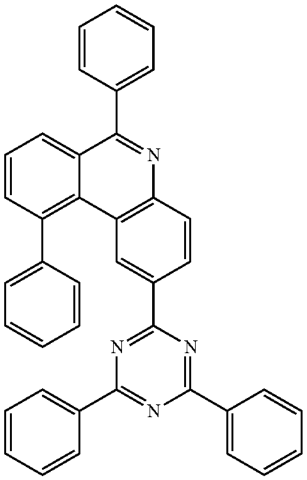
-continued
479
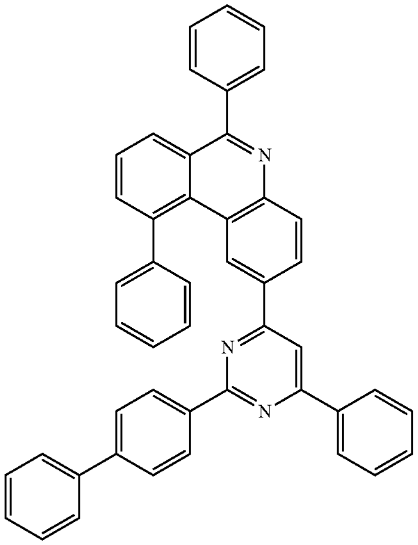
480
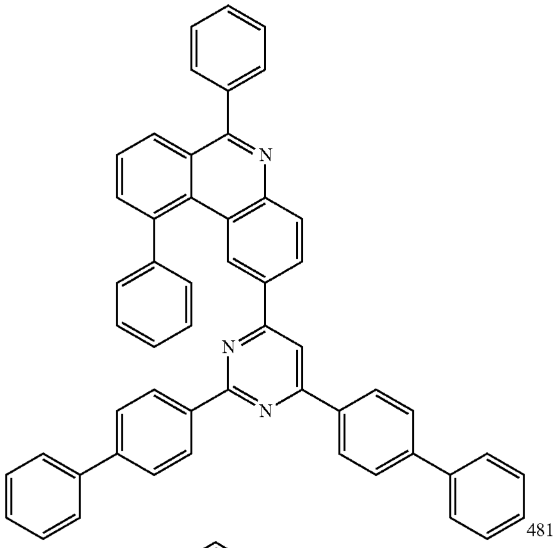
481
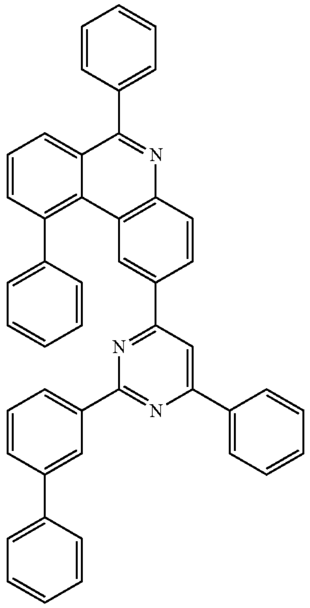

-continued
482
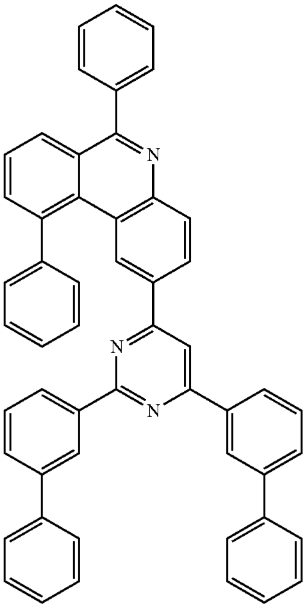
483
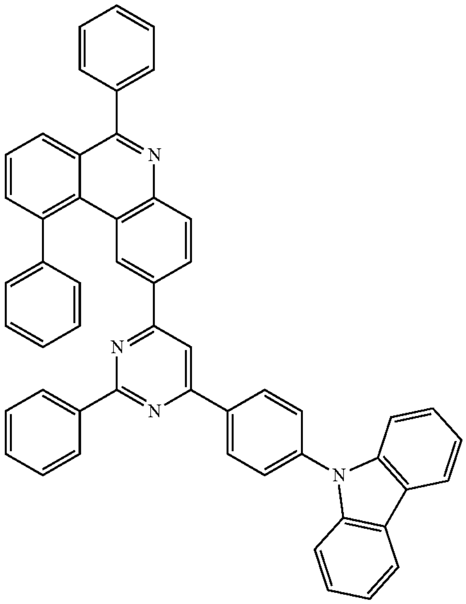
-continued
484
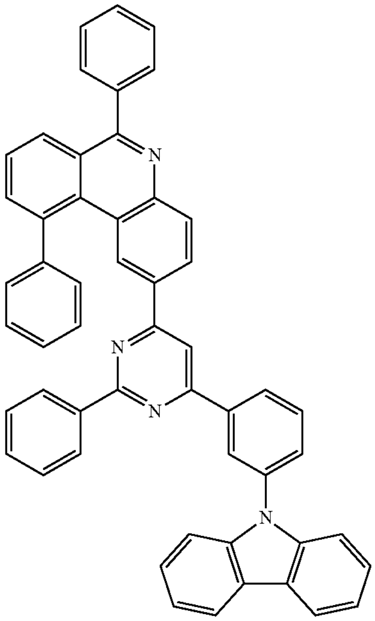
485
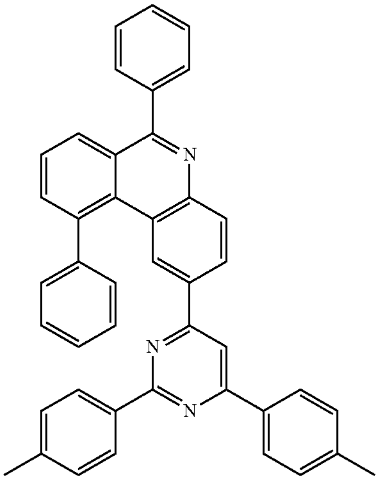
486
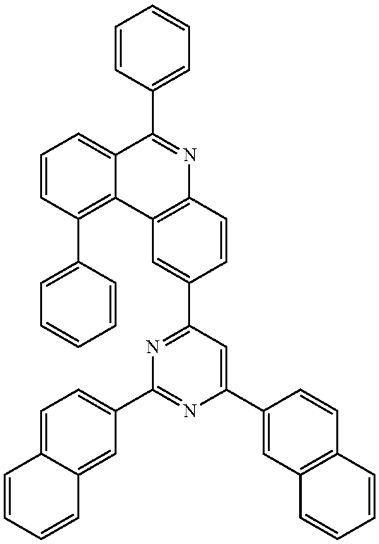

-continued
487
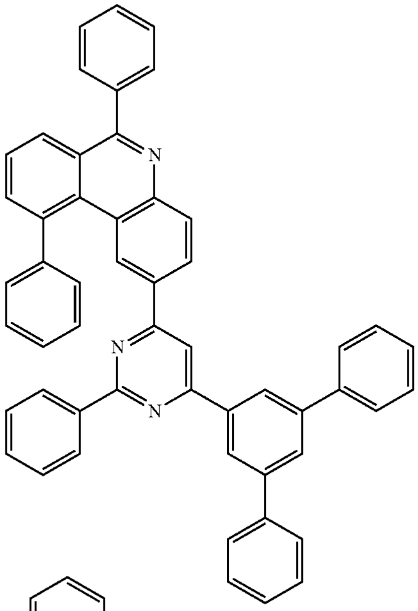
488
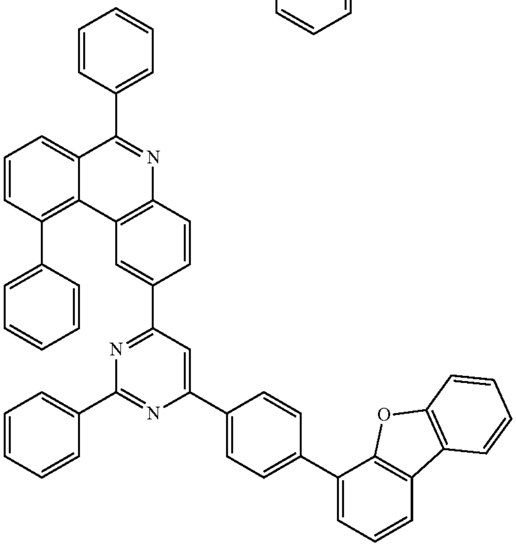
489
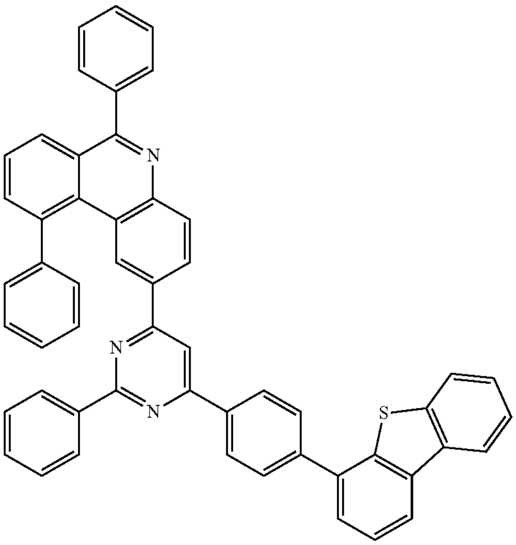
-continued
490
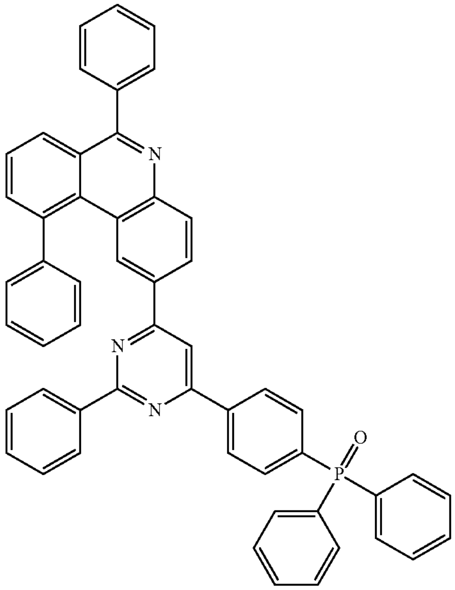
491
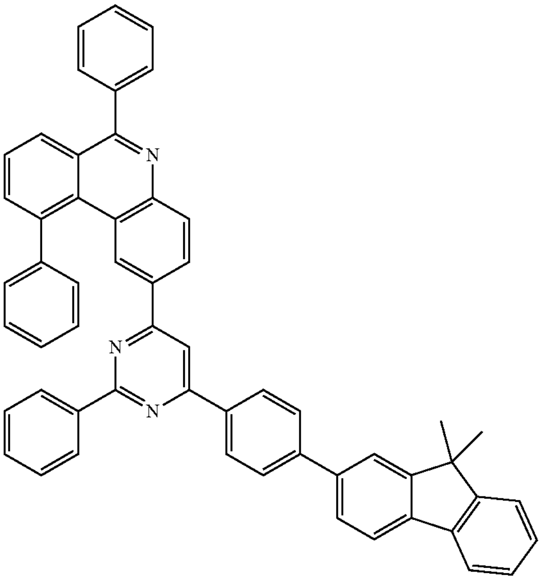

-continued
492
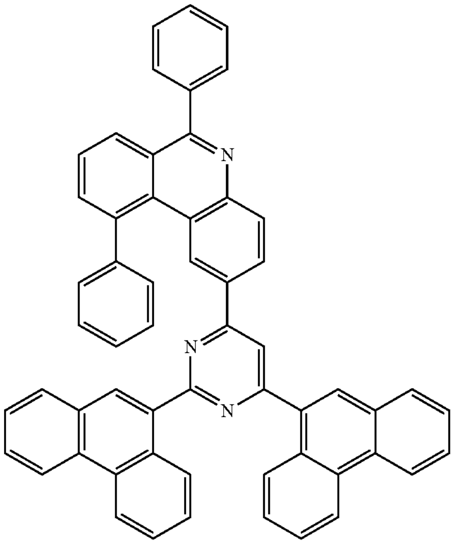
493
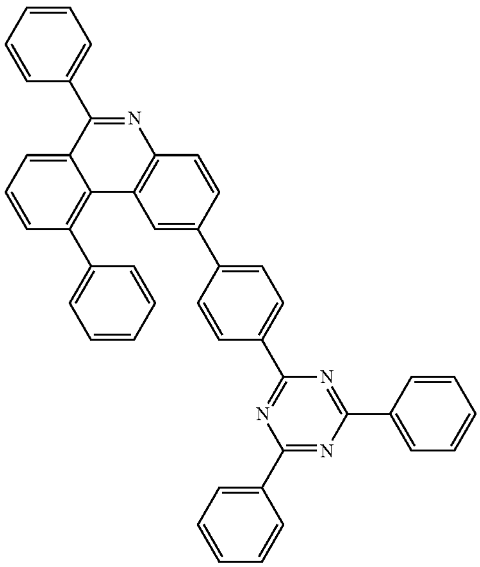
-continued
494
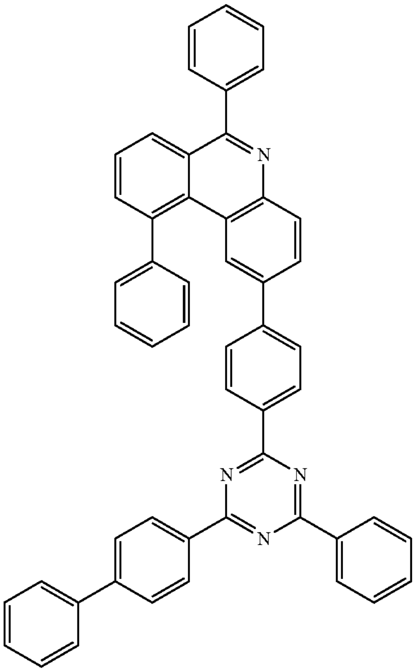
495
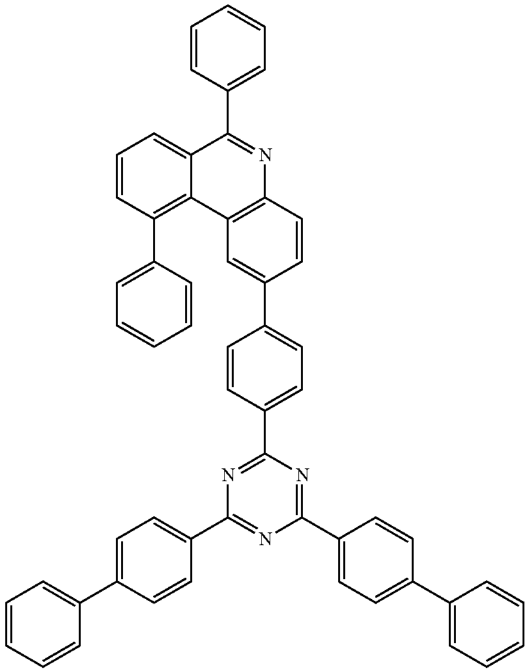

-continued
496
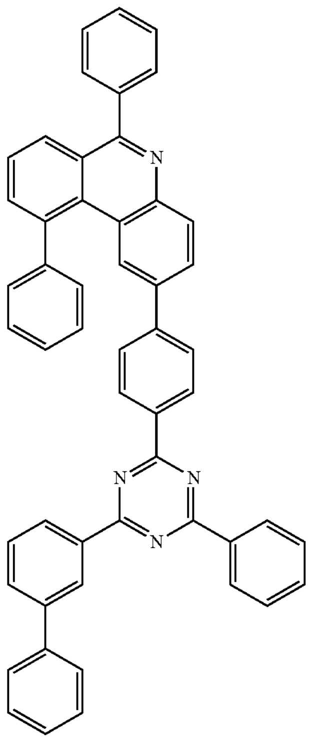
497
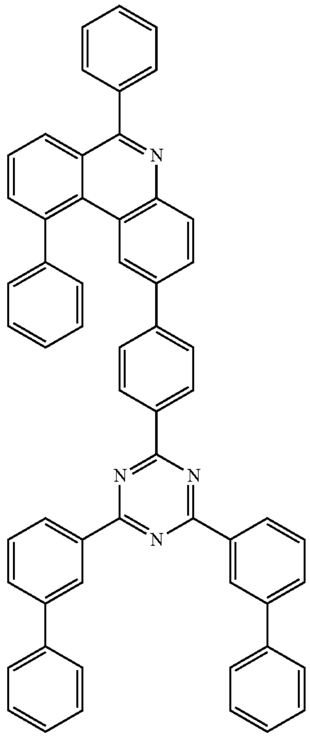
-continued
498
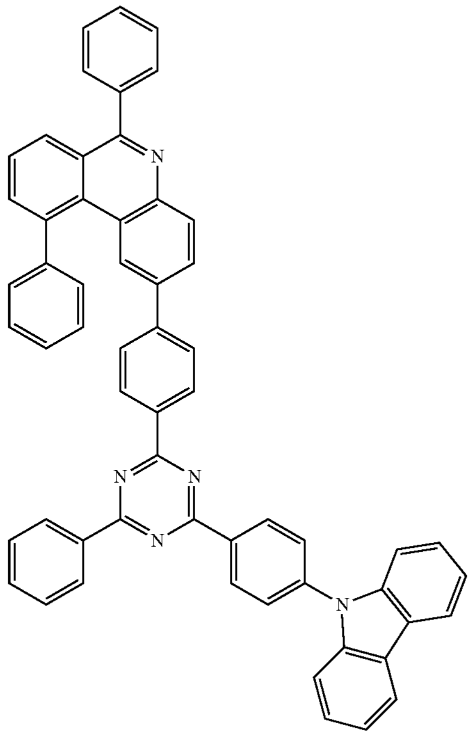
499
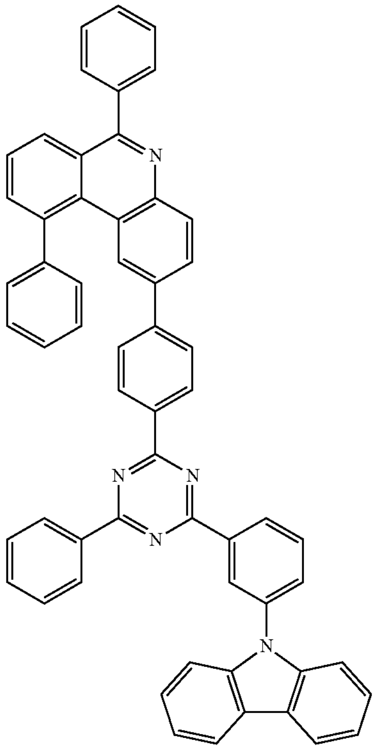

-continued
500
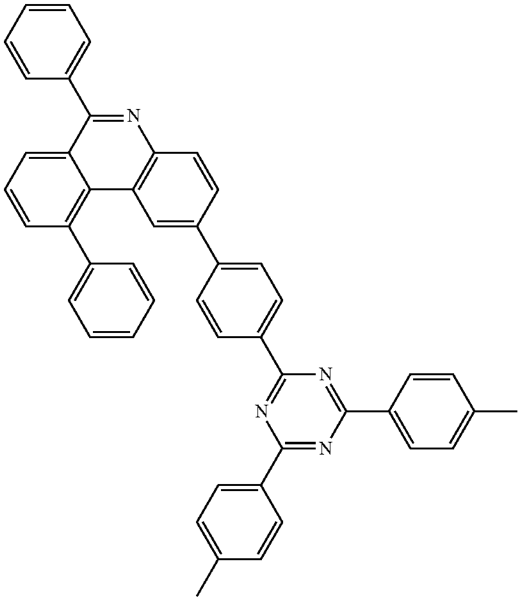
501
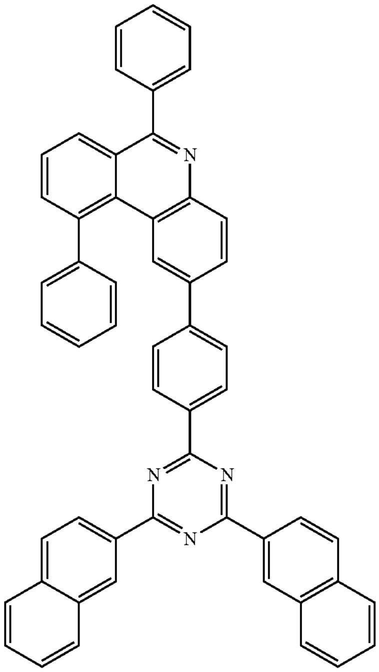
-continued
502
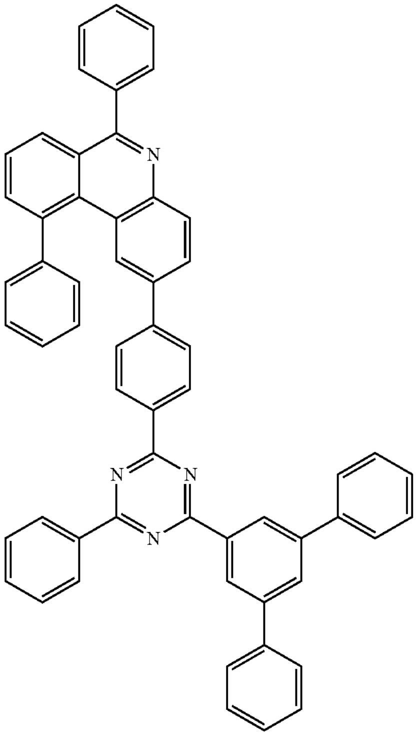
503
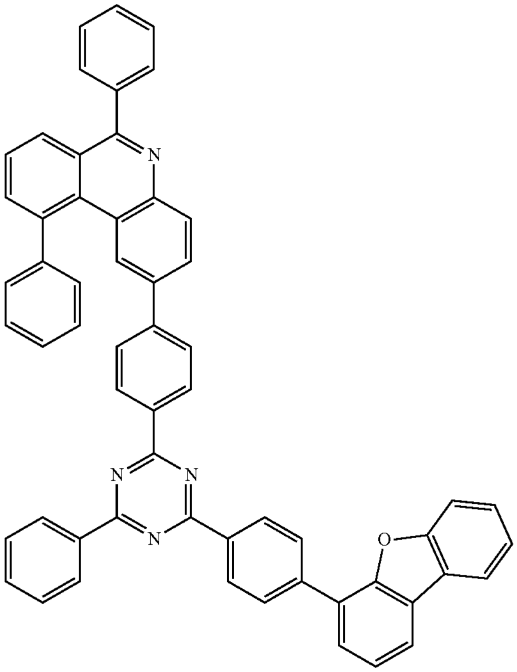

504
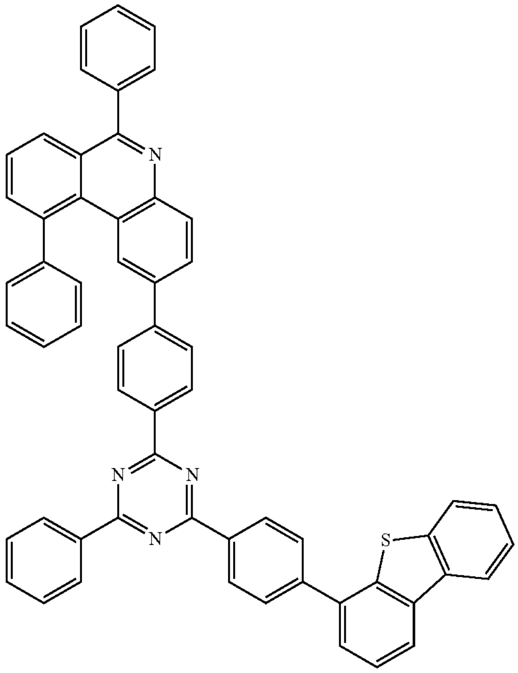
505
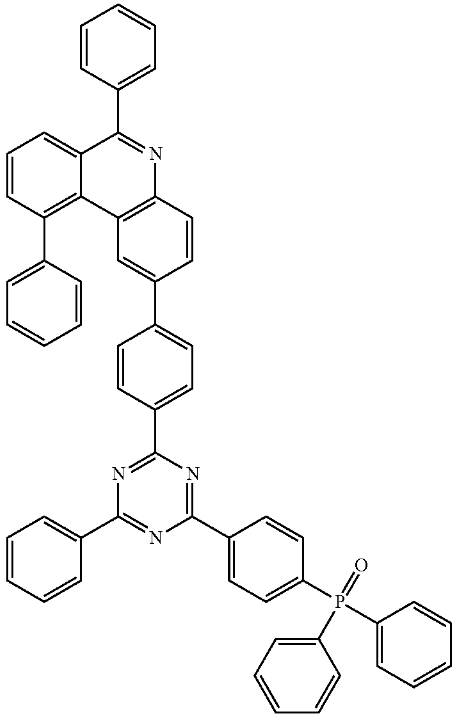
506
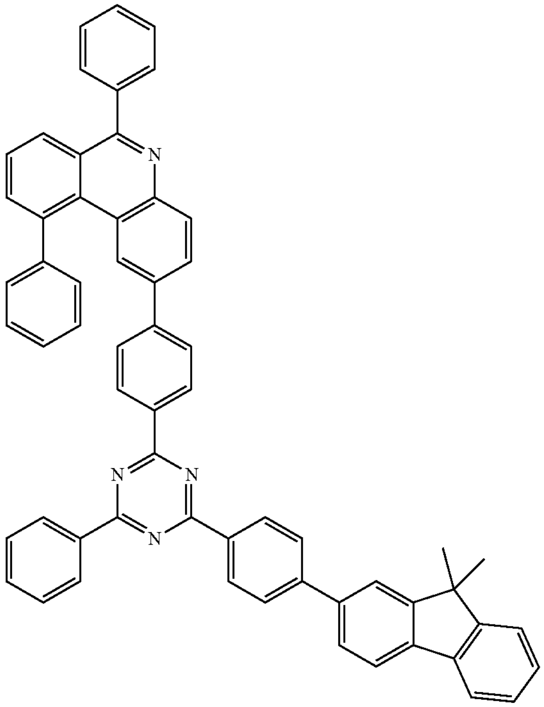
507
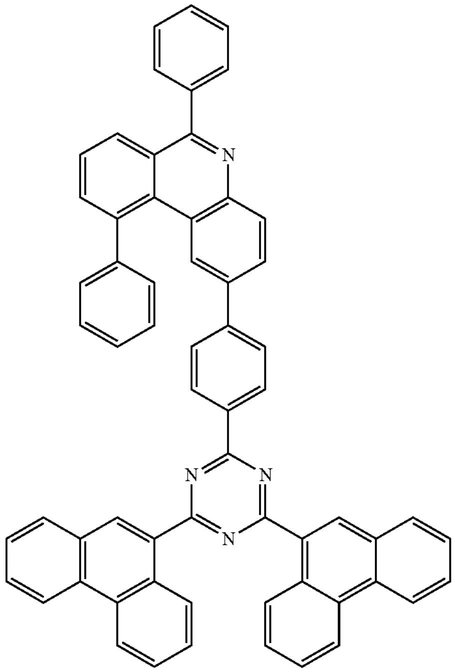

-continued
508
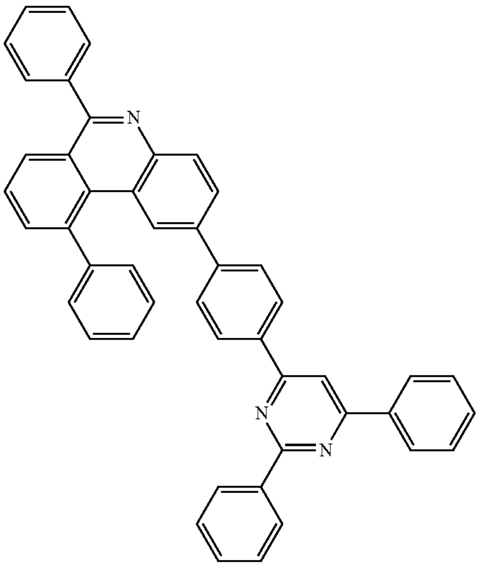
509
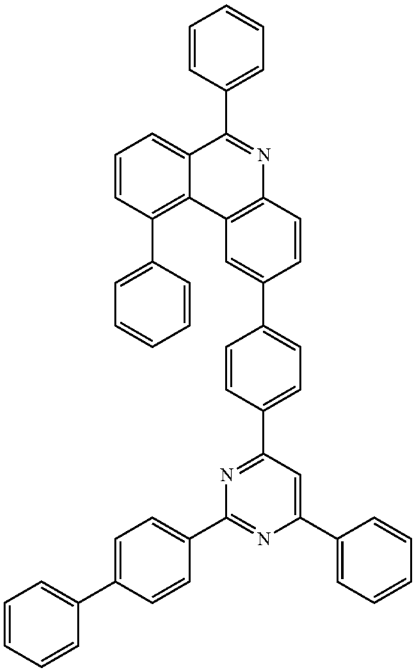
-continued
510
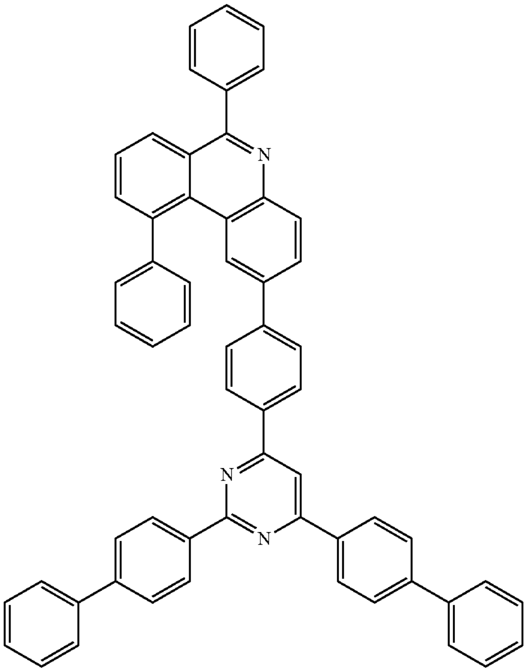
511
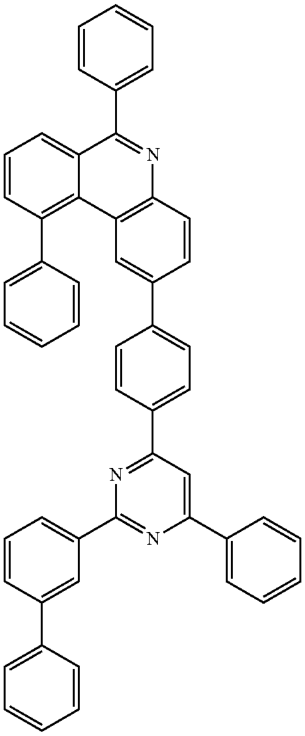

-continued
512
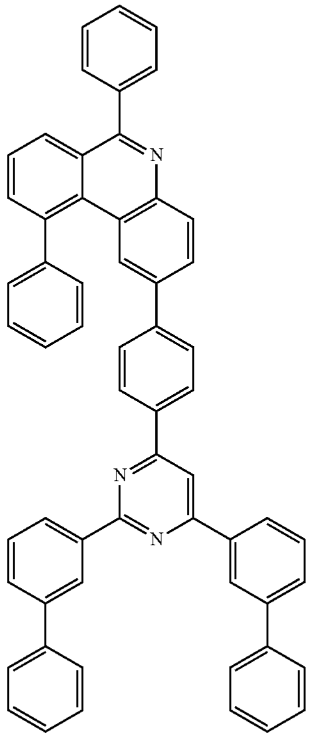
513
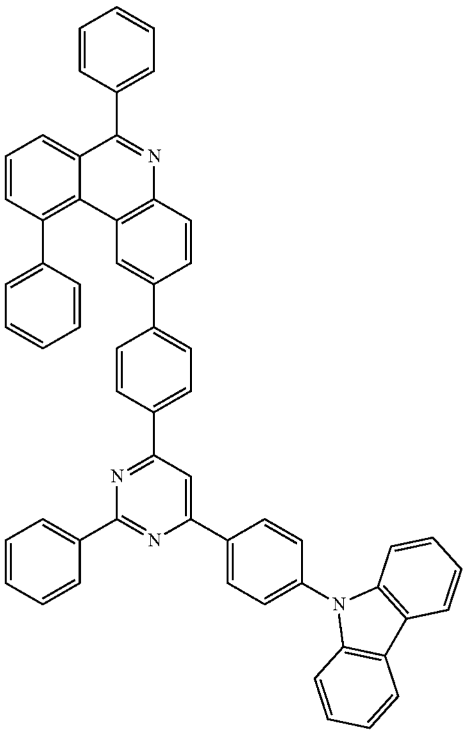
-continued
514
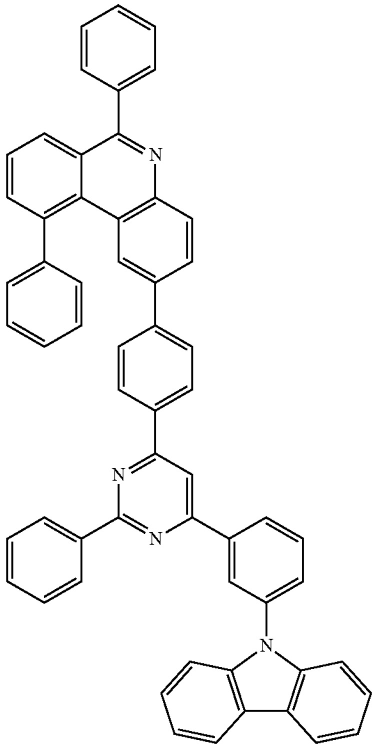
515
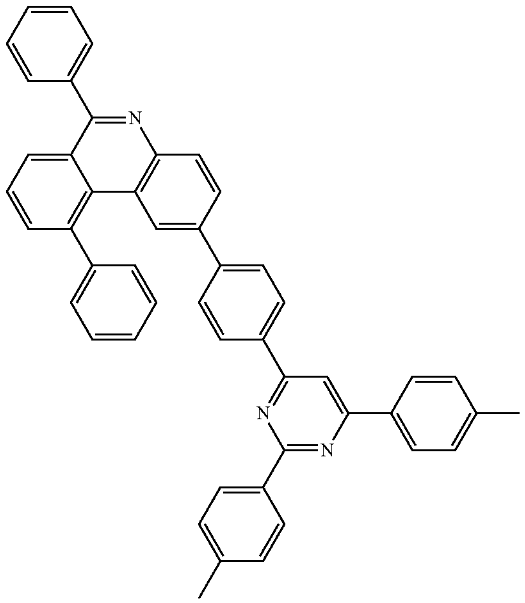

-continued
516
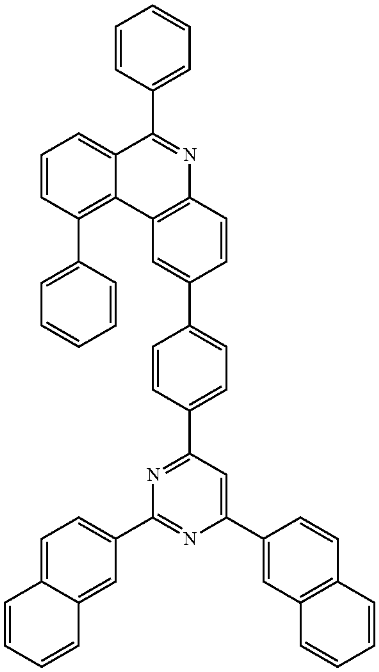
517
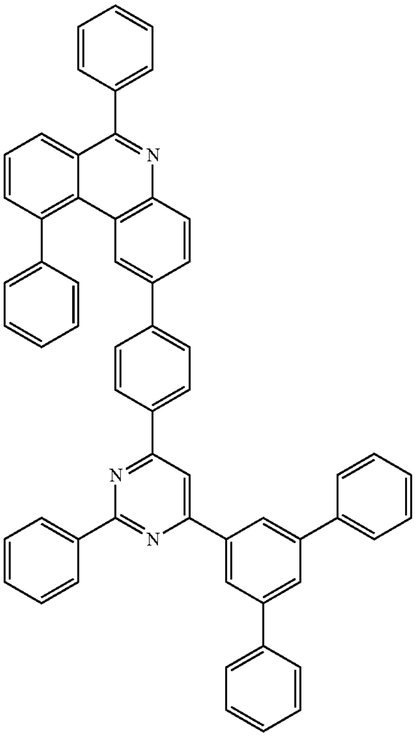
-continued
518
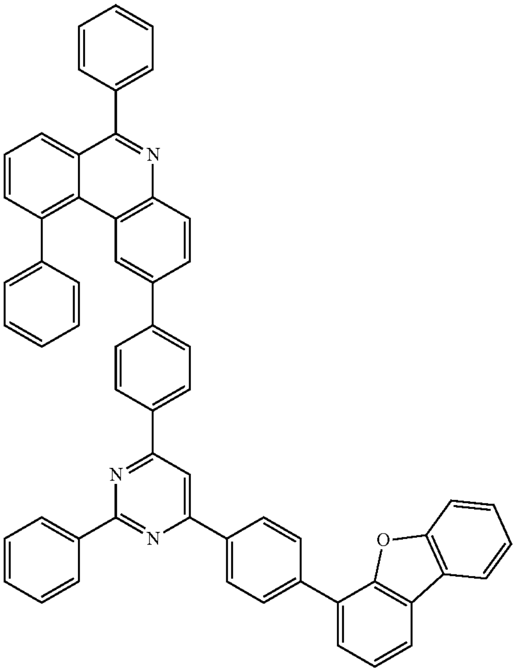
519
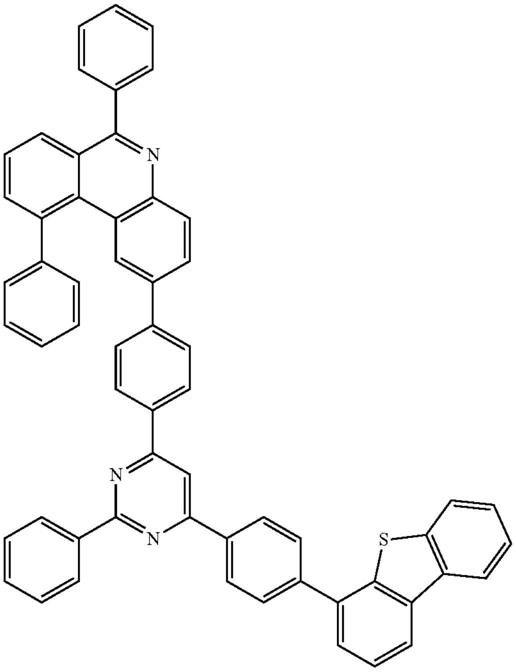

-continued
520
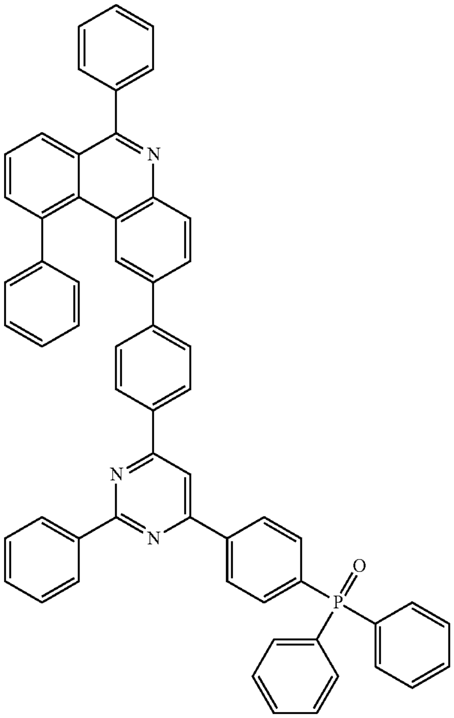
521
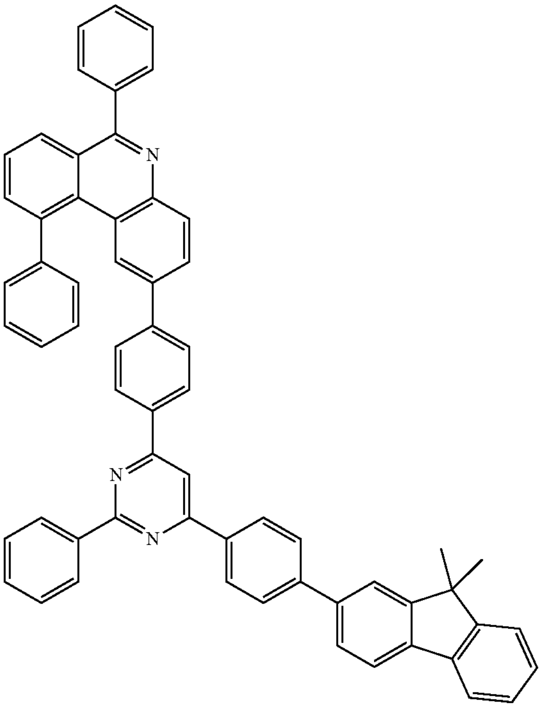
-continued
522
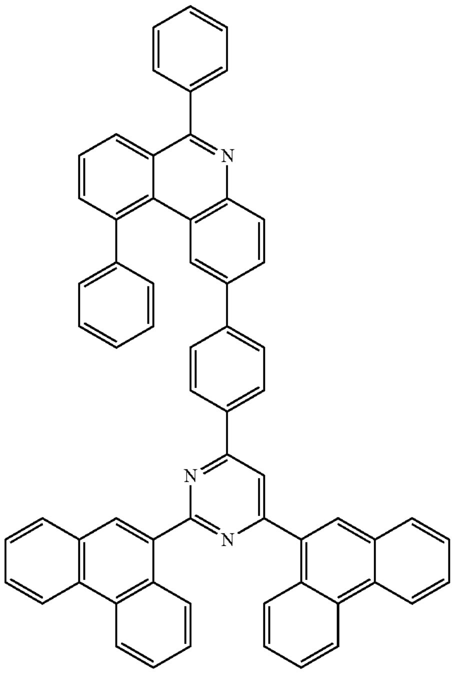
523
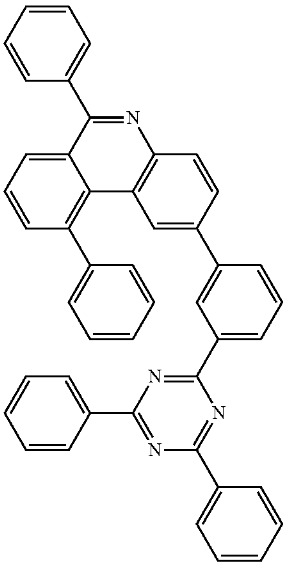

-continued
524
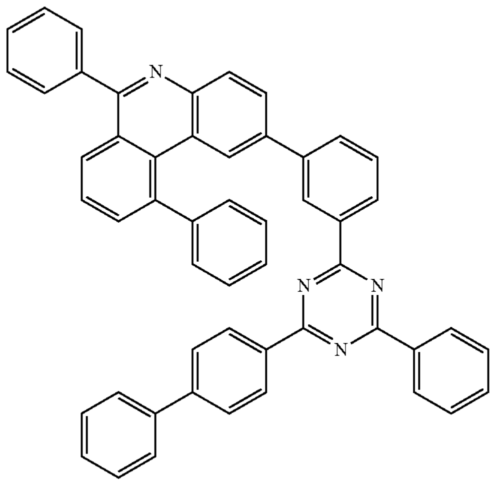
525
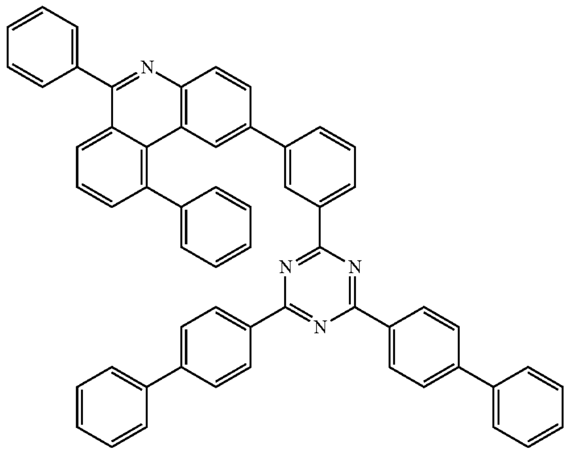
526
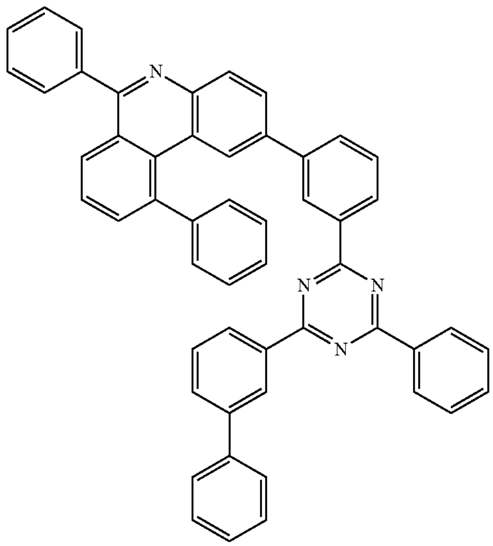
-continued
527
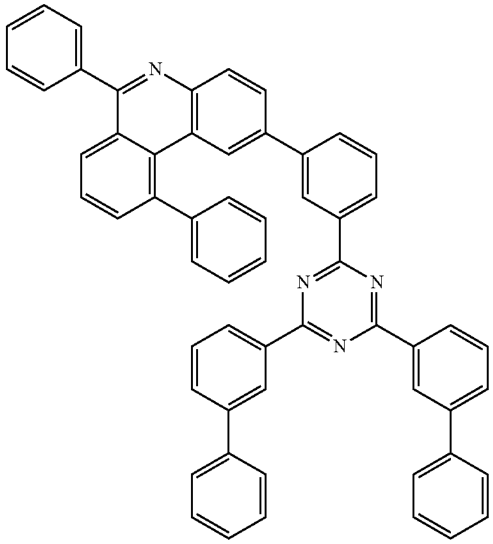
528
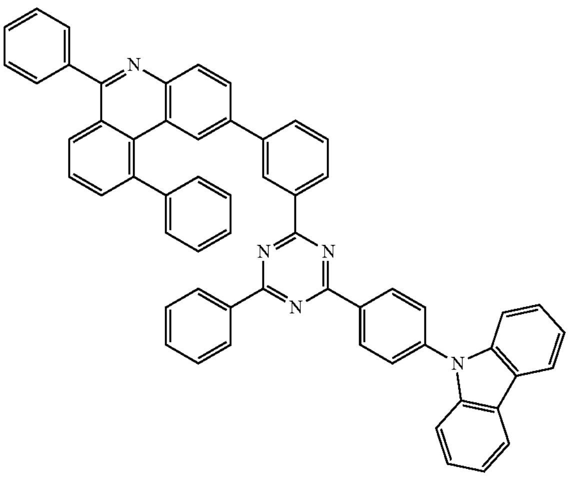
529
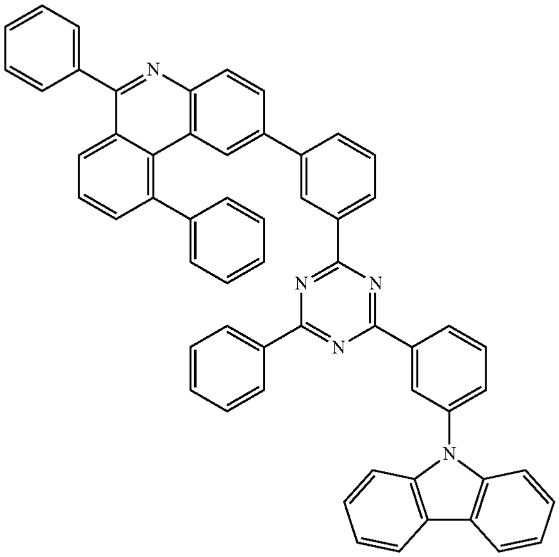

-continued
530
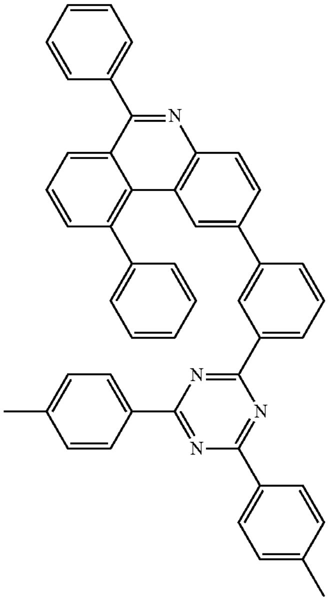
531
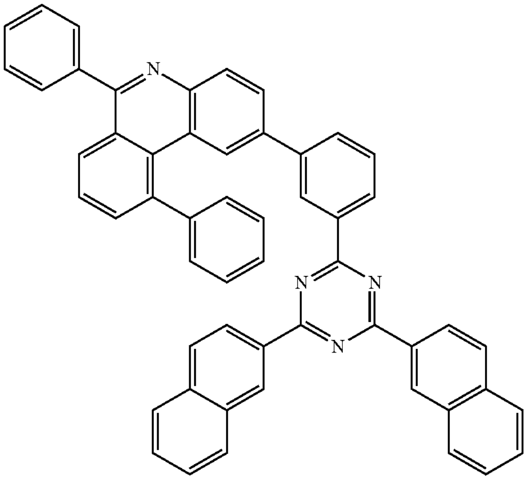
532
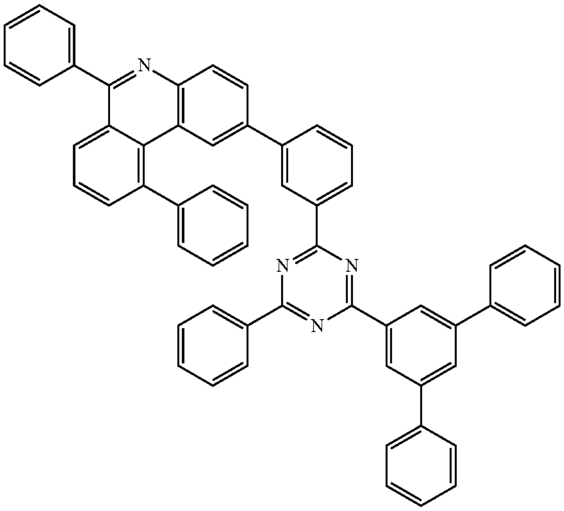
-continued
533
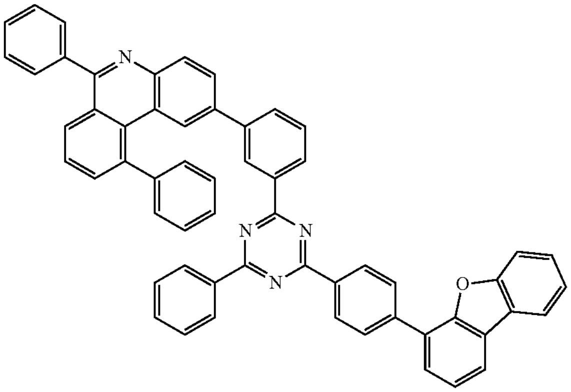
534
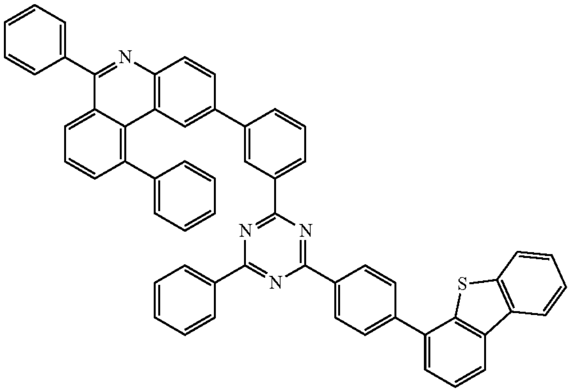
535
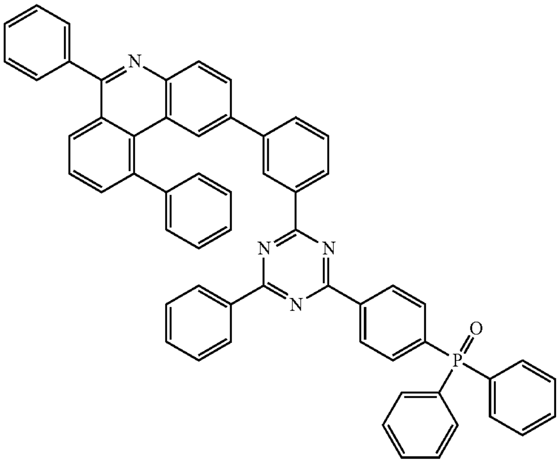

-continued
536
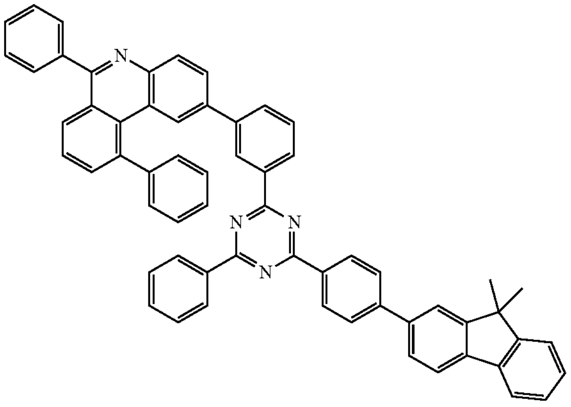
537
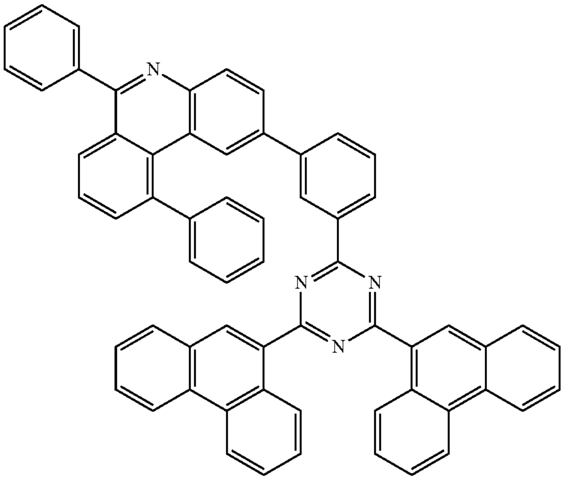
538
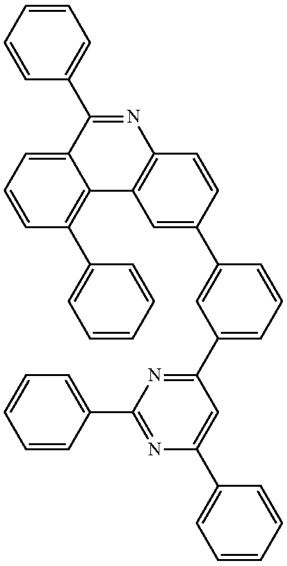
-continued
539
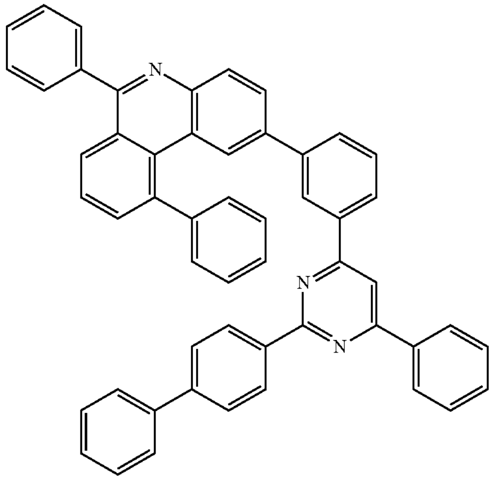
540
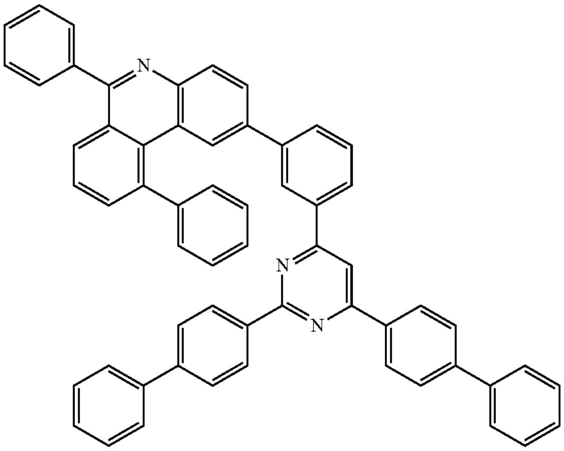
541
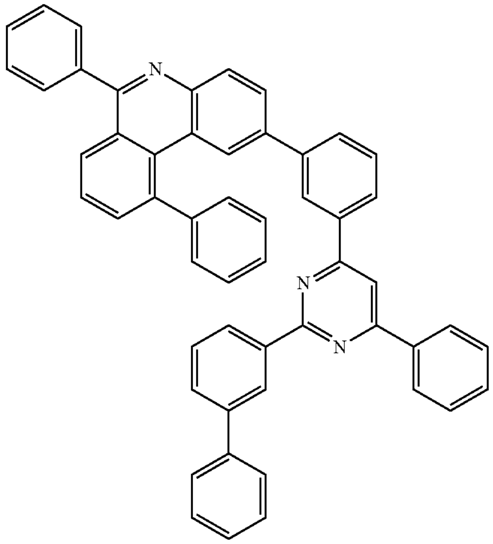

-continued
542
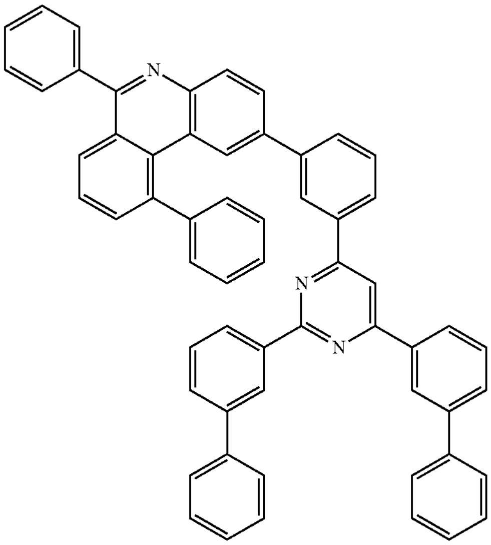
543
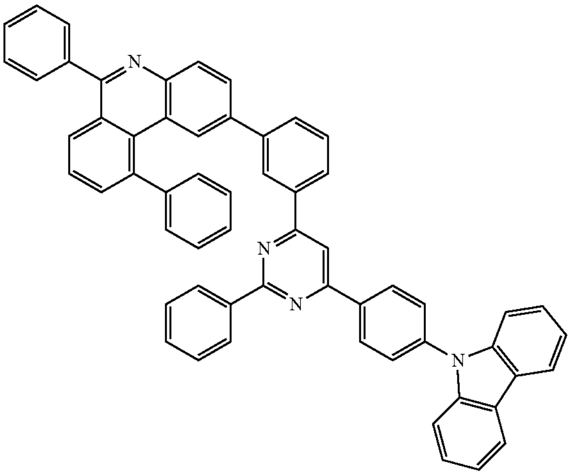
544
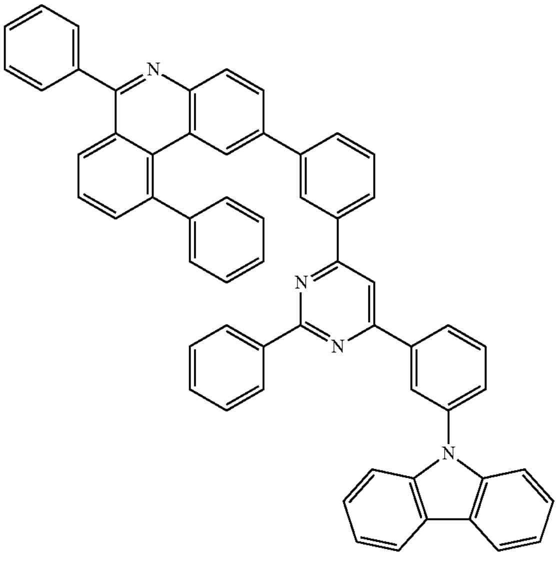
-continued
545
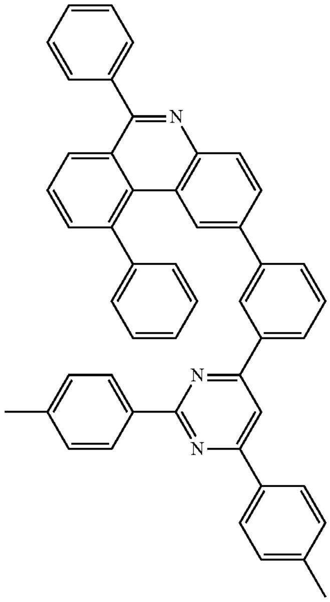
546
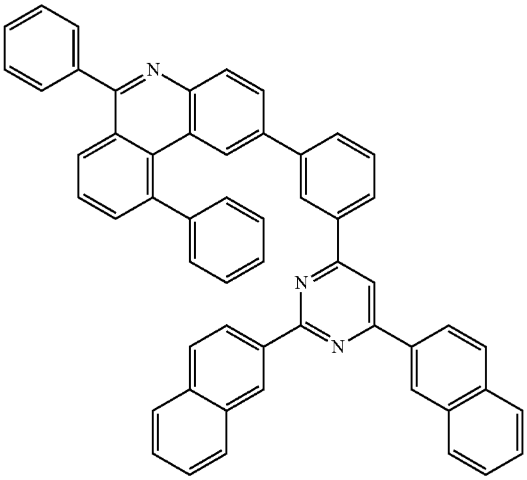
547
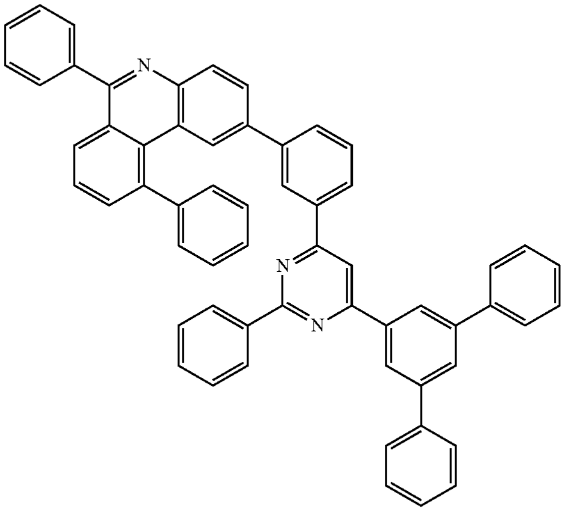

-continued
548
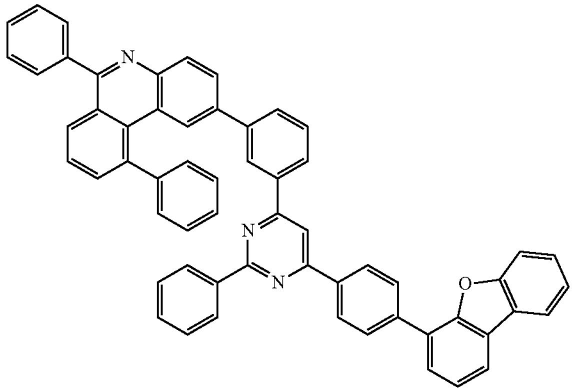
549
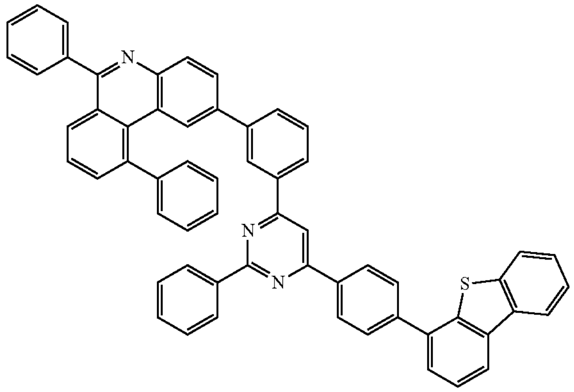
550
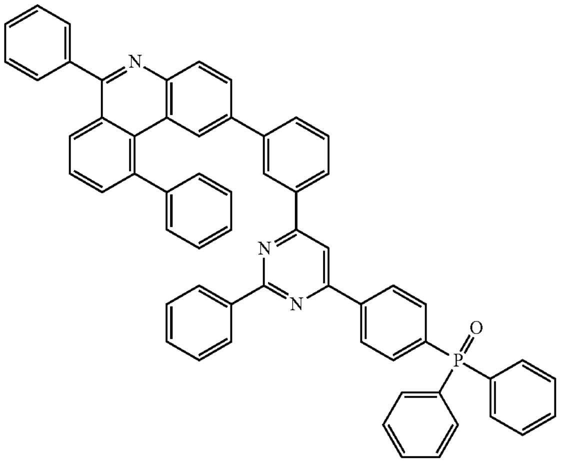
-continued
551
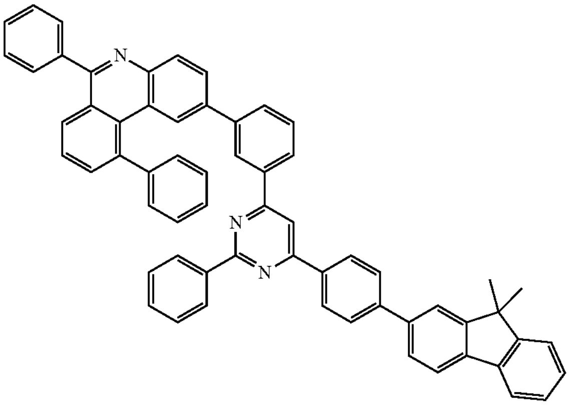
552
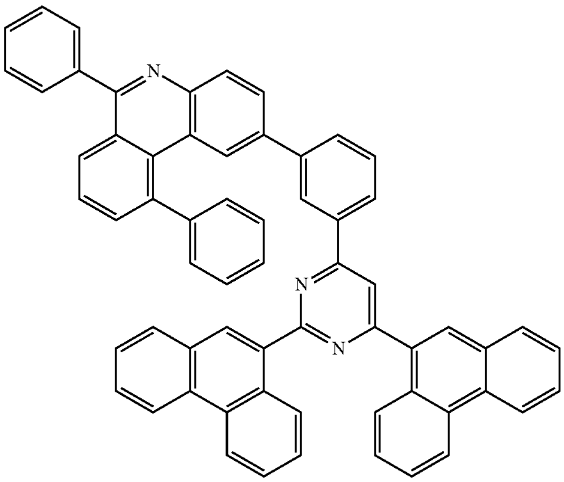
553
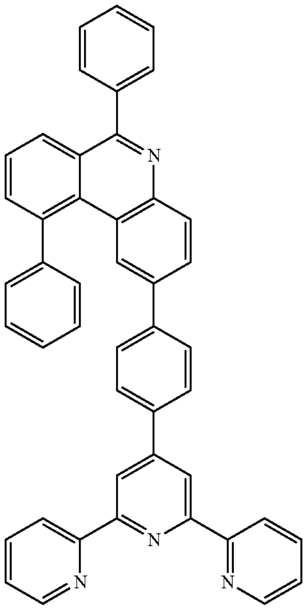

-continued
554
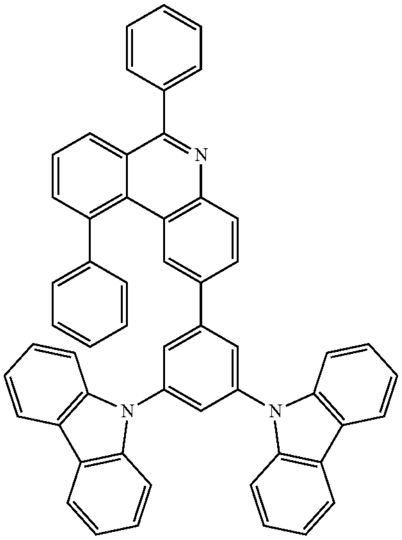
555
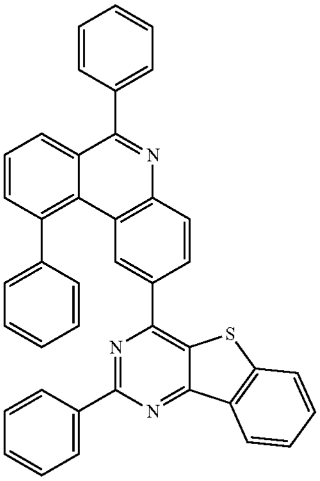
556
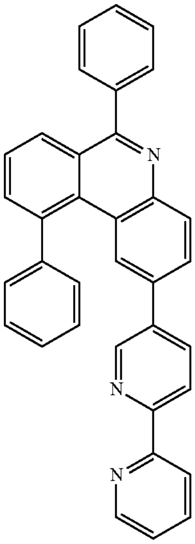
-continued
557
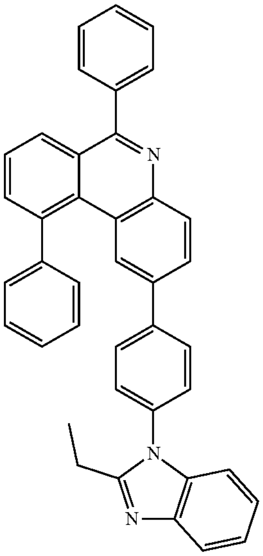
558
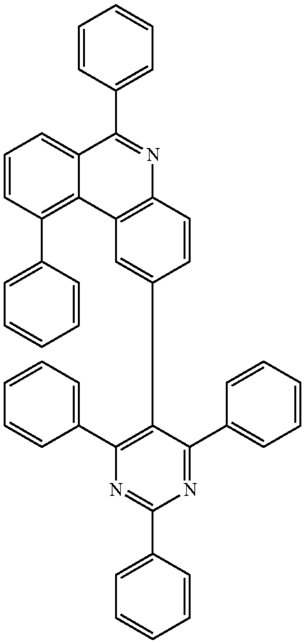

-continued
559
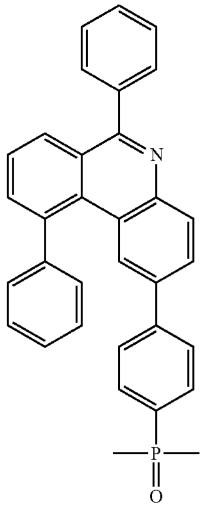
560
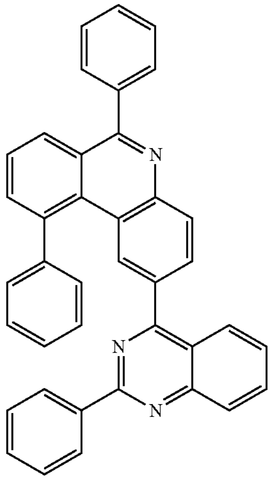
561
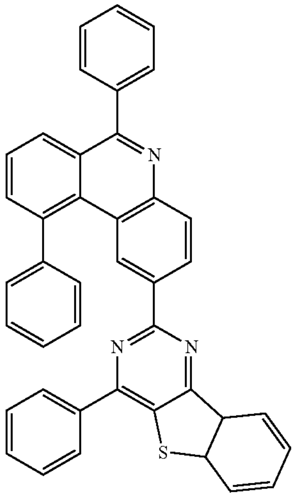
-continued
562
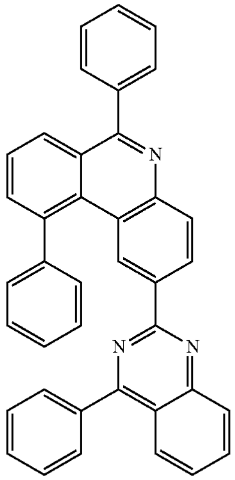
563
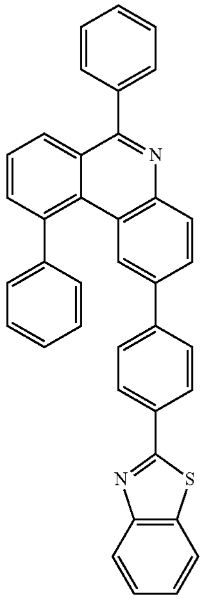

-continued
564
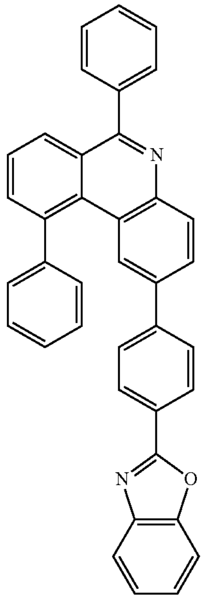
565
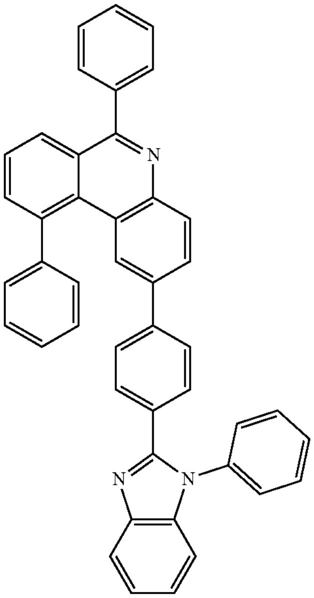
-continued
566
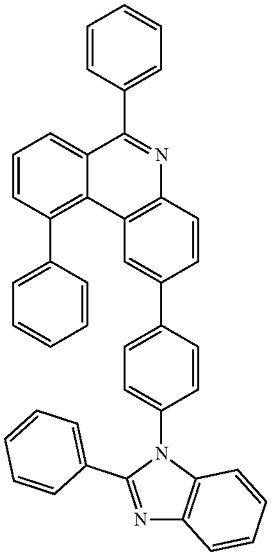
567
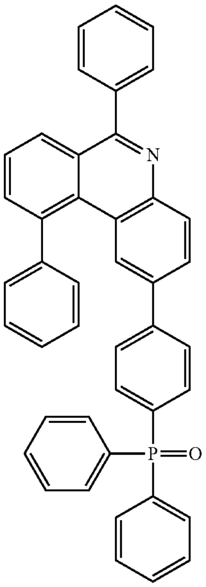
568
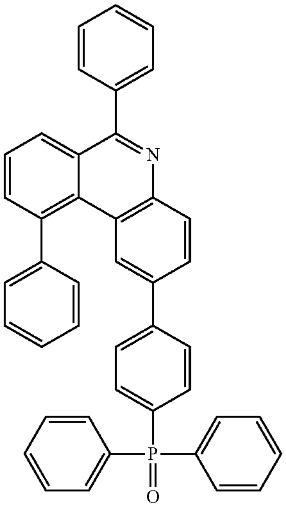

-continued
569
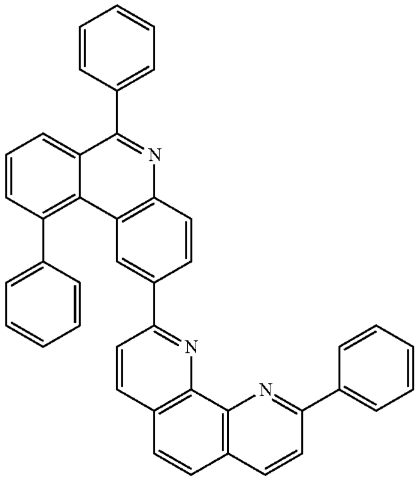
570
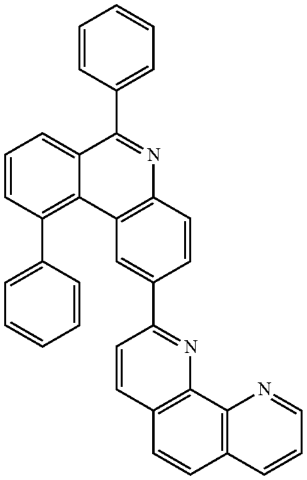
571
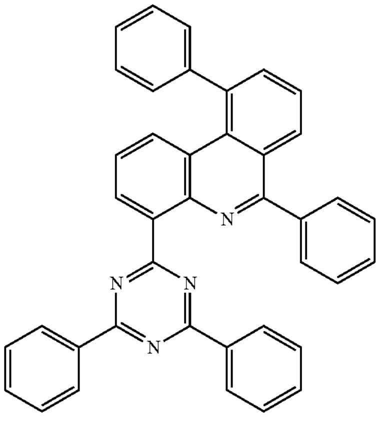
-continued
572
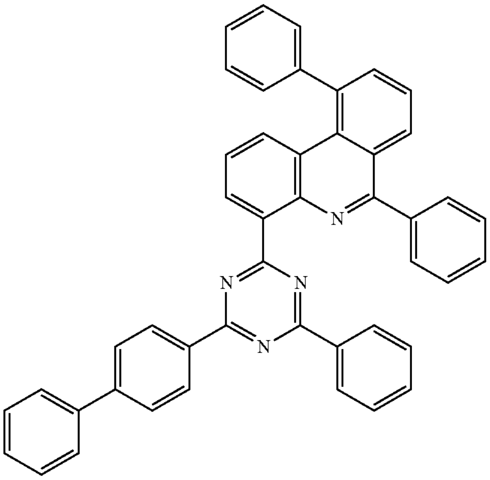
573
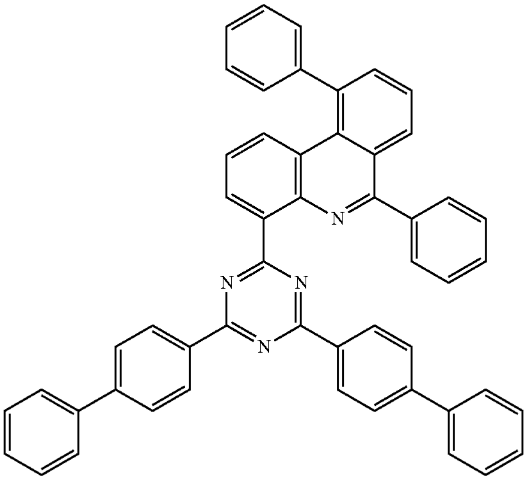
574
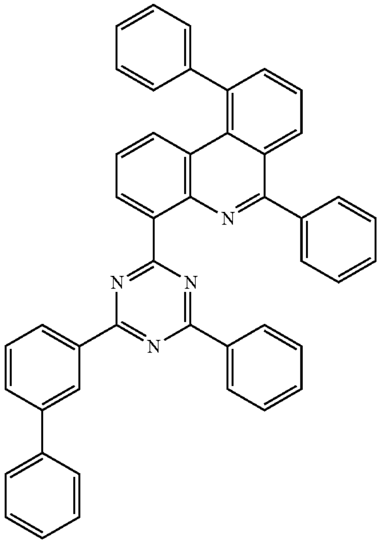

575
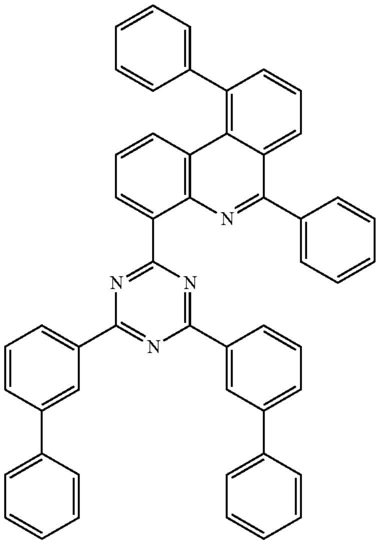
576
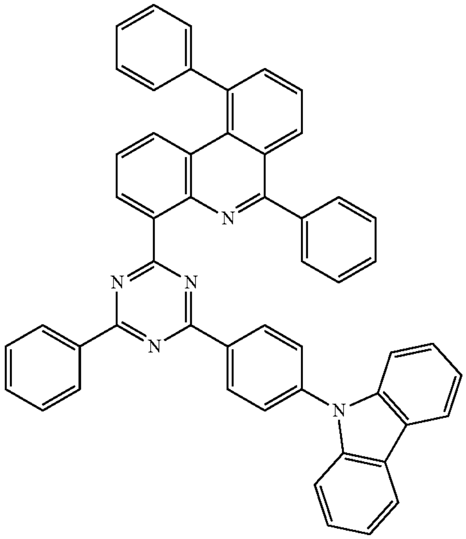
577
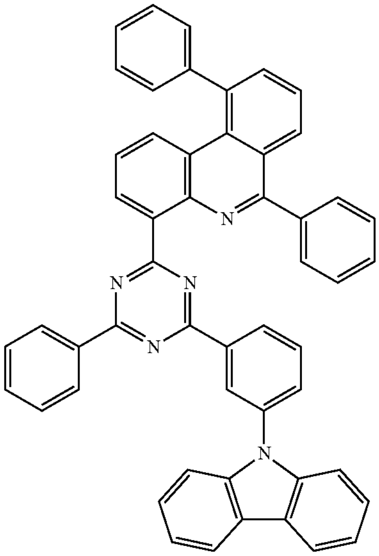
578
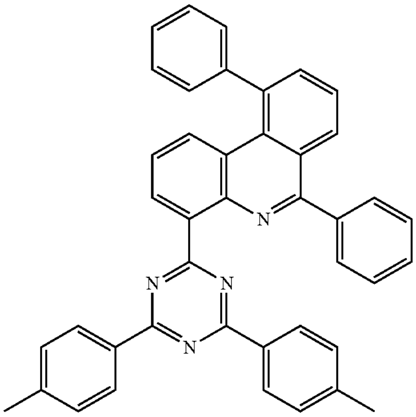
579
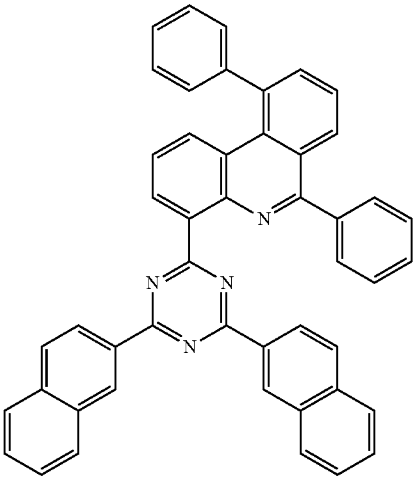
580
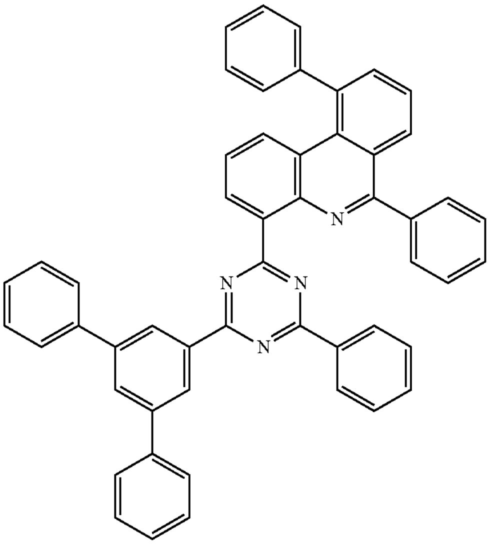

-continued
581
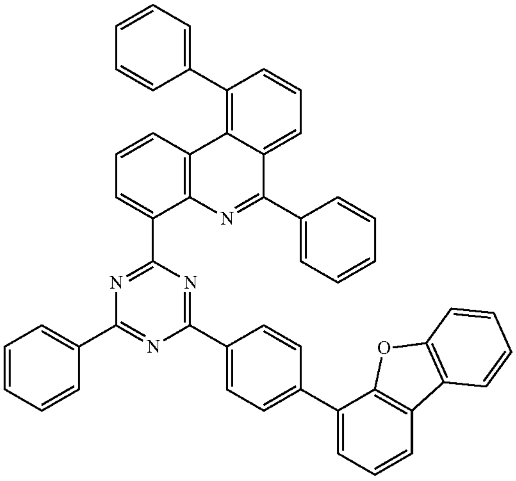
582
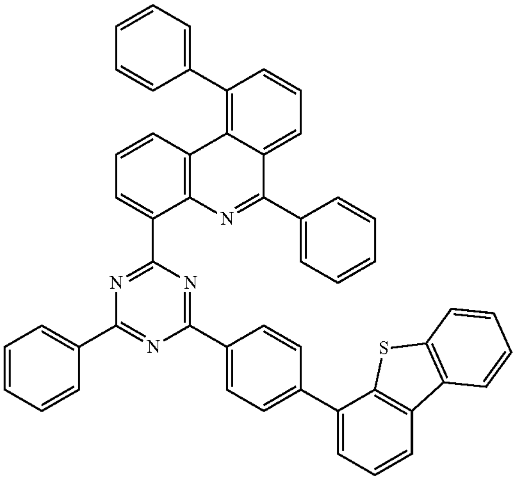
583
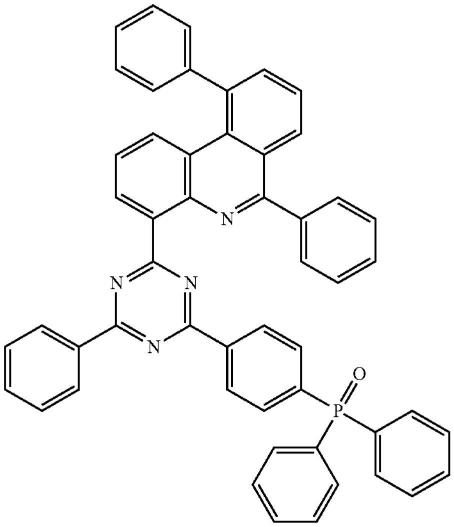
-continued
584
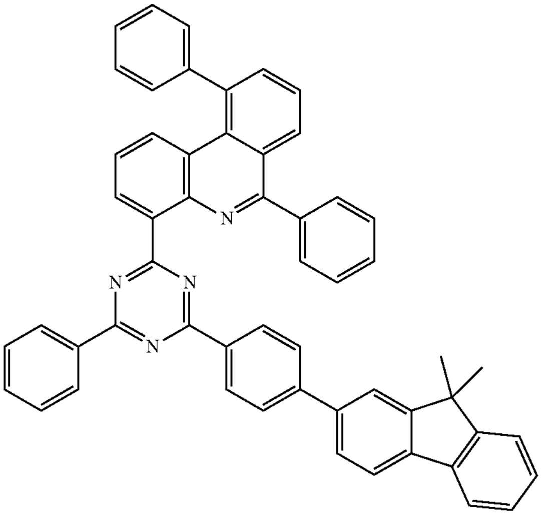
585
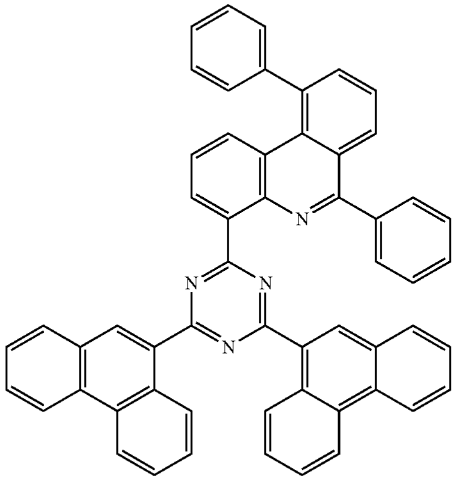
586
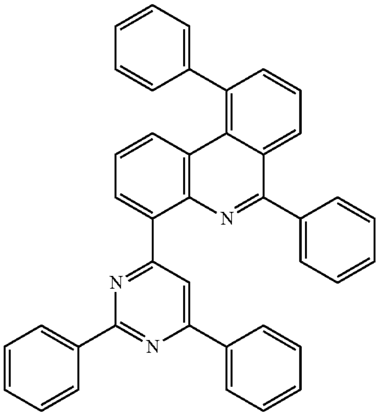

-continued
587
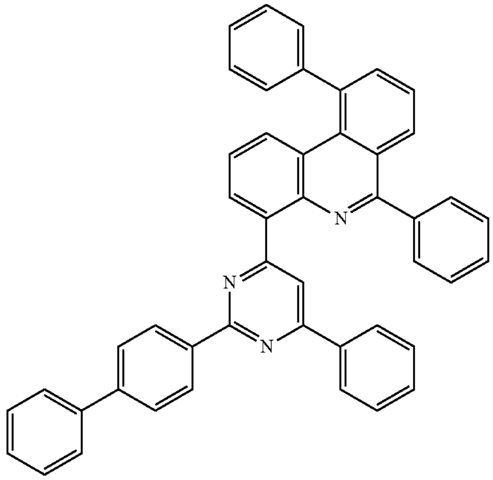
588
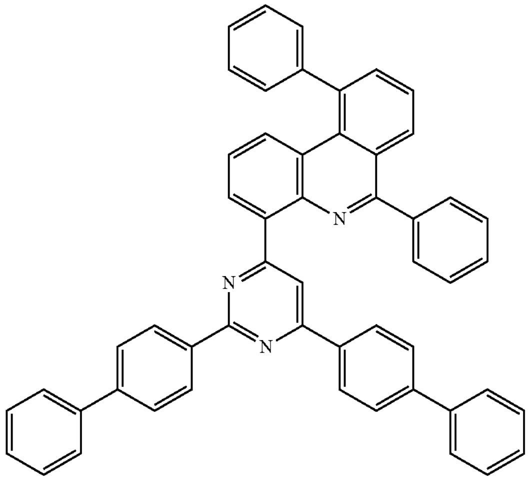
589
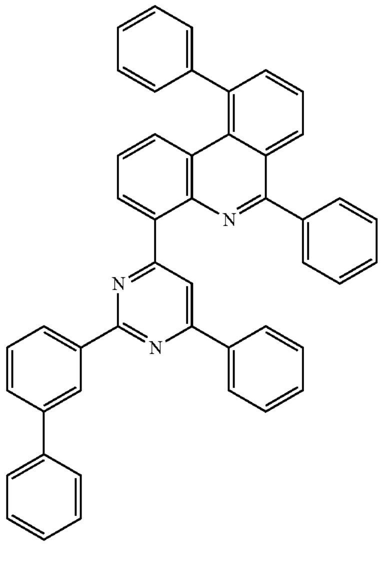
-continued
590
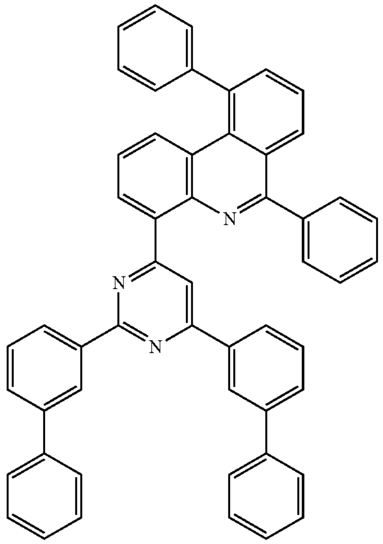
591
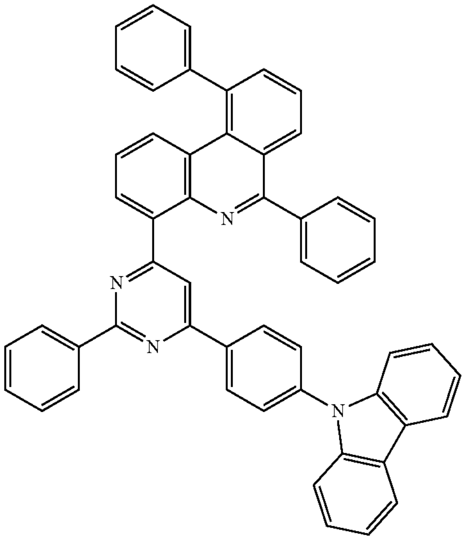
592
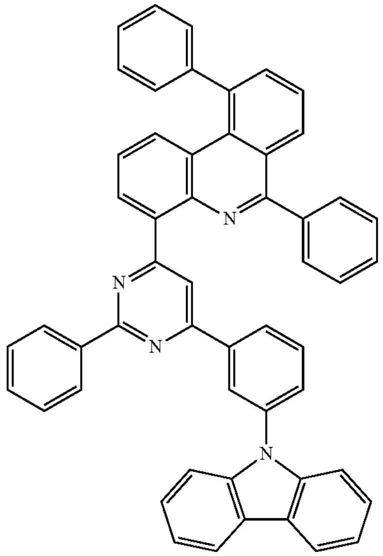

-continued
593
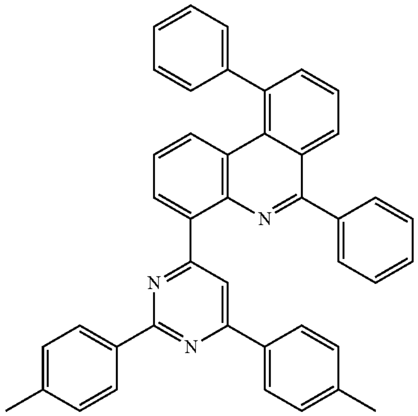
594
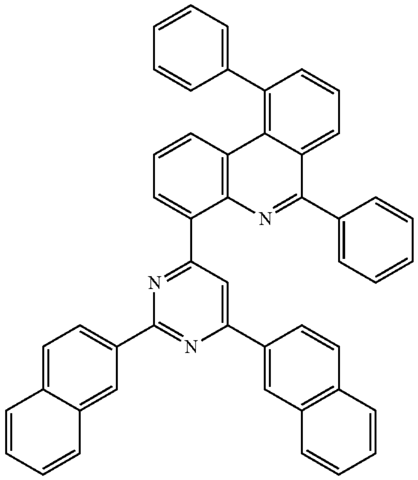
595
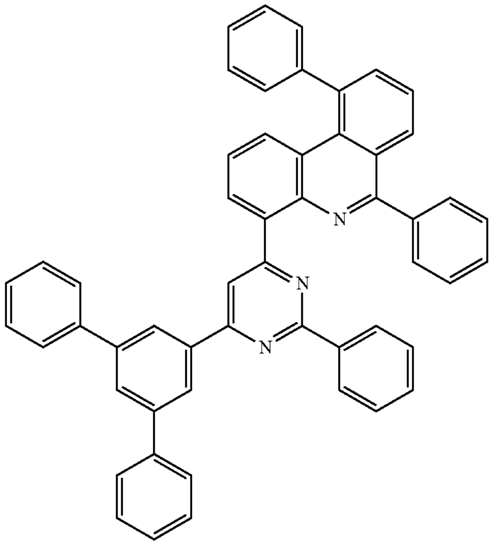
-continued
596
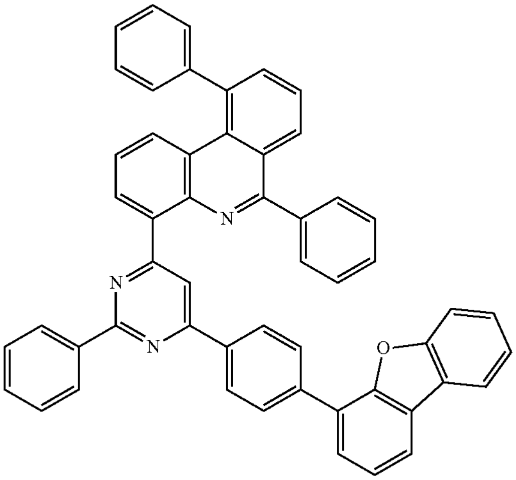
597
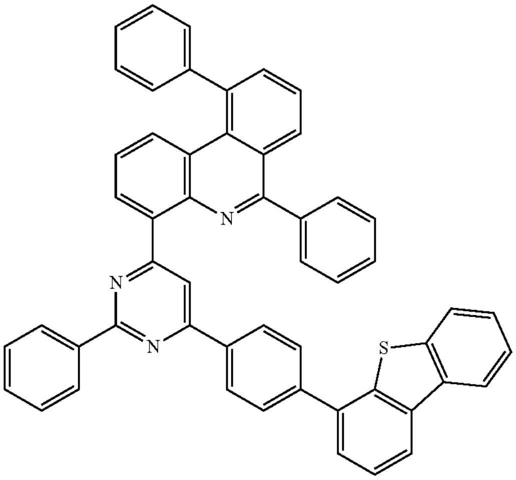
598
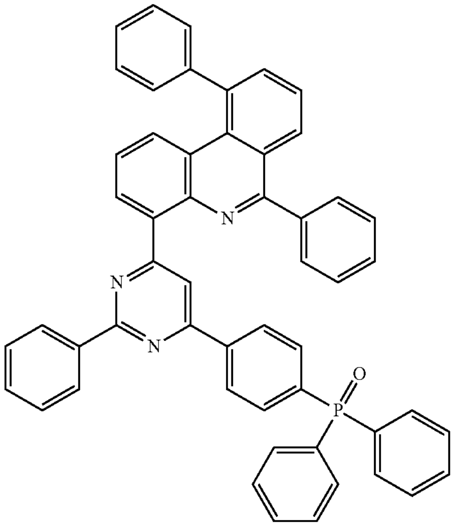

-continued
599
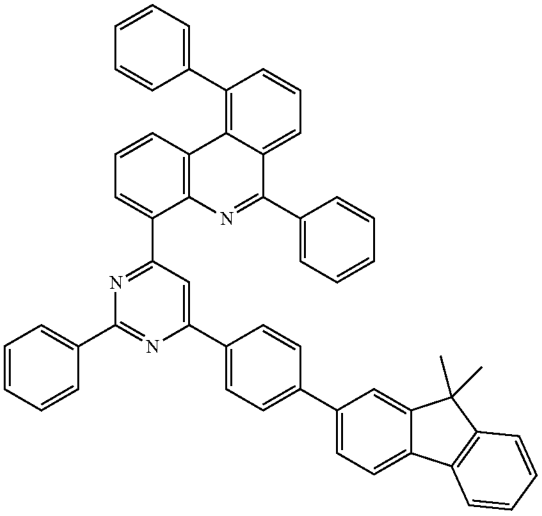
600
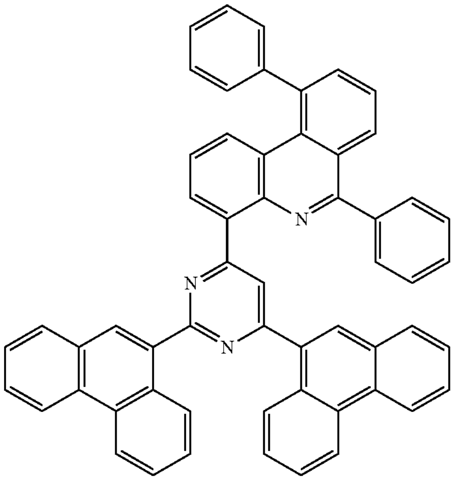
601
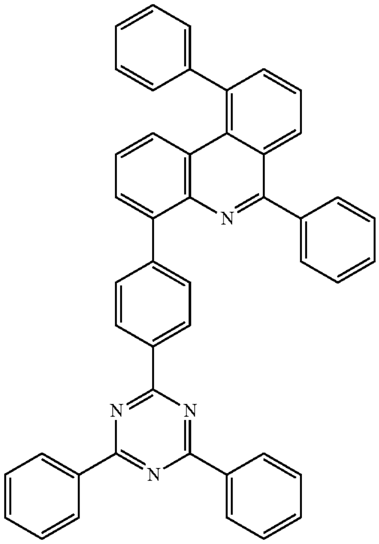
-continued
602
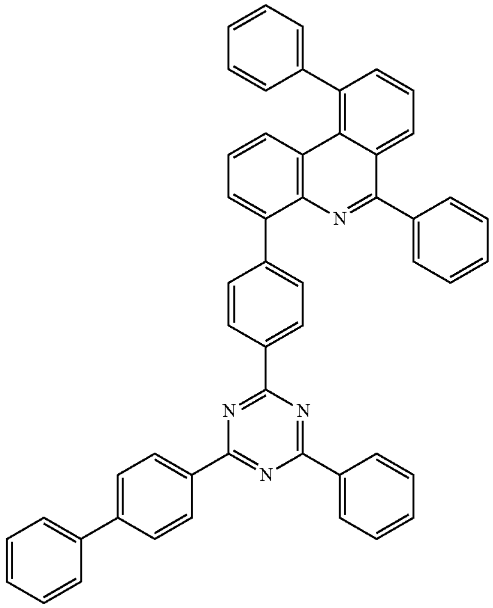
603
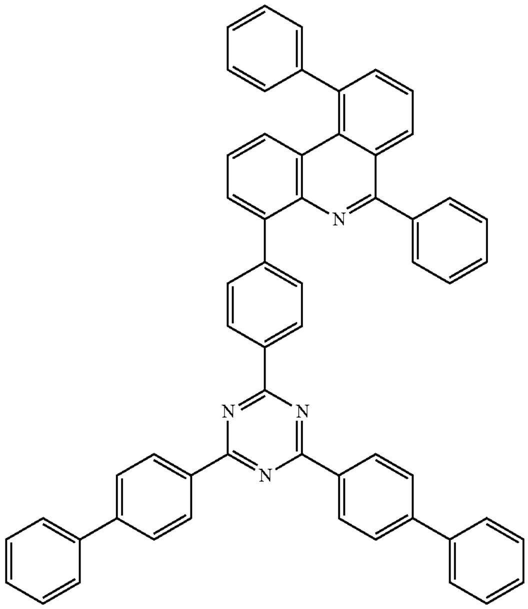

604
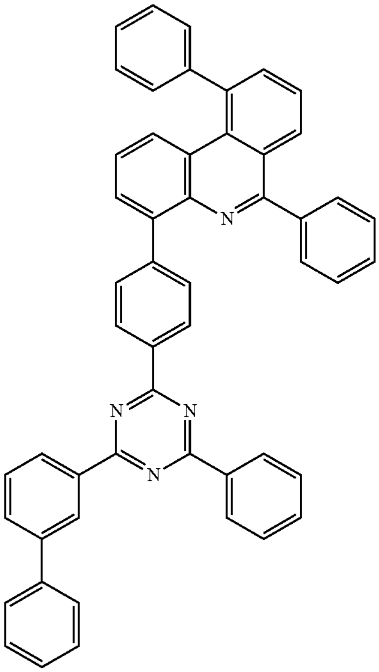
605
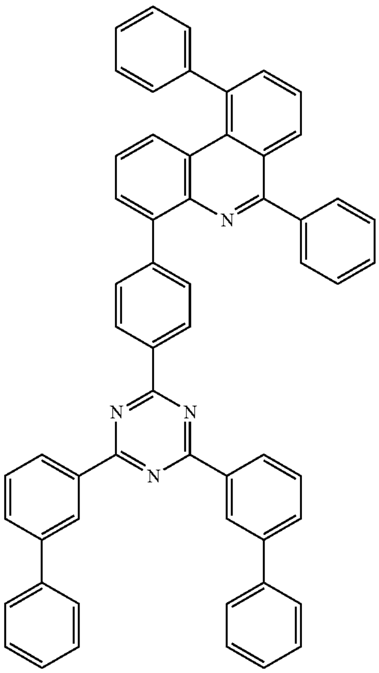
606
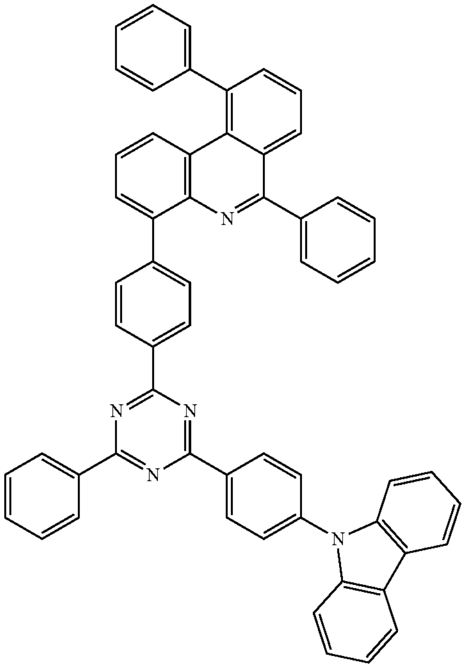
607
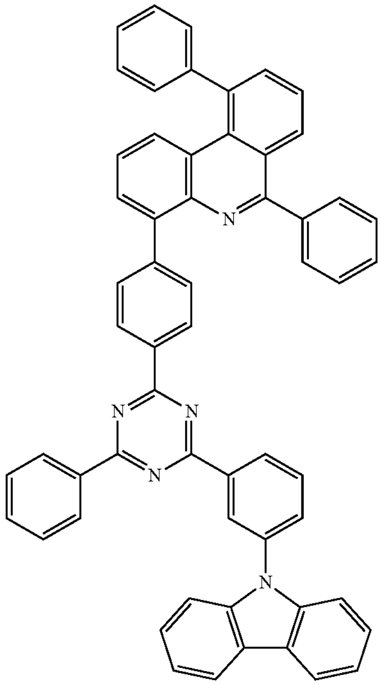

-continued
608
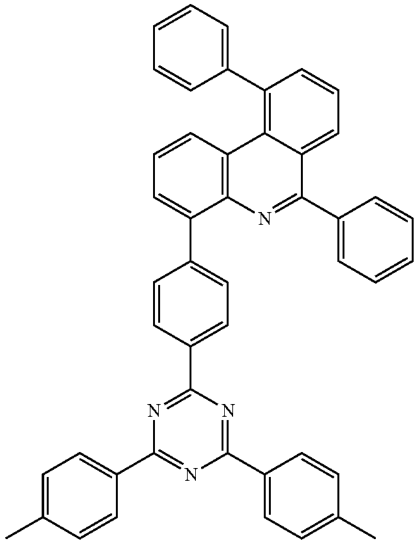
609
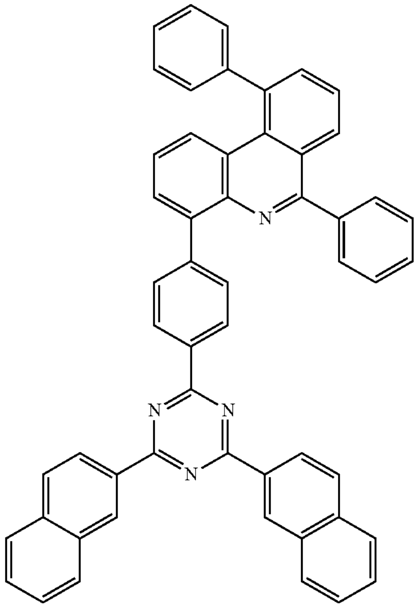
-continued
610
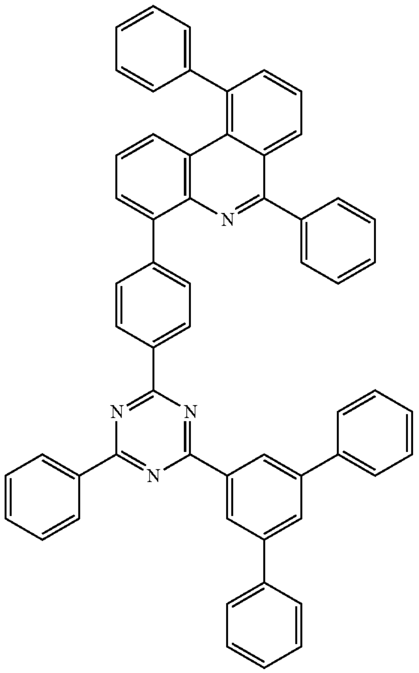
611
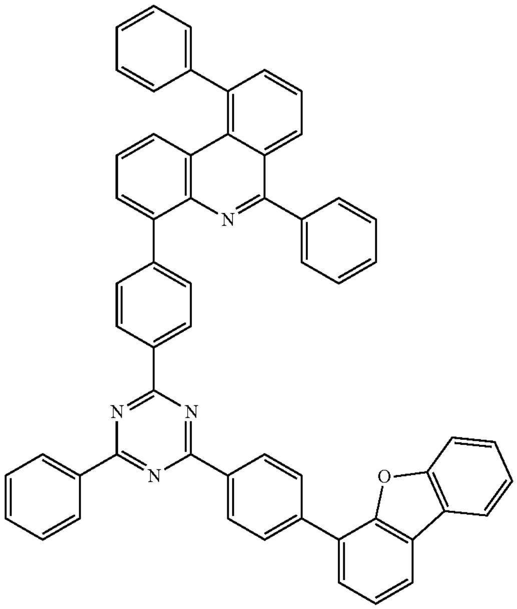

612
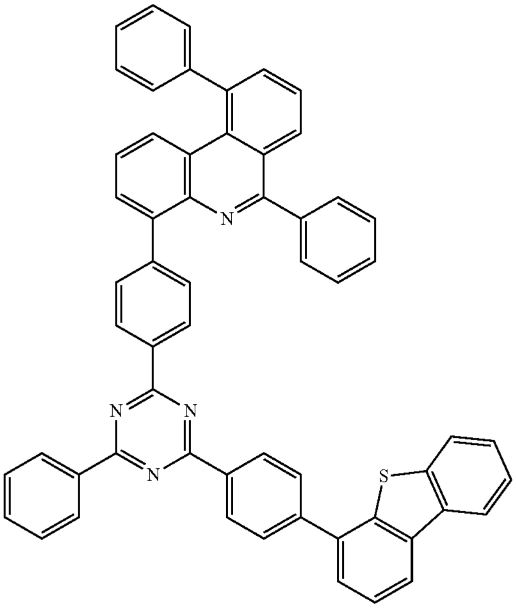
613
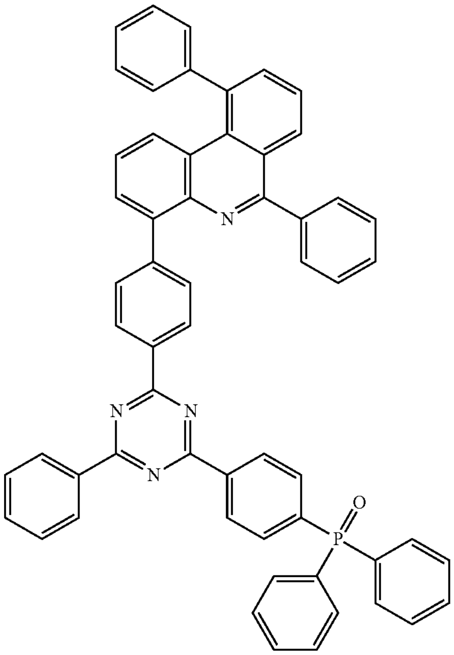
614
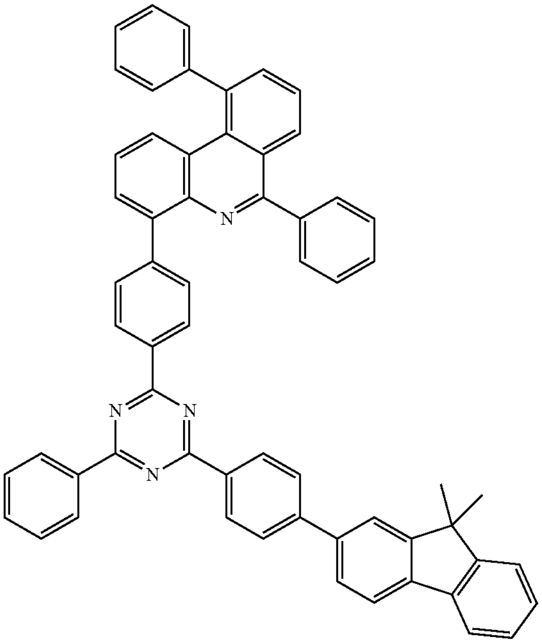
615
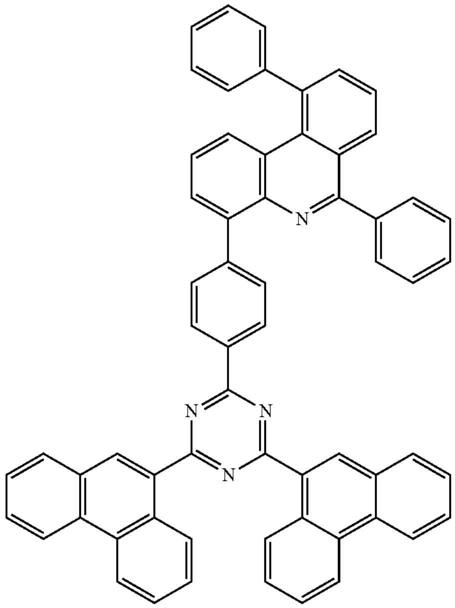

616
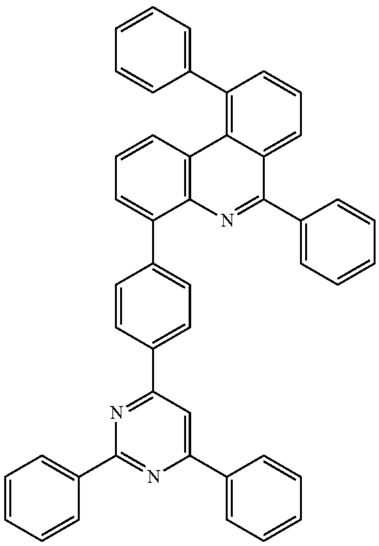
617
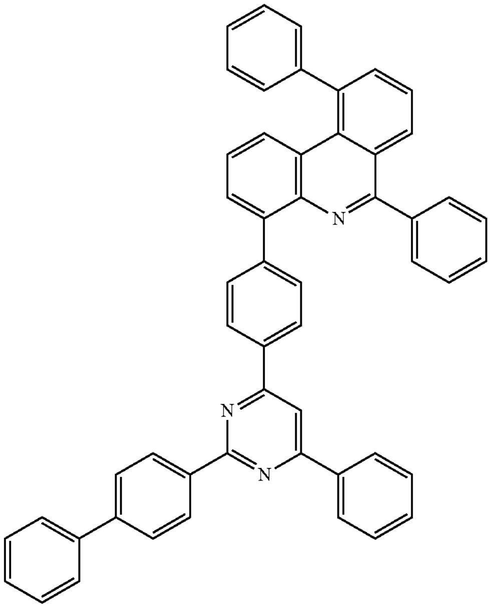
618
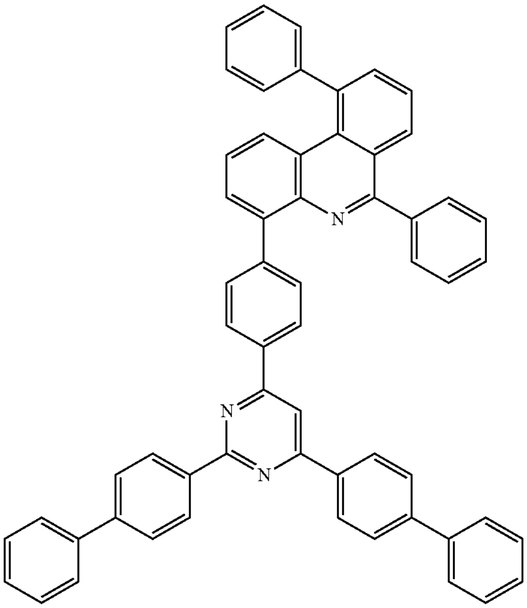
619
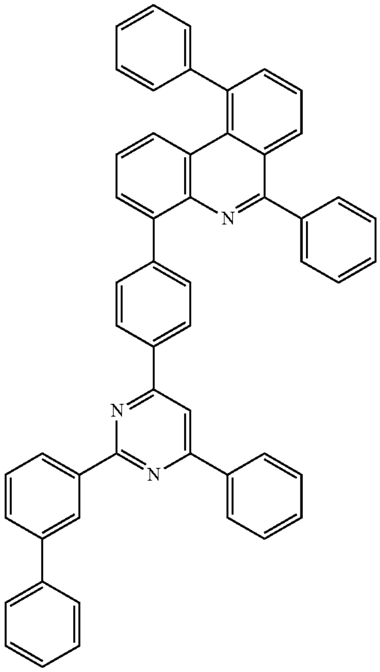

-continued
620
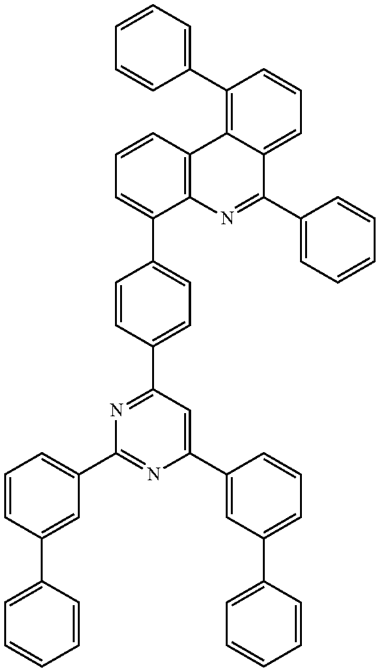
621
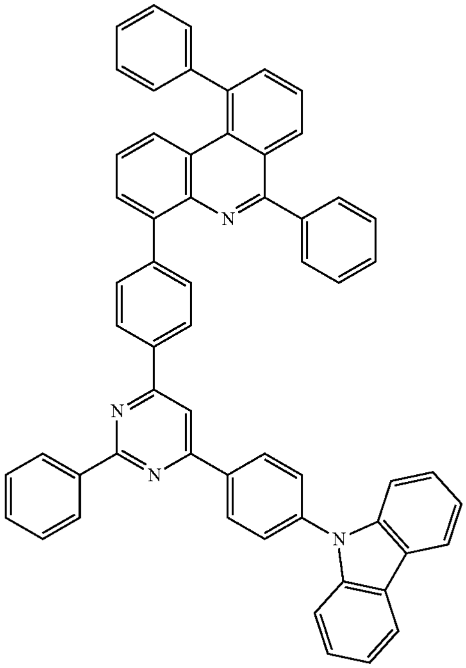
-continued
622
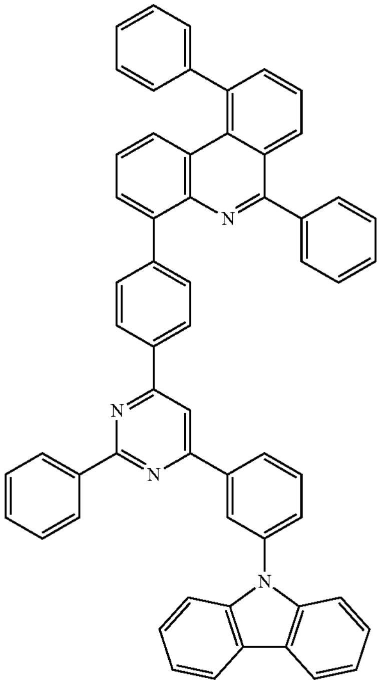
623
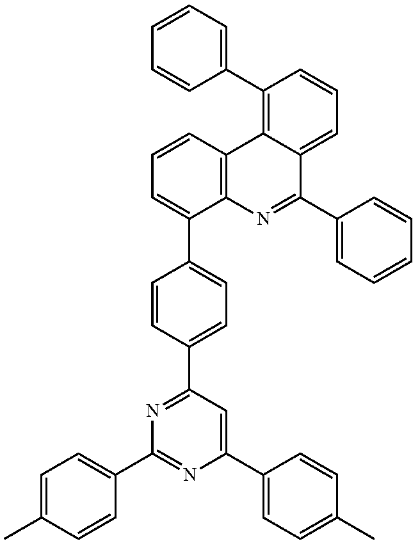

-continued
624
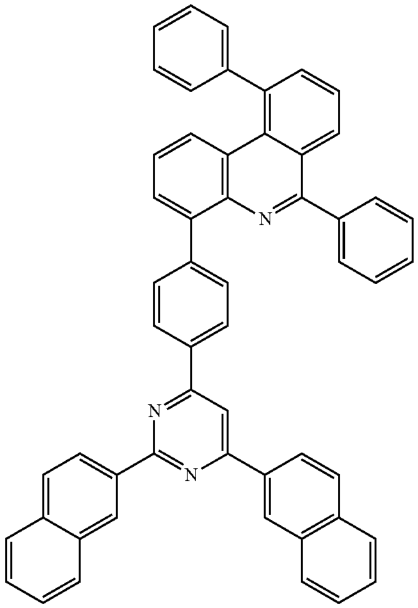
625
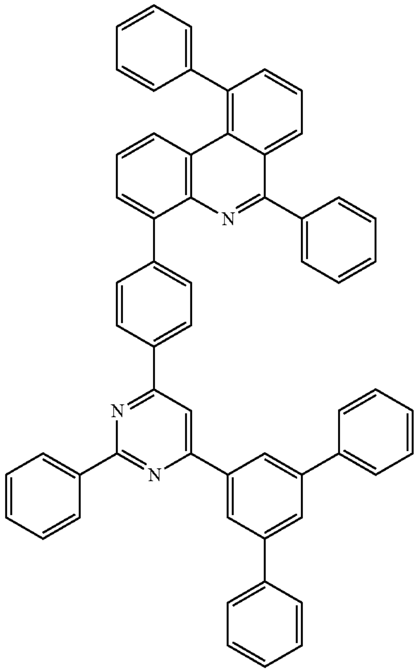
-continued
626
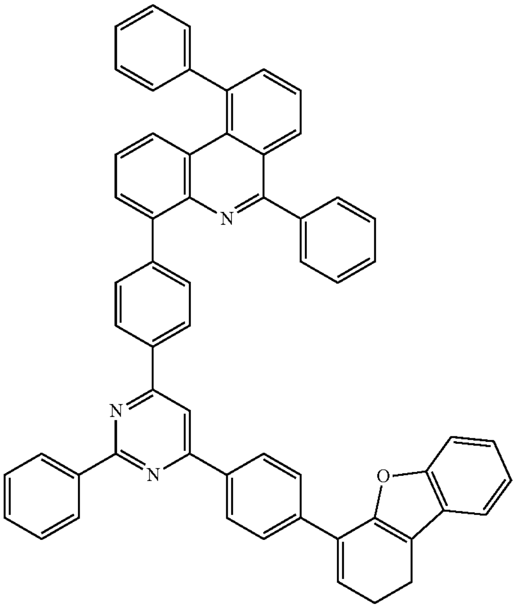
627
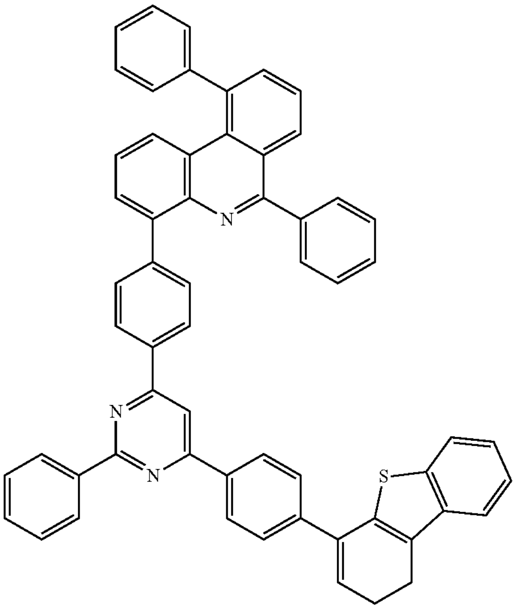

-continued
628
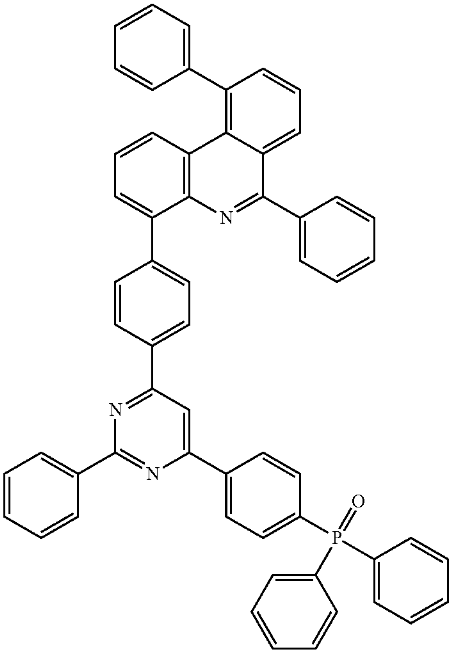
629
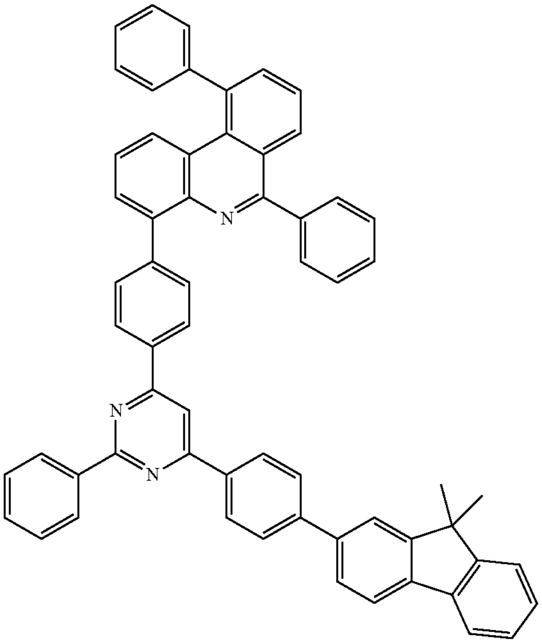
-continued
630
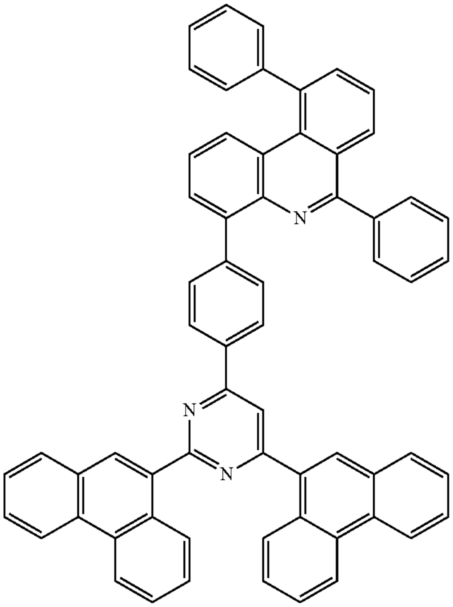
631
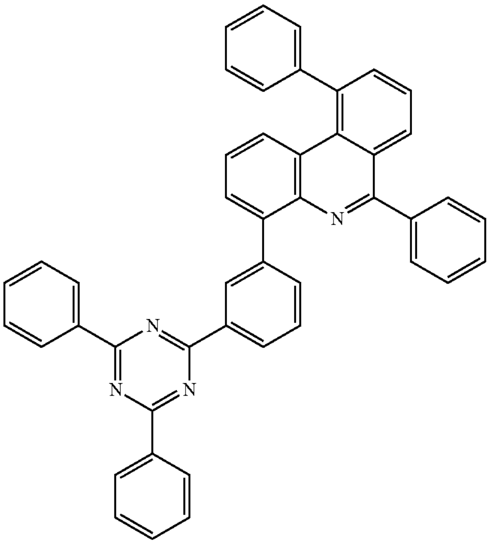
632
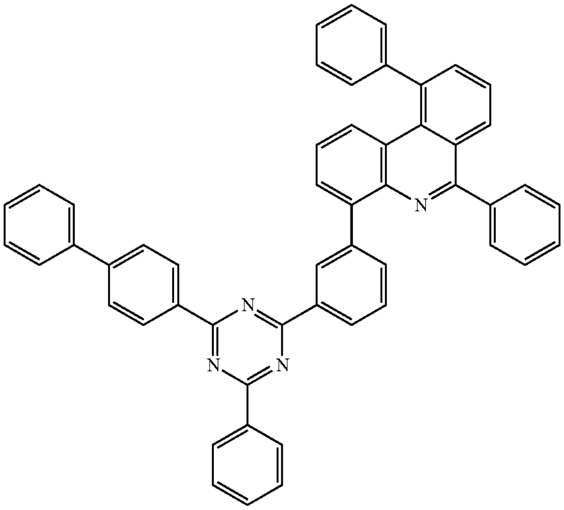

-continued
633
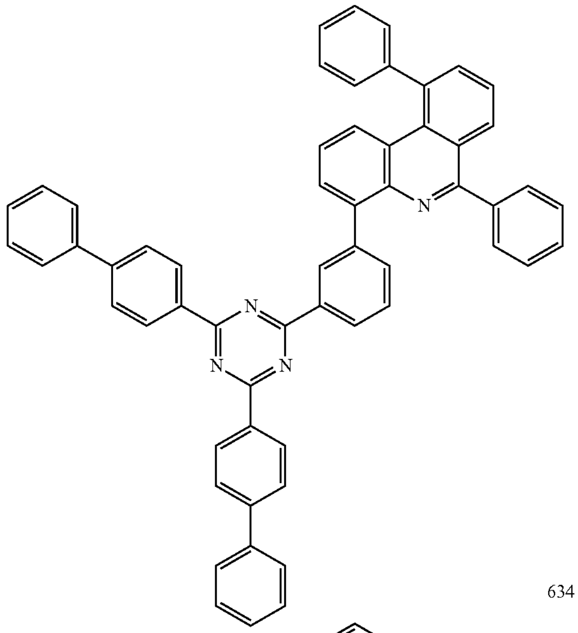
634
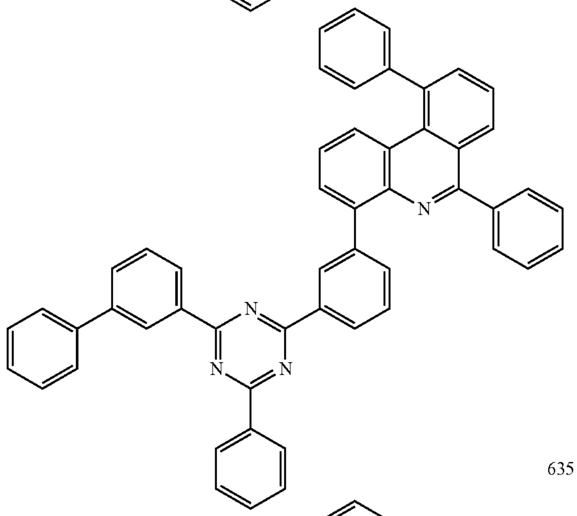
635
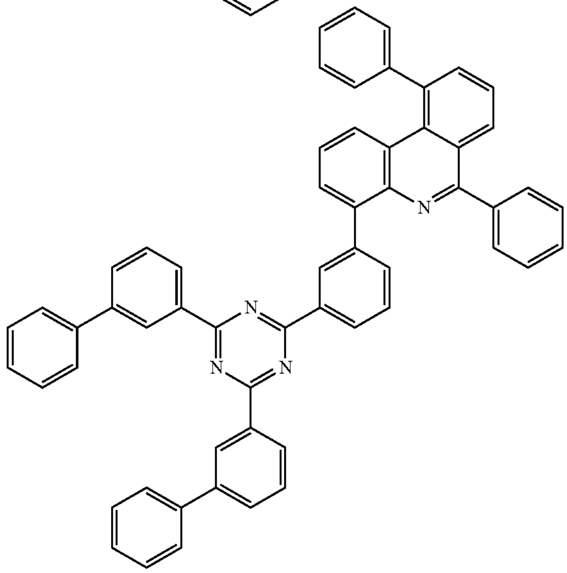
-continued
636
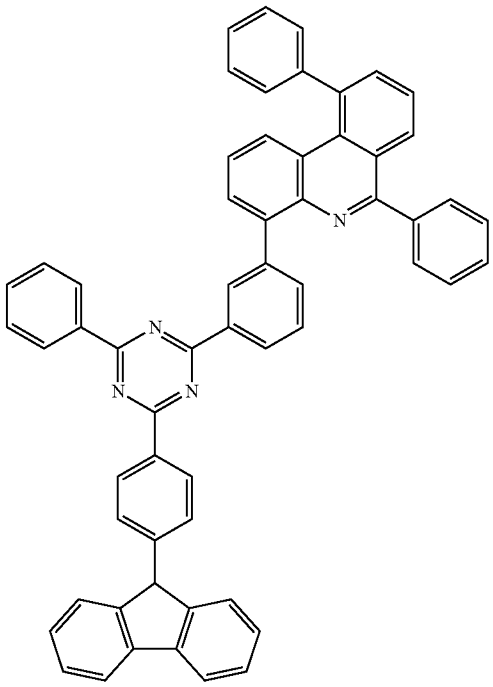
637
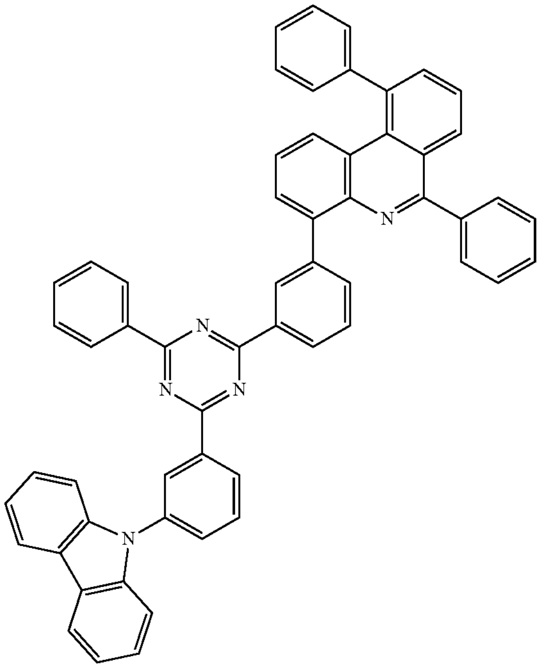

-continued
638
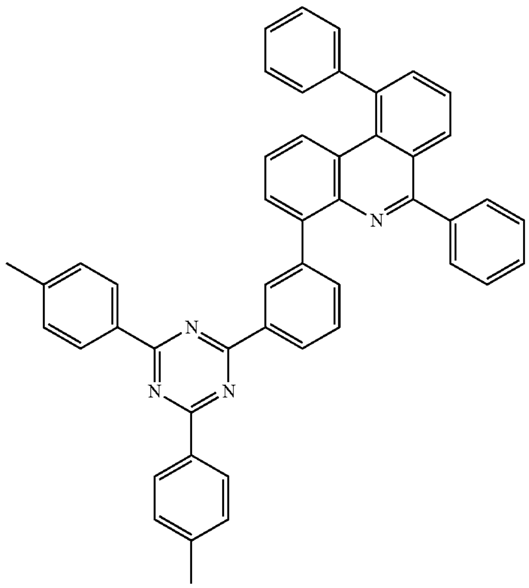
639
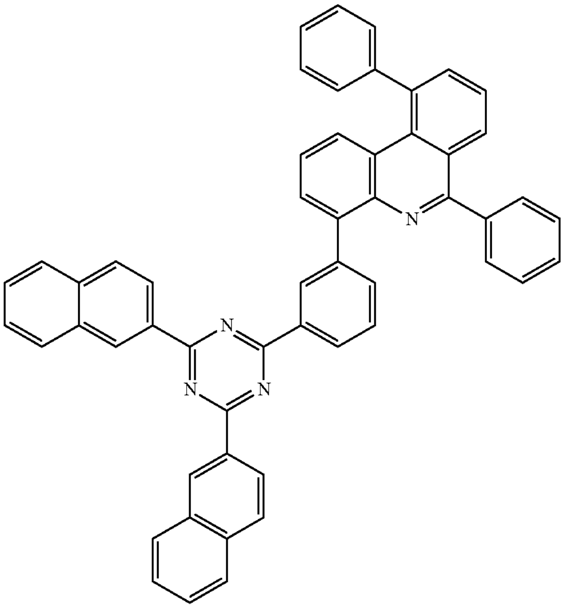
-continued
640
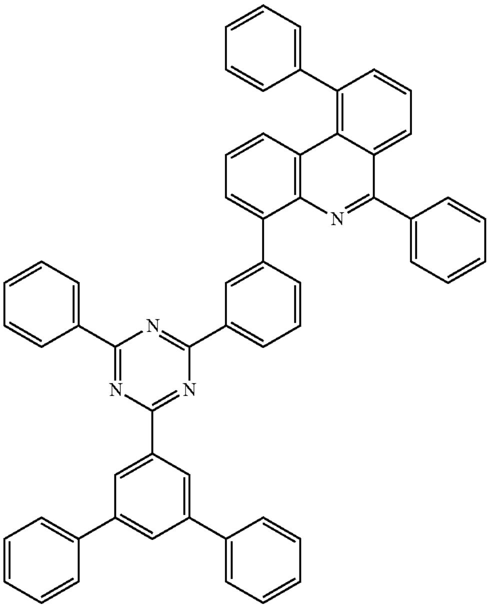
641
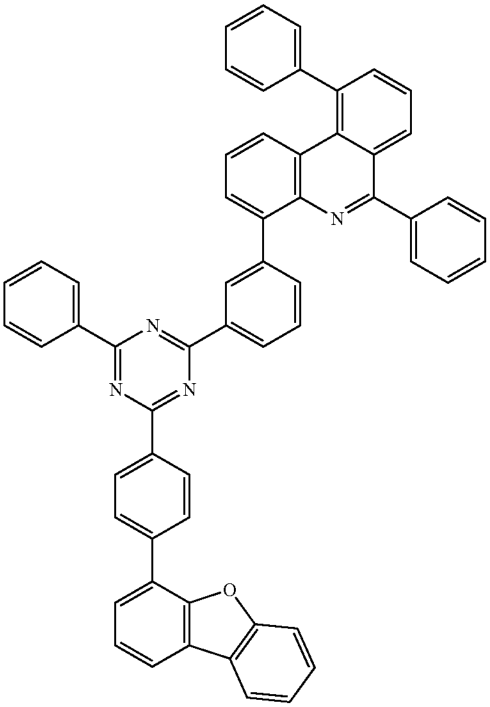

-continued
642
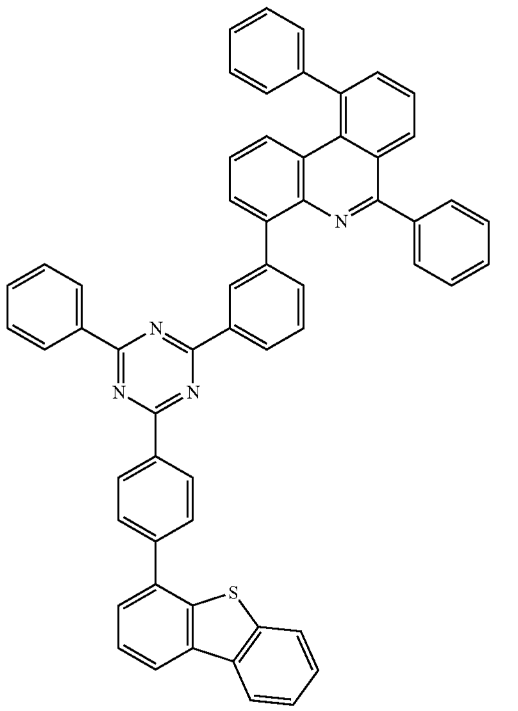
643
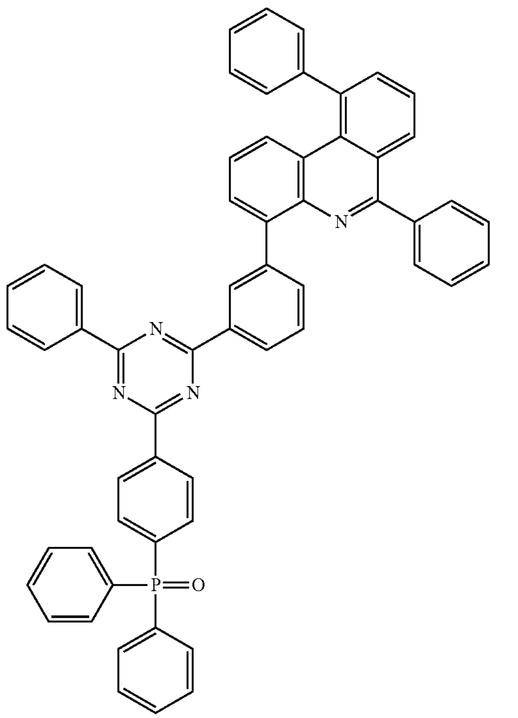
-continued
644
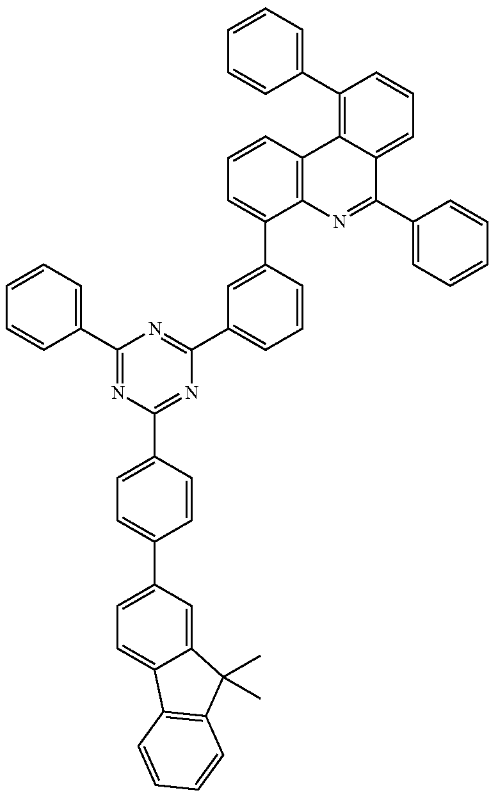
645
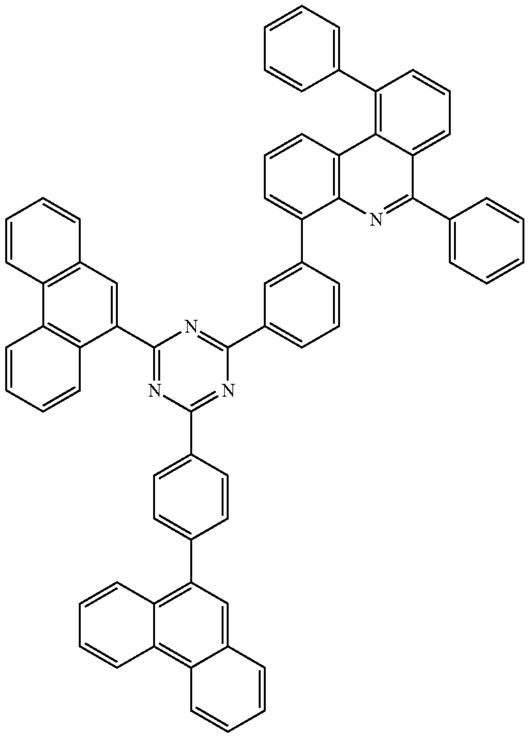

-continued
646
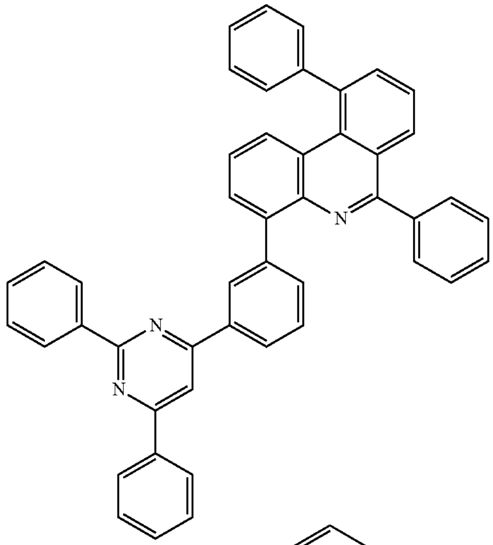
647
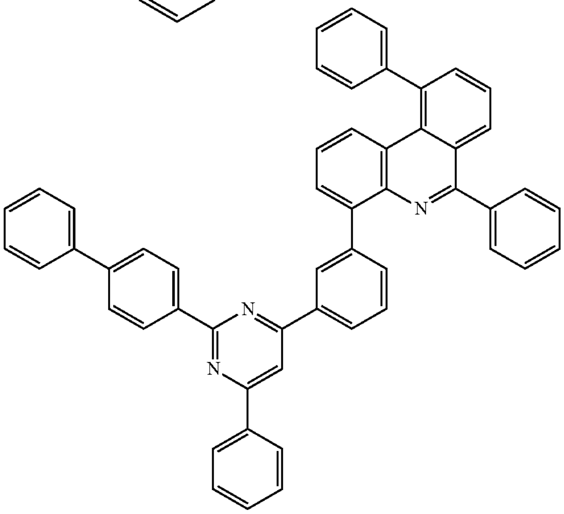
648
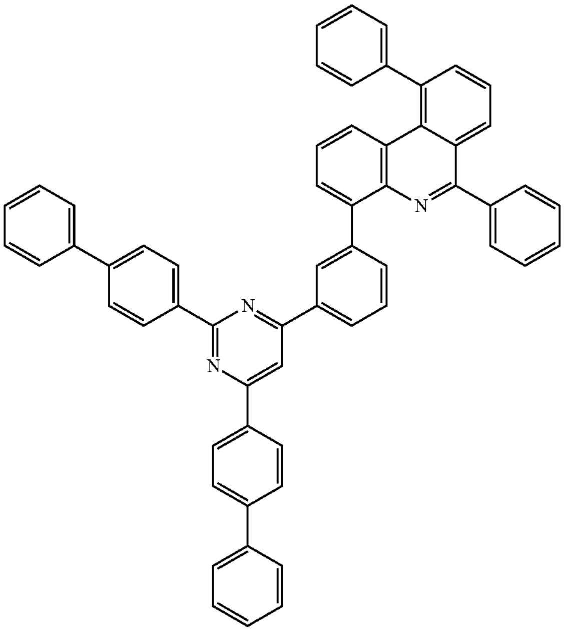
-continued
649
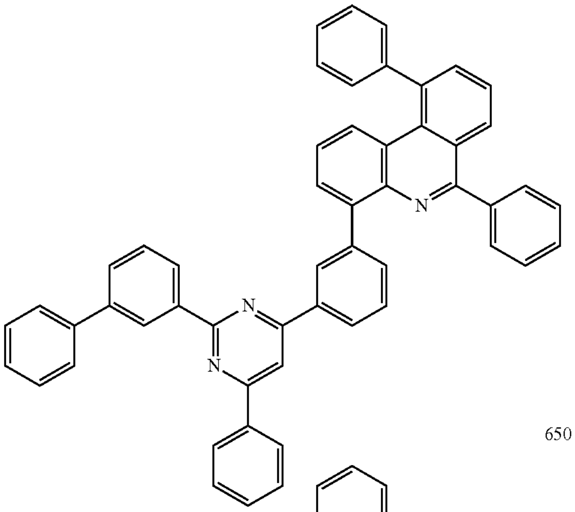
650
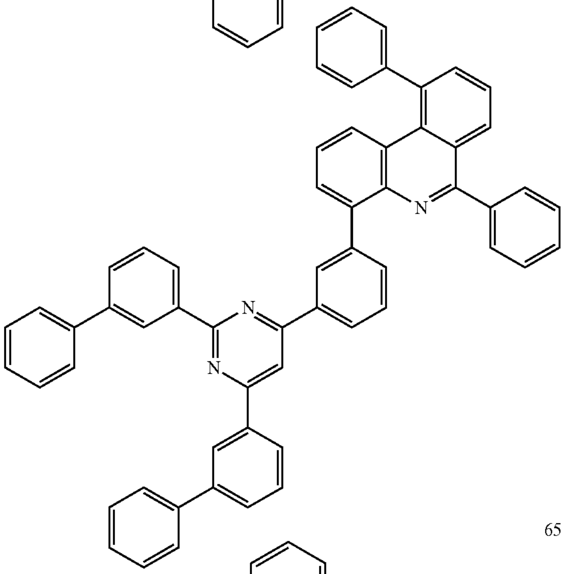
651
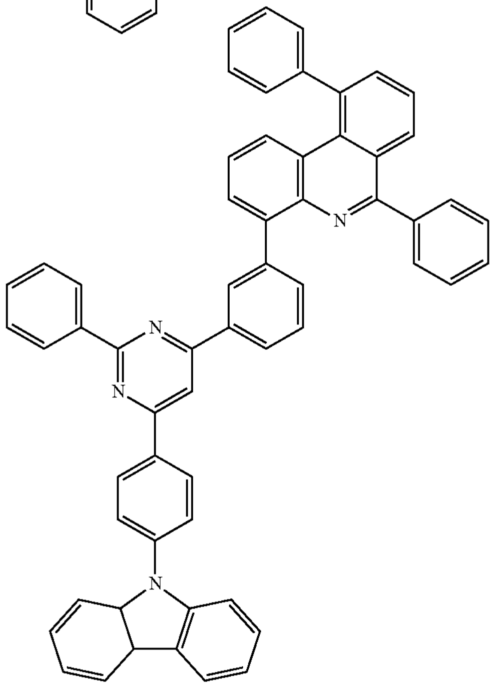

-continued
652
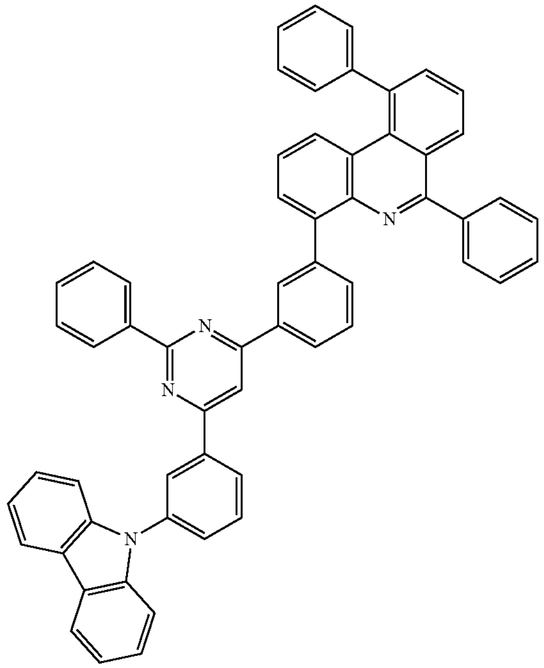
653
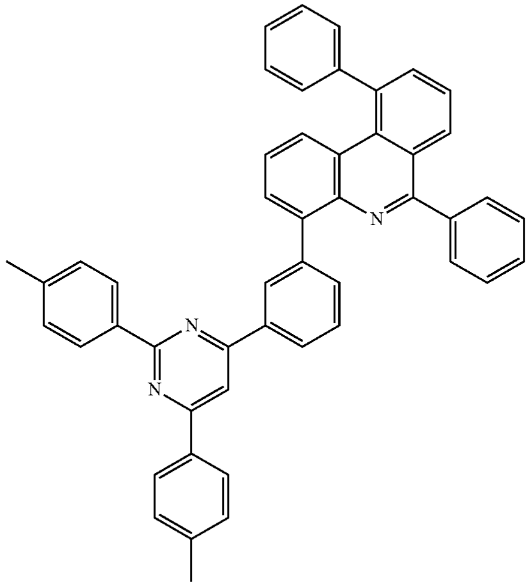
-continued
654
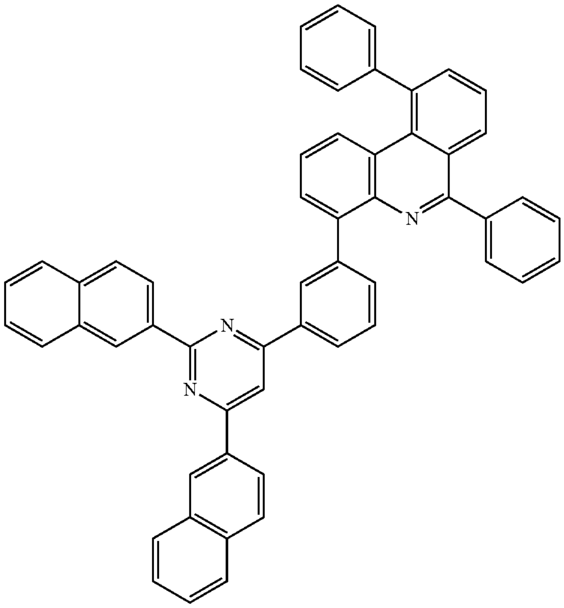
655
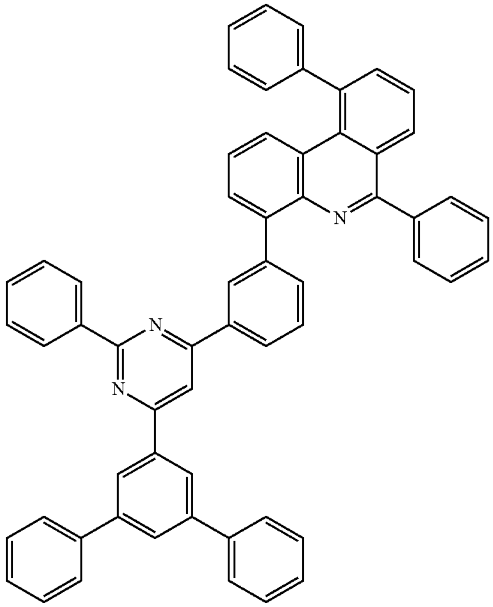

-continued
656
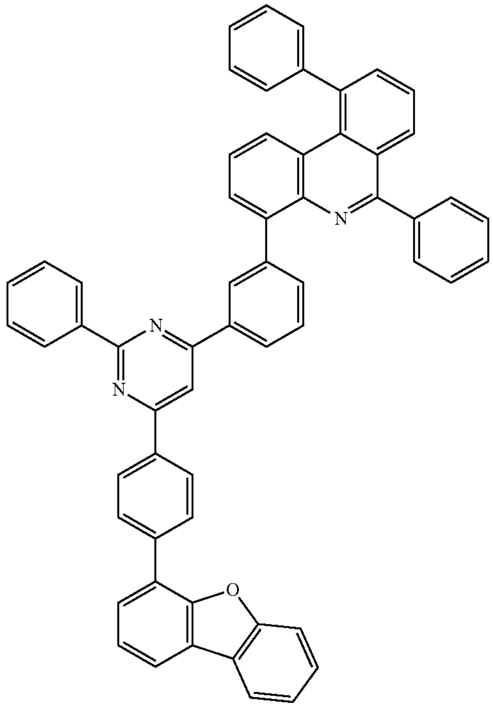
657
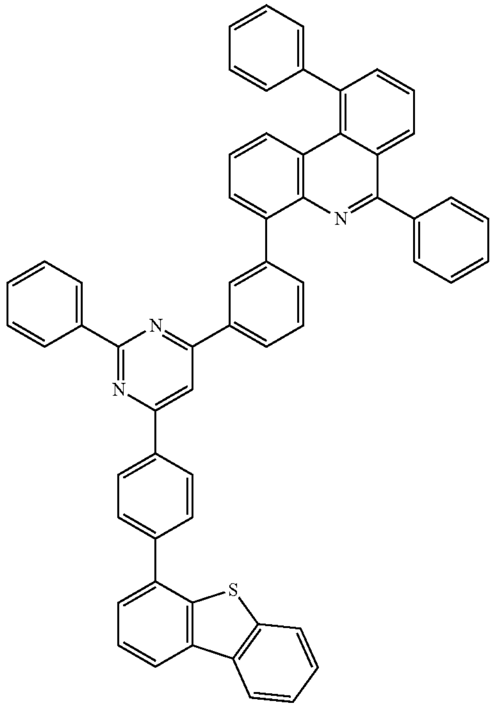
-continued
658
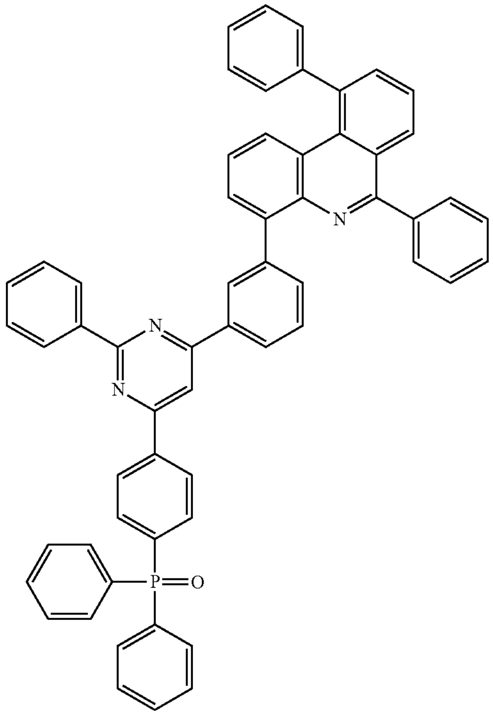
659
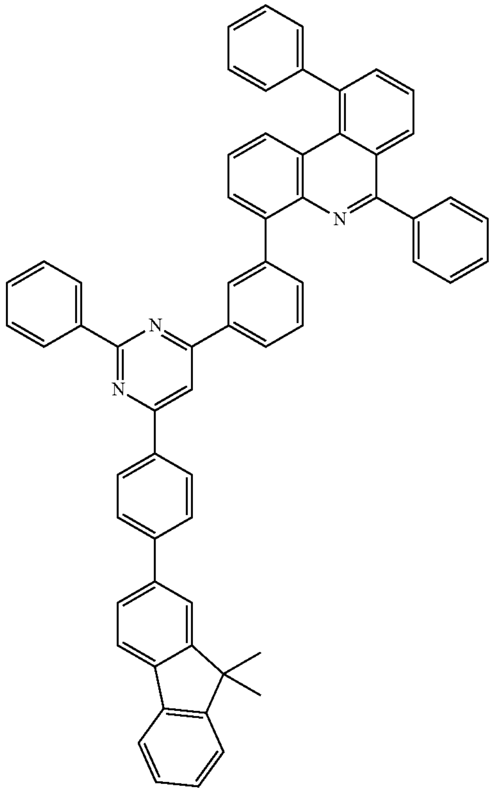

-continued
660
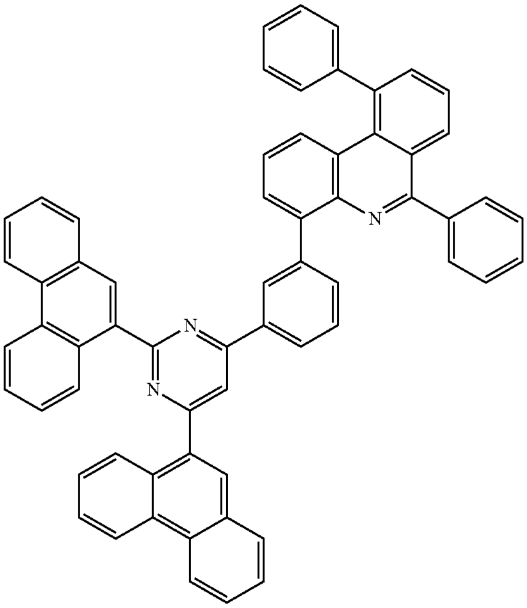
661
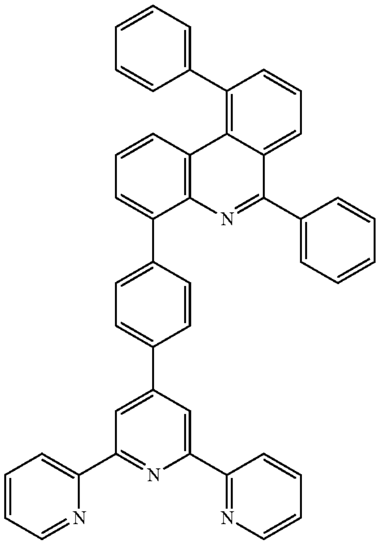
662
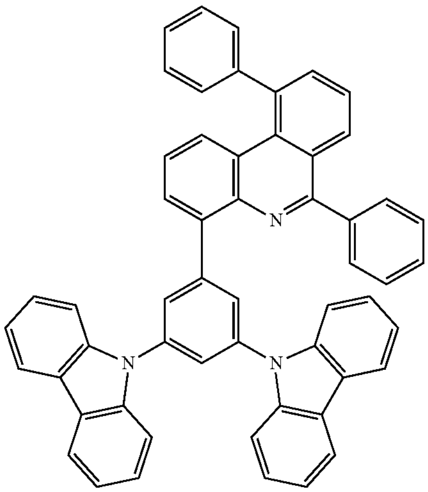
-continued
663
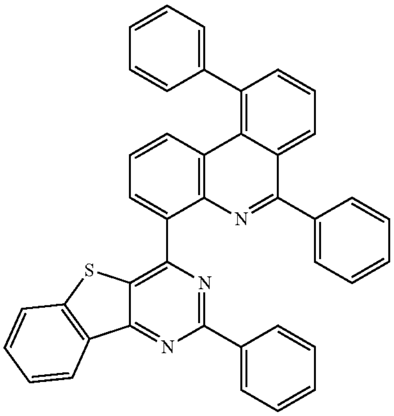
664
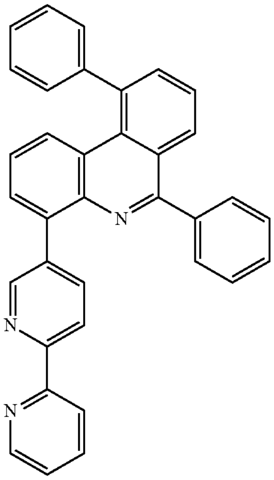
665
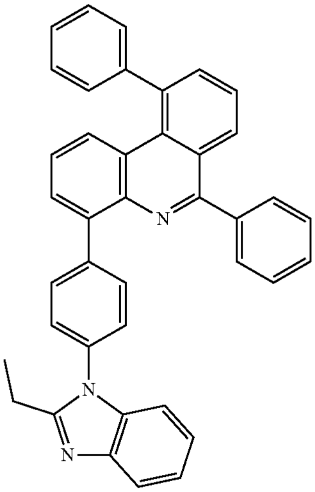

-continued
666
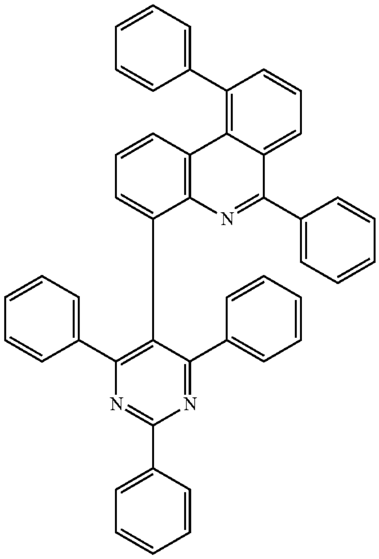
667
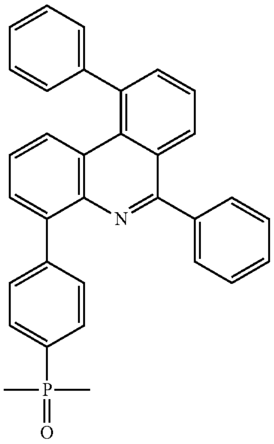
668
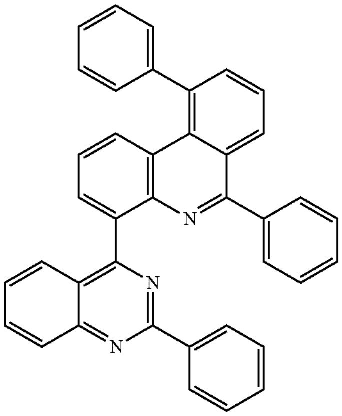
-continued
669
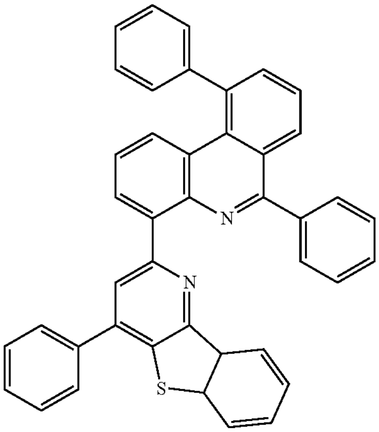
670
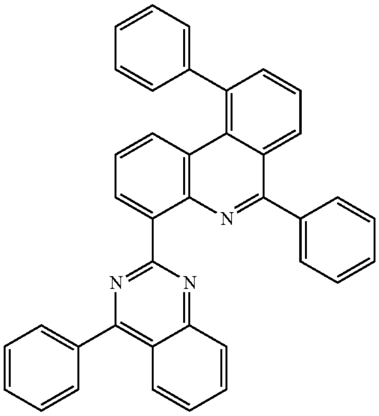
671
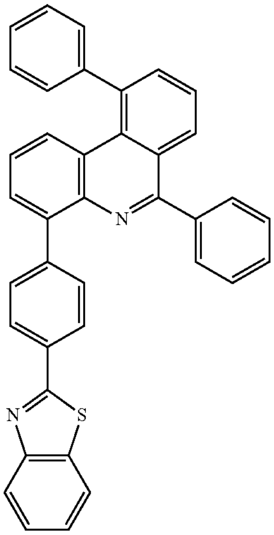

-continued
672
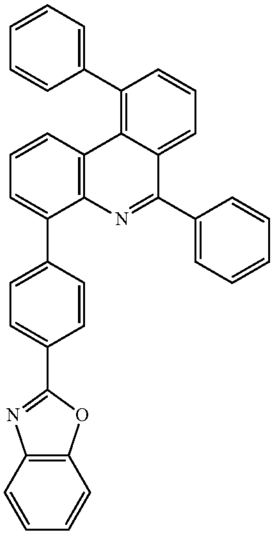
673
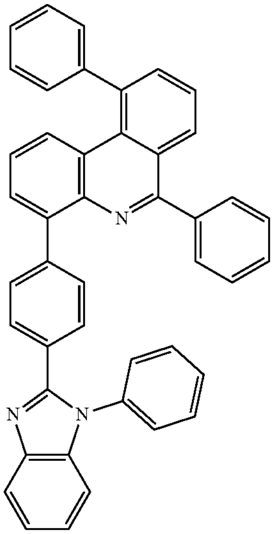
674
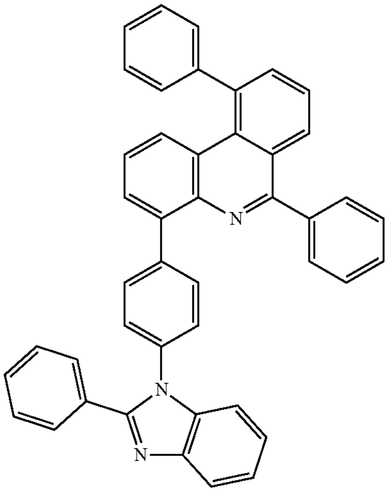
-continued
675
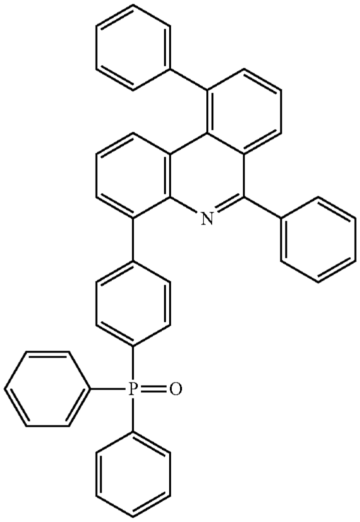
676
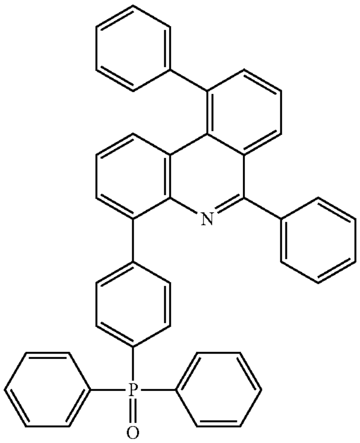
677
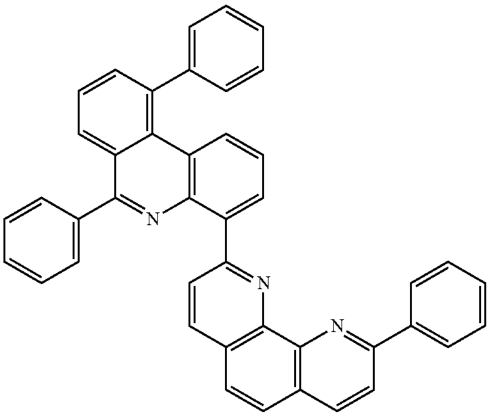

-continued
678
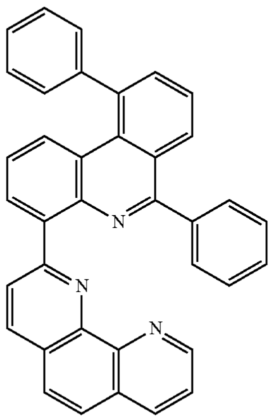
679
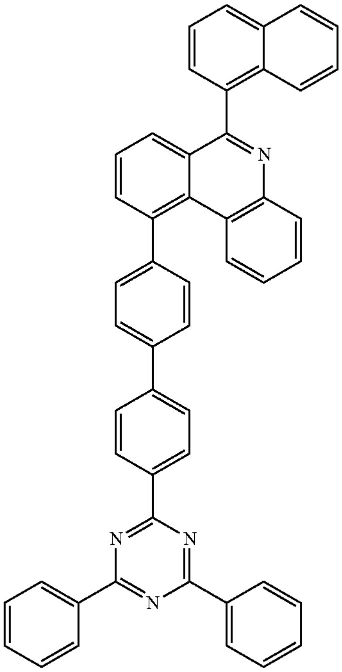
-continued
680
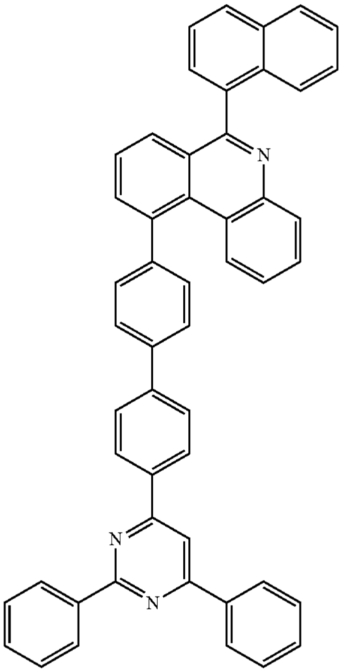
681
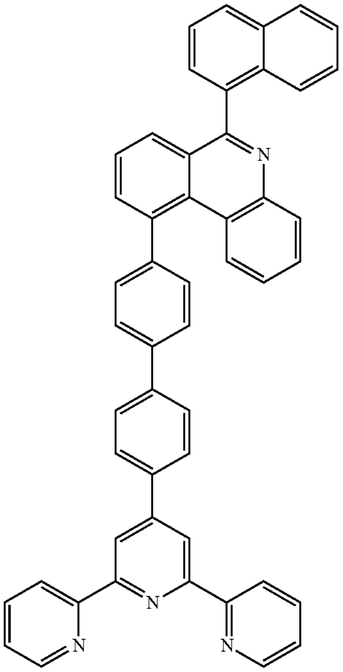

-continued
682
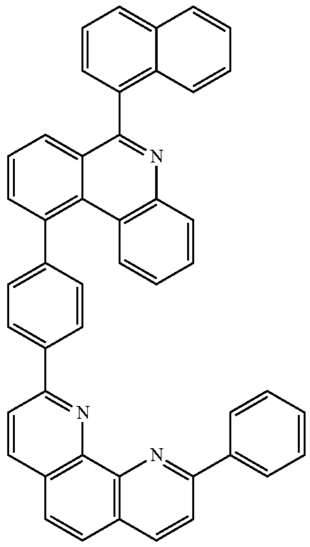
683
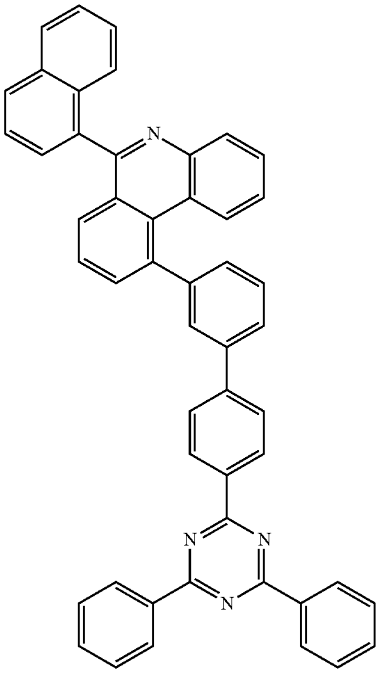
-continued
684
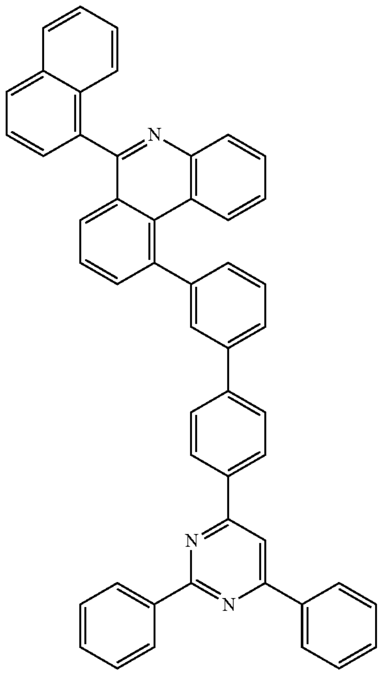
685
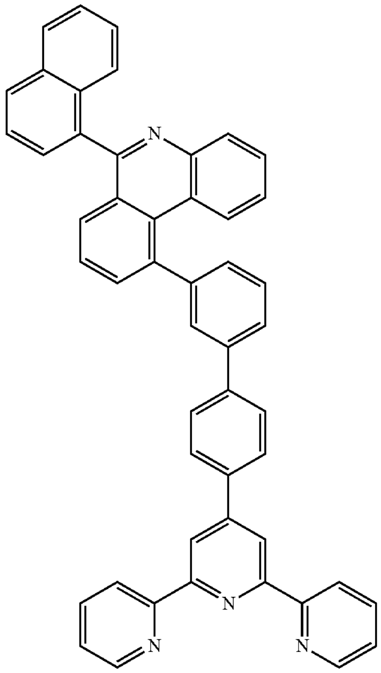

686
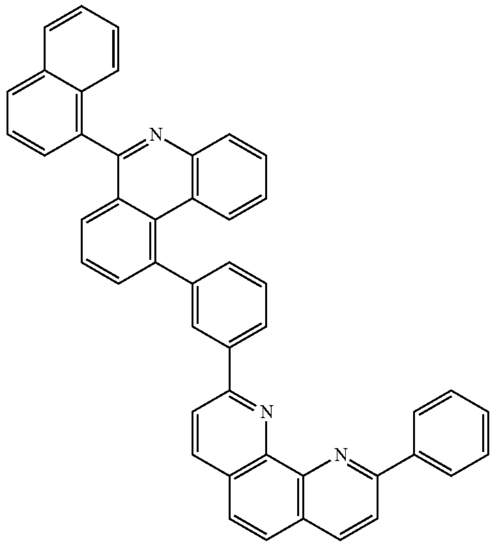
688
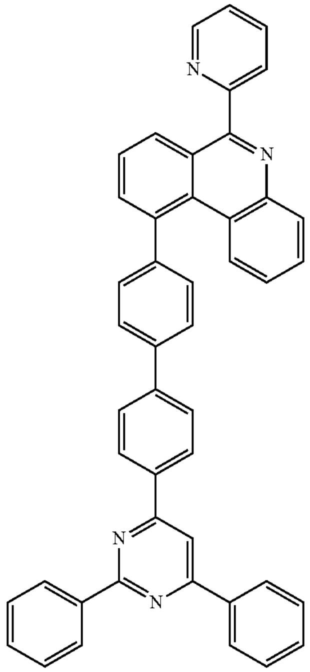
687
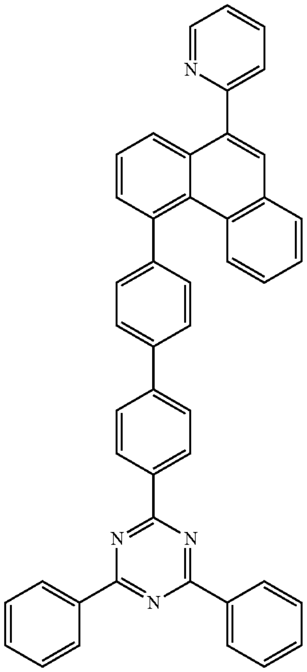
689
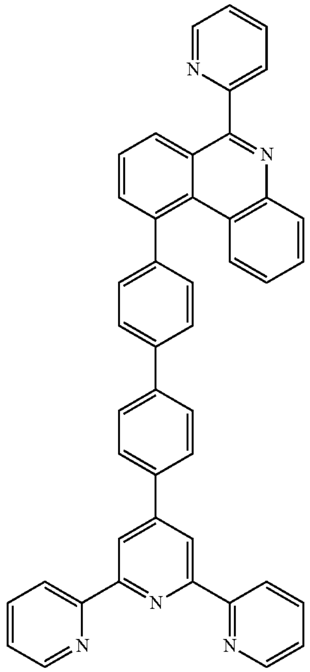

-continued
690
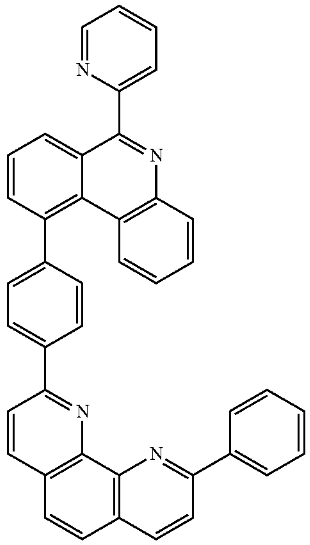
691
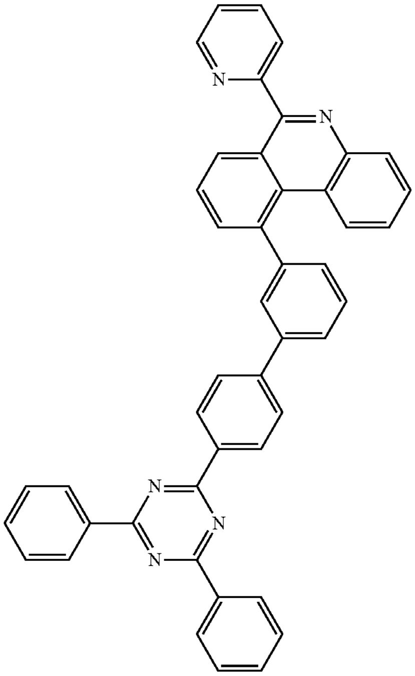
-continued
692
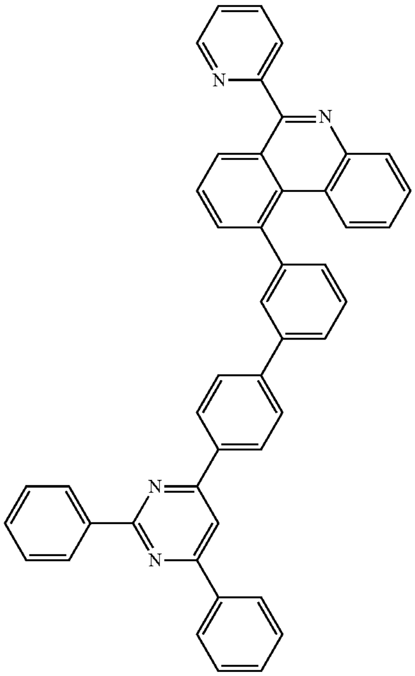
693
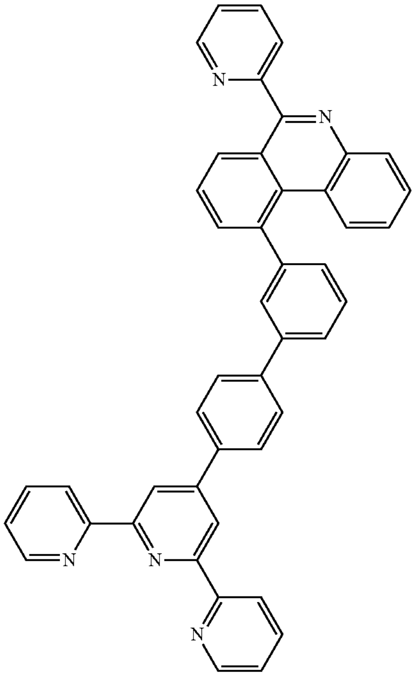

-continued
694
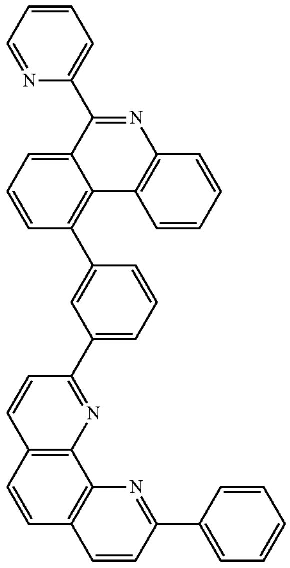
695
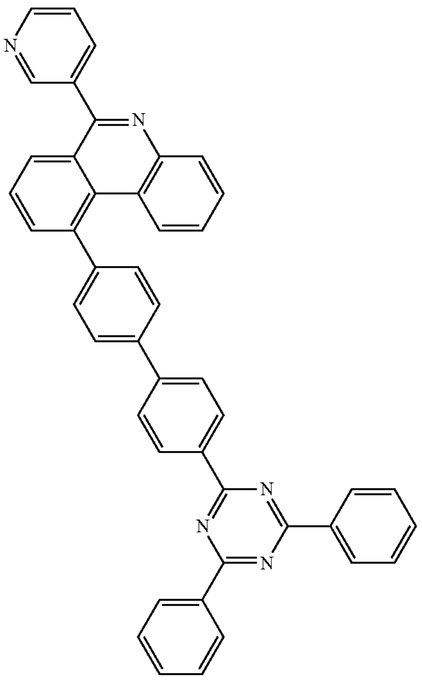
-continued
696
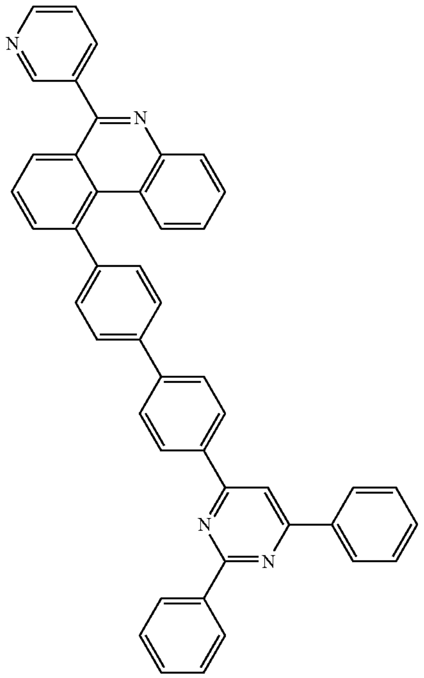
697
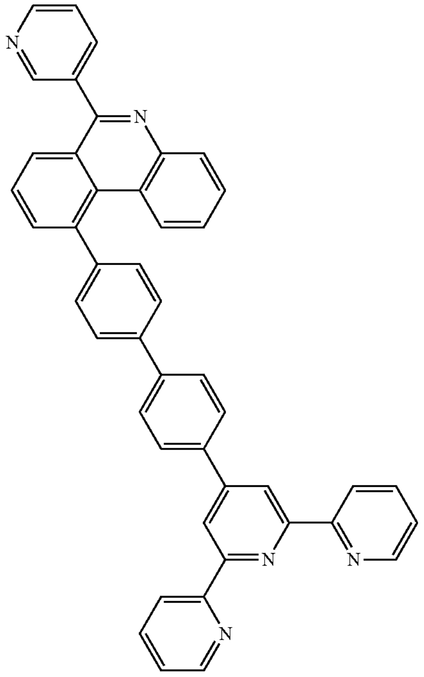

698
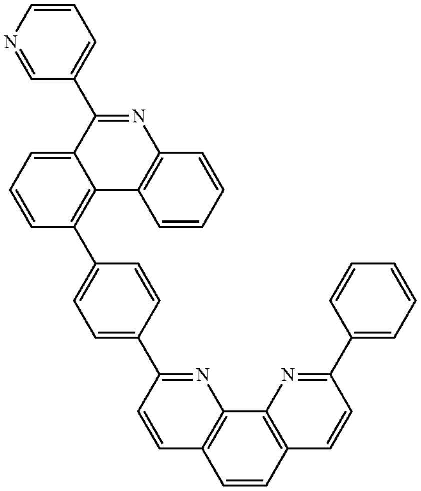
699
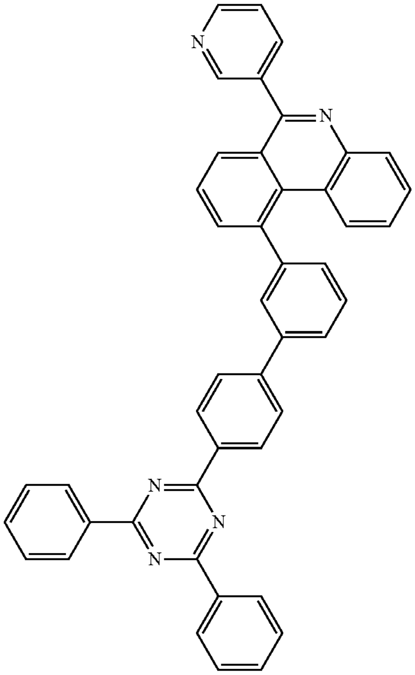
700
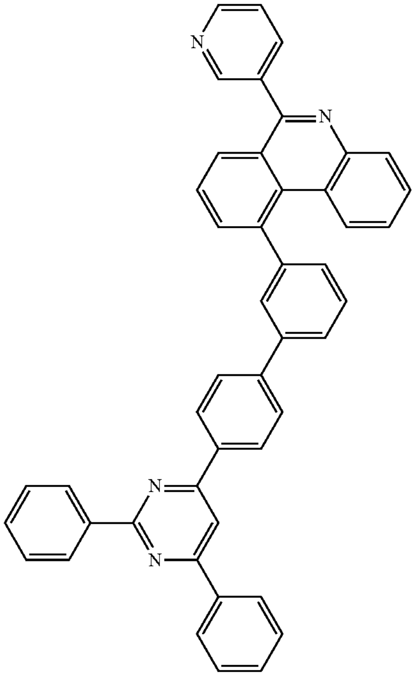
701
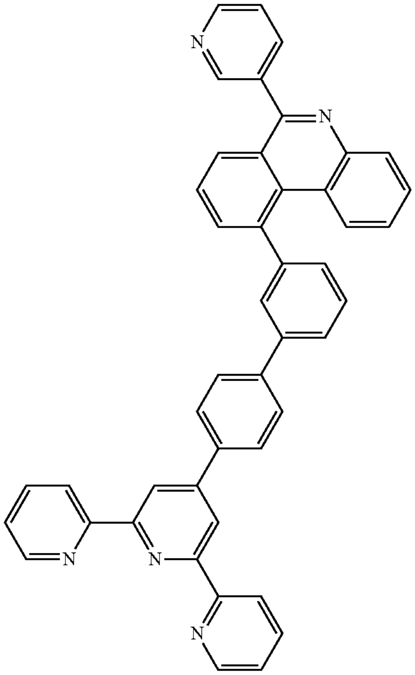

-continued
702
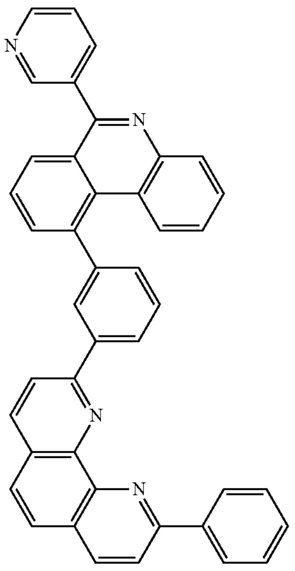
703
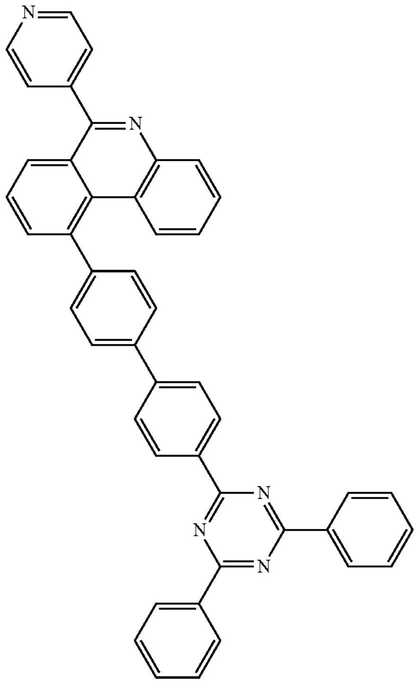
-continued
704
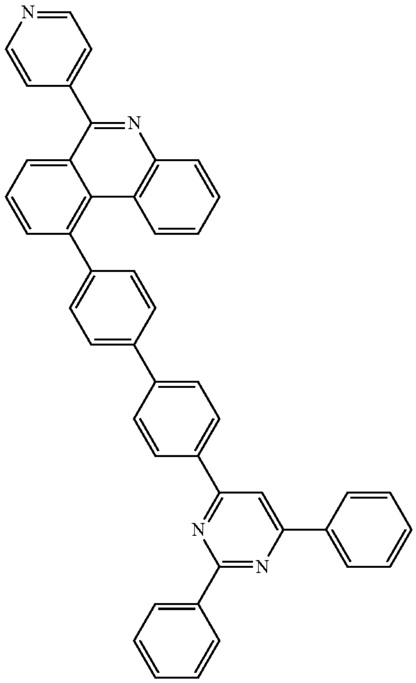
705
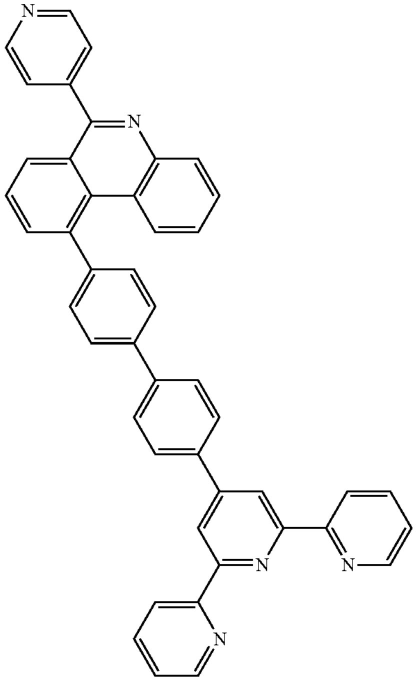

706
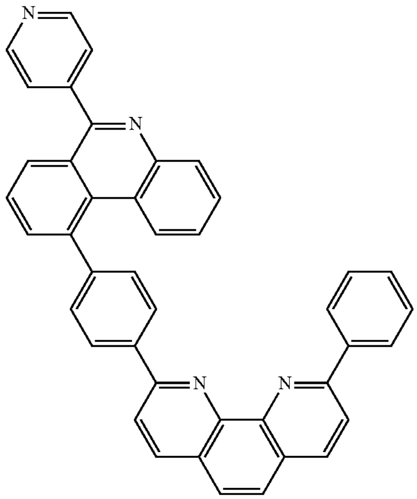
707
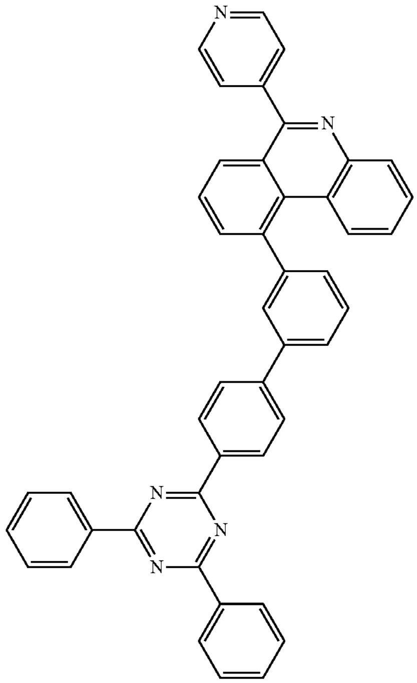
708
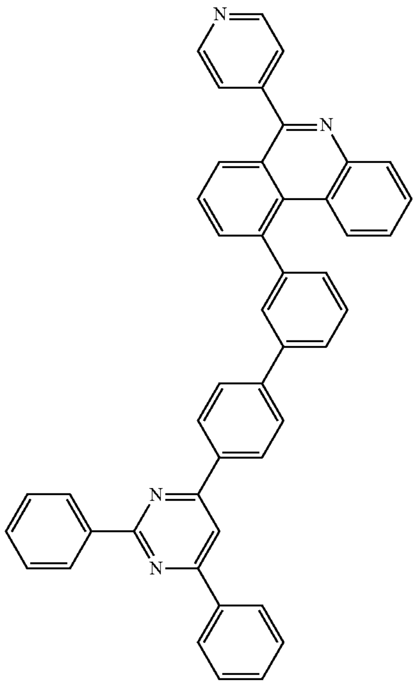
709
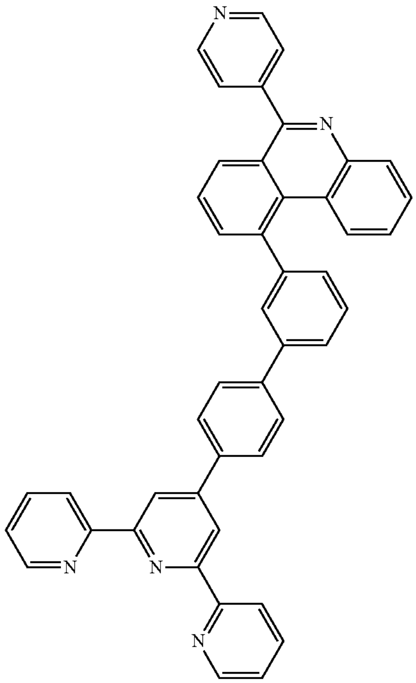

-continued
710
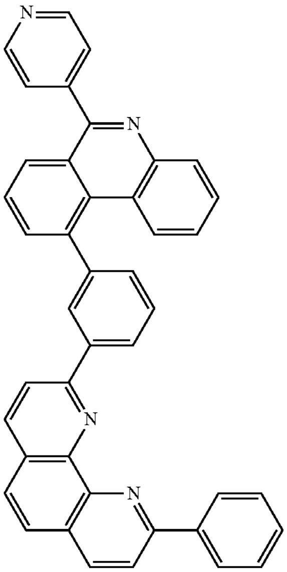
711
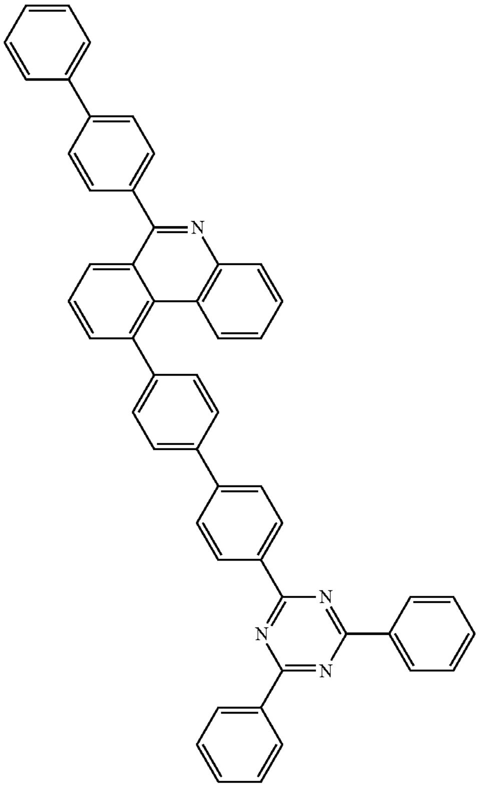
-continued
712
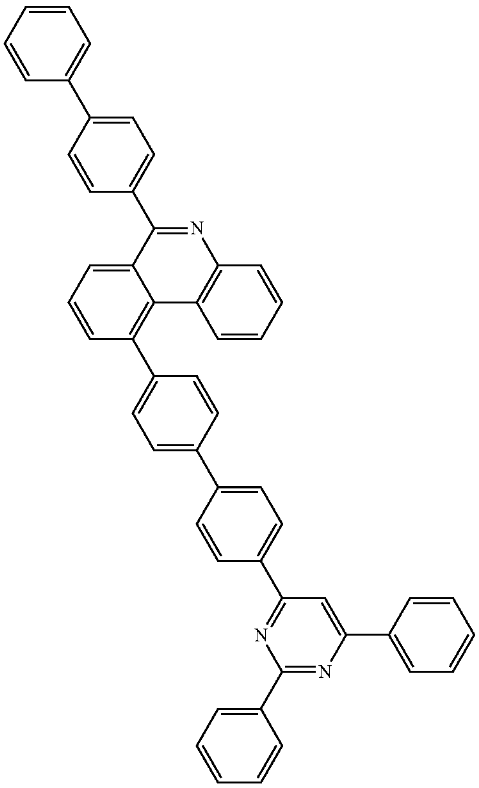
713
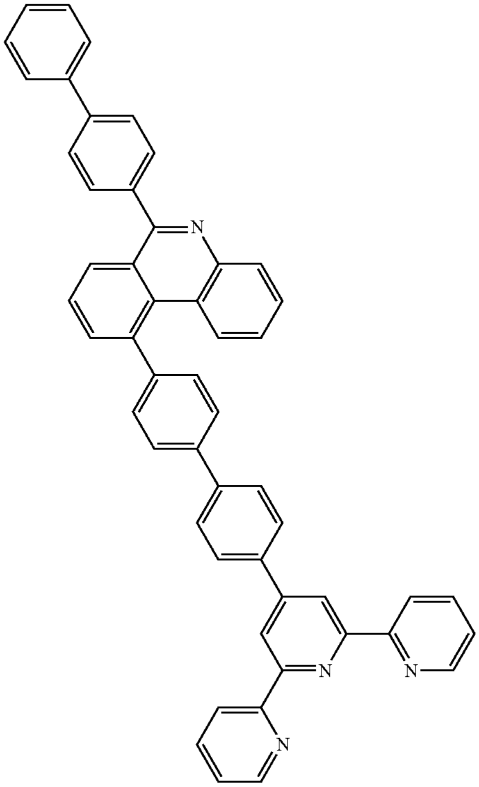

714
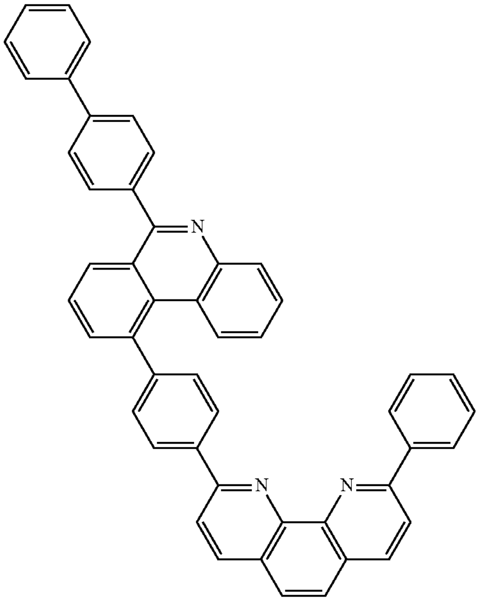
716
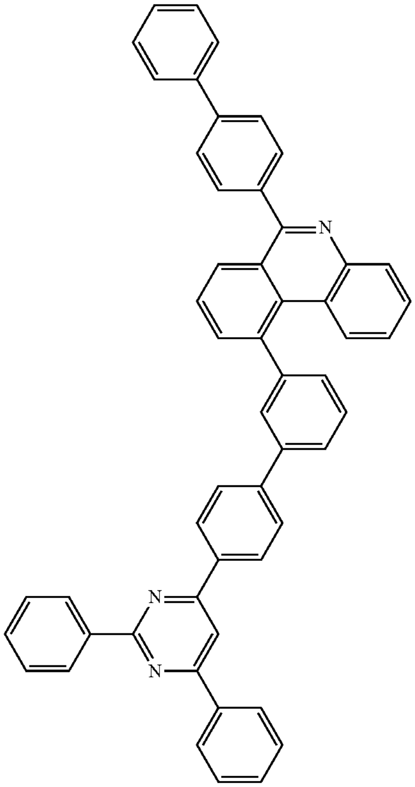
715
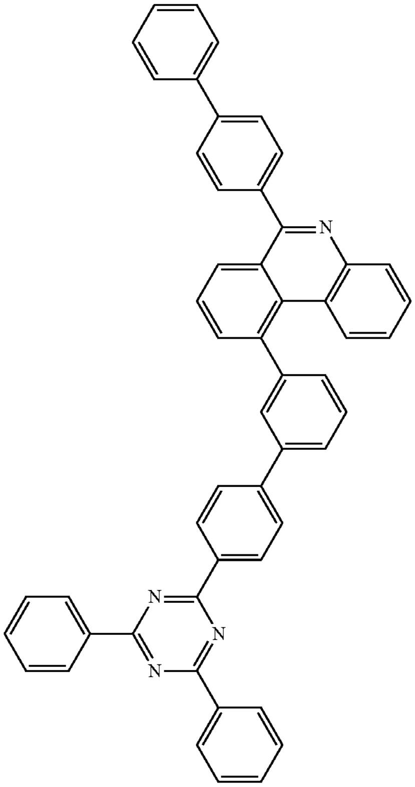
717
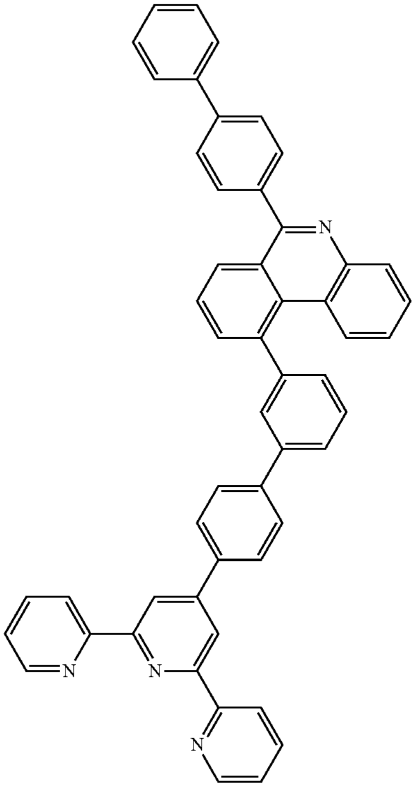

-continued
718
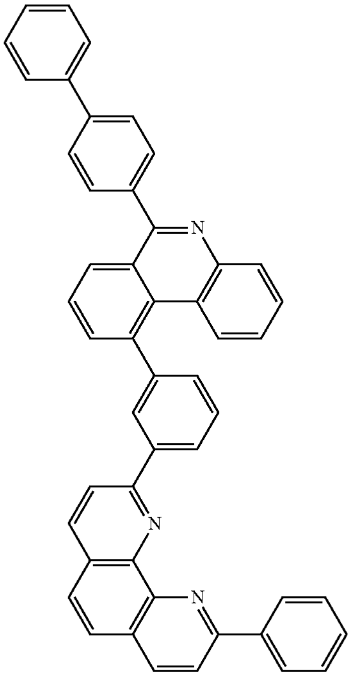
719
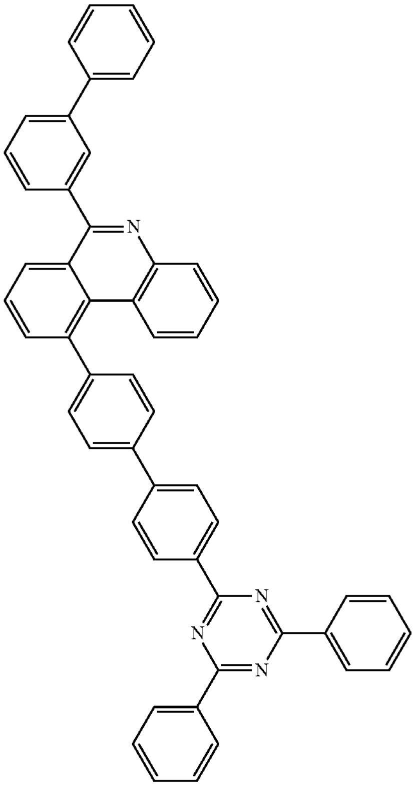
-continued
720
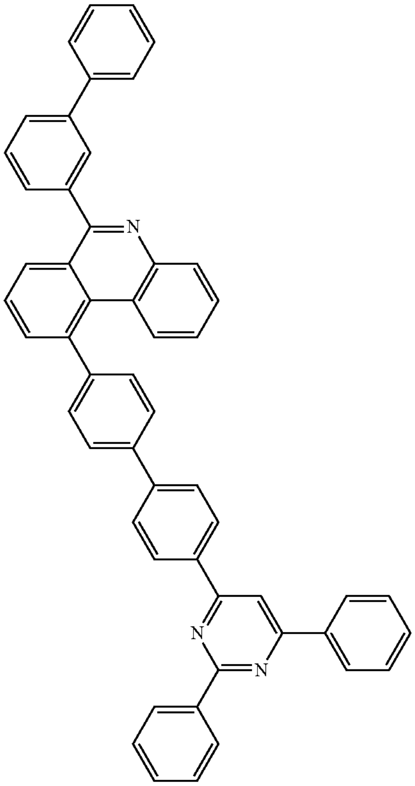
721
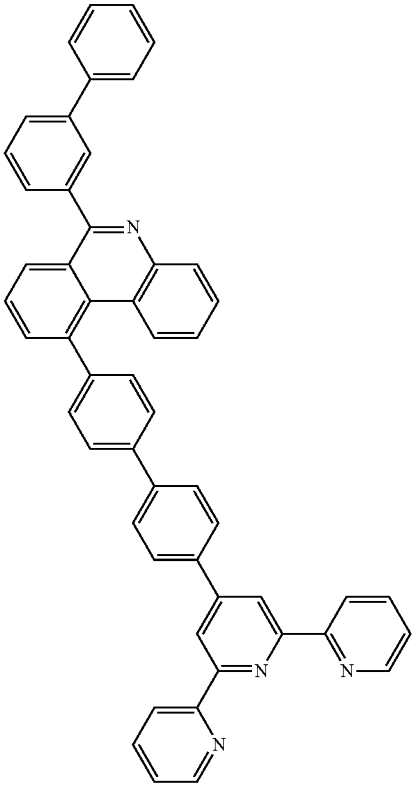

722
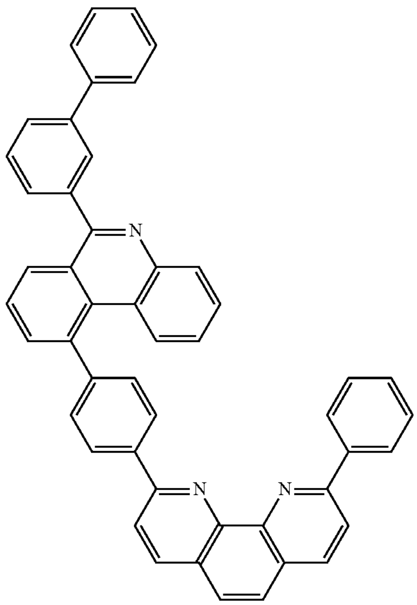
723
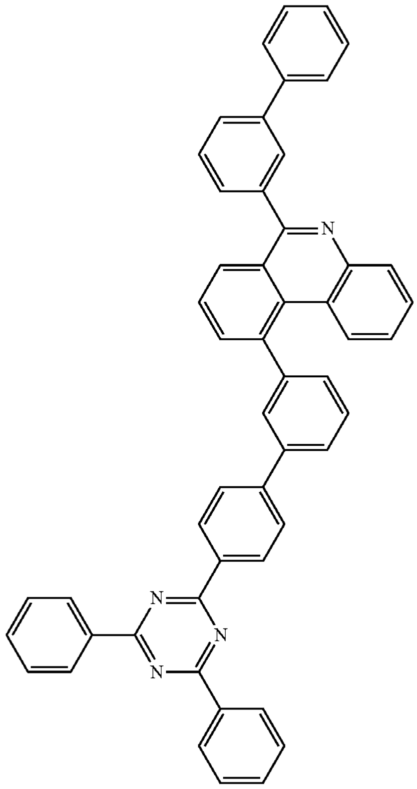
724
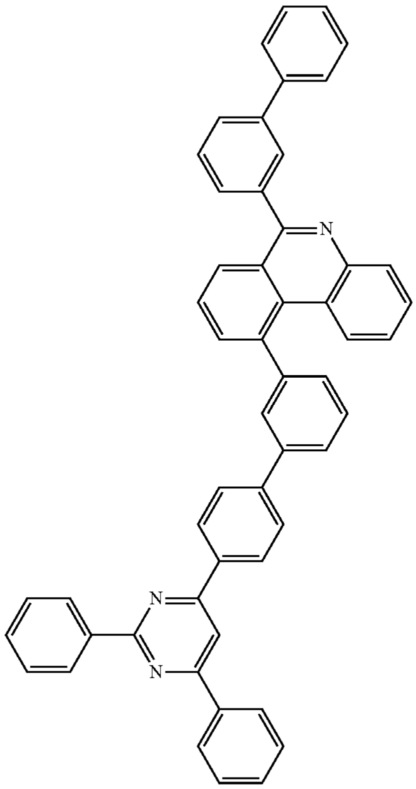
725
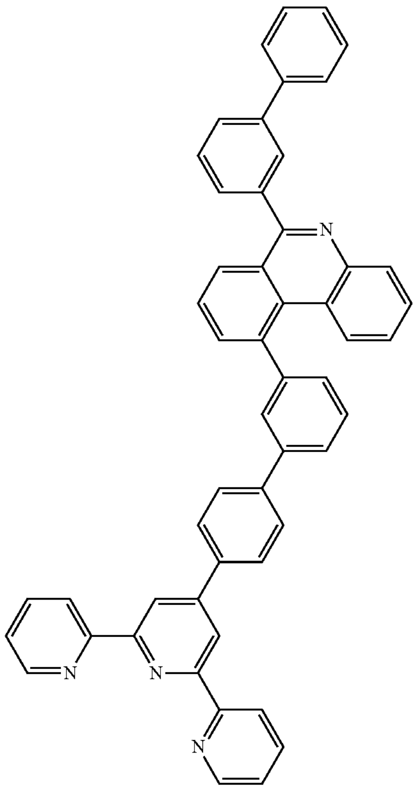

-continued
726
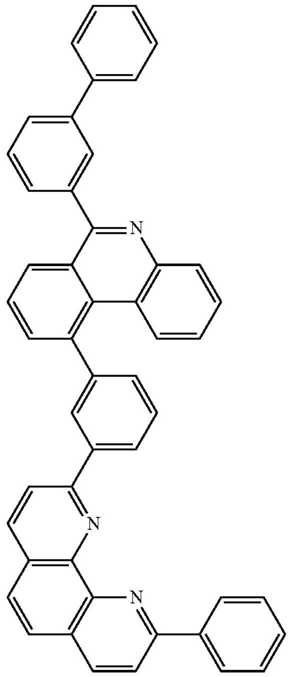
727
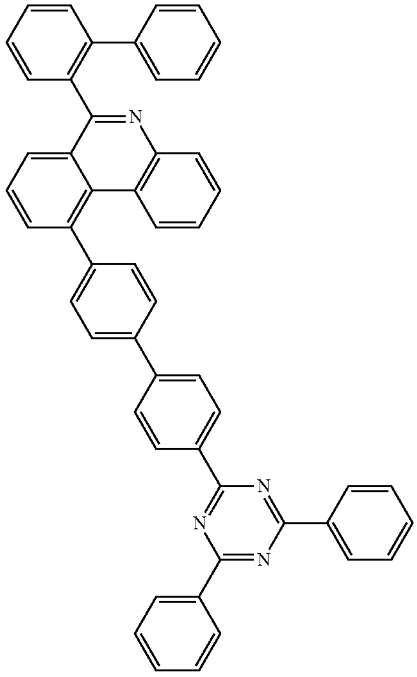
-continued
728
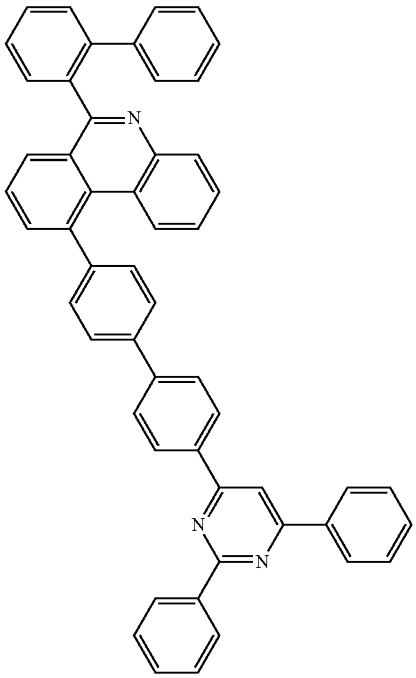
729
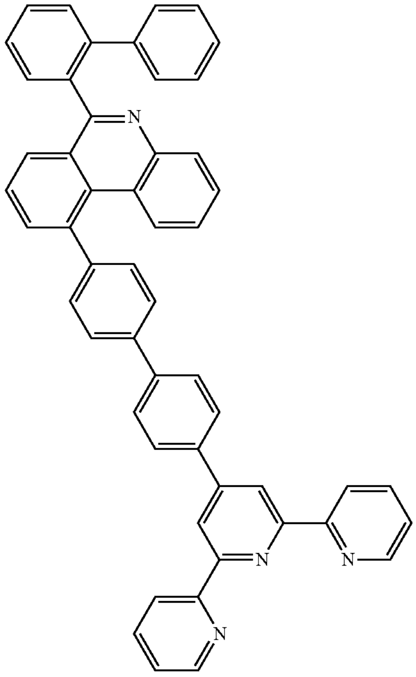

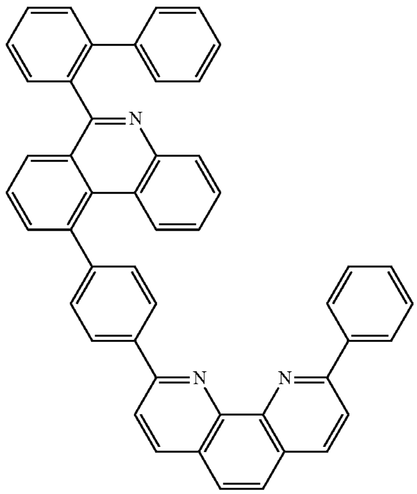
730
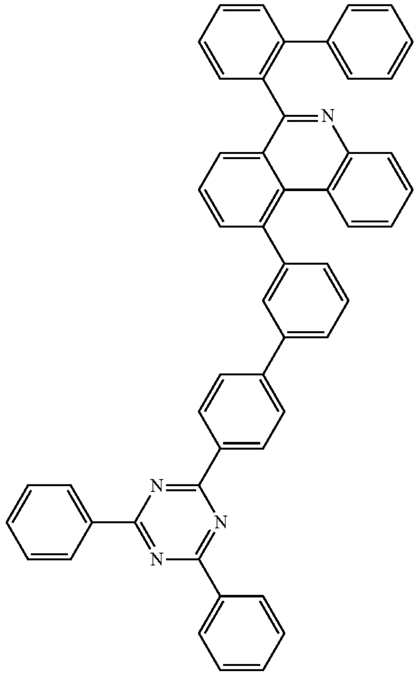
731
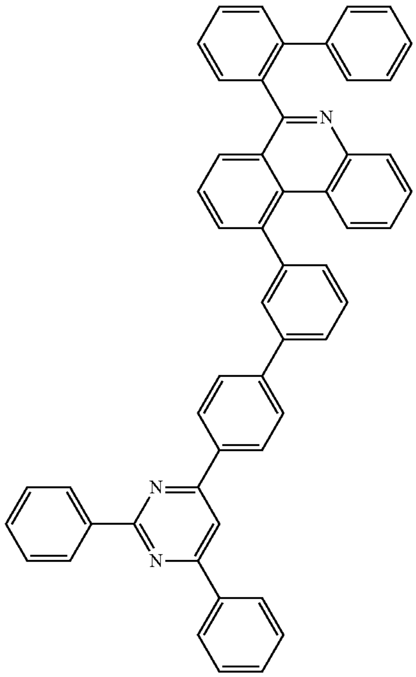
732
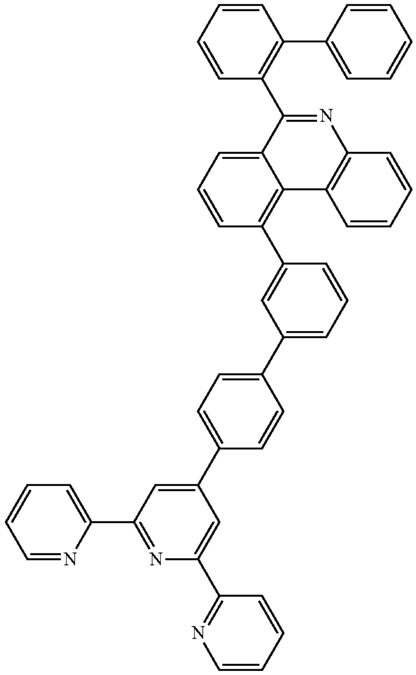
733

-continued
734
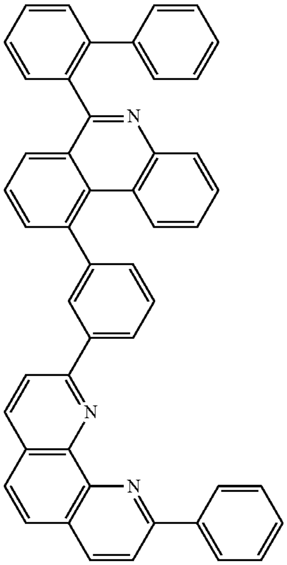
735
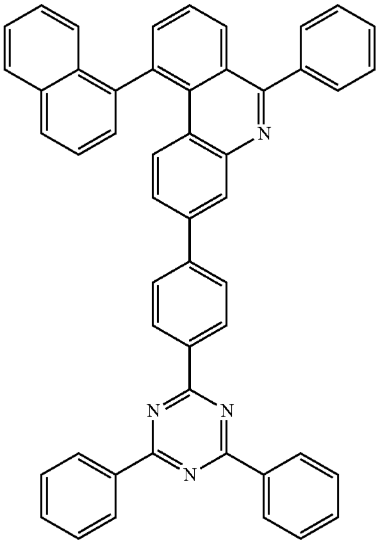
736
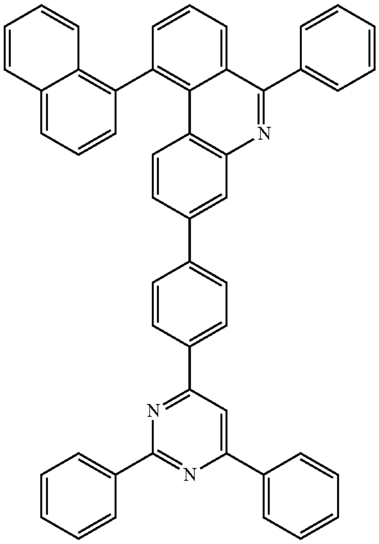
-continued
737
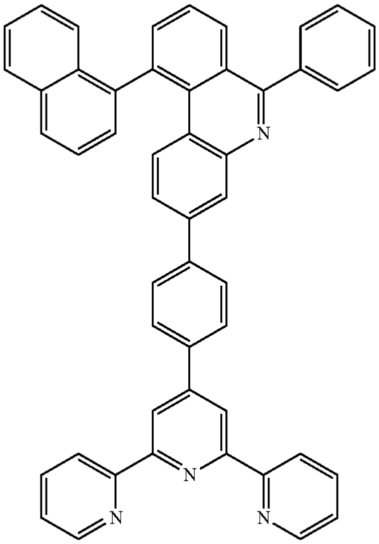
738
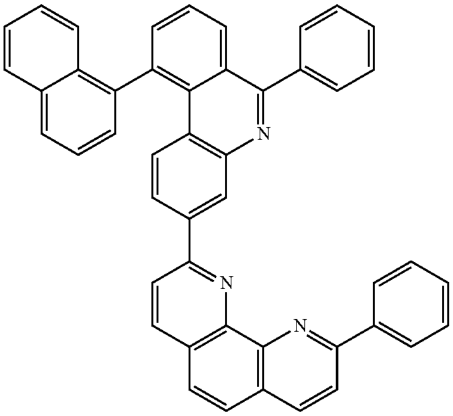
739
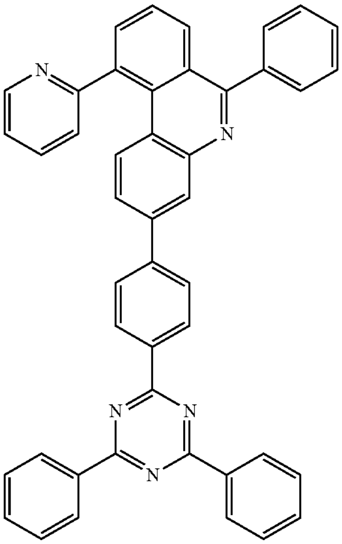

-continued
740
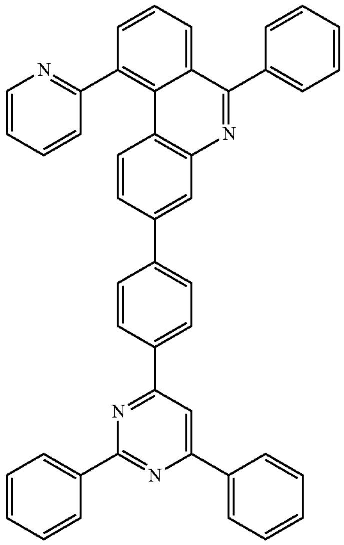
741
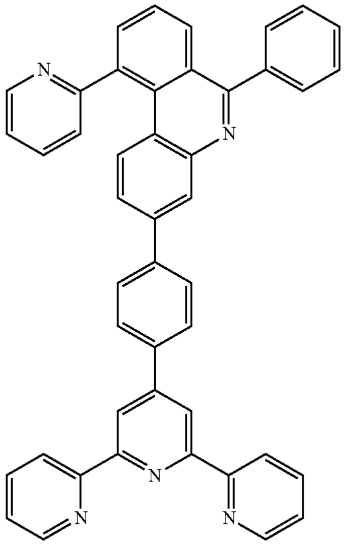
742
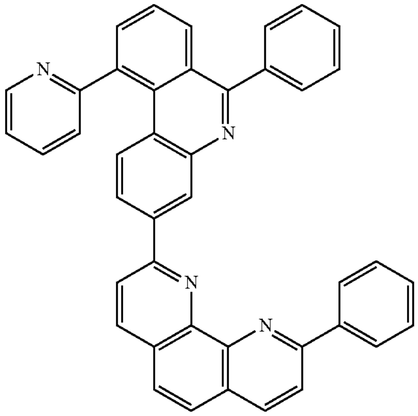
-continued
743
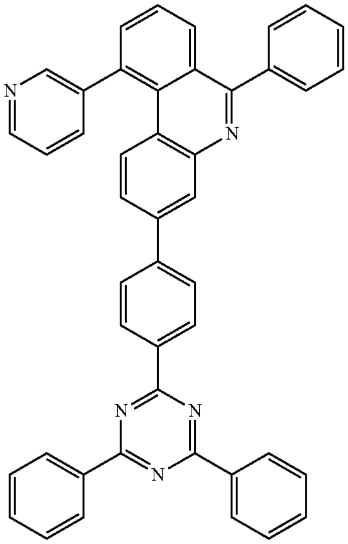
744
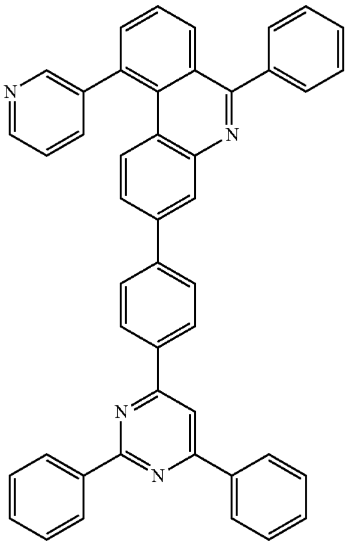
745
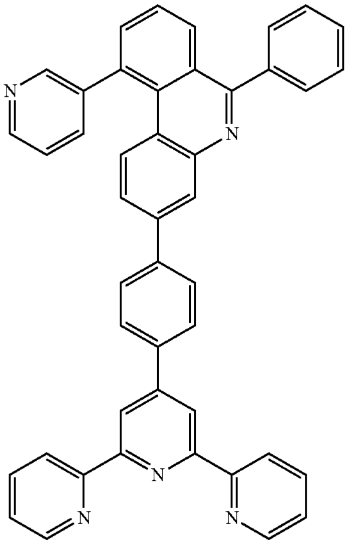

746
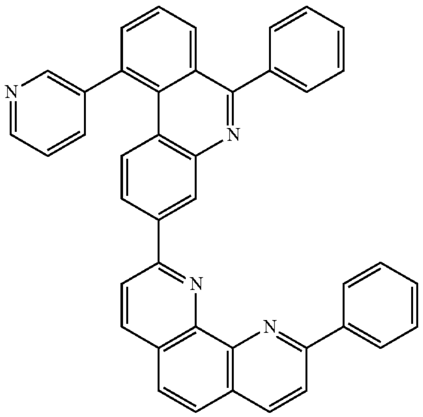
747
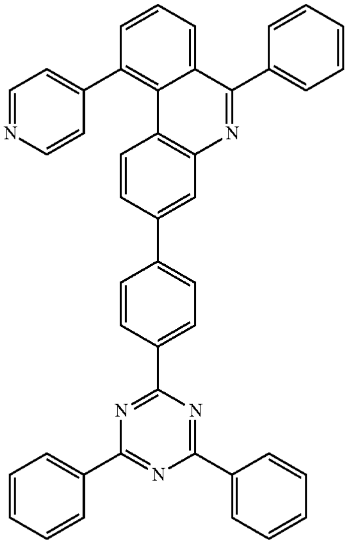
748
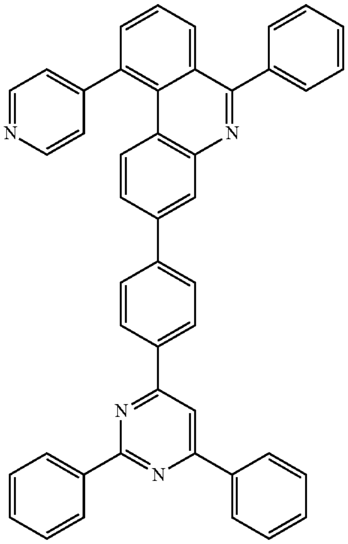
749
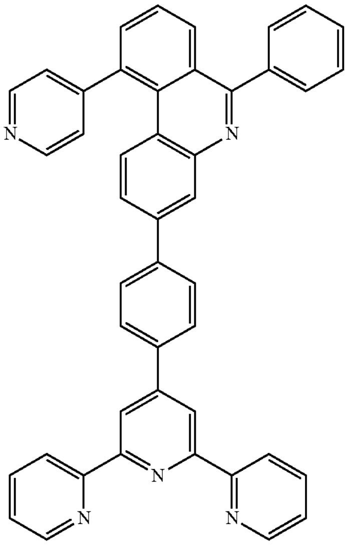
750
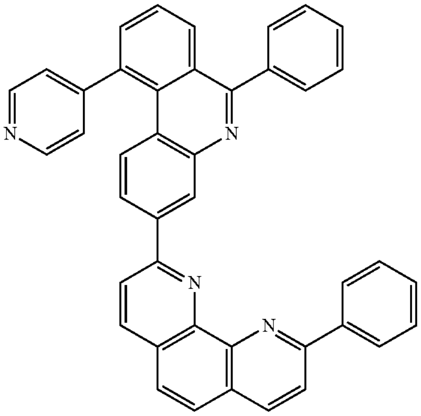
751
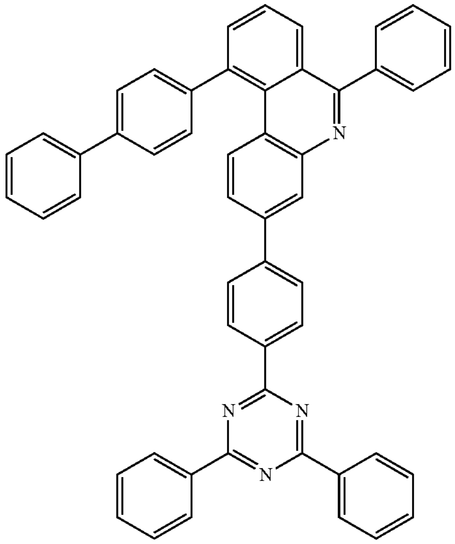

-continued
752
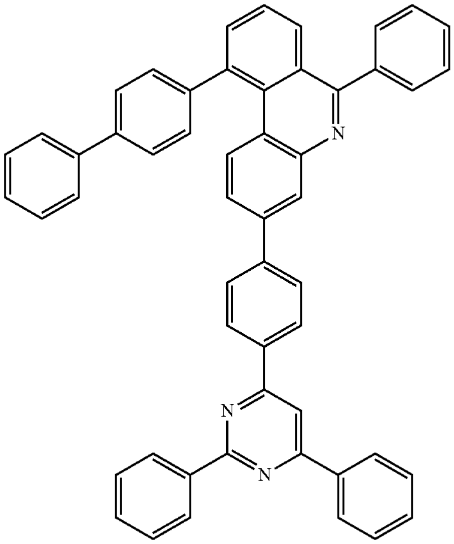
753
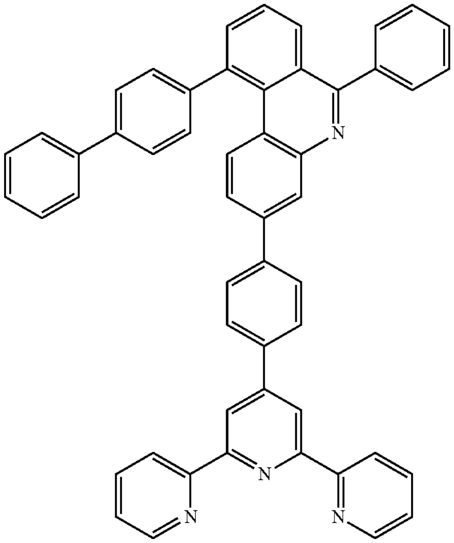
754
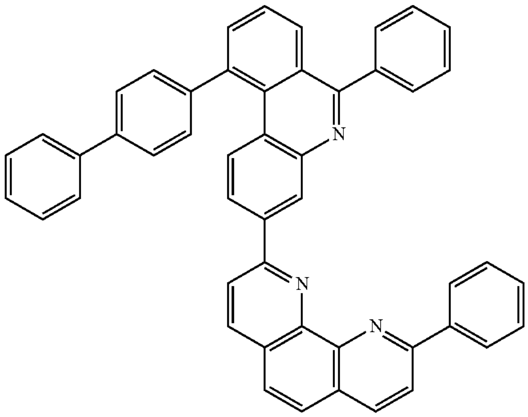
-continued
755
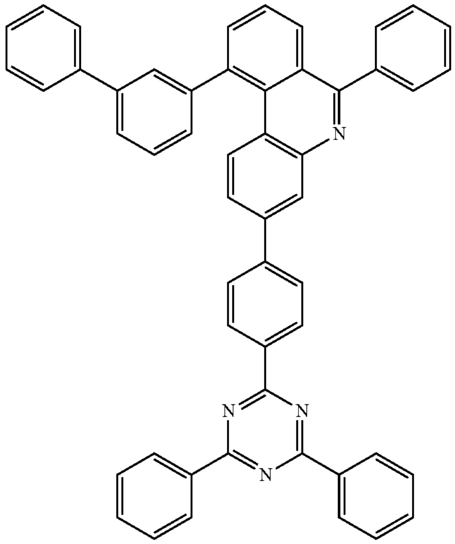
756
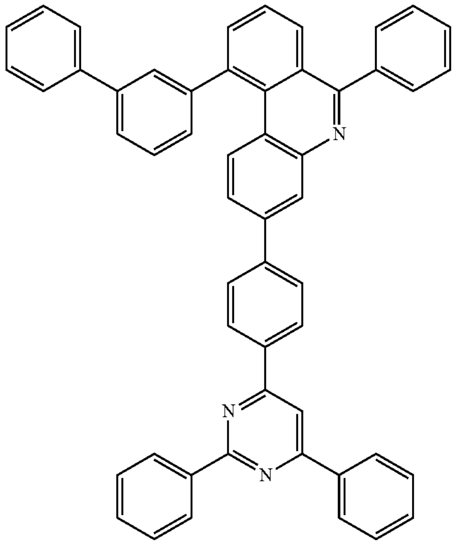
757
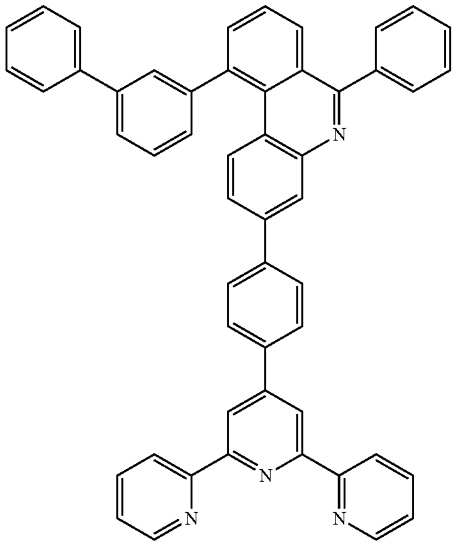

-continued
758
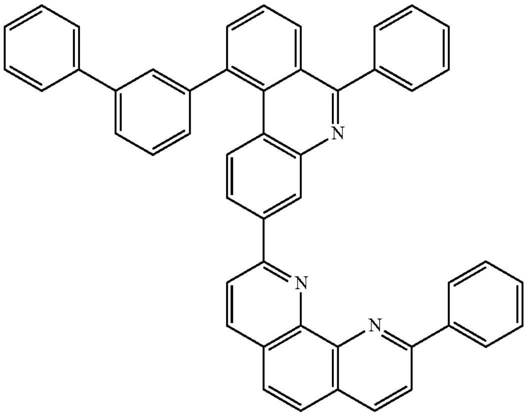
759
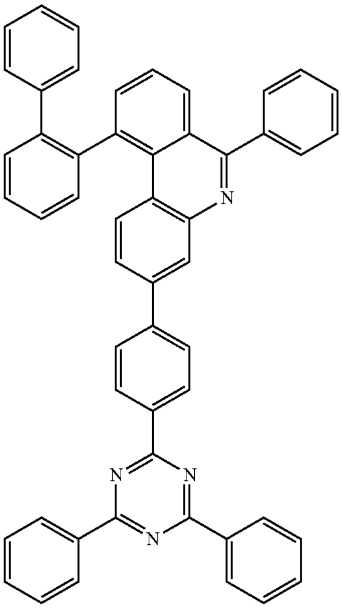
760
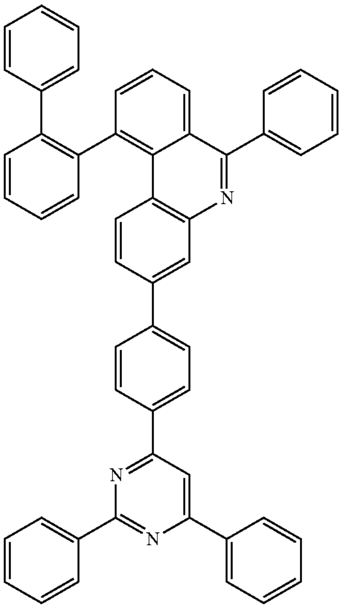
-continued
761
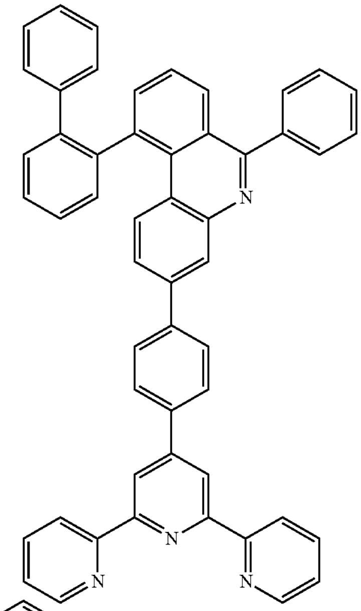
762
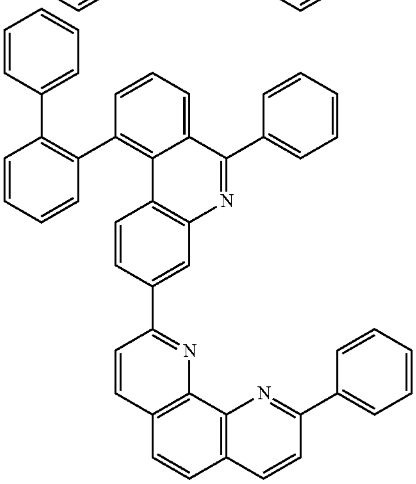
763
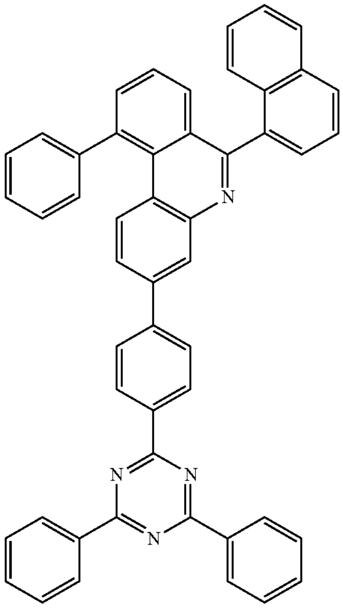

-continued
764
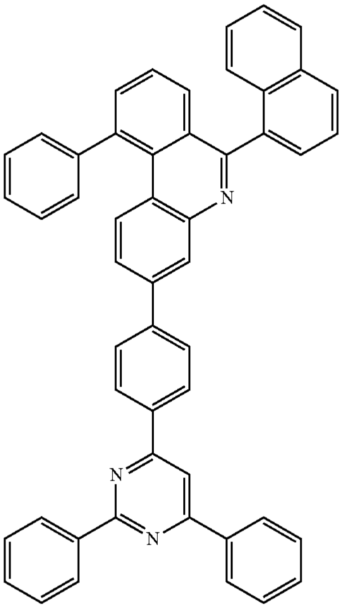
765
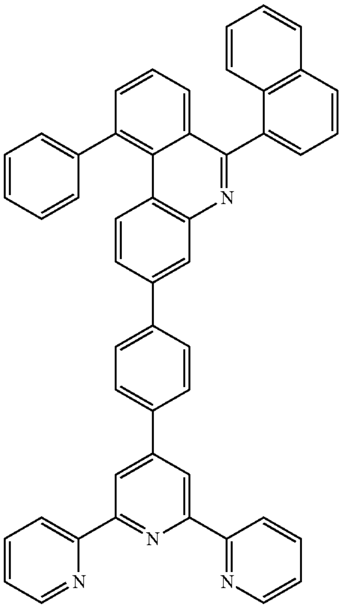
766
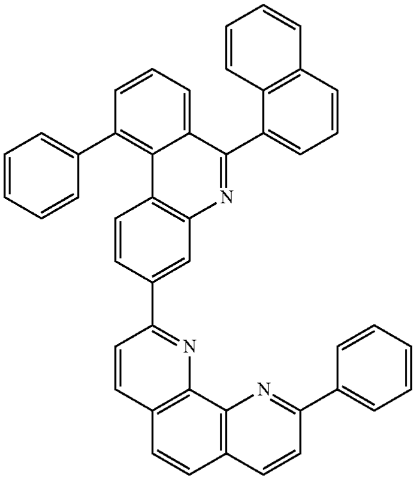
-continued
767
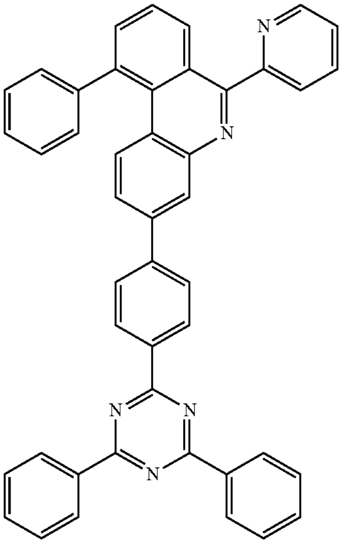
768
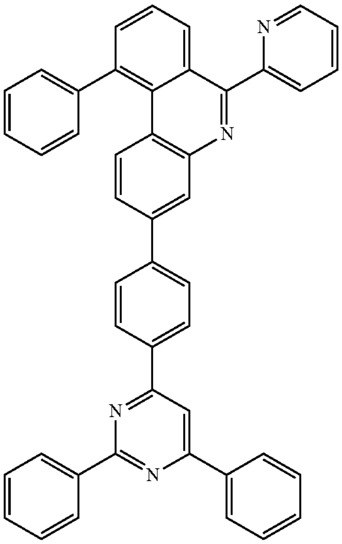
769
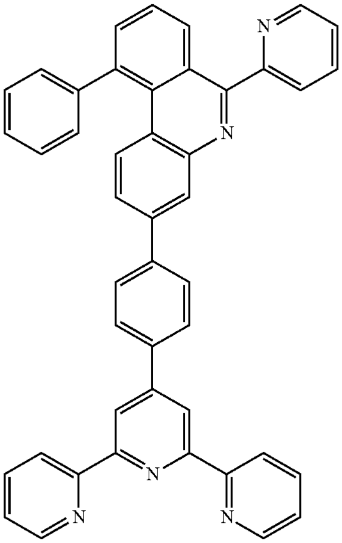

770
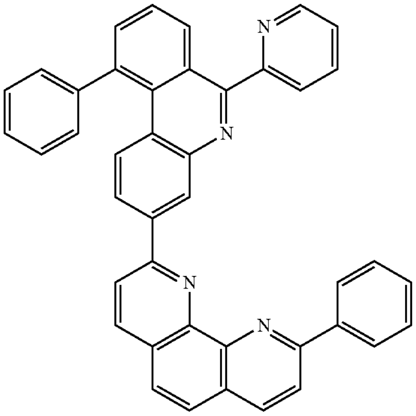
771
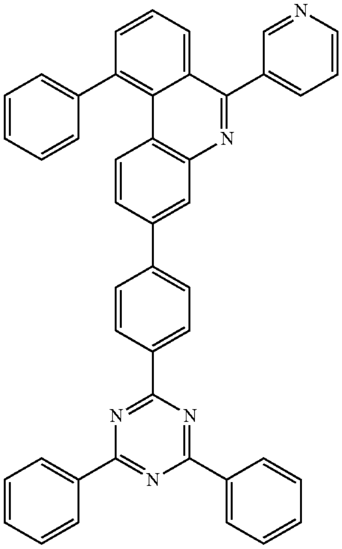
772
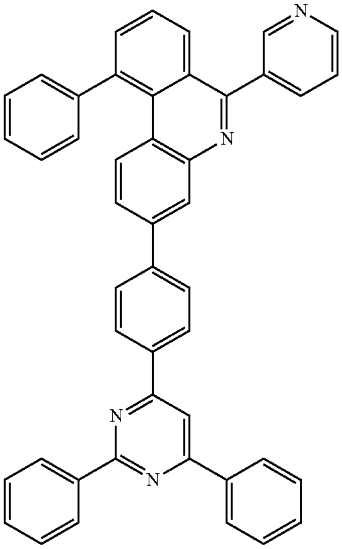
773
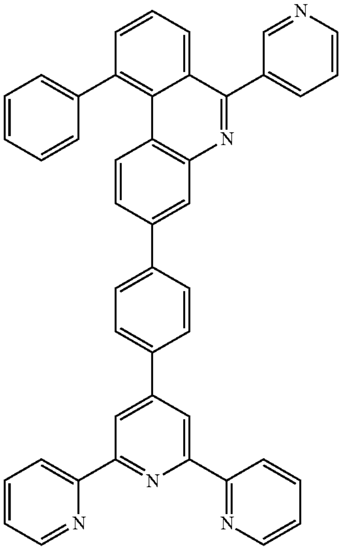
774
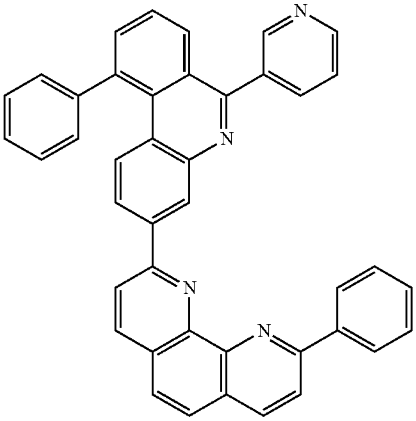
775
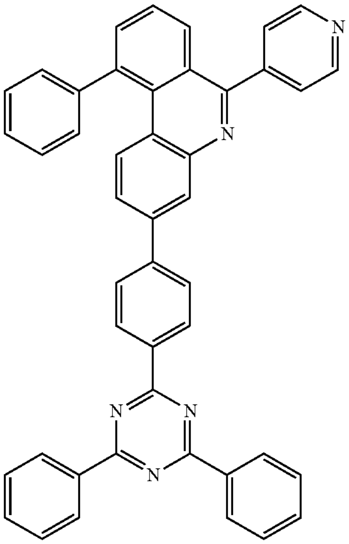

-continued
776
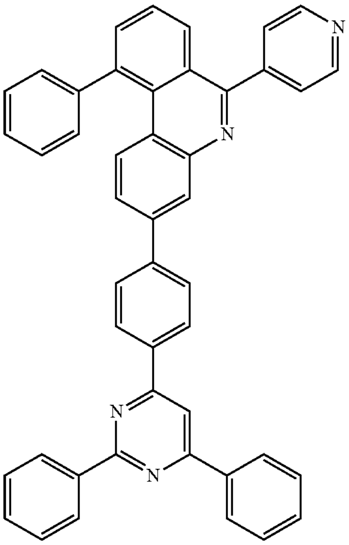
777
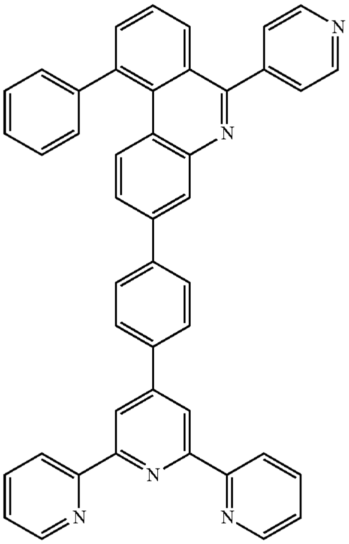
778
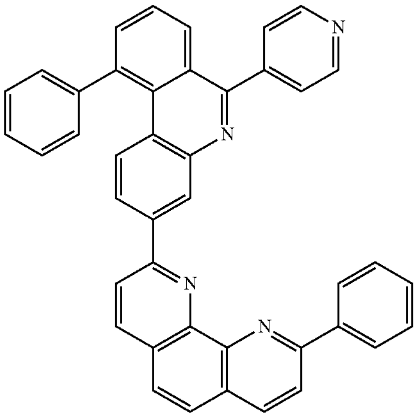
-continued
779
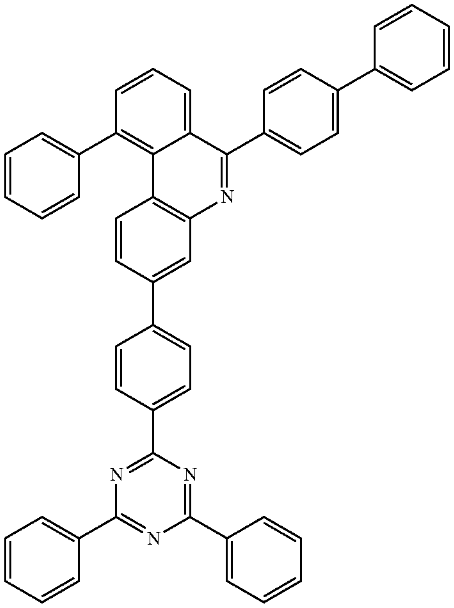
780
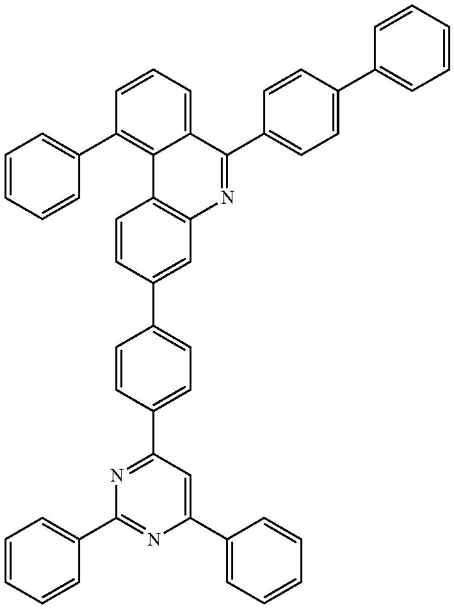

781
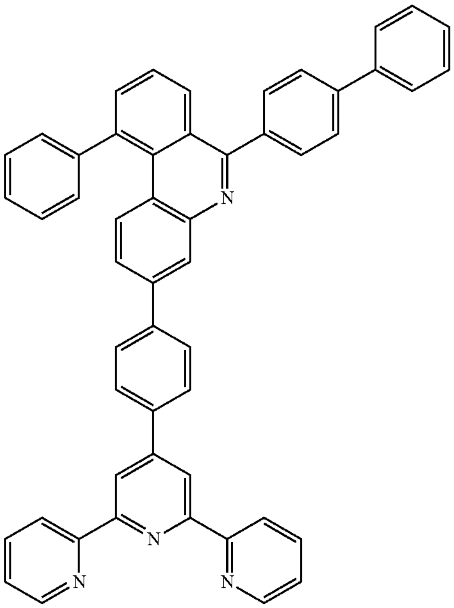
782
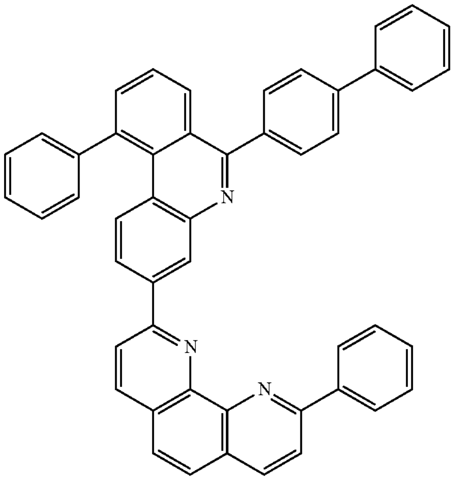
783
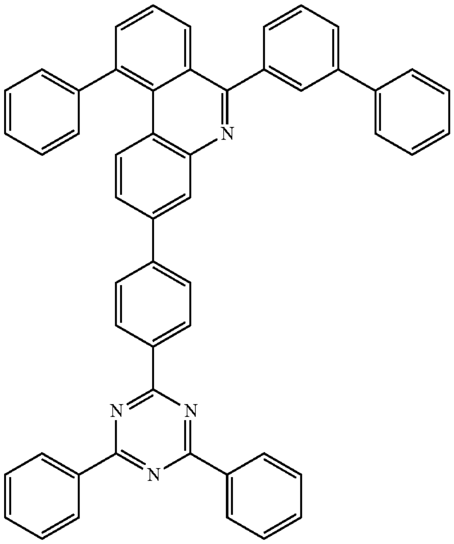
784
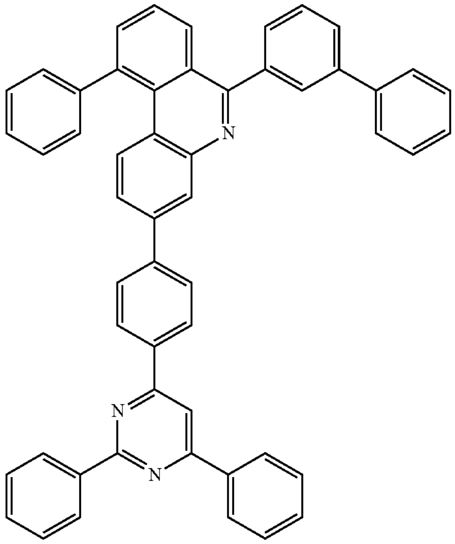
785
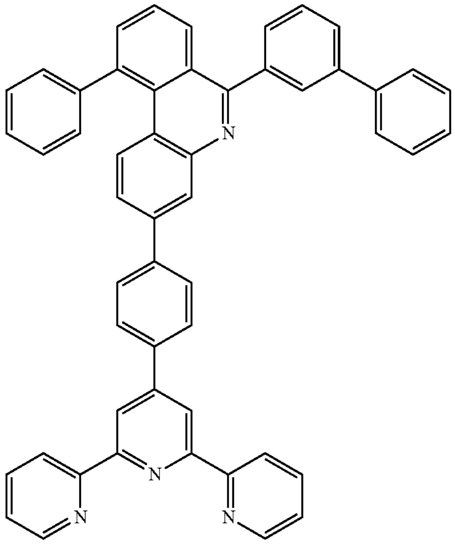
786
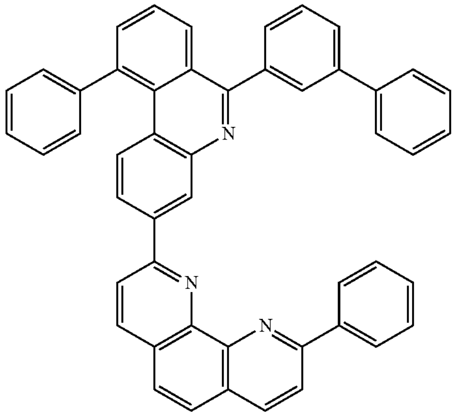

-continued
787
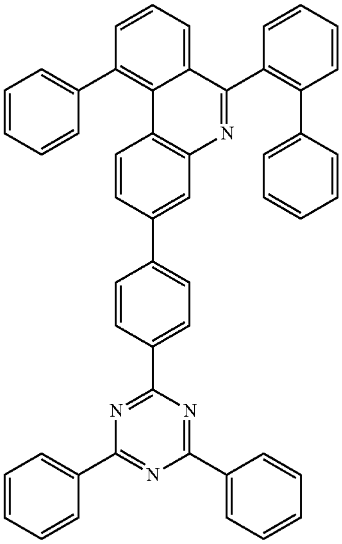
788
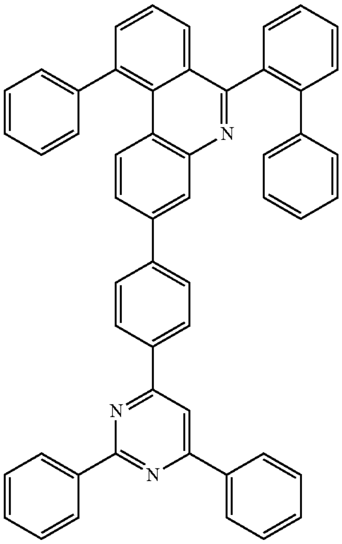
789
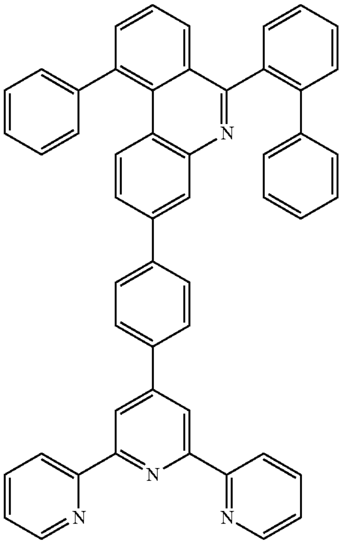
-continued
790
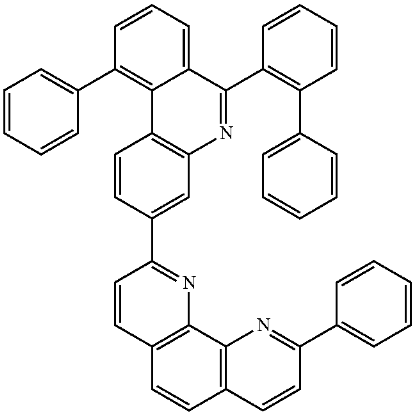
791
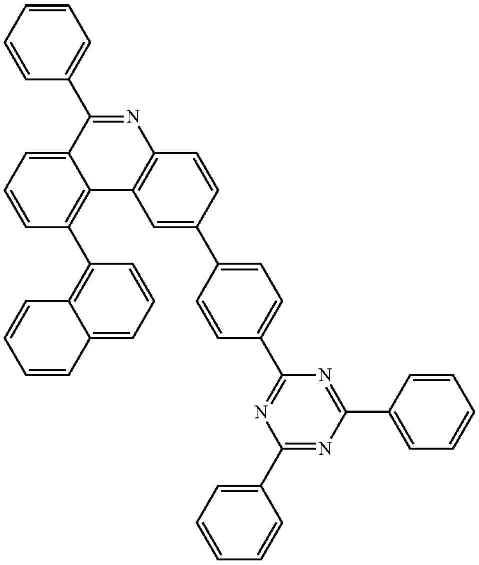
792
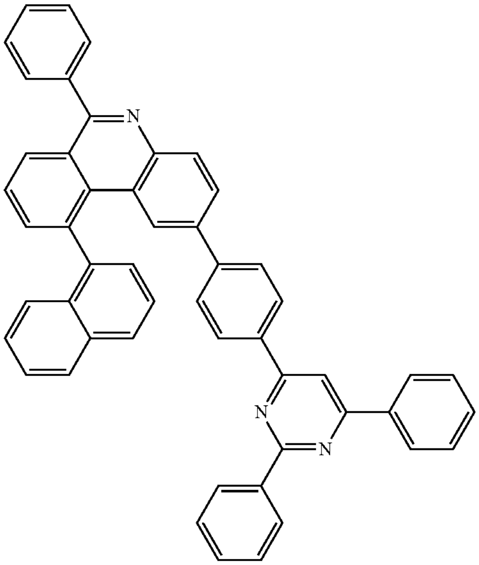

-continued
793
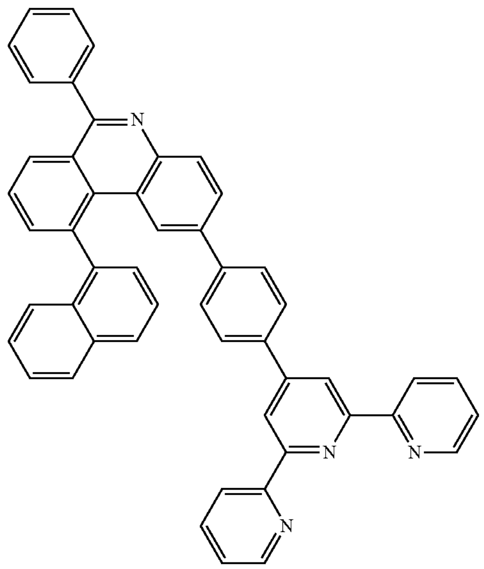
794
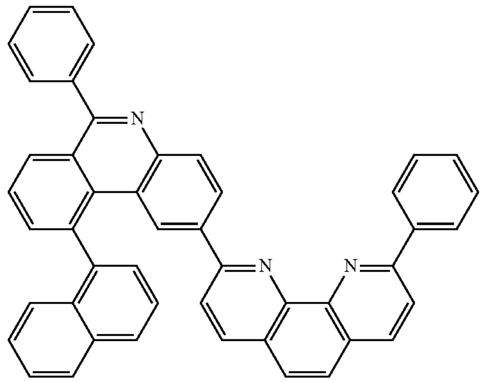
795
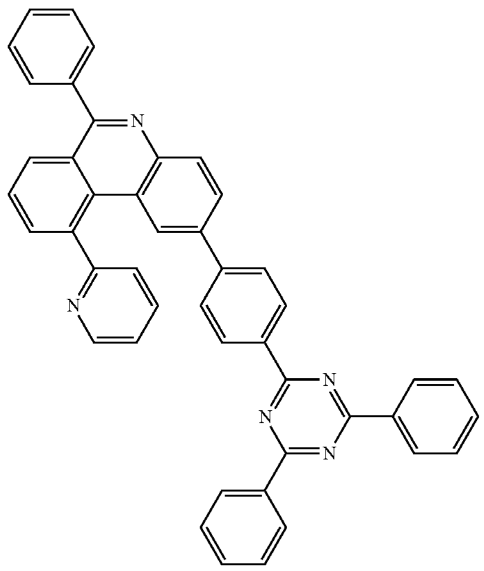
-continued
796
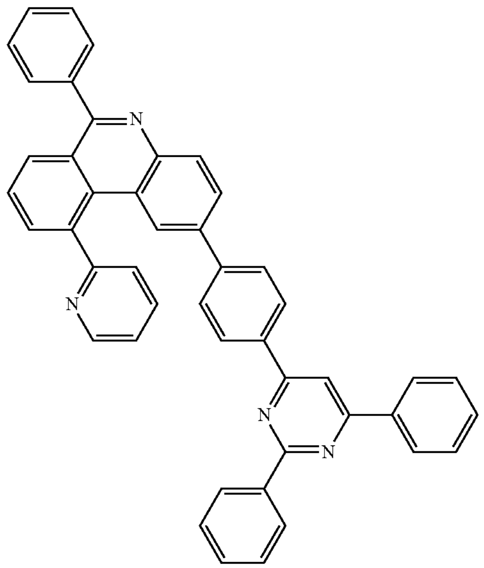
797
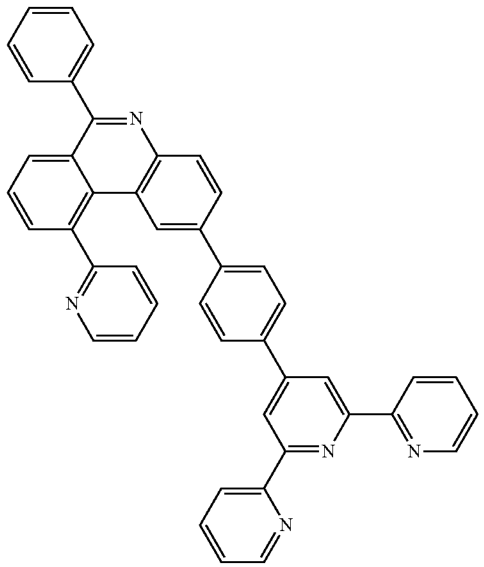
798
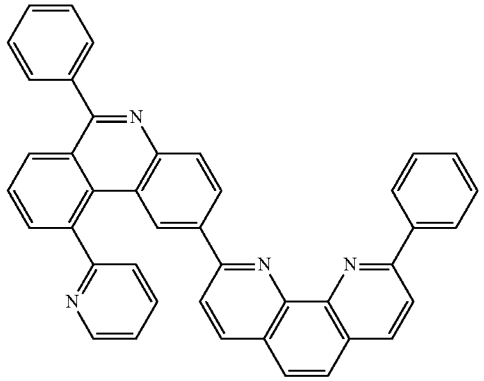

-continued
799
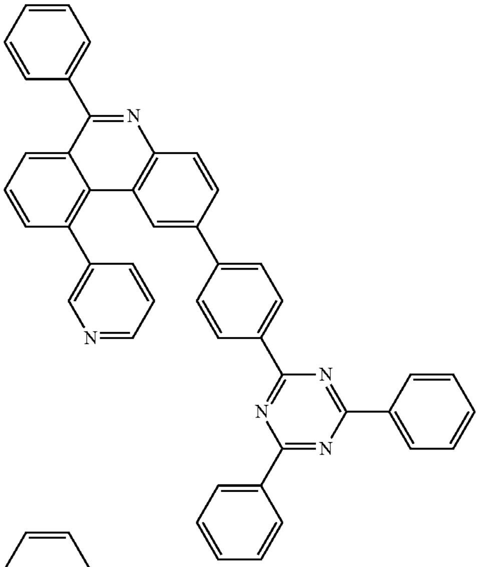
800
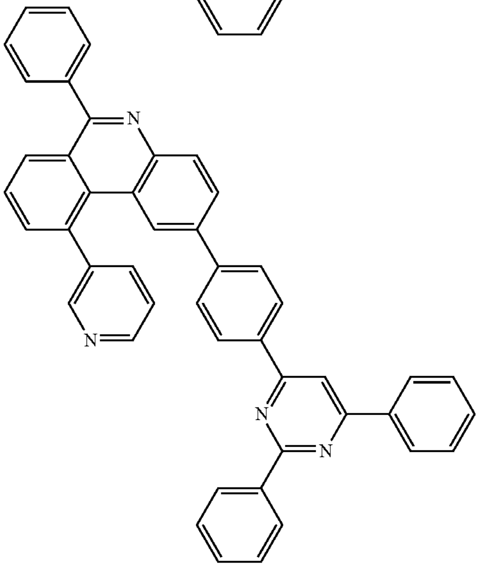
801
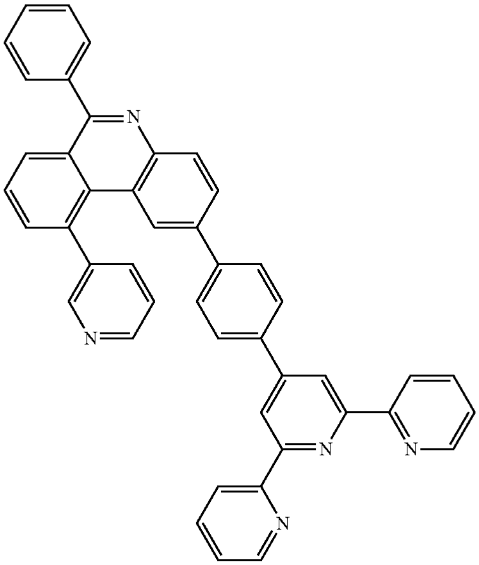
-continued
802
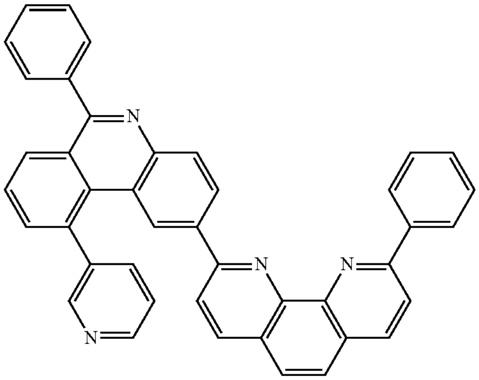
803
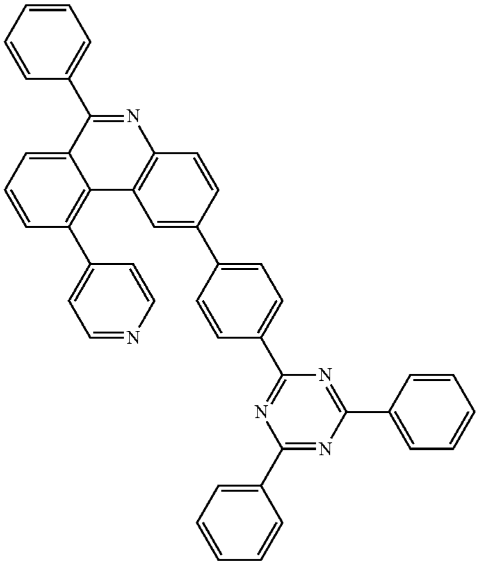
804
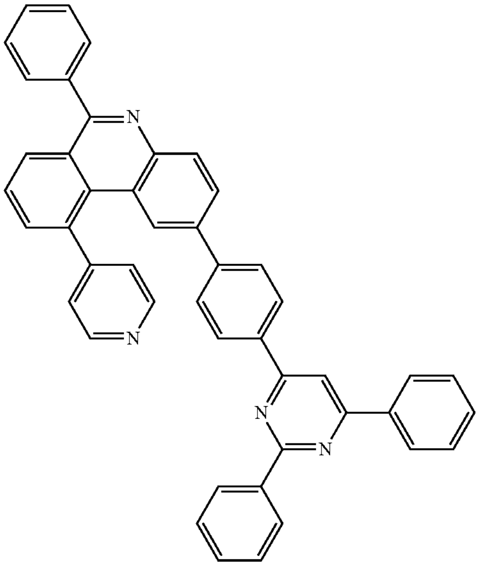

805
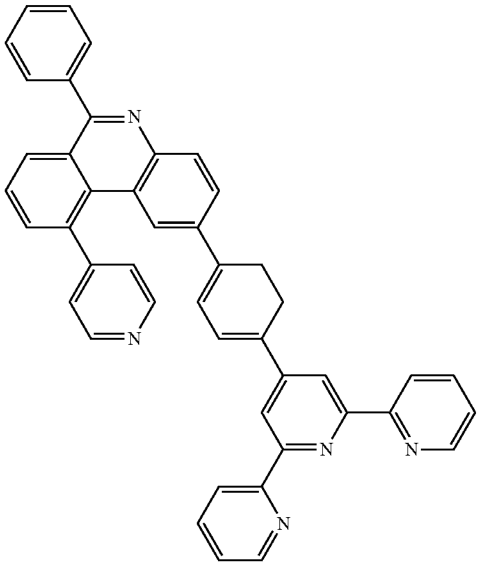
806
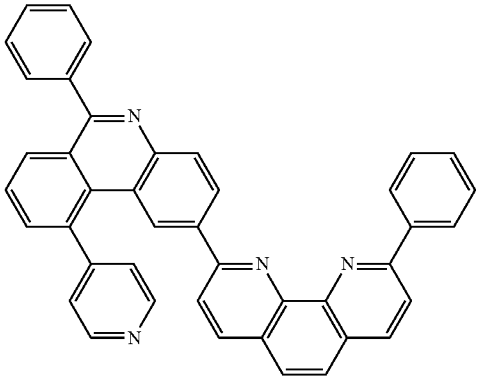
807
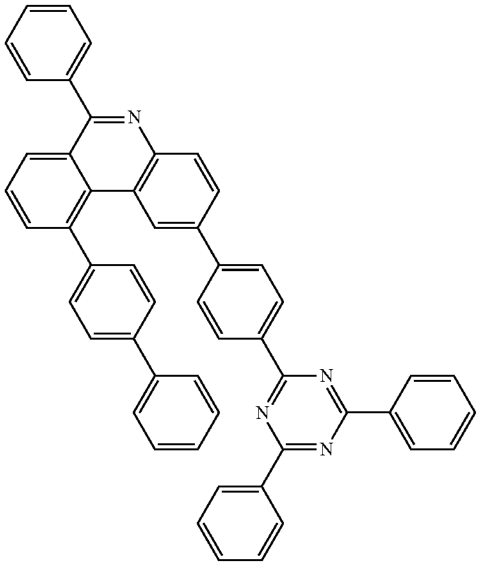
808
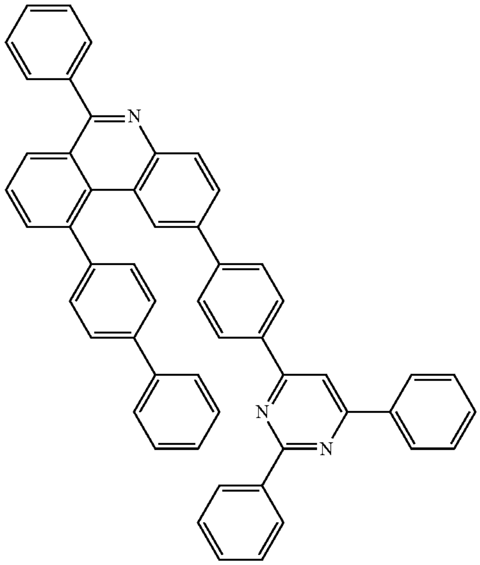
809
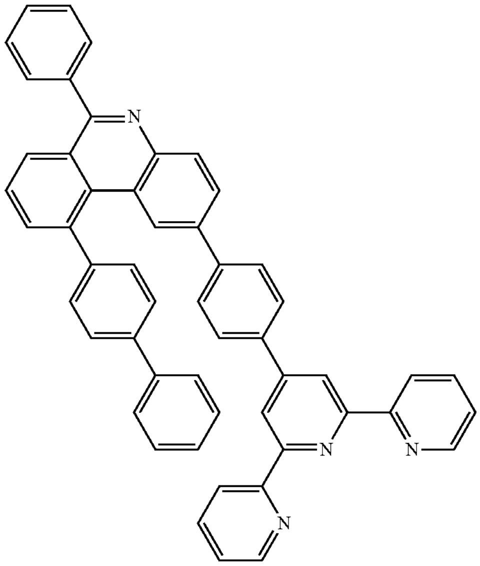
810
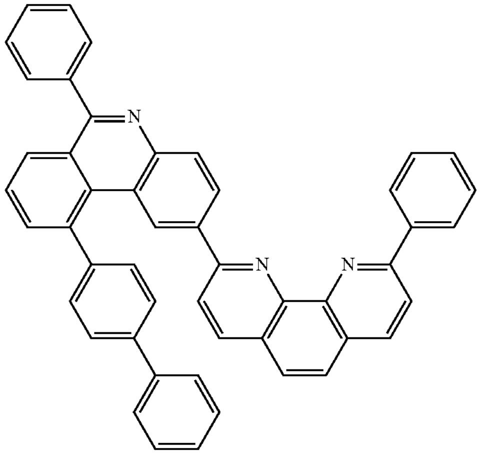

-continued
811
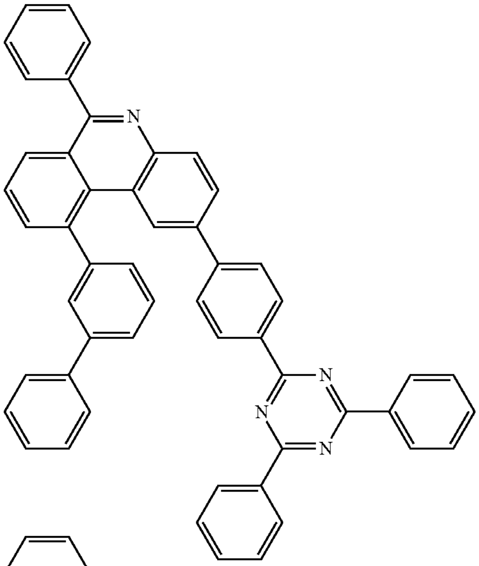
812
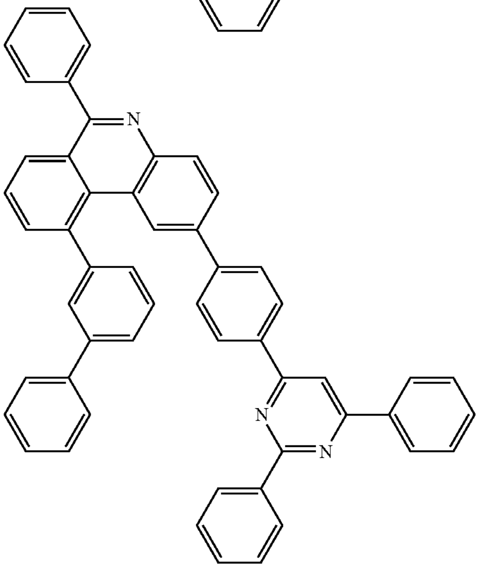
813
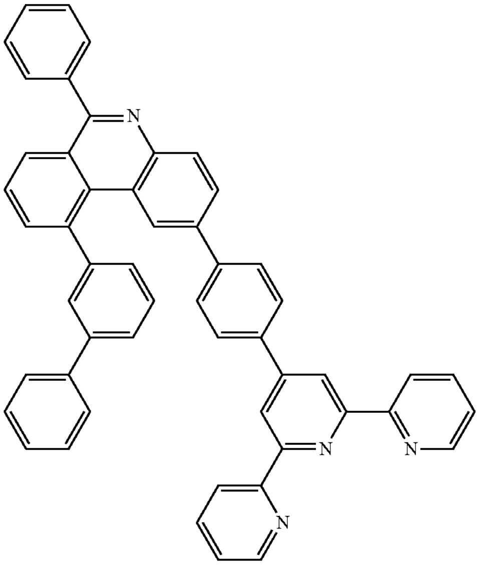
-continued
814
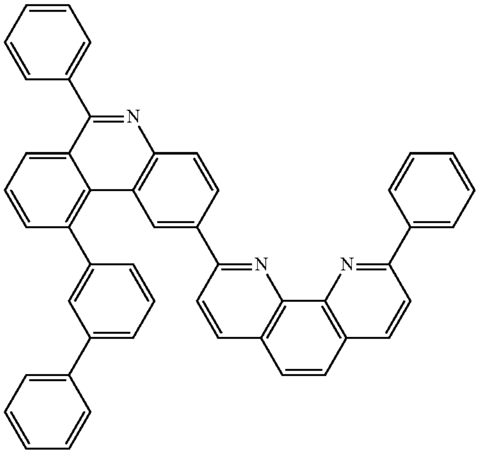
815
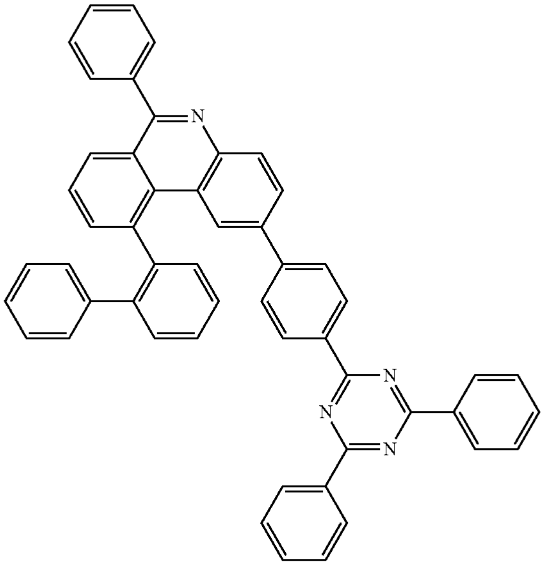
816
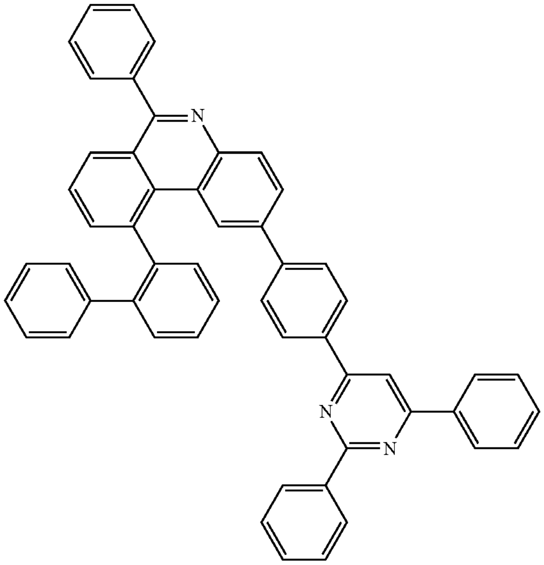

-continued
817
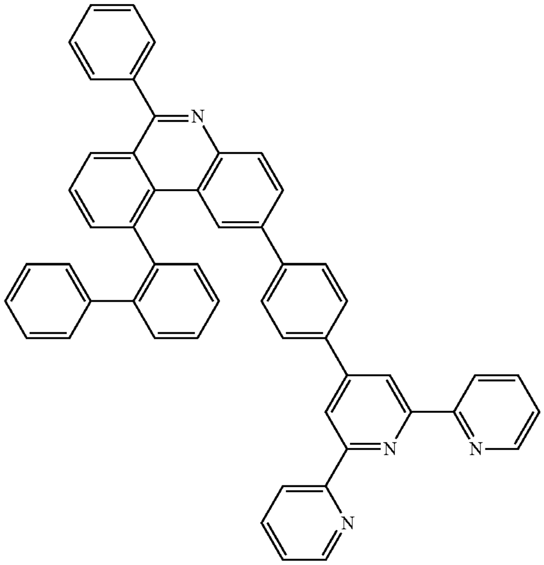
818
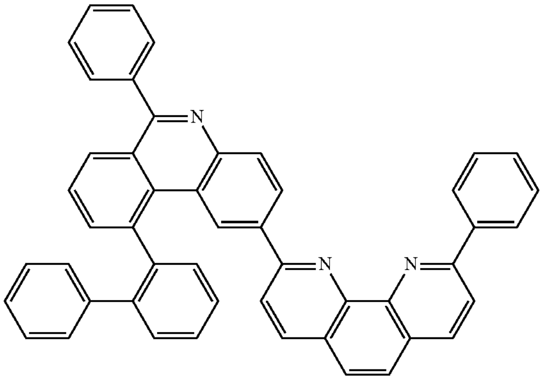
819
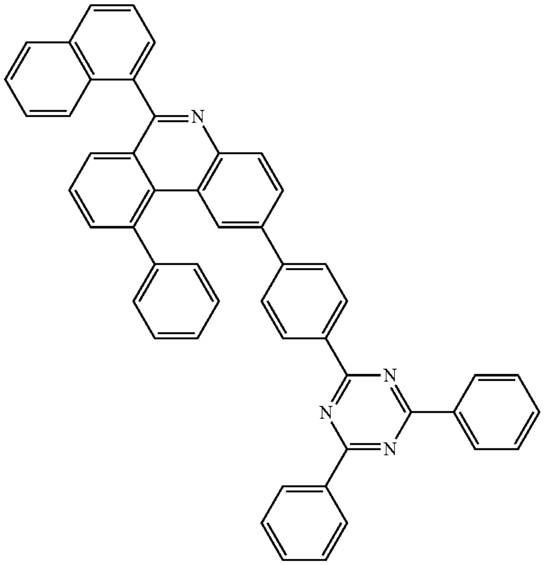
-continued
820
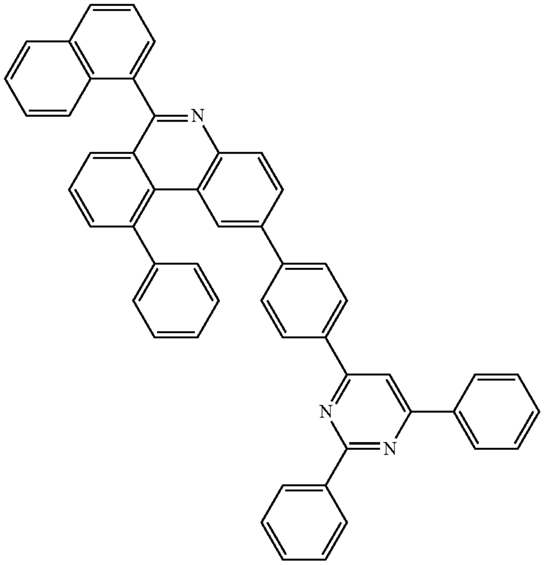
821
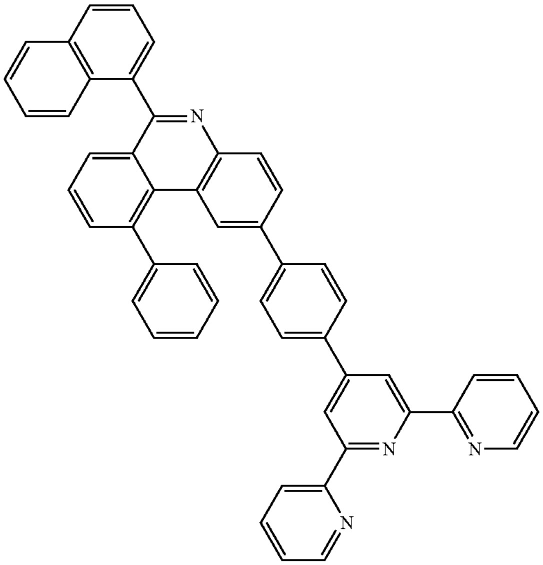
822
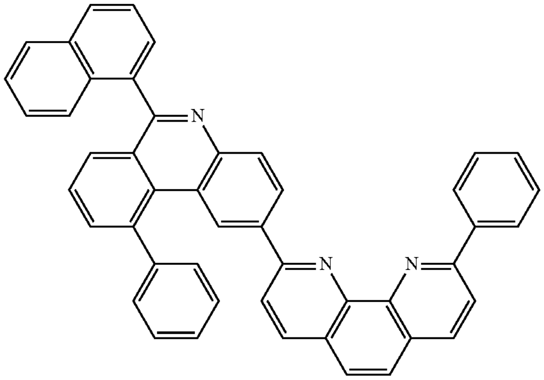

-continued
823
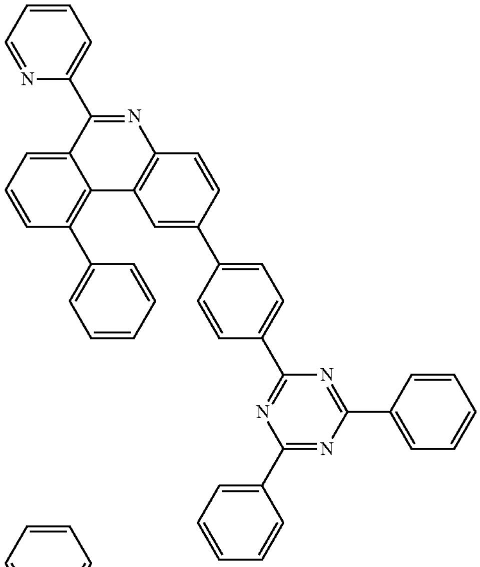
824
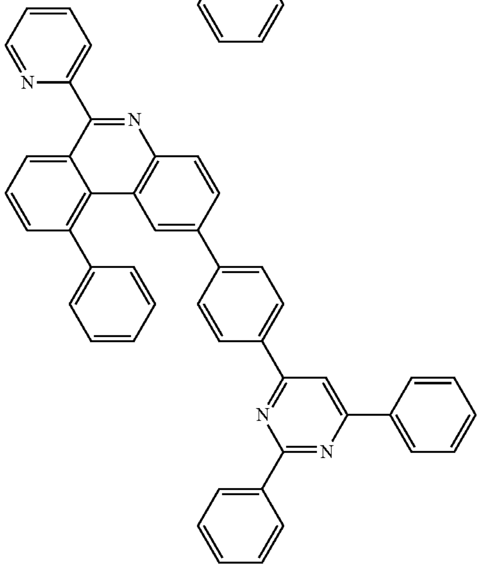
825
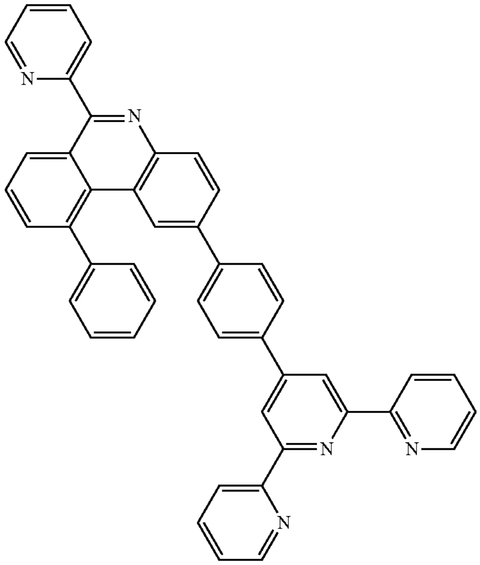
-continued
826
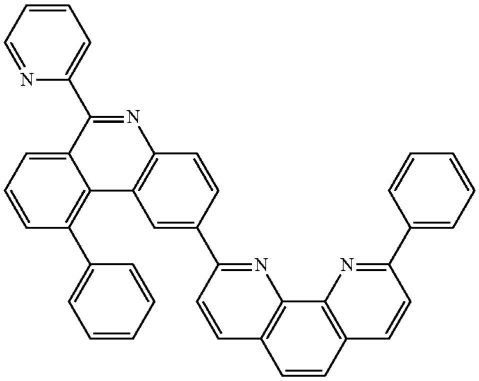
87
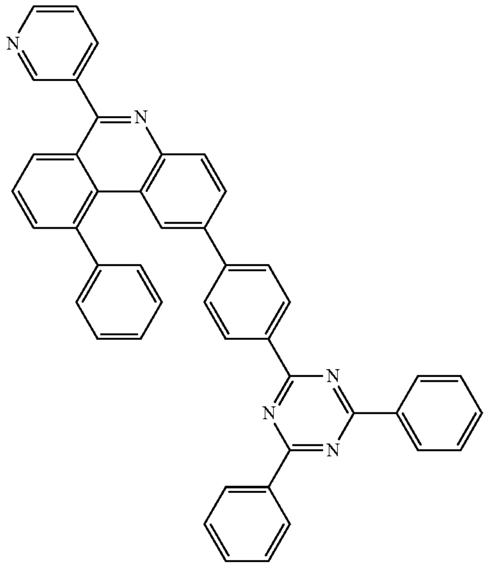
828
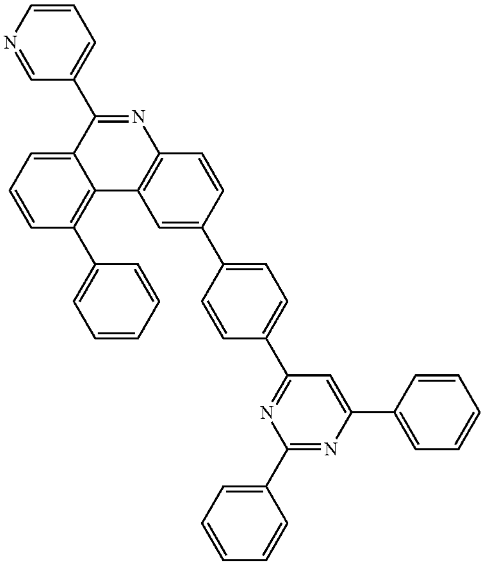

-continued
829
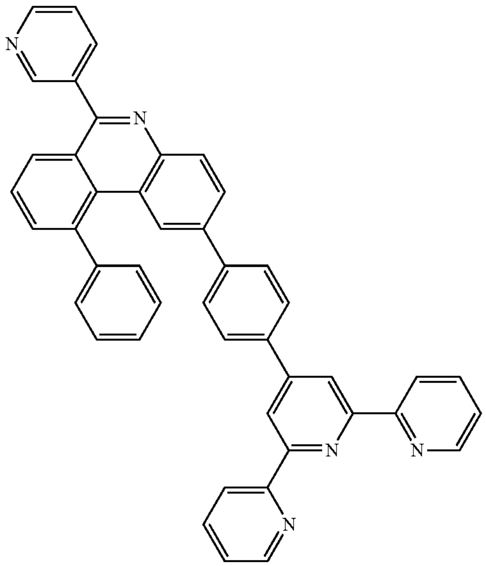
830
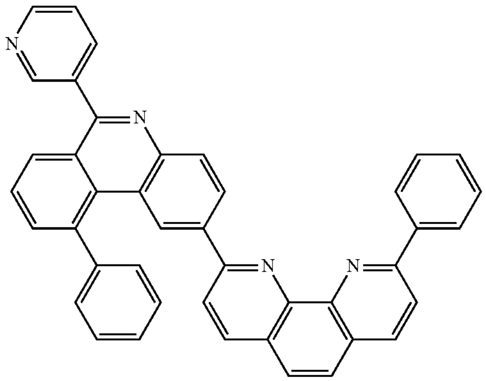
831
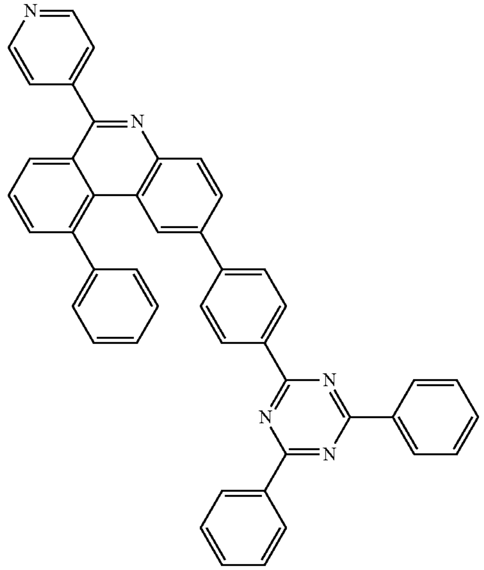
-continued
832
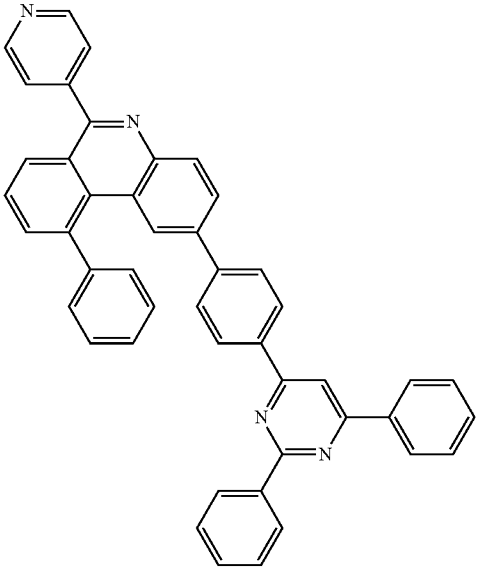
833
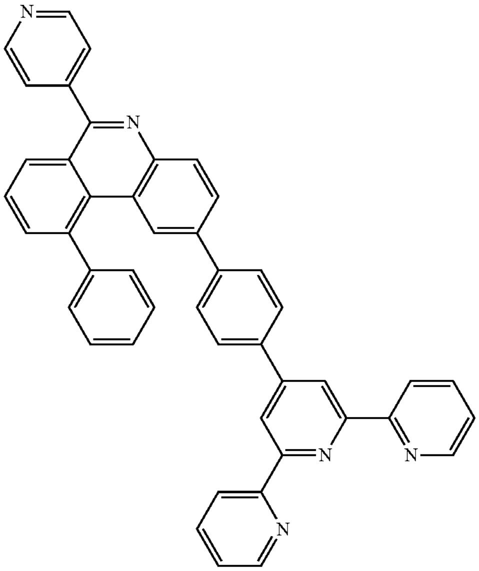
834
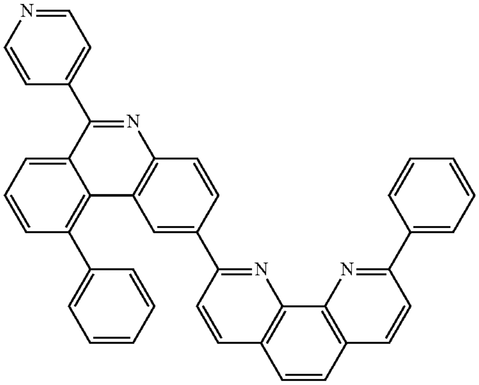

-continued
835
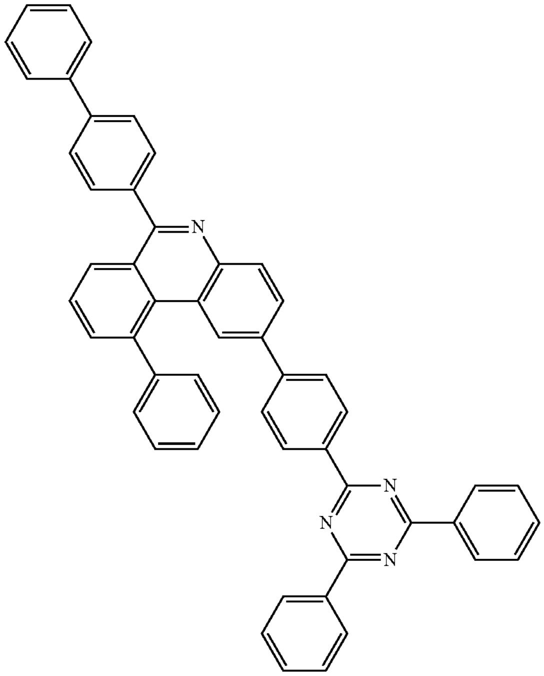
837
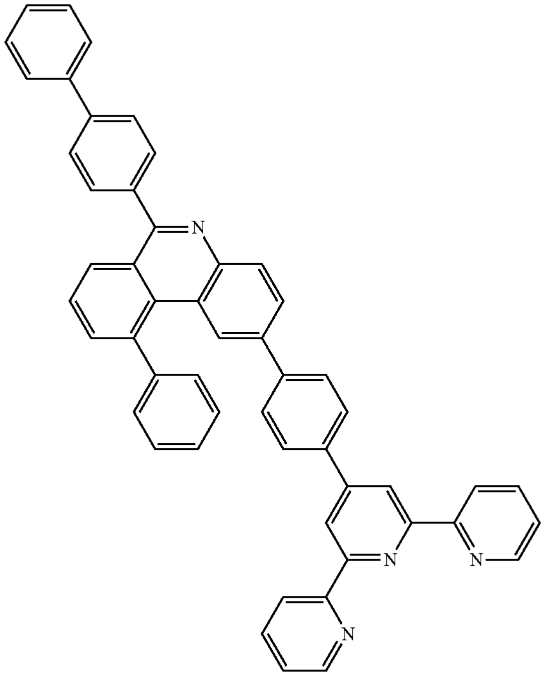
836
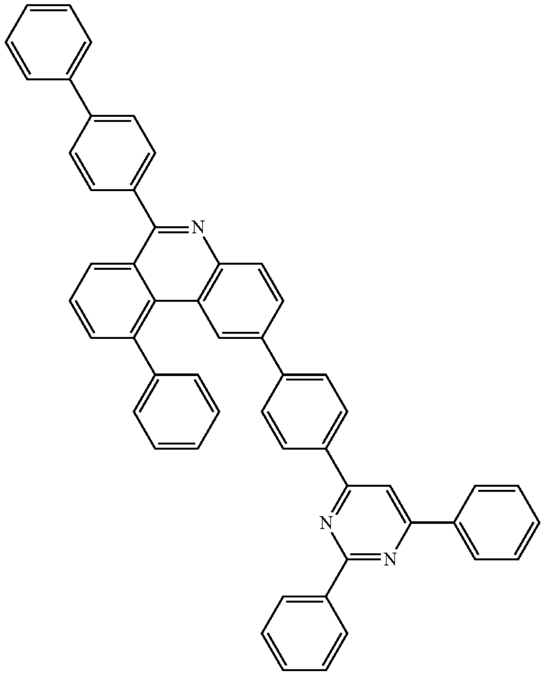
838
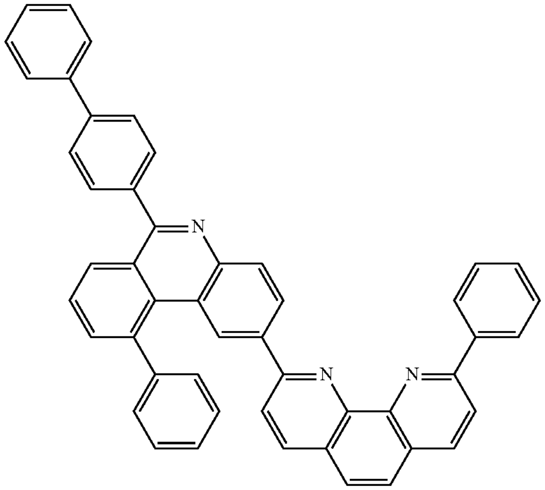

-continued
839
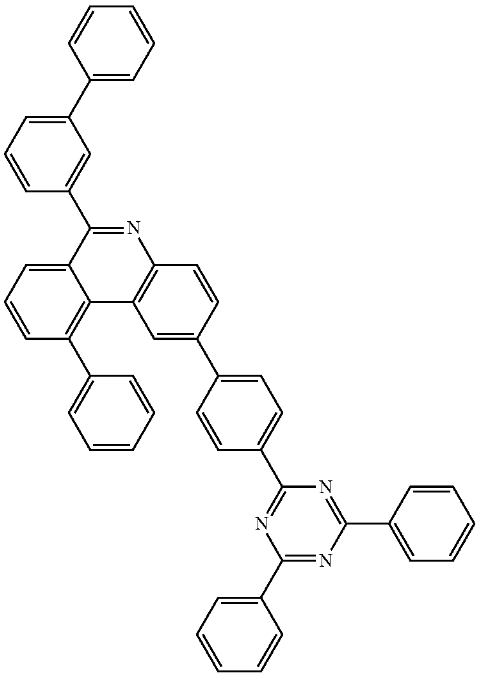
840
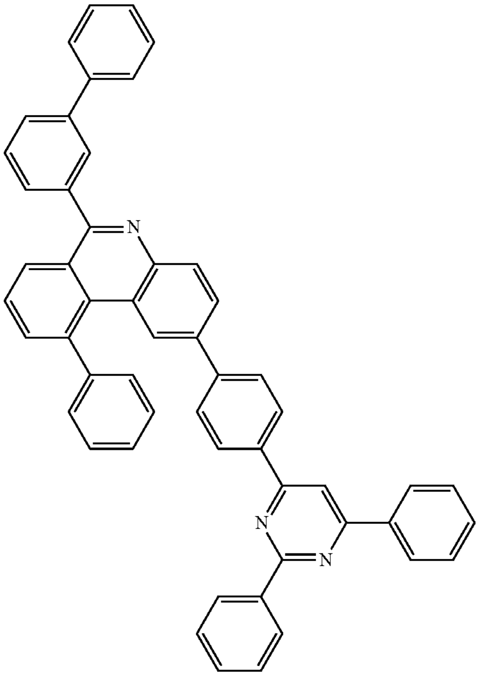
-continued
841
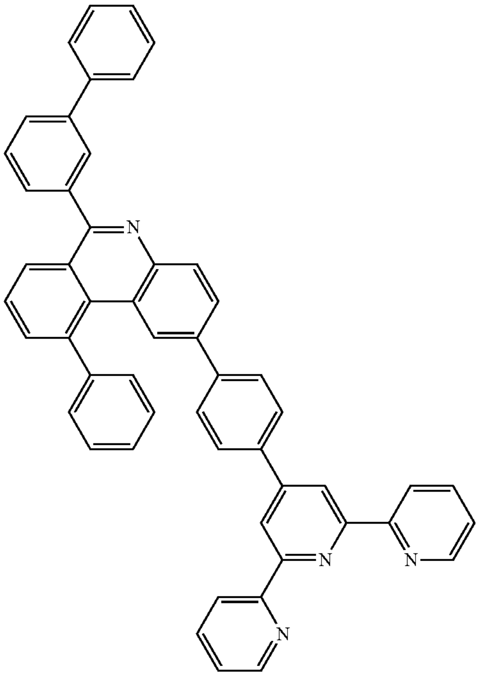
842
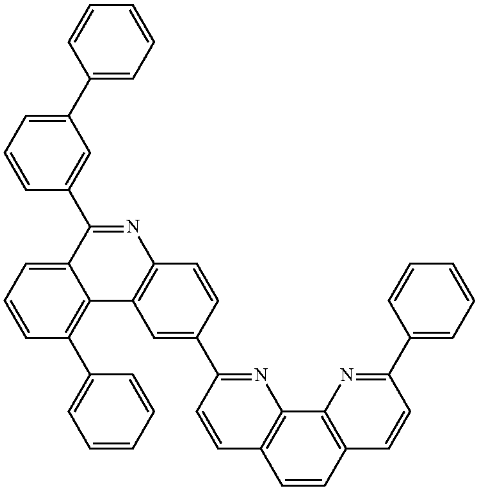

-continued
843
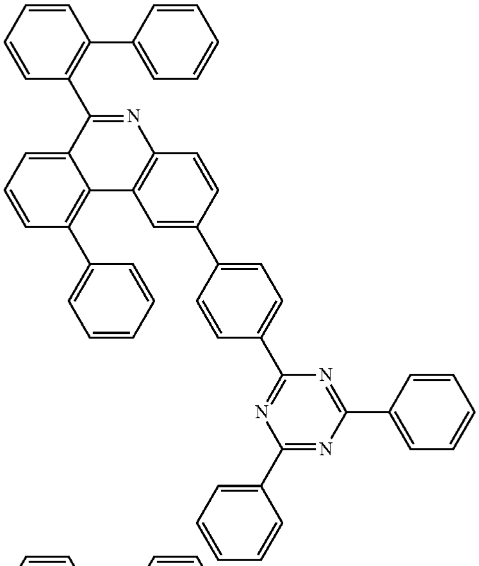
844
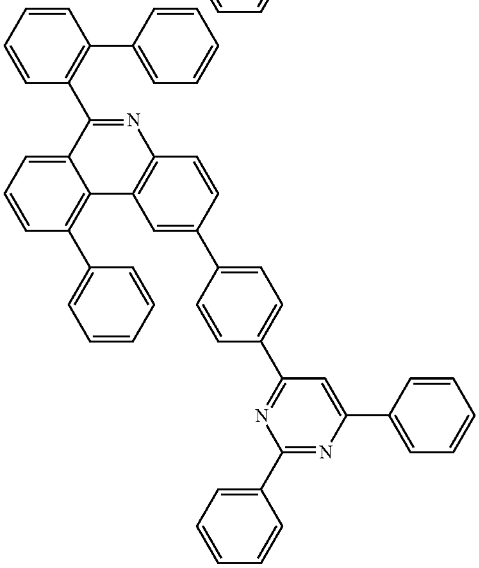
845
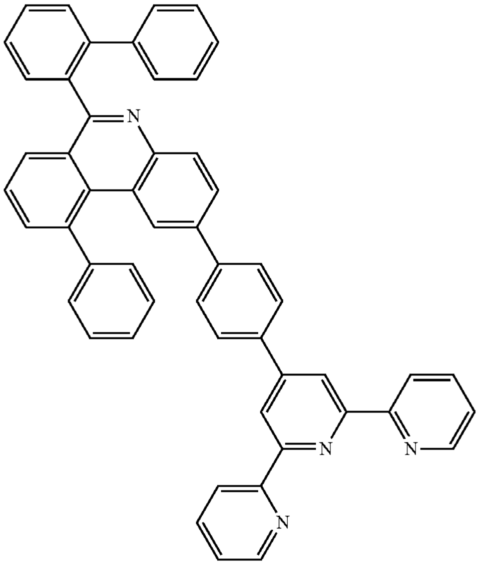
-continued
846
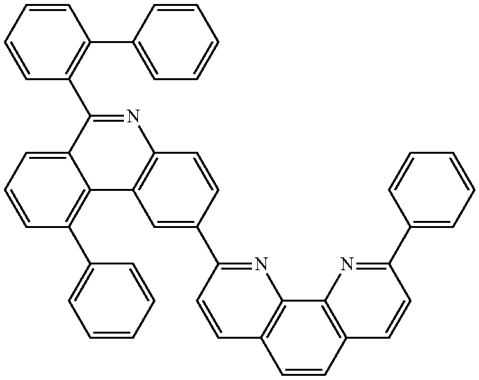
847
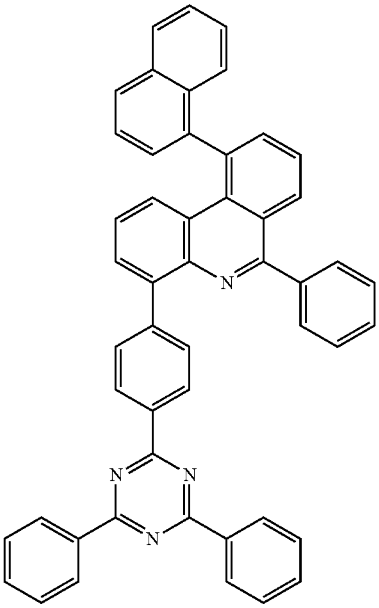
848
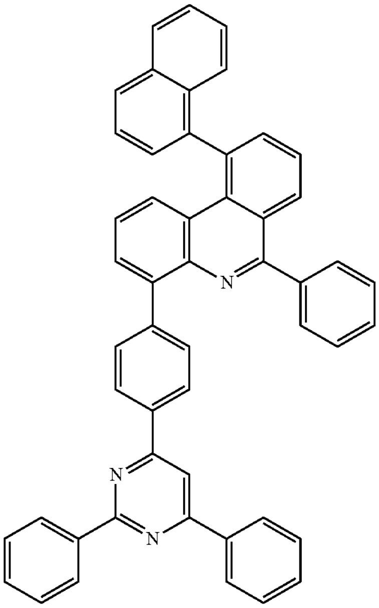

-continued
849
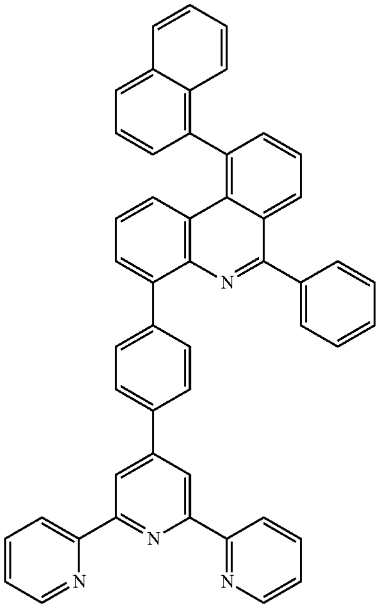
850
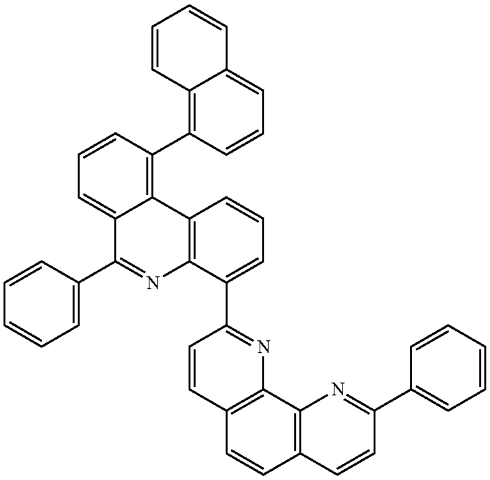
851
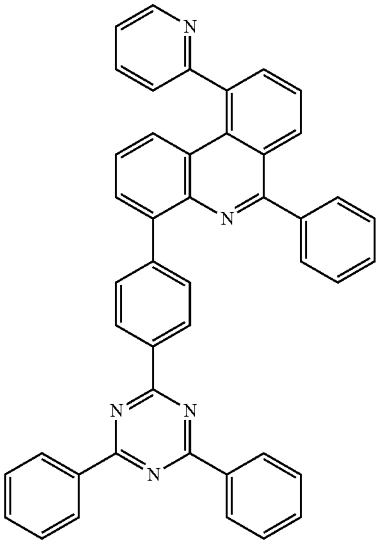
-continued
852
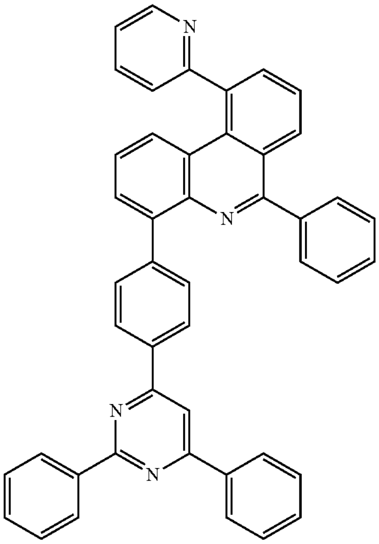
853
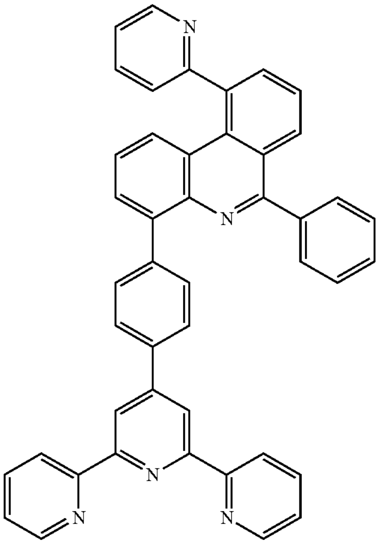
854
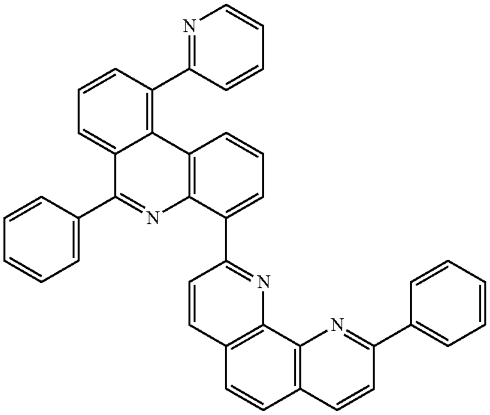

-continued
855
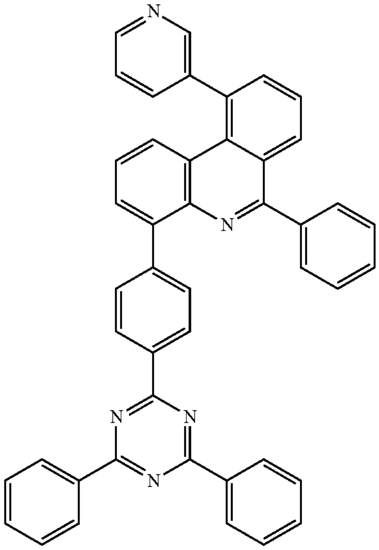
856
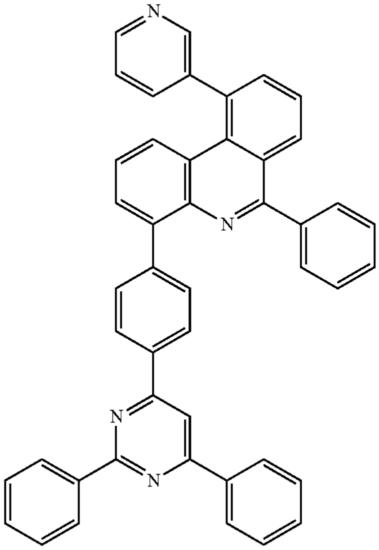
857
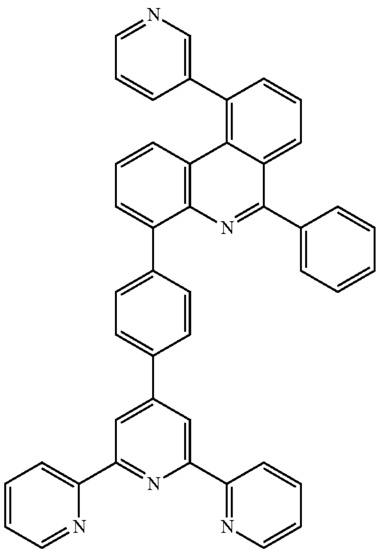
-continued
858
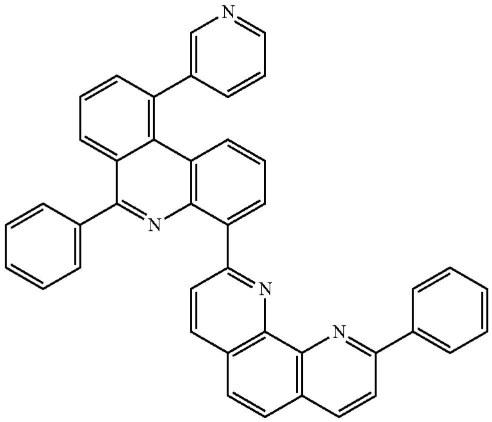
859
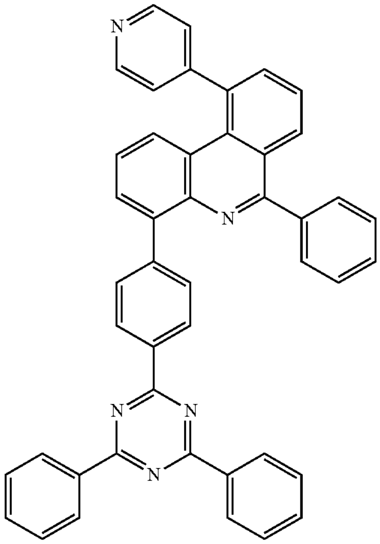
960
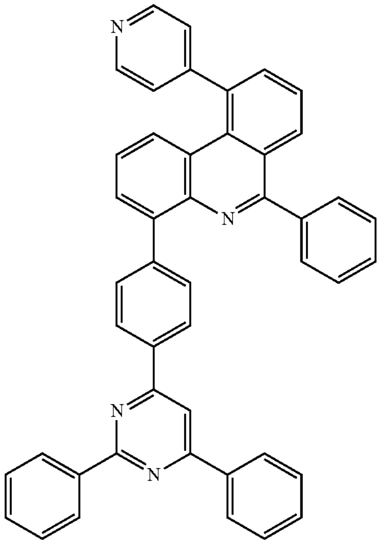

-continued
861
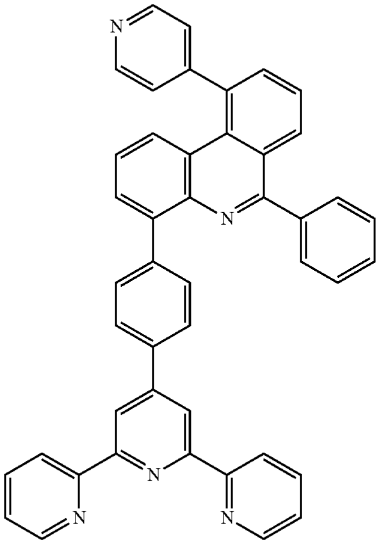
862
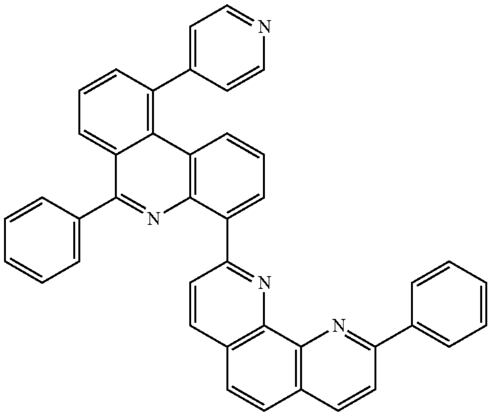
863
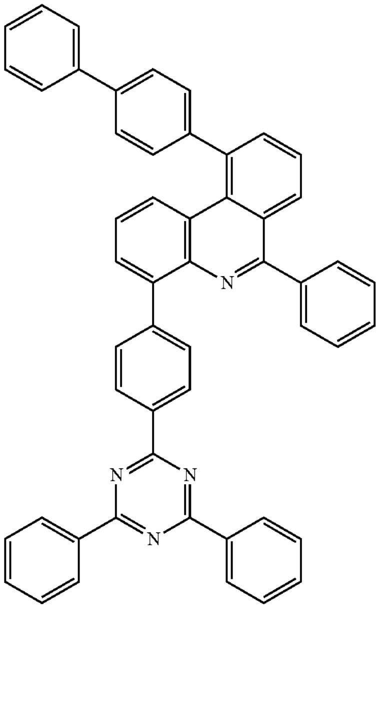
-continued
864
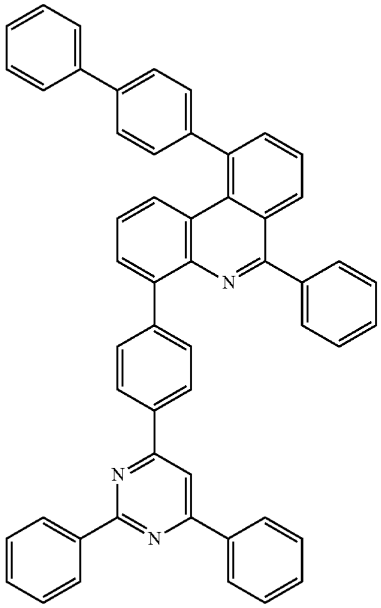
865
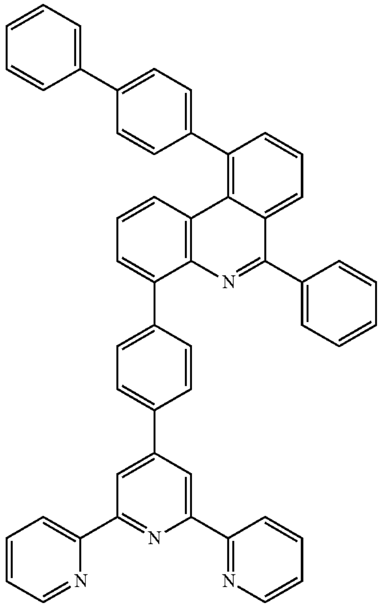
866
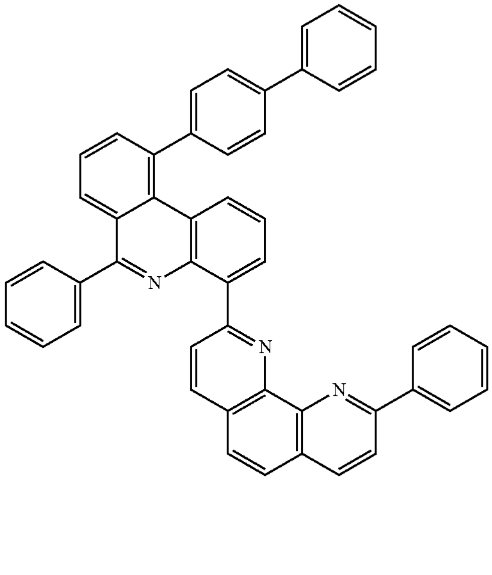

-continued
867
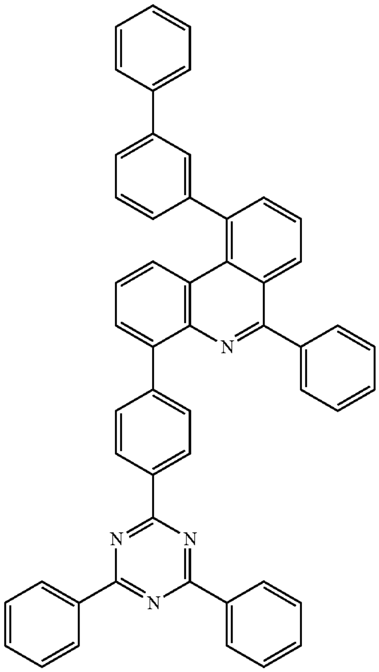
868
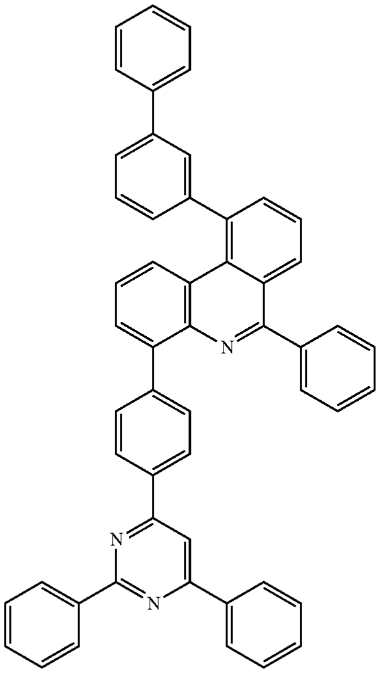
-continued
869
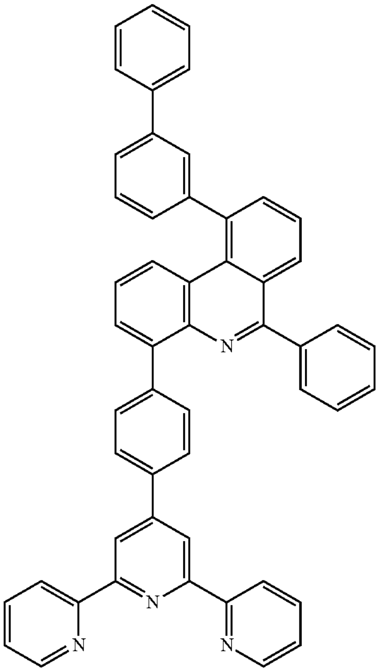
870
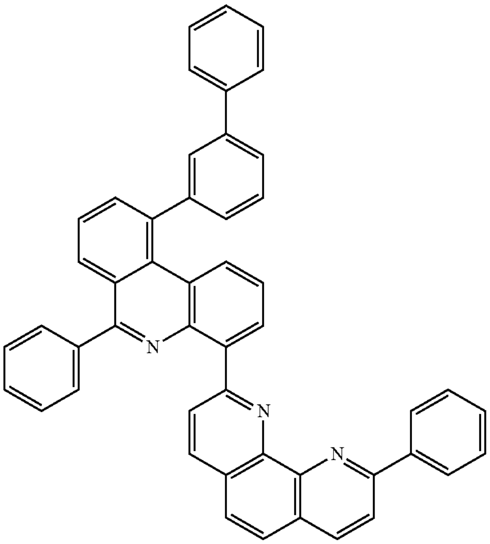

-continued
871
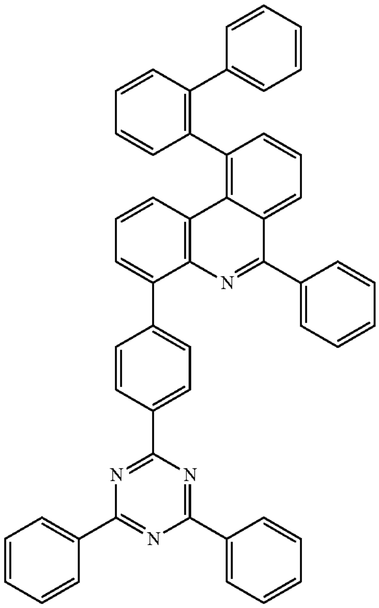
872
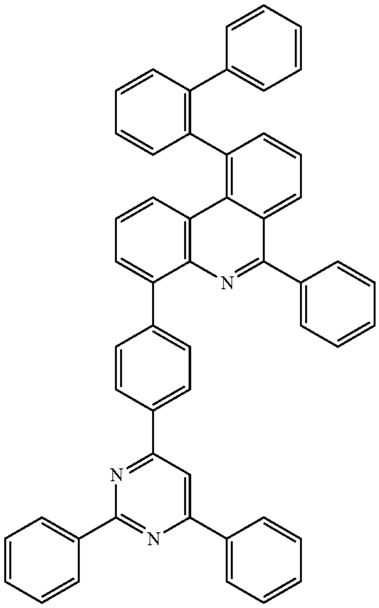
-continued
873
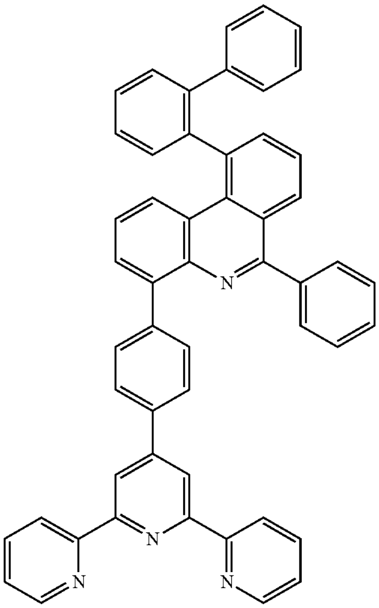
874
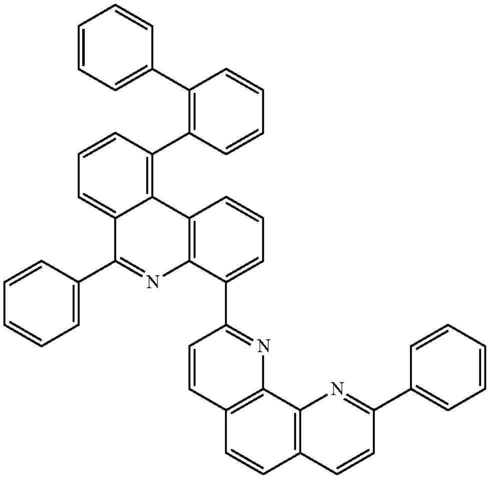
875
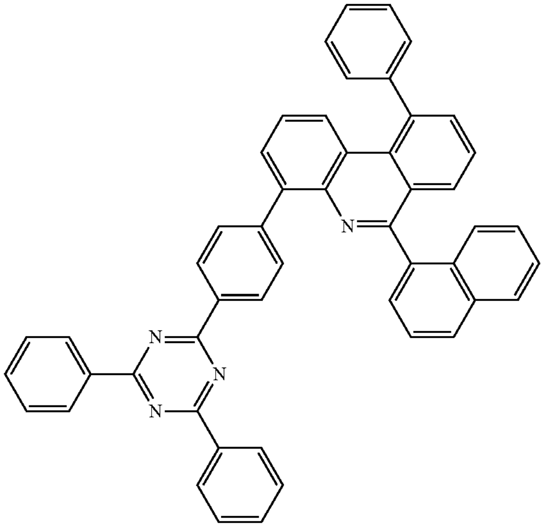

-continued
876
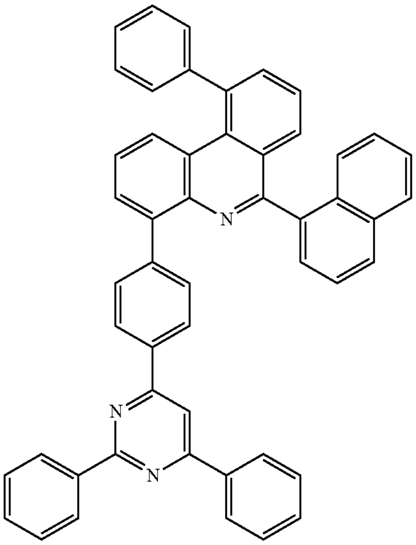
877
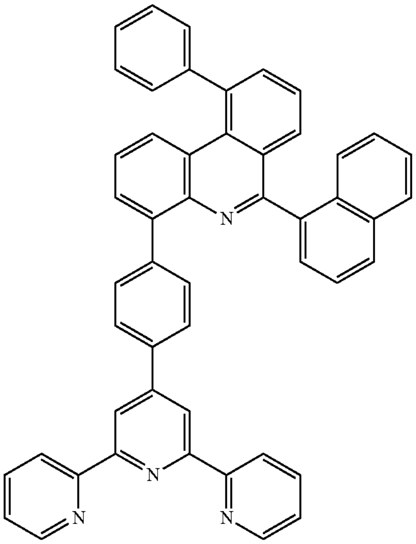
878
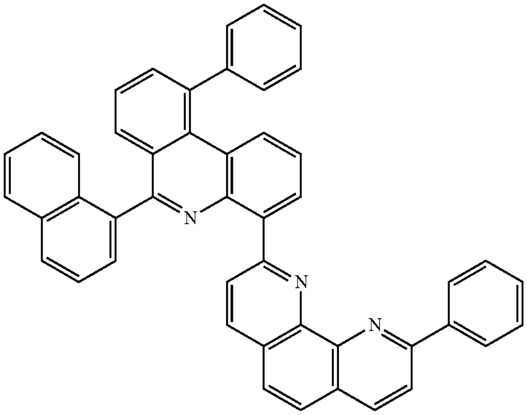
-continued
879
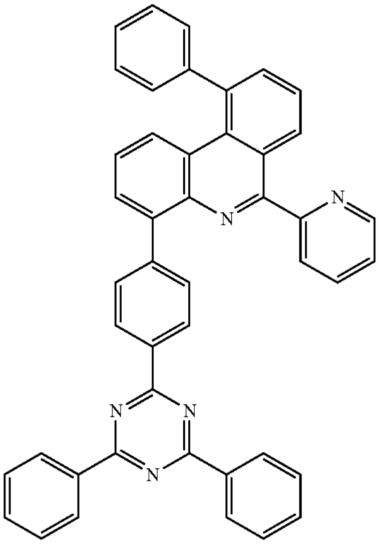
880
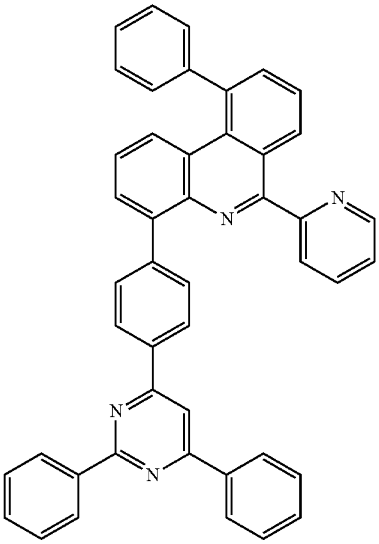
881
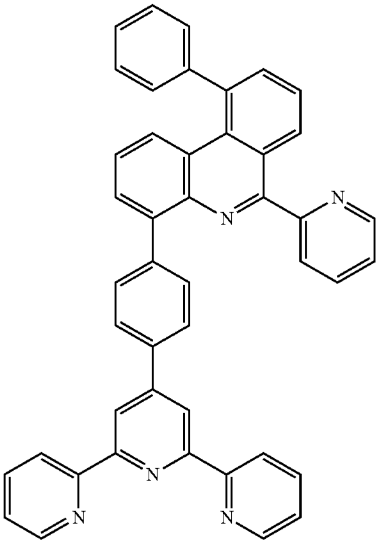

-continued
882
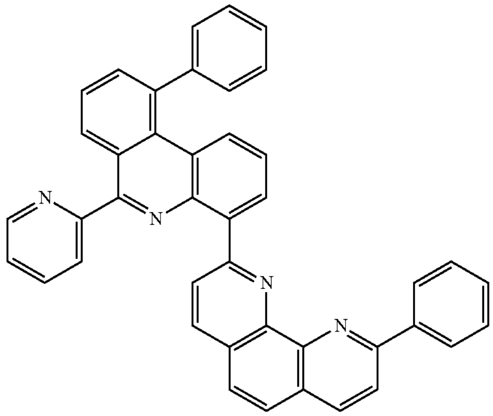
883
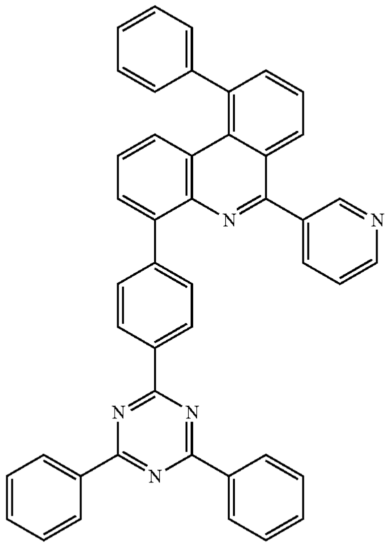
884
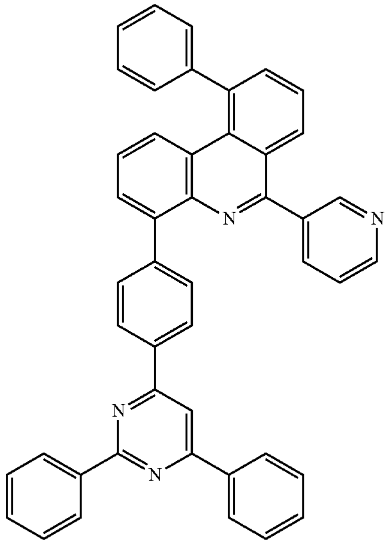
-continued
885
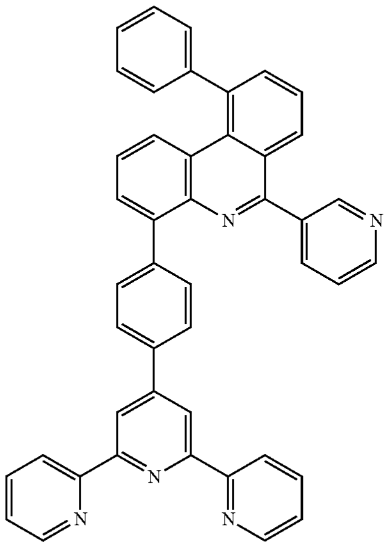
886
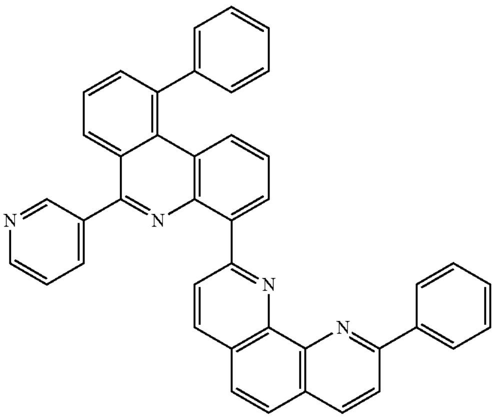
887
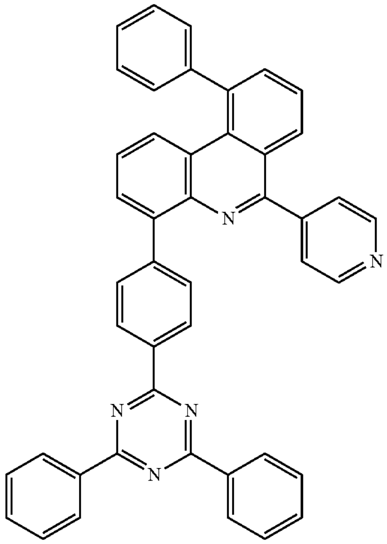

-continued
888
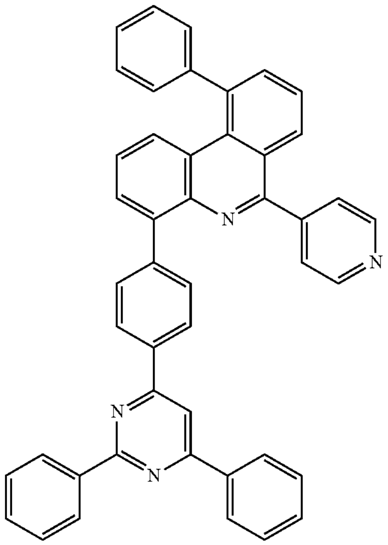
889
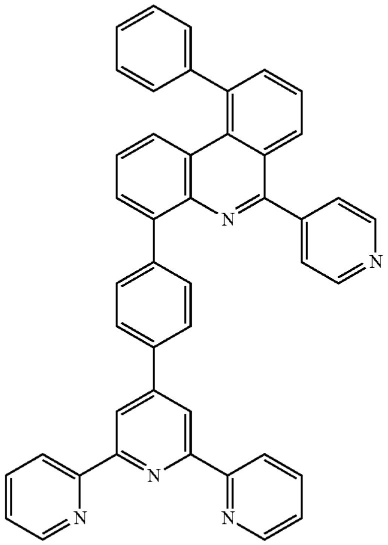
890
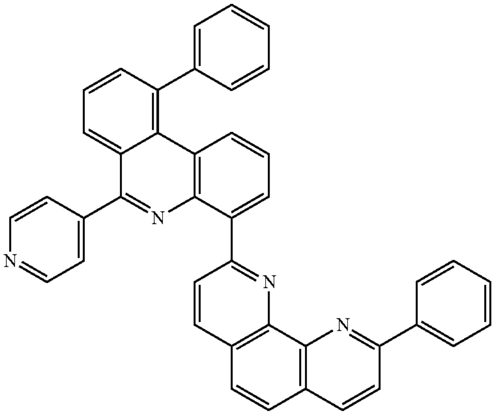
-continued
891
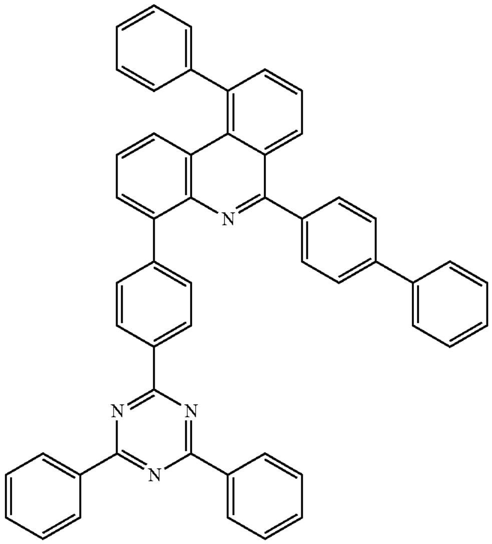
892
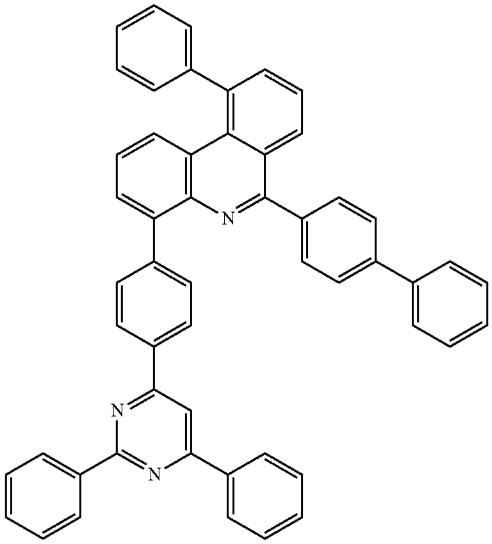
893
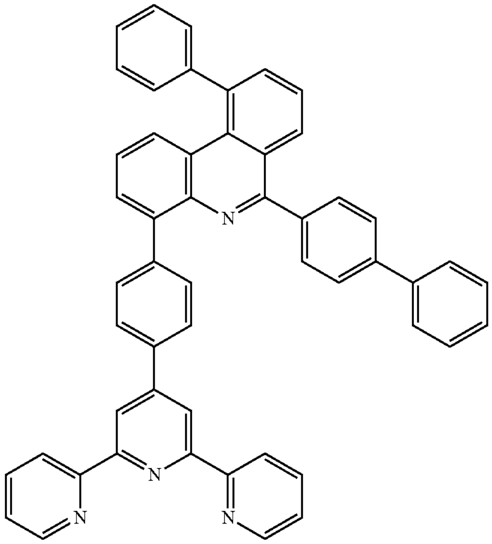

-continued
894
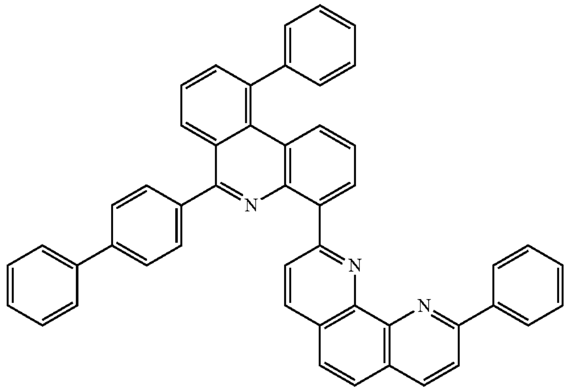
895
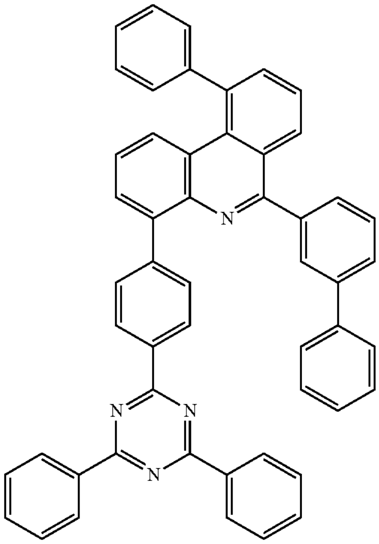
896
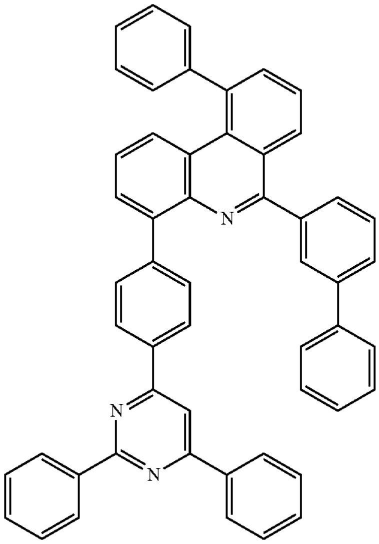
-continued
897
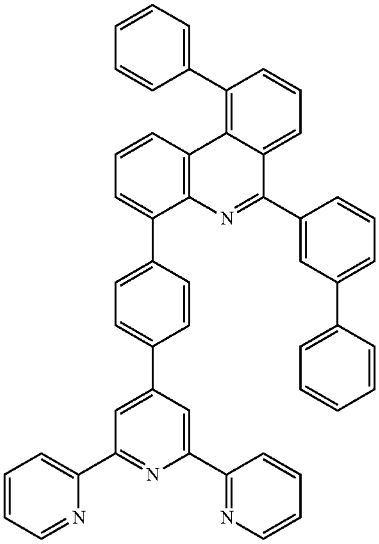
898
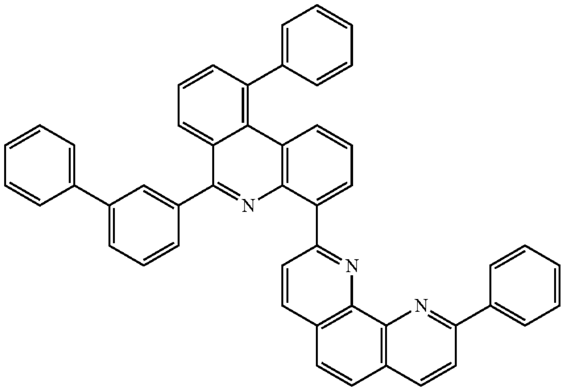
899
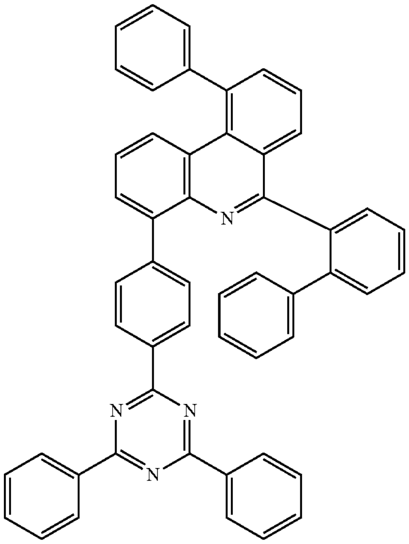

-continued
900
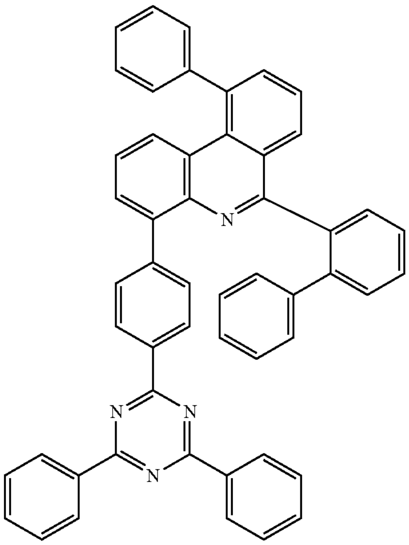
901
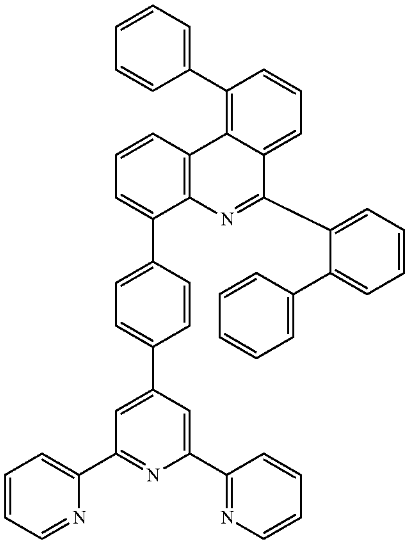
902
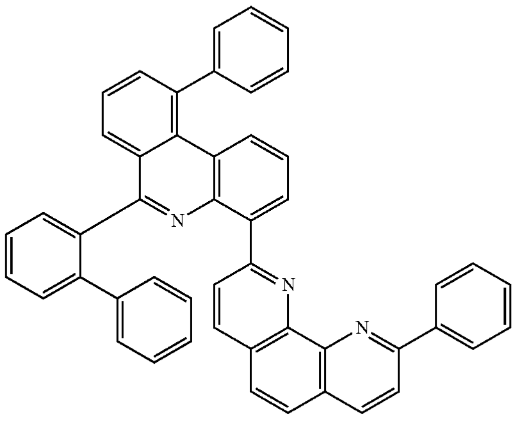
-continued
903
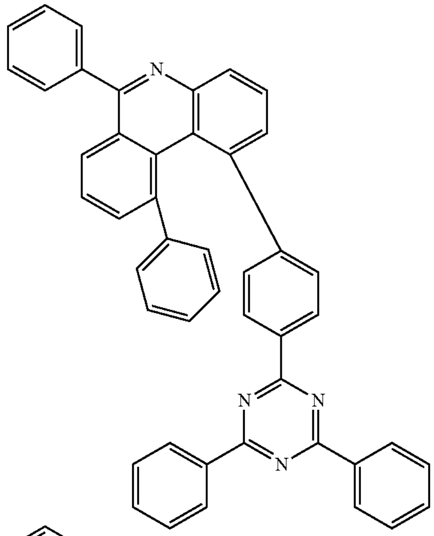
904
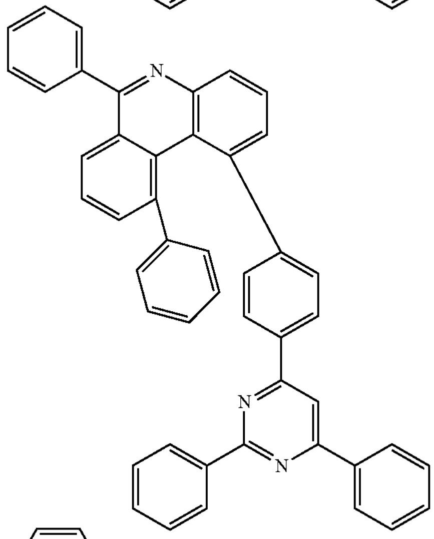
905
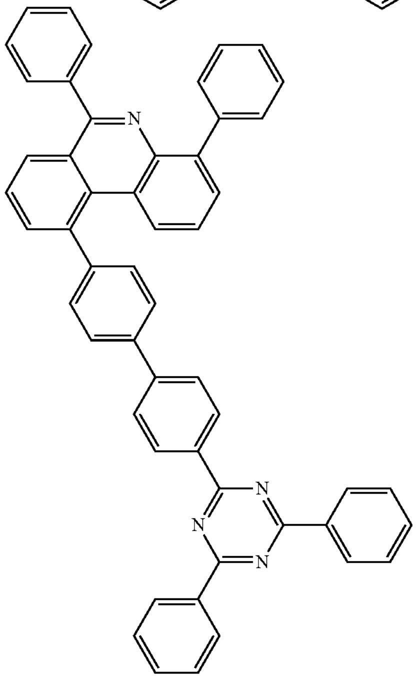

-continued
906
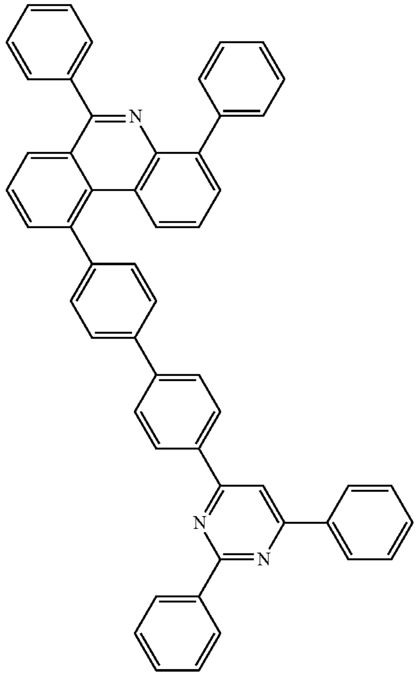
907
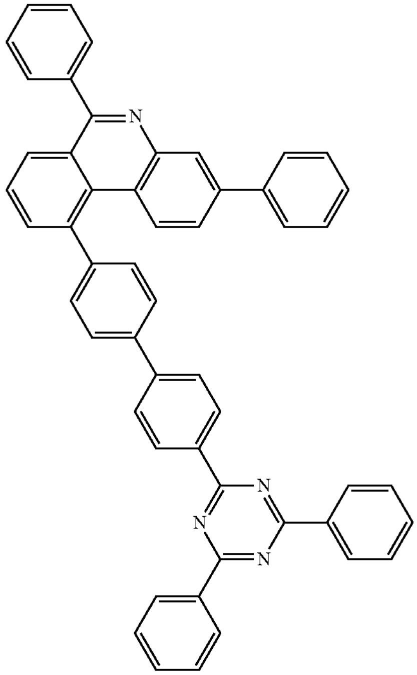
-continued
908
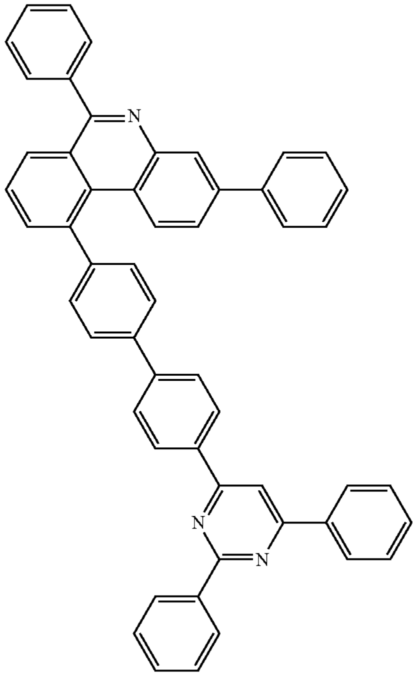
909
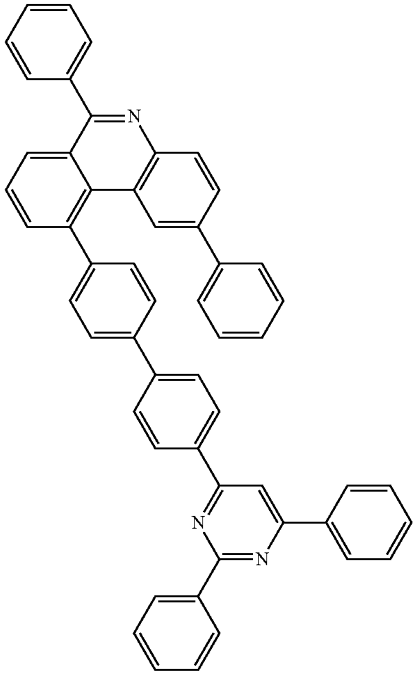

-continued
910
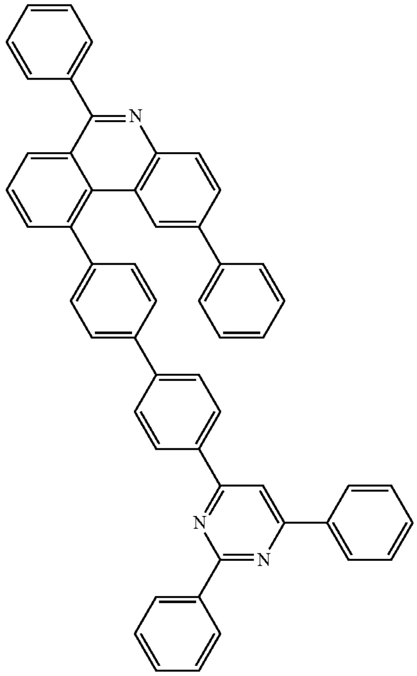
911
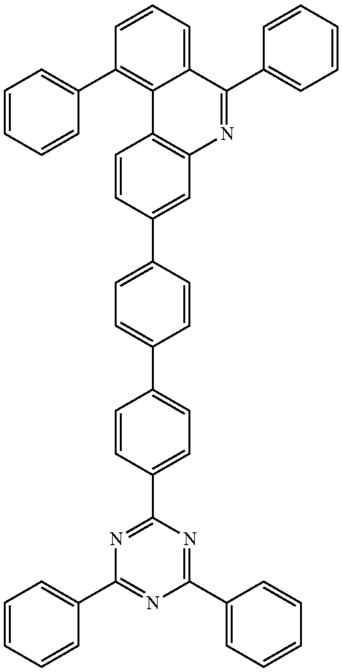
-continued
912
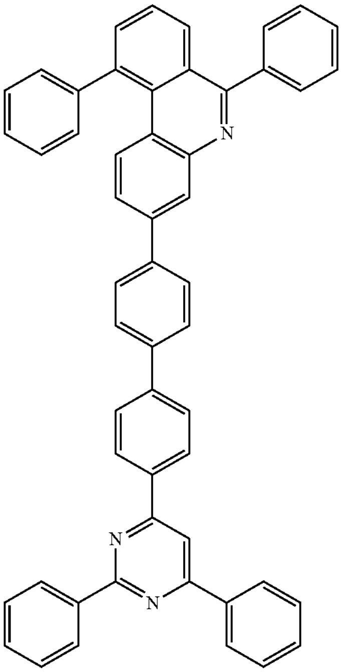
913
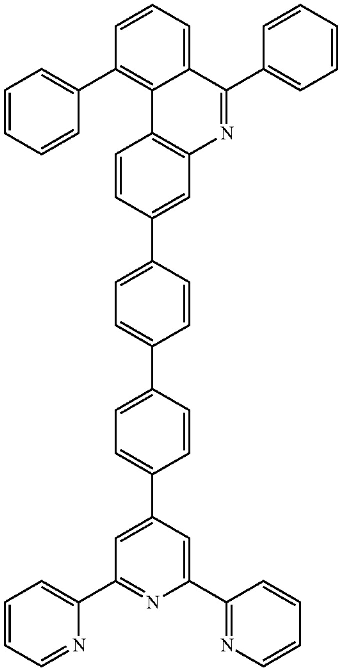

-continued
914
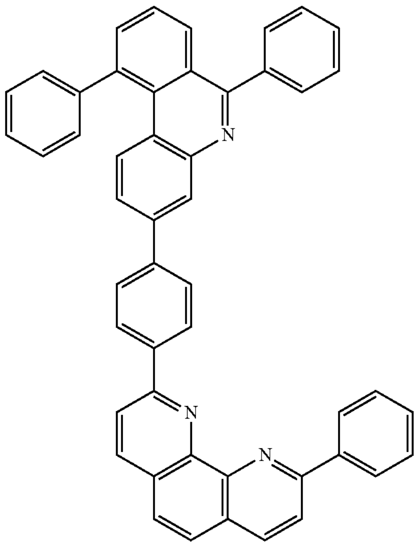
915
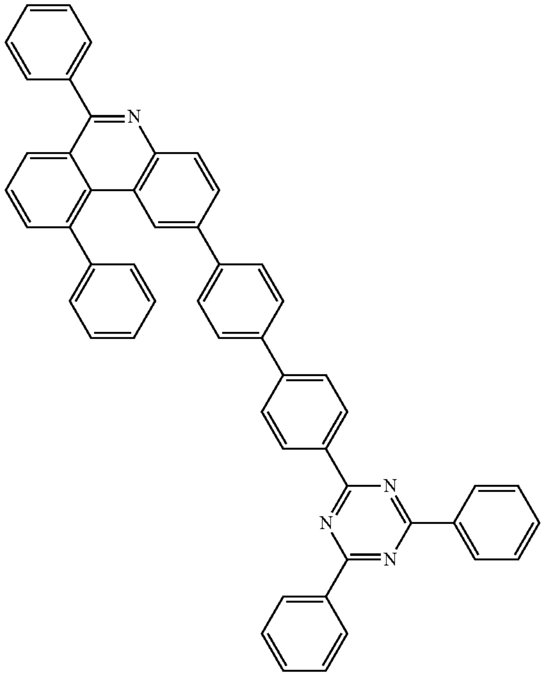
-continued
916
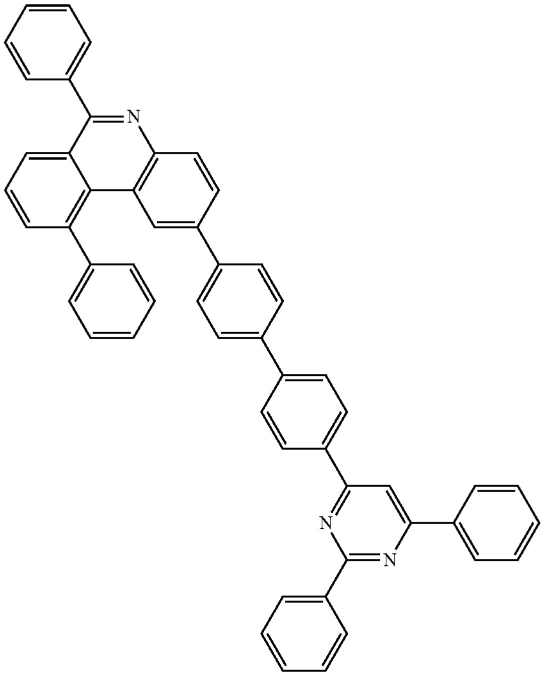
917
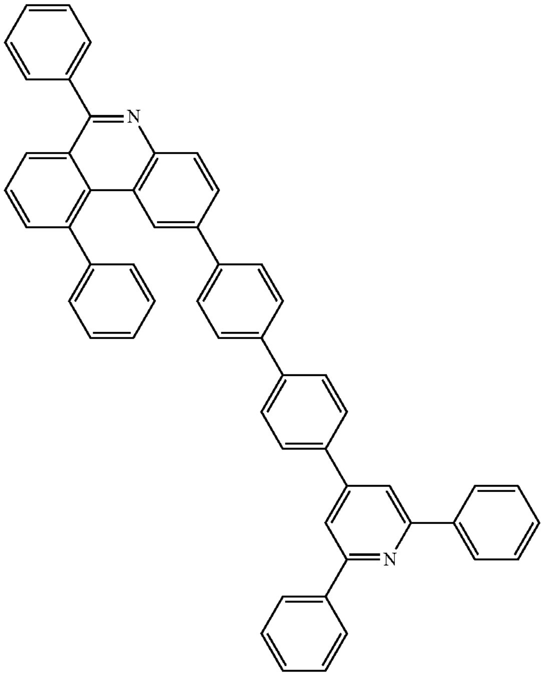

918
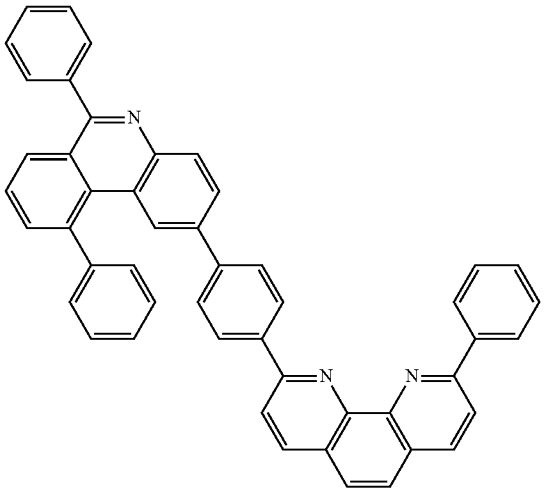
919
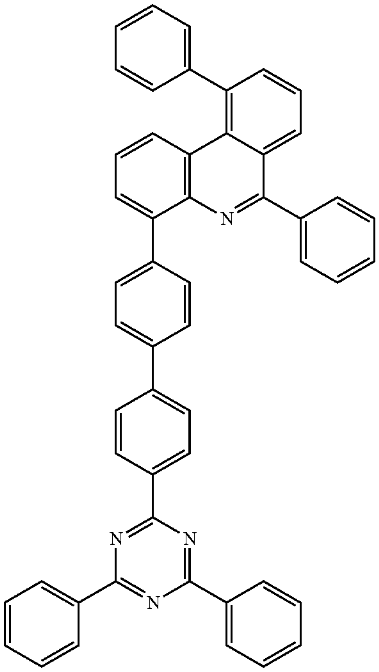
920
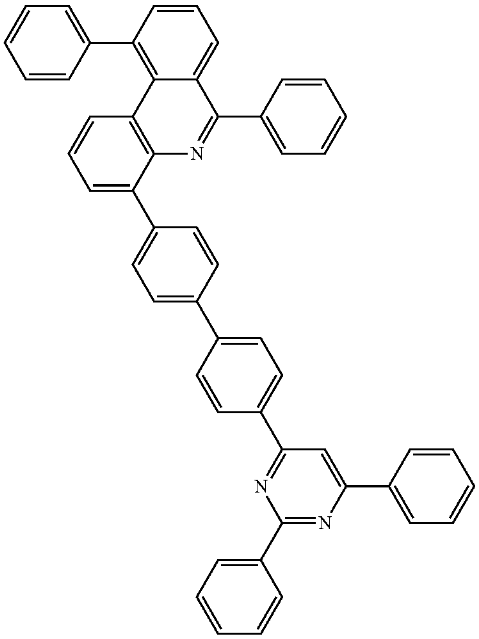
921
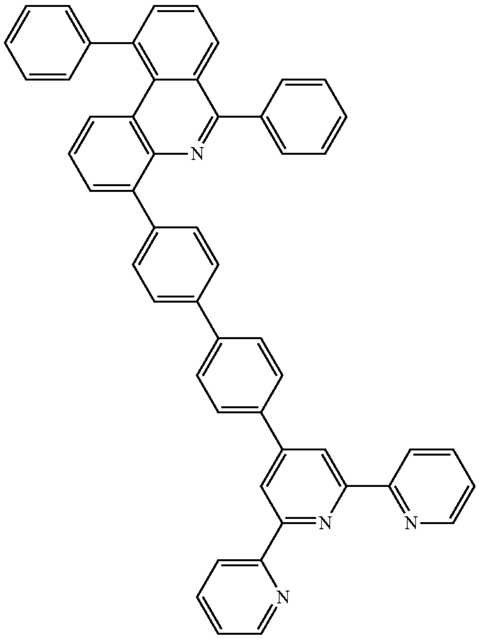

-continued
922
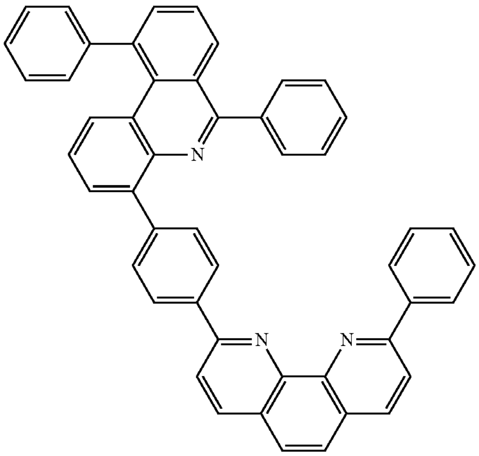
923
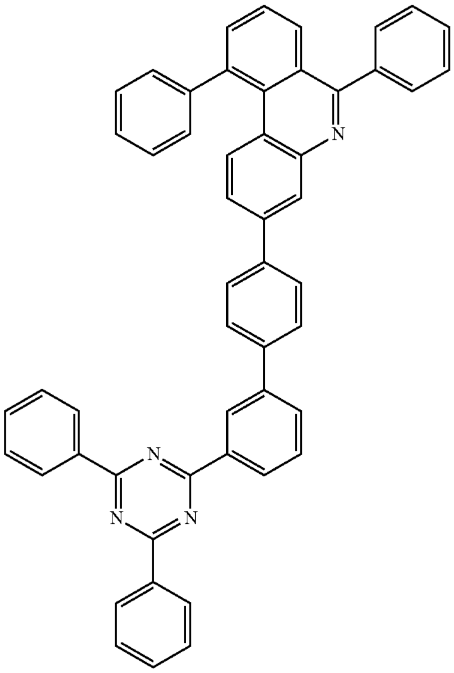
-continued
924
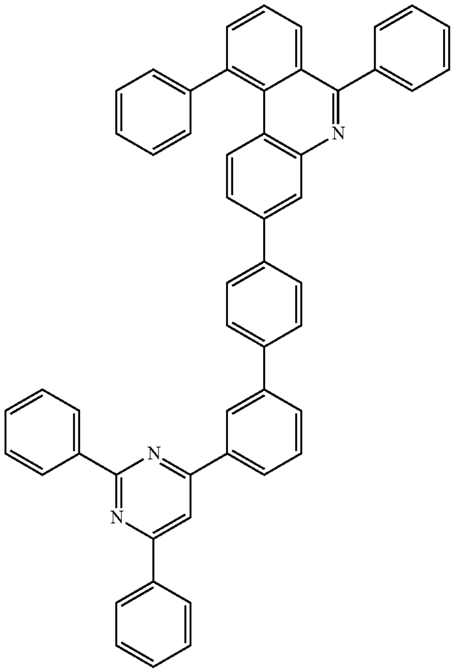
925
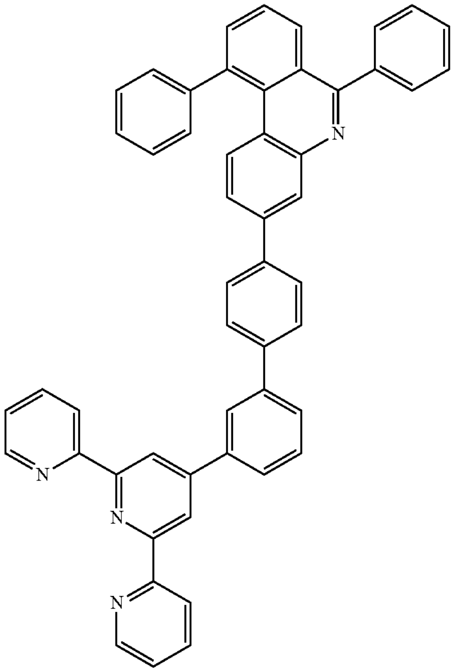

926
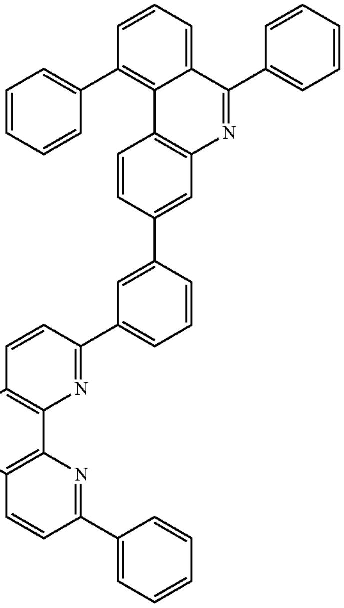
927
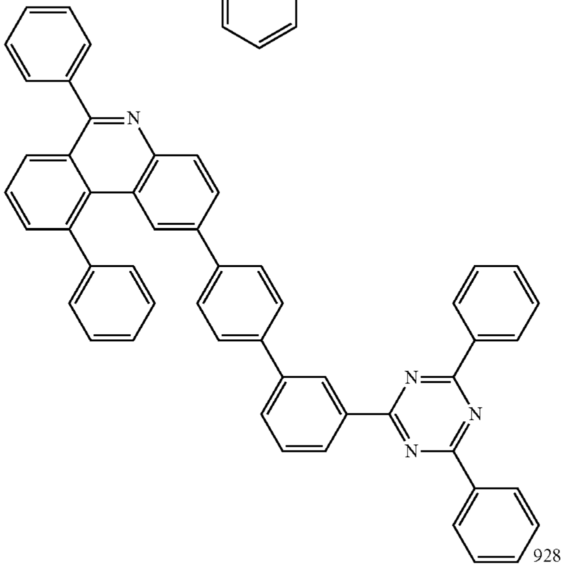
928
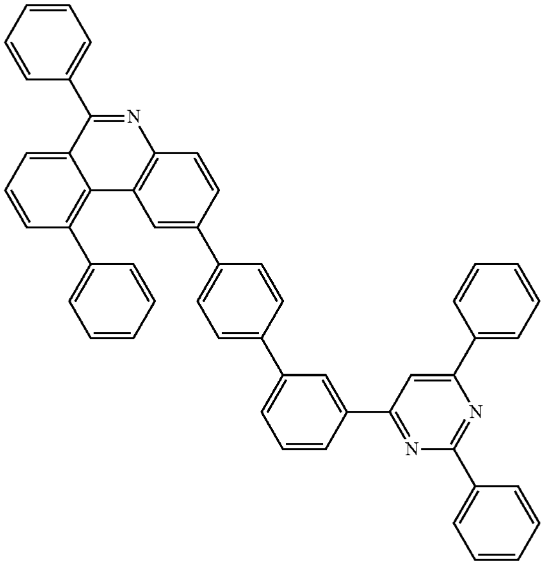
929
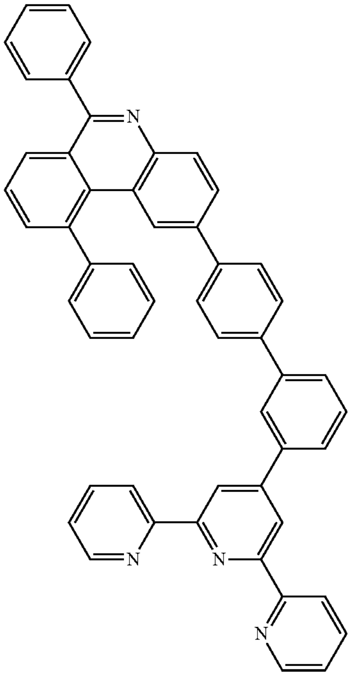
930
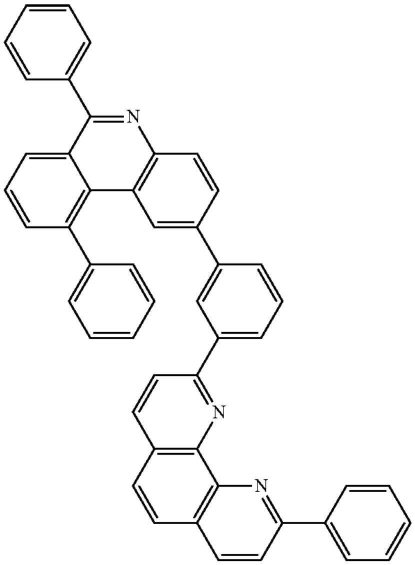

931
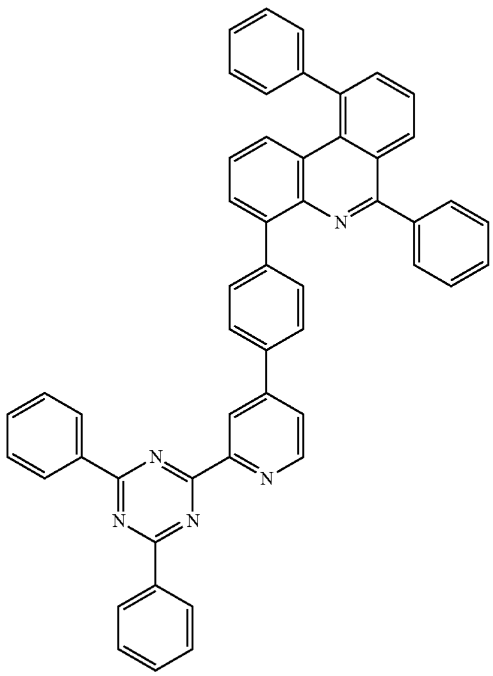
933
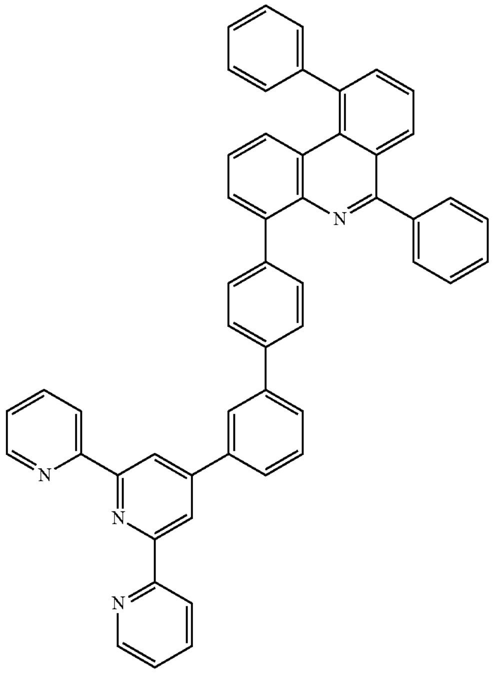
932
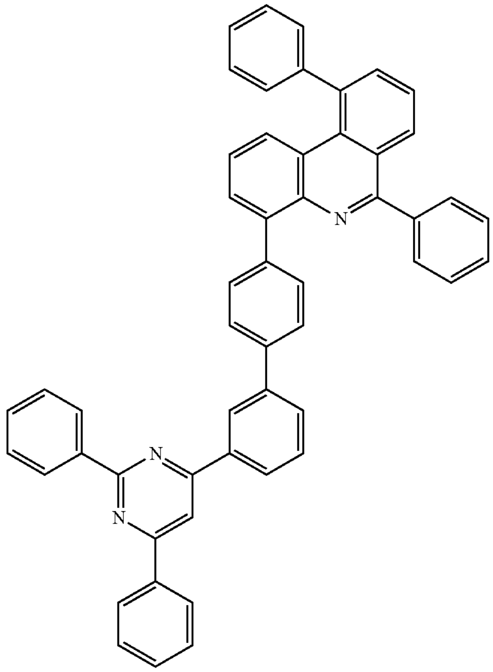
934
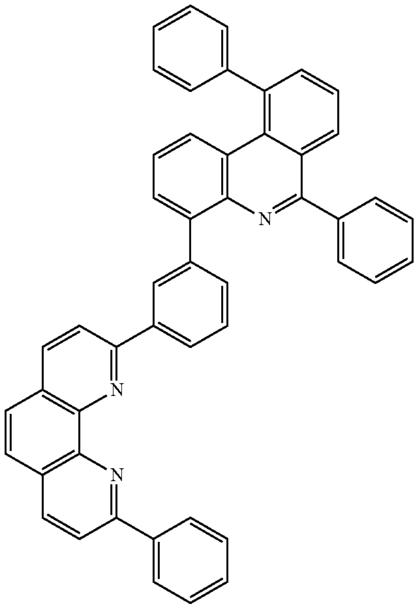

-continued
935
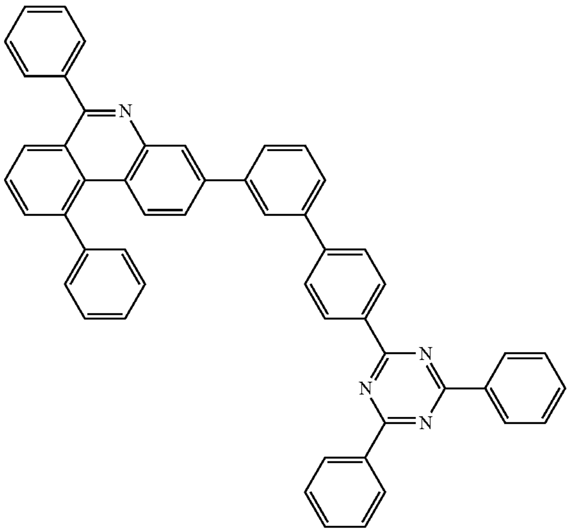
936
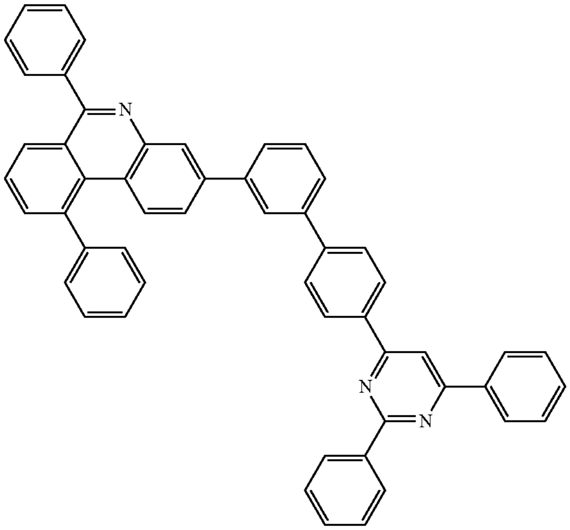
937
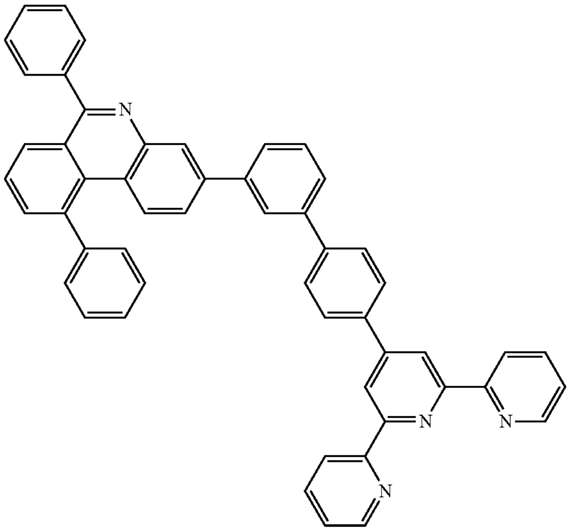
-continued
938
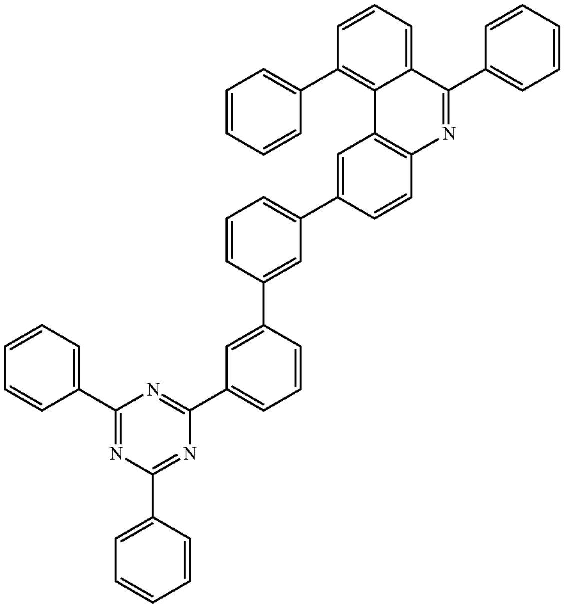
939
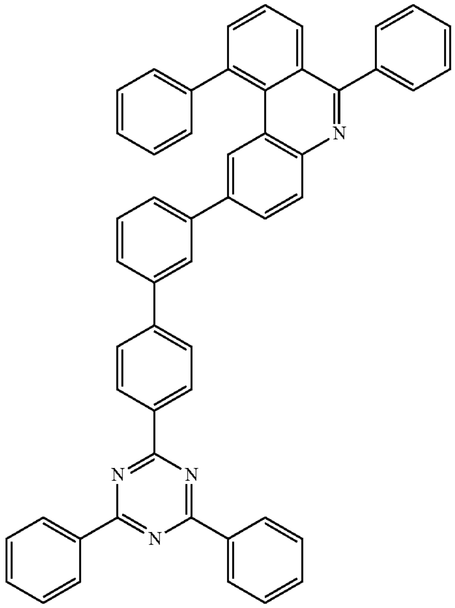

940
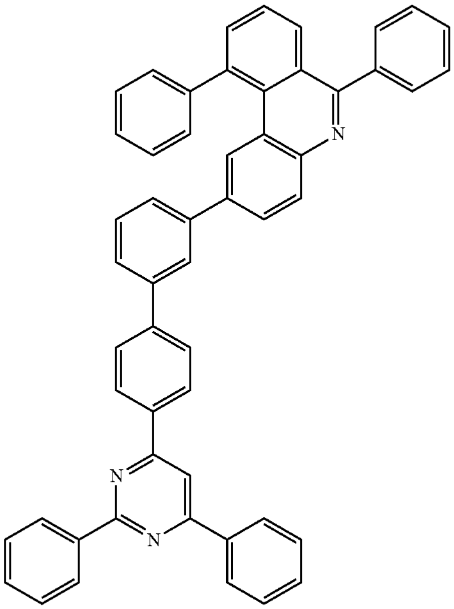
942
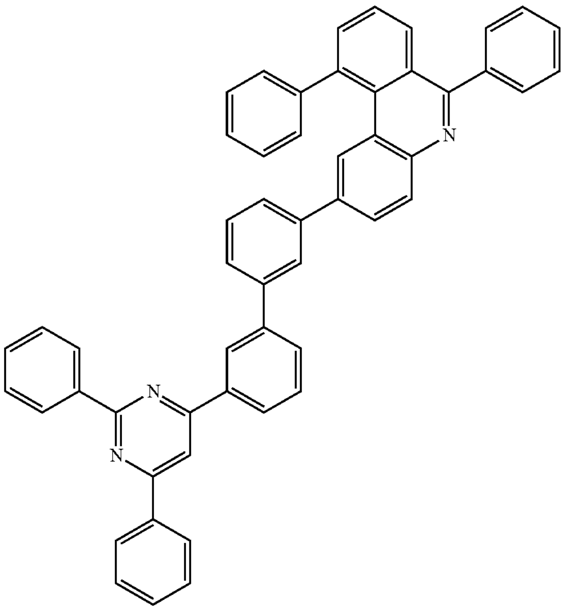
941
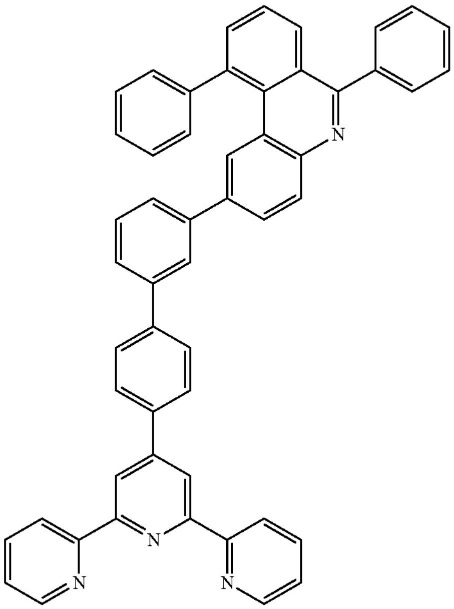
943
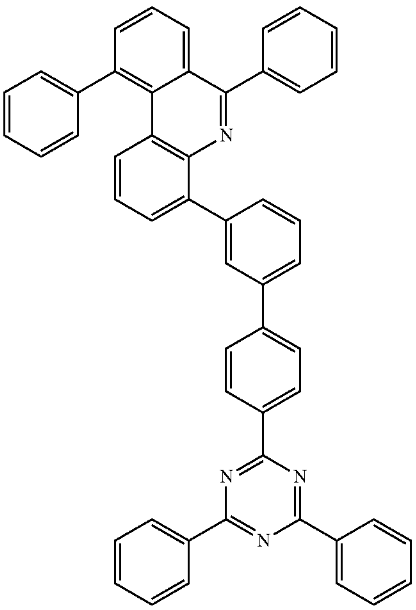

-continued
944
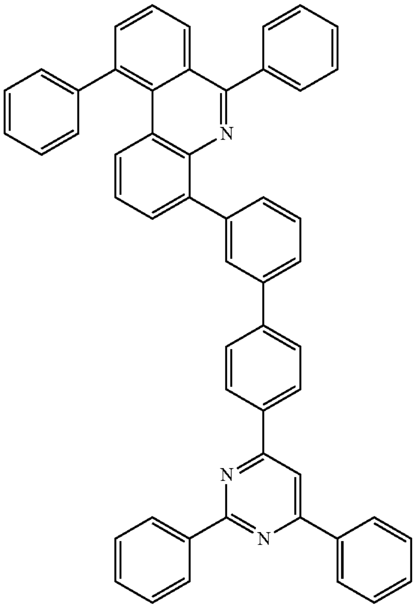
945
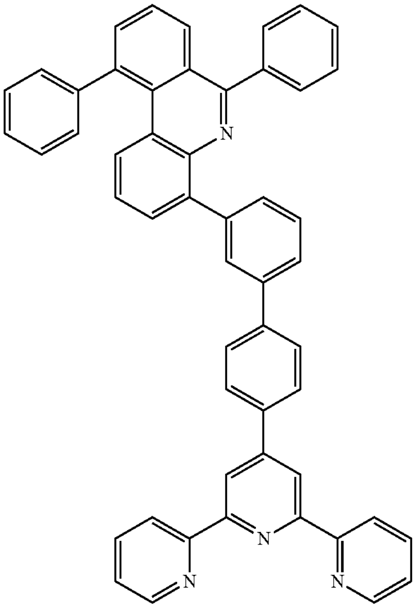
-continued
946
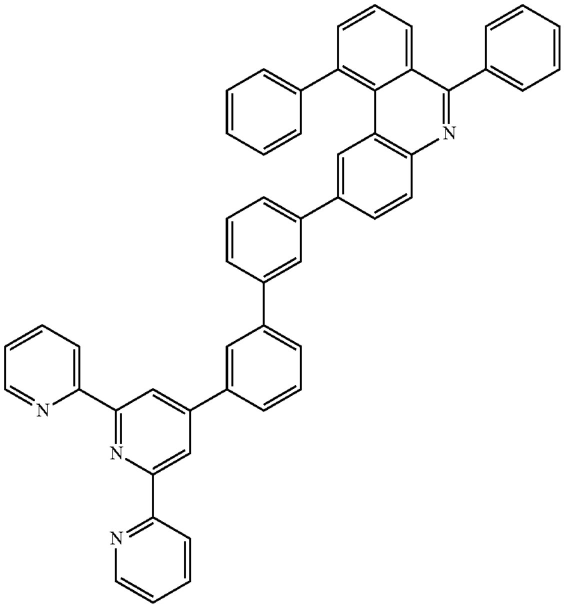
947
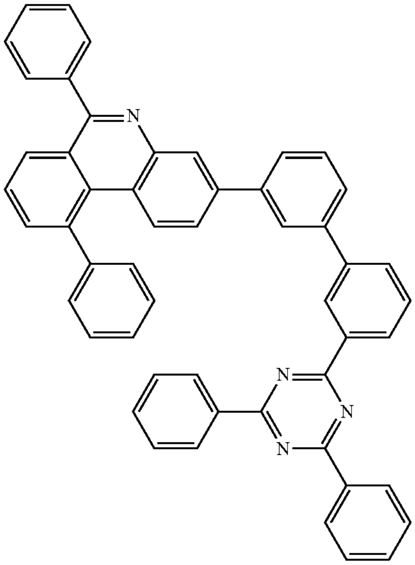

-continued

948

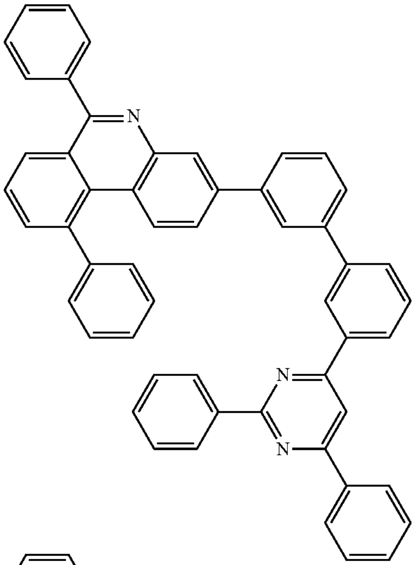

949

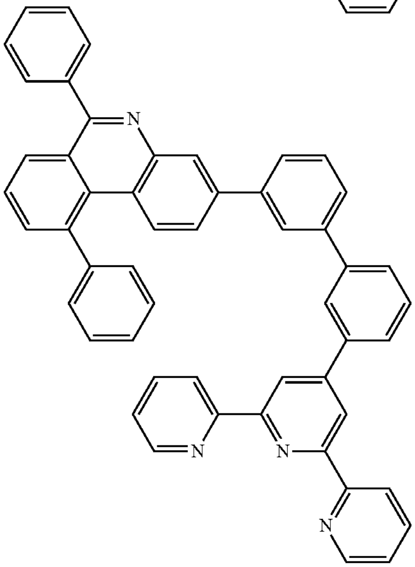

950

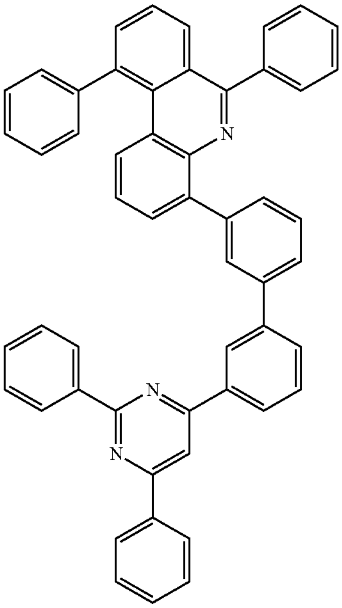

-continued

951

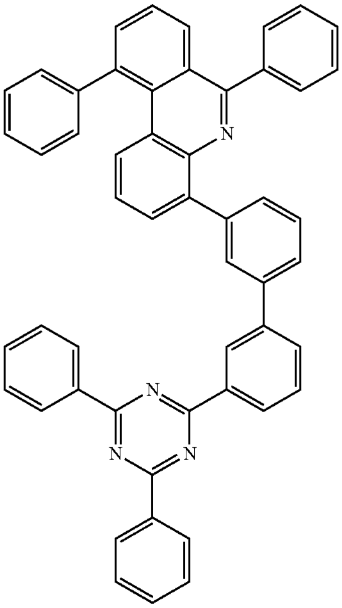

952

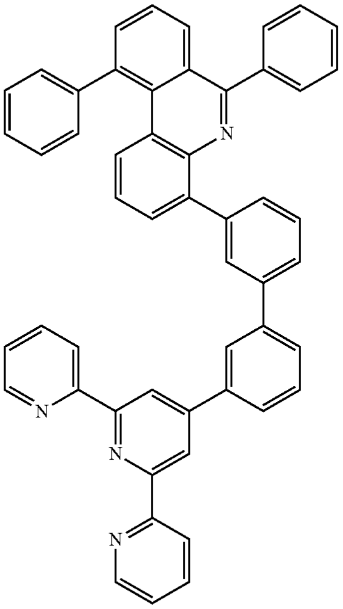

2. An organic light emitting device comprising:

a first electrode;

a second electrode provided opposite to the first electrode; and one or more organic material layers provided between the first electrode and the second electrode, wherein one or more layers of the organic material layers comprise the heterocyclic compound of claim 1.

3. The organic light emitting device of claim 2, wherein the organic material layer comprises a light emitting layer, and the light emitting layer comprises the heterocyclic compound.

4. The organic light emitting device of claim 2, wherein the organic material layer comprises an electron injection layer or an electron transfer layer, and the electron injection layer or the electron transfer layer comprises the heterocyclic compound.

5. The organic light emitting device of claim 2, wherein the organic material layer comprises an electron blocking layer or a hole blocking layer, and the electron blocking layer or the hole blocking layer comprises the heterocyclic compound.

6. The organic light emitting device of claim 2, further comprising one, two or more layers selected from the group consisting of a light emitting layer, a hole injection layer, a hole transfer layer, an electron injection layer, an electron transfer layer, an electron blocking layer and a hole blocking layer.

7. The organic light emitting device of claim 2, comprising:

a first electrode;

a first stack provided on the first electrode and comprising a first light emitting layer;

a charge generation layer provided on the first stack;

a second stack provided on the charge generation layer and comprising a second light emitting layer; and a second electrode provided on the second stack.

8. The organic light emitting device of claim 7, wherein the charge generation layer comprises the heterocyclic compound.

9. The organic light emitting device of claim 7, wherein the charge generation layer is an N-type charge generation layer, and the charge generation layer comprises the heterocyclic compound.

* * * * *